(12) United States Patent
Fujiwara et al.

(10) Patent No.: US 9,051,310 B2
(45) Date of Patent: *Jun. 9, 2015

(54) NICOTINAMIDE DERIVATIVE OR SALT THEREOF

(71) Applicant: FUJIFILM Corporation, Minato-ku, Tokyo (JP)

(72) Inventors: Hideyasu Fujiwara, Ashigarakami-gun (JP); Shinsuke Mizumoto, Ashigarakami-gun (JP); Yohei Kubo, Ashigarakami-gun (JP); Hiyoku Nakata, Ashigarakami-gun (JP); Shinji Hagiwara, Ashigarakami-gun (JP); Yasutaka Baba, Ashigarakami-gun (JP); Takashi Tamura, Ashigarakami-gun (JP); Hidenobu Kuniyoshi, Ashigarakami-gun (JP); Tomoyuki Mashiko, Ashigarakami-gun (JP); Mari Yamamoto, Toyama (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/317,001

(22) Filed: Jun. 27, 2014

(65) Prior Publication Data

US 2014/0309225 A1  Oct. 16, 2014

Related U.S. Application Data

(63) Continuation of application No. PCT/JP2011/080597, filed on Dec. 28, 2011.

(30) Foreign Application Priority Data

Dec. 28, 2011 (JP) .................. 2011-288205

(51) Int. Cl.
*C07D 213/82* (2006.01)
*C07D 413/12* (2006.01)
(Continued)

(52) U.S. Cl.
CPC ............ *C07D 413/12* (2013.01); *C07D 401/14* (2013.01); *C07D 405/14* (2013.01);
(Continued)

(58) Field of Classification Search
USPC ......... 514/332, 333, 336, 337, 338, 339, 353; 546/255, 256, 264, 268.1, 306
See application file for complete search history.

(56) References Cited

U.S. PATENT DOCUMENTS 6,797,706 B1   9/2004  Hisamichi et al.
8,895,585 B2  11/2014  Fujiwara et al.

(Continued)

FOREIGN PATENT DOCUMENTS

CN   101155800 A   4/2008
CN   101675034 A   3/2010
(Continued)

OTHER PUBLICATIONS

International Preliminary Report on Patentability dated Jul. 10, 2014, issued by the International Searching Authority in corresponding application No. PCT/JP2011/080597.
(Continued)

*Primary Examiner* — Kahsay Habte
(74) *Attorney, Agent, or Firm* — Sughrue Mion, PLLC

(57) ABSTRACT

The object of the present invention is to provide a compound and a pharmaceutical composition having excellent Syk inhibitory activity. According to the present invention, a nicotinamide derivative represented by the following formula (I) or a salt thereof is provided,

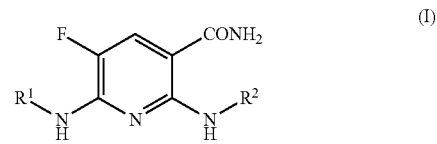

wherein
$R^1$ is a substituent represented by the following formula (II-1), (III-1), or (IV-1)

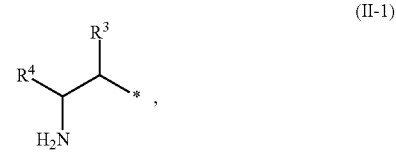

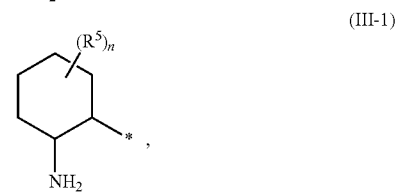

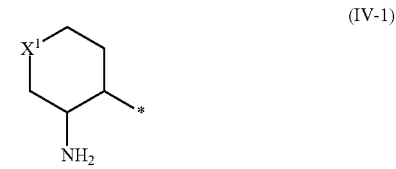

(wherein $R^3$, $R^4$, $R^5$, n, and $X^1$ have the same definitions as those described in the specification), and $R^2$ is a pyridyl, indazolyl, phenyl, pyrazolopyridyl, benzisoxazolyl, pyrimidinyl, or quinolyl group, each of which optionally has at least one substituent.

14 Claims, No Drawings

(51) Int. Cl.
| | |
|---|---|
| C07D 401/12 | (2006.01) |
| C07D 401/14 | (2006.01) |
| C07D 405/14 | (2006.01) |
| C07D 409/14 | (2006.01) |
| C07D 471/04 | (2006.01) |
| C07D 405/04 | (2006.01) |

(52) U.S. Cl.
CPC ............ *C07D213/82* (2013.01); *C07D 401/12* (2013.01); *C07D 409/14* (2013.01); *C07D 471/04* (2013.01); *C07D 405/04* (2013.01)

(56) References Cited

U.S. PATENT DOCUMENTS

| | | | |
|---|---|---|---|
| 2007/0197782 | A1 | 8/2007 | Clough et al. |
| 2008/0139561 | A1 | 6/2008 | Davies et al. |
| 2011/0230467 | A1 | 9/2011 | Shirakami et al. |
| 2012/0142671 | A1* | 6/2012 | Jia et al. .................. 514/212.08 |
| 2013/0116430 | A1 | 5/2013 | Fujiwara et al. |

FOREIGN PATENT DOCUMENTS

| | | |
|---|---|---|
| CN | 102958918 A | 3/2013 |
| EP | 1 184 376 A1 | 3/2002 |
| EP | 2 589 592 A1 | 5/2013 |
| JP | 2008-13499 A | 1/2008 |
| JP | 2008-528664 A | 7/2008 |
| WO | 00/75113 A1 | 12/2000 |
| WO | 2006/082392 A1 | 8/2006 |
| WO | 2007/120980 A2 | 10/2007 |
| WO | 2007/124221 A1 | 11/2007 |
| WO | 2008/140066 A2 | 11/2008 |
| WO | 2009/026107 A1 | 2/2009 |
| WO | 2009/036996 A2 | 3/2009 |
| WO | 2009/131687 A1 | 10/2009 |
| WO | 2009/136995 A2 | 11/2009 |
| WO | 2009/145856 A1 | 12/2009 |
| WO | 2010/144647 A1 | 12/2010 |
| WO | 2012/002577 A1 | 1/2012 |
| WO | 2012/061418 A2 | 5/2012 |
| WO | 2010/058846 A1 | 2/2015 |

OTHER PUBLICATIONS

International Search Report and Written Opinion dated Mar. 19, 2012, issued by the International Searching Authority in corresponding application No. PCT/JP2011/080597.
Takanobu Taniguchi et al., "Molecular Cloning of a Porcine Gene *syk* That Encodes a 72-kDa Protein-Tyrosine Kinase Showing High Susceptibility to Proteolysis", The Journal of Biological Chemistry, Aug. 25, 1991, pp. 15790-15796, vol. 266, No. 24.
Peter Valent et al., "Signal Transduction-Associated and Cell Activation-Linked Antigens Expressed in Human Mast Cells", International Journal of Hematology 2002, pp. 357-362, vol. 75, No. 4.
Tsung H. Lin et al., "Integrin-mediated Tyrosine Phosphorylation and Cytokine Message Induction in Monocytic Cells", The Journal of Biological Chemistry, Jul. 7, 1995, pp. 16189-16197, vol. 270, No. 27.
Elena Bulanova et al., "The IL-15Rα Chain Signals Through Association with Syk in Human B Cells", The Journal of Immunology 2001, pp. 6292-6302, vol. 167, No. 11.
Brian R. Wong et al., "Targeting Syk as a treatment for allergic and autoimmune disorders", Expert Opinion on Investigational Drugs 2004, pp. 743-762, vol. 13, No. 7.
Malini Bajpai, "Fostamatinib, a Syk inhibitor prodrug for the treatment of inflammatory diseases", IDrugs 2009, pp. 174-185, vol. 12, No. 3.
Marina Ulanova et al., "Spleen tyrosine kinase (Syk) as a novel target for allergic asthma and rhinitis", Expert Opinion on Therapeutic Targets 2005, pp. 901-921, vol. 9, No. 5.
Huan-Zhang Xie et al., "Pharmacophore modeling study based on known Spleen tyrosine kinase inhibitors together with virtual screening for identifying novel inhibitors", Bioorganic & Medicinal Chemistry Letters 2009, pp. 1944-1949, vol. 19, No. 7.
International Search Report for PCT/JP2011/080597 dated Mar. 19, 2012.
Chinese Office Action for CN 201180031719.6 dated May 5, 2014.
Supplementary European Search Report for EP 11 80 1034 dated Nov. 19, 2013.
International Preliminary Report on Patentability for PCT/JP2011/065530 issued on Jan. 8, 2013.
International Search Report and Written Opinion for PCT/JP2011/065530 dated Sep. 20, 2011.
Chinese Office Action for CN 201180031719.6 dated Aug. 22, 2013.
Office Action dated Sep. 25, 2014 from the Taiwanese Patent Office in counterpart Taiwanese Application No. 100123081.
Substantive Examination Report dated Aug. 29, 2014 from the Intellectual Property Office of the Philippines in counterpart Application No. 1/2012/502572.
Office Action dated Nov. 18, 2014, issued by the Intellectual Property Office of the Philippines in corresponding Philippines Application No. 1/2012/502572.
Communication from the Japanese Patent Office mailed Aug. 12, 2014 in corresponding Japanese Patent Application No. 2012-522731.
Office Action dated Feb. 10, 2015 from the State Intellectual Property Office of the People's Republic of China in counterpart Chinese Application No. 201180076091.1.
Office Action dated Feb. 10, 2015 from the Intellectual Property Office of Singapore in counterpart Singaporean Application No. 201209663-2.
Braselmann et al., "R406, an Orally Available Spleen Tyrosine Kinase Inhibitor Blocks Fc Receptor Signaling and Reduces Immune Complex-Mediated Inflammation," Journal of Pharmacology and Experimental Therapeutics, 2006, vol. 319, No. 3, pp. 996-1008 (11 total pages).
Meltzer et al., "An intranasal Syk-kinase inhibitor (R112) improves the symptoms of seasonal allergic rhinitis in a park environment," Journal of Allergy Clin. Immunol., 2005, vol. 115, No. 4, pp. 791-796 (6 pages total).
Yamamoto et al., "The Orally Available Spleen Tyrosine Kinase Inhibitor 2-[7-(3,4-Dimethoxyphenyl)- imidazo[1,2-c] pyrimidin-5-ylamino]-nicotinamide Dihydrochloride (BAY 61-3606) Blocks Antigen-Induced Airway Inflammation in Rodents," Journal of Pharmacology and Experimental Therapeutics, 2003, vol. 306, No. 3, pp. 1174-1181 (8 pages total).
Extended European Search Report dated Apr. 14, 2015, issued by the European Patent Office in corresponding EP Application No. 11878563.3.
Patani et al., "Bioisosterism: A Rational Approach in Drug Design", Chemical Review, American Chemical Society, US, Jan. 1, 1996, vol. 96, No. 8, pp. 3147-3176, XP 000652176.

\* cited by examiner

NICOTINAMIDE DERIVATIVE OR SALT THEREOF

CROSS-REFERENCE TO RELATED APPLICATIONS

This application is a Continuation of PCT International Application No. PCT/JP2011/080597 filed on Dec. 28, 2011, which claims priority under 35 U.S.C. §119(a) to Japanese Patent Application No. 2011-288205 filed on Dec. 28, 2011. Each of the above-application is hereby expressly incorporated by reference, in its entirety, into the present application.

TECHNICAL FIELD

The present invention relates to a nicotinamide derivative having Syk-inhibitory activity or a salt thereof.

BACKGROUND ART

Spleen Tyrosine Kinase (Syk), which is a non-receptor type intracellular tyrosine phosphatase, plays essential roles for activation of B cells and in an intracellular signaling system mediated by an Fc receptor. For example, Syk is associated with a FcεRI signal that is an immunoglobulin E receptor in mast cells, basophils, and other cells, and thus it regulates generation of inflammatory mediators, such as histamine or leukotrien, as well as cytokine from these cells. At the same time, Syk plays a role in transmitting activation signals caused by stimulation of Fcγ receptor into monocytes, dendritic cells, and other cells (Non Patent Literatures 1 and 2). Moreover, it has been reported that Syk is also associated with cytokine signaling caused by integrin, IL-13, IL-15, etc. (Non Patent Literatures 3 and 4).

In the case of a B-cell, a signal is transmitted into the cell mediated by a BCR (a B-cell antigen receptor) expressed on the cell membrane, so that activation and differentiation of the cell is induced, resulting in generation of an antibody. It has been reported that Syk is essential for such an activation and differentiation process (Non Patent Literature 5).

It is anticipated that it is possible to suppress various cell responses by inhibiting Syk (Non Patent Literatures 5 and 6).

In the case of a type I allergy, which is an immediate-type allergy reaction, for example, immunoglobulin E (IgE) binds to FcεRI, which is a high-affinity IgE receptor, and an allergen then binds thereto to promote activation of the FcεRI and the release of inflammatory mediator. As a result, allergic symptoms are expressed. It is anticipated that inhibition of Syk activity will lead to the suppression of the activation of the FcεRI, and that it will be useful for the treatment of representative type I allergy-related diseases such as bronchial asthma, allergic rhinitis, hives, and atopic dermatitis.

Moreover, it is considered that inhibition of Syk activity leads to the suppression of the activation and/or maturation of immune B cells and generation of antibodies, and that such inhibition of Syk activity can also regulate immune reactions other than type I allergy. Accordingly, it is also anticipated that inhibition of Syk activity will be effective for autoimmune diseases (rheumatoid arthritis, systemic lupus erythematosus, etc.), autoimmune hemolytic anemia, nephrotic syndrome, contact dermatitis, and the like. Furthermore, since inhibition of Syk activity also leads to the suppression of the activation of macrophages, it is anticipated that inhibition of Syk will be also effective for idiopathic thrombocytopenic purpura.

Further, inhibition of Syk activity suppresses not only immune and/or inflammatory diseases, but also activation and proliferation of lymphocytes, including B-cells as typical examples. Thus, it is anticipated that inhibition of Syk will be also effective for the treatment of various types of proliferative diseases such as lymphoma and lymphocytic leukemia. Still further, since inhibition of Syk activity regulates proliferation and differentiation of bone marrow cells, it is anticipated that it will be also effective for acute myelocytic leukemia.

On the other hand, Syk has been known to be involved in signaling mediated by integrin, which is a cell adhesion molecule. Since Syk is expressed in blood platelets and is involved in the activation thereof, an inhibitor of such Syk is anticipated to be effective as a therapeutic agent for diseases associated with the activation of blood platelets.

A large number of compounds having Syk-inhibitory activity have been reported (Patent Literatures 1 to 4). Useful compounds (Non Patent Literature 7) and compounds having Syk and/or JAK inhibitory activity (Patent Literatures 5 to 8) have been reported from clinical tests in which rheumatoid arthritis and idiopathic thrombocytopenic purpura have been targeted.

PRIOR ART LITERATURES

Patent Literature

[Patent Literature 1] International Publication WO00/75113
[Patent Literature 2] JP Patent Publication (Kokai) No. 2008-013499 A
[Patent Literature 3] International Publication WO07/120,980
[Patent Literature 4] International Publication WO07/124,221
[Patent Literature 5] International Publication WO09/026,107
[Patent Literature 6] International Publication WO09/131,687
[Patent Literature 7] International Publication WO09/136,995
[Patent Literature 8] International Publication WO09/145,856

Non Patent Literature

[Non Patent Literature 1] The Journal of Biological Chemistry, Vol. 266, pp. 15790-15796, 1991
[Non Patent Literature 2] International Journal of Hematology, Vol. 75, No. 4, pp. 357-362, 2002
[Non Patent Literature 3] The Journal of Biological Chemistry, Vol. 270, pp. 16189-16197, 1995
[Non Patent Literature 4] The Journal of Immunology, Vol. 167, No. 11, pp. 6292-6302, 2001
[Non Patent Literature 5] Expert Opinion on Investigational Drugs, Vol. 13, No. 7, pp. 743-762, 2004
[Non Patent Literature 6] Expert Opinion on Therapeutic Targets, Vol. 9, No. 5, pp. 901-921, 2005
[Non Patent Literature 7] IDrugs, Vol. 12, No. 3, pp. 174-185, 2009

SUMMARY OF INVENTION

Problem to be Solved by the Invention

To date, various Syk inhibitors have been reported, but they have not been placed on the market yet. It has been desired to develop a compound and a pharmaceutical composition, which have excellent Syk-inhibitory activity.

Means for Solution to Problem

As a result of intensive studies directed towards achieving the aforementioned object, the present inventors have found that a nicotinamide derivative having a specific structure or a salt thereof has excellent Syk-inhibitory activity, thereby completing the present invention.

Specifically, the nicotinamide derivative of the present invention or a pharmaceutically acceptable salt thereof is characterized in that it is represented by the following formula (I):

[Formula 1]

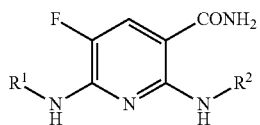
(I)

wherein
$R^1$ is a substituent represented by the following formula (II-1), (III-1), or (IV-1):

[Formula 2]

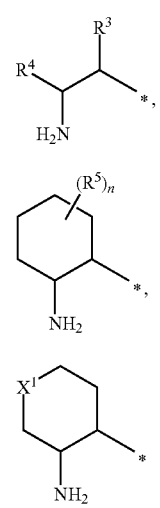

(wherein
$R^3$ represents a hydrogen atom or a $C_{1-6}$ alkyl, $C_{3-8}$ cycloalkyl, phenyl, pyridyl, or thienyl group, each of which optionally has at least one substituent,
$R^4$ represents a hydrogen atom, a $C_{1-6}$ alkyl group, or a $C_{3-8}$ cycloalkyl group,
$R^5$ represents a hydroxy group, a halogen atom, or a $C_{1-6}$ alkyl or $C_{1-6}$ alkoxy group, each of which optionally has at least one substituent,
n is an integer of 0-2,
$R^5$ may be the same or different, and two $R^5$s may, together with the carbon atom to which they bind, form a $C_{3-8}$ cycloalkane ring when n is 2,
$X^1$ represents an oxygen atom or —N($R^6$)— (wherein $R^6$ represents a hydrogen atom or an acyl group), "*" represents a binding site), and
$R^2$ represents a pyridyl, indazolyl, phenyl, pyrazolopyridyl, benzisoxazolyl, pyrimidinyl, or quinolyl group, each of which optionally has at least one substituent.

In addition, the present invention provides a pharmaceutical composition comprising the above-described nicotinamide derivative or a salt thereof, particularly, a pharmaceutical composition for use in the treatment of a Syk-related disease, which comprises the above-described nicotinamide derivative or a salt thereof, and a pharmaceutical composition for use in the treatment of a disease selected from the group consisting of rheumatoid arthritis and idiopathic thrombocytopenic purpura, which comprises the above-described nicotinamide derivative or a salt thereof.

From a further viewpoint, the present invention provides: use of the above-described nicotinamide derivative or a salt thereof for production of the above-described pharmaceutical composition; a method for treating a Syk-related disease, which comprises a step of administering a therapeutically effective amount of the above-described nicotinamide derivative or a salt thereof to mammals including a human; and a method for treating a disease selected from the group consisting of rheumatoid arthritis and idiopathic thrombocytopenic purpura, which comprises a step of administering a therapeutically effective amount of the above-described nicotinamide derivative or a salt thereof to mammals including a human.

Advantageous Effects of Invention

The nicotinamide derivative of the present invention or a salt thereof has excellent Syk-inhibitory activity, and it is useful as a pharmaceutical composition for use in the treatment of a Syk-related disease.

DESCRIPTION OF EMBODIMENTS

Hereinafter, the compound of the present invention will be described in detail.

It is to be noted that the following definitions are applied in the present specification, unless otherwise specified.

The term "halogen atom" is used herein to mean a fluorine atom, a chlorine atom, a bromine atom or an iodine atom.

The term "$C_{1-3}$ alkyl group" is used herein to mean a methyl, ethyl, propyl, or isopropyl group.

The term "$C_{1-4}$ alkyl group" is used herein to mean a methyl, ethyl, propyl, isopropyl, butyl, sec-butyl, isobutyl, or tert-butyl group.

The term "$C_{1-6}$ alkyl group" is used herein to mean a linear or branched $C_{1-6}$ alkyl group such as a methyl, ethyl, propyl, isopropyl, butyl, sec-butyl, isobutyl, tert-butyl, pentyl, isopentyl, or hexyl group.

The term "$C_{2-4}$ alkyl group" is used herein to mean an ethyl, propyl, isopropyl, butyl, sec-butyl, isobutyl, or tert-butyl group.

The term "$C_{4-6}$ alkyl group" is used herein to mean a linear or branched $C_{4-6}$ alkyl group such as a butyl, sec-butyl, isobutyl, tert-butyl, pentyl, isopentyl, or hexyl group.

The term "$C_{3-8}$ cycloalkyl group" is used herein to mean a $C_{3-8}$ cycloalkyl group such as a cyclopropyl, cyclobutyl, cyclopentyl, or cyclohexyl group.

The term "ar-$C_{1-6}$ alkyl group" is used herein to mean an ar-$C_{1-6}$ alkyl group such as a benzyl, diphenylmethyl, trityl, phenethyl, or naphthylmethyl group.

The term "$C_{1-3}$ alkoxy group" is used herein to mean a methoxy, ethoxy, propoxy, or isopropoxy group.

The term "$C_{1-6}$ alkoxy group" is used herein to mean a linear or branched $C_{1-6}$ alkyloxy group such as a methoxy, ethoxy, propoxy, isopropoxy, butoxy, isobutoxy, sec-butoxy, tert-butoxy, pentyloxy, or hexyloxy group.

The term "$C_{1-6}$ alkoxy $C_{1-6}$ alkyl group" is used herein to mean a $C_{1-6}$ alkoxy $C_{1-6}$ alkyl group such as a methoxymethyl or 1-ethoxyethyl group.

The term "$C_{1-3}$ alkylthio group" is used herein to mean a $C_{1-3}$ alkylthio group such as a methylthio, ethylthio, or propylthio group.

The term "$C_{1-6}$ alkylthio group" is used herein to mean a $C_{1-6}$ alkylthio group such as a methylthio, ethylthio, propylthio, butylthio, or pentylthio group.

The term "$C_{1-6}$ alkylsulfonyl group" is used herein to mean a $C_{1-6}$ alkylsulfonyl group such as a methylsulfonyl, ethylsulfonyl, or propylsulfonyl group.

The term "arylsulfonyl group" is used herein to mean a benzenesulfonyl, p-toluenesulfonyl, or naphthalenesulfonyl group.

The term "$C_{1-6}$ alkylsulfonyloxy group" is used herein to mean a $C_{1-6}$ alkylsulfonyloxy group such as a methylsulfonyloxy or ethylsulfonyloxy group.

The term "arylsulfonyloxy group" is used herein to mean a benzenesulfonyloxy or p-toluenesulfonyloxy group.

The term "$C_{2-12}$ alkanoyl group" is used herein to mean a linear or branched $C_{2-12}$ alkanoyl group such as an acetyl, propionyl, valeryl, isovaleryl, or pivaloyl group.

The term "aroyl group" is used herein to mean a benzoyl or naphthoyl group.

The term "acyl group" is used herein to mean a formyl group, a $C_{2-12}$ alkanoyl group, or an aroyl group.

The term "$C_{1-6}$ alkoxycarbonyl group" is used herein to mean a linear or branched $C_{1-6}$ alkoxycarbonyl group such as a methoxycarbonyl, ethoxycarbonyl, isopropoxycarbonyl, tert-butoxycarbonyl, or 1,1-dimethylpropoxycarbonyl group.

The term "ar-$C_{1-6}$ alkyloxycarbonyl group" is used herein to mean an ar-$C_{1-6}$ alkyloxycarbonyl group such as a benzyloxycarbonyl or phenethyloxycarbonyl group.

The term "aryloxycarbonyl group" is used herein to mean a phenyloxycarbonyl or naphthyloxycarbonyl group.

The term "$C_{1-6}$ alkylamino group" is used herein to mean a linear or branched $C_{1-6}$ alkylamino group such as a methylamino, ethylamino, propylamino, isopropylamino, butylamino, sec-butylamino, tert-butylamino, pentylamino, or hexylamino group.

The term "di-$C_{1-6}$ alkylamino group" is used herein to mean a linear or branched di-$C_{1-6}$ alkylamino group such as a dimethylamino, diethylamino, dipropylamino, diisopropylamino, dibutylamino, di(tert-butyl)amino, dipentylamino, dihexylamino, (ethyl)(methyl)amino, or (methyl)(propyl)amino group.

The term "(di)$C_{1-6}$ alkylamino group" is used herein to mean a $C_{1-6}$ alkylamino group or di-$C_{1-6}$ alkylamino group.

The term "silyl group" is used herein to mean a trimethylsilyl, triethylsilyl, or tributylsilyl group.

The term "$C_{3-8}$ cycloalkane" is used herein to mean a $C_{3-8}$ cycloalkane ring such as a cyclopropane, cyclobutane, cyclopentane, or cyclohexane ring.

The amino-protecting group includes all groups that can be used as protecting groups for ordinary amino groups. Examples of such an amino-protecting group include groups described in W. Greene et al., Protective Groups in Organic Synthesis, Vol. 4, pp. 696 to 926, 2007, John Wiley & Sons, INC. Specific examples include an ar-$C_{1-6}$ alkyl group, a $C_{1-6}$ alkoxy $C_{1-6}$ alkyl group, an acyl group, a $C_{1-6}$ alkoxycarbonyl group, an ar-$C_{1-6}$ alkyloxycarbonyl group, an aryloxycarbonyl group, a $C_{1-6}$ alkylsulfonyl group, an arylsulfonyl group, and a silyl group.

The hydroxy-protecting group includes all groups that can be used as protecting groups for ordinary hydroxy groups. Examples of such a hydroxy-protecting group include groups described in W. Greene et al., Protective Groups in Organic Synthesis, Vol. 4, pp. 16 to 299, 2007, John Wiley & Sons, INC. Specific examples include a $C_{1-6}$ alkyl group, an ar-$C_{1-6}$ alkyl group, a $C_{1-6}$ alkoxy $C_{1-6}$ alkyl group, acyl group, a $C_{1-6}$ alkoxycarbonyl group, an ar-$C_{1-6}$ alkyloxycarbonyl group, a $C_{1-6}$ alkylsulfonyl group, an arylsulfonyl group, a silyl group, a tetrahydrofuranyl group, and a tetrahydropyranyl group.

The carboxyl-protecting group includes all groups that can be used as protecting groups for ordinary carboxyl groups. Examples of such a carboxyl-protecting group include groups described in W. Greene et al., Protective Groups in Organic Synthesis, Vol. 4, pp. 533 to 643, 2007, John Wiley & Sons, INC. Specific examples include a $C_{1-6}$ alkyl group, an ar-$C_{1-6}$ alkyl group, a $C_{1-6}$ alkoxy $C_{1-6}$ alkyl group, an ar-$C_{1-6}$ alkyloxy $C_{1-6}$ alkyl group, and a silyl group.

Examples of a leaving group include a halogen atom, a $C_{1-6}$ alkylsulfonyloxy group, and an arylsulfonyloxy group.

Alcohols include methanol, ethanol, propanol, 2-propanol, butanol, and 2-methyl-2-propanol.

Aliphatic hydrocarbons include pentane, hexane, and cyclohexane.

Halogenated hydrocarbons include methylene chloride, chloroform, and dichloroethane.

Aromatic hydrocarbons include benzene, toluene, and xylene. Glycols include ethylene glycol, propylene glycol, and diethylene glycol.

Ethers include diethyl ether, diisopropyl ether, dioxane, tetrahydrofuran, anisole, ethylene glycol dimethyl ether, diethylene glycol dimethyl ether, and diethylene glycol diethyl ether.

Ketones include acetone, 2-butanone, and 4-methyl-2-pentanone.

Esters include methyl acetate, ethyl acetate, propyl acetate, and butyl acetate.

Amides include N,N-dimethylformamide, N,N-dimethylacetamide, and 1-methyl-2-pyrrolidone.

Nitriles include acetonitrile and propionitrile.

Sulfoxides include dimethyl sulfoxide.

Salts of the compound represented by the formula (I) include generally known salts, namely, the salts of basic groups such as amino groups, and the salts of acidic groups such as hydroxy or carboxyl groups.

Examples of the salts of basic groups include: salts with mineral acids such as hydrochloric acid, hydrobromic acid, nitric acid, and sulfuric acid; salts with organic carboxylic acids such as formic acid, acetic acid, citric acid, oxalic acid, fumaric acid, maleic acid, succinic acid, malic acid, tartaric acid, aspartic acid, trichloroacetic acid, and trifluoroacetic acid; and salts with sulfonic acids such as methanesulfonic acid, benzenesulfonic acid, p-toluenesulfonic acid, mesitylenesulfonic acid, and naphthalenesulfonic acid.

Examples of the salts of acidic groups include: salts with alkaline metals such as sodium and potassium; salts with alkaline earth metals such as calcium and magnesium; ammonium salts; and salts with nitrogen-containing organic bases such as trimethylamine, triethylamine, tributylamine, pyridine, N,N-dimethyl aniline, N-methyl piperidine, N-methyl morpholine, diethylamine, dicyclohexylamine, procaine, dibenzylamine, N-benzyl-β-phenethylamine, 1-ephenamine, and N,N'-dibenzylethylenediamine.

Among the above-described salts, pharmaceutically acceptable salts are preferable.

The nicotinamide derivative of the present invention is characterized in that it is represented by the following formula (I):

[Formula 3]

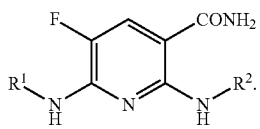
(I)

$R^1$ is a substituent represented by the following formula (II-1), (III-1), or (IV-1):

[Formula 4]

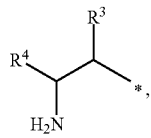
(II-1)

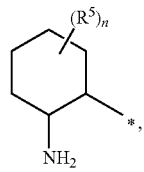
(III-1)

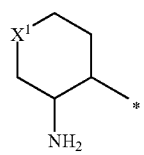
(IV-1)

(wherein $R^3$, $R^4$, $R^5$, n, and $X^1$ have the same definitions as those described above), preferably a substituent represented by the following formula (II-2), (III-2), or (IV-2):

[Formula 5]

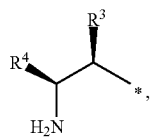
(II-2)

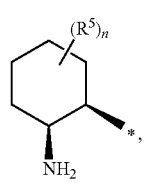
(III-2)

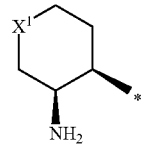
(IV-2)

(wherein $R^3$, $R^4$, $R^5$, n, and $X^1$ have the same definitions as those described above), and more preferably a substituent represented by the following formula (II-2) or (III-2):

[Formula 6]

(II-2)

(III-2)

(wherein $R^3$, $R^4$, $R^5$, and n have the same definitions as those described above).

$R^3$ is a hydrogen atom or a $C_{1-6}$ alkyl, $C_{3-8}$ cycloalkyl, phenyl, pyridyl, or thienyl group, each of which optionally has at least one substituent and preferably a $C_{1-6}$ alkyl or $C_{3-8}$ cycloalkyl group, each of which optionally has at least one substituent.

When $R^3$ is a $C_{1-6}$ alkyl or $C_{3-8}$ cycloalkyl group, each of which optionally has at least one substituent, toxicity of the compound can be further reduced.

$R^3$ is preferably a phenyl, pyridyl, or thienyl group, each of which optionally has at least one substituent. When $R^3$ is a phenyl, pyridyl, or thienyl group, each of which optionally has at least one substituent, pharmacological activity of the compound is improved.

When $R^3$ is a $C_{1-6}$ alkyl group, it is preferably a $C_{1-4}$ alkyl group. Preferred examples include methyl, ethyl, n-propyl, isopropyl, and isobutyl groups.

When $R^3$ is a $C_{3-8}$ cycloalkyl group, it is preferably a cyclopropyl or cyclobutyl group and more preferably a cyclopropyl group.

A substituent on a $C_{1-6}$ alkyl, $C_{3-8}$ cycloalkyl, phenyl, pyridyl, or thienyl group represented by $R^3$ is preferably selected from a substituent group $\alpha_{1-1}$ and more preferably selected from a substituent group $\alpha_{1-2}$. Toxicity of the compound having such a substituent can be further reduced.

The substituent group $\alpha_{1-1}$ includes a halogen atom and $C_{1-6}$ alkyl, $C_{3-8}$ cycloalkyl, $C_{1-6}$ alkoxy, $C_{1-6}$ alkylthio, phenyl, and pyrazolyl groups, each of which has at least one halogen atom.

The substituent group $\alpha_{1-2}$ includes a halogen atom, a $C_{1-6}$ alkyl group, and a $C_{1-6}$ alkoxy group.

A halogen atom in each of the substituent groups $\alpha_{1-1}$ and $\alpha_{1-2}$ is preferably a fluorine atom or a chlorine atom and more preferably a fluorine atom.

A $C_{1-6}$ alkyl group in each of the substituent groups $\alpha_{1-1}$ and $\alpha_{1-2}$ is preferably a $C_{1-3}$ alkyl group, more preferably a methyl group or an ethyl group, and further preferably a methyl group.

A $C_{3-8}$ cycloalkyl group in the substituent group $\alpha_{1-1}$ is preferably a cyclopropyl group or a cyclobutyl group and more preferably a cyclopropyl group.

A $C_{1-6}$ alkoxy group in each of the substituent groups $\alpha_{1-1}$ and $\alpha_{1-2}$ is preferably a $C_{1-3}$ alkoxy group, more preferably a methoxy group or an ethoxy group, and further preferably a methoxy group.

A $C_{1-6}$ alkylthio group in the substituent group $\alpha_{1-1}$ is preferably a $C_{1-3}$ alkylthio group, more preferably a methylthio group or an ethylthio group, and further preferably a methylthio group.

When $R^3$ is a $C_{1-6}$ alkyl group, the $C_{1-6}$ alkyl group is preferably unsubstituted or substituted with a halogen atom or a $C_{1-6}$ alkoxy group and more preferably unsubstituted or substituted with a $C_{1-6}$ alkoxy group.

When $R^3$ is a $C_{3-8}$ cycloalkyl group, the $C_{3-8}$ cycloalkyl group is preferably unsubstituted or substituted with a halogen atom or a $C_{1-6}$ alkyl group.

When $R^3$ is a thienyl group, the thienyl group is preferably unsubstituted or substituted with a $C_{1-6}$ alkyl group.

$R^4$ is a hydrogen atom, a $C_{1-6}$ alkyl group, or a $C_{3-8}$ cycloalkyl group, preferably a hydrogen atom or a $C_{1-3}$ alkyl group, more preferably a hydrogen atom, a methyl group, or an ethyl group, and further preferably a hydrogen atom or a methyl group.

When $R^3$ is a $C_{4-6}$ alkyl group, $R^4$ is preferably a hydrogen atom. When $R^3$ is a $C_{4-6}$ alkyl group, the $C_{4-6}$ alkyl group is preferably an isobutyl group. Toxicity of the compound having such a substituent can be further reduced.

When $R^3$ is a $C_{1-3}$ alkyl or thienyl group, $R^4$ is preferably a methyl group. Toxicity of the compound having such a substituent can be further reduced.

$R^5$ is a hydroxy group, a halogen atom, or a $C_{1-6}$ alkyl or $C_{1-6}$ alkoxy group, each of which optionally has at least one substituent.

Here, n is an integer of 0 to 2. When n is 2, $R^5$ may be the same or different. Also, two $R^5$s may, together with the carbon atom to which they bind, form a $C_{3-8}$ cycloalkane ring. The $C_{3-8}$ cycloalkane ring is preferably a cyclopropane or cyclobutane ring and more preferably a cyclopropane ring.

Here, $R^5$ is preferably a hydroxy group, a halogen atom, or a $C_{1-6}$ alkyl or $C_{1-6}$ alkoxy group, each of which optionally has at least one phenyl group and more preferably a hydroxy group or a halogen atom.

Here, n is an integer of 0-2, preferably an integer of 0 or 1, and more preferably an integer of 0.

$X^1$ is an oxygen atom or —N($R^6$)— (wherein $R^6$ has the same definition as that described above) and preferably an oxygen atom. When $X^1$ is an oxygen atom, pharmacological activity of the compound is improved.

$R^6$ is a hydrogen atom or an acyl group, preferably a hydrogen atom or an acetyl group, and more preferably an acetyl group.

$R^2$ is a pyridyl, indazolyl, phenyl, pyrazolopyridyl, benzisoxazolyl, pyrimidinyl, or quinolyl group, each of which optionally has at least one substituent, preferably a pyridyl or phenyl group, each of which optionally has at least one substituent, and more preferably a pyridyl group. When $R^2$ is a pyridyl or phenyl group, each of which optionally has at least one substituent, toxicity of the compound can be further reduced.

In addition, for idiopathic thrombocytopenic purpura (hereinafter also referred to as "ITP"), a pyridyl, phenyl, indazolyl, or pyrazolopyridyl group, each of which optionally has at least one substituent is preferable and an indazolyl or pyrazolopyridyl group, each of which optionally has at least one substituent is more preferable.

A substituent that binds to a pyridyl, indazolyl, phenyl, pyrazolopyridyl, benzisoxazolyl, pyrimidinyl, or quinolyl group is preferably a substituent selected from a substituent group $\alpha_{2-1}$.

The substituent group $\alpha_{2-1}$ includes: a halogen atom and $C_{1-6}$ alkyl, $C_{3-8}$ cycloalkyl, $C_{1-6}$ alkoxy, (di)$C_{1-6}$ alkylamino, acyl, pyrazolyl, triazolyl, morpholinyl, and pyrrolysyl groups, each of which optionally has at least one substituent selected from a substituent group $\beta_{2-1}$.

A halogen atom in the substituent group $\alpha_{2-1}$ is preferably a fluorine atom or a chlorine atom and more preferably a fluorine atom.

A $C_{1-6}$ alkyl group in the substituent group $\alpha_{2-1}$ is preferably a $C_{1-3}$ alkyl group, more preferably a methyl or ethyl group, and further preferably a methyl group.

A $C_{3-8}$ cycloalkyl group in the substituent group $\alpha_{2-1}$ is preferably a cyclopropyl or cyclobutyl group and more preferably a cyclopropyl group.

A $C_{1-6}$ alkoxy group in the substituent group $\alpha_{2-1}$ is preferably a $C_{1-3}$ alkoxy group, more preferably a methoxy or ethoxy group, and further preferably a methoxy group.

A (di)$C_{1-6}$ alkylamino group in the substituent group $\alpha_{2-1}$ is a mono-$C_{1-6}$ alkylamino or di-$C_{1-6}$ alkylamino group and preferably a di-$C_{1-6}$ alkylamino group. Here, a $C_{1-6}$ alkyl group that binds to a nitrogen atom is preferably a $C_{1-3}$ alkyl group, more preferably a methyl or ethyl group, and further preferably a methyl group.

Acyl in the substituent group $\alpha_{2-1}$ is preferably an acetyl group.

The substituent group $\beta_{2-1}$ includes a halogen atom, oxo, and $C_{1-6}$ alkyl and $C_{1-6}$ alkoxy groups.

A halogen atom in the substituent group $\beta_{2-1}$ is preferably a fluorine atom or a chlorine atom and more preferably a fluorine atom.

A $C_{1-6}$ alkyl group in the substituent group $\beta_{2-1}$ is preferably a $C_{1-3}$ alkyl group, more preferably a methyl or ethyl group, and further preferably a methyl group.

A $C_{1-6}$ alkoxy group in the substituent group $\beta_{2-1}$ is preferably a $C_{1-3}$ alkoxy group, more preferably a methoxy or ethoxy group, and further preferably a methoxy group.

When $R^2$ is pyridyl optionally having at least one substituent, a substituent that binds to the pyridyl group is preferably a substituent selected from the substituent group $\alpha_{2-1}$, more preferably a substituent selected from a substituent group $\alpha_{3-1}$, and further preferably a substituent selected from a substituent group $\alpha_{3-2}$.

The substituent group $\alpha_{3-1}$ includes a halogen atom and $C_{1-6}$ alkyl, $C_{3-8}$ cycloalkyl, $C_{1-6}$ alkoxy, (di)$C_{1-6}$ alkylamino, acyl, pyrazolyl, triazolyl, morpholinyl, and pyrrolysyl groups, each of which optionally has at least one substituent selected from the following substituent group $\beta_{3-1}$. The preferred ranges of the substituents are the same as those described for the substituent group $\alpha_{2-1}$.

The substituent group $\beta_{3-1}$ includes a halogen atom and $C_{1-6}$ alkyl and $C_{1-6}$ alkoxy groups. The preferred ranges of the substituents are the same as those described for the substituent group $\beta_{2-1}$.

The substituent group $\alpha_{3-2}$ includes a halogen atom and $C_{1-6}$ alkyl, $C_{3-8}$ cycloalkyl, $C_{1-6}$ alkoxy, (di)$C_{1-6}$ alkylamino, pyrazolyl, triazolyl, and morpholinyl groups, each of which optionally has at least one substituent selected from the following substituent group $\beta_{3-2}$. The preferred ranges of the substituents are the same as those described for the substituent group $\alpha_{2-1}$.

The substituent group $\beta_{3-2}$ includes a halogen atom and a $C_{1-6}$ alkyl group. The preferred ranges of the substituents are the same as those described for the substituent group $\beta_{2-1}$.

When $R^2$ is pyridyl optionally having at least one substituent, a pyridyl group is preferably a substituent represented by the following formula (V-1) or (V-2):

[Formula 7]

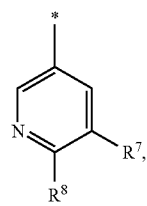

(V-1)

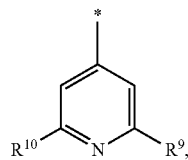

(V-2)

(wherein $R^7$, $R^8$, $R^9$, and $R^{10}$ may be the same or different and are each a hydrogen atom or a substituent selected from the substituent group $\alpha_{3\text{-}2}$), and more preferably a substituent represented by formula (V-1).

$R^7$ is a hydrogen atom or a substituent selected from the substituent group $\alpha_{3\text{-}2}$ and preferably a hydrogen atom or a substituent selected from a substituent group $\alpha_{3\text{-}3}$. Toxicity of a compound having such a substituent can be further reduced.

The substituent group $\alpha_{3\text{-}3}$ includes a halogen atom, a $C_{1\text{-}6}$ alkyl group, and $C_{1\text{-}6}$ alkyl, $C_{3\text{-}8}$ cycloalkyl, $C_{1\text{-}6}$ alkoxy, pyrazolyl, and triazolyl groups, each of which optionally has at least one $C_{1\text{-}6}$ alkyl group.

A halogen atom in the substituent group $\alpha_{3\text{-}3}$ is preferably a fluorine atom or chlorine atom and more preferably a fluorine atom.

A $C_{1\text{-}6}$ alkyl group in the substituent group $\alpha_{3\text{-}3}$ is preferably a $C_{1\text{-}3}$ alkyl group, more preferably a methyl or ethyl group, and further preferably a methyl group.

A $C_{3\text{-}8}$ cycloalkyl group in the substituent group $\alpha_{3\text{-}3}$ is preferably a cyclopropyl or cyclobutyl group and more preferably a cyclopropyl group.

A $C_{1\text{-}6}$ alkoxy group in the substituent group $\alpha_{3\text{-}3}$ is preferably a $C_{1\text{-}3}$ alkoxy group, more preferably a methoxy or ethoxy group, and further preferably a methoxy group.

$R^8$ is a hydrogen atom or a substituent selected from the substituent group $\alpha_{3\text{-}2}$ and preferably a hydrogen atom or a substituent selected from a substituent group $\alpha_{3\text{-}4}$. Toxicity of a compound having such a substituent can be further reduced.

The substituent group $\alpha_{3\text{-}4}$ includes $C_{1\text{-}6}$ alkyl, $C_{1\text{-}6}$ alkoxy, and morpholinyl groups, each of which optionally has at least one halogen atom.

A halogen atom in the substituent group $\alpha_{3\text{-}4}$ is preferably a fluorine atom or a chlorine atom and more preferably a fluorine atom.

A $C_{1\text{-}6}$ alkyl group in the substituent group $\alpha_{3\text{-}4}$ is preferably a $C_{1\text{-}3}$ alkyl group, more preferably a methyl or ethyl group, and further preferably a methyl group.

A $C_{1\text{-}6}$ alkoxy group in the substituent group $\alpha_{3\text{-}4}$ is preferably a $C_{1\text{-}3}$ alkoxy group, more preferably a methoxy or ethoxy group, and further preferably a methoxy group.

In addition, when $R^7$ is a pyrazolyl or triazolyl group, $R^8$ is preferably a hydrogen atom or a methyl group.

$R^9$ and $R^{10}$ may be the same or different and are each a hydrogen atom or a substituent selected from the substituent group $\alpha_{3\text{-}2}$ and preferably a hydrogen atom or a substituent selected from a substituent group $\alpha_{3\text{-}5}$. Toxicity of a compound having such a substituent can be further reduced.

The substituent group $\alpha_{3\text{-}5}$ includes $C_{1\text{-}6}$ alkyl and $C_{1\text{-}6}$ alkoxyl groups, each of which optionally has at least one halogen atom.

A halogen atom in the substituent group $\alpha_{3\text{-}5}$ is preferably a fluorine atom or a chlorine atom and more preferably a fluorine atom.

A $C_{1\text{-}6}$ alkyl group in the substituent group $\alpha_{3\text{-}5}$ is preferably a $C_{1\text{-}3}$ alkyl group, more preferably a methyl or ethyl group, and further preferably a methyl group.

A $C_{1\text{-}6}$ alkoxy group in the substituent group $\alpha_{3\text{-}5}$ is preferably a $C_{1\text{-}3}$ alkoxy group, more preferably a methoxy or ethoxy group, and further preferably a methoxy group.

When $R^2$ is an indazolyl group optionally having at least one substituent, a substituent that binds to the indazolyl group is preferably a substituent selected from the substituent group $\alpha_{2\text{-}1}$, more preferably a substituent selected from a substituent group $\alpha_{4\text{-}1}$, and further preferably a substituent selected from a substituent group $\alpha_{4\text{-}2}$.

The substituent group $\alpha_{4\text{-}1}$ includes a halogen atom and $C_{1\text{-}6}$ alkyl, $C_{1\text{-}6}$ alkoxy, (di)$C_{1\text{-}6}$ alkylamino, and pyrrolysyl groups, each of which optionally has at least one substituent selected from a substituent group $\beta_{4\text{-}1}$. The preferred ranges of the substituents are the same as those described for the substituent group $\alpha_{2\text{-}1}$.

The substituent group $\beta_{4\text{-}1}$ includes a halogen atom, oxo, and a $C_{1\text{-}6}$ alkoxy group. The preferred ranges of the substituents are the same as those described for the substituent group $\beta_{2\text{-}1}$.

The substituent group $\alpha_{4\text{-}2}$ includes a halogen atom and $C_{1\text{-}6}$ alkyl, $C_{1\text{-}6}$ alkoxy, and (di)$C_{1\text{-}6}$ alkylamino groups, each of which optionally has at least one substituent selected from a substituent group $\beta_{4\text{-}2}$. The preferred ranges of the substituents are the same as those described for the substituent group $\alpha_{2\text{-}1}$.

The substituent group $\beta_{4\text{-}2}$ includes a halogen atom and a $C_{1\text{-}6}$ alkoxy group. The preferred ranges of the substituents are the same as those described for the substituent group $\beta_{2\text{-}1}$.

When $R^2$ is an indazolyl group optionally having at least one substituent, the indazolyl group is preferably a substituent represented by the following formula (VI-1) or (VI-2):

[Formula 8]

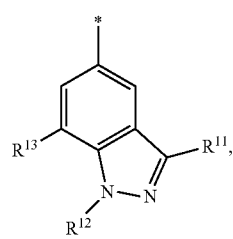

(VI-1)

-continued

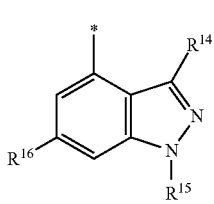

(VI-2)

(wherein $R^{11}$, $R^{12}$, $R^{13}$, $R^{14}$, $R^{15}$, and $R^{16}$ may be the same or different and are each a hydrogen atom or a substituent selected from the substituent group $\alpha_{4\text{-}2}$).

$R^{11}$ and $R^{14}$ are each a hydrogen atom or a substituent selected from the substituent group $\alpha_{4\text{-}2}$ and preferably a hydrogen atom or a substituent selected from a substituent group $\alpha_{4\text{-}3}$. Toxicity of the compound having such a substituent can be further reduced.

The substituent group $\alpha_{4\text{-}3}$ includes $C_{1\text{-}6}$ alkyl, $C_{1\text{-}6}$ alkoxy, and (di)$C_{1\text{-}6}$ alkylamino groups, each of which optionally has at least one halogen atom.

A halogen atom in the substituent group $\alpha_{4\text{-}3}$ is preferably a fluorine atom or a chlorine atom and more preferably a fluorine atom.

A $C_{1\text{-}6}$ alkyl group in the substituent group $\alpha_{4\text{-}3}$ is preferably a $C_{1\text{-}3}$ alkyl group, more preferably a methyl or ethyl group, and further preferably a methyl group.

A $C_{1\text{-}6}$ alkoxy group in the substituent group $\alpha_{4\text{-}3}$ is preferably a $C_{1\text{-}3}$ alkoxy group, more preferably a methoxy or ethoxy group, and further preferably a methoxy group.

A (di)$C_{1\text{-}6}$ alkylamino group in the substituent group $\alpha_{4\text{-}3}$ is a mono-$C_{1\text{-}6}$ alkylamino or di-$C_{1\text{-}6}$ alkylamino group and preferably a di-$C_{1\text{-}6}$ alkylamino group. Here, a $C_{1\text{-}6}$ alkyl group that binds to a nitrogen atom is preferably a $C_{1\text{-}3}$ alkyl group, more preferably a methyl or ethyl group, and further preferably a methyl group.

$R^{12}$ and $R^{15}$ are each a hydrogen atom or a substituent selected from the substituent group $\alpha_{4\text{-}2}$ and preferably a hydrogen atom or a substituent selected from a substituent group $\alpha_{4\text{-}4}$. Toxicity of the compound having such a substituent can be further reduced.

The substituent group $\alpha_{4\text{-}4}$ includes a $C_{1\text{-}6}$ alkyl group optionally having at least one substituent selected from a substituent group $\beta_{4\text{-}4}$.

A $C_{1\text{-}6}$ alkyl group in the substituent group $\alpha_{4\text{-}4}$ is preferably a $C_{1\text{-}3}$ alkyl group, more preferably a methyl or ethyl group, and further preferably a methyl group.

The substituent group $\beta_{4\text{-}4}$ includes a halogen atom and a $C_{1\text{-}6}$ alkoxy group.

A halogen atom in the substituent group $\beta_{4\text{-}4}$ is preferably a fluorine atom or a chlorine atom and more preferably a fluorine atom.

A $C_{1\text{-}6}$ alkoxy group in the substituent group $\beta_{4\text{-}4}$ is preferably a $C_{1\text{-}3}$ alkoxy group, more preferably a methoxy or ethoxy group, and further preferably a methoxy group.

$R^{13}$ and $R^{16}$ are each preferably a hydrogen atom or a halogen atom. A halogen atom is preferably a fluorine atom or a chlorine atom and more preferably a fluorine atom.

When $R^2$ is a phenyl group optionally having at least one substituent, a substituent that binds to the phenyl group is preferably a substituent selected from the substituent group $\alpha_{2\text{-}1}$, more preferably a substituent selected from a substituent group $\alpha_{5\text{-}1}$, and further preferably a substituent selected from a substituent group $\alpha_{5\text{-}2}$.

The substituent group $\alpha_{5\text{-}1}$ includes a halogen atom and $C_{1\text{-}6}$ alkyl, $C_{1\text{-}6}$ alkoxy, acyl, and triazolyl groups, each of which optionally has at least one halogen atom. The preferred ranges of the substituents are the same as those described for the substituent group $\alpha_{2\text{-}1}$.

The substituent group $\alpha_{5\text{-}2}$ includes a halogen atom, a $C_{1\text{-}6}$ alkoxy group, and $C_{1\text{-}6}$ alkyl and triazolyl groups, each of which optionally has at least one halogen atom. The preferred ranges of the substituents are the same as those described for the substituent group $\alpha_{2\text{-}1}$.

When $R^2$ is phenyl optionally having at least one substituent, a phenyl group is preferably a substituent represented by the following formula (VII-1):

[Formula 9]

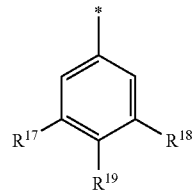

(VII-1)

(wherein $R^{17}$, $R^{18}$, and $R^{19}$ may be the same or different and are each a hydrogen atom or a substituent selected from the substituent group $\alpha_{5\text{-}2}$).

$R^{17}$ and $R^{18}$ are each a hydrogen atom or a substituent selected from the substituent group $\alpha_{5\text{-}2}$ and preferably a hydrogen atom or a substituent selected from a substituent group $\alpha_{5\text{-}3}$. Toxicity of the compound having such a substituent can be further reduced.

The substituent group $\alpha_{5\text{-}3}$ includes a halogen atom, a $C_{1\text{-}6}$ alkoxy group, a triazolyl group, and a $C_{1\text{-}6}$ alkyl group optionally having at least one halogen atom.

A halogen atom in the substituent group $\alpha_{5\text{-}3}$ is preferably a fluorine atom or a chlorine atom and more preferably a fluorine atom.

A $C_{1\text{-}6}$ alkoxy group in the substituent group $\alpha_{5\text{-}3}$ is preferably a $C_{1\text{-}3}$ alkoxy group, more preferably a methoxy or ethoxy group, and further preferably a methoxy group.

A $C_{1\text{-}6}$ alkyl group in the substituent group $\alpha_{5\text{-}3}$ is preferably a $C_{1\text{-}3}$ alkyl group, more preferably a methyl or ethyl group, and further preferably a methyl group.

$R^{19}$ is a hydrogen atom or a substituent selected from the substituent group $\alpha_{5\text{-}2}$ and preferably a hydrogen atom or a substituent selected from a substituent group $\alpha_{5\text{-}4}$. Toxicity of the compound having such a substituent can be further reduced.

The substituent group $\alpha_{5\text{-}4}$ includes a halogen atom, a $C_{1\text{-}6}$ alkoxy group, and a $C_{1\text{-}6}$ alkyl group optionally having at least one halogen atom.

A halogen atom in the substituent group $\alpha_{5\text{-}4}$ is preferably a fluorine atom or a chlorine atom, and more preferably a fluorine atom.

A $C_{1\text{-}6}$ alkoxy group in the substituent group $\alpha_{5\text{-}4}$ is preferably a $C_{1\text{-}3}$ alkoxy group, more preferably a methoxy or ethoxy group, and further preferably a methoxy group.

A $C_{1\text{-}6}$ alkyl group in the substituent group $\alpha_{5\text{-}4}$ is preferably a $C_{1\text{-}3}$ alkyl group, more preferably a methyl or ethyl group, and further preferably a methyl group.

When $R^2$ is a pyrazolopyridyl group optionally having at least one substituent, a substituent that binds to the pyrazolopyridyl group is preferably a substituent selected from the substituent group $\alpha_{2\text{-}1}$ and more preferably a substituent selected from a substituent group $\alpha_{6\text{-}1}$.

The substituent group $\alpha_{6-1}$ includes a halogen atom and $C_{1-6}$ alkyl, $C_{1-6}$ alkoxy, and (di)$C_{1-6}$ alkylamino groups, each of which optionally has at least one substituent selected from a substituent group $\beta_{6-1}$. The preferred ranges of the substituents are the same as those described for the substituent group $\alpha_{2-1}$.

The substituent group $\beta_{6-1}$ includes a halogen atom and a $C_{1-6}$ alkoxy group. The preferred ranges of the substituents are the same as those described for the substituent group $\beta_{2-1}$.

When $R^2$ is a pyrazolopyridyl group optionally having at least one substituent, the pyrazolopyridyl group is preferably a substituent represented by the following formula (VIII-1) or (VIII-2):

[Formula 10]

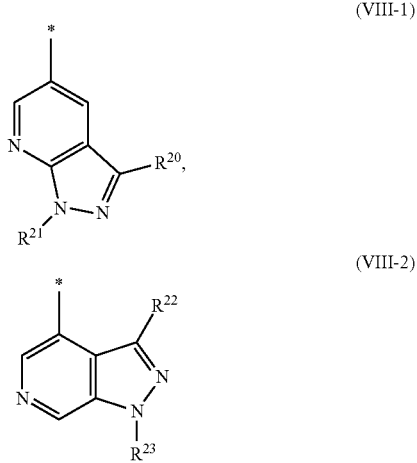

(wherein $R^{20}$, $R^{21}$, $R^{22}$, and $R^{23}$ may be the same or different and are each a hydrogen atom or a substituent selected from the substituent group $\alpha_{6-1}$).

$R^{20}$ is a hydrogen atom or a substituent selected from the substituent group $\alpha_{6-1}$. Toxicity of the compound having such a substituent can be further reduced.

$R^{21}$ and $R^{23}$ are each a hydrogen atom or a substituent selected from the substituent group $\alpha_{6-1}$ and preferably a hydrogen atom or a substituent selected from a substituent group $\alpha_{6-2}$. Toxicity of the compound having such a substituent can be further reduced.

The substituent group $\alpha_{6-2}$ includes a $C_{1-6}$ alkyl group optionally having at least one substituent selected from a halogen atom and a $C_{1-6}$ alkoxy group.

A halogen atom in the substituent group $\alpha_{6-2}$ is preferably a fluorine atom or a chlorine atom and more preferably a fluorine atom.

A $C_{1-6}$ alkoxy group in the substituent group $\alpha_{6-2}$ is preferably a $C_{1-3}$ alkoxy group, more preferably a methoxy or ethoxy group, and further preferably a methoxy group.

A $C_{1-6}$ alkyl group in the substituent group $\alpha_{6-2}$ is preferably a $C_{1-3}$ alkyl group, more preferably a methyl or ethyl group, and further preferably a methyl group.

$R^{22}$ is a hydrogen atom or a substituent selected from the substituent group $\alpha_{6-1}$ and preferably a hydrogen atom, a halogen atom, or a $C_{1-6}$ alkyl group. Here, a halogen atom is preferably a fluorine atom or a chlorine atom and more preferably a fluorine atom. In addition, a $C_{1-6}$ alkyl group is preferably a $C_{1-3}$ alkyl group, more preferably a methyl or ethyl group, and further preferably a methyl group.

When $R^2$ is a benzisoxazolyl group optionally having at least one substituent, a substituent that binds to the benzisoxazolyl group is preferably a substituent selected from the substituent group $\alpha_{2-1}$ and more preferably a $C_{1-6}$ alkoxy group. Here, a $C_{1-6}$ alkoxy group is preferably a $C_{1-3}$ alkoxy group, more preferably a methoxy or ethoxy group, and further preferably a methoxy group.

When $R^2$ is a pyrimidinyl group optionally having at least one substituent, a substituent that binds to the pyrimidinyl group is preferably a substituent selected from the substituent group $\alpha_{2-1}$ and more preferably $C_{1-6}$ alkyl, $C_{1-6}$ alkoxy, pyrazolyl, triazolyl, or morpholinyl. Here, a $C_{1-6}$ alkoxy group is preferably a $C_{1-3}$ alkoxy group, more preferably a methoxy or ethoxy group, and further preferably a methoxy group. A $C_{1-6}$ alkyl group is preferably a $C_{1-3}$ alkyl group, more preferably a methyl or ethyl group, and further preferably a methyl group.

When $R^2$ is a quinolyl group optionally having at least one substituent, a substituent that binds to the quinolyl group is preferably a substituent selected from the substituent group $\alpha_{2-1}$.

The nicotinamide derivative of the present invention is represented preferably by the following formula (I-1) and more preferably by the following formula (I-2):

[Formula 11]

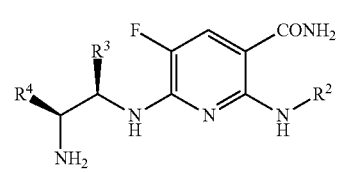

(wherein $R^2$, $R^3$, and $R^4$ are the same substituents as those described above and the preferred ranges thereof are also the same as those described above).

The nicotinamide derivative of the present invention is represented preferably by the following formula (I-3) and more preferably by the following formula (I-4):

[Formula 12]

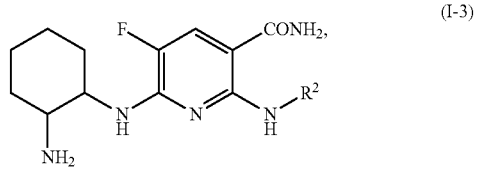

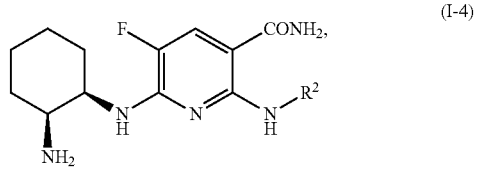

(wherein $R^2$ is the same substituent as that described above and the preferred range thereof is also the same as that described above).

The nicotinamide derivative of the present invention is represented preferably by the following formula (I-5) and more preferably by the following formula (I-6):

[Formula 13]

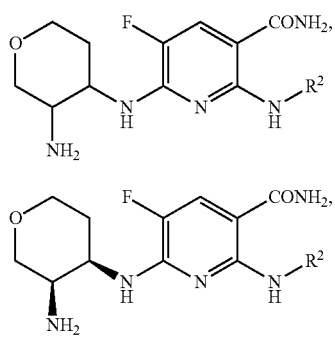

(I-5)

(I-6)

(wherein $R^2$ is the same substituent as that described above and the preferred range thereof is also the same as that described above).

Preferred examples of the compound represented by the formula (1) of the present invention include the following compounds:

EXAMPLE 2-1

6-(((1R,2S)-2-aminocyclohexyl)amino)-2-((3-(dimethylamino)-1-methyl-1H-indazol-5-yl)amino)-5-fluoronicotinamide

EXAMPLE 2-10

6-(((1R,2S)-2-amino-1-cyclobutyl propyl)amino)-5-fluoro-2-((1-methyl-1H-indazol-6-yl)amino)nicotinamide

EXAMPLE 2-123

6-(((1R,2S)-2-aminocyclohexyl)amino)-5-fluoro-2-((3-methoxy-1-(2-methoxy ethyl)-1H-indazol-5-yl)amino) nicotinamide

EXAMPLE 2-125

6-(((2S,3R)-2-aminopentan-3-yl)amino)-5-fluoro-2-((3-methoxy-1-(2-methoxyethyl)-1H-indazol-5-yl)amino) nicotinamide

EXAMPLE 2-126

6-(((2S,3R)-2-aminohexan-3-yl)amino)-5-fluoro-2-((3-methoxy-1-(2-methoxy ethyl)-1H-indazol-5-yl)amino) nicotinamide

EXAMPLE 2-130

(R)-6-(1-amino-4-methylpentan-2-yl)amino)-5-fluoro-2-((1-(2-methoxyethyl)-3-methyl-1H-indazol-5-yl)amino) nicotinamide

EXAMPLE 2-131

6-(((2S,3R)-2-aminopentan-3-yl)amino)-5-fluoro-2-((1-(2-methoxyethyl)-3-methyl-1H-indazol-5-yl)amino)nicotinamide

EXAMPLE 2-133

6-(((1R,2S)-2-amino-1-cyclopropylpropyl)amino)-5-fluoro-((1-(2-methoxyethyl)-3-methyl-1H-indazol-5-yl)amino) nicotinamide

EXAMPLE 2-137

(R)-6-(1-amino-4-methylpentan-2-yl)amino)-2-((1-(2,2-difluoroethyl)-3-methyl-1H-indazol-5-yl)amino)-5-fluoronicotinamide

EXAMPLE 2-138

6-(((2S,3R)-2-aminohexan-3-yl)amino)-2-(1-(2,2-difluoroethyl)-3-methyl-1H-indazol-5-yl)amino)-5-fluoronicotinamide

EXAMPLE 2-139

6-(((2S,3S)-3-amino-1-methoxybutan-2-yl)amino)-2-((1-(2,2-difluoroethyl)-3-methyl-1H-indazol-5-yl)amino)-5-fluoronicotinamide

EXAMPLE 2-142

6-(((1R,2S)-2-aminocyclohexyl)amino)-5-fluoro-2-((5-fluoro-6-methylpyridin-3-yl)amino)nicotinamide

EXAMPLE 2-148

6-(((2S,3R)-2-aminopentan-3-yl)amino)-2-((7-chloro-1-methyl-1H-indazol-5-yl)amino)-5-fluoronicotinamide

EXAMPLE 2-149

6-(((2S,3S)-3-amino-1-methoxybutan-2-yl)amino)-2-((7-chloro-1-methyl-1H-indazol-5-yl)amino)-5-fluoronicotinamide

EXAMPLE 2-159

6-(((2S,3S)-3-amino-1-methoxybutan-2-yl)amino)-5-fluoro-2-((7-fluoro-3-methoxy-1-methyl-1H-indazol-5-yl)amino)nicotinamide

EXAMPLE 2-17

6-(((2S,3R)-2-aminopentan-3-yl)amino)-2-((5,6-dimethylpyridin-3-yl)amino)-5-fluoronicotinamide

EXAMPLE 2-173

6-(((2S,3S)-3-amino-1-methoxybutan-2-yl)amino)-2-((3-(difluoromethoxy)-1-methyl-1H-indazol-5-yl)amino)-5-fluoronicotinamide

EXAMPLE 2-18

6-(((2S,3R)-2-amino-5-methylhexan-3-yl)amino)-2-((5,6-dimethylpyridin-3-yl)amino)-5-fluoronicotinamide

EXAMPLE 2-182

6-(((2S,3S)-3-amino-1-ethoxybutan-2-yl)amino)-2-((1-ethyl-1H-indazol-5-yl)amino)-5-fluoronicotinamide

EXAMPLE 2-184

6-(((1R,2S)-2-aminocyclohexyl)amino)-2-((3-(dimethylamino)-7-fluoro-1-methyl-1H-indazol-5-yl)amino)-5-fluoronicotinamide

EXAMPLE 2-186

6-(((2S,3R)-2-aminopentan-3-yl)amino)-2-((3-(dimethylamino)-7-fluoro-1-m ethyl-1H-indazol-5-yl)amino)-5-fluoronicotinamide

EXAMPLE 2-187

6-(((2S,3R)-2-aminohexan-3-yl)amino)-2-((3-(dimethylamino)-7-fluoro-1-methyl-1H-indazol-5-yl)amino)-5-fluoronicotinamide

EXAMPLE 2-188

6-(((1R,2S)-2-amino-1-cyclopropylpropyl)amino)-2-((3-(dimethylamino)-7-fluoro-1-methyl-1H-indazol-5-yl)amino)-5-fluoronicotinamide

EXAMPLE 2-196

6-(((2S,3S)-3-amino-1-methoxybutan-2-yl)amino)-2-((1,3-dimethyl-1H-indazol-5-yl)amino)-5-fluoronicotinamide

EXAMPLE 2-20

6-(((1R,2S)-2-aminocyclohexyl)amino)-2-((1-(2,2-difluoroethyl)-1H-indazol-4-yl)amino)-5-fluoronicotinamide

EXAMPLE 2-207

6-(((2S,3R)-2-aminohexan-3-yl)amino)-2-((6-ethoxy-5-(1H-1,2,3-triazol-1-yl)pyridin-3-yl)amino)-5-fluoronicotinamide

EXAMPLE 2-208

6-(((3R,4R)-3-aminotetrahydro-2H-pyran-4-yl)amino)-2-((1,3-dimethyl-1H-indazol-5-yl)amino)-5-fluoronicotinamide

EXAMPLE 2-209

6-(((3R,4R)-3-aminotetrahydro-2H-pyran-4-yl)amino)-5-fluoro-2-((3-fluoro-1-methyl-1H-indazol-5-yl)amino)nicotinamide

EXAMPLE 2-210

6-(((3R,4R)-3-aminotetrahydro-2H-pyran-4-yl)amino)-5-fluoro-2-((3-methoxy-1-methyl-1H-indazol-5-yl)amino)nicotinamide

EXAMPLE 2-211

6-(((3R,4R)-3-aminotetrahydro-2H-pyran-4-yl)amino)-5-fluoro-2-((7-fluoro-3-methoxy-1-methyl-1H-indazol-5-yl)amino)nicotinamide

EXAMPLE 2-213

6-(((3R,4R)-3-aminotetrahydro-2H-pyran-4-yl)amino)-2-((3-(dimethylamino)-7-fluoro-1-methyl-1H-indazol-5-yl)amino)-5-fluoronicotinamide

EXAMPLE 2-214

6-(((3R,4R)-3-aminotetrahydro-2H-pyran-4-yl)amino)-5-fluoro-2-((6-methyl-5-(2H-1,2,3-triazol-2-yl)pyridin-3-yl)amino)nicotinamide

EXAMPLE 2-218

6-(((3R,4R)-3-aminotetrahydro-2H-pyran-4-yl)amino)-5-fluoro-2-((5-methylpyridin-3-yl)amino)nicotinamide

EXAMPLE 2-23

6-(((2S,3R)-2-aminopentan-3-yl)amino)-2-((1-(2,2-difluoroethyl)-1H-indazol-4-yl)amino)-5-fluoronicotinamide

EXAMPLE 2-230

6-(((1S,2R)-1-amino-1-cyclopropylpropan-2-yl)amino)-2-((1-ethyl-1H-indazol-1-5-yl)amino)-5-fluoronicotinamide

EXAMPLE 2-235

6-(((2S,3R)-2-amino-5-methylhexan-3-yl)amino)-5-fluoro-2-((3-fluoro-2-morpholinopyridin-4-yl)amino)nicotinamide

EXAMPLE 2-249

6-(((1R,2S)-2-aminocyclohexyl)amino)-5-fluoro-2-((3-methoxy-1-methyl-1H-pyrazolo[3,4-b]pyridin-5-yl)amino)nicotinamide

EXAMPLE 2-253

6-(((1R,2S)-2-amino-1-cyclopropylpropyl)amino)-5-fluoro-2-((3-methoxy-1-methyl-1H-pyrazolo[3,4-b]pyridin-5-yl)amino)nicotinamide

EXAMPLE 2-265

6-(((1R,2S)-2-amino-1-cyclopropylpropyl)amino)-5-fluoro-2-((1-(2-methoxyethyl)-1H-indazol-5-yl)amino)nicotinamide

EXAMPLE 2-266

6-(((3R,4S)-4-aminohexan-3-yl)amino)-5-fluoro-2-((1-(2-methoxyethyl)-1H-indazol-5-yl)amino)nicotinamide

EXAMPLE 2-267

6-(((2S,3S)-3-amino-1-methoxybutan-2-yl)amino)-2-((3,5-dimethoxyphenyl)amino)-5-fluoronicotinamide

EXAMPLE 2-27

6-(((1R,2S)-2-amino-1-cyclobutyl propyl)amino)-5-fluoro-2-((3-methoxyphenyl)amino)nicotinamide

EXAMPLE 2-270

6-(((2R,3S)-3-aminopentan-2-yl)amino)-5-fluoro-2-((5-fluoro-6-methylpyridin-3-yl)amino)nicotinamide

EXAMPLE 2-273

6-(((1R,2S)-2-aminocyclohexyl)amino)-5-fluoro-2-((5-fluoro-6-(methylamino)pyridin-3-yl)amino)nicotinamide

EXAMPLE 2-28

6-(((1R,2S)-2-amino-1-cyclobutyl propyl)amino)-2-(3,5-dimethoxyphenyl)amino)-5-fluoronicotinamide

EXAMPLE 2-29

6-(((1R,2S)-2-amino-1-cyclobutyl propyl)amino)-2-(3,4-dimethoxyphenyl)amino)-5-fluoronicotinamide

EXAMPLE 2-31

6-(((2S,3R)-2-aminopentan-3-yl)amino)-5-fluoro-2-((6-methyl-5-(2H-1,2,3-triazol-2-yl)pyridin-3-yl)amino)nicotinamide

EXAMPLE 2-316

6-(((1R,2S)-2-aminocyclohexyl)amino)-2-(1-ethyl-1H-pyrazolo[3,4-c]pyridin-4-yl)amino)-5-fluoronicotinamide

EXAMPLE 2-317

6-(((3R,4R)-3-aminotetrahydro-2H-pyran-4-yl)amino)-2-((1-ethyl-1H-pyrazolo[3,4-c]pyridin-4-yl)amino)-5-fluoronicotinamide

EXAMPLE 2-319

6-(((2S,3R)-2-aminohexan-3-yl)amino)-2-((1-ethyl-1H-pyrazolo[3,4-c]pyridin-4-yl)amino)-5-fluoronicotinamide

EXAMPLE 2-320

6-(((1R,2S)-2-amino-1-cyclopropylpropyl)amino)-2-((1-ethyl-1H-pyrazolo[3,4-c]pyridin-4-yl)amino)-5-fluoronicotinamide

EXAMPLE 2-322

6-(((2S,3R)-2-amino-5-methylhexan-3-yl)amino)-2-((1-ethyl-1H-pyrazolo[3,4-c]pyridin-4-yl)amino)-5-fluoronicotinamide

EXAMPLE 2-326

6-(((3R,4R)-3-aminotetrahydro-2H-pyran-4-yl)amino)-2-((1-ethyl-1H-indazol-5-yl)amino)-5-fluoronicotinamide

EXAMPLE 2-328

6-(((3R,4R)-3-aminotetrahydro-2H-pyran-4-yl)amino)-2-((1-(2,2-difluoroethyl)-3-methyl-1H-indazol-5-yl)amino)-5-fluoronicotinamide

EXAMPLE 2-329

6-(((3R,4R)-3-aminotetrahydro-2H-pyran-4-yl)amino)-5-fluoro-2-((3-methoxy-1-(2-methoxyethyl)-1H-indazol-5-yl)amino)nicotinamide

EXAMPLE 2-330

6-(((3R,4R)-3-aminotetrahydro-2H-pyran-4-yl)-amino)-2-((1-ethyl-1H-indazol-4-yl)amino)-5-fluoronicotinamide

EXAMPLE 2-332

6-(((3R,4R)-3-aminotetrahydro-2H-pyran-4-yl)amino)-2-((1-(2,2-difluoroethyl)-1H-indazol-4-yl)amino)-5-fluoronicotinamide

EXAMPLE 2-362

6-(((1R,2S)-2-amino-1-cyclopropyl-butyl)amino)-2-(1-ethyl-1H-indazol-5-yl)amino)-5-fluoronicotinamide

EXAMPLE 2-37

6-(((2S,3R)-2-amino-5-methylhexan-3-yl)amino)-5-fluoro-2-((1-methyl-1H-indazol-6-yl)amino)nicotinamide

EXAMPLE 2-375

6-(((3R,4R)-3-aminotetrahydro-2H-pyran-4-yl)amino)-5-fluoro-2-((6-fluoro-1-(2-methoxyethyl)-1H-indazol-4-yl)amino)nicotinamide

EXAMPLE 2-376

6-(((2S,3R)-2-aminopentan-3-yl)amino)-5-fluoro-2-((6-fluoro-1-(2-methoxyethyl)-1H-indazol-4-yl)amino)nicotinamide

EXAMPLE 2-377

6-(((1R,2S)-2-amino-1-cyclopropylpropyl)amino)-5-fluoro-2-((6-fluoro-1-(2-methoxyethyl)-1H-indazol-4-yl)amino)nicotinamide

EXAMPLE 2-378

6-(((2R,3S)-3-aminopentan-2-yl)amino)-5-fluoro-2-((6-fluoro-1-(2-methoxyethyl)-1H-indazol-4-yl)amino)nicotinamide

EXAMPLE 2-38

6-(((2S,3R)-2-aminoheptan-3-yl)amino)-5-fluoro-2-((1-methyl-1H-indazol-6-yl)amino)nicotinamide

EXAMPLE 2-381

6-(((1S,2S)-2-amino-1-(pyridin-2-yl)propyl)amino)-2-(1-ethyl-1H-indazol-5-yl)amino)-5-fluoronicotinamide

EXAMPLE 2-39

6-(((2R,3S)-3-aminopentan-2-yl)amino)-5-fluoro-2-((1-methyl-1H-indazol-6-yl)amino)nicotinamide

EXAMPLE 2-4

6-(((2S,3R)-2-aminopentan-3-yl)amino)-2-(3-(dimethylamino)-1-methyl-1H-indazol-5-yl)amino)-5-fluoronicotinamide

EXAMPLE 2-40

6-(((2R,3S)-3-aminopentan-2-yl)amino)-5-fluoro-2-((1-methyl-1H-indazol-5-yl)amino)nicotinamide

EXAMPLE 2-404

6-(((1R,2S)-2-amino-1-cyclopropylpropyl)amino)-5-fluoro-2-(quinolin-5-ylamino)nicotinamide

EXAMPLE 2-41

6-(((2R,3S)-3-aminopentan-2-yl)amino)-2-((5-cyclopropylpyridin-3-yl)amino)-5-fluoronicotinamide

EXAMPLE 2-410

6-(((1R,2S)-2-amino-1-(2-fluorophenyl) propyl)amino)-2-((1-ethyl-1H-indazol-5-yl)amino)-5-fluoronicotinamide

EXAMPLE 2-413

6-(((1R,2S)-2-amino-1-(3-fluorophenyl) propyl)amino)-2-(1-ethyl-1H-indazol-5-yl)amino)-5-fluoronicotinamide

EXAMPLE 2-414

6-(((1R,2S)-2-amino-1-(3-fluorophenyl)propyl)amino)-2-(2,6-dimethoxypyridin-4-yl)amino)-5-fluoronicotinamide

EXAMPLE 2-416

6-(((1S,2S)-2-amino-1-(thiophen-2-yl)propyl)amino)-2-(1-ethyl-1H-indazol-5-yl)amino)-5-fluoronicotinamide

EXAMPLE 2-42:

6(((2R,3S)-3-aminopentan-2-yl)amino)-5-2-((2-(2-methoxyethoxy)pyridin-4-yl)amino)nicotinamide

EXAMPLE 2-434:

6-(((1R,2S)-2-aminocyclohexyl)amino)-5-fluoro-2-(m-tolylamino)nicotinamide

EXAMPLE 2-437

2-((3-(2H-1,2,3-triazol-2-yl)phenyl)amino)-6-(((1R,2S)-2-aminocyclohexyl)amino)-5-fluoronicotinamide

EXAMPLE 2-438

2-((3-(1H-1,2,3-triazol-1-yl)phenyl)amino)-6-(((1R,2S)-2-aminocyclohexyl)amino)-5-fluoronicotinamide

EXAMPLE 2-439

6-(((1R,2S)-2-aminocyclohexyl)amino)-2-((3-chlorophenyl)amino)-5-fluoronicotinamide

EXAMPLE 2-44

6-(((1R,2S)-2-amino-1-cyclopropylpropyl)amino)-5-fluoro-2-(m-tolylamino)nicotinamide

EXAMPLE 2-442

2-((3-acetylphenyl)amino)-6-(((1R,2S)-2-aminocyclohexyl)amino)-5-fluoronicotinamide

EXAMPLE 2-454

6-(((1R,2S)-2-amino-1-(3-fluorophenyl)propyl)amino)-5-fluoro-2-((1-(2-methoxyethyl)-1H-indazol-5-yl)amino)nicotinamide

EXAMPLE 2-46

6-(((1R,2S)-2-amino-1-cyclopropylpropyl)amino)-5-fluoro-2-((3-methoxyphenyl)amino)nicotinamide

EXAMPLE 2-47

6-(((1R,2S)-2-amino-1-cyclopropylpropyl)amino)-2-((3,5-dimethoxyphenyl)amino)-5-fluoronicotinamide

EXAMPLE 2-472

6-(((1R,2S)-2-aminocyclohexyl)amino)-5-fluoro-2-((5-(4-methyl-1H-pyrazol-1-yl)pyridin-3-yl)amino)nicotinamide

EXAMPLE 2-475

2-((3-(2H-1,2,3-triazol-2-yl)phenyl)amino)-6-(((2S,3R)-2-aminopentan-3-yl)amino)-5-fluoronicotinamide

EXAMPLE 2-476

2-((3-(1H-1,2,3-triazol-1-yl)phenyl)amino)-6-(((2S,3R)-2-aminopentan-3-yl)amino)-5-fluoronicotinamide

EXAMPLE 2-478

2-((3-acetylphenyl)amino)-6-(((2S,3R)-2-aminopentan-3-yl)amino)-5-fluoronicotinamide

EXAMPLE 2-479

2-((3-(2H-1,2,3-triazol-2-yl)phenyl)amino)-6-(((1R,2S)-2-amino-1-cyclopropylpropyl)amino)-5-fluoronicotinamide

EXAMPLE 2-48

6-(((1R,2S)-2-amino-1-cyclopropylpropyl)amino)-2-((3,4-dimethoxyphenyl)amino)-5-fluoronicotinamide

EXAMPLE 2-480

2-((3-(1H-1,2,3-triazol-1-yl)phenyl)amino)-6-(((1R,2S)-2-amino-1-cyclopropylpropyl)amino)-5-fluoronicotinamide

EXAMPLE 2-481

6-(((1R,2S)-2-amino-1-cyclopropylpropyl)amino)-2-((3,4-dimethylphenyl)amino)-5-fluoronicotinamide

EXAMPLE 2-482

2-((3-acetylphenyl)amino)-6-(((1R,2S)-2-amino-1-cyclopropylpropyl)amino)-5-fluoronicotinamide

EXAMPLE 2-5

6-(((1R,2S)-2-amino-1-cyclobutyl propyl)amino)-5-fluoro-2-((2-methoxypyridin-4-yl)amino)nicotinamide

EXAMPLE 2-508

6-(((1S,2S)-2-amino-1-(thiophen-2-yl)propyl)amino)-5-fluoro-2-((5-fluoro-6-morpholinopyridin-3-yl)amino)nicotinamide

EXAMPLE 2-518

2-((5-acetyl-6-methylpyridin-3-yl)amino)-6-(((1R,2S)-2-aminocyclohexyl)amino)-5-fluoronicotinamide

EXAMPLE 2-521

6-(((2S,3R)-2-aminopentan-3-yl)amino)-5-fluoro-2-((5-(4-methyl-1H-pyrazol-1-yl)pyridin-3-yl)amino)nicotinamide

EXAMPLE 2-57

6-(((2S,3R)-2-aminopentan-3-yl)amino)-5-fluoro-2-((3-methoxybenzo[d]isoxazol-5-yl)amino)nicotinamide

EXAMPLE 2-7

6-(((1R,2S)-2-amino-1-cyclobutyl propyl)amino)-5-fluoro-2-((2-(2-methoxyethoxy)pyridin-4-yl)amino)nicotinamide

EXAMPLE 2-71

6-(((1R,2S)-2-amino-1-cyclopropylpropyl)amino)-2-(1-(2,2-difluoroethyl)-1H-indazol-5-yl)amino)-5-fluoronicotinamide

EXAMPLE 2-74

6-(((1R,2S)-2-amino-1-cyclopropylpropyl)amino)-2-((1-(2,2-difluoroethyl)-3-methoxy-1H-indazol-5-yl)amino)-5-fluoronicotinamide

EXAMPLE 2-78

(R)-6-((1-amino-4-methylpentan-2-yl)amino)-5-fluoro-2-((3-methoxy-1-methyl-1H-indazol-5-yl)amino)nicotinamide

EXAMPLE 2-8

6-(((1R,2S)-2-amino-1-cyclobutyl propyl)amino)-5-fluoro-2-(quinolin-6-ylamino)nicotinamide

EXAMPLE 2-80

6-(((2S,3R)-2-aminohexan-3-yl)amino)-5-fluoro-2-((3-methoxy-1-methyl-1H-indazol-5-yl)amino)nicotinamide

EXAMPLE 2-9

6-(((1R,2S)-2-amino-1-cyclobutyl propyl)amino)-2-(1-ethyl-1H-indazol-5-yl)amino)-5-fluoronicotinamide The compound represented by the formula (1) of the present invention is preferably a compound having a Syk-inhibitory activity IC50, which is 50 nM or less, and also having IC50 in a TNFα generation assay, which is 130 nM or less. More specific examples of such a compound include compounds wherein, in Table 5 that shows the results of a test performed according to a test method described in a "Syk enzyme assay" in Test Example 1 below, the Syk-inhibitory activity $IC_{50}$ is 50 nM or less (that is, evaluation standards are A and B), and in Table 6 that shows the results of a test performed according to a test method described in a "TNFα generation assay" in Test Example 3 below, the $IC_{50}$ is 130 nM or less (that is, evaluation standards are A and B).

Examples of Syk-related diseases of the present invention include bronchial asthma, allergic rhinitis, hives, atopic dermatitis, rheumatoid arthritis, systemic lupus erythematosus, autoimmune hemolytic anemia, nephrotic syndrome, contact dermatitis, idiopathic thrombocytopenic purpura, lymphocytic leukemia, and acute myelocytic leukemia. Rheumatoid arthritis or idiopathic thrombocytopenic purpura is preferable. Idiopathic thrombocytopenic purpura is more preferable.

Next, a method for producing the compound of the present invention will be described.

The compound of the present invention can be produced by combining well-known methods. For example, the present compound can be produced according to production methods as described below.

[Production Method 1]

[Formula 14]

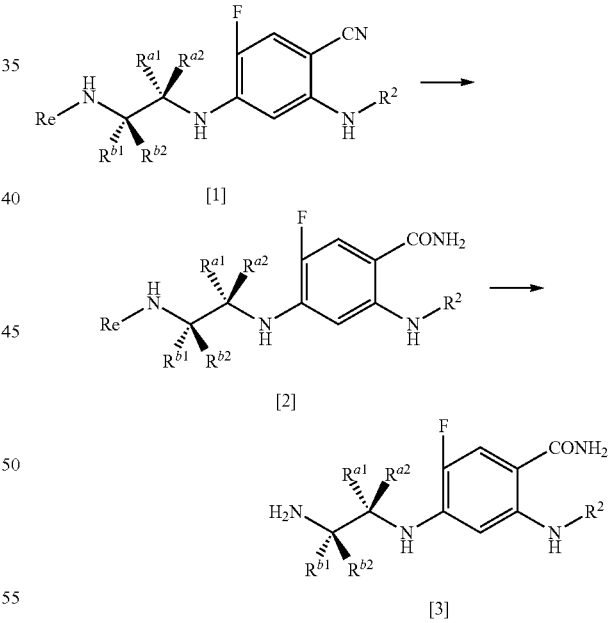

"wherein Re represents an amino protecting group, $R^{a1}$ and $R^{a2}$ may be the same or different and each have the same definition as that described above for $R^3$, $R^{b1}$ and $R^{b2}$ may be the same or different and each have the same definition as that described above for $R^4$, and $R^2$ has the same definition as that described above."

(A1-1)

The compound of the formula [2] can be produced by hydrolyzing the compound of the formula [1] in the presence of a base and in the presence of hydrogen peroxide.

The solvent used in this reaction is not particularly limited, as long as it does not affect the reaction. Examples of such a solvent include aliphatic hydrocarbons, halogenated hydrocarbons, alcohols, glycols, ethers, ketones, esters, amides, sulfoxides, aromatic hydrocarbons, and water. These substances may be used in combination.

Preferred solvents are alcohols and water.

Examples of the base used in this reaction include: metal alkoxides such as sodium methoxide, sodium ethoxide, potassium tert-butoxide, and sodium tert-butoxide; inorganic bases such as sodium hydroxide, potassium hydroxide, sodium hydrogencarbonate, sodium carbonate, potassium carbonate, sodium hydride, and potassium hydride; and organic bases such as triethylamine, diisopropylethylamine, and pyridine.

The base may be used in a molar concentration 1 time or more, and preferably 1 to 10 times, higher than that of the compound of the formula [1].

The hydrogen peroxide may be used in a molar concentration 1 time or more, and preferably 1 to 10 times, higher than that of the compound of the formula [1].

This reaction may be carried out at a temperature from 0° C. to the boiling point of a solvent, and preferably from 10° C. to 40° C., for 1 minute to 24 hours.

(A1-2)

The compound of the formula [3] can be produced by deprotecting the compound of the formula [2] in the presence of an acid. This reaction can be carried out, for example, by the method described in W. Greene et al., Protective Groups in Organic Synthesis, Vol. 4, pp. 696 to 926, 2007, John Wiley & Sons, INC.

Examples of the acid used in this reaction include: inorganic acids such as hydrochloric acid, sulfuric acid, phosphoric acid, hydrogen chloride, and hydrogen bromide; organic carboxylic acids such as acetic acid, trichloroacetic acid, and trifluoroacetic acid; and organic sulfonic acids such as methanesulfonic acid and p-toluenesulfonic acid.

The acid may be used in a molar concentration 1 time or more, and preferably 1 to 5 times, higher than that of the compound of the formula [2]. In addition, such an acid may be used as a solvent.

This reaction may be carried out in the coexistence of a solvent, as necessary. The solvent used is not particularly limited, as long as it does not affect the reaction. Examples of such a solvent include aliphatic hydrocarbons, halogenated hydrocarbons, alcohols, glycols, ethers, ketones, esters, amides, nitriles, sulfoxides, aromatic hydrocarbons, and water. These substances may be used in combination.

This reaction may be carried out at a temperature from 0° C. to the boiling point of a solvent, and preferably from 10° C. to 40° C., for 1 minute to 24 hours.

[Production Method 2]

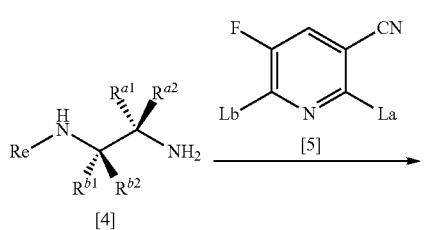

[Formula 15]

-continued

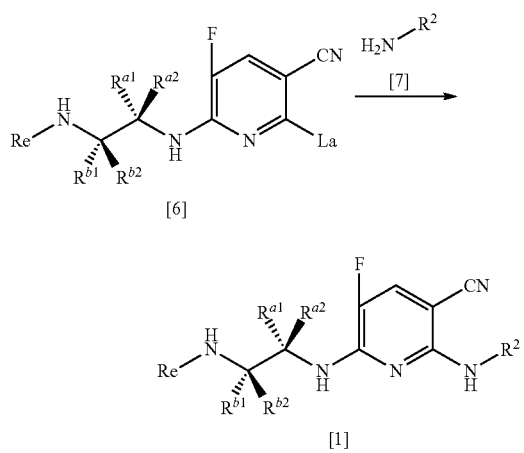

"wherein La and Lb may be the same or different, and a leaving group, Re, $R^{a1}$, $R^{a2}$, $R^{b1}$, $R^{b2}$, and $R^2$ have the same definitions as those described above."

(A2-1)

The compound of the formula [6] can be produced by allowing the compound of the formula [4] to react with the compound of the formula [5] in the presence of a base.

The compound of the formula [4] can be produced by, for example, Production Method 3 described below.

A known example of the compound of the formula [4] is tert-butyl ((1R,2S)-1-amino-1-cyclobutylpropan-2-yl)carbamate.

A known example of the compound of the formula [5] is 2,6-dichloro-5-fluoronicotinonitrile.

The solvent used in this reaction is not particularly limited, as long as it does not affect the reaction. Examples of such a solvent include aliphatic hydrocarbons, halogenated hydrocarbons, alcohols, glycols, ethers, ketones, esters, amides, nitriles, sulfoxides, aromatic hydrocarbons, and water. These substances may be used in combination.

Preferred solvents are amides and ethers.

Examples of the base used in this reaction include: inorganic bases such as sodium hydrogen carbonate, sodium carbonate, potassium carbonate, cesium carbonate, and tripotassium phosphate; and organic bases such as pyridine, 4-(dimethylamino)pyridine, triethylamine, and diisopropyl ethylamine.

The base may be used in a molar concentration 1 to 50 times, and preferably 1 to 5 times, higher than that of the compound of the formula [4].

The compound of the formula [5] may be used in a molar concentration 1 to 50 times, and preferably 1 to 2 times, higher than that of the compound of the formula [4].

This reaction may be carried out at a temperature from 0° C. to the boiling point of a solvent, and preferably from 10° C. to 40° C., for 1 minute to 24 hours.

(A2-2)

The compound of the formula [1] can be produced by allowing the compound of the formula [6] to react with the compound of the formula [7] in the presence or absence of a base, in the presence of a palladium catalyst, and in the presence or absence of a ligand.

A known example of the compound of the formula [7] is 5-fluoro-6-morpholinopyridin-3-amine.

The solvent used in this reaction is not particularly limited, as long as it does not affect the reaction. Examples of the solvent include aliphatic hydrocarbons, halogenated hydrocarbons, alcohols, glycols, ethers, ketones, esters, amides, nitriles, sulfoxides, aromatic hydrocarbons, and water. These substances may be used in combination.

Preferred solvents are ethers.

Examples of the base used in this reaction as desired include: inorganic bases such as sodium hydrogen carbonate, sodium carbonate, potassium carbonate, cesium carbonate, and tripotassium phosphate; and organic bases such as pyridine, 4-(dimethylamino)pyridine, triethylamine, and diisopropylethylamine.

The base may be used in a molar concentration 1 to 50 times, and preferably 1 to 5 times, higher than that of the compound of the formula [6].

Examples of the palladium catalyst used in this reaction include: metallic palladium such as palladium carbon and palladium black; inorganic palladium salts such as palladium chloride; organic palladium salts such as palladium acetate; organic palladium complexes such as tetrakis(triphenylphosphine)palladium (0), bis(triphenylphosphine)palladium (II) chloride, 1,1'-bis(diphenylphosphino)ferrocene-palladium (II) chloride, and tris(dibenzylideneacetone)dipalladium (0); and polymer-bound organic palladium complexes such as polymer-supported bis(acetate)triphenylphosphine palladium (II) and polymer-supported di(acetate)dicyclohexylphenylphosphine palladium (II). These compounds may be used in combination.

The palladium catalyst may be used in a molar concentration 0.00001 to 1 time, and preferably 0.001 to 0.1 time, as high as that of the compound of the formula [6].

Examples of the ligand used in this reaction as desired include: trialkylphosphines such as trimethylphosphine and tri-tert-butylphosphine; tricycloalkylphosphines such as tricyclohexylphosphine; triarylphosphines such as triphenylphosphine and tritolylphosphine; trialkylphosphites such as trimethylphosphite, triethylphosphite, and tributylphosphite; tricycloalkylphosphites such as tricyclohexylphosphite; triarylphosphites such as triphenylphosphite; imidazolium salts such as 1,3-bis(2,4,6-trimethylphenyl) imidazolium chloride; diketones such as acetylacetone and octafluoroacetylacetone; amines such as trimethylamine, triethylamine, tripropylamine, and triisopropylamine; and 4,5-bis(diphenylphosphino)-9,9-dimethyl-xanthene, 1,1'-bis(diphenylphosphino)ferrocene, 2,2'-bis(diphenylphosphino)-1,1'-binaphthyl, 2-dicyclohexylphosphino-2',6'-dimethoxybiphenyl, 2-dicyclohexylphosphino-2',4',6'-triisopropylbiphenyl, 2-(di-tert-butylphosphino)-2',4',6'-triisopropylbiphenyl, and 2-(di-tert-butylphosphino)biphenyl. These compounds may be used in combination.

Such a ligand may be used in a molar concentration 0.00001 to 1 time, and preferably 0.001 to 0.5 time, as high as that of the compound of the formula [6].

The compound of the formula [7] may be used in a molar concentration 1 to 50 times, and preferably 1 to 2 times, higher than that of the compound of the formula [6].

This reaction may be preferably carried out in an inert gas (e.g. nitrogen, argon) atmosphere at a temperature from 40° C. to 170° C. for 1 minute to 96 hours.

[Production Method 3]

[Formula 16]

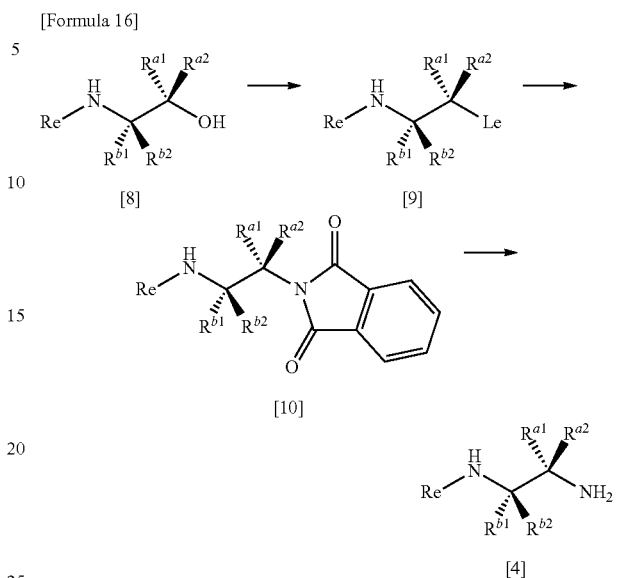

"wherein Le represents a leaving group, and Re, $R^{a1}$, $R^{a2}$, $R^{b1}$, and $R^{b2}$ have the same definitions as those described above."

(A3-1)

The compound of the formula [9] can be produced by allowing the compound of the formula [8] to react with a sulfonylchloride in the presence of a base.

A known example of the compound of the formula [8] is tert-butyl ((2S)-1-cyclopropyl-1-hydroxypropan-2-yl)carbamate.

The solvent used in this reaction is not particularly limited, as long as it does not affect the reaction. Examples of the solvent include aliphatic hydrocarbons, halogenated hydrocarbons, ethers, ketones, esters, nitriles, sulfoxides, and aromatic hydrocarbons. These substances may be used in combination.

Preferred solvents are ethers.

Examples of the sulfonyl chloride used in this reaction include methylsulfonyl chloride, ethylsulfonyl chloride, propylsulfonyl chloride, benzenesulfonyl chloride, p-toluenesulfonyl chloride, and naphthalenesulfonyl chloride.

Preferred sulfonyl chlorides include methylsulfonyl chloride and p-toluenesulfonyl chloride. Further, methylsulfonyl chloride is more preferable.

The sulfonyl chloride is used in a molar concentration of 1 time or more, and preferably 1 to 3 times, higher than that of the compound of the formula [8].

Examples of the base used in this reaction include: inorganic bases such as sodium hydrogen carbonate, sodium carbonate, potassium carbonate, cesium carbonate, and tripotassium phosphate; and organic bases such as pyridine, 4-(dimethylamino)pyridine, triethylamine, and diisopropylethylamine.

The base may be used in a molar concentration 1 time or more, and preferably 1 to 3 times, higher than that of the compound of the formula [8].

This reaction may be carried out at a temperature from −78° C. to the boiling point of a solvent, and preferably from 0° C. to 80° C., for 1 minute to 24 hours.

(A3-2)

The compound of the formula [10] can be produced by allowing the compound of the formula [9] to react with a phthalimide.

When the compound of the formula [9] is in the form of a diastereomeric mixture, the diastereomeric mixture may be separated in a step of isolating the compound of the formula [10].

The solvent used in this reaction is not particularly limited, as long as it does not affect the reaction. Examples of the solvent include aliphatic hydrocarbons, halogenated hydrocarbons, alcohols, glycols, ethers, ketones, esters, amides, nitriles, sulfoxides, aromatic hydrocarbons, and water. These substances may be used in combination.

Preferred solvents are amides.

Examples of the phthalimide used in this reaction include phthalimide sodium and phthalimide potassium. A preferred phthalimide is phthalimide potassium.

Such a phthalimide can also be produced in a reaction system.

Such a phthalimide is used in a molar concentration 1 time or more, and preferably 1 to 3 times, higher than that of the compound of the formula [9].

This reaction may be carried out at a temperature from 0° C. to the boiling point of a solvent, and preferably from 0° C. to 100° C., for 1 minute to 24 hours.

(A3-3)

The compound of the formula [4] can be produced by deprotecting the compound of the formula [10]. This reaction can be carried out, for example, by the method described in W. Greene et al., Protective Groups in Organic Synthesis, the fourth edition, pp. 696 to 926, 2007, John Wiley & Sons, INC.

In this reaction, deprotection is preferably carried out using hydrazine.

[Production Method 4]

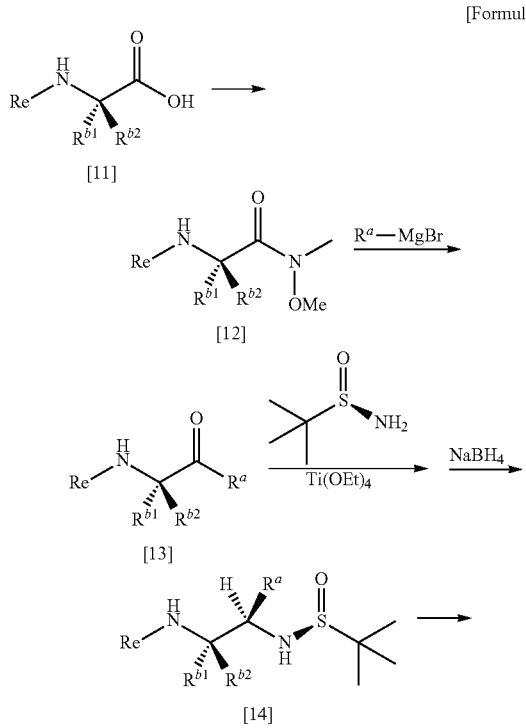

[Formula 17]

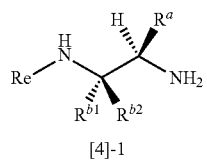

[4]-1

"wherein $R^a$ represents a $C_{1-6}$ alkyl, $C_{3-8}$ cycloalkyl, phenyl, pyridyl, or thienyl group, each of which optionally has at least one substituent, and Re, $R^{b1}$, $R^{b2}$, and Le have the same definitions as those described above."

(A4-1)

The compound of the formula [12] can be produced by activating a carboxyl group of the compound of the formula [11] and then allowing the compound to react with an amine under basic conditions.

The solvent used in this reaction is not particularly limited, as long as it does not affect the reaction. Examples of the solvent include, aliphatic hydrocarbons, halogenated hydrocarbons, alcohols, glycols, ethers, ketones, esters, amides, nitriles, sulfoxides, aromatic hydrocarbons, and water. These substances may be used in combination.

Preferred solvents are halogenated hydrocarbons and ethers.

Examples of a carboxyl activator used in this reaction include: carbodiimides such as N,N'-dicyclohexyl carbodiimide, N,N'-diisopropyl carbodiimide, and N-ethyl-N'-(3-dimethylaminopropyl)carbodiimide; azide phosphates such as diphenylphosphoryl azide; phosphoniums such as BOP reagents; carbonyldiimidazoles such as 1,1'-carbonyldiimidazole; and acid halides such as thionyl chloride.

Examples of the base used in this reaction include: metal alkoxides such as sodium methoxide, sodium ethoxide, potassium tert-butoxide, and sodium tert-butoxide; inorganic bases such as sodium hydroxide, potassium hydroxide, sodium hydrogen carbonate, sodium carbonate, potassium carbonate, sodium hydride, and potassium hydride; and organic bases such as triethylamine, diisopropylethylamine, and pyridine.

Preferred bases are organic bases.

Examples of the amine used in this reaction include methoxymethylamine.

The amine is used in a molar concentration 1 time or more, and preferably 1 to 3 times, higher than that of the compound of the formula [11].

The carboxyl activator is used in a molar concentration 1 time or more, and preferably 1 to 3 times, higher than that of the compound of the formula [11].

The base is used in a molar concentration 1 time or more, and preferably 1 to 3 times, higher than that of the compound of the formula [11].

This reaction may be carried out at a temperature from 0° C. to the boiling point of a solvent, and preferably from 0° C. to 100° C., for 1 minute to 24 hours.

(A4-2)

The compound of the formula [13] can be produced by allowing the compound of the formula [12] to react with a Grignard reagent.

The solvent used in this reaction is not particularly limited, as long as it does not affect the reaction. Examples of the solvent include aliphatic hydrocarbons, halogenated hydrocarbons, ethers, aromatic hydrocarbons, and water. These substances may be used in combination.

Preferred solvents are ethers.

The Grignard reagent is used in a molar concentration 1 time or more, and preferably 1 to 5 times, higher than that of the compound of the formula [12].

This reaction may be carried out at a temperature from 0° C. to the boiling point of a solvent, and preferably from 0° C. to 100° C., for 1 minute to 24 hours.

(A4-3)

The compound of the formula [14] can be produced by allowing the compound of the formula [13] to react with (R)-(+)-tert-butyl sulfinamide in the presence of an additive having the Lewis acid action and dehydrating action and then reducing a resulting imine.

(S)-(−)-tert-butyl sulfinamide may be used instead of (R)-(+)-tert-butyl sulfinamide.

The solvent used in a series of reactions is not particularly limited, as long as it does not affect the reaction. Examples of such a solvent include aliphatic hydrocarbons, halogenated hydrocarbons, ethers, amides, nitriles, sulfoxides, and aromatic hydrocarbons. These substances may be used in combination.

Preferred solvents are halogenated hydrocarbons, aromatic hydrocarbons, and ethers.

Examples of the additive having the Lewis acid action and dehydrating action used in this reaction include: carboxylic acids such as acetic acid, citric acid, and formic acid; and metal alkoxides such as tetraethyl orthotitanate.

Preferred additives are acetic acid and tetraethyl orthotitanate.

The acid is used in a molar concentration 1 time or more, and preferably 1 to 10 times, higher than that of the compound of the formula [13].

(R)-(+)-tert-butyl sulfinamide is used in a molar concentration 1 time or more, and preferably 1 to 10 times, higher than that of the compound of the formula [13].

The reaction of generating an imine may be carried out at a temperature from 0° C. to the boiling point of a solvent, and preferably from 0° C. to 100° C., for 1 minute to 24 hours.

Examples of a reducing agent to be used in a reaction of reducing an imine include boron hydrides such as sodium cyanoborohydride and sodium borohydride.

The boron hydride is used in a molar concentration 1 time or more, and preferably 1 to 10 times, higher than that of the compound of the formula [13].

The reaction of reducing an imine can be performed at −50° C. to the boiling point of a solvent and preferably at −50° C. to 100° C. for 1 minute to 24 hours.

(A4-4)

The compound of the formula [4]-1 can be produced through desulfinylation of the compound of the formula [14] under acidic conditions.

The solvent used in this reaction is not particularly limited, as long as it does not affect the reaction. Examples of the solvent include aliphatic hydrocarbons, halogenated hydrocarbons, alcohols, glycols, ethers, ketones, esters, amides, nitriles, sulfoxides, aromatic hydrocarbons, and water. These substances may be used in combination.

Preferred solvents are alcohols and ethers.

Examples of the acid used in this reaction include: inorganic acids such as hydrochloric acid, hydrogen bromide, and sulfuric acid; sulfonic acids such as methanesulfonic acid and p-toluenesulfonic acid; carboxylic acids such as acetic acid, citric acid, and formic acid.

Preferred acids are inorganic acids such as hydrogen halide and sulfuric acid.

The inorganic acid is used in a molar concentration 1 time or more, and preferably 1 to 5 times, higher than that of the compound of the formula [14].

This reaction may be carried out at a temperature from −50° C. to the boiling point of a solvent, and preferably from 0° C. to 100° C., for 1 minute to 24 hours.

[Production Method 5]

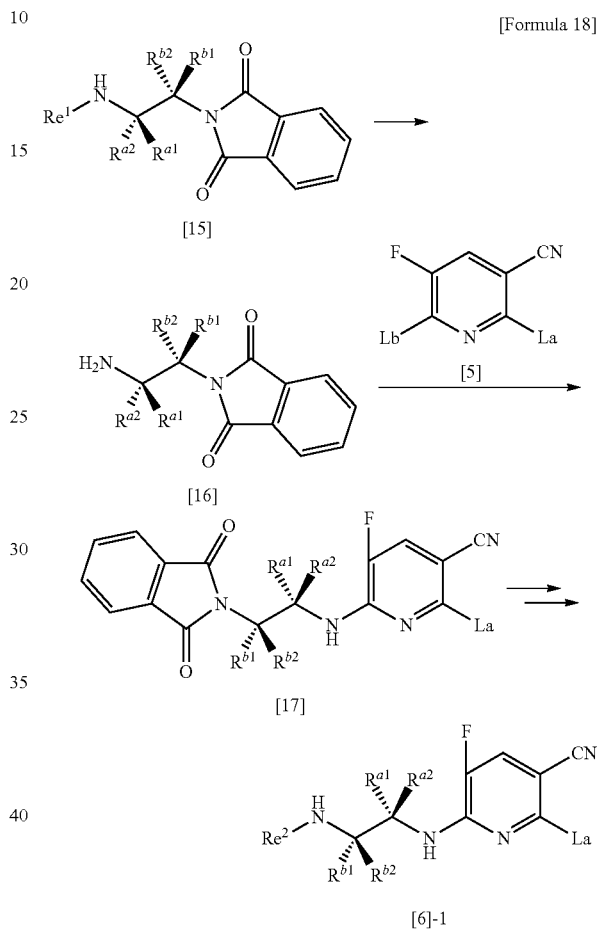

[Formula 18]

"wherein $Re^1$ and $Re^2$ may be the same or different, an amino protecting group, $R^{a1}$, $R^{a2}$, $R^{b1}$, $R^{b2}$, La, and Lb have the same definitions as those described above."

(A5-1)

The compound of the formula [16] can be produced by deprotecting the compound of the formula [15].

(A5-2)

The compound of the formula [17] can be produced by allowing the compound of the formula [16] to react with the compound of the formula [5] in accordance with Production Method 2.

(A5-3)

The compound of the formula [6]-1 can be produced by deprotecting the compound of the formula [17] with the use of hydrazine or the like and then protecting an amino group.

The compounds obtained by the above-described production methods can be induced to other compounds by subjecting them to well-known reactions such as condensation, addition, oxidation, reduction, dislocation, substitution, halogenation, dehydration or hydrolysis, or by combining these reactions, as appropriate.

When amino, hydroxy and/or carboxyl groups are present in the compounds obtained by the above-described production methods and the intermediates thereof, reactions can be carried out by replacing their protecting groups with other groups, as appropriate. In addition, when two or more protecting groups are present, such protecting groups can be selectively deprotected by subjecting them to well-known reactions.

Among compounds used in the above-described production methods, those that can be in the form of salts can be used as salts. Examples of such salts are the same as the examples of the salt of the compound represented by the formula (I) of the present invention.

When isomers (for example, optical isomers, geometric isomers, tautomers, etc.) are present for the compounds used in the above-described production methods, these isomers can also be used. In addition, when solvates, hydrates, and various forms of crystals are present, these solvates, hydrates, and various forms of crystals can also be used.

When the compound represented by the formula [1] of the present invention is used as a medicament, pharmaceutical additives commonly used in formulation of such a medicament, such as an excipient, a carrier, and a diluent, may be mixed into the compound of the present invention, as appropriate. The thus formulated medicament can be orally or parenterally administered in the form of a tablet, a capsule, a powdered medicine, a syrup, a granule, a pill, a suspending agent, an emulsion, a liquid agent, a powdery agent, a suppository, an eye drop, a nasal drop, an ear drop, a patch, an ointment, or an injection, according to ordinary methods. An administration method, a dosage, and a number of doses can be selected, as appropriate, depending on the age, body weight, and symptoms of a patient. In general, the medicament may be administered orally or parenterally (e.g. via injection, drip infusion, or administration into a rectal site) at a dosage from 0.01 to 1000 mg/kg to an adult per day, once or dividedly several times.

EXAMPLES

The present invention is hereafter described with reference to the Reference Examples and the Examples, although the scope of the present invention is not limited thereto.

LC/MS analysis was conducted under the following conditions.
LC/MS analyzer: Waters SQD
Column: Waters BEHC18 1.7 μm, 2.1×30 mm
Solvent: Liquid A: 0.1% formic acid-water
 Liquid B: 0.1% formic acid-acetonitrile
Gradient cycle: 0.00 min (Liquid A/Liquid B=95/5), 2.00 min (Liquid
A/Liquid B=5/95), 3.00 min (Liquid A/Liquid B=5/95), 3.01 min (Liquid
A/Liquid B=100/0), 3.80 min (Liquid A/Liquid B=100/0)
Flow rate: 0.5 mL/min (The column temperature was room temperature, and no temperature control was carried out.)
Ionization method: Electron Spray Ionization method (ESI positive and negative ion peaks were detected.)
UV detection: UV 254 nm
NMR spectra used herein are proton NMR spectra. NMR spectra were measured using a BRUKER AVANCE 300 (300 MHz spectrometer), and the δ value was expressed in ppm.
The carrier used for silica gel column chromatography is PSQ100B (spherical shape) (Fuji Silysia Chemical Ltd.), and the PLC glass plate used herein is a PLC glass plate silica gel 60 $F_{254}$ (Merck), unless otherwise specified.

The compound of the formula [1a] is a mixture of the compound of the formula [1b] and the compound of the formula [1c].

[Formula 19]

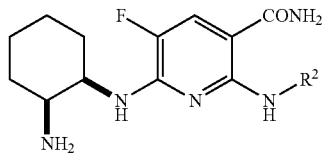
[1a]

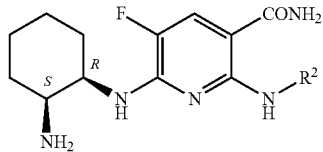
[1b]

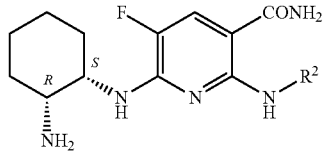
[1c]

Abbreviations used in the Reference Examples and the Examples stand for the terms given below.

Boc: tert-butoxycarbonyl
Bn: benzyl
CDI: carbonyldiimidazole
Cbz: benzyloxycarbonyl
$CHCl_3$: chloroform
$CH_2Cl_2$: dichloromethane
dba: 1,3-dibenzylideneacetone
DIAD: diisopropyl azodicarboxylate
DIPEA: N,N-diisopropyl ethylamine
DMAc: N,N-dimethylacetamide
DMAP: N,N-dimethylaminopyridine
DMF: N,N-dimethylformamide
DMSO: dimethyl sulfoxide
DMSO-$d_6$: deuterated dimethyl sulfoxide
DPPA: diphenylphosphoryl azide
Et: ethyl
IPE: diisopropylether
mCPBA: meta-chloroperoxybenzoic acid
Me: methyl
Ms: methanesulfonyl
Ph: phenyl
RT, rt: retention time
TBAI: tetrabutylammonium iodide
Tf: trifluoromethanesulfonyl
TFA: trifluoroacetic acid
THF: tetrahydrofuran
Py: pyridine Xantphos: 4,5-bis(diphenylphosphino)-9,9-dimethylxanthene Reference Example 1

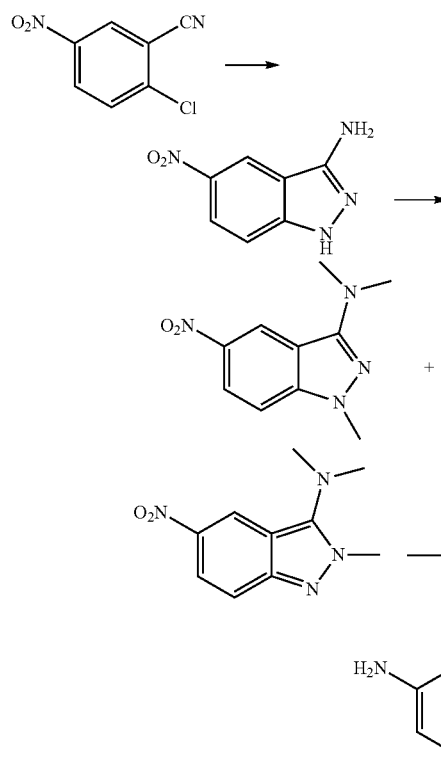

[Formula 20]

1st Step

Hydrazine monohydrate (4.87 ml) was added to an EtOH (19 ml) solution containing 2-chloro-5-nitrobenzonitrile (1.83 g), followed by stirring for 0.5 hour under ice cooling. Water was added to the reaction solution, and a solid precipitate was collected by filtration and washed with IPE and ethyl acetate. A red solid of 5-nitro-1H-indazol-3-amine (1.45 g) was thus obtained.

MS (ESI m/z): 179 (M+H)

RT (min): 0.77

2nd Step 5-nitro-1H-indazol-3-amine (254 mg) obtained in the 1st step and iodomethane (1 ml) were added to a DMF (3 ml) suspension containing sodium hydride (60% in oil) (171 mg) under ice cooling, followed by stirring at room temperature for 1 hour. Water was added to the reaction solution, followed by extraction with ethyl acetate. The organic layers were washed with water and saturated saline and dried over anhydrous sodium sulfate. Then, the solvent was distilled away under reduced pressure, and the obtained residue was purified by silica gel chromatography (n-hexane:ethyl acetate=1:0 to 1:1). A yellow solid of N,N,1-trimethyl-5-nitro-1H-indazol-3-amine (132 mg) and a yellow solid of N,N,2-trimethyl-5-nitro-2H-indazol-3-amine (72 mg) were thus obtained.

N,N,1-trimethyl-5-nitro-1H-indazol-3-amine

MS (ESI m/z): 221 (M+H)

RT (min): 1.24

N,N,2-trimethyl-5-nitro-2H-indazol-3-amine

MS (ESI m/z): 221 (M+H)

RT (min): 1.14

3rd Step

An MeOH (10 ml) solution containing N,N,1-trimethyl-5-nitro-1H-indazol-3-amine (132 mg) obtained in the 2nd step was prepared and subjected to a hydrogenation reaction (70° C.; 50 bar; flow rate: 2 ml/min; 10% Pd/C) using H-Cube™. The solvent was distilled away under reduced pressure. A red solid of $N^3,N^3,1$-trimethyl-1H-indazol-3,5-diamine (100 mg) was thus obtained.

MS (ESI m/z): 191 (M+H)

RT (min): 0.52

Reference Example 2

[Formula 21]

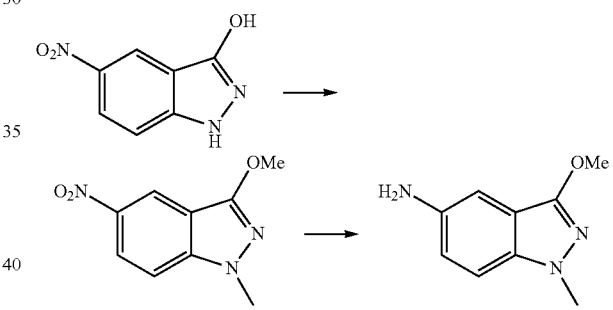

1st Step

5-Nitro-1H-indazol-3-ol (112 mg) and iodomethane (0.5 ml) was added to a DMF (2 ml) suspension containing sodium hydride (60% in oil) (60 mg), followed by stirring at room temperature for 10 minutes. Water was added to the reaction solution, followed by extraction with chloroform. The organic layers were dried over anhydrous sodium sulfate. The solvent was distilled away under reduced pressure, and the obtained residue was purified by silica gel chromatography (n-hexane:ethyl acetate=1:0 to 1:1). A yellow solid of 3-methoxy-1-methyl-5-nitro-1H-indazole (31 mg) was thus obtained.

3-Methoxy-1-methyl-5-nitro-1H-indazole

MS (ESI m/z): 208 (M+H)

RT (min): 1.33

2nd Step

The following compound was obtained as described in the 3rd step in Reference Example 1.

3-Methoxy-1-methyl-1H-indazol-5-amine

MS (ESI m/z): 178 (M+H)
RT (min): 0.44

Reference Example 3

[Formula 22]

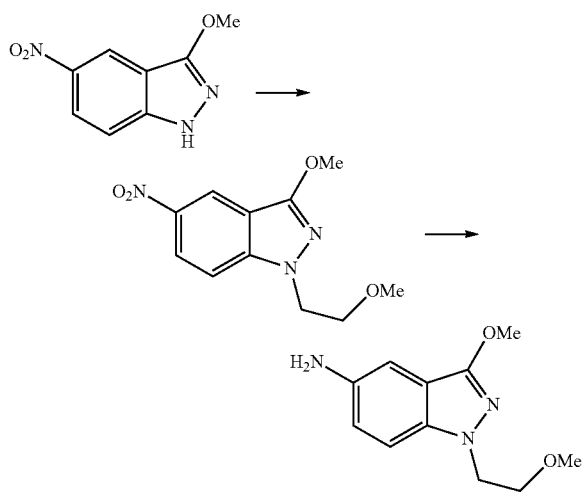

1st Step

3-Methoxy-5-nitro-1H-indazole (97 mg), 1-bromo-2-methoxyethane (70 μl, and TBAI (2 mg) were added to a DMF (1 ml) suspension containing sodium hydride (60% in oil) (24 mg) under ice cooling, followed by stirring at 100° C. for 1 hour. Water was added to the reaction solution, followed by extraction with ethyl acetate. The organic layers were washed with water and saturated saline and dried over anhydrous sodium sulfate. Then, the solvent was distilled away under reduced pressure, and the obtained residue was purified by silica gel chromatography (n-hexane:ethyl acetate=1:0 to 1:1). A 3-methoxy-1-(2-methoxyethyl)-5-nitro-1H-indazole (50 mg) was thus obtained.

MS (ESI m/z): 252 (M+H)
RT (min): 1.40

2nd Step

The following compound was obtained as described in the 3rd step in Reference Example 1.

3-Methoxy-1-(2-methoxyethyl)-1H-indazol-5-amine

Reference Example 4

The following compound was obtained as described in Reference Example 3.

[Formula 23]

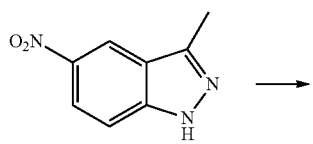

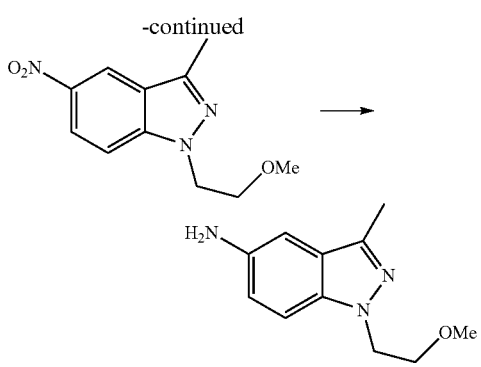

1-(2-Methoxyethyl)-3-methyl-1H-indazol-5-amine

MS (ESI m/z): 206 (M+H)
RT (min): 0.79

Reference Example 5

[Formula 24]

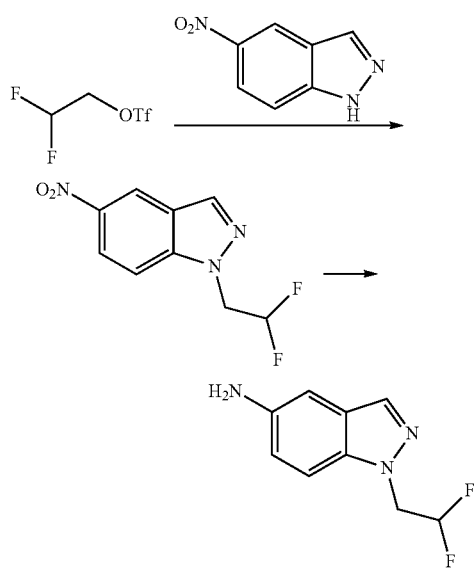

1st Step

A CH$_2$Cl$_2$ (10 ml) solution containing 2,2-difluoroethanol (5.0 g) and triethylamine (8.44 ml) was slowly added to a CH$_2$Cl$_2$ (10 ml) solution containing trifluoromethanesulfonic anhydride (10.2 ml) at −78° C. in a nitrogen atmosphere, followed by stirring for 45 minutes. The solvent was distilled away under reduced pressure. Colorless oily matter of 2,2-difluoroethyl trifluoromethane sulfonate (9.04 g) was thus obtained.

2nd Step 2,2-Difluoroethyl trifluoromethane sulfonate (2 ml) obtained in the 1st step and 5-nitroindazole (163 mg) were added to a DMF (2 ml) suspension containing sodium hydride (60% in oil) (44 mg) under ice cooling, followed by stirring at room temperature for 1 hour. Water was added to the reaction solution, followed by extraction with ethyl acetate. The organic layers were washed with water and saturated saline and dried over anhydrous sodium sulfate. The solvent was distilled away under reduced pressure, and the obtained residue was purified by silica gel chromatography (n-hexane: ethyl acetate=1:0 to 1:1). 1-(2,2-Difluoroethyl)-5-nitro-1H-indazole (113 mg) was thus obtained.

MS (ESI m/z): 228 (M+H)
RT (min): 1.25

3rd Step

The following compound was obtained as described in the 3rd step in Reference Example 1.

1-(2,2-Difluoroethyl)-1H-indazol-5-amine

MS (ESI m/z): 228 (M+H)
RT (min): 1.18

Reference Example 6

[Formula 25]

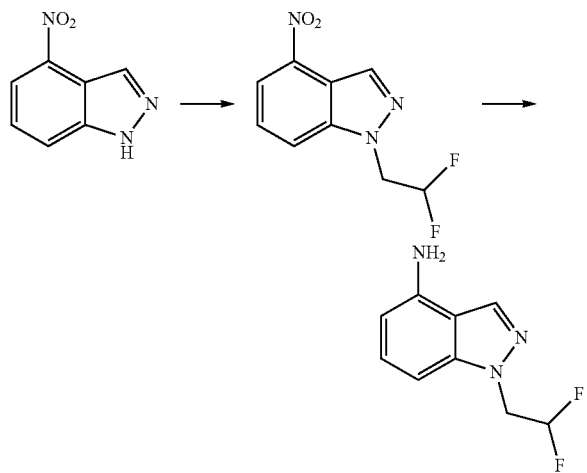

The following compound was obtained as described in Reference Example 5.

1st Step 1-(2,2-Difluoroethyl)-4-nitro-1H-indazole

2nd Step 1-(2,2-Difluoroethyl)-1H-indazol-4-amine

MS (ESI m/z): 198 (M+H)
RT (min): 0.88

Reference Example 7

[Formula 26]

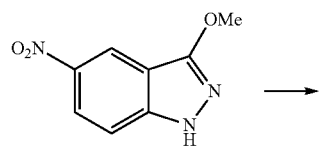

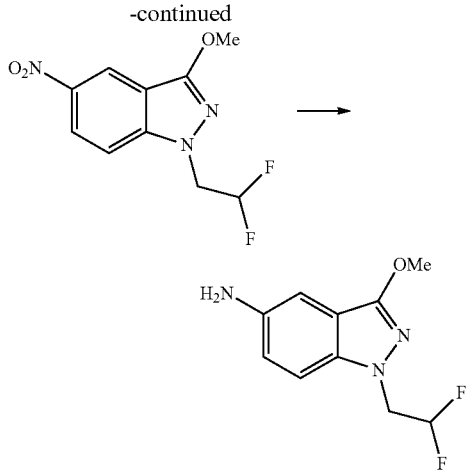

The following compound was obtained as described in Reference Example 5.

1st Step 1-(2,2-Difluoroethyl)-3-methoxy-5-nitro-1H-indazole

MS (ESI m/z): 258 (M+H)
RT (min): 1.40

2nd Step 1-(2,2-Difluoroethyl)-3-methoxy-1H-indazol-5-amine

Reference Example 8

[Formula 27]

The following compound was obtained as described in Reference Example 5.

1st Step 1-(2,2-Difluoroethyl)-3-methyl-5-nitro-1H-indazole

2nd Step 1-(2,2-Difluoroethyl)-3-methyl-1H-indazol-5-amine

MS (ESI m/z): 212 (M+H)
RT (min): 0.49

Reference Example 9

[Formula 28]

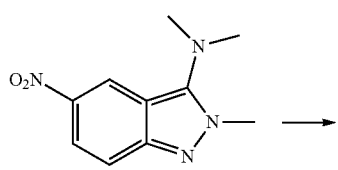

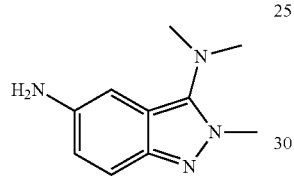

The following compound was obtained as described in the 3rd step in Reference Example 1.

$N^3,N^3$,1-trimethyl-2H-indazol-3,5-diamine

MS (ESI m/z): 191 (M+H)
RT (min): 0.47

Reference Example 10

The following compound was obtained with reference to WO2007/126841 A2.

[Formula 29]

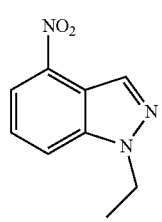

1-Ethyl-4-nitro-1H-indazole

Reference Example 11

The following compound was obtained as described in the 3rd step in Reference Example 1.

[Formula 30]

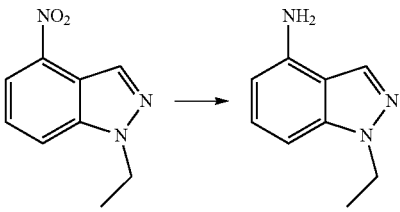

1-Ethyl-1H-indazol-4-amine

MS (ESI m/z): 162 (M+H)
RT (min): 0.92

Reference Example 12

The following compound was obtained with reference to US2009/76275 A1.

[Formula 31]

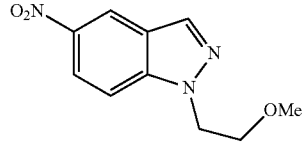

1-(2-Methoxyethyl)-5-nitro-1H-indazole

Reference Example 13

[Formula 32]

The following compound was obtained as described in the 3rd step in Reference Example 1.

1-(2-Methoxyethyl)-1H-indazol-5-amine

MS (ESI m/z): 192 (M+H)
RT (min): 0.39

Reference Example 14

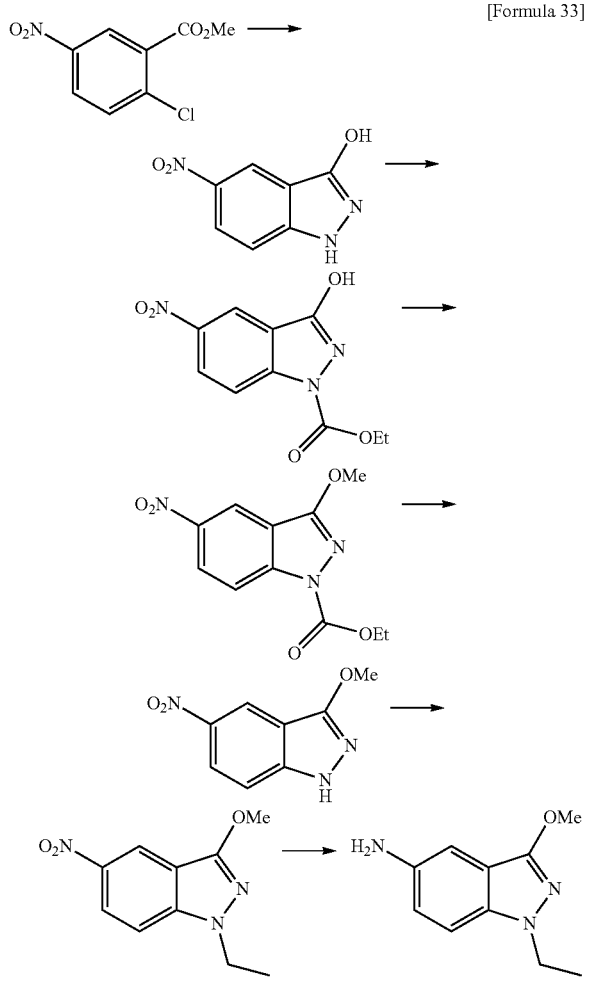

[Formula 33]

1st Step

Hydrazine monohydrate (19 ml) was added to an EtOH (15 ml) solution containing methyl 2-chloro-5-nitrobenzoate (10 g), followed by stirring at 90° C. for 1 hour. The reaction solution was adjusted to room temperature. Water and concentrated hydrochloric acid (32 ml) were added dropwise to the reaction solution. A solid precipitate was collected by filtration and washed with water. A brown solid of 5-nitro-1H-indazol-3-ol (5.42 g) was thus obtained.

MS (ESI m/z): 180 (M+H)

RT (min): 0.73

2nd Step

Ethyl chloroformate (5 ml) was added to a pyridine (30 ml) solution containing 5-nitro-1H-indazol-3-ol (5.42 g) obtained in the 1st step, followed by stirring at room temperature for 1.5 hours. Water and concentrated hydrochloric acid (32 ml) were added dropwise to the reaction solution and a solid precipitate was collected by filtration. The obtained residue was washed with water. A brown solid of ethyl 3-hydroxy-5-nitro-1H-indazol-1-carboxylate (7.5 g) was thus obtained.

MS (ESI m/z): 252 (M+H)

RT (min): 1.17

3rd Step

Iodomethane (10 ml) and cesium carbonate (4.89 g) were added to an acetone (20 ml) solution containing ethyl 3-hydroxy-5-nitro-1H-indazol-1-carboxylate (2.51 g) obtained in the 2nd step under ice cooling in a nitrogen atmosphere, followed by stirring at 80° C. for 0.5 hours. An insoluble precipitate was removed by filtration and the solvent was distilled away under reduced pressure. The obtained residue was purified by silica gel chromatography (n-hexane:ethyl acetate=1:0 to 4:1). A white solid of ethyl 3-methoxy-5-nitro-1H-indazol-1-carboxylate (1.24 g) was thus obtained.

MS (ESI m/z): 266 (M+H)

RT (min): 1.45

4th Step

Potassium hydroxide (0.6 g) was added to an EtOH (20 ml) solution containing ethyl 3-methoxy-5-nitro-1H-indazol-1-carboxylate (1.24 g) obtained in the 3rd step, followed by stirring at room temperature for 0.5 hours. Water and concentrated hydrochloric acid (1 ml) were added dropwise to the reaction solution. A solid precipitate was collected by filtration and washed with water. A light yellow solid of 3-methoxy-5-nitro-1H-indazole (636 mg) was thus obtained.

MS (ESI m/z): 194 (M+H)

RT (min): 1.15

5th Step 3-methoxy-5-nitro-1H-indazole (100 mg) and iodoethane (0.1 ml) were added to a DMF (1 ml) suspension containing sodium hydride (60% in oil) (23 mg), followed by stirring at room temperature for 0.5 hours. Water was added to the reaction solution. A solid precipitate was collected by filtration and purified by silica gel chromatography (n-hexane: ethyl acetate=1:0 to 1:1). 1-Ethyl-3-methoxy-5-nitro-1H-indazole (80 mg) was thus obtained.

MS (ESI m/z): 222 (M+H)

RT (min): 1.45

6th Step

The following compound was obtained as described in the 3rd step in Reference Example 1.

1-Ethyl-3-methoxy-1H-indazol-5-amine

Reference Example 15

The following compound was obtained with reference to Journal of Heterocyclic Chemistry, 1979, vol. 16, pp. 1599, 1600, and 1601.

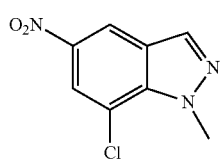

[Formula 34]

7-Chloro-1-methyl-5-nitro-1H-indazole

Reference Example 16

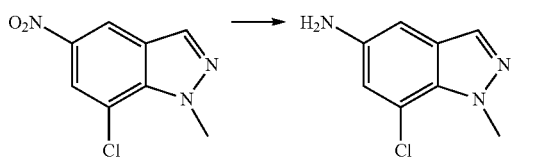

[Formula 35]

Tin (II) chloride (50 mg) was added to a ethanol (2 ml) solution containing 7-chloro-1-methyl-5-nitro-1H-indazole (30 mg), followed by stirring at 100° C. for 0.5 hours. The solvent was distilled away under reduced pressure and the obtained residue was purified by silica gel chromatography (n-hexane:ethyl acetate=1:0 to 0:1). 7-Chloro-1-methyl-1H-indazol-5-amine (10 mg) was thus obtained.

MS (ESI m/z): 182 (M+H)

RT (min): 0.64

Reference Example 17

The following compound was obtained with reference to EP1150962 B1, 2004.

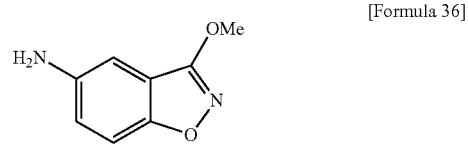 [SMILES: COc1noc2ccc(N)cc12]

[Formula 36]

3-Methoxybenz[d]isoxazol-5-amine

Reference Example 18

[Formula 37]

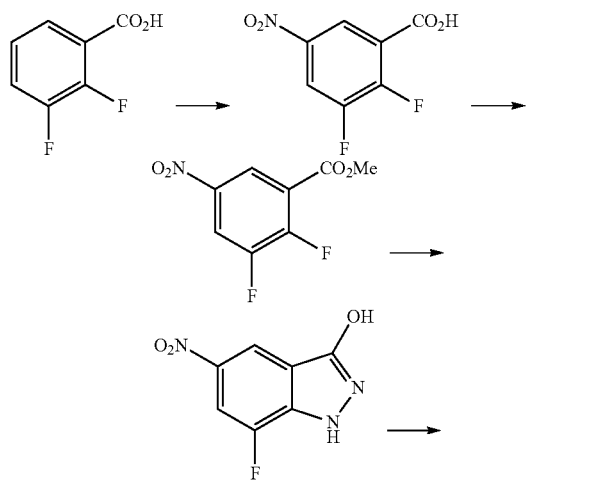

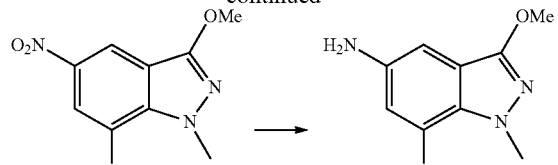

1st Step

Sodium nitrate (1.7 g) was added to a concentrated sulfuric acid (7 ml) solution containing 2,3-difluorobenzoic acid (1.58 g), followed by stirring at room temperature for 0.5 hours. The reaction solution was poured into ice water, followed by extraction with ethyl acetate. The organic layers were dried over anhydrous sodium sulfate. The solvent was distilled away under reduced pressure, the obtained residue was purified by silica gel chromatography (n-hexane:ethyl acetate=1:0 to 4:1). A light yellow solid of 2,3-difluoro-5-nitrobenzoic acid (1.61 g) was thus obtained.

MS (ESI m/z): 202 (M+H)

RT (min): 0.97

2nd Step

Oxalyl chloride (1 ml) and DMF (5 μl) were added to a CH$_2$Cl$_2$ (1.6 ml) solution containing 2,3-difluoro-5-nitrobenzoic acid (1.61 g) obtained in the 1st step, followed by stirring at room temperature for 15 minutes. The reaction solution was poured into a liquid mixture of MeOH/Py (100 ml/1.28 ml) and the solvent was distilled away under reduced pressure. The obtained residue was purified by silica gel chromatography (n-hexane:ethyl acetate=1:0 to 4:1). A light yellow solid of methyl 2,3-difluoro-5-nitrobenzoate (1.71 g) was thus obtained.

3rd Step

Hydrazine monohydrate (1.91 ml) was added to an EtOH (40 ml) solution containing methyl 2,3-difluoro-5-nitrobenzoate (1.71 g) obtained in the 2nd step, followed by stirring at room temperature for 10 minutes. An insoluble precipitate was removed by filtration and washed with EtOH. 7-Fluoro-5-nitro-1H-indazol-3-ol (956 mg) was thus obtained.

MS (ESI m/z): 198 (M+H)

RT (min): 0.90

4th Step

The following compound was obtained as described in the 1st step in Reference Example 2.

7-Fluoro-3-methoxy-1-methyl-5-nitro-1H-indazole

MS (ESI m/z): 226 (M+H)

RT (min): 0.92

5th Step

The following compound was obtained as described in the 3rd step in Reference Example 1.

7-Fluoro-3-methoxy-1-methyl-1H-indazol-5-amine

MS (ESI m/z): 196 (M+H)

RT (min): 0.61

Reference Example 19

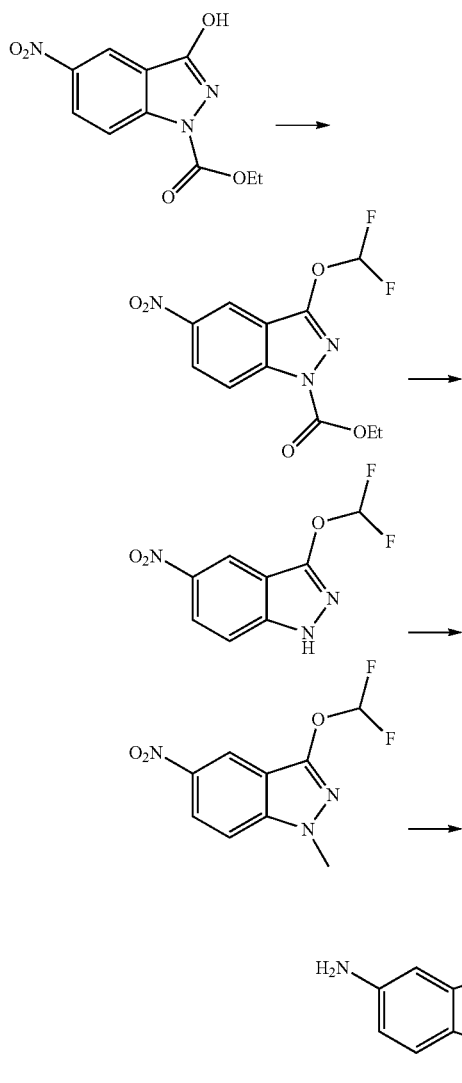

[Formula 38]

1st Step

Sodium chlorodifluoroacetate (4.75 g) and potassium carbonate (8.58 g) were added to a DMF (3 ml) solution containing ethyl 3-hydroxy-5-nitro-1H-indazol-1-carboxylate (1.56 g), followed by stirring at 80° C. for 1 hour. The reaction solution was adjusted to room temperature and ethyl acetate was added to remove an insoluble precipitate. The organic layers were washed with a saturated ammonium chloride aqueous solution, water, and saturated saline and dried over anhydrous sodium sulfate. Then, the solvent was distilled away under reduced pressure, and the obtained residue was purified by silica gel chromatography (n-hexane:ethyl acetate=1:0 to 4:1). A yellow solid of ethyl 3-(difluoromethoxy)-5-nitro-1H-indazol-1-carboxylate (1.14 g) was thus obtained.

MS (ESI m/z): 302 (M+H)
RT (min): 1.53

2nd Step

Water (6 ml) and lithium hydroxide monohydrate (640 mg) were added to a THF (19 ml) solution containing ethyl 3-(difluoromethoxy)-5-nitro-1H-indazol-1-carboxylate (1.14 g) obtained in the 1st step, followed by reflux at 80° C. for 3 hours. THF was distilled away under reduced pressure and a saturated ammonium chloride aqueous solution was added. An insoluble precipitate was removed by filtration. The obtained residue was washed with water, dissolved in ethyl acetate, and dried over anhydrous sodium sulfate. The solvent was distilled away under reduced pressure. A yellow solid of 3-(difluoromethoxy)-5-nitro-1H-indazole (921 mg) was thus obtained.

MS (ESI m/z): 230 (M+H)
RT (min): 1.04

3rd Step

The following compound was obtained as described in the 2nd step in Reference Example 1.

3-(Difluoromethoxy)-1-methyl-5-nitro-1H-indazole

MS (ESI m/z): 244 (M+H)
RT (min): 1.51

4th Step

The following compound was obtained as described in the 3rd step in Reference Example 1.

3-(Difluoromethoxy)-1-methyl-1H-indazol-5-amine

MS (ESI m/z): 214 (M+H)
RT (min): 0.59

Reference Example 20

[Formula 39]

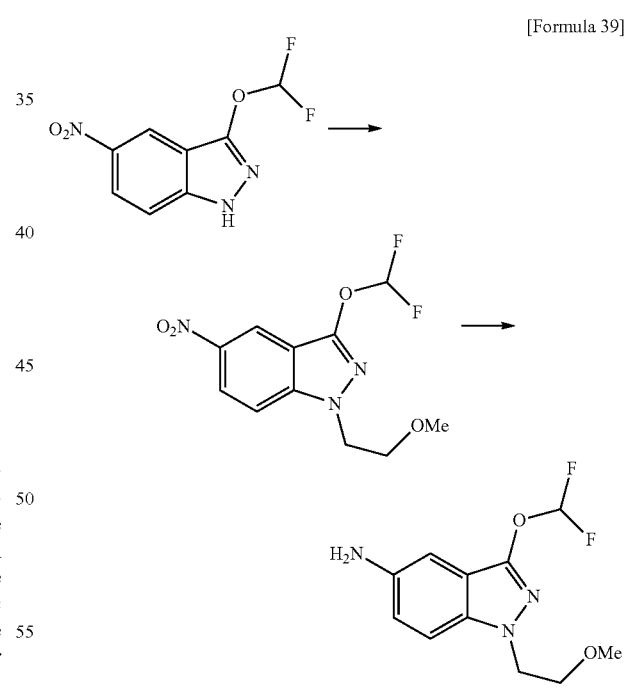

The following compound was obtained as described in Reference Example 3.

1st Step 3-(Difluoromethoxy)-1-(2-methoxyethyl)-5-nitro-1H-indazole

MS (ESI m/z): 288 (M+H)
RT (min): 1.55

2nd Step 3-(Difluoromethoxy)-1-(2-methoxyethyl)-1H-indazol-5-amine

MS (ESI m/z): 258 (M+H)
RT (min): 0.68

Reference Example 21

The following compound was obtained with reference to WO2010/114971 A1.

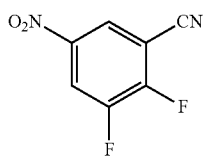

[Formula 40]

2,3-Difluoro-5-nitrobenzonitrile

Reference Example 22

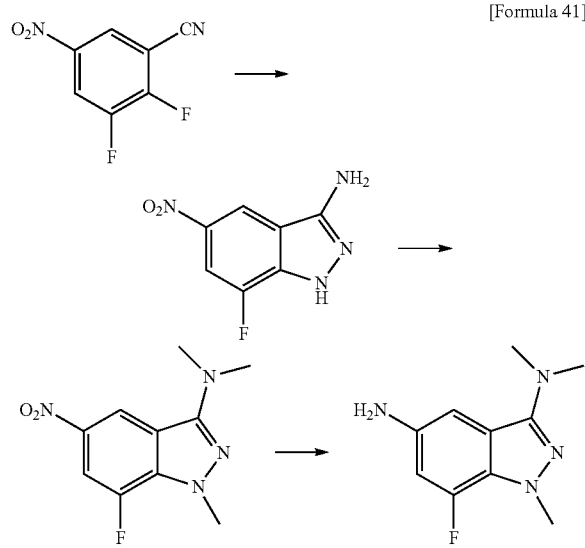

[Formula 41]

The following compound was obtained as described in Reference Example 1.

1st Step

7-Fluoro-5-nitro-1H-indazol-3-amine

MS (ESI m/z): 197 (M+H)
RT (min): 0.93

2nd Step

7-Fluoro-N,N,1-trimethyl-5-nitro-1H-indazol-3-amine

MS (ESI m/z): 239 (M+H)
RT (min): 1.66

3rd Step

7-Fluoro-$N^3,N^3$,1-trimethyl-1H-indazol-3,5-diamine

MS (ESI m/z): 209 (M+H)
RT (min): 0.70

Reference Example 23

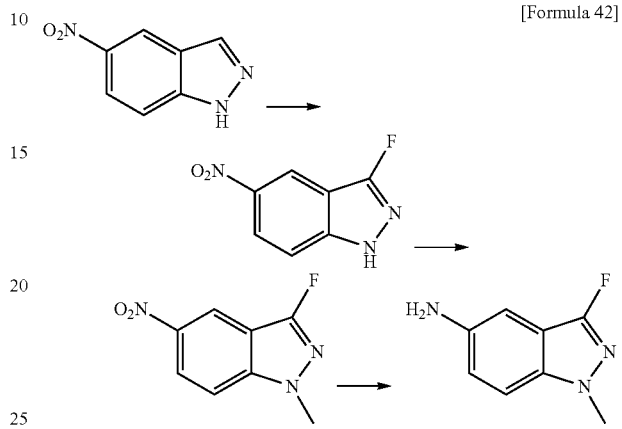

[Formula 42]

1st Step
Select flour (173 mg) and acetic acid (2.5 ml) were added to an acetonitrile (2.5 ml) solution containing 5-nitroindazole (615 mg), followed by microwave irradiation (Initiator™, 150° C., 0.5 hours, 2.45 GHz, 0-240 W). The obtained residue was purified by silica gel chromatography (n-hexane:ethyl acetate=1:0 to 1:1). 3-Fluoro-5-nitro-1H-indazole (404 mg) was thus obtained.

2nd Step
Methyl iodide (41 µl) and potassium carbonate (114 mg) were added to a 1,4-dioxane (2.5 ml) solution containing 3-fluoro-5-nitro-1H-indazole (100 mg), followed by stirring at 100° C. for 2 hours. Ethyl acetate was added to the reaction solution. An insoluble precipitate was removed by filtration, the solvent was distilled away under reduced pressure, and the obtained residue was purified by silica gel chromatography (n-hexane:ethyl acetate=1:0 to 1:1). 3-Fluoro-1-methyl-5-nitro-1H-indazole was thus obtained.

3rd Step
The following compound was obtained as described in the 3rd step in Reference Example 1.

3-Fluoro-1-methyl-1H-indazol-5-amine

MS (ESI m/z): 166 (M+H)
RT (min): 1.32

Reference Example 24

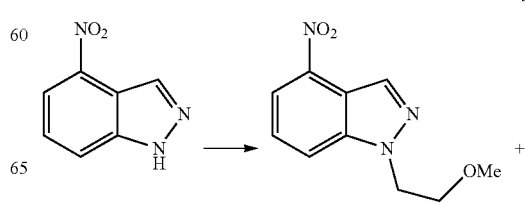

[Formula 43]

53

-continued

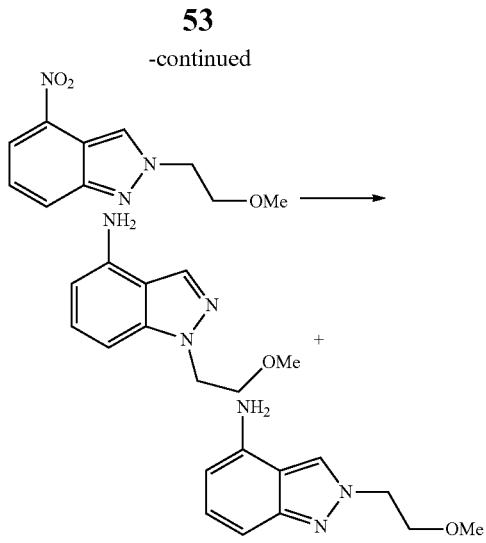

1st Step

Potassium carbonate (200 mg) and 2-chloroethylmethyl ether (0.1 ml) were added to a DMF (1.5 ml) solution containing 4-nitro-1H-indazole (80 mg), followed by stirring at 60° C. for 4 hours. An insoluble precipitate was collected by filtration and washed with ethyl acetate. A mixture of 1-(2-methoxyethyl)-4-nitro-1H-indazole and 2-(2-methoxyethyl)-4-nitro-2H-indazole was thus obtained.

1-(2-Methoxyethyl)-4-nitro-1H-indazole

MS (ESI m/z): 222 (M+H)

RT (min): 1.19

2-(2-Methoxyethyl)-4-nitro-2H-indazole

MS (ESI m/z): 222 (M+H)

RT (min): 1.12

2nd Step

Iron powder (170 mg), ammonium chloride (160 mg), and water (3 ml) were added to an EtOH (10 ml) solution containing the mixture of 1-(2-methoxyethyl)-4-nitro-1H-indazole and 2-(2-methoxyethyl)-4-nitro-2H-indazole obtained in the 1st step, followed by stirring at 80° C. for 2 hours. Ethyl acetate was added to the reaction solution, insoluble matter was removed by filtration, and the solvent was distilled away under reduced pressure. The obtained residue was purified by silica gel-alumina column chromatography. 1-(2-methoxyethyl)-1H-indazol-4-amine (49 mg) and 2-(2-methoxyethyl)-2H-indazol-4-amine (40 mg) were thus obtained.

1-(2-Methoxyethyl)-1H-indazol-4-amine

MS (ESI m/z): 192 (M+H)

RT (min): 0.72

2-(2-Methoxyethyl)-2H-indazol-4-amine

MS (ESI m/z): 192 (M+H)

RT (min): 0.53

54

Reference Example 25

[Formula 44]

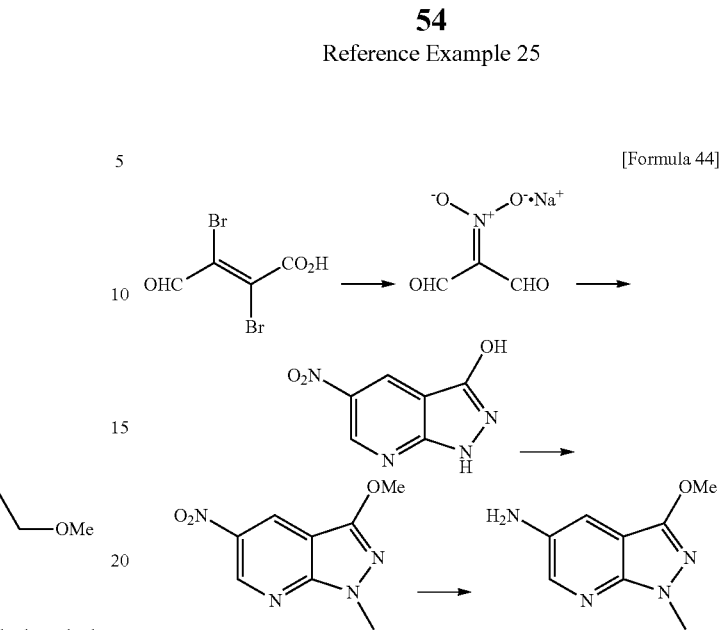

1st Step

An EtOH (12.5 ml) solution containing mucobromic acid (12.9 g) was added dropwise to a solution comprising sodium nitrate (13.1 g) and water (12.5 ml) at 50° C., followed by stirring for 0.5 hours. The reaction solution was adjusted to room temperature, a solid precipitate was collected by filtration. The obtained residue was washed with EtOH. A yellow solid of sodium (1,3-dioxopropan-2-ylidene)azinate (3.82 g) was thus obtained.

MS (ESI m/z): 116 (M−H)

RT (min): 0.31

2nd Step

Sodium (1,3-dioxopropan-2-ylidyne)azinate (864 mg) obtained in the 1st step was added to an acetic acid (5.5 ml) solution containing 3-amino-5-hydroxypyrazole (495 mg), followed by stirring in a sealed tube at 90° C. for 6 hours. The reaction solution was adjusted to room temperature and poured into water. A solid precipitate was collected by filtration. 5-Nitro-1H-pyrazolo[3,4-b]pyridin-3-ol (691 mg) was thus obtained.

MS (ESI m/z): 181 (M+H)

RT (min): 0.58

3rd Step

The following compound was obtained as described in Reference Example 2.

3-Methoxy-1-methyl-5-nitro-1H-pyrazolo[3,4-b]pyridine

MS (ESI m/z): 209 (M+H)

RT (min): 1.15

4th Step

The following compound was obtained as described in the 3rd step in Reference Example 1.

3-Methoxy-1-methyl-1H-pyrazolo[3,4-b]pyridin-5-amine

MS (ESI m/z): 179 (M+H)

RT (min): 0.49

Reference Example 26

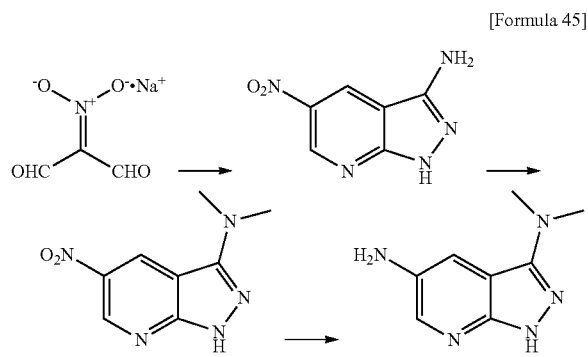

[Formula 45]

1st Step

Sodium (1,3-dioxopropan-2-ylidyne)azinate monohydrate (1.37 g) was added to an acetic acid (14 ml) solution containing pyrazole 3,5-diamine (2.41 g), followed by stirring in a sealed tube at 90° C. for 6 hours. The reaction solution was adjusted to room temperature and poured into a saturated sodium hydrogen carbonate aqueous solution. A solid precipitate was collected by filtration. A liquid mixture of ethyl acetate/MeOH/THF (2/1/0.1) was added to the obtained solid, insoluble matter was removed, and the organic layers were dried over anhydrous sodium sulfate. Then, the solvent was distilled away under reduced pressure, an orange-colored solid of 5-nitro-1H-pyrazolo[3,4-b]pyridin-3-amine (0.91 g) was thus obtained.

MS (ESI m/z): 180 (M+H)
RT (min): 0.55

2nd Step

The following compound was obtained as described in the 2nd step in Reference Example 1.

N,N,1-trimethyl-5-nitro-1H-pyrazolo[3,4-b]pyridin-3-amine

MS (ESI m/z): 222 (M+H)
RT (min): 1.17

3rd Step

The following compound was obtained as described in the 3rd step in Reference Example 1.

$N^3,N^3$,1-trimethyl-1H-pyrazolo[3,4-b]pyridin-3,5-diamine

MS (ESI m/z): 192 (M+H)
RT (min): 0.49

Reference Example 27

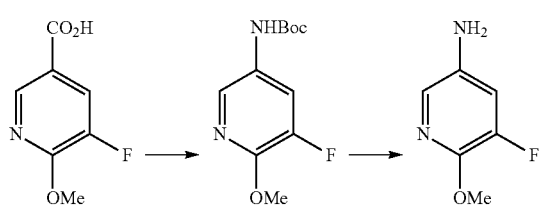

[Formula 46]

1st Step

Triethylamine (267 μl), tert-butanol (230 μl), and DPPA (413 μl) were added to a toluene (5 ml) solution containing 5-fluoro-6-methoxynicotinic acid (275 mg), followed by reflux for 3 hours. The reaction solution was adjusted to room temperature and water was added, followed by extraction with ethyl acetate. Next, the organic layers were washed with saturated saline and dried over anhydrous sodium sulfate and the solvent was distilled away under reduced pressure. Then, the obtained residue was purified by silica gel chromatography (n-hexane:ethyl acetate=10:1 to 3:1). Colorless oily matter of tert-butyl (5-fluoro-6-methoxypyridin-3-yl)carbamate (279 mg) was thus obtained.

MS (ESI m/z): 243 (M+H)
RT (min): 1.46

2nd Step

TFA (2 ml) was added to tert-butyl (5-fluoro-6-methoxypyridin-3-yl)carbamate (279 mg) obtained in the 1st step, followed by stirring at room temperature for 1 hour. The solvent was distilled away under reduced pressure and a 5M sodium hydroxide aqueous solution was added to the obtained residue at 0° C. so as to alkalify the mixture, followed by extraction with ethyl acetate. The organic layers were washed with saturated saline and dried over anhydrous sodium sulfate and the solvent was distilled away under reduced pressure. A light brown solid of 5-fluoro-6-methoxy-pyridin-3-amine (19 mg) was thus obtained.

MS (ESI m/z): 143 (M+H)
RT (min): 0.56

Reference Example 28

The following compound was obtained with reference to EP1932845 A1, 2008 and EP2070929 A1, 2009.

[Formula 47]

4-Bromo-1H-pyrazolo[3,4-c]pyridine

Reference Example 29

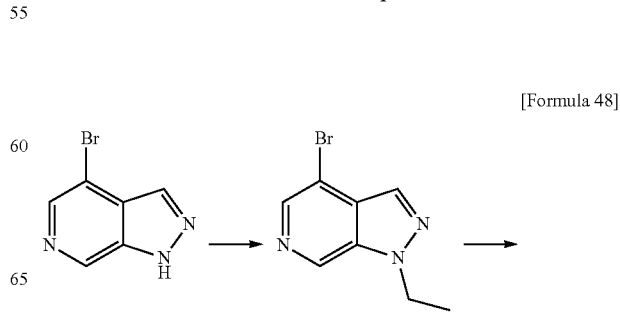

[Formula 48]

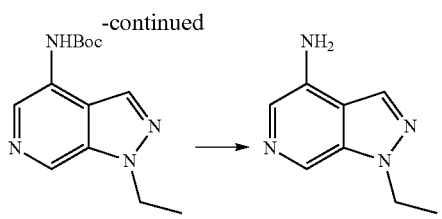

1st Step

The following compound was obtained as described in the 5th step in Reference Example 14.

4-Bromo-1-ethyl-1H-pyrazolo[3,4-c]pyridine

MS (ESI m/z): 226 (M+H)
RT (min): 1.12

2nd Step tert-Butyl carbamate (90 mg), cesium carbonate (500 mg), Pd$_2$(dba)$_3$ (46 mg), and Xantphos (58 mg) were added to a dioxane solution (2 ml) containing 4-bromo-1-ethyl-1H-pyrazolo[3,4-c]pyridine (115 mg) obtained in the 1st step, followed by microwave irradiation (Initiator™, 130° C., 1 hour, 2.45 GHz, 0-240 W). Ethyl acetate was added to the reaction solution, insoluble matter was removed by filtration, and the solvent was distilled away under reduced pressure. The obtained residue was purified by silica gel chromatography (n-hexane:ethyl acetate=1:0 to 3:1). A white solid of tert-butyl (1-ethyl-1H-pyrazolo[3,4-c]pyridin-4-yl)carbamate (113 mg) was thus obtained.

MS (ESI m/z): 263 (M+H)
RT (min): 0.84

3rd Step

The following compound was obtained as described in the 2nd step in Reference Example 27.

1-Ethyl-1H-pyrazolo[3,4-c]pyridin-4-amine

MS (ESI m/z): 163 (M+H)
RT (min): 0.42

Reference Example 30

[Formula 49]

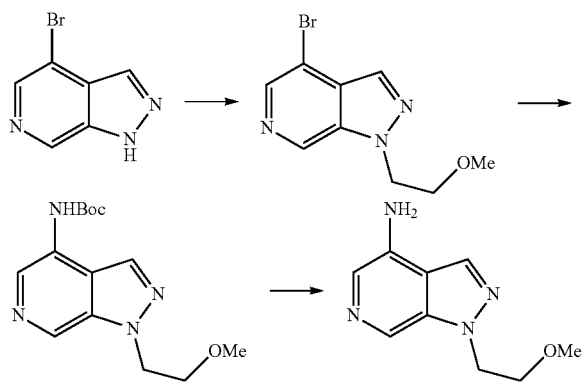

1st Step

The following compound was obtained as described in the 1st step in Reference Example 3.

4-Bromo-1-(2-methoxyethyl)-1H-pyrazolo[3,4-c]pyridine

MS (ESI m/z): 256 (M+H)
RT (min): 1.03

2nd Step

The following compound was obtained as described in the 2nd step in Reference Example 29.

tert-Butyl (1-(2-methoxyethyl)-1H-pyrazolo[3,4-c]pyridin-4-yl)carbamate

MS (ESI m/z): 293 (M+H)
RT (min): 0.87

3rd Step

The following compound was obtained as described in the 2nd step in Reference Example 27.

1-(2-Methoxyethyl)-1H-pyrazolo[3,4-c]pyridin-4-amine

Reference Example 31

The following compound was obtained with reference to WO2008/110863 A1, 2008 and WO2010/127855 A1, 2010.

[Formula 50]

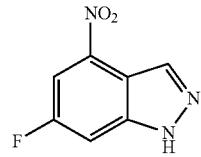

6-Fluoro-4-nitro-1H-indazole

Reference Example 32

[Formula 51]

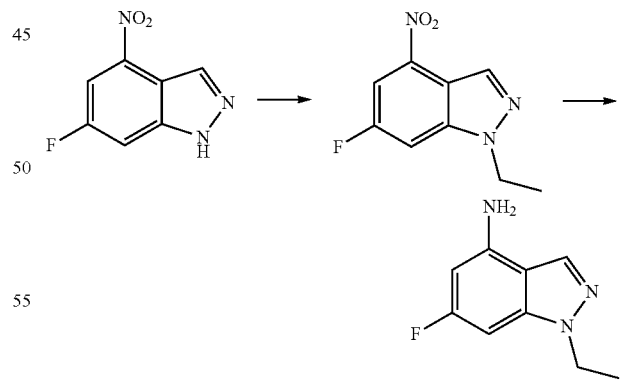

1st Step

The following compound was obtained as described in the 5th step in Reference Example 14.

1-Ethyl-6-fluoro-4-nitro-1H-indazole

MS (ESI m/z): 210 (M+H)
RT (min): 1.35

2nd Step

The following compound was obtained as described in the 3rd step in Reference Example 1.

1-Ethyl-6-fluoro-1H-indazol-4-amine

Reference Example 33

[Formula 52]

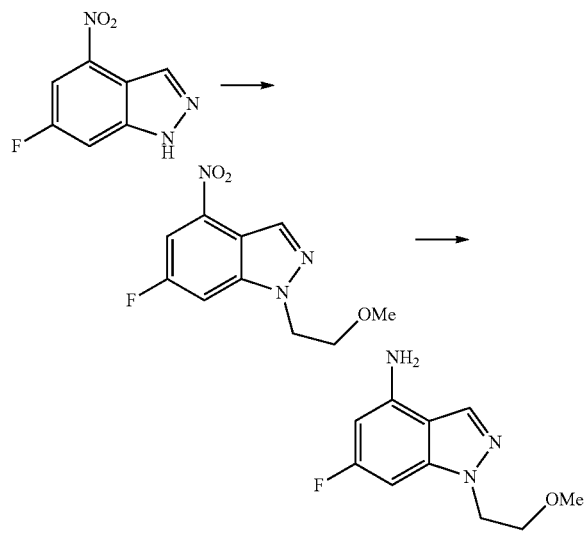

1st Step

The following compound was obtained as described in the 1st step in Reference Example 3.

6-Fluoro-1-(2-methoxyethyl)-4-nitro-1H-indazole

MS (ESI m/z): 240 (M+H)

RT (min): 1.31

2nd Step

The following compound was obtained as described in the 3rd step in Reference Example 1.

6-Fluoro-1-(2-methoxyethyl)-1H-indazol-4-amine

Reference Example 34

[Formula 53]

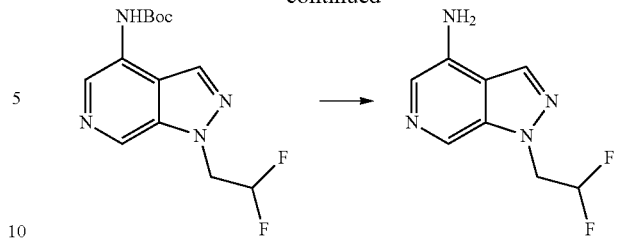

1st Step

The following compound was obtained as described in the 2nd step in Reference Example 5.

4-Bromo-1-(2,2-difluoroethyl)-1H-pyrazolo[3,4-c]pyridine

MS (ESI m/z): 264 (M+H)

RT (min): 1.12

The following compound was obtained as described in the 2nd and 3rd steps in Reference Example 29.

2nd Step tert-Butyl (1-(2,2-difluoroethyl)-1H-pyrazolo[3,4-c]pyridin-4-yl)carbamate MS (ESI m/z): 299 (M+H)

RT (min): 0.96

3rd Step 1-(2,2-Difluoroethyl)-1H-pyrazolo[3,4-c]pyridin-4-amine

Reference Example 35

[Formula 54]

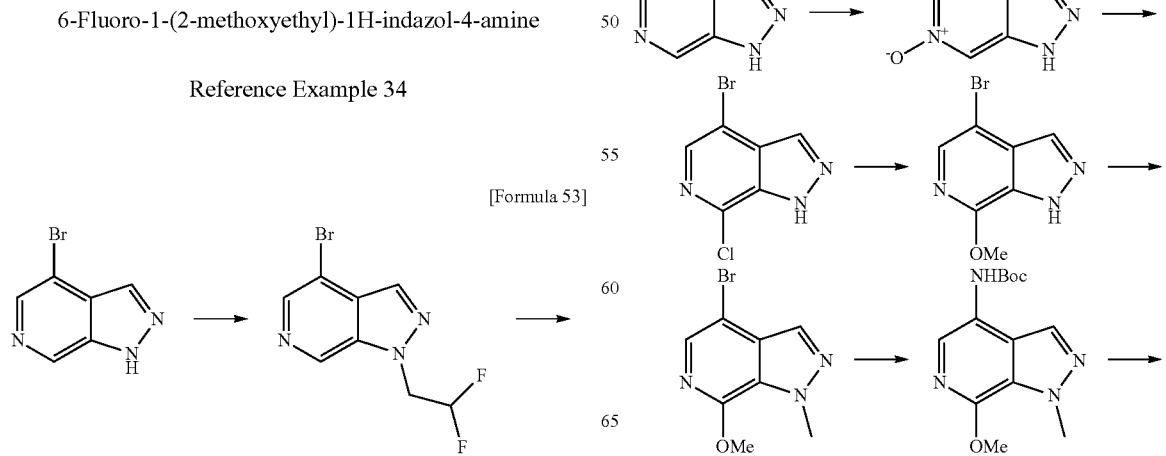

61

-continued

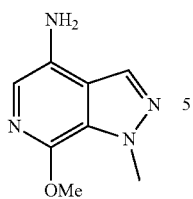

1st Step mCPBA (270 mg) was added to a CHCl₃ (5 ml) suspension containing 4-bromo-1H-pyrazolo[3,4-c]pyridine (197 mg), followed by stirring at room temperature for 10 minutes. IPE (10 ml) was added to the reaction solution and a solid precipitate was collected by filtration. A white solid of 4-bromo-1H-pyrazolo[3,4-c]pyridine 6-oxide (148 mg) was thus obtained.

MS (ESI m/z): 214 (M+H)

RT (min): 0.56

2nd Step

Phosphorus oxychloride (2 ml) was added to 4-bromo-1H-pyrazolo[3,4-c]pyridine 6-oxide (148 mg) obtained in the 1st step, followed by stirring at room temperature for 3 hours. The reaction solution was poured into water, followed by extraction with ethyl acetate. An insoluble precipitate was removed and then the solvent was distilled away under reduced pressure. A yellow solid of 4-bromo-7-chloro-1H-pyrazolo[3,4-c]pyridine (126 mg) was thus obtained.

MS (ESI m/z): 232 (M+H)

RT (min): 1.09

3rd Step

Sodium methoxide (28% in MeOH) (3 ml) was added to 4-bromo-7-chloro-1H-pyrazolo[3,4-c]pyridine (126 mg) obtained in the 2nd step, followed by stirring at 90° C. for 5 hours. A saturated ammonium chloride aqueous solution was added to the reaction solution and an insoluble precipitate was collected by filtration. The obtained residue was washed with water and a yellow solid of 4-bromo-7-methoxy-1H-pyrazolo[3,4-c]pyridine (133 mg) was thus obtained.

MS (ESI m/z): 228 (M+H)

RT (min): 1.12

The following compound was obtained as described in Reference Example 29.

4th Step

4-Bromo-7-methoxy-1-methyl-1H-pyrazolo[3,4-c]pyridine

MS (ESI m/z): 242 (M+H)

RT (min): 1.41

The following compound was obtained as described in the 2nd and 3rd steps in Reference Example 29.

5th Step tert-Butyl (7-methoxy-1-methyl-1H-pyrazolo[3,4-c]pyridin-4-yl)carbamate MS (ESI m/z): 279 (M+H)

RT (min): 1.30

62

6th Step

7-Methoxy-1-methyl-1H-pyrazolo[3,4-c]pyridin-4-amine

MS (ESI m/z): 179 (M+H)

RT (min): 0.58

Reference Example 36

[Formula 55]

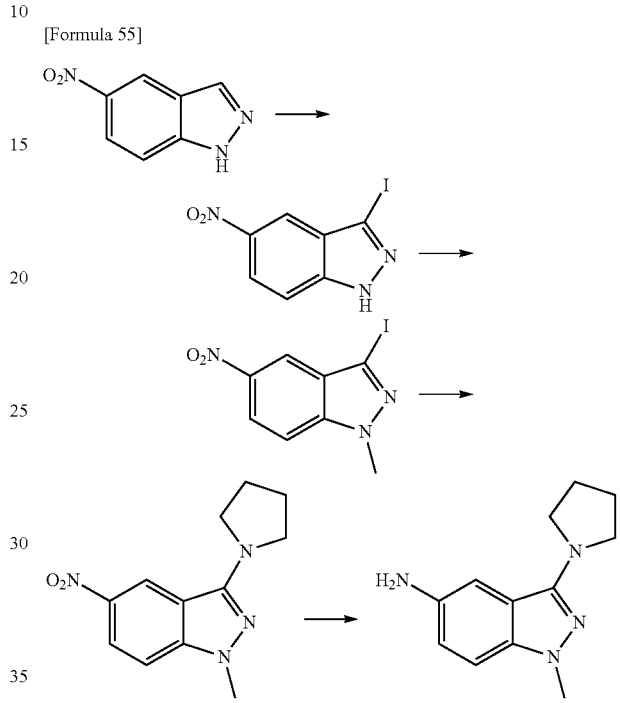

1st Step

Potassium hydroxide (6.45 g) and iodine (15.6 g) were added to a DMF (60 ml) solution containing 5-nitroindazole (5 g), followed by stirring at 65° C. for 1 hour. The reaction solution was poured into a saturated sodium hydrogen carbonate aqueous solution and a solid precipitate was collected by filtration. 3-Iodo-5-nitro-1H-indazole (8 g) was thus obtained.

2nd Step

The following compound was obtained as described in the 1st step in Reference Example 2.

3-Iodo-1-methyl-5-nitro-1H-indazole

MS (ESI m/z): 304 (M+H)

RT (min): 1.57

3rd Step

Pyrrolidine (90 mg), cesium carbonate (500 mg), Pd₂(dba)₃ (46 mg), and Xantphos (58 mg) were added to a dioxane solution (4 ml) containing 3-iodo-1-methyl-5-nitro-1H-indazole (303 mg) obtained in the 1st step, followed by microwave irradiation (Initiator™, 160° C., 15 minutes, 2.45 GHz, 0-240 W). Then, ethyl acetate was added to the obtained residue, insoluble matter was removed by filtration, and the solvent was distilled away under reduced pressure. 1-Methyl-5-nitro-3-(pyrrolidine-1-yl)-1H-indazole (50 mg) was thus obtained.

MS (ESI m/z): 247 (M+H)

RT (min): 1.37

4th Step

The following compound was obtained as described in the 3rd step in Reference Example 1.

1-Methyl-3-(pyrrolidine-1-yl)-1H-indazol-5-amine

Reference Example 37

The following compound was obtained as described in the 3rd and 4th steps in Reference Example 36.

[Formula 56]

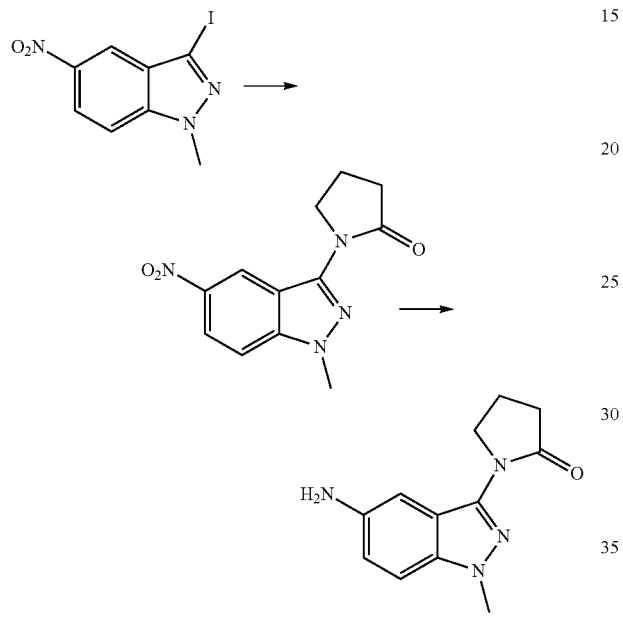

1st Step 1-(1-Methyl-5-nitro-1H-indazol-3-yl)pyrrolidin-2-one

MS (ESI m/z): 261 (M+H)
RT (min): 1.13

2nd Step 1-(5-Amino-1-methyl-1H-indazol-3-yl)pyrrolidin-2-one

MS (ESI m/z): 231 (M+H)
RT (min): 0.52

Reference Example 38

[Formula 57]

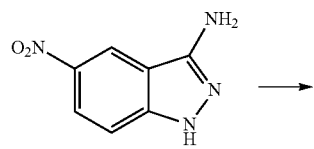

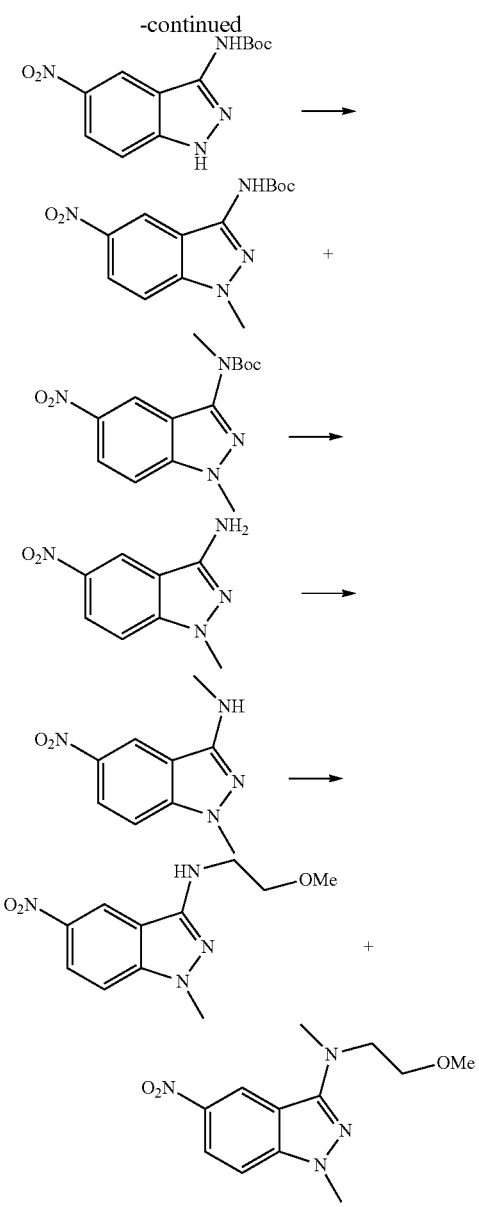

1st Step

Di-tert-butyl carbonate (1.76 g), triethylamine (1.13 ml), and DMAP (10 mg) were added to a THF (8.2 ml) solution containing 5-nitro-1H-indazol-3-amine (1.45 g) under ice cooling, followed by stirring for 20 minutes. A saturated ammonium chloride aqueous solution was added to the reaction solution, followed by extraction with ethyl acetate. The organic layers were extracted with water and saturated saline and dried over sodium sulfate and the solvent was distilled away under reduced pressure. The obtained residue was purified by silica gel chromatography (hexane:ethyl acetate=1:0 to 3:2) and a yellow solid of tert-butyl (5-nitro-1H-indazol-3-yl)carbamate (1.8 g) was thus obtained.

2nd Step

Sodium hydride (60% in oil) (250 mg) and iodomethane (458 ml) were added to a DMF (5 ml) solution containing tert-butyl (5-nitro-1H-indazol-3-yl)carbamate (680 mg) obtained in the 1st step under ice cooling, followed by stirring for 5 hours. Water was added to the reaction solution, followed by extraction with ethyl acetate and washing with water and saturated saline. The organic layers were dried over anhydrous sodium sulfate. Then, the solvent was distilled away under reduced pressure and the obtained residue was purified by silica gel chromatography (n-hexane:ethyl acetate=1:0 to 5:1) and directly used in the subsequent reaction.

3rd Step

The following compound was obtained as described in the 2nd step in Reference Example 27.

1-Methyl-5-nitro-1H-indazol-3-amine

N,1-dimethyl-5-nitro-1H-indazol-3-amine

4th Step

The following compound was obtained as described in the 1st step in Reference Example 3.

N-(2-methoxyethyl)-1-methyl-5-nitro-1H-indazol-3-amine

MS (ESI m/z): 251 (M+H)
RT (min): 1.11

N-(2-methoxyethyl)-N,1-dimethyl-5-nitro-1H-indazol-3-amine

MS (ESI m/z): 265 (M+H)
RT (min): 1.29

Reference Example 39

The following compound was obtained as described in the 3rd step in Reference Example 1.

[Formula 58]

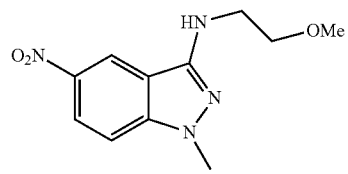
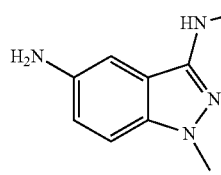

$N^3$-(2-methoxyethyl)-1-methyl-1H-indazol-3,5-diamine

[Formula 59]

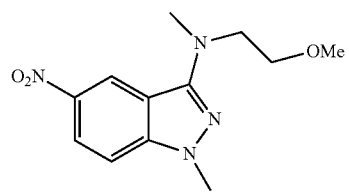

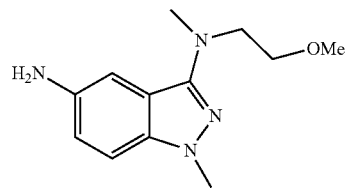

$N^3$-(2-methoxyethyl)-N,1-dimethyl-1H-indazol-3,5-diamine

Reference Example 40

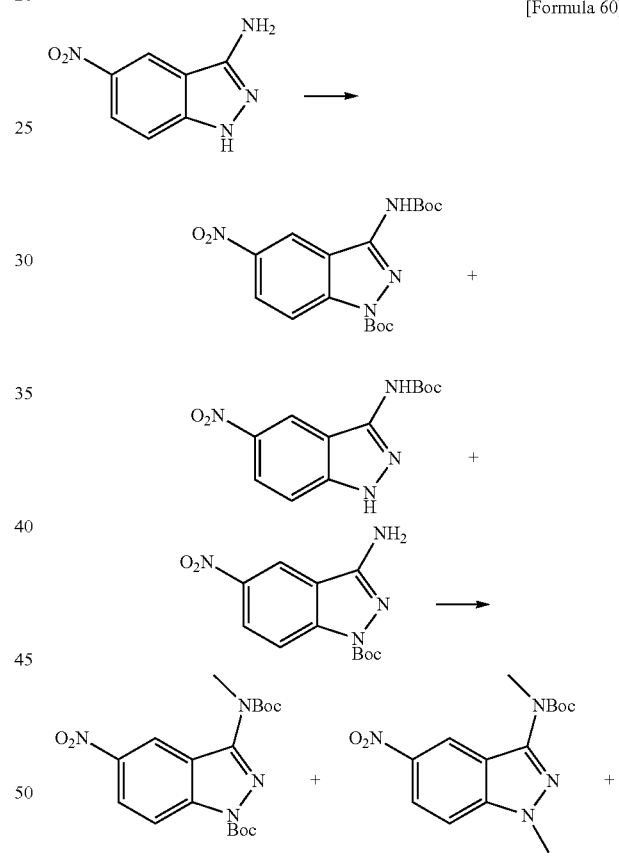
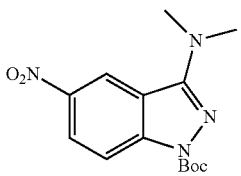
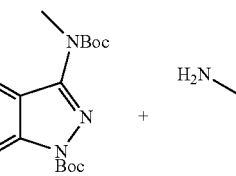

[Formula 60]

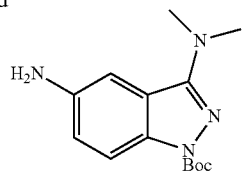

1st Step di-tert-Butyl carbonate (1.76 g), triethylamine (1.13 ml), and DMAP (10 mg) were added to a THF (8.2 ml) solution containing 5-nitro-1H-indazol-3-amine (1.45 g), followed by stirring for 20 minutes under ice cooling. A saturated ammonium chloride aqueous solution was added to the reaction solution, followed by extraction with ethyl acetate and washing with water and saturated saline. The obtained solution was dried over sodium sulfate and the solvent was distilled away under reduced pressure. The obtained residue was purified by silica gel chromatography (hexane:ethyl acetate=1:0 to 3:2) and a yellow solid mixture (1.8 g) of tert-butyl 3-((tert-butoxycarbonyl)amino)-5-nitro-1H-indazol-1-carboxylate, tert-butyl (5-nitro-1H-indazol-3-yl)carbamate, and tert-butyl 3-amino-5-nitro-1H-indazol-1-carboxylate was thus obtained.

2nd Step

The following compound was obtained as described in the 2nd step in Reference Example 1.

tert-Butyl 3-((tert-butoxycarbonyl)(methyl)amino)-5-nitro-1H-indazol-1-carboxylate MS (ESI m/z): 393 (M+H)
RT (min): 1.96 tert-Butyl methyl (1-methyl-5-nitro-1H-indazol-3-yl)carbamate

MS (ESI m/z): 307 (M+H)
RT (min): 1.59 tert-Butyl 3-(dimethylamino)-5-nitro-1H-indazol-1-carboxylate

MS (ESI m/z): 307 (M+H)
RT (min): 1.68

3rd Step

The following compound was obtained as described in the 3rd step in Reference Example 1.

tert-Butyl 5-amino-3-((tert-butoxycarbonyl)(methyl)amino)-1H-indazol-1-carboxylate MS (ESI m/z): 363 (M+H)
RT (min): 1.40 tert-Butyl (5-amino-1-methyl-1H-indazol-3-yl)(methyl)carbamate

MS (ESI m/z): 278 (M+H)
RT (min): 0.81 tert-Butyl 5-amino-3-(dimethylamino)-1H-indazol-1-carboxylate

MS (ESI m/z): 278 (M+H)
RT (min): 0.94

Reference Example 41

The following compound was obtained as described in the 3rd step in Reference Example 1.

[Formula 61]

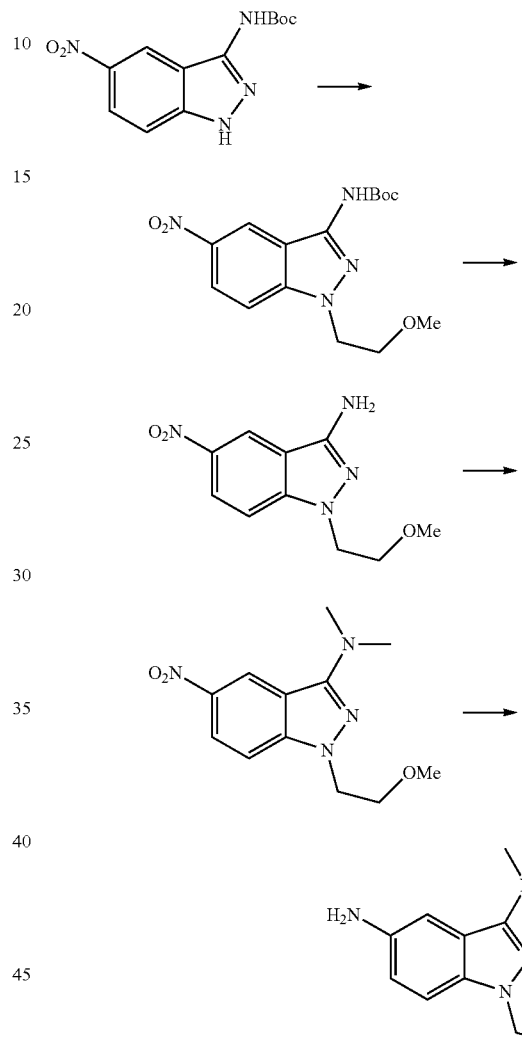

1st Step

The following compound was obtained as described in the 1st step in Reference Example 3.

tert-Butyl (1-(2-methoxyethyl)-5-nitro-1H-indazol-3-yl)carbamate

2nd Step

The following compound was obtained as described in the 2nd step in Reference Example 27.

1-(2-Methoxyethyl)-5-nitro-1H-indazol-3-amine

The following compound was obtained as described in the 2nd and 3rd steps in Reference Example 1.

3rd Step 1-(2-Methoxyethyl)-N,N-dimethyl-5-nitro-1H-indazol-3-amine

4th Step 1-(2-Methoxyethyl)-$N^3$,$N^3$-dimethyl-1H-indazol-3,5-diamine

MS (ESI m/z): 235 (M+H)
RT (min): 0.55

Reference Example 42

[Formula 62]

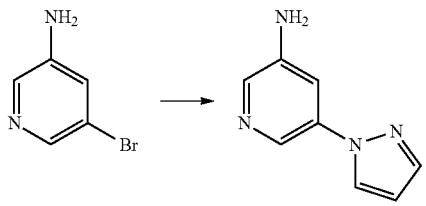

Pyrazole (42 mg), cesium carbonate (340 mg), trans-N,N'-dimethylcyclohexan-1,2-diamine (74 mg), and copper iodide (50 mg) were added to a DMAc (2 ml) solution containing 5-bromopyridin-3-amine (90 mg) in a nitrogen atmosphere, followed by stirring in a sealed tube at 150° C. for 15 hours. The reaction solution was adjusted to room temperature and water was added, followed by extraction with ethyl acetate. The organic layers were washed with saturated saline and dried over anhydrous sodium sulfate. The solvent was distilled away under reduced pressure. The obtained residue was purified by silica gel chromatography (chloroform:MeOH=1:0 to 10:1). A brown solid of 5-(pyrazol-1-yl)pyridin-3-amine (56.7 mg) was thus obtained.

MS (ESI m/z): 161 (M+H)
RT (min): 0.38

Reference Example 43

The following compound was obtained with reference to U.S. Pat. No. 6,133,253 A1.

[Formula 63]

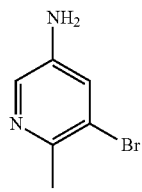

5-Bromo-6-methylpyridin-3-amine

Reference Example 44

[Formula 64]

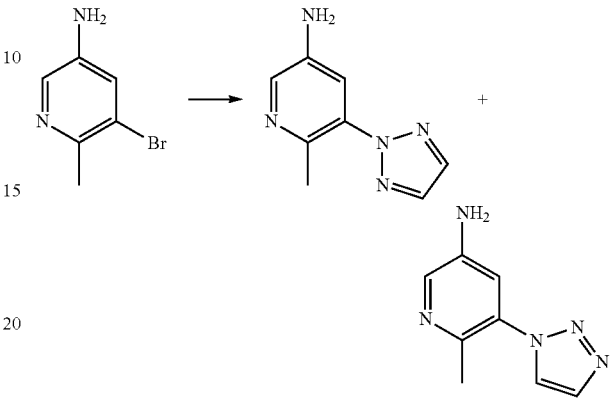

1,2,3-Triazole (45 mg), cesium carbonate (260 mg), trans-N,N'-dimethylcyclohexan-1,2-diamine (76 mg), and copper iodide (50 mg) were added to a DMAc (2 ml) solution containing 5-bromo-6-methylpyridin-3-amine (100 mg) in a nitrogen atmosphere, followed by stirring in a sealed tube at 110° C. for 8 hours. The reaction solution was adjusted to room temperature and water was added to the reaction solution, followed by extraction with ethyl acetate and washing with saturated saline. The organic layers were dried over anhydrous sodium sulfate. Next, the solvent was distilled away under reduced pressure and the obtained residue was purified by silica gel chromatography (chloroform:MeOH=1:0 to 20:1). A white solid of 6-methyl-5-(2H-1,2,3-triazol-2-yl)pyridin-3-amine (12.8 mg) and brown oily matter of 6-methyl-5-(1H-1,2,3-triazol-1-yl)pyridin-3-amine (6.7 mg) were thus obtained.

6-Methyl-5-(2H-1,2,3-triazol-2-yl)pyridin-3-amine

MS (ESI m/z): 176 (M+H)
RT (min): 0.44
$^1$H-NMR (DMSO-$d_6$, 300 MHz) δ: 8.11 (s, 2H), 7.96 (d, 1H, J=2.7 Hz), 7.25 (d, 1H, J=2.7 Hz), 5.52 (br, 2H), 2.32 (s, 3H)

6-Methyl-5-(1H-1,2,3-triazol-1-yl)pyridin-3-amine

MS (ESI m/z): 176 (M+H)
RT (min): 0.20, 0.27

Reference Example 45

[Formula 65]

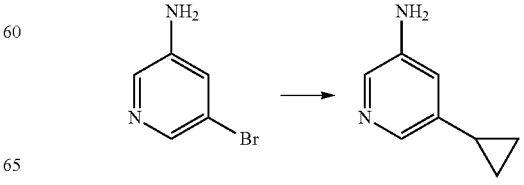

Cyclopropylboronic acid (360 mg), cesium carbonate (1.4 g), and Pd(PPh$_3$)$_4$ (166 mg) were added to a 1,4-dioxane/water (4.5 ml/0.5 ml) solution containing 5-bromopyridin-3-amine (500 mg) in a nitrogen atmosphere, followed by stirring in a sealed tube at 100° C. for 5 hours. The reaction solution was adjusted to room temperature and water was added to the reaction solution, followed by extraction with ethyl acetate. The organic layers were washed with saturated saline and dried over anhydrous sodium sulfate, the solvent was distilled away under reduced pressure, and the obtained residue was purified by silica gel chromatography (chloroform:MeOH=1:0 to 30:1). A brown solid of 5-cyclopropyl pyridin-3-amine (314 mg) was thus obtained.

MS (ESI m/z): 135 (M+H)
RT (min): 0.39

Reference Example 46

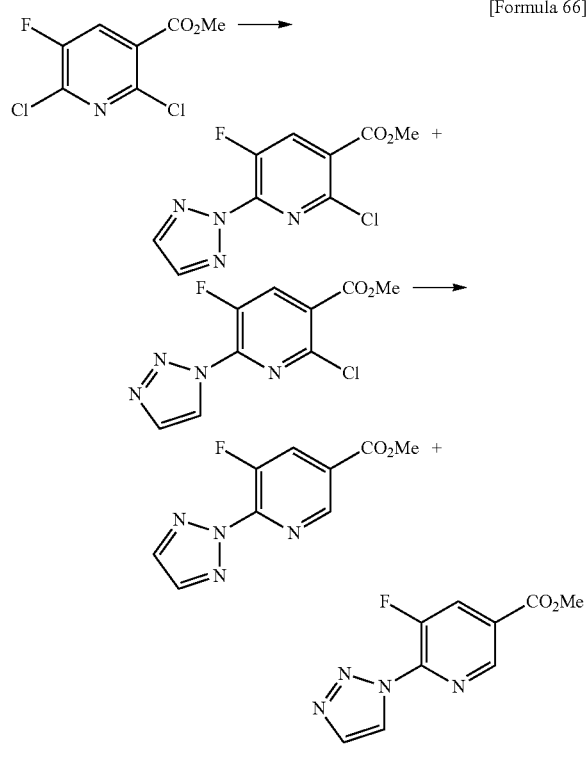

[Formula 66]

1st Step 1,2,3-triazole (340 mg) and cesium carbonate (1.74 g) were added to a DMAc (10 ml) solution containing methyl 2,6-dichloro-5-fluoronicotinate (1 g), followed by stirring at 70° C. to 80° C. for 1.5 hours. The reaction solution was adjusted to room temperature and water was added to the reaction solution, followed by extraction with ethyl acetate. The organic layers were washed with saturated saline and dried over anhydrous sodium sulfate. Next, the solvent was distilled away under reduced pressure. A mixture of methyl 2-chloro-5-fluoro-6-(2H-1,2,3-triazol-2-yl)nicotinate and methyl 2-chloro-5-fluoro-6-(1H-1,2,3-triazol-1-yl)nicotinate was thus obtained.

MS (ESI m/z): 257, 259 (M+H)
RT (min): 1.07, 1.13

2nd Step

The mixture of methyl 2-chloro-5-fluoro-6-(2H-1,2,3-triazol-2-yl)nicotinate and methyl 2-chloro-5-fluoro-6-(1H-1,2,3-triazol-1-yl)nicotinate obtained in the 1st step was dissolved in MeOH (5 ml) and ammonium formate (300 mg) and 10% Pd/C (200 mg) were added thereto, followed by reflux for 4.5 hours. The reaction solution was adjusted to room temperature and filtered through Celite, the filtrate was collected, and the solvent was distilled away under reduced pressure. The obtained residue was purified by silica gel chromatography (n-hexane:ethyl acetate=1:0 to 4:1). A white solid of methyl 5-fluoro-6-(2H-1,2,3-triazol-2-yl)nicotinate (250 mg) and a white solid of methyl 5-fluoro-6-(1H-1,2,3-triazol-1-yl)nicotinate (160 mg) were thus obtained.

Methyl 5-fluoro-6-(2H-1,2,3-triazol-2-yl)nicotinate

MS (ESI m/z): 223 (M+H)
RT (min): 0.90

Methyl 5-fluoro-6-(1H-1,2,3-triazol-1-yl)nicotinate

MS (ESI m/z): 223 (M+H)
RT (min): 0.95

Reference Example 47

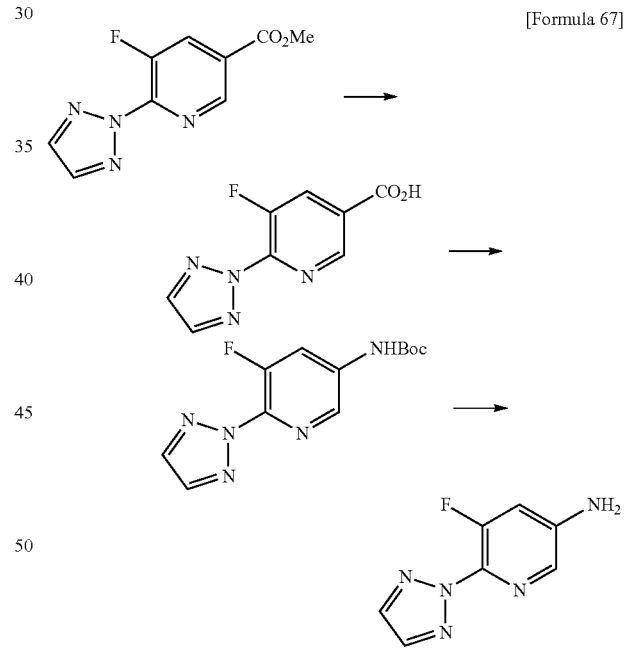

[Formula 67]

1st Step

A 5M potassium hydroxide aqueous solution (2 ml) was added to a THF/MeOH (2 ml/2 ml) solution containing methyl 5-fluoro-6-(2H-1,2,3-triazol-2-yl)nicotinate (250 mg), followed by stirring at room temperature for 1 hour. 6M hydrochloric acid was added to the reaction solution so as to acidify the reaction solution, followed by extraction with ethyl acetate. The organic layers were washed with saturated saline and dried over anhydrous sodium sulfate. The solvent was distilled away under reduced pressure and a white solid of 5-fluoro-6-(2H-1,2,3-triazol-2-yl)nicotinic acid (198 mg) was thus obtained.

MS (ESI m/z): 209 (M+H)
RT (min): 0.70
2nd Step

Triethylamine (158 µl), tert-butanol, and DPPA (246 µl) were added to a toluene (5 ml) solution containing 5-fluoro-6-(2H-1,2,3-triazol-2-yl)nicotinic acid (198 mg) obtained in the 1st step, followed by stirring at 100° C. for 1 hour. The reaction solution was adjusted to room temperature and the solvent was distilled away under reduced pressure. The obtained residue was purified by silica gel chromatography (n-hexane:ethyl acetate=4:1 to 1:1) and a white solid of tert-butyl (5-fluoro-6-(2H-1,2,3-triazol-2-yl)pyridin-3-yl)carbamate (94 mg) was thus obtained.

MS (ESI m/z): 180 (M+H)
RT (min): 0.64
3rd Step

TFA (1 ml) was added to tert-butyl (5-fluoro-6-(2H-1,2,3-triazol-2-yl)pyridin-3-yl)carbamate (30 mg) obtained in the 2nd step, followed by stirring at room temperature for 1 hour. The solvent was distilled away under reduced pressure, a 5M sodium hydroxide aqueous solution was added to the obtained residue at 0° C. so as to alkalify the mixture, followed by extraction with ethyl acetate. The organic layers were washed with saturated saline and dried over anhydrous sodium sulfate. The solvent was distilled away under reduced pressure and a light brown solid of 5-fluoro-6-(2H-1,2,3-triazol-2-yl)pyridin-3-amine (19 mg) was thus obtained.

MS (ESI m/z): 180 (M+H)
RT (min): 0.64

Reference Example 48

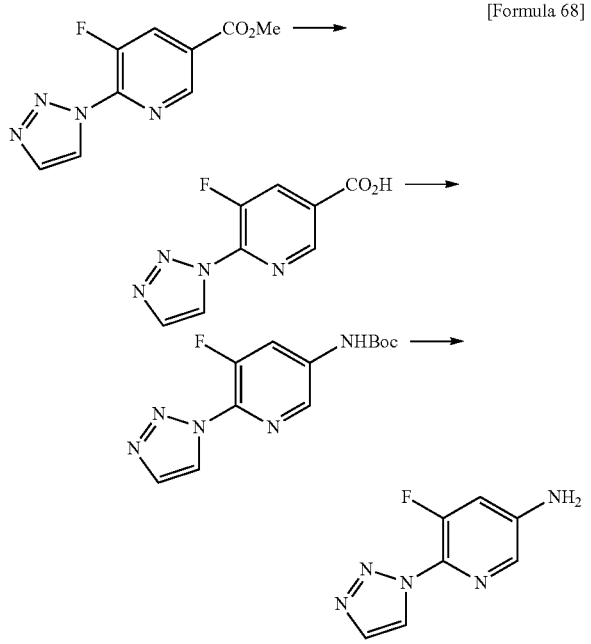

[Formula 68]

The following compound was obtained as described in Reference Example 47.
1st Step 5-Fluoro-6-(1H-1,2,3-triazol-1-yl)nicotinic acid MS (ESI m/z): 209 (M+H)
RT (min): 0.64

2nd Step tert-Butyl (5-fluoro-6-(1H-1,2,3-triazol-1-yl)pyridin-3-yl)carbamate

MS (ESI m/z): 280 (M+H)
RT (min): 1.20
3rd Step

5-Fluoro-6-(1H-1,2,3-triazol-1-yl)pyridin-3-amine

MS (ESI m/z): 180 (M+H)
RT (min): 0.59

Reference Example 49

The following compound was obtained with reference to Helvetica Chimica Acta, 1964, vol. 47, pp. 363, 376.

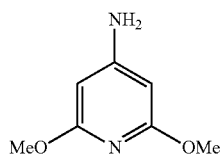

[Formula 69]

2,6-Dimethoxypyridin-4-amine

Reference Example 50

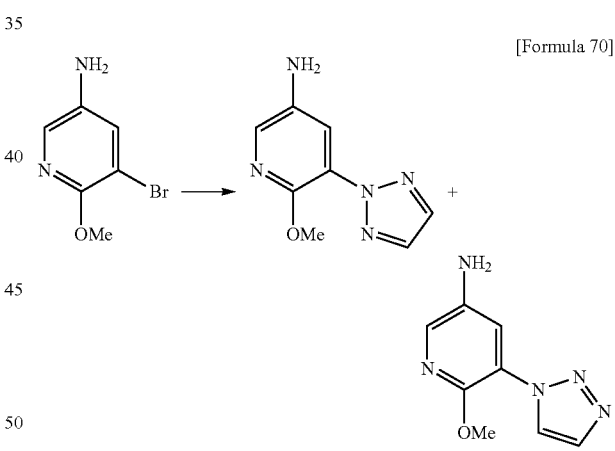

[Formula 70]

N,N-dimethylglycine (1.27 g), copper iodide (1.88 g), potassium tert-butoxide (4.1 g), and 1H-1,2,3,-triazole (1.7 g) were added to a DMSO (25 ml) solution containing 5-bromo-6-methoxypyridin-3-amine (25 g), followed by stirring at 130° C. for 2 hours. The reaction solution was adjusted to room temperature and water was added to the reaction solution. Then, 4M hydrochloric acid was added to adjust the pH to pH=4, followed by extraction with ethyl acetate. Next, the obtained organic layers were dried over anhydrous sodium sulfate. The solvent was distilled away under reduced pressure. The obtained residue was purified by silica gel chromatography (n-hexane:ethyl acetate=1:1). Yellow oily matter of 6-methoxy-5-(2H-1,2,3-triazol-2-yl)pyridin-3-amine (1 g) and a light yellow solid of 6-methoxy-5-(1H-1,2,3-triazol-1-yl)pyridin-3-amine (525 mg) was thus obtained.

6-Methoxy-5-(2H-1,2,3-triazol-2-yl)pyridin-3-amine

MS (ESI m/z): 192 (M+H)
RT (min): 0.58
$^1$H-NMR (CDCl$_3$, 300 MHz) δ: 7.87 (s, 2H), 7.77 (d, 1H, J=2.4Hz), 7.39 (d, 1H, J=2.4Hz), 3.98 (s, 3H), 3.53 (br, 2H)

6-Methoxy-5-(1H-1,2,3-triazol-2-yl)pyridin-3-amine

MS (ESI m/z): 192 (M+H)
RT (min): 0.56
$^1$H-NMR (CDCl$_3$, 300MHz) δ: 8.36-8.33 (m, 1H), 7.82 (s, 1H), 7.77-7.72 (m, 2H), 3.98 (s, 3H), 3.60 (br, 2H)

Reference Example 51

[Formula 71]

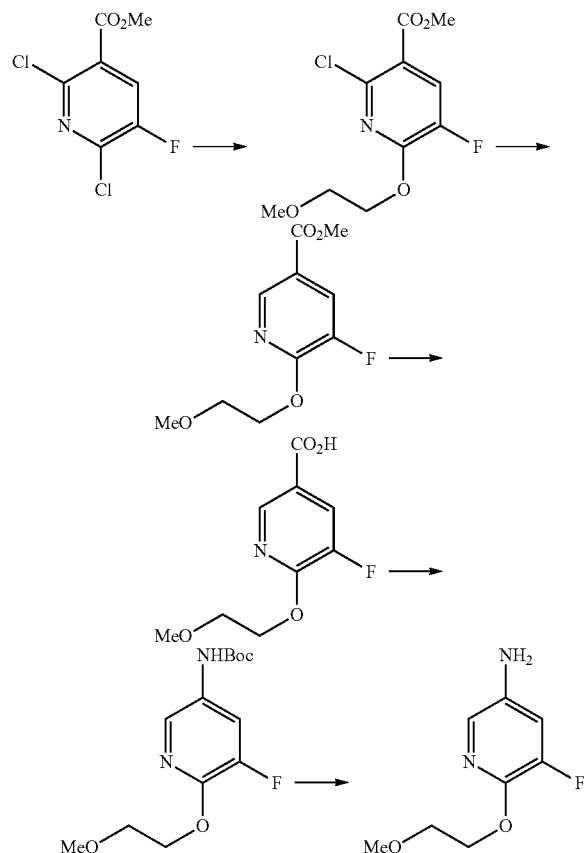

1st Step 2-methoxy ethanol (423 μl) and sodium hydride (60% in oil) (196 mg) were added to a THF (10 ml) solution containing methyl 2,6-dichloro-5-fluoronicotinate (1 g) under ice cooling in a nitrogen atmosphere, followed by stirring for 1.5 hours. Water was added to the reaction solution, followed by extraction with ethyl acetate. The organic layers were washed with saturated saline and dried over anhydrous sodium sulfate. The solvent was distilled away under reduced pressure and yellow oily matter of methyl 2-chloro-5-fluoro-6-(2-methoxyethoxy)nicotinate (1.07 g) was thus obtained.

MS (ESI m/z): 264 (M+H)
RT (min): 1.41

2nd Step

10% Pd/C (200 mg) and ammonium formate (200 mg) were added to an MeOH (10 ml) solution containing methyl 2-chloro-5-fluoro-6-(2-methoxyethoxy)nicotinate (1.07 g) obtained in the 1st step, followed by reflux for 1 hour. Next, insoluble matter was removed using Celite. The solvent was distilled away under reduced pressure. Then, the obtained residue was purified by silica gel chromatography (n-hexane: ethyl acetate=1:0 to 1:5). A white solid of methyl 5-fluoro-6-(2-methoxyethoxy)nicotinate (264 mg) was thus obtained.

MS (ESI m/z): 230 (M+H)
RT (min): 1.25

3rd Step

A 5M sodium hydroxide aqueous solution (2 ml) was added to a THF/MeOH (2 ml/2 ml) solution containing methyl 5-fluoro-6-(2-methoxyethoxy)nicotinate (264 mg) obtained in the 2nd step, followed by stirring at room temperature for 1 hour. Next, 6M hydrochloric acid (2 ml) was added to the reaction solution at 5° C. or less so as to acidify the reaction solution, followed by extraction with ethyl acetate. The organic layers were washed with saturated saline and dried over anhydrous sodium sulfate. The solvent was distilled away under reduced pressure and a white solid of 5-fluoro-6-(2-methoxyethoxy)nicotinic acid (197 mg) was thus obtained.

MS (ESI m/z): 216 (M+H)
RT (min): 0.95

4th Step

The following compound was obtained as described in the 2nd step in Reference Example 47.

tert-Butyl (5-fluoro-6-(2-methoxyethoxy)pyridin-3-yl)carbamate

MS (ESI m/z): 287 (M+H)
RT (min): 1.47

5th Step

The following compound was obtained as described in the 3rd step in Reference Example 47.

5-Fluoro-6-(2-methoxyethoxy)pyridin-3-amine

MS (ESI m/z): 187 (M+H)
RT (min): 0.67

Reference Example 52

[Formula 72]

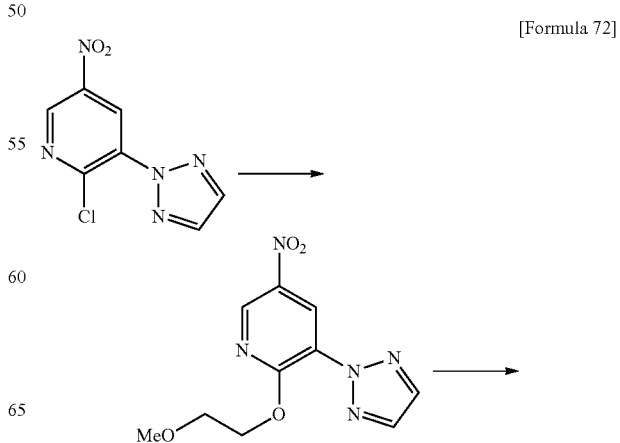

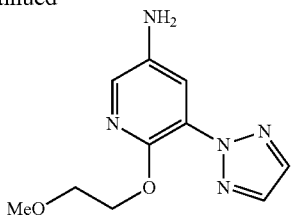

1st Step

The following compound was obtained as described in the 1st step in Reference Example 51.

2-(2-Methoxyethoxy)-5-nitro-3-(2H-1,2,3-triazol-2-yl)pyridine

MS (ESI m/z): 266 (M+H)
RT (min): 1.18

2nd Step

10% Pd/C (200 mg) and ammonium formate (200 mg) were added to an MeOH/ethyl acetate (5 ml/5 ml) solution containing 2-(2-methoxyethoxy)-5-nitro-3-(2H-1,2,3-triazol-2-yl)pyridine (286 mg) obtained in the 1st step, followed by reflux for 1 hour. Insoluble matter was removed using Celite and the solvent was distilled away under reduced pressure. The obtained residue was purified by silica gel chromatography (n-hexane:ethyl acetate=1:0 to 1:5) and a white solid of 6-(2-methoxyethoxy)-5-(2H-1,2,3-triazol-2-yl)pyridin-3-amine (240 mg) was thus obtained.

MS (ESI m/z): 236 (M+H)
RT (min): 0.69

Reference Example 53

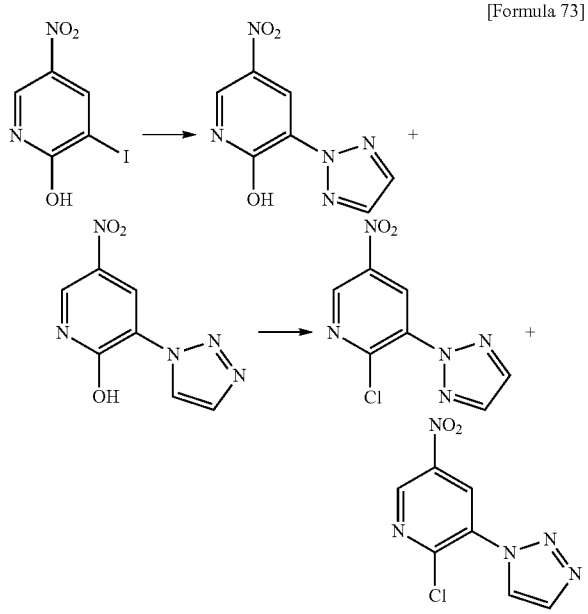

[Formula 73]

1st Step

Cesium carbonate (24.4 g), 1,2,3-triazole (4.35 ml), 2,2,6,6-tetramethyl-3,5-heptanedione (3.89 ml), and copper iodide (7.1 g) were added to a DMSO (100 ml) solution containing 3-iodo-5-nitropyridin-2-ol (10 g) in a nitrogen atmosphere, followed by stirring at 155° C. for 1 hour. The reaction solution was adjusted to room temperature and water was added to the reaction solution. An insoluble precipitate was removed by filtration. 1M hydrochloric acid (110 ml) was added to the resulting filtrate so as to acidify the reaction solution, followed by extraction with ethyl acetate. The organic layers were washed with saturated saline and dried over anhydrous sodium sulfate and the solvent was distilled away under reduced pressure. Ethyl acetate was added to the obtained residue and insoluble matter was collected by filtration. A yellow solid mixture (4.86 g) of 5-nitro-3-(2H-1,2,3-triazol-2-yl)pyridin-2-ol and 5-nitro-3-(1H-1,2,3-triazol-1-yl)pyridin-2-ol was thus obtained.

5-Nitro-3-(2H-1,2,3-triazol-2-yl)pyridin-2-ol

MS (ESI m/z): 208 (M+H)
RT (min): 0.69

5-Nitro-3-(1H-1,2,3-triazol-1-yl)pyridin-2-ol

MS (ESI m/z): 208 (M+H)
RT (min): 0.63

2nd Step

Thionyl chloride (19 ml) and DMF (4 ml) were added to a mixture (5.32 g) of 5-nitro-3-(2H-1,2,3-triazol-2-yl)pyridin-2-ol and 5-nitro-3-(1H-1,2,3-triazol-1-yl)pyridin-2-ol, followed by reflux for 1 hour. The reaction solution was poured into ice water, followed by extraction with ethyl acetate. The organic layers were washed with saturated saline and dried over anhydrous sodium sulfate. The solvent was distilled away under reduced pressure and the obtained residue was purified by silica gel chromatography (n-hexane:ethyl acetate=1:0 to 10:1). A light yellow solid of 2-chloro-5-nitro-3-(2H-1,2,3-triazol-2-yl)pyridine (0.72 g) and a yellow solid of 2-chloro-5-nitro-3-(1H-1,2,3-triazol-1-yl)pyridine (0.63 g) were thus obtained.

2-Chloro-5-nitro-3-(2H-1,2,3-triazol-2-yl)pyridine

MS (ESI m/z): 226 (M+H)
RT (min): 1.18

2-Chloro-5-nitro-3-(1H-1,2,3-triazol-1-yl)pyridine

MS (ESI m/z): 226 (M+H)
RT (min): 0.92

Reference Example 54

The following compound was obtained as described in Reference Example 52.

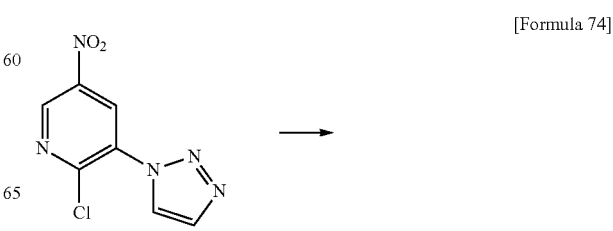

[Formula 74]

-continued

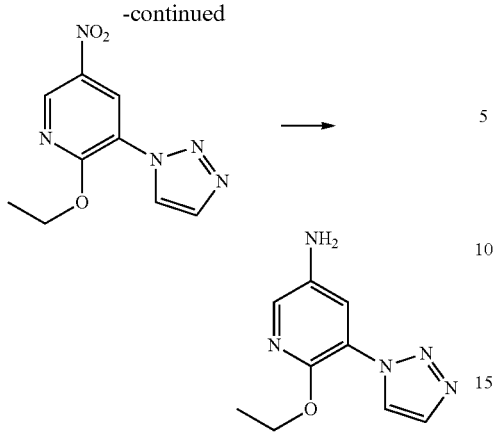

1st Step

2-Ethoxy-5-nitro-3-(1H-1,2,3-triazol-1-yl)pyridine

MS (ESI m/z): 236 (M+H)
RT (min): 1.21
2nd Step

6-Ethoxy-5-(1H-1,2,3-triazol-1-yl)pyridin-3-amine

MS (ESI m/z): 206 (M+H)
RT (min): 0.78
$^1$H-NMR (CDCl$_3$, 300 MHz) δ: 8.39 (s, 1H), 7.83-7.80 (m, 1H), 7.77 (d, 1H, J=2.7 Hz), 7.72 (d, 1H, J=2.7Hz), 4.43 (q, 2H, J=7.2Hz), 3.60 (br, 2H), 1.40 (t, 3H, J=7.2Hz)

Reference Example 55

[Formula 75]

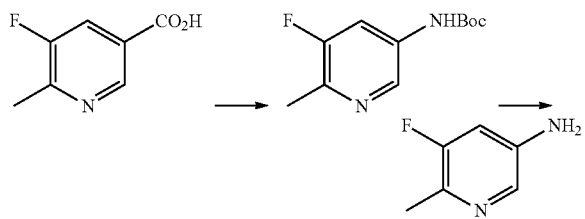

The following compound was obtained as described in the 2nd and 3rd steps in Reference Example 47.
1st Step tert-Butyl (5-fluoro-6-methylpyridin-3-yl)carbamate MS (ESI m/z): 227 (M+H)
RT (min): 1.32
2nd Step 5-Fluoro-6-methylpyridin-3-amine MS (ESI m/z): 127 (M+H)
RT (min): 0.23, 0.29

Reference Example 56

[Formula 76]

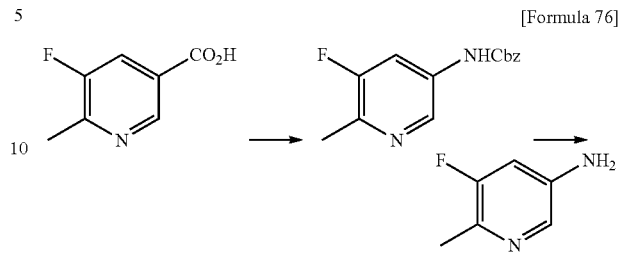

Triethylamine (0.99 ml), benzyl alcohol, and DPPA (1.53 ml) were added to a toluene (10 ml) solution containing 5-fluoro-6-(2H-1,2,3-triazol-2-yl)nicotinic acid (920 mg), followed by stirring at 100° C. for 1 hour. The reaction solution was adjusted to room temperature and the solvent was distilled away under reduced pressure. The obtained residue was purified by silica gel chromatography (n-hexane:ethyl acetate=4:1 to 1:1). A white solid of benzyl (5-fluoro-6-methylpyridin-3-yl)carbamate (94 mg) was thus obtained.
MS (ESI m/z): 261 (M+H)
RT (min): 1.35
The following compound was obtained as described in the 2nd step in Reference Example 46.

5-Fluoro-6-methylpyridin-3-amine

MS (ESI m/z): 127 (M+H)
RT (min): 0.23, 0.29

Reference Example 57

[Formula 77]

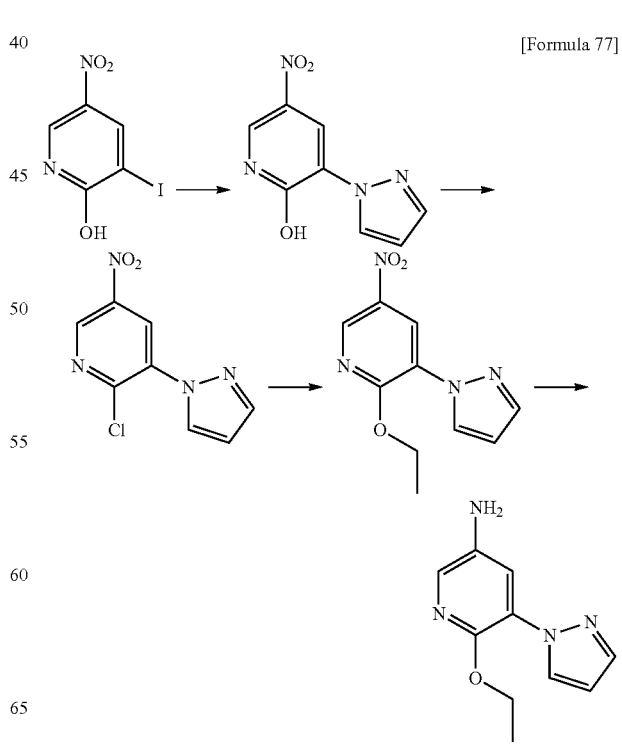

81

The following compound was obtained as described in Reference Example 53.

1st Step

5-Nitro-3-(pyrazol-1-yl)pyridin-2-ol

MS (ESI m/z): 207 (M+H)
RT (min): 0.88

2nd Step

2-Chloro-5-nitro-3-(pyrazol-1-yl)pyridine

MS (ESI m/z): 225, 227 (M+H)
RT (min): 1.17

The following compound was obtained as described in Reference Example 52.

3rd Step

2-Ethoxy-5-nitro-3-(pyrazol-1-yl)pyridine

MS (ESI m/z): 235 (M+H)
RT (min): 1.52

4th Step

6-Ethoxy-5-(pyrazol-1-yl)pyridin-3-amine

MS (ESI m/z): 205 (M+H)
RT (min): 0.93

Reference Example 58

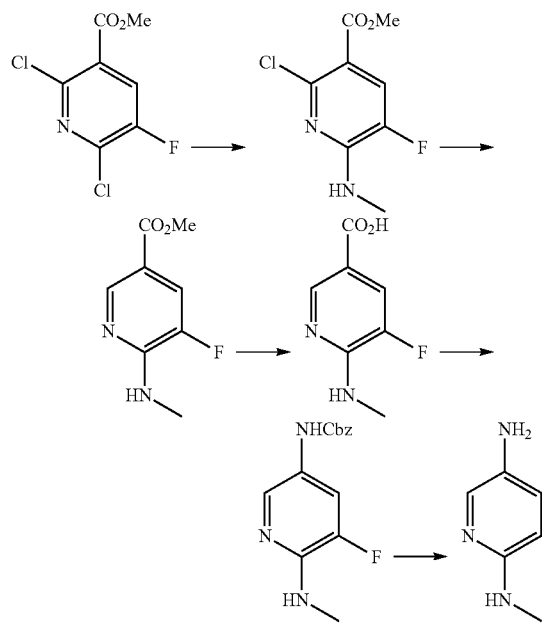

[Formula 78]

1st Step

Methylamine (9.8M in MeOH, 450 µl) was added to an MeOH (5 ml) solution containing methyl 2,6-dichloro-5-fluoronicotinate (0.5 g) under ice cooling, followed by stirring at 70° C. for 3.5 hours. The solvent and methylamine were distilled away under reduced pressure and methyl 2-chloro-5-fluoro-6-(methylamino)nicotinate was thus obtained.

82

MS (ESI m/z): 219, 221 (M+H)
RT (min): 1.20

2nd Step

The following compound was obtained as described in the 2nd step in Reference Example 46.

Methyl 5-fluoro-6-(methylamino)nicotinate

MS (ESI m/z): 185 (M+H)
RT (min): 0.88

The following compound was obtained as described in the 1st step in Reference Example 47.

3rd Step 5-fluoro-6-(methylamino)nicotinic acid

MS (ESI m/z): 171 (M+H)
RT (min): 0.50

The following compound was obtained as described in Reference Example 56.

4th Step

Benzozyl(5-fluoro-6-(methylamino)pyridin-3-yl) carbamate

MS (ESI m/z): 276 (M+H)
RT (min): 1.04

5th Step

3-Fluoro-$N^2$-methylpyridin-2,5-diamine

MS (ESI m/z): 142 (M+H)
RT (min): 0.22

Reference Example 59

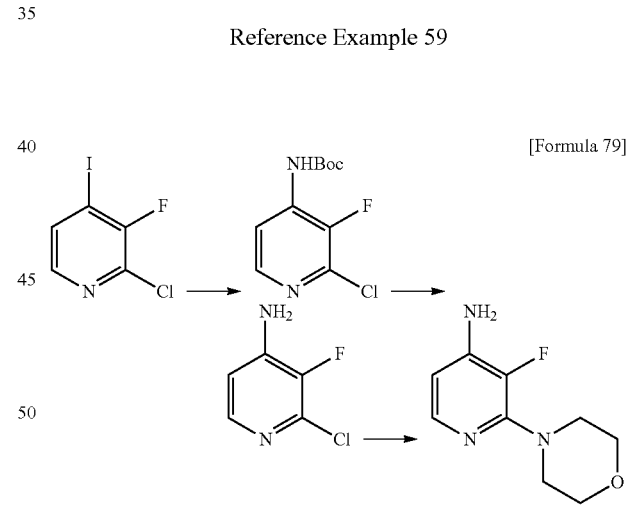

[Formula 79]

1st Step tert-Butyl carbamate (215 mg), cesium carbonate (1.14 g), $Pd_2(dba)_3$ (240 mg), and Xantphos (303 mg) were added to a toluene solution (9 ml) containing 2-chloro-3-fluoro-4-iodopyridine (450 mg), followed by stirring at 100° C. for 3 hours. The reaction solution was adjusted to room temperature and water was added to the reaction solution, followed by extraction with ethyl acetate. The organic layers were washed with saturated saline, dried over anhydrous sodium sulfate. Next, the solvent was distilled away under reduced pressure and the obtained residue was purified by silica gel chromatography (n-hexane:ethyl acetate=9:1 to 3:1). A yellow oily matter of tert-butyl (2-chloro-3-fluoropyridin-4-yl)carbamate (533 mg) was thus obtained.

MS (ESI m/z): 247, 249 (M+H)
RT (min): 1.46

2nd Step

The following compound was obtained as described in the 2nd step in Reference Example 27.

2-Chloro-3-fluoropyridin-4-amine

MS (ESI m/z): 147, 149 (M+H)
RT (min): 0.72

3rd Step

Morpholine (3 ml) was added to 2-chloro-3-fluoropyridin-4-amine (133 mg) obtained in the 2nd step, followed by microwave irradiation (Initiator™, 180° C., 20 minutes, 2.45 GHz, 0-240 W). A saturated ammonium chloride aqueous solution was added to the reaction solution, followed by extraction with ethyl acetate. The organic layers were washed with a saturated ammonium chloride aqueous solution and saturated saline and dried over anhydrous sodium sulfate. The solvent was distilled away under reduced pressure. A light brown solid of 3-fluoro-2-morpholinopyridin-4-amine (153 mg) was thus obtained.

3-Fluoro-2-morpholinopyridin-4-amine

MS (ESI m/z): 198 (M+H)
RT (min): 0.43

Reference Example 60

[Formula 80]

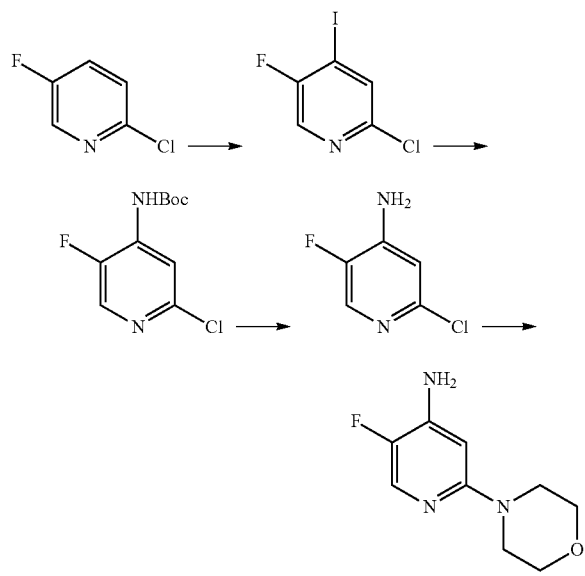

1st Step

Lithium N,N-diisopropyl amide (2M THF/ethylbenzene/heptane solution) (2.9 ml) was mixed with THF (20 ml), and a THF (5 ml) solution containing 2-chloro-5-fluoropyridine (500 mg) was added to the mixture in a nitrogen atmosphere at −75° C., followed by stirring for 3 hours. Subsequently, a THF (5 ml) solution containing iodine (1.16 g) was added to the mixture, followed by stirring at −75° C. for 1 hour. Next, water/THF (2 ml/8 ml), water (10 ml), and a 3M sodium thiosulfate aqueous solution were added to the reaction solution at −75° C., −50° C., and −35° C., respectively. The reaction solution was adjusted to room temperature, followed by extraction with ethyl acetate. The organic layers were washed with saturated saline and dried over anhydrous sodium sulfate. The solvent was distilled away under reduced pressure and the obtained residue was purified by silica gel chromatography (n-hexane:ethyl acetate=20:1 to 10:1). A white solid of 2-chloro-5-fluoro-4-iodopyridine (457 mg) was thus obtained.

2-Chloro-5-fluoro-4-iodopyridine $^1$H-NMR (CDCl$_3$, 300MHz) δ: 8.14 (s, 1H), 7.77 (d, 1H, J=4.3Hz)

2nd Step tert-Butyl carbamate (960 mg), cesium carbonate (5.06 g), Pd$_2$(dba)$_3$ (1.07 g), and Xantphos (1.35 g) were added to a toluene solution (40 ml) containing 2-chloro-5-fluoro-4-iodopyridine (2 g), followed by stirring at 100° C. for 3 hours. The reaction solution was adjusted to room temperature and water was added to the reaction solution, followed by extraction with ethyl acetate. The organic layers were washed with saturated saline and dried over anhydrous sodium sulfate. The solvent was distilled away under reduced pressure and the obtained residue was purified by silica gel chromatography (n-hexane:ethyl acetate=9:1 to 4:1). A yellow oily matter of tert-butyl (2-chloro-5-fluoropyridin-4-yl)carbamate (1.53 g) was thus obtained.

tert-Butyl (2-chloro-5-fluoropyridin-4-yl)carbamate

MS (ESI m/z): 247, 249 (M+H)
RT (min): 1.64

3rd Step

The following compound was obtained as described in the 2nd step in Reference Example 27.

2-Chloro-5-fluoropyridin-4-amine

MS (ESI m/z): 147, 149 (M+H)
RT (min): 0.68

4th Step

Morpholine (3 ml) was added to 2-chloro-5-fluoropyridin-4-amine (262 mg) obtained in the 2nd step, followed by microwave irradiation (Initiator™, 235° C., 2 hours, 2.45 GHz, 0-240 W). A saturated ammonium chloride aqueous solution was added to the reaction solution, followed by extraction with ethyl acetate. The organic layers were washed with a saturated ammonium chloride aqueous solution and saturated saline and dried over anhydrous sodium sulfate. Next, the solvent was distilled away under reduced pressure and a light brown solid of 5-fluoro-2-morpholinopyridin-4-amine (311 mg) was thus obtained.

5-Fluoro-2-morpholinopyridin-4-amine

MS (ESI m/z): 198 (M+H)
RT (min): 0.40

Reference Example 61

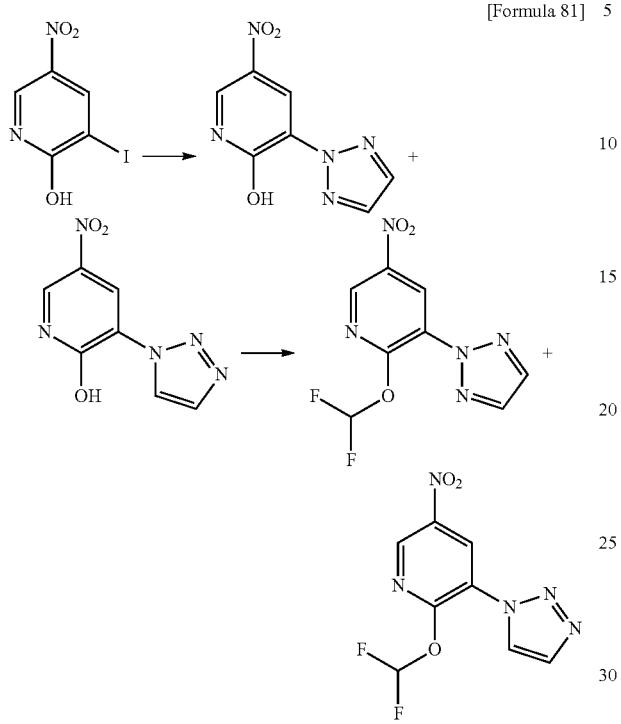

[Formula 81]

1st Step

Cesium carbonate (24.4 g), 1,2,3-triazole (4.35 ml), 2,2,6,6-tetramethyl-3,5-heptanedione (3.89 ml), and copper iodide (7.1 g) were added to a DMSO (100 ml) solution containing 3-iodo-5-nitropyridin-2-ol (10 g) in a nitrogen atmosphere, followed by stirring at 155° C. for 1 hour. The reaction solution was adjusted to room temperature and water was added to the reaction solution. An insoluble precipitate was removed by filtration. 1M hydrochloric acid (110 ml) was added to the resulting filtrate, followed by extraction with ethyl acetate. The organic layers were washed with saturated saline and dried over anhydrous sodium sulfate. The solvent was distilled away under reduced pressure, a small amount of ethyl acetate was added to the obtained residue, and insoluble matter was collected by filtration. A yellow solid mixture (4.86 g) of 5-nitro-3-(2H-1,2,3-triazol-2-yl)pyridin-2-ol and 5-nitro-3-(1H-1,2,3-triazol-1-yl)pyridin-2-ol was thus obtained.

5-Nitro-3-(2H-1,2,3-triazol-2-yl)pyridin-2-ol

MS (ESI m/z): 208 (M+H)
RT (min): 0.69

5-Nitro-3-(1H-1,2,3-triazol-1-yl)pyridin-2-ol

MS (ESI m/z): 208 (M+H)
RT (min): 0.63

2nd Step 2,2-difluoro-2-(fluorosulfonyl)acetic acid (189 μl) was added to an acetonitrile (2 ml) solution containing the mixture (105 mg) of 5-nitro-3-(2H-1,2,3-triazol-2-yl)pyridin-2-ol and 5-nitro-3-(1H-1,2,3-triazol-1-yl)pyridin-2-ol obtained in the 1st step, followed by stirring at room temperature for 21 hours. Subsequently, sodium sulfate (100 mg) and 2,2-difluoro-2-(fluorosulfonyl)acetic acid (126 μl) were added to the solution, followed by stirring at 70° C. for 7 hours. The reaction solution was adjusted to room temperature and a saturated sodium hydrogen carbonate solution was added to the reaction solution, followed by extraction with ethyl acetate. The organic layers were washed with saturated saline and dried over anhydrous sodium sulfate. The solvent was distilled away under reduced pressure and the obtained residue was, purified by silica gel chromatography (n-hexane: ethyl acetate=1:0 to 4:1). A light yellow solid of 2-(difluoromethoxy)-5-nitro-3-(2H-1,2,3-triazol-2-yl)pyridine (15 mg) was thus obtained.

MS (ESI m/z): 258 (M+H)
RT (min): 1.29

Reference Example 62

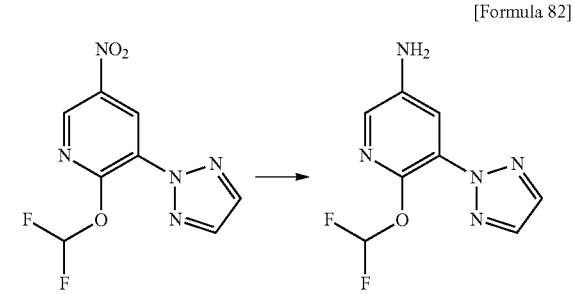 [SMILES: O=[N+]([O-])c1cnc(OC(F)F)c(-n2nccn2)c1 ; Nc1cnc(OC(F)F)c(-n2nccn2)c1]

[Formula 82]

1st Step

The following compound was obtained as described in the 3rd step in Reference Example 1.

6-(Difluoromethoxy)-5-(2H-1,2,3-triazol-2-yl)pyridin-3-amine

MS (ESI m/z): 228 (M+H)
RT (min): 0.93

Reference Example 63

The following compound was obtained with reference to WO2009/90548 A2, 2009.

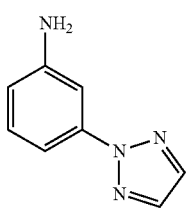

[Formula 83]

3-(2H-1,2,3-triazol-2-yl)aniline

Reference Example 64

The following compound was obtained with reference to Tetrahedron, 2011, vol. 67, #2, pp. 289-292, WO2009/90548 A2, 2009.

[Formula 84]

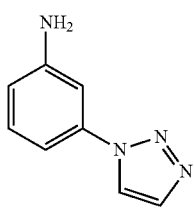

3-(1H-1,2,3-triazol-1-yl)aniline

Reference Example 65

[Formula 85]

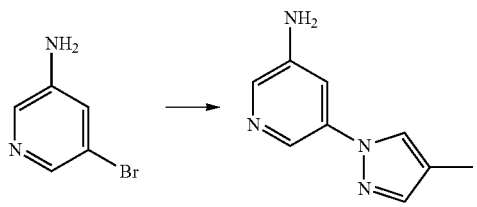

4-Methyl-1H-pyrazole (114 mg), cesium carbonate (753 mg), trans-N,N'-dimethylcyclohexan-1,2-diamine (164 mg), and copper iodide (110 mg) were added to a DMAc (5 ml) solution containing 5-bromopyridin-3-amine (200 mg) in a nitrogen atmosphere, followed by microwave irradiation (Initiator™, 170° C., 0.5 hours, 2.45 GHz, 0-240 W). Water was added to the reaction solution and the reaction solution was filtered through Celite and the filtrate was extracted with ethyl acetate. The organic layers were washed with saturated saline and dried over sodium sulfate. The solvent was distilled away under reduced pressure. The obtained residue was purified by silica gel chromatography (n-hexane:ethyl acetate=4:1 to 0:1). 5-(4-Methylpyrazol-1-yl)pyridin-3-amine (173 mg) was thus obtained.

MS (ESI m/z): 175 (M+H)
RT (min): 0.54

Reference Example 66

[Formula 86]

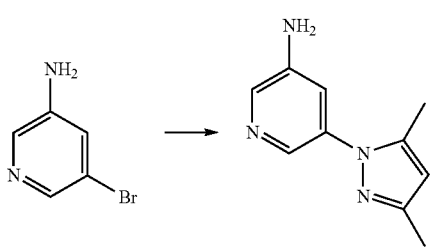

The following compound was obtained as described in Reference Example 65.

5-(3,5-Dimethylpyrazol-1-yl)pyridin-3-amine

MS (ESI m/z): 189 (M+H)
RT (min): 0.60

Reference Example 67

[Formula 87]

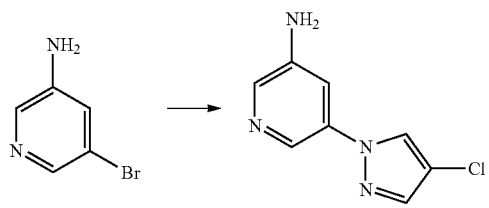

The following compound was obtained as described in Reference Example 65.

5-(4-Chloropyrazol-1-yl)pyridin-3-amine

MS (ESI m/z): 195, 197 (M+H)
RT (min): 0.66

Reference Example 68

[Formula 88]

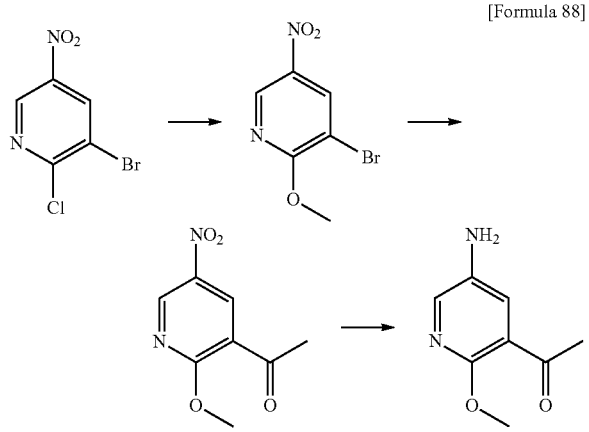

1st Step

A sodium ethoxide solution (28% in MeOH) (1 ml) was added to an MeOH (3 ml) solution containing 3-bromo-2-chloro-5-nitropyridine (100 mg), followed by stirring at room temperature for 0.5 hours. A saturated ammonium chloride aqueous solution was added to the reaction solution and MeOH was distilled away under reduced pressure. An insoluble precipitate was washed with water and a white solid of 3-bromo-2-methoxy-5-nitropyridine (69 mg) was thus obtained.

MS (ESI m/z): 233, 235 (M+H)
RT (min): 1.40

2nd Step

Pd(PPh$_3$)$_4$ (60 mg) and tributyl (1-ethoxyvinyl)tin were added to a DMAc (3 ml) solution containing 3-bromo-2- methoxy-5-nitropyridine (69 mg) obtained in the 1st step, followed by microwave irradiation (Initiator™, 180° C., 10 minutes, 2.45 GHz, 0-240 W). Saturated sodium hydrogen carbonate was added to the reaction solution, followed by extraction with ethyl acetate. The organic layers were dried over anhydrous sodium sulfate. The solvent was distilled away under reduced pressure and the obtained residue was purified by silica gel chromatography (n-hexane:ethyl acetate=9:1 to 3:7). A light yellow solid of 1-(2-methoxy-5-nitropyridin-3-yl)ethanone (72 mg) was thus obtained.

MS (ESI m/z): 197 (M+H)
RT (min): 1.14

3rd Step

The following compound was obtained as described in the 3rd step in Reference Example 1.

1-(5-Amino-2-methoxypyridin-3-yl)ethanone

MS (ESI m/z): 167 (M+H)
RT (min): 0.60

Reference Example 69

The following compound was obtained with reference to US2006/79522 A1.

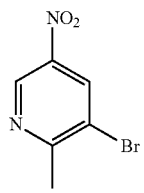

[Formula 89]

3-Bromo-2-methyl-5-nitropyridine

Reference Example 70

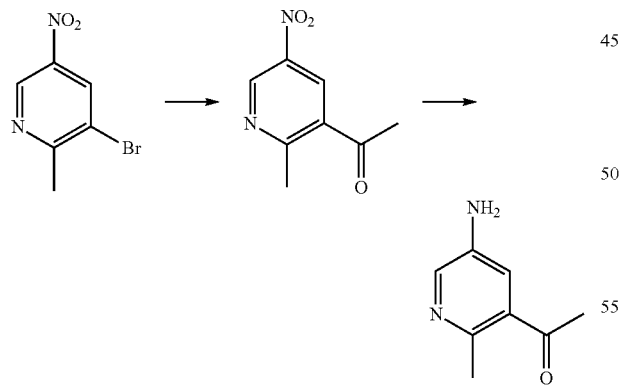

[Formula 90]

The following compound was obtained as described in the 2nd and 3rd steps in Reference Example 68.

1st Step 1-(2-Methyl-5-nitropyridin-3-yl)ethanone

MS (ESI m/z): 181 (M+H)
RT (min): 0.90

2nd Step 1-(5-amino-2-methylpyridin-3-yl)ethanone

MS (ESI m/z): 151 (M+H)
RT (min): 0.28

Reference Example 71

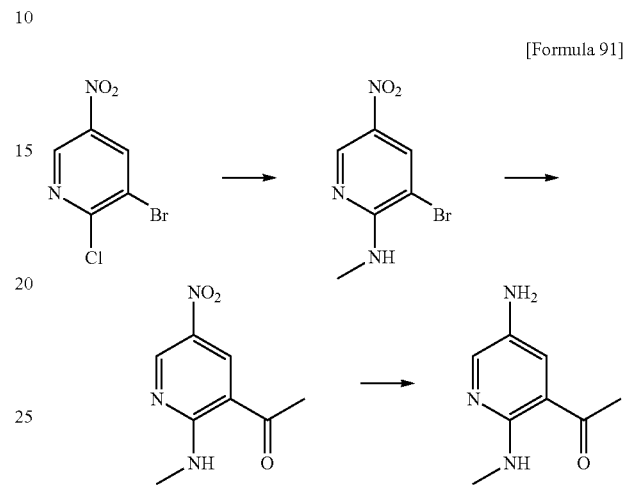

[Formula 91]

The following compound was obtained as described in Reference Example 68.

2-Methylamino-3-bromo-5-nitropyridine

MS (ESI m/z): 288, 290 (M+H)
RT (min): 1.36

1-(2-Methylamino-5-nitropyridin-3-yl)ethanone

MS (ESI m/z): 196 (M+H)
RT (min): 1.09

1-(5-Amino-2-methylaminopyridin-3-yl)ethanone

MS (ESI m/z): 166 (M+H)
RT (min): 0.32

Reference Example 72

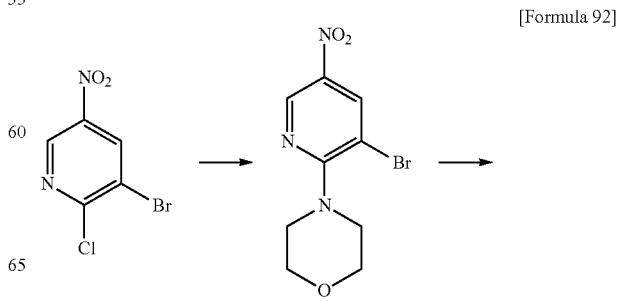

[Formula 92]

-continued

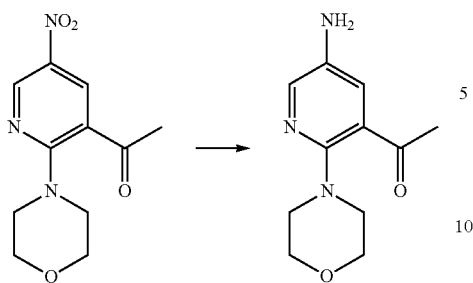

The following compound was obtained as described in Reference Example 68.

4-(3-Bromo-5-nitropyridin-2-yl)morpholine

MS (ESI m/z): 288, 290 (M+H)
RT (min): 1.36

1-(2-Morpholino-5-nitropyridin-3-yl)ethanone

MS (ESI m/z): 252 (M+H)
RT (min): 1.04

1-(5-Amino-2-morpholinopyridin-3-yl)ethanone

MS (ESI m/z): 222 (M+H)
RT (min): 0.53

Reference Example 73

[Formula 93]

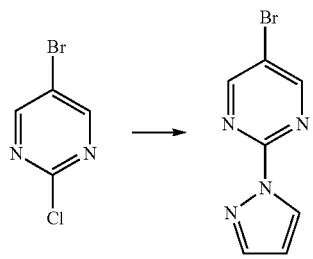

1st Step

Pyrazole (130 mg) and cesium carbonate (610 mg) were added to a DMAc (10 ml) solution containing 5-bromo-2-chloropyrimidine (300 mg), followed by stirring at 120° C. for 0.5 hours. The reaction mixture was adjusted to room temperature and water was added to the mixture. Next, the organic layers were collected, washed with saturated saline, and dried over anhydrous sodium sulfate. The solvent was distilled away under reduced pressure and a yellow solid of 5-bromo-2-(pyrazol-1-yl)pyrimidine (440 mg) was thus obtained.

MS (ESI m/z): 226 (M+H)
RT (min): 0.93

Reference Example 74

[Formula 94]

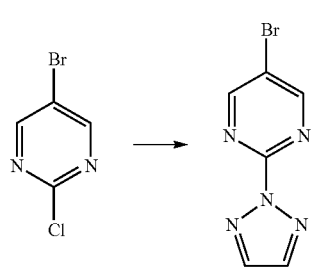

The following compound was obtained as described in Reference Example 73.

5-Bromo-2-(2H-1,2,3-triazol-2-yl)pyrimidine $^1$H-NMR: 1H-NMR (CDCl3) δ: 8.93 (2H, s), 8.01 (2H, s).
MS (ESI m/z): 227 (M+H)
RT (min): 0.68

Reference Example 75

The following compound was obtained with reference to Chemische Berichte, 1967, vol. 100, #11 pp. 3485-3494.

[Formula 95]

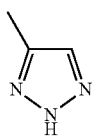

4-methyl-2H-1,2,3-triazole

Reference Example 76

[Formula 96]

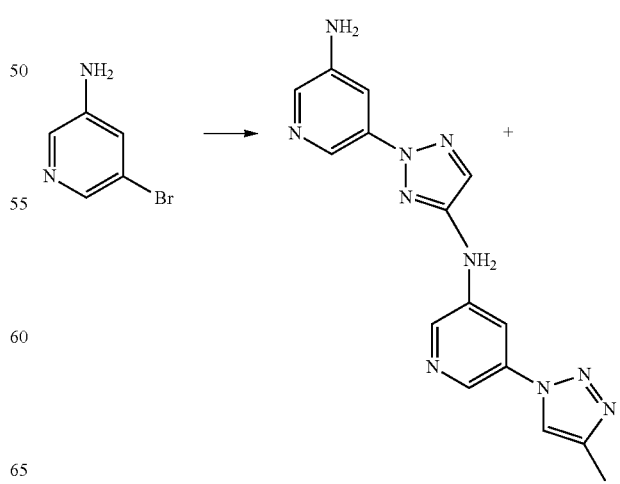

The following compound was obtained as described in Reference Example 50.

5-(4-Methyl-2H-1,2,3-triazol-2-yl)pyridin-3-amine

MS (ESI m/z): 176 (M+H)
RT (min): 0.56

5-(4-Methyl-1H-1,2,3-triazol-1-yl)pyridin-3-amine

MS (ESI m/z): 176 (M+H)
RT (min): 0.53

Reference Example 77

[Formula 97]

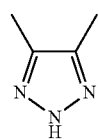

The following compound was obtained with reference to Chemische Berichte, 1967, vol. 100, #11 pp. 3485-3494.

4,5-Dimethyl-2H-1,2,3-triazole

Reference Example 78

[Formula 98]

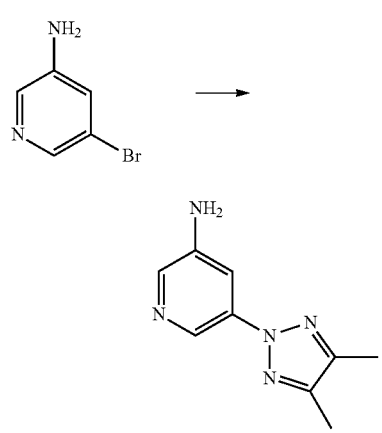

The following compound was obtained as described in Reference Example 50.

5-(4,5-Dimethyl-2H-1,2,3-triazol-2-yl)pyridin-3-amine

MS (ESI m/z): 190 (M+H)
RT (min): 0.62

5-(4,5-Dimethyl-1H-1,2,3-triazol-1-yl)pyridin-3-amine

MS (ESI m/z): 190 (M+H)
RT (min): 0.56

Reference Example 79

[Formula 99]

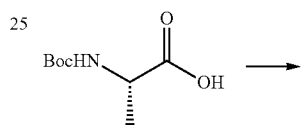
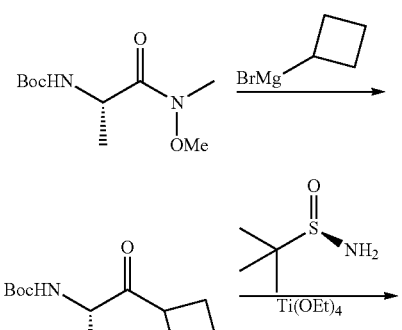
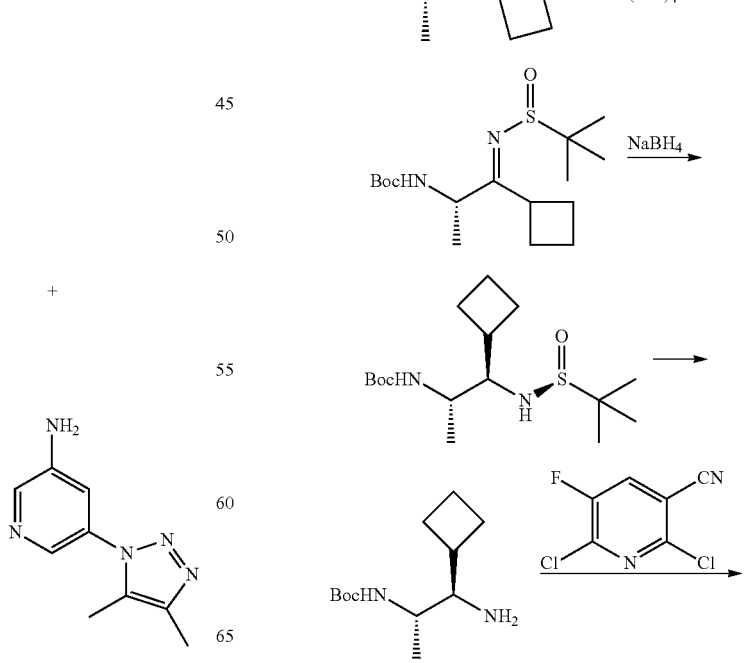

-continued

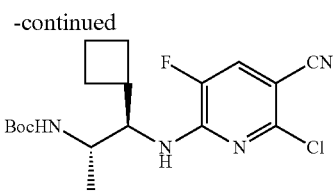

1st Step

CDI (185.6 g) was added to a dichloromethane (2000 ml) solution containing N-(tert-butoxycarbonyl)-L-alanine (200 g) at 5° C. or less, followed by stirring for 1 hour. Subsequently, triethylamine (115.8 g) and N-methoxy-N-methylamine hydrochloride (111.7 g) were added to the solution, followed by stirring at 15° C. or less for 1.5 hours. Dichloromethane (230 ml) was added to the reaction solution. The organic layers were washed with a 20% sodium hydroxide aqueous solution and the solvent was distilled away under reduced pressure. Heptane was added to the obtained residue for suspension and a solid was collected by filtration. A white solid of (S)-tert-butyl (1-(methoxy(methyl)amino)-1-oxopropan-2-yl)carbamate (237.8 g) was thus obtained.

2nd Step

Magnesium turnings (7 g) and THF (30 ml) were introduced into a reaction container in a nitrogen atmosphere and dibromoethane (10 μl) was added to the reaction container. After foaming was confirmed, a THF (150 ml) solution containing bromocyclobutane (40 g) was added dropwise at 70° C. or less for 0.5 hours. Next, (S)-tert-butyl (1-(methoxy (methyl)amino)-1-oxopropan-2-yl)carbamate (27.9 g) obtained in the 1st step was added, followed by stirring at 50° C. or less for 2 hours. The reaction solution was adjusted to room temperature and poured into a 10% citric acid aqueous solution (300 ml) so as to separate the organic layers. The obtained organic layers were dried over anhydrous sodium hydrogen sulfate and the solvent was distilled away under reduced pressure. A white solid of (S)-tert-butyl (1-cyclobutyl-3-oxobutan-2-yl)carbamate (36 g) was thus obtained.

3rd and 4th Steps

Tetraethyl orthotitanate (90.3 g), (S)-tert-butyl (3-oxobutan-2-yl)carbamate (36 g) obtained in the 2nd step and (R)-(+)-tert-butyl sulfinamide (23 g) were added to toluene (90 ml) in a nitrogen atmosphere, followed by stirring at 80° C. or less for 7 hours. Sodium borohydride (11.95 g) was added thereto at −30° C. or less, followed by stirring for 4 hours. Subsequently, the obtained mixture was adjusted to room temperature and MeOH was added so as to separate the organic layers. Next, the organic layers were washed with saturated saline and dried over anhydrous sodium sulfate. The solvent was distilled away under reduced pressure. Brown oily matter of tert-butyl ((2S)-1-((tert-butylsulfinyl)amino)-1-cyclobutylpropan-2-yl)carbamate (38 g) was thus obtained.

5th Step 4M hydrogen chloride/1,4-dioxane (100 ml) was added to an MeOH (900 ml) solution containing tert-butyl ((2S)-1-((tert-butylsulfinyl)amino)-1-cyclobutylpropan-2-yl)carbamate (38 g) obtained in the 4th step under ice cooling, followed by stirring for 30 minutes. The reaction solution was adjusted to room temperature and poured into a 1M sodium hydroxide aqueous solution (600 ml), followed by extraction with ethyl acetate. The solvent was distilled away under reduced pressure and used in the subsequent step.

6th Step

DIPEA (17 ml) was added to a DMF (30 ml) solution containing tert-butyl ((1R,2S)-1-amino-1-cyclobutylpropan-2-yl)carbamate and 2,6-dichloro-5-fluoronicotinonitrile (16.2 g) obtained in the 5th step at 70° C., followed by stirring for 3 hours. The reaction solution was adjusted to room temperature and water was added to the reaction solution, followed by extraction with ethyl acetate. The organic layers were washed with saturated saline and the organic layers were dried over anhydrous sodium sulfate. The obtained residue was purified by silica gel chromatography (n-hexane:ethyl acetate=10:1 to 1:1). A white solid of tert-butyl ((1R,2S)-1-((6-chloro-5-cyano-3-fluoropyridin-2-yl)amino)-1-cyclobutylpropan-2-yl)carbamate (16.5 g) was thus obtained.

$^1$H-NMR (CDCl$_3$) δ: 7.29 (1H, d, J=9.9 Hz), 5.59 (1H, Br), 4.84 (1H, Br), 4.36-4.24 (1H, m), 3.90-3.76 (1H, m), 2.54-2.43 (1H, m), 2.05-1.81 (6H, m), 1.45 (9H, s), 1.14 (3H, d, J=6.9 Hz).

MS (ESI m/z): 384 (M+H)

RT (min): 1.83

Reference Example 80

The following compound was obtained as described in Reference Example 79.

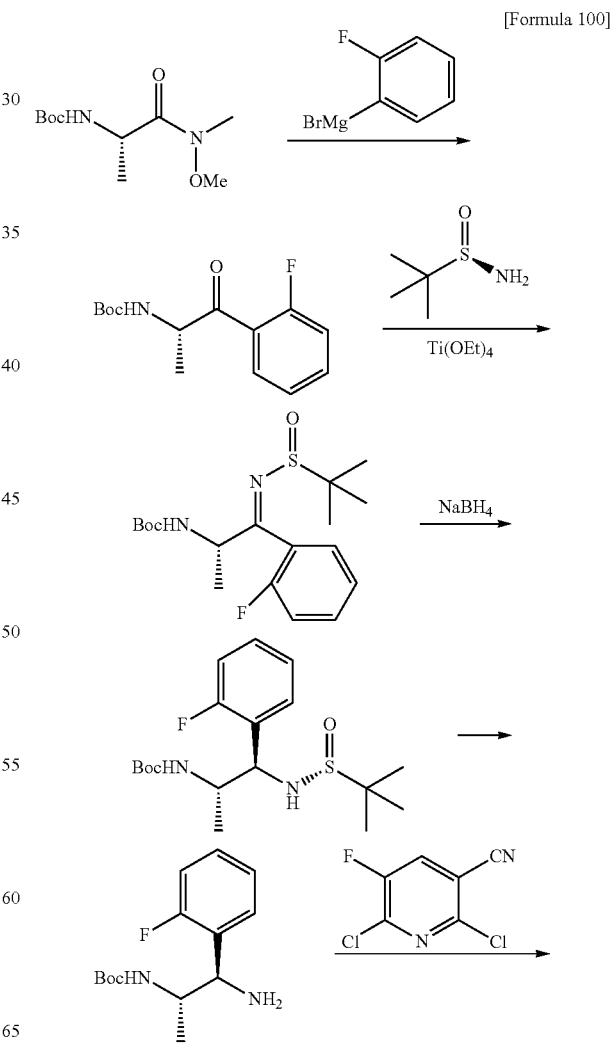

[Formula 100]

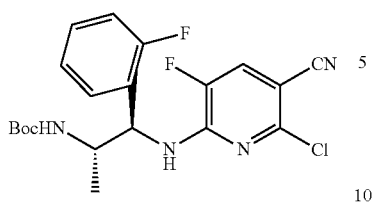

tert-Butyl ((2S)-1-((tert-butylsulfinyl)imino)-1-(2-fluorophenyl)propan-2-yl)carbamate MS (ESI m/z): 273 (M+H−Boc)
RT (min): 1.54 tert-Butyl ((1R,2S)-1-((6-chloro-5-cyano-3-fluoropyridin-2-yl)amino)-1-(2-fluorophenyl)propan-2-yl)carbamate $^1$H-NMR (CDCl3) δ: 8.09 (1H, s), 7.36-7.22 (1H, m), 7.07-6.92 (3H, m), 5.00 (1H, d, J=5.9 Hz), 4.32-4.24 (2H, m), 1.50 (9H, s), 1.14 (3H, d, J=6.6 Hz)
MS (ESI m/z): 323 (M+H−Boc)
RT (min): 1.83

Reference Example 81

The following compound was obtained as described in Reference Example 79.

[Formula 101]

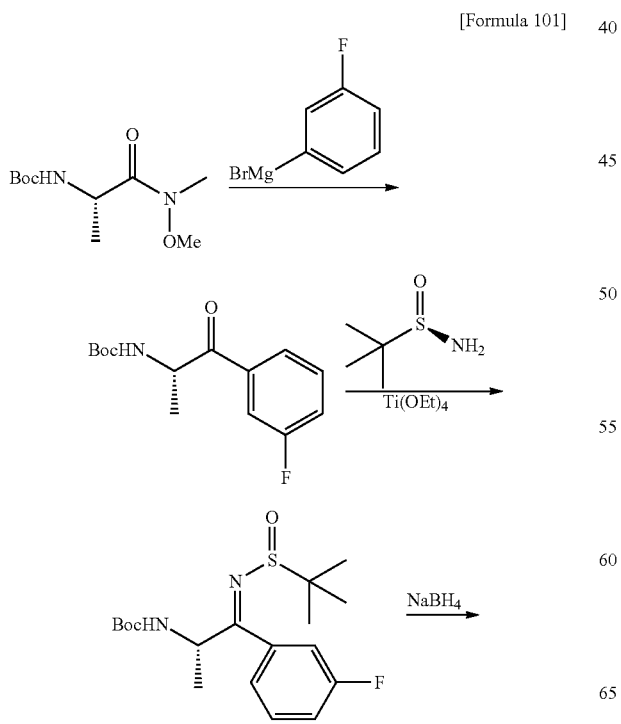

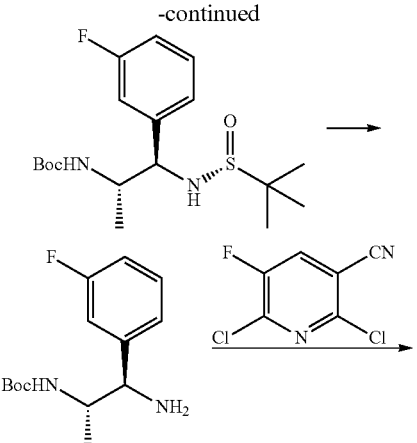

(S)-tert-butyl (1-(3-fluorophenyl)-1-oxopropan-2-yl)carbamate

MS (ESI m/z): 168 (M+H−Boc)
RT (min): 1.52 tert-Butyl ((1R,2S)-1-((R)-1,1-dimethylethylsulfinamide)-1-(3-fluorophenyl)propan-2-yl)carbamate MS (ESI m/z): 273 (M+H−Boc)
RT (min): 1.51 tert-Butyl ((1R,2S)-1-((6-chloro-5-cyano-3-fluoropyridin-2-yl)amino)-1-(3-fluorophenyl)propan-2-yl)carbamate $^1$H-NMR (CDCl3) δ: 7.92 (1H, s), 7.24-7.17 (2H, m), 7.13-7.06 (2H, m), 5.38 (1H, d, J=4.6 Hz), 4.39-4.25 (2H, m), 1.47 (9H, s), 1.16 (3H, d, J=6.6 Hz)
MS (ESI m/z): 323 (M+H−Boc)
RT (min): 1.83

Reference Example 82

The following compound was obtained as described in Reference Example 79.

[Formula 102]

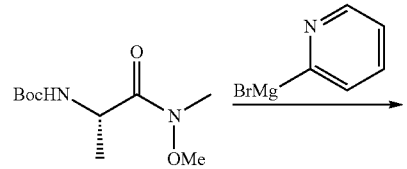
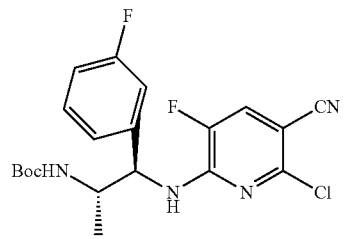

-continued

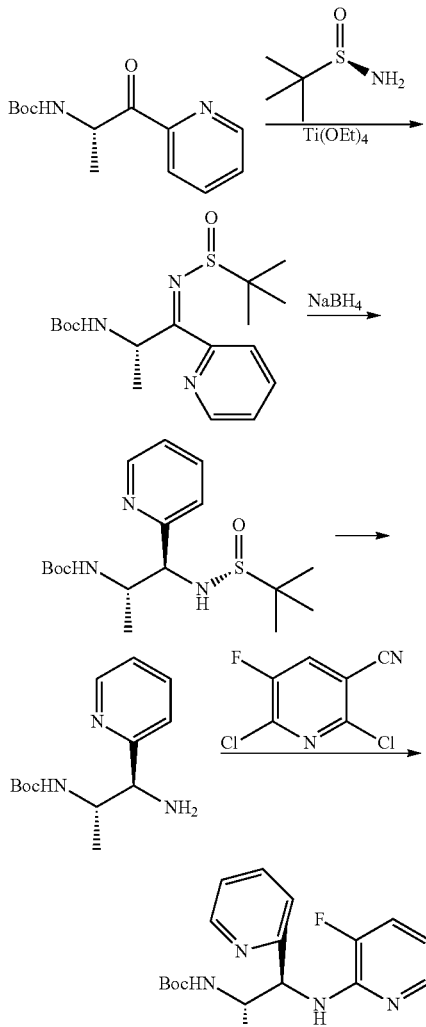

(S)-tert-butyl (1-oxo-1-(pyridin-2-yl)propan-2-yl)carbamate

MS (ESI m/z): 151 (M+H−Boc)
RT (min): 1.31 tert-Butyl ((2S)-1-((tert-butylsulfinyl)imino)-1-(pyridin-2-yl)propan-2-yl)carbamate MS (ESI m/z): 354 (M+H)
RT (min): 1.49 tert-Butyl ((1S,2S)-1-((R)-1,1-dimethylethylsulfinamide)-1-(pyridin-2-yl)propan-2-yl)carbamate MS (ESI m/z): 356 (M+H)
RT (min): 1.13 tert-Butyl ((1S,2S)-1-((6-chloro-5-cyano-3-fluoropyridin-2-yl)amino)-1-(pyridin-2-yl)propan-2-yl)carbamate $^1$H-NMR (CDCl3) δ: 8.60 (1H, d, J=4.6 Hz), 7.73 (1H, dd, J=7.3, 7.3 Hz), 7.41 (1H, d, J=7.9 Hz), 7.33-7.28 (2H, m), 5.49 (1H, s), 5.41-5.35 (1H, m), 4.29-4.19 (1H, m), 1.45 (9H, s), 1.05 (3H, d, J=6.6 Hz).

MS (ESI m/z): 406 (M+H)
RT (min): 1.53

Reference Example 83

The following compound was obtained as described in Reference Example 79.

[Formula 103]

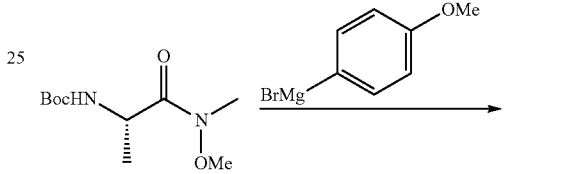

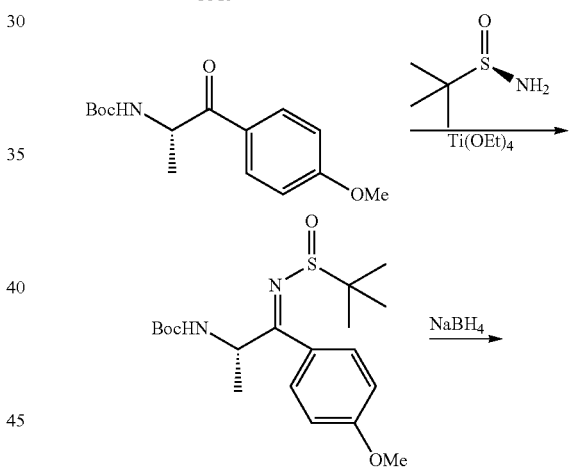

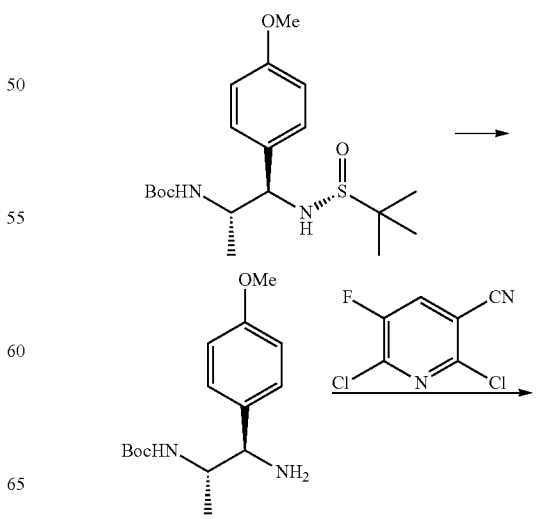

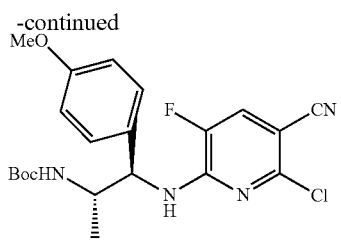

(S)-tert-butyl (1-(4-methoxyphenyl)-1-oxopropan-2-yl)carbamate

MS (ESI m/z): 180 (M+H−Boc)
RT (min): 1.48 tert-Butyl ((2S)-1-((tert-butylsulfinyl)imino)-1-(4-methoxyphenyl)propan-2-yl)carbamate MS (ESI m/z): 283 (M+H−Boc)
RT (min): 1.65 tert-Butyl ((1R,2S)-1-(R)-1,1-dimethylethylsulfinamide)-1-(4-methoxyphenyl)propan-2-yl)carbamate MS (ESI m/z): 385 (M+H)
RT (min): 1.50 tert-Butyl ((1R,2S)-1-((6-chloro-5-cyano-3-fluoropyridin-2-yl)amino)-1-(4-methoxyphenyl)propan-2-yl)carbamate $^1$H-NMR (CDCl3) δ: 7.89 (1H, s), 7.17 (2H, t, J=8.4 Hz), 6.88 (2H, t, J=8.4 Hz), 4.98 (1H, d, J=5.3 Hz), 4.34-4.20 (2H, m), 3.80 (3H, s), 1.48 (9H, s), 1.10 (3H, d, J=6.6 Hz).

MS (ESI m/z): 433 (M+H)
RT (min): 1.81

Reference Example 84

The following compound was obtained as described in Reference Example 79.

[Formula 104]

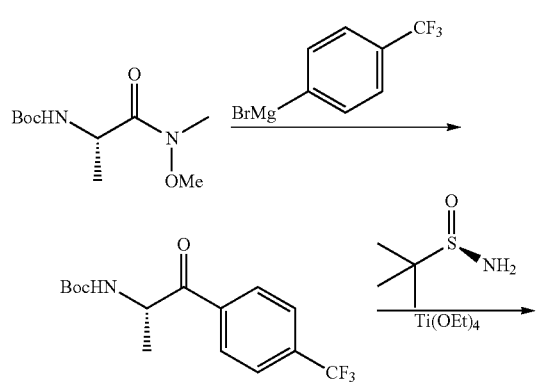

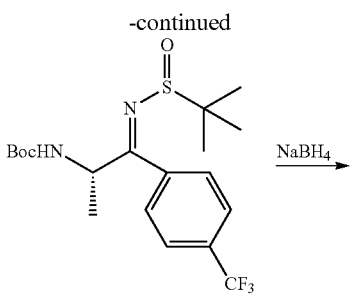

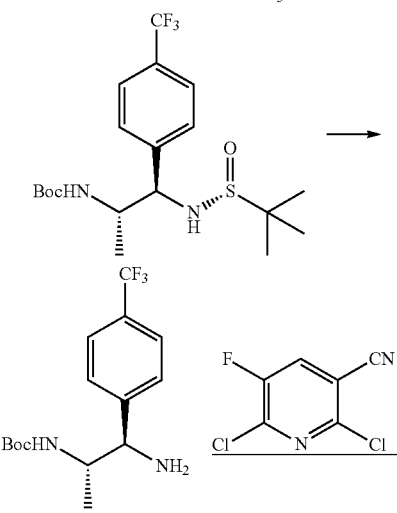

tert-Butyl ((1R,2S)-1-((R)-1,1-dimethylethylsulfinamide)-1-(4-(trifluoromethyl)phenyl)propan-2-yl)carbamate MS (ESI m/z): 323 (M+H−Boc)
RT (min): 1.71 tert-Butyl ((1R,2S)-1-(6-chloro-5-cyano-3-fluoropyridin-2-yl)amino)-1-(4-(trifluoromethyl)phenyl)propan-2-yl)carbamate $^1$H-NMR (CDCl3) δ: 8.21 (1H, s), 7.60 (2H, d, J=8.4 Hz), 7.38 (2H, d, J=8.4 Hz), 5.04 (1H, d, J=5.3 Hz), 4.38-4.26 (2H, m), 1.49 (9H, s), 1.13 (3H, d, J=6.6 Hz).

MS (ESI m/z): 373 (M+H)
RT (min): 1.91

Reference Example 85

The following compound was obtained as described in Reference Example 79.

103

[Formula 105]

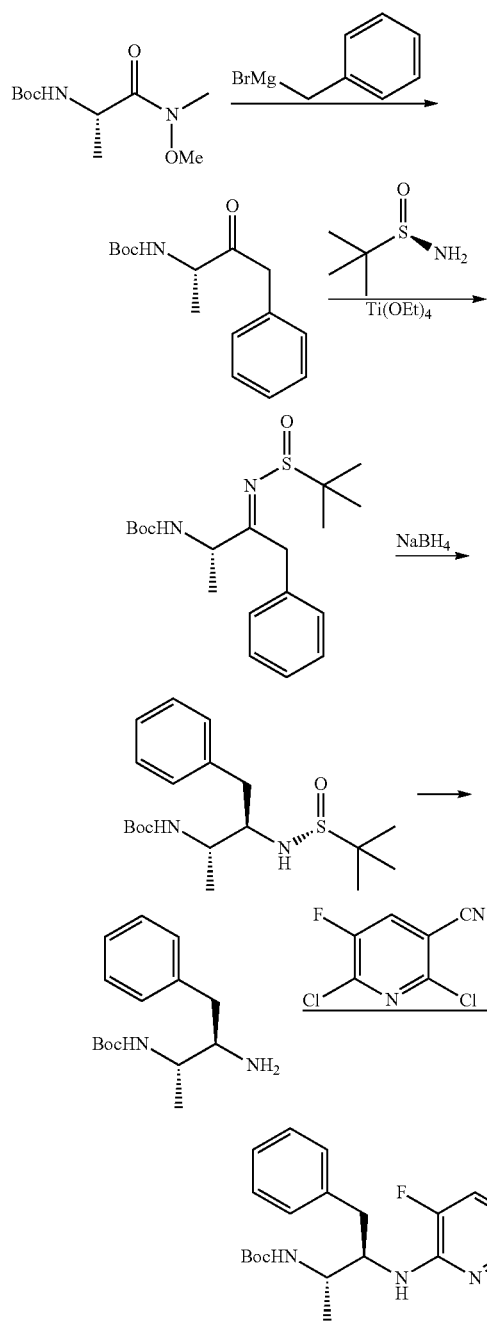

(S)-tert-butyl (3-oxo-4-phenylbutan-2-yl)carbamate

MS (ESI m/z): 164 (M+H−Boc)
RT (min): 1.48 tert-Butyl ((2S,3R)-3-((R)-1,1-dimethylethylsulfinamide)-4-phenylbutan-2-yl)carbamate MS (ESI m/z): 269 (M+H−Boc)
RT (min): 1.63

104 tert-Butyl ((2S,3R)-3-((6-chloro-5-cyano-3-fluoropyridin-2-yl)amino)-4-phenylbutan-2-yl)carbamate $^1$H-NMR (CDCl3) δ: 7.25-7.15 (5H, m), 6.13 (1H, s), 4.69 (1H, s), 4.56-4.50 (1H, m), 4.00-3.90 (1H, m), 2.99 (1H, dd, J=13.9, 5.4 Hz), 2.76 (1H, dd, J=13.9, 5.4 Hz), 1.45 (9H, s), 1.18 (3H, d, J=6.6 Hz).
MS (ESI m/z): 319 (M+H−Boc)
RT (min): 1.79

Reference Example 86

The following compound was obtained as described in Reference Example 79.

[Formula 106]

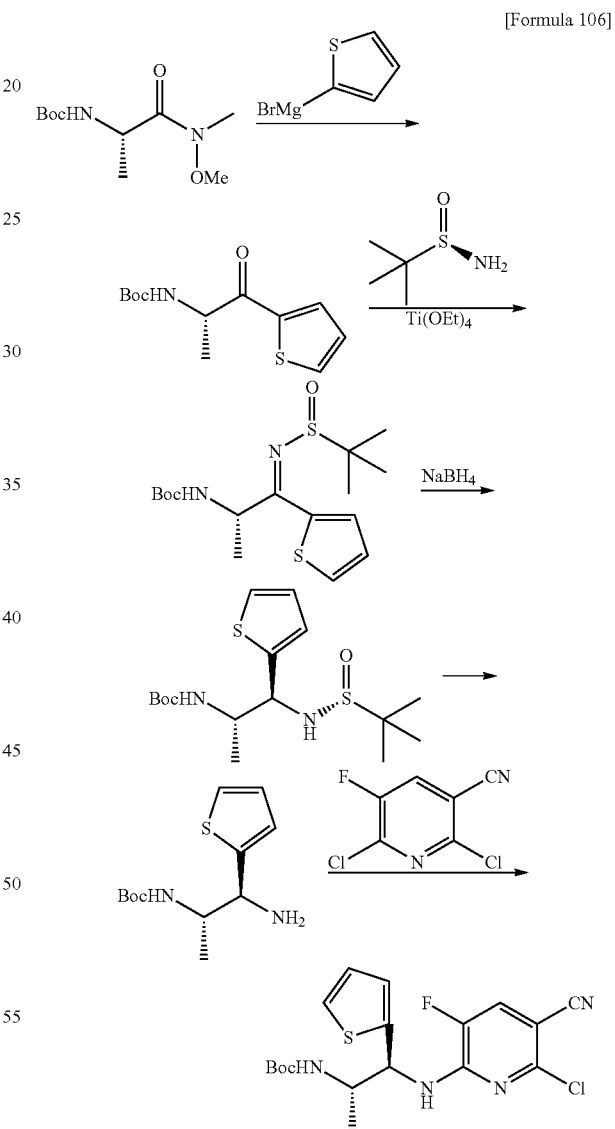

(S)-tert-butyl (1-oxo-1-(thiophen-2-yl)propan-2-yl)carbamate

MS (ESI m/z): 156 (M+H−Boc)
RT (min): 1.36 tert-Butyl ((2S)-1-((tert-butylsulfinyl)imino)-1-(thiophen-2-yl)propan-2-yl)carbamate MS (ESI m/z): 381 (M+Na)
RT (min): 1.69 tert-Butyl ((1S,2S)-1-((R)-1,1-dimethylethylsulfinamide)-1-(thiophen-2-yl)propan-2-yl)carbamate MS (ESI m/z): 261 (M+H–Boc)
RT (min): 1.52 tert-Butyl ((1S,2S)-1-((6-chloro-5-cyano-3-fluoropyridin-2-yl)amino)-1-(thiophen-2-yl)propan-2-yl)carbamate ¹H-NMR (CDCl3) δ: 7.87 (1H, s), 7.28-7.24 (1H, m), 7.06 (1H, d, J=3.0 Hz), 7.00 (1H, dd, J=5.3, 3.0 Hz), 5.37 (1H, d, J=4.6 Hz), 4.52 (1H, s), 4.33-4.24 (1H, m), 1.47 (9H, s), 1.18 (3H, d, J=6.6 Hz)
MS (ESI m/z): 409 (M–H)
RT (min): 1.78

Reference Example 87

The following compound was obtained as described in Reference Example 79.

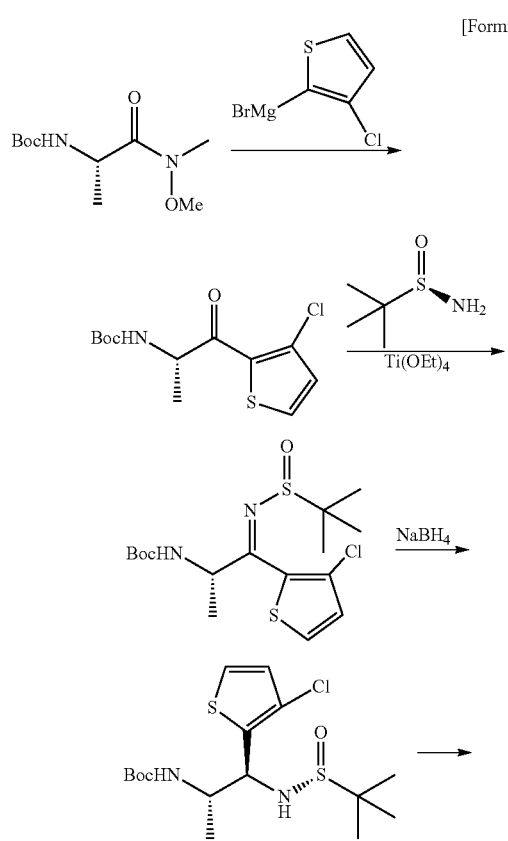

[Formula 107]

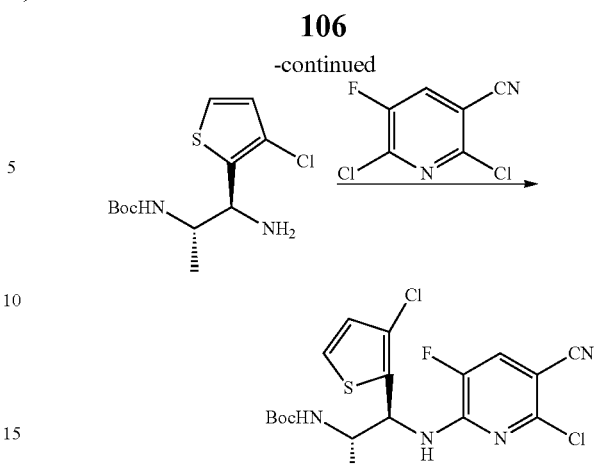

(S)-tert-butyl (1-(3-chlorothiophen-2-yl)-1-oxopropan-2-yl)carbamate

MS (ESI m/z): 190 (M+H–Boc)
RT (min): 1.59 tert-Butyl ((2S)-1-((tert-butylsulfinyl)imino)-1-(3-chlorothiophen-2-yl)propan-2-yl)carbamate MS (ESI m/z): 293 (M+H–Boc)
RT (min): 1.94 tert-Butyl ((1S,2S)-1-(3-chlorothiophen-2-yl)-1-((R)-1,1-dimethylethylsulfinamide)propan-2-yl)carbamate MS (ESI m/z): 295 (M+H–Boc)
RT (min): 1.59 tert-Butyl ((1S,2S)-1-((6-chloro-5-cyano-3-fluoropyridin-2-yl)amino)-1-(3-chlorothiophen-2-yl)propan-2-yl)carbamate MS (ESI m/z): 433 (M–H)
RT (min): 1.92

Reference Example 88

The following compound was obtained as described in Reference Example 79.

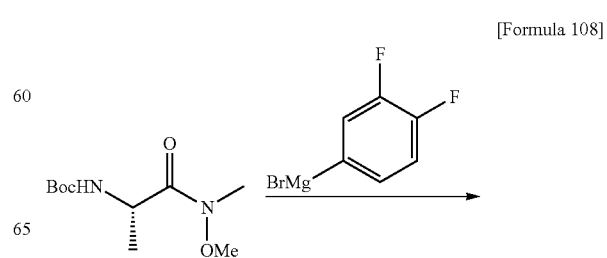

[Formula 108]

107

-continued

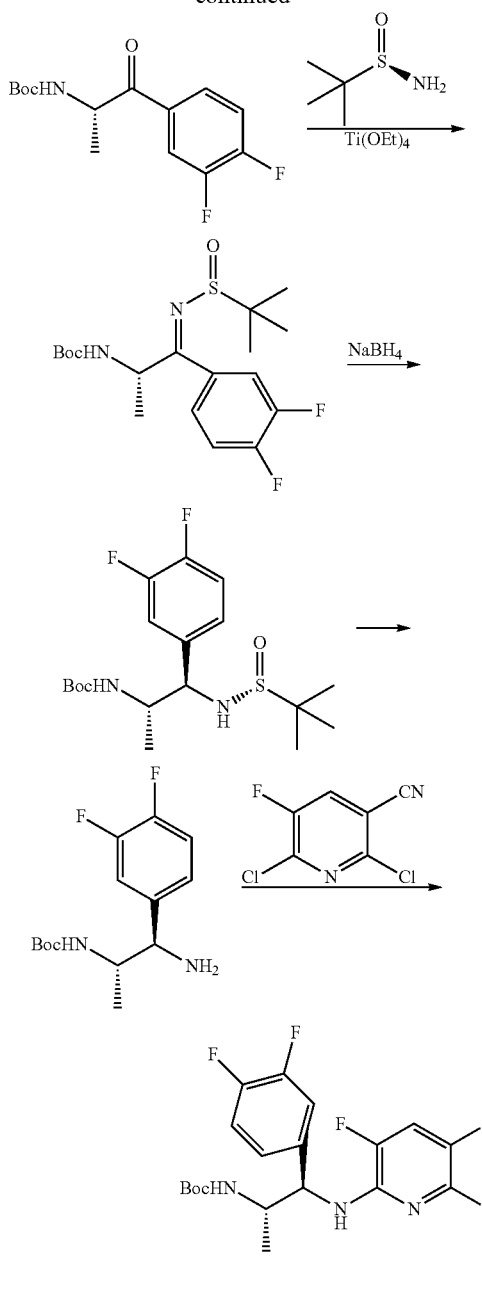

tert-Butyl ((1R,2S)-1-(3,4-difluorophenyl)-1-((R)-1,1-dimethylethylsulfinamide)propan-2-yl)carbamate MS (ESI m/z): 291 (M+H−Boc)
RT (min): 1.58 tert-Butyl ((1R,2S)-1-((6-chloro-5-cyano-3-fluoropyridin-2-yl)amino)-1-(3,4-difluorophenyl)propan-2-yl)carbamate ¹H-NMR (CDCl3) δ: 8.18 (1H, s), 6.80-6.72 (3H, m), 4.93 (1H, d, J=5.4 Hz), 4.32-4.21 (2H, m), 1.50 (9H, s), 1.16 (3H, d, J=6.6 Hz).
MS (ESI m/z): 341 (M+H−Boc)
RT (min): 1.83

108

Reference Example 89

The following compound was obtained as described in Reference Example 79.

[Formula 109]

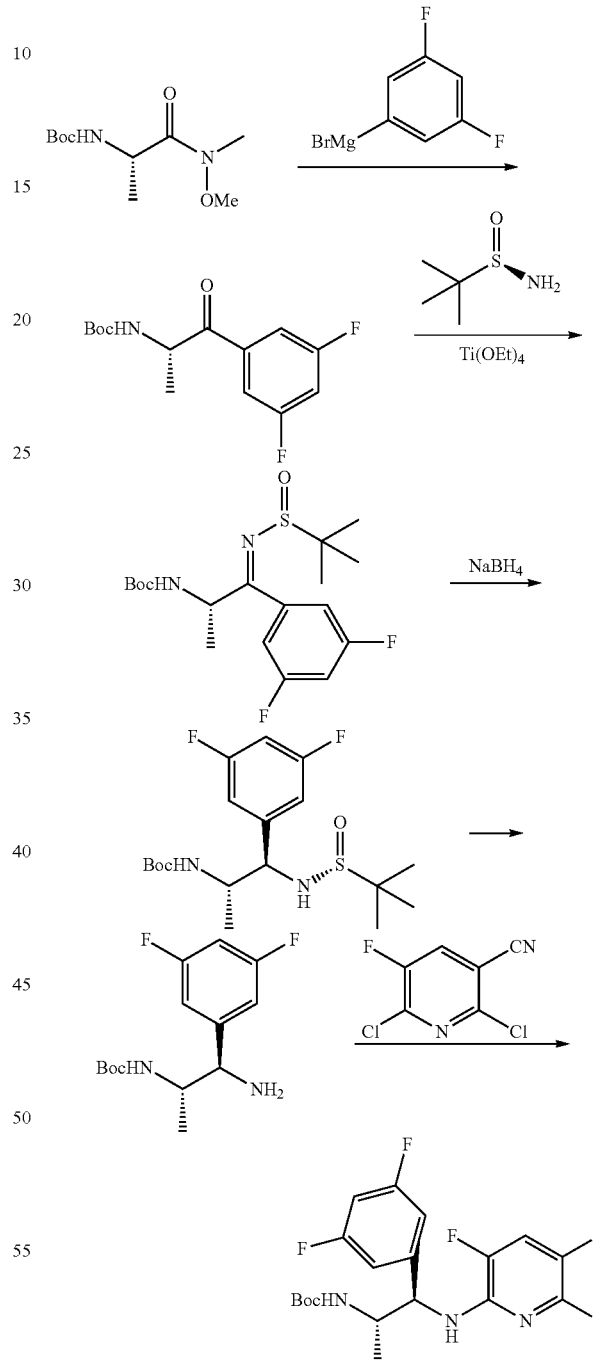

tert-Butyl ((1R,2S)-1-(3,5-difluorophenyl)-1-((R)-1,1-dimethylethylsulfinamide)propan-2-yl)carbamate MS (ESI m/z): 291 (M+H−Boc)
RT (min): 1.59

109 tert-Butyl ((1R,2S)-1-(6-chloro-5-cyano-3-fluoropyridin-2-yl)amino)-1-(3,5-difluorophenyl)propan-2-yl)carbamate $^1$H-NMR (CDCl$_3$) δ: 8.20 (1H, s), 6.82-6.71 (3H, m), 4.95 (1H, d, J=5.4 Hz), 4.32-4.18 (2H, m), 1.50 (9H, s), 1.13 (3H, d, J=6.6 Hz).
MS (ESI m/z): 341 (M+H−Boc)
RT (min): 1.83

Reference Example 90

The following compound was obtained as described in Reference Example 79.

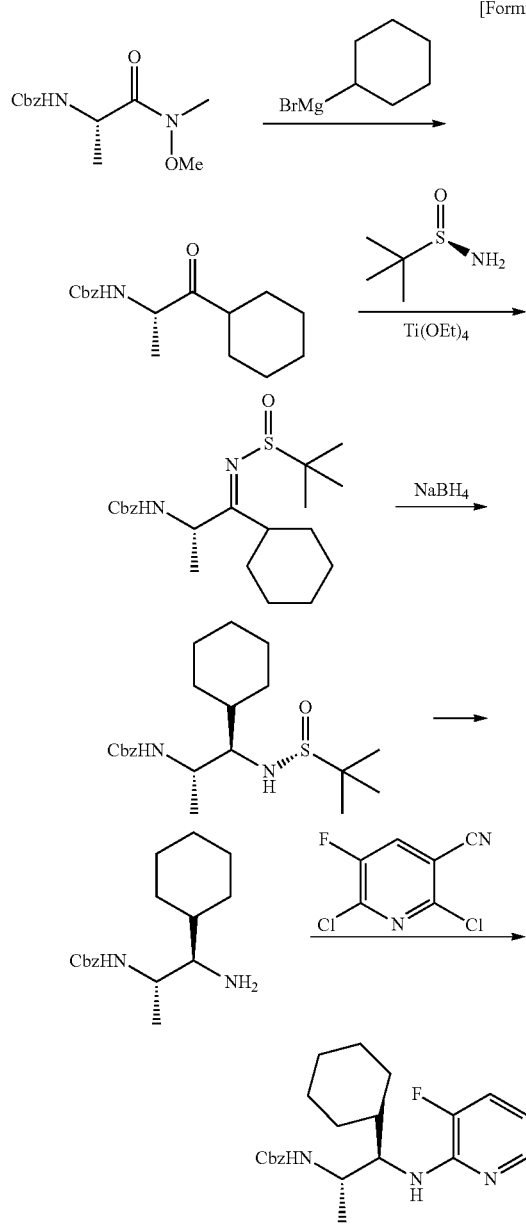

110

(S)-benzyl (1-cyclohexyl-1-oxopropan-2-yl)carbamate

MS (ESI m/z): 290 (M+H)
RT (min): 1.82

Benzyl ((1R,2S)-1-amino-1-cyclohexylpropan-2-yl)carbamate

MS (ESI m/z): 291 (M+H−Boc)
RT (min): 1.00

Benzyl ((1R,2S)-1-((6-chloro-5-cyano-3-fluoropyridin-2-yl)amino)-1-cyclohexylpropan-2-yl)carbamate MS (ESI m/z): 445 (M−H)
RT (min): 1.91

Reference Example 91

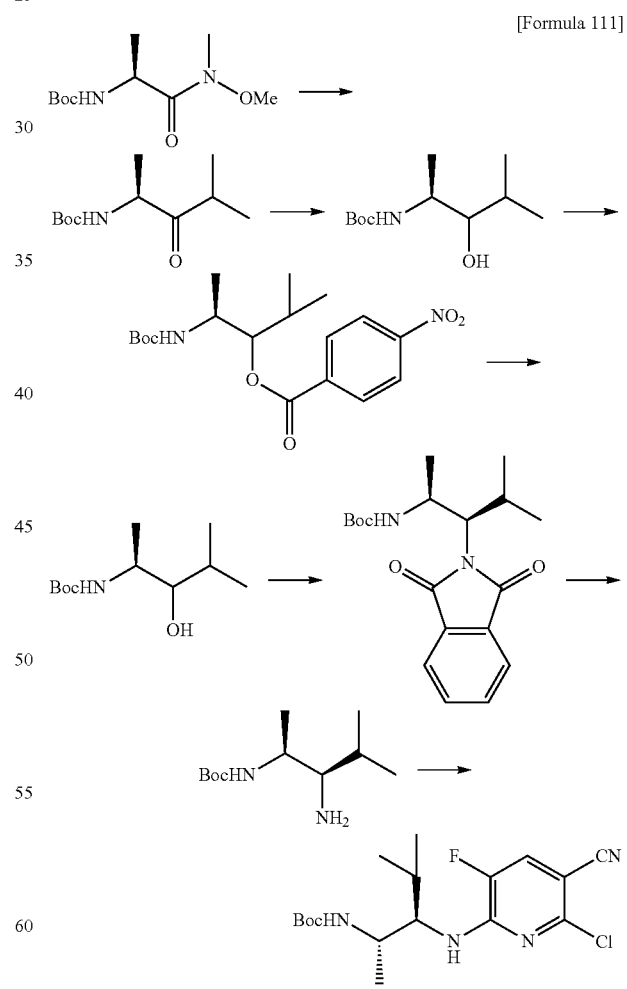

1st Step

The following compound was obtained as described in the 1st step in Reference Example 79.

S)-tert-butyl (4-methyl-3-oxopentan-2-yl)carbamate

2nd Step

Sodium borohydride (3.4 g) was added to an MeOH/isopropanol (20 ml/20 ml) solution containing (S)-tert-butyl (4-methyl-3-oxopentan-2-yl)carbamate (16 g) obtained in the 1st step, followed by stirring at room temperature for 30 minutes. Water was added to the reaction solution, followed by extraction with ethyl acetate. The organic layers were washed with saturated saline and dried over anhydrous sodium sulfate. The solvent was distilled away under reduced pressure and yellow oily matter of tert-butyl ((2S)-3-hydroxy-4-methylpentan-2-yl)carbamate (11.5 g) was thus obtained.

MS (ESI m/z): 218 (M+H)
RT (min): 1.22

3rd Step p-Nitrobenzoic acid (10.6 g), triphenylphosphine (20.8 g), and DIAD (42 ml) were added to a THF (50 ml) solution containing tert-butyl ((2S)-3-hydroxy-4-methylpentan-2-yl)carbamate (11.5 g) obtained in the 2nd step, followed by stirring at room temperature for 15 hours. The solvent was distilled away under reduced pressure and the obtained residue was purified by silica gel chromatography (hexane:ethyl acetate=1:0 to 5:1). Yellow oily matter of (2S)-2-((tert-butoxycarbonyl)amino)-4-methylpentan-3-yl 4-nitrobenzoate (10 g) was thus obtained.

MS (ESI m/z): 367 (M+H)
RT (min): 1.87

4th Step

A 1M lithium hydroxide aqueous solution (30 ml) was added to an MeOH (10 ml) solution containing (2S)-2-((tert-butoxycarbonyl)amino)-4-methylpentan-3-yl 4-nitrobenzoate (10 g) obtained in the 3rd step, followed by stirring at room temperature for 1 hour. The solvent was distilled away under reduced pressure, followed by extraction with ethyl acetate. The organic layers were washed with a saturated sodium hydrogen carbonate aqueous solution and saturated saline and dried over anhydrous sodium sulfate. The solvent was distilled away under reduced pressure. Yellow oily matter of tert-butyl ((2S)-3-hydroxy-4-methylpentan-2-yl)carbamate (5.3 g) was thus obtained.

MS (ESI m/z): 218 (M+H)
RT (min): 1.22

5th Step

Phthalimide (4.3 g), triphenylphosphine (9.6 g), and DIAD (19.2 ml) were added to a THF (40 ml) solution containing tert-butyl ((2S)-3-hydroxy-4-methylpentan-2-yl)carbamate (5.3 g) obtained in the 4th step, followed by stirring at room temperature for 16 hours. The solvent was distilled away under reduced pressure and the obtained residue was purified by silica gel chromatography (hexane:ethyl acetate=1:0 to 5:1). Yellow oily matter of tert-butyl ((2S,3R)-3-(1,3-dioxoisoindolin-2-yl)-4-methylpentan-2-yl)carbamate (3 g) was thus obtained.

$^1$H-NMR (CDCl3) δ: 7.89-7.81 (2H, m), 7.75-7.71 (2H, m), 4.44-4.24 (2H, m), 2.77-2.58 (1H, m), 1.46 (9H, s), 1.12 (6H, dd, J=24.1, 6.6 Hz), 0.86 (3H, d, J=6.6 Hz).

MS (ESI m/z): 347 (M+H)
RT (min): 1.73

6th Step

An ethanol (10 ml) solution containing tert-butyl ((2S,3R)-3-(1,3-dioxoisoindolin-2-yl)-4-methylpentan-2-yl)carbamate (3 g) obtained in the 5th step and hydrazine monohydrate (12.9 ml) was stirred at 80° C. to 90° C. for 48 hours. The solvent was distilled away under reduced pressure and an insoluble precipirate was removed. The obtained oily matter was used in the subsequent step.

tert-Butyl ((2S,3R)-3-(1,3-dioxoisoindolin-2-yl)-4-methylpentan-2-yl)carbamate

MS (ESI m/z): 217 (M+H)
RT (min): 0.75

7th Step

The following compound was obtained as described in the 6th step in Reference Example 79.

tert-Butyl ((2S,3R)-3-((6-chloro-5-cyano-3--fluoropyridin-2-yl)amino)-4-methylpentan-2-yl)carbamate $^1$H-NMR (CDCl3) δ: 7.32 (1H, d, J=9.9 Hz), 5.24 (1H, d, J=8.3 Hz), 4.74 (1H, d, J=7.6 Hz), 4.27-3.91 (2H, m), 1.95-1.77 (1H, m), 1.44 (9H, s), 1.19-0.88 (9H, m).

MS (ESI m/z): 371 (M+H)
RT (min): 1.71

Reference Example 92

[Formula 112]

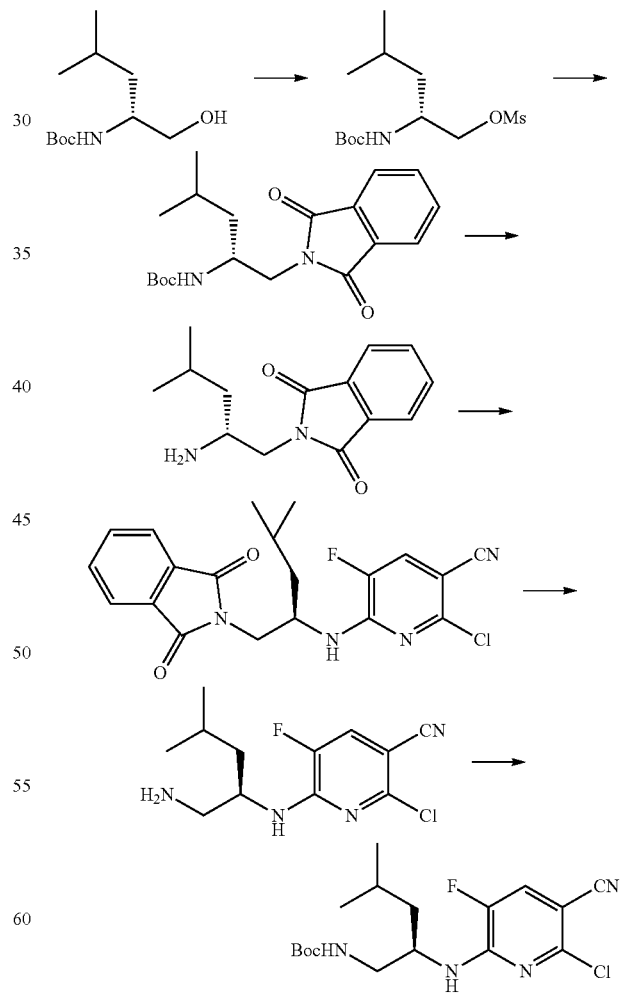

1st Step

Triethylamine (59 ml) and methanesulfonylchloride (25 ml) were added to a THF solution (200 ml) containing (R)-

113 tert-butyl (1-hydroxy-4-methylpentan-2-yl)carbamate (46.2 g) in an ice bath, followed by stirring for 0.5 hours. A saturated sodium hydrogen carbonate aqueous solution was added to the reaction solution, followed by extraction with ethyl acetate. The organic layers were dried over anhydrous sodium sulfate and the solvent was distilled away under reduced pressure. A white solid of (R)-2-((tert-butoxycarbonyl)amino)-4-methylpentyl methanesulfonate (60 g) was thus obtained.

2nd Step

Potassium phthalimide (47 g) was added to a DMF (100 ml) solution containing (R)-2-((tert-butoxycarbonyl)amino)-4-methylpentyl methanesulfonate (60 g) obtained in the 1st step, followed by stirring at 70° C. for 2 hours. The reaction solution was adjusted to room temperature and added dropwise to a saturated sodium hydrogen carbonate aqueous solution (1500 ml), followed by extraction with ethyl acetate. The organic layers were dried over anhydrous sodium sulfate and the solvent was distilled away under reduced pressure. (R)-tert-butyl (1-(1,3-dioxoindolin-2-yl)-4-methylpentan-2-yl)carbamate was thus obtained.

MS (ESI m/z): 347 (M+H)
RT (min): 1.65

3rd Step 4M hydrogen chloride/1,4-dioxane (100 ml) was added to a CHCl$_3$/MeOH (80 ml/40 ml) solution containing (R)-tert-butyl (1-(1,3-dioxoindolin-2-yl)-4-methylpentan-2-yl)carbamate obtained in the 2nd step, followed by stirring at room temperature for 6 hours. The solvent was distilled away under reduced pressure and a yellow solid of (R)-2-(2-amino-4-methylpentyl)isoindolin-1,3-dione hydrochloride (21 g) was thus obtained.

MS (ESI m/z): 247 (M+H)
RT (min): 0.75

4th Step

The following compound was obtained as described in the 7th step in Reference Example 91.

(R)-2-chloro-6-((1-(1,3-dioxoindolin-2-yl)-4-methylpentan-2-yl)amino)-5-fluoronicotinonitrile MS (ESI m/z): 401 (M+H)
RT (min): 1.73

5th Step

The following compound was obtained as described in the 6th step in Reference Example 91.

(R)-6-((1-amino-4-methylpentan-2-yl)amino)-2-chloro-5-fluoronicotinonitrile

MS (ESI m/z): 271 (M+H)
RT (min): 0.96

6th Step

The following compound was obtained as described in the 1st step in Reference Example 38.

(R)-tert-butyl (2-((6-chloro-5-cyano-3-fluoropyridin-2-yl)amino)-4-methylpentyl)carbamate $^1$H-NMR (CDCl$_3$,300 MHz) δ: 7.27 (d, 1H, J=9.3 Hz), 5.74 (d, 1H, J=5.9 Hz), 4.79 (br, 1H), 4.42-4.24 (m, 1H), 3.42-3.22 (m, 2H), 1.72-1.30 (m, 12H), 1.00-0.92 (m, 6H)
MS (ESI m/z): 371 (M+H)
RT (min): 1.81

Reference Example 93

The following compound was obtained as described in Reference Example 91.

114

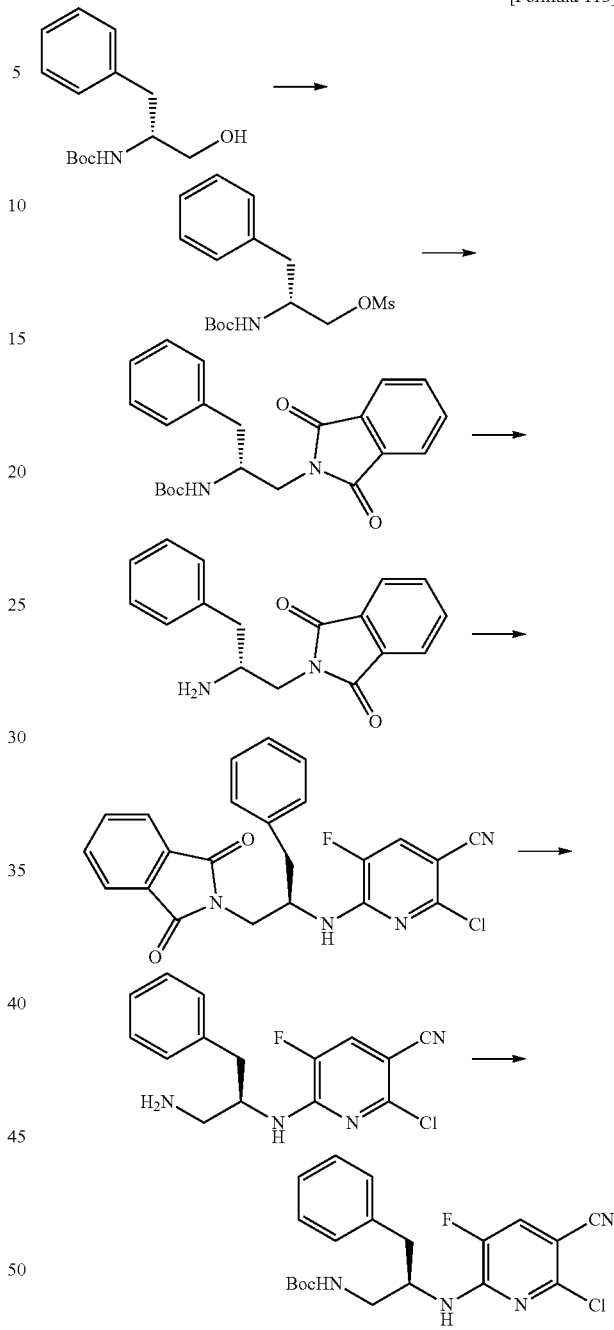

[Formula 113]

(R)-tert-butyl (1-(1,3-dioxoisoindolin-2-yl)-3-phenylpropan-2-yl)carbamate

MS (ESI m/z): 281 (M+H–Boc)
RT (min): 1.64

(R)-2-(2-amino-3-phenylpropyl)isoindolin-1,3-dione

MS (ESI m/z): 281 (M+H)
RT (min): 0.85

(R)-2-chloro-6-((1-(1,3-dioxoisoindolin-2-yl)-3-phenylpropan-2-yl)amino)-5-fluoronicotinonitrile MS (ESI m/z): 435 (M+H)
RT (min): 1.70

(R)-6-((1-amino-3-phenylpropan-2-yl)amino)-2-chloro-5-fluoronicotinonitrile

MS (ESI m/z): 305 (M+H)
RT (min): 0.99

(R)-tert-butyl (2-((6-chloro-5-cyano-3-fluoropyridin-2-yl)amino)-3-phenylpropyl)carbamate $^1$H-NMR (CDCl3) δ: 7.37-7.18 (6H, m), 6.55 (1H, d, J=5.3 Hz), 4.83-4.70 (1H, m), 4.41-4.26 (1H, m), 3.43-3.21 (2H, m), 3.10 (1H, dd, J=13.5, 5.0 Hz), 2.73 (1H, dd, J=13.7, 8.8 Hz), 1.42 (9H, s).
MS (ESI m/z): 405 (M+H)
RT (min): 1.78

Reference Example 94

The following compound was obtained as described in Reference Example 91.

[Formula 114]

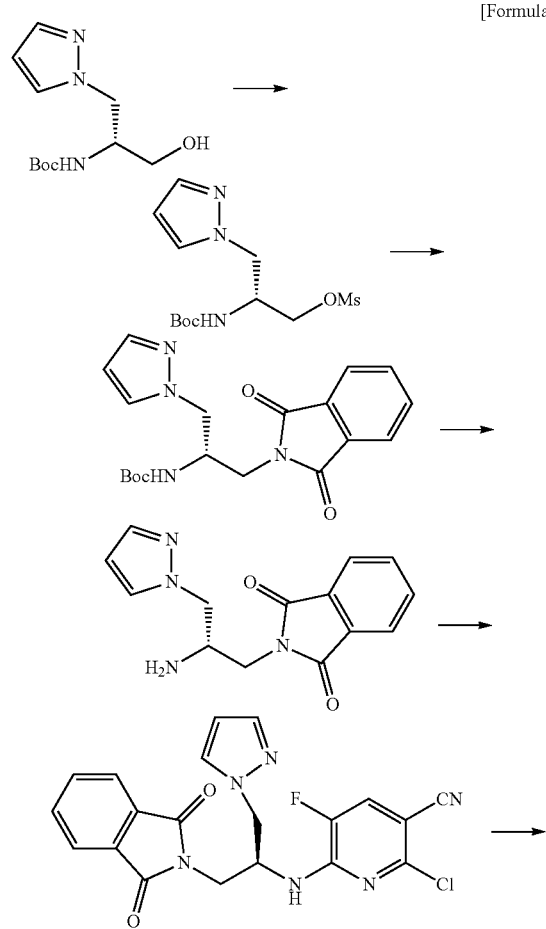

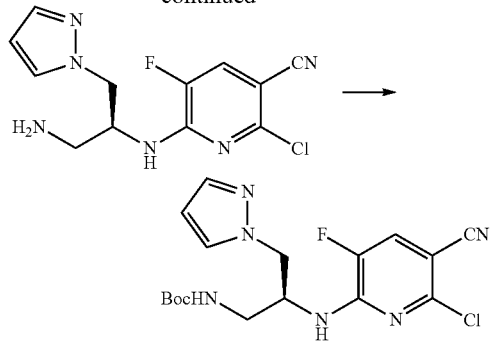

-continued (S)-tert-butyl (1-(1,3-dioxoisoindolin-2-yl)-3-(pyrazol-1-yl)propan-2-yl)carbamate MS (ESI m/z): 371 (M+H)
RT (min): 1.34

(S)-2-(2-amino-3-(pyrazol-1-yl)propyl)isoindolin-1,3-dione

MS (ESI m/z): 271 (M+H)
RT (min): 0.57

(S)-2-chloro-6-((1-(1,3-dioxoisoindolin-2-yl)-3-(pyrazol-1-yl)propan-2-yl)amino)-5-fluoronicotinonitrile MS (ESI m/z): 425 (M+H)
RT (min): 1.38

(S)-6-(1-amino-3-(pyrazol-1-yl)propan-2-yl)amino)-2-chloro-5-fluoronicotinonitrile MS (ESI m/z): 295 (M+H)
RT (min): 0.75

(S)-tert-butyl (2-((6-chloro-5-cyano-3-fluoropyridin-2-yl)amino)-3-(pyrazol-1-yl)propyl)carbamate MS (ESI m/z): 395 (M+H)
RT (min): 1.42

Reference Example 95

The following compound was synthesized with reference to WO2010/097248.

[Formula 115]

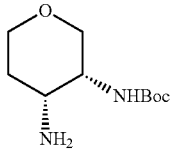

tert-Butyl ((3R,4R)-4-aminotetrahydro-2H-pyran-3-yl)carbamate

Reference Example 96

The following compound was obtained as described in Reference Example 91.

117

[Formula 116]

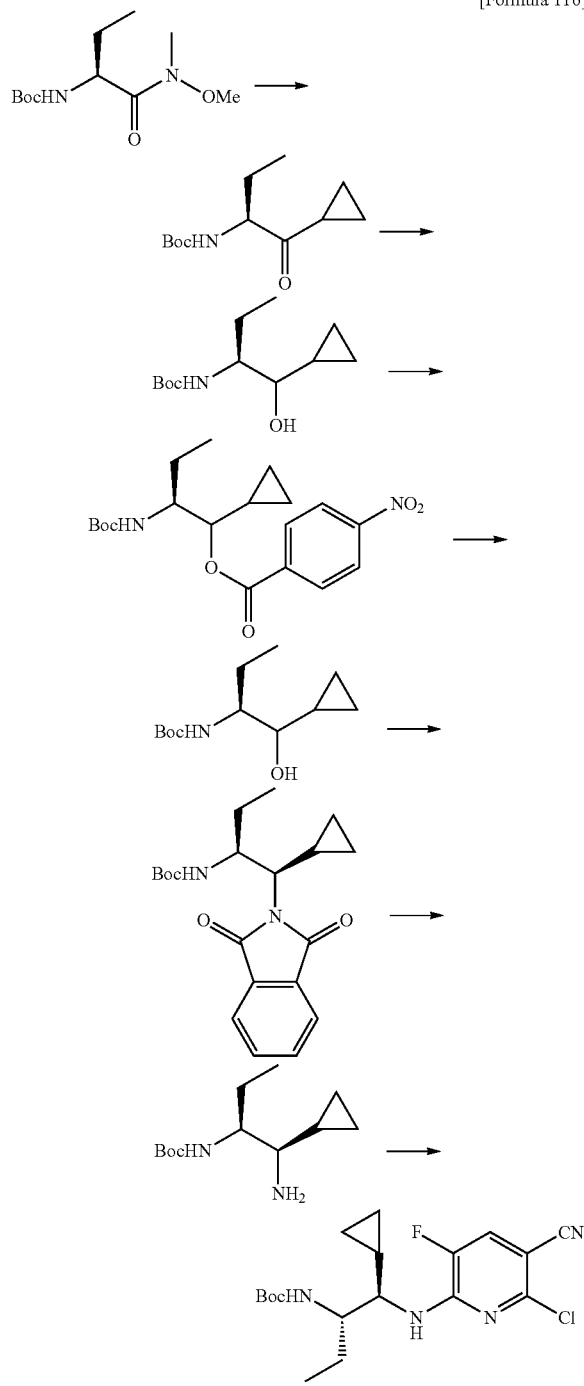

(2S)-2-((tert-butoxycarbonyl)amino)-1-cyclopropyl-
butyl 4-nitrobenzoate

MS (ESI m/z): 379 (M+H)
RT (min): 1.80 tert-Butyl ((1R,2S)-1-cyclopropyl-1-(1,3-dioxoisoin-
dolin-2-yl)butan-2-yl)carbamate MS (ESI m/z): 359 (M+H)
RT (min): 1.69 tert-Butyl ((1R,2S)-1-amino-1-cyclopropylbutan-2-
yl)carbamate

MS (ESI m/z): 229 (M+H)
RT (min): 0.79 tert-Butyl ((1R,2S)-1-((6-chloro-5-cyano-3-fluoropyridin-2-
yl)amino)-1-cyclopropylbutan-2-yl)carbamate $^1$H-NMR (CDCl$_3$) δ: 7.32 (1H, d, J=9.9 Hz), 6.22 (1H, Br), 4.60 (1H, Br), 3.84-3.62 (2H, m), 1.79-1.57 (2H, m), 1.48 (9H, t, J=9.2 Hz), 1.01 (3H, t, J=7.3 Hz), 0.95-0.83 (1H, m), 0.70-0.35 (4H, m)

MS (ESI m/z): 383 (M+H).
RT (min): 1.79

Reference Example 97

The following compound was obtained as described in Reference Example 91.

[Formula 117]

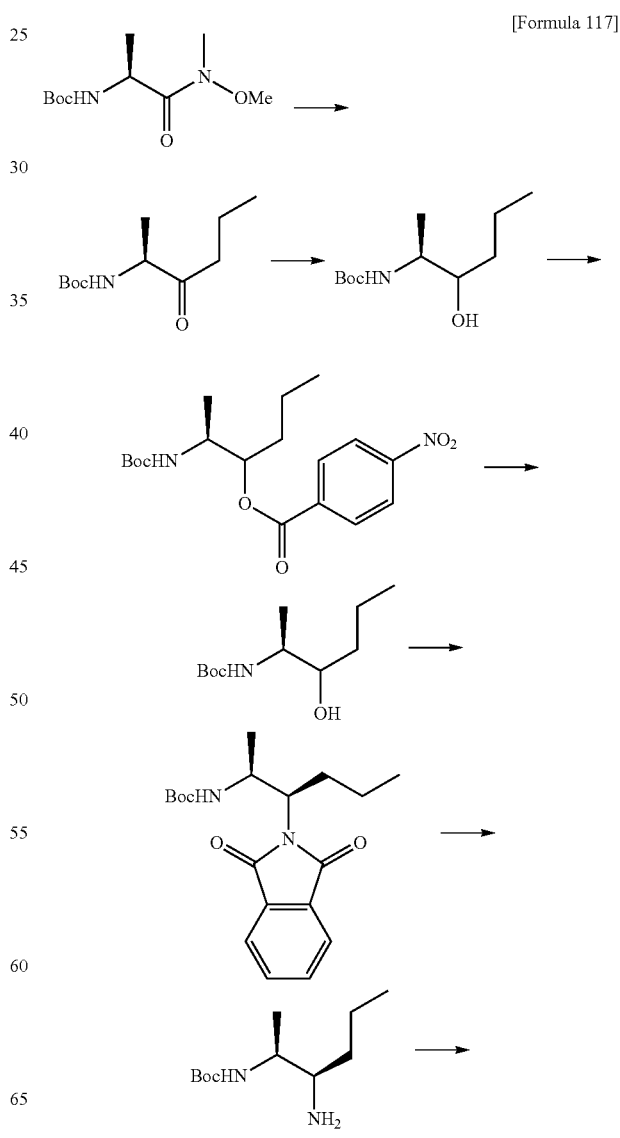

-continued

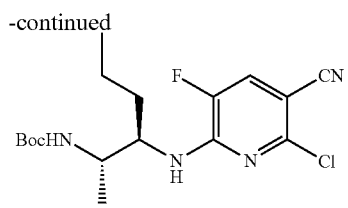

(S)-tert-butyl (3-oxohexan-2-yl)carbamate

MS (ESI m/z): 216 (M+H)
RT (min): 1.37

((2S)-3-hydroxyhexan-2-yl)carbamate

MS (ESI m/z): 218 (M+H)
RT (min): 1.27

(2S)-2-((tert-butoxycarbonyl)amino)hexan-3-yl 4-nitrobenzoate

MS (ESI m/z): 367 (M+H)
RT (min): 1.86 tert-Butyl ((2S)-3-hydroxyhexan-2-yl)carbamate

MS (ESI m/z): 218 (M+H)
RT (min): 1.27 tert-Butyl ((2S,3R)-3-(1,3-dioxoisoindolin-2-yl)hexan-2-yl)carbamate $^1$H-NMR (CDCl$_3$, 300 MHz) δ: 7.88-7.79 (m, 2H), 7.76-7.65 (m, 2H), 4.62-4.42 (m, 1H), 4.33-4.00 (m, 2H), 2.40-2.20 (m, 1H), 1.81-1.62 (m, 1H), 1.44 (s, 9H), 1.35-1.20 (m, 2H), 1.11 (d, 3H, J=6.6 Hz), 0.89 (t, 3H, J=7.3 Hz)
MS (ESI m/z): 347 (M+H)
RT (min): 1.70 tert-Butyl ((2S,3R)-3-aminohexan-2-yl)carbamate

MS (ESI m/z): 217 (M+H)
RT (min): 0.79

7th Step tert-Butyl ((2S,3R)-3-((6-chloro-5-cyano-3-fluoropyridin-2-yl)amino)hexan-2-yl)carbamate $^1$H-NMR (CDCl$_3$, 300 MHz) δ: 7.29 (d, 1H, J=9.3 Hz), 5.76 (d, 1H, J=7.3 Hz), 4.67 (d, 1H, J=6.6 Hz), 4.36-4.20 (m, 1H), 3.96-3.80 (m, 1H), 1.70-1.29 (m, 13H), 1.17 (d, 3H, J=6.6 Hz), 0.94 (t, 3H, J=7.3 Hz)
MS (ESI m/z): 371 (M+H)
RT (min): 1.78

Reference Example 98

The following compound was obtained as described in Reference Example 91.

[Formula 118]

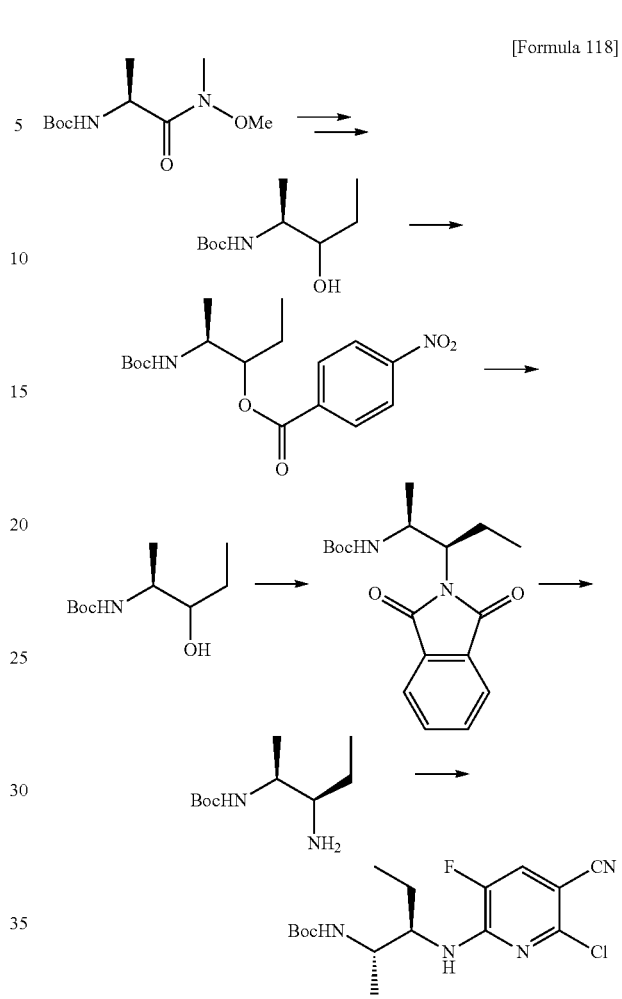

tert-Butyl ((2S)-3-hydroxypentan-2-yl)carbamate

MS (ESI m/z): 204 (M+H)
RT (min): 1.12

(2S)-2-((tert-butoxycarbonyl)amino)pentan-3-yl 4-nitrobenzoate

MS (ESI m/z): 353 (M+H)
RT (min): 1.75 tert-Butyl ((2S)-3-hydroxypentan-2-yl)carbamate

MS (ESI m/z): 204 (M+H)
RT (min): 1.13 tert-Butyl ((2S,3R)-3-(1,3-dioxoisoindolin-2-yl)pentan-2-yl)carbamate $^1$H-NMR (CDCl$_3$, 300 MHz) δ: 7.84 (dd, 2H, J=3.3, 5.4 Hz), 7.72 (dd, 2H, J=3.3, 5.4 Hz), 4.60-4.50 (m, 1H), 4.35-4.20 (m, 1H), 4.10-3.95 (m, 1H), 2.38-2.17 (m, 1H), 1.93-1.80 (m, 1H), 1.43 (s, 9H), 1.11 (d, 3H, J=6.6 Hz), 0.86 (d, 3H, J=7.3 Hz)
MS (ESI m/z): 333 (M+H)
RT (min): 1.56

121 tert-Butyl ((2S,3R)-3-aminopentan-2-yl)carbamate

MS (ESI m/z): 203 (M+H)
RT (min): 0.69 tert-Butyl ((2S,3R)-3-((6-chloro-5-cyano-3-fluoropyridin-2-yl)amino)pentan-2-yl)carbamate $^1$H-NMR (CDCl$_3$, 300 MHz) δ: 7.29 (d, 1H, J=9.9 Hz), 5.76 (d, 1H, J=6.6 Hz), 4.68 (d, 1H, J=6.6 Hz), 4.26-4.14 (m, 1H), 3.98-3.84 (m, 1H), 1.80-1.62 (m, 1H), 1.49-1.36 (m, 10H), 1.17 (d, 3H, J=7.2 Hz), 0.97 (t, 3H, J=7.7 Hz)
MS (ESI m/z): 357 (M+H)
RT (min): 1.67

Reference Example 99

The following compound was obtained as described in Reference Example 91.

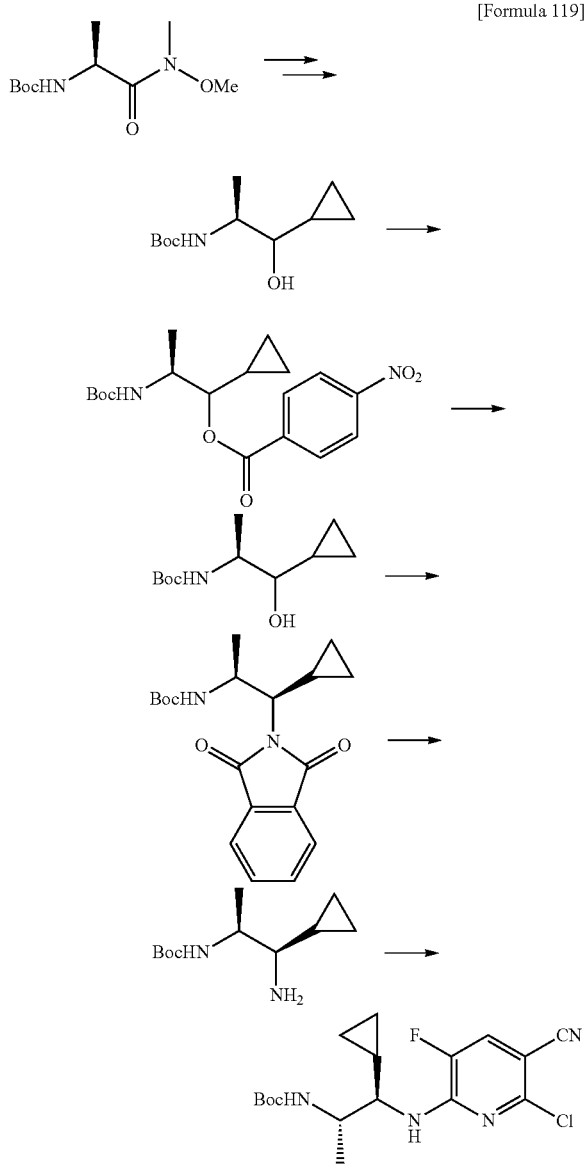

[Formula 119]

122 tert-Butyl ((2S)-1-cyclopropyl-1-hydroxypropan-2-yl)carbamate

MS (ESI m/z): 216 (M+H)
RT (min): 1.14

(2S)-2-((tert-butoxycarbonyl)amino)-1-cyclopropylpropyl-4-nitrobenzoate

MS (ESI m/z): 365 (M+H)
RT (min): 1.76 tert-Butyl ((2S)-1-cyclopropyl-1-hydroxypropan-2-yl)carbamate

MS (ESI m/z): 216 (M+H)
RT (min): 1.14 tert-Butyl ((1R,2S)-1-cyclopropyl-1-(1,3-dioxoindolin-2-yl)propan-2-yl)carbamate $^1$H-NMR (CDCl$_3$, 300 MHz) δ: 7.87-7.68 (m, 4H), 4.62 (br, 1H), 4.45-4.28 (m, 1H), 3.31 (dd, 1H, J=10.7, 6.8 Hz), 2.25-1.75 (m, 1H), 1.40 (s, 9H), 1.18 (t, 3H, J=6.9 Hz), 0.85-0.72 (m, 1H), 0.52-0.38 (m, 2H), 0.16-0.04 (m, 1H)
MS (ESI m/z): 345 (M+H)
RT (min): 1.60 tert-Butyl ((1R,2S)-1-((6-chloro-5-cyano-3-fluoropyridin-2-yl)amino)-1-cyclopropylpropan-2-yl)carbamate $^1$H-NMR (CDCl$_3$, 300 MHz) δ: 7.32-7.28 (m, 1H), 6.20 (br, 1H), 4.90-4.74 (m, 1H), 4.12-3.98 (m, 1H), 3.68-3.50 (m, 1H), 1.44 (s, 9H), 1.27 (t, 3H, J=3.3 Hz), 0.98-0.85 (m, 1H), 0.73-0.40 (m, 4H)
MS (ESI m/z): 369 (M+H)
RT (min): 1.72

Reference Example 100

The following compound was obtained as described in Reference Example 91.

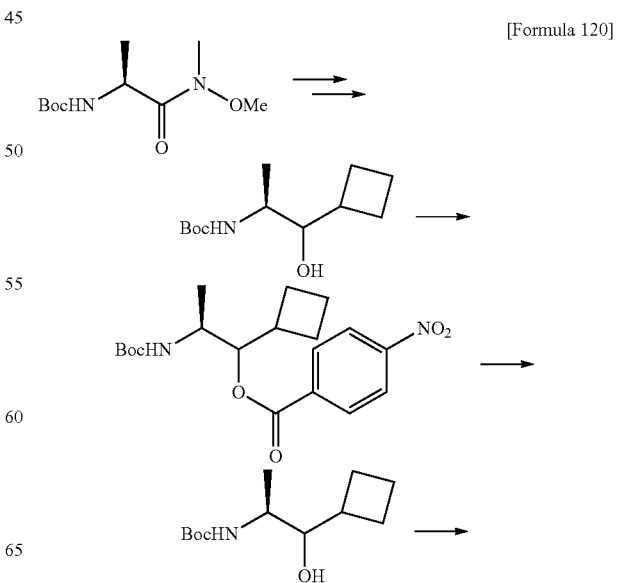

[Formula 120]

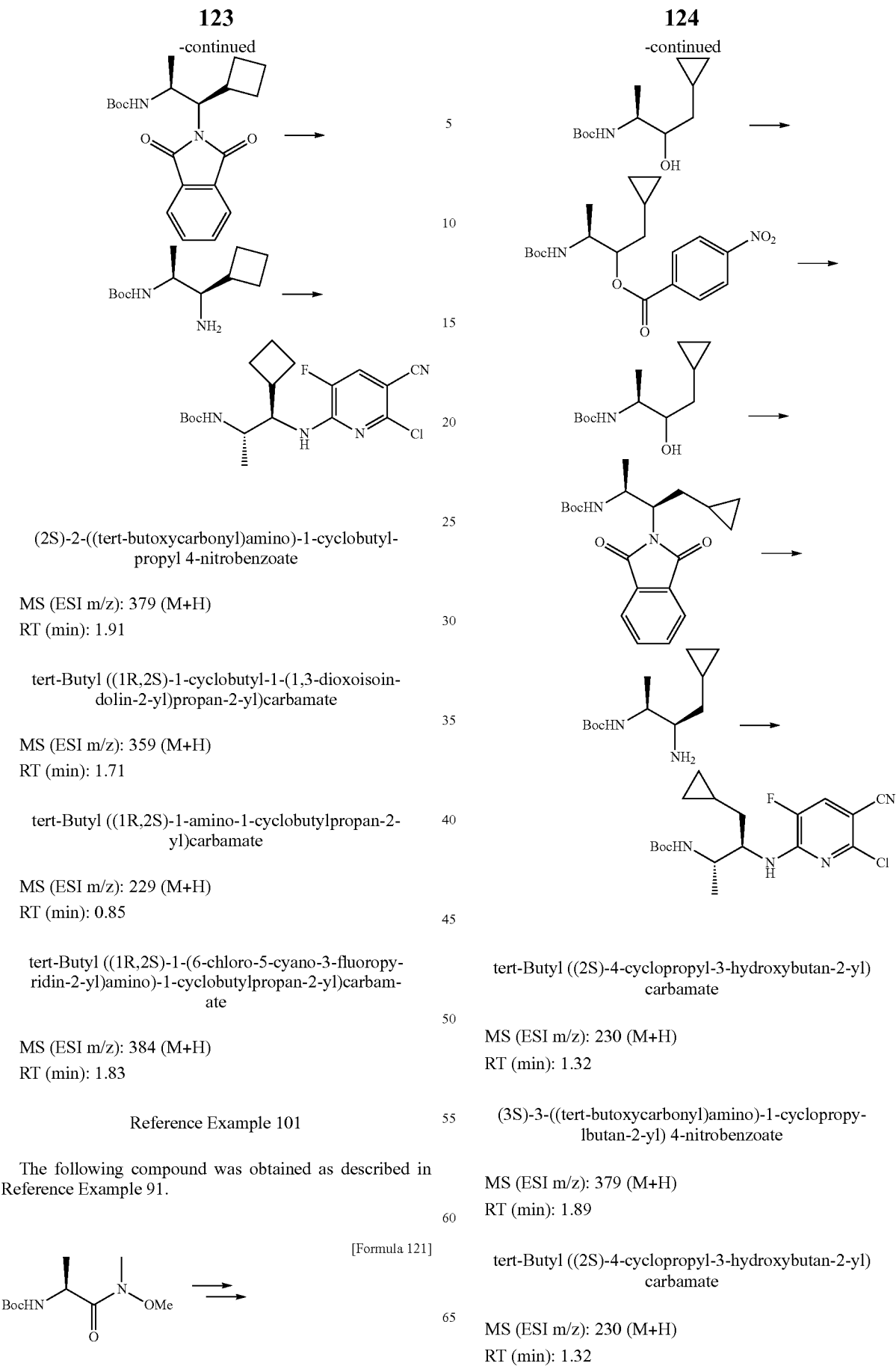

(2S)-2-((tert-butoxycarbonyl)amino)-1-cyclobutyl-propyl 4-nitrobenzoate

MS (ESI m/z): 379 (M+H)
RT (min): 1.91 tert-Butyl ((1R,2S)-1-cyclobutyl-1-(1,3-dioxoisoindolin-2-yl)propan-2-yl)carbamate MS (ESI m/z): 359 (M+H)
RT (min): 1.71 tert-Butyl ((1R,2S)-1-amino-1-cyclobutylpropan-2-yl)carbamate

MS (ESI m/z): 229 (M+H)
RT (min): 0.85 tert-Butyl ((1R,2S)-1-(6-chloro-5-cyano-3-fluoropyridin-2-yl)amino)-1-cyclobutylpropan-2-yl)carbamate MS (ESI m/z): 384 (M+H)
RT (min): 1.83

Reference Example 101

The following compound was obtained as described in Reference Example 91.

[Formula 121]

tert-Butyl ((2S)-4-cyclopropyl-3-hydroxybutan-2-yl)carbamate

MS (ESI m/z): 230 (M+H)
RT (min): 1.32

(3S)-3-((tert-butoxycarbonyl)amino)-1-cyclopropylbutan-2-yl) 4-nitrobenzoate

MS (ESI m/z): 379 (M+H)
RT (min): 1.89 tert-Butyl ((2S)-4-cyclopropyl-3-hydroxybutan-2-yl)carbamate

MS (ESI m/z): 230 (M+H)
RT (min): 1.32

125 tert-Butyl ((2S,3R)-4-cyclopropyl-3-(1,3-dioxoisoindolin-2-yl)butan-2-yl)carbamate ¹H-NMR (CDCl₃, 300 MHz) δ: 7.87-7.69 (m, 4H), 5.81-5.66 (m, 1H), 5.00-4.82 (m, 2H), 4.58-4.46 (br, 1H), 4.33-4.06 (m, 2H), 2.55-1.80 (m, 2H), 1.44 (s, 9H), 1.34-1.26 (m, 2H), 1.11 (d, 3H, J=6.6 Hz)

MS (ESI m/z): 359 (M+H)

RT (min): 1.70 tert-Butyl ((2S,3R)-3-amino-4-cyclopropylbutan-2-yl)carbamate

MS (ESI m/z): 229 (M+H)

RT (min): 0.89 tert-Butyl ((2S,3R)-3-((6-chloro-5-cyano-3-fluoropyridin-2-yl)amino)-4-cyclopropylbutan-2-yl)carbamate ¹H-NMR (CDCl₃, 300 MHz) δ: 7.29 (d, 1H, J=9.9 Hz), 5.94-5.74 (m, 1H), 5.06-4.95 (m, 2H), 4.62 (br, 1H), 4.34-4.25 (m, 1H), 3.96-3.87 (m, 1H), 2.17-2.08 (m, 2H), 1.78-1.67 (m, 1H), 1.55-1.46 (m, 2H), 1.44 (s, 9H), 1.18 (d, 3H, J=7.3 Hz)

MS (ESI m/z): 383 (M+H)

RT (min): 1.77

Reference Example 102

The following compound was obtained as described in Reference Example 91.

[Formula 122]

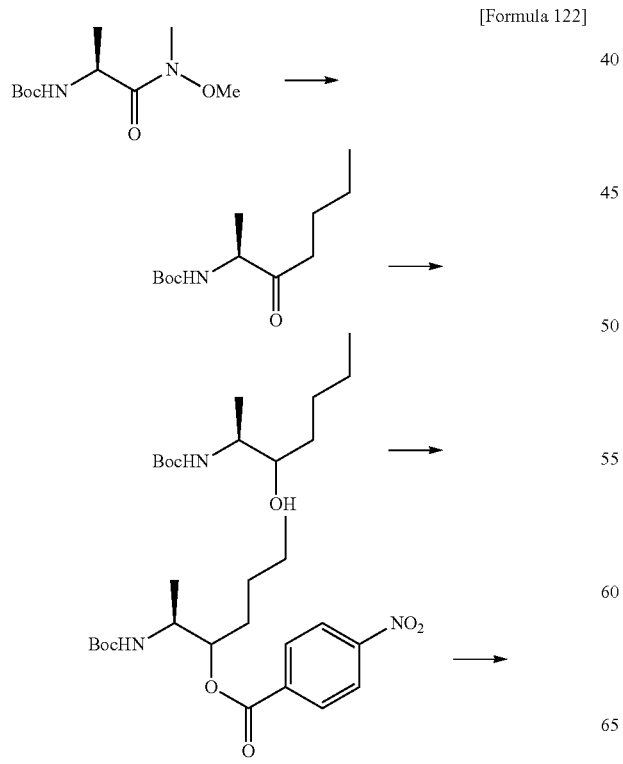

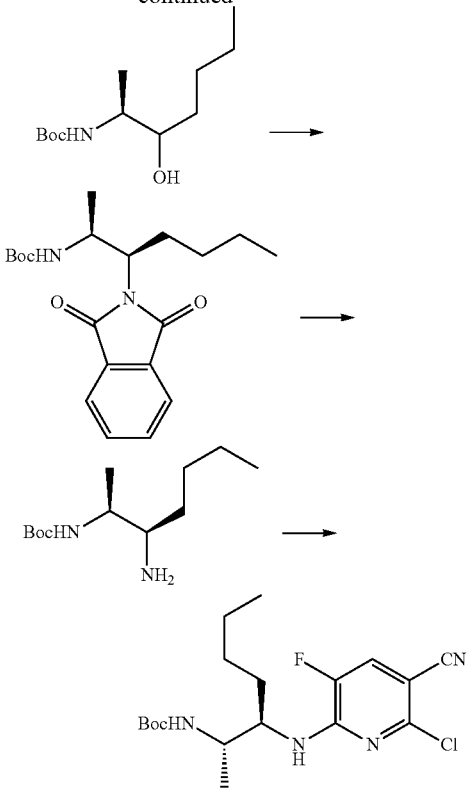

(S)-tert-butyl (3-oxoheptan-2-yl)carbamate

MS (ESI m/z): 230 (M+H)

RT (min): 1.53 tert-Butyl ((2S)-3-hydroxyheptan-2-yl)carbamate

MS (ESI m/z): 232 (M+H)

RT (min): 1.40

(2S)-2-((tert-butoxycarbonyl)amino)heptan-3-yl 4-nitrobenzoate

MS (ESI m/z): 381 (M+H)

RT (min): 1.96 tert-Butyl ((2S)-3-hydroxyheptan-2-yl)carbamate

MS (ESI m/z): 232 (M+H)

RT (min): 1.43 tert-Butyl ((2S,3R)-3-(1,3-dioxoisoindolin-2-yl)heptan-2-yl)carbamate

¹H-NMR (CDCl₃, 300 MHz) δ: 7.87-7.79 (m, 2H), 7.76-7.68 (m, 2H), 4.53 (br, 1H), 4.32-3.99 (m, 2H), 2.40-2.17 (m, 1H), 1.86-1.69 (m, 1H), 1.44 (s, 9H), 1.36-1.04 (m, 7H), 0.83 (t, 3H, J=7.2 Hz)

MS (ESI m/z): 361 (M+H)

RT (min): 1.81 tert-Butyl ((2S,3R)-3-aminoheptan-2-yl)carbamate

MS (ESI m/z): 231 (M+H)
RT (min): 0.89 tert-Butyl ((2S,3R)-3-((6-chloro-5-cyano-3-fluoropyridin-2-yl)amino)heptan-2-yl)carbamate ¹H-NMR (CDCl₃, 300 MHz) δ: 7.29 (d, 1H, J=9.9 Hz), 5.74 (d, 1H, J=7.3 Hz), 4.68 (d, 1H, J=6.6 Hz), 4.34-4.18 (m, 1H), 3.97-3.80 (m, 1H), 1.71-1.22 (m, 15H), 1.17 (t, 3H, J=6.6 Hz), 0.89 (t, 3H, J=6.3 Hz)
MS (ESI m/z): 385 (M+H)
RT (min): 1.87

Reference Example 103

The following compound was obtained as described in Reference Example 91.

[Formula 123]

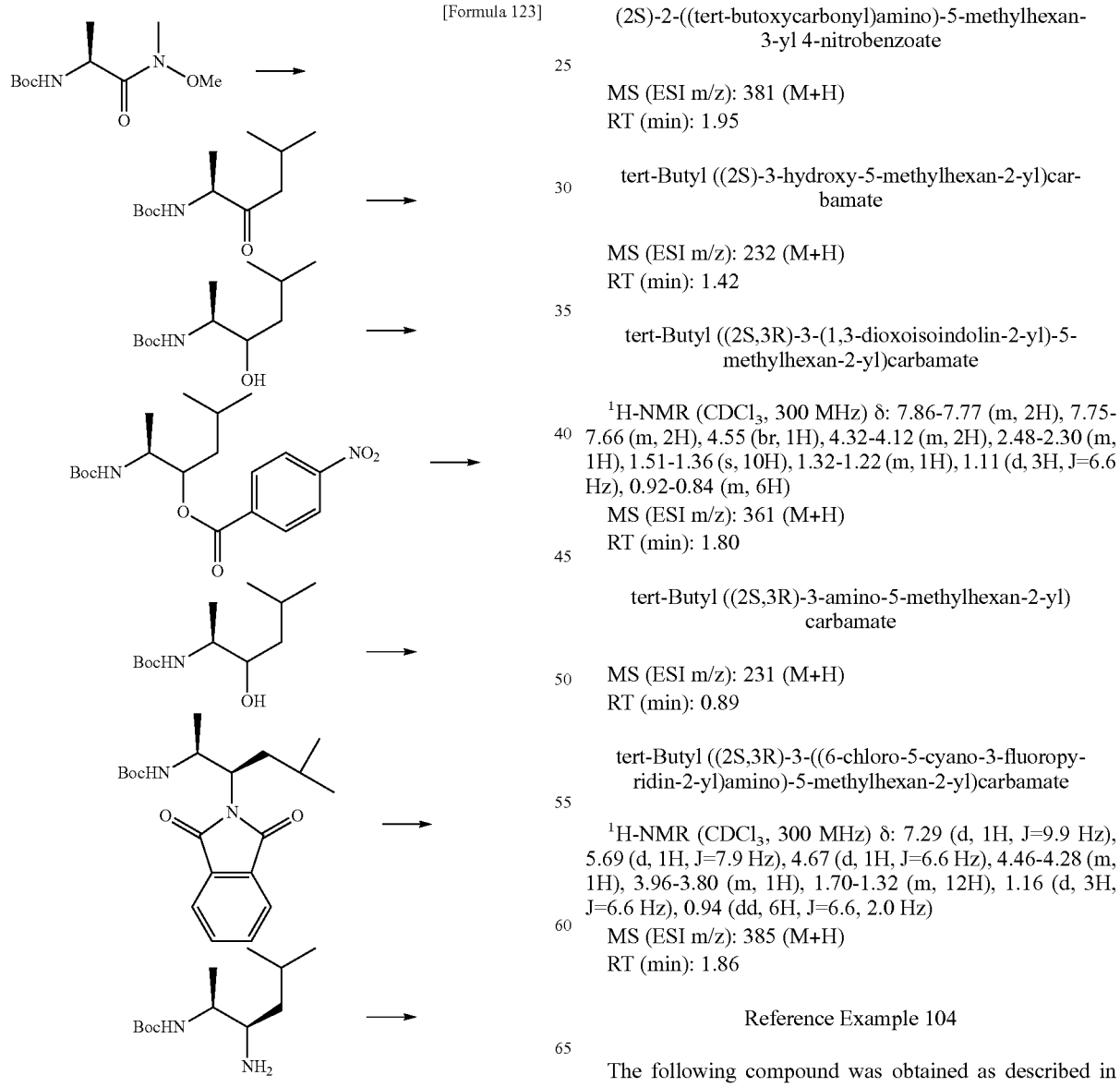

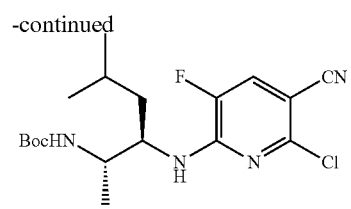

(S)-tert-butyl (5-methyl-3-oxohexan-2-yl)carbamate

MS (ESI m/z): 230 (M+H)
RT (min): 1.53 tert-Butyl ((2S)-3-hydroxy-5-methylhexan-2-yl)carbamate

MS (ESI m/z): 232 (M+H)
RT (min): 1.42

(2S)-2-((tert-butoxycarbonyl)amino)-5-methylhexan-3-yl 4-nitrobenzoate

MS (ESI m/z): 381 (M+H)
RT (min): 1.95 tert-Butyl ((2S)-3-hydroxy-5-methylhexan-2-yl)carbamate

MS (ESI m/z): 232 (M+H)
RT (min): 1.42 tert-Butyl ((2S,3R)-3-(1,3-dioxoisoindolin-2-yl)-5-methylhexan-2-yl)carbamate

¹H-NMR (CDCl₃, 300 MHz) δ: 7.86-7.77 (m, 2H), 7.75-7.66 (m, 2H), 4.55 (br, 1H), 4.32-4.12 (m, 2H), 2.48-2.30 (m, 1H), 1.51-1.36 (s, 10H), 1.32-1.22 (m, 1H), 1.11 (d, 3H, J=6.6 Hz), 0.92-0.84 (m, 6H)
MS (ESI m/z): 361 (M+H)
RT (min): 1.80 tert-Butyl ((2S,3R)-3-amino-5-methylhexan-2-yl)carbamate

MS (ESI m/z): 231 (M+H)
RT (min): 0.89 tert-Butyl ((2S,3R)-3-((6-chloro-5-cyano-3-fluoropyridin-2-yl)amino)-5-methylhexan-2-yl)carbamate ¹H-NMR (CDCl₃, 300 MHz) δ: 7.29 (d, 1H, J=9.9 Hz), 5.69 (d, 1H, J=7.9 Hz), 4.67 (d, 1H, J=6.6 Hz), 4.46-4.28 (m, 1H), 3.96-3.80 (m, 1H), 1.70-1.32 (m, 12H), 1.16 (d, 3H, J=6.6 Hz), 0.94 (dd, 6H, J=6.6, 2.0 Hz)
MS (ESI m/z): 385 (M+H)
RT (min): 1.86

Reference Example 104

The following compound was obtained as described in Reference Example 91.

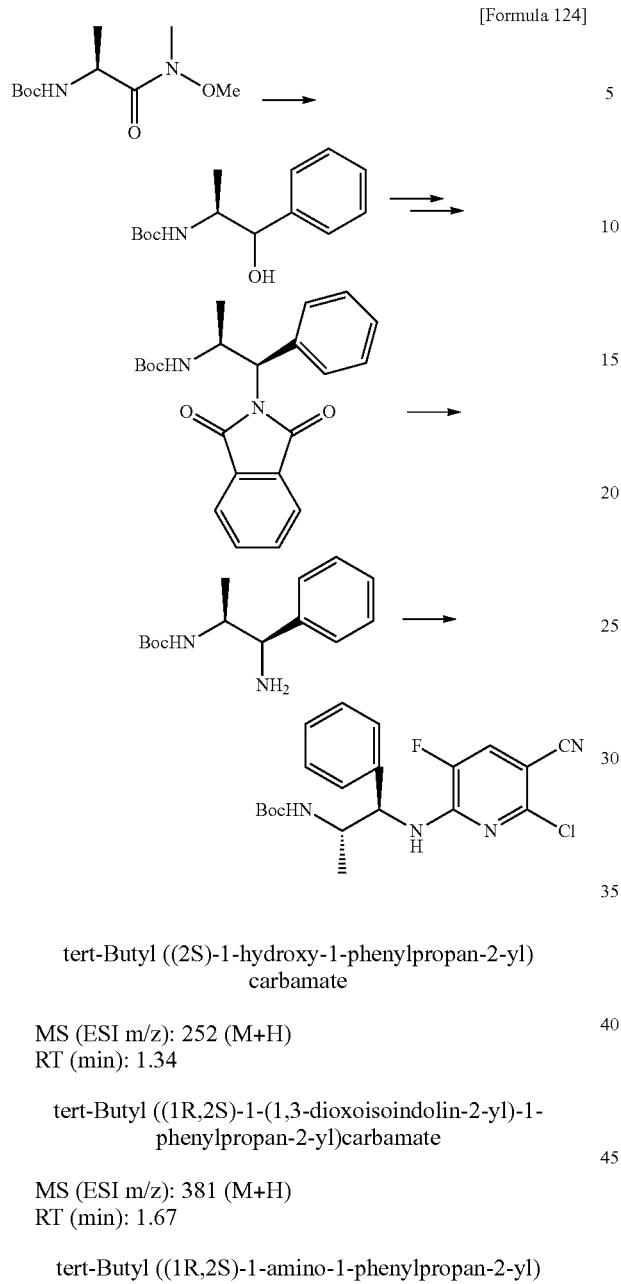
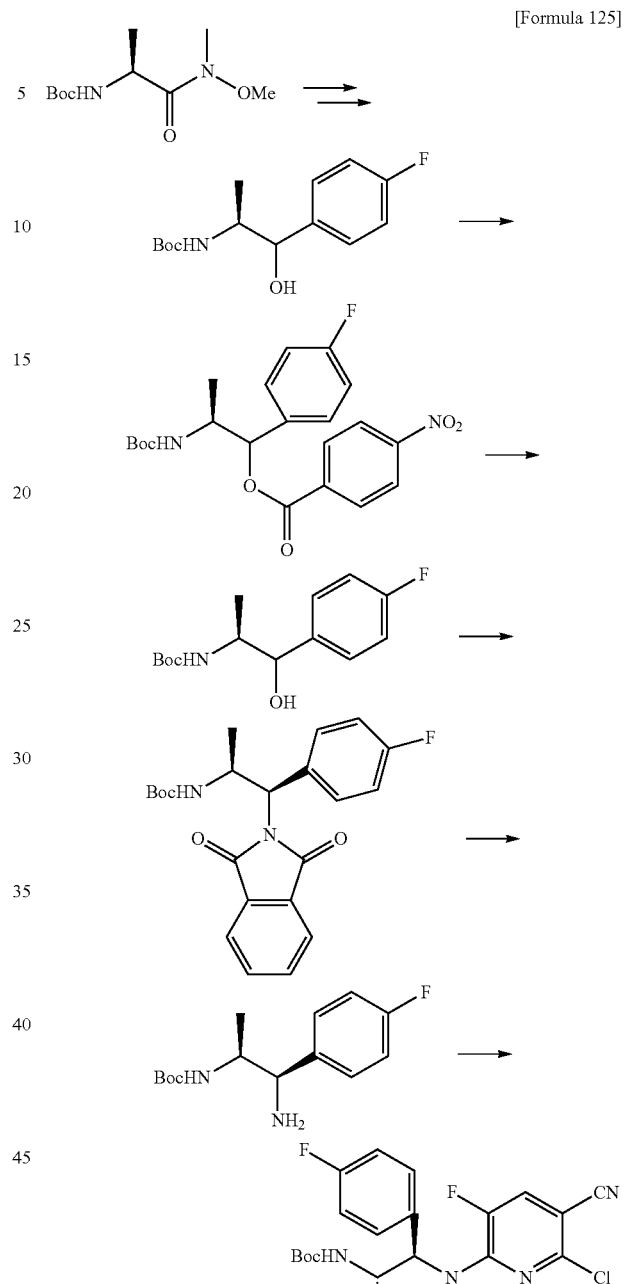

tert-Butyl ((2S)-1-hydroxy-1-phenylpropan-2-yl)carbamate

MS (ESI m/z): 252 (M+H)
RT (min): 1.34 tert-Butyl ((1R,2S)-1-(1,3-dioxoisoindolin-2-yl)-1-phenylpropan-2-yl)carbamate

MS (ESI m/z): 381 (M+H)
RT (min): 1.67 tert-Butyl ((1R,2S)-1-amino-1-phenylpropan-2-yl)carbamate

MS (ESI m/z): 251
RT (min): 0.86 tert-Butyl ((1R,2S)-1-(6-chloro-5-cyano-3-fluoropyridin-2-yl)amino)-1-phenylpropan-2-yl)carbamate $^1$H-NMR (CDCl$_3$, 300 MHz) δ: 7.95 (br, 1H), 7.42-7.19 (m, 6H), 5.04 (d, 1H, J=6.3 Hz), 4.37-4.20 (m, 2H), 1.49 (s, 9H), 1.13 (d, 3H, J=6.3 Hz)
MS (ESI m/z): 405 (M+H)
RT (min): 1.96

Reference Example 105

The following compound was obtained as described in Reference Example 91.

tert-Butyl ((2S)-1-(4-fluorophenyl)-1-hydroxypropan-2-yl)carbamate

MS (ESI m/z): 270 (M+H)
RT (min): 1.57

(2S)-2-((tert-butoxycarbonyl)amino)-1-(4-fluorophenyl)propyl-4-nitrobenzoate

MS (ESI m/z): 419 (M+H)
RT (min): 1.85 tert-Butyl ((2S)-1-(4-fluorophenyl)-1-hydroxypropan-2-yl)carbamate

MS (ESI m/z): 270 (M+H)
RT (min): 1.57 tert-Butyl ((1R,2S)-1-(1,3-dioxoisoindolin-2-yl)-1-(4-fluorophenyl)propan-2-yl)carbamate MS (ESI m/z): 399 (M+H)
RT (min): 1.74 tert-Butyl ((1R,2S)-1-amino-1-(4-fluorophenyl)propan-2-yl)carbamate

MS (ESI m/z): 269 (M+H)
RT (min): 0.89 tert-Butyl ((1R,2S)-1-((6-chloro-5-cyano-3-fluoropyridin-2-yl)amino)-1-(4-fluorophenyl)propan-2-yl)carbamate $^1$H-NMR (CDCl$_3$, 300 MHz) δ: 8.07 (br, 1H), 7.25-7.16 (m, 3H), 7.09-6.98 (m, 2H), 4.99 (d, 1H, J=5.9 Hz), 4.36-4.16 (m, 2H), 1.50 (s, 9H), 1.12 (d, 3H, J=6.6 Hz)
MS (ESI m/z): 423 (M+H)
RT (min): 1.81

Reference Example 106

The following compound was obtained as described in Reference Example 91.

[Formula 126]

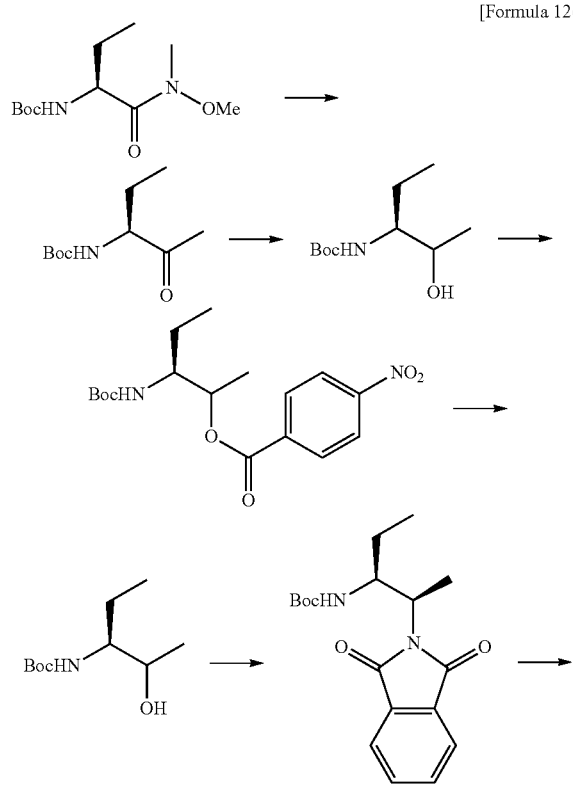

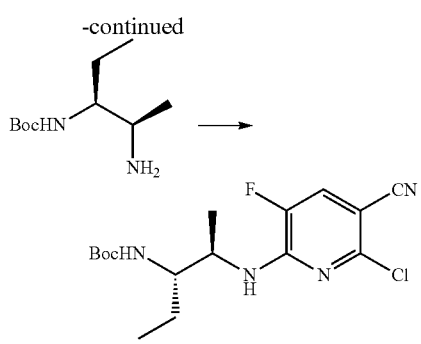

(S)-tert-butyl (2-oxopentan-3-yl)carbamate

MS (ESI m/z): 202 (M+H)
RT (min): 1.19 tert-Butyl ((3S)-2-hydroxypentan-3-yl)carbamate

MS (ESI m/z): 204 (M+H)
RT (min): 1.09

(3S)-3-((tert-butoxycarbonyl)amino)pentan-2-yl-4-nitrobenzoate

MS (ESI m/z): 353 (M+H)
RT (min): 1.75 tert-Butyl ((3S)-2-hydroxypentan-3-yl)carbamate

MS (ESI m/z): 204 (M+H)
RT (min): 1.09 tert-Butyl ((2R,3S)-2-(1,3-dioxoisoindolin-2-yl)pentan-3-yl)carbamate

1H-NMR (CDCl$_3$, 300 MHz) δ: 7.89-7.75 (m, 2H), 7.76-7.66 (m, 2H), 4.46 (d, 1H, J=8.6 Hz), 4.36-4.02 (m, 2H), 1.41 (s, 9H), 1.37-1.22 (m, 5H), 0.92 (t, 3H, J=7.2)
MS (ESI m/z): 333 (M+H)
RT (min): 1.58 tert-Butyl ((2R,3S)-2-aminopentan-3-yl)carbamate

MS (ESI m/z): 203 (M+H)
RT (min): 0.69 tert-Butyl ((2R,3S)-2-((6-chloro-5-cyano-3-fluoropyridin-2-yl)amino)pentan-3-yl)carbamate $^1$H-NMR (CDCl$_3$, 300 MHz) δ: 7.25 (d, 1H, J=9.9 Hz), 6.79 (d, 1H, J=5.4 Hz), 4.46 (d, 1H, J=7.9 Hz), 4.30-4.15 (m, 1H), 3.80-3.68 (m, 1H), 1.71-1.30 (m, 11H), 1.17 (d, 3H, J=6.6 Hz), 1.02 (t, 3H, J=7.6 Hz)
MS (ESI m/z): 357 (M+H)
RT (min): 1.72

Reference Example 107

The following compound was obtained as described in Reference Example 91.

[Formula 127]

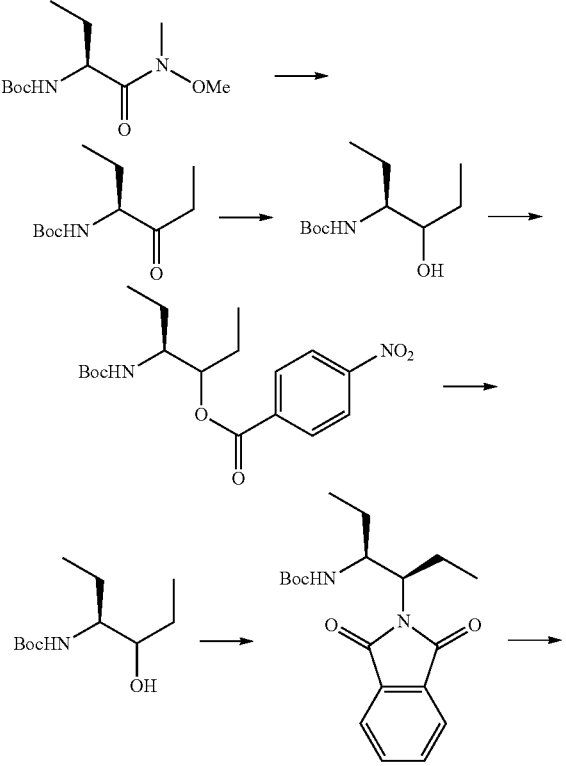

(S)-tert-butyl (4-oxohexan-3-yl)carbamate

MS (ESI m/z): 216 (M+H)
RT (min): 1.36 tert-Butyl ((3S)-4-hydroxyhexan-3-yl)carbamate

MS (ESI m/z): 218 (M+H)
RT (min): 1.26

(4S)-4-((tert-butoxycarbonyl)amino)hexan-3-yl-4-nitrobenzoate

MS (ESI m/z): 367 (M+H)
RT (min): 1.85 tert-Butyl ((3S)-4-hydroxyhexan-3-yl)carbamate

MS (ESI m/z): 218 (M+H)
RT (min): 1.26 tert-Butyl ((3S,4R)-4-(1,3-dioxoisoindolin-2-yl)hexan-3-yl)carbamate $^1$H-NMR (CDCl$_3$, 300 MHz) δ: 7.89-7.78 (m, 2H), 7.76-7.66 (m, 2H), 4.46 (d, 1H, J=8.6 Hz), 4.36-3.90 (m, 2H), 2.39-2.15 (m, 1H), 1.96-1.76 (m, 1H), 1.67-1.40 (m, 10H), 1.34-1.16 (m, 1H), 0.96-0.80 (m, 6H)
MS (ESI m/z): 347 (M+H)
RT (min): 1.68 tert-Butyl ((3S,4R)-4-aminohexan-3-yl)carbamate

MS (ESI m/z): 217 (M+H)
RT (min): 0.75 tert-Butyl ((3S,4R)-4-((6-chloro-5-cyano-3-fluoropyridin-2-yl)amino)hexan-3-yl)carbamate $^1$H-NMR (CDCl$_3$, 300 MHz) δ: 7.28 (d, 1H, J=9.9 Hz), 5.80 (d, 1H, J=7.9 Hz), 4.43 (d, 1H, J=8.6 Hz), 4.29-4.05 (m, 1H), 3.74-3.60 (m, 1H), 1.78-1.27 (m, 13H), 1.00 (t, 3H, J=7.7 Hz), 0.96 (t, 3H, J=7.5 Hz)
MS (ESI m/z): 371 (M+H)
RT (min.): 1.77

Reference Example 108

[Formula 128]

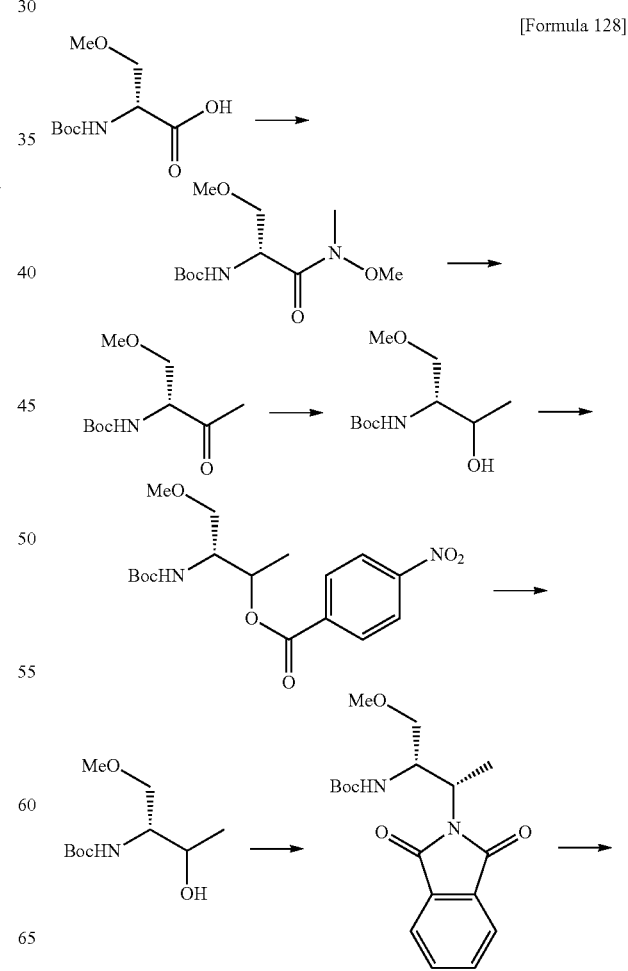

-continued

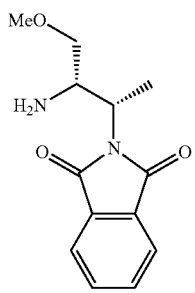

1st Step

The following compound was obtained as described in the 1st step in Reference Example 79.

(R)-tert-butyl (3-methoxy-1-(methoxy(methyl)amino)-1-oxopropan-2-yl)carbamate

MS (ESI m/z): 263 (M+H)
RT (min): 1.03

The following compound was obtained as described in the 1st to 5th steps in Reference Example 91.

2nd Step (R)-tert-butyl (1-methoxy-3-oxobutan-2-yl)carbamate

MS (ESI m/z): 218 (M+H)
RT (min): 1.07

3rd Step tert-Butyl ((2R)-3-hydroxy-1-methoxybutan-2-yl)carbamate

MS (ESI, m/z): 220 (M+H)
RT (min): 0.92

4th Step (3R)-3-((tert-butoxycarbonyl)amino)-4-methoxybutan-2-yl-4-nitrobenzoate MS (ESI m/z): 369 (M+H)
RT (min): 1.67

5th step tert-Butyl ((2R)-3-hydroxy-1-methoxybutan-2-yl)carbamate

MS (ESI m/z): 220 (M+H)
RT (min): 0.92

6th Step tert-Butyl ((2S,3S)-3-(1,3-dioxoisoindolin-2-yl)-1-methoxybutan-2-yl)carbamate $^1$H-NMR (CDCl$_3$, 300 MHz) δ: 7.85-7.78 (m, 2H), 7.74-7.66 (m, 2H), 5.08-4.92 (m, 1H), 4.54-4.34 (m, 2H), 3.44-3.26 (m, 2H), 3.22 (s, 3H), 1.52 (d, 3H, J=6.6 Hz), 1.45 (s, 9H)
MS (ESI m/z): 349 (M+H)
RT (min): 1.50

7th Step

The following compound was obtained as described in the 3rd step in Reference Example 47.

2-((2S,3S)-3-amino-4-methoxybutan-2-yl)isoindolin-1,3-dione

MS (ESI m/z): 249 (M+H),
RT (min): 0.64

Reference Example 109

[Formula 129]

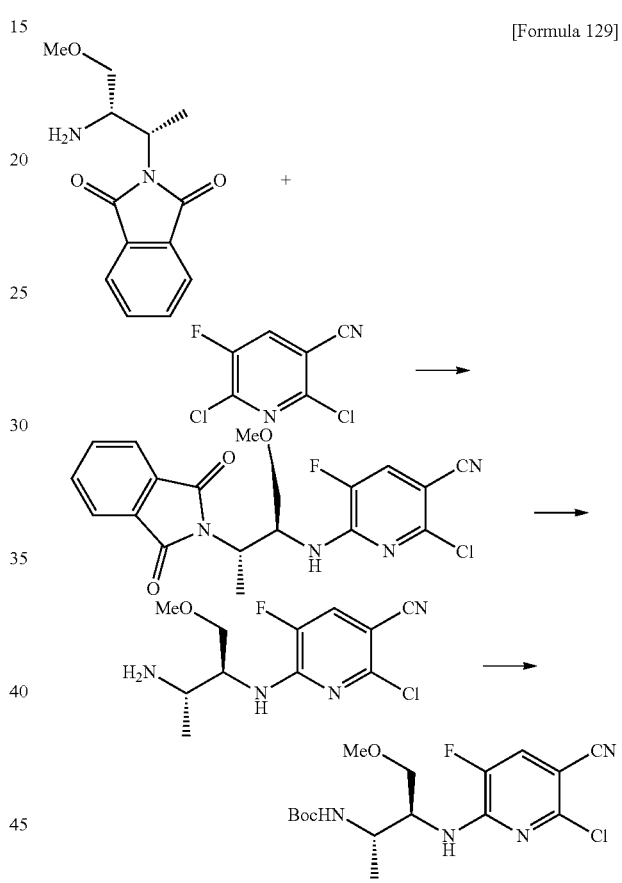

1st Step

The following compound was obtained as described in the 6th step in Reference Example 79.

2-chloro-6-(((2S,3S)-3-(1,3-dioxoisoindolin-2-yl)-1-methoxybutan-2-yl)amino)-5-fluoronicotinonitrile MS (ESI m/z): 403 (M+H),
RT (min): 1.59

2nd Step

The following compound was obtained as described in the 6th step in Reference Example 91.

6-(((2S,3S)-3-amino-1-methoxybutan-2-yl)amino)-2-chloro-5-fluoronicotinonitrile

MS (ESI m/z): 273 (M+H),
RT (min): 0.72

3rd Step

The following compound was obtained as described in the 1st step in Reference Example 38.

tert-Butyl ((2S,3S)-3-((6-chloro-5-cyano-3-fluoropyridin-2-yl)amino)-4-methoxybutan-2-yl)carbamate $^1$H-NMR (CDCl$_3$, 300 MHz) δ: 7.31 (d, 1H, J=9.6 Hz), 6.10 (d, 1H, J=7.6 Hz), 5.17 (d, 1H, J=8.9 Hz), 4.36-4.19 (m, 1H), 4.12-3.94 (m, 1H), 3.89 (s, 3H), 3.84-3.75 (m, 1H), 3.58-3.48 (m, 1H), 1.44 (s, 9H), 1.24 (d, 3H, J=7.2 Hz)

MS (ESI m/z): 373 (M+H)

RT (min): 1.60

Reference Example 110

The following compound was obtained as described in Reference Example 108.

[Formula 130]

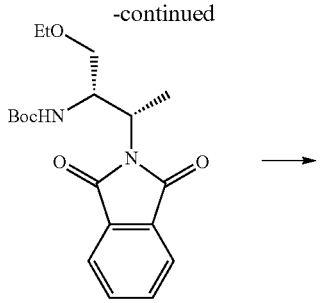

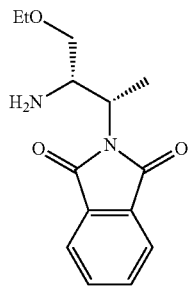

1st Step (R)-tert-butyl (3-ethoxy1-(methoxy(methyl)amino)-1-oxopropan-2-yl)carbamate $^1$H-NMR (CDCl$_3$) δ: 5.38 (1H, d, J=8.6 Hz), 4.90-4.78 (1H, m), 3.78 (3H, s), 3.72-3.43 (4H, m), 3.23 (3H, s), 1.46 (9H, s), 1.17 (3H, t, J=7.1 Hz).

MS (ESI m/z): 117 (M+H−Boc)

RT (min): 1.17

2nd Step (R)-tert-butyl (1-ethoxy3-oxobutan-2-yl)carbamate

1H-NMR (CDCl3) δ: 5.55-5.45 (1H, br), 4.37-4.28 (1H, m), 3.92-3.41 (4H, m), 2.21 (3H, s), 1.47 (9H, d, J=7.3 Hz), 1.17 (3H, q, J=7.3 Hz).

MS (ESI m/z): 132 (M+H−Boc)

RT (min): 1.22

3rd Step tert-Butyl ((2R)-3-hydroxy-1-ethoxybutan-2-yl)carbamate

MS (ESI, m/z): 234 (M+H)

RT (min): 1.07

4th Step (3R)-3-((tert-butoxycarbonyl)amino)-4-ethoxybutan-2-yl-4-nitrobenzoate MS (ESI m/z): 383 (M+H)

RT (min): 1.71

5th Step tert-Butyl ((2R)-3-hydroxy-1-ethoxybutan-2-yl)carbamate

MS (ESI m/z): 234 (M+H)

RT (min): 1.06

6th Step tert-Butyl ((2S,3S)-3-((1,3-dioxoisoindolin-2-yl)-1-ethoxybutan-2-yl)carbamate $^1$H-NMR (CDCl$_3$) δ: 7.86-7.81 (2H, m), 7.73-7.67 (2H, m), 5.10-4.95 (1H, m), 4.54-4.35 (2H, m), 3.47-3.25 (4H, m), 1.46 (9H, s), 1.32 (3H, d, J=6.3 Hz), 1.02 (3H, t, J=6.9 Hz).
MS (ESI m/z): 363 (M+H)
RT (min): 1.63

7th Step 2-((2S,3S)-3-amino-4-ethoxybutan-2-yl)isoindolin-1,3-dione

MS (ESI m/z): 263 (M+H),
RT (min): 0.77

Reference Example 111

The following compound was obtained as described in Reference Example 109.

3rd Step tert-Butyl ((2S,3S)-3-((6-chloro-5-cyano-3-fluoropyridin-2-yl)amino)-4-ethoxybutan-2-yl)carbamate $^1$H-NMR (CDCl$_3$) δ: 7.31 (1H, d, J=9.6 Hz), 6.14 (1H, d, J=6.9 Hz), 5.25 (1H, d, J=8.9 Hz), 4.33-4.19 (1H, dd, J=7.9, 3.6 Hz), 4.11-3.93 (1H, m), 3.79 (1H, dd, J=9.9, 2.6 Hz), 3.62-3.43 (4H, m), 1.44 (9H, s), 1.31-1.19 (6H, m).
MS (ESI m/z): 387 (M+H)
RT (min): 1.71

Reference Example 112

The following compound was obtained as described in Reference Example 108.

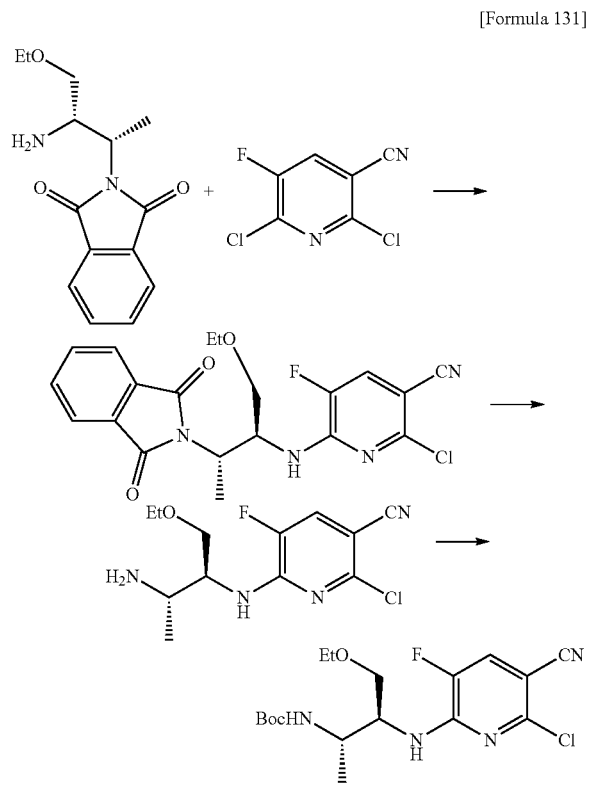

[Formula 131]

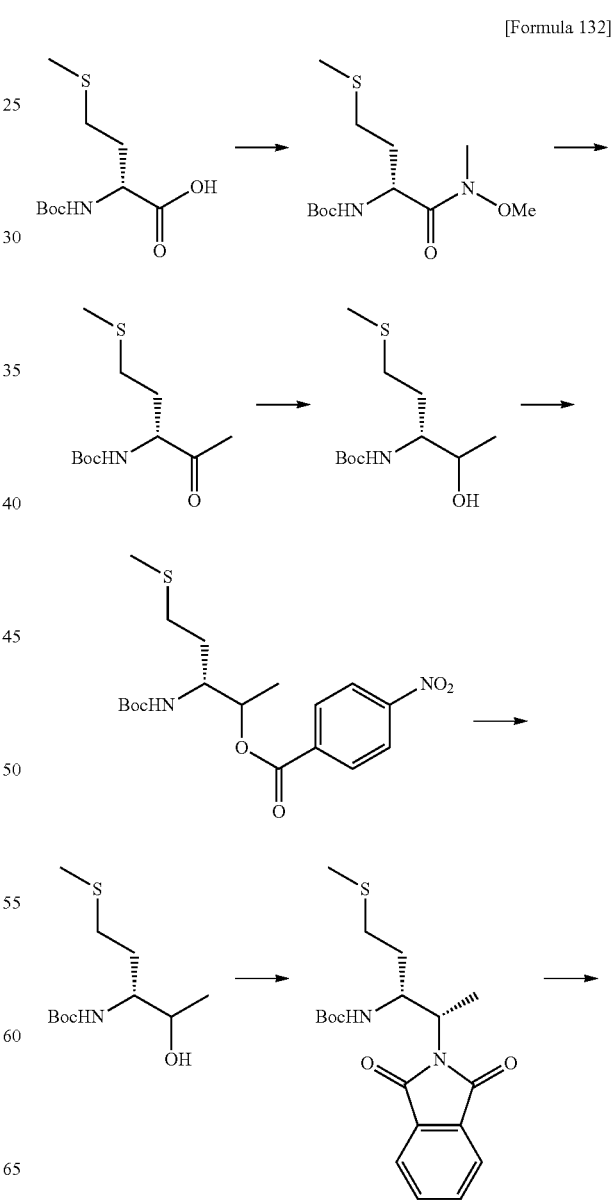

[Formula 132]

1st Step

2-Chloro-6-(((2S,3S)-3-(1,3-dioxoisoindolin-2-yl)-1-ethoxybutan-2-yl)amino)-5-fluoronicotinonitrile MS (ESI m/z): 417 (M+H)
RT (min): 1.41

2nd Step 6-(((2S,3S)-3-amino-1-ethoxybutan-2-yl)amino)-2-chloro-5-fluoronicotinonitrile MS (ESI m/z): 287 (M+H)
RT (min): 0.82

141
-continued

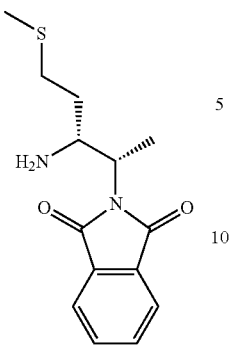

(R)-tert-butyl (1-(methoxy(methyl)amino)-4-(methylthio)-1-oxobutan-2-yl)carbamate MS (ESI m/z): 293 (M+H)
RT (min): 1.24

(3R)-3-((tert-butoxycarbonyl)amino)-5-(methylthio) pentan-2-yl 4-nitrobenzoate

MS (ESI m/z): 399 (M+H)
RT (min): 1.78 tert-Butyl ((3R,4S)-4-(1,3-dioxoisoindolin-2-yl)-1-(methylthio)pentan-3-yl)carbamate MS (ESI m/z): 379 (M+H)
RT (min): 1.60

2-((2S,3R)-3-amino-5-(methylthio)pentan-2-yl) isoindolin-1,3-dione

MS (ESI m/z): 279 (M+H)
RT (min): 0.75

Reference Example 113

The following compound was obtained as described in Reference Example 109.

[Formula 133]

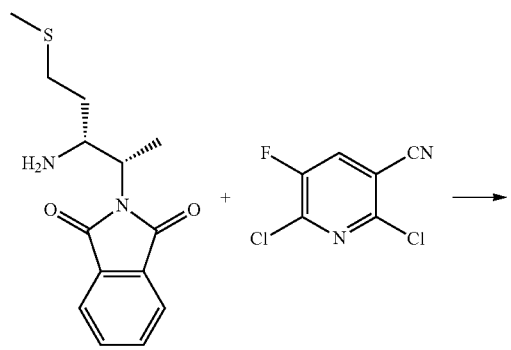

142
-continued

1st Step

2-Chloro-6-(((3R,4S)-4-(1,3-dioxoisoindolin-2-yl)-1-(methylthio)pentan-3-yl)amino)-5-fluoronicotinonitrile MS (ESI m/z): 433 (M+H)
RT (min): 1.67

2nd Step 6-(((3R,4S)-4-amino-1-(methylthio)pentan-3-yl)amino)-2-chloro-5-fluoronicotinonitrile MS (ESI m/z): 303 (M+H)
RT (min): 0.85

3rd Step tert-Butyl ((2S,3R)-3-((6-chloro-5-cyano-3-fluoropyridin-2-yl)amino)-5-(methylthio)pentan-2-yl)carbamate MS (ESI m/z): 403 (M+H)
RT (min): 1.70

Reference Example 114

The following compound was obtained as described in Reference Example 108.

[Formula 134]

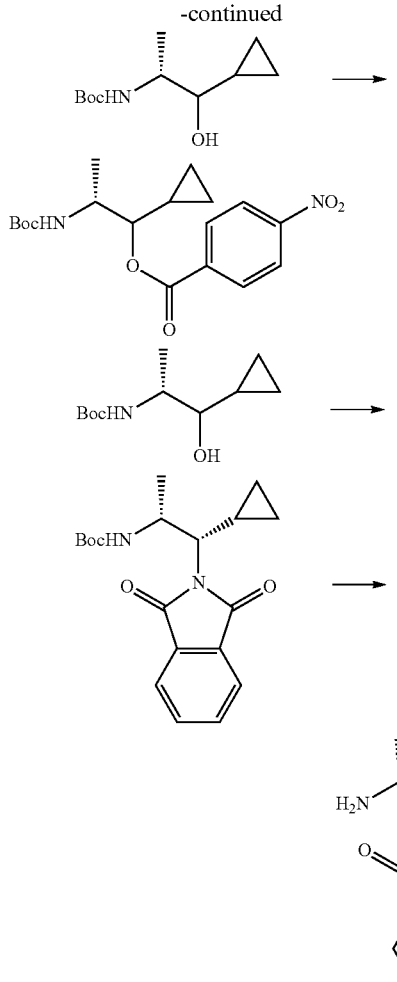

(2R)-2-((tert-butoxycarbonyl)amino)-1-cyclopropyl-propyl-4-nitrobenzoate

MS (ESI m/z): 365 (M+H)
RT (min): 1.78 tert-Butyl ((1S,2R)-1-cyclopropyl-1-(1,3-dioxoisoindolin-2-yl)propan-2-yl)carbamate MS (ESI m/z): 399 (M+H)
RT (min): 1.73

2-((1S,2R)-2-amino-1-cyclopropylpropyl)isoindolin-1,3-dione

MS (ESI m/z): 299 (M+H)
RT (min): 0.73

Reference Example 115

The following compound was obtained as described in Reference Example 109.

[Formula 135]

2-Chloro-6-((((1S,2R)-1-cyclopropyl-1-(1,3-dioxoisoindolin-2-yl)propan-2-yl)amino)-5-fluoronicotinonitrile MS (ESI m/z): 400 (M+H)
RT (min): 1.74

6-(((1S,2)-1-amino-1-cyclopropylpropan-2-yl)amino)-2-chloro-5-fluoronicotinonitrile MS (ESI m/z): 270 (M+H)
RT (min): 0.84 tert-Butyl ((1S,2R)-2-((6-chloro-5-cyano-3-fluoropyridin-2-yl)amino)-1-cyclopropylpropyl)carbamate MS (ESI m/z): 370 (M+H)
RT (min): 1.75

Reference Example 116

The following compound was obtained with reference to Archiv der Pharmazie (Weinheim, Germany), 2004, vol. 337, #12 pp. 654-667.

145

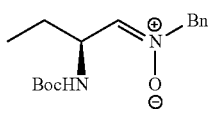

[Formula 136]

(S,Z)—N-(2-((tert-butoxycarbonyl)amino)butylidyne)-1--phenylmethaneamine oxide

Reference Example 117

[Formula 137]

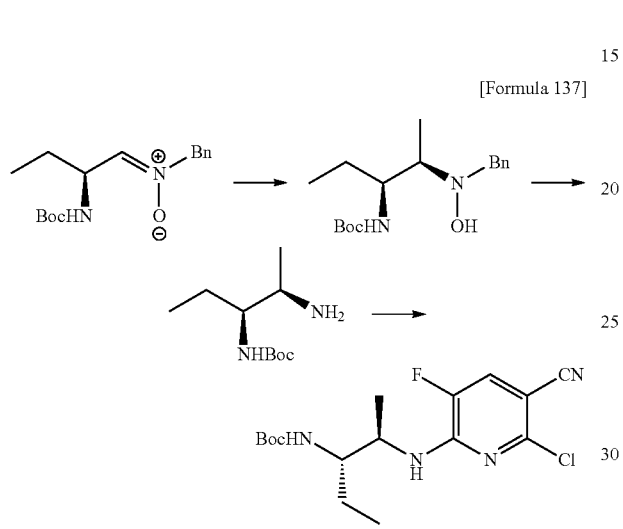

1st Step

Methylmagnesium bromide (3M diethyl ether solution, 0.86 ml) was added dropwise to a THF (5 ml) solution containing (S,Z)—N-(2-((tert-butoxycarbonyl)amino)butylidyne)-1-phenylmethaneamineoxide (250 mg) at −50° C., followed by stirring at −50° C. to −35° C. for 2 hours. Further, methylmagnesium bromide (3M diethyl ether solution, 0.86 ml) was added dropwise to the reaction solution, followed by stirring at −45° C. to −40° C. for 1 hour. A saturated ammonium chloride aqueous solution was added to the reaction solution, followed by extraction with ethyl acetate. The organic layers were washed with saturated saline and dried over anhydrous sodium sulfate. The solvent was distilled away under reduced pressure and the obtained residue was purified by silica gel chromatography (n-hexane:ethyl acetate=19:1 to 4:1). tert-Butyl ((3S,4R)-4-(benzyl (hydroxy)amino)pentan-3-yl)carbamate (39 mg) was thus obtained.

$^1$H-NMR (CDCl$_3$, 300 MHz) δ: 7.39-7.18 (m, 5H), 6.70 (s, 1H), 4.43 (d, 1H, J=10.2 Hz), 4.11 (d, 1H, J=13.9 Hz), 4.10-3.97 (m, 1H), 3.64 (d, 1H, J=13.9 Hz), 2.78-2.68 (m, 1H), 1.47 (s, 9H), 1.44-1.26 (m, 2H), 1.03-0.94 (m, 9H)

2nd Step

An MeOH (20 ml) solution containing tert-butyl ((3S,4R)-4-(benzyl (hydroxy)amino)pentan-3-yl)carbamate (39 mg) was subjected to a hydrogenation reaction (45° C.; 100 bar; flow rate: 1 ml/min; 20% Pd(OH)$_2$/C) using H-Cube™. Then, the solvent was distilled away under reduced pressure. Colorless oily matter of tert-butyl ((3S,4R)-4-aminopentan-3-yl)carbamate (27 mg) was thus obtained.

3rd Step

The following compound was obtained as described in the 7th step in Reference Example 417.

146 tert-Butyl ((2R,3S)-2-((6-chloro-5-cyano-3-fluoropyridin-2-yl)amino)pentan-3-yl)carbamate MS (ESI m/z): 357 (M+H), 355 (M−H)

Reference Example 118

The following compound was obtained as described in Reference Example 117.

[Formula 138]

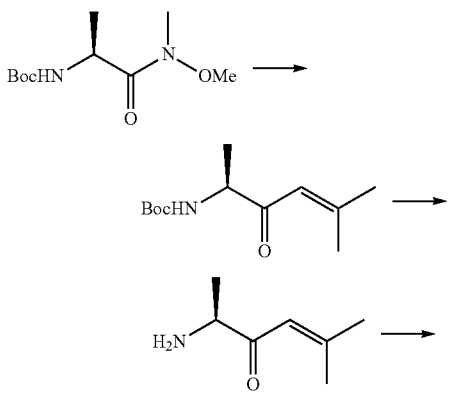

tert-Butyl ((3S,4R)-4-(benzyl (hydroxy)amino) hexan-3-yl)carbamate $^1$H-NMR (CDCl$_3$, 300 MHz) δ: 7.40-7.20 (m, 5H), 5.88 (s, 1H), 4.62 (d, 1H, J=9.6 Hz), 4.07 (d, 1H, J=13.9 Hz), 4.01-3.88 (m, 1H), 3.73 (d, 1H, J=13.9 Hz), 2.59-2.50 (m, 1H), 1.69-1.32 (m, 4H), 1.45 (s, 9H), 1.05 (t, 3H, J=7.6 Hz), 0.98 (t, 3H, J=7.3 Hz)

tert-Butyl ((3S,4R)-4-((6-chloro-5-cyano-3-fluoropyridin-2-yl)amino)hexan-3-yl)carbamate MS (ESI m/z): 371 (M+H), 369 (M−H)

Reference Example 119

[Formula 139]

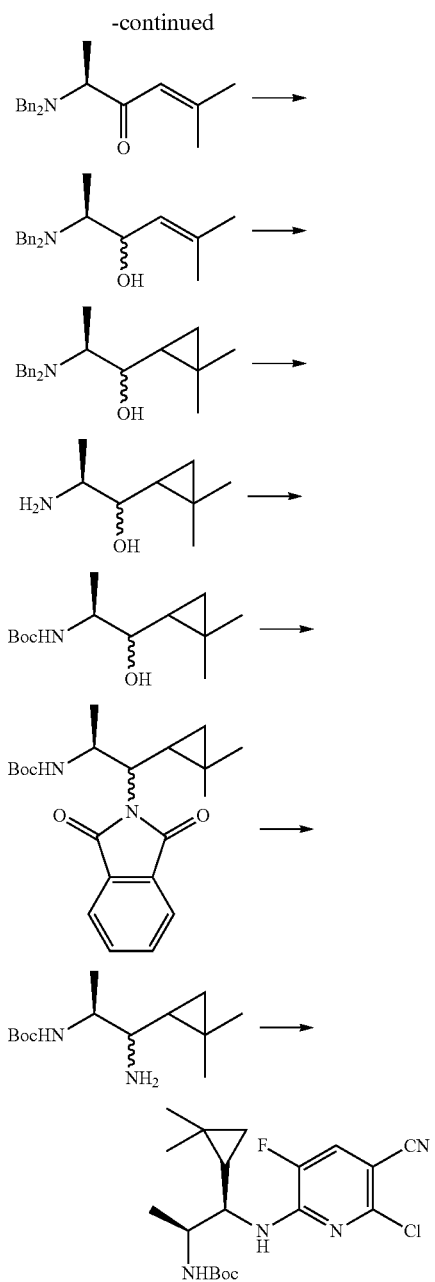

1st, 2nd, and 3rd Steps (S)-tert-butyl (1-(methoxy(methyl)amino)-1-oxopropan-2-yl)carbamate (10 g) was added to (2-methyl-1-propen-1-yl)magnesium bromide (0.5 M in THF) (258.3 ml), followed by stirring at 50° C. for 40 minutes. The reaction solution was adjusted to room temperature and poured into a 10% citric acid aqueous solution, followed by extraction with ethyl acetate. The organic layers were washed with water and saturated saline and dried over anhydrous sodium sulfate. The solvent was distilled away under reduced pressure. TFA (20 ml) was added to the obtained residue, followed by stirring at room temperature for 30 minutes. Next, the solvent was distilled away under reduced pressure. DMF (30 ml), potassium carbonate (13.8 g), and benzyl bromide (10.7 ml) were added to the obtained residue, followed by stirring at 70° C. for 50 minutes. Water was added to the reaction solution, followed by extraction with ethyl acetate. The organic layers were washed with water and saturated saline and dried over anhydrous sodium sulfate. The solvent was distilled away under reduced pressure and the obtained residue was purified by silica gel chromatography (n-hexane:ethyl acetate=1:0 to 1:0.2). A yellow liquid of (S)-2-(dibenzylamino)-5-methyl-4-hexen-3-one (4.46 g) was thus obtained.

MS (ESI m/z): 308 (M+H)
RT (min): 1.56

4th Step

A methanol solution (10 ml) containing sodium borohydride (1.5 g) and (S)-2-(dibenzylamino)-5-methyl-4-hexen-3-one (4.2 g) obtained in the 3rd step were added to an MeOH (30 ml) solution containing cerium chloride (10 g), followed by stirring for 7 hours. Water was added to the reaction solution, followed by extraction with ethyl acetate. The organic layers were washed with water and saturated saline and dried over anhydrous sodium sulfate. Then, the solvent was distilled away under reduced pressure and the obtained residue was purified by silica gel chromatography (n-hexane:ethyl acetate=1:0 to 1:0.2). A yellow liquid of (2S)-2-(dibenzylamino)-5-methyl-4-hexen-3-ol (3.5 g) was thus obtained.

MS (ESI m/z): 310 (M+H)
RT (min): 1.06

5th Step

A $CH_2Cl_2$ (5 ml) solution containing diiodomethane (3.5 ml) and a methylene chloride (5 ml) solution containing (2S)-2-amino-5-methyl-4-hexen-3-ol (2.7 g) obtained in the 4th step were added to a methylene chloride (40 ml) solution containing diethyl zinc (43.6 ml), followed by stirring at room temperature for 15 hours. Methanol and sodium hydrogen carbonate were added to the reaction solution, followed by filtration through Celite. The filtrate was extracted with ethyl acetate. The organic layers were washed with water and saturated saline and dried over anhydrous sodium sulfate. Then, the solvent was distilled away under reduced pressure and the obtained residue was purified by silica gel chromatography (n-hexane:ethyl acetate=1:0 to 1:0.2). (2S)-2-(dibenzylamino)-1-(2,2-dimethylcyclopropyl)propan-1-ol (2.4 g) was thus obtained.

MS (ESI m/z): 324 (M+H)
RT (min): 1.13

6th and 7th Steps

Formic acid (2.4 ml) and 10% Pd/C (0.4 g) were added to an ethanol solution (60 ml) containing (1S,2S)-2-(dibenzylamino)-1-(2,2-dimethylcyclopropyl)propan-1-ol (2.4 g) obtained in the 5th step, followed by stirring at 90° C. for 5 hours. The reaction solution was filtered through Celite and the filtrate was distilled away under reduced pressure. Diisopropyl ethylamine (1.5 ml) and di-tert-butyl carbonate (1.75 g) were added to a THF (5 ml) solution containing the obtained residue, followed by stirring at room temperature for 40 minutes. Water and a 10% citric acid aqueous solution were added to the reaction solution, followed by extraction with ethyl acetate. The organic layers were washed with water and saturated saline and dried over anhydrous sodium sulfate. Then, the solvent was distilled away under reduced pressure and the obtained residue was purified by silica gel chromatography (n-hexane:ethyl acetate=1:0 to 1:0.2). A yellow liquid of tert-butyl ((2S)-1-(2,2-dimethylcyclopropyl)-1-hydroxypropan-2-yl)carbamate (0.45 g) was thus obtained.

MS (ESI m/z): 244 (M+H)
RT (min): 1.36

8th Step

Phthalimide (0.147 g), triphenylphosphine (0.34 g), and diisopropyl azodicarboxylate (0.684 ml) were added to a THF (5 ml) solution containing tert-butyl ((2S)-1-(2,2-dimethyl-cyclopropyl)-1-hydroxypropan-2-yl)carbamate (0.20 g), followed by stirring at room temperature for 1.5 hours. The solvent was distilled away under reduced pressure and the obtained residue was purified by silica gel chromatography (n-hexane:ethyl acetate=1:0 to 1:0.2). A yellow liquid of tert-butyl ((2S)-1-(2,2-dimethylcyclopropyl)-1-(1,3-dioxoisoindolin-2-yl)propan-2-yl)carbamate (22.4 mg) was thus obtained.

MS (ESI m/z): 373 (M+H)
RT (min): 1.80

9th and 10th Steps

Hydrazine monohydrate (0.4 ml) was added to an ethanol solution (5 ml) containing tert-butyl ((2S)-1-(2,2-dimethylcyclopropyl)-1-(1,3-dioxoisoindolin-2-yl)propan-2-yl)carbamate (22.4 mg), followed by stirring at 90° C. for 3 hours. Water was added to the reaction solution, followed by extraction with ethyl acetate. The organic layers were washed with saturated saline and dried over anhydrous sodium sulfate. Then, the solvent was distilled away under reduced pressure. 2,6-Dichloro-5-fluoronicotinonitrile (15.3 mg) and diisopropyl ethylamine (0.1 ml) were added to the obtained residue, followed by stirring at 70° C. for 50 minutes. Water was added to the reaction solution, followed by extraction with ethyl acetate. The organic layers were washed with water and saturated saline and dried over anhydrous sodium sulfate. Then, the solvent was distilled away under reduced pressure and the obtained residue was purified by silica gel chromatography (n-hexane:ethyl acetate=1:0 to 1:0.2). A yellow liquid of tert-butyl ((1R,2S)-1-((6-chloro-5-cyano-3-fluoropyridin-2-yl)amino)-1-(S)-2,2-dimethylcyclopropyl)propan-2-yl)carbamate (6 mg) was thus obtained.

MS (ESI m/z): 397 (M+H)
RT (min): 1.89

Reference Example 120

[Formula 140]

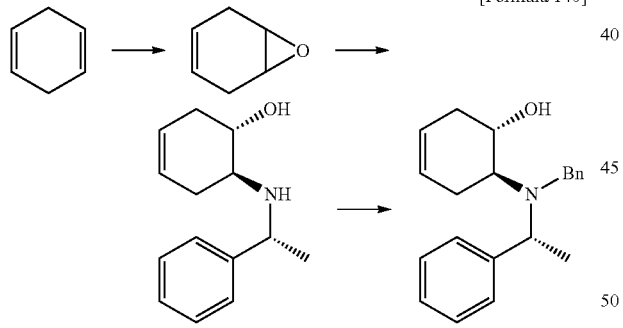

1st and 2nd Steps

A CH$_2$Cl$_2$ (125 ml) solution containing 1,4-hexadiene (8.0 g) was added to a solution comprising sodium hydrogen carbonate (12.6 g) and water (75 ml) at room temperature and mCPBA (16.4 g) was further added under ice cooling, followed by stirring for 1 hour and stirring at room temperature 10 hours. A 5% sodium thiosulfate aqueous solution was added to the reaction solution, followed by extraction with methylene chloride. The organic layers were washed with a saturated sodium hydrogen carbonate aqueous solution and saturated saline and dried over anhydrous sodium sulfate. The solvent was distilled away under reduced pressure. n-Butanol (20 ml) was added to the obtained residue. Next, (R)-(−)-1-phenylethylamine was added, followed by stirring at 90° C. for 5 hours. The solvent was distilled away under reduced pressure and the obtained residue was purified by silica gel chromatography (n-hexane:ethyl acetate=1:0 to 1:0.2). A yellow oily matter of (1S,6S)-6-(((R)-1-phenylethyl)amino)cyclohexyl-3-enol (2.6 g) was thus obtained.

3rd Step

Potassium carbonate (1.9 g) and benzyl bromide (1.53 ml) were added to a DMF (5 ml) solution containing (1S,6S)-6-(((R)-1-phenylethyl)amino)cyclohexyl-3-enol (2.5 g) obtained in the 2nd step, followed by stirring at 90° C. for 1 hour. Water was added to the reaction solution, followed by extraction with ethyl acetate. The organic layers were washed with water and saturated saline and dried over anhydrous sodium sulfate. The solvent was distilled away under reduced pressure and the obtained residue was purified by silica gel chromatography (n-hexane:ethyl acetate=1:0 to 1:0.2). Yellow oily matter of (1S,6S)-6-(benzyl ((R)-1-phenylethyl)amino)cyclohexan-3-ol (1.6 g) was thus obtained.

MS (ESI m/z): 308 (M+H)
RT (min): 0.98

Reference Example 121

[Formula 141]

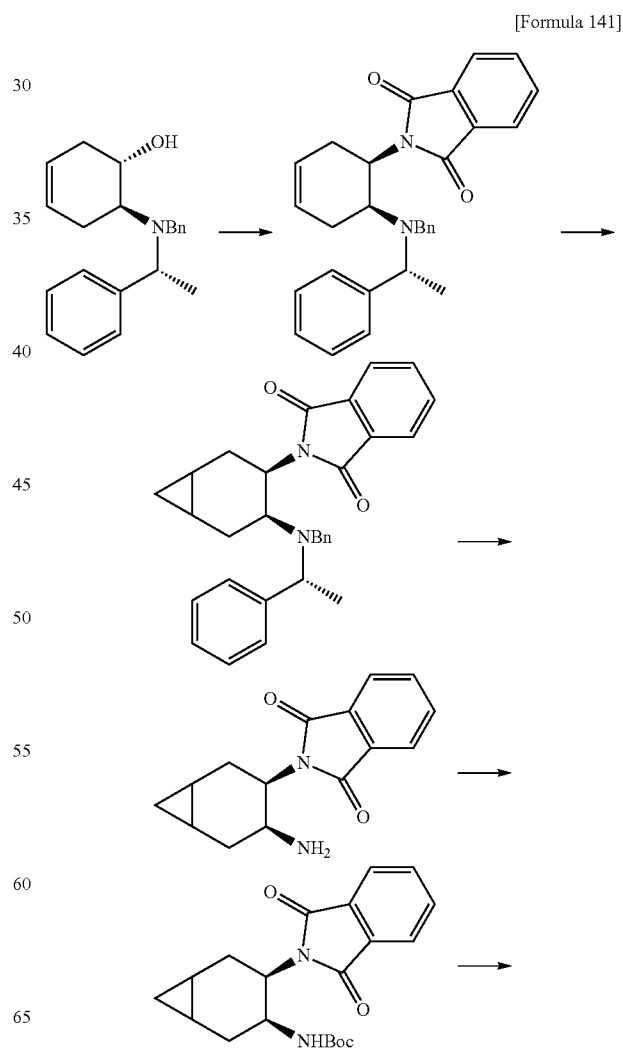

-continued

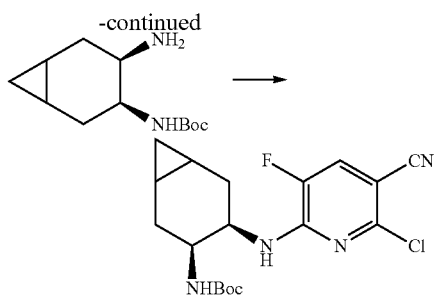

1st Step

Phthalimide (0.63 g), triphenylphosphine (1.3 g), and DIAD (1.9M in toluene solution) (2.6 ml) were added to a THF (50 ml) solution containing (1S,6S)-6-(benzyl ((R)-1-phenylethyl)amino)cyclohexan-3-ol (1.2 g), followed by stirring at room temperature for 15 hours. The solvent was distilled away under reduced pressure and the obtained residue was purified by silica gel chromatography (hexane:ethyl acetate=1:0 to 5:1). Yellow oily matter of 2-((1R,6S)-6-(benzyl ((R)-1-phenylethyl)amino)cyclohex-3-en-1-yl)isoindolin-1,3-dione (1.5 g) was thus obtained.

MS (ESI m/z): 438 (M+H)
RT (min): 2.21

2nd Step

A methylene chloride (3 ml) solution containing diiodomethane (0.2 ml) and a methylene chloride solution (3 ml) containing 2-((1R,6S)-6-(benzyl ((R)-1-phenylethyl)amino)-3-cyclohexen-1-yl)isoindolin-1,3-dione (0.36 g) obtained in the 1st step were added to a methylene chloride solution (10 ml) containing diethyl zinc (1M in hexane) (2.47 ml), followed by stirring for 15 hours. Methanol and sodium hydrogen carbonate were added to the reaction solution. The reaction solution was filtered through Celite. The filtrate was extracted with ethyl acetate. The organic layers were washed with water and saturated saline and dried over anhydrous sodium sulfate. The solvent was distilled away under reduced pressure and the obtained residue was purified by silica gel chromatography (n-hexane:ethyl acetate=1:0 to 1:0.2). A 2-((3R,4S)-4-(benzyl ((R)-1-phenylethyl)amino)bicyclo[4.1.0]heptan-3-yl)isoindolin-1,3-dione (0.20 g) was thus obtained.

MS (ESI m/z): 451 (M+H)
RT (min): 2.27

3rd and 4th Steps

Ammonium formate (0.084 g) and 10% Pd/C (0.1 g) were added to an ethanol solution (3 ml) containing 2-((3R,4S)-4-(benzyl ((R)-1-phenylethyl)amino)bicyclo[4.1.0]heptan-3-yl)isoindolin-1,3-dione (0.1 g) obtained in the 2nd step, followed by stirring 90° C. for 8 hours. The reaction solution was filtered through Celite and the filtrate was distilled away under reduced pressure. Diisopropyl ethylamine (0.2 ml) and di-tert-butyl carbonate (0.1 g) were added to a dimethylformamide solution (1 ml) containing the obtained residue, followed by stirring at room temperature for 45 minutes. Water and a 10% citric acid aqueous solution were added to the reaction solution, followed by extraction with ethyl acetate. The organic layers were washed with water and saturated saline and dried over anhydrous sodium sulfate. Then, the solvent was distilled away under reduced pressure and the obtained residue was purified by silica gel chromatography (n-hexane:ethyl acetate=1:0 to 1:0.2). Yellow oily matter of tert-butyl (3S,4R)-4-(1,3-dioxoisoindolin-2-yl)bicyclo[4.1.0]heptan-3-yl)carbamate (0.028 g) was thus obtained.

MS (ESI m/z): 357 (M+H)
RT (min): 1.81

5th and 6th Steps tert-Butyl (3S,4R)-4-(1,3-dioxoisoindolin-2-yl)bicyclo[4.1.0]heptan-3-yl)carbamate (0.028 g) obtained in the 4th step and an ethanol (5 ml) solution containing hydrazine monohydrate (0.2 ml) was stirred at 90° C. for 48 hours. The solvent was distilled away under reduced pressure and an insoluble precipitate was removed. Then, DMF (1 ml) containing 2,6-dichloro-5-fluoronicotinonitrile (0.02 g) and DIPEA (0.1 ml) were added to the obtained oily matter, followed by stirring for 4 hours. The reaction solution was adjusted to room temperature and water was added to the reaction solution, followed by extraction with ethyl acetate and washing with saturated saline. The organic layers were dried over anhydrous sodium sulfate. The obtained residue was purified by silica gel chromatography(n-hexane:ethyl acetate=10:1 to 1:1). A white solid of tert-butyl (3S,4R)-4-(6-chloro-5-cyano-3-fluoropyridin-2-yl)amino)bicyclo[4.1.0]hepta n-3-yl)carbamate (0.008 g) was thus obtained.

$^1$H-NMR (CDCl$_3$) δ: 7.23 (1H, d, J=9.9 Hz), 6.39 (1H, br), 4.48 (1H, d, J=7.9 Hz), 3.86-3.72 (1H, m), 3.47-3.33 (1H, m), 2.75-2.65 (1H, m), 2.33 (1H, dd, J=12.6, 4.6 Hz), 1.80 (1H, td, J=12.6, 4.6 Hz), 1.38 (9H, s), 1.29-0.69 (4H, m), 0.20-0.11 (1H, m)

MS (ESI m/z): 381 (M+H)
RT (min): 1.8

Reference Example 122

[Formula 142]

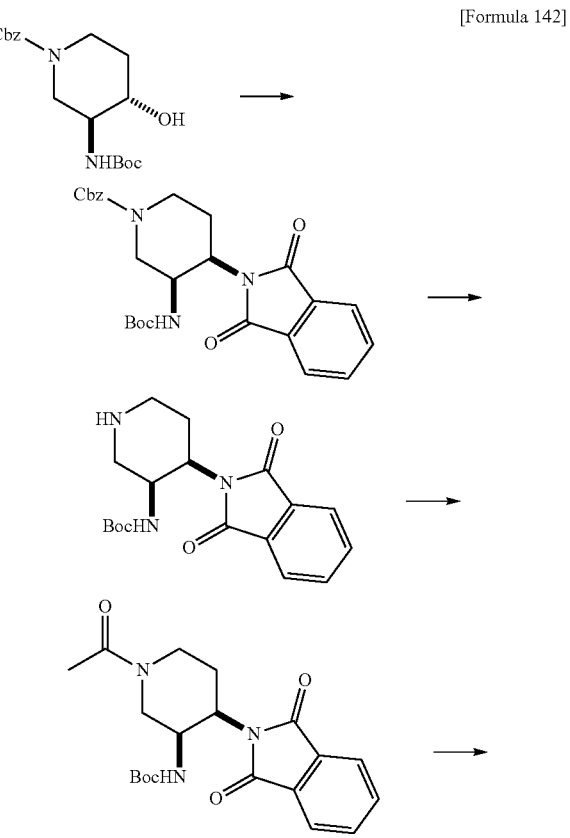

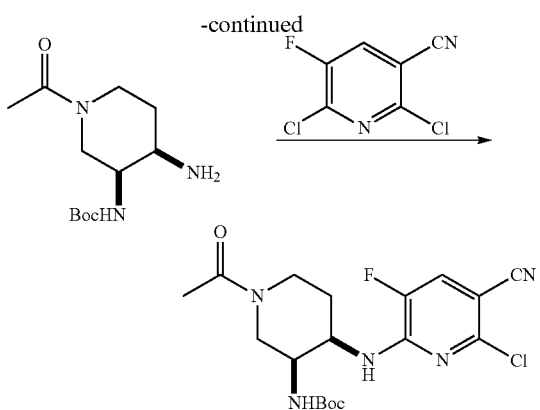

1st Step

PPh$_3$ (412 mg), phthalimide (252 mg), and diethyl azodicarboxylate (40% in toluene solution) (0.712 ml) were added to a THF (5 ml) solution containing benzyl 3-((tert-butoxycarbonyl)amino)-4-hydroxypiperidin-1-carboxylate (500 mg), followed by stirring at room temperature for 4 hours. Water was added to the reaction solution, followed by extraction with ethyl acetate. The organic layers were washed with saturated saline and dried over anhydrous sodium sulfate. The solvent was distilled away under reduced pressure. The obtained residue was purified by silica gel column chromatography (hexane:ethyl acetate=9:1 to 15:7). Colorless oily matter of benzyl 3-((tert-butoxycarbonyl)amino)-4-(1,3-dioxoisoindolin-2-yl)piperidin-1-carboxylate (205 mg) was thus obtained.

2nd Step

Ammonium formate (419 mg) and 10% Pd/C (84 mg) were added to an ethyl acetate/MeOH (4 ml/4 ml) solution containing benzyl 3-((tert-butoxycarbonyl)amino)-4-(1,3-dioxoisoindolin-2-yl)piperidin-1-carboxylate (419 mg) obtained in the 1st step, followed by stirring at 60° C. for 1 hour. The reaction solution was cooled to room temperature and insoluble matter was removed through Celite. Filter cake was washed with ethyl acetate and water. Subsequently, the filtrate was mixed with wash liquid and sodium chloride was added to the mixture. The organic layers were separated and washed with saturated saline. The organic layers were dried over anhydrous sodium sulfate and the solvent was distilled away under reduced pressure. A white solid of tert-butyl (4-(1,3-dioxoisoindolin-2-yl)piperidin-3-yl)carbamate (280 mg) was thus obtained.

MS (ESI m/z): 346 (M+H)

RT (min): 0.89

3rd Step

Sodium hydrogen carbonate (341 mg) and acetyl chloride (0.086 ml) were added to a THF/water (2 ml/2 ml) solution containing tert-butyl (4-(1,3-dioxoisoindolin-2-yl)piperidin-3-yl)carbamate (280 mg) obtained in the 2nd step under ice cooling, followed by stirring at room temperature for 0.5 hours. Ethyl acetate was added to the reaction solution. The organic layers were washed with saturated saline and dried over anhydrous sodium sulfate. Next, the solvent was distilled away under reduced pressure. A white solid of tert-butyl (1-acetyl-4-(1,3-dioxoisoindolin-2-yl)piperidin-3-yl)carbamate (301 mg) was thus obtained.

MS (ESI m/z): 388 (M+H)

RT (min): 1.17

4th Step

Hydrazine monohydrate (1 ml) was added to an ethanol (5 ml) solution containing tert-butyl (1-acetyl-4-(1,3-dioxoisoindolin-2-yl)piperidin-3-yl)carbamate (301 mg) obtained in the 3rd step, followed by heating and stirring at 50° C. for 0.5 hours. Ethyl acetate was added to the reaction solution. The reaction solution was washed with water and saturated saline and dried over anhydrous sodium sulfate. Next, the solvent was distilled away under reduced pressure. Colorless oily matter of tert-butyl (1-acetyl-4-aminopiperidin-3-yl)carbamate (147 mg) was thus obtained.

MS (ESI m/z): 258 (M+H)

RT (min): 0.50

5th Step

Triethylamine (0.096 ml) and 2,6-dichloro-5-fluoronicotinonitrile (109 mg) were added to a DMSO (2 ml) solution containing tert-butyl (1-acetyl-4-aminopiperidin-3-yl)carbamate (147 mg) obtained in the 4th step, followed by stirring at room temperature for 1 hour. Ethyl acetate was added to the reaction solution. The reaction solution was washed with water and saturated saline and dried over anhydrous sodium sulfate. Next, the solvent was distilled away under reduced pressure. The obtained residue was purified by silica gel column chromatography (hexane:ethyl acetate=4:1 to 2:3). A light yellow solid of tert-butyl (1-acetyl-4-((6-chloro-5-cyano-3-fluoropyridin-2-yl)amino)piperidin-3-yl)carbamate (91 mg) was thus obtained.

MS (ESI m/z): 412, 414 (M+H)

RT (min): 1.28

Reference Example 123

The following compound was obtained with reference to Journal of Medicinal Chemistry, 2010, 53, 7107.

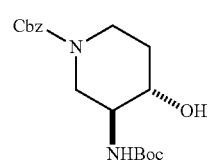

[Formula 143]

Benzyl 3-((tert-butoxycarbonyl)amino)-4-hydroxypiperidin-1-carboxylate

Reference Example 124

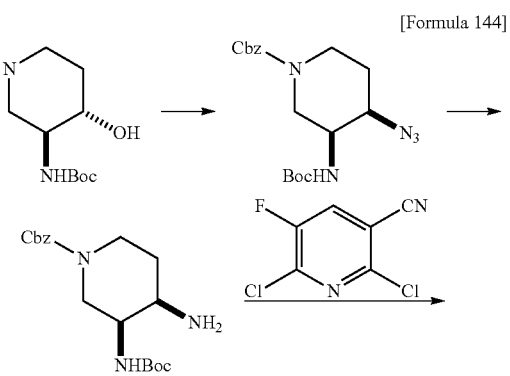

[Formula 144]

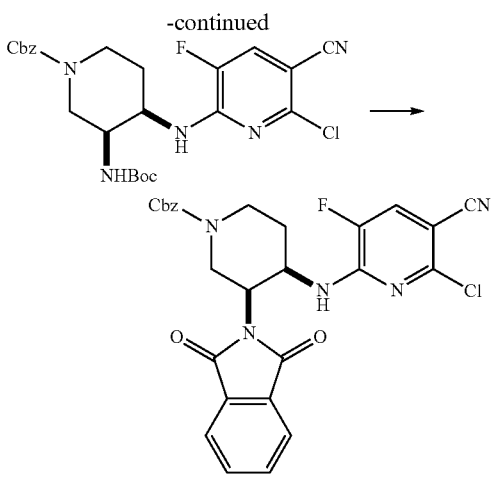

1st Step

Triphenylphosphine (840 mg), diisopropyl azodicarboxylate (40% in toluene) (1.68 ml), and DPPA (0.86 ml) were added to a THF (9.3 ml) solution containing benzyl 3-((tert-butoxycarbonyl)amino)-4-hydroxypiperidin-1-carboxylate (930 mg) under ice cooling, followed by stirring at 50° C. for 2 hours. The reaction solution was cooled to room temperature and water was added to the reaction solution, followed by extraction with ethyl acetate. The organic layers were washed with saturated saline and dried over anhydrous sodium sulfate. The solvent was distilled away under reduced pressure. The obtained residue was purified by silica gel column chromatography (hexane:ethyl acetate=9:1 to 17:3). Light yellow oily matter of benzyl 4-azide-3-((tert-butoxycarbonyl)amino)piperidin-1-carboxylate (780 mg) was thus obtained.

2nd Step

Triphenylphosphine (820 mg) was added to a THF/water (7.8 ml/0.78 ml) solution containing benzyl 4-azide-3-((tert-butoxycarbonyl)amino)piperidin-1-carboxylate (780 mg) obtained in the 1st step, followed by heating and stirring at 80° C. for 3 hours. The reaction solution was cooled to room temperature. Water and a 2M hydrochloric acid aqueous solution were added to the reaction solution so as to acidify the reaction solution. The reaction solution was washed with ethyl acetate. Next, the aqueous layers were collected and a 5M sodium hydroxide aqueous solution was added so as to alkalify the aqueous layers. The aqueous layers were subjected to extraction twice with ethyl acetate. The organic layers were washed with saturated saline and dried over anhydrous sodium sulfate and the solvent was distilled away under reduced pressure. Yellow oily matter of benzyl 4-amino-3-((tert-butoxycarbonyl)amino)piperidin-1-carboxylate (470 mg) was thus obtained.

3rd Step

Triethylamine (0.22 ml) and 2,6-dichloro-5-fluoronicotinonitrile (470 mg) were added to a DMSO (2.4 ml) solution containing benzyl 4-amino-3-((tert-butoxycarbonyl)amino)piperidin-1-carboxylate (470 mg) obtained in the 2nd step, followed by stirring at room temperature for 0.5 hours. Ethyl acetate and water were added to the reaction solution for extraction. The organic layers were washed with saturated saline and dried over anhydrous sodium sulfate. The solvent was distilled away under reduced pressure. The obtained residue was purified by silica gel column chromatography (hexane:ethyl acetate=19:1 to 15:3) and a white solid of benzyl 3-((tert-butoxycarbonyl)amino)-4-((6-chloro-5-cyano-3-fluoropyridin-2-yl)amino)piperidin-1-carboxylate (500 mg) was thus obtained.

MS (ESI m/z): 504, 506 (M+H)

RT (min): 1.88

4th Step

Benzyl 3-((tert-butoxycarbonyl)amino)-4-((6-chloro-5-cyano-3-fluoropyridin-2-yl)amino)piperidin-1-carboxylate (50 mg) obtained in the 3rd step was mixed with TFA (1 ml), followed by stirring at room temperature for 15 minutes. TFA was distilled away under reduced pressure. Water (5 ml), a 5M sodium hydroxide aqueous solution (1 ml), and chloroform were added to the obtained residue and the organic layers were collected. Subsequently, the organic layers were washed with saturated saline and dried over anhydrous sodium sulfate and the solvent was distilled away under reduced pressure.

Next, DMF (1 ml) and phthalic anhydride (29 mg) were added to the obtained residue, followed by heating and stirring at 150° C. for 1 hour. The reaction solution was cooled to room temperature. Ethyl acetate was added to the reaction solution. The reaction solution was washed with a saturated sodium hydrogen carbonate aqueous solution and saturated saline and dried over anhydrous sodium sulfate. The solvent was distilled away under reduced pressure. A white solid of benzyl 4-((6-chloro-5-cyano-3-fluoropyridin-2-yl)amino)-3-(1,3-dioxoisoindolin-2-yl)piperidin-1-carboxylate (37 mg) was thus obtained.

MS (ESI m/z): 534, 536 (M+H)

RT (min): 1.75

Reference Example 125

[Formula 145]

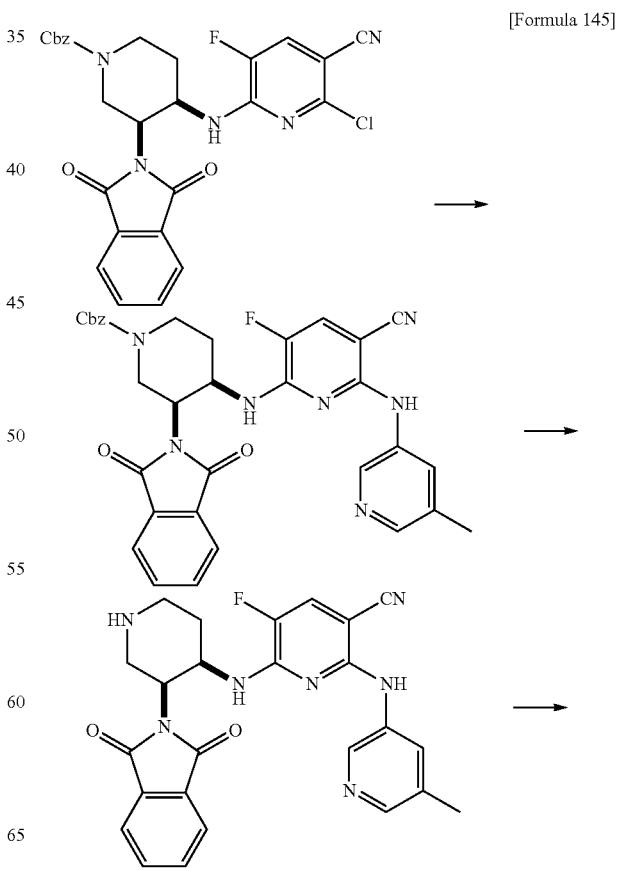

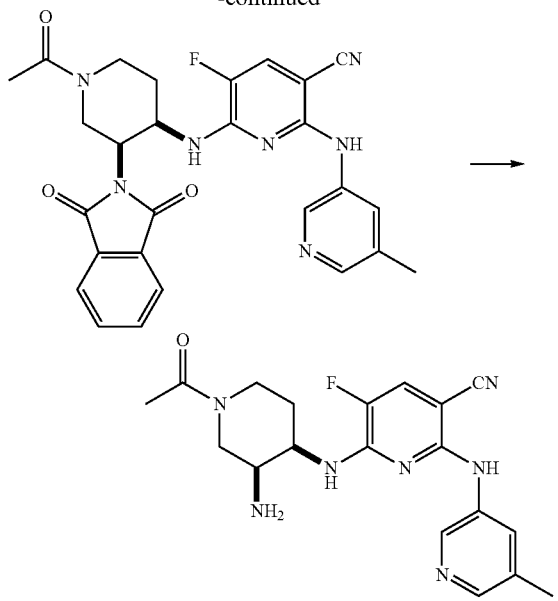

1st Step

3-Amino-3-methylpyridine (9 mg), cesium carbonate (45 mg), Pd$_2$(dba)$_3$ (10 mg), and Xantphos (12 mg) were added to a dioxane (3 ml) solution containing benzyl 4-((6-chloro-5-cyano-3-fluoropyridin-2-yl)amino)-3-(1,3-dioxoisoindolin-2-yl)piperidin-1-carboxylate (37 mg), followed by microwave irradiation (Initiator™, 160° C., 10 minutes, 2.45 GHz, 0-240 W). The obtained residue was filtered through Celite and filter cake was washed with ethyl acetate. Subsequently, the solvent was distilled away from the filtrate under reduced pressure. The obtained residue was purified by silica gel column chromatography (hexane:ethyl acetate=4:1 to 1:1). Yellow oily matter of benzyl 4-((5-cyano-3-fluoro-6-((5-methylpyridin-3-yl)amino)pyridin-2-yl)amino)-3-(1,3-dioxoisoindolin-2-yl)piperidin-1-carboxylate (28 mg) was thus obtained.

MS (ESI m/z): 606 (M+H)
RT (min): 1.30

2nd Step

Ammonium formate (6 mg) and 10% Pd/C (6 mg) were added to an ethyl acetate/MeOH (1 ml/1 ml) solution containing benzyl 4-((5-cyano-3-fluoro-6-((5-methylpyridin-3-yl)amino)pyridin-2-yl)amino)-3-(1,3-dioxoisoindolin-2-yl)piperidin-1-carboxylate (37 mg) obtained in the 1st step in a nitrogen atmosphere, followed by heating and stirring at 70° C. for 1 hour. Next, ammonium formate (30 mg) and 10% Pd/C (30 mg) were added to the solution, followed by heating and stirring at 70° C. for 1 hour. The reaction solution was cooled to room temperature and insoluble matter was removed by filtration through Celite. Filter cake was washed with ethyl acetate. The resulting filtrate was mixed with wash liquid. The obtained organic layers were washed with saturated saline and dried over anhydrous sodium sulfate. The solvent was distilled away under reduced pressure. A white solid of 6-((3-(1,3-dioxoisoindolin-2-yl)piperidin-4-yl)amino)-5-fluoro-2-((5-methylpyridin-3-yl)amino)nicotinonitrile (15 mg) was thus obtained.

3rd Step

Sodium hydrogen carbonate (13 mg) and acetyl chloride (0.005 ml) were added to a THF/water (0.5 ml/0.5 ml) solution containing 6-((3-(1,3-dioxoisoindolin-2-yl)piperidin-4-yl)amino)-5-fluoro-2-((5-methylpyridin-3-yl)amino)nicotinonitrile (15 mg) obtained in the 2nd step under ice cooling, followed by stirring at room temperature for 0.5 hours. Ethyl acetate was added to the reaction solution. The obtained organic layers were washed with saturated saline and dried over anhydrous sodium sulfate. Then, the solvent was distilled away under reduced pressure. Yellow oily matter of 6-((1-acetyl-3-(1,3-dioxoisoindolin-2-yl)piperidin-4-yl)amino)-5-fluoro-2-((5-methylpyridin-3-yl)amino)nicotinonitrile (12 mg) was thus obtained.

MS (ESI m/z): 514 (M+H)
RT (min): 0.86

4th Step

Hydrazine monohydrate (0.1 ml) was added to an EtOH (1 ml) solution containing 6-((1-acetyl-3-(1,3-dioxoisoindolin-2-yl)piperidin-4-yl)amino)-5-fluoro-2-((5-methylpyridin-3-yl)amino)nicotinonitrile (12 mg) obtained in the 3rd step at room temperature, followed by heating and stirring at 50° C. for 0.5 hours. Ethyl acetate was added to the reaction solution. The obtained organic layers were washed with saturated saline and dried over anhydrous sodium sulfate. The solvent was distilled away under reduced pressure. Next, ethyl acetate (1 ml) and 4M hydrochloric acid/1,4-dioxane (0.008 ml) were added to the obtained residue, followed by stirring at room temperature for 0.5 hours. The solvent was removed under reduced pressure and the obtained solid was washed with ethyl acetate. A yellow solid of 6-((1-acetyl-3-aminopiperidin-4-yl)amino)-5-fluoro-2-((5-methylpyridin-3-yl)amino)nicotinonitrile hydrochloride (6 mg) was thus obtained.

MS (ESI m/z): 384 (M+H)
RT (min): 0.54

Reference Example 126

The following compound was obtained with reference to J. Org. Chem., 1985, 50, 4154-4155 and Synth. Commun., 1992, 22, 3003-3012.

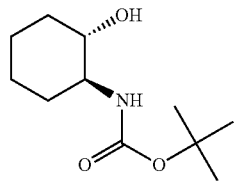

[Formula 146]

tert-Butyl ((1S,2S)-2-hydroxycyclohexyl)carbamate

Reference Example 127

The following compound was obtained with reference to US 2003/0119855 A1.

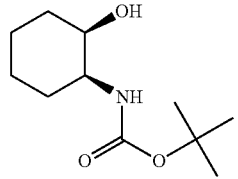

[Formula 147]

tert-Butyl ((1S,2R)-2-aminocyclohexyl)carbamate

1H NMR (CDCl₃, 300Mz): 1.3-1.7 (17H, m), 2.9-3.0 (1H, m), 3.6-3.7 (1H, m), 4.9-5.0 (1H, m).

Reference Example 128

[Formula 148]

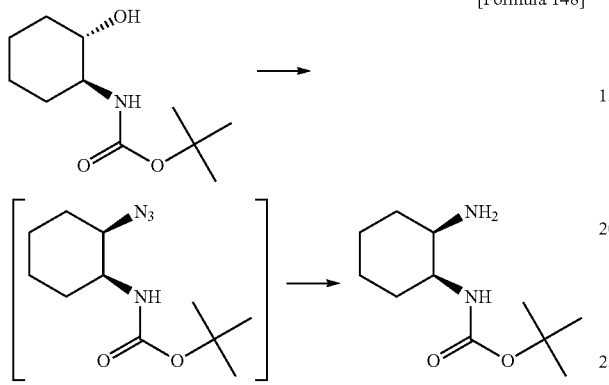

Triphenylphosphine (14.3 g) was added to a THF (190 ml) solution containing tert-butyl ((1S,2S)-2-hydroxycyclohexyl)carbamate (10.0 g), followed by ice cooling. Diethyl azodicarboxylate (40% in toluene) (24.3 g) and DPPA (15.3 g) were added dropwise to the reaction solution, followed by stirring at room temperature for 1 hour. The reaction solution was left overnight. The solvent was distilled away under reduced pressure. Water was added and then a 20% sodium hydroxide aqueous solution was added. Then, the organic layers were collected. Water (30 ml) was added to the obtained organic layers, followed by heating to 60° C. A THF (40 ml) solution containing triphenylphosphine (14.3 g) was added dropwise, followed by reflux for 2.5 hours. The solvent was distilled away under ordinary pressure. Toluene was added and the pH was adjusted with 3M hydrochloric acid to pH=1 or less. Then, the resulting aqueous layers were collected, ethyl acetate was added, and the pH was adjusted with a 20% sodium hydroxide aqueous solution to pH 12. The organic layers were collected and dried over anhydrous sodium sulfate. Light yellow oily matter of tert-butyl ((1S,2R)-2-aminocyclohexyl)carbamate (5.24 g) was thus obtained.

Reference Example 129

The following compound was obtained with reference to ChemCatChem, 2010, 2, 1215-1218 (optical resolution by lipase).

[Formula 149]

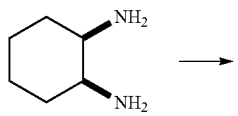

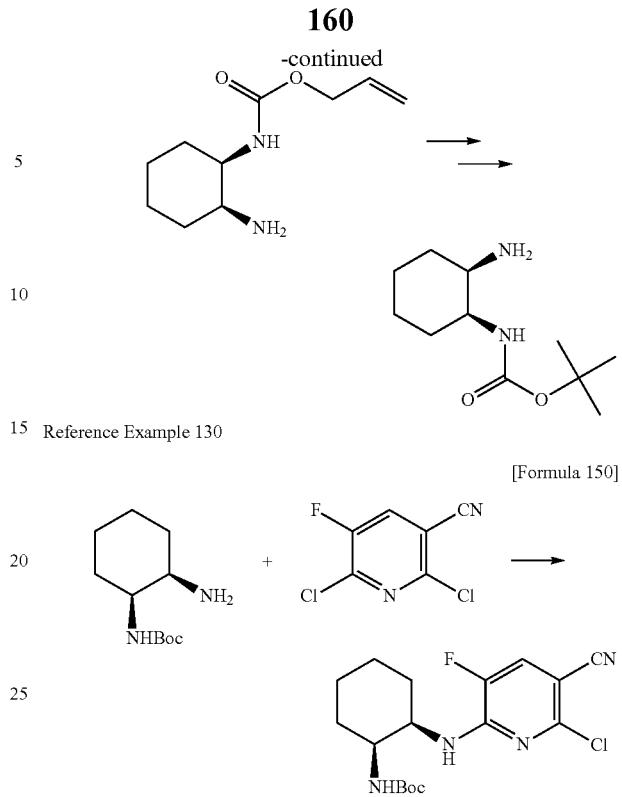

Reference Example 130

[Formula 150]

Potassium carbonate (3.62 g) and 2,6-dichloro-5-fluoronicotinonitrile (5.00 g) were added to a THF (50 ml) solution containing tert-butyl ((1S,2R)-2-aminocyclohexyl)carbamate (5.61 g), followed by reflux at 60° C. for 8 hours. Then, the solvent was distilled away at 70° C. 1,4-dioxane (100 ml) was added to the resulting solution, followed by stirring at 100° C. for 10 hours. The reaction solution was adjusted to room temperature. Ethyl acetate and 2M hydrochloric acid were added to the reaction solution. The organic layers were collected. The organic layers were washed with saturated saline and dried over anhydrous sodium sulfate. The solvent was distilled away under reduced pressure and the obtained residue was purified by silica gel chromatography (n-hexane: ethyl acetate=9:1 to 2:1). Diisopropyl ether was added to the obtained oily matter and a solid precipitate was collected by filtration. A white solid of tert-butyl ((1S,2R)-2-((6-chloro-5-cyano-3-fluoropyridin-2-yl)amino)cyclohexyl)carbamate (5.77 g) was thus obtained.

Reference Example 131

[Formula 151]

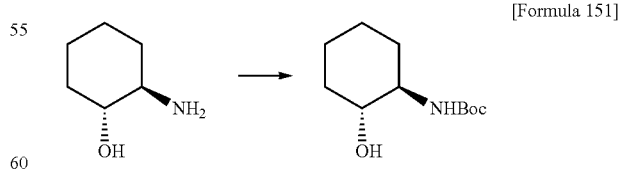

Water (100 ml) was added to (1R,2R)-2-aminocyclohexan-1-ol (47.8 g) and a THF (200 ml) solution containing di-tert-butyl dicarbonate (95.1 g) was added dropwise, followed by stirring at room temperature 3 hours. The organic layers were collected at 36° C., followed by cooling. Then, a solid precipitate was collected by filtration and washed with hexane and ethyl acetate. A white solid of tert-butyl ((1R,2R)-2-hydroxycyclohexyl)carbamate (73.7 g) was thus obtained.

Reference Example 132

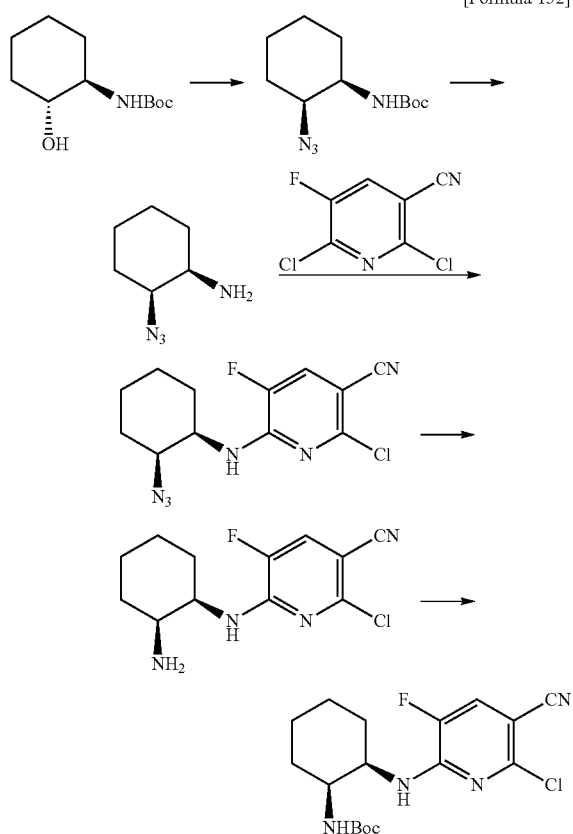

[Formula 152]

1st Step

Diethyl azodicarboxylate (40% in toluene) (36.4 g) and DPPA (23.0 g) were added dropwise to a THF (190 ml) solution containing tert-butyl ((1R,2R)-2-hydroxycyclohexyl)carbamate (15.0 g) and triphenylphosphine (21.9 g) under ice cooling, followed by stirring at room temperature for 7 hours. The solvent of the reaction solution was distilled away under reduced pressure and the obtained residue was purified by silica gel chromatography (n-hexane:ethyl acetate=4:1). Light yellow oily matter of tert-butyl ((1R,2S)-2-azide cyclohexyl)carbamate (21.1 g) was thus obtained.

2nd Step p-Toluene sulfonic acid monohydrate (13.3 g) was added to a 2-propanol (100 ml) solution containing tert-butyl ((1R,2S)-2-azide cyclohexyl)carbamate (21.1 g), followed by reflux for 40 minutes. After cooling, toluene and water were added, and aqueous layers were collected. Isopropyl acetate was added to the obtained aqueous layers. A 20% sodium hydroxide aqueous solution was added to adjust the pH to pH 12-13. Then, the organic layers were collected. The obtained organic layers were dried over anhydrous sodium sulfate and the solvent was distilled away under reduced pressure. (1R,2S)-2-azide cyclohexan-1-amine (8.7 g) was thus obtained.

3rd Step (Liquid A)

Potassium carbonate (0.87 g) was added to a DMSO (5 ml) solution containing 2,6-dichloro-5-fluoronicotinonitrile (1.00 g) at room temperature. The solution was heated to 50° C. and a DMSO (0.5 ml) solution containing (1R,2S)-2-azide cyclohexan-1-amine (0.73 g) was added to the solution. Subsequently, a DMSO (0.5 ml) solution containing (1R,2S)-2-azide cyclohexan-1-amine (0.22 g) was added, followed by stirring for 20 minutes. Further, a DMSO (0.5 ml) solution containing (1R,2S)-2-azide cyclohexan-1-amine (0.22 g) was added, followed by stirring for 20 minutes.

(Liquid B)

A toluene (25 ml) solution containing sodium carbonate (4.9 g) and (1R,2S)-2-azide cyclohexan-1-amine (7.5 g) was added dropwise to a DMSO (15 ml) solution containing 2,6-dichloro-5-fluoronicotinonitrile (7.3 g), followed by stirring at 45° C. for 2.5 hours.

4th Step

Water, 6M hydrochloric acid, and toluene were added to a mixture of liquid A and liquid B. The organic layers were collected. The solvent was distilled away under reduced pressure. THF (25 ml) and water (30 ml) were added to the obtained residue, followed by heating to 60° C. A THF (25 ml) solution containing triphenylphosphine (11.4 g) was added dropwise, followed by reflux for 3 hours. After cooling, toluene, water and 6M hydrochloric acid were added, and aqueous layers were collected. Isopropyl acetate and a 20% sodium hydroxide aqueous solution were added to the obtained aqueous layers, and organic layers were collected. The solvent was distilled away under reduced pressure. A residue was thus obtained.

5th Step

An ethyl acetate (15 ml) solution containing di-tert-butyl dicarbonate (8.1 g) was added dropwise to an ethyl acetate (50 ml) solution containing the residue obtained in the 4th step, followed by stirring at room temperature for 40 minutes. Next, an ethyl acetate (5 ml) solution containing di-tert-butyl dicarbonate (0.81 g) was added dropwise, followed by stirring at room temperature for 9 hours. Water and ethyl acetate were added to the reaction solution, and organic layers were collected. The solvent was distilled away under reduced pressure. 2-Propanol was added to the obtained residue. The solvent was distilled away under reduced pressure. Water and seed crystals were added, followed by stirring. Further, 2-propanol and water were added and a solid precipitate was collected by filtration. A white solid of tert-butyl ((1S,2R)-2-((6-chloro-5-cyano-3-fluoropyridin-2-yl)amino)cyclohexyl)carbamate (7.5 g) was thus obtained.

tert-Butyl ((1S,2R)-2-((6-chloro-5-cyano-3-fluoropyridin-2-yl)amino)cyclohexyl)carbamate obtained in the 5th step in Reference Example 132 was analyzed under the following conditions. It was confirmed that an optically-active substance was synthesized.

<Chiral HPLC conditions>

Apparatus: SHIMAZU 10A series

Column: Daicel CHIRALPAK IC-3

Mobile phase: n-Hex/IPA/i-PrNH2=95/5/0.1

Flow rate: 1.0 mL/min

Temperature: 40° C.

Wavelength: 210 nm

Retention time (minute): (R,S) 7.6, (S,R) 8.7

Reference Example 133

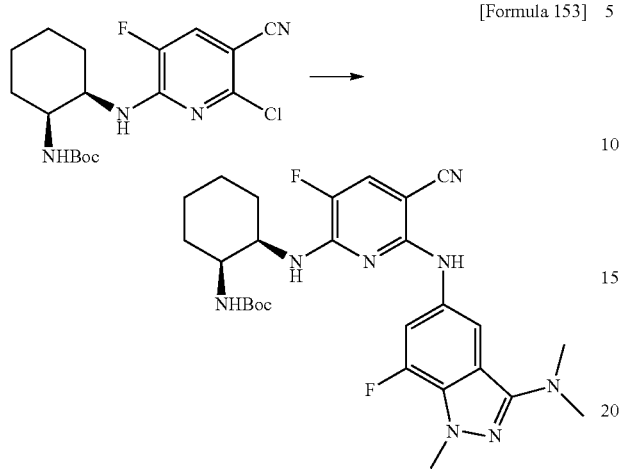

[Formula 153]

1st Step

7-Fluoro-N³,N³,1-trimethyl-1H-indazol-3,5-diamine (200 mg), cesium carbonate (625 mg), Pd₂(dba)₃ (132 mg), and Xantphos (167 mg) were added to a toluene (11 ml) solution containing tert-butyl cis-2-(6-chloro-5-cyano-3-fluoropyridin-2-ylamino)cyclohexylcarbamate (354 mg), followed by stirring at 100° C. for 6 hours in a nitrogen atmosphere. The reaction mixture was cooled to room temperature, insoluble matter was removed by filtration, and filter cake was washed with ethyl acetate. Then, the solvent was distilled away under reduced pressure. The obtained residue was purified by silica gel column chromatography (hexane:ethyl acetate=4:1 to 2:3). Brown oily matter of tert-butyl ((1S,2R)-2-(5-cyano-6-((3-dimethylamino-7-fluoro-1-methyl-1H-indazole5-yl)amino)-3-fluoropyridin-2-yl)amino)cyclohexylcarbamate (277 mg) was thus obtained.

MS (ESI m/z): 541 (M+H)
RT (min): 1.88

Reference Example 134

The compounds shown in table 1 were obtained as described in Reference Example 133.

TABLE 1

| Reference Example | Structure | Compound name | MS(ESI m/z): (M + H) | RT(min) |
|---|---|---|---|---|
| Reference Example 134-1 | 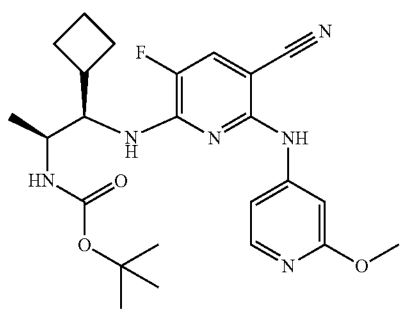 [SMILES: COc1cc(Nc2nc(N[C@H](C3CCC3)[C@H](C)NC(=O)OC(C)(C)C)c(F)cc2C#N)ccn1] | tert-butyl ((1R,2S)-1-((5-cyano-3-fluoro-6-((2-methoxypyridin-4-yl)amino)pyridin-2-yl)amino)-1-cyclobutylpropan-2-yl)carbamate | 471 | 1.35 |
| Reference Example 134-2 | 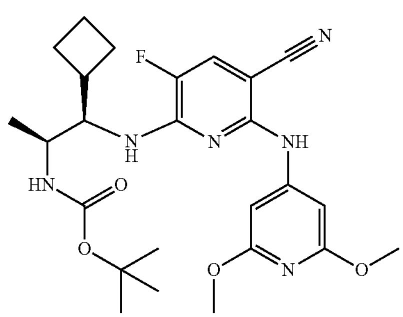 [SMILES: COc1cc(Nc2nc(N[C@H](C3CCC3)[C@H](C)NC(=O)OC(C)(C)C)c(F)cc2C#N)cc(OC)n1] | tert-butyl ((1R,2S)-1-((5-cyano-6-((2,6-dimethoxypyridin-4-yl)amino)-3-fluoropyridin-2-yl)amino)-1-cyclobutylpropan-2-yl)carbamate | 501 | 1.94 |
| Reference Example 134-3 | 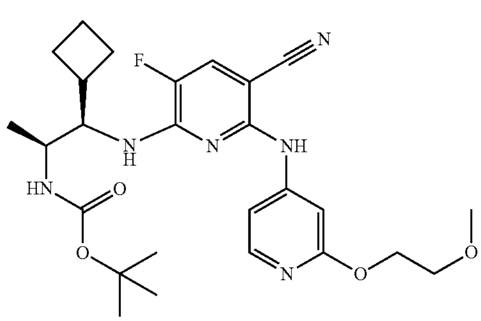 [SMILES: COCCOc1cc(Nc2nc(N[C@H](C3CCC3)[C@H](C)NC(=O)OC(C)(C)C)c(F)cc2C#N)ccn1] | tert-butyl ((1R,2S)-1-((5-cyano-3-fluoro-6-((2-(2-methoxyethoxy)pyridin-4-yl)amino)pyridin-2-yl)amino)-1-cyclobutylpropan-2-yl)carbamate | 515 | 1.42 |

TABLE 1-continued

| Reference Example | Structure | Compound name | MS(ESI m/z): (M + H) | RT(min) |
|---|---|---|---|---|
| Reference Example 134-4 | 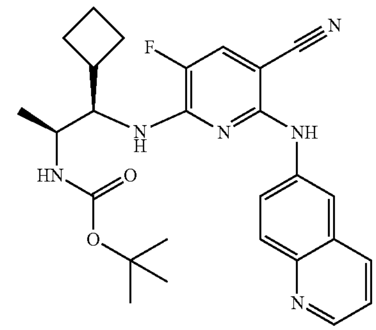 [SMILES: C[C@H](NC(=O)OC(C)(C)C)[C@H](Nc1nc(Nc2ccc3ncccc3c2)c(C#N)cc1F)C1CCC1] | tert-butyl ((1R,2S)-1-((5-cyano-3-fluoro-6-(quinolin-6-ylamino)pyridin-2-yl)amino)-1-cyclobutylpropan-2-yl)carbamate | 490 | 1.38 |
| Reference Example 134-5 | 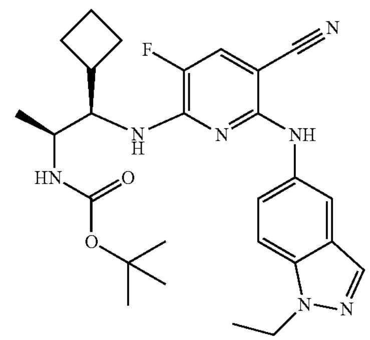 [SMILES: CCn1ncc2cc(Nc3nc(N[C@H](C4CCC4)[C@H](C)NC(=O)OC(C)(C)C)c(F)cc3C#N)ccc21] | tert-butyl ((1R,2S)-1-((5-cyano-6-((1-ethyl-1H-indazol-5-yl)amino)-3-fluoropyridin-2-yl)amino)-1-cyclobutylpropan-2-yl)carbamate | 508 | 1.80 |
| Reference Example 134-6 | 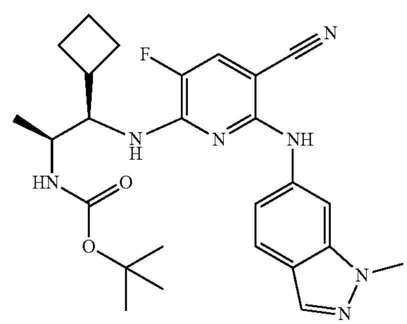 [SMILES: C[C@H](NC(=O)OC(C)(C)C)[C@H](Nc1nc(Nc2ccc3cnn(C)c3c2)c(C#N)cc1F)C1CCC1] | tert-butyl ((1R,2S)-1-((5-cyano-3-fluoro-6-((1-methyl-1H-indazol-6-yl)amino)pyridin-2-yl)amino)-1-cyclobutylpropan-2-yl)carbamate | 494 | 1.76 |
| Reference Example 134-7 | 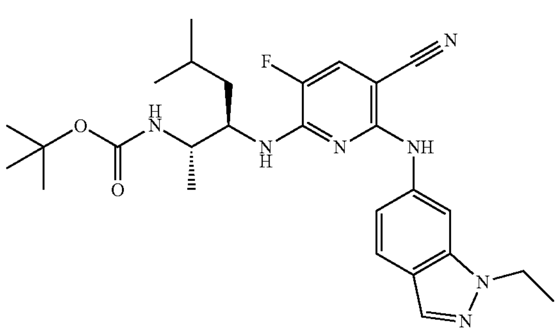 [SMILES: CCn1ncc2ccc(Nc3nc(N[C@H](CC(C)C)[C@H](C)NC(=O)OC(C)(C)C)c(F)cc3C#N)cc21] | tert-butyl ((2S,3R)-3-((5-cyano-6-((1-ethyl-1H-indazol-6-yl)amino)-3-fluoropyridin-2-yl)amino)-5-methylhexan-2-yl)carbamate | 510 | 1.86 |

TABLE 1-continued

| Reference Example | Structure | Compound name | MS(ESI m/z): (M + H) | RT(min) |
|---|---|---|---|---|
| Reference Example 134-8 | 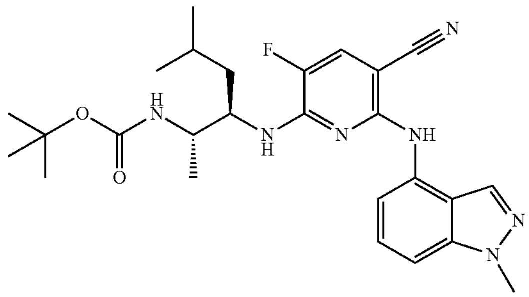 [SMILES: CC(C)C[C@@H](Nc1nc(Nc2cccc3c2cnn3C)c(C#N)cc1F)[C@H](C)NC(=O)OC(C)(C)C] | tert-butyl ((2S,3R)-3-((5-cyano-3-fluoro-6-((1-methyl-1H-indazol-4-yl)amino)pyridin-2-yl)amino)-5-methylhexan-2-yl)carbamate | 495 | 1.83 |
| Reference Example 134-9 | 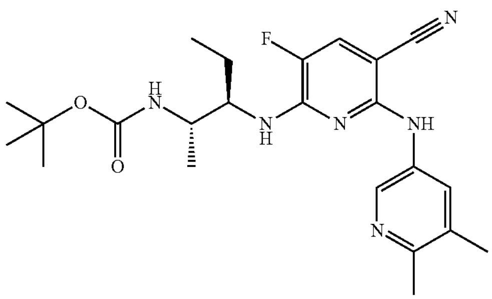 [SMILES: CC[C@@H](Nc1nc(Nc2cnc(C)c(C)c2)c(C#N)cc1F)[C@H](C)NC(=O)OC(C)(C)C] | tert-butyl ((2S,3R)-3-((5-cyano-6-((5,6-dimethylpyridin-3-yl)amino)-3-fluoropyridin-2-yl)amino)pentan-2-yl)carbamate | 461 | 1.10 |
| Reference Example 134-10 | 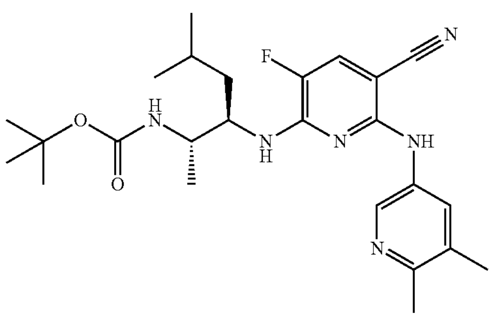 [SMILES: Cc1cc(Nc2nc(N[C@H](CC(C)C)[C@H](C)NC(=O)OC(C)(C)C)c(F)cc2C#N)cnc1C] | tert-butyl ((2S,3R)-3-((5-cyano-6-((5,6-dimethylpyridin-3-yl)amino)-3-fluoropyridin-2-yl)amino)-5-methylhexan-2-yl)carbamate | 489 | 1.24 |
| Reference Example 134-11 | 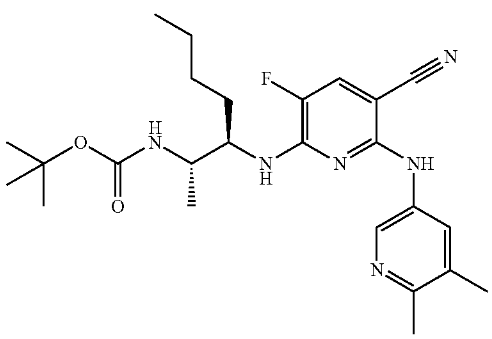 [SMILES: CCCC[C@@H](Nc1nc(Nc2cnc(C)c(C)c2)c(C#N)cc1F)[C@H](C)NC(=O)OC(C)(C)C] | tert-butyl ((2S,3R)-3-((5-cyano-6-((5,6-dimethylpyridin-3-yl)amino)-3-fluoropyridin-2-yl)amino)heptan-2-yl)carbamate | 489 | 1.25 |
| Reference Example 134-12 | 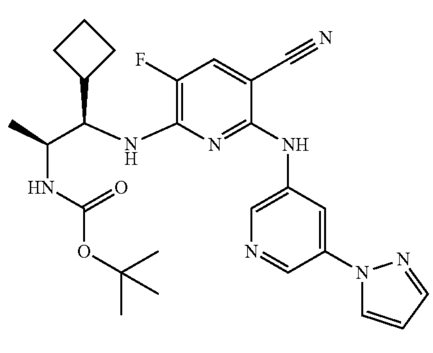 [SMILES: C[C@H](NC(=O)OC(C)(C)C)[C@H](Nc1nc(Nc2cncc(-n3cccn3)c2)c(C#N)cc1F)C1CCC1] | tert-butyl ((1R,2S)-1-((6-((5-(1H-pyrazol-1-yl)pyridin-3-yl)amino)-5-cyano-3-fluoropyridin-2-yl)amino)-1-cyclobutylpropan-2-yl)carbamate | 507 | 1.63 |

TABLE 1-continued

| Reference Example | Structure | Compound name | MS(ESI m/z): (M + H) | RT(min) |
|---|---|---|---|---|
| Reference Example 134-13 | 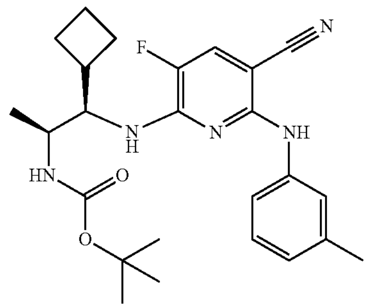 [SMILES: Cc1cccc(Nc2nc(N[C@H](C3CCC3)[C@H](C)NC(=O)OC(C)(C)C)c(F)cc2C#N)c1] | tert-butyl ((1R,2S)-1-((5-cyano-3-fluoro-6-(m-tolylamino)pyridin-2-yl)amino)-1-cyclobutylpropan-2-yl)carbamate | 454 | 1.98 |
| Reference Example 134-14 | 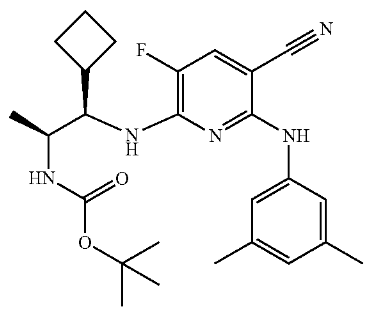 [SMILES: Cc1cc(C)cc(Nc2nc(N[C@H](C3CCC3)[C@H](C)NC(=O)OC(C)(C)C)c(F)cc2C#N)c1] | tert-butyl ((1R,2S)-1-((5-cyano-6-((3,5-dimethylphenyl)amino)-3-fluoropyridin-2-yl)amino)-1-cyclobutylpropan-2-yl)carbamate | 468 | 2.08 |
| Reference Example 134-15 | 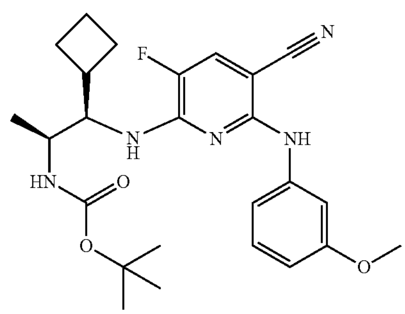 [SMILES: COc1cccc(Nc2nc(N[C@H](C3CCC3)[C@H](C)NC(=O)OC(C)(C)C)c(F)cc2C#N)c1] | tert-butyl ((1R,2S)-1-((5-cyano-3-fluoro-6-((3-methoxyphenyl)amino)pyridin-2-yl)amino)-1-cyclobutylpropan-2-yl)carbamate | 470 | 1.93 |
| Reference Example 134-16 | 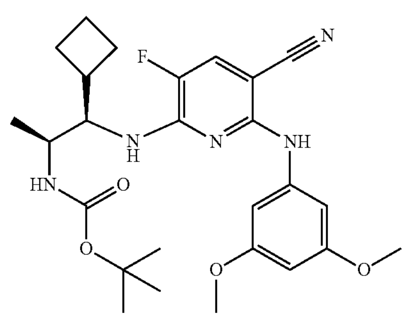 [SMILES: COc1cc(Nc2nc(N[C@H](C3CCC3)[C@H](C)NC(=O)OC(C)(C)C)c(F)cc2C#N)cc(OC)c1] | tert-butyl ((1R,2S)-1-((5-cyano-6-((3,5-dimethoxyphenyl)amino)-3-fluoropyridin-2-yl)amino)-1-cyclobutylpropan-2-yl)carbamate | 500 | 1.92 |
| Reference Example 134-17 | 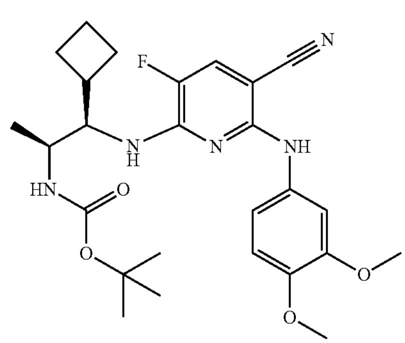 [SMILES: COc1ccc(Nc2nc(N[C@H](C3CCC3)[C@H](C)NC(=O)OC(C)(C)C)c(F)cc2C#N)cc1OC] | tert-butyl ((1R,2S)-1-((5-cyano-6-((3,4-dimethoxyphenyl)amino)-3-fluoropyridin-2-yl)amino)-1-cyclobutylpropan-2-yl)carbamate | 500 | 1.80 |

TABLE 1-continued

| Reference Example | Structure | Compound name | MS(ESI m/z): (M + H) | RT(min) |
|---|---|---|---|---|
| Reference Example 134-18 | 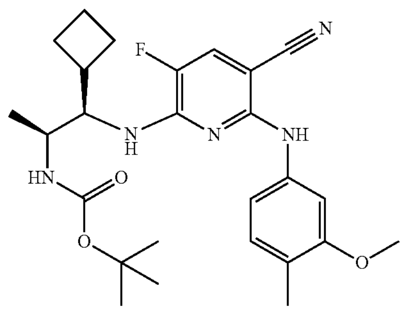 [SMILES: COc1cc(Nc2nc(N[C@H](C3CCC3)[C@H](C)NC(=O)OC(C)(C)C)c(F)cc2C#N)ccc1C] | tert-butyl ((1R,2S)-1-((5-cyano-3-fluoro-6-((3-methoxy-4-methylphenyl)amino)pyridin-2-yl)amino)-1-cyclobutylpropan-2-yl)carbamate | 484 | 2.05 |
| Reference Example 134-19 | 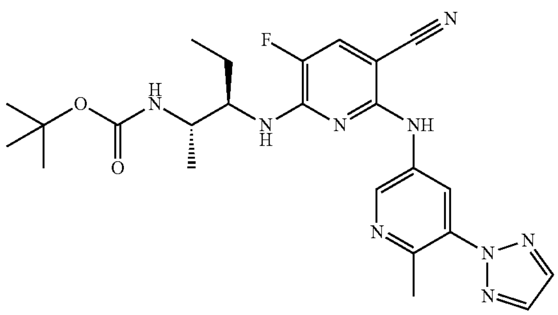 [SMILES: CC[C@@H](Nc1nc(Nc2cnc(C)c(-n3nccn3)c2)c(C#N)cc1F)[C@H](C)NC(=O)OC(C)(C)C] | tert-butyl ((2S,3R)-3-((5-cyano-3-fluoro-6-((6-methyl-5-(2H-1,2,3-triazol-2-yl)pyridin-3-yl)amino)pyridin-2-yl)amino)pentan-2-yl)carbamate | 514 | 1.44 |
| Reference Example 134-20 | 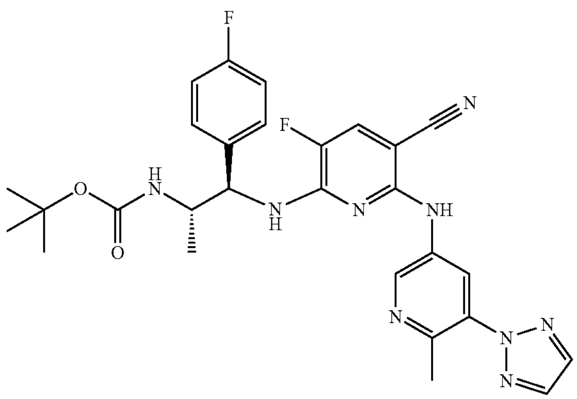 [SMILES: Cc1ncc(Nc2nc(N[C@H](c3ccc(F)cc3)[C@H](C)NC(=O)OC(C)(C)C)c(F)cc2C#N)cc1-n1nccn1] | tert-butyl ((1R,2S)-1-((5-cyano-3-fluoro-6-((6-methyl-5-(2H-1,2,3-triazol-2-yl)pyridin-3-yl)amino)pyridin-2-yl)amino)-1-(4-fluorophenyl)propan-2-yl)carbamate | 580 | 1.60 |
| Reference Example 134-21 | 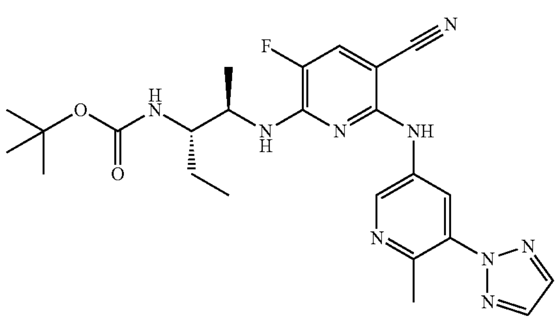 [SMILES: CC[C@H](NC(=O)OC(C)(C)C)[C@@H](C)Nc1nc(Nc2cnc(C)c(-n3nccn3)c2)c(C#N)cc1F] | tert-butyl ((2R,3S)-2-((5-cyano-3-fluoro-6-((6-methyl-5-(2H-1,2,3-triazol-2-yl)pyridin-3-yl)amino)pyridin-2-yl)amino)pentan-3-yl)carbamate | 514 | 1.48 |
| Reference Example 134-22 | 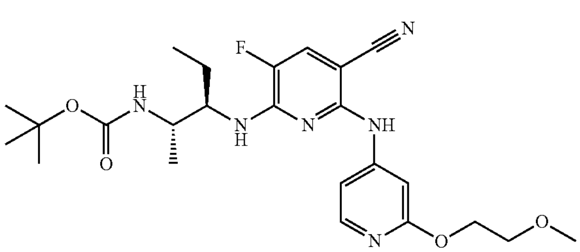 [SMILES: CC[C@@H](Nc1nc(Nc2ccnc(OCCOC)c2)c(C#N)cc1F)[C@H](C)NC(=O)OC(C)(C)C] | tert-butyl ((2S,3R)-3-((5-cyano-3-fluoro-6-((2-(2-methoxyethoxy)pyridin-4-yl)amino)pyridin-2-yl)amino)pentan-2-yl)carbamate | 507 | 1.12 |

TABLE 1-continued

| Reference Example | Structure | Compound name | MS(ESI m/z): (M + H) | RT(min) |
|---|---|---|---|---|
| Reference Example 134-23 | 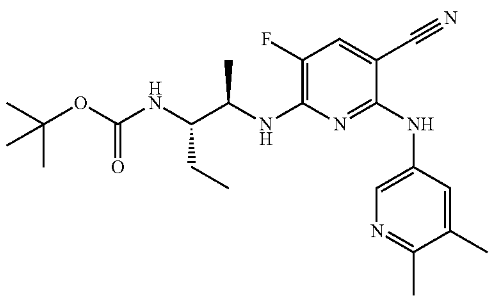 [SMILES: CC[C@H](NC(=O)OC(C)(C)C)[C@@H](C)Nc1nc(Nc2cnc(C)c(C)c2)c(C#N)cc1F] | tert-butyl ((2R,3S)-2-((5-cyano-6-((5,6-dimethylpyridin-3-yl)amino)-3-fluoropyridin-2-yl)amino)pentan-3-yl)carbamate | 461 | 1.10 |
| Reference Example 134-24 | 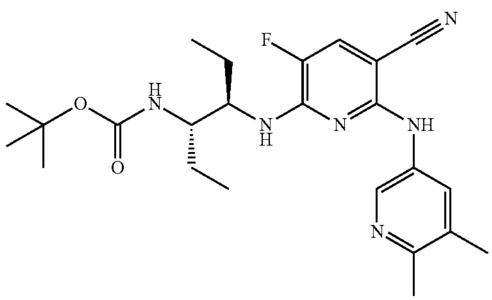 [SMILES: CC[C@H](NC(=O)OC(C)(C)C)[C@@H](CC)Nc1nc(Nc2cnc(C)c(C)c2)c(C#N)cc1F] | tert-butyl ((3S,4R)-4-((5-cyano 6-((5,6-dimethylpyridin-3-yl)amino)-3-fluoropyridin-2-yl)amino)hexan-3-yl)carbamate | 475 | 1.16 |
| Reference Example 134-25 | 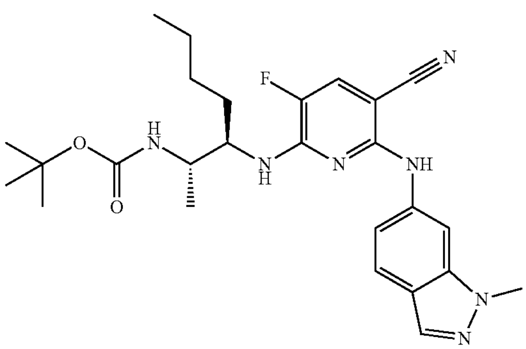 [SMILES: CCCC[C@@H](Nc1nc(Nc2ccc3cnn(C)c3c2)c(C#N)cc1F)[C@H](C)NC(=O)OC(C)(C)C] | tert-butyl ((2S,3R)-3-((5-cyano-3-fluoro-6-((1-methyl-1H-indazol-6-yl)amino)pyridin-2-yl)amino)heptan-2-yl)carbamate | 514 | 1.63 |
| Reference Example 134-26 | 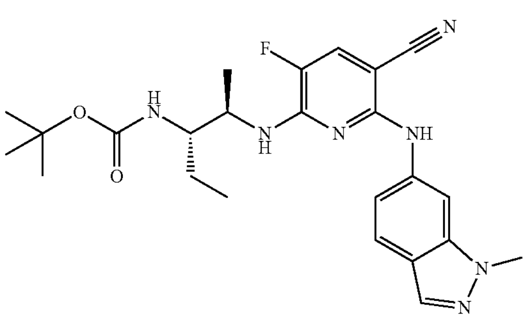 [SMILES: CC[C@H](NC(=O)OC(C)(C)C)[C@@H](C)Nc1nc(Nc2ccc3cnn(C)c3c2)c(C#N)cc1F] | tert-butyl ((2R,3S)-2-((5-cyano-3-fluoro-6-((1-methyl-1H-indazol-6-yl)amino)pyridin-2-yl)amino)pentan-3-yl)carbamate | 486 | 1.50 |

TABLE 1-continued

| Reference Example | Structure | Compound name | MS(ESI m/z): (M + H) | RT(min) |
|---|---|---|---|---|
| Reference Example 134-27 | 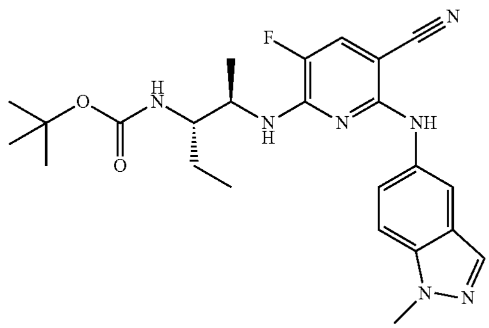 [SMILES: CC[C@H](NC(=O)OC(C)(C)C)[C@@H](C)Nc1nc(Nc2ccc3c(cnn3C)c2)c(C#N)cc1F] | tert-butyl ((2R,3S)-2-((5-cyano-3-fluoro-6-((1-methyl-1H-indazol-5-yl)amino)pyridin-2-yl)amino)pentan-3-yl)carbamate | 486 | 1.44 |
| Reference Example 134-28 | 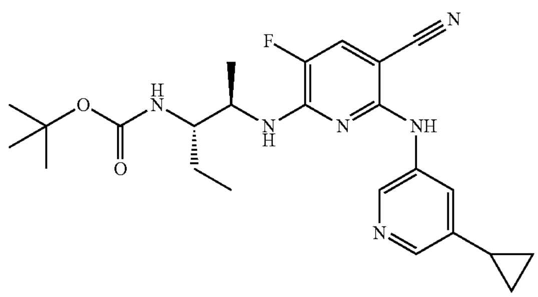 [SMILES: CC[C@H](NC(=O)OC(C)(C)C)[C@@H](C)Nc1nc(Nc2cncc(C3CC3)c2)c(C#N)cc1F] | tert-butyl ((2R,3S)-2-((5-cyano-6-((5-cyclopropylpyridin-3-yl)amino)-3-fluoropyridin-2-yl)amino)pentan-3-yl)carbamate | 473 | 1.20 |
| Reference Example 134-29 | 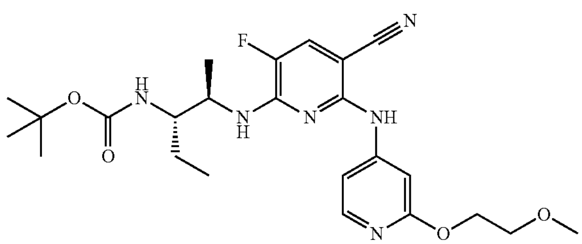 [SMILES: CC[C@H](NC(=O)OC(C)(C)C)[C@@H](C)Nc1nc(Nc2ccnc(OCCOC)c2)c(C#N)cc1F] | tert-butyl ((2R,3S)-2-((5-cyano-3-fluoro-6-((2-(2-methoxyethoxy)pyridin-4-yl)amino)pyridin-2-yl)amino)pentan-3-yl)carbamate | 507 | 1.16 |
| Reference Example 134-30 | 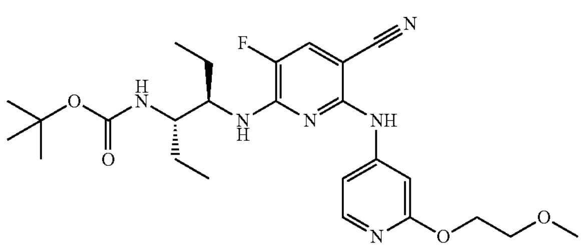 [SMILES: CC[C@H](NC(=O)OC(C)(C)C)[C@@H](CC)Nc1nc(Nc2ccnc(OCCOC)c2)c(C#N)cc1F] | tert-butyl ((3S,4R)-4-((5-cyano-3-fluoro-6-((2-(2-methoxyethoxy)pyridin-4-yl)amino)pyridin-2-yl)amino)hexan-3-yl)carbamate | 521 | 1.19 |
| Reference Example 134-31 | 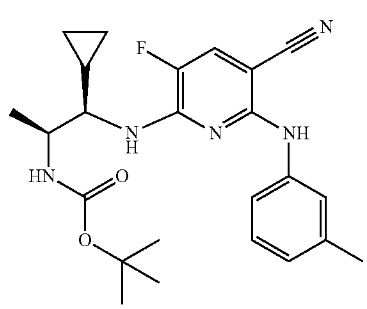 [SMILES: Cc1cccc(Nc2nc(N[C@H](C3CC3)[C@H](C)NC(=O)OC(C)(C)C)c(F)cc2C#N)c1] | tert-butyl ((1R,2S)-1-((5-cyano-3-fluoro-6-(m-tolylamino)pyridin-2-yl)amino)-1-cyclopropylpropan-2-yl)carbamate | 440 | 1.93 |

TABLE 1-continued

| Reference Example | Structure | Compound name | MS(ESI m/z): (M + H) | RT(min) |
|---|---|---|---|---|
| Reference Example 134-32 | 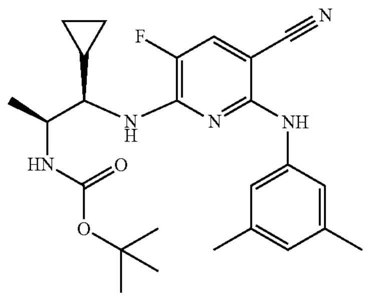 [SMILES: Cc1cc(C)cc(Nc2nc(N[C@H](C3CC3)[C@H](C)NC(=O)OC(C)(C)C)c(F)cc2C#N)c1] | tert-butyl ((1R,2S)-1-((5-cyano-6-((3,5-dimethylphenyl)amino)-3-fluoropyridin-2-yl)amino)-1-cyclopropylpropan-2-yl)carbamate | 454 | 2.02 |
| Reference Example 134-33 | 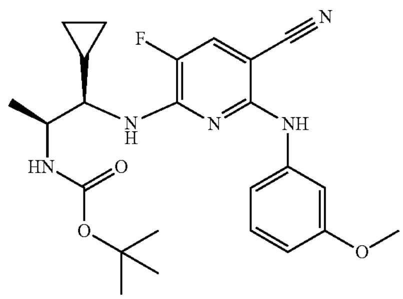 [SMILES: COc1cccc(Nc2nc(N[C@H](C3CC3)[C@H](C)NC(=O)OC(C)(C)C)c(F)cc2C#N)c1] | tert-butyl ((1R,2S)-1-((5-cyano-3-fluoro-6-((3-methoxyphenyl)amino)pyridin-2-yl)amino)-1-cyclopropylpropan-2-yl)carbamate | 456 | 1.83 |
| Reference Example 134-34 | 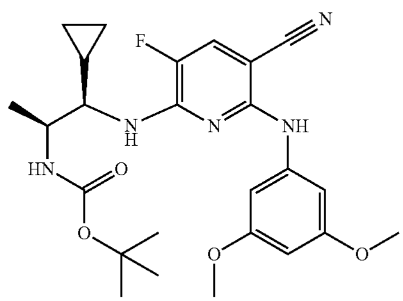 [SMILES: COc1cc(Nc2nc(N[C@H](C3CC3)[C@H](C)NC(=O)OC(C)(C)C)c(F)cc2C#N)cc(OC)c1] | tert-butyl ((1R,2S)-1-((5-cyano-6-((3,5-dimethoxyphenyl)amino)-3-fluoropyridin-2-yl)amino)-1-cyclopropylpropan-2-yl)carbamate | 486 | 1.82 |
| Reference Example 134-35 | 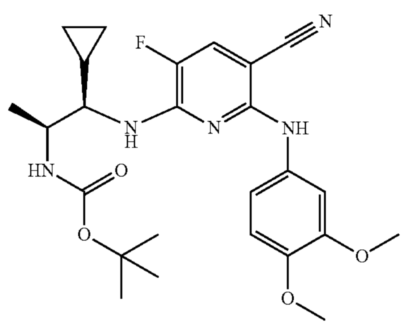 [SMILES: COc1ccc(Nc2nc(N[C@H](C3CC3)[C@H](C)NC(=O)OC(C)(C)C)c(F)cc2C#N)cc1OC] | tert-butyl ((1R,2S)-1-((5-cyano-6-((3,4-dimethoxyphenyl)amino)-3-fluoropyridin-2-yl)amino)-1-cyclopropylpropan-2-yl)carbamate | 486 | 1.69 |
| Reference Example 134-36 | 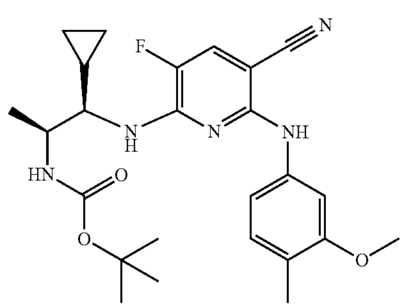 [SMILES: COc1cc(Nc2nc(N[C@H](C3CC3)[C@H](C)NC(=O)OC(C)(C)C)c(F)cc2C#N)ccc1C] | tert-butyl ((1R,2S)-1-((5-cyano-3-fluoro-6-((3-methoxy-4-methylphenyl)amino)pyridin-2-yl)amino)-1-cyclopropylpropan-2-yl)carbamate | 470 | 1.94 |

TABLE 1-continued

| Reference Example | Structure | Compound name | MS(ESI m/z): (M + H) | RT(min) |
|---|---|---|---|---|
| Reference Example 134-37 | 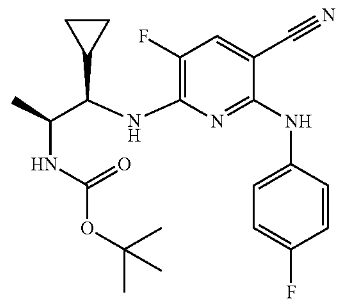 [SMILES: C[C@H](NC(=O)OC(C)(C)C)[C@H](Nc1nc(Nc2ccc(F)cc2)c(C#N)cc1F)C1CC1] | tert-butyl ((1R,2S)-1-((5-cyano-3-fluoro-6-((4-fluorophenyl)amino)pyridin-2-yl)amino)-1-cyclopropylpropan-2-yl)carbamate | 444 | 1.84 |
| Reference Example 134-38 | 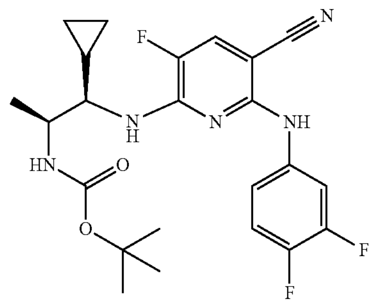 [SMILES: C[C@H](NC(=O)OC(C)(C)C)[C@H](Nc1nc(Nc2ccc(F)c(F)c2)c(C#N)cc1F)C1CC1] | tert-butyl ((1R,2S)-1-((5-cyano-6-((3,4-difluorophenyl)amino)-3-fluoropyridin-2-yl)amino)-1-cyclopropylpropan-2-yl)carbamate | 462 | 1.87 |
| Reference Example 134-39 | 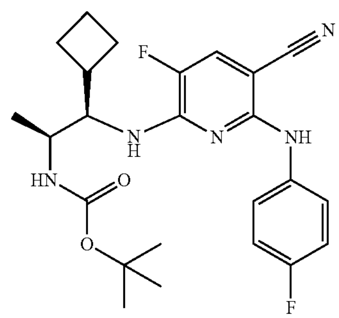 [SMILES: C[C@H](NC(=O)OC(C)(C)C)[C@H](Nc1nc(Nc2ccc(F)cc2)c(C#N)cc1F)C1CCC1] | tert-butyl ((1R,2S)-1-((5-cyano-3-fluoro-6-((4-fluorophenyl)amino)pyridin-2-yl)amino)-1-cyclobutylpropan-2-yl)carbamate | 458 | 1.95 |
| Reference Example 134-40 | 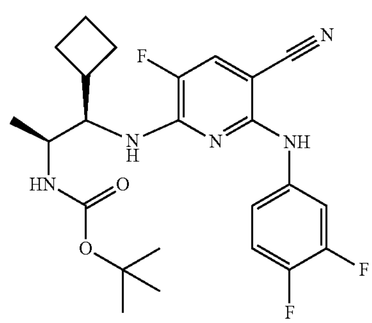 [SMILES: C[C@H](NC(=O)OC(C)(C)C)[C@H](Nc1nc(Nc2ccc(F)c(F)c2)c(C#N)cc1F)C1CCC1] | tert-butyl ((1R,2S)-1-((5-cyano-6-((3,4-difluorophenyl)amino)-3-fluoropyridin-2-yl)amino)-1-cyclobutylpropan-2-yl)carbamate | 476 | 1.98 |
| Reference Example 134-41 | 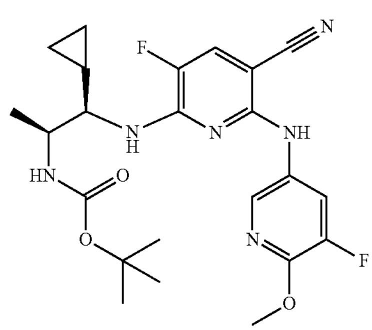 [SMILES: COc1ncc(Nc2nc(N[C@H](C3CC3)[C@H](C)NC(=O)OC(C)(C)C)c(F)cc2C#N)cc1F] | tert-butyl ((1R,2S)-1-((5-cyano-3-fluoro-6-((5-fluoro-6-methoxypyridin-3-yl)amino)pyridin-2-yl)amino)-1-cyclopropylpropan-2-yl)carbamate | 475 | 1.76 |

TABLE 1-continued

| Reference Example | Structure | Compound name | MS(ESI m/z): (M + H) | RT(min) |
|---|---|---|---|---|
| Reference Example 134-42 | 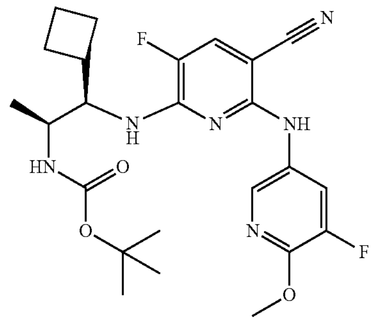 [SMILES: COc1ncc(Nc2nc(N[C@H](C3CCC3)[C@H](C)NC(=O)OC(C)(C)C)c(F)cc2C#N)cc1F] | tert-butyl ((1R,2S)-1-((5-cyano-3-fluoro-6-((5-fluoro-6-methoxypyridin-3-yl)amino)pyridin-2-yl)amino)-1-cyclobutylpropan-2-yl)carbamate | 489 | 1.87 |
| Reference Example 134-43 | 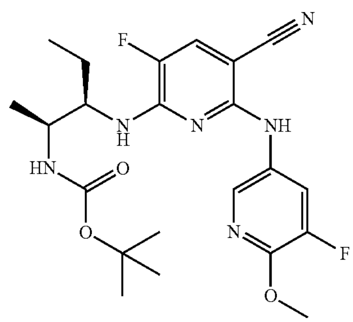 [SMILES: CC[C@@H](Nc1nc(Nc2cnc(OC)c(F)c2)c(C#N)cc1F)[C@H](C)NC(=O)OC(C)(C)C] | tert-butyl ((2S,3R)-3-((5-cyano-3-fluoro-6-((5-fluoro-6-methoxypyridin-3-yl)amino)pyridin-2-yl)amino)pentan-2-yl)carbamate | 463 | 1.75 |
| Reference Example 134-44 | 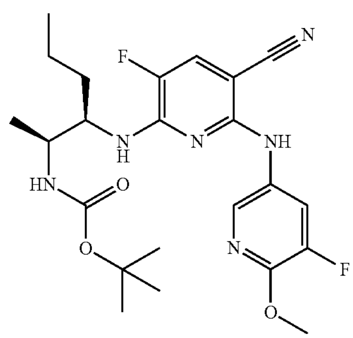 [SMILES: CCC[C@@H](Nc1nc(Nc2cnc(OC)c(F)c2)c(C#N)cc1F)[C@H](C)NC(=O)OC(C)(C)C] | tert-butyl ((2S,3R)-3-((5-cyano-3-fluoro-6-((5-fluoro-6-methoxypyridin-3-yl)amino)pyridin-2-yl)amino)hexan-2-yl)carbamate | 477 | 1.84 |
| Reference Example 134-45 | 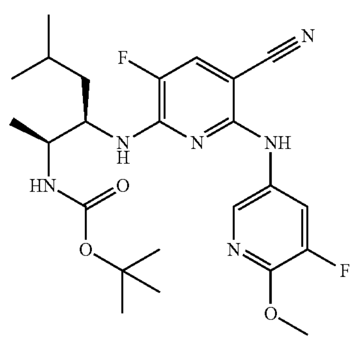 [SMILES: COc1ncc(Nc2nc(N[C@H](CC(C)C)[C@H](C)NC(=O)OC(C)(C)C)c(F)cc2C#N)cc1F] | tert-butyl ((2S,3R)-3-((5-cyano-3-fluoro-6-((5-fluoro-6-methoxypyridin-3-yl)amino)pyridin-2-yl)amino)-5-methylhexan-2-yl)carbamate | 491 | 1.90 |

TABLE 1-continued

| Reference Example | Structure | Compound name | MS(ESI m/z): (M + H) | RT(min) |
|---|---|---|---|---|
| Reference Example 134-46 | 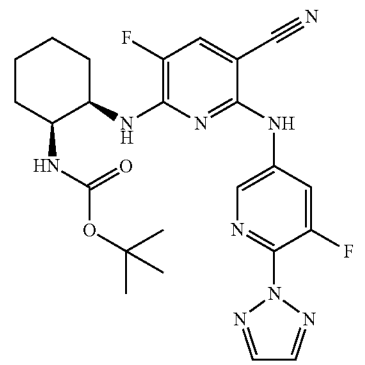 [SMILES: CC(C)(C)OC(=O)N[C@H]1CCCC[C@H]1Nc1nc(Nc2cnc(-n3nccn3)c(F)c2)c(C#N)cc1F] | tert-butyl ((1S,2R)-2-((5-cyano-3-fluoro-6-((5-fluoro-6-(2H-1,2,3-triazol-2-yl)pyridin-3-yl)amino)pyridin-2-yl)amino)cyclohexyl)carbamate | 512 | 1.66 |
| Reference Example 134-47 | 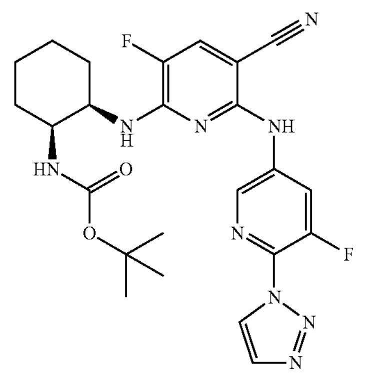 [SMILES: CC(C)(C)OC(=O)N[C@H]1CCCC[C@H]1Nc1nc(Nc2cnc(-n3ccnn3)c(F)c2)c(C#N)cc1F] | tert-butyl ((1S,2R)-2-((5-cyano-3-fluoro-6-((5-fluoro-6-(1H-1,2,3-triazol-1-yl)pyridin-3-yl)amino)pyridin-2-yl)amino)cyclohexyl)carbamate | 512 | 1.59 |
| Reference Example 134-48 | 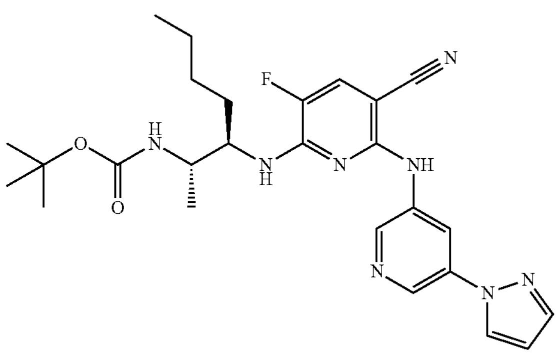 [SMILES: CCCC[C@@H](Nc1nc(Nc2cncc(-n3cccn3)c2)c(C#N)cc1F)[C@H](C)NC(=O)OC(C)(C)C] | tert-butyl ((2S,3R)-3-((6-((5-(1H-pyrazol-1-yl)pyridin-3-yl)amino)-5-cyano-3-fluoropyridin-2-yl)amino)heptan-2-yl)carbamate | 509 | 1.76 |
| Reference Example 134-49 | 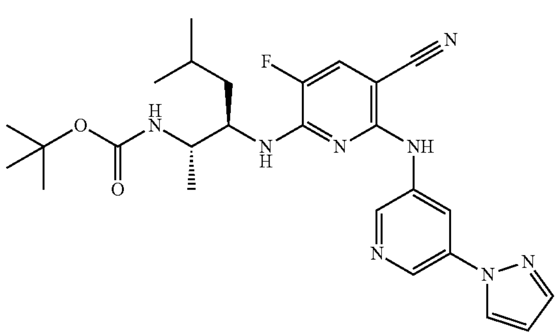 [SMILES: CC(C)C[C@@H](Nc1nc(Nc2cncc(-n3cccn3)c2)c(C#N)cc1F)[C@H](C)NC(=O)OC(C)(C)C] | tert-butyl ((2S,3R)-3-((6-((5-(1H-pyrazol-1-yl)pyridin-3-yl)amino)-5-cyano-3-fluoropyridin-2-yl)amino)-5-methylhexan-2-yl)carbamate | 509 | 1.74 |

TABLE 1-continued

| Reference Example | Structure | Compound name | MS(ESI m/z): (M + H) | RT(min) |
|---|---|---|---|---|
| Reference Example 134-50 | 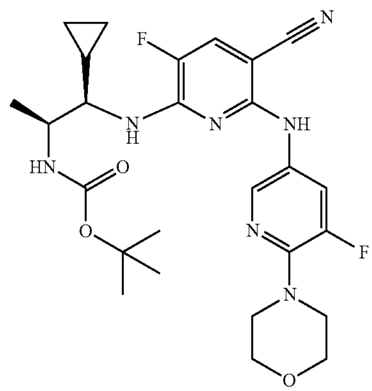 [SMILES: C[C@H](NC(=O)OC(C)(C)C)[C@H](Nc1nc(Nc2cnc(N3CCOCC3)c(F)c2)c(C#N)cc1F)C1CC1] | tert-butyl ((1R,2S)-1-((5-cyano-3-fluoro-6-((5-fluoro-6-morpholinopyridin-3-yl)amino)pyridin-2-yl)amino)-1-cyclopropylpropan-2-yl)carbamate | 530 | 1.64 |
| Reference Example 134-51 | 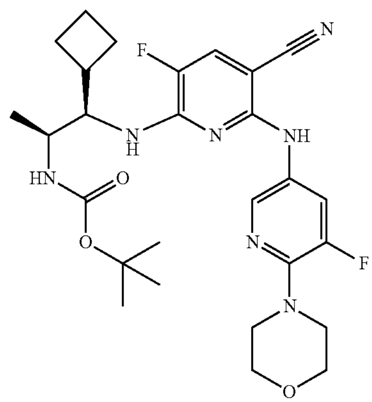 [SMILES: C[C@H](NC(=O)OC(C)(C)C)[C@H](Nc1nc(Nc2cnc(N3CCOCC3)c(F)c2)c(C#N)cc1F)C1CCC1] | tert-butyl ((1R,2S)-1-((5-cyano-3-fluoro-6-((5-fluoro-6-morpholinopyridin-3-yl)amino)pyridin-2-yl)amino)-1-cyclobutylpropan-2-yl)carbamate | 544 | 1.75 |
| Reference Example 134-52 | 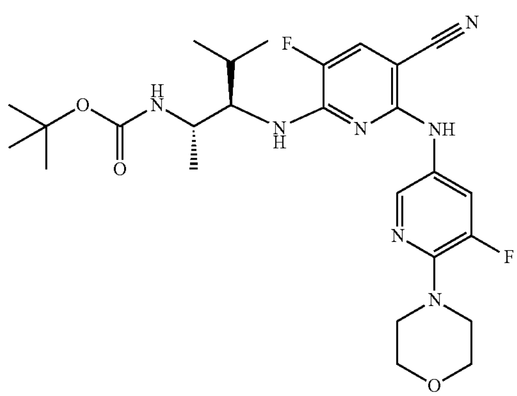 [SMILES: CC(C)[C@@H](Nc1nc(Nc2cnc(N3CCOCC3)c(F)c2)c(C#N)cc1F)[C@H](C)NC(=O)OC(C)(C)C] | tert-butyl ((2S,3R)-3-((5-cyano-3-fluoro-6-((5-fluoro-6-morpholinopyridin-3-yl)amino)pyridin-2-yl)amino)-4-methylpentan-2-yl)carbamate | 532 | 1.76 |
| Reference Example 134-53 | 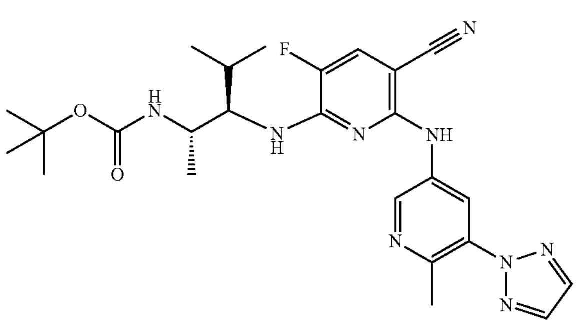 [SMILES: Cc1ncc(Nc2nc(N[C@H](C(C)C)[C@H](C)NC(=O)OC(C)(C)C)c(F)cc2C#N)cc1-n1nccn1] | tert-butyl ((2S,3R)-3-((5-cyano-3-fluoro-6-((6-methyl-5-(2H-1,2,3-triazol-2-yl)pyridin-3-yl)amino)pyridin-2-yl)amino)-4-methylpentan-2-yl)carbamate | 510 | 1.71 |

TABLE 1-continued

| Reference Example | Structure | Compound name | MS(ESI m/z): (M + H) | RT(min) |
|---|---|---|---|---|
| Reference Example 134-54 | 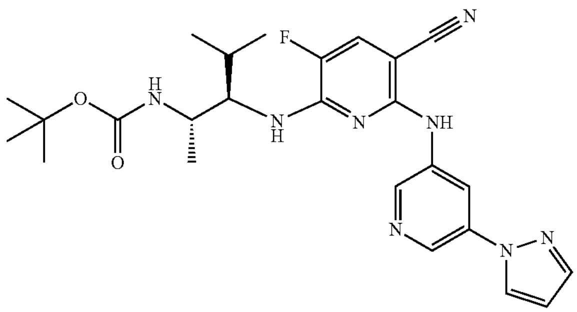 [SMILES: CC(C)[C@@H](Nc1nc(Nc2cncc(-n3cccn3)c2)c(C#N)cc1F)[C@H](C)NC(=O)OC(C)(C)C] | tert-butyl ((2S,3R)-3-((6-((5-(1H-pyrazol-1-yl)pyridin-3-yl)amino)-5-cyano-3-fluoropyridin-2-yl)amino)-4-methylpentan-2-yl)carbamate | 495 | 1.67 |
| Reference Example 134-55 | 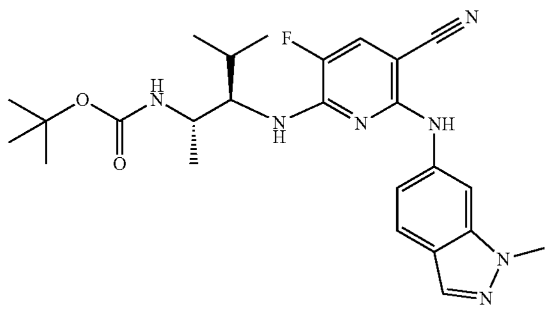 [SMILES: CC(C)[C@@H](Nc1nc(Nc2ccc3cnn(C)c3c2)c(C#N)cc1F)[C@H](C)NC(=O)OC(C)(C)C] | tert-butyl ((2S,3R)-3-((5-cyano-3-fluoro-6-((1-methyl-1H-indazol-6-yl)amino)pyridin-2-yl)amino)-4-methylpentan-2-yl)carbamate | 482 | 1.72 |
| Reference Example 134-56 | 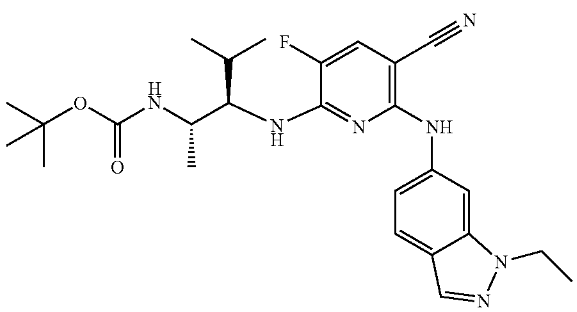 [SMILES: CCn1ncc2ccc(Nc3nc(N[C@H](C(C)C)[C@H](C)NC(=O)OC(C)(C)C)c(F)cc3C#N)cc21] | tert-butyl ((2S,3R)-3-((5-cyano-6-((1-ethyl-1H-indazol-6-yl)amino)-3-fluoropyridin-2-yl)amino)-4-methylpentan-2-yl)carbamate | 496 | 1.80 |
| Reference Example 134-57 | 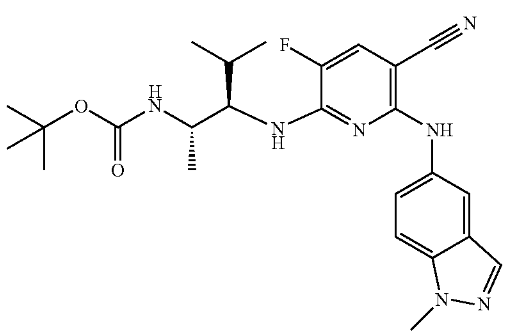 [SMILES: CC(C)[C@@H](Nc1nc(Nc2ccc3c(cnn3C)c2)c(C#N)cc1F)[C@H](C)NC(=O)OC(C)(C)C] | tert-butyl ((2S,3R)-3-((5-cyano-3-fluoro-6-((1-methyl-1H-indazol-5-yl)amino)pyridin-2-yl)amino)-4-methylpentan-2-yl)carbamate | 482 | 1.70 |
| Reference Example 134-58 | 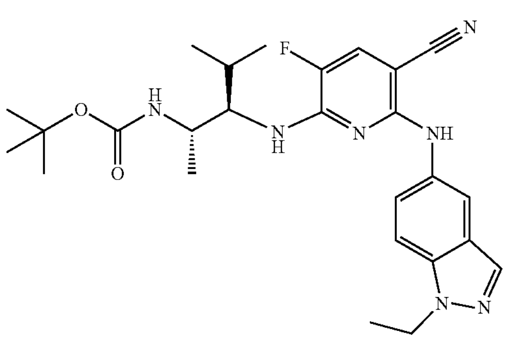 [SMILES: CCn1ncc2cc(Nc3nc(N[C@H](C(C)C)[C@H](C)NC(=O)OC(C)(C)C)c(F)cc3C#N)ccc21] | tert-butyl ((2S,3R)-3-((5-cyano-6-((1-ethyl-1H-indazol-5-yl)amino)-3-fluoropyridin-2-yl)amino)-4-methylpentan-2-yl)carbamate | 496 | 1.78 |

TABLE 1-continued

| Reference Example | Structure | Compound name | MS(ESI m/z): (M + H) | RT(min) |
|---|---|---|---|---|
| Reference Example 134-59 | 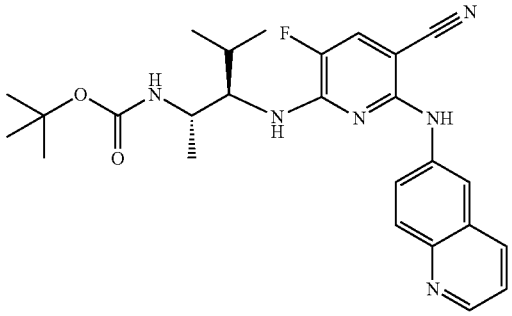 [SMILES: CC(C)[C@@H](Nc1nc(Nc2ccc3ncccc3c2)c(C#N)cc1F)[C@H](C)NC(=O)OC(C)(C)C] | tert-butyl ((2S,3R)-3-((5-cyano-3-fluoro-6-(quinolin-6-ylamino)pyridin-2-yl)amino)-4-methylpentan-2-yl)carbamate | 497 | 1.20 |
| Reference Example 134-60 | 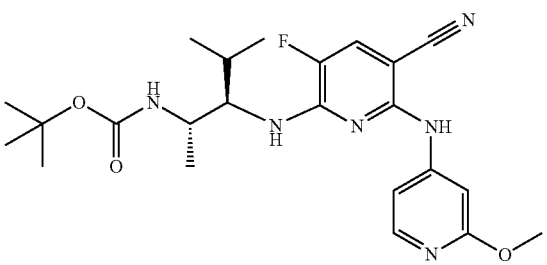 [SMILES: COc1cc(Nc2nc(N[C@H](C(C)C)[C@H](C)NC(=O)OC(C)(C)C)c(F)cc2C#N)ccn1] | tert-butyl ((2S,3R)-3-((5-cyano-3-fluoro-6-((2-methoxypyridin-4-yl)amino)pyridin-2-yl)amino)-4-methylpentan-2-yl)carbamate | 477 | 1.13 |
| Reference Example 134-61 | 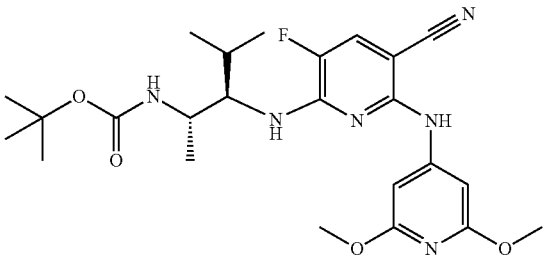 [SMILES: COc1cc(Nc2nc(N[C@H](C(C)C)[C@H](C)NC(=O)OC(C)(C)C)c(F)cc2C#N)cc(OC)n1] | tert-butyl ((2S,3R)-3-((5-cyano-6-((2,6-dimethoxypyridin-4-yl)amino)-3-fluoropyridin-2-yl)amino)-4-methylpentan-2-yl)carbamate | 507 | 1.70 |
| Reference Example 134-62 | 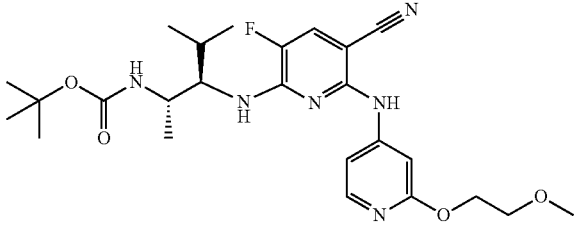 [SMILES: COCCOc1cc(Nc2nc(N[C@H](C(C)C)[C@H](C)NC(=O)OC(C)(C)C)c(F)cc2C#N)ccn1] | tert-butyl ((2S,3R)-3-((5-cyano-3-fluoro-6-((2-(2-methoxyethoxy)pyridin-4-yl)amino)pyridin-2-yl)amino)-4-methylpentan-2-yl)carbamate | 521 | 1.18 |
| Reference Example 134-63 | 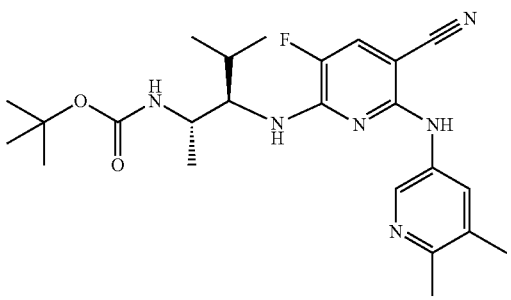 [SMILES: Cc1cc(Nc2nc(N[C@H](C(C)C)[C@H](C)NC(=O)OC(C)(C)C)c(F)cc2C#N)cnc1C] | tert-butyl ((2S,3R)-3-((5-cyano-6-((5,6-dimethylpyridin-3-yl)amino)-3-fluoropyridin-2-yl)amino)-4-methylpentan-2-yl)carbamate | 475 | 1.18 |

TABLE 1-continued

| Reference Example | Structure | Compound name | MS(ESI m/z): (M + H) | RT(min) |
|---|---|---|---|---|
| Reference Example 134-64 | 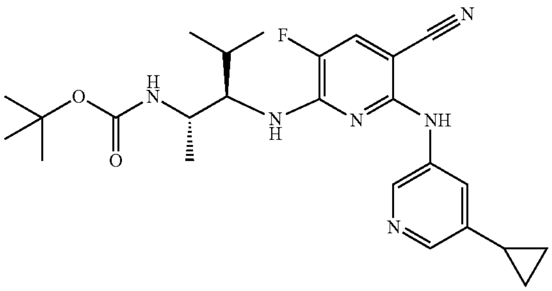 [SMILES: CC(C)[C@@H](Nc1nc(Nc2cncc(C3CC3)c2)c(C#N)cc1F)[C@H](C)NC(=O)OC(C)(C)C] | tert-butyl ((2S,3R)-3-((5-cyano-6-((5-cyclopropylpyridin-3-yl)amino)-3-fluoropyridin-2-yl)amino)-4-methylpentan-2-yl)carbamate | 487 | 1.22 |
| Reference Example 134-65 | 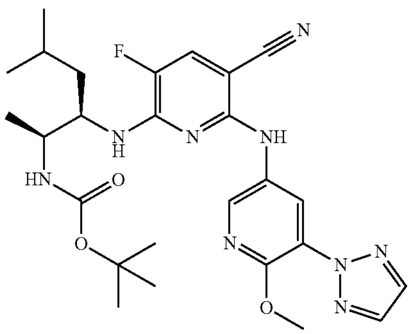 [SMILES: COc1ncc(Nc2nc(N[C@H](CC(C)C)[C@H](C)NC(=O)OC(C)(C)C)c(F)cc2C#N)cc1-n1nccn1] | tert-butyl ((2S,3R)-3-((5-cyano-3-fluoro-6-((6-methoxy-5-(2H-1,2,3-triazol-2-yl)pyridin-3-yl)amino)pyridin-2-yl)amino)-5-methylhexan-2-yl)carbamate | 540 | 1.81 |
| Reference Example 134-66 | 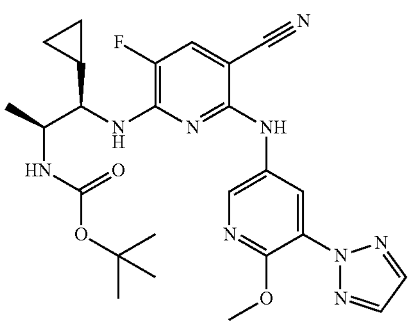 [SMILES: COc1ncc(Nc2nc(N[C@H](C3CC3)[C@H](C)NC(=O)OC(C)(C)C)c(F)cc2C#N)cc1-n1nccn1] | tert-butyl ((1R,2S)-1-((5-cyano-3-fluoro-6-((6-methoxy-5-(2H-1,2,3-triazol-2-yl)pyridin-3-yl)amino)pyridin-2-yl)amino)-1-cyclopropylpropan-2-yl)carbamate | 524 | 1.67 |
| Reference Example 134-67 | 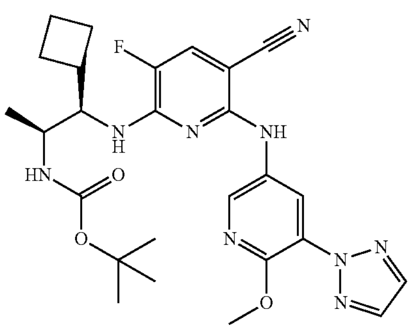 [SMILES: COc1ncc(Nc2nc(N[C@H](C3CCC3)[C@H](C)NC(=O)OC(C)(C)C)c(F)cc2C#N)cc1-n1nccn1] | tert-butyl ((1R,2S)-1-((5-cyano-3-fluoro-6-((6-methoxy-5-(2H-1,2,3-triazol-2-yl)pyridin-3-yl)amino)pyridin-2-yl)amino)-1-cyclobutylpropan-2-yl)carbamate | 538 | 1.77 |

TABLE 1-continued

| Reference Example | Structure | Compound name | MS(ESI m/z): (M + H) | RT(min) |
|---|---|---|---|---|
| Reference Example 134-68 | 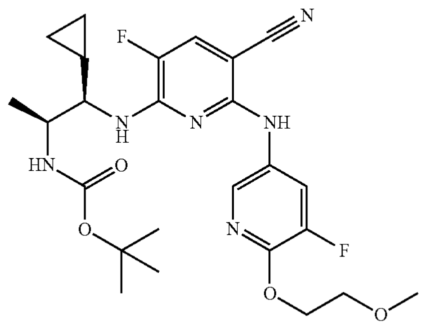 [SMILES: COCCOc1ncc(Nc2nc(N[C@H](C3CC3)[C@H](C)NC(=O)OC(C)(C)C)c(F)cc2C#N)cc1F] | tert-butyl ((1R,2S)-1-((5-cyano-3-fluoro-6-((5-fluoro-6-(2-methoxyethoxy)pyridin-3-yl)amino)pyridin-2-yl)amino)-1-cyclopropylpropan-2-yl)carbamate | 519 | 1.73 |
| Reference Example 134-69 | 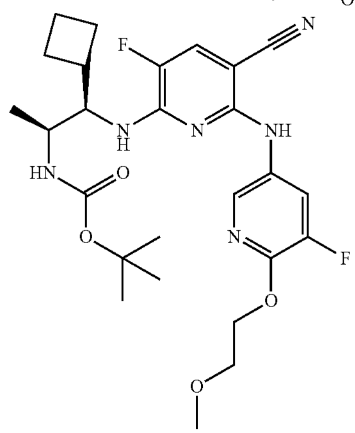 | tert-butyl ((1R,2S)-1-((5-cyano-3-fluoro-6-((5-fluoro-6-(2-methoxyethoxy)pyridin-3-yl)amino)pyridin-2-yl)amino)-1-cyclobutylpropan-2-yl)carbamate | 533 | 1.83 |
| Reference Example 134-70 | 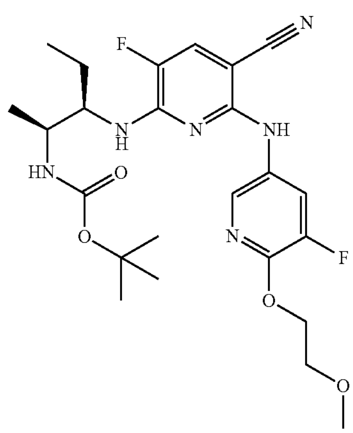 [SMILES: CC[C@@H](Nc1nc(Nc2cnc(OCCOC)c(F)c2)c(C#N)cc1F)[C@H](C)NC(=O)OC(C)(C)C] | tert-butyl ((2S,3R)-3-((5-cyano-3-fluoro-6-((5-fluoro-6-(2-methoxyethoxy)pyridin-3-yl)amino)pyridin-2-yl)amino)pentan-2-yl)carbamate | 507 | 1.72 |
| Reference Example 134-71 | 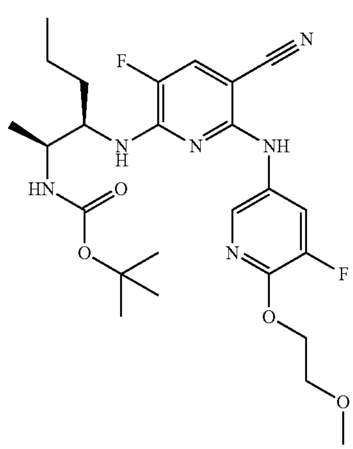 [SMILES: CCC[C@@H](Nc1nc(Nc2cnc(OCCOC)c(F)c2)c(C#N)cc1F)[C@H](C)NC(=O)OC(C)(C)C] | tert-butyl ((2S,3R)-3-((5-cyano-3-fluoro-6-((5-fluoro-6-(2-methoxyethoxy)pyridin-3-yl)amino)pyridin-2-yl)amino)hexan-2-yl)carbamate | 521 | 1.80 |

TABLE 1-continued

| Reference Example | Structure | Compound name | MS(ESI m/z): (M + H) | RT(min) |
|---|---|---|---|---|
| Reference Example 134-72 | 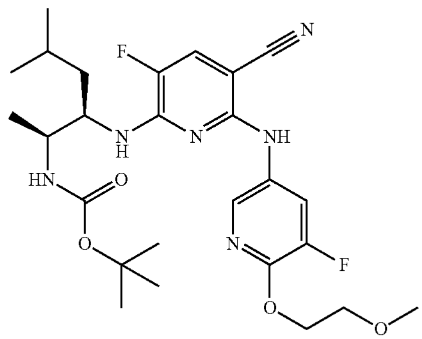 [SMILES: COCCOc1ncc(Nc2nc(N[C@H](CC(C)C)[C@H](C)NC(=O)OC(C)(C)C)c(F)cc2C#N)cc1F] | tert-butyl ((2S,3R)-3-((5-cyano-3-fluoro-6-((5-fluoro-6-(2-methoxyethoxy)pyridin-3-yl)amino)pyridin-2-yl)amino)-5-methylhexan-2-yl)carbamate | 507 | 1.72 |
| Reference Example 134-73 | 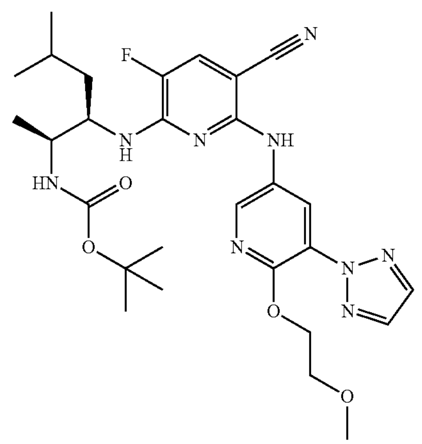 [SMILES: COCCOc1ncc(Nc2nc(N[C@H](CC(C)C)[C@H](C)NC(=O)OC(C)(C)C)c(F)cc2C#N)cc1-n1nccn1] | tert-butyl ((2S,3R)-3-((5-cyano-3-fluoro-6-((6-(2-methoxyethoxy)-5-(2H-1,2,3-triazol-2-yl)pyridin-3-yl)amino)pyridin-2-yl)amino)-5-methylhexan-2-yl)carbamate | 584 | 1.85 |
| Reference Example 134-74 | 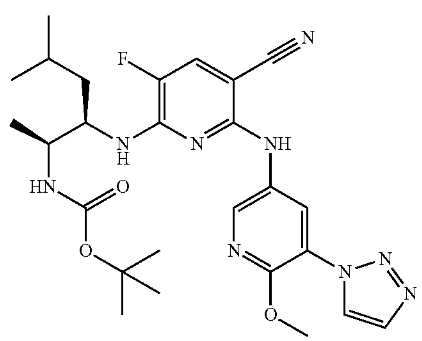 [SMILES: COc1ncc(Nc2nc(N[C@H](CC(C)C)[C@H](C)NC(=O)OC(C)(C)C)c(F)cc2C#N)cc1-n1ccnn1] | tert-butyl ((2S,3R)-3-((5-cyano-3-fluoro-6-((6-methoxy-5-(1H-1,2,3-triazol-1-yl)pyridin-3-yl)amino)pyridin-2-yl)amino)-5-methylhexan-2-yl)carbamate | 540 | 1.83 |
| Reference Example 134-75 | 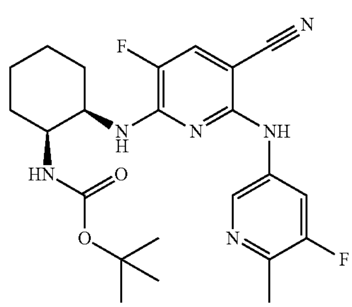 [SMILES: Cc1ncc(Nc2nc(N[C@@H]3CCCC[C@@H]3NC(=O)OC(C)(C)C)c(F)cc2C#N)cc1F] | tert-butyl ((1S,2R)-2-((5-cyano-3-fluoro-6-((5-fluoro-6-methylpyridin-3-yl)amino)pyridin-2-yl)amino)cyclohexyl)carbamate | 459 | 1.74 |

TABLE 1-continued

| Reference Example | Structure | Compound name | MS(ESI m/z): (M + H) | RT(min) |
|---|---|---|---|---|
| Reference Example 134-76 | 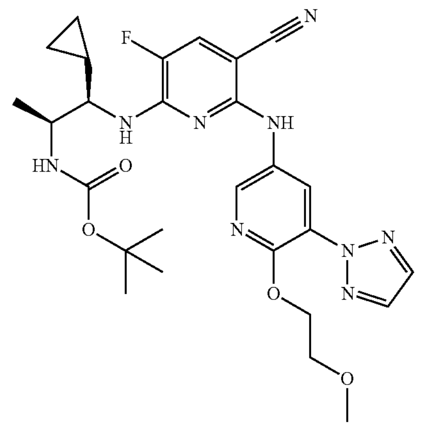 [SMILES: COCCOc1ncc(Nc2nc(N[C@H](C3CC3)[C@H](C)NC(=O)OC(C)(C)C)c(F)cc2C#N)cc1-n1nccn1] | tert-butyl ((1R,2S)-1-((5-cyano-3-fluoro-6-((6-(2-methoxyethoxy)-5-(2H-1,2,3-triazol-2-yl)pyridin-3-yl)amino)pyridin-2-yl)amino)-1-cyclopropylpropan-2-yl)carbamate | 568 | 1.70 |
| Reference Example 134-77 | 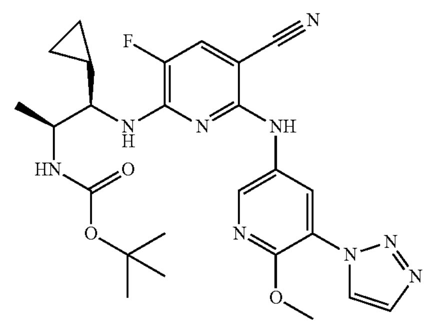 [SMILES: COc1ncc(Nc2nc(N[C@H](C3CC3)[C@H](C)NC(=O)OC(C)(C)C)c(F)cc2C#N)cc1-n1ccnn1] | tert-butyl ((1R,2S)-1-((5-cyano-3-fluoro-6-((6-methoxy-5-(1H-1,2,3-triazol-1-yl)pyridin-3-yl)amino)pyridin-2-yl)amino)-1-cyclopropylpropan-2-yl)carbamate | 524 | 1.69 |
| Reference Example 134-78 | 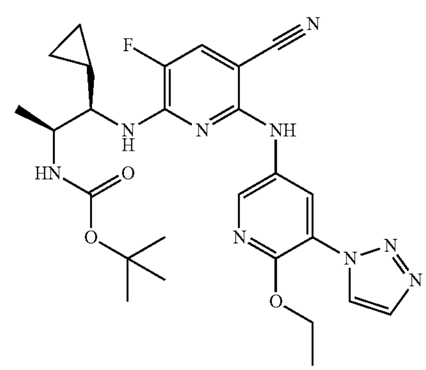 [SMILES: CCOc1ncc(Nc2nc(N[C@H](C3CC3)[C@H](C)NC(=O)OC(C)(C)C)c(F)cc2C#N)cc1-n1ccnn1] | tert-butyl ((1R,2S)-1-((5-cyano-6-((6-ethoxy-5-(1H-1,2,3-triazol-1-yl)pyridin-3-yl)amino)-3-fluoropyridin-2-yl)amino)-1-cyclopropylpropan-2-yl)carbamate | 538 | 1.79 |
| Reference Example 134-79 | 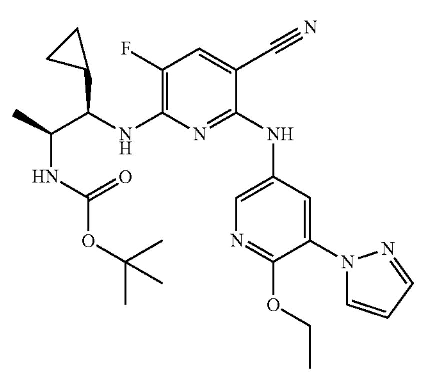 [SMILES: CCOc1ncc(Nc2nc(N[C@H](C3CC3)[C@H](C)NC(=O)OC(C)(C)C)c(F)cc2C#N)cc1-n1cccn1] | tert-butyl ((1R,2S)-1-((5-cyano-6-((6-ethoxy-5-(1H-pyrazol-1-yl)pyridin-3-yl)amino)-3-fluoropyridin-2-yl)amino)-1-cyclopropylpropan-2-yl)carbamate | 537 | 1.96 |

TABLE 1-continued

| Reference Example | Structure | Compound name | MS(ESI m/z): (M + H) | RT(min) |
|---|---|---|---|---|
| Reference Example 134-80 | 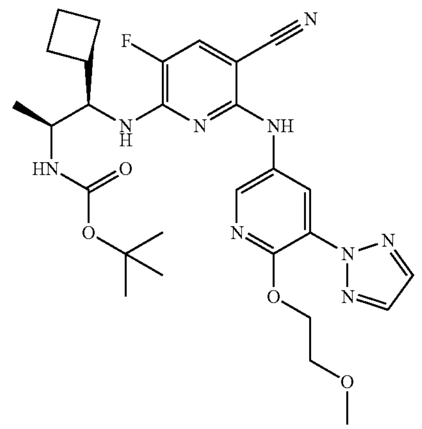 [SMILES: COCCOc1ncc(Nc2nc(N[C@H](C3CCC3)[C@H](C)NC(=O)OC(C)(C)C)c(F)cc2C#N)cc1-n1nccn1] | tert-butyl ((1R,2S)-1-((5-cyano-3-fluoro-6-((6-(2-methoxyethoxy)-5-(2H-1,2,3-triazol-2-yl)pyridin-3-yl)amino)pyridin-2-yl)amino)-1-cyclobutylpropan-2-yl)carbamate | 582 | 1.80 |
| Reference Example 134-81 | 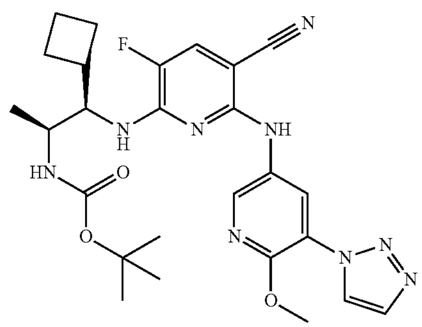 [SMILES: COc1ncc(Nc2nc(N[C@H](C3CCC3)[C@H](C)NC(=O)OC(C)(C)C)c(F)cc2C#N)cc1-n1ccnn1] | tert-butyl ((1R,2S)-1-((5-cyano-3-fluoro-6-((6-methoxy-5-(1H-1,2,3-triazol-1-yl)pyridin-3-yl)amino)pyridin-2-yl)amino)-1-cyclobutylpropan-2-yl)carbamate | 438 | 1.79 |
| Reference Example 134-82 | 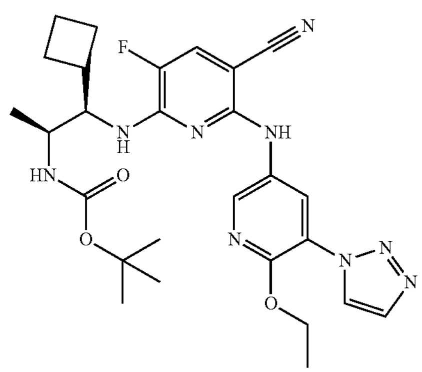 [SMILES: CCOc1ncc(Nc2nc(N[C@H](C3CCC3)[C@H](C)NC(=O)OC(C)(C)C)c(F)cc2C#N)cc1-n1ccnn1] | tert-butyl ((1R,2S)-1-((5-cyano-6-((6-ethoxy-5-(1H-1,2,3-triazol-1-yl)pyridin-3-yl)amino)-3-fluoropyridin-2-yl)amino)-1-cyclobutylpropan-2-yl)carbamate | 552 | 1.89 |
| Reference Example 134-83 | 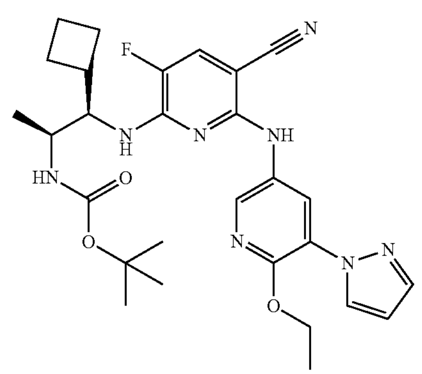 [SMILES: CCOc1ncc(Nc2nc(N[C@H](C3CCC3)[C@H](C)NC(=O)OC(C)(C)C)c(F)cc2C#N)cc1-n1cccn1] | tert-butyl ((1R,2S)-1-((5-cyano-6-((6-ethoxy-5-(1H-pyrazol-1-yl)pyridin-3-yl)amino)-3-fluoropyridin-2-yl)amino)-1-cyclobutylpropan-2-yl)carbamate | 551 | 2.07 |

TABLE 1-continued

| Reference Example | Structure | Compound name | MS(ESI m/z): (M + H) | RT(min) |
|---|---|---|---|---|
| Reference Example 134-84 | 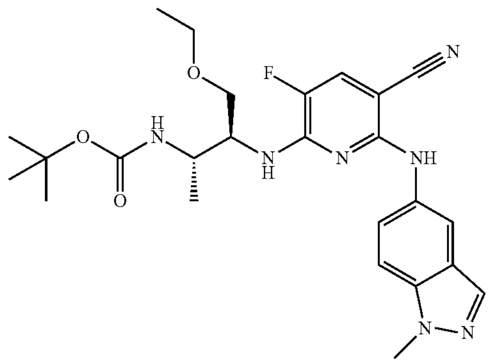 [SMILES: CCOC[C@@H](Nc1nc(Nc2ccc3c(cnn3C)c2)c(C#N)cc1F)[C@H](C)NC(=O)OC(C)(C)C] | tert-butyl ((2S,3S)-3-((5-cyano-3-fluoro-6-((1-methyl-1H-indazol-5-yl)amino)pyridin-2-yl)amino)-4-ethoxybutan-2-yl)carbamate | 516 | 1.53 |
| Reference Example 134-85 | 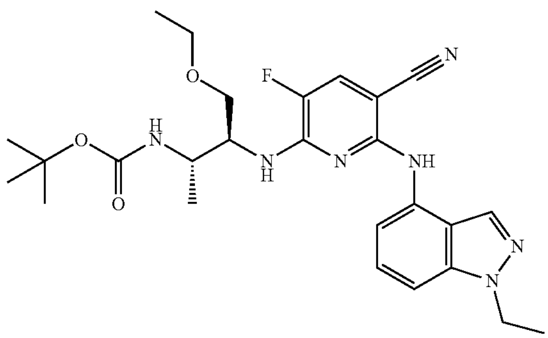 [SMILES: CCOC[C@@H](Nc1nc(Nc2cccc3c2cnn3CC)c(C#N)cc1F)[C@H](C)NC(=O)OC(C)(C)C] | tert-butyl ((2S,3S)-3-((5-cyano-6-((1-ethyl-1H-indazol-4-yl)amino)-3-fluoropyridin-2-yl)amino)-4-ethoxybutan-2-yl)carbamate | 530 | 1.72 |
| Reference Example 134-86 | 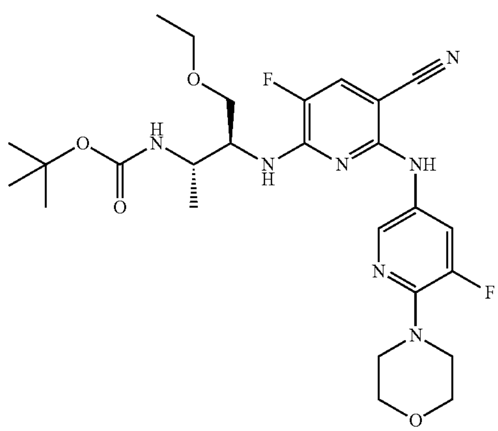 | tert-butyl ((2S,3S)-3-((5-cyano-3-fluoro-6-((5-fluoro-6-morpholinopyridin-3-yl)amino)pyridin-2-yl)amino)-4-ethoxybutan-2-yl)carbamate | 566 | 1.62 |
| Reference Example 134-87 | 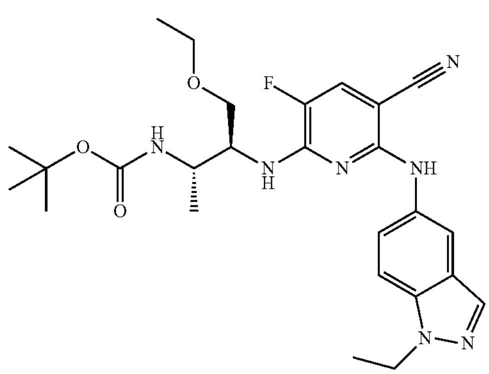 [SMILES: CCOC[C@@H](Nc1nc(Nc2ccc3c(cnn3CC)c2)c(C#N)cc1F)[C@H](C)NC(=O)OC(C)(C)C] | tert-butyl ((2S,3S)-3-((5-cyano-6-((1-ethyl-1H-indazol-5-yl)amino)-3-fluoropyridin-2-yl)amino)-4-ethoxybutan-2-yl)carbamate | 530 | 1.62 |

TABLE 1-continued

| Reference Example | Structure | Compound name | MS(ESI m/z): (M + H) | RT(min) |
|---|---|---|---|---|
| Reference Example 134-88 | 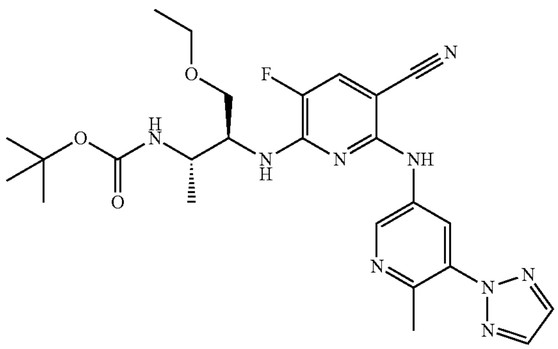 [SMILES: CCOC[C@@H](Nc1nc(Nc2cnc(C)c(-n3nccn3)c2)c(C#N)cc1F)[C@H](C)NC(=O)OC(C)(C)C] | tert-butyl ((2S,3S)-3-((5-cyano-3-fluoro-6-((6-methyl-5-(2H-1,2,3-triazol-2-yl)pyridin-3-yl)amino)pyridin-2-yl)amino)-4-ethoxybutan-2-yl)carbamate | 544 | 1.56 |
| Reference Example 134-89 | 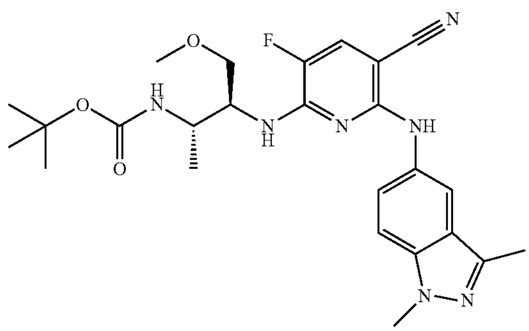 [SMILES: COC[C@@H](Nc1nc(Nc2ccc3c(c2)c(C)nn3C)c(C#N)cc1F)[C@H](C)NC(=O)OC(C)(C)C] | tert-butyl ((2S,3S)-3-((5-cyano-6-((1,3-dimethyl-1H-indazol-5-yl)amino)-3-fluoropyridin-2-yl)amino)-4-methoxybutan-2-yl)carbamate | 498 | 1.66 |
| Reference Example 134-90 | 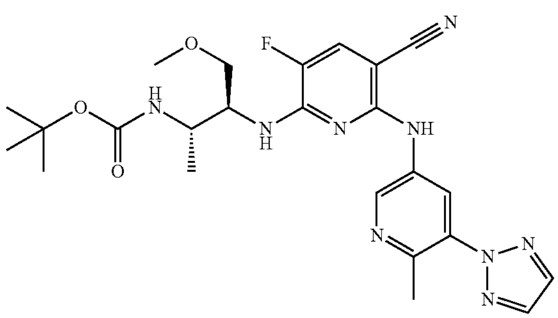 [SMILES: COC[C@@H](Nc1nc(Nc2cnc(C)c(-n3nccn3)c2)c(C#N)cc1F)[C@H](C)NC(=O)OC(C)(C)C] | tert-butyl ((2S,3S)-3-((5-cyano-3-fluoro-6-((6-methyl-5-(2H-1,2,3-triazol-2-yl)pyridin-3-yl)amino)pyridin-2-yl)amino)-4-methoxybutan-2-yl)carbamate | 512 | 1.62 |
| Reference Example 134-91 | 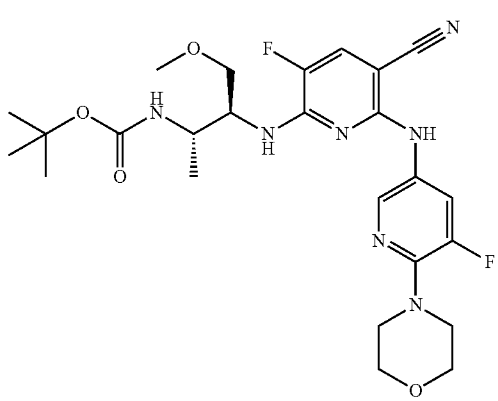 [SMILES: COC[C@@H](Nc1nc(Nc2cnc(N3CCOCC3)c(F)c2)c(C#N)cc1F)[C@H](C)NC(=O)OC(C)(C)C] | tert-butyl ((2S,3S)-3-((5-cyano-3-fluoro-6-((5-fluoro-6-morpholinopyridin-3-yl)amino)pyridin-2-yl)amino)-4-methoxybutan-2-yl)carbamate | 534 | 1.68 |

TABLE 1-continued

| Reference Example | Structure | Compound name | MS(ESI m/z): (M + H) | RT(min) |
|---|---|---|---|---|
| Reference Example 134-92 | 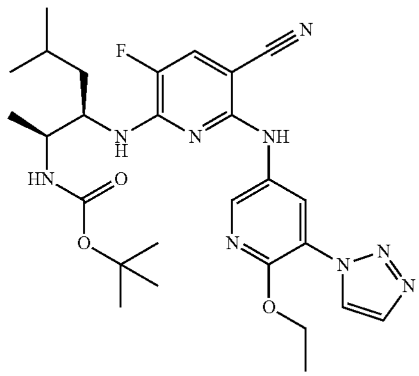 [SMILES: CCOc1ncc(Nc2nc(N[C@H](CC(C)C)[C@H](C)NC(=O)OC(C)(C)C)c(F)cc2C#N)cc1-n1ccnn1] | tert-butyl ((2S,3R)-3-((5-cyano-6-((6-ethoxy-5-(1H-1,2,3-triazol-1-yl)pyridin-3-yl)amino)-3-fluoropyridin-2-yl)amino)-5-methylhexan-2-yl)carbamate | 554 | 1.95 |
| Reference Example 134-93 | 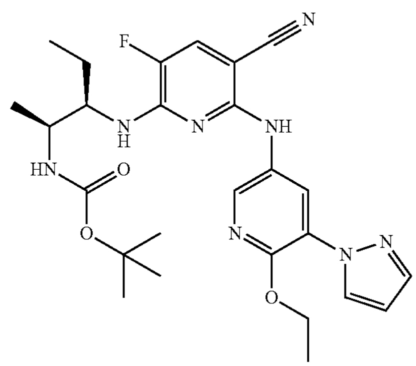 [SMILES: CCOc1ncc(Nc2nc(N[C@H](CC)[C@H](C)NC(=O)OC(C)(C)C)c(F)cc2C#N)cc1-n1cccn1] | tert-butyl ((2S,3R)-3-((5-cyano-6-((6-ethoxy-5-(1H-pyrazol-1-yl)pyridin-3-yl)amino)-3-fluoropyridin-2-yl)amino)pentan-2-yl)carbamate | 525 | 2.00 |
| Reference Example 134-94 | 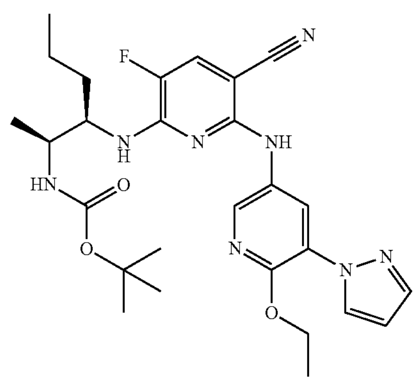 [SMILES: CCC[C@@H](Nc1nc(Nc2cnc(OCC)c(-n3cccn3)c2)c(C#N)cc1F)[C@H](C)NC(=O)OC(C)(C)C] | tert-butyl ((2S,3R)-3-((5-cyano-6-((6-ethoxy-5-(1H-pyrazol-1-yl)pyridin-3-yl)amino)-3-fluoropyridin-2-yl)amino)hexan-2-yl)carbamate | 539 | 2.08 |
| Reference Example 134-95 | 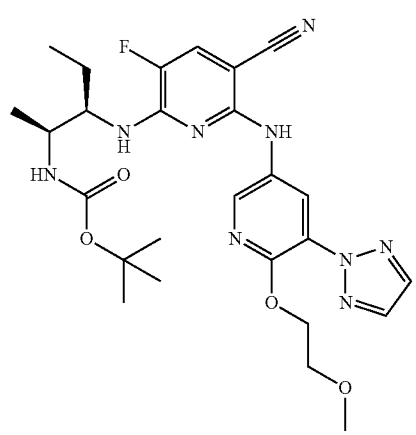 [SMILES: CC[C@@H](Nc1nc(Nc2cnc(OCCOC)c(-n3nccn3)c2)c(C#N)cc1F)[C@H](C)NC(=O)OC(C)(C)C] | tert-butyl ((2S,3R)-3-((5-cyano-3-fluoro-6-((6-(2-methoxyethoxy)-5-(2H-1,2,3-triazol-2-yl)pyridin-3-yl)amino)pyridin-2-yl)amino)pentan-2-yl)carbamate | 556 | 1.73 |

TABLE 1-continued

| Reference Example | Structure | Compound name | MS(ESI m/z): (M + H) | RT(min) |
|---|---|---|---|---|
| Reference Example 134-96 | 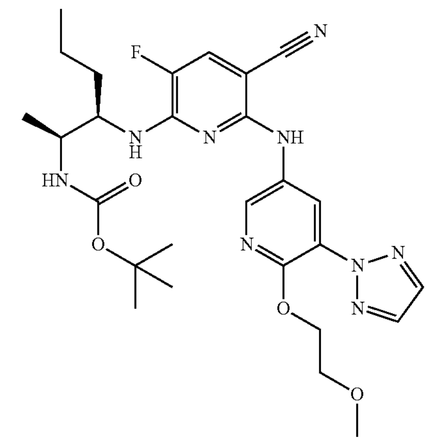 [SMILES: CCC[C@@H](Nc1nc(Nc2cnc(OCCOC)c(-n3nccn3)c2)c(C#N)cc1F)[C@H](C)NC(=O)OC(C)(C)C] | tert-butyl ((2S,3R)-3-((5-cyano-3-fluoro-6-((6-(2-methoxyethoxy)-5-(2H-1,2,3-triazol-2-yl)pyridin-3-yl)amino)pyridin-2-yl)amino)hexan-2-yl)carbamate | 570 | 1.81 |
| Reference Example 134-97 | 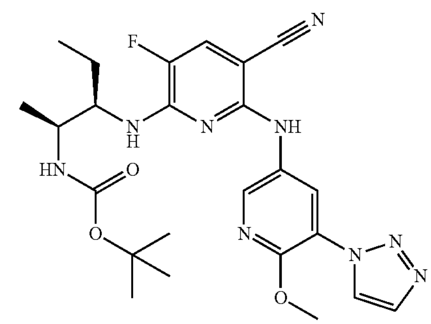 [SMILES: CC[C@@H](Nc1nc(Nc2cnc(OC)c(-n3ccnn3)c2)c(C#N)cc1F)[C@H](C)NC(=O)OC(C)(C)C] | tert-butyl ((2S,3R)-3-((5-cyano-3-fluoro-6-((6-methoxy-5-(1H-1,2,3-triazol-1-yl)pyridin-3-yl)amino)pyridin-2-yl)amino)pentan-2-yl)carbamate | 512 | 1.71 |
| Reference Example 134-98 | 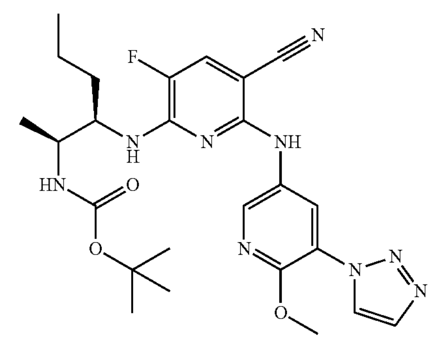 [SMILES: CCC[C@@H](Nc1nc(Nc2cnc(OC)c(-n3ccnn3)c2)c(C#N)cc1F)[C@H](C)NC(=O)OC(C)(C)C] | tert-butyl ((2S,3R)-3-((5-cyano-3-fluoro-6-((6-methoxy-5-(1H-1,2,3-triazol-1-yl)pyridin-3-yl)amino)pyridin-2-yl)amino)hexan-2-yl)carbamate | 526 | 1.79 |
| Reference Example 134-99 | 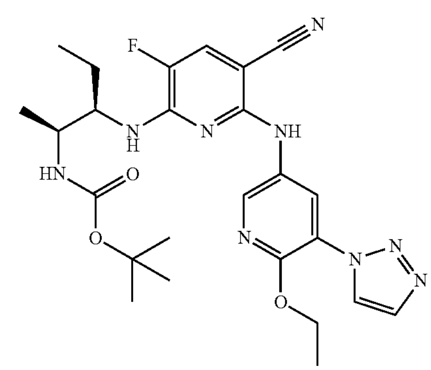 [SMILES: CCOc1ncc(Nc2nc(N[C@H](CC)[C@H](C)NC(=O)OC(C)(C)C)c(F)cc2C#N)cc1-n1ccnn1] | tert-butyl ((2S,3R)-3-((5-cyano-6-((6-ethoxy-5-(1H-1,2,3-triazol-1-yl)pyridin-3-yl)amino)-3-fluoropyridin-2-yl)amino)pentan-2-yl)carbamate | 526 | 1.82 |

TABLE 1-continued

| Reference Example | Structure | Compound name | MS(ESI m/z): (M + H) | RT(min) |
|---|---|---|---|---|
| Reference Example 134-100 | 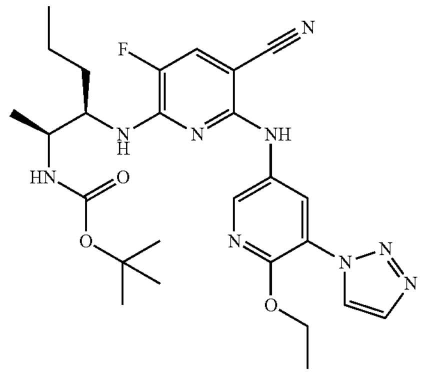 [SMILES: CCC[C@@H](Nc1nc(Nc2cnc(OCC)c(-n3ccnn3)c2)c(C#N)cc1F)[C@H](C)NC(=O)OC(C)(C)C] | tert-butyl ((2S,3R)-3-((5-cyano-6-((6-ethoxy-5-(1H-1,2,3-triazol-1-yl)pyridin-3-yl)amino)-3-fluoropyridin-2-yl)amino)hexan-2-yl)carbamate | 540 | 1.90 |
| Reference Example 134-101 | 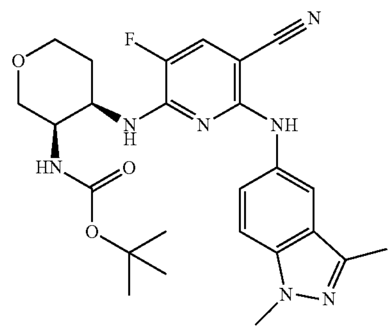 [SMILES: Cc1nn(C)c2ccc(Nc3nc(N[C@@H]4CCOC[C@@H]4NC(=O)OC(C)(C)C)c(F)cc3C#N)cc12] | tert-butyl ((3R,4R)-4-((5-cyano-6-((1,3-dimethyl-1H-indazol-5-yl)amino)-3-fluoropyridin-2-yl)amino)tetrahydro-2H-pyran-3-yl)carbamate | 496 | 1.41 |
| Reference Example 134-102 | 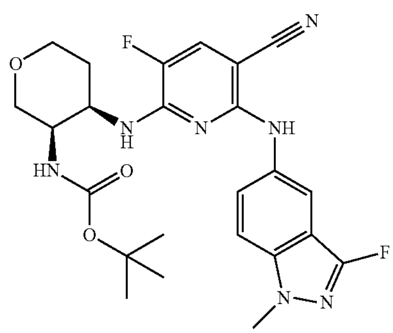 [SMILES: Cn1nc(F)c2cc(Nc3nc(N[C@@H]4CCOC[C@@H]4NC(=O)OC(C)(C)C)c(F)cc3C#N)ccc21] | tert-butyl ((3R,4R)-4-((5-cyano-3-fluoro-6-((3-fluoro-1-methyl-1H-indazol-5-yl)amino)pyridin-2-yl)amino)tetrahydro-2H-pyran-3-yl)carbamate | 500 | 1.53 |
| Reference Example 134-103 | 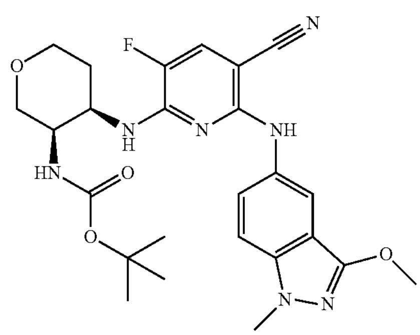 [SMILES: COc1nn(C)c2ccc(Nc3nc(N[C@@H]4CCOC[C@@H]4NC(=O)OC(C)(C)C)c(F)cc3C#N)cc12] | tert-butyl ((3R,4R)-4-((5-cyano-3-fluoro-6-((3-methoxy-1-methyl-1H-indazol-5-yl)amino)pyridin-2-yl)amino)tetrahydro-2H-pyran-3-yl)carbamate | 512 | 1.54 |

TABLE 1-continued

| Reference Example | Structure | Compound name | MS(ESI m/z): (M + H) | RT(min) |
|---|---|---|---|---|
| Reference Example 134-104 | 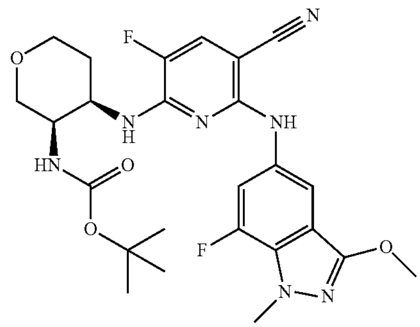 [SMILES: COc1nn(C)c2c(F)cc(Nc3nc(N[C@@H]4CCOC[C@@H]4NC(=O)OC(C)(C)C)c(F)cc3C#N)cc12] | tert-butyl ((3R,4R)-4-((5-cyano-3-fluoro-6-((7-fluoro-3-methoxy-1-methyl-1H-indazol-5-yl)amino)pyridin-2-yl)amino)tetrahydro-2H-pyran-3-yl)carbamate | 530 | 1.63 |
| Reference Example 134-105 | 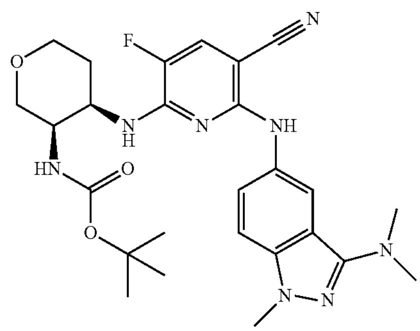 [SMILES: CN(C)c1nn(C)c2ccc(Nc3nc(N[C@@H]4CCOC[C@@H]4NC(=O)OC(C)(C)C)c(F)cc3C#N)cc12] | tert-butyl ((3R,4R)-4-((5-cyano-6-((3-(dimethylamino)-1-methyl-1H-indazol-5-yl)amino)-3-fluoropyridin-2-yl)amino)tetrahydro-2H-pyran-3-yl)carbamate | 525 | 1.48 |
| Reference Example 134-106 | 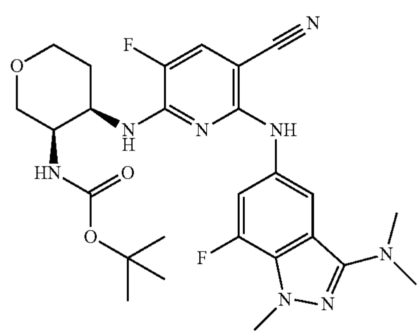 [SMILES: CN(C)c1nn(C)c2c(F)cc(Nc3nc(N[C@@H]4CCOC[C@@H]4NC(=O)OC(C)(C)C)c(F)cc3C#N)cc12] | tert-butyl ((3R,4R)-4-((5-cyano-6-((3-(dimethylamino)-7-fluoro-1-methyl-1H-indazol-5-yl)amino)-3-fluoropyridin-2-yl)amino)tetrahydro-2H-pyran-3-yl)carbamate | 543 | 1.64 |
| Reference Example 134-107 | 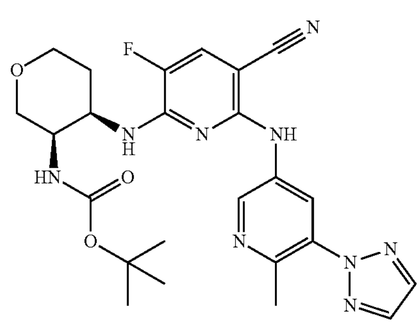 [SMILES: Cc1ncc(Nc2nc(N[C@@H]3CCOC[C@@H]3NC(=O)OC(C)(C)C)c(F)cc2C#N)cc1-n1nccn1] | tert-butyl ((3R,4R)-4-((5-cyano-3-fluoro-6-((6-methyl-5-(2H-1,2,3-triazol-2-yl)pyridin-3-yl)amino)pyridin-2-yl)amino)tetrahydro-2H-pyran-3-yl)carbamate | 510 | 1.38 |

TABLE 1-continued

| Reference Example | Structure | Compound name | MS(ESI m/z): (M + H) | RT(min) |
|---|---|---|---|---|
| Reference Example 134-108 | 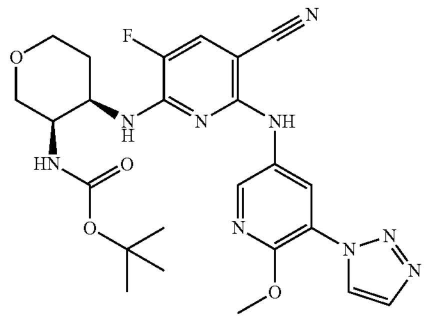 [SMILES: COc1ncc(Nc2nc(N[C@@H]3CCOC[C@@H]3NC(=O)OC(C)(C)C)c(F)cc2C#N)cc1-n1ccnn1] | tert-butyl ((3R,4R)-4-((5-cyano-3-fluoro-6-((6-methoxy-5-(1H-1,2,3-triazol-1-yl)pyridin-3-yl)amino)pyridin-2-yl)amino)tetrahydro-2H-pyran-3-yl)carbamate | 526 | 1.41 |
| Reference Example 134-109 | 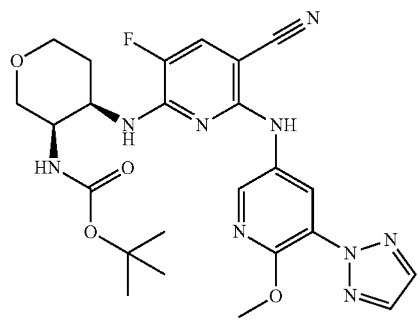 [SMILES: COc1ncc(Nc2nc(N[C@@H]3CCOC[C@@H]3NC(=O)OC(C)(C)C)c(F)cc2C#N)cc1-n1nccn1] | tert-butyl ((3R,4R)-4-((5-cyano-3-fluoro-6-((6-methoxy-5-(2H-1,2,3-triazol-2-yl)pyridin-3-yl)amino)pyridin-2-yl)amino)tetrahydro-2H-pyran-3-yl)carbamate | 526 | 1.43 |
| Reference Example 134-110 | 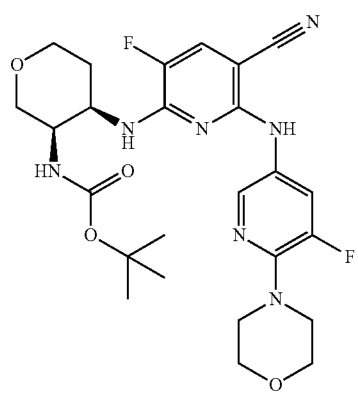 [SMILES: CC(C)(C)OC(=O)N[C@H]1COCC[C@H]1Nc1nc(Nc2cnc(N3CCOCC3)c(F)c2)c(C#N)cc1F] | tert-butyl ((3R,4R)-4-((5-cyano-3-fluoro-6-((5-fluoro-6-morpholinopyridin-3-yl)amino)pyridin-2-yl)amino)tetrahydro-2H-pyran-3-yl)carbamate | 532 | 1.49 |
| Reference Example 134-111 | 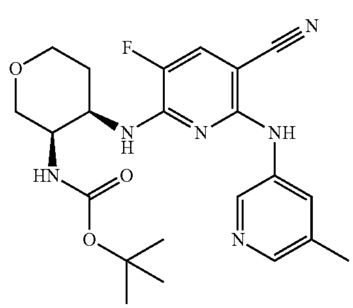 [SMILES: Cc1cncc(Nc2nc(N[C@@H]3CCOC[C@@H]3NC(=O)OC(C)(C)C)c(F)cc2C#N)c1] | tert-butyl ((3R,4R)-4-((5-cyano-3-fluoro-6-((5-methylpyridin-3-yl)amino)pyridin-2-yl)amino)tetrahydro-2H-pyran-3-yl)carbamate | 443 | 1.03 |

TABLE 1-continued

| Reference Example | Structure | Compound name | MS(ESI m/z): (M + H) | RT(min) |
|---|---|---|---|---|
| Reference Example 134-112 | 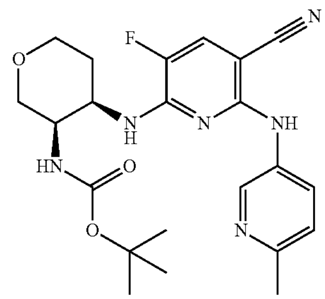 [SMILES: Cc1ccc(Nc2nc(N[C@@H]3CCOC[C@@H]3NC(=O)OC(C)(C)C)c(F)cc2C#N)cn1] | tert-butyl ((3R,4R)-4-((5-cyano-3-fluoro-6-((6-methylpyridin-3-yl)amino)pyridin-2-yl)amino)tetrahydro-2H-pyran-3-yl)carbamate | 443 | 1.00 |
| Reference Example 134-113 | 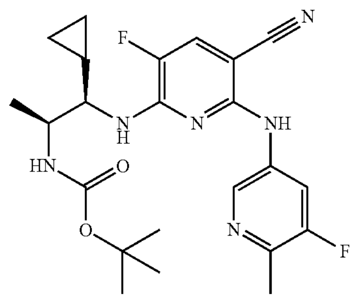 [SMILES: Cc1ncc(Nc2nc(N[C@H](C3CC3)[C@H](C)NC(=O)OC(C)(C)C)c(F)cc2C#N)cc1F] | tert-butyl ((1R,2S)-1-((5-cyano-3-fluoro-6-((5-fluoro-6-methylpyridin-3-yl)amino)pyridin-2-yl)amino)-1-cyclopropylpropan-2-yl)carbamate | 459 | 1.61 |
| Reference Example 134-114 | 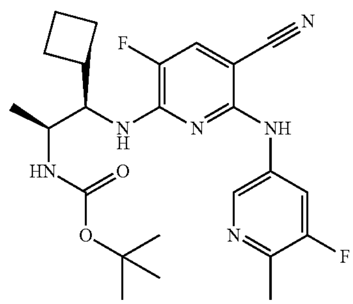 [SMILES: Cc1ncc(Nc2nc(N[C@H](C3CCC3)[C@H](C)NC(=O)OC(C)(C)C)c(F)cc2C#N)cc1F] | tert-butyl ((1R,2S)-1-((5-cyano-3-fluoro-6-((5-fluoro-6-methylpyridin-3-yl)amino)pyridin-2-yl)amino)-1-cyclobutylpropan-2-yl)carbamate | 473 | 1.72 |
| Reference Example 134-115 | 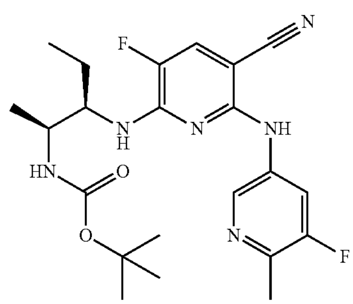 [SMILES: CC[C@@H](Nc1nc(Nc2cnc(C)c(F)c2)c(C#N)cc1F)[C@H](C)NC(=O)OC(C)(C)C] | tert-butyl ((2S,3R)-3-((5-cyano-3-fluoro-6-((5-fluoro-6-methylpyridin-3-yl)amino)pyridin-2-yl)amino)pentan-2-yl)carbamate | 447 | 1.59 |
| Reference Example 134-116 | 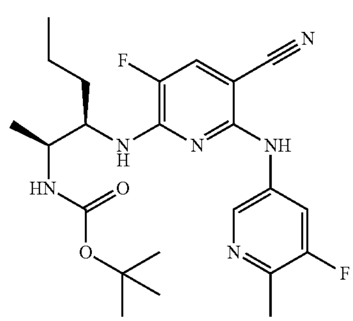 [SMILES: CCC[C@@H](Nc1nc(Nc2cnc(C)c(F)c2)c(C#N)cc1F)[C@H](C)NC(=O)OC(C)(C)C] | tert-butyl ((2S,3R)-3-((5-cyano-3-fluoro-6-((5-fluoro-6-methylpyridin-3-yl)amino)pyridin-2-yl)amino)hexan-2-yl)carbamate | 461 | 1.69 |

TABLE 1-continued

| Reference Example | Structure | Compound name | MS(ESI m/z): (M + H) | RT(min) |
|---|---|---|---|---|
| Reference Example 134-117 | 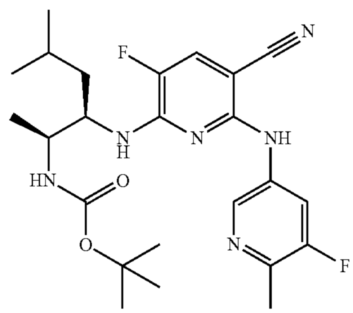 [SMILES: Cc1ncc(Nc2nc(N[C@H](CC(C)C)[C@H](C)NC(=O)OC(C)(C)C)c(F)cc2C#N)cc1F] | tert-butyl ((2S,3R)-3-((5-cyano-3-fluoro-6-((5-fluoro-6-methylpyridin-3-yl)amino)pyridin-2-yl)amino)-5-methylhexan-2-yl)carbamate | 475 | 1.77 |
| Reference Example 134-118 | 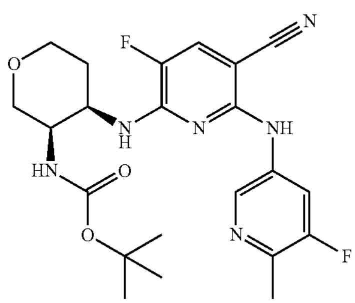 [SMILES: Cc1ncc(Nc2nc(N[C@@H]3CCOC[C@@H]3NC(=O)OC(C)(C)C)c(F)cc2C#N)cc1F] | tert-butyl ((3R,4R)-4-((5-cyano-3-fluoro-6-((5-fluoro-6-methylpyridin-3-yl)amino)pyridin-2-yl)amino)tetrahydro-2H-pyran-3-yl)carbamate | 461 | 1.40 |
| Reference Example 134-119 | 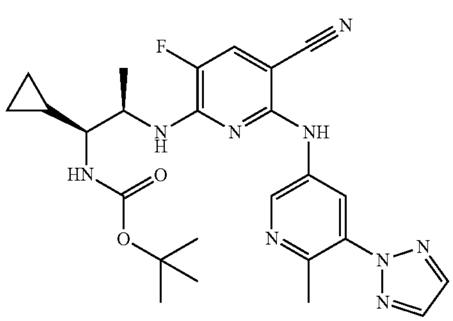 [SMILES: Cc1ncc(Nc2nc(N[C@H](C)[C@@H](NC(=O)OC(C)(C)C)C3CC3)c(F)cc2C#N)cc1-n1nccn1] | tert-butyl ((1S,2R)-2-((5-cyano-3-fluoro-6-((6-methyl-5-(2H-1,2,3-triazol-2-yl)pyridin-3-yl)amino)pyridin-2-yl)amino)-1-cyclopropylpropyl)carbamate | 508 | 1.65 |
| Reference Example 134-120 | 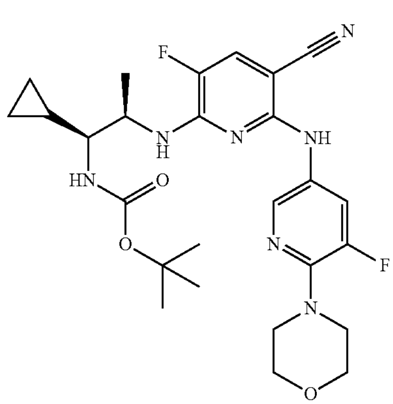 [SMILES: C[C@@H](Nc1nc(Nc2cnc(N3CCOCC3)c(F)c2)c(C#N)cc1F)[C@@H](NC(=O)OC(C)(C)C)C1CC1] | tert-butyl ((1S,2R)-2-((5-cyano-3-fluoro-6-((5-fluoro-6-morpholinopyridin-3-yl)amino)pyridin-2-yl)amino)-1-cyclopropylpropyl)carbamate | 530 | 1.70 |

TABLE 1-continued

| Reference Example | Structure | Compound name | MS(ESI m/z): (M + H) | RT(min) |
|---|---|---|---|---|
| Reference Example 134-121 | 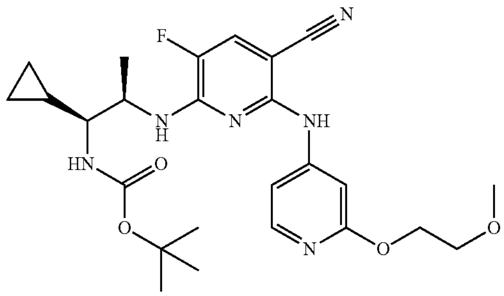 [SMILES: COCCOc1cc(Nc2nc(N[C@H](C)[C@@H](NC(=O)OC(C)(C)C)C3CC3)c(F)cc2C#N)ccn1] | tert-butyl ((1S,2R)-2-((5-cyano-3-fluoro-6-((2-(2-methoxyethoxy)pyridin-4-yl)amino)pyridin-2-yl)amino)-1-cyclopropylpropyl)carbamate | 501 | 1.31 |
| Reference Example 134-122 | 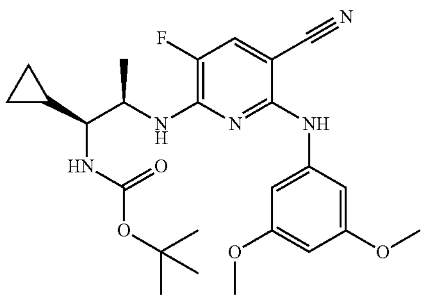 [SMILES: COc1cc(Nc2nc(N[C@H](C)[C@@H](NC(=O)OC(C)(C)C)C3CC3)c(F)cc2C#N)cc(OC)c1] | tert-butyl ((1S,2R)-2-((5-cyano-6-((3,5-dimethoxyphenyl)amino)-3-fluoropyridin-2-yl)amino)-1-cyclopropylpropyl)carbamate | 486 | 1.83 |
| Reference Example 134-123 | 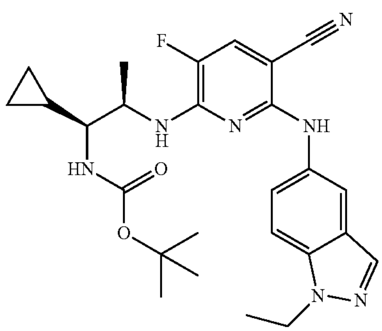 [SMILES: CCn1ncc2cc(Nc3nc(N[C@H](C)[C@@H](NC(=O)OC(C)(C)C)C4CC4)c(F)cc3C#N)ccc21] | tert-butyl ((1S,2R)-2-((5-cyano-6-((1-ethyl-1H-indazol-5-yl)amino)-3-fluoropyridin-2-yl)amino)-1-cyclopropylpropyl)carbamate | 494 | 1.71 |
| Reference Example 134-124 | 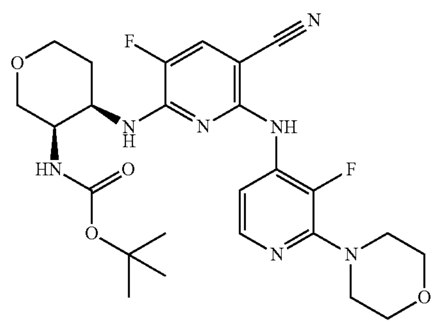 [SMILES: CC(C)(C)OC(=O)N[C@H]1COCC[C@H]1Nc1nc(Nc2ccnc(N3CCOCC3)c2F)c(C#N)cc1F] | tert-butyl ((3R,4R)-4-((5-cyano-3-fluoro-6-((3-fluoro-2-morpholinopyridin-4-yl)amino)pyridin-2-yl)amino)tetrahydro-2H-pyran-3-yl)carbamate | 532 | 1.33 |
| Reference Example 134-125 | 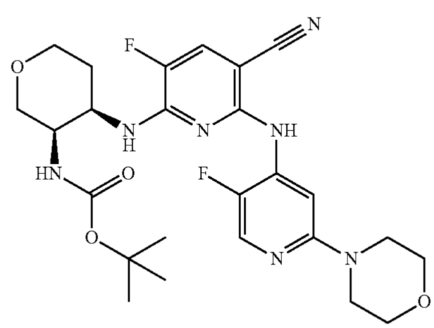 [SMILES: CC(C)(C)OC(=O)N[C@H]1COCC[C@H]1Nc1nc(Nc2cc(N3CCOCC3)ncc2F)c(C#N)cc1F] | tert-butyl ((3R,4R)-4-((5-cyano-3-fluoro-6-((5-fluoro-2-morpholinopyridin-4-yl)amino)pyridin-2-yl)amino)tetrahydro-2H-pyran-3-yl)carbamate | 532 | 1.19 |

TABLE 1-continued

| Reference Example | Structure | Compound name | MS(ESI m/z): (M + H) | RT(min) |
|---|---|---|---|---|
| Reference Example 134-126 | 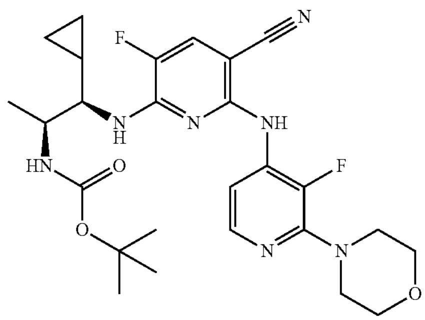 [SMILES: C[C@H](NC(=O)OC(C)(C)C)[C@H](Nc1nc(Nc2ccnc(N3CCOCC3)c2F)c(C#N)cc1F)C1CC1] | tert-butyl ((1R,2S)-1-((5-cyano-3-fluoro-6-((3-fluoro-2-morpholinopyridin-4-yl)amino)pyridin-2-yl)amino)-1-cyclopropylpropan-2-yl)carbamate | 530 | 1.53 |
| Reference Example 134-127 | 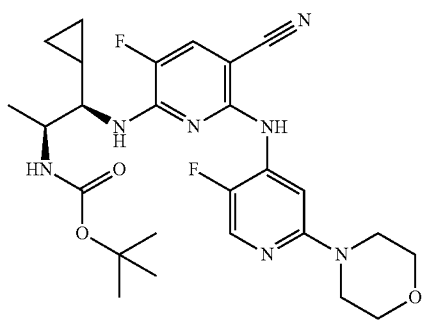 [SMILES: C[C@H](NC(=O)OC(C)(C)C)[C@H](Nc1nc(Nc2cc(N3CCOCC3)ncc2F)c(C#N)cc1F)C1CC1] | tert-butyl ((1R,2S)-1-((5-cyano-3-fluoro-6-((5-fluoro-2-morpholinopyridin-4-yl)amino)pyridin-2-yl)amino)-1-cyclopropylpropan-2-yl)carbamate | 530 | 1.44 |
| Reference Example 134-128 | 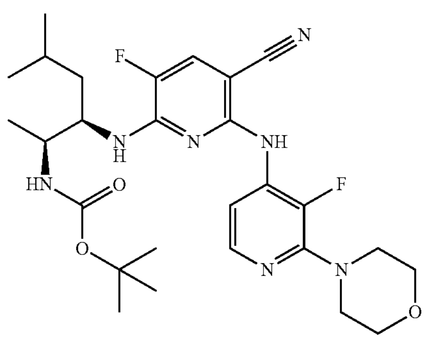 [SMILES: CC(C)C[C@@H](Nc1nc(Nc2ccnc(N3CCOCC3)c2F)c(C#N)cc1F)[C@H](C)NC(=O)OC(C)(C)C] | tert-butyl ((2S,3R)-3-((5-cyano-3-fluoro-6-((3-fluoro-2-morpholinopyridin-4-yl)amino)pyridin-2-yl)amino)-5-methylhexan-2-yl)carbamate | 546 | 1.71 |
| Reference Example 134-129 | 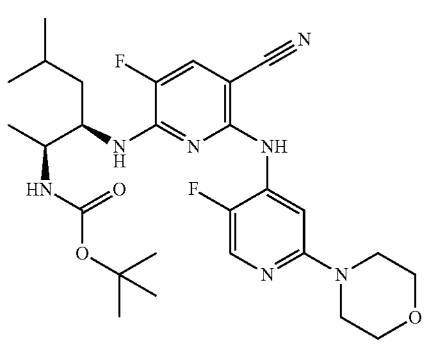 [SMILES: CC(C)C[C@@H](Nc1nc(Nc2cc(N3CCOCC3)ncc2F)c(C#N)cc1F)[C@H](C)NC(=O)OC(C)(C)C] | tert-butyl ((2S,3R)-3-((5-cyano-3-fluoro-6-((5-fluoro-2-morpholinopyridin-4-yl)amino)pyridin-2-yl)amino)-5-methylhexan-2-yl)carbamate | 546 | 1.63 |

TABLE 1-continued

| Reference Example | Structure | Compound name | MS(ESI m/z): (M + H) | RT(min) |
|---|---|---|---|---|
| Reference Example 134-130 | 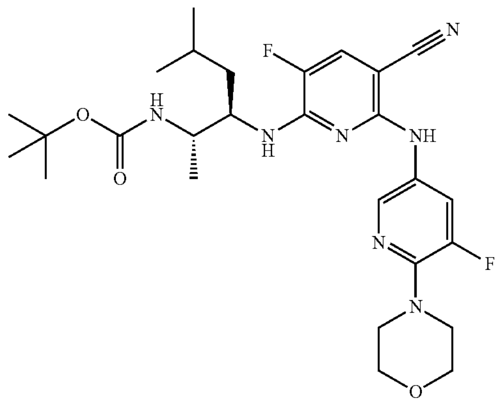 [SMILES: CC(C)C[C@@H](Nc1nc(Nc2cnc(N3CCOCC3)c(F)c2)c(C#N)cc1F)[C@H](C)NC(=O)OC(C)(C)C] | tert-butyl ((2S,3R)-3-((5-cyano-3-fluoro-6-((5-fluoro-6-morpholinopyridin-3-yl)amino)pyridin-2-yl)amino)-5-methylhexan-2-yl)carbamate | 546 | 1.82 |
| Reference Example 134-131 | 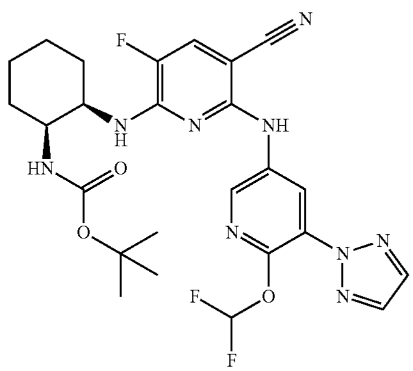 [SMILES: CC(C)(C)OC(=O)N[C@H]1CCCC[C@H]1Nc1nc(Nc2cnc(OC(F)F)c(-n3nccn3)c2)c(C#N)cc1F] | tert-butyl ((1S,2R)-2-((5-cyano-6-((6-(difluoromethoxy)-5-(2H-1,2,3-triazol-2-yl)pyridin-3-yl)amino)-3-fluoropyridin-2-yl)amino)cyclohexyl)carbamate | 560 | 1.79 |
| Reference Example 134-132 | 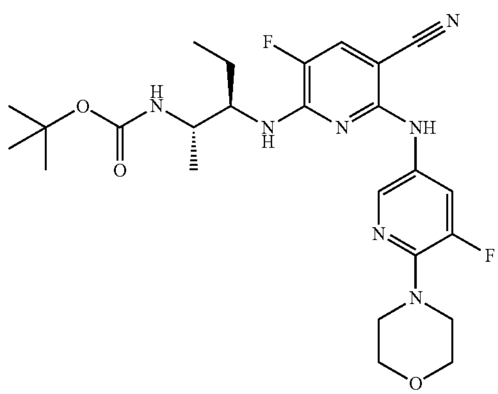 [SMILES: CC[C@@H](Nc1nc(Nc2cnc(N3CCOCC3)c(F)c2)c(C#N)cc1F)[C@H](C)NC(=O)OC(C)(C)C] | tert-butyl ((2S,3R)-3-((5-cyano-3-fluoro-6-((5-fluoro-6-morpholinopyridin-3-yl)amino)pyridin-2-yl)amino)pentan-2-yl)carbamate | 536 | 1.51 |
| Reference Example 134-133 | 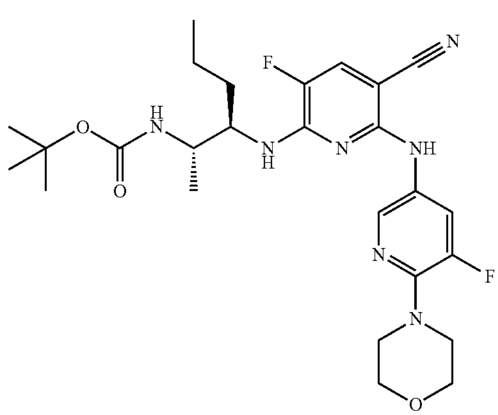 [SMILES: CCC[C@@H](Nc1nc(Nc2cnc(N3CCOCC3)c(F)c2)c(C#N)cc1F)[C@H](C)NC(=O)OC(C)(C)C] | tert-butyl ((2S,3R)-3-((5-cyano-3-fluoro-6-((5-fluoro-6-morpholinopyridin-3-yl)amino)pyridin-2-yl)amino)hexan-2-yl)carbamate | 550 | 1.59 |

TABLE 1-continued

| Reference Example | Structure | Compound name | MS(ESI m/z): (M + H) | RT(min) |
|---|---|---|---|---|
| Reference Example 134-134 | 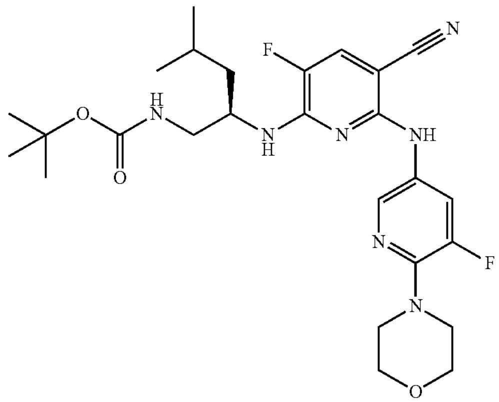 [SMILES: CC(C)C[C@H](CNC(=O)OC(C)(C)C)Nc1nc(Nc2cnc(N3CCOCC3)c(F)c2)c(C#N)cc1F] | (R)-tert-butyl (2-((5-cyano-3-fluoro-6-((5-fluoro-6-morpholinopyridin-3-yl)amino)pyridin-2-yl)amino)-4-methylpentyl)carbamate | 550 | 1.63 |
| Reference Example 134-135 | 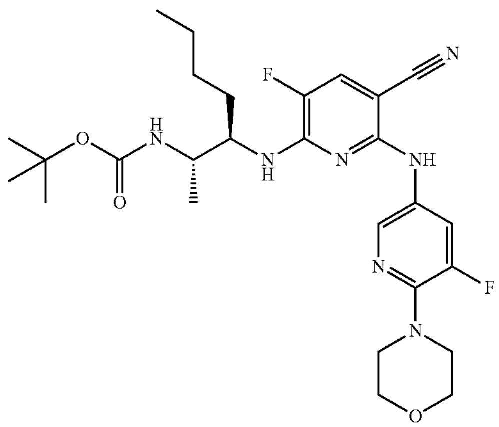 [SMILES: CCCC[C@@H](Nc1nc(Nc2cnc(N3CCOCC3)c(F)c2)c(C#N)cc1F)[C@H](C)NC(=O)OC(C)(C)C] | tert-butyl ((2S,3R)-3-((5-cyano-3-fluoro-6-((5-fluoro-6-morpholinopyridin-3-yl)amino)pyridin-2-yl)amino)heptan-2-yl)carbamate | 564 | 1.69 |
| Reference Example 134-136 | 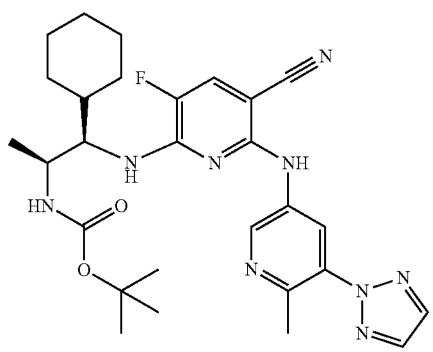 [SMILES: Cc1ncc(Nc2nc(N[C@H](C3CCCCC3)[C@H](C)NC(=O)OC(C)(C)C)c(F)cc2C#N)cc1-n1nccn1] | tert-butyl ((1R,2S)-1-((5-cyano-3-fluoro-6-((6-methyl-5-(2H-1,2,3-triazol-2-yl)pyridin-3-yl)amino)pyridin-2-yl)amino)-1-cyclohexylpropan-2-yl)carbamate | 584 | 1.84 |
| Reference Example 134-137 | 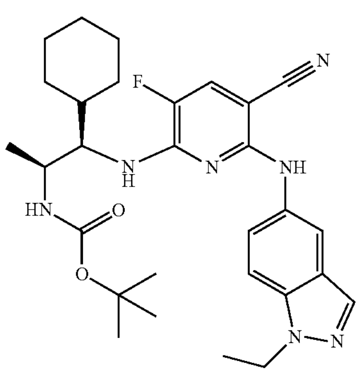 [SMILES: CCn1ncc2cc(Nc3nc(N[C@H](C4CCCCC4)[C@H](C)NC(=O)OC(C)(C)C)c(F)cc3C#N)ccc21] | tert-butyl ((1R,2S)-1-((5-cyano-6-((1-ethyl-1H-indazol-5-yl)amino)-3-fluoropyridin-2-yl)amino)-1-cyclohexylpropan-2-yl)carbamate | 570 | 1.91 |

TABLE 1-continued

| Reference Example | Structure | Compound name | MS(ESI m/z): (M + H) | RT(min) |
|---|---|---|---|---|
| Reference Example 134-138 | 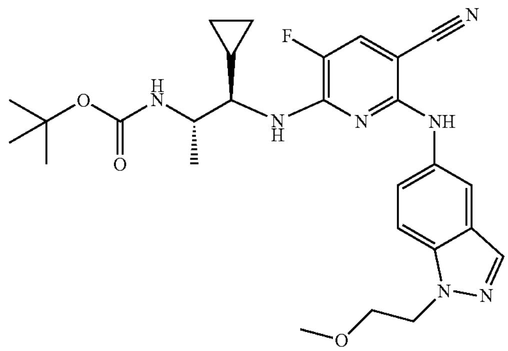 [SMILES: COCCn1ncc2cc(Nc3nc(N[C@H](C4CC4)[C@H](C)NC(=O)OC(C)(C)C)c(F)cc3C#N)ccc21] | tert-butyl ((1R,2S)-1-((5-cyano-3-fluoro-6-((1-(2-methoxyethyl)-1H-indazol-5-yl)amino)pyridin-2-yl)amino)-1-cyclopropylpropan-2-yl)carbamate | 542 | 1.45 |
| Reference Example 134-139 | 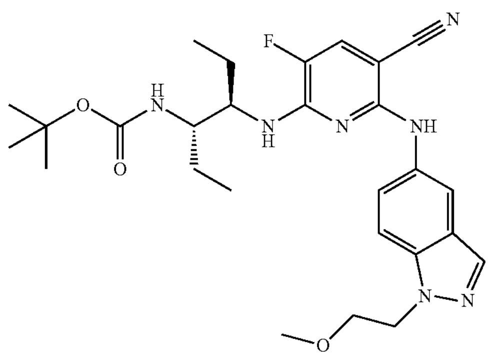 [SMILES: CC[C@H](NC(=O)OC(C)(C)C)[C@@H](CC)Nc1nc(Nc2ccc3c(cnn3CCOC)c2)c(C#N)cc1F] | tert-butyl ((3S,4R)-4-((5-cyano-3-fluoro-6-((1-(2-methoxyethyl)-1H-indazol-5-yl)amino)pyridin-2-yl)amino)hexan-3-yl)carbamate | 544 | 1.50 |
| Reference Example 134-140 | 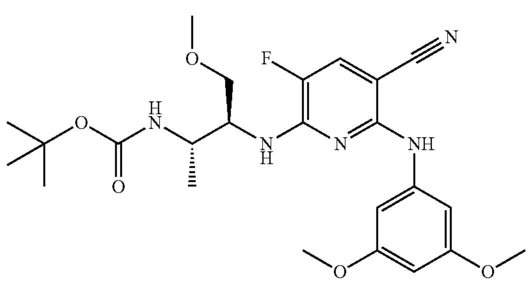 [SMILES: COC[C@@H](Nc1nc(Nc2cc(OC)cc(OC)c2)c(C#N)cc1F)[C@H](C)NC(=O)OC(C)(C)C] | tert-butyl ((2S,3S)-3-((5-cyano-6-((3,5-dimethoxyphenyl)amino)-3-fluoropyridin-2-yl)amino)-4-methoxybutan-2-yl)carbamate | 508 | 1.58 |
| Reference Example 134-141 | 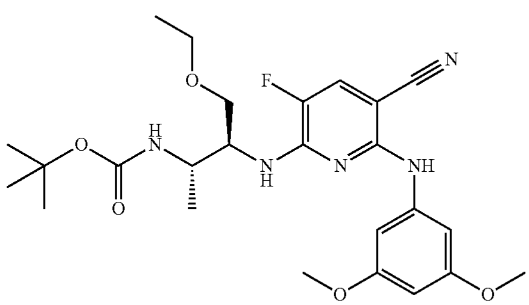 [SMILES: CCOC[C@@H](Nc1nc(Nc2cc(OC)cc(OC)c2)c(C#N)cc1F)[C@H](C)NC(=O)OC(C)(C)C] | tert-butyl ((2S,3S)-3-((5-cyano-6-((3,5-dimethoxyphenyl)amino)-3-fluoropyridin-2-yl)amino)-4-ethoxybutan-2-yl)carbamate | 522 | 1.68 |

TABLE 1-continued

| Reference Example | Structure | Compound name | MS(ESI m/z): (M + H) | RT(min) |
|---|---|---|---|---|
| Reference Example 134-142 | 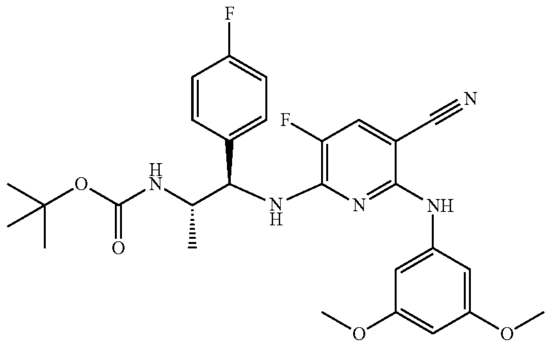 [SMILES: COc1cc(Nc2nc(N[C@H](c3ccc(F)cc3)[C@H](C)NC(=O)OC(C)(C)C)c(F)cc2C#N)cc(OC)c1] | tert-butyl ((1R,2S)-1-((5-cyano-6-((3,5-dimethoxyphenyl)amino)-3-fluoropyridin-2-yl)amino)-1-(4-fluorophenyl)propan-2-yl)carbamate | 558 | 1.75 |
| Reference Example 134-143 | 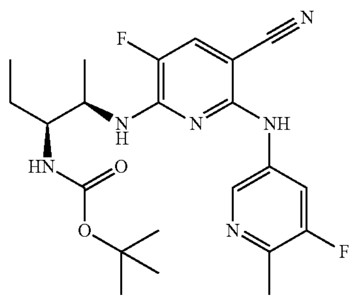 [SMILES: CC[C@H](NC(=O)OC(C)(C)C)[C@@H](C)Nc1nc(Nc2cnc(C)c(F)c2)c(C#N)cc1F] | tert-butyl ((2R,3S)-2-((5-cyano-3-fluoro-6-((5-fluoro-6-methylpyridin-3-yl)amino)pyridin-2-yl)amino)pentan-3-yl)carbamate | 447 | 1.58 |
| Reference Example 134-144 | 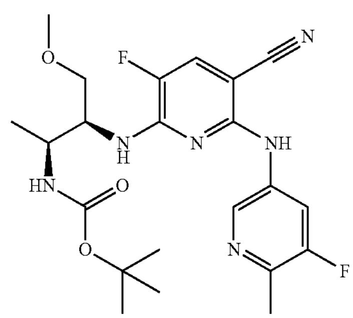 [SMILES: COC[C@@H](Nc1nc(Nc2cnc(C)c(F)c2)c(C#N)cc1F)[C@H](C)NC(=O)OC(C)(C)C] | tert-butyl ((2S,3S)-3-((5-cyano-3-fluoro-6-((5-fluoro-6-methylpyridin-3-yl)amino)pyridin-2-yl)amino)-4-methoxybutan-2-yl)carbamate | 463 | 1.67 |
| Reference Example 134-145 | 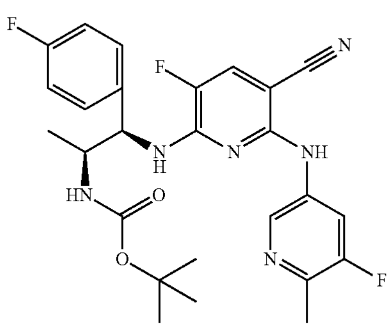 [SMILES: Cc1ncc(Nc2nc(N[C@H](c3ccc(F)cc3)[C@H](C)NC(=O)OC(C)(C)C)c(F)cc2C#N)cc1F] | tert-butyl ((1R,2S)-1-((5-cyano-3-fluoro-6-((5-fluoro-6-methylpyridin-3-yl)amino)pyridin-2-yl)amino)-1-(4-fluorophenyl)propan-2-yl)carbamate | 513 | 1.82 |

TABLE 1-continued

| Reference Example | Structure | Compound name | MS(ESI m/z): (M + H) | RT(min) |
|---|---|---|---|---|
| Reference Example 134-146 | 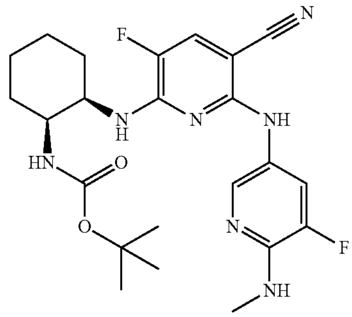 [SMILES: CNc1ncc(Nc2nc(N[C@@H]3CCCC[C@@H]3NC(=O)OC(C)(C)C)c(F)cc2C#N)cc1F] | tert-butyl ((1S,2R)-2-((5-cyano-3-fluoro-6-((5-fluoro-6-(methylamino)pyridin-3-yl)amino)pyridin-2-yl)amino)cyclohexyl)carbamate | 474 | 1.42 |
| Reference Example 134-147 | 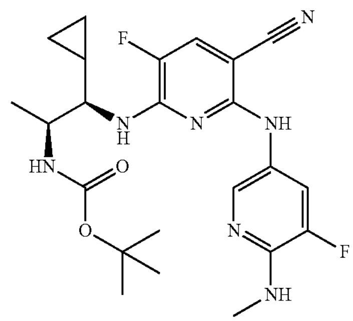 [SMILES: CNc1ncc(Nc2nc(N[C@H](C3CC3)[C@H](C)NC(=O)OC(C)(C)C)c(F)cc2C#N)cc1F] | tert-butyl ((1R,2S)-1-((5-cyano-3-fluoro-6-((5-fluoro-6-(methylamino)pyridin-3-yl)amino)pyridin-2-yl)amino)-1-cyclopropylpropan-2-yl)carbamate | 474 | 1.37 |
| Reference Example 134-148 | 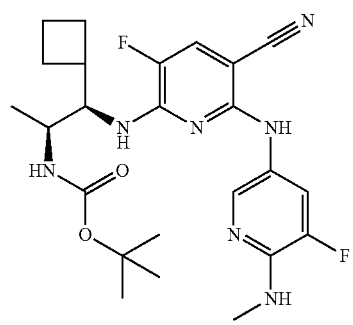 [SMILES: CNc1ncc(Nc2nc(N[C@H](C3CCC3)[C@H](C)NC(=O)OC(C)(C)C)c(F)cc2C#N)cc1F] | tert-butyl ((1R,2S)-1-((5-cyano-3-fluoro-6-((5-fluoro-6-(methylamino)pyridin-3-yl)amino)pyridin-2-yl)amino)-1-cyclobutylpropan-2-yl)carbamate | 488 | 1.48 |
| Reference Example 134-149 | 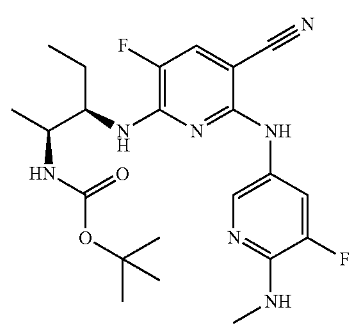 [SMILES: CC[C@@H](Nc1nc(Nc2cnc(NC)c(F)c2)c(C#N)cc1F)[C@H](C)NC(=O)OC(C)(C)C] | tert-butyl ((2S,3R)-3-((5-cyano-3-fluoro-6-((5-fluoro-6-(methylamino)pyridin-3-yl)amino)pyridin-2-yl)amino)pentan-2-yl)carbamate | 462 | 1.34 |

TABLE 1-continued

| Reference Example | Structure | Compound name | MS(ESI m/z): (M + H) | RT(min) |
|---|---|---|---|---|
| Reference Example 134-150 | 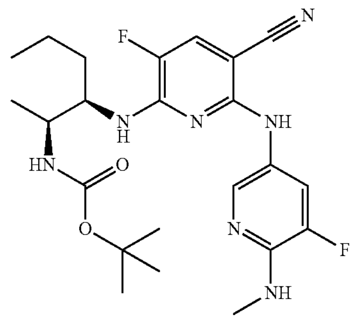 [SMILES: CCC[C@@H](Nc1nc(Nc2cnc(NC)c(F)c2)c(C#N)cc1F)[C@H](C)NC(=O)OC(C)(C)C] | tert-butyl ((2S,3R)-3-((5-cyano-3-fluoro-6-((5-fluoro-6-(methylamino)pyridin-3-yl)amino)pyridin-2-yl)amino)hexan-2-yl)carbamate | 476 | 1.45 |
| Reference Example 134-151 | 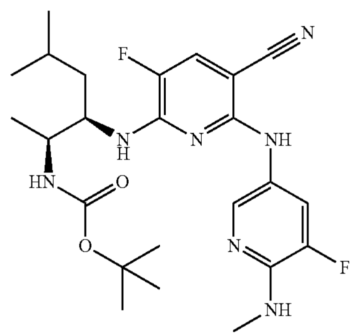 [SMILES: CNc1ncc(Nc2nc(N[C@H](CC(C)C)[C@H](C)NC(=O)OC(C)(C)C)c(F)cc2C#N)cc1F] | tert-butyl ((2S,3R)-3-((5-cyano-3-fluoro-6-((5-fluoro-6-(methylamino)pyridin-3-yl)amino)pyridin-2-yl)amino)-5-methylhexan-2-yl)carbamate | 490 | 1.54 |
| Reference Example 134-152 | 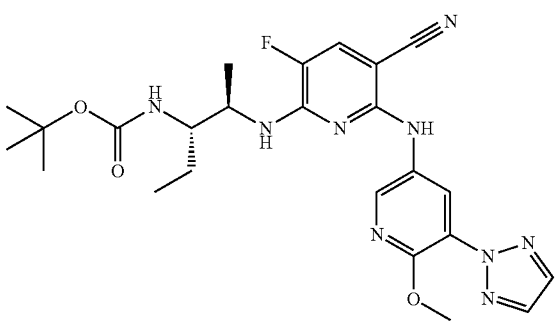 [SMILES: CC[C@H](NC(=O)OC(C)(C)C)[C@@H](C)Nc1nc(Nc2cnc(OC)c(-n3nccn3)c2)c(C#N)cc1F] | tert-butyl ((2R,3S)-2-((5-cyano-3-fluoro-6-((6-methoxy-5-(2H-1,2,3-triazol-2-yl)pyridin-3-yl)amino)pyridin-2-yl)amino)pentan-3-yl)carbamate | 530 | 1.52 |
| Reference Example 134-153 | 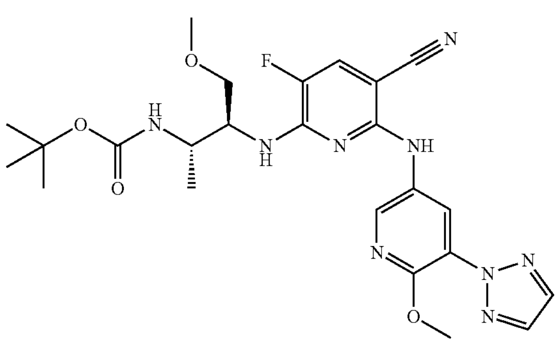 [SMILES: COC[C@@H](Nc1nc(Nc2cnc(OC)c(-n3nccn3)c2)c(C#N)cc1F)[C@H](C)NC(=O)OC(C)(C)C] | tert-butyl ((2S,3S)-3-((5-cyano-3-fluoro-6-((6-methoxy-5-(2H-1,2,3-triazol-2-yl)pyridin-3-yl)amino)pyridin-2-yl)amino)-4-methoxybutan-2-yl)carbamate | 546 | 1.44 |

| Reference Example | Structure | Compound name | MS(ESI m/z): (M + H) | RT(min) |
|---|---|---|---|---|
| Reference Example 134-154 | 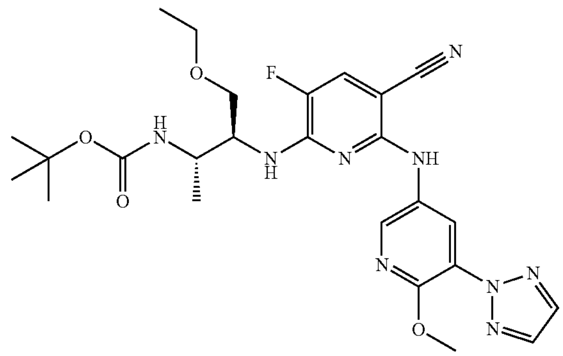 [SMILES: CCOC[C@@H](Nc1nc(Nc2cnc(OC)c(-n3nccn3)c2)c(C#N)cc1F)[C@H](C)NC(=O)OC(C)(C)C] | tert-butyl ((2S,3S)-3-((5-cyano-3-fluoro-6-((6-methoxy-5-(2H-1,2,3-triazol-2-yl)pyridin-3-yl)amino)pyridin-2-yl)amino)-4-ethoxybutan-2-yl)carbamate | 560 | 1.53 |
| Reference Example 134-155 | 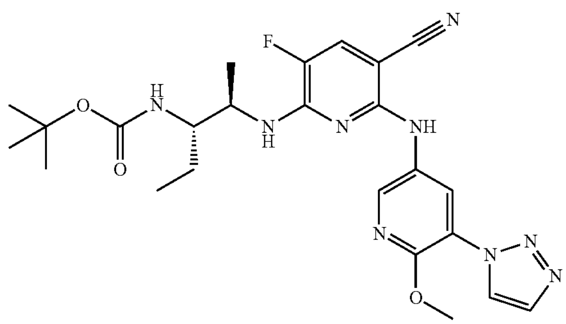 [SMILES: CC[C@H](NC(=O)OC(C)(C)C)[C@@H](C)Nc1nc(Nc2cnc(OC)c(-n3ccnn3)c2)c(C#N)cc1F] | tert-butyl ((2R,3S)-2-((5-cyano-3-fluoro-6-((6-methoxy-5-(1H-1,2,3-triazol-1-yl)pyridin-3-yl)amino)pyridin-2-yl)amino)pentan-3-yl)carbamate | 530 | 1.52 |
| Reference Example 134-156 | 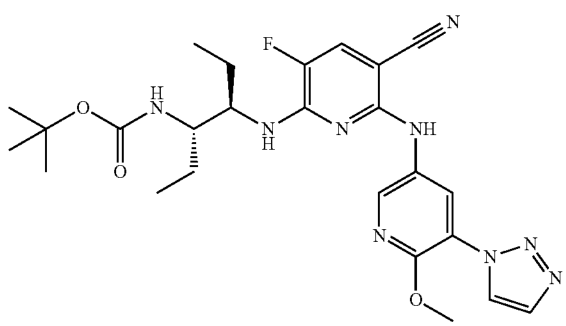 [SMILES: CC[C@H](NC(=O)OC(C)(C)C)[C@@H](CC)Nc1nc(Nc2cnc(OC)c(-n3ccnn3)c2)c(C#N)cc1F] | tert-butyl ((3S,4R)-4-((5-cyano-3-fluoro-6-((6-methoxy-5-(1H-1,2,3-triazol-1-yl)pyridin-3-yl)amino)pyridin-2-yl)amino)hexan-3-yl)carbamate | 542 | 1.58 |
| Reference Example 134-157 | 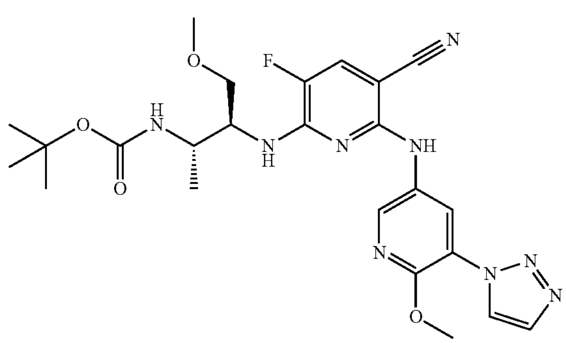 [SMILES: COC[C@@H](Nc1nc(Nc2cnc(OC)c(-n3ccnn3)c2)c(C#N)cc1F)[C@H](C)NC(=O)OC(C)(C)C] | tert-butyl ((2S,3S)-3-((5-cyano-3-fluoro-6-((6-methoxy-5-(1H-1,2,3-triazol-1-yl)pyridin-3-yl)amino)pyridin-2-yl)amino)-4-methoxybutan-2-yl)carbamate | 546 | 1.44 |

TABLE 1-continued

| Reference Example | Structure | Compound name | MS(ESI m/z): (M + H) | RT(min) |
|---|---|---|---|---|
| Reference Example 134-158 | 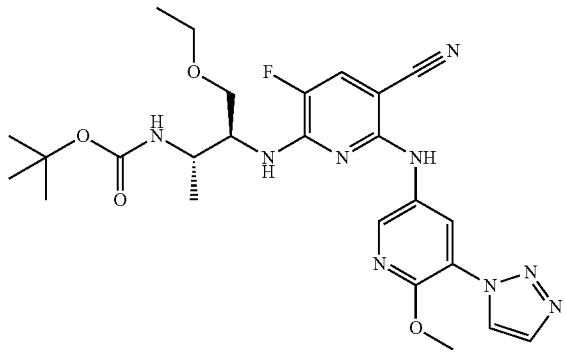 [SMILES: CCOC[C@@H](Nc1nc(Nc2cnc(OC)c(-n3ccnn3)c2)c(C#N)cc1F)[C@H](C)NC(=O)OC(C)(C)C] | tert-butyl ((2S,3S)-3-((5-cyano-3-fluoro-6-((6-methoxy-5-(1H-1,2,3-triazol-1-yl)pyridin-3-yl)amino)pyridin-2-yl)amino)-4-ethoxybutan-2-yl)carbamate | 558 | 1.54 |
| Reference Example 134-159 | 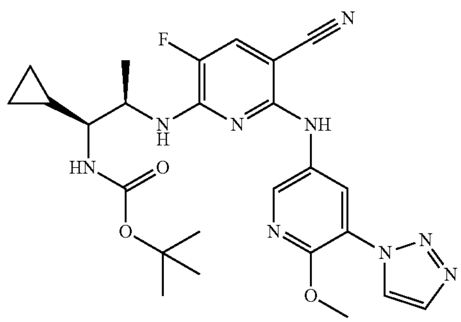 [SMILES: COc1ncc(Nc2nc(N[C@H](C)[C@@H](NC(=O)OC(C)(C)C)C3CC3)c(F)cc2C#N)cc1-n1ccnn1] | tert-butyl ((1S,2R)-2-((5-cyano-3-fluoro-6-((6-methoxy-5-(1H-1,2,3-triazol-1-yl)pyridin-3-yl)amino)pyridin-2-yl)amino)-1-cyclopropylpropyl)carbamate | 524 | 1.66 |
| Reference Example 134-160 | 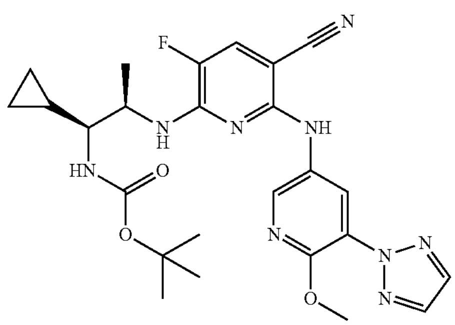 [SMILES: COc1ncc(Nc2nc(N[C@H](C)[C@@H](NC(=O)OC(C)(C)C)C3CC3)c(F)cc2C#N)cc1-n1nccn1] | tert-butyl ((1S,2R)-2-((5-cyano-3-fluoro-6-((6-methoxy-5-(2H-1,2,3-triazol-2-yl)pyridin-3-yl)amino)pyridin-2-yl)amino)-1-cyclopropylpropyl)carbamate | 524 | 1.69 |
| Reference Example 134-161 | 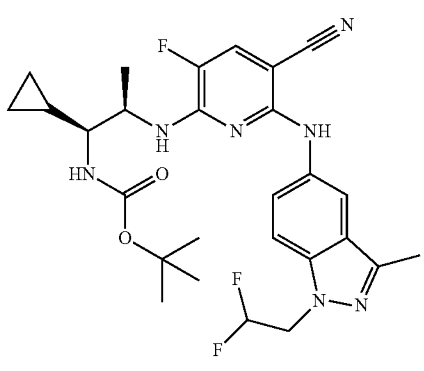 [SMILES: Cc1nn(CC(F)F)c2ccc(Nc3nc(N[C@H](C)[C@@H](NC(=O)OC(C)(C)C)C4CC4)c(F)cc3C#N)cc12] | tert-butyl ((1S,2R)-2-((5-cyano-6-((1-(2,2-difluoroethyl)-3-methyl-1H-indazol-5-yl)amino)-3-fluoropyridin-2-yl)amino)-1-cyclopropylpropyl)carbamate | 544 | 1.75 |

TABLE 1-continued

| Reference Example | Structure | Compound name | MS(ESI m/z): (M + H) | RT(min) |
|---|---|---|---|---|
| Reference Example 134-162 | 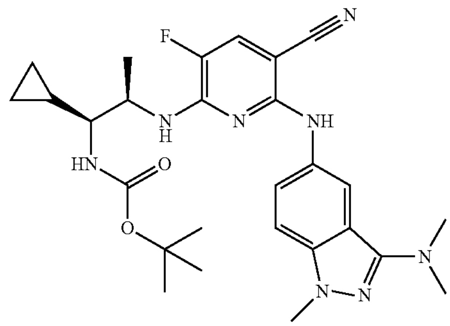 [SMILES: C[C@@H](Nc1nc(Nc2ccc3c(c2)c(N(C)C)nn3C)c(C#N)cc1F)[C@@H](NC(=O)OC(C)(C)C)C1CC1] | tert-butyl ((1S,2R)-2-((5-cyano-6-((3-(dimethylamino)-1-methyl-1H-indazol-5-yl)amino)-3-fluoropyridin-2-yl)amino)-1-cyclopropylpropyl)carbamate | 523 | 1.70 |
| Reference Example 134-163 | 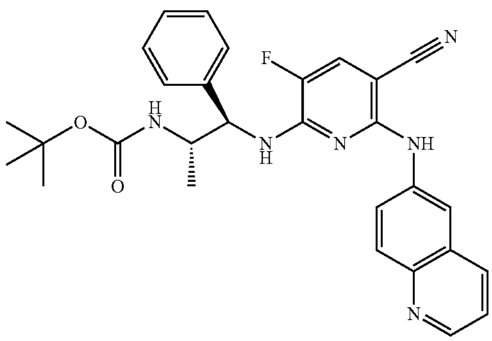 [SMILES: C[C@H](NC(=O)OC(C)(C)C)[C@H](Nc1nc(Nc2ccc3ncccc3c2)c(C#N)cc1F)c1ccccc1] | tert-butyl ((1R,2S)-1-((5-cyano-3-fluoro-6-(quinolin-6-ylamino)pyridin-2-yl)amino)-1-phenylpropan-2-yl)carbamate | 513 | 1.45 |
| Reference Example 134-164 | 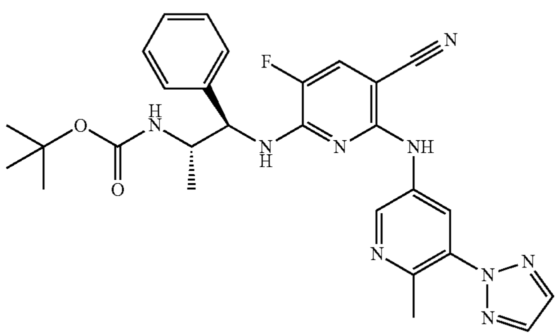 [SMILES: Cc1ncc(Nc2nc(N[C@H](c3ccccc3)[C@H](C)NC(=O)OC(C)(C)C)c(F)cc2C#N)cc1-n1nccn1] | tert-butyl ((1R,2S)-1-((5-cyano-3-fluoro-6-((6-methyl-5-(2H-1,2,3-triazol-2-yl)pyridin-3-yl)amino)pyridin-2-yl)amino)-1-phenylpropan-2-yl)carbamate | 544 | 1.73 |
| Reference Example 134-165 | 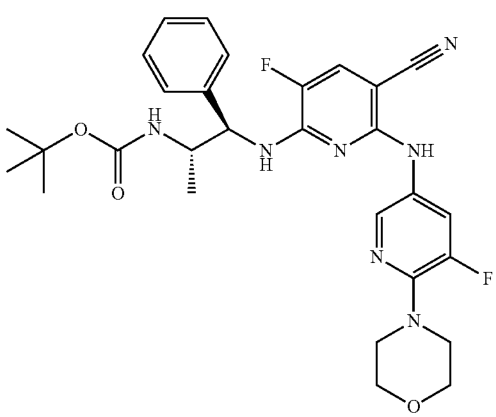 [SMILES: C[C@H](NC(=O)OC(C)(C)C)[C@H](Nc1nc(Nc2cnc(N3CCOCC3)c(F)c2)c(C#N)cc1F)c1ccccc1] | tert-butyl ((1R,2S)-1-((5-cyano-3-fluoro-6-((5-fluoro-6-morpholinopyridin-3-yl)amino)pyridin-2-yl)amino)-1-phenylpropan-2-yl)carbamate | 566 | 1.80 |

TABLE 1-continued

| Reference Example | Structure | Compound name | MS(ESI m/z): (M + H) | RT(min) |
|---|---|---|---|---|
| Reference Example 134-166 | 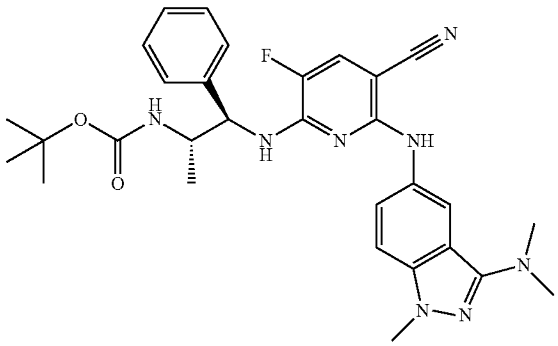 [SMILES: C[C@H](NC(=O)OC(C)(C)C)[C@H](Nc1nc(Nc2ccc3c(c2)c(N(C)C)nn3C)c(C#N)cc1F)c1ccccc1] | tert-butyl ((1R,2S)-1-((5-cyano-6-((3-(dimethylamino)-1-methyl-1H-indazol-5-yl)amino)-3-fluoropyridin-2-yl)amino)-1-phenylpropan-2-yl)carbamate | 559 | 1.78 |
| Reference Example 134-167 | 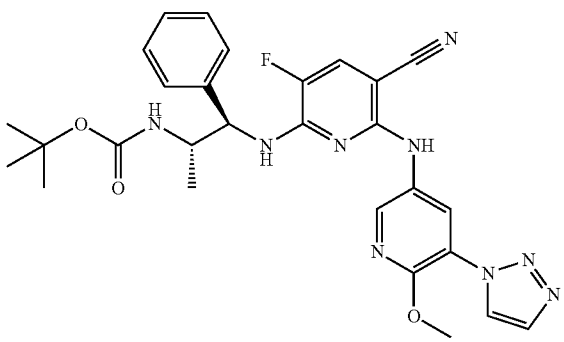 [SMILES: COc1ncc(Nc2nc(N[C@H](c3ccccc3)[C@H](C)NC(=O)OC(C)(C)C)c(F)cc2C#N)cc1-n1ccnn1] | tert-butyl ((1R,2S)-1-((5-cyano-3-fluoro-6-((6-methoxy-5-(1H-1,2,3-triazol-1-yl)pyridin-3-yl)amino)pyridin-2-yl)amino)-1-phenylpropan-2-yl)carbamate | 460 (+H − Boc) | 1.74 |
| Reference Example 134-168 | 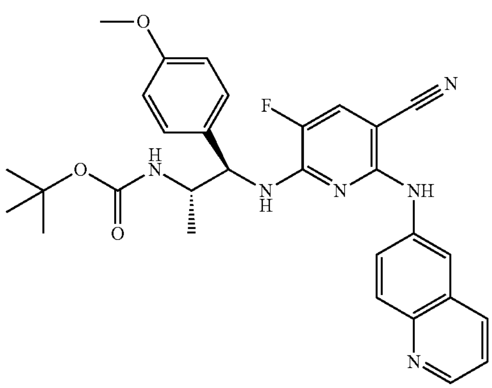 [SMILES: COc1ccc([C@@H](Nc2nc(Nc3ccc4ncccc4c3)c(C#N)cc2F)[C@H](C)NC(=O)OC(C)(C)C)cc1] | tert-butyl ((1R,2S)-1-((5-cyano-3-fluoro-6-(quinolin-6-ylamino)pyridin-2-yl)amino)-1-(4-methoxyphenyl)propan-2-yl)carbamate | 543 | 1.44 |
| Reference Example 134-169 | 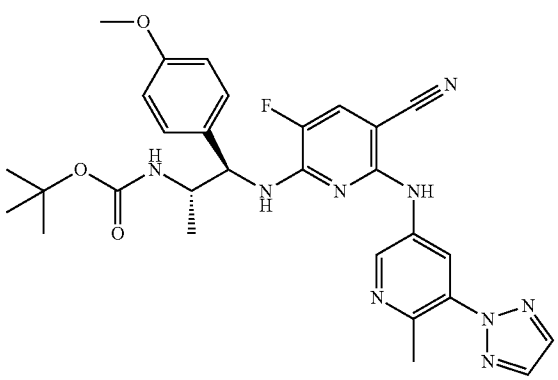 [SMILES: COc1ccc([C@@H](Nc2nc(Nc3cnc(C)c(-n4nccn4)c3)c(C#N)cc2F)[C@H](C)NC(=O)OC(C)(C)C)cc1] | tert-butyl ((1R,2S)-1-((5-cyano-3-fluoro-6-((6-methyl-5-(2H-1,2,3-triazol-2-yl)pyridin-3-yl)amino)pyridin-2-yl)amino)-1-(4-methoxyphenyl)propan-2-yl)carbamate | 574 | 1.71 |

TABLE 1-continued

| Reference Example | Structure | Compound name | MS(ESI m/z): (M + H) | RT(min) |
|---|---|---|---|---|
| Reference Example 134-170 | 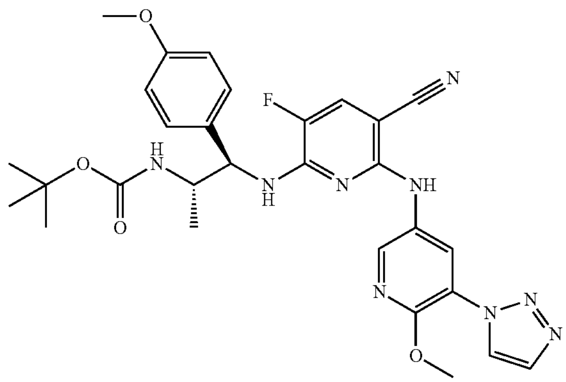 [SMILES: COc1ccc([C@@H](Nc2nc(Nc3cnc(OC)c(-n4ccnn4)c3)c(C#N)cc2F)[C@H](C)NC(=O)OC(C)(C)C)cc1] | tert-butyl ((1R,2S)-1-((5-cyano-3-fluoro-6-((6-methoxy-5-(1H-1,2,3-triazol-1-yl)pyridin-3-yl)amino)pyridin-2-yl)amino)-1-(4-methoxyphenyl)propan-2-yl)carbamate | 490 (+H − Boc) | 1.72 |
| Reference Example 134-171 | 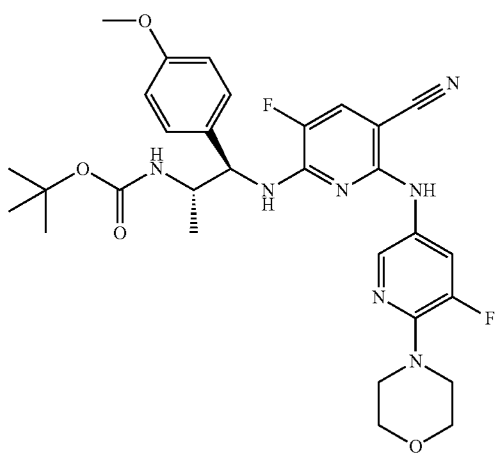 [SMILES: COc1ccc([C@@H](Nc2nc(Nc3cnc(N4CCOCC4)c(F)c3)c(C#N)cc2F)[C@H](C)NC(=O)OC(C)(C)C)cc1] | tert-butyl ((1R,2S)-1-((5-cyano-3-fluoro-6-((5-fluoro-6-morpholinopyridin-3-yl)amino)pyridin-2-yl)amino)-1-(4-methoxyphenyl)propan-2-yl)carbamate | 596 | 1.77 |
| Reference Example 134-172 | 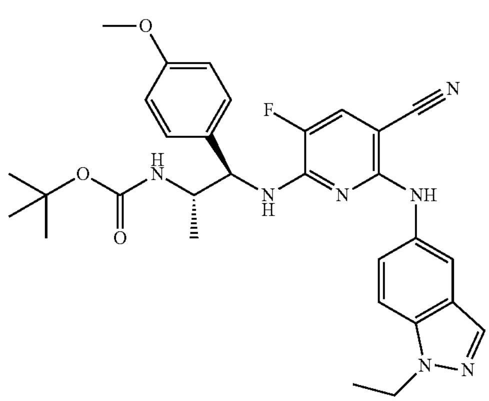 [SMILES: CCn1ncc2cc(Nc3nc(N[C@H](c4ccc(OC)cc4)[C@H](C)NC(=O)OC(C)(C)C)c(F)cc3C#N)ccc21] | tert-butyl ((1R,2S)-1-((5-cyano-6-((1-ethyl-1H-indazol-5-yl)amino)-3-fluoropyridin-2-yl)amino)-1-(4-methoxyphenyl)propan-2-yl)carbamate | 560 | 1.77 |

TABLE 1-continued

| Reference Example | Structure | Compound name | MS(ESI m/z): (M + H) | RT(min) |
|---|---|---|---|---|
| Reference Example 134-173 | 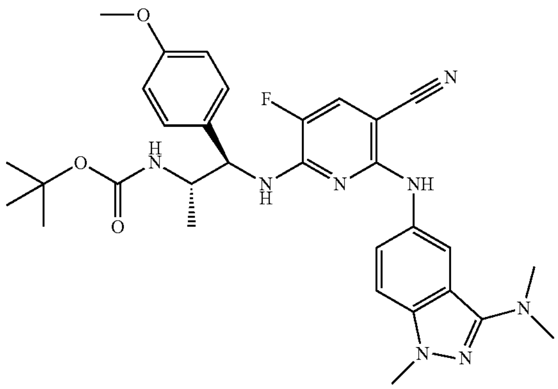 [SMILES: COc1ccc([C@@H](Nc2nc(Nc3ccc4c(c3)c(N(C)C)nn4C)c(C#N)cc2F)[C@H](C)NC(=O)OC(C)(C)C)cc1] | tert-butyl ((1R,2S)-1-((5-cyano-6-((3-(dimethylamino)-1-methyl-1H-indazol-5-yl)amino)-3-fluoropyridin-2-yl)amino)-1-(4-methoxyphenyl)propan-2-yl)carbamate | 587 | 1.76 |
| Reference Example 134-174 | 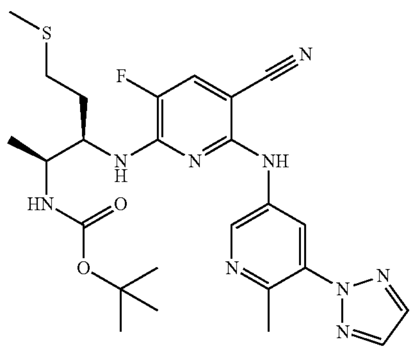 [SMILES: CSCC[C@@H](Nc1nc(Nc2cnc(C)c(-n3nccn3)c2)c(C#N)cc1F)[C@H](C)NC(=O)OC(C)(C)C] | tert-butyl ((2S,3R)-3-((5-cyano-3-fluoro-6-((6-methyl-5-(2H-1,2,3-triazol-2-yl)pyridin-3-yl)amino)pyridin-2-yl)amino)-5-(methylthio)pentan-2-yl)carbamate | 542 | 1.61 |
| Reference Example 134-175 | 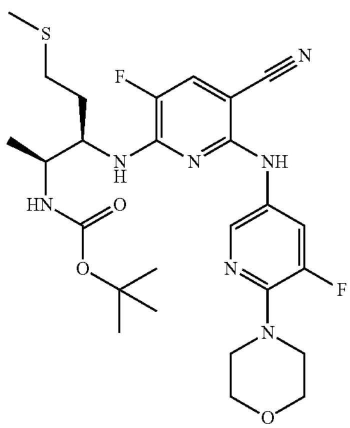 [SMILES: CSCC[C@@H](Nc1nc(Nc2cnc(N3CCOCC3)c(F)c2)c(C#N)cc1F)[C@H](C)NC(=O)OC(C)(C)C] | tert-butyl ((2S,3R)-3-((5-cyano-3-fluoro-6-((5-fluoro-6-morpholinopyridin-3-yl)amino)pyridin-2-yl)amino)-5-(methylthio)pentan-2-yl)carbamate | 564 | 1.61 |
| Reference Example 134-176 | 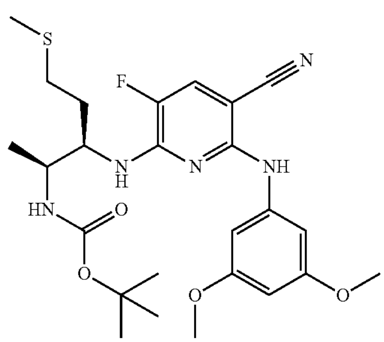 [SMILES: COc1cc(Nc2nc(N[C@H](CCSC)[C@H](C)NC(=O)OC(C)(C)C)c(F)cc2C#N)cc(OC)c1] | tert-butyl ((2S,3R)-3-((5-cyano-6-((3,5-dimethoxyphenyl)amino)-3-fluoropyridin-2-yl)amino)-5-(methylthio)pentan-2-yl)carbamate | 535 | 1.26 |

TABLE 1-continued

| Reference Example | Structure | Compound name | MS(ESI m/z): (M + H) | RT(min) |
|---|---|---|---|---|
| Reference Example 134-177 | 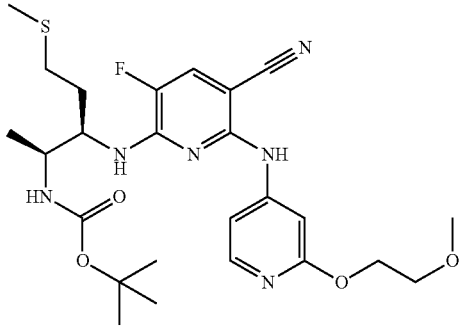 [SMILES: COCCOc1cc(Nc2nc(N[C@H](CCSC)[C@H](C)NC(=O)OC(C)(C)C)c(F)cc2C#N)ccn1] | tert-butyl ((2S,3R)-3-((5-cyano-3-fluoro-6-((2-(2-methoxyethoxy)pyridin-4-yl)amino)pyridin-2-yl)amino)-5-(methylthio)pentan-2-yl)carbamate | 520 | 1.74 |
| Reference Example 134-178 | 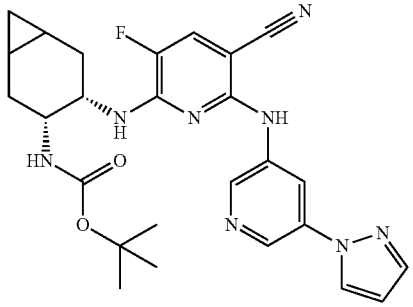 [SMILES: CC(C)(C)OC(=O)N[C@@H]1CC2CC2C[C@@H]1Nc1nc(Nc2cncc(-n3cccn3)c2)c(C#N)cc1F] | tert-butyl ((3R,4S)-4-((6-((5-(1H-pyrazol-1-yl)pyridin-3-yl)amino)-5-cyano-3-fluoropyridin-2-yl)amino)bicyclo[4.1.0]heptan-3-yl)carbamate | 505 | 1.66 |
| Reference Example 134-179 | 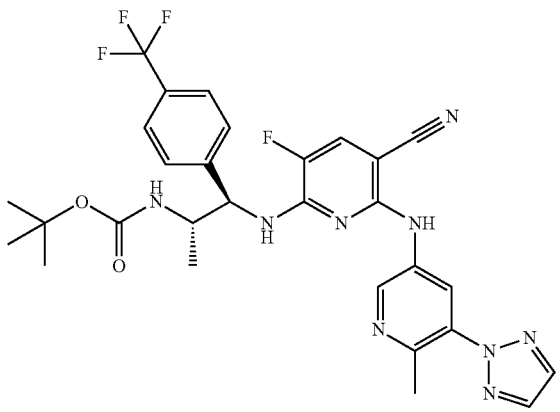 [SMILES: Cc1ncc(Nc2nc(N[C@H](c3ccc(C(F)(F)F)cc3)[C@H](C)NC(=O)OC(C)(C)C)c(F)cc2C#N)cc1-n1nccn1] | tert-butyl ((1R,2S)-1-((5-cyano-3-fluoro-6-((6-methyl-5-(2H-1,2,3-triazol-2-yl)pyridin-3-yl)amino)pyridin-2-yl)amino)-1-(4-(trifluoromethyl)phenyl)propan-2-yl)carbamate | 612 | 1.85 |
| Reference Example 134-180 | 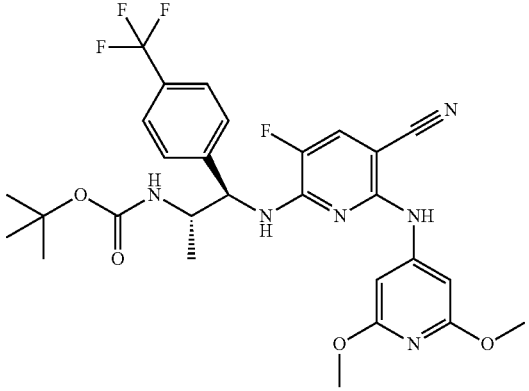 [SMILES: COc1cc(Nc2nc(N[C@H](c3ccc(C(F)(F)F)cc3)[C@H](C)NC(=O)OC(C)(C)C)c(F)cc2C#N)cc(OC)n1] | tert-butyl ((1R,2S)-1-((5-cyano-6-((2,6-dimethoxypyridin-4-yl)amino)-3-fluoropyridin-2-yl)amino)-1-(4-(trifluoromethyl)phenyl)propan-2-yl)carbamate | 591 | 2.03 |

TABLE 1-continued

| Reference Example | Structure | Compound name | MS(ESI m/z): (M + H) | RT(min) |
|---|---|---|---|---|
| Reference Example 134-181 | 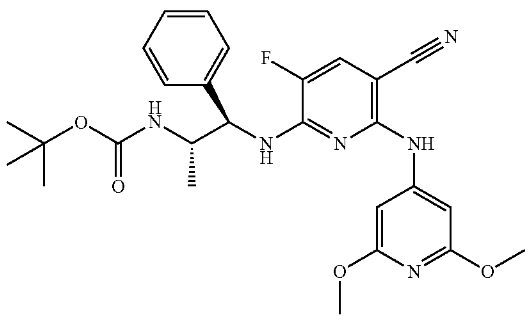 [SMILES: COc1cc(Nc2nc(N[C@H](c3ccccc3)[C@H](C)NC(=O)OC(C)(C)C)c(F)cc2C#N)cc(OC)n1] | tert-butyl ((1R,2S)-1-((5-cyano-6-((2,6-dimethoxypyridin-4-yl)amino)-3-fluoropyridin-2-yl)amino)-1-phenylpropan-2-yl)carbamate | 523 | 1.93 |
| Reference Example 134-182 | 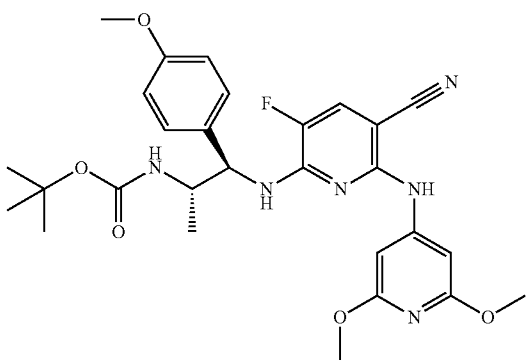 [SMILES: COc1ccc([C@@H](Nc2nc(Nc3cc(OC)nc(OC)c3)c(C#N)cc2F)[C@H](C)NC(=O)OC(C)(C)C)cc1] | tert-butyl ((1R,2S)-1-((5-cyano-6-((2,6-dimethoxypyridin-4-yl)amino)-3-fluoropyridin-2-yl)amino)-1-(4-methoxyphenyl)propan-2-yl)carbamate | 553 | 1.89 |
| Reference Example 134-183 | 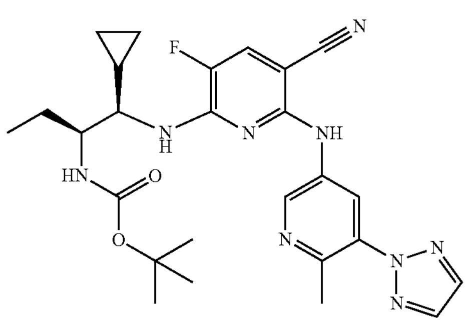 [SMILES: CC[C@H](NC(=O)OC(C)(C)C)[C@H](Nc1nc(Nc2cnc(C)c(-n3nccn3)c2)c(C#N)cc1F)C1CC1] | tert-butyl ((1R,2S)-1-((5-cyano-3-fluoro-6-((6-methyl-5-(2H-1,2,3-triazol-2-yl)pyridin-3-yl)amino)pyridin-2-yl)amino)-1-cyclopropylbutan-2-yl)carbamate | 522 | 1.68 |
| Reference Example 134-184 | 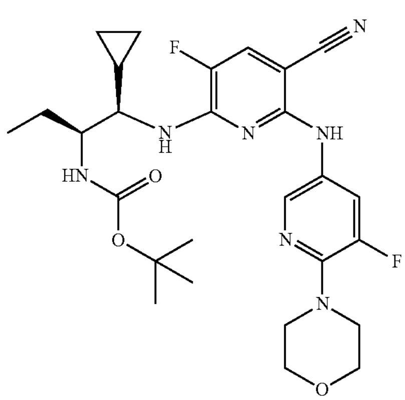 [SMILES: CC[C@H](NC(=O)OC(C)(C)C)[C@H](Nc1nc(Nc2cnc(N3CCOCC3)c(F)c2)c(C#N)cc1F)C1CC1] | tert-butyl ((1R,2S)-1-((5-cyano-3-fluoro-6-((5-fluoro-6-morpholinopyridin-3-yl)amino)pyridin-2-yl)amino)-1-cyclopropylbutan-2-yl)carbamate | 544 | 1.74 |

TABLE 1-continued

| Reference Example | Structure | Compound name | MS(ESI m/z): (M + H) | RT(min) |
|---|---|---|---|---|
| Reference Example 134-185 | 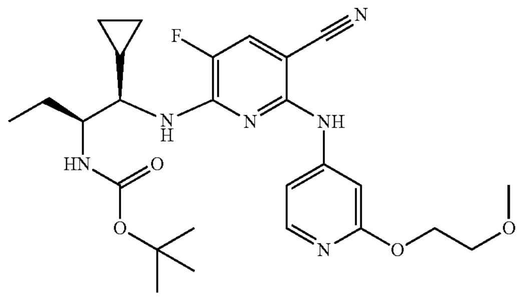 [SMILES: CC[C@H](NC(=O)OC(C)(C)C)[C@H](Nc1nc(Nc2ccnc(OCCOC)c2)c(C#N)cc1F)C1CC1] | tert-butyl ((1R,2S)-1-((5-cyano-3-fluoro-6-((2-(2-methoxyethoxy)pyridin-4-yl)amino)pyridin-2-yl)amino)-1-cyclopropylbutan-2-yl)carbamate | 515 | 1.41 |
| Reference Example 134-186 | 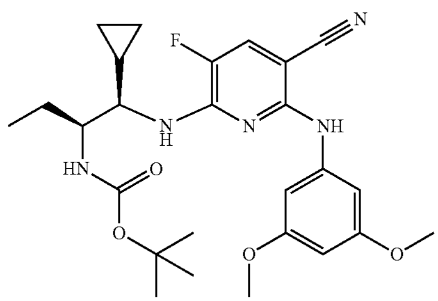 [SMILES: CC[C@H](NC(=O)OC(C)(C)C)[C@H](Nc1nc(Nc2cc(OC)cc(OC)c2)c(C#N)cc1F)C1CC1] | tert-butyl ((1R,2S)-1-((5-cyano-6-((3,5-dimethoxyphenyl)amino)-3-fluoropyridin-2-yl)amino)-1-cyclopropylbutan-2-yl)carbamate | 500 | 1.86 |
| Reference Example 134-187 | 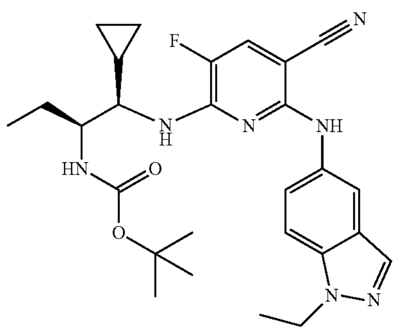 [SMILES: CC[C@H](NC(=O)OC(C)(C)C)[C@H](Nc1nc(Nc2ccc3c(cnn3CC)c2)c(C#N)cc1F)C1CC1] | tert-butyl ((1R,2S)-1-((5-cyano-6-((1-ethyl-1H-indazol-5-yl)amino)-3-fluoropyridin-2-yl)amino)-1-cyclopropylbutan-2-yl)carbamate | 508 | 1.75 |
| Reference Example 134-188 | 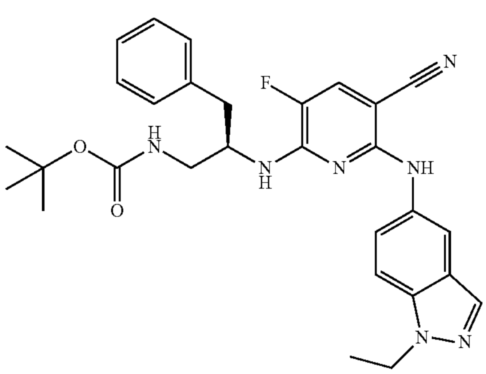 [SMILES: CCn1ncc2cc(Nc3nc(N[C@@H](CNC(=O)OC(C)(C)C)Cc4ccccc4)c(F)cc3C#N)ccc21] | (R)-tert-butyl (2-((5-cyano-6-((1-ethyl-1H-indazol-5-yl)amino)-3-fluoropyridin-2-yl)amino)-3-phenylpropyl)carbamate | 548 | 1.60 |

TABLE 1-continued

| Reference Example | Structure | Compound name | MS(ESI m/z): (M + H) | RT(min) |
|---|---|---|---|---|
| Reference Example 134-189 | 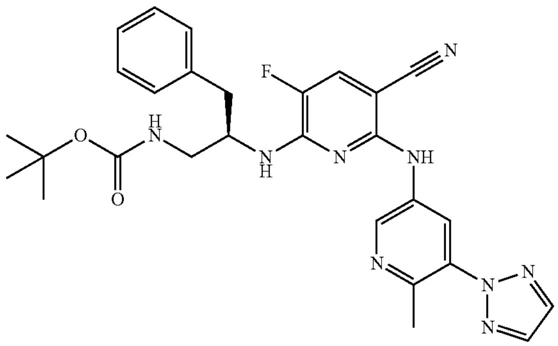 [SMILES: Cc1ncc(Nc2nc(N[C@@H](CNC(=O)OC(C)(C)C)Cc3ccccc3)c(F)cc2C#N)cc1-n1nccn1] | (R)-tert-butyl (2-((5-cyano-3-fluoro-6-((6-methyl-5-(2H-1,2,3-triazol-2-yl)pyridin-3-yl)amino)pyridin-2-yl)amino)-3-phenylpropyl)carbamate | 562 | 1.51 |
| Reference Example 134-190 | 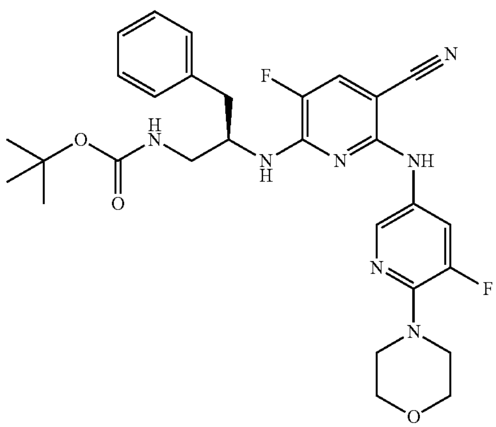 [SMILES: CC(C)(C)OC(=O)NC[C@@H](Cc1ccccc1)Nc1nc(Nc2cnc(N3CCOCC3)c(F)c2)c(C#N)cc1F] | (R)-tert-butyl (2-((5-cyano-3-fluoro-6-((5-fluoro-6-morpholinopyridin-3-yl)amino)pyridin-2-yl)amino)-3-phenylpropyl)carbamate | 548 | 1.60 |
| Reference Example 134-191 | 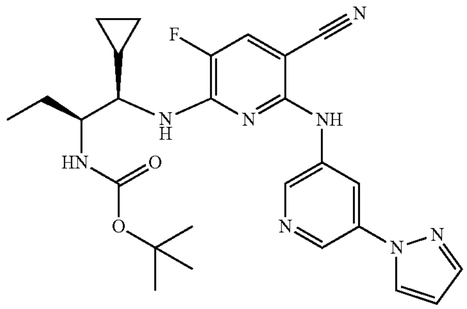 [SMILES: CC[C@H](NC(=O)OC(C)(C)C)[C@H](Nc1nc(Nc2cncc(-n3cccn3)c2)c(C#N)cc1F)C1CC1] | tert-butyl ((1R,2S)-1-((6-((5-(1H-pyrazol-1-yl)pyridin-3-yl)amino)-5-cyano-3-fluoropyridin-2-yl)amino)-1-cyclopropylbutan-2-yl)carbamate | 507 | 1.63 |
| Reference Example 134-192 | 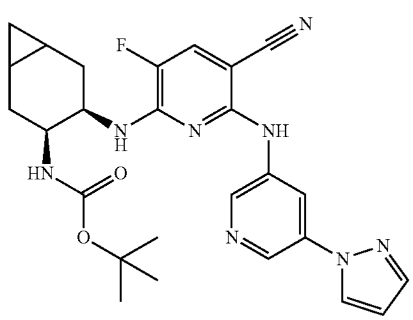 [SMILES: CC(C)(C)OC(=O)N[C@H]1CC2CC2C[C@H]1Nc1nc(Nc2cncc(-n3cccn3)c2)c(C#N)cc1F] | tert-butyl ((3S,4R)-4-((6-((5-(1H-pyrazol-1-yl)pyridin-3-yl)amino)-5-cyano-3-fluoropyridin-2-yl)amino)bicyclo[4.1.0]heptan-3-yl)carbamate | 505 | 1.66 |

TABLE 1-continued

| Reference Example | Structure | Compound name | MS(ESI m/z): (M + H) | RT(min) |
|---|---|---|---|---|
| Reference Example 134-193 | 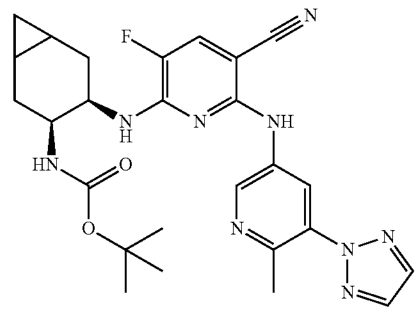 [SMILES: Cc1ncc(Nc2nc(N[C@@H]3CC4CC4C[C@@H]3NC(=O)OC(C)(C)C)c(F)cc2C#N)cc1-n1nccn1] | tert-butyl ((3S,4R)-4-((5-cyano-3-fluoro-6-((6-methyl-5-(2H-1,2,3-triazol-2-yl)pyridin-3-yl)amino)pyridin-2-yl)amino)bicyclo[4.1.0]heptan-3-yl)carbamate | 520 | 1.70 |
| Reference Example 134-194 | 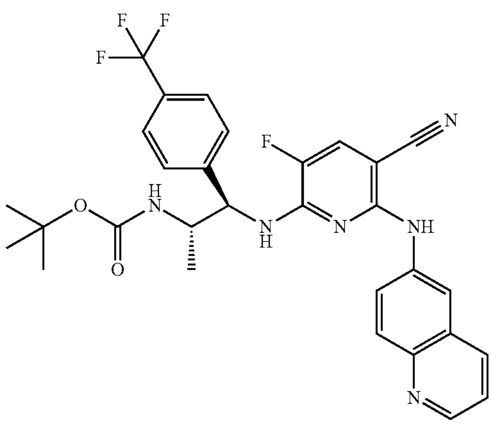 [SMILES: C[C@H](NC(=O)OC(C)(C)C)[C@H](Nc1nc(Nc2ccc3ncccc3c2)c(C#N)cc1F)c1ccc(C(F)(F)F)cc1] | tert-butyl ((1R,2S)-1-((5-cyano-3-fluoro-6-(quinolin-6-ylamino)pyridin-2-yl)amino)-1-(4-(trifluoromethyl)phenyl)propan-2-yl)carbamate | 581 | 1.63 |
| Reference Example 134-195 | 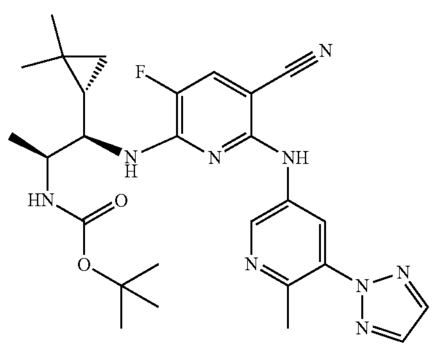 [SMILES: Cc1ncc(Nc2nc(N[C@@H]([C@H](C)NC(=O)OC(C)(C)C)[C@H]3CC3(C)C)c(F)cc2C#N)cc1-n1nccn1] | tert-butyl ((1R,2S)-1-((5-cyano-3-fluoro-6-((6-methyl-5-(2H-1,2,3-triazol-2-yl)pyridin-3-yl)amino)pyridin-2-yl)amino)-1-((S)-2,2-dimethylcyclopropyl)propan-2-yl)carbamate | 536 | 1.75 |
| Reference Example 134-196 | 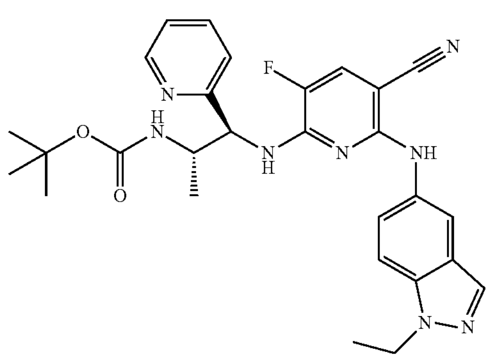 [SMILES: CCn1ncc2cc(Nc3nc(N[C@H](c4ccccn4)[C@H](C)NC(=O)OC(C)(C)C)c(F)cc3C#N)ccc21] | tert-butyl ((1S,2S)-1-((5-cyano-6-((1-ethyl-1H-indazol-5-yl)amino)-3-fluoropyridin-2-yl)amino)-1-(pyridin-2-yl)propan-2-yl)carbamate | 531 | 1.47 |

TABLE 1-continued

| Reference Example | Structure | Compound name | MS(ESI m/z): (M + H) | RT(min) |
|---|---|---|---|---|
| Reference Example 134-197 | 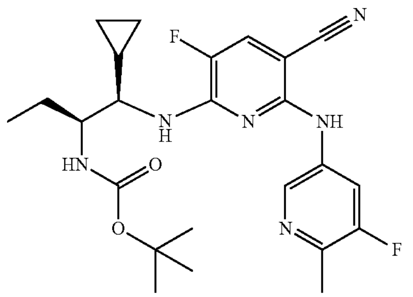 [SMILES: CC[C@H](NC(=O)OC(C)(C)C)[C@H](Nc1nc(Nc2cnc(C)c(F)c2)c(C#N)cc1F)C1CC1] | tert-butyl ((1R,2S)-1-((5-cyano-3-fluoro-6-((5-fluoro-6-methylpyridin-3-yl)amino)pyridin-2-yl)amino)-1-cyclopropylbutan-2-yl)carbamate | 473 | 1.68 |
| Reference Example 134-198 | 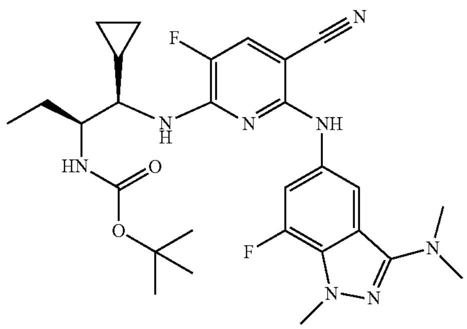 [SMILES: CC[C@H](NC(=O)OC(C)(C)C)[C@H](Nc1nc(Nc2cc(F)c3c(c2)c(N(C)C)nn3C)c(C#N)cc1F)C1CC1] | tert-butyl ((1R,2S)-1-((5-cyano-6-((3-(dimethylamino)-7-fluoro-1-methyl-1H-indazol-5-yl)amino)-3-fluoropyridin-2-yl)amino)-1-cyclopropylbutan-2-yl)carbamate | 555 | 1.87 |
| Reference Example 134-199 | 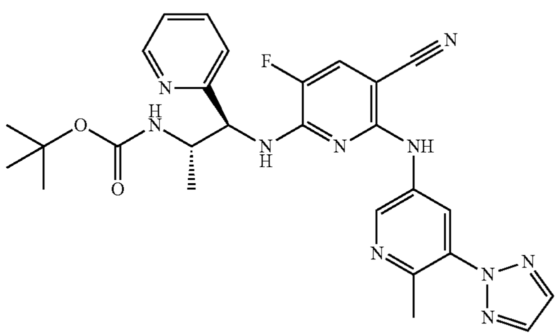 [SMILES: Cc1ncc(Nc2nc(N[C@H](c3ccccn3)[C@H](C)NC(=O)OC(C)(C)C)c(F)cc2C#N)cc1-n1nccn1] | tert-butyl ((1S,2S)-1-((5-cyano-3-fluoro-6-((6-methyl-5-(2H-1,2,3-triazol-2-yl)pyridin-3-yl)amino)pyridin-2-yl)amino)-1-(pyridin-2-yl)propan-2-yl)carbamate | 545 | 1.46 |
| Reference Example 134-200 | 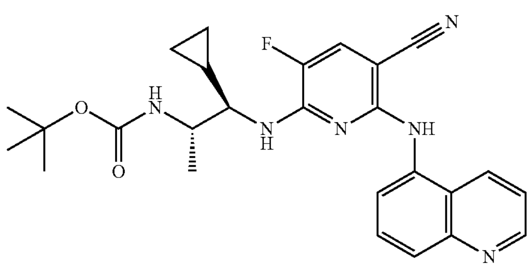 [SMILES: C[C@H](NC(=O)OC(C)(C)C)[C@H](Nc1nc(Nc2cccc3ncccc23)c(C#N)cc1F)C1CC1] | tert-butyl ((1R,2S)-1-((5-cyano-3-fluoro-6-(quinolin-5-ylamino)pyridin-2-yl)amino)-1-cyclopropylpropan-2-yl)carbamate | 477 | 1.33 |
| Reference Example 134-201 | 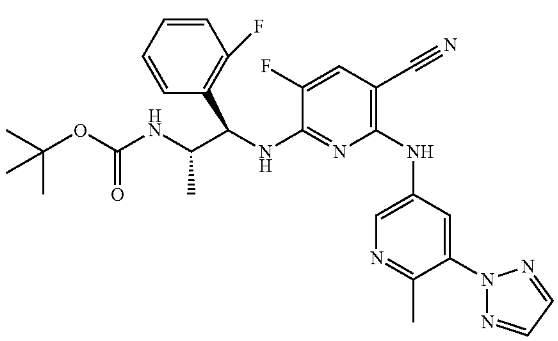 [SMILES: Cc1ncc(Nc2nc(N[C@H](c3ccccc3F)[C@H](C)NC(=O)OC(C)(C)C)c(F)cc2C#N)cc1-n1nccn1] | tert-butyl ((1R,2S)-1-((5-cyano-3-fluoro-6-((6-methyl-5-(2H-1,2,3-triazol-2-yl)pyridin-3-yl)amino)pyridin-2-yl)amino)-1-(2-fluorophenyl)propan-2-yl)carbamate | 562 | 1.73 |

TABLE 1-continued

| Reference Example | Structure | Compound name | MS(ESI m/z): (M + H) | RT(min) |
|---|---|---|---|---|
| Reference Example 134-202 | 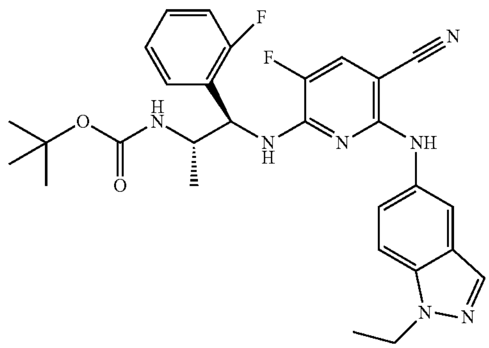 [SMILES: CCn1ncc2cc(Nc3nc(N[C@H](c4ccccc4F)[C@H](C)NC(=O)OC(C)(C)C)c(F)cc3C#N)ccc21] | tert-butyl ((1R,2S)-1-((5-cyano-6-((1-ethyl-1H-indazol-5-yl)amino)-3-fluoropyridin-2-yl)amino)-1-(2-fluorophenyl)propan-2-yl)carbamate | 548 | 1.79 |
| Reference Example 134-203 | 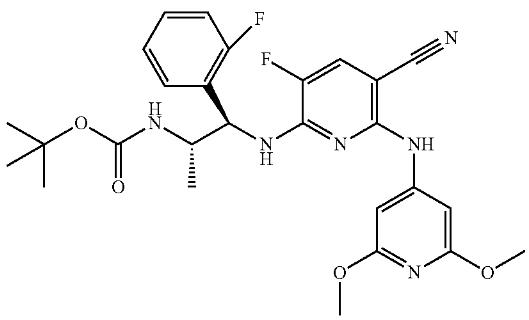 [SMILES: COc1cc(Nc2nc(N[C@H](c3ccccc3F)[C@H](C)NC(=O)OC(C)(C)C)c(F)cc2C#N)cc(OC)n1] | tert-butyl ((1R,2S)-1-((5-cyano-6-((2,6-dimethoxypyridin-4-yl)amino)-3-fluoropyridin-2-yl)amino)-1-(2-fluorophenyl)propan-2-yl)carbamate | 541 | 1.91 |
| Reference Example 134-204 | 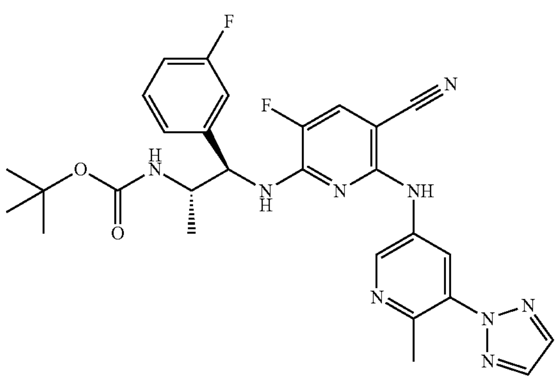 [SMILES: Cc1ncc(Nc2nc(N[C@H](c3cccc(F)c3)[C@H](C)NC(=O)OC(C)(C)C)c(F)cc2C#N)cc1-n1nccn1] | tert-butyl ((1R,2S)-1-((5-cyano-3-fluoro-6-((6-methyl-5-(2H-1,2,3-triazol-2-yl)pyridin-3-yl)amino)pyridin-2-yl)amino)-1-(3-fluorophenyl)propan-2-yl)carbamate | 562 | 1.70 |
| Reference Example 134-205 | 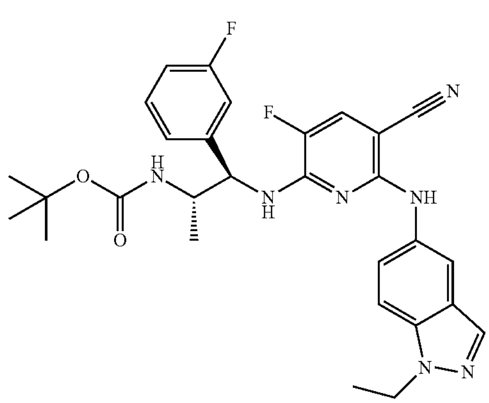 [SMILES: CCn1ncc2cc(Nc3nc(N[C@H](c4cccc(F)c4)[C@H](C)NC(=O)OC(C)(C)C)c(F)cc3C#N)ccc21] | tert-butyl ((1R,2S)-1-((5-cyano-6-((1-ethyl-1H-indazol-5-yl)amino)-3-fluoropyridin-2-yl)amino)-1-(3-fluorophenyl)propan-2-yl)carbamate | 548 | 1.79 |

TABLE 1-continued

| Reference Example | Structure | Compound name | MS(ESI m/z): (M + H) | RT(min) |
|---|---|---|---|---|
| Reference Example 134-206 | 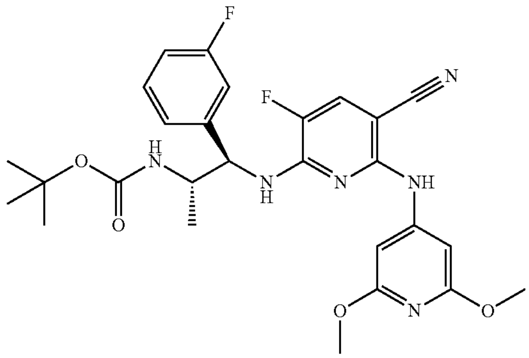 [SMILES: COc1cc(Nc2nc(N[C@H](c3cccc(F)c3)[C@H](C)NC(=O)OC(C)(C)C)c(F)cc2C#N)cc(OC)n1] | tert-butyl ((1R,2S)-1-((5-cyano-6-((2,6-dimethoxypyridin-4-yl)amino)-3-fluoropyridin-2-yl)amino)-1-(3-fluorophenyl)propan-2-yl)carbamate | 541 | 1.89 |
| Reference Example 134-207 | 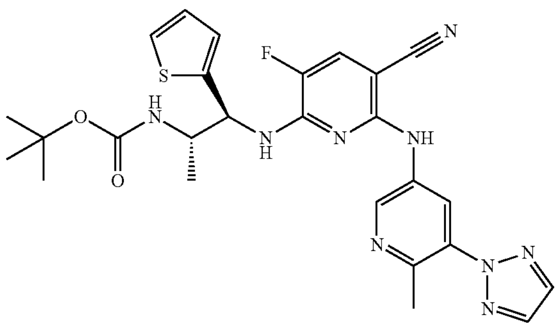 [SMILES: Cc1ncc(Nc2nc(N[C@H](c3cccs3)[C@H](C)NC(=O)OC(C)(C)C)c(F)cc2C#N)cc1-n1nccn1] | tert-butyl ((1S,2S)-1-((5-cyano-3-fluoro-6-((6-methyl-5-(2H-1,2,3-triazol-2-yl)pyridin-3-yl)amino)pyridin-2-yl)amino)-1-(thiophen-2-yl)propan-2-yl)carbamate | 550 | 1.70 |
| Reference Example 134-208 | 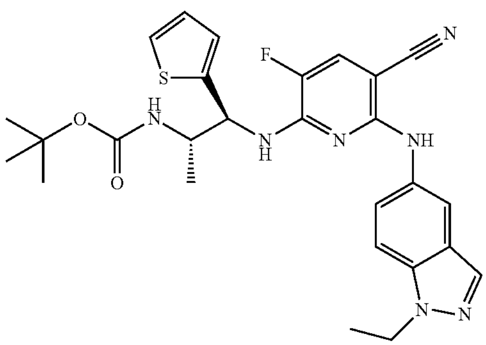 [SMILES: CCn1ncc2cc(Nc3nc(N[C@H](c4cccs4)[C@H](C)NC(=O)OC(C)(C)C)c(F)cc3C#N)ccc21] | tert-butyl ((1S,2S)-1-((5-cyano-6-((1-ethyl-1H-indazol-5-yl)amino)-3-fluoropyridin-2-yl)amino)-1-(thiophen-2-yl)propan-2-yl)carbamate | 536 | 1.77 |
| Reference Example 134-209 | 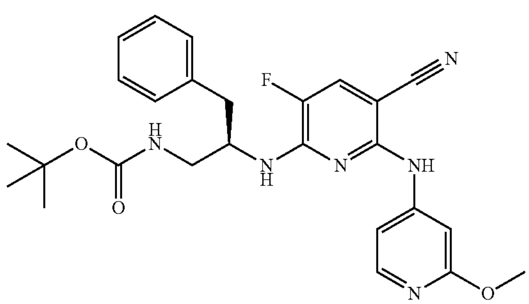 [SMILES: COc1cc(Nc2nc(N[C@@H](CNC(=O)OC(C)(C)C)Cc3ccccc3)c(F)cc2C#N)ccn1] | (R)-tert-butyl (2-((5-cyano-3-fluoro-6-((2-methoxypyridin-4-yl)amino)pyridin-2-yl)amino)-3-phenylpropyl)carbamate | ND | ND |

TABLE 1-continued

| Reference Example | Structure | Compound name | MS(ESI m/z): (M + H) | RT(min) |
|---|---|---|---|---|
| Reference Example 134-210 | 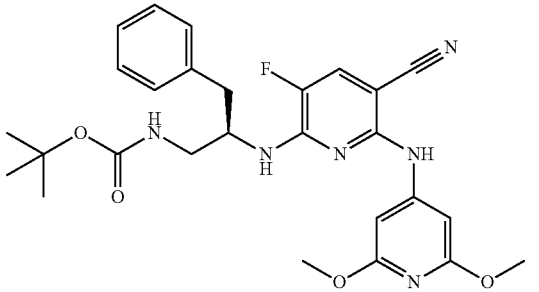 [SMILES: COc1cc(Nc2nc(N[C@@H](CNC(=O)OC(C)(C)C)Cc3ccccc3)c(F)cc2C#N)cc(OC)n1] | (R)-tert-butyl (2-((5-cyano-6-((2,6-dimethoxypyridin-4-yl)amino)-3-fluoropyridin-2-yl)amino)-3-phenylpropyl)carbamate | 541 | 1.75 |
| Reference Example 134-211 | 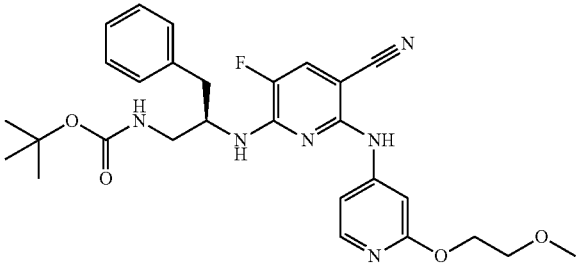 [SMILES: COCCOc1cc(Nc2nc(N[C@@H](CNC(=O)OC(C)(C)C)Cc3ccccc3)c(F)cc2C#N)ccn1] | (R)-tert-butyl (2-((5-cyano-3-fluoro-6-((2-(2-methoxyethoxy)pyridin-4-yl)amino)pyridin-2-yl)amino)-3-phenylpropyl)carbamate | 555 | 1.20 |
| Reference Example 134-212 | 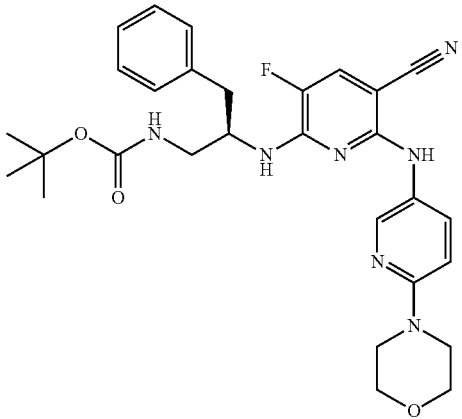 [SMILES: CC(C)(C)OC(=O)NC[C@@H](Cc1ccccc1)Nc1nc(Nc2ccc(N3CCOCC3)nc2)c(C#N)cc1F] | (R)-tert-butyl (2-((5-cyano-3-fluoro-6-((6-morpholinopyridin-3-yl)amino)pyridin-2-yl)amino)-3-phenylpropyl)carbamate | 566 | 1.20 |
| Reference Example 134-213 | 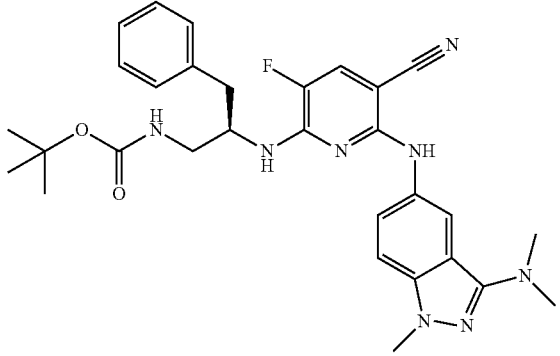 [SMILES: CN(C)c1nn(C)c2ccc(Nc3nc(N[C@@H](CNC(=O)OC(C)(C)C)Cc4ccccc4)c(F)cc3C#N)cc12] | (R)-tert-butyl (2-((5-cyano-6-((3-(dimethylamino)-1-methyl-1H-indazol-5-yl)amino)-3-fluoropyridin-2-yl)amino)-3-phenylpropyl)carbamate | 577 | 1.58 |

TABLE 1-continued

| Reference Example | Structure | Compound name | MS(ESI m/z): (M + H) | RT(min) |
|---|---|---|---|---|
| Reference Example 134-214 | 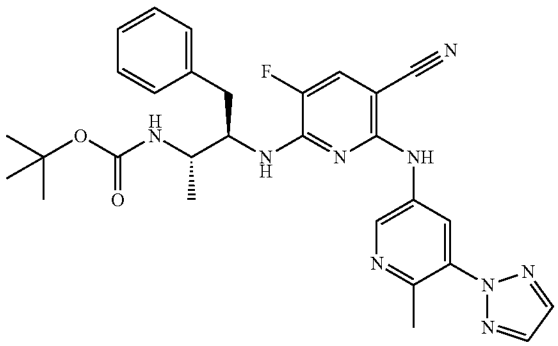 [SMILES: Cc1ncc(Nc2nc(N[C@H](Cc3ccccc3)[C@H](C)NC(=O)OC(C)(C)C)c(F)cc2C#N)cc1-n1nccn1] | tert-butyl ((2S,3R)-3-((5-cyano-3-fluoro-6-((6-methyl-5-(2H-1,2,3-triazol-2-yl)pyridin-3-yl)amino)pyridin-2-yl)amino)-4-phenylbutan-2-yl)carbamate | 558 | 1.72 |
| Reference Example 134-215 | 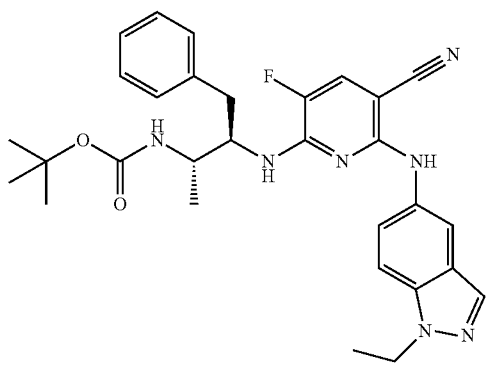 [SMILES: CCn1ncc2cc(Nc3nc(N[C@H](Cc4ccccc4)[C@H](C)NC(=O)OC(C)(C)C)c(F)cc3C#N)ccc21] | tert-butyl ((2S,3R)-3-((5-cyano-6-((1-ethyl-1H-indazol-5-yl)amino)-3-fluoropyridin-2-yl)amino)-4-phenylbutan-2-yl)carbamate | 544 | 1.77 |
| Reference Example 134-216 | 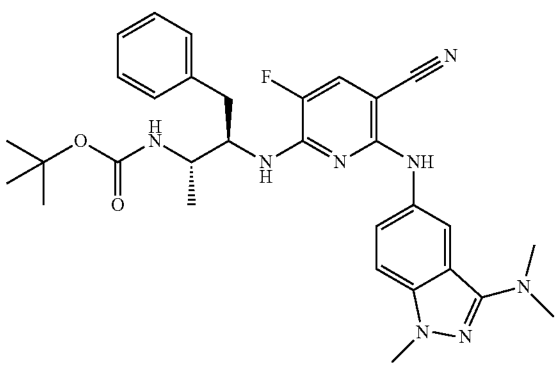 [SMILES: C[C@H](NC(=O)OC(C)(C)C)[C@@H](Cc1ccccc1)Nc1nc(Nc2ccc3c(c2)c(N(C)C)nn3C)c(C#N)cc1F] | tert-butyl ((2S,3R)-3-((5-cyano-6-((3-(dimethylamino)-1-methyl-1H-indazol-5-yl)amino)-3-fluoropyridin-2-yl)amino)-4-phenylbutan-2-yl)carbamate | 573 | 1.77 |
| Reference Example 134-217 | 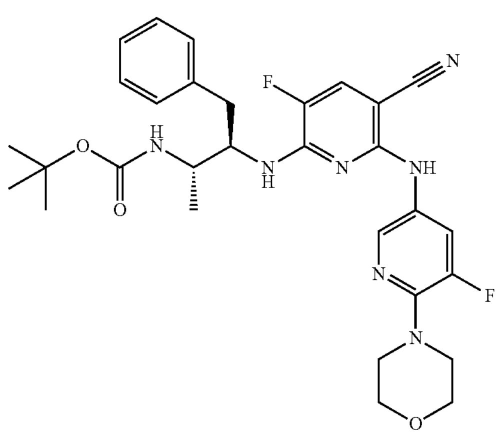 [SMILES: C[C@H](NC(=O)OC(C)(C)C)[C@@H](Cc1ccccc1)Nc1nc(Nc2cnc(N3CCOCC3)c(F)c2)c(C#N)cc1F] | tert-butyl ((2S,3R)-3-((5-cyano-3-fluoro-6-((5-fluoro-6-morpholinopyridin-3-yl)amino)pyridin-2-yl)amino)-4-phenylbutan-2-yl)carbamate | 580 | 1.75 |

TABLE 1-continued

| Reference Example | Structure | Compound name | MS(ESI m/z): (M + H) | RT(min) |
|---|---|---|---|---|
| Reference Example 134-218 | 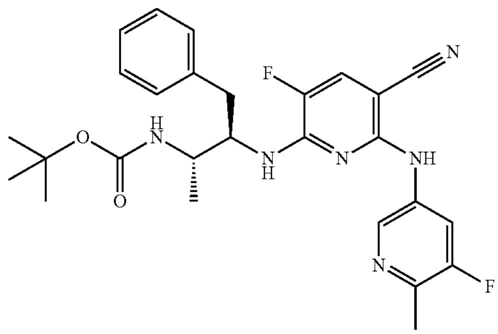 [SMILES: Cc1ncc(Nc2nc(N[C@H](Cc3ccccc3)[C@H](C)NC(=O)OC(C)(C)C)c(F)cc2C#N)cc1F] | tert-butyl ((2S,3R)-3-((5-cyano-3-fluoro-6-((5-fluoro-6-methylpyridin-3-yl)amino)pyridin-2-yl)amino)-4-phenylbutan-2-yl)carbamate | 507 | 1.70 |
| Reference Example 134-219 | 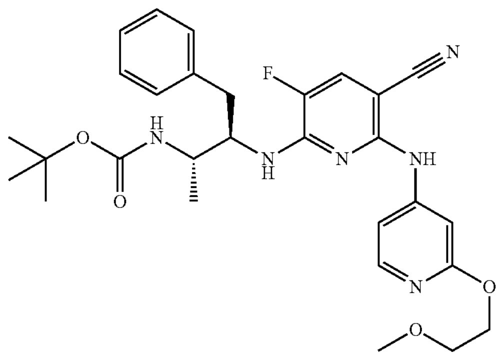 [SMILES: COCCOc1cc(Nc2nc(N[C@H](Cc3ccccc3)[C@H](C)NC(=O)OC(C)(C)C)c(F)cc2C#N)ccn1] | tert-butyl ((2S,3R)-3-((5-cyano-3-fluoro-6-((2-(2-methoxyethoxy)pyridin-4-yl)amino)pyridin-2-yl)amino)-4-phenylbutan-2-yl)carbamate | 551 | 1.43 |
| Reference Example 134-220 | 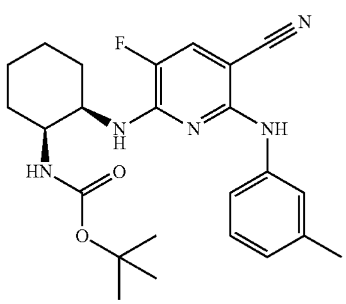 [SMILES: Cc1cccc(Nc2nc(N[C@@H]3CCCC[C@@H]3NC(=O)OC(C)(C)C)c(F)cc2C#N)c1] | tert-butyl ((1S,2R)-2-((5-cyano-3-fluoro-6-(m-tolylamino)pyridin-2-yl)amino)cyclohexyl)carbamate | 440 | 1.96 |
| Reference Example 134-221 | 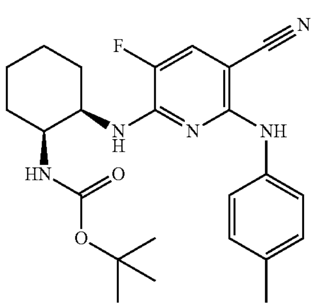 [SMILES: Cc1ccc(Nc2nc(N[C@@H]3CCCC[C@@H]3NC(=O)OC(C)(C)C)c(F)cc2C#N)cc1] | tert-butyl ((1S,2R)-2-((5-cyano-3-fluoro-6-(p-tolylamino)pyridin-2-yl)amino)cyclohexyl)carbamate | 440 | 1.96 |
| Reference Example 134-222 | 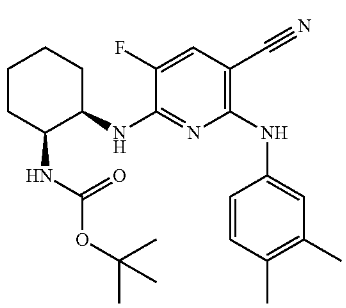 [SMILES: Cc1ccc(Nc2nc(N[C@@H]3CCCC[C@@H]3NC(=O)OC(C)(C)C)c(F)cc2C#N)cc1C] | tert-butyl ((1S,2R)-2-((5-cyano-6-((3,4-dimethylphenyl)amino)-3-fluoropyridin-2-yl)amino)cyclohexyl)carbamate | 454 | 2.03 |

TABLE 1-continued

| Reference Example | Structure | Compound name | MS(ESI m/z): (M + H) | RT(min) |
|---|---|---|---|---|
| Reference Example 134-223 | 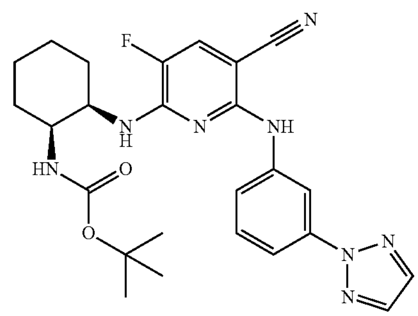 [SMILES: CC(C)(C)OC(=O)N[C@H]1CCCC[C@H]1Nc1nc(Nc2cccc(-n3nccn3)c2)c(C#N)cc1F] | tert-butyl ((1S,2R)-2-((6-((3-(2H-1,2,3-triazol-2-yl)phenyl)amino)-5-cyano-3-fluoropyridin-2-yl)amino)cyclohexyl)carbamate | 493 | 1.85 |
| Reference Example 134-224 | 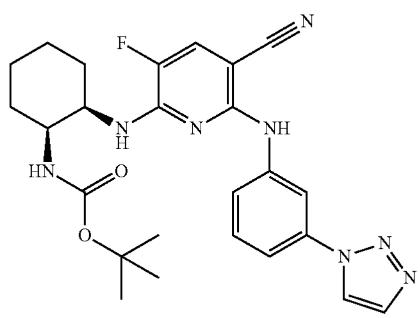 [SMILES: CC(C)(C)OC(=O)N[C@H]1CCCC[C@H]1Nc1nc(Nc2cccc(-n3ccnn3)c2)c(C#N)cc1F] | tert-butyl ((1S,2R)-2-((6-((3-(1H-1,2,3-triazol-1-yl)phenyl)amino)-5-cyano-3-fluoropyridin-2-yl)amino)cyclohexyl)carbamate | 493 | 1.61 |
| Reference Example 134-225 | 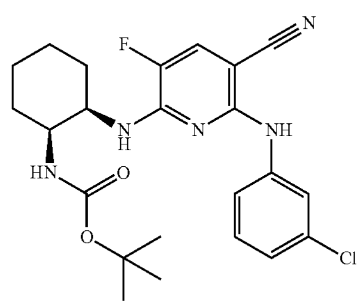 [SMILES: CC(C)(C)OC(=O)N[C@H]1CCCC[C@H]1Nc1nc(Nc2cccc(Cl)c2)c(C#N)cc1F] | tert-butyl ((1S,2R)-2-((6-((3-chlorophenyl)amino)-5-cyano-3-fluoropyridin-2-yl)amino)cyclohexyl)carbamate | 460 462 | 1.99 |
| Reference Example 134-226 | 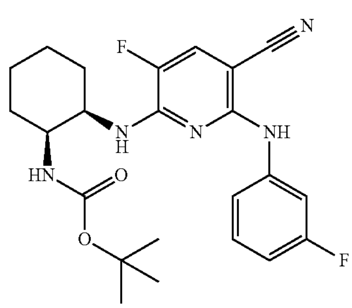 [SMILES: CC(C)(C)OC(=O)N[C@H]1CCCC[C@H]1Nc1nc(Nc2cccc(F)c2)c(C#N)cc1F] | tert-butyl ((1S,2R)-2-((5-cyano-3-fluoro-6-((3-fluorophenyl)amino)pyridin-2-yl)amino)cyclohexyl)carbamate | 444 | 1.90 |
| Reference Example 134-227 | 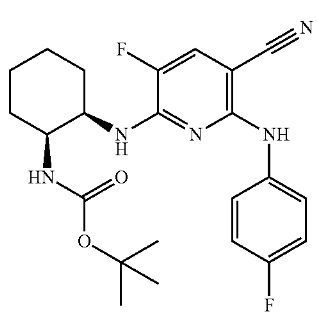 [SMILES: CC(C)(C)OC(=O)N[C@H]1CCCC[C@H]1Nc1nc(Nc2ccc(F)cc2)c(C#N)cc1F] | tert-butyl ((1S,2R)-2-((5-cyano-3-fluoro-6-((4-fluorophenyl)amino)pyridin-2-yl)amino)cyclohexyl)carbamate | 444 | 1.87 |

TABLE 1-continued

| Reference Example | Structure | Compound name | MS(ESI m/z): (M + H) | RT(min) |
|---|---|---|---|---|
| Reference Example 134-228 | 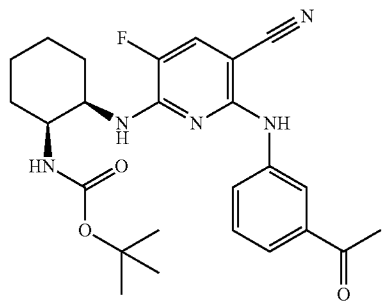 [SMILES: CC(=O)c1cccc(Nc2nc(N[C@@H]3CCCC[C@@H]3NC(=O)OC(C)(C)C)c(F)cc2C#N)c1] | tert-butyl ((1S,2R)-2-((6-((3-acetylphenyl)amino)-5-cyano-3-fluoropyridin-2-yl)amino)cyclohexyl)carbamate | 468 | 1.74 |
| Reference Example 134-229 | 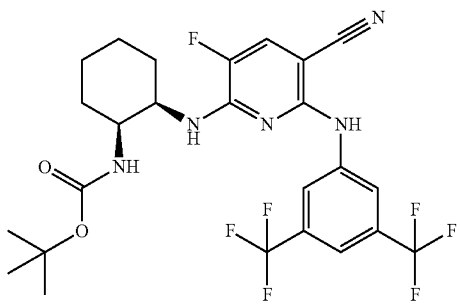 [SMILES: CC(C)(C)OC(=O)N[C@H]1CCCC[C@H]1Nc1nc(Nc2cc(C(F)(F)F)cc(C(F)(F)F)c2)c(C#N)cc1F] | tert-butyl ((1S,2R)-2-((6-((3,5-bis(trifluoromethyl)phenyl)amino)-5-cyano-3-fluoropyridin-2-yl)amino)cyclohexyl)carbamate | 561 | 2.16 |
| Reference Example 134-230 | 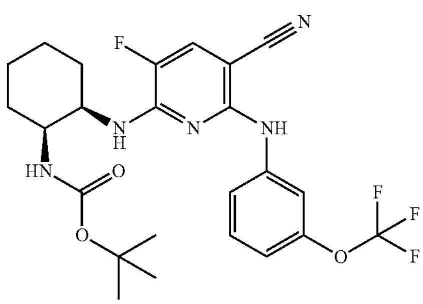 [SMILES: CC(C)(C)OC(=O)N[C@H]1CCCC[C@H]1Nc1nc(Nc2cccc(OC(F)(F)F)c2)c(C#N)cc1F] | tert-butyl ((1S,2R)-2-((5-cyano-3-fluoro-6-((3-(trifluoromethoxy)phenyl)amino)pyridin-2-yl)amino)cyclohexyl)carbamate | 510 | 2.04 |
| Reference Example 134-231 | 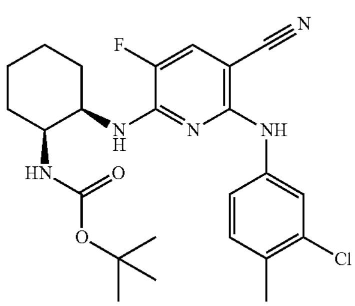 [SMILES: Cc1ccc(Nc2nc(N[C@@H]3CCCC[C@@H]3NC(=O)OC(C)(C)C)c(F)cc2C#N)cc1Cl] | tert-butyl ((1S,2R)-2-((6-((3-chloro-4-methylphenyl)amino)-5-cyano-3-fluoropyridin-2-yl)amino)cyclohexyl)carbamate | 474 | 2.09 |
| Reference Example 134-232 | 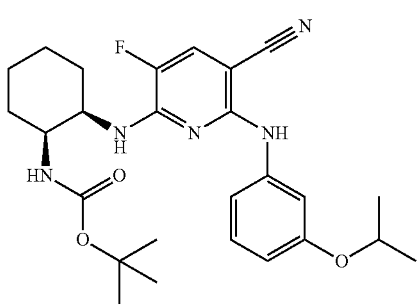 [SMILES: CC(C)Oc1cccc(Nc2nc(N[C@@H]3CCCC[C@@H]3NC(=O)OC(C)(C)C)c(F)cc2C#N)c1] | tert-butyl ((1S,2R)-2-((5-cyano-3-fluoro-6-((3-isopropoxyphenyl)amino)pyridin-2-yl)amino)cyclohexyl)carbamate | 484 | 2.01 |

TABLE 1-continued

| Reference Example | Structure | Compound name | MS(ESI m/z): (M + H) | RT(min) |
|---|---|---|---|---|
| Reference Example 134-233 | 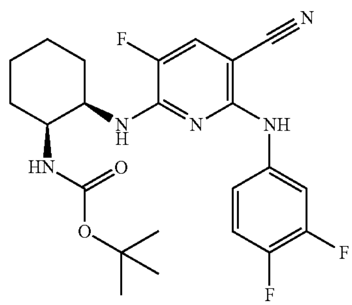 [SMILES: CC(C)(C)OC(=O)N[C@H]1CCCC[C@H]1Nc1nc(Nc2ccc(F)c(F)c2)c(C#N)cc1F] | tert-butyl ((1S,2R)-2-((5-cyano-6-((3,4-difluorophenyl)amino)-3-fluoropyridin-2-yl)amino)cyclohexyl)carbamate | 462 | 1.92 |
| Reference Example 134-234 | 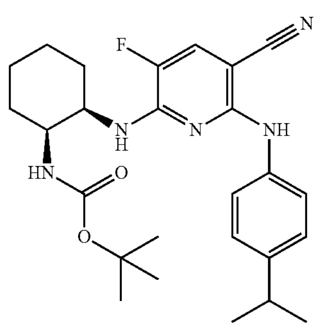 [SMILES: CC(C)c1ccc(Nc2nc(N[C@@H]3CCCC[C@@H]3NC(=O)OC(C)(C)C)c(F)cc2C#N)cc1] | tert-butyl ((1S,2R)-2-((5-cyano-3-fluoro-6-((4-isopropylphenyl)amino)pyridin-2-yl)amino)cyclohexyl)carbamate | 468 | 2.11 |
| Reference Example 134-235 | 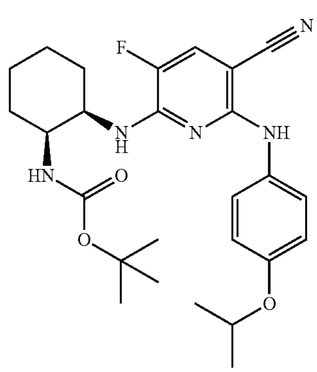 [SMILES: CC(C)Oc1ccc(Nc2nc(N[C@@H]3CCCC[C@@H]3NC(=O)OC(C)(C)C)c(F)cc2C#N)cc1] | tert-butyl ((1S,2R)-2-((5-cyano-3-fluoro-6-((4-isopropoxyphenyl)amino)pyridin-2-yl)amino)cyclohexyl)carbamate | 484 | 1.98 |
| Reference Example 134-236 | 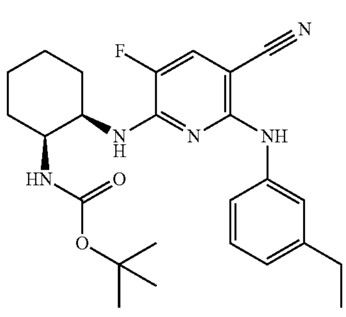 [SMILES: CCc1cccc(Nc2nc(N[C@@H]3CCCC[C@@H]3NC(=O)OC(C)(C)C)c(F)cc2C#N)c1] | tert-butyl ((1S,2R)-2-((5-cyano-6-((3-ethylphenyl)amino)-3-fluoropyridin-2-yl)amino)cyclohexyl)carbamate | 454 | 2.04 |

TABLE 1-continued

| Reference Example | Structure | Compound name | MS(ESI m/z): (M + H) | RT(min) |
|---|---|---|---|---|
| Reference Example 134-237 | 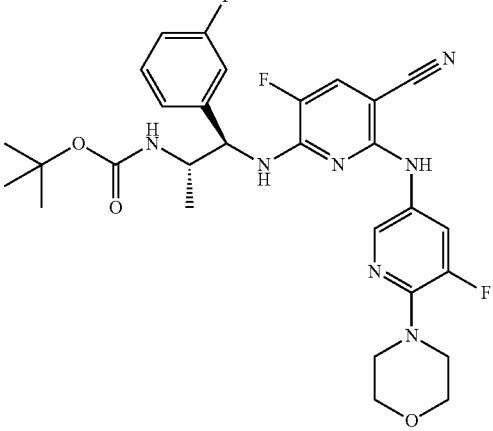 | tert-butyl ((1R,2S)-1-((5-cyano-3-fluoro-6-((5-fluoro-6-morpholinopyridin-3-yl)amino)pyridin-2-yl)amino)-1-(3-fluorophenyl)propan-2-yl)carbamate | 584 | 1.78 |
| Reference Example 134-238 | 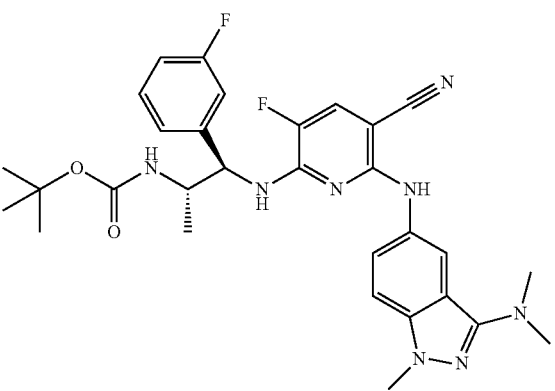 [SMILES: C[C@H](NC(=O)OC(C)(C)C)[C@H](Nc1nc(Nc2ccc3c(c2)c(N(C)C)nn3C)c(C#N)cc1F)c1cccc(F)c1] | tert-butyl ((1R,2S)-1-((5-cyano-6-((3-(dimethylamino)-1-methyl-1H-indazol-5-yl)amino)-3-fluoropyridin-2-yl)amino)-1-(3-fluorophenyl)propan-2-yl)carbamate | 577 | 1.77 |
| Reference Example 134-239 | 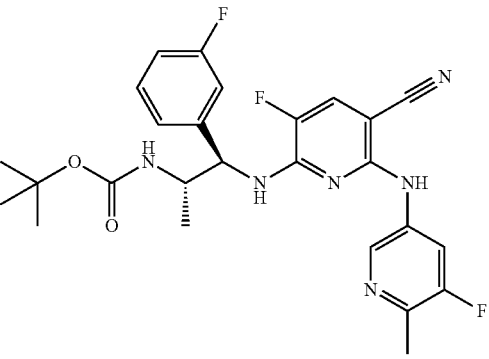 [SMILES: Cc1ncc(Nc2nc(N[C@H](c3cccc(F)c3)[C@H](C)NC(=O)OC(C)(C)C)c(F)cc2C#N)cc1F] | tert-butyl ((1R,2S)-1-((5-cyano-3-fluoro-6-((5-fluoro-6-methylpyridin-3-yl)amino)pyridin-2-yl)amino)-1-(3-fluorophenyl)propan-2-yl)carbamate | 513 | 1.73 |
| Reference Example 134-240 | 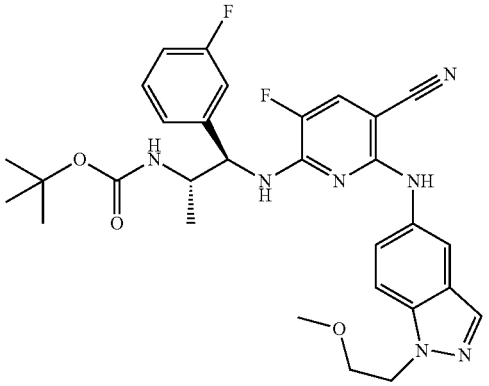 [SMILES: COCCn1ncc2cc(Nc3nc(N[C@H](c4cccc(F)c4)[C@H](C)NC(=O)OC(C)(C)C)c(F)cc3C#N)ccc21] | tert-butyl ((1R,2S)-1-((5-cyano-3-fluoro-6-((1-(2-methoxyethyl)-1H-indazol-5-yl)amino)pyridin-2-yl)amino)-1-(3-fluorophenyl)propan-2-yl)carbamate | 578 | 1.74 |

TABLE 1-continued

| Reference Example | Structure | Compound name | MS(ESI m/z): (M + H) | RT(min) |
|---|---|---|---|---|
| Reference Example 134-241 | 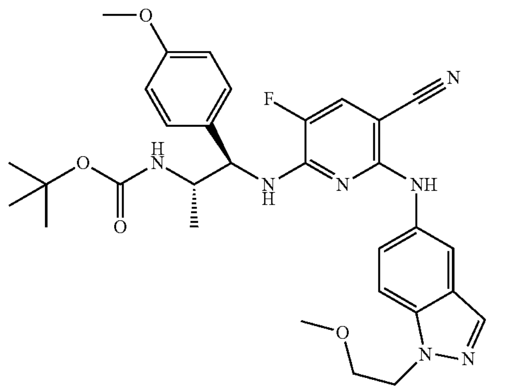 [SMILES: COCCn1ncc2cc(Nc3nc(N[C@H](c4ccc(OC)cc4)[C@H](C)NC(=O)OC(C)(C)C)c(F)cc3C#N)ccc21] | tert-butyl ((1R,2S)-1-((5-cyano-3-fluoro-6-((1-(2-methoxyethyl)-1H-indazol-5-yl)amino)pyridin-2-yl)amino)-1-(4-rnethoxyphenyl)propan-2-yl)carbamate | 590 | 1.71 |
| Reference Example 134-242 | 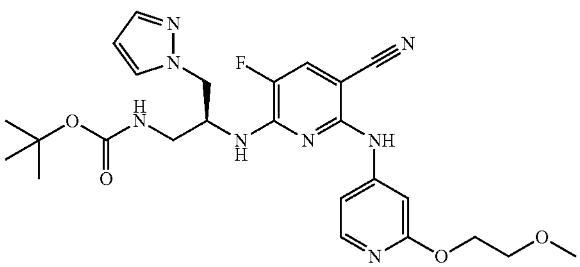 [SMILES: COCCOc1cc(Nc2nc(N[C@@H](CNC(=O)OC(C)(C)C)Cn3cccn3)c(F)cc2C#N)ccn1] | (S)-tert-butyl (2-((5-cyano-3-fluoro-6-((2-(2-methoxyethoxy)pyridin-4-yl)amino)pyridin-2-yl)amino)-3-(1H-pyrazol-1-yl)propyl)carbamate | 545 | 1.00 |
| Reference Example 134-243 | 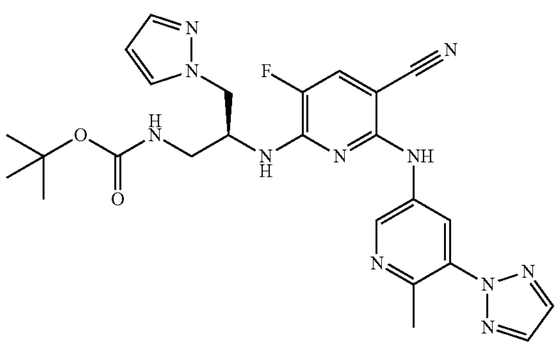 [SMILES: Cc1ncc(Nc2nc(N[C@@H](CNC(=O)OC(C)(C)C)Cn3cccn3)c(F)cc2C#N)cc1-n1nccn1] | (S)-tert-butyl (2-((5-cyano-3-fluoro-6-((6-methyl-5-(2H-1,2,3-triazol-2-yl)pyridin-3-yl)amino)pyridin-2-yl)amino)-3-(1H-pyrazol-1-yl)propyl)carbamate | 552 | 1.23 |
| Reference Example 134-244 | 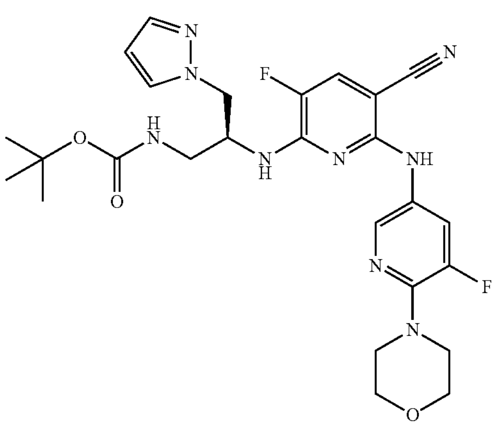 [SMILES: CC(C)(C)OC(=O)NC[C@@H](Cn1cccn1)Nc1nc(Nc2cnc(N3CCOCC3)c(F)c2)c(C#N)cc1F] | (S)-tert-butyl (2-((5-cyano-3-fluoro-6-((5-fluoro-6-morpholinopyridin-3-yl)amino)pyridin-2-yl)amino)-3-(1H-pyrazol-1-yl)propyl)carbamate | 574 | 1.32 |

TABLE 1-continued

| Reference Example | Structure | Compound name | MS(ESI m/z): (M + H) | RT(min) |
|---|---|---|---|---|
| Reference Example 134-245 | 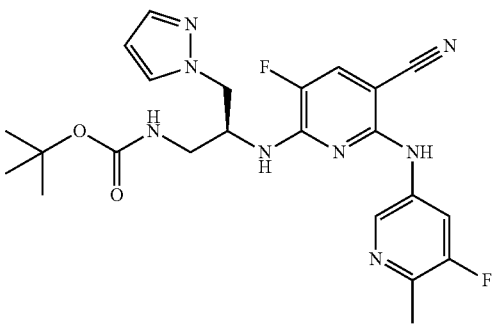 [SMILES: Cc1ncc(Nc2nc(N[C@@H](CNC(=O)OC(C)(C)C)Cn3cccn3)c(F)cc2C#N)cc1F] | (S)-tert-butyl (2-((5-cyano-3-fluoro-6-((5-fluoro-6-methylpyridin-3-yl)amino)pyridin-2-yl)amino)-3-(1H-pyrazol-1-yl)propyl)carbamate | 503 | 1.18 |
| Reference Example 134-246 | 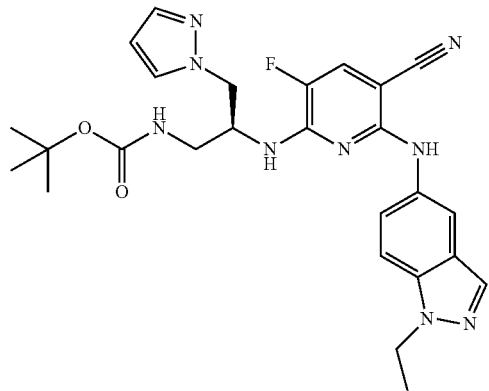 [SMILES: CCn1ncc2cc(Nc3nc(N[C@@H](CNC(=O)OC(C)(C)C)Cn4cccn4)c(F)cc3C#N)ccc21] | (S)-tert-butyl (2-((5-cyano-6-((1-ethyl-1H-indazol-5-yl)amino)-3-fluoropyridin-2-yl)amino)-3-(1H-pyrazol-1-yl)propyl)carbamate | 538 | 1.34 |
| Reference Example 134-247 | 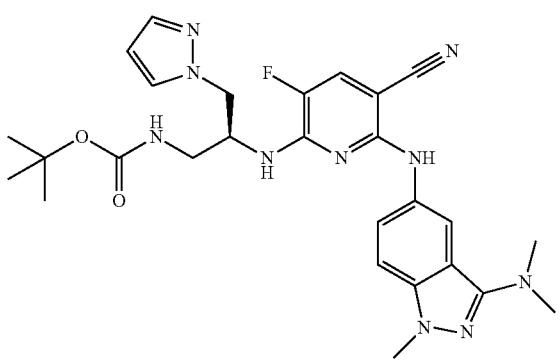 [SMILES: CN(C)c1nn(C)c2ccc(Nc3nc(N[C@@H](CNC(=O)OC(C)(C)C)Cn4cccn4)c(F)cc3C#N)cc12] | (S)-tert-butyl (2-((5-cyano-6-((3-(dimethylamino)-1-methyl-1H-indazol-5-yl)amino)-3-fluoropyridin-2-yl)amino)-3-(1H-pyrazol-1-yl)propyl)carbamate | 567 | 1.31 |
| Reference Example 134-248 | 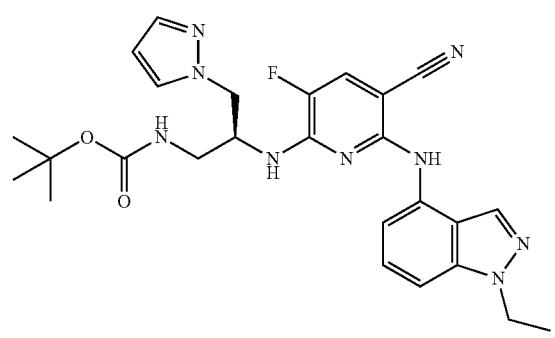 [SMILES: CCn1ncc2c(Nc3nc(N[C@@H](CNC(=O)OC(C)(C)C)Cn4cccn4)c(F)cc3C#N)cccc21] | (S)-tert-butyl (2-((5-cyano-6-((1-ethyl-1H-indazol-4-yl)amino)-3-fluoropyridin-2-yl)amino)-3-(1H-pyrazol-1-yl)propyl)carbamate | 538 | 1.42 |

TABLE 1-continued

| Reference Example | Structure | Compound name | MS(ESI m/z): (M + H) | RT(min) |
|---|---|---|---|---|
| Reference Example 134-249 | 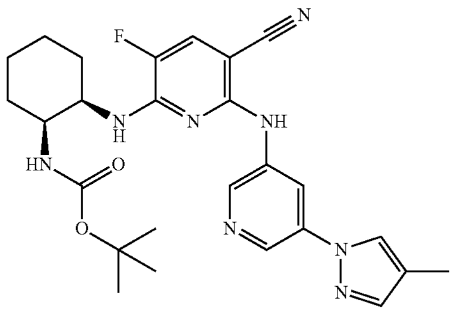 [SMILES: Cc1cnn(-c2cncc(Nc3nc(N[C@@H]4CCCC[C@@H]4NC(=O)OC(C)(C)C)c(F)cc3C#N)c2)c1] | tert-butyl ((1S,2R)-2-((5-cyano-3-fluoro-6-((5-(4-methyl-1H-pyrazol-1-yl)pyridin-3-yl)amino)pyridin-2-yl)amino)cyclohexyl)carbamate | 507 | 1.65 |
| Reference Example 134-250 | 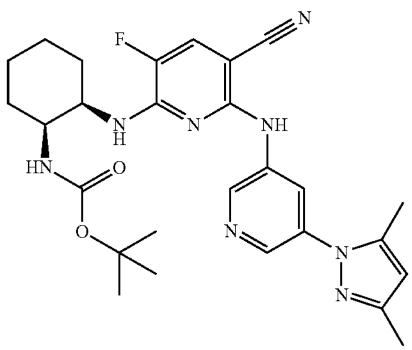 [SMILES: Cc1cc(C)n(-c2cncc(Nc3nc(N[C@@H]4CCCC[C@@H]4NC(=O)OC(C)(C)C)c(F)cc3C#N)c2)n1] | tert-butyl ((1S,2R)-2-((5-cyano-6-((5-(3,5-dimethyl-1H-pyrazol-1-yl)pyridin-3-yl)amino)-3-fluoropyridin-2-yl)amino)cyclohexyl)carbamate | 521 | 1.62 |
| Reference Example 134-251 | 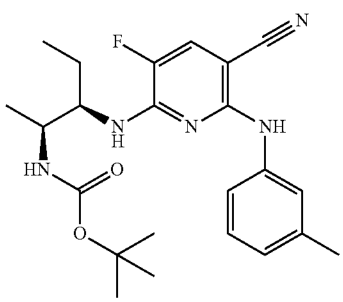 [SMILES: CC[C@@H](Nc1nc(Nc2cccc(C)c2)c(C#N)cc1F)[C@H](C)NC(=O)OC(C)(C)C] | tert-butyl ((2S,3R)-3-((5-cyano-3-fluoro-6-(m-tolylamino)pyridin-2-yl)amino)pentan-2-yl)carbamate | 428 | 1.89 |
| Reference Example 134-252 | 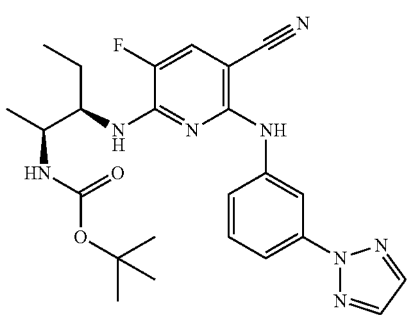 [SMILES: CC[C@@H](Nc1nc(Nc2cccc(-n3nccn3)c2)c(C#N)cc1F)[C@H](C)NC(=O)OC(C)(C)C] | tert-butyl ((2S,3R)-3-((6-((3-(2H-1,2,3-triazol-2-yl)phenyl)amino)-5-cyano-3-fluoropyridin-2-yl)amino)pentan-2-yl)carbamate | 481 | 1.84 |
| Reference Example 134-253 | 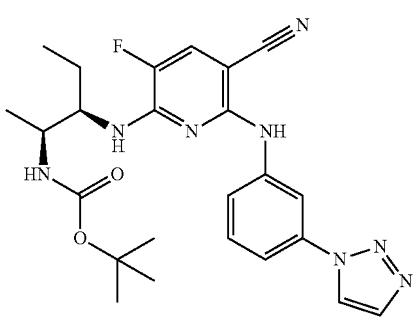 [SMILES: CC[C@@H](Nc1nc(Nc2cccc(-n3ccnn3)c2)c(C#N)cc1F)[C@H](C)NC(=O)OC(C)(C)C] | tert-butyl ((2S,3R)-3-((6-((3-(1H-1,2,3-triazol-1-yl)phenyl)amino)-5-cyano-3-fluoropyridin-2-yl)amino)pentan-2-yl)carbamate | 481 | 1.60 |

TABLE 1-continued

| Reference Example | Structure | Compound name | MS(ESI m/z): (M + H) | RT(min) |
|---|---|---|---|---|
| Reference Example 134-254 | 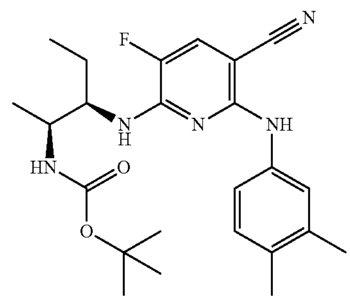 [SMILES: CC[C@@H](Nc1nc(Nc2ccc(C)c(C)c2)c(C#N)cc1F)[C@H](C)NC(=O)OC(C)(C)C] | tert-butyl ((2S,3R)-3-((5-cyano-6-((3,4-dimethylphenyl)amino)-3-fluoropyridin-2-yl)amino)pentan-2-yl)carbamate | 442 | 1.95 |
| Reference Example 134-255 | 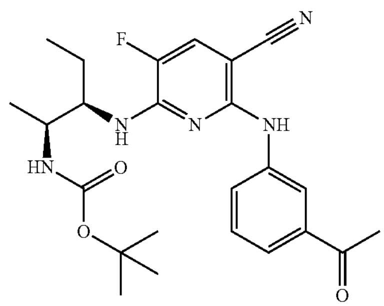 [SMILES: CC[C@@H](Nc1nc(Nc2cccc(C(C)=O)c2)c(C#N)cc1F)[C@H](C)NC(=O)OC(C)(C)C] | tert-butyl ((2S,3R)-3-((6-((3-acetylphenyl)amino)-5-cyano-3-fluoropyridin-2-yl)amino)pentan-2-yl)carbamate | 456 | 1.72 |
| Reference Example 134-256 | 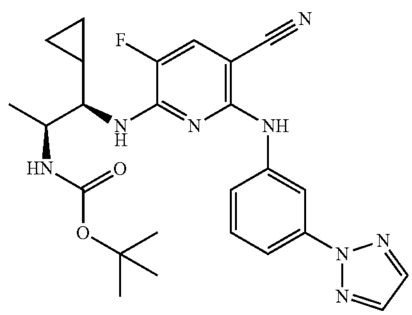 [SMILES: C[C@H](NC(=O)OC(C)(C)C)[C@H](Nc1nc(Nc2cccc(-n3nccn3)c2)c(C#N)cc1F)C1CC1] | tert-butyl ((1R,2S)-1-((6-((3-(2H-1,2,3-triazol-2-yl)phenyl)amino)-5-cyano-3-fluoropyridin-2-yl)amino)-1-cyclopropylpropan-2-yl)carbamate | 493 | 1.84 |
| Reference Example 134-257 | 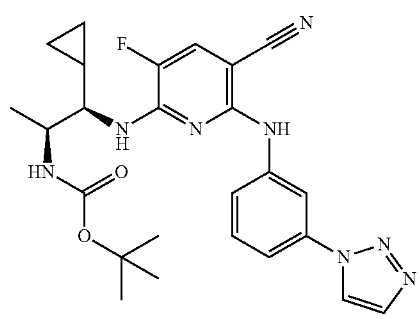 [SMILES: C[C@H](NC(=O)OC(C)(C)C)[C@H](Nc1nc(Nc2cccc(-n3ccnn3)c2)c(C#N)cc1F)C1CC1] | tert-butyl ((1R,2S)-1-((6-((3-(1H-1,2,3-triazol-1-yl)phenyl)amino)-5-cyano-3-fluoropyridin-2-yl)amino)-1-cyclopropylpropan-2-yl)carbamate | 493 | 1.61 |
| Reference Example 134-258 | 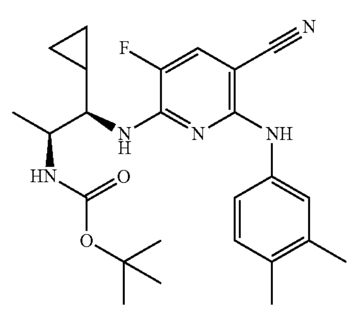 [SMILES: Cc1ccc(Nc2nc(N[C@H](C3CC3)[C@H](C)NC(=O)OC(C)(C)C)c(F)cc2C#N)cc1C] | tert-butyl ((1R,2S)-1-((5-cyano-6-((3,4-dimethylphenyl)amino)-3-fluoropyridin-2-yl)amino)-1-cyclopropylpropan-2-yl)carbamate | 454 | 1.96 |

TABLE 1-continued

| Reference Example | Structure | Compound name | MS(ESI m/z): (M + H) | RT(min) |
|---|---|---|---|---|
| Reference Example 134-259 | 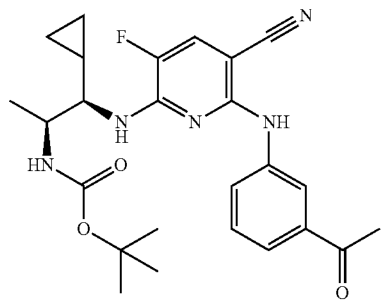 [SMILES: CC(=O)c1cccc(Nc2nc(N[C@H](C3CC3)[C@H](C)NC(=O)OC(C)(C)C)c(F)cc2C#N)c1] | tert-butyl ((1R,2S)-1-((6-((3-acetylphenyl)amino)-5-cyano-3-fluoropyridin-2-yl)amino)-1-cyclopropylpropan-2-yl)carbamate | 468 | 1.73 |
| Reference Example 134-260 | 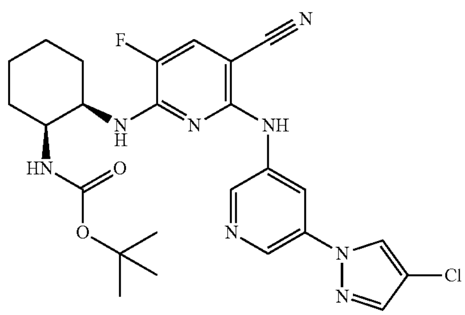 [SMILES: CC(C)(C)OC(=O)N[C@H]1CCCC[C@H]1Nc1nc(Nc2cncc(-n3cc(Cl)cn3)c2)c(C#N)cc1F] | tert-butyl ((1S,2R)-2-((6-((5-(4-chloro-1H-pyrazol-1-yl)pyridin-3-yl)amino)-5-cyano-3-fluoropyridin-2-yl)amino)cyclohexyl)carbamate | 527 529 | 1.76 |
| Reference Example 134-261 | 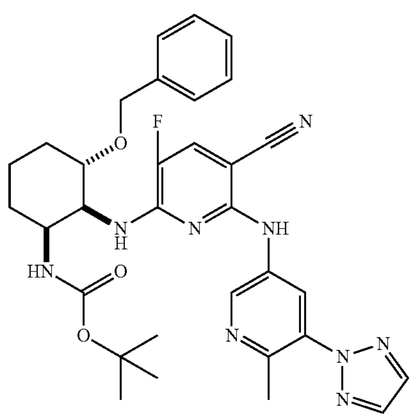 [SMILES: Cc1ncc(Nc2nc(N[C@H]3[C@@H](NC(=O)OC(C)(C)C)CCC[C@@H]3OCc3ccccc3)c(F)cc2C#N)cc1-n1nccn1] | Mixture of tert-butyl (3-(benzyloxy)-2-((5-cyano-3-fluoro-6-((6-methyl-5-(2H-1,2,3-triazol-2-yl)pyridin-3-yl)amino)pyridin-2-yl)amino)cyclohexyl)carbamate (1S,2S,3S),(1R,2R,3R) | 614 | 1.78 |
| Reference Example 134-262 | 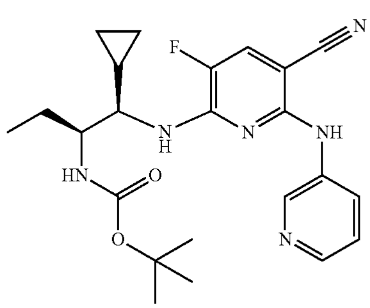 [SMILES: CC[C@H](NC(=O)OC(C)(C)C)[C@H](Nc1nc(Nc2cccnc2)c(C#N)cc1F)C1CC1] | tert-butyl ((1R,2S)-1-((5-cyano-3-fluoro-6-(pyridin-3-ylamino)pyridin-2-yl)amino)-1-cyclopropylbutan-2-yl)carbamate | 441 | 1.23 |

TABLE 1-continued

| Reference Example | Structure | Compound name | MS(ESI m/z): (M + H) | RT(min) |
|---|---|---|---|---|
| Reference Example 134-263 | 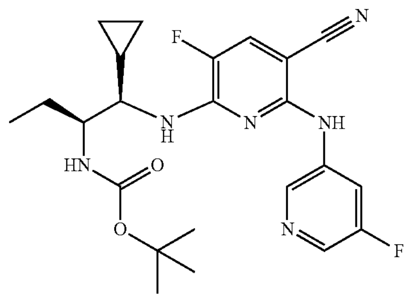 [SMILES: CC[C@H](NC(=O)OC(C)(C)C)[C@H](Nc1nc(Nc2cncc(F)c2)c(C#N)cc1F)C1CC1] | tert-butyl ((1R,2S)-1-((5-cyano-3-fluoro-6-((5-fluoropyridin-3-yl)amino)pyridin-2-yl)amino)-1-cyclopropylbutan-2-yl)carbamate | 459 | 1.64 |
| Reference Example 134-264 | 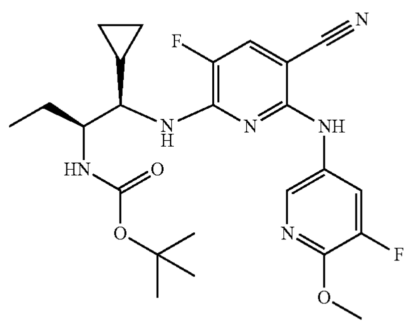 [SMILES: CC[C@H](NC(=O)OC(C)(C)C)[C@H](Nc1nc(Nc2cnc(OC)c(F)c2)c(C#N)cc1F)C1CC1] | tert-butyl ((1R,2S)-1-((5-cyano-3-fluoro-6-((5-fluoro-6-methoxypyridin-3-yl)amino)pyridin-2-yl)amino)-1-cyclopropylbutan-2-yl)carbamate | 489 | 1.79 |
| Reference Example 134-265 | 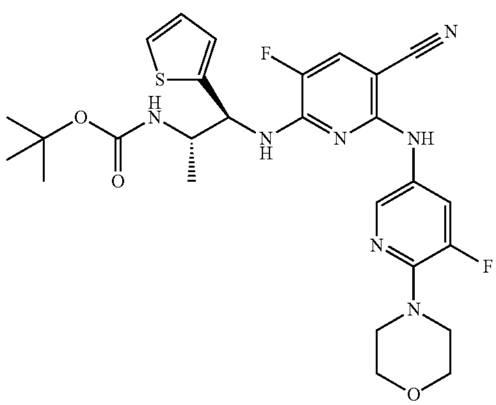 [SMILES: C[C@H](NC(=O)OC(C)(C)C)[C@H](Nc1nc(Nc2cnc(N3CCOCC3)c(F)c2)c(C#N)cc1F)c1cccs1] | tert-butyl ((1S,2S)-1-((5-cyano-3-fluoro-6-((5-fluoro-6-morpholinopyridin-3-yl)amino)pyridin-2-yl)amino)-1-(thiophen-2-yl)propan-2-yl)carbamate | 572 | 1.78 |
| Reference Example 134-266 | 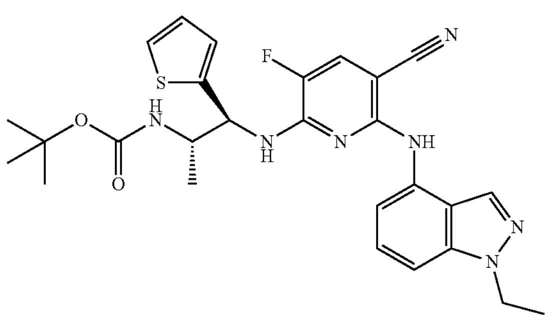 [SMILES: CCn1ncc2c(Nc3nc(N[C@H](c4cccs4)[C@H](C)NC(=O)OC(C)(C)C)c(F)cc3C#N)cccc21] | tert-butyl ((1S,2S)-1-((5-cyano-6-((1-ethyl-1H-indazol-4-yl)amino)-3-fluoropyridin-2-yl)amino)-1-(thiophen-2-yl)propan-2-yl)carbamate | 536 | 1.82 |

TABLE 1-continued

| Reference Example | Structure | Compound name | MS(ESI m/z): (M + H) | RT(min) |
|---|---|---|---|---|
| Reference Example 134-267 | 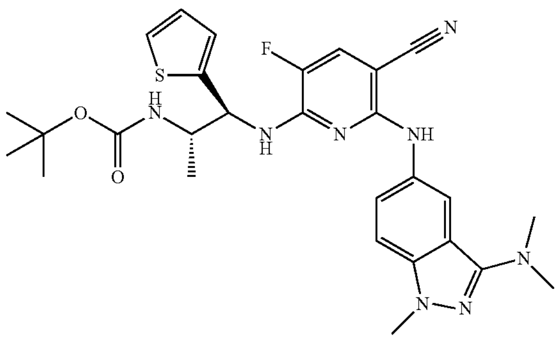 [SMILES: C[C@H](NC(=O)OC(C)(C)C)[C@H](Nc1nc(Nc2ccc3c(c2)c(N(C)C)nn3C)c(C#N)cc1F)c1cccs1] | tert-butyl ((1S,2S)-1-((5-cyano-6-((3-(dimethylamino)-1-methyl-1H-indazol-5-yl)amino)-3-fluoropyridin-2-yl)amino)-1-(thiophen-2-yl)propan-2-yl)carbamate | 565 | 1.77 |
| Reference Example 134-268 | 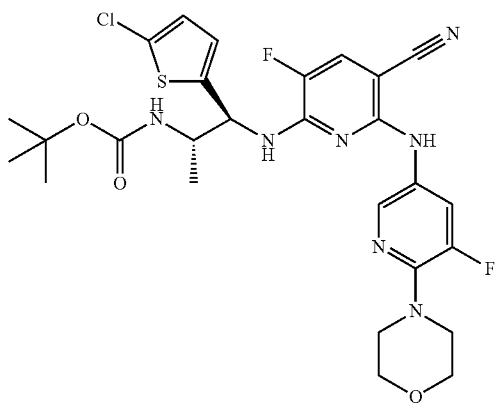 [SMILES: C[C@H](NC(=O)OC(C)(C)C)[C@H](Nc1nc(Nc2cnc(N3CCOCC3)c(F)c2)c(C#N)cc1F)c1ccc(Cl)s1] | tert-butyl ((1S,2S)-1-(5-chlorothiophen-2-yl)-1-((5-cyano-3-fluoro-6-((5-fluoro-6-morpholinopyridin-3-yl)amino)pyridin-2-yl)amino)propan-2-yl)carbamate | 606 | 1.90 |
| Reference Example 134-269 | 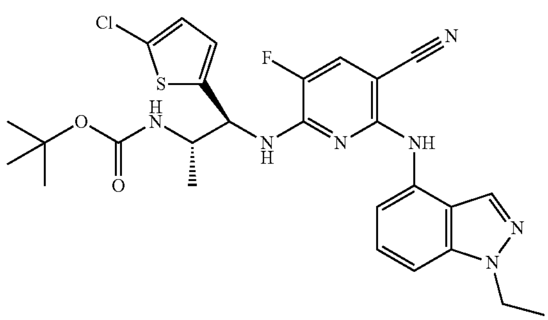 [SMILES: CCn1ncc2c(Nc3nc(N[C@H](c4ccc(Cl)s4)[C@H](C)NC(=O)OC(C)(C)C)c(F)cc3C#N)cccc21] | tert-butyl ((1S,2S)-1-(5-chlorothiophen-2-yl)-1-((5-cyano-6-((1-ethyl-1H-indazol-4-yl)amino)-3-fluoropyridin-2-yl)amino)propan-2-yl)carbamate | 570 | 1.94 |
| Reference Example 134-270 | 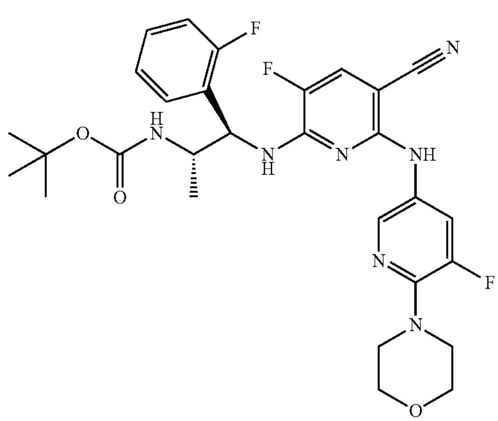 [SMILES: C[C@H](NC(=O)OC(C)(C)C)[C@H](Nc1nc(Nc2cnc(N3CCOCC3)c(F)c2)c(C#N)cc1F)c1ccccc1F] | tert-butyl ((1R,2S)-1-((5-cyano-3-fluoro-6-((5-fluoro-6-morpholinopyridin-3-yl)amino)pyridin-2-yl)amino)-1-(2-fluorophenyl)propan-2-yl)carbamate | 584 | 1.80 |

TABLE 1-continued

| Reference Example | Structure | Compound name | MS(ESI m/z): (M + H) | RT(min) |
|---|---|---|---|---|
| Reference Example 134-271 | 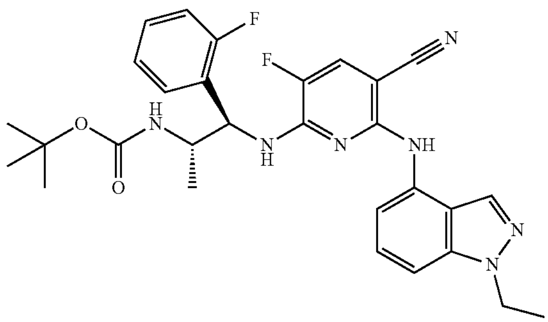 [SMILES: CCn1ncc2c(Nc3nc(N[C@H](c4ccccc4F)[C@H](C)NC(=O)OC(C)(C)C)c(F)cc3C#N)cccc21] | tert-butyl ((1R,2S)-1-((5-cyano-6-((1-ethyl-1H-indazol-4-yl)amino)-3-fluoropyridin-2-yl)amino)-1-(2-fluorophenyl)propan-2-yl)carbamate | 548 | 1.83 |
| Reference Example 134-272 | 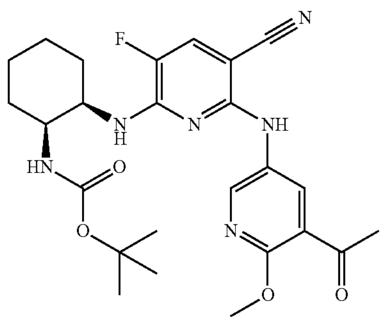 [SMILES: COc1ncc(Nc2nc(N[C@@H]3CCCC[C@@H]3NC(=O)OC(C)(C)C)c(F)cc2C#N)cc1C(C)=O] | tert-butyl ((1S,2R)-2-((6-((5-acetyl-6-methoxypyridin-3-yl)amino)-5-cyano-3-fluoropyridin-2-yl)amino)cyclohexyl)carbamate | 499 | 1.76 |
| Reference Example 134-273 | 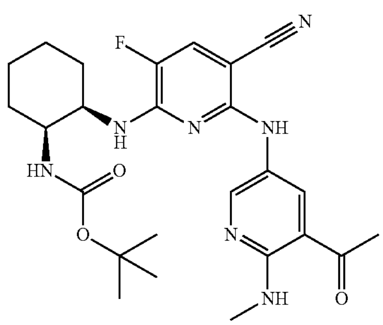 [SMILES: CNc1ncc(Nc2nc(N[C@@H]3CCCC[C@@H]3NC(=O)OC(C)(C)C)c(F)cc2C#N)cc1C(C)=O] | tert-butyl ((1S,2R)-2-((6-((5-acetyl-6-(methylamino)pyridin-3-yl)amino)-5-cyano-3-fluoropyridin-2-yl)amino)cyclohexyl)carbamate | 498 | 1.50 |
| Reference Example 134-274 | 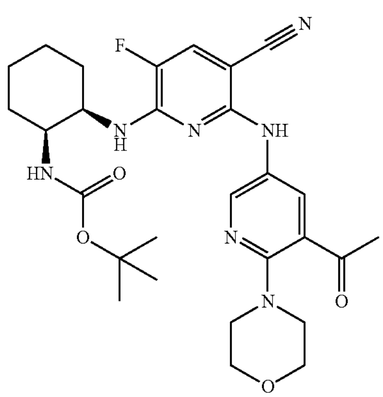 [SMILES: CC(=O)c1cc(Nc2nc(N[C@@H]3CCCC[C@@H]3NC(=O)OC(C)(C)C)c(F)cc2C#N)cnc1N1CCOCC1] | tert-butyl ((1S,2R)-2-((6-((5-acetyl-6-morpholinopyridin-3-yl)amino)-5-cyano-3-fluoropyridin-2-yl)amino)cyclohexyl)carbamate | 554 | 1.63 |

TABLE 1-continued

| Reference Example | Structure | Compound name | MS(ESI m/z): (M + H) | RT(min) |
|---|---|---|---|---|
| Reference Example 134-275 | 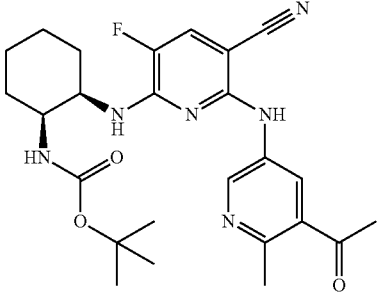 [SMILES: CC(=O)c1cc(Nc2nc(N[C@@H]3CCCC[C@@H]3NC(=O)OC(C)(C)C)c(F)cc2C#N)cnc1C] | tert-butyl ((1S,2R)-2-((6-((5-acetyl-6-methylpyridin-3-yl)amino)-5-cyano-3-fluoropyridin-2-yl)amino)cyclohexyl)carbamate | 483 | 1.43 |
| Reference Example 134-276 | 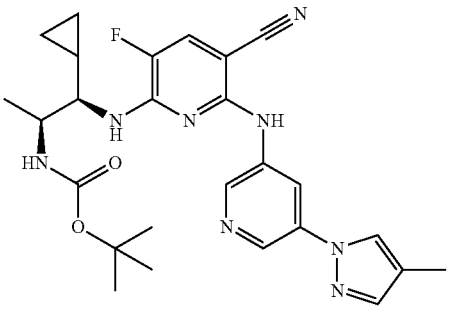 [SMILES: Cc1cnn(-c2cncc(Nc3nc(N[C@H](C4CC4)[C@H](C)NC(=O)OC(C)(C)C)c(F)cc3C#N)c2)c1] | tert-butyl ((1R,2S)-1-((5-cyano-3-fluoro-6-((5-(4-methyl-1H-pyrazol-1-yl)pyridin-3-yl)amino)pyridin-2-yl)amino)-1-cyclopropylpropan-2-yl)carbamate | 507 | 1.64 |
| Reference Example 134-277 | 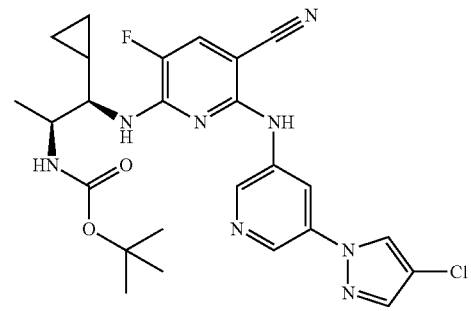 [SMILES: C[C@H](NC(=O)OC(C)(C)C)[C@H](Nc1nc(Nc2cncc(-n3cc(Cl)cn3)c2)c(C#N)cc1F)C1CC1] | tert-butyl ((1R,2S)-1-((6-((5-(4-chloro-1H-pyrazol-1-yl)pyridin-3-yl)amino)-5-cyano-3-fluoropyridin-2-yl)amino)-1-cyclopropylpropan-2-yl)carbamate | 527 529 | 1.74 |
| Reference Example 134-278 | 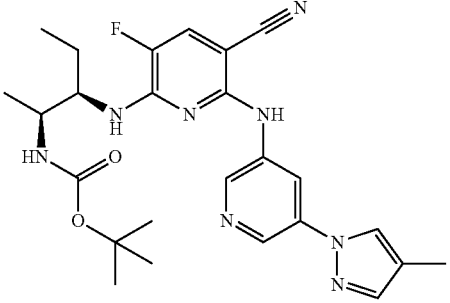 [SMILES: CC[C@@H](Nc1nc(Nc2cncc(-n3cc(C)cn3)c2)c(C#N)cc1F)[C@H](C)NC(=O)OC(C)(C)C] | tert-butyl ((2S,3R)-3-((5-cyano-3-fluoro-6-((5-(4-methyl-1H-pyrazol-1-yl)pyridin-3-yl)amino)pyridin-2-yl)amino)pentan-2-yl)carbamate | 495 | 1.64 |
| Reference Example 134-279 | 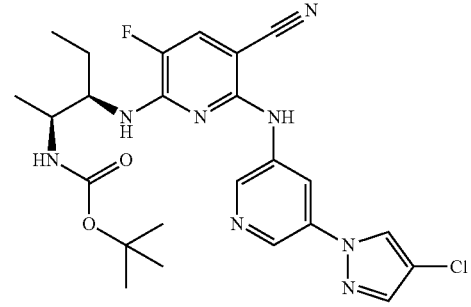 [SMILES: CC[C@@H](Nc1nc(Nc2cncc(-n3cc(Cl)cn3)c2)c(C#N)cc1F)[C@H](C)NC(=O)OC(C)(C)C] | tert-butyl ((2S,3R)-3-((6-((5-(4-chloro-1H-pyrazol-1-yl)pyridin-3-yl)amino)-5-cyano-3-fluoropyridin-2-yl)amino)pentan-2-yl)carbamate | 515 517 | 1.74 |

TABLE 1-continued

| Reference Example | Structure | Compound name | MS(ESI m/z): (M + H) | RT(min) |
|---|---|---|---|---|
| Reference Example 134-280 | 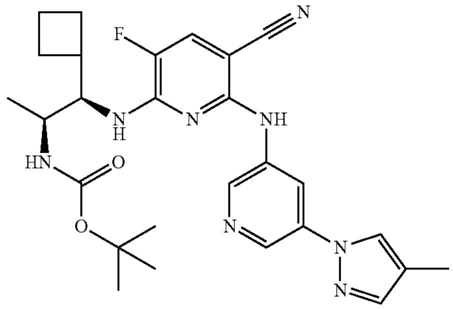 [SMILES: Cc1cnn(-c2cncc(Nc3nc(N[C@H](C4CCC4)[C@H](C)NC(=O)OC(C)(C)C)c(F)cc3C#N)c2)c1] | tert-butyl ((1R,2S)-1-((5-cyano-3-fluoro-6-((5-(4-methyl-1H-pyrazol-1-yl)pyridin-3-yl)amino)pyridin-2-yl)amino)-1-cyclobutylpropan-2-yl)carbamate | 521 | 1.75 |
| Reference Example 134-281 | 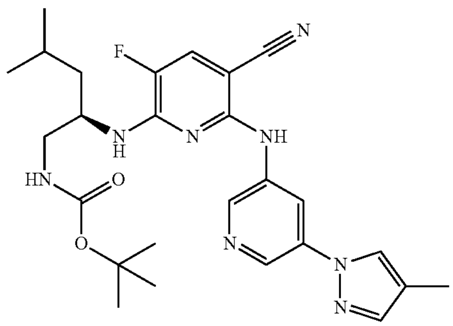 [SMILES: Cc1cnn(-c2cncc(Nc3nc(N[C@@H](CNC(=O)OC(C)(C)C)CC(C)C)c(F)cc3C#N)c2)c1] | (R)-tert-butyl (2-((5-cyano-3-fluoro-6-((5-(4-methyl-1H-pyrazol-1-yl)pyridin-3-yl)amino)pyridin-2-yl)amino)-4-methylpentyl)carbamate | 509 | 1.75 |
| Reference Example 134-282 | 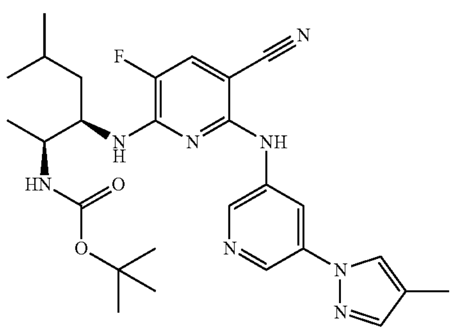 [SMILES: Cc1cnn(-c2cncc(Nc3nc(N[C@H](CC(C)C)[C@H](C)NC(=O)OC(C)(C)C)c(F)cc3C#N)c2)c1] | tert-butyl ((2S,3R)-3-((5-cyano-3-fluoro-6-((5-(4-methyl-1H-pyrazol-1-yl)pyridin-3-yl)amino)pyridin-2-yl)amino)-5-methylhexan-2-yl)carbamate | 523 | 1.80 |
| Reference Example 134-283 | 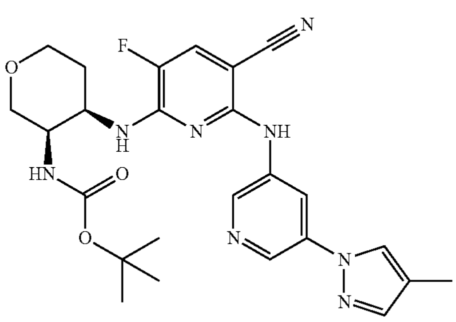 [SMILES: Cc1cnn(-c2cncc(Nc3nc(N[C@@H]4CCOC[C@@H]4NC(=O)OC(C)(C)C)c(F)cc3C#N)c2)c1] | tert-butyl ((3R,4R)-4-((5-cyano-3-fluoro-6-((5-(4-methyl-1H-pyrazol-1-yl)pyridin-3-yl)amino)pyridin-2-yl)amino)tetrahydro-2H-pyran-3-yl)carbamate | 509 | 1.41 |

TABLE 1-continued

| Reference Example | Structure | Compound name | MS(ESI m/z): (M + H) | RT(min) |
|---|---|---|---|---|
| Reference Example 134-284 | 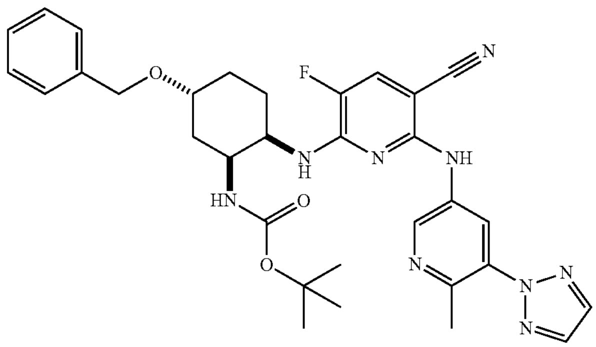 [SMILES: Cc1ncc(Nc2nc(N[C@@H]3CC[C@@H](OCc4ccccc4)C[C@@H]3NC(=O)OC(C)(C)C)c(F)cc2C#N)cc1-n1nccn1] | Mixture of tert-butyl (5-(benzyloxy)-2-((5-cyano-3-fluoro-6-((6-methyl-5-(2H-1,2,3-triazol-2-yl)pyridin-3-yl)amino)pyridin-2-yl)amino)cyclohexyl)carbamate (1S,2R,5R),(1R,2S,5S) | 614 | 1.80 |
| Reference Example 134-285 | 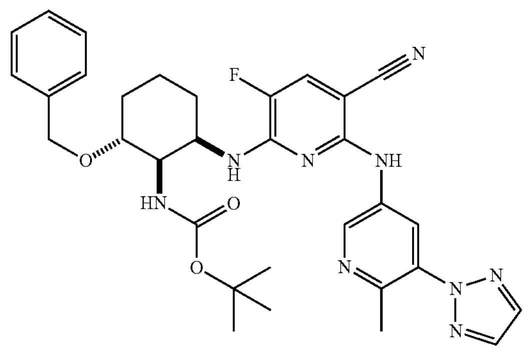 [SMILES: Cc1ncc(Nc2nc(N[C@@H]3CCC[C@@H](OCc4ccccc4)[C@@H]3NC(=O)OC(C)(C)C)c(F)cc2C#N)cc1-n1nccn1] | Mixture of tert-butyl (2-(benzyloxy)-6-((5-cyano-3-fluoro-6-((6-methyl-5-(2H-1,2,3-triazol-2-yl)pyridin-3-yl)amino)pyridin-2-yl)amino)cyclohexyl)carbamate (1R,2R,6R),(1S,2S,6S) | 614 | 1.80 |
| Reference Example 134-286 | 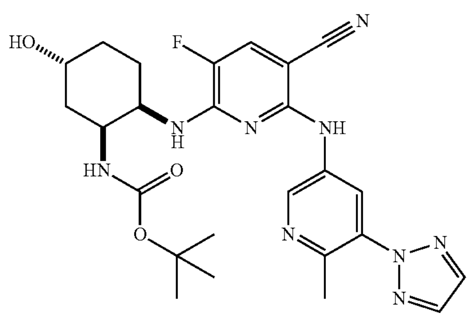 [SMILES: Cc1ncc(Nc2nc(N[C@@H]3CC[C@@H](O)C[C@@H]3NC(=O)OC(C)(C)C)c(F)cc2C#N)cc1-n1nccn1] | Mixture of tert-butyl (2-((5-cyano-3-fluoro-6-((6-methyl-5-(2H-1,2,3-triazol-2-yl)pyridin-2-yl)amino)pyridin-2-yl)amino)-5-hydroxycyclohexyl)carbamate (1S,2R,5R),(1R,2S,5S) | 614 | 1.80 |
| Reference Example 134-287 | 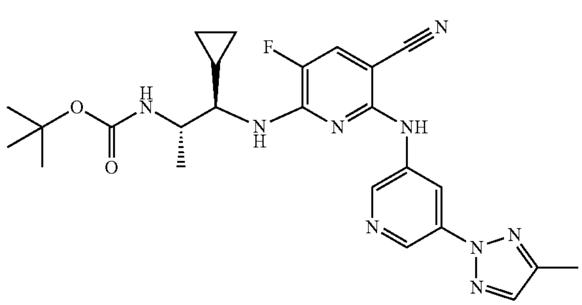 [SMILES: Cc1cnn(-c2cncc(Nc3nc(N[C@H](C4CC4)[C@H](C)NC(=O)OC(C)(C)C)c(F)cc3C#N)c2)n1] | tert-butyl ((1R,2S)-1-((5-cyano-3-fluoro-6-((5-(4-methyl-2H-1,2,3-triazol-2-yl)pyridin-3-yl)amino)pyridin-2-yl)amino)-1-cyclopropylpropan-2-yl)carbamate | 526 | 1.54 |

TABLE 1-continued

| Reference Example | Structure | Compound name | MS(ESI m/z): (M + H) | RT(min) |
|---|---|---|---|---|
| Reference Example 134-288 | 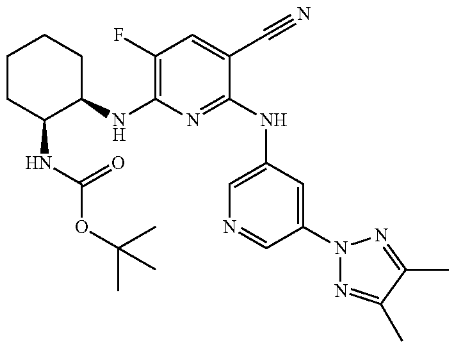 [SMILES: Cc1nn(-c2cncc(Nc3nc(N[C@@H]4CCCC[C@@H]4NC(=O)OC(C)(C)C)c(F)cc3C#N)c2)nc1C] | tert-butyl ((1S,2R)-2-((5-cyano-6-((5-(4,5-dimethyl-2H-1,2,3-triazol-2-yl)pyridin-3-yl)amino)-3-fluoropyridin-2-yl)amino)cyclohexyl)carbamate | 540 | 1.59 |
| Reference Example 134-289 | 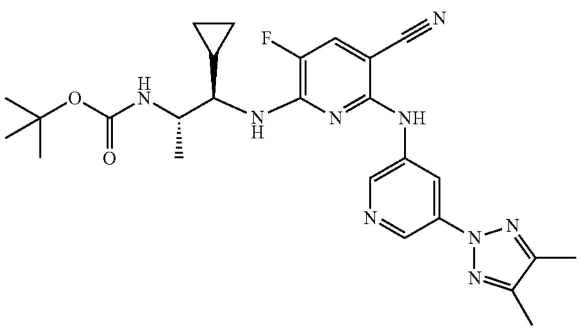 [SMILES: Cc1nn(-c2cncc(Nc3nc(N[C@H](C4CC4)[C@H](C)NC(=O)OC(C)(C)C)c(F)cc3C#N)c2)nc1C] | tert-butyl ((1R,2S)-1-((5-cyano-6-((5-(4,5-dimethyl-2H-1,2,3-triazol-2-yl)pyridin-3-yl)amino)-3-fluoropyridin-2-yl)amino)-1-cyclopropylpropan-2-yl)carbamate | 540 | 1.56 |
| Reference Example 134-290 | 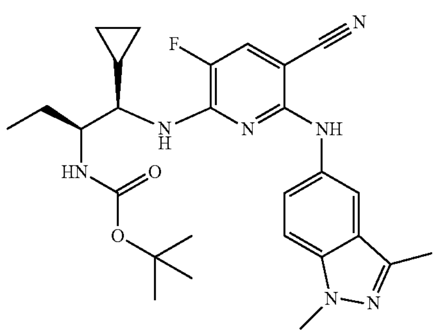 [SMILES: CC[C@H](NC(=O)OC(C)(C)C)[C@H](Nc1nc(Nc2ccc3c(c2)c(C)nn3C)c(C#N)cc1F)C1CC1] | tert-butyl ((1R,2S)-1-((5-cyano-6-((1,3-dimethyl-1H-indazol-5-yl)amino)-3-fluoropyridin-2-yl)amino)-1-cyclopropylbutan-2-yl)carbamate | 508 | 1.71 |
| Reference Example 134-291 | 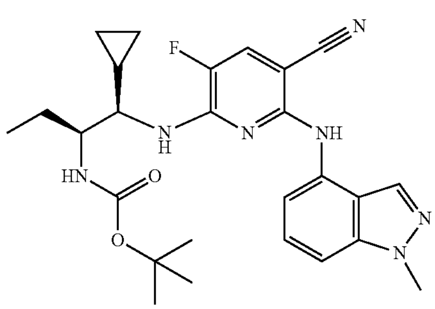 [SMILES: CC[C@H](NC(=O)OC(C)(C)C)[C@H](Nc1nc(Nc2cccc3c2cnn3C)c(C#N)cc1F)C1CC1] | tert-butyl ((1R,2S)-1-((5-cyano-3-fluoro-6-(((1-methyl-1H-indazol-4-yl)amino)pyridin-2-yl)amino)-1-cyclopropylbutan-2-yl)carbamate | 494 | 1.70 |

TABLE 1-continued

| Reference Example | Structure | Compound name | MS(ESI m/z): (M + H) | RT(min) |
|---|---|---|---|---|
| Reference Example 134-292 | 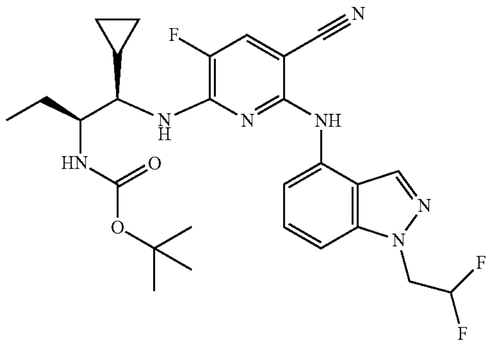 [SMILES: CC[C@H](NC(=O)OC(C)(C)C)[C@H](Nc1nc(Nc2cccc3c2cnn3CC(F)F)c(C#N)cc1F)C1CC1] | tert-butyl ((1R,2S)-1-((5-cyano-6-((1-(2,2-difluoroethyl)-1H-indazol-4-yl)amino)-3-fluoropyridin-2-yl)amino)-1-cyclopropylbutan-2-yl)carbamate | 544 | 1.74 |
| Reference Example 134-293 | 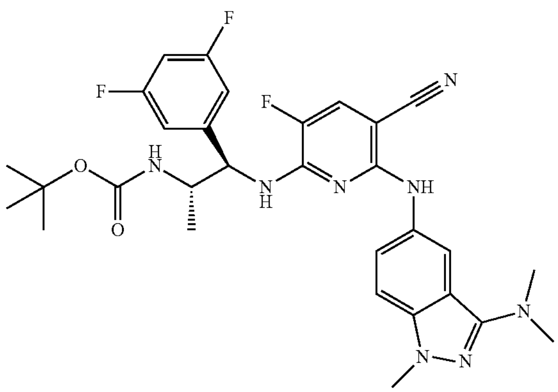 [SMILES: C[C@H](NC(=O)OC(C)(C)C)[C@H](Nc1nc(Nc2ccc3c(c2)c(N(C)C)nn3C)c(C#N)cc1F)c1cc(F)cc(F)c1] | tert-butyl ((1R,2S)-1-((5-cyano-6-((3-(dimethylamino)-1-methyl-1H-indazol-5-yl)amino)-3-fluoropyridin-2-yl)amino)-1-(3,5-difluorophenyl)propan-2-yl)carbamate | 595 | 1.82 |
| Reference Example 134-294 | 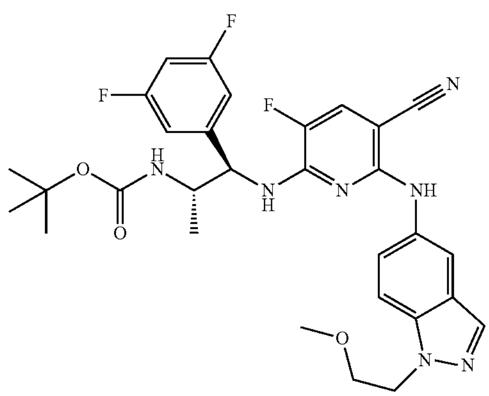 [SMILES: COCCn1ncc2cc(Nc3nc(N[C@H](c4cc(F)cc(F)c4)[C@H](C)NC(=O)OC(C)(C)C)c(F)cc3C#N)ccc21] | tert-butyl ((1R,2S)-1-((5-cyano-3-fluoro-6-((1-(2-methoxyethyl)-1H-indazol-5-yl)amino)pyridin-2-yl)amino)-1-(3,5-difluorophenyl)propan-2-yl)carbamate | 594 | 1.76 |
| Reference Example 134-295 | 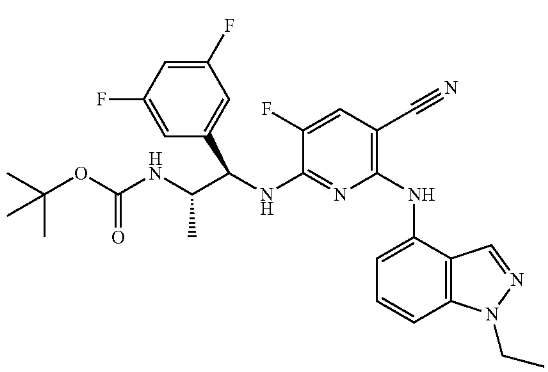 [SMILES: CCn1ncc2c(Nc3nc(N[C@H](c4cc(F)cc(F)c4)[C@H](C)NC(=O)OC(C)(C)C)c(F)cc3C#N)cccc21] | tert-butyl ((1R,2S)-1-((5-cyano-6-((1-ethyl-1H-indazol-4-yl)amino)-3-fluoropyridin-2-yl)amino)-1-(3,5-difluorophenyl)propan-2-yl)carbamate | 566 | 1.86 |

TABLE 1-continued

| Reference Example | Structure | Compound name | MS(ESI m/z): (M + H) | RT(min) |
|---|---|---|---|---|
| Reference Example 134-296 | 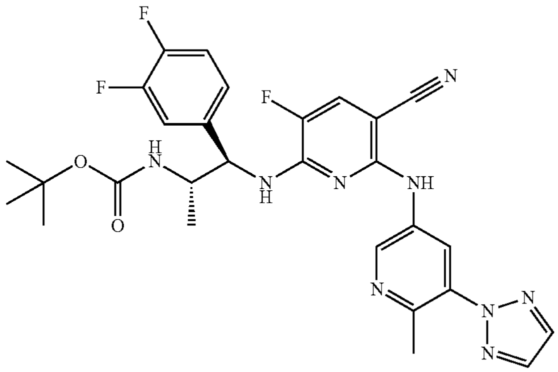 [SMILES: Cc1ncc(Nc2nc(N[C@H](c3ccc(F)c(F)c3)[C@H](C)NC(=O)OC(C)(C)C)c(F)cc2C#N)cc1-n1nccn1] | tert-butyl ((1R,2S)-1-((5-cyano-3-fluoro-6-((6-methyl-5-(2H-1,2,3-triazol-2-yl)pyridin-3-yl)amino)pyridin-2-yl)amino)-1-(3,4-difluorophenyl)propan-2-yl)carbamate | 580 | 1.78 |
| Reference Example 134-297 | 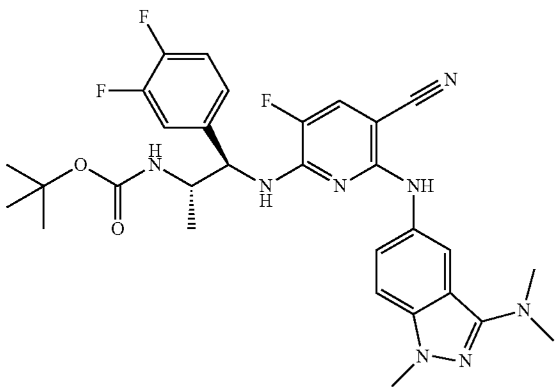 [SMILES: C[C@H](NC(=O)OC(C)(C)C)[C@H](Nc1nc(Nc2ccc3c(c2)c(N(C)C)nn3C)c(C#N)cc1F)c1ccc(F)c(F)c1] | tert-butyl ((1R,2S)-1-((5-cyano-6-((3-(dimethylamino)-1-methyl-1H-indazol-5-yl)amino)-3-fluoropyridin-2-yl)amino)-1-(3,4-difluorophenyl)propan-2-yl)carbamate | 595 | 1.82 |
| Reference Example 134-298 | 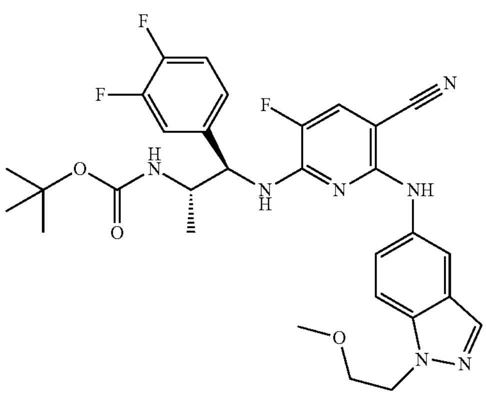 [SMILES: COCCn1ncc2cc(Nc3nc(N[C@H](c4ccc(F)c(F)c4)[C@H](C)NC(=O)OC(C)(C)C)c(F)cc3C#N)ccc21] | tert-butyl ((1R,2S)-1-((5-cyano-3-fluoro-6-((1-(2-methoxyethyl)-1H-indazol-5-yl)amino)pyridin-2-yl)amino)-1-(3,4-difluorophenyl)propan-2-yl)carbamate | 596 | 1.76 |
| Reference Example 134-299 | 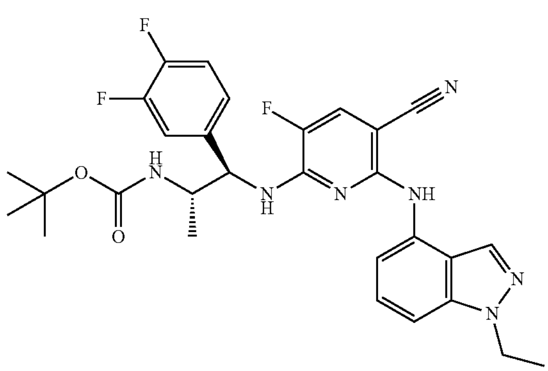 [SMILES: CCn1ncc2c(Nc3nc(N[C@H](c4ccc(F)c(F)c4)[C@H](C)NC(=O)OC(C)(C)C)c(F)cc3C#N)cccc21] | tert-butyl ((1R,2S)-1-((5-cyano-6-((1-ethyl-1H-indazol-4-yl)amino)-3-fluoropyridin-2-yl)amino)-1-(3,4-difluorophenyl)propan-2-yl)carbamate | 564 | 1.85 |

TABLE 1-continued

| Reference Example | Structure | Compound name | MS(ESI m/z): (M + H) | RT(min) |
|---|---|---|---|---|
| Reference Example 134-300 | 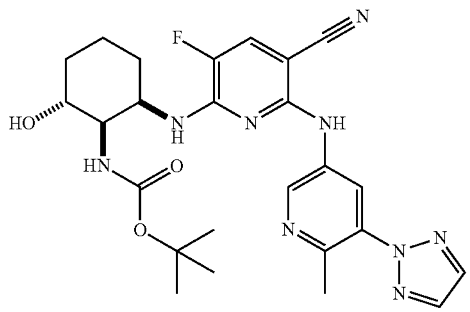 [SMILES: Cc1ncc(Nc2nc(N[C@@H]3CCC[C@@H](O)[C@@H]3NC(=O)OC(C)(C)C)c(F)cc2C#N)cc1-n1nccn1] | Mixture of tert-butyl (2-((5-cyano-3-fluoro-6-((6-methyl-5-(2H-1,2,3-triazol-2-yl)pyridin-3-yl)amino)pyridin-2-yl)amino)-6-hydroxycyclohexyl)carbamate (1R,2R,6R),(1S,2S,6S) | 614 | 1.80 |
| Reference Example 134-301 | 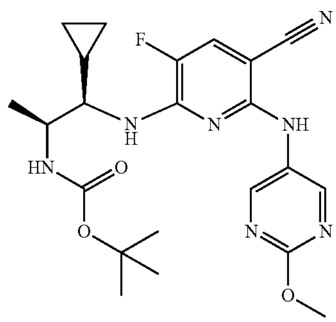 [SMILES: COc1ncc(Nc2nc(N[C@H](C3CC3)[C@H](C)NC(=O)OC(C)(C)C)c(F)cc2C#N)cn1] | tert-butyl ((1R,2S)-1-((5-cyano-3-fluoro-6-((2-methoxypyrimidine-5-yl)amino)pyridin-2-yl)amino)-1-cyclopropylpropan-2-yl)carbamate | 458 | 1.49 |
| Reference Example 134-302 | 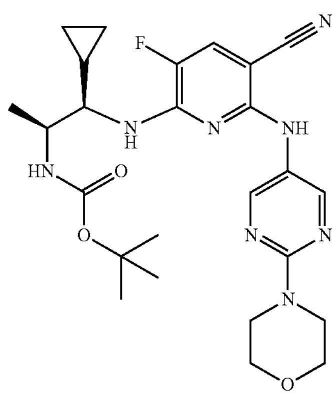 [SMILES: C[C@H](NC(=O)OC(C)(C)C)[C@H](Nc1nc(Nc2cnc(N3CCOCC3)nc2)c(C#N)cc1F)C1CC1] | tert-butyl ((1R,2S)-1-((5-cyano-3-fluoro-6-((2-morpholinopyrimidin-5-yl)amino)pyridin-2-yl)amino)-1-cyclopropylpropan-2-yl)carbamate | 513 | 1.56 |
| Reference Example 134-303 | 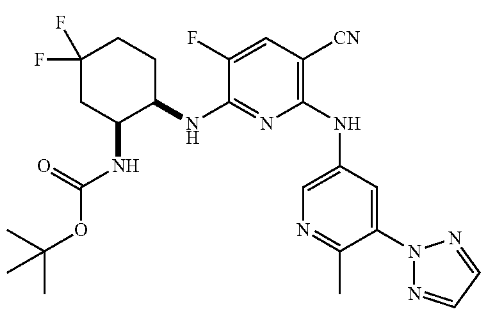 [SMILES: Cc1ncc(Nc2nc(N[C@@H]3CCC(F)(F)C[C@@H]3NC(=O)OC(C)(C)C)c(F)cc2C#N)cc1-n1nccn1] | Mixture of tert-butyl (2-((5-cyano-3-fluoro-6-((6-methyl-5-(2H-1,2,3-triazol-2-yl)pyridin-3-yl)amino)pyridin-2-yl)amino)-5,5-difluorocyclohexyl)carbamate (1S,2R),(1R,2S) | 544 | 1.62 |

TABLE 1-continued

| Reference Example | Structure | Compound name | MS(ESI m/z): (M + H) | RT(min) |
|---|---|---|---|---|
| Reference Example 134-304 | 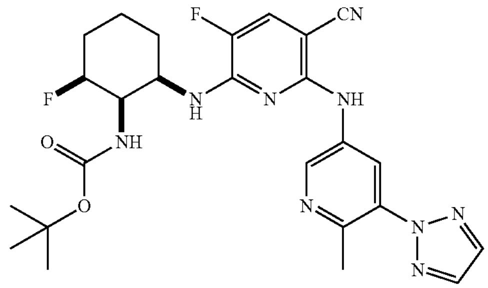 [SMILES: Cc1ncc(Nc2nc(N[C@@H]3CCC[C@H](F)[C@@H]3NC(=O)OC(C)(C)C)c(F)cc2C#N)cc1-n1nccn1] | Mixture of tert-butyl (2-((5-cyano-3-fluoro-6-((6-methyl-5-(2H-1,2,3-triazol-2-yl)pyridin-3-ylamino)pyridin-2-yl)amino)-6-fluorocyclohexyl)carbamate (1R,2R,6S),(1S,2S,6R) | 614 | 1.80 |

Reference Example 135

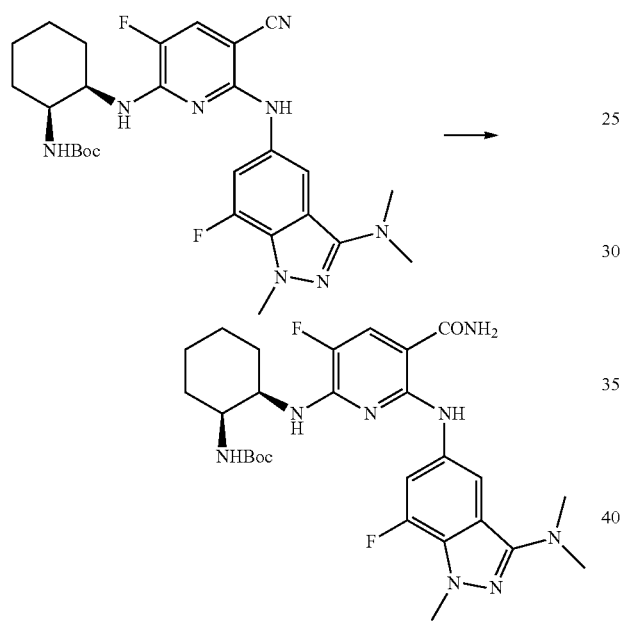

[Formula 154]

A 5N sodium hydroxide aqueous solution (0.512 ml) and a 30% hydrogen peroxide solution (0.29 ml) were added to a DMSO/EtOH (3 ml/3 ml) mixed solution containing tert-butyl ((1S,2R)-2-((5-cyano-6-((3-dimethylamino-7-fluoro-1-methyl-1H-indazol-5-yl)amino)-3-fluoropyridin-2-yl)amino)cyclohexylcarbamate (277 mg), followed by stirring at room temperature for 30 minutes. Water was added to the reaction solution and a solid was collected by filtration. A yellow solid of tert-butyl ((1S,2R)-2-((5-carbamoyl-6-((3-(dimethylamino)-7-fluoro-1-methyl-1H-indazole-5-yl)amino)-3-fluoropyridin-2-yl)amino)cyclohexyl)carbamate (283 mg) was thus obtained.

MS (ESI m/z): 559 (M+H)

RT (min): 1.72

Reference Example 136

The compounds shown in table 2 were obtained as described in

Reference Example 135

TABLE 2

| Reference Example | Structure | Compound name | MS (ESI m/z): (M + H) | RT (min) |
|---|---|---|---|---|
| Reference Example 136-1 | 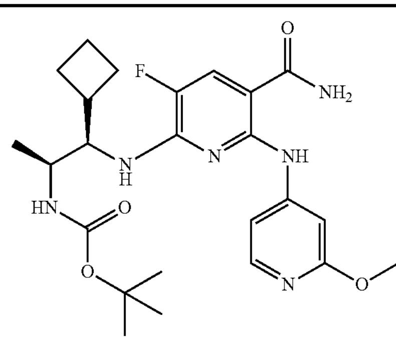 | tert-butyl ((1R,2S)-1-((5-carbamoyl-3-fluoro-6-((2-methoxypyridin-4-yl)amino)pyridin-2-yl)amino)-1-cyclobutylpropan-2-yl)carbamate | 489 | 1.11 |

TABLE 2-continued

| Reference Example | Structure | Compound name | MS (ESI m/z): (M + H) | RT (min) |
|---|---|---|---|---|
| Reference Example 136-2 | 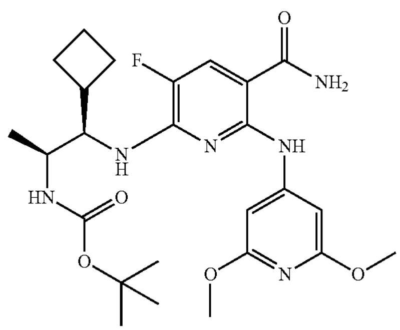 [SMILES: COc1cc(Nc2nc(N[C@H](C3CCC3)[C@H](C)NC(=O)OC(C)(C)C)c(F)cc2C(N)=O)cc(OC)n1] | tert-butyl ((1R,2S)-1-((5-carbamoyl-6-((2,6-dimethoxypyridin-4-yl)amino)-3-fluoropyridin-2-yl)amino)-1-cyclobutylpropan-2-yl)carbamate | 519 | 1.70 |
| Reference Example 136-3 | 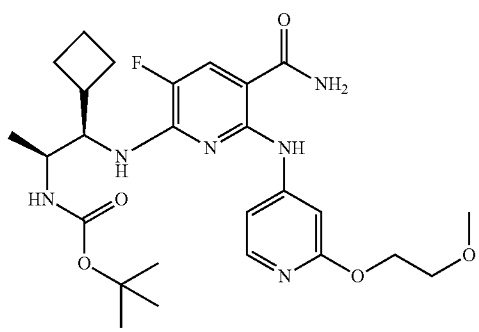 [SMILES: COCCOc1cc(Nc2nc(N[C@H](C3CCC3)[C@H](C)NC(=O)OC(C)(C)C)c(F)cc2C(N)=O)ccn1] | tert-butyl ((1R,2S)-1-((5-carbamoyl-3-fluoro-6-((2-(2-methoxyethoxy)pyridin-4-yl)amino)pyridin-2-yl)amino)-1-cyclobutylpropan-2-yl)carbamate | 433 | 1.16 |
| Reference Example 136-4 | 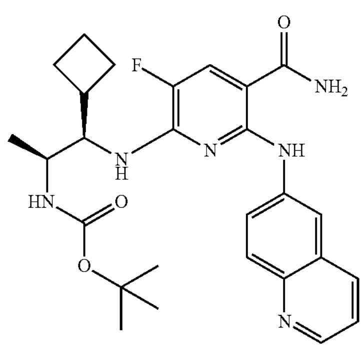 [SMILES: C[C@H](NC(=O)OC(C)(C)C)[C@H](Nc1nc(Nc2ccc3ncccc3c2)c(C(N)=O)cc1F)C1CCC1] | tert-butyl ((1R,2S)-1-((5-carbamoyl-3-fluoro-6-(quinolin-6-ylamino)pyridin-2-yl)amino)-1-cyclobutylpropan-2-yl)carbamate | 509 | 1.17 |
| Reference Example 136-5 | 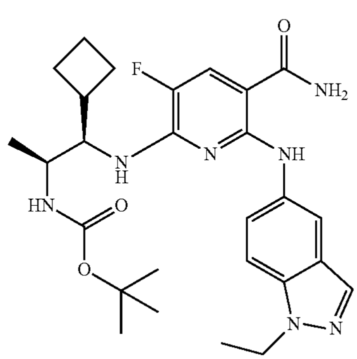 [SMILES: CCn1ncc2cc(Nc3nc(N[C@H](C4CCC4)[C@H](C)NC(=O)OC(C)(C)C)c(F)cc3C(N)=O)ccc21] | tert-butyl ((1R,2S)-1-((5-carbamoyl-6-((1-ethyl-1H-indazol-5-yl)amino)-3-fluoropyridin-2-yl)amino)-1-cyclobutylpropan-2-yl)carbamate | 526 | 1.59 |

TABLE 2-continued

| Reference Example | Structure | Compound name | MS (ESI m/z): (M + H) | RT (min) |
|---|---|---|---|---|
| Reference Example 136-6 | 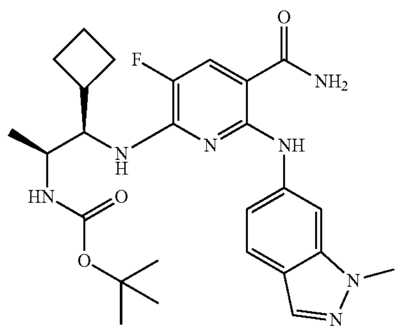 [SMILES: C[C@H](NC(=O)OC(C)(C)C)[C@H](Nc1nc(Nc2ccc3cnn(C)c3c2)c(C(N)=O)cc1F)C1CCC1] | tert-butyl ((1R,2S)-1-((5-carbamoyl-3-fluoro-6-((1-methyl-1H-indazol-6-yl)amino)pyridin-2-yl)amino)-1-cyclobutylpropan-2-yl)carbamate | 512 | 1.52 |
| Reference Example 136-7 | 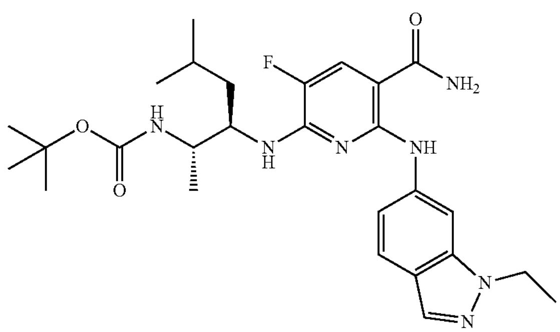 [SMILES: CCn1ncc2ccc(Nc3nc(N[C@H](CC(C)C)[C@H](C)NC(=O)OC(C)(C)C)c(F)cc3C(N)=O)cc21] | tert-butyl ((2S,3R)-3-((5-carbamoyl-6-((1-ethyl-1H-indazol-6-yl)amino)-3-fluoropyridin-2-yl)amino)-5-methylhexan-2-yl)carbamate | 528 | 1.68 |
| Reference Example 136-8 | 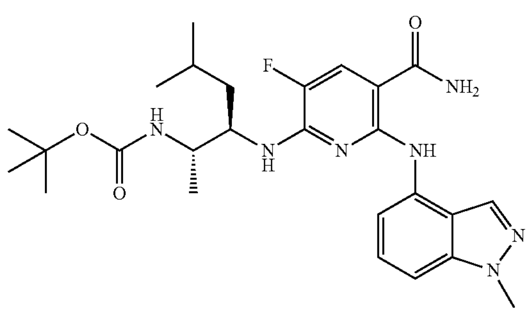 [SMILES: CC(C)C[C@@H](Nc1nc(Nc2cccc3c2cnn3C)c(C(N)=O)cc1F)[C@H](C)NC(=O)OC(C)(C)C] | tert-butyl ((2S,3R)-3-((5-carbamoyl-3-fluoro-6-((1-methyl-1H-indazol-4-yl)amino)pyridin-2-yl)amino)-5-methylhexan-2-yl)carbamate | 514 | 1.71 |
| Reference Example 136-9 | 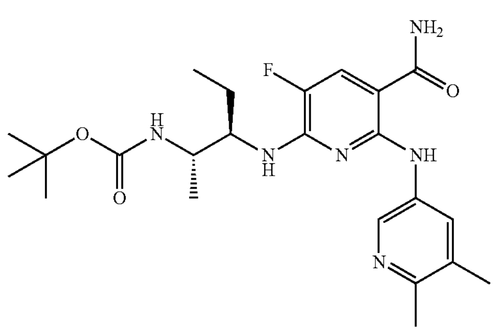 [SMILES: CC[C@@H](Nc1nc(Nc2cnc(C)c(C)c2)c(C(N)=O)cc1F)[C@H](C)NC(=O)OC(C)(C)C] | tert-butyl ((2S,3R)-3-((5-carbamoyl-6-((5,6-dimethylpyridin-3-yl)amino)-3-fluoropyridin-2-yl)amino)pentan-2-yl)carbamate | 461 | 1.10 |

TABLE 2-continued

| Reference Example | Structure | Compound name | MS (ESI m/z): (M + H) | RT (min) |
|---|---|---|---|---|
| Reference Example 136-10 | 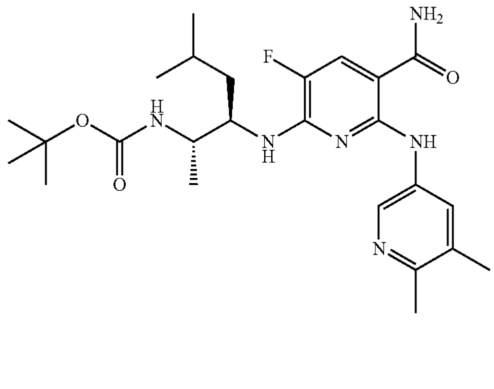 [SMILES: Cc1cc(Nc2nc(N[C@H](CC(C)C)[C@H](C)NC(=O)OC(C)(C)C)c(F)cc2C(N)=O)cnc1C] | tert-butyl ((2S,3R)-3-((5-carbamoyl-6-((5,6-dimethylpyridin-3-yl)amino)-3-fluoropyridin-2-yl)amino)-5-methylhexan-2-yl)carbamate | 489 | 1.24 |
| Reference Example 136-11 | 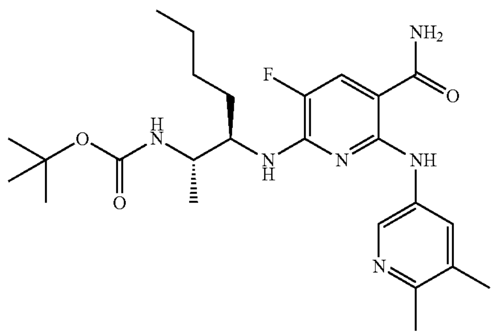 [SMILES: CCCC[C@@H](Nc1nc(Nc2cnc(C)c(C)c2)c(C(N)=O)cc1F)[C@H](C)NC(=O)OC(C)(C)C] | tert-butyl ((2S,3R)-3-((5-carbamoyl-6-((5,6-dimethylpyridin-3-yl)amino)-3-fluoropyridin-2-yl)amino)heptan-2-yl)carbamate | 489 | 1.25 |
| Reference Example 136-12 | 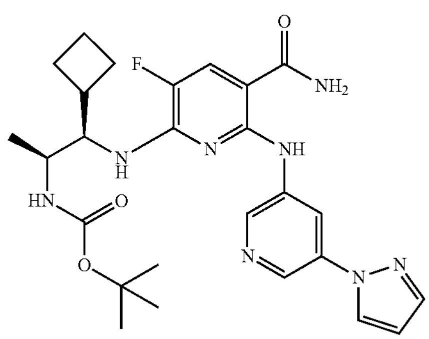 [SMILES: C[C@H](NC(=O)OC(C)(C)C)[C@H](Nc1nc(Nc2cncc(-n3cccn3)c2)c(C(N)=O)cc1F)C1CCC1] | tert-butyl ((1R,2S)-1-((6-((5-(1H-pyrazol-1-yl)pyridin-3-yl)amino)-5-carbamoyl-3-fluoropyridin-2-yl)amino)-1-cyclobutylpropan-2-yl)carbamate | 525 | 1.53 |
| Reference Example 136-13 | 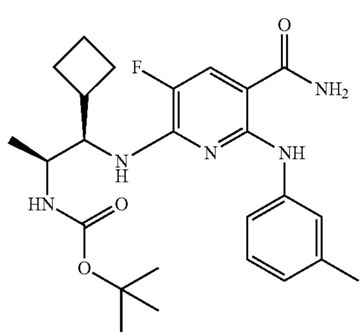 [SMILES: Cc1cccc(Nc2nc(N[C@H](C3CCC3)[C@H](C)NC(=O)OC(C)(C)C)c(F)cc2C(N)=O)c1] | tert-butyl ((1R,2S)-1-((5-carbamoyl-3-fluoro-6-(m-tolylamino)pyridin-2-yl)amino)-1-cyclobutylpropan-2-yl)carbamate | 472 | 1.89 |

TABLE 2-continued

| Reference Example | Structure | Compound name | MS (ESI m/z): (M + H) | RT (min) |
|---|---|---|---|---|
| Reference Example 136-14 | 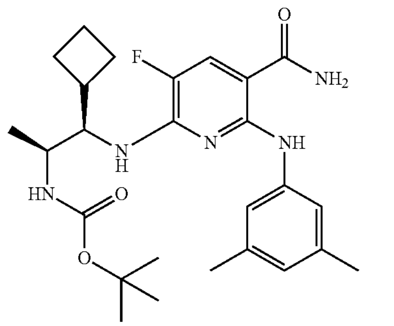 [SMILES: Cc1cc(C)cc(Nc2nc(N[C@H](C3CCC3)[C@H](C)NC(=O)OC(C)(C)C)c(F)cc2C(N)=O)c1] | tert-butyl ((1R,2S)-1-((5-carbamoyl-6-((3,5-dimethylphenyl)amino)-3-fluoropyridin-2-yl)amino)-1-cyclobutylpropan-2-yl)carbamate | 486 | 1.98 |
| Reference Example 136-15 | 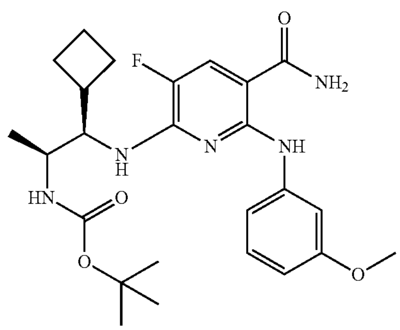 [SMILES: COc1cccc(Nc2nc(N[C@H](C3CCC3)[C@H](C)NC(=O)OC(C)(C)C)c(F)cc2C(N)=O)c1] | tert-butyl ((1R,2S)-1-((5-carbamoyl-3-fluoro-6-((3-methoxyphenyl)amino)pyridin-2-yl)amino)-1-cyclobutylpropan-2-yl)carbamate | 488 | 1.78 |
| Reference Example 136-16 | 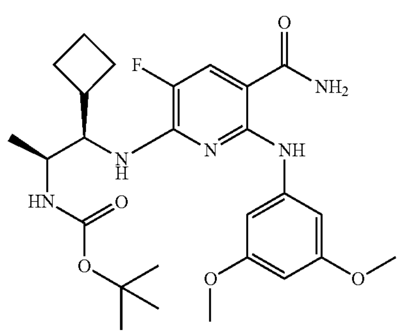 [SMILES: COc1cc(Nc2nc(N[C@H](C3CCC3)[C@H](C)NC(=O)OC(C)(C)C)c(F)cc2C(N)=O)cc(OC)c1] | tert-butyl ((1R,2S)-1-((5-carbamoyl-6-((3,5-dimethoxyphenyl)amino)-3-fluoropyridin-2-yl)amino)-1-cyclobutylpropan-2-yl)carbamate | 518 | 1.76 |
| Reference Example 136-17 | 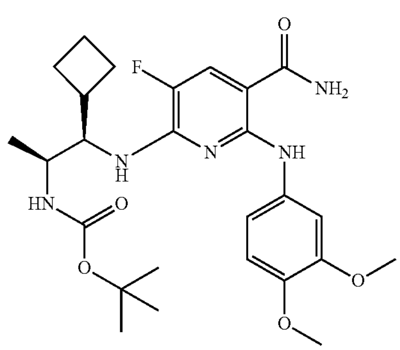 [SMILES: COc1ccc(Nc2nc(N[C@H](C3CCC3)[C@H](C)NC(=O)OC(C)(C)C)c(F)cc2C(N)=O)cc1OC] | tert-butyl ((1R,2S)-1-((5-carbamoyl-6-((3,4-dimethoxyphenyl)amino)-3-fluoropyridin-2-yl)amino)-1-cyclobutylpropan-2-yl)carbamate | 518 | 1.61 |

TABLE 2-continued

| Reference Example | Structure | Compound name | MS (ESI m/z): (M + H) | RT (min) |
|---|---|---|---|---|
| Reference Example 136-18 | 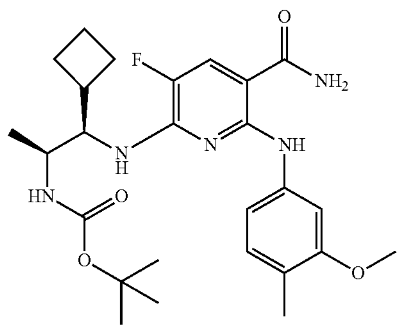 [SMILES: COc1cc(Nc2nc(N[C@H](C3CCC3)[C@H](C)NC(=O)OC(C)(C)C)c(F)cc2C(N)=O)ccc1C] | tert-butyl ((1R,2S)-1-((5-carbamoyl-3-fluoro-6-((3-methoxy-4-methylphenyl)amino)pyridin-2-yl)amino)-1-cyclobutylpropan-2-yl)carbamate | 502 | 1.85 |
| Reference Example 136-19 | 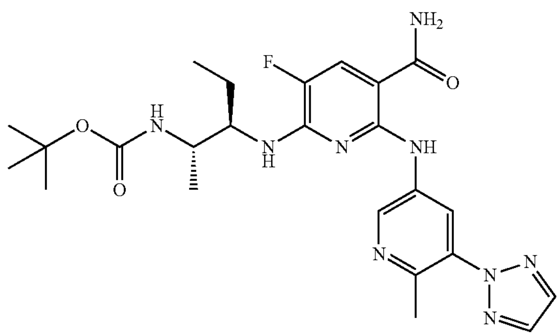 [SMILES: CC[C@@H](Nc1nc(Nc2cnc(C)c(-n3nccn3)c2)c(C(N)=O)cc1F)[C@H](C)NC(=O)OC(C)(C)C] | tert-butyl ((2S,3R)-3-((5-carbamoyl-3-fluoro-6-((6-methyl-5-(2H-1,2,3-triazol-2-yl)pyridin-3-yl)amino)pyridin-2-yl)amino)pentan-2-yl)carbamate | 514 | 1.44 |
| Reference Example 136-20 | 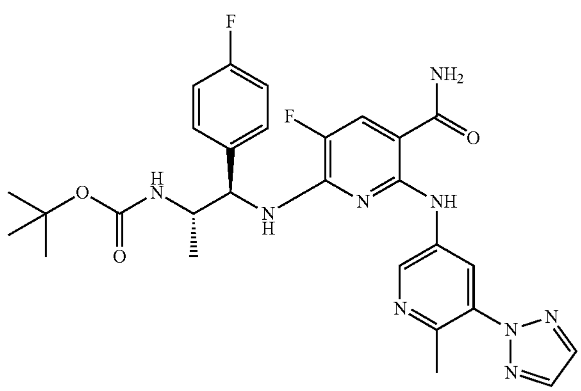 [SMILES: Cc1ncc(Nc2nc(N[C@H](c3ccc(F)cc3)[C@H](C)NC(=O)OC(C)(C)C)c(F)cc2C(N)=O)cc1-n1nccn1] | tert-butyl ((1R,2S)-1-((5-carbamoyl-3-fluoro-6-((6-methyl-5-(2H-1,2,3-triazol-2-yl)pyridin-3-yl)amino)pyridin-2-yl)amino)-1-(4-fluorophenyl)propan-2-yl)carbamate | 580 | 1.60 |
| Reference Example 136-21 | 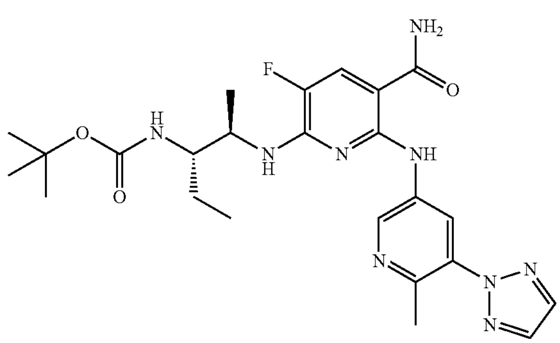 [SMILES: CC[C@H](NC(=O)OC(C)(C)C)[C@@H](C)Nc1nc(Nc2cnc(C)c(-n3nccn3)c2)c(C(N)=O)cc1F] | tert-butyl ((2R,3S)-2-((5-carbamoyl-3-fluoro-6-((6-methyl-5-(2H-1,2,3-triazol-2-yl)pyridin-3-yl)amino)pyridin-2-yl)amino)pentan-3-yl)carbamate | 514 | 1.48 |

TABLE 2-continued

| Reference Example | Structure | Compound name | MS (ESI m/z): (M + H) | RT (min) |
|---|---|---|---|---|
| Reference Example 136-22 | 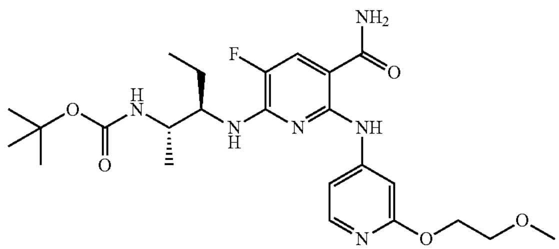 [SMILES: CC[C@@H](Nc1nc(Nc2ccnc(OCCOC)c2)c(C(N)=O)cc1F)[C@H](C)NC(=O)OC(C)(C)C] | tert-butyl ((2S,3R)-3-((5-carbamoyl-3-fluoro-6-((2-(2-methoxyethoxy)pyridin-4-yl)amino)pyridin-2-yl)amino)pentan-2-yl)carbamate | 507 | 1.12 |
| Reference Example 136-23 | 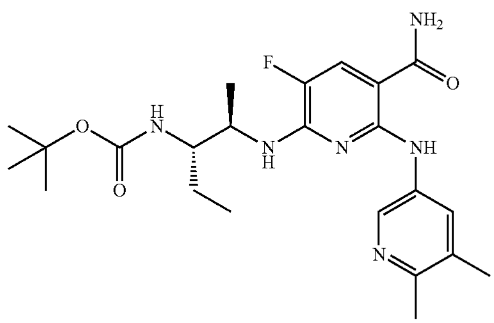 [SMILES: CC[C@H](NC(=O)OC(C)(C)C)[C@@H](C)Nc1nc(Nc2cnc(C)c(C)c2)c(C(N)=O)cc1F] | tert-butyl ((2R,3S)-2-((5-carbamoyl-6-((5,6-dimethylpyridin-3-yl)amino)-3-fluoropyridin-2-yl)amino)pentan-3-yl)carbamate | 461 | 1.10 |
| Reference Example 136-24 | 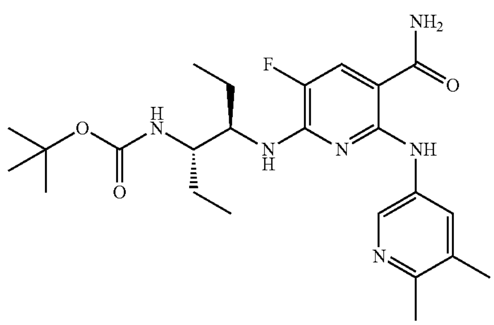 [SMILES: CC[C@H](NC(=O)OC(C)(C)C)[C@@H](CC)Nc1nc(Nc2cnc(C)c(C)c2)c(C(N)=O)cc1F] | tert-butyl ((3S,4R)-4-((5-carbamoyl-6-((5,6-dimethylpyridin-3-yl)amino)-3-fluoropyridin-2-yl)amino)hexan-3-yl)carbamate | 475 | 1.16 |
| Reference Example 136-25 | 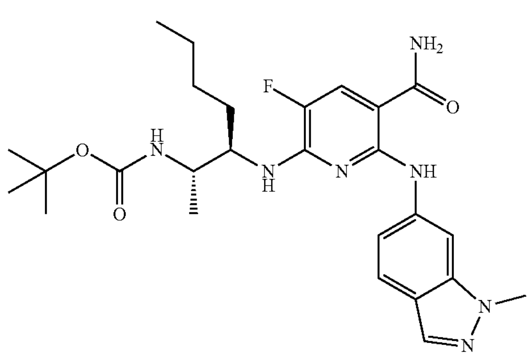 [SMILES: CCCC[C@@H](Nc1nc(Nc2ccc3cnn(C)c3c2)c(C(N)=O)cc1F)[C@H](C)NC(=O)OC(C)(C)C] | tert-butyl ((2S,3R)-3-((5-carbamoyl-3-fluoro-6-((1-methyl-1H-indazol-6-yl)amino)pyridin-2-yl)amino)heptan-2-yl)carbamate | 514 | 1.63 |

TABLE 2-continued

| Reference Example | Structure | Compound name | MS (ESI m/z): (M + H) | RT (min) |
|---|---|---|---|---|
| Reference Example 136-26 | 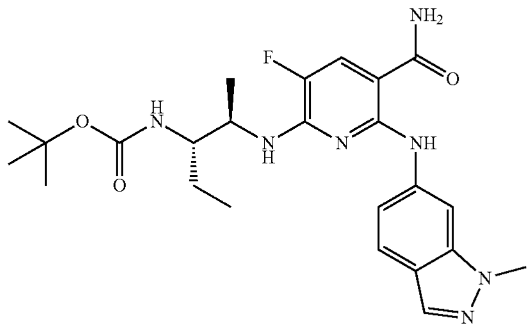 [SMILES: CC[C@H](NC(=O)OC(C)(C)C)[C@@H](C)Nc1nc(Nc2ccc3cnn(C)c3c2)c(C(N)=O)cc1F] | tert-butyl ((2R,3S)-2-((5-carbamoyl-3-fluoro-6-((1-methyl-1H-indazol-6-yl)amino)pyridin-2-yl)amino)pentan-3-yl)carbamate | 486 | 1.50 |
| Reference Example 136-27 | 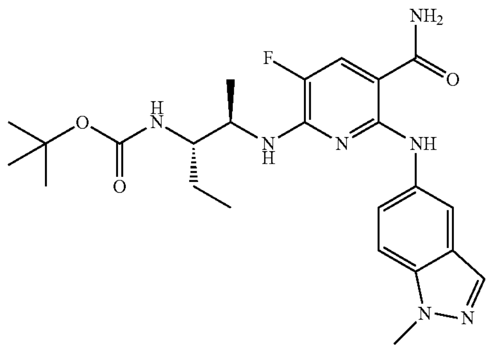 [SMILES: CC[C@H](NC(=O)OC(C)(C)C)[C@@H](C)Nc1nc(Nc2ccc3c(cnn3C)c2)c(C(N)=O)cc1F] | tert-butyl ((2R,3S)-2-((5-carbamoyl-3-fluoro-6-((1-methyl-1H-indazol-5-yl)amino)pyridin-2-yl)amino)pentan-3-yl)carbamate | 486 | 1.44 |
| Reference Example 136-28 | 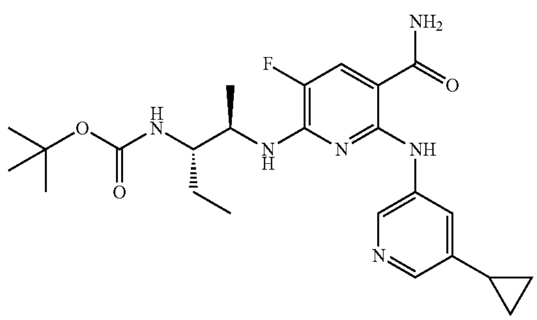 [SMILES: CC[C@H](NC(=O)OC(C)(C)C)[C@@H](C)Nc1nc(Nc2cncc(C3CC3)c2)c(C(N)=O)cc1F] | tert-butyl ((2R,3S)-2-((5-carbamoyl-6-((5-cyclopropylpyridin-3-yl)amino)-3-fluoropyridin-2-yl)amino)pentan-3-yl)carbamate | 473 | 1.20 |
| Reference Example 136-29 | 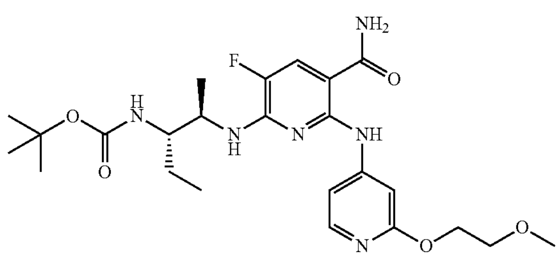 [SMILES: CC[C@H](NC(=O)OC(C)(C)C)[C@@H](C)Nc1nc(Nc2ccnc(OCCOC)c2)c(C(N)=O)cc1F] | tert-butyl ((2R,3S)-2-((5-carbamoyl-3-fluoro-6-((2-(2-methoxyethoxy)pyridin-4-yl)amino)pyridin-2-yl)amino)pentan-3-yl)carbamate | 507 | 1.16 |
| Reference Example 136-30 | 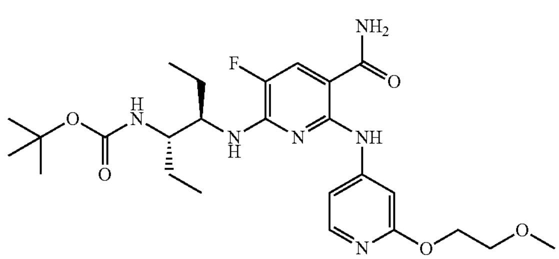 [SMILES: CC[C@H](NC(=O)OC(C)(C)C)[C@@H](CC)Nc1nc(Nc2ccnc(OCCOC)c2)c(C(N)=O)cc1F] | tert-butyl ((3S,4R)-4-((5-carbamoyl-3-fluoro-6-((2-(2-methoxyethoxy)pyridin-4-yl)amino)pyridin-2-yl)amino)hexan-3-yl)carbamate | 521 | 1.19 |

TABLE 2-continued

| Reference Example | Structure | Compound name | MS (ESI m/z): (M + H) | RT (min) |
|---|---|---|---|---|
| Reference Example 136-31 | 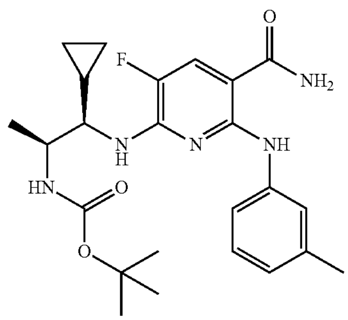 [SMILES: Cc1cccc(Nc2nc(N[C@H](C3CC3)[C@H](C)NC(=O)OC(C)(C)C)c(F)cc2C(N)=O)c1] | tert-butyl ((1R,2S)-1-((5-carbamoyl-3-fluoro-6-(m-tolylamino)pyridin-2-yl)amino)-1-cyclopropylpropan-2-yl)carbamate | 458 | 1.78 |
| Reference Example 136-32 | 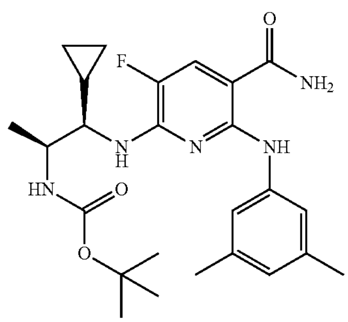 [SMILES: Cc1cc(C)cc(Nc2nc(N[C@H](C3CC3)[C@H](C)NC(=O)OC(C)(C)C)c(F)cc2C(N)=O)c1] | tert-butyl ((1R,2S)-1-((5-carbamoyl-6-((3,5-dimethylphenyl)amino)-3-fluoropyridin-2-yl)amino)-1-cyclopropylpropan-2-yl)carbamate | 472 | 1.87 |
| Reference Example 136-33 | 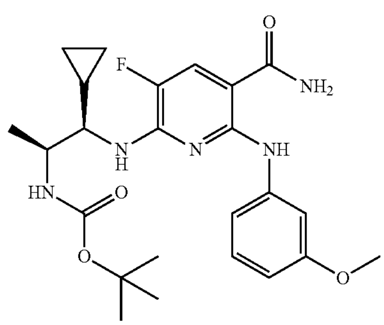 [SMILES: COc1cccc(Nc2nc(N[C@H](C3CC3)[C@H](C)NC(=O)OC(C)(C)C)c(F)cc2C(N)=O)c1] | tert-butyl ((1R,2S)-1-((5-carbamoyl-3-fluoro-6-((3-methoxyphenyl)amino)pyridin-2-yl)amino)-1-cyclopropylpropan-2-yl)carbamate | 474 | 1.68 |
| Reference Example 136-34 | 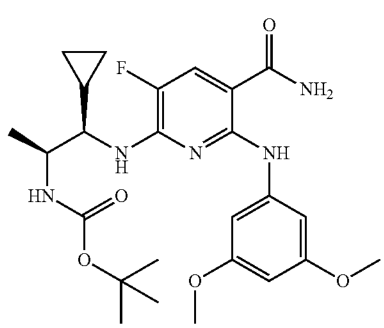 [SMILES: COc1cc(Nc2nc(N[C@H](C3CC3)[C@H](C)NC(=O)OC(C)(C)C)c(F)cc2C(N)=O)cc(OC)c1] | tert-butyl ((1R,2S)-1-((5-carbamoyl-6-((3,5-dimethoxyphenyl)amino)-3-fluoropyridin-2-yl)amino)-1-cyclopropylpropan-2-yl)carbamate | 504 | 1.67 |

| Reference Example | Structure | Compound name | MS (ESI m/z): (M + H) | RT (min) |
|---|---|---|---|---|
| Reference Example 136-35 | 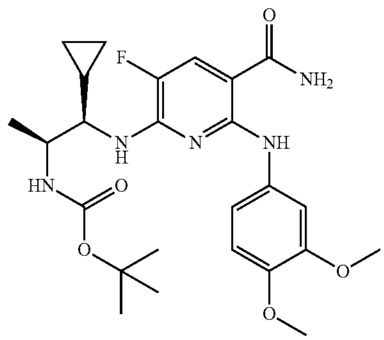 [SMILES: COc1ccc(Nc2nc(N[C@H](C3CC3)[C@H](C)NC(=O)OC(C)(C)C)c(F)cc2C(N)=O)cc1OC] | tert-butyl ((1R,2S)-1-((5-carbamoyl-6-((3,4-dimethoxyphenyl)amino)-3-fluoropyridin-2-yl)amino)-1-cyclopropylpropan-2-yl)carbamate | 504 | 1.52 |
| Reference Example 136-36 | 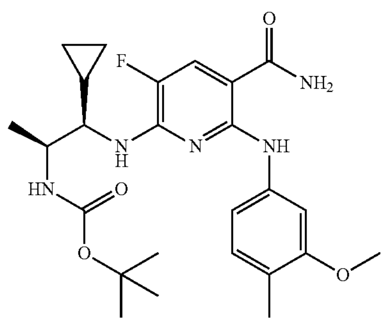 [SMILES: COc1cc(Nc2nc(N[C@H](C3CC3)[C@H](C)NC(=O)OC(C)(C)C)c(F)cc2C(N)=O)ccc1C] | tert-butyl ((1R,2S)-1-((5-carbamoyl-3-fluoro-6-((3-methoxy-4-methylphenyl)amino)pyridin-2-yl)amino)-1-cyclopropylpropan-2-yl)carbamate | 488 | 1.79 |
| Reference Example 136-37 | 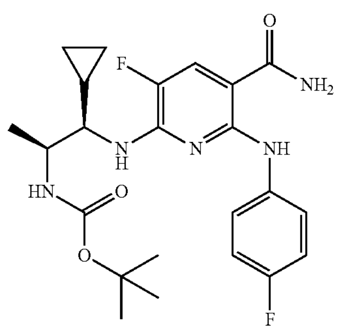 [SMILES: C[C@H](NC(=O)OC(C)(C)C)[C@H](Nc1nc(Nc2ccc(F)cc2)c(C(N)=O)cc1F)C1CC1] | tert-butyl ((1R,2S)-1-((5-carbamoyl-3-fluoro-6-((4-fluorophenyl)amino)pyridin-2-yl)amino)-1-cyclopropylpropan-2-yl)carbamate | 462 | 1.70 |
| Reference Example 136-38 | 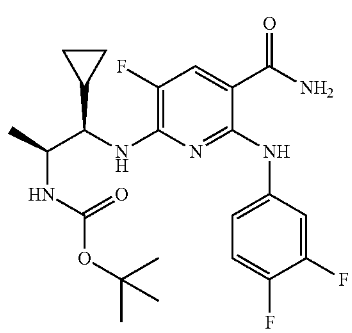 [SMILES: C[C@H](NC(=O)OC(C)(C)C)[C@H](Nc1nc(Nc2ccc(F)c(F)c2)c(C(N)=O)cc1F)C1CC1] | tert-butyl ((1R,2S)-1-((5-carbamoyl-6-((3,4-difluorophenyl)amino)-3-fluoropyridin-2-yl)amino)-1-cyclopropylpropan-2-yl)carbamate | 480 | 1.76 |

TABLE 2-continued

| Reference Example | Structure | Compound name | MS (ESI m/z): (M + H) | RT (min) |
|---|---|---|---|---|
| Reference Example 136-39 | 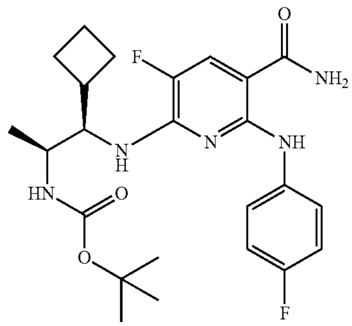 [SMILES: C[C@H](NC(=O)OC(C)(C)C)[C@H](Nc1nc(Nc2ccc(F)cc2)c(C(N)=O)cc1F)C1CCC1] | tert-butyl ((1R,2S)-1-((5-carbamoyl-3-fluoro-6-((4-fluorophenyl)amino)pyridin-2-yl)amino)-1-cyclobutylpropan-2-yl)carbamate | 478 | 1.81 |
| Reference Example 136-40 | 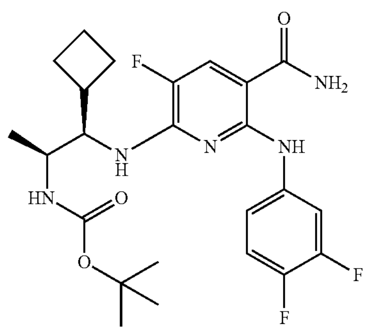 [SMILES: C[C@H](NC(=O)OC(C)(C)C)[C@H](Nc1nc(Nc2ccc(F)c(F)c2)c(C(N)=O)cc1F)C1CCC1] | tert-butyl ((1R,2S)-1-((5-carbamoyl-6-((3,4-difluorophenyl)amino)-3-fluoropyridin-2-yl)amino)-1-cyclobutylpropan-2-yl)carbamate | 494 | 1.86 |
| Reference Example 136-41 | 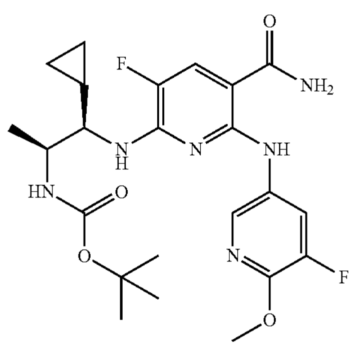 [SMILES: COc1ncc(Nc2nc(N[C@H](C3CC3)[C@H](C)NC(=O)OC(C)(C)C)c(F)cc2C(N)=O)cc1F] | tert-butyl ((1R,2S)-1-((5-carbamoyl-3-fluoro-6-((5-fluoro-6-methoxypyridin-3-yl)amino)pyridin-2-yl)amino)-1-cyclopropylpropan-2-yl)carbamate | 493 | 1.61 |
| Reference Example 136-42 | 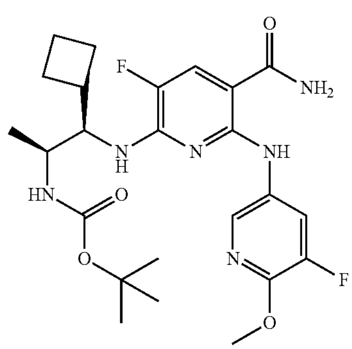 [SMILES: COc1ncc(Nc2nc(N[C@H](C3CCC3)[C@H](C)NC(=O)OC(C)(C)C)c(F)cc2C(N)=O)cc1F] | tert-butyl ((1R,2S)-1-((5-carbamoyl-3-fluoro-6-((5-fluoro-6-methoxypyridin-3-yl)amino)pyridin-2-yl)amino)-1-cyclobutylpropan-2-yl)carbamate | 507 | 1.72 |

TABLE 2-continued

| Reference Example | Structure | Compound name | MS (ESI m/z): (M + H) | RT (min) |
|---|---|---|---|---|
| Reference Example 136-43 | 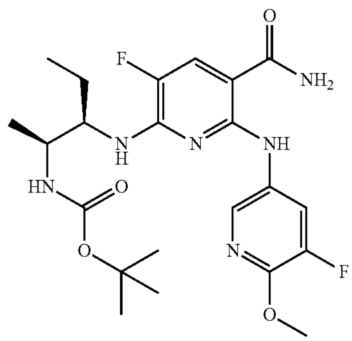 [SMILES: CC[C@@H](Nc1nc(Nc2cnc(OC)c(F)c2)c(C(N)=O)cc1F)[C@H](C)NC(=O)OC(C)(C)C] | tert-butyl ((2S,3R)-3-((5-carbamoyl-3-fluoro-6-((5-fluoro-6-methoxypyridin-3-yl)amino)pyridin-2-yl)amino)pentan-2-yl)carbamate | 481 | 1.61 |
| Reference Example 136-44 | 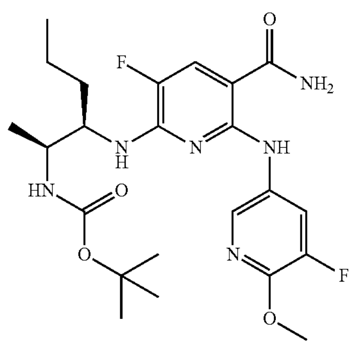 [SMILES: CCC[C@@H](Nc1nc(Nc2cnc(OC)c(F)c2)c(C(N)=O)cc1F)[C@H](C)NC(=O)OC(C)(C)C] | tert-butyl ((2S,3R)-3-((5-carbamoyl-3-fluoro-6-((5-fluoro-6-methoxypyridin-3-yl)amino)pyridin-2-yl)amino)hexan-2-yl)carbamate | 495 | 1.69 |
| Reference Example 136-45 | 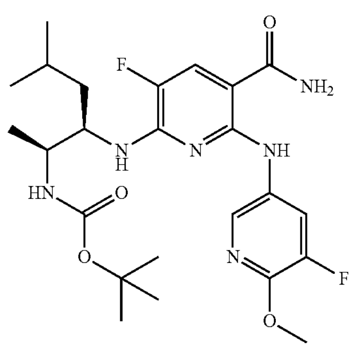 [SMILES: COc1ncc(Nc2nc(N[C@H](CC(C)C)[C@H](C)NC(=O)OC(C)(C)C)c(F)cc2C(N)=O)cc1F] | tert-butyl ((2S,3R)-3-((5-carbamoyl-3-fluoro-6-((5-fluoro-6-methoxypyridin-3-yl)amino)pyridin-2-yl)amino)-5-methylhexan-2-yl)carbamate | 509 | 1.77 |
| Reference Example 136-46 | 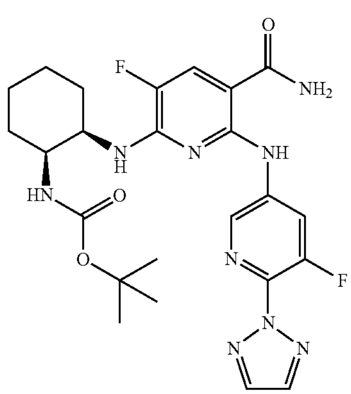 [SMILES: CC(C)(C)OC(=O)N[C@H]1CCCC[C@H]1Nc1nc(Nc2cnc(-n3nccn3)c(F)c2)c(C(N)=O)cc1F] | tert-butyl ((1S,2R)-2-((5-carbamoyl-3-fluoro-6-((5-fluoro-6-(2H-1,2,3-triazol-2-yl)pyridin-3-yl)amino)pyridin-2-yl)amino)cyclohexyl)carbamate | 530 | 1.56 |

TABLE 2-continued

| Reference Example | Structure | Compound name | MS (ESI m/z): (M + H) | RT (min) |
|---|---|---|---|---|
| Reference Example 136-47 | 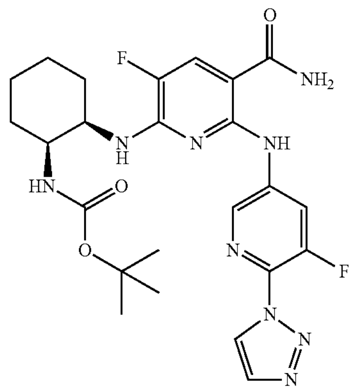 [SMILES: CC(C)(C)OC(=O)N[C@H]1CCCC[C@H]1Nc1nc(Nc2cnc(-n3ccnn3)c(F)c2)c(C(N)=O)cc1F] | tert-butyl ((1S,2R)-2-((5-carbamoyl-3-fluoro-6-((5-fluoro-6-(1H-1,2,3-triazol-1-yl)pyridin-3-yl)amino)pyridin-2-yl)amino)cyclohexyl)carbamate | 530 | 1.47 |
| Reference Example 136-48 | 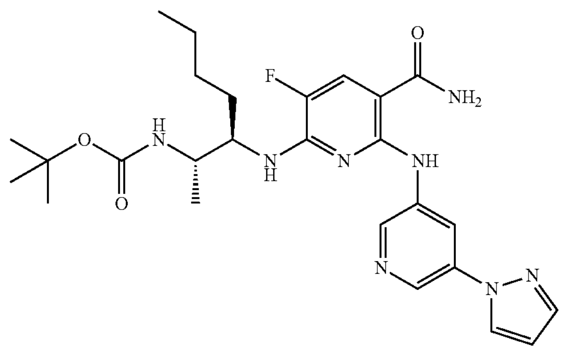 [SMILES: CCCC[C@@H](Nc1nc(Nc2cncc(-n3cccn3)c2)c(C(N)=O)cc1F)[C@H](C)NC(=O)OC(C)(C)C] | tert-butyl ((2S,3R)-3-((6-((5-(1H-pyrazol-1-yl)pyridin-3-yl)amino)-5-carbamoyl-3-fluoropyridin-2-yl)amino)heptan-2-yl)carbamate | 527 | 1.61 |
| Reference Example 136-49 | 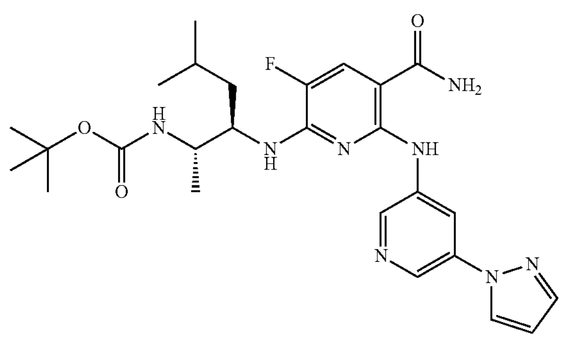 [SMILES: CC(C)C[C@@H](Nc1nc(Nc2cncc(-n3cccn3)c2)c(C(N)=O)cc1F)[C@H](C)NC(=O)OC(C)(C)C] | tert-butyl ((2S,3R)-3-((6-((5-(1H-pyrazol-1-yl)pyridin-3-yl)amino)-5-carbamoyl-3-fluoropyridin-2-yl)amino)-5-methylhexan-2-yl)carbamate | 527 | 1.60 |
| Reference Example 136-50 | 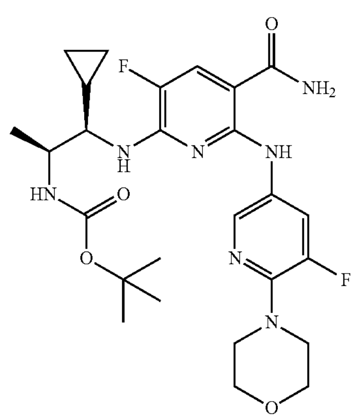 [SMILES: C[C@H](NC(=O)OC(C)(C)C)[C@H](Nc1nc(Nc2cnc(N3CCOCC3)c(F)c2)c(C(N)=O)cc1F)C1CC1] | tert-butyl ((1R,2S)-1-((5-carbamoyl-3-fluoro-6-((5-fluoro-6-morpholinopyridin-3-yl)amino)pyridin-2-yl)amino)-1-cyclopropylpropan-2-yl)carbamate | 548 | 1.48 |

TABLE 2-continued

| Reference Example | Structure | Compound name | MS (ESI m/z): (M + H) | RT (min) |
|---|---|---|---|---|
| Reference Example 136-51 | 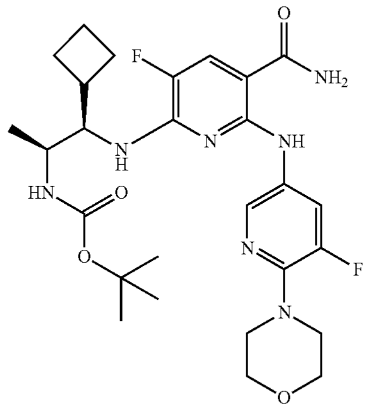 [SMILES: C[C@H](NC(=O)OC(C)(C)C)[C@H](Nc1nc(Nc2cnc(N3CCOCC3)c(F)c2)c(C(N)=O)cc1F)C1CCC1] | tert-butyl ((1R,2S)-1-((5-carbamoyl-3-fluoro-6-((5-fluoro-6-morpholinopyridin-3-yl)amino)pyridin-2-yl)amino)-1-cyclobutylpropan-2-yl)carbamate | 562 | 1.59 |
| Reference Example 136-52 | 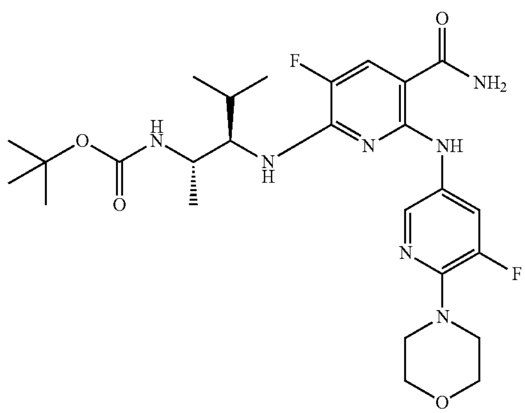 [SMILES: CC(C)[C@@H](Nc1nc(Nc2cnc(N3CCOCC3)c(F)c2)c(C(N)=O)cc1F)[C@H](C)NC(=O)OC(C)(C)C] | tert-butyl ((2S,3R)-3-((5-carbamoyl-3-fluoro-6-((5-fluoro-6-morpholinopyridin-3-yl)amino)pyridin-2-yl)amino)-4-methylpentan-2-yl)carbamate | 550 | 1.61 |
| Reference Example 136-53 | 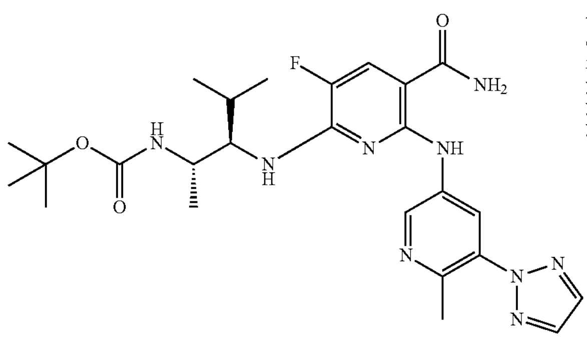 | tert-butyl ((2S,3R)-3-((5-carbamoyl-3-fluoro-6-((6-methyl-5-(2H-1,2,3-triazol-2-yl)pyridin-3-yl)amino)pyridin-2-yl)amino)-4-methylpentan-2-yl)carbamate | 528 | 1.55 |
| Reference Example 136-54 | 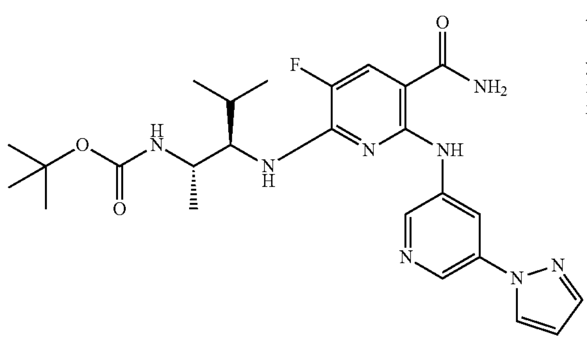 [SMILES: CC(C)[C@@H](Nc1nc(Nc2cncc(-n3cccn3)c2)c(C(N)=O)cc1F)[C@H](C)NC(=O)OC(C)(C)C] | tert-butyl ((2S,3R)-3-((6-((5-(1H-pyrazol-1-yl)pyridin-3-yl)amino)-5-carbamoyl-3-fluoropyridin-2-yl)amino)-4-methylpentan-2-yl)carbamate | 513 | 1.53 |

TABLE 2-continued

| Reference Example | Structure | Compound name | MS (ESI m/z): (M + H) | RT (min) |
|---|---|---|---|---|
| Reference Example 136-55 | 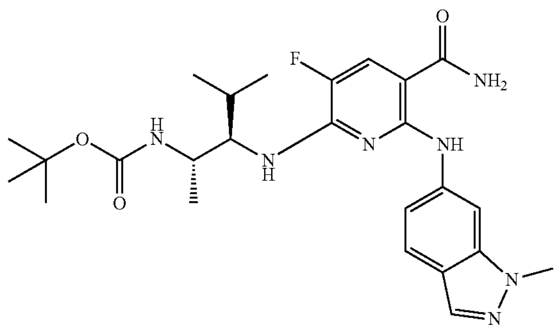 [SMILES: CC(C)[C@@H](Nc1nc(Nc2ccc3cnn(C)c3c2)c(C(N)=O)cc1F)[C@H](C)NC(=O)OC(C)(C)C] | tert-butyl ((2S,3R)-3-((5-carbamoyl-3-fluoro-6-((1-methyl-1H-indazol-6-yl)amino)pyridin-2-yl)amino)-4-methylpentan-2-yl)carbamate | 500 | 1.53 |
| Reference Example 136-56 | 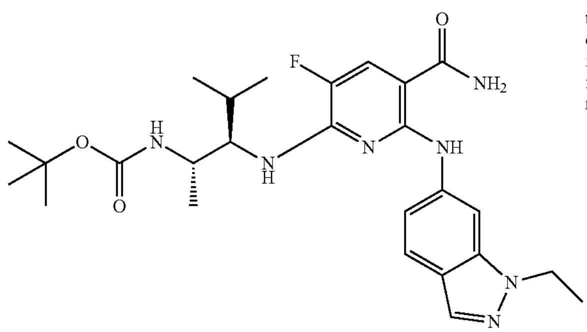 [SMILES: CCn1ncc2ccc(Nc3nc(N[C@H](C(C)C)[C@H](C)NC(=O)OC(C)(C)C)c(F)cc3C(N)=O)cc21] | tert-butyl ((2S,3R)-3-((5-carbamoyl-6-((1-ethyl-1H-indazol-6-yl)amino)-3-fluoropyridin-2-yl)amino)-4-methylpentan-2-yl)carbamate | 514 | 1.61 |
| Reference Example 136-57 | 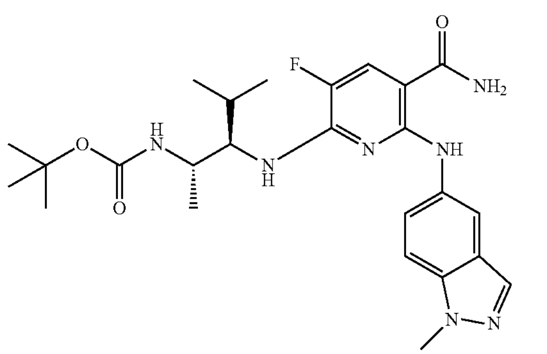 [SMILES: CC(C)[C@@H](Nc1nc(Nc2ccc3c(cnn3C)c2)c(C(N)=O)cc1F)[C@H](C)NC(=O)OC(C)(C)C] | tert-butyl ((2S,3R)-3-((5-carbamoyl-3-fluoro-6-((1-methyl-1H-indazol-5-yl)amino)pyridin-2-yl)amino)-4-methylpentan-2-yl)carbamate | 500 | 1.52 |
| Reference Example 136-58 | 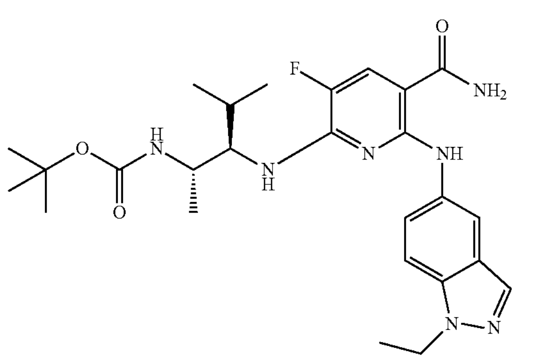 [SMILES: CCn1ncc2cc(Nc3nc(N[C@H](C(C)C)[C@H](C)NC(=O)OC(C)(C)C)c(F)cc3C(N)=O)ccc21] | tert-butyl ((2S,3R)-3-((5-carbamoyl-6-((1-ethyl-1H-indazol-5-yl)amino)-3-fluoropyridin-2-yl)amino)-4-methylpentan-2-ycarbamate | 514 | 1.60 |

TABLE 2-continued

| Reference Example | Structure | Compound name | MS (ESI m/z): (M + H) | RT (min) |
|---|---|---|---|---|
| Reference Example 136-59 | 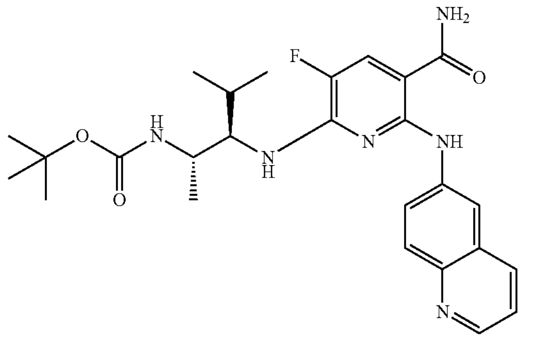 [SMILES: CC(C)[C@@H](Nc1nc(Nc2ccc3ncccc3c2)c(C(N)=O)cc1F)[C@H](C)NC(=O)OC(C)(C)C] | tert-butyl ((2S,3R)-3-((5-carbamoyl-3-fluoro-6-(quinolin-6-ylamino)pyridin-2-yl)amino)-4-methylpentan-2-yl)carbamate | 497 | 1.20 |
| Reference Example 136-60 | 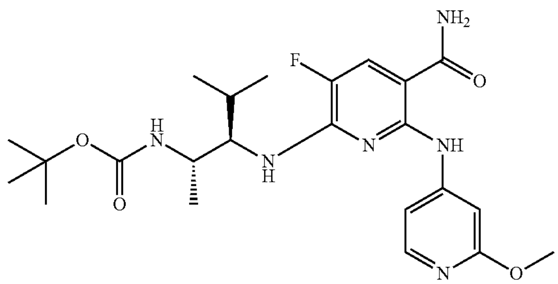 [SMILES: COc1cc(Nc2nc(N[C@H](C(C)C)[C@H](C)NC(=O)OC(C)(C)C)c(F)cc2C(N)=O)ccn1] | tert-butyl ((2S,3R)-3-((5-carbamoyl-3-fluoro-6-((2-methoxypyridin-4-yl)amino)pyridin-2-yl)amino)-4-methylpentan-2-yl)carbamate | 477 | 1.13 |
| Reference Example 136-61 | 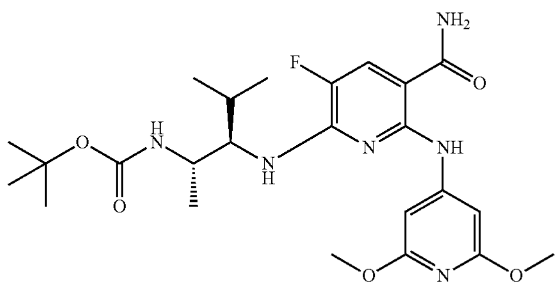 [SMILES: COc1cc(Nc2nc(N[C@H](C(C)C)[C@H](C)NC(=O)OC(C)(C)C)c(F)cc2C(N)=O)cc(OC)n1] | tert-butyl ((2S,3R)-3-((5-carbamoyl-6-((2,6-dimethoxypyridin-4-yl)amino)-3-fluoropyridin-2-yl)amino)-4-methylpentan-2-yl)carbamate | 507 | 1.70 |
| Reference Example 136-62 | 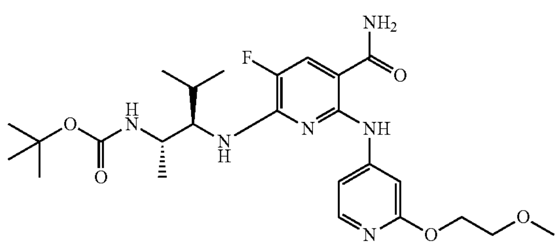 [SMILES: COCCOc1cc(Nc2nc(N[C@H](C(C)C)[C@H](C)NC(=O)OC(C)(C)C)c(F)cc2C(N)=O)ccn1] | tert-butyl ((2S,3R)-3-((5-carbamoyl-3-fluoro-6-((2-(2-methoxyethoxy)pyridin-4-yl)amino)pyridin-2-yl)amino)-4-methylpentan-2-yl)carbamate | 521 | 1.18 |
| Reference Example 136-63 | 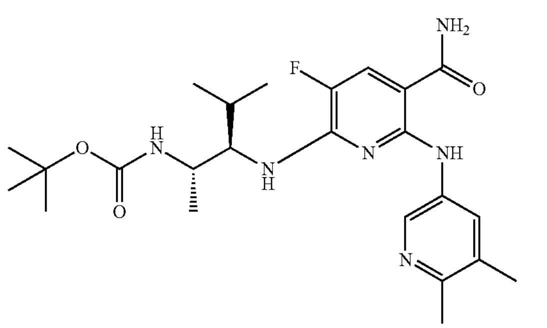 [SMILES: Cc1cc(Nc2nc(N[C@H](C(C)C)[C@H](C)NC(=O)OC(C)(C)C)c(F)cc2C(N)=O)cnc1C] | tert-butyl ((2S,3R)-3-((5-carbamoyl-6-((5,6-dimethylpyridin-3-yl)amino)-3-fluoropyridin-2-yl)amino)-4-methylpentan-2-yl)carbamate | 475 | 1.18 |

TABLE 2-continued

| Reference Example | Structure | Compound name | MS (ESI m/z): (M + H) | RT (min) |
|---|---|---|---|---|
| Reference Example 136-64 | 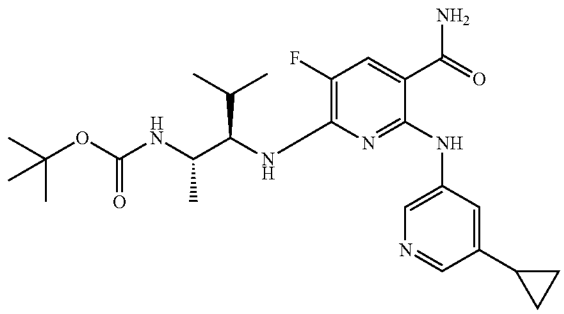 [SMILES: CC(C)[C@@H](Nc1nc(Nc2cncc(C3CC3)c2)c(C(N)=O)cc1F)[C@H](C)NC(=O)OC(C)(C)C] | tert-butyl ((2S,3R)-3-((5-carbamoyl-6-((5-cyclopropylpyridin-3-yl)amino)-3-fluoropyridin-2-yl)amino)-4-methylpentan-2-yl)carbamate | 487 | 1.22 |
| Reference Example 136-65 | 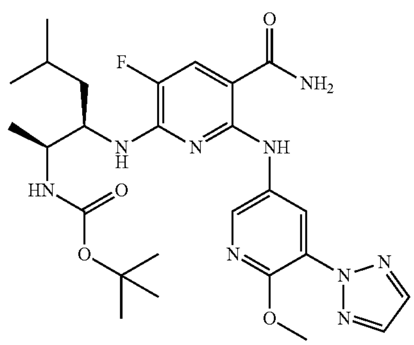 [SMILES: COc1ncc(Nc2nc(N[C@H](CC(C)C)[C@H](C)NC(=O)OC(C)(C)C)c(F)cc2C(N)=O)cc1-n1nccn1] | tert-butyl ((2S,3R)-3-((5-carbamoyl-3-fluoro-6-((6-methoxy-5-(2H-1,2,3-triazol-2-yl)pyridin-3-yl)amino)pyridin-2-yl)amino)-5-methylhexan-2-yl)carbamate | 558 | 1.66 |
| Reference Example 136-66 | 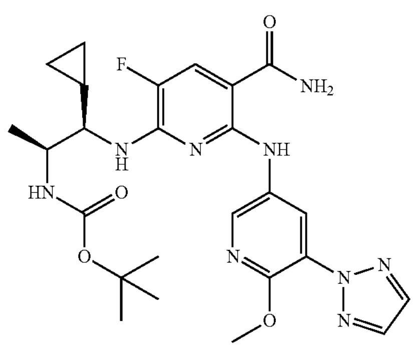 [SMILES: COc1ncc(Nc2nc(N[C@H](C3CC3)[C@H](C)NC(=O)OC(C)(C)C)c(F)cc2C(N)=O)cc1-n1nccn1] | tert-butyl ((1R,2S)-1-((5-carbamoyl-3-fluoro-6-((6-methoxy-5-(2H-1,2,3-triazol-2-yl)pyridin-3-yl)amino)pyridin-2-yl)amino)-1-cyclopropylpropan-2-yl)carbamate | 542 | 1.52 |
| Reference Example 136-67 | 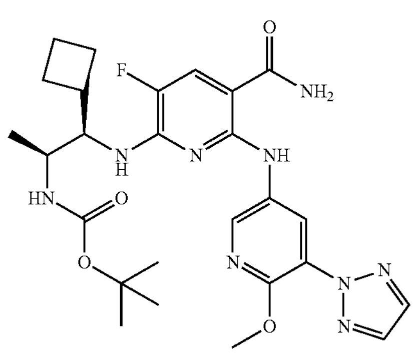 [SMILES: COc1ncc(Nc2nc(N[C@H](C3CCC3)[C@H](C)NC(=O)OC(C)(C)C)c(F)cc2C(N)=O)cc1-n1nccn1] | tert-butyl ((1R,2S)-1-((5-carbamoyl-3-fluoro-6-((6-methoxy-5-(2H-1,2,3-triazol-2-yl)pyridin-3-yl)amino)pyridin-2-yl)amino)-1-cyclobutylpropan-2-yl)carbamate | 556 | 1.61 |

TABLE 2-continued

| Reference Example | Structure | Compound name | MS (ESI m/z): (M + H) | RT (min) |
|---|---|---|---|---|
| Reference Example 136-68 | 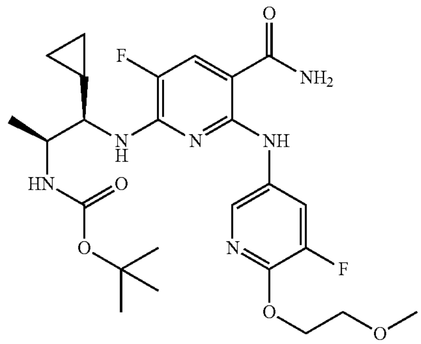 [SMILES: COCCOc1ncc(Nc2nc(N[C@H](C3CC3)[C@H](C)NC(=O)OC(C)(C)C)c(F)cc2C(N)=O)cc1F] | tert-butyl ((1R,2S)-1-((5-carbamoyl-3-fluoro-6-((5-fluoro-6-(2-methoxyethoxy)pyridin-3-yl)amino)pyridin-2-yl)amino)-1-cyclopropylpropan-2-yl)carbamate | 537 | 1.59 |
| Reference Example 136-69 | 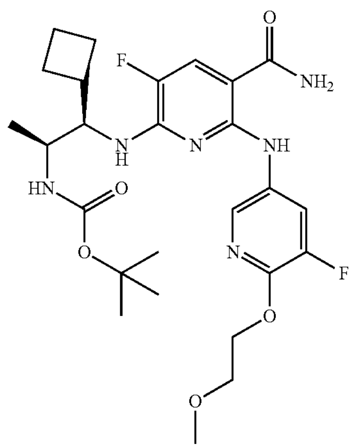 [SMILES: COCCOc1ncc(Nc2nc(N[C@H](C3CCC3)[C@H](C)NC(=O)OC(C)(C)C)c(F)cc2C(N)=O)cc1F] | tert-butyl ((1R,2S)-1-((5-carbamoyl-3-fluoro-6-((5-fluoro-6-(2-methoxyethoxy)pyridin-3-yl)amino)pyridin-2-yl)amino)-1-cyclobutylpropan-2-yl)carbamate | 551 | 1.69 |
| Reference Example 136-70 | 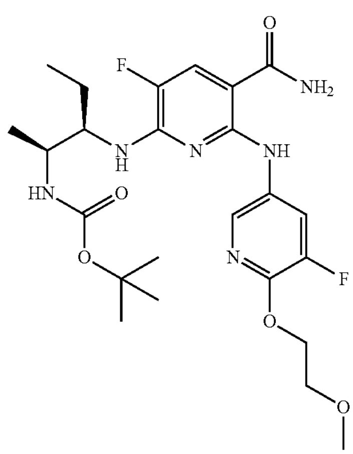 [SMILES: CC[C@@H](Nc1nc(Nc2cnc(OCCOC)c(F)c2)c(C(N)=O)cc1F)[C@H](C)NC(=O)OC(C)(C)C] | tert-butyl ((2S,3R)-3-((5-carbamoyl-3-fluoro-6-((5-fluoro-6-(2-methoxyethoxy)pyridin-3-yl)amino)pyridin-2-yl)amino)pentan-2-yl)carbamate | 525 | 1.57 |

TABLE 2-continued

| Reference Example | Structure | Compound name | MS (ESI m/z): (M + H) | RT (min) |
|---|---|---|---|---|
| Reference Example 136-71 | 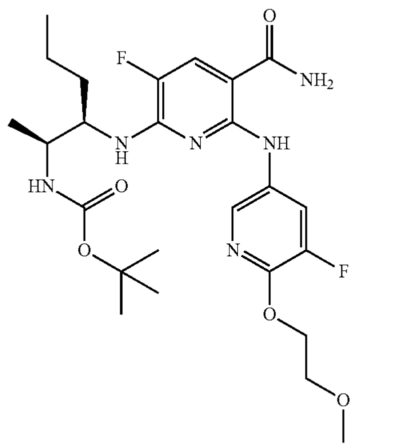 | tert-butyl ((2S,3R)-3-((5-carbamoyl-3-fluoro-6-((5-fluoro-6-(2-methoxyethoxy)pyridin-3-yl)amino)pyridin-2-yl)amino)hexan-2-yl)carbamate | 539 | 1.66 |
| Reference Example 136-72 | 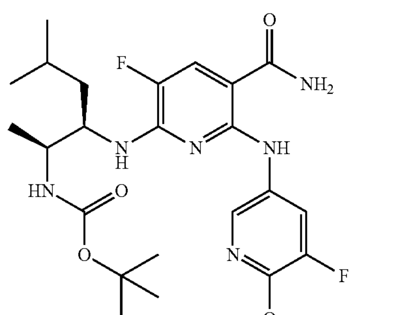 | tert-butyl ((2S,3R)-3-((5-carbamoyl-3-fluoro-6-((5-fluoro-6-(2-methoxyethoxy)pyridin-3-yl)amino)pyridin-2-yl)amino)-5-methylhexan-2-yl)carbamate | 553 | 1.72 |
| Reference Example 136-73 | 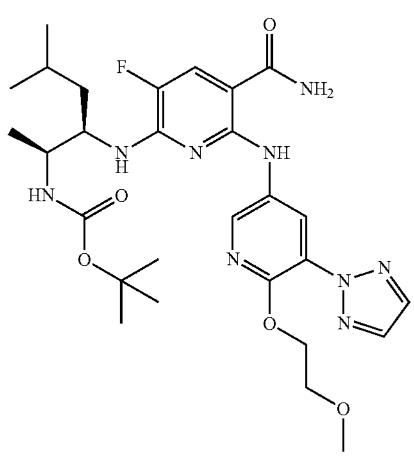 [SMILES: COCCOc1ncc(Nc2nc(N[C@H](CC(C)C)[C@H](C)NC(=O)OC(C)(C)C)c(F)cc2C(N)=O)cc1-n1nccn1] | tert-butyl ((2S,3R)-3-((5-carbamoyl-3-fluoro-6-((6-(2-methoxyethoxy)-5-(2H-1,2,3-triazol-2-yl)pyridin-3-yl)amino)pyridin-2-yl)amino)-5-methylhexan-2-yl)carbamate | 602 | 1.71 |

TABLE 2-continued

| Reference Example | Structure | Compound name | MS (ESI m/z): (M + H) | RT (min) |
|---|---|---|---|---|
| Reference Example 136-74 | 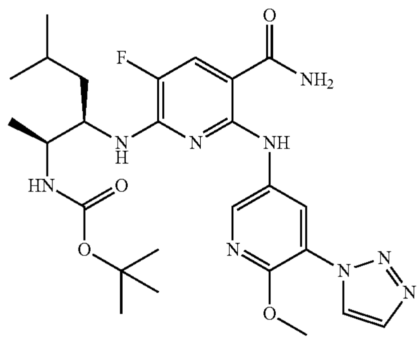 [SMILES: COc1ncc(Nc2nc(N[C@H](CC(C)C)[C@H](C)NC(=O)OC(C)(C)C)c(F)cc2C(N)=O)cc1-n1ccnn1] | tert-butyl ((2S,3R)-3-((5-carbamoyl-3-fluoro-6-((6-methoxy-5-(1H-1,2,3-triazol-1-yl)pyridin-3-yl)amino)pyridin-2-yl)amino)-5-methylhexan-2-yl)carbamate | 558 | 1.71 |
| Reference Example 136-75 | 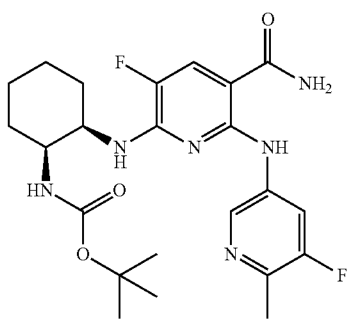 [SMILES: Cc1ncc(Nc2nc(N[C@@H]3CCCC[C@@H]3NC(=O)OC(C)(C)C)c(F)cc2C(N)=O)cc1F] | tert-butyl ((1S,2R)-2-((5-carbamoyl-3-fluoro-6-((5-fluoro-6-methylpyridin-3-yl)amino)pyridin-2-yl)amino)cyclohexyl)carbamate | 477 | 1.57 |
| Reference Example 136-76 | 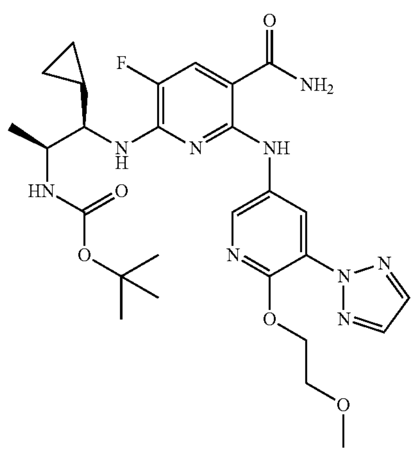 [SMILES: COCCOc1ncc(Nc2nc(N[C@H](C3CC3)[C@H](C)NC(=O)OC(C)(C)C)c(F)cc2C(N)=O)cc1-n1nccn1] | tert-butyl ((1R,2S)-1-((5-carbamoyl-3-fluoro-6-((6-(2-methoxyethoxy)-5-(2H-1,2,3-triazol-2-y)pyridin-3-yl)amino)pyridin-2-yl)amino)-1-cyclopropylpropan-2-yl)carbamate | 586 | 1.55 |
| Reference Example 136-77 | 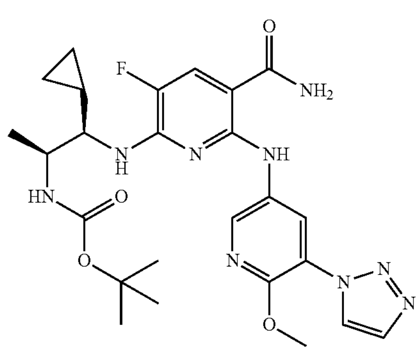 [SMILES: COc1ncc(Nc2nc(N[C@H](C3CC3)[C@H](C)NC(=O)OC(C)(C)C)c(F)cc2C(N)=O)cc1-n1ccnn1] | tert-butyl ((1R,2S)-1-((5-carbamoyl-3-fluoro-6-((6-methoxy-5-(1H-1,2,3-triazol-1-yl)pyridin-3-yl)amino)pyridin-2-yl)amino)-1-cyclopropylpropan-2-yl)carbamate | 542 | 1.56 |

TABLE 2-continued

| Reference Example | Structure | Compound name | MS (ESI m/z): (M + H) | RT (min) |
|---|---|---|---|---|
| Reference Example 136-78 | 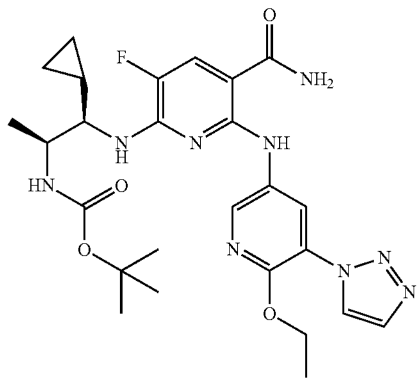 [SMILES: CCOc1ncc(Nc2nc(N[C@H](C3CC3)[C@H](C)NC(=O)OC(C)(C)C)c(F)cc2C(N)=O)cc1-n1ccnn1] | tert-butyl ((1R,2S)-1-((5-carbamoyl-6-((6-ethoxy-5-(1H-1,2,3-triazol-1-yl)pyridin-3-yl)amino)-3-fluoropyridin-2-yl)amino)-1-cyclopropylpropan-2-yl)carbamate | 556 | 1.68 |
| Reference Example 136-79 | 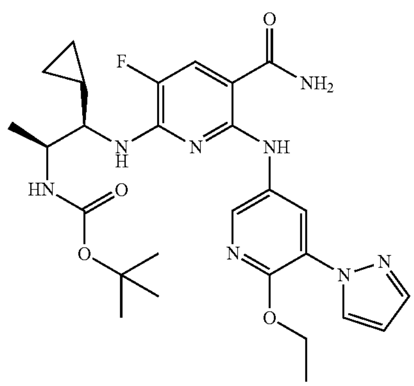 [SMILES: CCOc1ncc(Nc2nc(N[C@H](C3CC3)[C@H](C)NC(=O)OC(C)(C)C)c(F)cc2C(N)=O)cc1-n1cccn1] | tert-butyl ((1R,2S)-1-((5-carbamoyl-6-((6-ethoxy-5-(1H-pyrazol-1-yl)pyridin-3-yl)amino)-3-fluoropyridin-2-yl)amino)-1-cyclopropylpropan-2-yl)carbamate | 555 | 1.85 |
| Reference Example 136-80 | 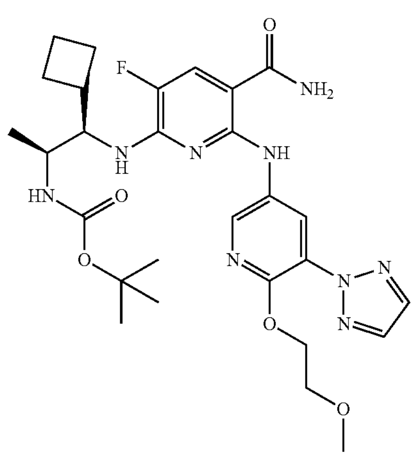 [SMILES: COCCOc1ncc(Nc2nc(N[C@H](C3CCC3)[C@H](C)NC(=O)OC(C)(C)C)c(F)cc2C(N)=O)cc1-n1nccn1] | tert-butyl ((1R,2S)-1-((5-carbamoyl-3-fluoro-6-(((6-(2-methoxyethoxy)-5-(2H-1,2,3-triazol-2-yl)pyridin-3-yl)amino)pyridin-2-yl)amino)-1-cyclobutylpropan-2-yl)carbamate | 600 | 1.65 |

TABLE 2-continued

| Reference Example | Structure | Compound name | MS (ESI m/z): (M + H) | RT (min) |
|---|---|---|---|---|
| Reference Example 136-81 | 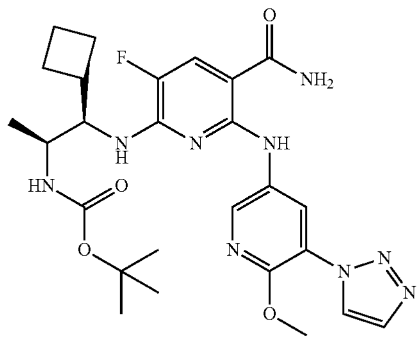 [SMILES: COc1ncc(Nc2nc(N[C@H](C3CCC3)[C@H](C)NC(=O)OC(C)(C)C)c(F)cc2C(N)=O)cc1-n1ccnn1] | tert-butyl ((1R,2S)-1-((5-carbamoyl-3-fluoro-6-((6-methoxy-5-(1H-1,2,3-triazol-1-yl)pyridin-3-yl)amino)pyridin-2-yl)amino)-1-cyclobutylpropan-2-yl)carbamate | 556 | 1.66 |
| Reference Example 136-82 | 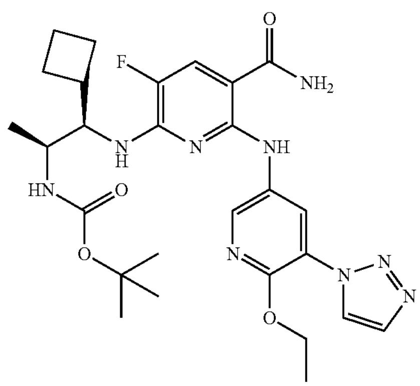 [SMILES: CCOc1ncc(Nc2nc(N[C@H](C3CCC3)[C@H](C)NC(=O)OC(C)(C)C)c(F)cc2C(N)=O)cc1-n1ccnn1] | tert-butyl ((1R,2S)-1-((5-carbamoyl-6-((6-ethoxy-5-(1H-1,2,3-triazol-1-yl)pyridin-3-yl)amino)-3-fluoropyridin-2-yl)amino)-1-cyclobutylpropan-2-yl)carbamate | 570 | 1.77 |
| Reference Example 136-83 | 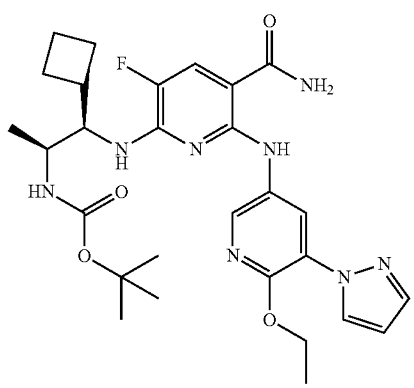 [SMILES: CCOc1ncc(Nc2nc(N[C@H](C3CCC3)[C@H](C)NC(=O)OC(C)(C)C)c(F)cc2C(N)=O)cc1-n1cccn1] | tert-butyl ((1R,2S)-1-((5-carbamoyl-6-((6-ethoxy-5-(1H-pyrazol-1-yl)pyridin-3-yl)amino)-3-fluoropyridin-2-yl)amino)-1-cyclobutylpropan-2-yl)carbamate | 569 | 1.95 |
| Reference Example 136-84 | 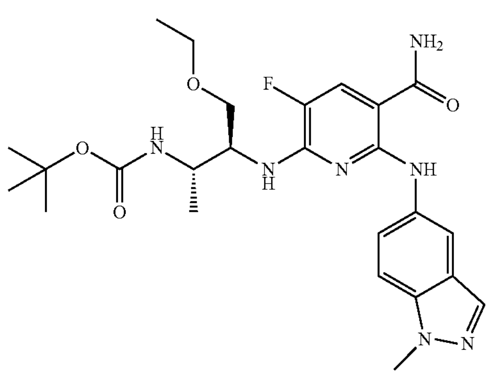 [SMILES: CCOC[C@@H](Nc1nc(Nc2ccc3c(cnn3C)c2)c(C(N)=O)cc1F)[C@H](C)NC(=O)OC(C)(C)C] | tert-butyl ((2S,3S)-3-((5-carbamoyl-3-fluoro-6-((1-methyl-1H-indazol-5-yl)amino)pyridin-2-yl)amino)-4-ethoxybutan-2-yl)carbamate | 516 | 1.53 |

TABLE 2-continued

| Reference Example | Structure | Compound name | MS (ESI m/z): (M + H) | RT (min) |
|---|---|---|---|---|
| Reference Example 136-85 | 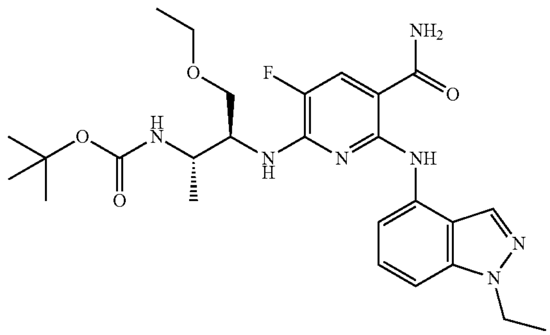 [SMILES: CCOC[C@@H](Nc1nc(Nc2cccc3c2cnn3CC)c(C(N)=O)cc1F)[C@H](C)NC(=O)OC(C)(C)C] | tert-butyl ((2S,3S)-3-((5-carbamoyl-6-((1-ethyl-1H-indazol-4-yl)amino)-3-fluoropyridin-2-yl)amino)-4-ethoxybutan-2-yl)carbamate | 530 | 1.72 |
| Reference Example 136-86 | 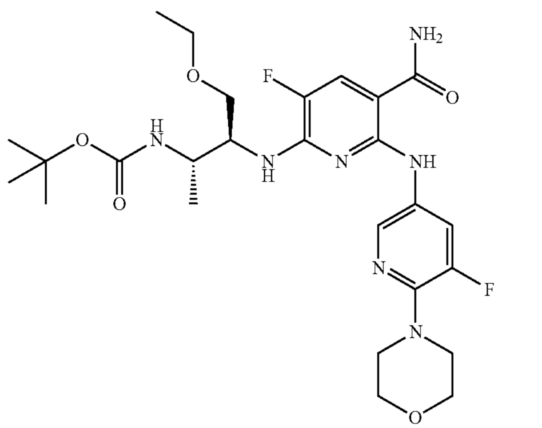 [SMILES: CCOC[C@@H](Nc1nc(Nc2cnc(N3CCOCC3)c(F)c2)c(C(N)=O)cc1F)[C@H](C)NC(=O)OC(C)(C)C] | tert-butyl ((2S,3S)-3-((5-carbamoyl-3-fluoro-6-((5-fluoro-6-morpholinopyridin-3-yl)amino)pyridin-2-yl)amino)-4-ethoxybutan-2-yl)carbamate | 566 | 1.62 |
| Reference Example 136-87 | 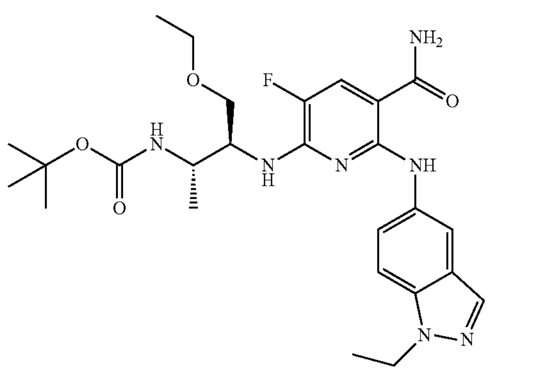 [SMILES: CCOC[C@@H](Nc1nc(Nc2ccc3c(cnn3CC)c2)c(C(N)=O)cc1F)[C@H](C)NC(=O)OC(C)(C)C] | tert-butyl ((2S,3S)-3-((5-carbamoyl-6-((1-ethyl-1H-indazol-5-yl)amino)-3-fluoropyridin-2-yl)amino)-4-ethoxybutan-2-yl)carbamate | 530 | 1.62 |
| Reference Example 136-88 | 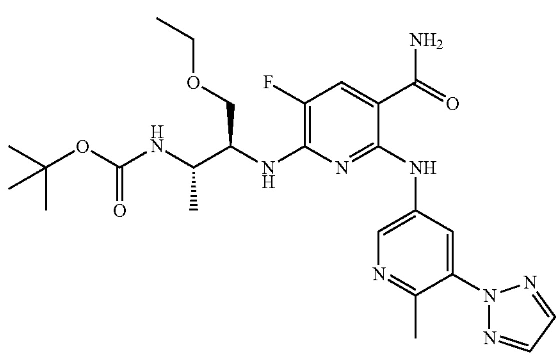 [SMILES: CCOC[C@@H](Nc1nc(Nc2cnc(C)c(-n3nccn3)c2)c(C(N)=O)cc1F)[C@H](C)NC(=O)OC(C)(C)C] | tert-butyl ((2S,3S)-3-((5-carbamoyl-3-fluoro-6-((6-methyl-5-(2H-1,2,3-triazol-2-yl)pyridin-3-yl)amino)pyridin-2-yl)amino)-4-ethoxybutan-2-yl)carbamate | 544 | 1.56 |

TABLE 2-continued

| Reference Example | Compound name | MS (ESI m/z): (M + H) | RT (min) |
|---|---|---|---|
| Reference Example 136-89 | tert-butyl ((2S,3S)-3-((5-carbamoyl-6-((1,3-dimethyl-1H-indazol-5-yl)amino)-3-fluoropyridin-2-yl)amino)-4-methoxybutan-2-yl)carbamate | 516 | 1.49 |
| Reference Example 136-90 | tert-butyl ((2S,3R)-3-((5-carbamoyl-6-((6-ethoxy-5-(1H-1,2,3-triazol-1-yl)pyridin-3-yl)amino)-3-fluoropyridin-2-yl)amino)-5-methylhexan-2-yl)carbamate | 572 | 1.84 |
| Reference Example 136-91 | tert-butyl ((2S,3R)-3-((5-carbamoyl-6-((6-ethoxy-5-(1H-pyrazol-1-yl)pyridin-3-yl)amino)-3-fluoropyridin-2-yl)amino)pentan-2-yl)carbamate | 543 | 1.89 |
| Reference Example 136-92 | tert-butyl ((2S,3R)-3-((5-carbamoyl-6-((6-ethoxy-5-(1H-pyrazol-1-yl)pyridin-3-yl)amino)-3-fluoropyridin-2-yl)amino)hexan-2-yl)carbamate | 557 | 1.97 |

TABLE 2-continued

| Reference Example | Structure | Compound name | MS (ESI m/z): (M + H) | RT (min) |
|---|---|---|---|---|
| Reference Example 136-93 | 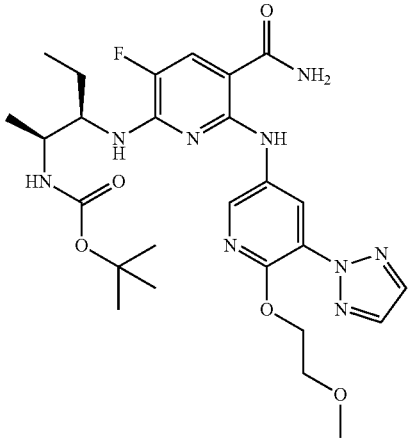 [SMILES: CC[C@@H](Nc1nc(Nc2cnc(OCCOC)c(-n3nccn3)c2)c(C(N)=O)cc1F)[C@H](C)NC(=O)OC(C)(C)C] | tert-butyl ((2S,3R)-3-((5-carbamoyl-3-fluoro-6-((6-(2-methoxyethoxy)-5-(2H-1,2,3-triazol-2-yl)pyridin-3-yl)amino)pyridin-2-yl)amino)pentan-2-yl)carbamate | 574 | 1.59 |
| Reference Example 136-94 | 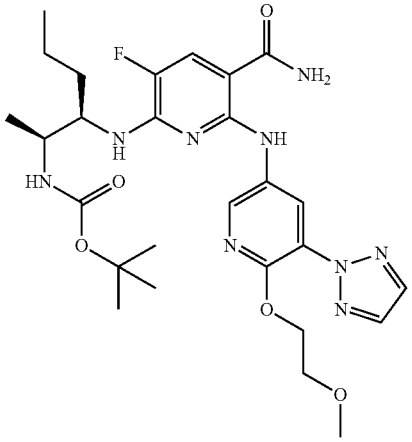 | tert-butyl ((2S,3R)-3-((5-carbamoyl-3-fluoro-6-((6-(2-methoxyethoxy)-5-(2H-1,2,3-triazol-2-yl)pyridin-3-yl)amino)pyridin-2-yl)amino)hexan-2-yl)carbamate | 588 | 1.67 |
| Reference Example 136-95 | 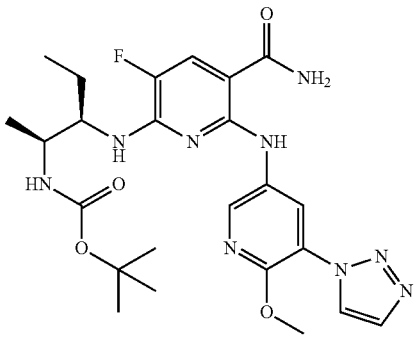 [SMILES: CC[C@@H](Nc1nc(Nc2cnc(OC)c(-n3ccnn3)c2)c(C(N)=O)cc1F)[C@H](C)NC(=O)OC(C)(C)C] | tert-butyl ((2S,3R)-3-((5-carbamoyl-3-fluoro-6-((6-methoxy-5-(1H-1,2,3-triazol-1-yl)pyridin-3-yl)amino)pyridin-2-yl)amino)pentan-2-yl)carbamate | 530 | 1.59 |

TABLE 2-continued

| Reference Example | Structure | Compound name | MS (ESI m/z): (M + H) | RT (min) |
|---|---|---|---|---|
| Reference Example 136-96 | 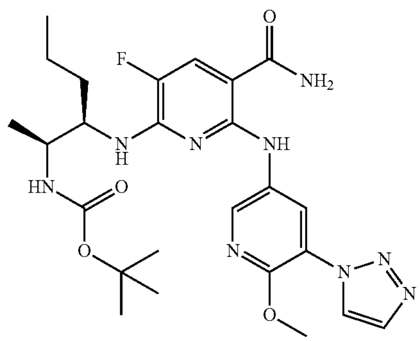 [SMILES: CCC[C@@H](Nc1nc(Nc2cnc(OC)c(-n3ccnn3)c2)c(C(N)=O)cc1F)[C@H](C)NC(=O)OC(C)(C)C] | tert-butyl ((2S,3R)-3-((5-carbamoyl-3-fluoro-6-((6-methoxy-5-(1H-1,2,3-triazol-1-yl)pyridin-3-yl)amino)pyridin-2-yl)amino)hexan-2-yl)carbamate | 544 | 1.67 |
| Reference Example 136-97 | 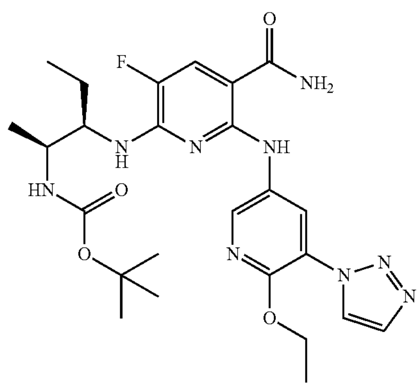 [SMILES: CCOc1ncc(Nc2nc(N[C@H](CC)[C@H](C)NC(=O)OC(C)(C)C)c(F)cc2C(N)=O)cc1-n1ccnn1] | tert-butyl ((2S,3R)-3-((5-carbamoyl-6-((6-ethoxy-5-(1H-1,2,3-triazol-1-yl)pyridin-3-yl)amino)-3-fluoropyridin-2-yl)amino)pentan-2-yl)carbamate | 544 | 1.70 |
| Reference Example 136-98 | 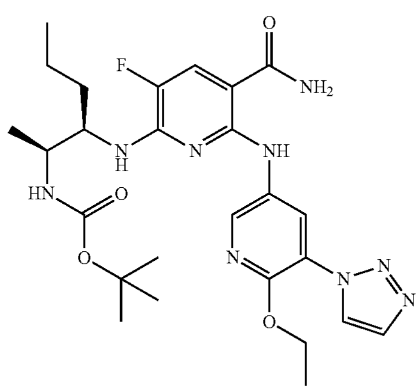 [SMILES: CCC[C@@H](Nc1nc(Nc2cnc(OCC)c(-n3ccnn3)c2)c(C(N)=O)cc1F)[C@H](C)NC(=O)OC(C)(C)C] | tert-butyl ((2S,3R)-3-((5-carbamoyl-6-((6-ethoxy-5-(1H-1,2,3-triazol-1-yl)pyridin-3-yl)amino)-3-fluoropyridin-2-yl)amino)hexan-2-yl)carbamate | 558 | 1.78 |
| Reference Example 136-99 | 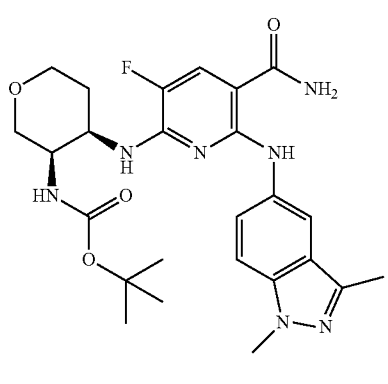 [SMILES: Cc1nn(C)c2ccc(Nc3nc(N[C@@H]4CCOC[C@@H]4NC(=O)OC(C)(C)C)c(F)cc3C(N)=O)cc12] | tert-butyl ((3R,4R)-4-((5-carbamoyl-6-((1,3-dimethyl-1H-indazol-5-yl)amino)-3-fluoropyridin-2-yl)amino)tetrahydro-2H-pyran-3-yl)carbamate | 514 | 1.32 |

TABLE 2-continued

| Reference Example | Structure | Compound name | MS (ESI m/z): (M + H) | RT (min) |
|---|---|---|---|---|
| Reference Example 136-100 | 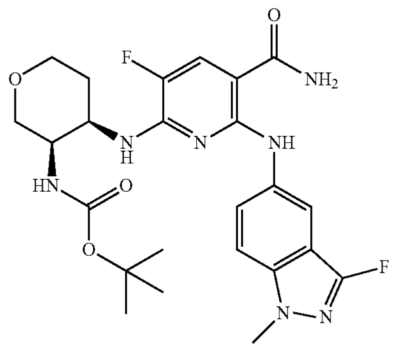 [SMILES: Cn1nc(F)c2cc(Nc3nc(N[C@@H]4CCOC[C@@H]4NC(=O)OC(C)(C)C)c(F)cc3C(N)=O)ccc21] | tert-butyl ((3R,4R)-4-((5-carbamoyl-3-fluoro-6-((3-fluoro-1-methyl-1H-indazol-5-yl)amino)pyridin-2-yl)amino)tetrahydro-2H-pyran-3-yl)carbamate | 518 | 1.44 |
| Reference Example 136-101 | 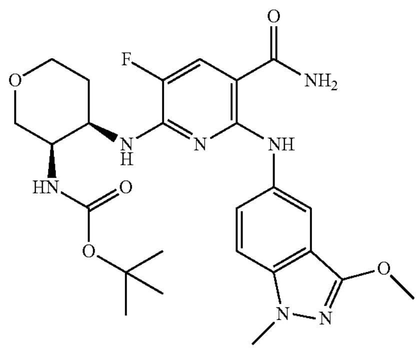 [SMILES: COc1nn(C)c2ccc(Nc3nc(N[C@@H]4CCOC[C@@H]4NC(=O)OC(C)(C)C)c(F)cc3C(N)=O)cc12] | tert-butyl ((3R,4R)-4-((5-carbamoyl-3-fluoro-6-((3-methoxy-1-methyl-1H-indazol-5-yl)amino)pyridin-2-yl)amino)tetrahydro-2H-pyran-3-yl)carbamate | 530 | 1.37 |
| Reference Example 136-102 | 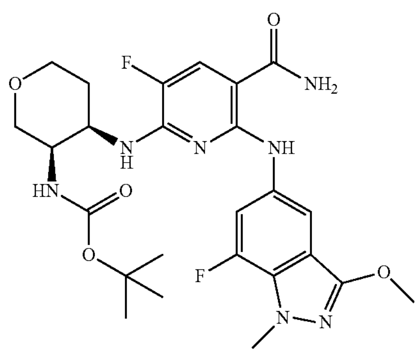 [SMILES: COc1nn(C)c2c(F)cc(Nc3nc(N[C@@H]4CCOC[C@@H]4NC(=O)OC(C)(C)C)c(F)cc3C(N)=O)cc12] | tert-butyl ((3R,4R)-4-((5-carbamoyl-3-fluoro-6-((7-fluoro-3-methoxy-1-methyl-1H-indazol-5-yl)amino)pyridin-2-yl)amino)tetrahydro-2H-pyran-3-yl)carbamate | 548 | 1.52 |
| Reference Example 136-103 | 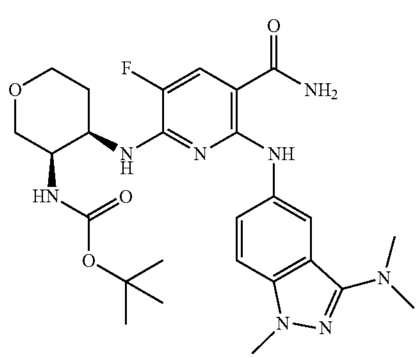 [SMILES: CN(C)c1nn(C)c2ccc(Nc3nc(N[C@@H]4CCOC[C@@H]4NC(=O)OC(C)(C)C)c(F)cc3C(N)=O)cc12] | tert-butyl ((3R,4R)-4-((5-carbamoyl-6-((3-(dimethylamino)-1-methyl-1H-indazol-5-yl)amino)-3-fuoropyridin-2-yl)amino)tetrahydro-2H-pyran-3-yl)carbamate | 543 | 1.24 |

TABLE 2-continued

| Reference Example | Structure | Compound name | MS (ESI m/z): (M + H) | RT (min) |
|---|---|---|---|---|
| Reference Example 136-104 | 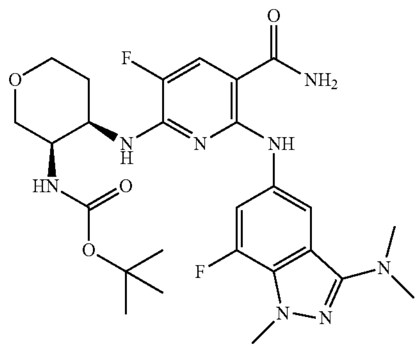 [SMILES: CN(C)c1nn(C)c2c(F)cc(Nc3nc(N[C@@H]4CCOC[C@@H]4NC(=O)OC(C)(C)C)c(F)cc3C(N)=O)cc12] | tert-butyl ((3R,4R)-4-((5-carbamoyl-6-((3-(dimethylamino)-7-fluoro-1-methyl-1H-indazol-5-yl)amino)-3-fluoropyridin-2-yl)amino)tetrahydro-2H-pyran-3-yl)carbamate | 561 | 1.41 |
| Reference Example 136-105 | 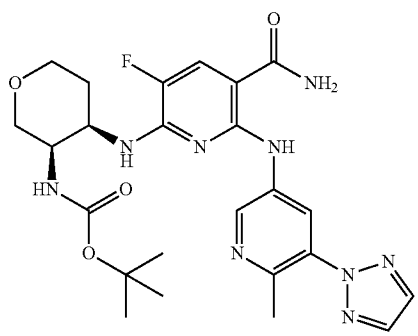 [SMILES: Cc1ncc(Nc2nc(N[C@@H]3CCOC[C@@H]3NC(=O)OC(C)(C)C)c(F)cc2C(N)=O)cc1-n1nccn1] | tert-butyl ((3R,4R)-4-((5-carbamoyl-3-fluoro-6-((6-methyl-5-(2H-1,2,3-triazol-2-yl)pyridin-3-yl)amino)pyridin-2-yl)amino)tetrahydro-2H-pyran-3-yl)carbamate | 528 | 1.17 |
| Reference Example 136-106 | 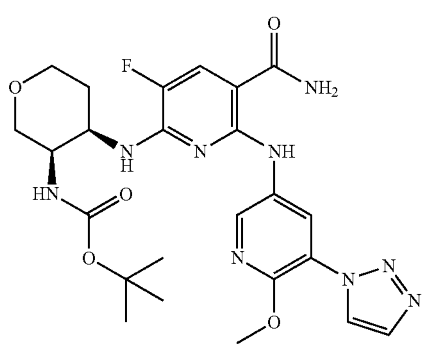 [SMILES: COc1ncc(Nc2nc(N[C@@H]3CCOC[C@@H]3NC(=O)OC(C)(C)C)c(F)cc2C(N)=O)cc1-n1ccnn1] | tert-butyl ((3R,4R)-4-((5-carbamoyl-3-fluoro-6-((6-methoxy-5-(1H-1,2,3-triazol-1-yl)pyridin-3-yl)amino)pyridin-2-yl)amino)tetrahydro-2H-pyran-3-yl)carbamate | 544 | 1.22 |
| Reference Example 136-107 | 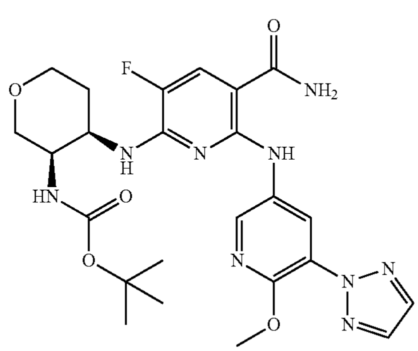 [SMILES: COc1ncc(Nc2nc(N[C@@H]3CCOC[C@@H]3NC(=O)OC(C)(C)C)c(F)cc2C(N)=O)cc1-n1nccn1] | tert-butyl ((3R,4R)-4-((5-carbamoyl-3-fluoro-6-((6-methoxy-5-(2H-1,2,3-triazol-2-yl)pyridin-3-yl)amino)pyridin-2-yl)amino)tetrahydro-2H-pyran-3-yl)carbamate | 544 | 1.24 |

TABLE 2-continued

| Reference Example | Structure | Compound name | MS (ESI m/z): (M + H) | RT (min) |
|---|---|---|---|---|
| Reference Example 136-108 | 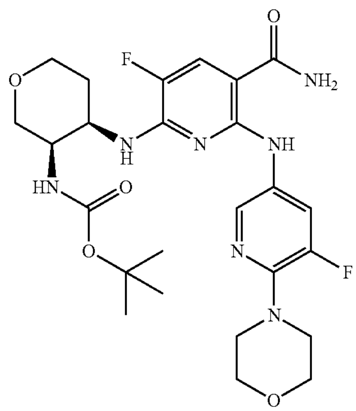 [SMILES: CC(C)(C)OC(=O)N[C@H]1COCC[C@H]1Nc1nc(Nc2cnc(N3CCOCC3)c(F)c2)c(C(N)=O)cc1F] | tert-butyl ((3R,4R)-4-((5-carbamoyl-3-fluoro-6-((5-fluoro-6-morpholinopyridin-3-yl)amino)pyridin-2-yl)amino)tetrahydro-2H-pyran-3-yl)carbamate | 550 | 1.30 |
| Reference Example 136-109 | 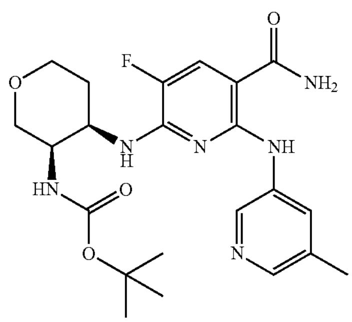 [SMILES: Cc1cncc(Nc2nc(N[C@@H]3CCOC[C@@H]3NC(=O)OC(C)(C)C)c(F)cc2C(N)=O)c1] | tert-butyl ((3R,4R)-4-((5-carbamoyl-3-fluoro-6-((5-methylpyridin-3-yl)amino)pyridin-2-yl)amino)tetrahydro-2H-pyran-3-yl)carbamate | 461 | 0.88 |
| Reference Example 136-110 | 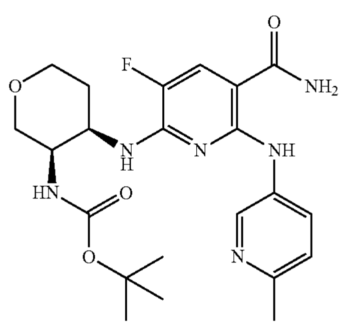 [SMILES: Cc1ccc(Nc2nc(N[C@@H]3CCOC[C@@H]3NC(=O)OC(C)(C)C)c(F)cc2C(N)=O)cn1] | tert-butyl ((3R,4R)-4-((5-carbamoyl-3-fluoro-6-((6-methylpyridin-3-yl)amino)pyridin-2-yl)amino)tetrahydro-2H-pyran-3-yl)carbamate | 461 | 0.86 |
| Reference Example 136-111 | 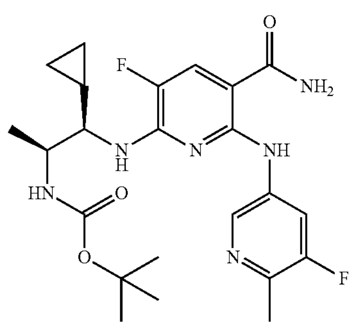 [SMILES: Cc1ncc(Nc2nc(N[C@H](C3CC3)[C@H](C)NC(=O)OC(C)(C)C)c(F)cc2C(N)=O)cc1F] | tert-butyl ((1R,2S)-1-((5-carbamoyl-3-fluoro-6-((5-fluoro-6-methylpyridin-3-yl)amino)pyridin-2-yl)amino)-1-cyclopropylpropan-2-yl)carbamate | 477 | 1.55 |

TABLE 2-continued

| Reference Example | Structure | Compound name | MS (ESI m/z): (M + H) | RT (min) |
|---|---|---|---|---|
| Reference Example 136-112 | 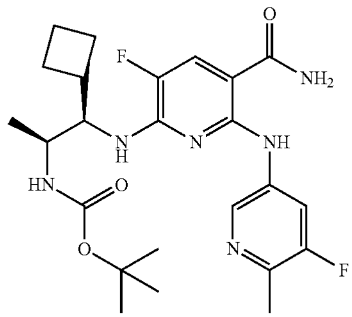 [SMILES: Cc1ncc(Nc2nc(N[C@H](C3CCC3)[C@H](C)NC(=O)OC(C)(C)C)c(F)cc2C(N)=O)cc1F] | tert-butyl ((1R,2S)-1-((5-carbamoyl-3-fluoro-6-((5-fluoro-6-methylpyridin-3-yl)amino)pyridin-2-yl)amino)-1-cyclobutylpropan-2-yl)carbamate | 491 | 1.67 |
| Reference Example 136-113 | 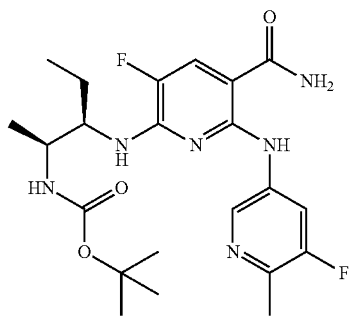 [SMILES: CC[C@@H](Nc1nc(Nc2cnc(C)c(F)c2)c(C(N)=O)cc1F)[C@H](C)NC(=O)OC(C)(C)C] | tert-butyl ((2S,3R)-3-((5-carbamoyl-3-fluoro-6-((5-fluoro-6-methylpyridin-3-yl)amino)pyridin-2-yl)amino)pentan-2-yl)carbamate | 465 | 1.43 |
| Reference Example 136-114 | 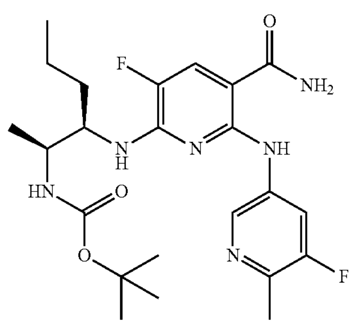 [SMILES: CCC[C@@H](Nc1nc(Nc2cnc(C)c(F)c2)c(C(N)=O)cc1F)[C@H](C)NC(=O)OC(C)(C)C] | tert-butyl ((2S,3R)-3-((5-carbamoyl-3-fluoro-6-((5-fluoro-6-methylpyridin-3-yl)amino)pyridin-2-yl)amino)hexan-2-yl)carbamate | 479 | 1.53 |
| Reference Example 136-115 | 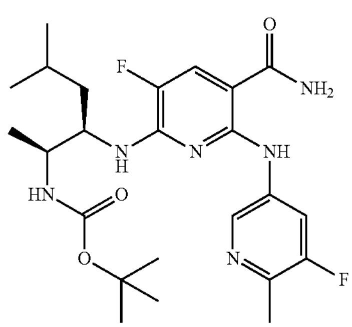 [SMILES: Cc1ncc(Nc2nc(N[C@H](CC(C)C)[C@H](C)NC(=O)OC(C)(C)C)c(F)cc2C(N)=O)cc1F] | tert-butyl ((2S,3R)-3-((5-carbamoyl-3-fluoro-6-((5-fluoro-6-methylpyridin-3-yl)amino)pyridin-2-yl)amino)-5-methylhexan-2-yl)carbamate | 493 | 1.61 |

TABLE 2-continued

| Reference Example | Structure | Compound name | MS (ESI m/z): (M + H) | RT (min) |
|---|---|---|---|---|
| Reference Example 136-116 | 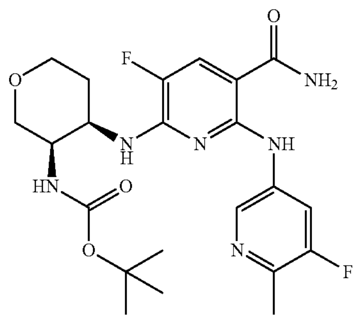 [SMILES: Cc1ncc(Nc2nc(N[C@@H]3CCOC[C@@H]3NC(=O)OC(C)(C)C)c(F)cc2C(N)=O)cc1F] | tert-butyl ((3R,4R)-4-((5-carbamoyl-3-fluoro-6-((5-fluoro-6-methylpyridin-3-yl)amino)pyridin-2-yl)amino)tetrahydro-2H-pyran-3-yl)carbamate | 479 | 1.24 |
| Reference Example 136-117 | 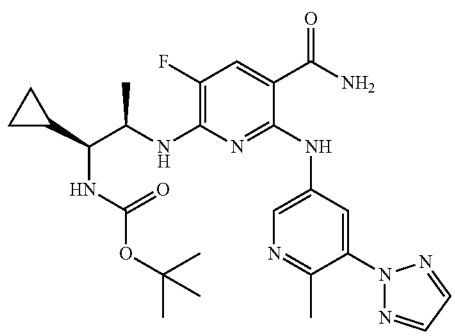 [SMILES: Cc1ncc(Nc2nc(N[C@H](C)[C@@H](NC(=O)OC(C)(C)C)C3CC3)c(F)cc2C(N)=O)cc1-n1nccn1] | tert-butyl ((1S,2R)-2-((5-carbamoyl-3-fluoro-6-((6-methyl-5-(2H-1,2,3-triazol-2-yl)pyridin-3-y)amino)pyridin-2-yl)amino)-1-cyclopropylpropyl)carbamate | 526 | 1.48 |
| Reference Example 136-118 | 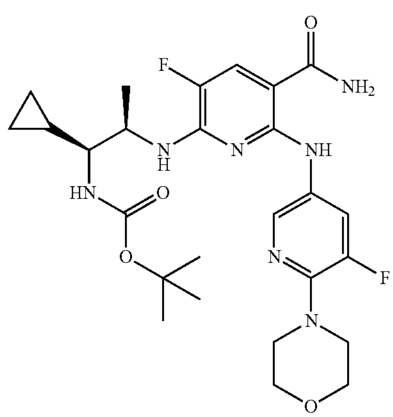 [SMILES: C[C@@H](Nc1nc(Nc2cnc(N3CCOCC3)c(F)c2)c(C(N)=O)cc1F)[C@@H](NC(=O)OC(C)(C)C)C1CC1] | tert-butyl ((1S,2R)-2-((5-carbamoyl-3-fluoro-6-((5-fluoro-6-morpholinopyridin-3-yl)amino)pyridin-2-yl)amino)-1-cyclopropylpropyl)carbamate | 548 | 1.54 |
| Reference Example 136-119 | 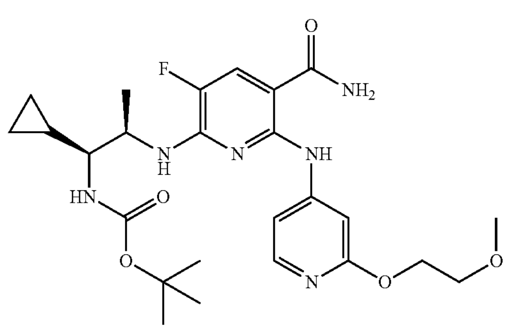 [SMILES: COCCOc1cc(Nc2nc(N[C@H](C)[C@@H](NC(=O)OC(C)(C)C)C3CC3)c(F)cc2C(N)=O)ccn1] | tert-butyl (1S,2R)-2-((5-carbamoyl-3-fluoro-6-((2-(2-methoxyethoxy)pyridin-4-yl)amino)pyridin-2-yl)amino)-1-cyclopropylpropyl)carbamate | 519 | 1.16 |

TABLE 2-continued

| Reference Example | Structure | Compound name | MS (ESI m/z): (M + H) | RT (min) |
|---|---|---|---|---|
| Reference Example 136-120 | 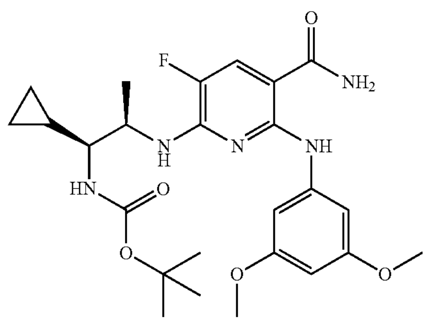 [SMILES: COc1cc(Nc2nc(N[C@H](C)[C@@H](NC(=O)OC(C)(C)C)C3CC3)c(F)cc2C(N)=O)cc(OC)c1] | tert-butyl ((1S,2R)-2-((5-carbamoyl-6-((3,5-dimethoxyphenyl)amino)-3-fluoropyridin-2-yl)amino)-1-cyclopropylpropyl)carbamate | 504 | 1.67 |
| Reference Example 136-121 | 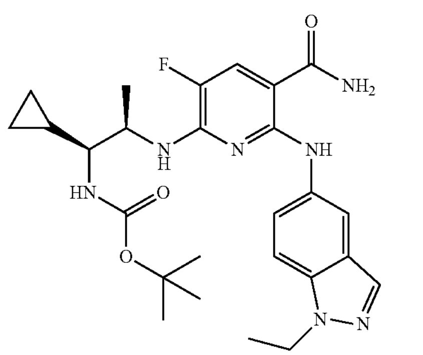 [SMILES: CCn1ncc2cc(Nc3nc(N[C@H](C)[C@@H](NC(=O)OC(C)(C)C)C4CC4)c(F)cc3C(N)=O)ccc21] | tert-butyl ((1S,2R)-2-((5-carbamoyl-6-((1-ethyl-1H-indazol-5-yl)amino)-3-fluoropyridin-2-yl)amino)-1-cyclopropylpropyl)carbamate | 512 | — |
| Reference Example 136-122 | 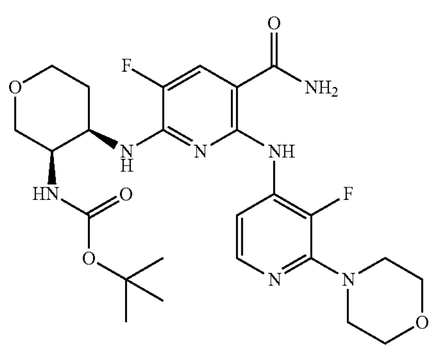 [SMILES: CC(C)(C)OC(=O)N[C@H]1COCC[C@H]1Nc1nc(Nc2ccnc(N3CCOCC3)c2F)c(C(N)=O)cc1F] | tert-butyl ((3R,4R)-4-((5-carbamoyl-3-fluoro-6-((3-fluoro-2-morpholinopyridin-4-yl)amino)pyridin-2-yl)amino)tetrahydro-2H-pyran-3-yl)carbamate | 550 | 1.05 |
| Reference Example 136-123 | 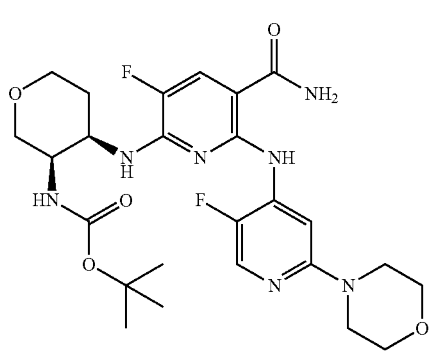 [SMILES: CC(C)(C)OC(=O)N[C@H]1COCC[C@H]1Nc1nc(Nc2cc(N3CCOCC3)ncc2F)c(C(N)=O)cc1F] | tert-butyl ((3R,4R)-4-((5-carbamoyl-3-fluoro-6-((5-fluoro-2-morpholinopyridin-4-yl)amino)pyridin-2-yl)amino)tetrahydro-2H-pyran-3-yl)carbamate | 550 | 0.99 |

TABLE 2-continued

| Reference Example | Structure | Compound name | MS (ESI m/z): (M + H) | RT (min) |
|---|---|---|---|---|
| Reference Example 136-124 | 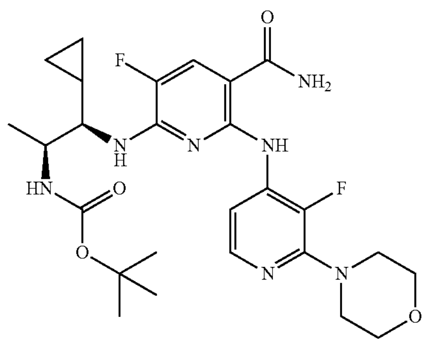 [SMILES: C[C@H](NC(=O)OC(C)(C)C)[C@H](Nc1nc(Nc2ccnc(N3CCOCC3)c2F)c(C(N)=O)cc1F)C1CC1] | tert-butyl ((1R,2S)-1-((5-carbamoyl-3-fluoro-6-((3-fluoro-2-morpholinopyridin-4-yl)amino)pyridin-2-yl)amino)-1-cyclopropylpropan-2-yl)carbamate | 548 | 1.21 |
| Reference Example 136-125 | 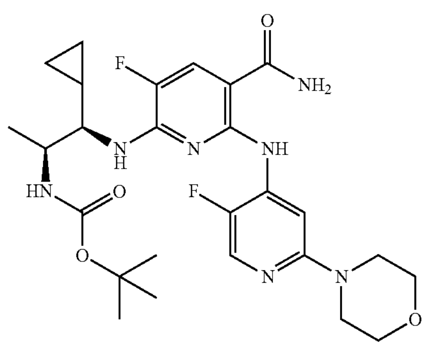 [SMILES: C[C@H](NC(=O)OC(C)(C)C)[C@H](Nc1nc(Nc2cc(N3CCOCC3)ncc2F)c(C(N)=O)cc1F)C1CC1] | tert-butyl ((1R,2S)-1-((5-carbamoyl-3-fluoro-6-((5-fluoro-2-morpholinopyridin-4-yl)amino)pyridin-2-yl)amino)-1-cyclopropylpropan-2-yl)carbamate | 548 | 1.15 |
| Reference Example 136-126 | 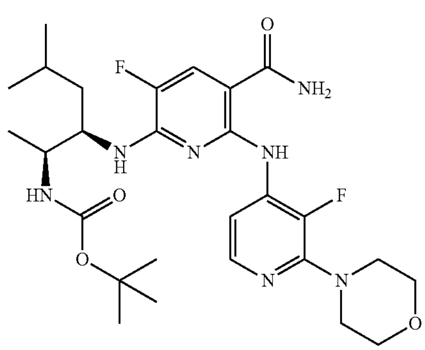 [SMILES: CC(C)C[C@@H](Nc1nc(Nc2ccnc(N3CCOCC3)c2F)c(C(N)=O)cc1F)[C@H](C)NC(=O)OC(C)(C)C] | tert-butyl ((2S,3R)-3-((5-carbamoyl-3-fluoro-6-((3-fluoro-2-morpholinopyridin-4-yl)amino)pyridin-2-yl)amino)-5-methylhexan-2-yl)carbamate | 564 | 1.34 |
| Reference Example 136-127 | 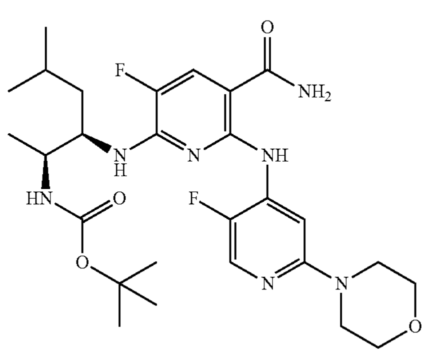 [SMILES: CC(C)C[C@@H](Nc1nc(Nc2cc(N3CCOCC3)ncc2F)c(C(N)=O)cc1F)[C@H](C)NC(=O)OC(C)(C)C] | tert-butyl ((2S,3R)-3-((5-carbamoyl-3-fluoro-6-((5-fluoro-2-morpholinopyridin-4-yl)amino)pyridin-2-yl)amino)-5-methylhexan-2-yl)carbamate | 564 | 1.26 |

TABLE 2-continued

| Reference Example | Structure | Compound name | MS (ESI m/z): (M + H) | RT (min) |
|---|---|---|---|---|
| Reference Example 136-128 | 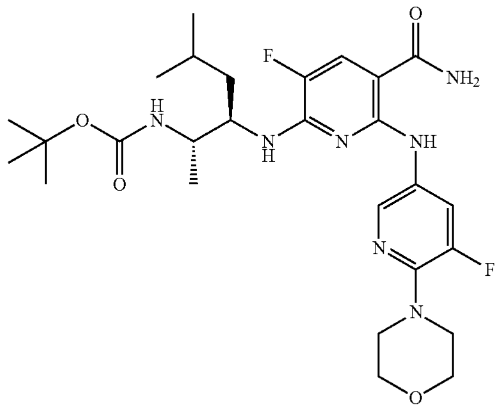 [SMILES: CC(C)C[C@@H](Nc1nc(Nc2cnc(N3CCOCC3)c(F)c2)c(C(N)=O)cc1F)[C@H](C)NC(=O)OC(C)(C)C] | tert-butyl ((2S,3R)-3-((5-carbamoyl-3-fluoro-6-((5-fluoro-6-morpholinopyridin-3-yl)amino)pyridin-2-yl)amino)-5-methylhexan-2-yl)carbamate | 564 | 1.67 |
| Reference Example 136-129 | 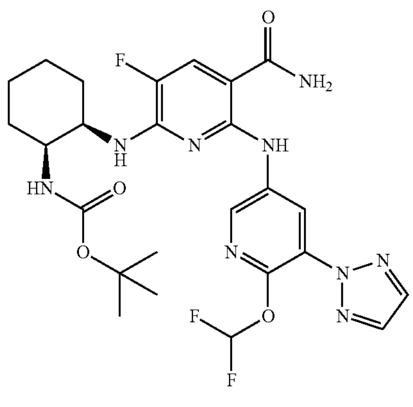 [SMILES: CC(C)(C)OC(=O)N[C@H]1CCCC[C@H]1Nc1nc(Nc2cnc(OC(F)F)c(-n3nccn3)c2)c(C(N)=O)cc1F] | tert-butyl ((1S,2R)-2-((5-carbamoyl-6-((6-(difluoromethoxy)-5-(2H-1,2,3-triazol-2-yl)pyridin-3-yl)amino)-3-fluoropyridin-2-yl)amino)cyclohexyl)carbamate | 578 | 1.67 |
| Reference Example 136-130 | 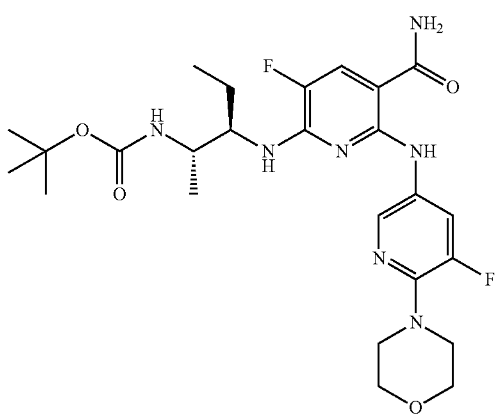 [SMILES: CC[C@@H](Nc1nc(Nc2cnc(N3CCOCC3)c(F)c2)c(C(N)=O)cc1F)[C@H](C)NC(=O)OC(C)(C)C] | tert-butyl ((2S,3R)-3-((5-carbamoyl-3-fluoro-6-((5-fluoro-6-morpholinopyridin-3-yl)amino)pyridin-2-yl)amino)pentan-2-yl)carbamate | 536 | 1.51 |

TABLE 2-continued

| Reference Example | Structure | Compound name | MS (ESI m/z): (M + H) | RT (min) |
|---|---|---|---|---|
| Reference Example 136-131 | 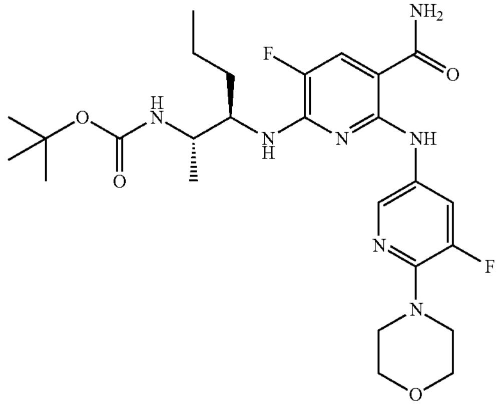 [SMILES: CCC[C@@H](Nc1nc(Nc2cnc(N3CCOCC3)c(F)c2)c(C(N)=O)cc1F)[C@H](C)NC(=O)OC(C)(C)C] | tert-butyl ((2S,3R)-3-((5-carbamoyl-3-fluoro-6-((5-fluoro-6-morpholinopyridin-3-yl)amino)pyridin-2-yl)amino)hexan-2-yl)carbamate | 550 | 1.59 |
| Reference Example 136-132 | 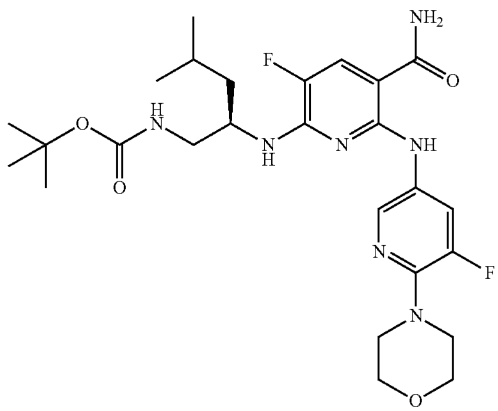 [SMILES: CC(C)C[C@H](CNC(=O)OC(C)(C)C)Nc1nc(Nc2cnc(N3CCOCC3)c(F)c2)c(C(N)=O)cc1F] | (R)-tert-butyl (2-((5-carbamoyl-3-fluoro-6-((5-fluoro-6-morpholinopyridin-3-yl)amino)pyridin-2-yl)amino)-4-methylpentyl)carbamate | 550 | 1.63 |
| Reference Example 136-133 | 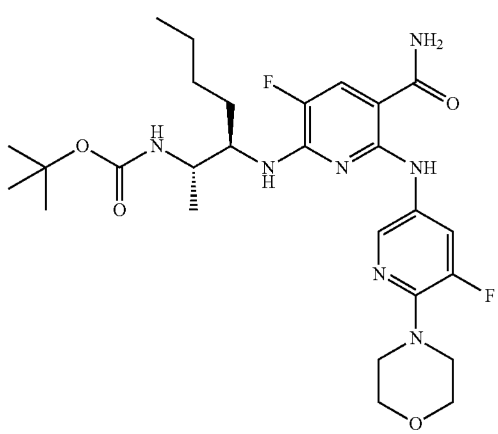 [SMILES: CCCC[C@@H](Nc1nc(Nc2cnc(N3CCOCC3)c(F)c2)c(C(N)=O)cc1F)[C@H](C)NC(=O)OC(C)(C)C] | tert-butyl ((2S,3R)-3-((5-carbamoyl-3-fluoro-6-((5-fluoro-6-morpholinopyridin-3-yl)amino)pyridin-2-yl)amino)heptan-2-yl)carbamate | 564 | 1.69 |

TABLE 2-continued

| Reference Example | Structure | Compound name | MS (ESI m/z): (M + H) | RT (min) |
|---|---|---|---|---|
| Reference Example 136-134 | 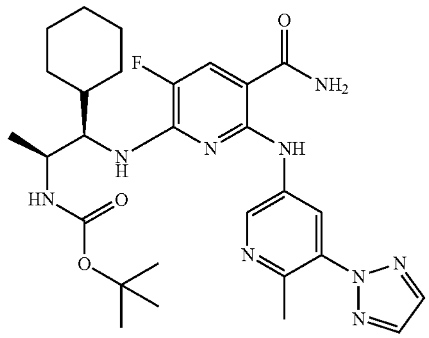 [SMILES: Cc1ncc(Nc2nc(N[C@H](C3CCCCC3)[C@H](C)NC(=O)OC(C)(C)C)c(F)cc2C(N)=O)cc1-n1nccn1] | tert-butyl ((1R,2S)-1-((5-carbamoyl-3-fluoro-6-((6-methyl-5-(2H-1,2,3-triazol-2-yl)pyridin-3-yl)amino)pyridin-2-yl)amino)-1-cyclohexylpropan-2-yl)carbamate | 568 | 1.67 |
| Reference Example 136-135 | 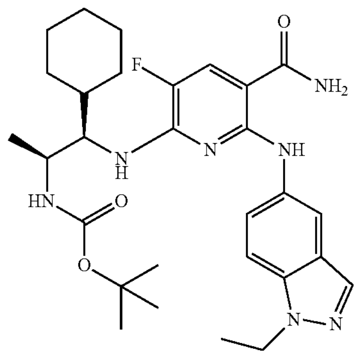 [SMILES: CCn1ncc2cc(Nc3nc(N[C@H](C4CCCCC4)[C@H](C)NC(=O)OC(C)(C)C)c(F)cc3C(N)=O)ccc21] | tert-butyl ((1R,2S)-1-((5-carbamoyl-6-((1-ethyl-1H-indazol-5-yl)amino)-3-fluoropyridin-2-yl)amino)-1-cyclohexylpropan-2-yl)carbamate | 554 | 1.75 |
| Reference Example 136-136 | 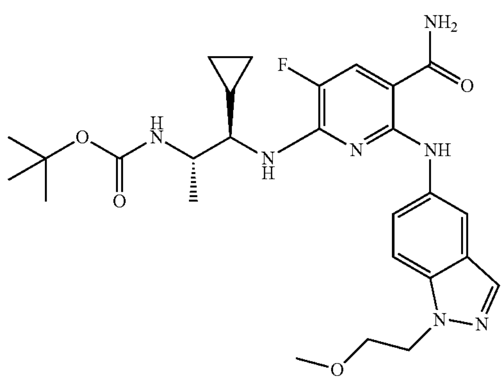 [SMILES: COCCn1ncc2cc(Nc3nc(N[C@H](C4CC4)[C@H](C)NC(=O)OC(C)(C)C)c(F)cc3C(N)=O)ccc21] | tert-butyl ((1R,2S)-1-((5-carbamoyl-3-fluoro-6-((1-(2-methoxyethyl)-1H-indazol-5-yl)amino)pyridin-2-yl)amino)-1-cyclopropylpropan-2-yl)carbamate | 542 | 1.45 |
| Reference Example 136-137 | 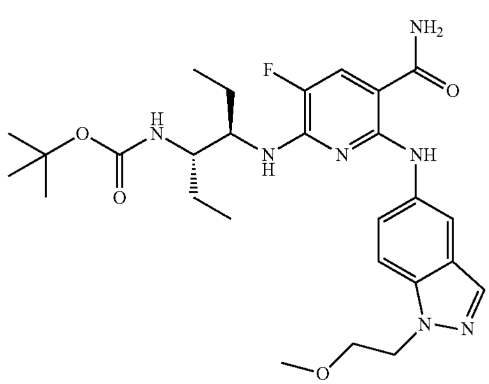 [SMILES: CC[C@H](NC(=O)OC(C)(C)C)[C@@H](CC)Nc1nc(Nc2ccc3c(cnn3CCOC)c2)c(C(N)=O)cc1F] | tert-butyl ((3S,4R)-4-((5-carbamoyl-3-fluoro-6-((1-(2-methoxyethyl)-1H-indazol-5-yl)amino)pyridin-2-yl)amino)hexan-3-yl)carbamate | 544 | 1.50 |

TABLE 2-continued

| Reference Example | Structure | Compound name | MS (ESI m/z): (M + H) | RT (min) |
|---|---|---|---|---|
| Reference Example 136-138 | 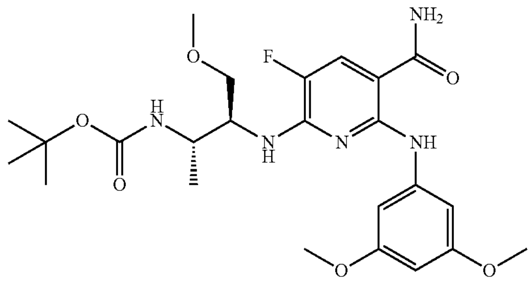 [SMILES: COC[C@@H](Nc1nc(Nc2cc(OC)cc(OC)c2)c(C(N)=O)cc1F)[C@H](C)NC(=O)OC(C)(C)C] | tert-butyl ((2S,3S)-3-((5-carbamoyl-6-((3,5-dimethoxyphenyl)amino)-3-fluoropyridin-2-yl)amino)-4-methoxybutan-2-yl)carbamate | 508 | 1.58 |
| Reference Example 136-139 | 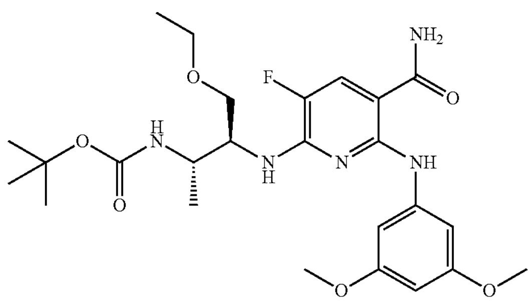 [SMILES: CCOC[C@@H](Nc1nc(Nc2cc(OC)cc(OC)c2)c(C(N)=O)cc1F)[C@H](C)NC(=O)OC(C)(C)C] | tert-butyl ((2S,3S)-3-((5-carbamoyl-6-((3,5-dimethoxyphenyl)amino)-3-fluoropyridin-2-yl)amino)-4-ethoxybutan-2-yl)carbamate | 522 | 1.68 |
| Reference Example 136-140 | 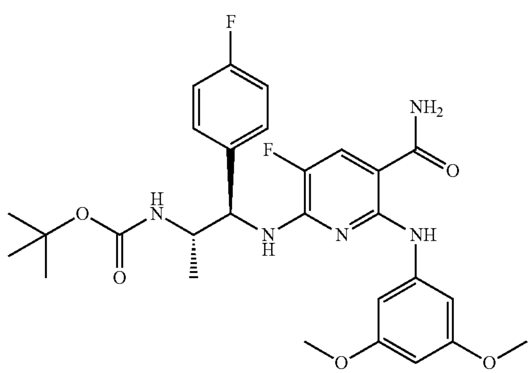 [SMILES: COc1cc(Nc2nc(N[C@H](c3ccc(F)cc3)[C@H](C)NC(=O)OC(C)(C)C)c(F)cc2C(N)=O)cc(OC)c1] | tert-butyl ((1R,2S)-1-((5-carbamoyl-6-((3,5-dimethoxyphenyl)amino)-3-fluoropyridin-2-yl)amino)-1-(4-fluorophenyl)propan-2-yl)carbamate | 558 | 1.75 |
| Reference Example 136-141 | 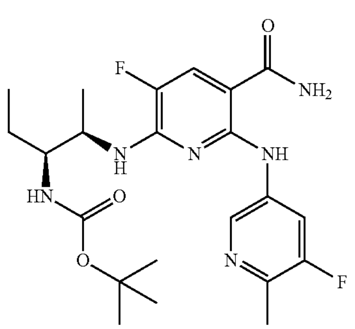 [SMILES: CC[C@H](NC(=O)OC(C)(C)C)[C@@H](C)Nc1nc(Nc2cnc(C)c(F)c2)c(C(N)=O)cc1F] | tert-butyl ((2R,3S)-2-((5-carbamoyl-3-fluoro-6-((5-fluoro-6-methylpyridin-3-yl)amino)pyridin-2-yl)amino)pentan-3-yl)carbamate | 465 | 1.44 |

TABLE 2-continued

| Reference Example | Structure | Compound name | MS (ESI m/z): (M + H) | RT (min) |
|---|---|---|---|---|
| Reference Example 136-142 | 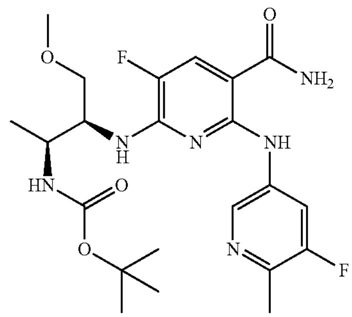 [SMILES: COC[C@@H](Nc1nc(Nc2cnc(C)c(F)c2)c(C(N)=O)cc1F)[C@H](C)NC(=O)OC(C)(C)C] | tert-butyl ((2S,3S)-3-((5-carbamoyl-3-fluoro-6-((5-fluoro-6-methylpyridin-3-yl)amino)pyridin-2-yl)amino)-4-methoxybutan-2-yl)carbamate | 481 | 1.33 |
| Reference Example 136-143 | 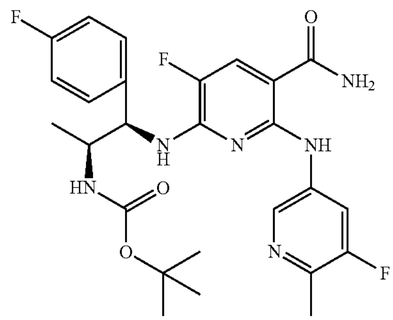 [SMILES: Cc1ncc(Nc2nc(N[C@H](c3ccc(F)cc3)[C@H](C)NC(=O)OC(C)(C)C)c(F)cc2C(N)=O)cc1F] | tert-butyl ((1R,2S)-1-((5-carbamoyl-3-fluoro-6-((5-fluoro-6-methylpyridin-3-yl)amino)pyridin-2-yl)amino)-1-(4-fluorophenyl)propan-2-yl)carbamate | 531 | 1.60 |
| Reference Example 136-144 | 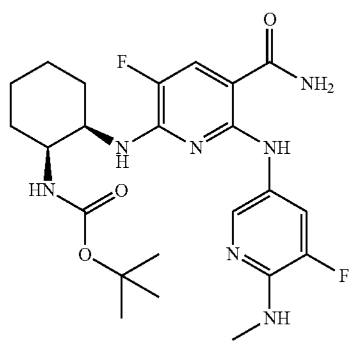 [SMILES: CNc1ncc(Nc2nc(N[C@@H]3CCCC[C@@H]3NC(=O)OC(C)(C)C)c(F)cc2C(N)=O)cc1F] | tert-butyl ((1S,2R)-2-((5-carbamoyl-3-fluoro-6-((5-fluoro-6-(methylamino)pyridin-3-yl)amino)pyridin-2-yl)amino)cyclohexyl)carbamate | 492 | 1.19 |
| Reference Example 136-145 | 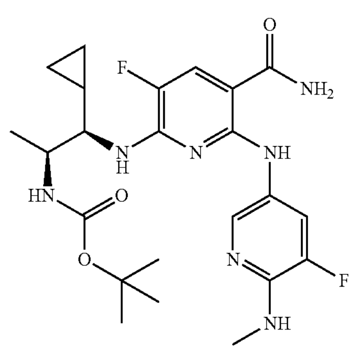 [SMILES: CNc1ncc(Nc2nc(N[C@H](C3CC3)[C@H](C)NC(=O)OC(C)(C)C)c(F)cc2C(N)=O)cc1F] | tert-butyl ((1R,2S)-1-((5-carbamoyl-3-fluoro-6-((5-fluoro-6-(methylamino)pyridin-3-yl)amino)pyridin-2-yl)amino)-1-cyclopropylpropan-2-yl)carbamate | 492 | 1.15 |

TABLE 2-continued

| Reference Example | Structure | Compound name | MS (ESI m/z): (M + H) | RT (min) |
|---|---|---|---|---|
| Reference Example 136-146 | 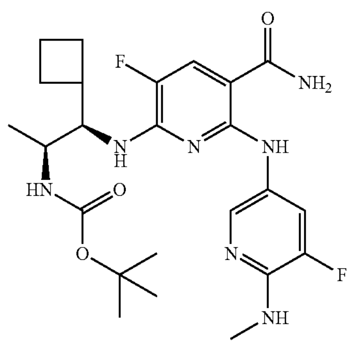 [SMILES: CNc1ncc(Nc2nc(N[C@H](C3CCC3)[C@H](C)NC(=O)OC(C)(C)C)c(F)cc2C(N)=O)cc1F] | tert-butyl ((1R,2S)-1-((5-carbamoyl-3-fluoro-6-((5-fluoro-6-(methylamino)pyridin-3-yl)amino)pyridin-2-yl)amino)-1-cyclobutylpropan-2-yl)carbamate | 506 | 1.24 |
| Reference Example 136-147 | 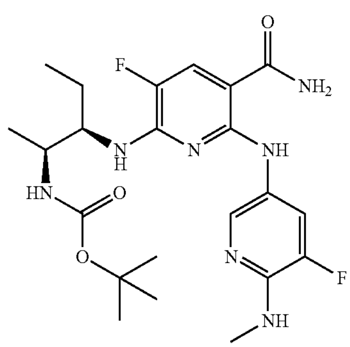 [SMILES: CC[C@@H](Nc1nc(Nc2cnc(NC)c(F)c2)c(C(N)=O)cc1F)[C@H](C)NC(=O)OC(C)(C)C] | tert-butyl ((2S,3R)-3-((5-carbamoyl-3-fluoro-6-((5-fluoro-6-(methylamino)pyridin-3-yl)amino)pyridin-2-yl)amino)pentan-2-yl)carbamate | 480 | 1.13 |
| Reference Example 136-148 | 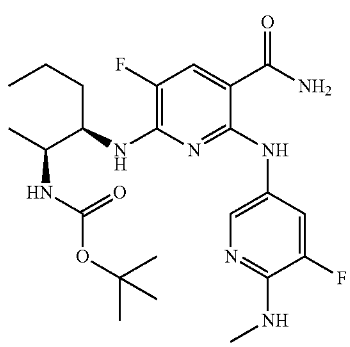 [SMILES: CCC[C@@H](Nc1nc(Nc2cnc(NC)c(F)c2)c(C(N)=O)cc1F)[C@H](C)NC(=O)OC(C)(C)C] | tert-butyl ((2S,3R)-3-((5-carbamoyl-3-fluoro-6-((5-fluoro-6-(methylamino)pyridin-3-yl)amino)pyridin-2-yl)amino)hexan-2-yl)carbamate | 494 | 1.22 |
| Reference Example 136-149 | 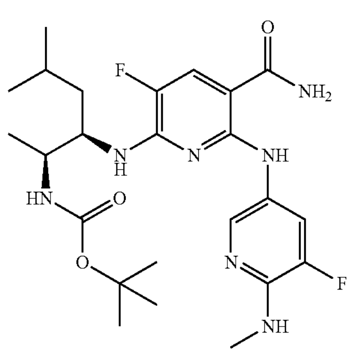 [SMILES: CNc1ncc(Nc2nc(N[C@H](CC(C)C)[C@H](C)NC(=O)OC(C)(C)C)c(F)cc2C(N)=O)cc1F] | tert-butyl ((2S,3R)-3-((5-carbamoyl-3-fluoro-6-((5-fluoro-6-(methylamino)pyridin-3-yl)amino)pyridin-2-yl)amino)-5-methylhexan-2-yl)carbamate | 508 | 1.30 |

TABLE 2-continued

| Reference Example | Structure | Compound name | MS (ESI m/z): (M + H) | RT (min) |
|---|---|---|---|---|
| Reference Example 136-150 | 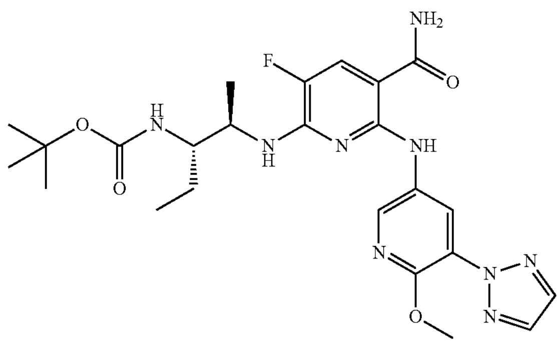 [SMILES: CC[C@H](NC(=O)OC(C)(C)C)[C@@H](C)Nc1nc(Nc2cnc(OC)c(-n3nccn3)c2)c(C(N)=O)cc1F] | tert-butyl ((2R,3S)-2-((5-carbamoyl-3-fluoro-6-((6-methoxy-5-(2H-1,2,3-triazol-2-yl)pyridin-3-yl)amino)pyridin-2-yl)amino)pentan-3-yl)carbamate | 530 | 1.52 |
| Reference Example 136-151 | 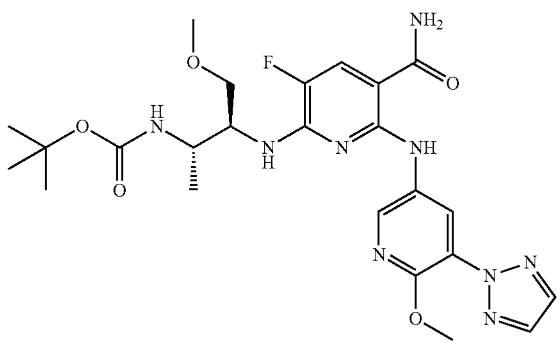 [SMILES: COC[C@@H](Nc1nc(Nc2cnc(OC)c(-n3nccn3)c2)c(C(N)=O)cc1F)[C@H](C)NC(=O)OC(C)(C)C] | tert-butyl ((2S,3S)-3-((5-carbamoyl-3-fluoro-6-((6-methoxy-5-(2H-1,2,3-triazol-2-yl)pyridin-3-yl)amino)pyridin-2-yl)amino)-4-methoxybutan-2-yl)carbamate | 546 | 1.44 |
| Reference Example 136-152 | 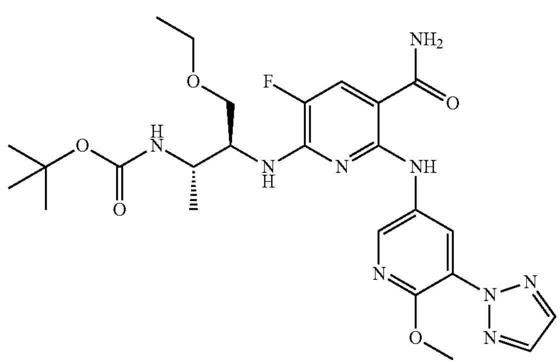 [SMILES: CCOC[C@@H](Nc1nc(Nc2cnc(OC)c(-n3nccn3)c2)c(C(N)=O)cc1F)[C@H](C)NC(=O)OC(C)(C)C] | tert-butyl ((2S,3S)-3-((5-carbamoyl-3-fluoro-6-((6-methoxy-5-(2H-1,2,3-triazol-2-yl)pyridin-3-yl)amino)pyridin-2-yl)amino)-4-ethoxybutan-2-yl)carbamate | 560 | 1.53 |
| Reference Example 136-153 | 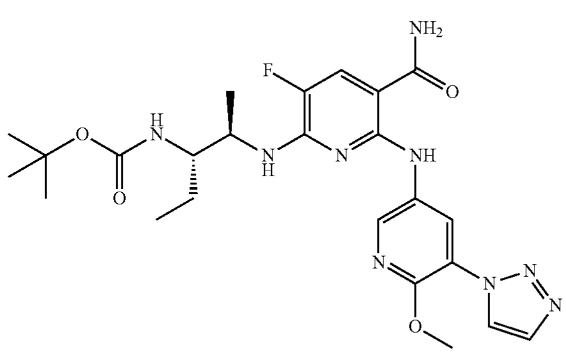 [SMILES: CC[C@H](NC(=O)OC(C)(C)C)[C@@H](C)Nc1nc(Nc2cnc(OC)c(-n3ccnn3)c2)c(C(N)=O)cc1F] | tert-butyl ((2R,3S)-2-((5-carbamoyl-3-fluoro-6-((6-methoxy-5-(1H-1,2,3-triazol-1-yl)pyridin-3-yl)amino)pyridin-2-yl)amino)pentan-3-yl)carbamate | 530 | 1.52 |

TABLE 2-continued

| Reference Example | Structure | Compound name | MS (ESI m/z): (M + H) | RT (min) |
|---|---|---|---|---|
| Reference Example 136-154 | 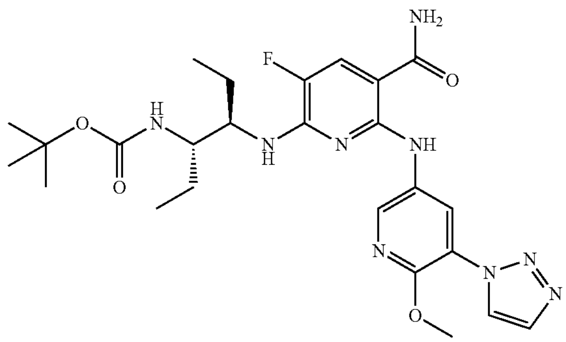 [SMILES: CC[C@H](NC(=O)OC(C)(C)C)[C@@H](CC)Nc1nc(Nc2cnc(OC)c(-n3ccnn3)c2)c(C(N)=O)cc1F] | tert-butyl ((3S,4R)-4-((5-carbamoyl-3-fluoro-6-((6-methoxy-5-(1H-1,2,3-triazol-1-yl)pyridin-3-yl)amino)pyridin-2-yl)amino)hexan-3-yl)carbamate | 542 | 1.58 |
| Reference Example 136-155 | 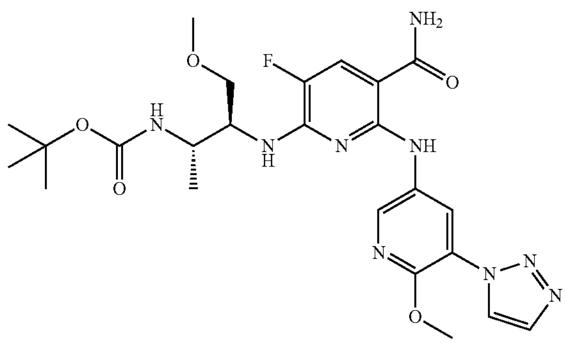 [SMILES: COC[C@@H](Nc1nc(Nc2cnc(OC)c(-n3ccnn3)c2)c(C(N)=O)cc1F)[C@H](C)NC(=O)OC(C)(C)C] | tert-butyl ((2S,3S)-3-((5-carbamoyl-3-fluoro-6-((6-methoxy-5-(1H-1,2,3-triazol-1-yl)pyridin-3-yl)amino)pyridin-2-yl)amino)-4-methoxybutan-2-yl)carbamate | 546 | 1.44 |
| Reference Example 136-156 | 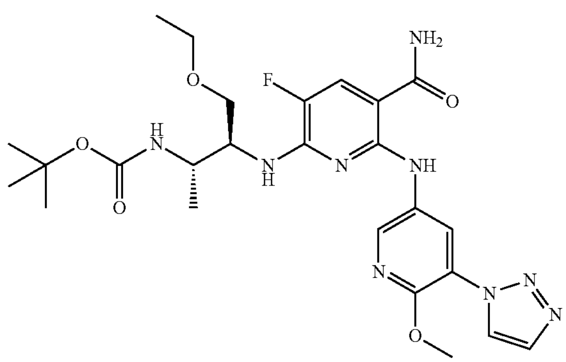 [SMILES: CCOC[C@@H](Nc1nc(Nc2cnc(OC)c(-n3ccnn3)c2)c(C(N)=O)cc1F)[C@H](C)NC(=O)OC(C)(C)C] | tert-butyl ((2S,3S)-3-((5-carbamoyl-3-fluoro-6-((6-methoxy-5-(1H-1,2,3-triazol-1-yl)pyridin-3-yl)amino)pyridin-2-yl)amino)-4-ethoxybutan-2-yl)carbamate | 558 | 1.54 |
| Reference Example 136-157 | 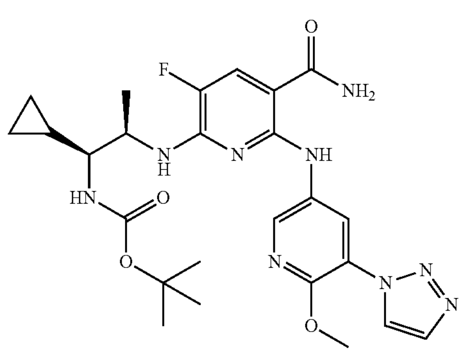 [SMILES: COc1ncc(Nc2nc(N[C@H](C)[C@@H](NC(=O)OC(C)(C)C)C3CC3)c(F)cc2C(N)=O)cc1-n1ccnn1] | tert-butyl ((1S,2R)-2-((5-carbamoyl-3-fluoro-6-((6-methoxy-5-(1H-1,2,3-triazol-1-yl)pyridin-3-yl)amino)pyridin-2-yl)amino)-1-cyclopropylpropyl)carbamate | 542 | 1.54 |

TABLE 2-continued

| Reference Example | Structure | Compound name | MS (ESI m/z): (M + H) | RT (min) |
|---|---|---|---|---|
| Reference Example 136-158 | 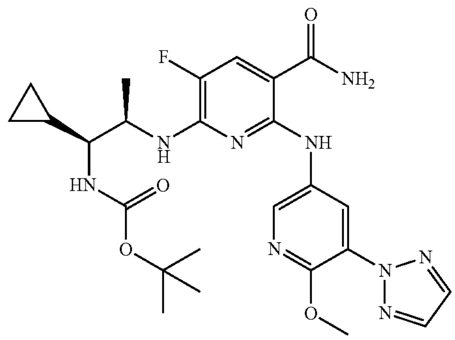 [SMILES: COc1ncc(Nc2nc(N[C@H](C)[C@@H](NC(=O)OC(C)(C)C)C3CC3)c(F)cc2C(N)=O)cc1-n1nccn1] | tert-butyl ((1S,2R)-2-((5-carbamoyl-3-fluoro-6-((6-methoxy-5-(2H-1,2,3-triazol-2-yl)pyridin-3-yl)amino)pyridin-2-yl)amino)-1-cyclopropylpropyl)carbamate | 542 | 1.54 |
| Reference Example 136-159 | 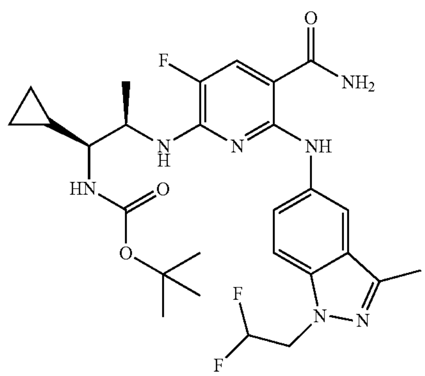 [SMILES: Cc1nn(CC(F)F)c2ccc(Nc3nc(N[C@H](C)[C@@H](NC(=O)OC(C)(C)C)C4CC4)c(F)cc3C(N)=O)cc12] | tert-butyl ((1S,2R)-2-((5-carbamoyl-6-((1-(2,2-difluoroethyl)-3-methyl-1H-indazol-5-yl)amino)-3-fluoropyridin-2-yl)amino)-1-cyclopropylpropyl)carbamate | 562 | 1.59 |
| Reference Example 136-160 | 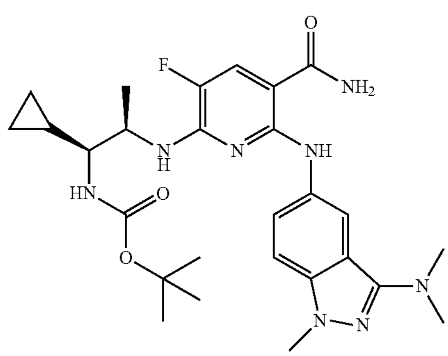 [SMILES: C[C@@H](Nc1nc(Nc2ccc3c(c2)c(N(C)C)nn3C)c(C(N)=O)cc1F)[C@@H](NC(=O)OC(C)(C)C)C1CC1] | tert-butyl ((1S,2R)-2-((5-carbamoyl-6-((3-(dimethylamino)-1-methyl-1H-indazol-5-yl)amino)-3-fluoropyridin-2-yl)amino)-1-cyclopropylpropyl)carbamate | 541 | 1.51 |
| Reference Example 136-161 | 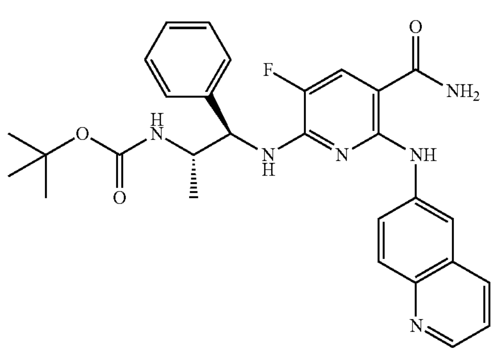 [SMILES: C[C@H](NC(=O)OC(C)(C)C)[C@H](Nc1nc(Nc2ccc3ncccc3c2)c(C(N)=O)cc1F)c1ccccc1] | tert-butyl ((1R,2S)-1-((5-carbamoyl-3-fluoro-6-(quinolin-6-ylamino)pyridin-2-yl)amino)-1-phenylpropan-2-yl)carbamate | 531 | 1.30 |

TABLE 2-continued

| Reference Example | Structure | Compound name | MS (ESI m/z): (M + H) | RT (min) |
|---|---|---|---|---|
| Reference Example 136-162 | 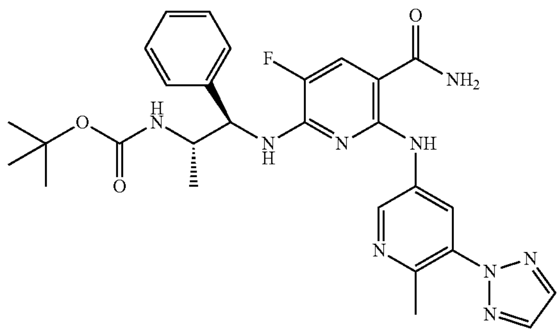 [SMILES: Cc1ncc(Nc2nc(N[C@H](c3ccccc3)[C@H](C)NC(=O)OC(C)(C)C)c(F)cc2C(N)=O)cc1-n1nccn1] | tert-butyl ((1R,2S)-1-((5-carbamoyl-3-fluoro-6-((6-methyl-5-(2H-1,2,3-triazol-2-yl)pyridin-3-yl)amino)pyridin-2-yl)amino)-1-phenylpropan-2-yl)carbamate | 562 | 1.56 |
| Reference Example 136-163 | 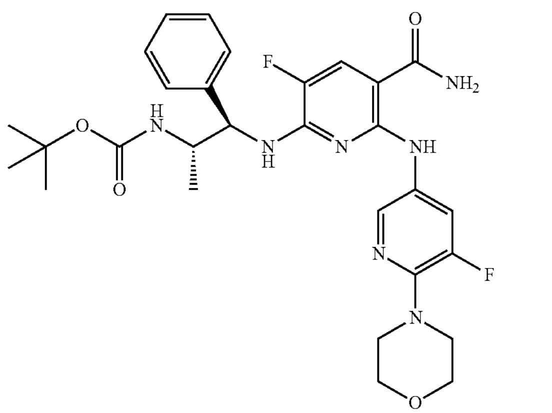 [SMILES: C[C@H](NC(=O)OC(C)(C)C)[C@H](Nc1nc(Nc2cnc(N3CCOCC3)c(F)c2)c(C(N)=O)cc1F)c1ccccc1] | tert-butyl ((1R,2S)-1-((5-carbamoyl-3-fluoro-6-((5-fluoro-6-morpholinopyridin-3-yl)amino)pyridin-2-yl)amino)-1-phenylpropan-2-yl)carbamate | 584 | 1.64 |
| Reference Example 136-164 | 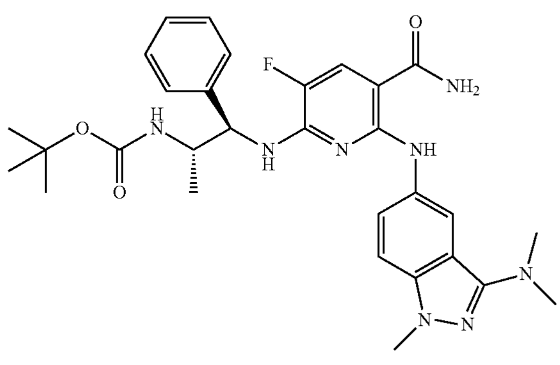 [SMILES: C[C@H](NC(=O)OC(C)(C)C)[C@H](Nc1nc(Nc2ccc3c(c2)c(N(C)C)nn3C)c(C(N)=O)cc1F)c1ccccc1] | tert-butyl ((1R,2S)-1-((5-carbamoyl-6-((3-(dimethylamino)-1-methyl-1H-indazol-5-yamino)-3-fluoropyridin-2-yl)amino)-1-phenylpropan-2-yl)carbamate | 577 | 1.60 |
| Reference Example 136-165 | 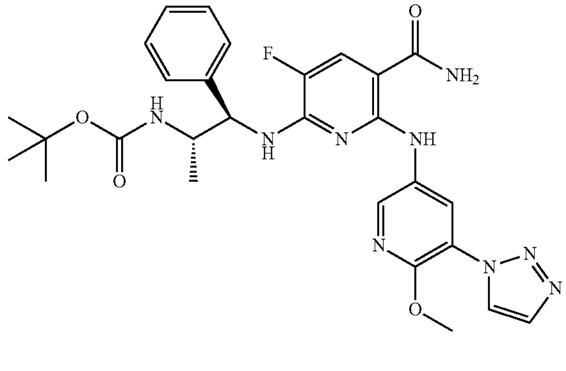 [SMILES: COc1ncc(Nc2nc(N[C@H](c3ccccc3)[C@H](C)NC(=O)OC(C)(C)C)c(F)cc2C(N)=O)cc1-n1ccnn1] | tert-butyl ((1R,2S)-1-((5-carbamoyl-3-fluoro-6-((6-methoxy-5-(1H-1,2,3-triazol-1-yl)pyridin-3-yl)amino)pyridin-2-yl)amino)-1-phenylpropan-2-yl)carbamate | 578 | 1.61 |

TABLE 2-continued

| Reference Example | Structure | Compound name | MS (ESI m/z): (M + H) | RT (min) |
|---|---|---|---|---|
| Reference Example 136-166 | 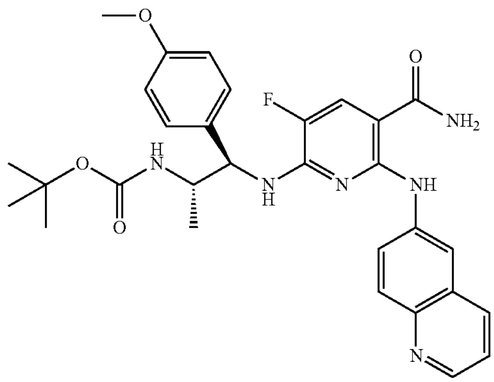 [SMILES: COc1ccc([C@@H](Nc2nc(Nc3ccc4ncccc4c3)c(C(N)=O)cc2F)[C@H](C)NC(=O)OC(C)(C)C)cc1] | tert-butyl ((1R,2S)-1-((5-carbamoyl-3-fluoro-6-(quinolin-6-ylamino)pyridin-2-yl)amino)-1-(4-methoxyphenyl)propan-2-yl)carbamate | 561 | 1.29 |
| Reference Example 136-167 | 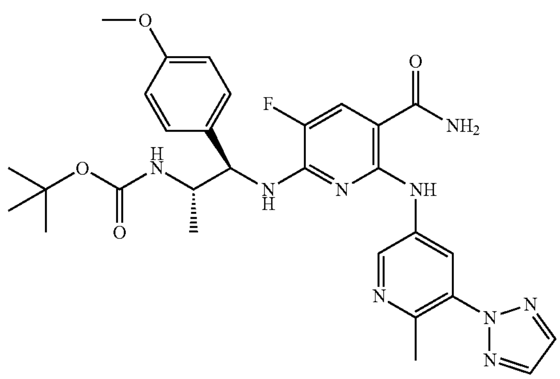 [SMILES: COc1ccc([C@@H](Nc2nc(Nc3cnc(C)c(-n4nccn4)c3)c(C(N)=O)cc2F)[C@H](C)NC(=O)OC(C)(C)C)cc1] | tert-butyl ((1R,2S)-1-((5-carbamoyl-3-fluoro-6-((6-methyl-5-(2H-1,2,3-triazol-2-yl)pyridin-3-yl)amino)pyridin-2-yl)amino)-1-(4-methoxyphenyl)propan-2-yl)carbamate | 592 | 1.54 |
| Reference Example 136-168 | 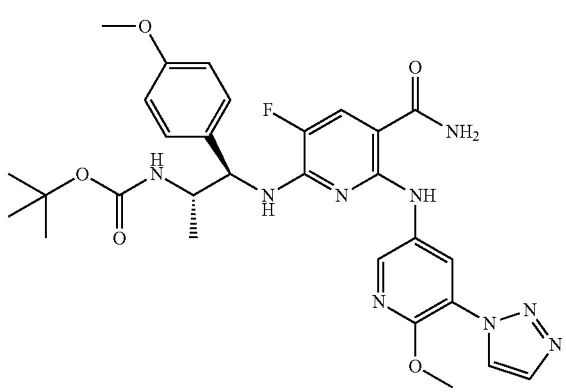 [SMILES: COc1ccc([C@@H](Nc2nc(Nc3cnc(OC)c(-n4ccnn4)c3)c(C(N)=O)cc2F)[C@H](C)NC(=O)OC(C)(C)C)cc1] | tert-butyl ((1R,2S)-1-((5-carbamoyl-3-fluoro-6-((6-methoxy-5-(1H-1,2,3-triazol-1-yl)pyridin-3-yl)amino)pyridin-2-yl)amino)-1-(4-methoxyphenyl)propan-2-yl)carbamate | 608 | 1.59 |

TABLE 2-continued

| Reference Example | Structure | Compound name | MS (ESI m/z): (M + H) | RT (min) |
|---|---|---|---|---|
| Reference Example 136-169 | 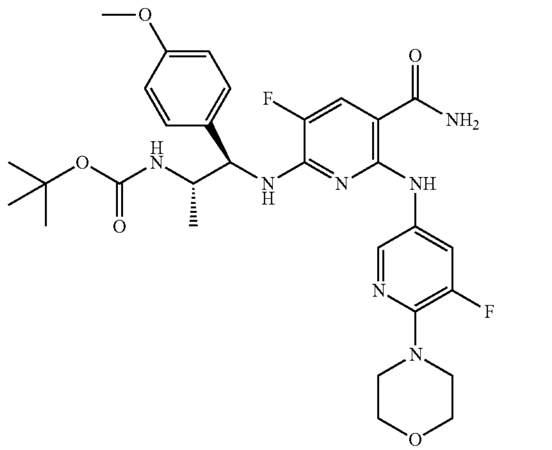 [SMILES: COc1ccc([C@@H](Nc2nc(Nc3cnc(N4CCOCC4)c(F)c3)c(C(N)=O)cc2F)[C@H](C)NC(=O)OC(C)(C)C)cc1] | tert-butyl ((1R,2S)-1-((5-carbamoyl-3-fluoro-6-((5-fluoro-6-morpholinopyridin-3-yl)amino)pyridin-2-yl)amino)-1-(4-methoxyphenyl)propan-2-yl)carbamate | 614 | 1.62 |
| Reference Example 136-170 | 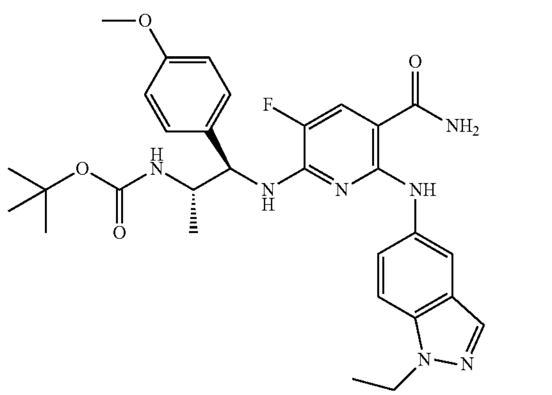 [SMILES: CCn1ncc2cc(Nc3nc(N[C@H](c4ccc(OC)cc4)[C@H](C)NC(=O)OC(C)(C)C)c(F)cc3C(N)=O)ccc21] | tert-butyl ((1R,2S)-1-((5-carbamoyl-6-((1-ethyl-1H-indazol-5-yl)amino)-3-fluoropyridin-2-yl)amino)-1-(4-methoxyphenyl)propan-2-yl)carbamate | 578 | 1.60 |
| Reference Example 136-171 | 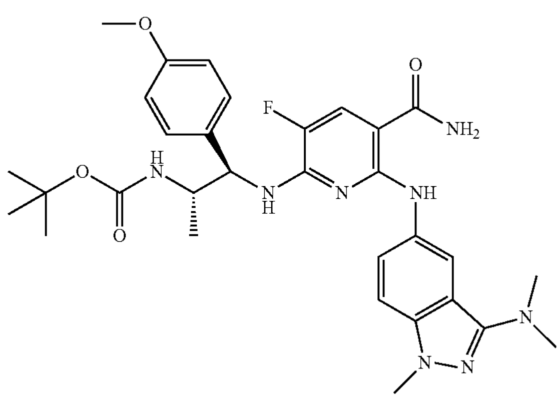 [SMILES: COc1ccc([C@@H](Nc2nc(Nc3ccc4c(c3)c(N(C)C)nn4C)c(C(N)=O)cc2F)[C@H](C)NC(=O)OC(C)(C)C)cc1] | tert-butyl ((1R,2S)-1-((5-carbamoyl-6-((3-(dimethylamino)-1-methyl-1H-indazol-5-yl)amino)-3-fluoropyridin-2-yl)amino)-1-(4-methoxyphenyl)propan-2-yl)carbamate | 607 | 1.57 |

TABLE 2-continued

| Reference Example | Structure | Compound name | MS (ESI m/z): (M + H) | RT (min) |
|---|---|---|---|---|
| Reference Example 136-172 | 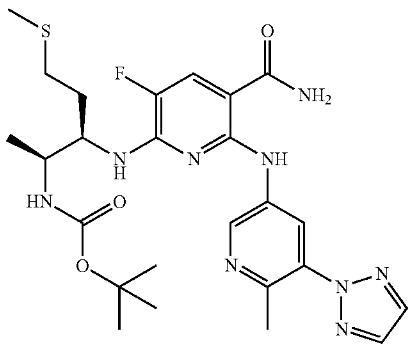 [SMILES: CSCC[C@@H](Nc1nc(Nc2cnc(C)c(-n3nccn3)c2)c(C(N)=O)cc1F)[C@H](C)NC(=O)OC(C)(C)C] | tert-butyl ((2S,3R)-3-((5-carbamoyl-3-fluoro-6-((6-methyl-5-(2H-1,2,3-triazol-2-yl)pyridin-3-yl)amino)pyridin-2-yl)amino)-5-(methylthio)pentan-2-yl)carbamate | 560 | — |
| Reference Example 136-173 | 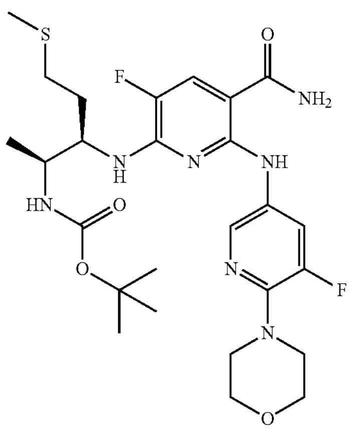 [SMILES: CSCC[C@@H](Nc1nc(Nc2cnc(N3CCOCC3)c(F)c2)c(C(N)=O)cc1F)[C@H](C)NC(=O)OC(C)(C)C] | tert-butyl ((2S,3R)-3-((5-carbamoyl-3-fluoro-6-((5-fluoro-6-morpholinopyridin-3-yl)amino)pyridin-2-yl)amino)-5-(methylthio)pentan-2-yl)carbamate | 582 | — |
| Reference Example 136-174 | 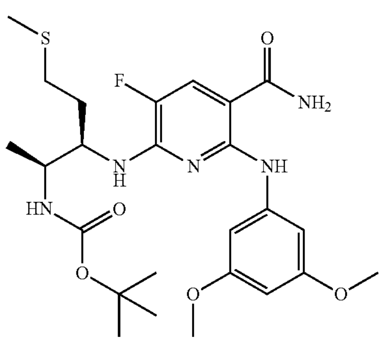 [SMILES: COc1cc(Nc2nc(N[C@H](CCSC)[C@H](C)NC(=O)OC(C)(C)C)c(F)cc2C(N)=O)cc(OC)c1] | tert-butyl ((2S,3R)-3-((5-carbamoyl-6-((3,5-dimethoxyphenyl)amino)-3-fluoropyridin-2-yl)amino)-5-(methylthio)pentan-2-yl)carbamate | 553 | — |
| Reference Example 136-175 | 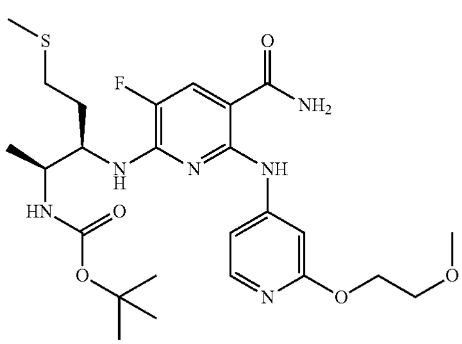 [SMILES: COCCOc1cc(Nc2nc(N[C@H](CCSC)[C@H](C)NC(=O)OC(C)(C)C)c(F)cc2C(N)=O)ccn1] | tert-butyl ((2S,3R)-3-((5-carbamoyl-3-fluoro-6-((2-(2-methoxyethoxy)pyridin-4-yl)amino)pyridin-2-yl)amino)-5-(methylthio)pentan-2-yl)carbamate | 538 | — |

TABLE 2-continued

| Reference Example | Structure | Compound name | MS (ESI m/z): (M + H) | RT (min) |
|---|---|---|---|---|
| Reference Example 136-176 | 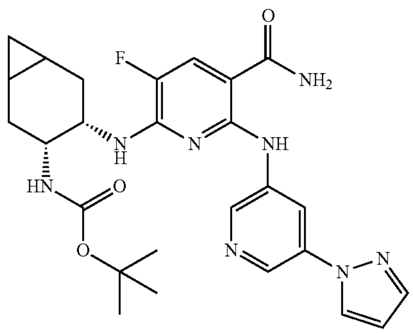 [SMILES: CC(C)(C)OC(=O)N[C@@H]1CC2CC2C[C@@H]1Nc1nc(Nc2cncc(-n3cccn3)c2)c(C(N)=O)cc1F] | tert-butyl ((3R,4S)-4-((6-((5-(1H-pyrazol-1-yl)pyridin-3-yl)amino)-5-carbamoyl-3-fluoropyridin-2-yl)amino)bicyclo[4.1.0]heptan-3-yl)carbamate | 523 | 1.50 |
| Reference Example 136-177 | 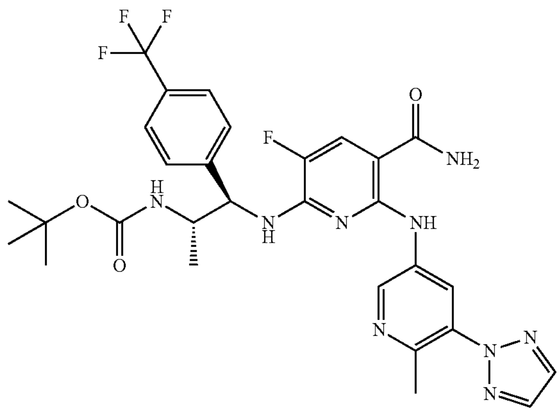 [SMILES: Cc1ncc(Nc2nc(N[C@H](c3ccc(C(F)(F)F)cc3)[C@H](C)NC(=O)OC(C)(C)C)c(F)cc2C(N)=O)cc1-n1nccn1] | tert-butyl ((1R,2S)-1-((5-carbamoyl-3-fluoro-6-((6-methyl-5-(2H-1,2,3-triazol-2-yl)pyridin-3-yl)amino)pyridin-2-yl)amino)-1-(4-(trifluoromethyl)phenyl)propan-2-yl)carbamate | 630 | 1.71 |
| Reference Example 136-178 | 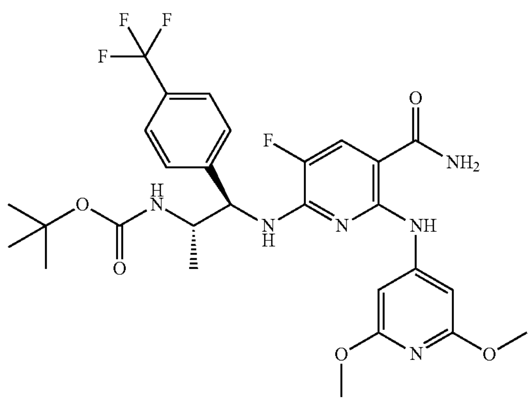 [SMILES: COc1cc(Nc2nc(N[C@H](c3ccc(C(F)(F)F)cc3)[C@H](C)NC(=O)OC(C)(C)C)c(F)cc2C(N)=O)cc(OC)n1] | tert-butyl ((1R,2S)-1-((5-carbamoyl-6-((2,6-dimethoxypyridin-4-yl)amino)-3-fluoropyridin-2-yl)amino)-1-(4-(trifluoromethyl)phenyl)propan-2-yl)carbamate | 609 | 1.90 |
| Reference Example 136-179 | 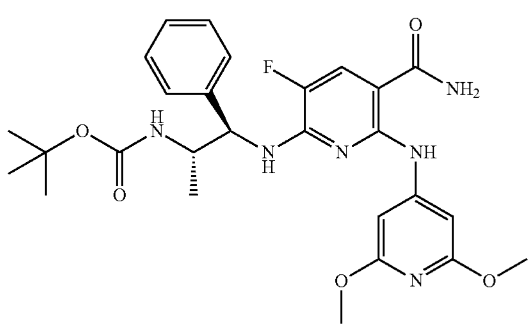 [SMILES: COc1cc(Nc2nc(N[C@H](c3ccccc3)[C@H](C)NC(=O)OC(C)(C)C)c(F)cc2C(N)=O)cc(OC)n1] | tert-butyl ((1R,2S)-1-((5-carbamoyl-6-((2,6-dimethoxypyridin-4-yl)amino)-3-fluoropyridin-2-yl)amino)-1-phenylpropan-2-yl)carbamate | 541 | 1.78 |

TABLE 2-continued

| Reference Example | Structure | Compound name | MS (ESI m/z): (M + H) | RT (min) |
|---|---|---|---|---|
| Reference Example 136-180 | 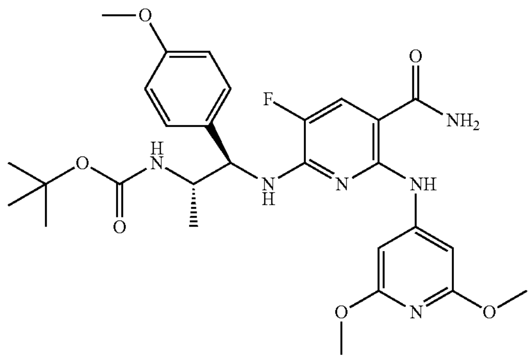 [SMILES: COc1ccc([C@@H](Nc2nc(Nc3cc(OC)nc(OC)c3)c(C(N)=O)cc2F)[C@H](C)NC(=O)OC(C)(C)C)cc1] | tert-butyl ((1R,2S)-1-((5-carbamoyl-6-((2,6-dimethoxypyridin-4-yl)amino)-3-fluoropyridin-2-yl)amino)-1-(4-methoxyphenyl)propan-2-yl)carbamate | 571 | 1.74 |
| Reference Example 136-181 | 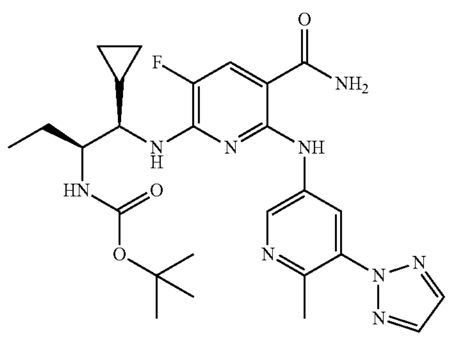 [SMILES: CC[C@H](NC(=O)OC(C)(C)C)[C@H](Nc1nc(Nc2cnc(C)c(-n3nccn3)c2)c(C(N)=O)cc1F)C1CC1] | tert-butyl ((1R,2S)-1-((5-carbamoyl-3-fluoro-6-((6-methyl-5-(2H-1,2,3-triazol-2-yl)pyridin-3-yl)amino)pyridin-2-yl)amino)-1-cyclopropylbutan-2-yl)carbamate | 540 | 1.75 |
| Reference Example 136-182 | 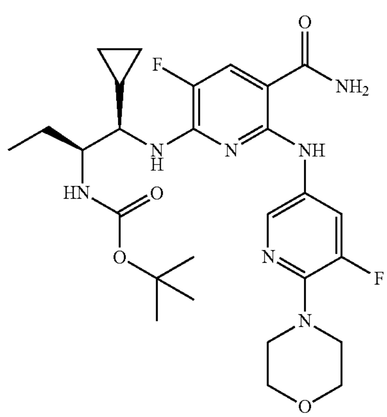 [SMILES: CC[C@H](NC(=O)OC(C)(C)C)[C@H](Nc1nc(Nc2cnc(N3CCOCC3)c(F)c2)c(C(N)=O)cc1F)C1CC1] | tert-butyl ((1R,2S)-1-((5-carbamoyl-3-fluoro-6-((5-fluoro-6-morpholinopyridin-3-yl)amino)pyridin-2-yl)amino)-1-cyclopropylbutan-2-yl)carbamate | 562 | 1.72 |
| Reference Example 136-183 | 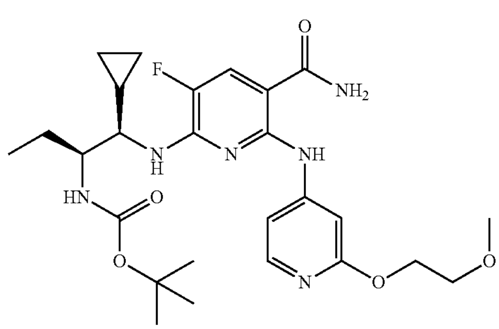 [SMILES: CC[C@H](NC(=O)OC(C)(C)C)[C@H](Nc1nc(Nc2ccnc(OCCOC)c2)c(C(N)=O)cc1F)C1CC1] | tert-butyl ((1R,2S)-1-((5-carbamoyl-3-fluoro-6-((2-(2-methoxyethoxy)pyridin-4-yl)amino)pyridin-2-yl)amino)-1-cyclopropylbutan-2-yl)carbamate | 533 | 1.22 |

TABLE 2-continued

| Reference Example | Structure | Compound name | MS (ESI m/z): (M + H) | RT (min) |
|---|---|---|---|---|
| Reference Example 136-184 | 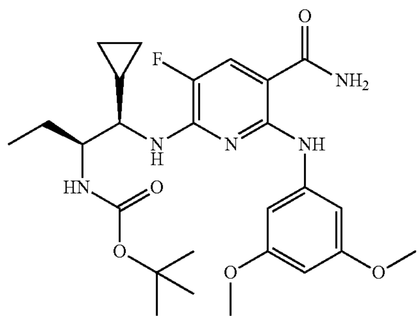 [SMILES: CC[C@H](NC(=O)OC(C)(C)C)[C@H](Nc1nc(Nc2cc(OC)cc(OC)c2)c(C(N)=O)cc1F)C1CC1] | tert-butyl ((1R,2S)-1-((5-carbamoyl-6-((3,5-dimethoxyphenyl)amino)-3-fluoropyridin-2-yl)amino)-1-cyclopropylbutan-2-yl)carbamate | 518 | 1.72 |
| Reference Example 136-185 | 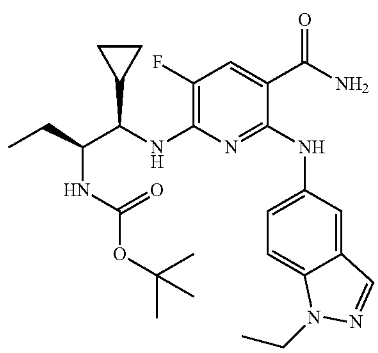 [SMILES: CC[C@H](NC(=O)OC(C)(C)C)[C@H](Nc1nc(Nc2ccc3c(cnn3CC)c2)c(C(N)=O)cc1F)C1CC1] | tert-butyl ((1R,2S)-1-((5-carbamoyl-6-((1-ethyl-1 indazol-5-yl)amino)-3-fluoropyridin-2-yl)amino)-1-cyclopropylbutan-2-yl)carbamate | 526 | 1.58 |
| Reference Example 136-186 | 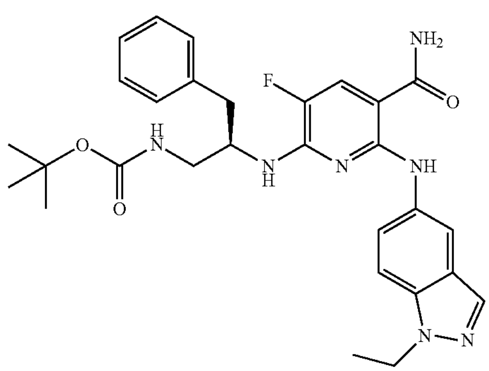 [SMILES: CCn1ncc2cc(Nc3nc(N[C@@H](CNC(=O)OC(C)(C)C)Cc4ccccc4)c(F)cc3C(N)=O)ccc21] | (R)-tert-butyl (2-((5-carbamoyl-6-((1-ethyl-1H-indazol-5-yl)amino)-3-fluoropyridin-2-yl)amino)-3-phenylpropyl)carbamate | 548 | 1.60 |
| Reference Example 136-187 | 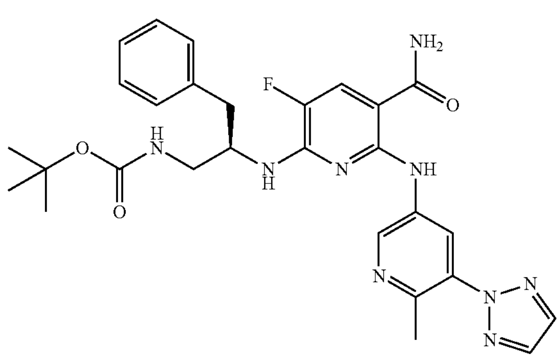 [SMILES: Cc1ncc(Nc2nc(N[C@@H](CNC(=O)OC(C)(C)C)Cc3ccccc3)c(F)cc2C(N)=O)cc1-n1nccn1] | (R)-tert-butyl (2-((5-carbamoyl-3-fluoro-6-((6-methyl-5-(2H-1,2,3-triazol-2-yl)pyridin-3-yl)amino)pyridin-2-yl)amino)-3-phenylpropyl)carbamate | 562 | 1.51 |

TABLE 2-continued

| Reference Example | Structure | Compound name | MS (ESI m/z): (M + H) | RT (min) |
|---|---|---|---|---|
| Reference Example 136-188 | 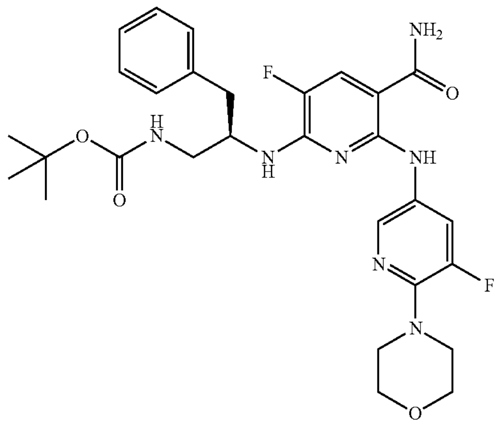 [SMILES: CC(C)(C)OC(=O)NC[C@@H](Cc1ccccc1)Nc1nc(Nc2cnc(N3CCOCC3)c(F)c2)c(C(N)=O)cc1F] | (R)-tert-butyl (2-((5-carbamoyl-3-fluoro-6-((5-fluoro-6-morpholinopyridin-3-yl)amino)pyridin-2-yl)amino)-3-phenylpropyl)carbamate | 548 | 1.60 |
| Reference Example 136-189 | 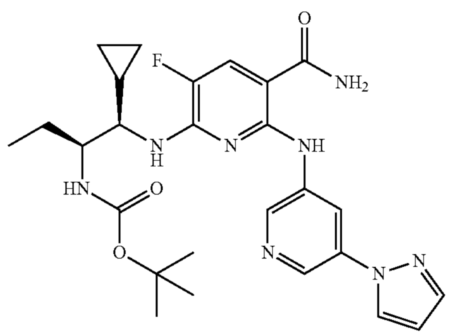 [SMILES: CC[C@H](NC(=O)OC(C)(C)C)[C@H](Nc1nc(Nc2cncc(-n3cccn3)c2)c(C(N)=O)cc1F)C1CC1] | tert-butyl ((1R,2S)-1-((6-((5-(1H-pyrazol-1-yl)pyridin-3-yl)amino)-5-carbamoyl-3-fluoropyridin-2-yl)amino)-1-cyclopropylbutan-2-yl)carbamate | 525 | 1.49 |
| Reference Example 136-190 | 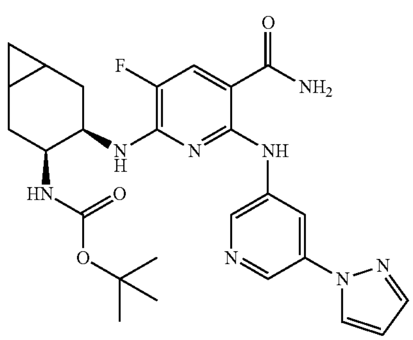 [SMILES: CC(C)(C)OC(=O)N[C@H]1CC2CC2C[C@H]1Nc1nc(Nc2cncc(-n3cccn3)c2)c(C(N)=O)cc1F] | tert-butyl ((3S,4R)-4-((6-((5-(1H-pyrazol-1-yl)pyridin-3-yl)amino)-5-carbamoyl-3-fluoropyridin-2-yl)amino)bicyclo[4.1.0]heptan-3-yl)carbamate | 523 | 1.50 |
| Reference Example 136-191 | 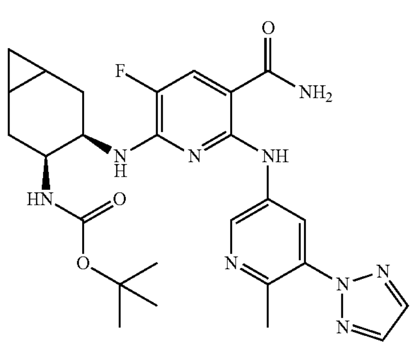 [SMILES: Cc1ncc(Nc2nc(N[C@@H]3CC4CC4C[C@@H]3NC(=O)OC(C)(C)C)c(F)cc2C(N)=O)cc1-n1nccn1] | tert-butyl ((3S,4R)-4-((5-carbamoyl-3-fluoro-6-((6-methyl-5-(2H-1,2,3-triazol-2-yl)pyridin-3-yl)amino)pyridin-2-yl)amino)bicyclo[4.1.0]heptan-3-yl)carbamate | 538 | 1.53 |

TABLE 2-continued

| Reference Example | Structure | Compound name | MS (ESI m/z): (M + H) | RT (min) |
|---|---|---|---|---|
| Reference Example 136-192 | 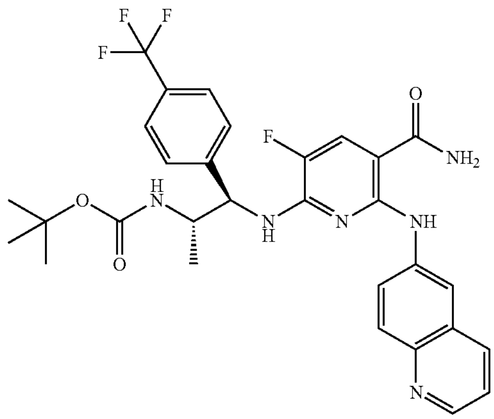 [SMILES: C[C@H](NC(=O)OC(C)(C)C)[C@H](Nc1nc(Nc2ccc3ncccc3c2)c(C(N)=O)cc1F)c1ccc(C(F)(F)F)cc1] | tert-butyl ((1R,2S)-1-((5-carbamoyl-3-fluoro-6-(quinolin-6-ylamino)pyridin-2-yl)amino)-1-(4-(trifluoromethyl)phenyl)propan-2-yl)carbamate | 599 | 1.43 |
| Reference Example 136-193 | 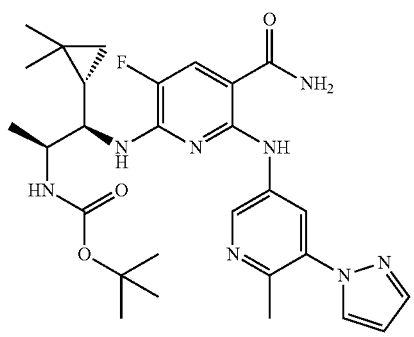 [SMILES: Cc1ncc(Nc2nc(N[C@@H]([C@H](C)NC(=O)OC(C)(C)C)[C@H]3CC3(C)C)c(F)cc2C(N)=O)cc1-n1cccn1] | tert-butyl ((1R,2S)-1-((5-carbamoyl-3-fluoro-6-((6-methyl-5-(2H-1,2,3-triazol-2-yl)pyridin-3-yl)amino)pyridin-2-yl)amino)-1-((S)-2,2-dimethylcyclopropyl)propan-2-yl)carbamate | 554 | 1.62 |
| Reference Example 136-194 | 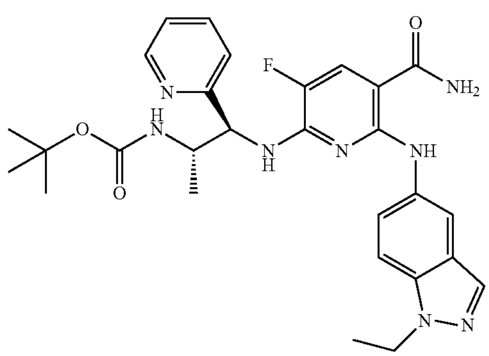 [SMILES: CCn1ncc2cc(Nc3nc(N[C@H](c4ccccn4)[C@H](C)NC(=O)OC(C)(C)C)c(F)cc3C(N)=O)ccc21] | tert-butyl ((1S,2S)-1-((5-carbamoyl-6-((1-ethyl-1H-indazol-5-yl)amino)-3-fluoropyridin-2-yl)amino)-1-(pyridin-2-yl)propan-2-yl)carbamate | 549 | 1.30 |
| Reference Example 136-195 | 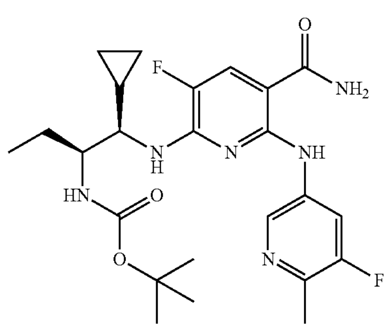 [SMILES: CC[C@H](NC(=O)OC(C)(C)C)[C@H](Nc1nc(Nc2cnc(C)c(F)c2)c(C(N)=O)cc1F)C1CC1] | tert-butyl ((1R,2S)-1-((5-carbamoyl-3-fluoro-6-((5-fluoro-6-methylpyridin-3-yl)amino)pyridin-2-yl)amino)-1-cyclopropylbutan-2-yl)carbamate | 491 | 1.51 |

TABLE 2-continued

| Reference Example | Structure | Compound name | MS (ESI m/z): (M + H) | RT (min) |
|---|---|---|---|---|
| Reference Example 136-196 | 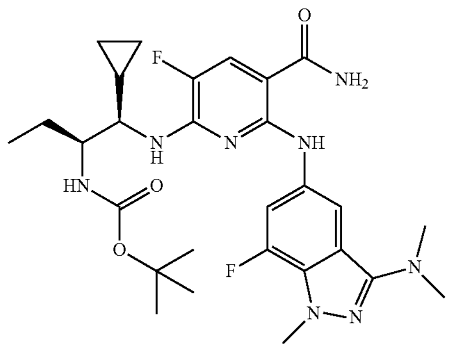 [SMILES: CC[C@H](NC(=O)OC(C)(C)C)[C@H](Nc1nc(Nc2cc(F)c3c(c2)c(N(C)C)nn3C)c(C(N)=O)cc1F)C1CC1] | tert-butyl ((1R,2S)-1-((5-carbamoyl-6-((3-dimethyl)amino)-7-fluoro-1-methyl-1H-indazol-5-yl)amino)-3-fluoropyridin-2-yl)amino)-1-cyclopropylbutan-2-yl)carbamate | 573 | 1.72 |
| Reference Example 136-197 | 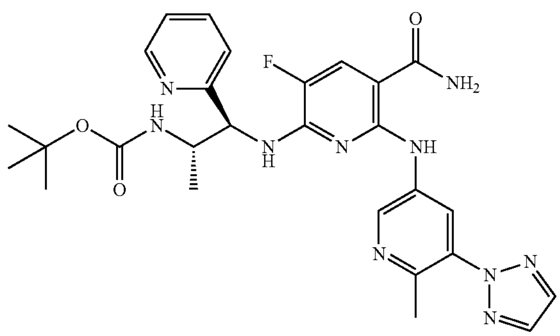 [SMILES: Cc1ncc(Nc2nc(N[C@H](c3ccccn3)[C@H](C)NC(=O)OC(C)(C)C)c(F)cc2C(N)=O)cc1-n1nccn1] | tert-butyl ((1S,2S)-1-((5-carbamoyl-3-fluoro-6-((6-methyl-5-(2H-1,2,3-triazol-2-yl)pyridin-3-yl)amino)pyridin-2-yl)amino)-1-(pyridin-2-yl)propen-2-yl)carbamate | 563 | 1.29 |
| Reference Example 136-198 | 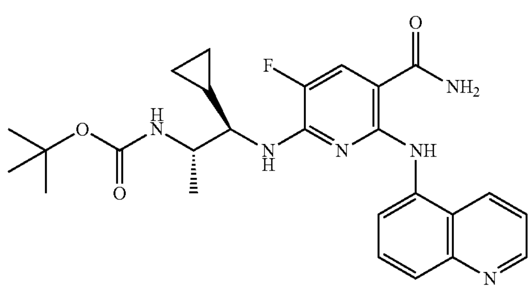 [SMILES: C[C@H](NC(=O)OC(C)(C)C)[C@H](Nc1nc(Nc2cccc3ncccc23)c(C(N)=O)cc1F)C1CC1] | tert-butyl ((1R,2S)-1-((5-carbamoyl-3-fluoro-6-(quinolin-5-ylamino)pyridin-2-yl)amino)-1-cyclopropylpropan-2-yl)carbamate | 495 | 1.18 |
| Reference Example 136-199 | 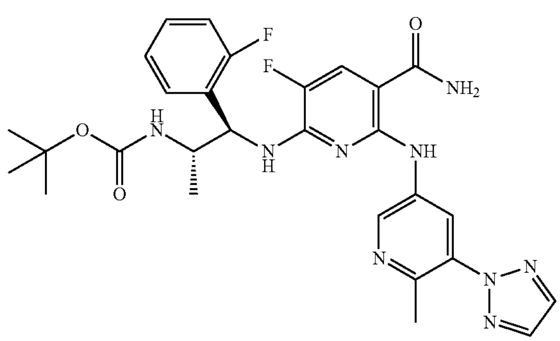 [SMILES: Cc1ncc(Nc2nc(N[C@H](c3ccccc3F)[C@H](C)NC(=O)OC(C)(C)C)c(F)cc2C(N)=O)cc1-n1nccn1] | tert-butyl ((1R,2S)-1-((5-carbamoyl-3-fluoro-6-((6-methyl-5-(2H-1,2,3-triazol-2-yl)pyridin-3-yl)amino)pyridin-2-yl)amino)-1-(2-fluorophenyl)propan-2-yl)carbamate | 580 | 1.58 |

TABLE 2-continued

| Reference Example | Structure | Compound name | MS (ESI m/z): (M + H) | RT (min) |
|---|---|---|---|---|
| Reference Example 136-200 | 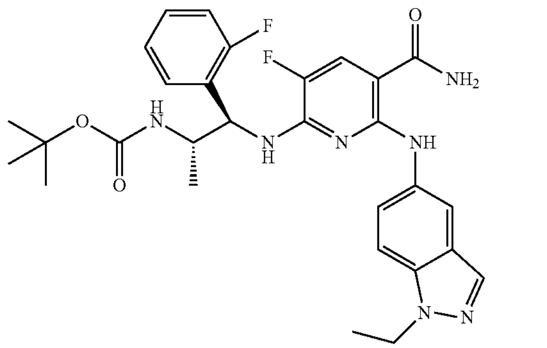 [SMILES: CCn1ncc2cc(Nc3nc(N[C@H](c4ccccc4F)[C@H](C)NC(=O)OC(C)(C)C)c(F)cc3C(N)=O)ccc21] | tert-butyl ((1R,2S)-1-((5-carbamoyl-6-((1-ethyl-1H-indazol-5-yl)amino)-3-fluoropyridin-2-yl)amino)-1-(2-fluorophenyl)propan-2-yl)carbamate | 566 | 1.63 |
| Reference Example 136-201 | 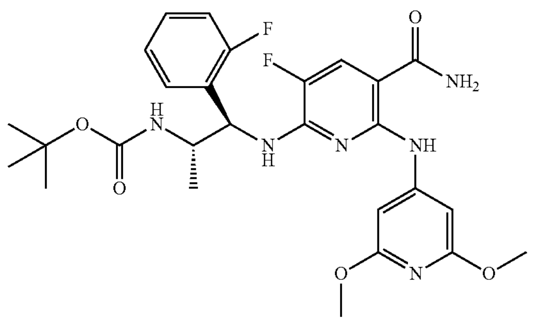 [SMILES: COc1cc(Nc2nc(N[C@H](c3ccccc3F)[C@H](C)NC(=O)OC(C)(C)C)c(F)cc2C(N)=O)cc(OC)n1] | tert-butyl ((1R,2S)-1-((5-carbamoyl-6-((2,6-dimethoxypyridin-4-yl)amino)-3-fluoropyridin-2-yl)amino)-1-(2-fluorophenyl)propan-2-yl)carbamate | 559 | 1.78 |
| Reference Example 136-202 | 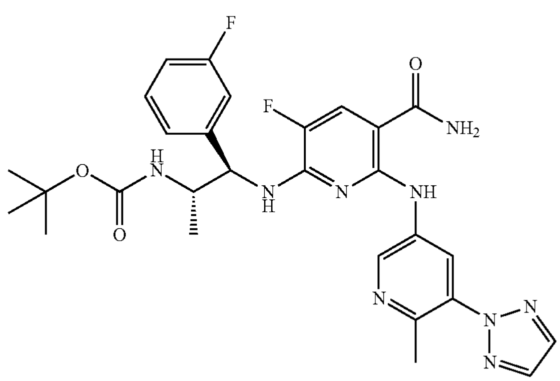 [SMILES: Cc1ncc(Nc2nc(N[C@H](c3cccc(F)c3)[C@H](C)NC(=O)OC(C)(C)C)c(F)cc2C(N)=O)cc1-n1nccn1] | tert-butyl ((1R,2S)-1-((5-carbamoyl-3-fluoro-6-((6-methyl-5-(2H-1,2,3-triazol-2-yl)pyridin-3-yl)amino)pyridin-2-yl)amino)-1-(3-fluorophenyl)propan-2-yl)carbamate | 580 | 1.55 |
| Reference Example 136-203 | 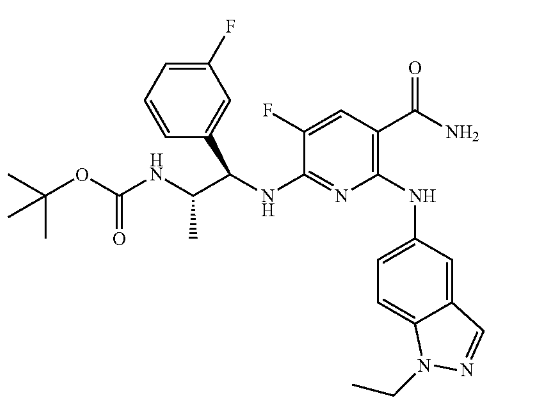 [SMILES: CCn1ncc2cc(Nc3nc(N[C@H](c4cccc(F)c4)[C@H](C)NC(=O)OC(C)(C)C)c(F)cc3C(N)=O)ccc21] | tert-butyl ((1R,2S)-1-((5-carbamoyl-6-((1-ethyl-1H-indazol-5-yl)amino)-3-fluoropyridin-2-yl)amino)-1-(3-fluorophenyl)propan-2-yl)carbamate | 566 | 1.62 |

TABLE 2-continued

| Reference Example | Structure | Compound name | MS (ESI m/z): (M + H) | RT (min) |
|---|---|---|---|---|
| Reference Example 136-204 | 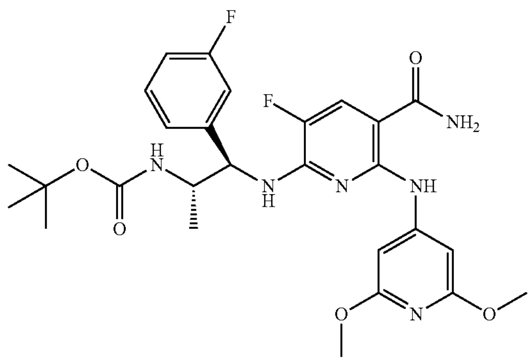 [SMILES: COc1cc(Nc2nc(N[C@H](c3cccc(F)c3)[C@H](C)NC(=O)OC(C)(C)C)c(F)cc2C(N)=O)cc(OC)n1] | tert-butyl ((1R,2S)-1-((5-carbamoyl-6-((2,6-dimethoxypyridin-4-yl)amino)-3-fluoropyridin-2-yl)amino)-1-(3-fluorophenyl)propan-2-yl)carbamate | 559 | 1.74 |
| Reference Example 136-205 | 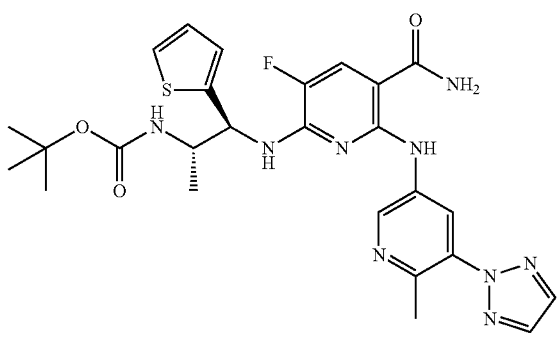 [SMILES: Cc1ncc(Nc2nc(N[C@H](c3cccs3)[C@H](C)NC(=O)OC(C)(C)C)c(F)cc2C(N)=O)cc1-n1nccn1] | tert-butyl ((1S,2S)-1-((5-carbamoyl-3-fluoro-6-((6-methyl-5-(2H-1,2,3-triazol-2-yl)pyridin-3-yl)amino)pyridin-2-yl)amino)-1-(thiophen-2-yl)propan-2-yl)carbamate | 568 | 1.53 |
| Reference Example 136-206 | 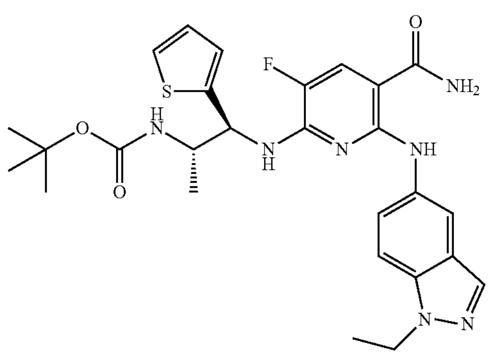 [SMILES: CCn1ncc2cc(Nc3nc(N[C@H](c4cccs4)[C@H](C)NC(=O)OC(C)(C)C)c(F)cc3C(N)=O)ccc21] | tert-butyl ((1S,2S)-1-((5-carbamoyl-6-((1-ethyl-1H-indazol-5-yl)amino)-3-fluoropyridin-2-yl)amino)-1-(thiophen-2-yl)propan-2-yl)carbamate | 554 | 1.59 |
| Reference Example 136-207 | 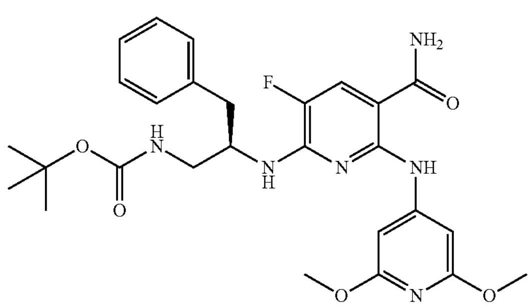 [SMILES: COc1cc(Nc2nc(N[C@@H](CNC(=O)OC(C)(C)C)Cc3ccccc3)c(F)cc2C(N)=O)cc(OC)n1] | (R)-tert-butyl (2-((5-carbamoyl-6-((2,6-dimethoxypyridin-4-yl)amino)-3-fluoropyridin-2-yl)amino)-3-phenylpropyl)carbamate | 541 | 1.75 |

TABLE 2-continued

| Reference Example | Structure | Compound name | MS (ESI m/z): (M + H) | RT (min) |
|---|---|---|---|---|
| Reference Example 136-208 | 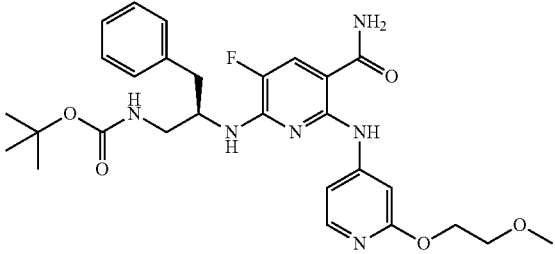 [SMILES: COCCOc1cc(Nc2nc(N[C@@H](CNC(=O)OC(C)(C)C)Cc3ccccc3)c(F)cc2C(N)=O)ccn1] | (R)-tert-butyl (2-((5-carbamoyl-3-fluoro-6-((2-(2-methoxyethoxy)pyridin-4-yl)amino)pyridin-2-yl)amino)-3-phenylpropyl)carbamate | 555 | 1.20 |
| Reference Example 136-209 | 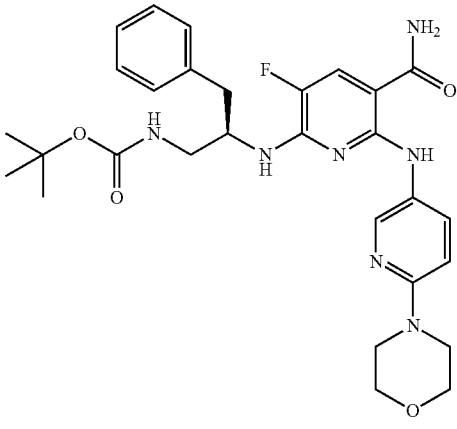 [SMILES: CC(C)(C)OC(=O)NC[C@@H](Cc1ccccc1)Nc1nc(Nc2ccc(N3CCOCC3)nc2)c(C(N)=O)cc1F] | (R)-tert-butyl (2-((5-carbamoyl-3-fluoro-6-((6-morpholinopyridin-3-yl)amino)pyridin-2-yl)amino)-3-phenylpropyl)carbamate | 566 | 1.20 |
| Reference Example 136-210 | 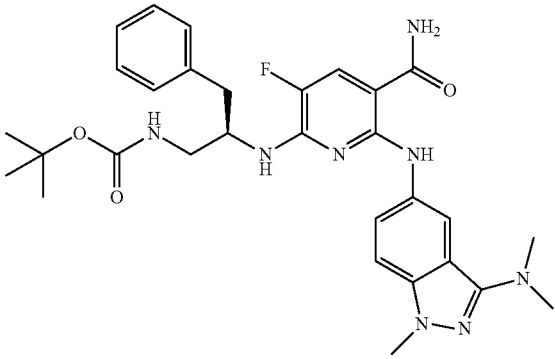 [SMILES: CN(C)c1nn(C)c2ccc(Nc3nc(N[C@@H](CNC(=O)OC(C)(C)C)Cc4ccccc4)c(F)cc3C(N)=O)cc12] | (R)-tert-butyl (2-((5-carbamoyl-6-((3-(dimethylamino)-1-methyl-1H-indazol-5-yl)amino)-3-fluoropyridin-2-yl)amino)-3-phenylpropyl)carbamate | 577 | 1.58 |
| Reference Example 136-211 | 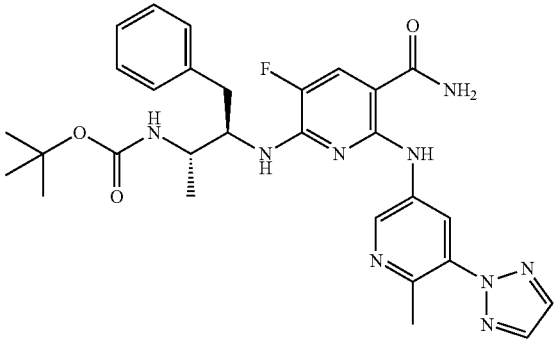 [SMILES: Cc1ncc(Nc2nc(N[C@H](Cc3ccccc3)[C@H](C)NC(=O)OC(C)(C)C)c(F)cc2C(N)=O)cc1-n1nccn1] | tert-butyl ((2S,3R)-3-((5-carbamoyl-3-fluoro-6-((6-methyl-5-(2H-1,2,3-triazol-2-yl)pyridin-3-yl)amino)pyridin-2-yl)amino)-4-phenylbutan-2-yl)carbamate | 576 | 1.56 |

TABLE 2-continued

| Reference Example | Structure | Compound name | MS (ESI m/z): (M + H) | RT (min) |
|---|---|---|---|---|
| Reference Example 136-212 | 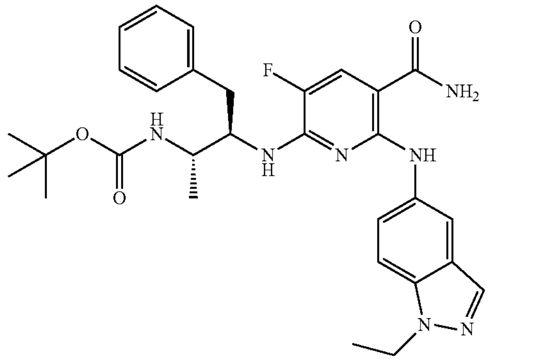 [SMILES: CCn1ncc2cc(Nc3nc(N[C@H](Cc4ccccc4)[C@H](C)NC(=O)OC(C)(C)C)c(F)cc3C(N)=O)ccc21] | tert-butyl ((2S,3R)-3-((5-carbamoyl-6-((1-ethyl-1H-indazol-5-yl)amino)-3-fluoropyridin-2-yl)amino)-4-phenylbutan-2-yl)carbamate | 562 | 1.60 |
| Reference Example 136-213 | 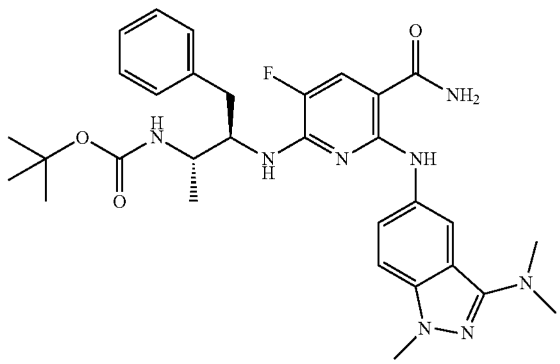 [SMILES: C[C@H](NC(=O)OC(C)(C)C)[C@@H](Cc1ccccc1)Nc1nc(Nc2ccc3c(c2)c(N(C)C)nn3C)c(C(N)=O)cc1F] | tert-butyl ((2S,3R)-3-((5-carbamoyl-6-((3-(dimethylamino)-1-methyl-1H-indazol-5-yl)amino)-3-fluoropyridin-2-yl)amino)-4-phenylbutan-2-yl)carbamate | 591 | 1.59 |
| Reference Example 136-214 | 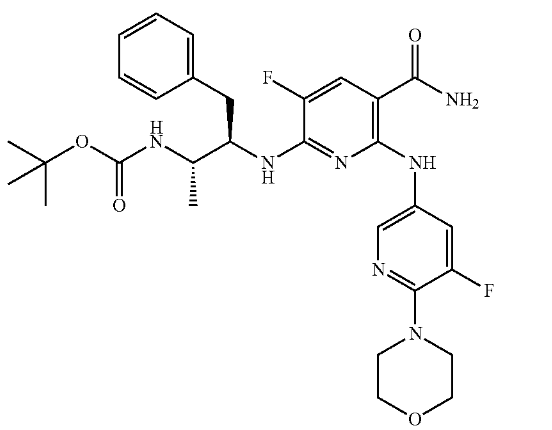 [SMILES: C[C@H](NC(=O)OC(C)(C)C)[C@@H](Cc1ccccc1)Nc1nc(Nc2cnc(N3CCOCC3)c(F)c2)c(C(N)=O)cc1F] | tert-butyl ((2S,3R)-3-((5-carbamoyl-3-fluoro-6-((5-fluoro-6-morpholinopyridin-3-yl)amino)pyridin-2-yl)amino)-4-phenylbutan-2-yl)carbamate | 598 | 1.60 |
| Reference Example 136-215 | 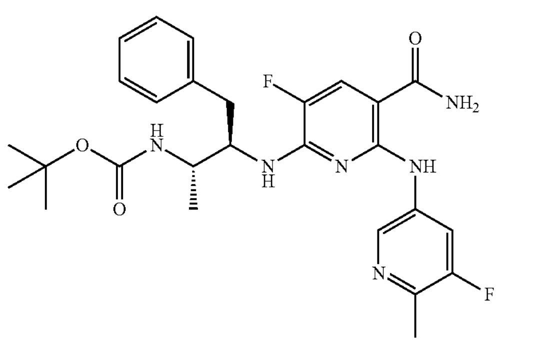 [SMILES: Cc1ncc(Nc2nc(N[C@H](Cc3ccccc3)[C@H](C)NC(=O)OC(C)(C)C)c(F)cc2C(N)=O)cc1F] | tert-butyl ((2S,3R)-3-((5-carbamoyl-3-fluoro-6-((5-fluoro-6-methylpyridin-3-yl)amino)pyridin-2-yl)amino)-4-phenylbutan-2-yl)carbamate | 527 | 1.53 |

TABLE 2-continued

| Reference Example | Structure | Compound name | MS (ESI m/z): (M + H) | RT (min) |
|---|---|---|---|---|
| Reference Example 136-216 | 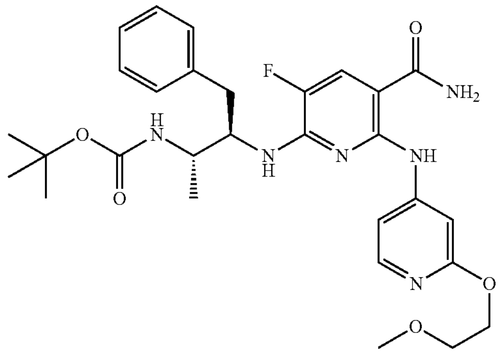 [SMILES: COCCOc1cc(Nc2nc(N[C@H](Cc3ccccc3)[C@H](C)NC(=O)OC(C)(C)C)c(F)cc2C(N)=O)ccn1] | tert-butyl ((2S,3R)-3-((5-carbamoyl-3-fluoro-6-((2-(2-methoxyethoxy)pyridin-4-yl)amino)pyridin-2-yl)amino)-4-phenylbutan-2-yl)carbamate | 569 | 1.23 |
| Reference Example 136-217 | 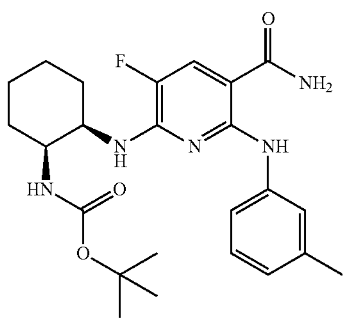 [SMILES: Cc1cccc(Nc2nc(N[C@@H]3CCCC[C@@H]3NC(=O)OC(C)(C)C)c(F)cc2C(N)=O)c1] | tert-butyl ((1S,2R)-2-((5-carbamoyl-3-fluoro-6-(m-tolylamino)pyridin-2-yl)amino)cyclohexyl)carbamate | 458 | 1.82 |
| Reference Example 136-218 | 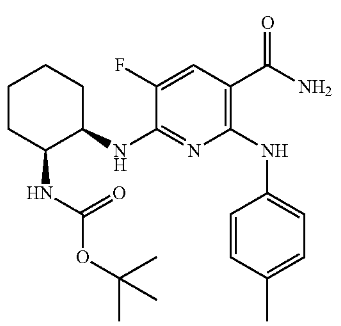 [SMILES: Cc1ccc(Nc2nc(N[C@@H]3CCCC[C@@H]3NC(=O)OC(C)(C)C)c(F)cc2C(N)=O)cc1] | tert-butyl ((1S,2R)-2-((5-carbamoyl-3-fluoro-6-(p-tolylamino)pyridin-2-yl)amino)cyclohexyl)carbamate | 458 | 1.82 |
| Reference Example 136-219 | 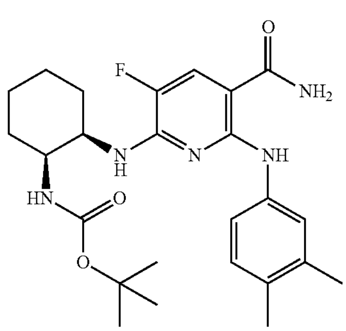 [SMILES: Cc1ccc(Nc2nc(N[C@@H]3CCCC[C@@H]3NC(=O)OC(C)(C)C)c(F)cc2C(N)=O)cc1C] | tert-butyl ((1S,2R)-2-((5-carbamoyl-6-((3,4-dimethylphenyl)amino)-3-fluoropyridin-2-yl)amino)cyclohexyl)carbamate | 472 | 1.89 |

TABLE 2-continued

| Reference Example | Structure | Compound name | MS (ESI m/z): (M + H) | RT (min) |
|---|---|---|---|---|
| Reference Example 136-220 | 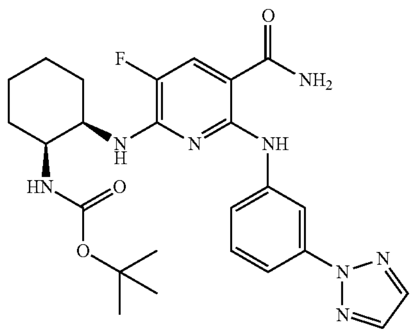 [SMILES: CC(C)(C)OC(=O)N[C@H]1CCCC[C@H]1Nc1nc(Nc2cccc(-n3nccn3)c2)c(C(N)=O)cc1F] | tert-butyl ((1S,2R)-2-((6-((3-(2H-1,2,3-triazol-2-yl)phenyl)amino)-5-carbamoyl-3-fluoropyridin-2-yl)amino)cyclohexyl)carbamate | 511 | 1.73 |
| Reference Example 136-221 | 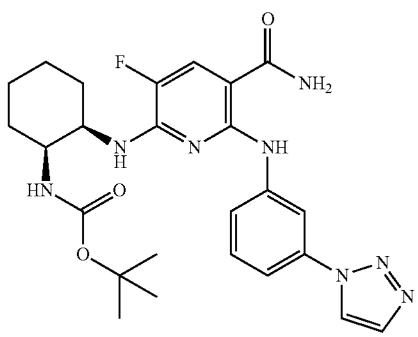 [SMILES: CC(C)(C)OC(=O)N[C@H]1CCCC[C@H]1Nc1nc(Nc2cccc(-n3ccnn3)c2)c(C(N)=O)cc1F] | tert-butyl ((1S,2R)-2-((6-((3-(1H-1,2,3-triazol-1-yl)phenyl)amino)-5-carbamoyl-3-fluoropyridin-2-yl)amino)cyclohexyl)carbamate | 511 | 1.47 |
| Reference Example 136-222 | 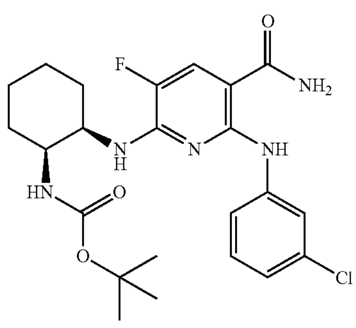 [SMILES: CC(C)(C)OC(=O)N[C@H]1CCCC[C@H]1Nc1nc(Nc2cccc(Cl)c2)c(C(N)=O)cc1F] | tert-butyl ((1S,2R)-2-((5-carbamoyl-6-((3-chlorophenyl)amino)-3-fluoropyridin-2-yl)amino)cyclohexyl)carbamate | 478 480 | 1.88 |
| Reference Example 136-223 | 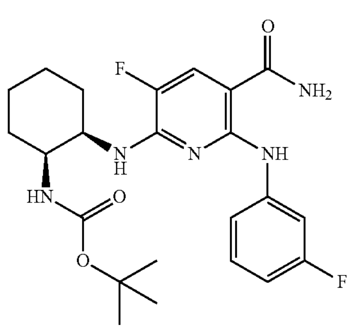 [SMILES: CC(C)(C)OC(=O)N[C@H]1CCCC[C@H]1Nc1nc(Nc2cccc(F)c2)c(C(N)=O)cc1F] | tert-butyl ((1S,2R)-2-((5-carbamoyl-3-fluoro-6-((3-fluorophenyl)amino)pyridin-2-yl)amino)cyclohexyl)carbamate | 462 | 1.78 |

TABLE 2-continued

| Reference Example | Structure | Compound name | MS (ESI m/z): (M + H) | RT (min) |
|---|---|---|---|---|
| Reference Example 136-224 | 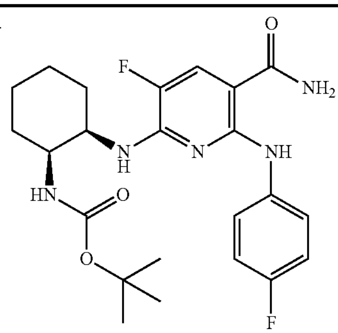 | tert-butyl ((1S,2R)-2-((5-carbamoyl-3-fluoro-6-((4-fluorophenyl)amino)pyridin-2-yl)amino)cyclohexyl)carbamate | 462 | 1.75 |
| Reference Example 136-225 | 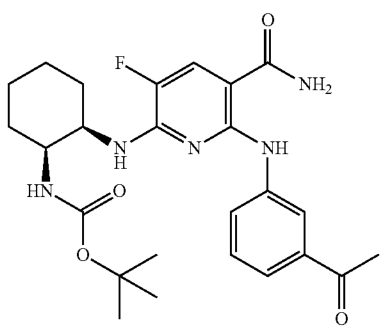 [SMILES: CC(=O)c1cccc(Nc2nc(N[C@@H]3CCCC[C@@H]3NC(=O)OC(C)(C)C)c(F)cc2C(N)=O)c1] | tert-butyl ((1S,2R)-2-((6-((3-acetylphenyl)amino)-5-carbamoyl-3-fluoropyridin-2-yl)amino)cyclohexyl)carbamate | 486 | 1.61 |
| Reference Example 136-226 | 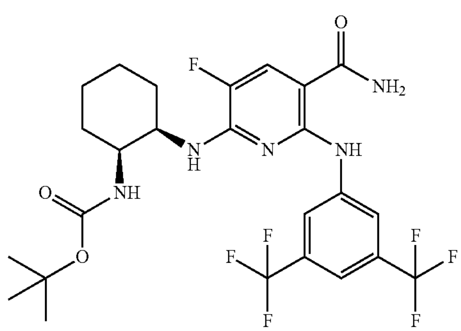 [SMILES: CC(C)(C)OC(=O)N[C@H]1CCCC[C@H]1Nc1nc(Nc2cc(C(F)(F)F)cc(C(F)(F)F)c2)c(C(N)=O)cc1F] | tert-butyl ((1S,2R)-2-((6-((3,5-bis(trifluoromethyl)phenyl)amino)-5-carbamoyl-3-fluoropyridin-2-yl)amino)cyclohexyl)carbamate | 580 | 2.09 |
| Reference Example 136-227 | 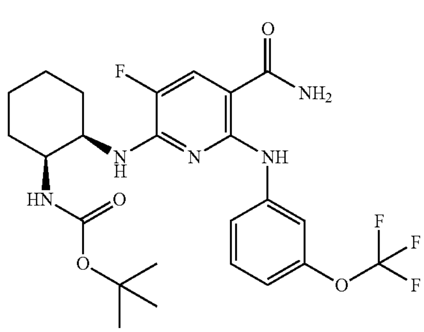 [SMILES: CC(C)(C)OC(=O)N[C@H]1CCCC[C@H]1Nc1nc(Nc2cccc(OC(F)(F)F)c2)c(C(N)=O)cc1F] | tert-butyl ((1S,2R)-2-((5-carbamoyl-3-fluoro-6-((3-(trifluoromethoxy)phenyl)amino)pyridin-2-yl)amino)cyclohexyl)carbamate | 528 | 2.00 |

TABLE 2-continued

| Reference Example | Structure | Compound name | MS (ESI m/z): (M + H) | RT (min) |
|---|---|---|---|---|
| ReferenceExample 136-228 | 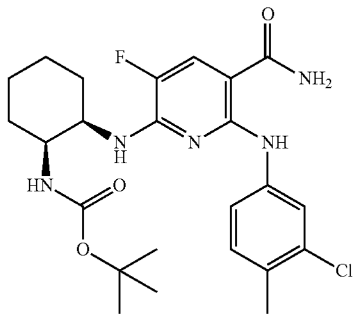 [SMILES: Cc1ccc(Nc2nc(N[C@@H]3CCCC[C@@H]3NC(=O)OC(C)(C)C)c(F)cc2C(N)=O)cc1Cl] | tert-butyl ((1S,2R)-2-((5-carbamoyl-6-((3-chloro-4-methylphenyl)amino)-3-fluoropyridin-2-yl)amino)cyclohexyl)carbamate | 492 494 | 2.25 |
| Reference Example 136-229 | 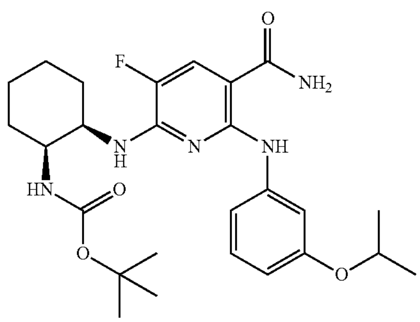 [SMILES: CC(C)Oc1cccc(Nc2nc(N[C@@H]3CCCC[C@@H]3NC(=O)OC(C)(C)C)c(F)cc2C(N)=O)c1] | tert-butyl ((1S,2R)-2-((5-carbamoyl-3-fluoro-6-((3-isopropoxyphenyl)amino)pyridin-2-yl)amino)cyclohexyl)carbamate | 502 | 2.07 |
| Reference Example 136-230 | 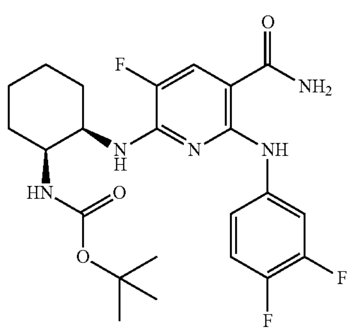 [SMILES: CC(C)(C)OC(=O)N[C@H]1CCCC[C@H]1Nc1nc(Nc2ccc(F)c(F)c2)c(C(N)=O)cc1F] | tert-butyl ((1S,2R)-2-((5-carbamoyl-6-((3,4-difluorophenyl)amino)-3-fluoropyridin-2-yl)amino)cyclohexyl)carbamate | 480 | 1.87 |
| Reference Example 136-231 | 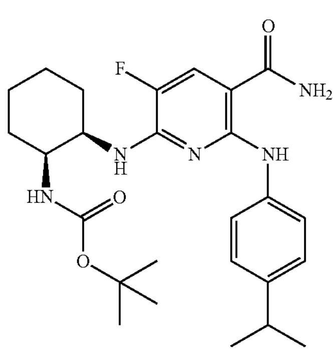 [SMILES: CC(C)c1ccc(Nc2nc(N[C@@H]3CCCC[C@@H]3NC(=O)OC(C)(C)C)c(F)cc2C(N)=O)cc1] | tert-butyl ((1S,2R)-2-((5-carbamoyl-3-fluoro-6-((4-isopropylphenyl)amino)pyridin-2-yl)amino)cyclohexyl)carbamate | 486 | 2.00 |

TABLE 2-continued

| Reference Example | Structure | Compound name | MS (ESI m/z): (M + H) | RT (min) |
|---|---|---|---|---|
| Reference Example 136-232 | 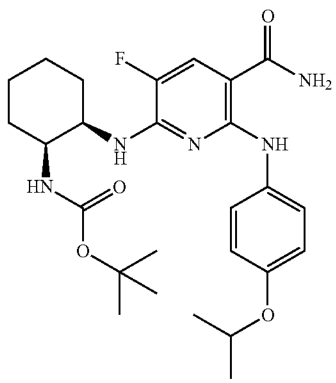 [SMILES: CC(C)Oc1ccc(Nc2nc(N[C@@H]3CCCC[C@@H]3NC(=O)OC(C)(C)C)c(F)cc2C(N)=O)cc1] | tert-butyl ((1S,2R)-2-((5-carbamoyl-3-fluoro-6-((4-isopropoxyphenyl)amino)pyridin-2-yl)amino)cyclohexyl)carbamate | 502 | 1.84 |
| Reference Example 136-233 | 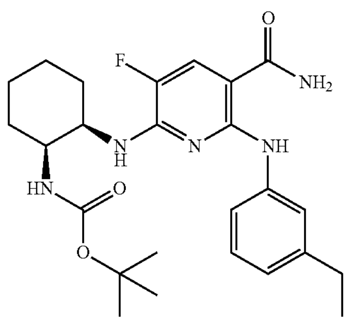 [SMILES: CCc1cccc(Nc2nc(N[C@@H]3CCCC[C@@H]3NC(=O)OC(C)(C)C)c(F)cc2C(N)=O)c1] | tert-butyl ((1S,2R)-2-((5-carbamoyl-6-((3-ethylphenyl)amino)-3-fluoropyridin-2-yl)amino)cyclohexyl)carbamate | 472 | 1.91 |
| Reference Example 136-234 | 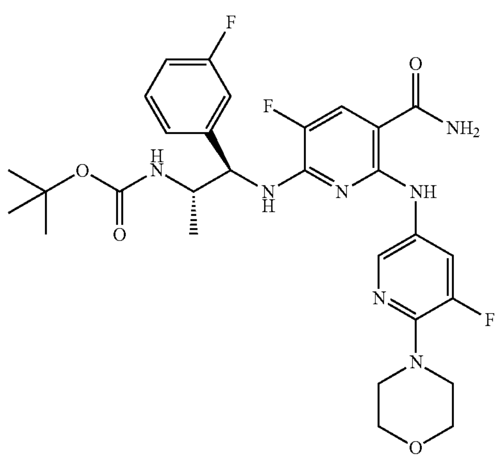 [SMILES: C[C@H](NC(=O)OC(C)(C)C)[C@H](Nc1nc(Nc2cnc(N3CCOCC3)c(F)c2)c(C(N)=O)cc1F)c1cccc(F)c1] | tert-butyl ((1R,2S)-1-((5-carbamoyl-3-fluoro-6-((5-fluoro-6-morpholinopyridin-3-yl)amino)pyridin-2-yl)amino)-1-(3-fluorophenyl)propan-2-yl)carbamate | 602 | 1.62 |
| Reference Example 136-235 | 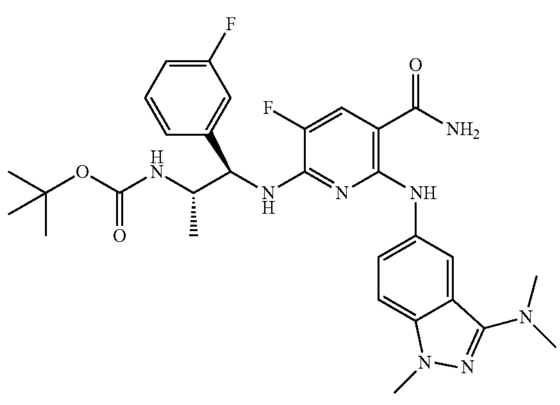 [SMILES: C[C@H](NC(=O)OC(C)(C)C)[C@H](Nc1nc(Nc2ccc3c(c2)c(N(C)C)nn3C)c(C(N)=O)cc1F)c1cccc(F)c1] | tert-butyl ((1R,2S)-1-((5-carbamoyl-6-((3-(dimethylamino)-1-methyl-1H-indazol-5-yl)amino)-3-fluoropyridin-2-yl)amino)-1-(3-fluorophenyl)propan-2-yl)carbamate | 595 | 1.58 |

| Reference Example | Structure | Compound name | MS (ESI m/z): (M+H) | RT (min) |
|---|---|---|---|---|
| Reference Example 136-236 | 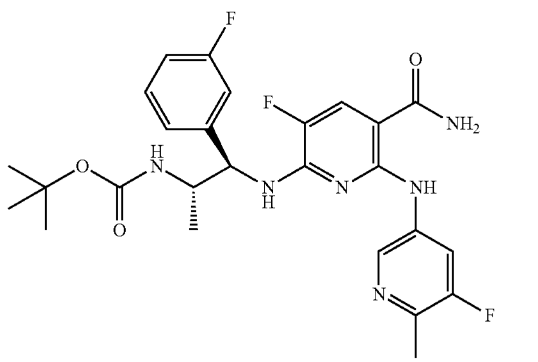 [SMILES: Cc1ncc(Nc2nc(N[C@H](c3cccc(F)c3)[C@H](C)NC(=O)OC(C)(C)C)c(F)cc2C(N)=O)cc1F] | tert-butyl ((1R,2S)-1-((5-carbamoyl-3-fluoro-6-((5-fluoro-6-methylpyridin-3-yl)amino)pyridin-2-yl)amino)-1-(3-fluorophenyl)propan-2-yl)carbamate | 531 | 1.55 |
| Reference Example 136-237 | 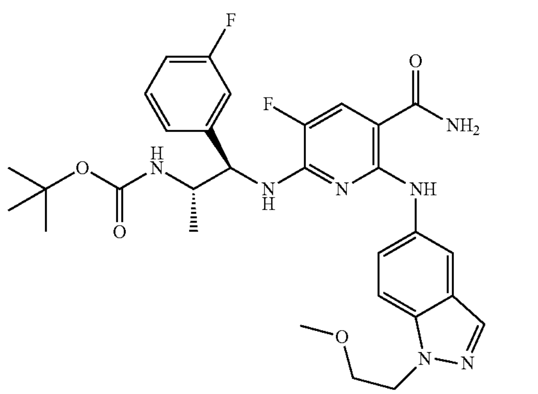 [SMILES: COCCn1ncc2cc(Nc3nc(N[C@H](c4cccc(F)c4)[C@H](C)NC(=O)OC(C)(C)C)c(F)cc3C(N)=O)ccc21] | tert-butyl ((1R,2S)-1-((5-carbamoyl-3-fluoro-6-((1-(2-methoxyethyl)-1H-indazol-5-yl)amino)pyridin-2-yl)amino)-1-(3-fluorophenyl)propan-2-yl)carbamate | 596 | 1.55 |
| Reference Example 136-238 | 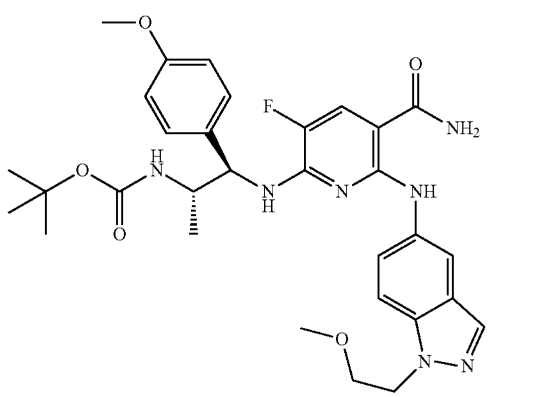 [SMILES: COCCn1ncc2cc(Nc3nc(N[C@H](c4ccc(OC)cc4)[C@H](C)NC(=O)OC(C)(C)C)c(F)cc3C(N)=O)ccc21] | tert-butyl ((1R,2S)-1-((5-carbamoyl-3-fluoro-6-((1-(2-methoxyethyl)-1H-indazol-5-yl)amino)pyridin-2-yl)amino)-1-(4-methoxyphenyl)propan-2-yl)carbamate | 608 | 1.50 |
| Reference Example 136-239 | 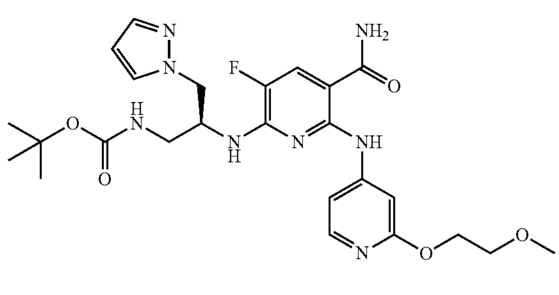 [SMILES: COCCOc1cc(Nc2nc(N[C@@H](CNC(=O)OC(C)(C)C)Cn3cccn3)c(F)cc2C(N)=O)ccn1] | (S)-tert-butyl (2-((5-carbamoyl-3-fluoro-6-((2-(2-methoxyethoxy)pyridin-4-yl)amino)pyridin-2-yl)amino)-3-(1H-pyrazol-1-yl)propyl)carbamate | 545 | 1.00 |

TABLE 2-continued

| Reference Example | Structure | Compound name | MS (ESI m/z): (M + H) | RT (min) |
|---|---|---|---|---|
| Reference Example 136-240 | 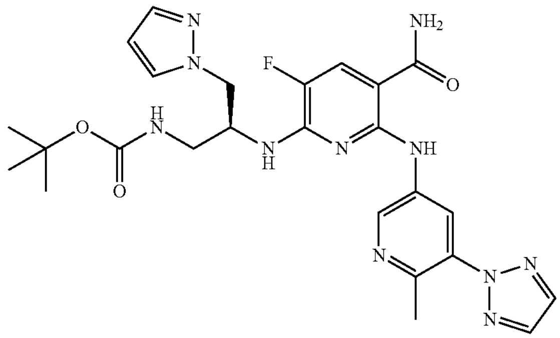 [SMILES: Cc1ncc(Nc2nc(N[C@@H](CNC(=O)OC(C)(C)C)Cn3cccn3)c(F)cc2C(N)=O)cc1-n1nccn1] | (S)-tert-butyl (2-((5-carbamoyl-3-fluoro-6-((6-methyl-5-(2H-1,2,3-triazol-2-yl)pyridin-3-yl)amino)pyridin-2-yl)amino)-3-(1H-pyrazol-1-yl)propyl)carbamate | 552 | 1.23 |
| Reference Example 136-241 | 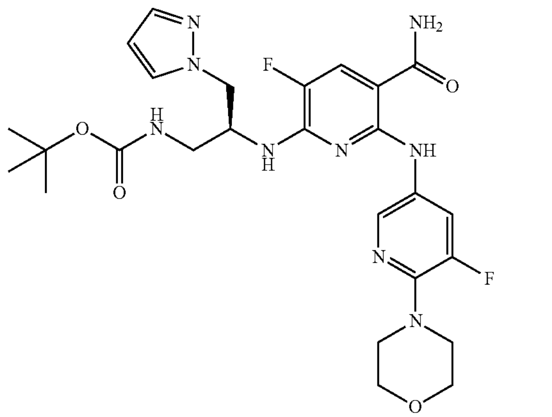 [SMILES: CC(C)(C)OC(=O)NC[C@@H](Cn1cccn1)Nc1nc(Nc2cnc(N3CCOCC3)c(F)c2)c(C(N)=O)cc1F] | (S)-tert-butyl (2-((5-carbamoyl-3-fluoro-6-((5-fluoro-6-morpholinopyridin-3-yl)amino)pyridin-2-yl)amino)-3-(1H-pyrazol-1-yl)propyl)carbamate | 574 | 1.32 |
| Reference Example 136-242 | 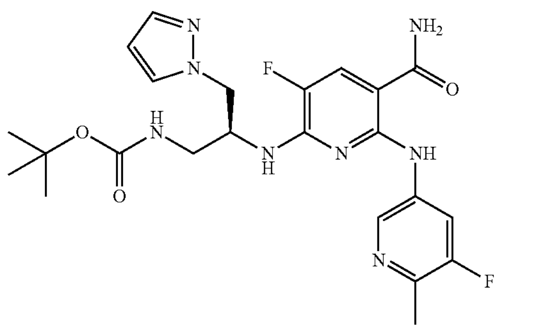 [SMILES: Cc1ncc(Nc2nc(N[C@@H](CNC(=O)OC(C)(C)C)Cn3cccn3)c(F)cc2C(N)=O)cc1F] | (S)-tert-butyl (2-((5-carbamoyl-3-fluoro-6-((5-fluoro-6-methylpyridin-3-yl)amino)pyridin-2-yl)amino)-3-(1H-pyrazol-1-yl)propyl)carbamate | 503 | 1.18 |
| Reference Example 136-243 | 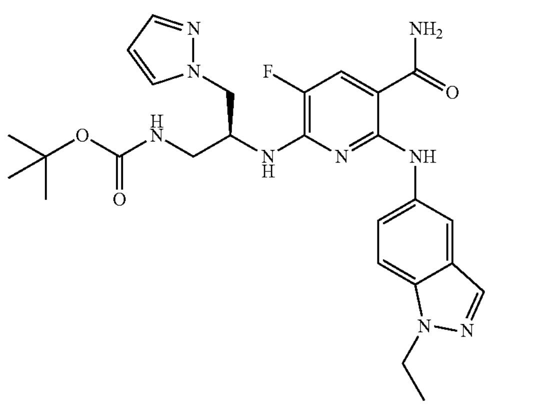 [SMILES: CCn1ncc2cc(Nc3nc(N[C@@H](CNC(=O)OC(C)(C)C)Cn4cccn4)c(F)cc3C(N)=O)ccc21] | (S)-tert-butyl (2-((5-carbamoyl-6-((1-ethyl-1H-indazol-5-yl)amino)-3-fluoropyridin-2-yl)amino)-3-(1H-pyrazol-1-yl)propyl)carbamate | 538 | 1.34 |

TABLE 2-continued

| Reference Example | Structure | Compound name | MS (ESI m/z): (M + H) | RT (min) |
|---|---|---|---|---|
| Reference Example 136-244 | 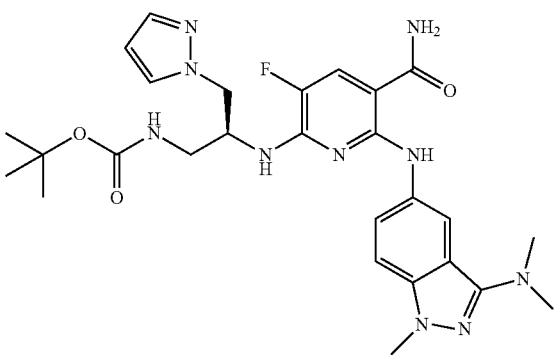 [SMILES: CN(C)c1nn(C)c2ccc(Nc3nc(N[C@@H](CNC(=O)OC(C)(C)C)Cn4cccn4)c(F)cc3C(N)=O)cc12] | (S)-tert-butyl (2-((5-carbamoyl-6-((3-(dimethylamino)-1-methyl-1H-indazol-5-yl)amino)-3-fluoropyridin-2-yl)amino)-3-(1H-pyrazol-1-yl)propyl)carbamate | 567 | 1.31 |
| Reference Example 136-245 | 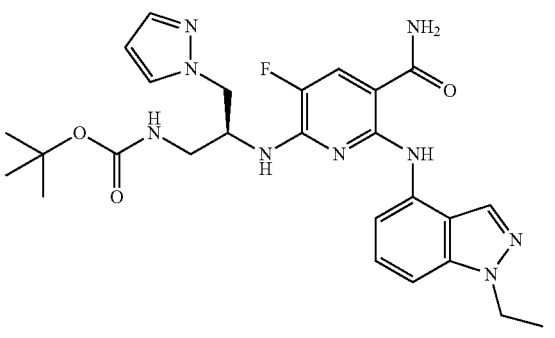 [SMILES: CCn1ncc2c(Nc3nc(N[C@@H](CNC(=O)OC(C)(C)C)Cn4cccn4)c(F)cc3C(N)=O)cccc21] | (S)-tert-butyl (2-((5-carbamoyl-6-((1-ethyl-1H-indazol-4-yl)amino)-3-fluoropyridin-2-yl)amino)-3-(1H-pyrazol-1-yl)propyl)carbamate | 538 | 1.42 |
| Reference Example 136-246 | 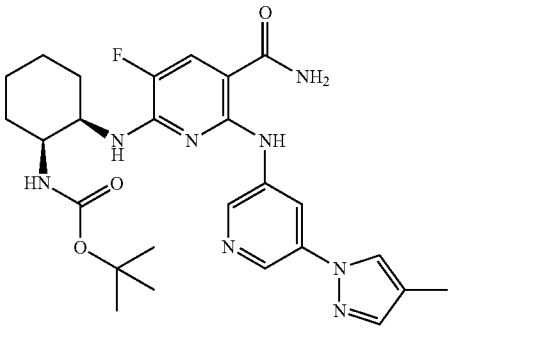 [SMILES: Cc1cnn(-c2cncc(Nc3nc(N[C@@H]4CCCC[C@@H]4NC(=O)OC(C)(C)C)c(F)cc3C(N)=O)c2)c1] | tert-butyl ((1S,2R)-2-((5-carbamoyl-3-fluoro-6-((5-(4-methyl-1H-pyrazol-1-yl)pyridin-3-yl)amino)pyridin-2-yl)amino)cyclohexyl)carbamate | 525 | 1.49 |
| Reference Example 136-247 | 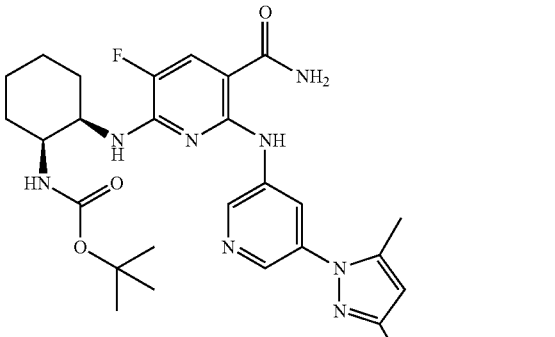 | tert-butyl ((1S,2R)-2-((5-carbamoyl-6-((5-(3,5-dimethyl-1H-pyrazol-1-yl)pyridin-3-yl)amino)-3-fluoropyridin-2-yl)amino)cyclohexyl)carbamate | 539 | 1.46 |

TABLE 2-continued

| Reference Example | Structure | Compound name | MS (ESI m/z): (M + H) | RT (min) |
|---|---|---|---|---|
| Reference Example 136-248 | 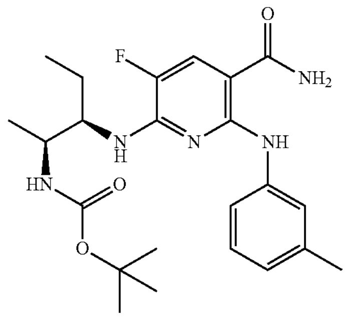 [SMILES: CC[C@@H](Nc1nc(Nc2cccc(C)c2)c(C(N)=O)cc1F)[C@H](C)NC(=O)OC(C)(C)C] | tert-butyl ((2S,3R)-3-((5-carbamoyl-3-fluoro-6-(m-tolylamino)pyridin-2-yl)amino)pentan-2-yl)carbamate | 446 | 1.74 |
| Reference Example 136-249 | 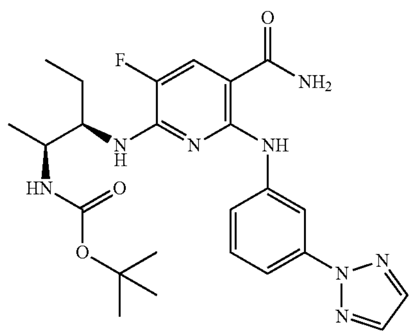 [SMILES: CC[C@@H](Nc1nc(Nc2cccc(-n3nccn3)c2)c(C(N)=O)cc1F)[C@H](C)NC(=O)OC(C)(C)C] | tert-butyl ((2S,3R)-3-((6-((3-(2H-1,2,3-triazol-2-yl)phenyl)amino)-5-carbamoyl-3-fluoropyridin-2-yl)amino)pentan-2-yl)carbamate | 499 | 1.76 |
| Reference Example 136-250 | 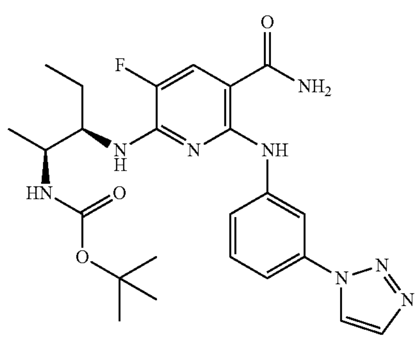 [SMILES: CC[C@@H](Nc1nc(Nc2cccc(-n3ccnn3)c2)c(C(N)=O)cc1F)[C@H](C)NC(=O)OC(C)(C)C] | tert-butyl ((2S,3R)-3-((6-((3-(1H-1,2,3-triazol-1-yl)phenyl)amino)-5-carbamoyl-3-fluoropyridin-2-yl)amino)pentan-2-yl)carbamate | 499 | 1.55 |
| Reference Example 136-251 | 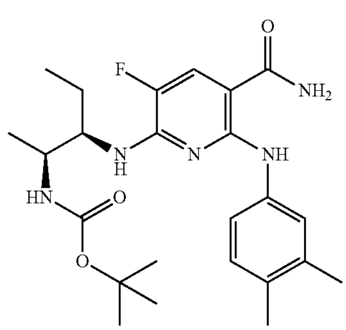 [SMILES: CC[C@@H](Nc1nc(Nc2ccc(C)c(C)c2)c(C(N)=O)cc1F)[C@H](C)NC(=O)OC(C)(C)C] | tert-butyl ((2S,3R)-3-((5-carbamoyl-6-((3,4-dimethylphenyl)amino)-3-fluoropyridin-2-yl)amino)pentan-2-yl)carbamate | 460 | 1.93 |

TABLE 2-continued

| Reference Example | Structure | Compound name | MS (ESI m/z): (M + H) | RT (min) |
|---|---|---|---|---|
| Reference Example 136-252 | 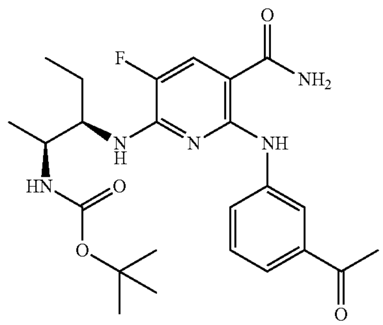 [SMILES: CC[C@@H](Nc1nc(Nc2cccc(C(C)=O)c2)c(C(N)=O)cc1F)[C@H](C)NC(=O)OC(C)(C)C] | tert-butyl ((2S,3R)-3-((6-((3-acetylphenyl)amino)-5-carbamoyl-3-fluoropyridin-2-yl)amino)pentan-2-yl)carbamate | 474 | 1.64 |
| Reference Example 136-253 | 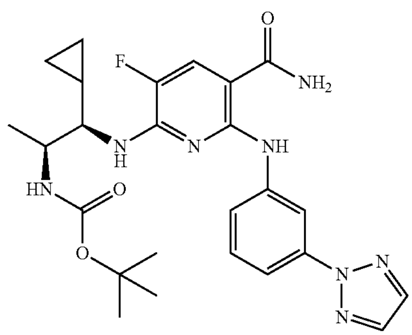 [SMILES: C[C@H](NC(=O)OC(C)(C)C)[C@H](Nc1nc(Nc2cccc(-n3nccn3)c2)c(C(N)=O)cc1F)C1CC1] | tert-butyl ((1R,2S)-1-((6-((3-(2H-1,2,3-triazol-2-yl)phenyl)amino)-5-carbamoyl-3-fluoropyridin-2-yl)amino)-1-cyclopropylpropan-2-yl)carbamate | 511 | 1.73 |
| Reference Example 136-254 | 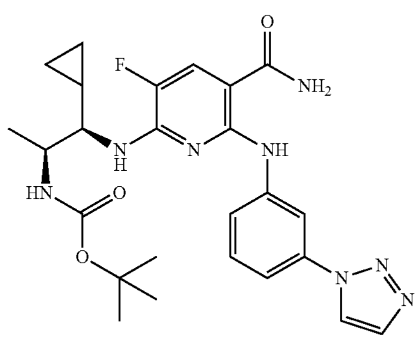 [SMILES: C[C@H](NC(=O)OC(C)(C)C)[C@H](Nc1nc(Nc2cccc(-n3ccnn3)c2)c(C(N)=O)cc1F)C1CC1] | tert-butyl ((1R,2S)-1-((6-((3-(1H-1,2,3-triazol-1-yl)phenyl)amino)-5-carbamoyl-3-fluoropyridin-2-yl)amino)-1-cyclopropylpropan-2-yl)carbamate | 511 | 1.49 |
| Reference Example 136-255 | 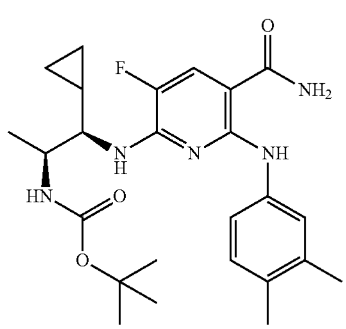 [SMILES: Cc1ccc(Nc2nc(N[C@H](C3CC3)[C@H](C)NC(=O)OC(C)(C)C)c(F)cc2C(N)=O)cc1C] | tert-butyl ((1R,2S)-1-((5-carbamoyl-6-((3,4-dimethylphenyl)amino)-3-fluoropyridin-2-yl)amino)-1-cyclopropylpropan-2-yl)carbamate | 472 | 1.83 |

TABLE 2-continued

| Reference Example | Structure | Compound name | MS (ESI m/z): (M + H) | RT (min) |
|---|---|---|---|---|
| Reference Example 136-256 | 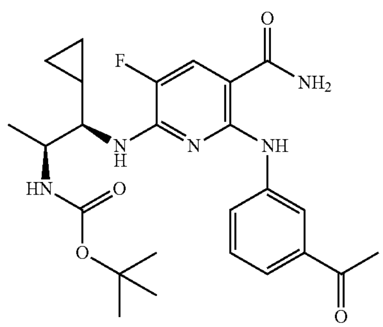 [SMILES: CC(=O)c1cccc(Nc2nc(N[C@H](C3CC3)[C@H](C)NC(=O)OC(C)(C)C)c(F)cc2C(N)=O)c1] | tert-butyl ((1R,2S)-1-((6-((3-acetylphenyl)amino)-5-carbamoyl-3-fluoropyridin-2-yl)amino)-1-cyclopropylpropan-2-yl)carbamate | 486 | 1.62 |
| Reference Example 136-257 | 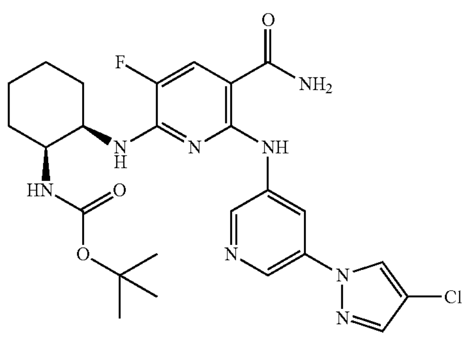 [SMILES: CC(C)(C)OC(=O)N[C@H]1CCCC[C@H]1Nc1nc(Nc2cncc(-n3cc(Cl)cn3)c2)c(C(N)=O)cc1F] | tert-butyl ((1S,2R)-2-((5-carbamoyl-6-((5-(4-chloro-1H-pyrazol-1-yl)pyridin-3-yl)amino)-3-fluoropyridin-2-yl)amino)cyclohexyl)carbamate | 545 547 | 1.65 |
| Reference Example 136-258 | 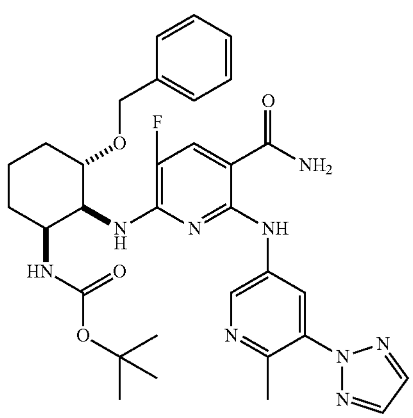 | Mixture of tert-butyl (3-(benzyloxy)-2-((5-carbamoyl-3-fluoro-6-((6-methyl-5-(2H-1,2,3-triazol-2-yl)pyridin-3-yl)amino)pyridin-2-yl)amino)cyclohexyl)carbamate (1S,2S,3S), (1R,2R,3R) | 632 | 1.64 |
| Reference Example 136-259 | 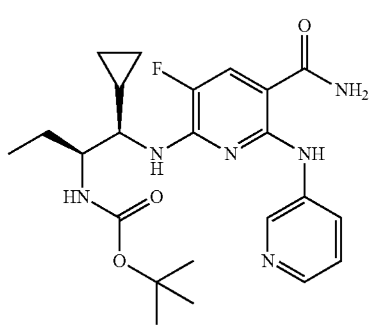 [SMILES: CC[C@H](NC(=O)OC(C)(C)C)[C@H](Nc1nc(Nc2cccnc2)c(C(N)=O)cc1F)C1CC1] | tert-butyl ((1R,2S)-1-((5-carbamoyl-3-fluoro-6-(pyridin-3-ylamino)pyridin-2-yl)amino)-1-cyclopropylbutan-2-yl)carbamate | 459 | 1.09 |

TABLE 2-continued

| Reference Example | Structure | Compound name | MS (ESI m/z): (M + H) | RT (min) |
|---|---|---|---|---|
| Reference Example 136-260 | 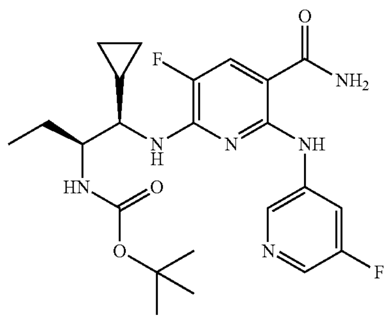 [SMILES: CC[C@H](NC(=O)OC(C)(C)C)[C@H](Nc1nc(Nc2cncc(F)c2)c(C(N)=O)cc1F)C1CC1] | tert-butyl ((1R,2S)-1-((5-carbamoyl-3-fluoro-6-((5-fluoropyridin-3-yl)amino)pyridin-2-yl)amino)-1-cyclopropylbutan-2-yl)carbamate | 477 | 1.51 |
| Reference Example 136-261 | 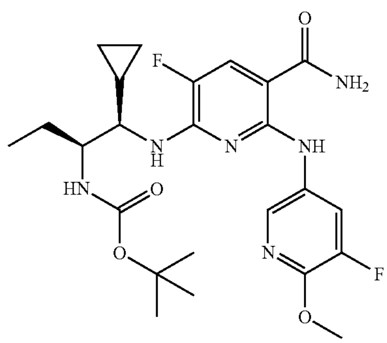 [SMILES: CC[C@H](NC(=O)OC(C)(C)C)[C@H](Nc1nc(Nc2cnc(OC)c(F)c2)c(C(N)=O)cc1F)C1CC1] | tert-butyl ((1R,2S)-1-((5-carbamoyl-3-fluoro-6-((5-fluoro-6-methoxypyridin-3-yl)amino)pyridin-2-yl)amino)-1-cyclopropylbutan-2-yl)carbamate | 507 | 1.66 |
| Reference Example 136-262 | 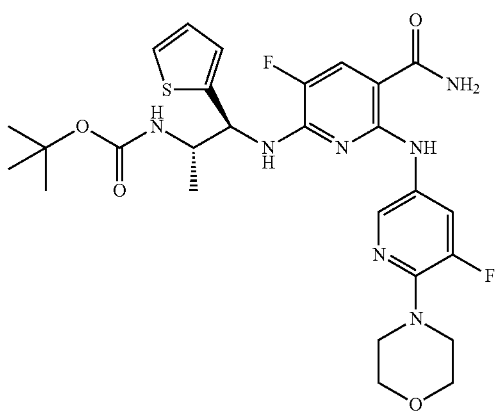 [SMILES: C[C@H](NC(=O)OC(C)(C)C)[C@H](Nc1nc(Nc2cnc(N3CCOCC3)c(F)c2)c(C(N)=O)cc1F)c1cccs1] | tert-butyl ((1S,2S)-1-((5-carbamoyl-3-fluoro-6-((5-fluoro-6-morpholinopyridin-3-yl)amino)pyridin-2-yl)amino)-1-(thiophen-2-yl)propan-2-yl)carbamate | 590 | 1.63 |
| Reference Example 136-263 | 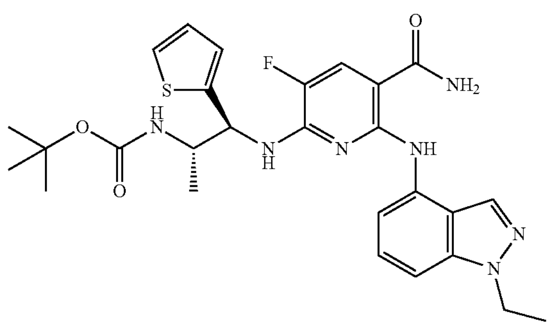 [SMILES: CCn1ncc2c(Nc3nc(N[C@H](c4cccs4)[C@H](C)NC(=O)OC(C)(C)C)c(F)cc3C(N)=O)cccc21] | tert-butyl ((1S,2S)-1-((5-carbamoyl-6-((1-ethyl-1H-indazol-4-yl)amino)-3-fluoropyridin-2-yl)amino)-1-(thiophen-2-yl)propan-2-yl)carbamate | 554 | 1.71 |

TABLE 2-continued

| Reference Example | Compound name | MS (ESI m/z): (M + H) | RT (min) |
|---|---|---|---|
| Reference Example 136-264 | tert-butyl ((1S,2S)-1-((5-carbamoyl-6-((3-(dimethylamino)-1-methyl-1H-indazol-5-yl)amino)-3-fluoropyridin-2-yl)amino)-1-(thiophen-2-yl)propan-2-yl)carbamate | 583 | 1.57 |
| Reference Example 136-265 | tert-butyl ((1S,2S)-1-((5-carbamoyl-3-fluoro-6-((5-fluoro-6-morpholinopyridin-3-yl)amino)pyridin-2-yl)amino)-1-(5-chlorothiophen-2-yl)propan-2-yl)carbamate | 624 | 1.75 |
| Reference Example 136-266 | tert-butyl ((1S,2S)-1-((5-carbamoyl-6-((1-ethyl-1H-indazol-4-yl)amino)-3-fluoropyridin-2-yl)amino)-1-(5-chlorothiophen-2-yl)propan-2-yl)carbamate | 588 | 1.81 |
| Reference Example 136-267 | tert-butyl ((1R,2S)-1-((5-carbamoyl-3-fluoro-6-((5-fluoro-6-morpholinopyridin-3-yl)amino)pyridin-2-yl)amino)-1-(2-fluorophenyl)propan-2-yl)carbamate | 602 | 1.63 |

TABLE 2-continued

| Reference Example | Structure | Compound name | MS (ESI m/z): (M + H) | RT (min) |
|---|---|---|---|---|
| Reference Example 136-268 | 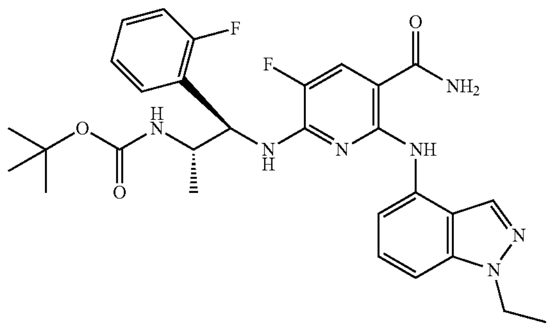 [SMILES: CCn1ncc2c(Nc3nc(N[C@H](c4ccccc4F)[C@H](C)NC(=O)OC(C)(C)C)c(F)cc3C(N)=O)cccc21] | tert-butyl ((1R,2S)-1-((5-carbamoyl-6-((1-ethyl-1H-indazol-4-yl)amino)-3-fluoropyridin-2-yl)amino)-1-(2-fluorophenyl)propan-2-yl)carbamate | 566 | 1.71 |
| Reference Example 136-269 | 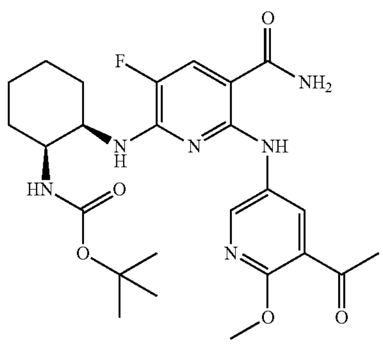 [SMILES: COc1ncc(Nc2nc(N[C@@H]3CCCC[C@@H]3NC(=O)OC(C)(C)C)c(F)cc2C(N)=O)cc1C(C)=O] | tert-butyl ((1S,2R)-2-((6-((5-acetyl-6-methoxypyridin-3-yl)amino)-5-carbamoyl-3-fluoropyridin-2-yl)amino)cyclohexyl)carbamate | 517 | 1.65 |
| Reference Example 136-270 | 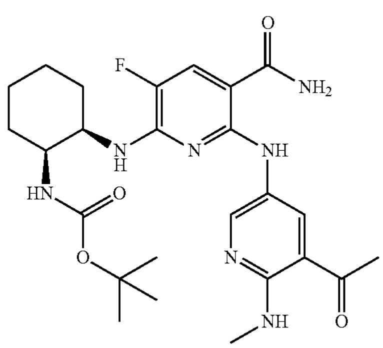 [SMILES: CNc1ncc(Nc2nc(N[C@@H]3CCCC[C@@H]3NC(=O)OC(C)(C)C)c(F)cc2C(N)=O)cc1C(C)=O] | tert-butyl ((1S,2R)-2-((6-((5-acetyl-6-(methylamino)pyridin-3-yl)amino)-5-carbamoyl-3-fluoropyridin-2-yl)amino)cyclohexyl)carbamate | 516 | 1.26 |
| Reference Example 136-271 | 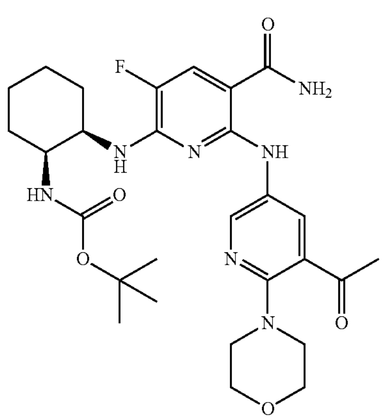 [SMILES: CC(=O)c1cc(Nc2nc(N[C@@H]3CCCC[C@@H]3NC(=O)OC(C)(C)C)c(F)cc2C(N)=O)cnc1N1CCOCC1] | tert-butyl ((1S,2R)-2-((6-((5-acetyl-6-morpholinopyridin-3-yl)amino)-5-carbamoyl-3-fluoropyridin-2-yl)amino)cyclohexyl)carbamate | 572 | 1.49 |

TABLE 2-continued

| Reference Example | Structure | Compound name | MS (ESI m/z): (M + H) | RT (min) |
|---|---|---|---|---|
| Reference Example 136-272 | 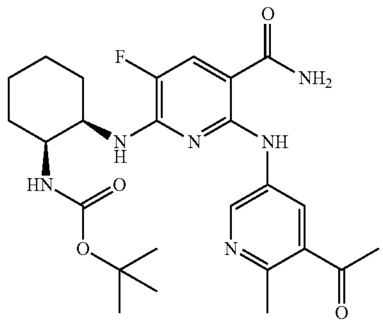 [SMILES: CC(=O)c1cc(Nc2nc(N[C@@H]3CCCC[C@@H]3NC(=O)OC(C)(C)C)c(F)cc2C(N)=O)cnc1C] | tert-butyl ((1S,2R)-2-((6-((5-acetyl-6-methylpyridin-3-yl)amino)-5-carbamoyl-3-fluoropyridin-2-yl)amino)cyclohexyl)carbamate | 501 | 1.23 |
| Reference Example 136-273 | 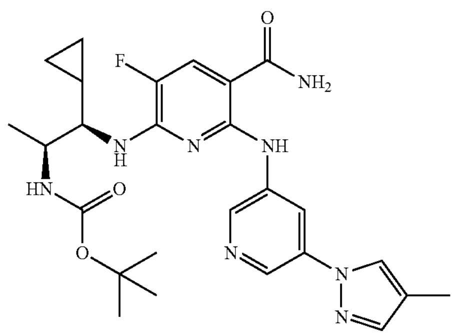 [SMILES: Cc1cnn(-c2cncc(Nc3nc(N[C@H](C4CC4)[C@H](C)NC(=O)OC(C)(C)C)c(F)cc3C(N)=O)c2)c1] | tert-butyl ((1R,2S)-1-((5-carbamoyl-3-fluoro-6-((5-(4-methyl-1H-pyrazol-1-yl)pyridin-3-yl)amino)pyridin-2-yl)amino)-1-cyclopropylpropan-2-yl)carbamate | 525 | 1.50 |
| Reference Example 136-274 | 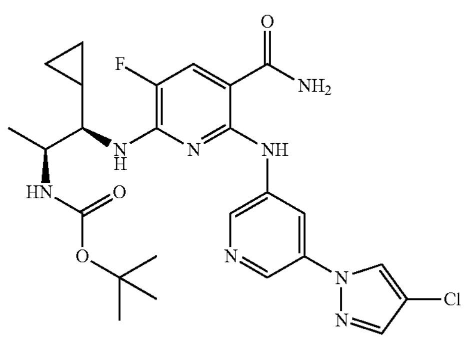 [SMILES: C[C@H](NC(=O)OC(C)(C)C)[C@H](Nc1nc(Nc2cncc(-n3cc(Cl)cn3)c2)c(C(N)=O)cc1F)C1CC1] | tert-butyl ((1R,2S)-1-((5-carbamoyl-6-((5-(4-chloro-1H-pyrazol-1-yl)pyridin-3-yl)amino)-3-fluoropyridin-2-yl)amino)-1-cyclopropylpropan-2-yl)carbamate | 545 547 | 1.63 |
| Reference Example 136-275 | 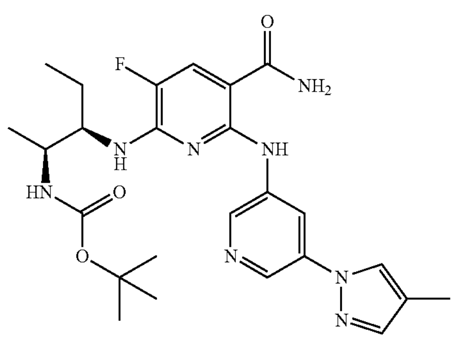 [SMILES: CC[C@@H](Nc1nc(Nc2cncc(-n3cc(C)cn3)c2)c(C(N)=O)cc1F)[C@H](C)NC(=O)OC(C)(C)C] | tert-butyl ((2S,3R)-3-((5-carbamoyl-3-fluoro-6-((5-(4-methyl-1H-pyrazol-1-yl)pyridin-3-yl)amino)pyridin-2-yl)amino)pentan-2-yl)carbamate | 513 | 1.49 |

TABLE 2-continued

| Reference Example | Structure | Compound name | MS (ESI m/z): (M + H) | RT (min) |
|---|---|---|---|---|
| Reference Example 136-276 | 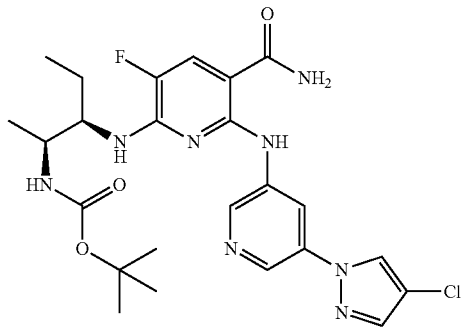 [SMILES: CC[C@@H](Nc1nc(Nc2cncc(-n3cc(Cl)cn3)c2)c(C(N)=O)cc1F)[C@H](C)NC(=O)OC(C)(C)C] | tert-butyl ((2S,3R)-3-((5-carbamoyl-6-((5-(4-chloro-1H-pyrazol-1-yl)pyridin-3-yl)amino)-3-fluoropyridin-2-yl)amino)pentan-2-yl)carbamate | 533 535 | 1.62 |
| Reference Example 136-277 | 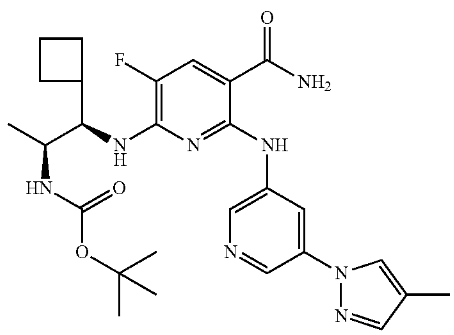 [SMILES: Cc1cnn(-c2cncc(Nc3nc(N[C@H](C4CCC4)[C@H](C)NC(=O)OC(C)(C)C)c(F)cc3C(N)=O)c2)c1] | tert-butyl ((1R,2S)-1-((5-carbamoyl-3-fluoro-6-((5-(4-methyl-1H-pyrazol-1-yl)pyridin-3-yl)amino)pyridin-2-yl)amino)-1-cyclobutylpropan-2-yl)carbamate | 539 | 1.60 |
| Reference Example 136-278 | 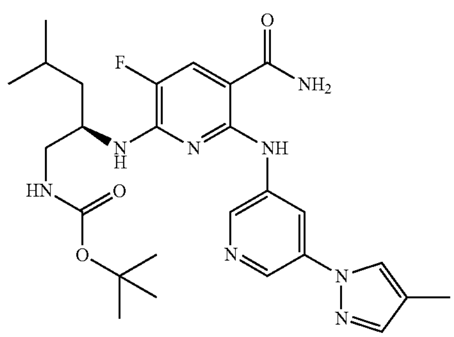 [SMILES: Cc1cnn(-c2cncc(Nc3nc(N[C@@H](CNC(=O)OC(C)(C)C)CC(C)C)c(F)cc3C(N)=O)c2)c1] | (R)-tert-butyl (2-((5-carbamoyl-3-fluoro-6-((5-(4-methyl-1H-pyrazol-1-yl)pyridin-3-yl)amino)pyridin-2-yl)amino)-4-methylpentyl)carbamate | 527 | 1.60 |
| Reference Example 136-279 | 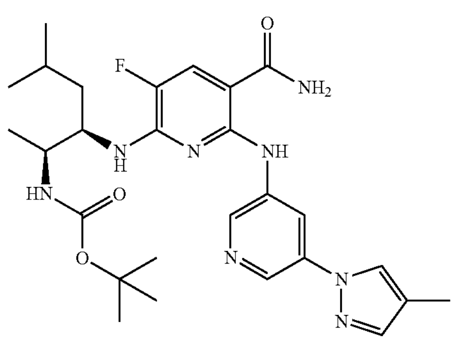 [SMILES: Cc1cnn(-c2cncc(Nc3nc(N[C@H](CC(C)C)[C@H](C)NC(=O)OC(C)(C)C)c(F)cc3C(N)=O)c2)c1] | tert-butyl ((2S,3R)-3-((5-carbamoyl-3-fluoro-6-((5-(4-methyl-1H-pyrazol-1-yl)pyridin-3-yl)amino)pyridin-2-yl)amino)-5-methylhexan-2-yl)carbamate | 541 | 1.66 |

TABLE 2-continued

| Reference Example | Structure | Compound name | MS (ESI m/z): (M + H) | RT (min) |
|---|---|---|---|---|
| Reference Example 136-280 | 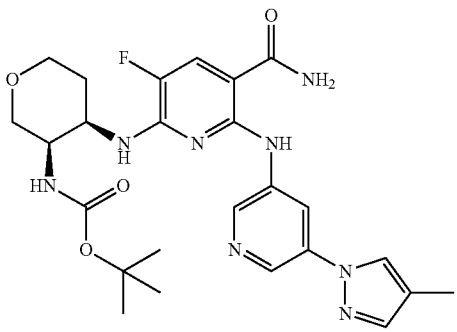 [SMILES: Cc1cnn(-c2cncc(Nc3nc(N[C@@H]4CCOC[C@@H]4NC(=O)OC(C)(C)C)c(F)cc3C(N)=O)c2)c1] | tert-butyl ((3R,4R)-4-((5-carbamoyl-3-fluoro-6-((5-(4-methyl-1H-pyrazol-1-yl)pyridin-3-yl)amino)pyridin-2-yl)amino)tetrahydro-2H-pyran-3-yl)carbamate | 527 | 1.25 |
| Reference Example 136-281 | 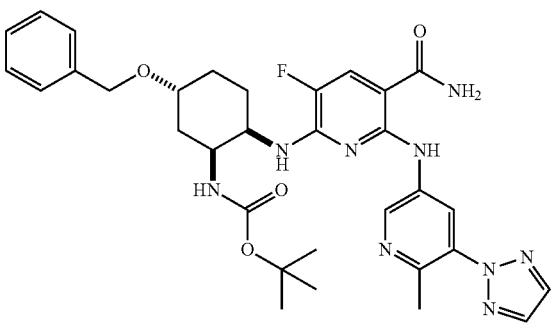 | Mixture of tert-butyl (5-(benzyloxy)-2-((5-carbamoyl-3-fluoro-6-((6-methyl-5-(2H-1,2,3-triazol-2-yl)pyridin-3-yl)amino)pyridin-2-yl)amino)cyclohexyl)carbamate (1S,2R,5R), (1R,2S,5S) | 632 | 1.66 |
| Reference Example 136-282 | 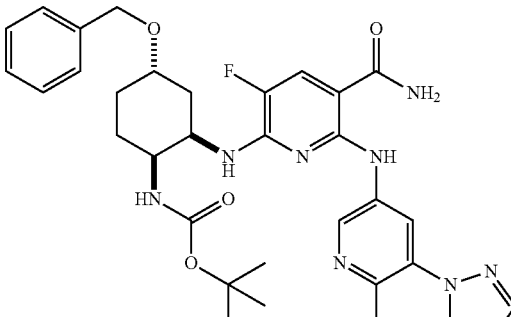 | tert-butyl ((1S,2R,4S)-4-(benzyloxy)-2-((5-carbamoyl-3-fluoro-6-((6-methyl-5-(2H-1,2,3-triazol-2-yl)pyridin-3-yl)amino)pyridin-2-yl)amino)cyclohexyl)carbamate | 632 | 1.57 |
| Reference Example 136-283 | 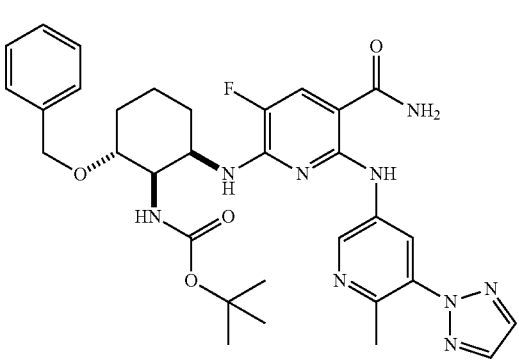 | Mixture of tert-butyl (2-(benzyloxy)-6-((5-carbamoyl-3-fluoro-6-((6-methyl-5-(2H-1,2,3-triazol-2-yl)pyridin-3-yl)amino)pyridin-2-yl)amino)cyclohexyl)carbamate (1R,2R,6R), (1S,2S,6S) | 632 | 1.63 |

TABLE 2-continued

| Reference Example | Structure | Compound name | MS (ESI m/z): (M + H) | RT (min) |
|---|---|---|---|---|
| Reference Example 136-284 | 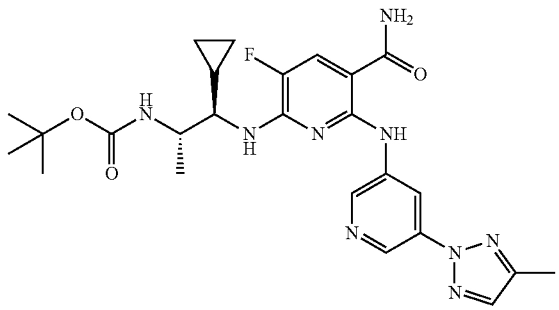 [SMILES: Cc1cnn(-c2cncc(Nc3nc(N[C@H](C4CC4)[C@H](C)NC(=O)OC(C)(C)C)c(F)cc3C(N)=O)c2)n1] | tert-butyl ((1R,2S)-1-((5-carbamoyl-3-fluoro-6-((5-(4-methyl-2H-1,2,3-triazol-2-yl)pyridin-3-yl)amino)pyridin-2-yl)amino)-1-cyclopropylpropan-2-yl)carbamate | 526 | 1.54 |
| Reference Example 136-285 | 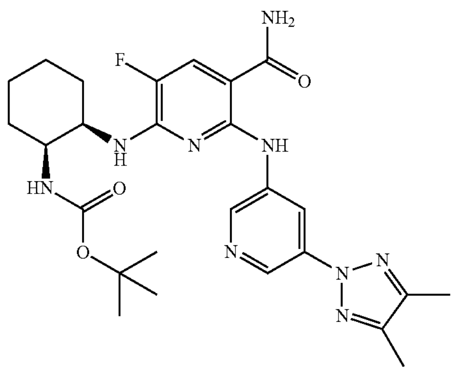 [SMILES: Cc1nn(-c2cncc(Nc3nc(N[C@@H]4CCCC[C@@H]4NC(=O)OC(C)(C)C)c(F)cc3C(N)=O)c2)nc1C] | tert-butyl ((1S,2R)-2-((5-carbamoyl-6-((5-(4,5-dimethyl-2H-1,2,3-triazol-2-yl)pyridin-3-y)amino)-3-fluoropyridin-2-yl)amino)cyclohexyl)carbamate | 540 | 1.59 |
| Reference Example 136-286 | 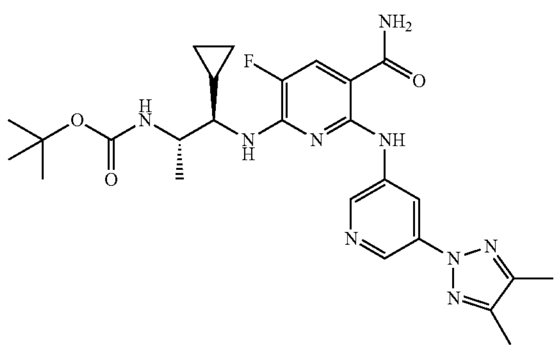 [SMILES: Cc1nn(-c2cncc(Nc3nc(N[C@H](C4CC4)[C@H](C)NC(=O)OC(C)(C)C)c(F)cc3C(N)=O)c2)nc1C] | tert-butyl ((1R,2S)-1-((5-carbamoyl-6-((5-(4,5-dimethyl-2H-1,2,3-triazol-2-yl)pyridin-3-yl)amino)-3-fluoropyridin-2-yl)amino)-1-cyclopropylpropan-2-yl)carbamate | 540 | 1.56 |
| Reference Example 136-287 | 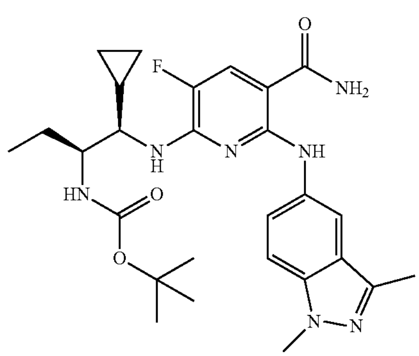 [SMILES: CC[C@H](NC(=O)OC(C)(C)C)[C@H](Nc1nc(Nc2ccc3c(c2)c(C)nn3C)c(C(N)=O)cc1F)C1CC1] | tert-butyl ((1R,2S)-1-((5-carbamoyl-6-((1,3-dimethyl-1H-indazol-5-yl)amino)-3-fluoropyridin-2-yl)amino)-1-cyclopropylbutan-2-yl)carbamate | 526 | 1.52 |

TABLE 2-continued

| Reference Example | Structure | Compound name | MS (ESI m/z): (M + H) | RT (min) |
|---|---|---|---|---|
| Reference Example 136-288 | 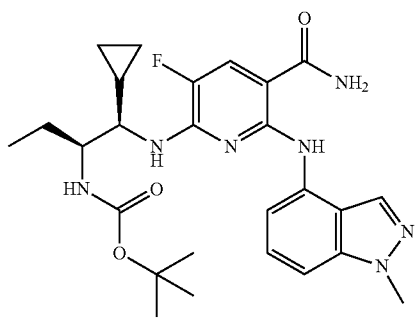 [SMILES: CC[C@H](NC(=O)OC(C)(C)C)[C@H](Nc1nc(Nc2cccc3c2cnn3C)c(C(N)=O)cc1F)C1CC1] | tert-butyl ((1R,2S)-1-((5-carbamoyl-3-fluoro-6-((1-methyl-1H-indazol-4-yl)amino)pyridin-2-yl)amino)-1-cyclopropylbutan-2-yl)carbamate | 512 | 1.60 |
| Reference Example 136-289 | 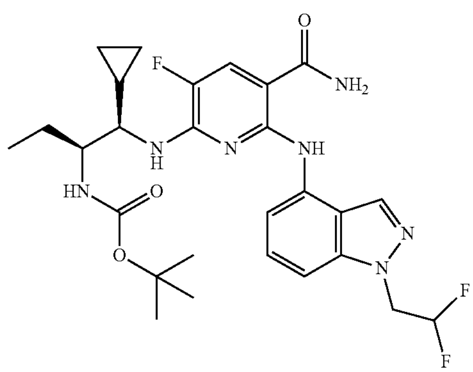 [SMILES: CC[C@H](NC(=O)OC(C)(C)C)[C@H](Nc1nc(Nc2cccc3c2cnn3CC(F)F)c(C(N)=O)cc1F)C1CC1] | tert-butyl ((1R,2S)-1-((5-carbamoyl-6-((1-(2,2-difluoroethyl)-1H-indazol-4-yl)amino)-3-fluoropyridin-2-yl)amino)-1-cyclopropylbutan-2-yl)carbamate | 562 | 1.65 |
| Reference Example 136-290 | 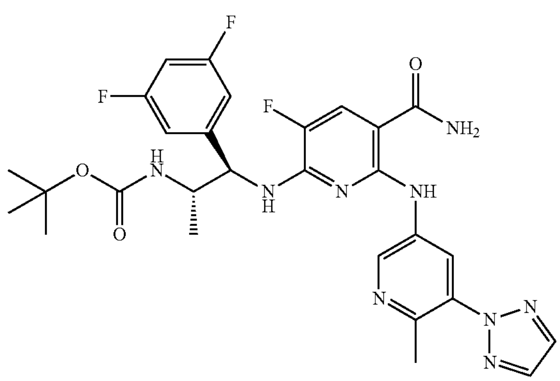 [SMILES: Cc1ncc(Nc2nc(N[C@H](c3cc(F)cc(F)c3)[C@H](C)NC(=O)OC(C)(C)C)c(F)cc2C(N)=O)cc1-n1nccn1] | tert-butyl ((1R,2S)-1-((5-carbamoyl-3-fluoro-6-((6-methyl-5-(2H-1,2,3-triazol-2-yl)pyridin-3-yl)amino)pyridin-2-yl)amino)-1-(3,5-difluorophenyl)propan-2-yl)carbamate | 598 | 1.63 |
| Reference Example 136-291 | 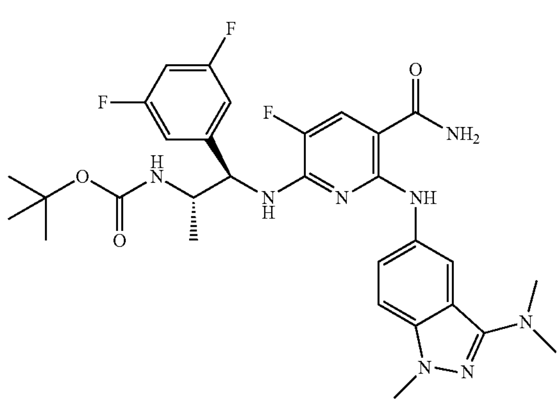 [SMILES: C[C@H](NC(=O)OC(C)(C)C)[C@H](Nc1nc(Nc2ccc3c(c2)c(N(C)C)nn3C)c(C(N)=O)cc1F)c1cc(F)cc(F)c1] | tert-butyl ((1R,2S)-1-((5-carbamoyl-6-((3-(dimethylamino)-1-methyl-1H-indazol-5-yl)amino)-3-fluoropyridin-2-yl)amino)-1-(3,5-difluorophenyl)propan-2-yl)carbamate | 613 | 1.62 |

TABLE 2-continued

| Reference Example | Structure | Compound name | MS (ESI m/z): (M + H) | RT (min) |
|---|---|---|---|---|
| Reference Example 136-292 | 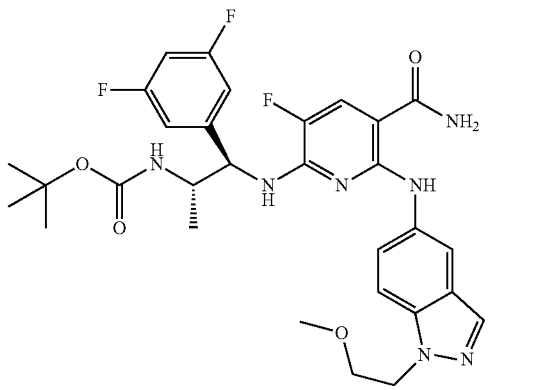 [SMILES: COCCn1ncc2cc(Nc3nc(N[C@H](c4cc(F)cc(F)c4)[C@H](C)NC(=O)OC(C)(C)C)c(F)cc3C(N)=O)ccc21] | tert-butyl,((1R,2S)-1-((5-carbamoyl-3-fluoro-6-((1-(2-(2-methoxyethyl)-1H-indazol-5-yl)amino)pyridin-2-yl)amino)-1-(3,5-difluorophenyl)propan-2-yl)carbamate | 614 | 1.58 |
| Reference Example 136-293 | 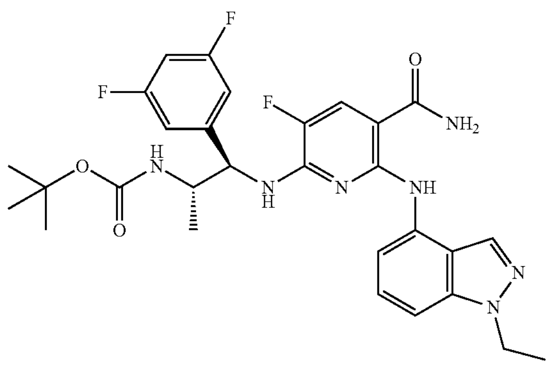 [SMILES: CCn1ncc2c(Nc3nc(N[C@H](c4cc(F)cc(F)c4)[C@H](C)NC(=O)OC(C)(C)C)c(F)cc3C(N)=O)cccc21] | tert-butyl ((1R,2S)-1-((5-carbamoyl-6-((1-ethyl-1H-indazol-4-yl)amino)-3-fluoropyridin-2-yl)amino)-1-(3,5-difluorophenyl)propan-2-yl)carbamate | 584 | 1.74 |
| Reference Example 136-294 | 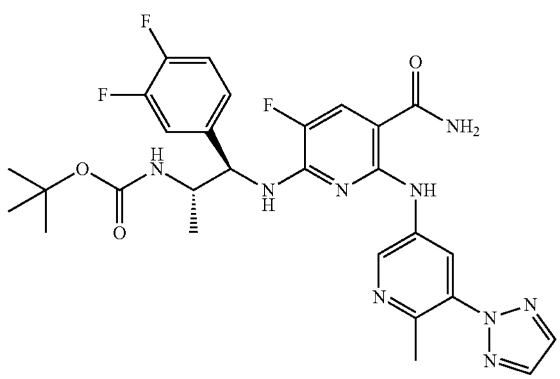 [SMILES: Cc1ncc(Nc2nc(N[C@H](c3ccc(F)c(F)c3)[C@H](C)NC(=O)OC(C)(C)C)c(F)cc2C(N)=O)cc1-n1nccn1] | tert-butyl ((1R,2S)-1-((5-carbamoyl-3-fluoro-6-((6-methyl-5-(2H-1,2,3-triazol-2-yl)pyridin-3-yl)amino)pyridin-2-yl)amino)-1-(3,4-difluorophenyl)propan-2-yl)carbamate | 598 | 1.61 |
| Reference Example 136-295 | 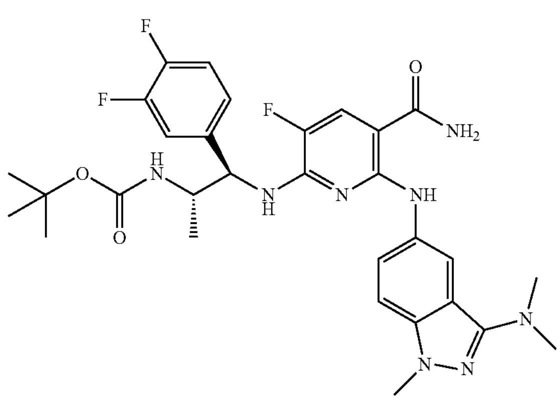 [SMILES: C[C@H](NC(=O)OC(C)(C)C)[C@H](Nc1nc(Nc2ccc3c(c2)c(N(C)C)nn3C)c(C(N)=O)cc1F)c1ccc(F)c(F)c1] | tert-butyl ((1R,2S)-1-((5-carbamoyl-6-((3-(dimethylamino)-1-methyl-1H-indazol-5-yl)amino)-3-fluoropyridin-2-yl)amino)-1-(3,4-difluorophenyl)propan-2-yl)carbamate | 613 | 1.62 |

TABLE 2-continued

| Reference Example | Structure | Compound name | MS (ESI m/z): (M + H) | RT (min) |
|---|---|---|---|---|
| Reference Example 136-296 | 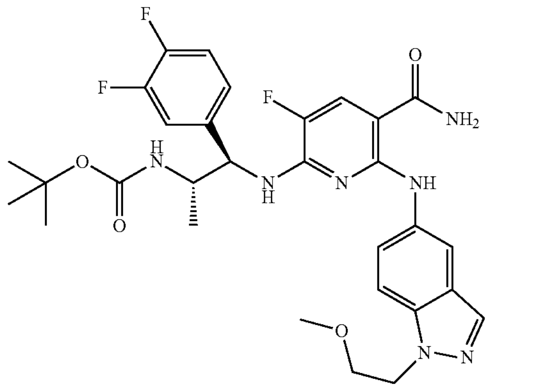 [SMILES: COCCn1ncc2cc(Nc3nc(N[C@H](c4ccc(F)c(F)c4)[C@H](C)NC(=O)OC(C)(C)C)c(F)cc3C(N)=O)ccc21] | tert-butyl ((1R,2S)-1-((5-carbamoyl-3-fluoro-6-((1-(2-methoxyethyl)-1H-indazol-5-yl)amino)pyridin-2-yl)amino)-1-(3,4-difluorophenyl)propan-2-yl)carbamate | 614 | 1.58 |
| Reference Example 136-297 | 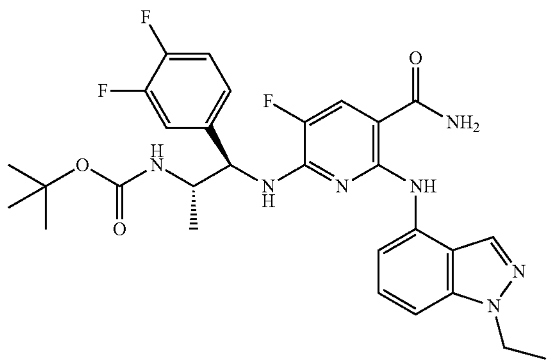 [SMILES: CCn1ncc2c(Nc3nc(N[C@H](c4ccc(F)c(F)c4)[C@H](C)NC(=O)OC(C)(C)C)c(F)cc3C(N)=O)cccc21] | tert-butyl ((1R,2S)-1-((5-carbamoyl-6-((1-ethyl-1H-indazol-4-yl)amino)-3-fluoropyridin-2-yl)amino)-1-(3,4-difluorophenyl)propan-2-yl)carbamate | 584 | 1.72 |
| Reference Example 136-298 | 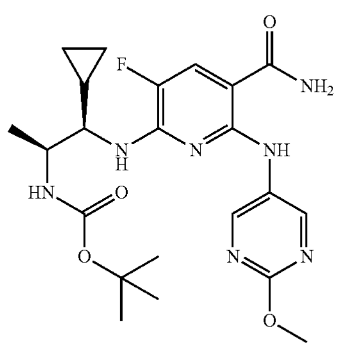 [SMILES: COc1ncc(Nc2nc(N[C@H](C3CC3)[C@H](C)NC(=O)OC(C)(C)C)c(F)cc2C(N)=O)cn1] | tert-butyl ((1R,2S)-1-((5-carbamoyl-3-fluoro-6-((2-methoxypyrimidine-5-yl)amino)pyridin-2-yl)amino)-1-cyclopropylpropan-2-yl)carbamate | 476 | — |
| Reference Example 136-299 | 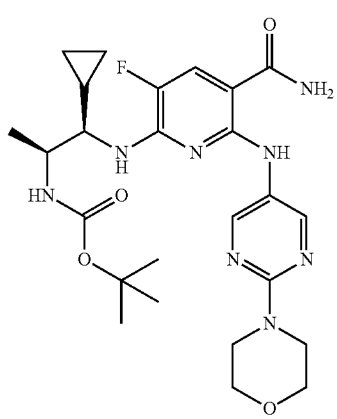 [SMILES: C[C@H](NC(=O)OC(C)(C)C)[C@H](Nc1nc(Nc2cnc(N3CCOCC3)nc2)c(C(N)=O)cc1F)C1CC1] | tert-butyl ((1R,2S)-1-((5-carbamoyl-3-fluoro-6-((2-morpholinopyrimidine-5-yl)amino)pyridin-2-yl)amino)-1-cyclopropylpropan-2-yl)carbamate | 531 | 1.37 |

TABLE 2-continued

| Reference Example | Structure | Compound name | MS (ESI m/z): (M + H) | RT (min) |
|---|---|---|---|---|
| Reference Example 136-300 | 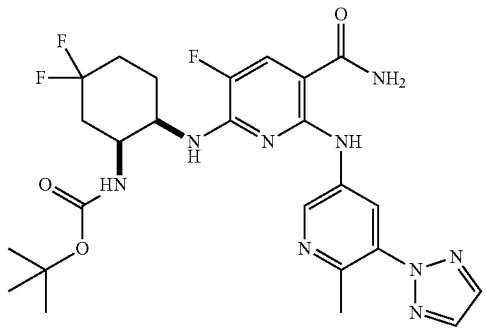 | Mixture of tert-butyl (2-((5-carbamoyl-3-fluoro-6-((6-methyl-5-(2H-1,2,3-triazol-2-yl)pyridin-3-yl)amino)pyridin-2-yl)amino)-5,5-difluorocyclohexyl)carbamate (1S,2R), (1R,2S) | 562 | 1.47 |

Example 1

Example 2-184

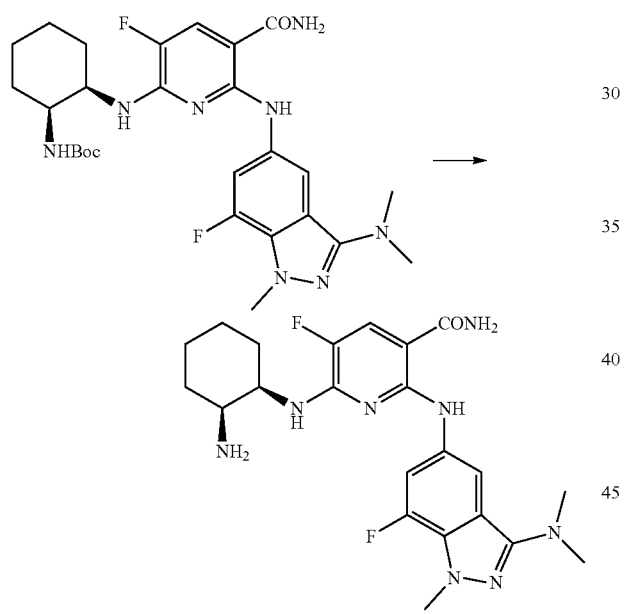

[Formula 155]

A mixture of tert-butyl ((1S,2R)-2-((5-carbamoyl-6-((3-(dimethylamino)-7-fluoro-1-methyl-1H-indazol-5-yl)amino)-3-fluoropyridin-2-yl)amino)cyclohexyl)carbamate (283 mg) and TFA (3 ml) was stirred at room temperature for 30 minutes. The solvent was distilled away under reduced pressure. 4N hydrogen chloride/1,4-dioxane (0.253 ml) was added to an ethyl acetate (10 ml) suspension containing the obtained residue, followed by stirring at room temperature for 30 minutes. A solid was collected by filtration and washed with ethyl acetate. A light yellow solid of 6-(((1R,2S)-2-aminocyclohexyl)amino)-2-((3-(dimethylamino)-7-fluoro-1-methyl-1H-indazol-5-yl)amino)-5-fluoronicotinamide hydrochloride (241 mg) was thus obtained.

(Table 3 (Example 2-184) lists $^1$H-NMR data and MS data.)

Example 2

The compounds shown in table 3 were obtained as described in Example 1.

TABLE 3

| Example | Structure | Compound name | MS (ESI m/z): (M + H) | RT (min) | HNMR |
|---|---|---|---|---|---|
| Example 2-1 | 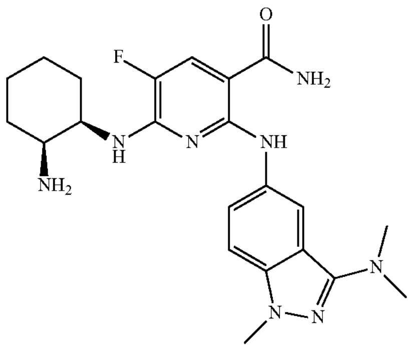 [SMILES: CN(C)c1nn(C)c2ccc(Nc3nc(N[C@@H]4CCCC[C@@H]4N)c(F)cc3C(N)=O)cc12] | 6-(((1R,2S)-2-aminocyclohexyl)amino)-2-((3-(dimethyl)amino)-1-methyl-1H-indazol-5-yl)amino)-5-fluoronicotinamide | 441 | 0.9 | 1H-NMR (MeOD) δ: 8.01 (1H, br s), 7.83 (1H, br s), 7.79 (1H, br s), 7.58 (1H, br s), 4.32-4.29 (1H, m), 3.91 (3H, s), 3.70-3.66 (1H, br s), 3.38 (6H, br s), 1.79-1.50 (8H, m). |
| Example 2-2 | 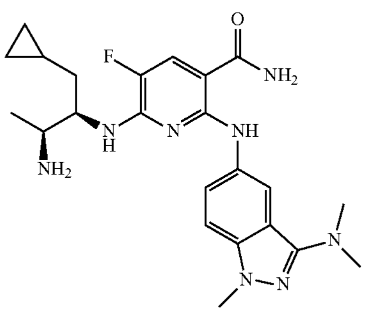 [SMILES: C[C@H](N)[C@@H](CC1CC1)Nc1nc(Nc2ccc3c(c2)c(N(C)C)nn3C)c(C(N)=O)cc1F] | 6-(((2R,3S)-3-amino-1-cyclopropylbutan-2-yl)amino)-2-((3-(dimethyl)amino)-1-methyl-1H-indazol-5-yl)amino)-5-fluoronicotinamide | 455 | 0.95 | |
| Example 2-3 | 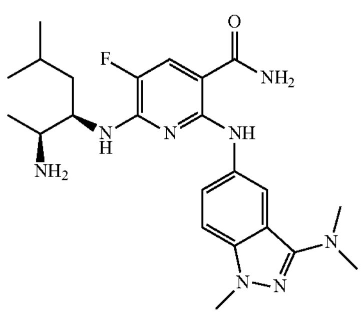 [SMILES: CC(C)C[C@@H](Nc1nc(Nc2ccc3c(c2)c(N(C)C)nn3C)c(C(N)=O)cc1F)[C@H](C)N] | 6-(((2S,3R)-2-amino-5-methylhexan-3-yl)amino)-2-((3-(dimethyl)amino)-1-methyl-1H-indazol-5-yl)amino)-5-fluoronicotinamide | 457 | 1.03 | 1H-NMR (MeOD) δ: 8.05 (1H, br s), 7.79 (1H, br s), 7.75 (1H, br s), 7.62 (1H, br s), 4.35-4.30 (1H, m), 3.94 (3H, s), 3.54-3.48 (1H, m), 3.43 (6H, s), 1.71-1.56 (2H, m), 1.39-1.27 (1H, m), 1.21 (3H, d, J = 6.6 Hz), 0.95 (3H, d, J = 6.6 Hz), 0.84 (3H, d, J = 6.6 Hz). |

TABLE 3-continued

| Example | Structure | Compound name | MS (ESI m/z): (M + H) | RT (min) | HNMR |
|---|---|---|---|---|---|
| Example 2-4 | 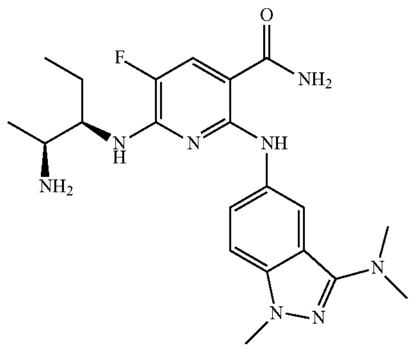 [SMILES: CC[C@@H](Nc1nc(Nc2ccc3c(c2)c(N(C)C)nn3C)c(C(N)=O)cc1F)[C@H](C)N] | 6-(((2S,3R)-2-aminopentan-3-yl)amino)-2-((3-(dimethylamino)-1-methyl-1H-indazol-5-yl)amino)-5-fluoronicotinamide | 429 | 0.89 | |
| Example 2-5 | 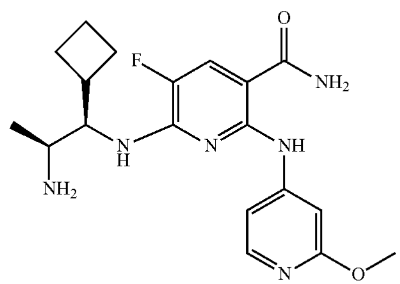 [SMILES: COc1cc(Nc2nc(N[C@H](C3CCC3)[C@H](C)N)c(F)cc2C(N)=O)ccn1] | 6-(((1R,2S)-2-amino-1-cyclobutylpropyl)amino)-5-fluoro-2-((2-methoxypyridin-4-yl)amino)nicotinamide | 389 | 0.72 | |
| Example 2-6 | 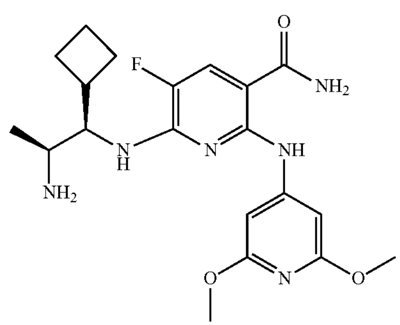 [SMILES: COc1cc(Nc2nc(N[C@H](C3CCC3)[C@H](C)N)c(F)cc2C(N)=O)cc(OC)n1] | 6-(((1R,2S)-2-amino-1-cyclobutylpropyl)amino)-2-((2,6-dimethoxypyridin-4-yl)amino)-5-fluoronicotinamide | 419 | 1.07 | |

TABLE 3-continued

| Example | Structure | Compound name | MS (ESI m/z): (M + H) | RT (min) | HNMR |
|---|---|---|---|---|---|
| Example 2-7 | 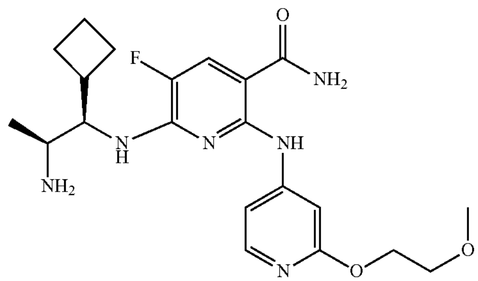 [SMILES: COCCOc1cc(Nc2nc(N[C@H](C3CCC3)[C@H](C)N)c(F)cc2C(N)=O)ccn1] | 6-(((1R,2S)-2-amino-1-cyclobutylpropyl)amino)-5-fluoro-2-((2-(2-methoxyethoxy)pyridin-4-yl)amino)nicotinamide | 433 | 0.79 | |
| Example 2-8 | 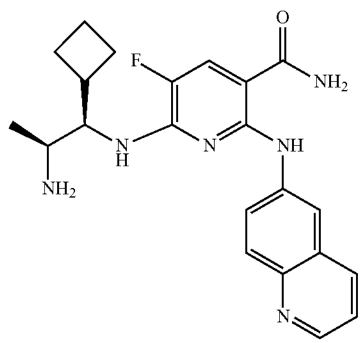 [SMILES: C[C@H](N)[C@H](Nc1nc(Nc2ccc3ncccc3c2)c(C(N)=O)cc1F)C1CCC1] | 6-(((1R,2S)-2-amino-1-cyclobutylpropyl)amino)-5-fluoro-2-(quinolin-6-ylamino)nicotinamide | 409 | 0.78 | |
| Example 2-9 | 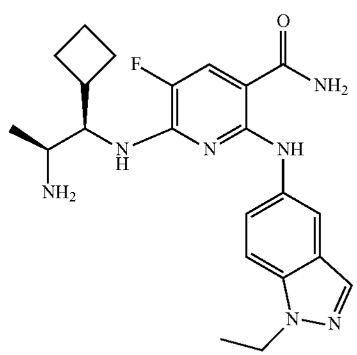 [SMILES: CCn1ncc2cc(Nc3nc(N[C@H](C4CCC4)[C@H](C)N)c(F)cc3C(N)=O)ccc21] | 6-(((1R,2S)-2-amino-1-cyclobutylpropyl)amino)-2-((1-ethyl-1H-indazol-5-yl)amino)-5-fluoronicotinamide | 426 | 1.01 | |

TABLE 3-continued

| Example | Structure | Compound name | MS (ESI m/z): (M + H) | RT (min) | HNMR |
|---|---|---|---|---|---|
| Example 2-10 | 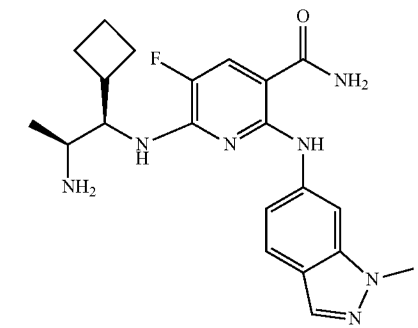 [SMILES: C[C@H](N)[C@H](Nc1nc(Nc2ccc3cnn(C)c3c2)c(C(N)=O)cc1F)C1CCC1] | 6-(((1R,2S)-2-amino-1-cyclobutylpropyl)amino)-5-fluoro-2-((1-methyl-1H-indazol-6-yl)amino)nicotinamide | 412 | 0.96 | |
| Example 2-11 | 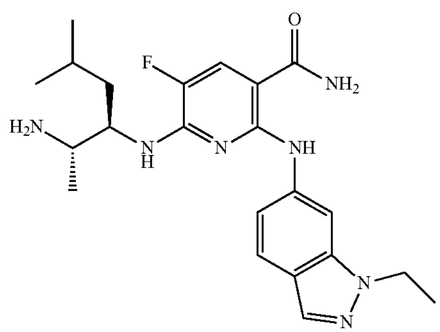 [SMILES: CCn1ncc2ccc(Nc3nc(N[C@H](CC(C)C)[C@H](C)N)c(F)cc3C(N)=O)cc21] | 6-(((2S,3R)-2-amino-5-methylhexan-3-yl)amino)-2-((1-ethyl-1H-indazol-6-yl)amino)-5-fluoronicotinamide | 428 | 1.07 | |
| Example 2-12 | 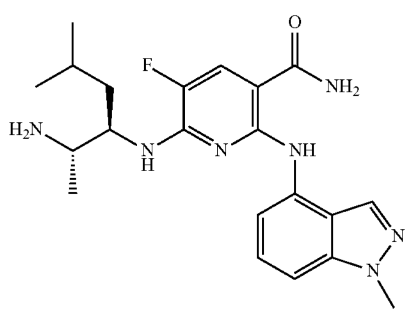 [SMILES: CC(C)C[C@@H](Nc1nc(Nc2cccc3c2cnn3C)c(C(N)=O)cc1F)[C@H](C)N] | 6-(((2S,3R)-2-amino-5-methylhexan-3-yl)amino)-5-fluoro-2-((1-methyl-1H-indazol-4-yl)amino)nicotinamide | 414 | 1.05 | |

TABLE 3-continued

| Example | Structure | Compound name | MS (ESI m/z): (M + H) | RT (min) | HNMR |
|---|---|---|---|---|---|
| Example 2-13 | 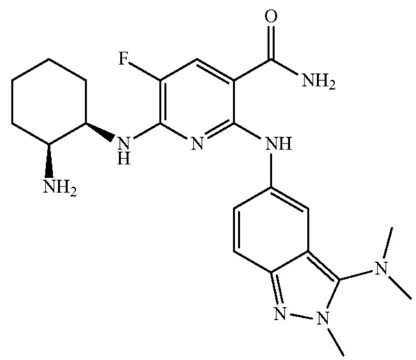 [SMILES: CN(C)c1c2cc(Nc3nc(N[C@@H]4CCCC[C@@H]4N)c(F)cc3C(N)=O)ccc2nn1C] | 6-(((1R,2S)-2-aminocyclohexyl)amino)-2-((3-(dimethylamino)-2-methyl-2H-indazol-5-yl)amino)-5-fluoronicotinamide | 441 | 0.85 | |
| Example 2-14 | 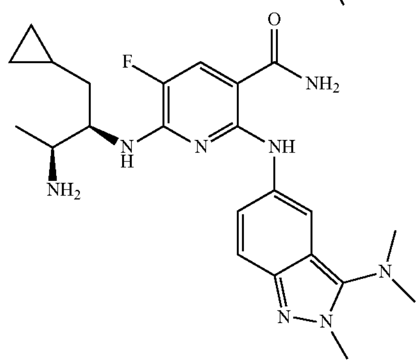 | 6-(((2R,3S)-3-amino-1-cyclopropylbutan-2-yl)amino)-2-((3-(dimethylamino)-2-methyl-2H-indazol-5-yl)amino)-5-fluoronicotinamide | 455 | 0.88 | |
| Example 2-15 | 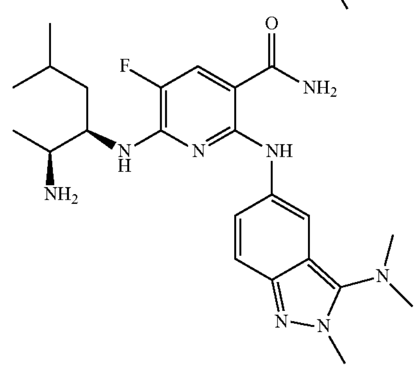 | 6-(((2S,3R)-2-amino-5-methylhexan-3-yl)amino)-2-((3-(dimethylamino)-2-methyl-2H-indazol-5-yl)amino)-5-fluoronicotinamide | 457 | 0.94 | |

TABLE 3-continued

| Example | Structure | Compound name | MS (ESI m/z): (M + H) | RT (min) | HNMR |
|---|---|---|---|---|---|
| Example 2-16 | 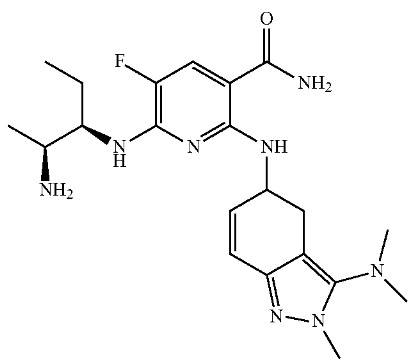 [SMILES: CC[C@@H](Nc1nc(NC2C=Cc3nn(C)c(N(C)C)c3C2)c(C(N)=O)cc1F)[C@H](C)N] | 6-(((2S,3R)-2-aminopentan-3-yl)amino)-2-((3-(dimethylamino)-2-methyl-2H-indazol-5-yl)amino)-5-fluoronicotinamide | 429 | 0.82 | |
| Example 2-17 | 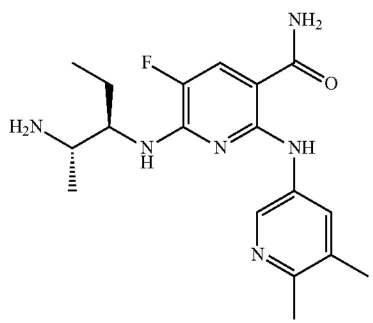 [SMILES: CC[C@@H](Nc1nc(Nc2cnc(C)c(C)c2)c(C(N)=O)cc1F)[C@H](C)N] | 6-(((2S,3R)-2-aminopentan-3-yl)amino)-2-((5,6-dimethylpyridin-3-yl)amino)-5-fluoronicotinamide | 361 | 0.62 | |
| Example 2-18 | 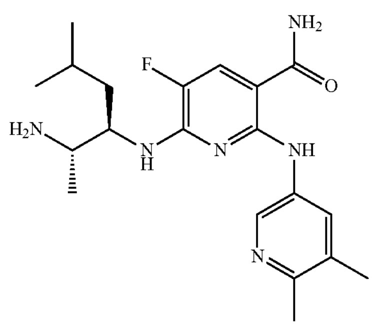 [SMILES: Cc1cc(Nc2nc(N[C@H](CC(C)C)[C@H](C)N)c(F)cc2C(N)=O)cnc1C] | 6-(((2S,3R)-2-amino-5-methylhexan-3-yl)amino)-2-((5,6-dimethylpyridin-3-yl)amino)-5-fluoronicotinamide | 389 | 0.77 | 1H-NMR (MeOD) δ: 9.34 (1H, s), 8.14 (1H, s), 7.82 (1H, d, J = 11.7 Hz), 4.65-4.55 (1H, m), 3.58-3.49 (1H, m), 2.67 (3H, s), 2.47 (3H, s), 1.72-1.33 (6H, m), 0.98 (3H, d, 6.3 Hz), 0.91 (3H, d, 6.3 Hz). |

TABLE 3-continued

| Example | Structure | Compound name | MS (ESI m/z): (M + H) | RT (min) | HNMR |
|---|---|---|---|---|---|
| Example 2-19 | 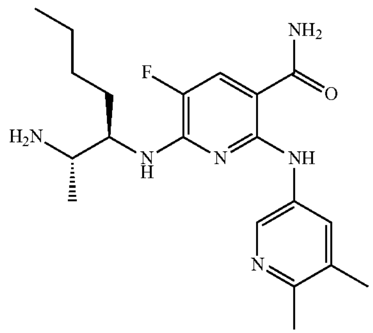 [SMILES: CCCC[C@@H](Nc1nc(Nc2cnc(C)c(C)c2)c(C(N)=O)cc1F)[C@H](C)N] | 6-(((2S,3R)-aminoheptan-3-yl)amino)-2-((5,6-dimethylpyridin-3-yl)amino)-5-fluoronicotinamide | 389 | 0.76 | |
| Example 2-20 | 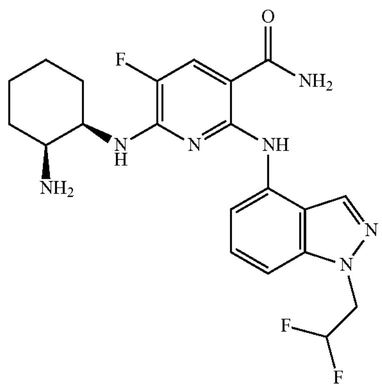 [SMILES: NC(=O)c1cc(F)c(N[C@@H]2CCCC[C@@H]2N)nc1Nc1cccc2c1cnn2CC(F)F] | 6-(((1R,2S)-aminocyclohexyl)amino)-2-((1-(2,2-difluoroethyl)-1H-indazol-4-yl)amino)-5-fluoronicotinamide | 448 | 0.98 | |

TABLE 3-continued

| Example | Structure | Compound name | MS (ESI m/z): (M + H) | RT (min) | HNMR |
|---|---|---|---|---|---|
| Example 2-21 | 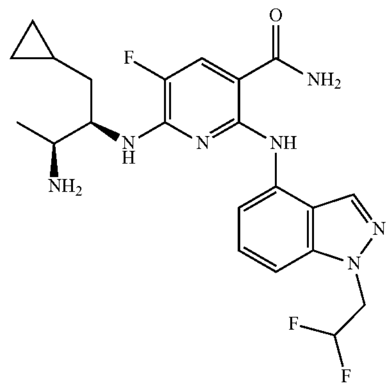 [SMILES: C[C@H](N)[C@@H](CC1CC1)Nc1nc(Nc2cccc3c2cnn3CC(F)F)c(C(N)=O)cc1F] | 6-(((2R,3S)-3-amino-1-cyclopropylbutan-2-yl)amino)-2-((1-(2,2-difluoroethyl)-1H-indazol-4-yl)amino)-5-fluoronicotinamide | 462 | 1 | |
| Example 2-22 | 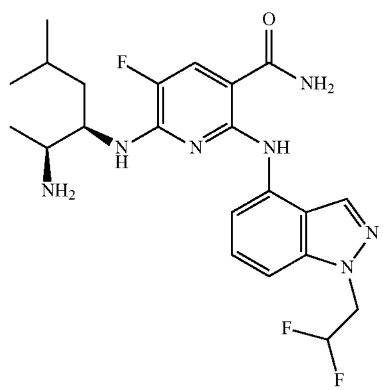 [SMILES: CC(C)C[C@@H](Nc1nc(Nc2cccc3c2cnn3CC(F)F)c(C(N)=O)cc1F)[C@H](C)N] | 6-(((2S,3R)-2-amino-5-methylhexan-3-yl)amino)-2-((1-(2,2-difluoroethyl)-1H-indazol-4-yl)amino)-5-fluoronicotinamide | 464 | 1.05 | |

TABLE 3-continued

| Example | Structure | Compound name | MS (ESI m/z): (M + H) | RT (min) | HNMR |
|---|---|---|---|---|---|
| Example 2-23 | 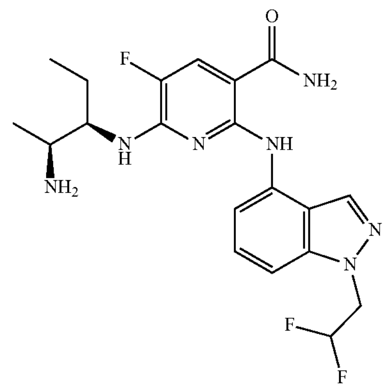 [SMILES: CC[C@@H](Nc1nc(Nc2cccc3c2cnn3CC(F)F)c(C(N)=O)cc1F)[C@H](C)N] | 6-(((2S,3R)-2-aminopentan-3-yl)amino)-2-((1-(2,2-difluoroethyl)-1H-indazol-4-yl)amino)-5-fluoronicotinamide | 436 | 0.94 | |
| Example 2-24 | 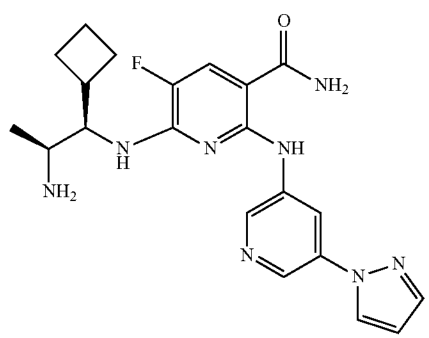 [SMILES: C[C@H](N)[C@H](Nc1nc(Nc2cncc(-n3cccn3)c2)c(C(N)=O)cc1F)C1CCC1] | 2-((5-(1H-pyrazol-1-yl)pyridin-3-yl)amino)-6-(((1R,2S)-2-amino-1-cyclobutylpropyl)amino)-5-fluoronicotinamide | 425 | 0.97 | |
| Example 2-25 | 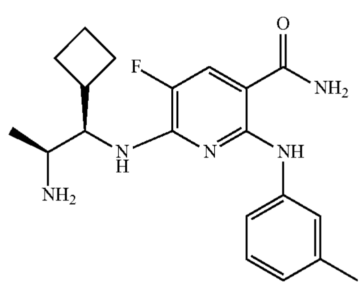 [SMILES: Cc1cccc(Nc2nc(N[C@H](C3CCC3)[C@H](C)N)c(F)cc2C(N)=O)c1] | 6-(((1R,2S)-2-amino-1-cyclobutylpropyl)amino)-5-fluoro-2-(m-tolylamino)nicotinamide | 372 | 1.1 | |

TABLE 3-continued

| Example | Structure | Compound name | MS (ESI m/z): (M + H) | RT (min) | HNMR |
|---|---|---|---|---|---|
| Example 2-26 | 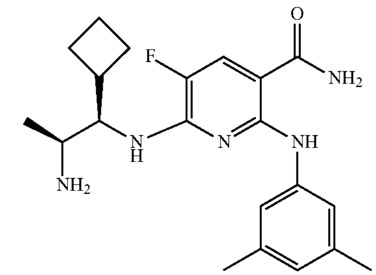 [SMILES: Cc1cc(C)cc(Nc2nc(N[C@H](C3CCC3)[C@H](C)N)c(F)cc2C(N)=O)c1] | 6-(((1R,2S)-2-amino-1-cyclobutylpropyl)amino)-2-((3,5-dimethylphenyl)amino)-5-fluoronicotinamide | 386 | 1.18 | |
| Example 2-27 | 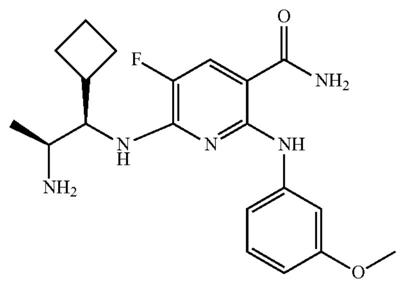 [SMILES: COc1cccc(Nc2nc(N[C@H](C3CCC3)[C@H](C)N)c(F)cc2C(N)=O)c1] | 6-(((1R,2S)-2-amino-1-cyclobutylpropyl)amino)-5-fluoro-2-((3-methoxyphenyl)amino)nicotinamide | 388 | 1.05 | |
| Example 2-28 | 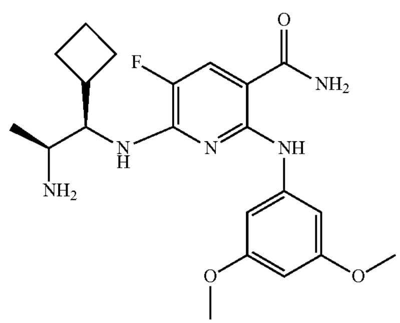 [SMILES: COc1cc(Nc2nc(N[C@H](C3CCC3)[C@H](C)N)c(F)cc2C(N)=O)cc(OC)c1] | 6-(((1R,2S)-2-amino-1-cyclobutylpropyl)amino)-2-((3,5-dimethoxyphenyl)amino)-5-fluoronicotinamide | 418 | 1.07 | 1H-NMR (DMSO-d6) δ: 11.58 (1H, s), 7.91-7.60 (6H, m), 6.90-6.40 (4H, m), 6.17-6.13 (1H, m), 4.47-4.33 (1H, m), 3.80 (3H, s), 3.74 (3H, s), 3.35-3.26 (1H, m), 2.74-2.60 (1H, m), 2.10-1.60 (6H, m), 1.17 (3H, d, J = 7.5 Hz). |

TABLE 3-continued

| Example | Structure | Compound name | MS (ESI m/z): (M + H) | RT (min) | HNMR |
|---|---|---|---|---|---|
| Example 2-29 | 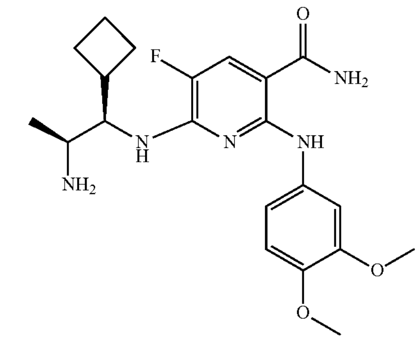 [SMILES: COc1ccc(Nc2nc(N[C@H](C3CCC3)[C@H](C)N)c(F)cc2C(N)=O)cc1OC] | 6-(((1R,2S)-2-amino-1-cyclobutylpropyl)amino)-2-((3,4-dimethoxyphenyl)amino)-5-fluoronicotinamide | 418 | 0.97 | 1H-NMR (DMSO-d6) δ: 11.35 (1H, s), 7.91-7.40 (5H, m), 7.25-6.77 (5H, m), 4.36-4.25 (1H, m), 3.80 (3H, s), 3.74 (3H, s), 3.25-3.35 (1H, m), 2.74-2.60 (1H, m), 2.10-1.62 (6H, m), 1.14 (3H, d, J = 7.5 Hz). |
| Example 2-30 | 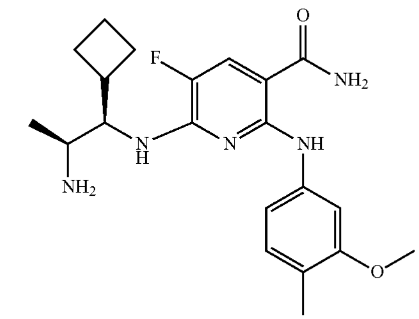 [SMILES: COc1cc(Nc2nc(N[C@H](C3CCC3)[C@H](C)N)c(F)cc2C(N)=O)ccc1C] | 6-(((1R,2S)-2-amino-1-cyclobutylpropyl)amino)-5-Fluoro-2-((3-methoxy-4-methylphenyl)amino) nicotinamide | 402 | 1.13 | |
| Example 2-31 | 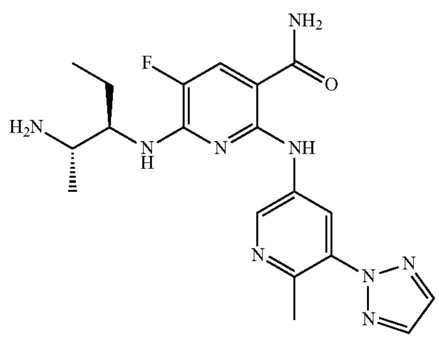 [SMILES: CC[C@@H](Nc1nc(Nc2cnc(C)c(-n3nccn3)c2)c(C(N)=O)cc1F)[C@H](C)N] | 6-(((2S,3R)-2-aminopentan-3-yl)amino)-5-fluoro-2-((6-methyl-5-(2H-1,2,3-triazol-2-yl)pyridin-3-yl)amino)nicotinamide | 414 | 0.86 | 1H-NMR (MeOD) δ: 9.30 (1H, d, J = 2.3 Hz), 8.83-8.78 (1H, m), 8.15 (2H, s), 7.87 (1H, d, J = 11.9 Hz), 4.72-4.63 (1H, m), 3.66-3.55 (1H, m), 2.84 (3H, s), 1.89-1.57 (2H, m), 1.31 (3H, d, J = 6.6 Hz), 0.98 (3H, t, J = 7.3 Hz). |

TABLE 3-continued

| Example | Structure | Compound name | MS (ESI m/z): (M + H) | RT (min) | HNMR |
|---|---|---|---|---|---|
| Example 2-32 | 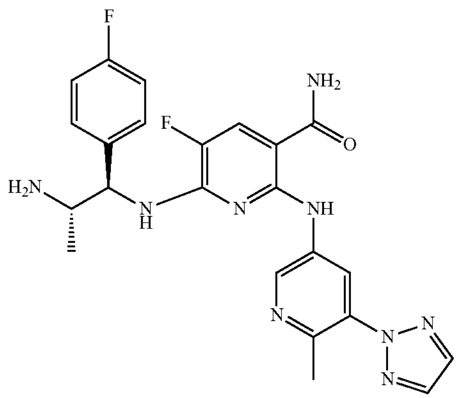 [SMILES: Cc1ncc(Nc2nc(N[C@H](c3ccc(F)cc3)[C@H](C)N)c(F)cc2C(N)=O)cc1-n1nccn1] | 6-(((1R,2S)-2-amino-1-(4-fluorophenyl)propyl)amino)-5-fluoro-2-((6-methyl-5-(2H-1,2,3-triazol-2-yl)pyridin-3-yl)amino)nicotinamide | 480 | 0.96 | |
| Example 2-33 | 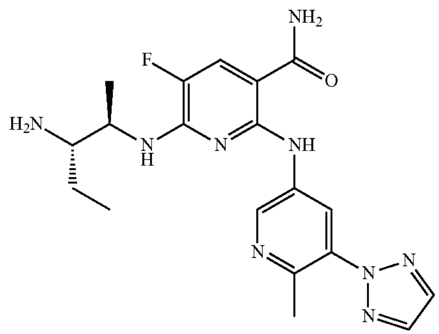 [SMILES: CC[C@H](N)[C@@H](C)Nc1nc(Nc2cnc(C)c(-n3nccn3)c2)c(C(N)=O)cc1F] | 6-(((2R,3S)-3-aminopentan-2-yl)amino)-5-fluoro-2-((6-methyl-5-(2H-1,2,3-triazol-2-yl)pyridin-3-yl)amino)nicotinamide | 414 | 0.83 | |
| Example 2-34 | 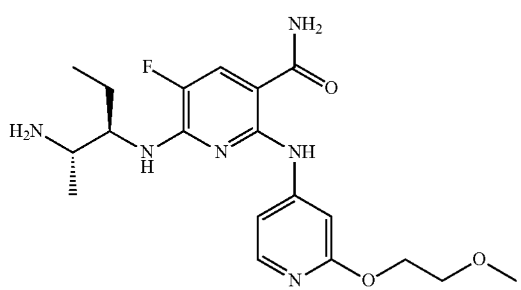 [SMILES: CC[C@@H](Nc1nc(Nc2ccnc(OCCOC)c2)c(C(N)=O)cc1F)[C@H](C)N] | 6-(((2S,3R)-2-aminopentan-3-yl)amino)-5-fluoro-2-((2-(2-methoxyethoxy)pyridin-4-yl)amino)nicotinamide | 407 | 0.67 | |

TABLE 3-continued

| Example | Structure | Compound name | MS (ESI m/z): (M + H) | RT (min) | HNMR |
|---|---|---|---|---|---|
| Example 2-35 | 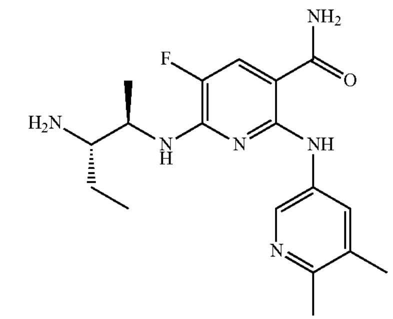 [SMILES: CC[C@H](N)[C@@H](C)Nc1nc(Nc2cnc(C)c(C)c2)c(C(N)=O)cc1F] | 6-(((2R,3S)-3-aminopentan-2-yl)amino)-2-((5,6-dimethylpyridin-3-yl)amino)-5-fluoronicotinamide | 361 | 0.52 | |
| Example 2-36 | 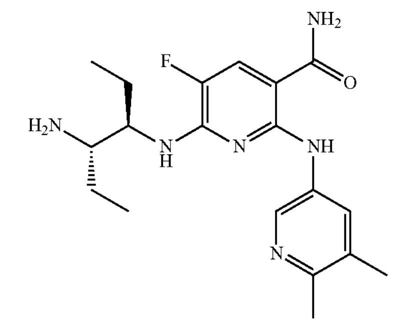 [SMILES: CC[C@H](N)[C@@H](CC)Nc1nc(Nc2cnc(C)c(C)c2)c(C(N)=O)cc1F] | 6-(((3R,4S)-4-aminohexan-3-yl)amino)-2-((5,6-dimethylpyridin-3-yl)amino)-5-fluoronicotinamide | 375 | 0.64 | |
| Example 2-37 | 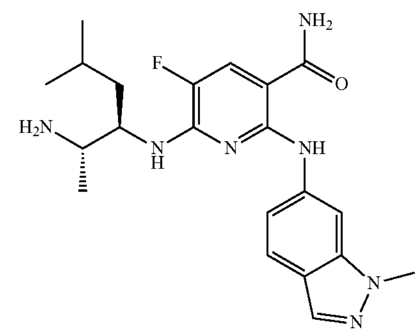 [SMILES: CC(C)C[C@@H](Nc1nc(Nc2ccc3cnn(C)c3c2)c(C(N)=O)cc1F)[C@H](C)N] | 6-(((2S,3R)-2-amino-5-methylhexan-3-yl)amino)-5-fluoro-2-((1-methyl-1H-indazol-6-yl)amino)nicotinamide | 414 | 1.02 | |

TABLE 3-continued

| Example | Structure | Compound name | MS (ESI m/z): (M + H) | RT (min) | HNMR |
|---|---|---|---|---|---|
| Example 2-38 | 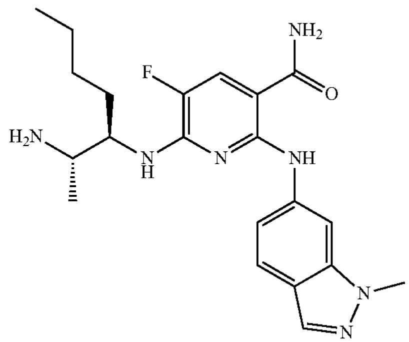 [SMILES: CCCC[C@@H](Nc1nc(Nc2ccc3cnn(C)c3c2)c(C(N)=O)cc1F)[C@H](C)N] | 6-(((2S,3R)-2-aminoheptan-3-yl)amino)-5-fluoro-2-((1-methyl-1H-indazol-6-yl)amino)nicotinamide | 414 | 1.01 | |
| Example 2-39 | 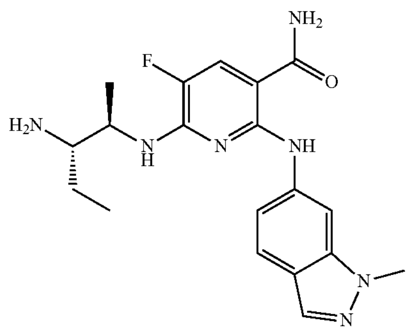 [SMILES: CC[C@H](N)[C@@H](C)Nc1nc(Nc2ccc3cnn(C)c3c2)c(C(N)=O)cc1F] | 6-(((2R,3S)-3-aminopentan-2-yl)amino)-5-fluoro-2-((1-methyl-1H-indazol-6-yl)amino)nicotinamide | 386 | 0.85 | |
| Example 2-40 | 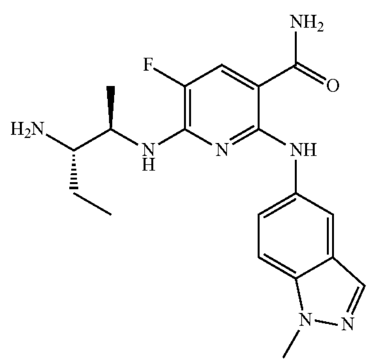 [SMILES: CC[C@H](N)[C@@H](C)Nc1nc(Nc2ccc3c(cnn3C)c2)c(C(N)=O)cc1F] | 6-(((2R,3S)-3-aminopentan-2-yl)amino)-5-fluoro-2-((1-methyl-1H-indazol-5-yl)amino)nicotinamide | 386 | 0.83 | 1H-NMR (MeOD) δ: 7.94 (1H, s), 7.92-7.89 (1H, m), 7.74 (1H, d, J = 11.9 Hz), 7.53 (1H, d, J = 8.9 Hz), 7.42 (1H, dd, J = 8.9, 2.0 Hz), 4.36-4.24 (1H, m), 4.06 (3H, s), 3.46-3.33 (1H, m), 1.67-1.40 (2H, m), 1.28 (3H, d, J = 7.3 Hz), 0.68 (3H, t, J = 7.6 Hz). |

TABLE 3-continued

| Example | Structure | Compound name | MS (ESI m/z): (M + H) | RT (min) | HNMR |
|---|---|---|---|---|---|
| Example 2-41 | 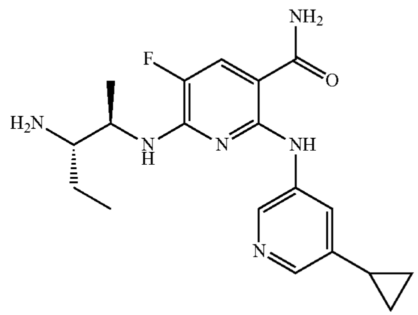 [SMILES: CC[C@H](N)[C@@H](C)Nc1nc(Nc2cncc(C3CC3)c2)c(C(N)=O)cc1F] | 6-(((2R,3S)-3-aminopentan-2-yl)amino)-2-((5-cyclopropylpyridin-3-yl)amino)-5-fluoronicotinamide | 373 | 0.64 | |
| Example 2-42 | 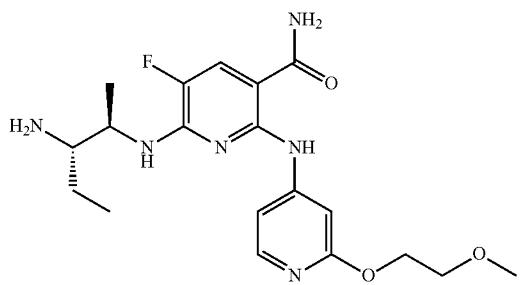 [SMILES: CC[C@H](N)[C@@H](C)Nc1nc(Nc2ccnc(OCCOC)c2)c(C(N)=O)cc1F] | 6-(((2R,3S)-3-aminopentan-2-yl)amino)-5-fluoro-2-((2-(2-methoxyethoxy)pyridin-4-yl)amino)nicotinamide | 407 | 0.65 | |
| Example 2-43 | 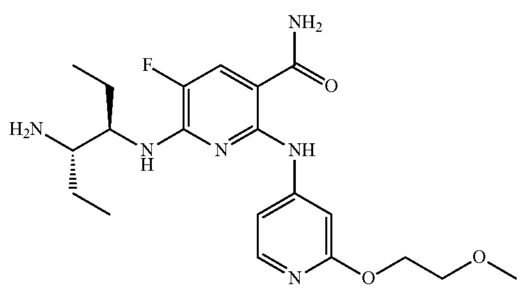 [SMILES: CC[C@H](N)[C@@H](CC)Nc1nc(Nc2ccnc(OCCOC)c2)c(C(N)=O)cc1F] | 6-(((3R,4S)-4-aminohexan-3-yl)amino)-5-fluoro-2-((2-(2-methoxyethoxy)pyridin-4-yl)amino)nicotinamide | 421 | 0.71 | |

TABLE 3-continued

| Example | Structure | Compound name | MS (ESI m/z): (M + H) | RT (min) | HNMR |
|---|---|---|---|---|---|
| Example 2-44 | 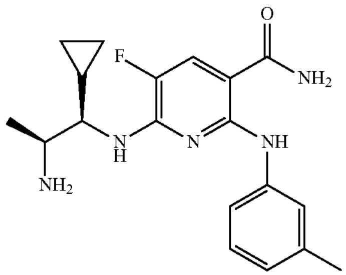 [SMILES: Cc1cccc(Nc2nc(N[C@H](C3CC3)[C@H](C)N)c(F)cc2C(N)=O)c1] | 6-(((1R,2S)-2-amino-1-cyclopropylpropyl)amino)-5-fluoro-2-(m-tolylamino)nicotinamide | 358 | 1.03 | 1H-NMR (DMSO) δ: 11.52 (1H, s), 7.95-7.05 (10H, m), 6.76 (1H, d, J = 7.3 Hz), 3.72-3.61 (1H, m), 3.50-3.42 (1H, m), 2.28, (3H, s), 1.26 (3H, d, J = 8.4 Hz), 1.21-1.08 (1H, m), 0.66-0.34 (4H, m) |
| Example 2-45 | 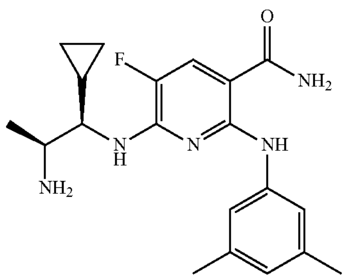 [SMILES: Cc1cc(C)cc(Nc2nc(N[C@H](C3CC3)[C@H](C)N)c(F)cc2C(N)=O)c1] | 6-(((1R,2S)-2-amino-1-cyclopropylpropyl)amino)-2-(3,5-dimethylphenyl)amino)-5-fluoronicotinamide | 372 | 1.11 | |
| Example 2-46 | 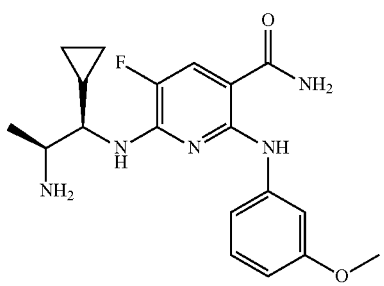 [SMILES: COc1cccc(Nc2nc(N[C@H](C3CC3)[C@H](C)N)c(F)cc2C(N)=O)c1] | 6-(((1R,2S)-2-amino-1-cyclopropylpropyl)amino)-5-fluoro-2-((3-methoxyphenyl)amino) nicotinamide | 374 | 0.98 | 1H-NMR (DMSO-d6) δ: 11.57 (1H, s), 7.95-7.50 (5H, m), 7.30-7.00 (5H, m), 6.54 (1H, d, J = 7.8 Hz), 3.74 (3H, s), 3.72-3.61 (1H, m), 3.50-3.42 (1H, m), 1.29 (3H, d, J = 8.4 Hz), 1.16-1.00 (1H, m), 0.69-0.25 (4H, m) |

TABLE 3-continued

| Example | Structure | Compound name | MS (ESI m/z): (M + H) | RT (min) | HNMR |
|---|---|---|---|---|---|
| Example 2-47 | 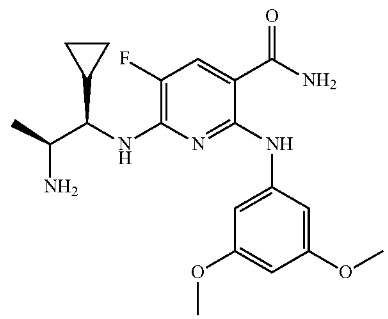 [SMILES: COc1cc(Nc2nc(N[C@H](C3CC3)[C@H](C)N)c(F)cc2C(N)=O)cc(OC)c1] | 6-(((1R,2S)-2-amino-1-cyclopropylpropyl)amino)-2-((3,5-dimethoxyphenyl)amino)-5-fluoronicotinamide | 404 | 1 | 1H-NMR (DMSO-d6) δ: 11.55 (1H, s), 7.89-6.90 (7H, m), 6.68 (2H, d, J = 3.0 Hz), 6.17-6.13 (1H, m), 3.72 (6H, s), 3.72-3.61 (1H, m), 3.60-3.45 (1H, m), 1.29 (3H, d, J = 8.4 Hz), 1.16-1.00 (1H, m), 0.70-0.28 (4H, m) |
| Example 2-48 | 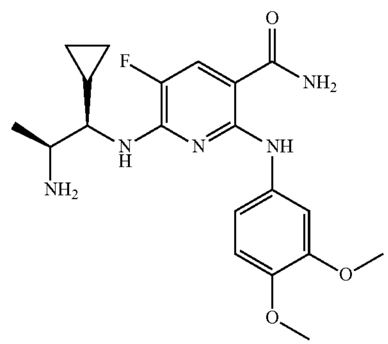 [SMILES: COc1ccc(Nc2nc(N[C@H](C3CC3)[C@H](C)N)c(F)cc2C(N)=O)cc1OC] | 6-(((1R,2S)-2-amino-1-cyclopropylpropyl)amino)-2-((3,4-dimethoxyphenyl)amino)-5-fluoronicotinamide | 404 | 0.89 | 1H-NMR (DMSO-d6) δ: 11.31 (1H, s), 7.90-7.50 (5H, m), 7.20-6.65 (6H, m), 3.75 (3H, s), 3.73 (3H, s), 3.69-3.58 (1H, m), 3.60-3.45 (1H, m), 1.23 (3H, d, J = 8.4 Hz), 1.16-1.00 (1H, m), 0.64-0.25 (4H, m) |
| Example 2-49 | 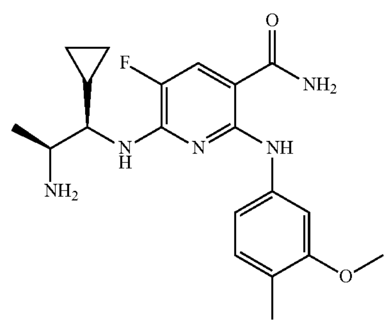 [SMILES: COc1cc(Nc2nc(N[C@H](C3CC3)[C@H](C)N)c(F)cc2C(N)=O)ccc1C] | 6-(((1R,2S)-2-amino-1-cyclopropylpropyl)amino)-5-fluoro-2-((3-methoxy-4-methylphenyl)amino)nicotinamide | 388 | 1.06 | |

TABLE 3-continued

| Example | Structure | Compound name | MS (ESI m/z): (M + H) | RT (min) | HNMR |
|---|---|---|---|---|---|
| Example 2-50 | 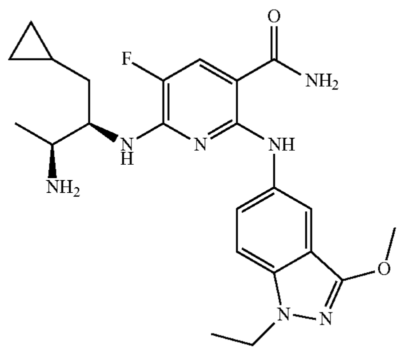 [SMILES: CCn1nc(OC)c2cc(Nc3nc(N[C@H](CC4CC4)[C@H](C)N)c(F)cc3C(N)=O)ccc21] | 6-(((2R,3S)-3-amino-1-cyclopropylbutan-2-yl)amino)-2-((1-ethyl-3-methoxy-1H-indazol-5-yl)amino)-5-fluoronicotinamide | 456 | 1.1 | |
| Example 2-51 | 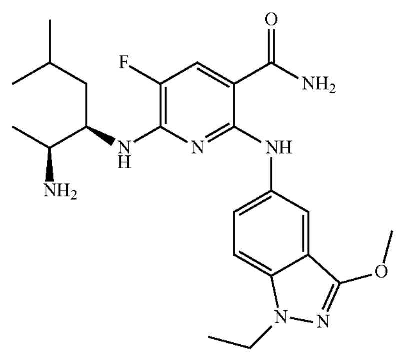 [SMILES: CCn1nc(OC)c2cc(Nc3nc(N[C@H](CC(C)C)[C@H](C)N)c(F)cc3C(N)=O)ccc21] | 6-(((2S,3R)-2-amino-5-methylhexan-3-yl)amino)-2-((1-ethyl-3-methoxy-1H-indazol-5-yl)amino)-5-fluoronicotinamide | 458 | 1.16 | |
| Example 2-52 | 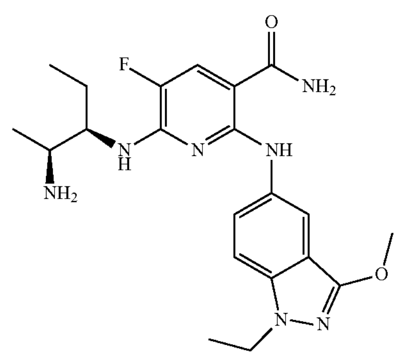 [SMILES: CC[C@@H](Nc1nc(Nc2ccc3c(c2)c(OC)nn3CC)c(C(N)=O)cc1F)[C@H](C)N] | 6-(((2S,3R)-2-aminopentan-3-yl)amino)-2-((1-ethyl-3-methoxy-1H-indazol-5-yl)amino)-5-fluoronicotinamide | 430 | 1.01 | 1H-NMR (MeOD) δ: 7.92 (1H, d, J = 2.0 Hz), 7.75 (1H, d, J = 11.9 Hz), 7.37 (1H, d, J = 9.2 Hz), 7.29 (1H, dd, J = 9.2, 2.0 Hz), 4.25 (2H, q, J = 7.3 Hz), 4.24-4.18 (1H, m), 4.06 (3H, s), 3.48 (1H, dd, J = 6.9, 3.6 Hz), 1.76-1.56 (2H, m), 1.38 (3H, t, J = 7.3 Hz), 1.22 (3H, d, J = 6.6 Hz), 1.07 (3H, t, J = 7.3 Hz). |

TABLE 3-continued

| Example | Structure | Compound name | MS (ESI m/z): (M + H) | RT (min) | HNMR |
|---|---|---|---|---|---|
| Example 2-53 | 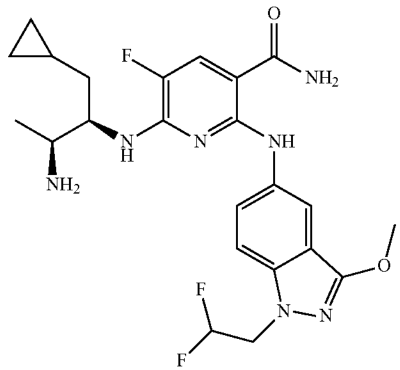 [SMILES: COc1nn(CC(F)F)c2ccc(Nc3nc(N[C@H](CC4CC4)[C@H](C)N)c(F)cc3C(N)=O)cc12] | 6-(((2R,3S)-3-amino-1-cyclopropylbutan-2-yl)amino)-2-((1-(2,2-difluoroethyl)-3-methoxy-1H-indazol-5-yl)amino)-5-fluoronicotinamide | 492 | 1.11 | |
| Example 2-54 | 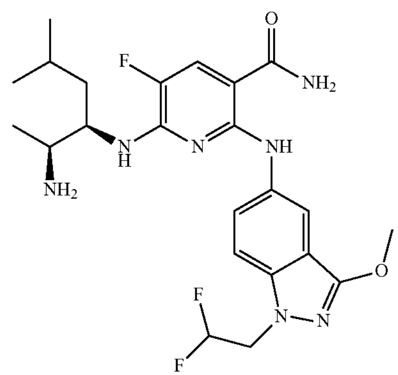 [SMILES: COc1nn(CC(F)F)c2ccc(Nc3nc(N[C@H](CC(C)C)[C@H](C)N)c(F)cc3C(N)=O)cc12] | 6-(((2S,3R)-2-amino-5-methylhexan-3-yl)amino)-2-((1-(2,2-difluoroethyl)-3-methoxy-1H-indazol-5-yl)amino)-5-fluoronicotinamide | 494 | 1.15 | |

TABLE 3-continued

| Example | Structure | Compound name | MS (ESI m/z): (M + H) | RT (min) | HNMR |
|---|---|---|---|---|---|
| Example 2-55 | 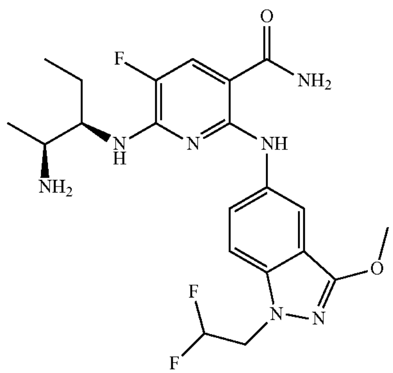 [SMILES: CC[C@@H](Nc1nc(Nc2ccc3c(c2)c(OC)nn3CC(F)F)c(C(N)=O)cc1F)[C@H](C)N] | 6-(((2S,3R)-2-aminopentan-3-yl)amino)-2-((1-(2,2-difluoroethyl)-3-methoxy-1H-indazol-5-yl)amino)-5-fluoronicotinamide | 466 | 1.03 | |
| Example 2-56 | 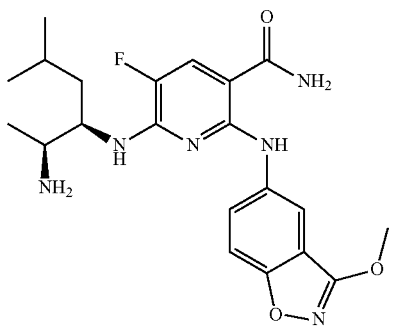 [SMILES: COc1noc2ccc(Nc3nc(N[C@H](CC(C)C)[C@H](C)N)c(F)cc3C(N)=O)cc12] | 6-(((2S,3R)-2-amino-5-methylhexan-3-yl)amino)-5-fluoro-2-((3-methoxybenzo[d]isoxazol-5-yl)amino)nicotinamide | 431 | 1.15 | |
| Example 2-57 | 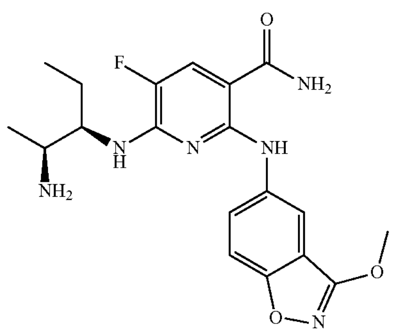 [SMILES: CC[C@@H](Nc1nc(Nc2ccc3onc(OC)c3c2)c(C(N)=O)cc1F)[C@H](C)N] | 6-(((2S,3R)-2-aminopentan-3-yl)amino)-5-fluoro-2-((3-methoxybenzo[d]isoxazol-5-yl)amino)nicotinamide | 403 | 0.87 | |

TABLE 3-continued

| Example | Structure | Compound name | MS (ESI m/z): (M + H) | RT (min) | HNMR |
|---|---|---|---|---|---|
| Example 2-58 | 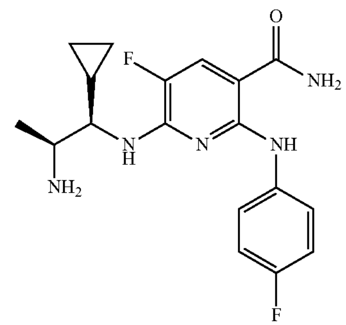 [SMILES: C[C@H](N)[C@H](Nc1nc(Nc2ccc(F)cc2)c(C(N)=O)cc1F)C1CC1] | 6-(((1R,2S)-2-amino-1-cyclopropylpropyl)amino)-5-fluoro-2-((4-fluorophenyl)amino)nicotinamide | 362 | 0.98 | |
| Example 2-59 | 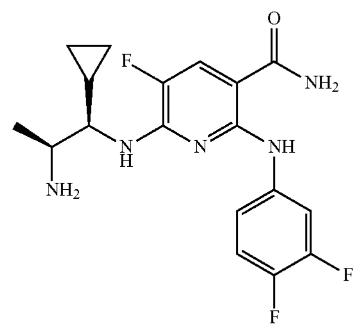 [SMILES: C[C@H](N)[C@H](Nc1nc(Nc2ccc(F)c(F)c2)c(C(N)=O)cc1F)C1CC1] | 6-(((1R,2S)-2-amino-1-cyclopropylpropyl)amino)-2-((3,4-difluorophenyl)amino)-5-fluoronicotinamide | 380 | 1.03 | |
| Example 2-60 | 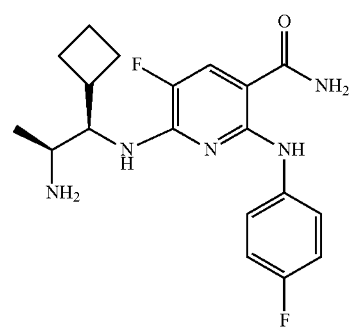 [SMILES: C[C@H](N)[C@H](Nc1nc(Nc2ccc(F)cc2)c(C(N)=O)cc1F)C1CCC1] | 6-(((1R,2S)-2-amino-1-cyclobutylpropyl)amino)-5-fluoro-2-((4-fluorophenyl)amino)nicotinamide | 376 | 1.07 | |

TABLE 3-continued

| Example | Structure | Compound name | MS (ESI m/z): (M + H) | RT (min) | HNMR |
|---|---|---|---|---|---|
| Example 2-61 | 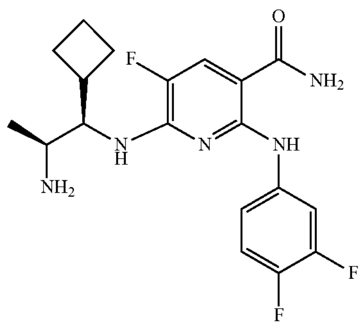 [SMILES: C[C@H](N)[C@H](Nc1nc(Nc2ccc(F)c(F)c2)c(C(N)=O)cc1F)C1CCC1] | 6-(((1R,2S)-2-amino-1-cyclobutylpropyl)amino)-2-((3,4-difluorophenyl)amino)-5-fluoronicotinamide | 394 | 1.13 | |
| Example 2-62 | 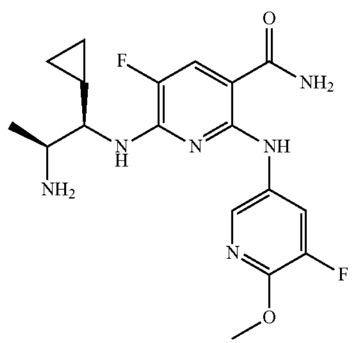 [SMILES: COc1ncc(Nc2nc(N[C@H](C3CC3)[C@H](C)N)c(F)cc2C(N)=O)cc1F] | 6-(((1R,2S)-2-amino-1-cyclopropylpropyl)amino)-5-fluoro-2-((5-fluoro-6-methoxypyridin-3-yl)amino)nicotinamide. | 393 | 0.94 | 1H-NMR (DMSO-d6) δ: 11.41 (1H, s), 8.02 (1H, dd, J = 2.4, 12.9 Hz), 7.95-7.65 (6H, m), 7.40-7.10 (2H, m), 3.91 (3H, s), 3.65-3.40 (2H, m), 1.25 (3H, d, J = 6.6 Hz), 1.14-1.10 (1H, m), 0.68-0.54 (1H, m), 0.48-0.22 (3H, m) |
| Example 2-63 | 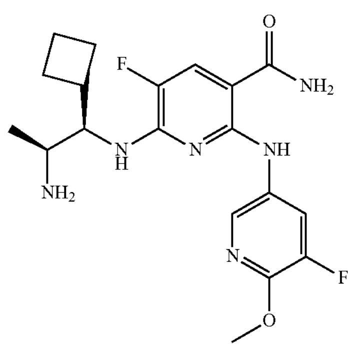 [SMILES: COc1ncc(Nc2nc(N[C@H](C3CCC3)[C@H](C)N)c(F)cc2C(N)=O)cc1F] | 6-(((1R,2S)-2-amino-1-cyclobutylpropyl)amino)-5-fluoro-2-((5-fluoro-6-methoxypyridin-3-yl)amino)nicotinamide. | 407 | 1.02 | 1H-NMR (DMSO-d6) δ: 11.44 (1H, s), 8.18 (1H, dd, J = 2.1, 12.6 Hz), 7.99 (1H, d, J = 2.1 Hz), 7.91 (1H, d, J = 12.6 Hz), 7.85-7.60 (4H, m), 7.42-7.10 (1H, m), 6.88 (1H, d, J = 9.9 Hz), 4.37-4.25 (1H, m), 3.92 (3H, s), 3.40-3.25 (1H, m), 2.70-2.54 (1H, m), 2.10-1.62 (6H, m), 1.15 (3H, d, J = 6.6 Hz) |

TABLE 3-continued

| Example | Structure | Compound name | MS (ESI m/z): (M + H) | RT (min) | HNMR |
|---|---|---|---|---|---|
| Example 2-64 | 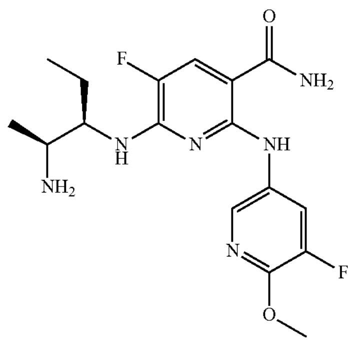 [SMILES: CC[C@@H](Nc1nc(Nc2cnc(OC)c(F)c2)c(C(N)=O)cc1F)[C@H](C)N] | 6-(((2S,3R)-2-aminopentan-3-yl)amino)-5-fluoro-2-((5-fluoro-6-methoxypyridin-3-yl)amino)nicotinamide | 381 | 0.93 | |
| Example 2-65 | 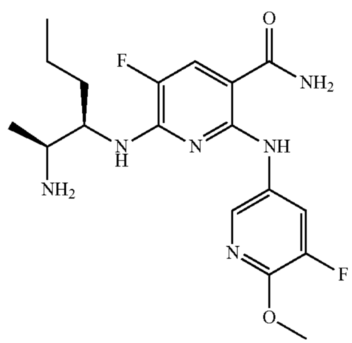 [SMILES: CCC[C@@H](Nc1nc(Nc2cnc(OC)c(F)c2)c(C(N)=O)cc1F)[C@H](C)N] | 6-(((2S,3R)-2-aminohexan-3-yl)amino)-5-fluoro-2-((5-fluoro-6-methoxypyridin-3-yl)amino)nicotinamide | 395 | 1.02 | 1H-NMR (DMSO-d6) δ: 11.44 (1H, s), 8.08-7.97 (2H, m), 7.92 (1H, d, J = 12.6 Hz), 7.92-7.65 (4H, m), 7.40-7.16 (1H, m), 6.99 (1H, d, J = 8.4 Hz), 4.20-4.06 (1H, m), 3.91 (3H, s), 3.46-3.26 (1H, m), 1.64-1.48 (2H, m), 1.47-1.13 (5H, m), 0.85 (3H, t, J = 7.4 Hz) |
| Example 2-66 | 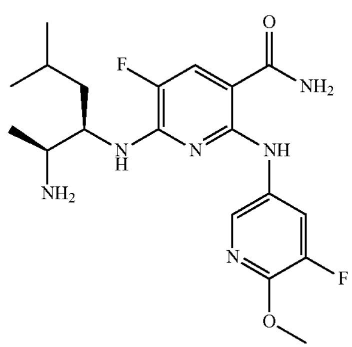 [SMILES: COc1ncc(Nc2nc(N[C@H](CC(C)C)[C@H](C)N)c(F)cc2C(N)=O)cc1F] | 6-(((2S,3R)-2-amino-5-methylhexan-3-yl)amino)-5-fluoro-2-((5-fluoro-6-methoxypyridin-3-yl)amino)nicotinamide | 409 | 1.08 | 1H-NMR (DMSO-d6) δ: 11.40 (1H, s), 8.08-7.97 (2H, m), 7.91 (1H, d, J = 12.6 Hz), 7.85-7.62 (4H, m), 7.40-7.10 (1H, m), 7.00 (1H, d, J = 8.4 Hz), 4.26-4.12 (1H, m), 3.90 (3H, s), 3.40-3.26 (1H, m), 1.66-1.48 (2H, m), 1.38-1.24 (1H, m), 1.17 (3H, d, J = 6.6 Hz), 0.89 (3H, d, J = 6.6 Hz), 0.76 (3H, d, J = 6.6 Hz) |

TABLE 3-continued

| Example | Structure | Compound name | MS (ESI m/z): (M + H) | RT (min) | HNMR |
|---|---|---|---|---|---|
| Example 2-67 | 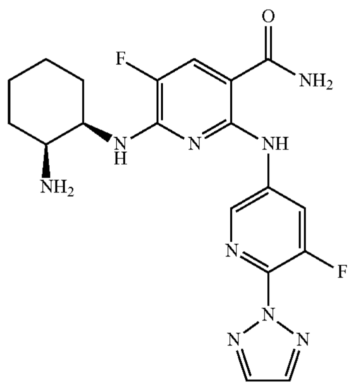 [SMILES: NC(=O)c1cc(F)c(N[C@@H]2CCCC[C@@H]2N)nc1Nc1cnc(-n2nccn2)c(F)c1] | 6-(((1R,2S)-2-aminocyclohexyl)amino)-5-fluoro-2-((5-fluoro-6-(2H-1,2,3-triazol-2-yl)pyridin-3-yl)amino)nicotinamide | 430 | 0.9 | 1H-NMR (DMSO-d6) δ: 12.23 (1H, s), 8.58-8.47 (2H, m), 8.17 (2H, s), 8.03(1H, d, J = 12.0 Hz), 8.02-7.80 (4H, m), 7.58-7.40 (1H, m), 7.11 (1H, d, J = 6.6 Hz), 4.37-4.22 (1H, m), 3.76-3.62 (1H, m), 2.02-1.80 (2H, m), 1.80-1.54 (4H, m), 1.52-1.34 (2H, m) |
| Example 2-68 | 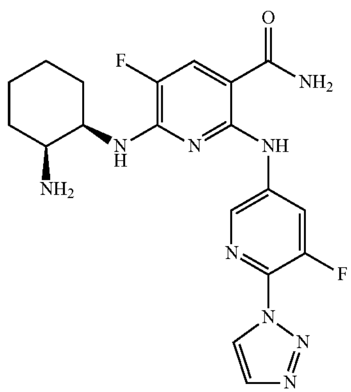 [SMILES: NC(=O)c1cc(F)c(N[C@@H]2CCCC[C@@H]2N)nc1Nc1cnc(-n2ccnn2)c(F)c1] | 6-(((1R,2S)-2-aminocyclohexyl)amino)-5-fluoro-2-((5-fluoro-6-(1H-1,2,3-triazol-1-yl)pyridin-3-yl)amino)nicotinamide | 430 | 0.86 | 1H-NMR (DMSO-d6) δ: 12.24 (1H, s), 8.67-8.48 (3H, m), 8.15-7.75 (6H, m), 7.60-7.40 (1H, m), 7.11 (1H, d, J = 6.6 Hz), 4.38-4.23 (1H, m), 3.75-3.60 (1H, m), 2.04-1.80 (2H, m), 1.80-1.54 (4H, m), 1.54-1.32 (2H, m) |

| Example | Structure | Compound name | MS (ESI m/z): (M + H) | RT (min) | HNMR |
|---|---|---|---|---|---|
| Example 2-69 | 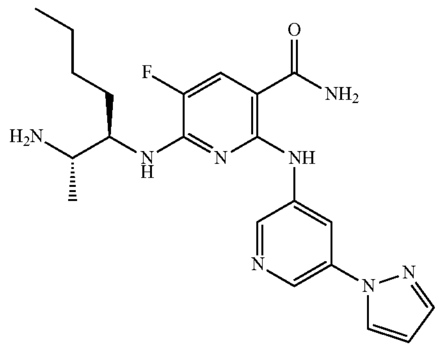 [SMILES: CCCC[C@@H](Nc1nc(Nc2cncc(-n3cccn3)c2)c(C(N)=O)cc1F)[C@H](C)N] | 2-((5-(1H-pyrazol-1-yl)pyridin-3-yl)amino)-6-(((2S,3R)-2-aminoheptan-3-yl)amino)-5-fluoronicotinamide | 427 | 1.02 | |
| Example 2-70 | 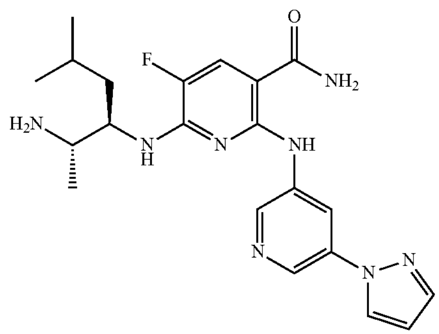 [SMILES: CC(C)C[C@@H](Nc1nc(Nc2cncc(-n3cccn3)c2)c(C(N)=O)cc1F)[C@H](C)N] | 2-((5-(1H-pyrazol-1-yl)pyridin-3-yl)amino)-6-(((2S,3R)-2-amino-5-methylhexan-3-yl)amino)-5-fluoronicotinamide | 427 | 1.02 | |

TABLE 3-continued
| Example | Structure | Compound name | MS (ESI m/z): (M + H) | RT (min) | HNMR |
|---|---|---|---|---|---|
| Example 2-71 | 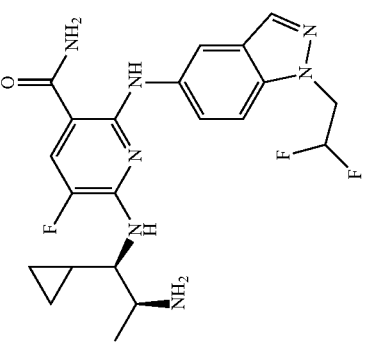 | 6-(((1R,2S)-2-amino-1-cyclopropylpropyl)amino)-2-((1-2,2-difluoroethyl)-1H-indazol-5-yl)amino)-5-fluoronicotinamide | 448 | 0.94 | |
| Example 2-72 | 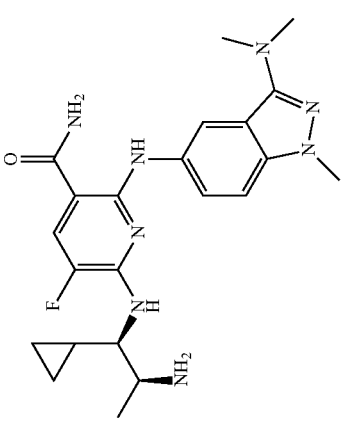 | 6-(((1R,2S)-2-amino-1-cyclopropylpropyl)amino)-2-((3-(dimethylamino)-1-methyl-1H-indazol-5-yl)amino)-5-fluoronicotinamide | 441 | 0.9 | |

TABLE 3-continued

| Example | Structure | Compound name | MS (ESI m/z): (M + H) | RT (min) | HNMR |
|---|---|---|---|---|---|
| Example 2-73 | 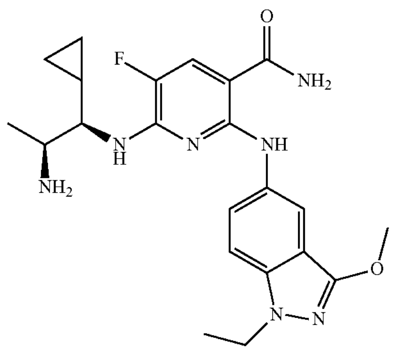 [SMILES: CCn1nc(OC)c2cc(Nc3nc(N[C@H](C4CC4)[C@H](C)N)c(F)cc3C(N)=O)ccc21] | 6-(((1R,2S)-2-amino-1-cyclopropyl)propyl)amino)-2-((1-ethyl-3-methoxy-1H-indazol-5-yl)amino)-5-fluoronicotinamide | 442 | 1.01 | |
| Example 2-74 | 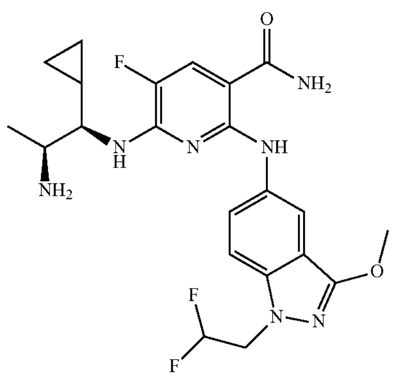 [SMILES: COc1nn(CC(F)F)c2ccc(Nc3nc(N[C@H](C4CC4)[C@H](C)N)c(F)cc3C(N)=O)cc12] | 6-(((1R,2S)-2-amino-1-cyclopropyl)propyl)amino)-2-((1-(2,2-difluoroethyl)-3-methoxy-1H-indazol-5-yl)amino)-5-fluoronicotinamide | 478 | 0.97 | |

TABLE 3-continued

| Example | Structure | Compound name | MS (ESI m/z): (M + H) | RT (min) | HNMR |
|---|---|---|---|---|---|
| Example 2-75 | 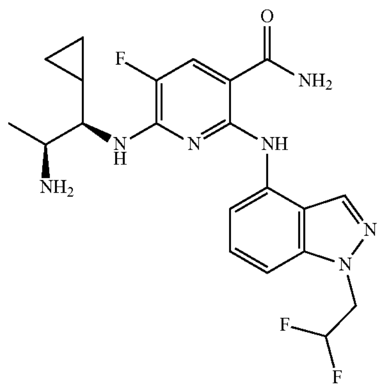 [SMILES: C[C@H](N)[C@H](Nc1nc(Nc2cccc3c2cnn3CC(F)F)c(C(N)=O)cc1F)C1CC1] | 6-(((1R,2S)-2-amino-1-cyclopropylpropyl)amino)-2-((1-(2,2-difluoroethyl)-1H-indazol-4-yl)amino)-5-fluoronicotinamide | 448 | 0.97 | |
| Example 2-76 | 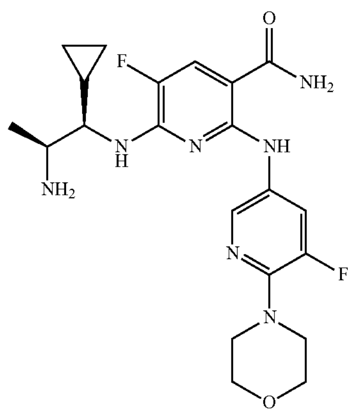 [SMILES: C[C@H](N)[C@H](Nc1nc(Nc2cnc(N3CCOCC3)c(F)c2)c(C(N)=O)cc1F)C1CC1] | 6-(((1R,2S)-2-amino-1-cyclopropylpropyl)amino)-5-fluoro-2-((5-fluoro-6-morpholinopyridin-3-yl)amino)nicotinamide | 448 | 0.87 | 1H-NMR (DMSO-d6) δ: 11.46 (1H, m), 8.10-7.55 (6H, m), 7.45-6.98 (3H, m), 3.74 (4H, t, J = 4.6 Hz), 3.69-3.68 (1H, m), 3.60-3.45 (1H, m), 3.24 (4H, t, J = 4.6 Hz), 1.23 (3H, d, J = 8.4 Hz), 1.13-1.00 (1H, m), 0.68-0.20 (4H, m) |

TABLE 3-continued

| Example | Structure | Compound name | MS (ESI m/z): (M + H) | RT (min) | HNMR |
|---|---|---|---|---|---|
| Example 2-77 | 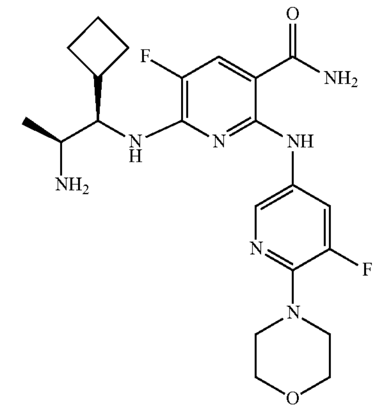 [SMILES: C[C@H](N)[C@H](Nc1nc(Nc2cnc(N3CCOCC3)c(F)c2)c(C(N)=O)cc1F)C1CCC1] | 6-(((1R,2S)-2-amino-1-cyclobutylpropyl)amino)-5-fluoro-2-((5-fluoro-6-morpholinopyridin-3-yl)amino)nicotinamide | 462 | 0.96 | 1H-NMR (DMSO-d6) δ: 11.49 (1H, s), 8.20-7.50 (7H, m), 7.40-6.75 (3H, m), 4.45-4.30 (m, 1H), 3.74 (4H, t, J = 4.6 Hz), 3.35-3.25 (4H, m), 2.74-2.60 (1H, m), 2.10-1.62 (6H, m), 1.14 (3H, d, J = 7.5 Hz) |
| Example 2-78 | 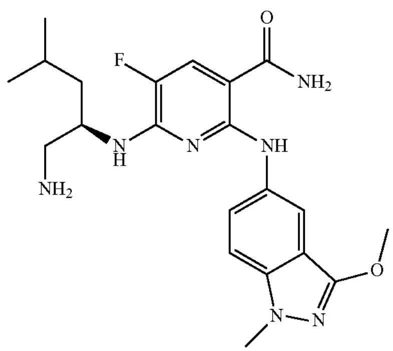 [SMILES: COc1nn(C)c2ccc(Nc3nc(N[C@@H](CN)CC(C)C)c(F)cc3C(N)=O)cc12] | (R)-6-((1-amino-4-methylpentan-2-yl)amino)-5-fluoro-2-((3-methoxy-1-methyl-1H-indazol-5-yl)amino)nicotinamide | 430 | 1.06 | 1H-NMR (MeOD) δ: 7.96 (1H, br s), 7.73 (1H, d, J = 11.9 Hz), 7.32 (1H, br s), 7.32 (3H, s), 4.44-4.37 (1H, m), 4.05 (3H, s), 3.84 (3H, s), 3.18-3.98 (2H, m), 1.77-1.60 (2H, m), 1.46-1.35 (1H, m), 0.93 (6H, t, J = 7.0 Hz). |

TABLE 3-continued

| Example | Structure | Compound name | MS (ESI m/z): (M + H) | RT (min) | HNMR |
|---|---|---|---|---|---|
| Example 2-79 | 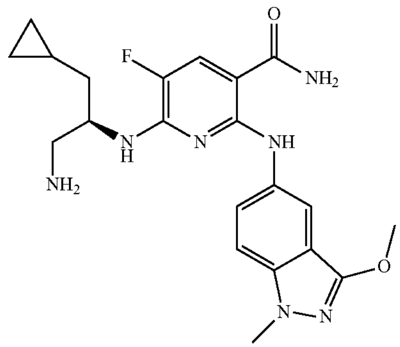 [SMILES: COc1nn(C)c2ccc(Nc3nc(N[C@@H](CN)CC4CC4)c(F)cc3C(N)=O)cc12] | (R)-6-((1-amino-3-cyclopropylpropan-2-yl)amino)-5-fluoro-2-((3-methoxy-1-methyl-1H-indazol-5-yl)amino)nicotinamide | 428 | 1.02 | |
| Example 2-80 | 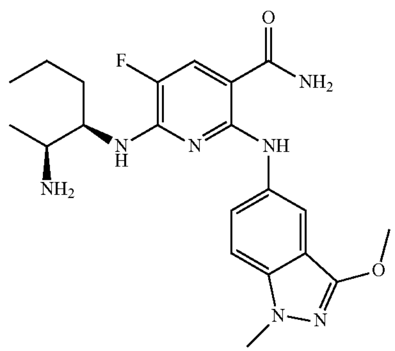 [SMILES: CCC[C@@H](Nc1nc(Nc2ccc3c(c2)c(OC)nn3C)c(C(N)=O)cc1F)[C@H](C)N] | 6-(((2S,3R)-2-aminohexan-3-yl)amino)-5-fluoro-2-((3-methoxy-1-methyl-1H-indazol-5-yl)amino)nicotinamide | 430 | 1 | |
| Example 2-81 | 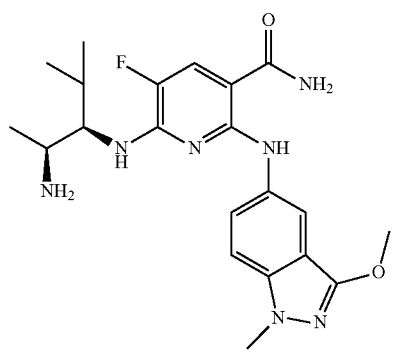 [SMILES: COc1nn(C)c2ccc(Nc3nc(N[C@H](C(C)C)[C@H](C)N)c(F)cc3C(N)=O)cc12] | 6-(((2S,3R)-2-amino-4-methylpentan-3-yl)amino)-5-fluoro-2-((3-methoxy-1-methyl-1H-indazol-5-yl)amino)nicotinamide | 430 | 1 | |

TABLE 3-continued

| Example | Structure | Compound name | MS (ESI m/z): (M + H) | RT (min) | HNMR |
|---|---|---|---|---|---|
| Example 2-82 | 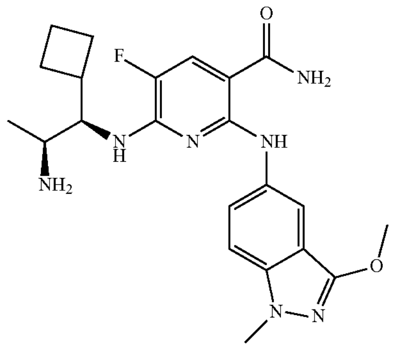 [SMILES: COc1nn(C)c2ccc(Nc3nc(N[C@H](C4CCC4)[C@H](C)N)c(F)cc3C(N)=O)cc12] | 6-(((1R,2S)-2-amino-1-cyclobutylpropyl)amino)-5-fluoro-2-((3-methoxy-1-methyl-1H-indazol-5-yl)amino)nicotinamide | 442 | 1.05 | |
| Example 2-83 | 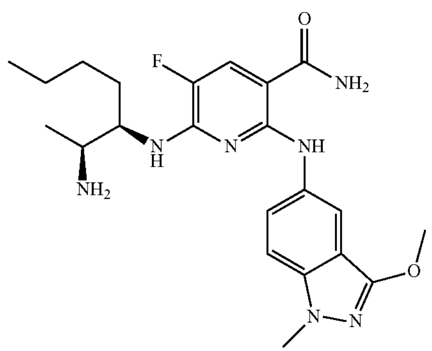 [SMILES: CCCC[C@@H](Nc1nc(Nc2ccc3c(c2)c(OC)nn3C)c(C(N)=O)cc1F)[C@H](C)N] | 6-(((2S,3R)-2-aminoheptan-3-yl)amino)-5-fluoro-2-((3-methoxy-1-methyl-1H-indazol-5-yl)amino)nicotinamide | 444 | 1.1 | 1H-NMR (MeOD) δ: 7.92 (1H, d, J = 1.3 Hz), 7.75 (1H, d, J = 11.9 Hz), 7.35 (1H, d, J = 9.2 Hz), 7.29 (1H, dd, J = 8.9, 1.7 Hz), 4.34-4.27 (1H, m), 4.04 (3H, s), 3.85 (3H, s), 3.46-3.41 (1H, m), 1.68-1.58 (2H, m), 1.51-1.34 (4H, m), 1.22 (3H, d, J = 7.3 Hz), 0.93 (3H, t, J = 6.9 Hz). |

TABLE 3-continued

| Example | Structure | Compound name | MS (ESI m/z): (M + H) | RT (min) | HNMR |
|---|---|---|---|---|---|
| Example 2-84 | 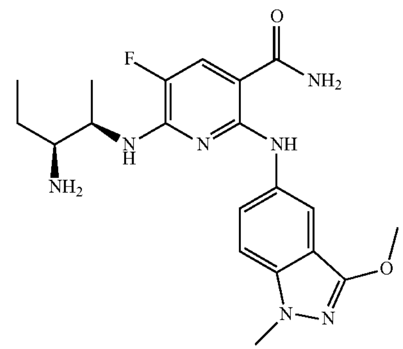 [SMILES: CC[C@H](N)[C@@H](C)Nc1nc(Nc2ccc3c(c2)c(OC)nn3C)c(C(N)=O)cc1F] | 6-(((2R,3S)-3-aminopentan-2-yl)amino)-5-fluoro-2-((3-methoxy-1-methyl-1H-indazol-5-yl)amino)nicotinamide | 416 | 0.93 | |
| Example 2-85 | 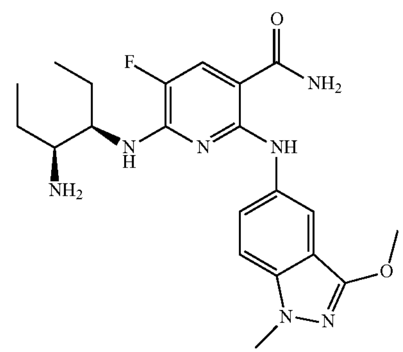 [SMILES: CC[C@H](N)[C@@H](CC)Nc1nc(Nc2ccc3c(c2)c(OC)nn3C)c(C(N)=O)cc1F] | 6-(((3R,4S)-4-aminohexan-3-yl)amino)-5-fluoro-2-((3-methoxy-1-methyl-1H-indazol-5-yl)amino)nicotinamide | 430 | 0.97 | |
| Example 2-86 | 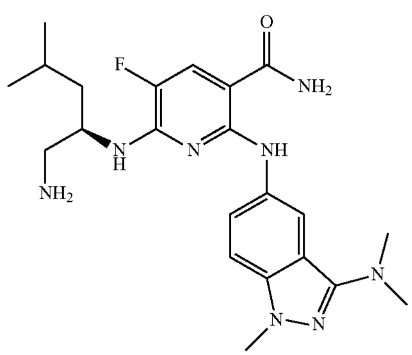 [SMILES: CC(C)C[C@H](CN)Nc1nc(Nc2ccc3c(c2)c(N(C)C)nn3C)c(C(N)=O)cc1F] | (R)-6-((1-amino-4-methylpentan-2-yl)amino)-2-((3-(dimethylamino)-1-methyl-1H-indazol-5-yl)amino)-5-fluoronicotinamide | 443 | 1.04 | |

TABLE 3-continued

| Example | Structure | Compound name | MS (ESI m/z): (M + H) | RT (min) | HNMR |
|---|---|---|---|---|---|
| Example 2-87 | 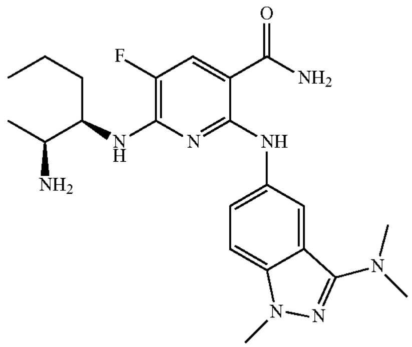 [SMILES: CCC[C@@H](Nc1nc(Nc2ccc3c(c2)c(N(C)C)nn3C)c(C(N)=O)cc1F)[C@H](C)N] | 6-(((2S,3R)-2-aminohexan-3-yl)amino)-2-((3-(dimethylamino)-1-methyl-1H-indazol-5-yl)amino)-5-fluoronicotinamide | 443 | 1 | |
| Example 2-88 | 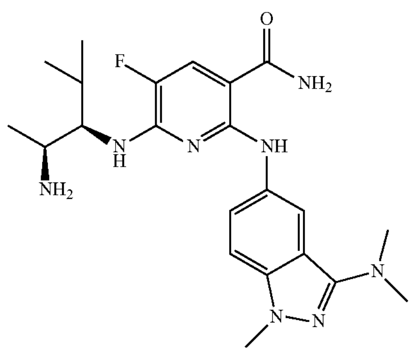 [SMILES: CC(C)[C@@H](Nc1nc(Nc2ccc3c(c2)c(N(C)C)nn3C)c(C(N)=O)cc1F)[C@H](C)N] | 6-(((2S,3R)-2-amino-4-methylpentan-3-yl)amino)-2-((3-(dimethylamino)-1-methyl-1H-indazol-5-yl)amino)-5-fluoronicotinamide | 443 | 0.98 | |

TABLE 3-continued

| Example | Structure | Compound name | MS (ESI m/z): (M + H) | RT (min) | HNMR |
|---|---|---|---|---|---|
| Example 2-89 | 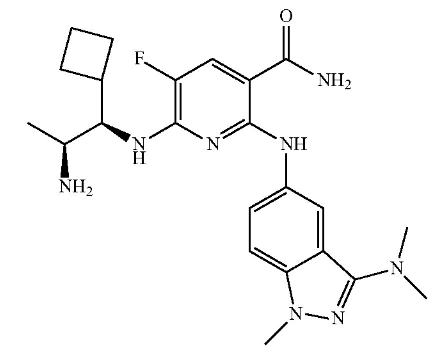 [SMILES: C[C@H](N)[C@H](Nc1nc(Nc2ccc3c(c2)c(N(C)C)nn3C)c(C(N)=O)cc1F)C1CCC1] | 6-(((1R,2S)-2-amino-1-cyclobutylpropyl)amino)-2-((3-(dimethylamino)-1-methyl-1H-indazol-5-yl)amino)-5-fluoronicotinamide | 455 | 1.02 | 1H-NMR (MeOD) δ: 7.99 (1H, d, J = 9.2 Hz), 7.84 (1H, s), 7.77 (1H, d, J = 11.9 Hz), 7.63 (1H, d, J = (8.6 Hz), 4.29 (1H, dd, J = 9.9, 3.3 Hz), 4.14-4.05 (1H, m), 3.95 (3H, s), 3.40 (6H, s), 2.69-2.54 (1H, m), 2.13-2.02 (2H, m), 1.98-1.78 (4H, m), 1.18 (3H, d, J = 7.3 Hz). |
| Example 2-90 | 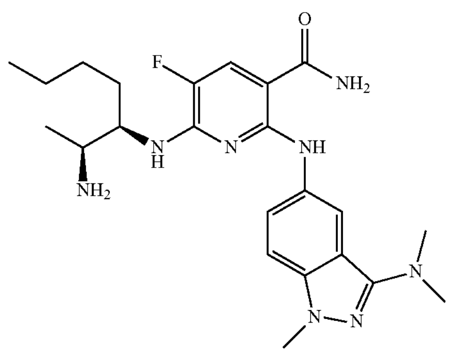 [SMILES: CCCC[C@@H](Nc1nc(Nc2ccc3c(c2)c(N(C)C)nn3C)c(C(N)=O)cc1F)[C@H](C)N] | 6-(((2S,3R)-2-aminoheptan-3-yl)amino)-2-((3-(dimethylamino)-1-methyl-1H-indazol-5-yl)amino)-5-fluoronicotinamide | 457 | 1.07 | |
| Example 2-91 | 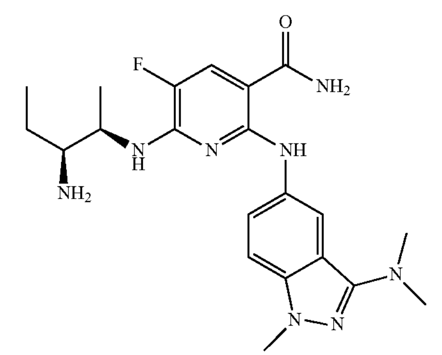 [SMILES: CC[C@H](N)[C@@H](C)Nc1nc(Nc2ccc3c(c2)c(N(C)C)nn3C)c(C(N)=O)cc1F] | 6-(((2R,3S)-3-aminopentan-2-yl)amino)-2-((3-(dimethylamino)-1-methyl-1H-indazol-5-yl)amino)-5-fluoronicotinamide | 429 | 0.88 | |

TABLE 3-continued

| Example | Structure | Compound name | MS (ESI m/z): (M + H) | RT (min) | HNMR |
|---|---|---|---|---|---|
| Example 2-92 | 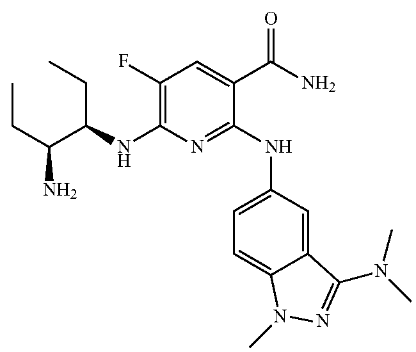 [SMILES: CC[C@H](N)[C@@H](CC)Nc1nc(Nc2ccc3c(c2)c(N(C)C)nn3C)c(C(N)=O)cc1F] | 6-(((3R,4S)-4-aminohexan-3-yl)amino)-2-((3-(dimethylamino)-1-methyl-1H-indazol-5-yl)amino)-5-fluoronicotinamide | 443 | 0.95 | |
| Example 2-93 | 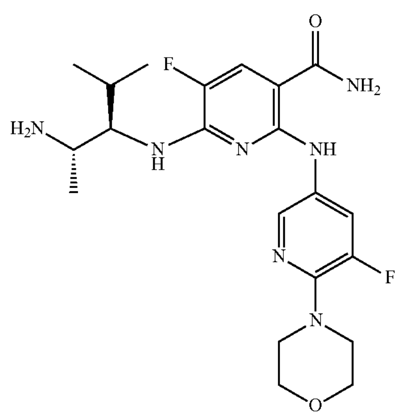 [SMILES: CC(C)[C@@H](Nc1nc(Nc2cnc(N3CCOCC3)c(F)c2)c(C(N)=O)cc1F)[C@H](C)N] | 6-(((2S,3R)-2-amino-4-methylpentan-3-yl)amino)-5-fluoro-2-((5-fluoro-6-morpholinopyridin-3-yl)amino)nicotinamide | 450 | 0.99 | |

TABLE 3-continued

| Example | Structure | Compound name | MS (ESI m/z): (M + H) | RT (min) | HNMR |
|---|---|---|---|---|---|
| Example 2-94 | 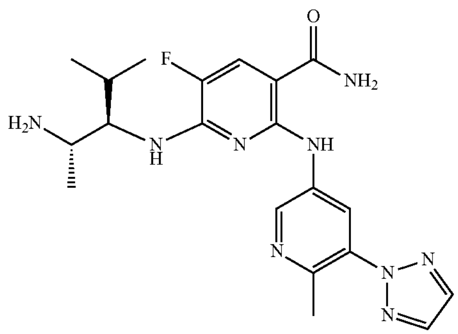 [SMILES: Cc1ncc(Nc2nc(N[C@H](C(C)C)[C@H](C)N)c(F)cc2C(N)=O)cc1-n1nccn1] | 6-(((2S,3R)-2-amino-4-methylpentan-3-yl)amino)-5-fluoro-2-((6-methyl-5-(2H-1,2,3-triazol-2-yl)pyridin-3-yl)amino)nicotinamide | 428 | 0.95 | |
| Example 2-95 | 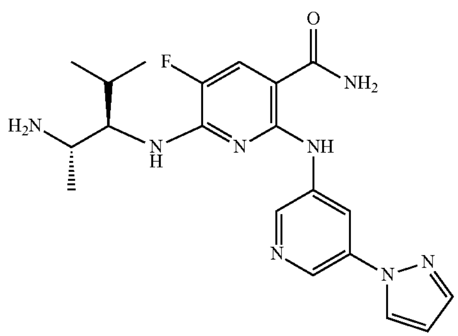 [SMILES: CC(C)[C@@H](Nc1nc(Nc2cncc(-n3cccn3)c2)c(C(N)=O)cc1F)[C@H](C)N] | 2-((5-(1H-pyrazol-1-yl)pyridin-3-yl)amino)-6-(((2S,3R)-2-amino-4-methylpentan-3-yl)amino)-5-fluoronicotinamide | 413 | 0.94 | |
| Example 2-96 | 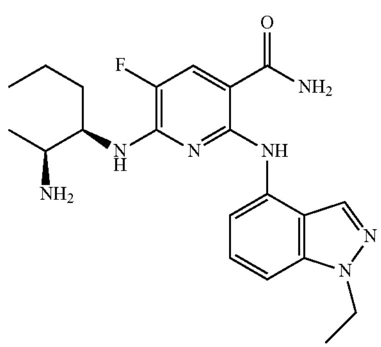 [SMILES: CCC[C@@H](Nc1nc(Nc2cccc3c2cnn3CC)c(C(N)=O)cc1F)[C@H](C)N] | 6-(((2S,3R)-2-aminohexan-3-yl)amino)-2-((1-ethyl-1H-indazol-4-yl)amino)-5-fluoronicotinamide | 414 | 1.01 | |

TABLE 3-continued

| Example | Structure | Compound name | MS (ESI m/z): (M + H) | RT (min) | HNMR |
|---|---|---|---|---|---|
| Example 2-97 | 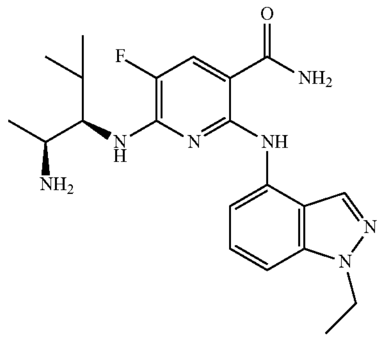 [SMILES: CCn1ncc2c(Nc3nc(N[C@H](C(C)C)[C@H](C)N)c(F)cc3C(N)=O)cccc21] | 6-(((2S,3R)-2-amino-4-methylpentan-3-yl)amino)-2-((1-ethyl-1H-indazol-4-yl)amino)-5-fluoronicotinamide | 414 | 0.97 | |
| Example 2-98 | 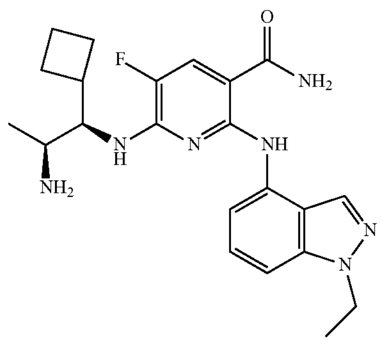 [SMILES: CCn1ncc2c(Nc3nc(N[C@H](C4CCC4)[C@H](C)N)c(F)cc3C(N)=O)cccc21] | 6-(((1R,2S)-2-amino-1-cyclobutylpropyl)amino)-2-((1-ethyl-1H-indazol-4-yl)amino)-5-fluoronicotinamide | 426 | 1.02 | |
| Example 2-99 | 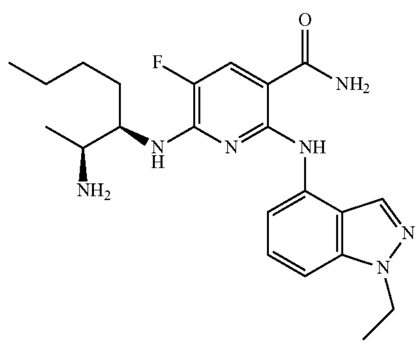 [SMILES: CCCC[C@@H](Nc1nc(Nc2cccc3c2cnn3CC)c(C(N)=O)cc1F)[C@H](C)N] | 6-(((2S,3R)-2-aminoheptan-3-yl)amino)-2-((1-ethyl-1H-indazol-4-yl)amino)-5-fluoronicotinamide | 428 | 1.08 | |

TABLE 3-continued

| Example | Structure | Compound name | MS (ESI m/z): (M + H) | RT (min) | HNMR |
|---|---|---|---|---|---|
| Example 2-100 | 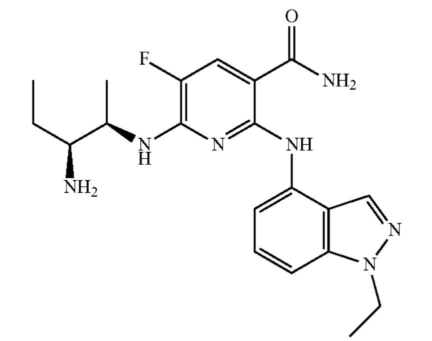 [SMILES: CC[C@H](N)[C@@H](C)Nc1nc(Nc2cccc3c2cnn3CC)c(C(N)=O)cc1F] | 6-(((2R,3S)-3-aminopentan-2-yl)amino)-2-((1-ethyl-1H-indazol-4-yl)amino)-5-fluoronicotinamide | 400 | 0.93 | |
| Example 2-101 | 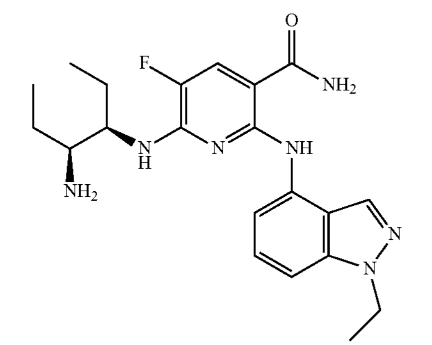 [SMILES: CC[C@H](N)[C@@H](CC)Nc1nc(Nc2cccc3c2cnn3CC)c(C(N)=O)cc1F] | 6-(((3R,4S)-4-aminohexan-3-yl)amino)-2-((1-ethyl-1H-indazol-4-yl)amino)-5-fluoronicotinamide | 414 | 0.98 | 1H-NMR (MeOD) δ: 8.06 (1H, s), 7.83 (1H, d, J = 11.0 Hz), 7.80 (1H, d, J = 6.6 Hz), 7.38 (1H, t, J = 7.9 Hz), 7.19 (1H, d, J = 8.6 Hz), 4.45 (2H, q, J = 7.0 Hz), 4.31 (1H, td, J = 7.3, 3.3 Hz), 3.42-3.34 (1H, m), 1.81-1.67 (2H, m), 1.67-1.53 (2H, m), 1.47 (3H, t, J = 7.0 Hz), 1.08 (3H, t, J = 7.3 Hz), 0.93 (3H, t, J = 7.6 Hz). |
| Example 2-102 | 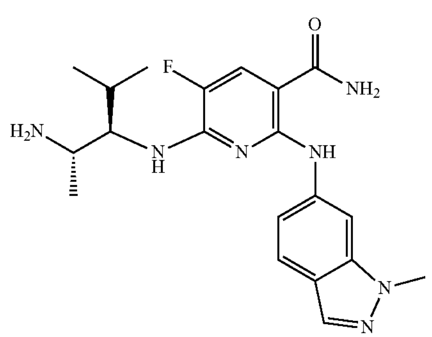 [SMILES: CC(C)[C@@H](Nc1nc(Nc2ccc3cnn(C)c3c2)c(C(N)=O)cc1F)[C@H](C)N] | 6-(((2S,3R)-2-amino-4-methylpentan-3-yl)amino)-5-fluoro-2-((1-methyl-1H-indazol-6-yl)amino)nicotinamide | 400 | 0.93 | |

TABLE 3-continued

| Example | Structure | Compound name | MS (ESI m/z): (M + H) | RT (min) | HNMR |
|---|---|---|---|---|---|
| Example 2-103 | 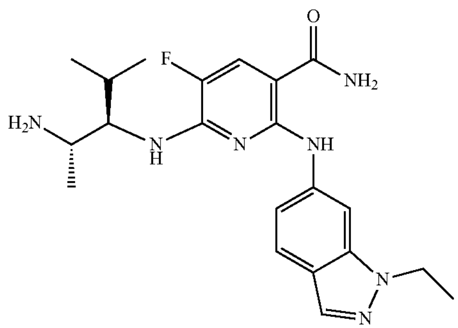 [SMILES: CCn1ncc2ccc(Nc3nc(N[C@H](C(C)C)[C@H](C)N)c(F)cc3C(N)=O)cc21] | 6-(((2S,3R)-2-amino-4-methylpentan-3-yl)amino)-2-((1-ethyl-1H-indazol-6-yl)amino)-5-fluoronicotinamide | 414 | 0.99 | |
| Example 2-104 | 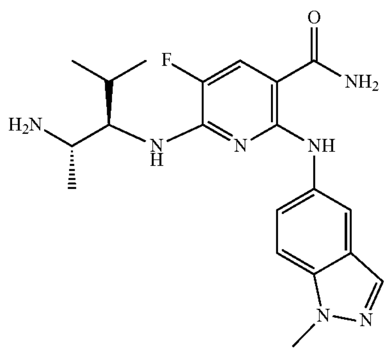 [SMILES: CC(C)[C@@H](Nc1nc(Nc2ccc3c(cnn3C)c2)c(C(N)=O)cc1F)[C@H](C)N] | 6-(((2S,3R)-2-amino-4-methylpentan-3-yl)amino)-5-fluoro-2-((1-methyl-1H-indazol-5-yl)amino)nicotinamide | 400 | 0.91 | |
| Example 2-105 | 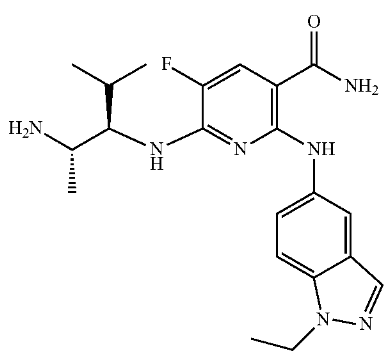 [SMILES: CCn1ncc2cc(Nc3nc(N[C@H](C(C)C)[C@H](C)N)c(F)cc3C(N)=O)ccc21] | 6-(((2S,3R)-2-amino-4-methylpentan-3-yl)amino)-2-((1-ethyl-1H-indazol-5-yl)amino)-5-fluoronicotinamide | 414 | 0.98 | |

TABLE 3-continued

| Example | Structure | Compound name | MS (ESI m/z): (M + H) | RT (min) | HNMR |
|---|---|---|---|---|---|
| Example 2-106 | 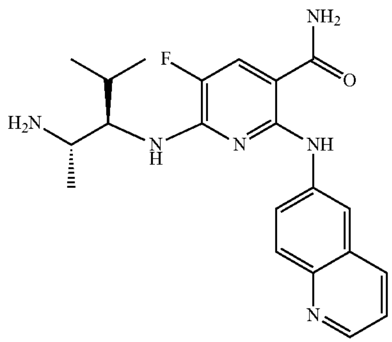 [SMILES: CC(C)[C@@H](Nc1nc(Nc2ccc3ncccc3c2)c(C(N)=O)cc1F)[C@H](C)N] | 6-(((2S,3R)-2-amino-4-methylpentan-3-yl)amino)-5-fluoro-2-(quinolin-6-ylamino)nicotinamide | 397 | 0.72 | |
| Example 2-107 | 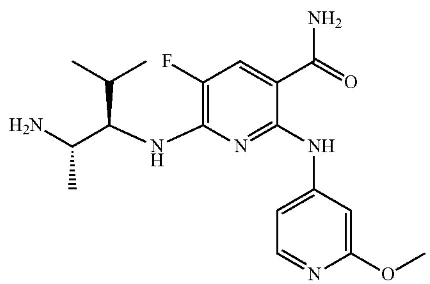 [SMILES: COc1cc(Nc2nc(N[C@H](C(C)C)[C@H](C)N)c(F)cc2C(N)=O)ccn1] | 6-(((2S,3R)-2-amino-4-methylpentan-3-yl)amino)-5-fluoro-2-((2-methoxypyridin-4-yl)amino)nicotinamide | 377 | 0.6 | |
| Example 2-108 | 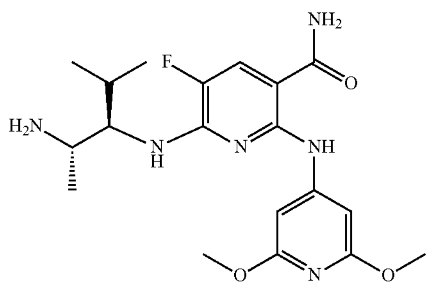 [SMILES: COc1cc(Nc2nc(N[C@H](C(C)C)[C@H](C)N)c(F)cc2C(N)=O)cc(OC)n1] | 6-(((2S,3R)-2-amino-4-methylpentan-3-yl)amino)-2-((2,6-dimethoxypyridin-4-yl)amino)-5-fluoronicotinamide | 407 | 1.01 | |

TABLE 3-continued

| Example | Structure | Compound name | MS (ESI m/z): (M + H) | RT (min) | HNMR |
|---|---|---|---|---|---|
| Example 2-109 | 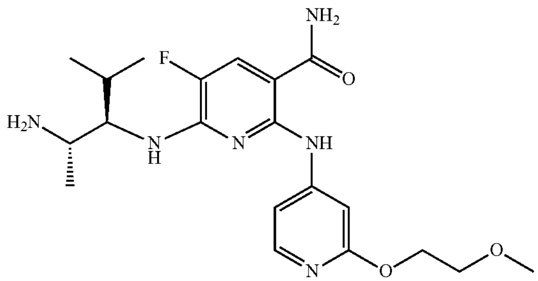 [SMILES: COCCOc1cc(Nc2nc(N[C@H](C(C)C)[C@H](C)N)c(F)cc2C(N)=O)ccn1] | 6-(((2S,3R)-2-amino-4-methylpentan-3-yl)amino)-5-fluoro-2-((2-(2-methoxyethoxy)pyridin-4-yl)amino)nicotinamide | 421 | 0.72 | |
| Example 2-110 | 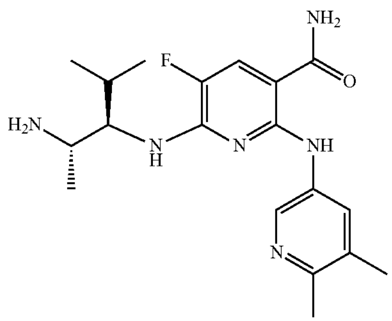 [SMILES: Cc1cc(Nc2nc(N[C@H](C(C)C)[C@H](C)N)c(F)cc2C(N)=O)cnc1C] | 6-(((2S,3R)-2-amino-4-methylpentan-3-yl)amino)-2-((5,6-dimethylpyridin-3-yl)amino)-5-fluoronicotinamide | 375 | 0.68 | |
| Example 2-111 | 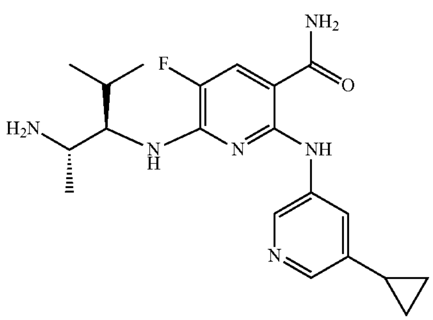 [SMILES: CC(C)[C@@H](Nc1nc(Nc2cncc(C3CC3)c2)c(C(N)=O)cc1F)[C@H](C)N] | 6-(((2S,3R)-2-amino-4-methylpentan-3-yl)amino)-2-((5-cyclopropylpyridin-3-yl)amino)-5-fluoronicotinamide | 387 | 0.76 | |

TABLE 3-continued

| Example | Structure | Compound name | MS (ESI m/z): (M + H) | RT (min) | HNMR |
|---|---|---|---|---|---|
| Example 2-112 | 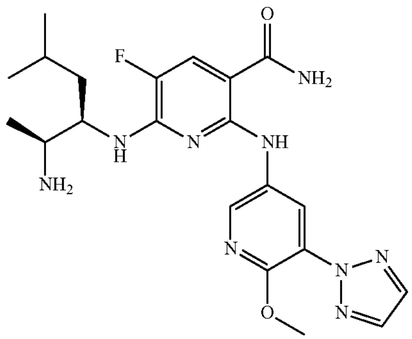 [SMILES: COc1ncc(Nc2nc(N[C@H](CC(C)C)[C@H](C)N)c(F)cc2C(N)=O)cc1-n1nccn1] | 6-(((2S,3R)-2-amino-5-methylhexan-3-yl)amino)-5-fluoro-2-((6-methoxy-5-(2H-1,2,3-triazol-3-yl)pyridin-3-yl)amino)nicotinamide | 458 | 1.02 | 1H-NMR (DMSO-d6) δ: 11.56 (1H, s), 8.53 (1H, d, J = 2.7 Hz), 8.27 (1H, d, J = 2.7 Hz), 8.12 (2H, s), 7.93 (1H, d, J = 12.3 Hz), 7.85-7.55 (4H, m), 7.45-7.15 (1H, m), 7.03 (1H, d, J = 8.7 Hz), 4.34-4.20 (1H, m), 3.89 (3H, s), 3.40-3.20 (1H, m), 1.64-1.44 (2H, m), 1.34-1.12 (1H, m), 1.02 (3H, d, J = 7.2 H), 0.84 (3H, d, J = 6.0 Hz), 0.63 (3H, d, J = 5.7 Hz) |
| Example 2-113 | 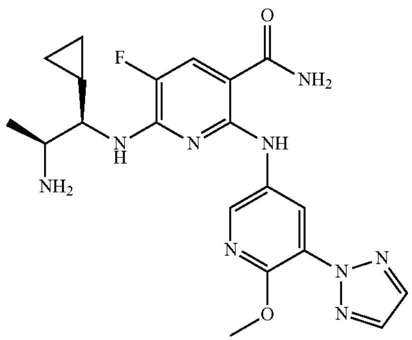 [SMILES: COc1ncc(Nc2nc(N[C@H](C3CC3)[C@H](C)N)c(F)cc2C(N)=O)cc1-n1nccn1] | 6-(((1R,2S)-2-amino-1-cyclopropylpropyl)amino)-5-fluoro-2-((6-methoxy-5-(2H-1,2,3-triazol-3-yl)pyridin-3-yl)amino)nicotinamide | 442 | 0.89 | 1H-NMR (DMSO-d6) δ: 11.51 (1H, s), 8.39 (1H, d, J = 2.7 Hz), 8.26 (1H, d, J = 2.7 Hz), 8.12 (2H, s), 8.05-7.70 (5H, m), 7.40-7.17 (1H, m), 7.17 (1H, d, J = 8.7 Hz), 3.89 (3H, s), 3.68-3.54 (1H, m), 3.50-3.30 (1H, m), 1.14 (3H, d, J = 6.6 Hz), 1.08-0.94 (1H, m), 0.54-0.42 (1H, m), 0.42-0.30 (1H, m), 0.26-0.10 (2H, m) |
| Example 2-114 | 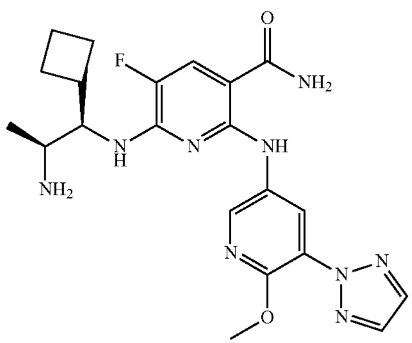 [SMILES: COc1ncc(Nc2nc(N[C@H](C3CCC3)[C@H](C)N)c(F)cc2C(N)=O)cc1-n1nccn1] | 6-(((1R,2S)-2-amino-1-cyclobutylpropyl)amino)-5-fluoro-2-((6-methoxy-5-(2H-1,2,3-triazol-3-yl)pyridin-3-yl)amino)nicotinamide | 456 | 0.98 | 1H-NMR (DMSO-d6) δ: 11.56 (1H, s), 8.58 (1H, d, J = 2.3 Hz), 8.27 (1H, d, J = 2.3 Hz), 8.14 (2H, s), 7.92 (1H, d, J = 12.6 Hz), 7.85-7.55 (4H, m), 7.50-7.10 (1H, m), 6.91 (1H, d, J = 8.7 Hz), 4.40-4.28 (1H, m), 3.90 (3H, s), 3.40-3.26 (1H, m), 2.62-2.50 (1H, m), 1.95-1.80 (2H, m), 1.80-1.52 (4H, m), 1.06 (3H, d, J = 7.5 Hz) |

TABLE 3-continued

| Example | Structure | Compound name | MS (ESI m/z): (M + H) | RT (min) | HNMR |
|---|---|---|---|---|---|
| Example 2-115 | 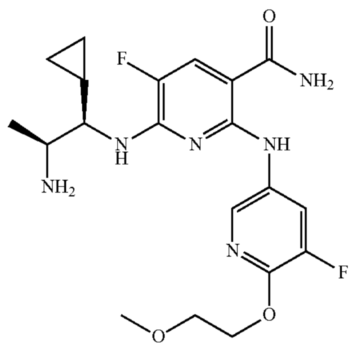 [SMILES: COCCOc1ncc(Nc2nc(N[C@H](C3CC3)[C@H](C)N)c(F)cc2C(N)=O)cc1F] | 6-(((1R,2S)-2-amino-1-cyclopropylpropyl)amino)-5-fluoro-2-((5-fluoro-6-(2-methoxyethoxy)pyridin-3-yl)amino)nicotinamide | 437 | 0.95 | |
| Example 2-116 | 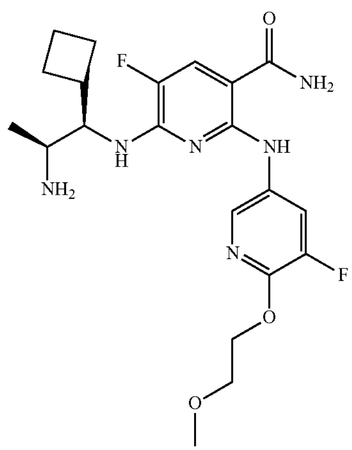 [SMILES: COCCOc1ncc(Nc2nc(N[C@H](C3CCC3)[C@H](C)N)c(F)cc2C(N)=O)cc1F] | 6-(((1R,2S)-2-amino-1-cyclobutylpropyl)amino)-5-fluoro-2-((5-fluoro-6-(2-methoxyethoxy)pyridin-3-yl)amino)nicotinamide | 451 | 1.03 | 1H-NMR (DMSO-d6) δ: 11.44 (1H, s), 8.18 (1H, dd, J = 2.3, 12.6 Hz), 7.98 (1H, d, J = 2.3 Hz), 7.91 (1H, d, J = 12.6 Hz), 7.88-7.66 (4H, m), 7.40-7.12 (1H, m), 6.90 (1H, d, J = 8.7 Hz), 4.46-4.39 (2H, m), 4.37-4.25 (1H, m), 3.72-3.65 (2H, m), 3.40-3.26 (4H, m), 2.75-2.55 (1H, m), 2.15-1.62 (6H, m), 1.16 (3H, d, J = 6.6 Hz) |

TABLE 3-continued

| Example | Structure | Compound name | MS (ESI m/z): (M + H) | RT (min) | HNMR |
|---|---|---|---|---|---|
| Example 2-117 | 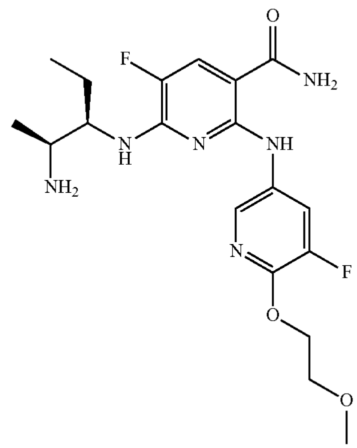 [SMILES: CC[C@@H](Nc1nc(Nc2cnc(OCCOC)c(F)c2)c(C(N)=O)cc1F)[C@H](C)N] | 6-(((2S,3R)-2-aminopentan-3-yl)amino)-5-fluoro-2-((5-fluoro-6-(2-methoxyethoxy)pyridin-3-yl)amino)nicotinamide | 425 | 0.94 | |
| Example 2-118 | 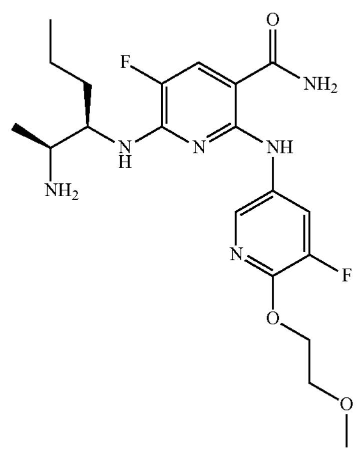 [SMILES: CCC[C@@H](Nc1nc(Nc2cnc(OCCOC)c(F)c2)c(C(N)=O)cc1F)[C@H](C)N] | 6-(((2S,3R)-2-aminohexan-3-yl)amino)-5-fluoro-2-((5-fluoro-6-(2-methoxyethoxy)pyridin-3-yl)amino)nicotinamide | 439 | 1.02 | |

TABLE 3-continued

| Example | Structure | Compound name | MS (ESI m/z): (M + H) | RT (min) | HNMR |
|---|---|---|---|---|---|
| Example 2-119 | 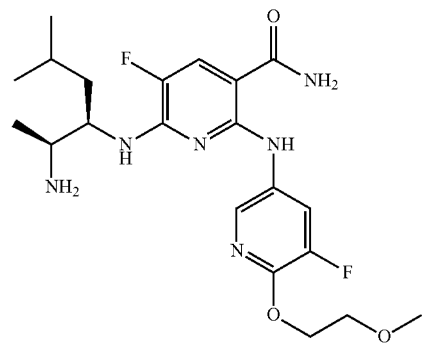 [SMILES: COCCOc1ncc(Nc2nc(N[C@H](CC(C)C)[C@H](C)N)c(F)cc2C(N)=O)cc1F] | 6-(((2S,3R)-2-amino-5-methylhexan-3-yl)amino)-5-fluoro-2-((5-fluoro-6-(2-methoxyethoxy)pyridin-3-yl)amino)nicotinamide | 453 | 1.08 | |
| Example 2-120 | 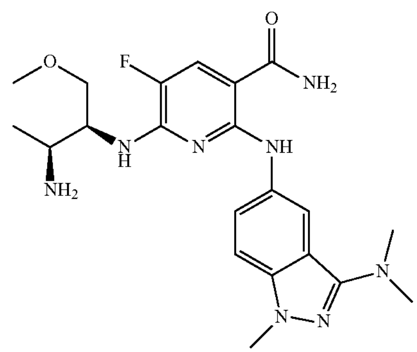 [SMILES: COC[C@@H](Nc1nc(Nc2ccc3c(c2)c(N(C)C)nn3C)c(C(N)=O)cc1F)[C@H](C)N] | 6-(((2S,3S)-3-amino-1-methoxybutan-2-yl)amino)-2-((3-(dimethylamino)-1-methyl-1H-indazol-5-yl)amino)-5-fluoronicotinamide | 445 | 0.81 | |
| Example 2-121 | 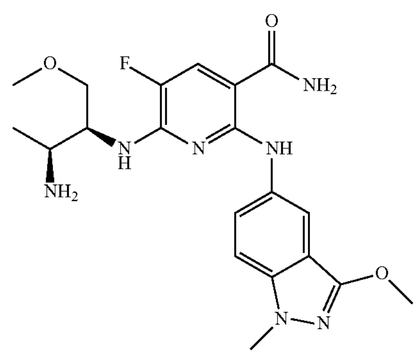 [SMILES: COC[C@@H](Nc1nc(Nc2ccc3c(c2)c(OC)nn3C)c(C(N)=O)cc1F)[C@H](C)N] | 6-(((2S,3S)-3-amino-1-methoxybutan-2-yl)amino)-5-fluoro-2-((3-methoxy-1-methyl-1H-indazol-5-yl)amino)nicotinamide | 432 | 0.84 | |

TABLE 3-continued

| Example | Structure | Compound name | MS (ESI m/z): (M + H) | RT (min) | HNMR |
|---|---|---|---|---|---|
| Example 2-122 | 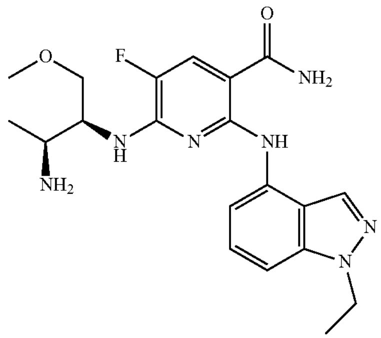 [SMILES: CCn1ncc2c(Nc3nc(N[C@H](COC)[C@H](C)N)c(F)cc3C(N)=O)cccc21] | 6-(((2S,3S)-3-amino-1-methoxybutan-2-yl)amino)-2-((1-ethyl-1H-indazol-4-yl)amino)-5-fluoronicotinamide | 416 | 0.87 | |
| Example 2-123 | 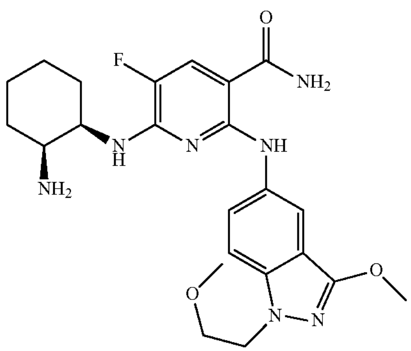 [SMILES: COCCn1nc(OC)c2cc(Nc3nc(N[C@@H]4CCCC[C@@H]4N)c(F)cc3C(N)=O)ccc21] | 6-(((1R,2S)-2-aminocyclohexyl)amino)-5-fluoro-2-((3-methoxy-1-(2-methoxyethyl)-1H-indazol-5-yl)amino)nicotinamide | 472 | 0.94 | 1H-NMR (MeOD) δ: 8.10 (1H, s), 7.74 (1H, d, J = 11.9 Hz), 7.36 (1H, d, J = 8.6 Hz), 7.23 (1H, d, J = 9.2 Hz), 4.61-4.57 (1H, m), 4.34 (2H, t, J = 5.3 Hz), 4.06 (3H, s), 3.76 (2H, t, J = 5.3 Hz), 3.58-3.54 (1H, m), 3.13 (3H, s), 1.52-1.37 (8H, m). |

TABLE 3-continued

| Example | Structure | Compound name | MS (ESI m/z): (M + H) | RT (min) | HNMR |
|---|---|---|---|---|---|
| Example 2-124 | 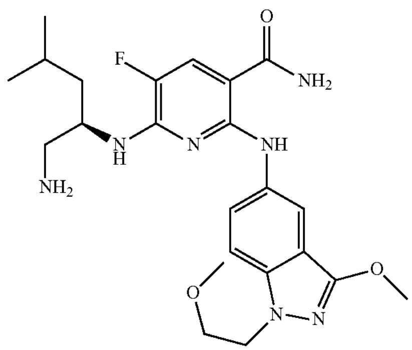 [SMILES: COCCn1nc(OC)c2cc(Nc3nc(N[C@@H](CN)CC(C)C)c(F)cc3C(N)=O)ccc21] | (R)-6-((1-amino-4-methylpentan-2-yl)amino)-5-fluoro-2-((3-methoxy-1-(2-methoxyethyl)-1H-indazol-5-yl)amino)nicotinamide | 474 | 1.02 | |
| Example 2-125 | 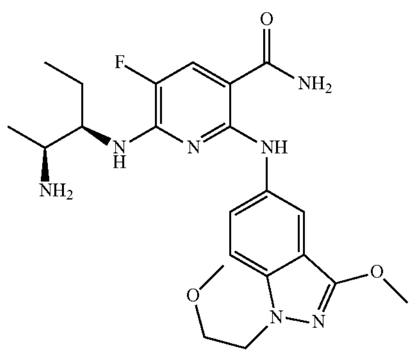 [SMILES: CC[C@@H](Nc1nc(Nc2ccc3c(c2)c(OC)nn3CCOC)c(C(N)=O)cc1F)[C@H](C)N] | 6-(((2S,3R)-2-aminopentan-3-yl)amino)-5-fluoro-2-((3-methoxy-1-(2-methoxyethyl)-1H-indazol-5-yl)amino)nicotinamide | 460 | 0.9 | |
| Example 2-126 | 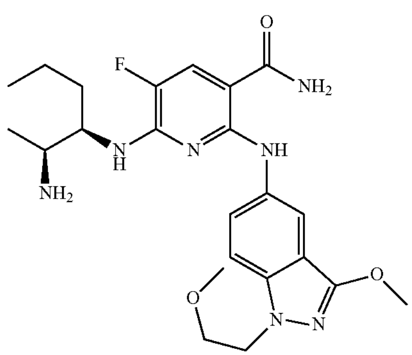 [SMILES: CCC[C@@H](Nc1nc(Nc2ccc3c(c2)c(OC)nn3CCOC)c(C(N)=O)cc1F)[C@H](C)N] | 6-(((2S,3R)-2-aminohexan-3-yl)amino)-5-fluoro-2-((3-methoxy-1-(2-methoxyethyl)-1H-indazol-5-yl)amino)nicotinamide | 474 | 0.98 | |

TABLE 3-continued

| Example | Structure | Compound name | MS (ESI m/z): (M + H) | RT (min) | HNMR |
|---|---|---|---|---|---|
| Example 2-127 | 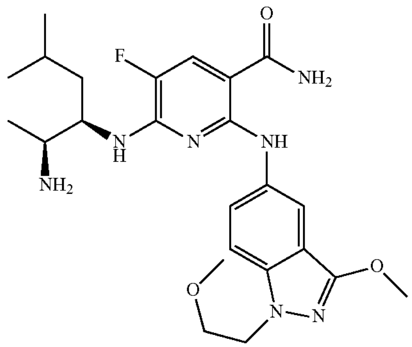 [SMILES: COCCn1nc(OC)c2cc(Nc3nc(N[C@H](CC(C)C)[C@H](C)N)c(F)cc3C(N)=O)ccc21] | 6-(((2S,3R)-2-amino-5-methylhexan-3-yl)amino)-5-fluoro-2-((3-methoxy-1-(2-methoxyethyl)-1H-indazol-5-yl)amino)nicotinamide | 488 | 1.11 | |
| Example 2-128 | 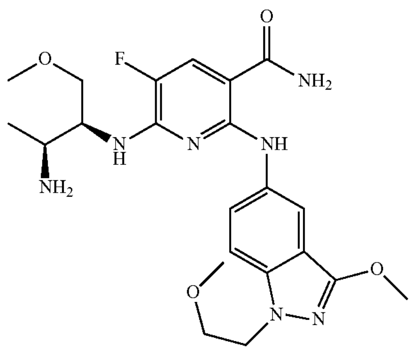 [SMILES: COCCn1nc(OC)c2cc(Nc3nc(N[C@H](COC)[C@H](C)N)c(F)cc3C(N)=O)ccc21] | 6-(((2S,3S)-3-amino-1-methoxybutan-2-yl)amino)-5-fluoro-2-((3-methoxy-1-(2-methoxyethyl)-1H-indazol-5-yl)amino)nicotinamide | 476 | 0.93 | |

TABLE 3-continued

| Example | Structure | Compound name | MS (ESI m/z): (M + H) | RT (min) | HNMR |
|---|---|---|---|---|---|
| Example 2-129 | 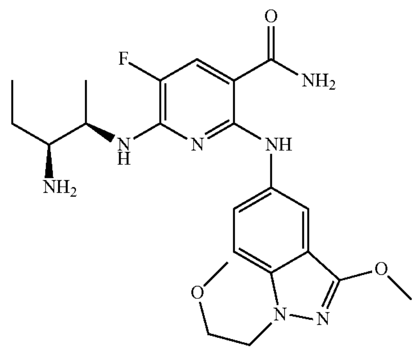 [SMILES: CC[C@H](N)[C@@H](C)Nc1nc(Nc2ccc3c(c2)c(OC)nn3CCOC)c(C(N)=O)cc1F] | 6-(((2R,3S)-3-aminopentan-2-yl)amino)-5-fluoro-2-((3-methoxy-1-(2-methoxyethyl)-1H-indazol-5-yl)amino)nicotinamide | 460 | 0.94 | |
| Example 2-130 | 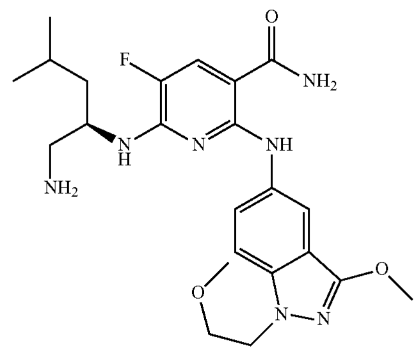 [SMILES: COCCn1nc(OC)c2cc(Nc3nc(N[C@@H](CN)CC(C)C)c(F)cc3C(N)=O)ccc21] | (R)-6-((1-amino-4-methylpentan-2-yl)amino)-5-fluoro-2-((1-(2-methoxyethyl)-3-methyl-1H-indazol-5-yl)amino)nicotinamide | 458 | 1.02 | |
| Example 2-131 | 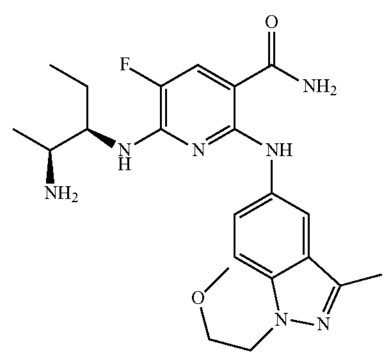 [SMILES: CC[C@@H](Nc1nc(Nc2ccc3c(c2)c(C)nn3CCOC)c(C(N)=O)cc1F)[C@H](C)N] | 6-(((2S,3R)-2-aminopentan-3-yl)amino)-5-fluoro-2-((1-(2-methoxyethyl)-3-methyl-1H-indazol-5-yl)amino)nicotinamide | 444 | 0.9 | |

TABLE 3-continued

| Example | Structure | Compound name | MS (ESI m/z): (M + H) | RT (min) | HNMR |
|---|---|---|---|---|---|
| Example 2-132 | 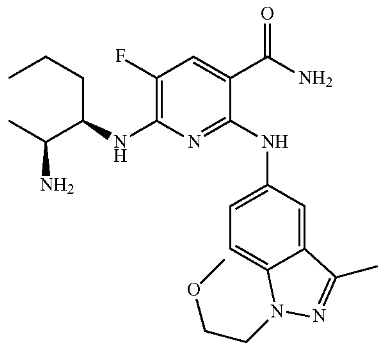 [SMILES: CCC[C@@H](Nc1nc(Nc2ccc3c(c2)c(C)nn3CCOC)c(C(N)=O)cc1F)[C@H](C)N] | 6-(((2S,3R)-2-aminohexan-3-yl)amino)-5-fluoro-2-((1-(2-methoxyethyl)-3-methyl-1H-indazol-5-yl)amino)nicotinamide | 458 | 0.99 | |
| Example 2-133 | 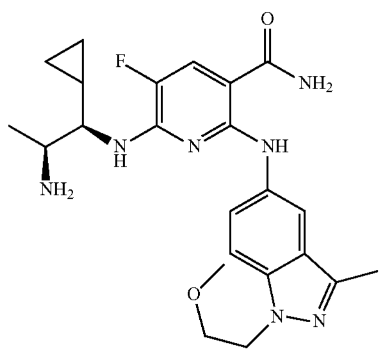 [SMILES: COCCn1nc(C)c2cc(Nc3nc(N[C@H](C4CC4)[C@H](C)N)c(F)cc3C(N)=O)ccc21] | 6-(((1R,2S)-2-amino-1-cyclopropylpropyl)amino)-5-fluoro-2-((1-(2-methoxyethyl)-3-methyl-1H-indazol-5-yl)amino)nicotinamide | 456 | 0.94 | |

TABLE 3-continued

| Example | Compound name | MS (ESI m/z): (M + H) | RT (min) | HNMR |
|---|---|---|---|---|
| Example 2-134 | 6-(((2S,3R)-2-amino-5-methylhexan-3-yl)amino)-5-fluoro-2-((1-(2-methoxyethyl)-3-methyl-1H-indazol-5-yl)amino)nicotinamide | 472 | 1.05 | |
| Example 2-135 | 6-(((2S,3S)-3-amino-1-methoxybutan-2-yl)amino)-5-fluoro-2-((1-(2-methoxyethyl)-3-methyl-1H-indazol-5-yl)amino)nicotinamide | 460 | 0.88 | 1H-NMR (MeOD) δ: 7.86 (1H, s), 7.77(1H, d, J = 11.9 Hz), 7.52 (1H, br s), 7.52 (1H, br s), 4.52 (2H, t, J = 5.3 Hz), 4.44-4.38 (1H, m), 3.73 (2H, t, J = 5.3 Hz), 3.78-3.74 (1H, m), 3.65-3.55 (2H, m), 3.40 (3H, s), 3.28 (3H, s), 2.58 (3H, s), 1.21 (3H, d, J = 6.6 Hz). |
| Example 2-136 | 6-(((2R,3S)-3-aminopentan-2-yl)amino)-5-fluoro-2-((1-(2-methoxyethyl)-3-methyl-1H-indazol-5-yl)amino)nicotinamide | 444 | 0.88 | |

TABLE 3-continued

| Example | Structure | Compound name | MS (ESI m/z): (M + H) | RT (min) | HNMR |
|---|---|---|---|---|---|
| Example 2-137 | 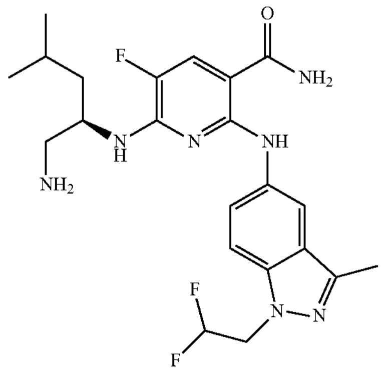 [SMILES: Cc1nn(CC(F)F)c2ccc(Nc3nc(N[C@@H](CN)CC(C)C)c(F)cc3C(N)=O)cc12] | (R)-6-((1-amino-4-methylpentan-2-yl)amino)-2-((1-(2,2-difluoroethyl)-3-methyl-1H-indazol-5-yl)amino)-5-fluoronicotinamide | 464 | 1.03 | |
| Example 2-138 | 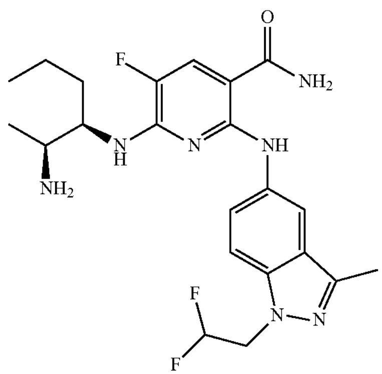 [SMILES: CCC[C@@H](Nc1nc(Nc2ccc3c(c2)c(C)nn3CC(F)F)c(C(N)=O)cc1F)[C@H](C)N] | 6-(((2S,3R)-2-aminohexan-3-yl)amino)-2-((1-(2,2-difluoroethyl)-3-methyl-1H-indazol-5-yl)amino)-5-fluoronicotinamide | 464 | 1.02 | |

TABLE 3-continued

| Example | Structure | Compound name | MS (ESI m/z): (M + H) | RT (min) | HNMR |
|---|---|---|---|---|---|
| Example 2-139 | 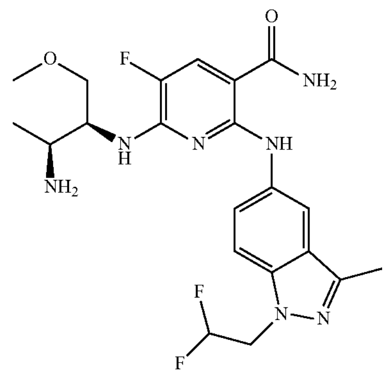 | 6-(((2S,3S)-3-amino-1-methoxybutan-2-yl)amino)-2-((1-(2,2-difluoroethyl)-3-methyl-1H-indazol-5-yl)amino)-5-fluoronicotinamide | 466 | 0.92 | |
| Example 2-140 | 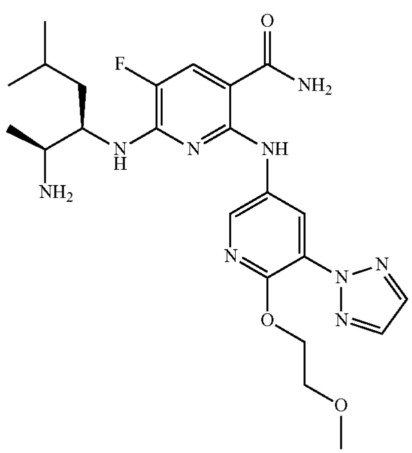 [SMILES: COCCOc1ncc(Nc2nc(N[C@H](CC(C)C)[C@H](C)N)c(F)cc2C(N)=O)cc1-n1nccn1] | 6-(((2S,3R)-2-amino-5-methylhexan-3-yl)amino)-5-fluoro-2-((6-(2-methoxyethoxy)-5-(2H-1,2,3-triazol-2-yl)pyridin-3-yl)amino)nicotinamide | 502 | 1.07 | |

TABLE 3-continued

| Example | Structure | Compound name | MS (ESI m/z): (M + H) | RT (min) | HNMR |
|---|---|---|---|---|---|
| Example 2-141 | 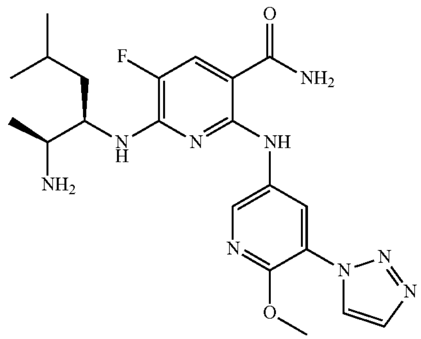 [SMILES: COc1ncc(Nc2nc(N[C@H](CC(C)C)[C@H](C)N)c(F)cc2C(N)=O)cc1-n1ccnn1] | 6-(((2S,3R)-2-amino-5-methylhexan-3-yl)amino)-5-fluoro-2-((6-methoxy-5-(1H-1,2,3-triazol-1-yl)pyridin-3-yl)amino)nicotinamide | 458 | 1.05 | |
| Example 2-142 | 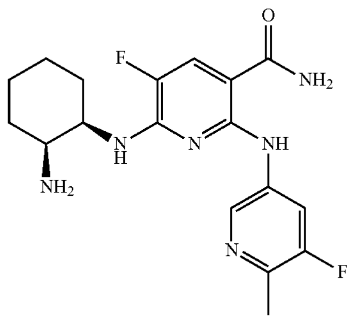 [SMILES: Cc1ncc(Nc2nc(N[C@@H]3CCCC[C@@H]3N)c(F)cc2C(N)=O)cc1F] | 6-(((1R,2S)-2-aminocyclohexyl)amino)-5-fluoro-2-((5-fluoro-6-methylpyridin-3-yl)amino)nicotinamide | 377 | 0.89 | 1H-NMR (DMSO-d6) δ: 11.84 (1H, s), 8.40-8.34 (1H, m), 8.20-8.11 (1H, m), 8.00-7.75 (5H, m), 7.46-7.28 (1H, m), 7.01 (1H, d, J = 7.2 Hz), 4.30-4.16 (1H, m), 3.50-3.40 (1H, m), 2.39 (3H, d, J = 2.7 Hz), 2.00-1.80 (2H, m), 1.79-1.54 (4H, m), 1.54-1.34 (2H, m) |
| Example 2-143 | 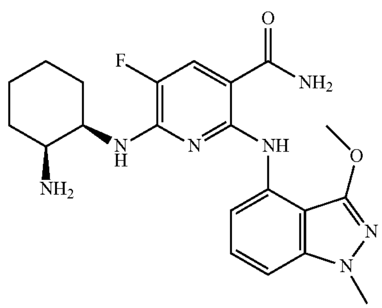 [SMILES: COc1nn(C)c2cccc(Nc3nc(N[C@@H]4CCCC[C@@H]4N)c(F)cc3C(N)=O)c12] | 6-(((1R,2S)-2-aminocyclohexyl)amino)-5-fluoro-2-((3-methoxy-1-methyl-1H-indazol-4-yl)amino)nicotinamide | 427 | 1.06 | |

TABLE 3-continued

| Example | Structure | Compound name | MS (ESI m/z): (M + H) | RT (min) | HNMR |
|---|---|---|---|---|---|
| Example 2-144 | 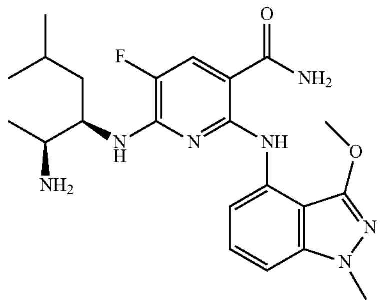 [SMILES: COc1nn(C)c2cccc(Nc3nc(N[C@H](CC(C)C)[C@H](C)N)c(F)cc3C(N)=O)c12] | 6-(((2S,3R)-2-amino-5-methylhexan-3-yl)amino)-5-fluoro-2-((3-methoxy-1-methyl-1H-indazol-4-yl)amino)nicotinamide | 444 | 1.36 | |
| Example 2-145 | 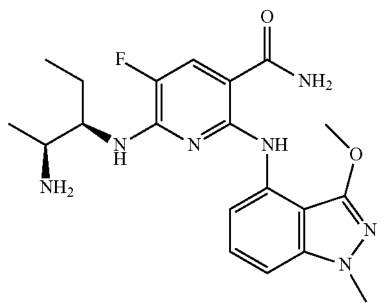 [SMILES: CC[C@@H](Nc1nc(Nc2cccc3c2c(OC)nn3C)c(C(N)=O)cc1F)[C@H](C)N] | 6-(((2S,3R)-2-aminopentan-3-yl)amino)-5-fluoro-2-((3-methoxy-1-methyl-1H-indazol-4-yl)amino)nicotinamide | 415 | 1.07 | |
| Example 2-146 | 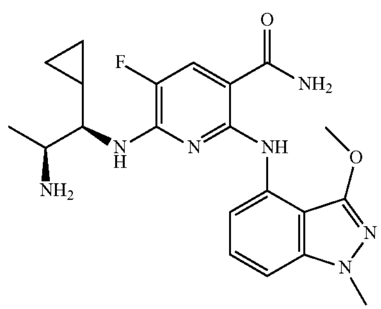 [SMILES: COc1nn(C)c2cccc(Nc3nc(N[C@H](C4CC4)[C@H](C)N)c(F)cc3C(N)=O)c12] | 6-(((1R,2S)-2-amino-1-cyclopropylpropyl)amino)-5-fluoro-2-((3-methoxy-1-methyl-1H-indazol-4-yl)amino)nicotinamide | 428 | 1.03 | |

TABLE 3-continued

| Example | Structure | Compound name | MS (ESI m/z): (M + H) | RT (min) | HNMR |
|---|---|---|---|---|---|
| Example 2-147 | 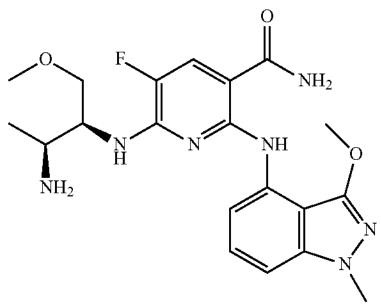 [SMILES: COC[C@@H](Nc1nc(Nc2cccc3c2c(OC)nn3C)c(C(N)=O)cc1F)[C@H](C)N] | 6-(((2S,3S)-3-amino-1-methoxybutan-2-yl)amino)-5-fluoro-2-((3-methoxy-1-methyl-1H-indazol-4-yl)amino)nicotinamide | 432 | 0.95 | |
| Example 2-148 | 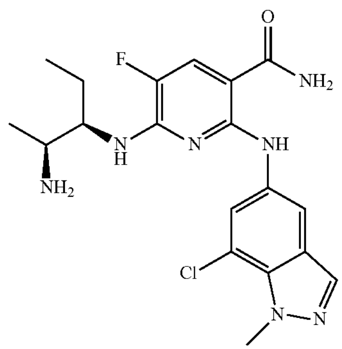 [SMILES: CC[C@@H](Nc1nc(Nc2cc(Cl)c3c(cnn3C)c2)c(C(N)=O)cc1F)[C@H](C)N] | 6-(((2S,3R)-2-aminopentan-3-yl)amino)-2-((7-chloro-1-methyl-1H-indazol-5-yl)amino)-5-fluoronicotinamide | 420 | 1.01 | |
| Example 2-149 | 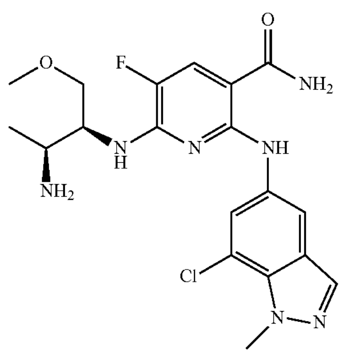 [SMILES: COC[C@@H](Nc1nc(Nc2cc(Cl)c3c(cnn3C)c2)c(C(N)=O)cc1F)[C@H](C)N] | 6-(((2S,3S)-3-amino-1-methoxybutan-2-yl)amino)-2-((7-chloro-1-methyl-1H-indazol-5-yl)amino)-5-fluoronicotinamide | 436 | 0.97 | |

TABLE 3-continued

| Example | Structure | Compound name | MS (ESI m/z): (M + H) | RT (min) | HNMR |
|---|---|---|---|---|---|
| Example 2-150 | 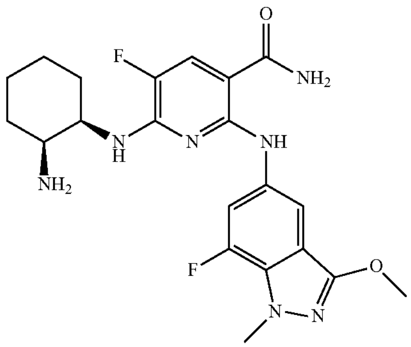 [SMILES: COc1nn(C)c2c(F)cc(Nc3nc(N[C@@H]4CCCC[C@@H]4N)c(F)cc3C(N)=O)cc12] | 6-(((1R,2S)-2-aminocyclohexyl)amino)-5-fluoro-2-((7-fluoro-3-methoxy-1-methyl-1H-indazol-5-yl)amino)nicotinamide | 446 | 1.06 | |
| Example 2-151 | 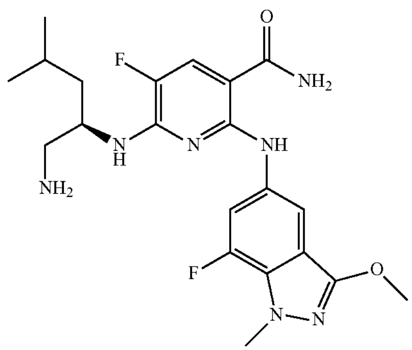 [SMILES: COc1nn(C)c2c(F)cc(Nc3nc(N[C@@H](CN)CC(C)C)c(F)cc3C(N)=O)cc12] | (R)-6-((1-amino-4-methylpentan-2-yl)amino)-5-fluoro-2-((7-fluoro-3-methoxy-1-methyl-1H-indazol-5-yl)amino)nicotinamide | 448 | 1.12 | |
| Example 2-152 | 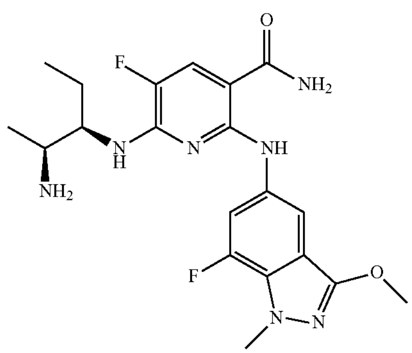 [SMILES: CC[C@@H](Nc1nc(Nc2cc(F)c3c(c2)c(OC)nn3C)c(C(N)=O)cc1F)[C@H](C)N] | 6-(((2S,3R)-2-aminopentan-3-yl)amino)-5-fluoro-2-((7-fluoro-3-methoxy-1-methyl-1H-indazol-5-yl)amino)nicotinamide | 434 | 1.04 | |

TABLE 3-continued

| Example | Structure | Compound name | MS (ESI m/z): (M + H) | RT (min) | HNMR |
|---|---|---|---|---|---|
| Example 2-153 | 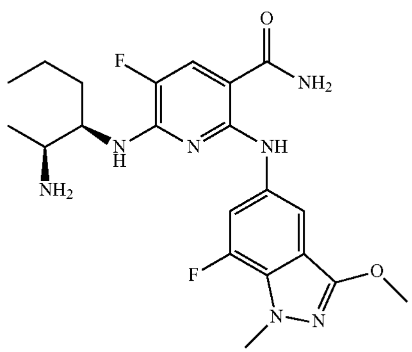 [SMILES: CCC[C@@H](Nc1nc(Nc2cc(F)c3c(c2)c(OC)nn3C)c(C(N)=O)cc1F)[C@H](C)N] | 6-(((2S,3R)-2-aminohexan-3-yl)amino)-5-fluoro-2-((7-fluoro-3-methoxy-1-methyl-1H-indazol-5-yl)amino)nicotinamide | 448 | 1.06 | |
| Example 2-154 | 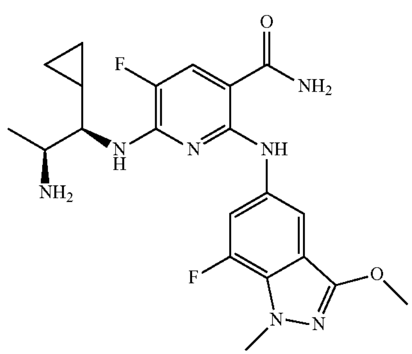 [SMILES: COc1nn(C)c2c(F)cc(Nc3nc(N[C@H](C4CC4)[C@H](C)N)c(F)cc3C(N)=O)cc12] | 6-(((1R,2S)-2-amino-1-cyclopropylpropyl)amino)-5-fluoro-2-((7-fluoro-3-methoxy-1-methyl-1H-indazol-5-yl)amino)nicotinamide | 446 | 1.07 | |

TABLE 3-continued

| Example | Structure | Compound name | MS (ESI m/z): (M + H) | RT (min) | HNMR |
|---|---|---|---|---|---|
| Example 2-155 | 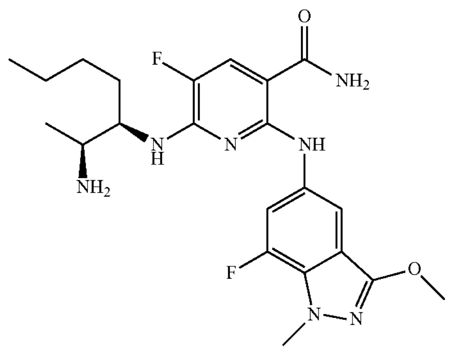 [SMILES: CCCC[C@@H](Nc1nc(Nc2cc(F)c3c(c2)c(OC)nn3C)c(C(N)=O)cc1F)[C@H](C)N] | 6-(((2S,3R)-2-aminoheptan-3-yl)amino)-5-fluoro-2-((7-fluoro-3-methoxy-1-methyl-1H-indazol-5-yl)amino)nicotinamide | 462 | 1.17 | |
| Example 2-156 | 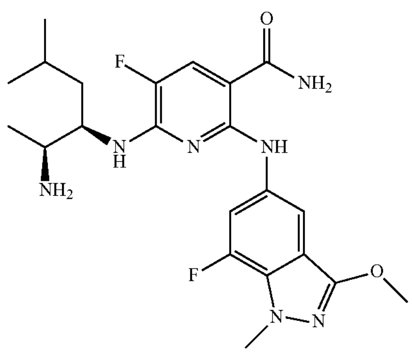 [SMILES: COc1nn(C)c2c(F)cc(Nc3nc(N[C@H](CC(C)C)[C@H](C)N)c(F)cc3C(N)=O)cc12] | 6-(((2S,3R)-2-amino-5-methylhexan-3-yl)amino)-5-fluoro-2-((7-fluoro-3-methoxy-1-methyl-1H-indazol-5-yl)amino)nicotinamide | 462 | 1.15 | |
| Example 2-157 | 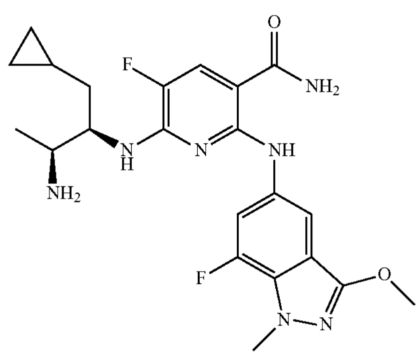 [SMILES: COc1nn(C)c2c(F)cc(Nc3nc(N[C@H](CC4CC4)[C@H](C)N)c(F)cc3C(N)=O)cc12] | 6-(((2R,3S)-3-amino-1-cyclopropylbutan-2-yl)amino)-5-fluoro-2-((7-fluoro-3-methoxy-1-methyl-1H-indazol-5-yl)amino)nicotinamide | 460 | 1.13 | |

TABLE 3-continued

| Example | Structure | Compound name | MS (ESI m/z): (M + H) | RT (min) | HNMR |
|---|---|---|---|---|---|
| Example 2-158 | 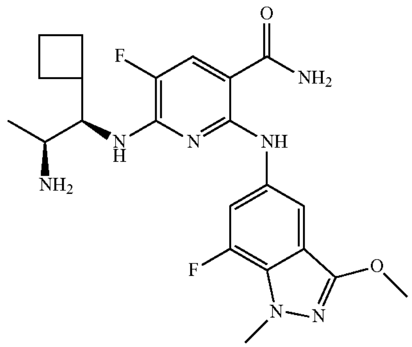 [SMILES: COc1nn(C)c2c(F)cc(Nc3nc(N[C@H](C4CCC4)[C@H](C)N)c(F)cc3C(N)=O)cc12] | 6-(((1R,2S)-2-amino-1-cyclobutylpropyl)amino)-5-fluoro-2-((7-fluoro-3-methoxy-1-methyl-1H-indazol-5-yl)amino)nicotinamide | 460 | 1.13 | |
| Example 2-159 | 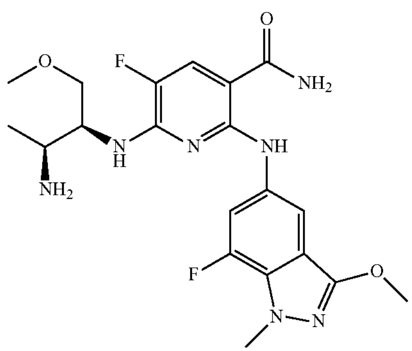 [SMILES: COC[C@@H](Nc1nc(Nc2cc(F)c3c(c2)c(OC)nn3C)c(C(N)=O)cc1F)[C@H](C)N] | 6-(((2S,3S)-3-amino-1-methoxybutan-2-yl)amino)-5-fluoro-2-((7-fluoro-3-methoxy-1-methyl-1H-indazol-5-yl)amino)nicotinamide | 450 | 1 | |

TABLE 3-continued
| Example | Structure | Compound name | MS (ESI m/z): (M + H) | RT (min) | HNMR |
|---|---|---|---|---|---|
| Example 2-160 | 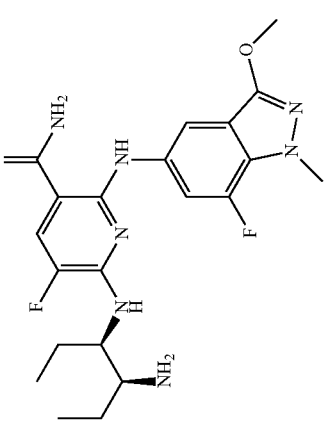 | 6-(((3R,4S)-4-aminohexan-3-yl)amino)-5-fluoro-2-((7-fluoro-3-methoxy-1-methyl-1H-indazol-5-yl)amino)nicotinamide | 448 | 1.04 | |
| Example 2-161 | 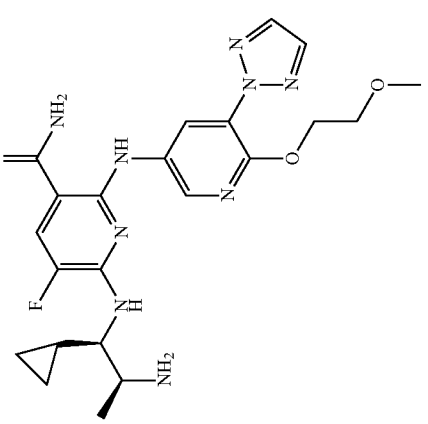 | 6-(((1R,2S)-2-amino-1-cyclopropylpropyl)amino)-5-fluoro-2-((6-(2-methoxyethoxy)-5-(2H-1,2,3-triazol-2-yl)pyridin-3-yl)amino)nicotinamide | 486 | 1 | |

TABLE 3-continued

| Example | Structure | Compound name | MS (ESI m/z): (M + H) | RT (min) | HNMR |
|---|---|---|---|---|---|
| Example 2-162 | 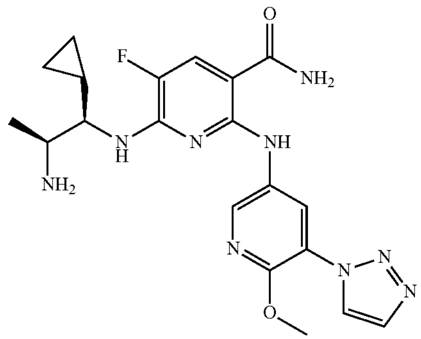 [SMILES: COc1ncc(Nc2nc(N[C@H](C3CC3)[C@H](C)N)c(F)cc2C(N)=O)cc1-n1ccnn1] | 6-(((1R,2S)-2-amino-1-cyclopropylpropyl)amino)-5-fluoro-2-(((6-methoxy-5-(1H-1,2,3-triazol-1-yl)pyridin-3-yl)amino)nicotinamide | 442 | 0.98 | 1H-NMR (DMSO-d6) δ: 11.63 (1H, s), 8.74 (1H, d, J = 2.4 Hz), 8.65-8.61 (1H, m), 8.22 (1H, d, J = 2.4 Hz), 8.00-7.97 (1H, m), 7.94 (1H, d, J = 12.3 Hz), 7.90-7.60 (4H, m), 7.40-7.20 (1H, m), 7.19 (1H, d, J = 8.7 Hz), 3.96 (3H, s), 3.80-3.66 (1H, m), 3.54-3.40 (1H, m), 1.15 (3H, d, J = 6.6 Hz), 1.10-0.96 (1H, m), 0.55-0.28 (3H, m), 0.20-0.10 (1H, m) |
| Example 2-163 | 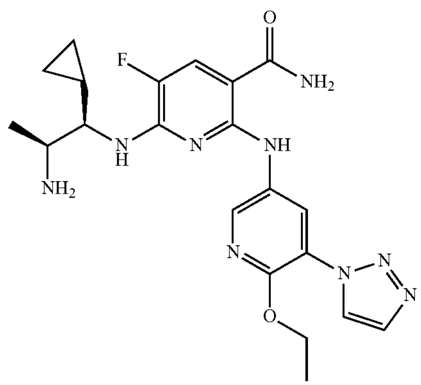 [SMILES: CCOc1ncc(Nc2nc(N[C@H](C3CC3)[C@H](C)N)c(F)cc2C(N)=O)cc1-n1ccnn1] | 6-(((1R,2S)-2-amino-1-cyclopropylpropyl)amino)-2-((6-ethoxy-5-(1H-1,2,3-triazol-1-yl)pyridin-3-yl)amino)-5-fluoronicotinamide | 456 | 1.07 | 1H-NMR (DMSO-d6) δ: 11.63 (1H, s), 8.75 (1H, d, J = 2.4 Hz), 8.66-8.62 (1H, m), 8.20 (1H, d, J = 2.4 Hz), 8.02-7.62 (6H, m), 7.40-7.12 (2H, m), 4.42 (2H, q, J = 6.9 Hz), 3.80-3.68 (1H, m), 3.56-3.40 (1H, m), 1.34 (3H, t, J = 6.9 Hz), 1.15 (3H, d, J = 6.6 Hz), 1.12-0.98 (1H, m), 0.54-0.30 (3H, m), 0.22-0.10 (1H, m) |

TABLE 3-continued

| Example | Structure | Compound name | MS (ESI m/z): (M + H) | RT (min) | HNMR |
|---|---|---|---|---|---|
| Example 2-164 | 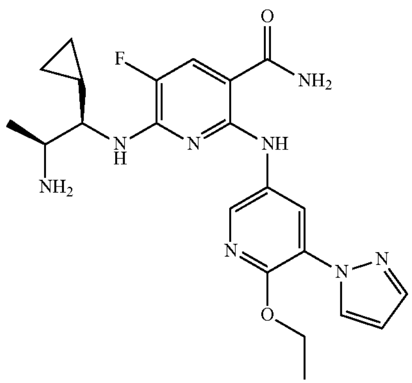 [SMILES: CCOc1ncc(Nc2nc(N[C@H](C3CC3)[C@H](C)N)c(F)cc2C(N)=O)cc1-n1cccn1] | 6-(((1R,2S)-2-amino-1-cyclopropylpropyl)amino)-2-((6-ethoxy-5-(1H-pyrazol-1-yl)pyridin-3-yl)amino)-5-fluoronicotinamide | 455 | 1.2 | |
| Example 2-165 | 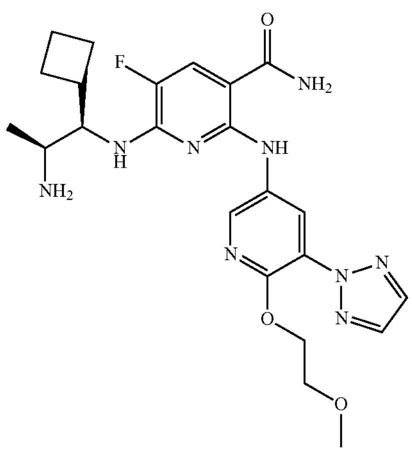 [SMILES: COCCOc1ncc(Nc2nc(N[C@H](C3CCC3)[C@H](C)N)c(F)cc2C(N)=O)cc1-n1nccn1] | 6-(((1R,2S)-2-amino-1-cyclobutylpropyl)amino)-5-fluoro-2-((6-(2-methoxyethoxy)-5-(2H-1,2,3-triazol-2-yl)pyridin-3-yl)amino)nicotinamide | 500 | 1.04 | |

TABLE 3-continued

| Example | Structure | Compound name | MS (ESI m/z): (M + H) | RT (min) | HNMR |
|---|---|---|---|---|---|
| Example 2-166 | 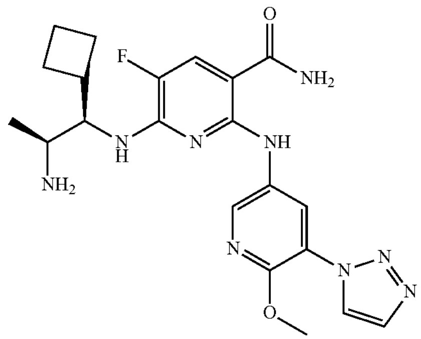 [SMILES: COc1ncc(Nc2nc(N[C@H](C3CCC3)[C@H](C)N)c(F)cc2C(N)=O)cc1-n1ccnn1] | 6-(((1R,2S)-2-amino-1-cyclobutylpropyl)amino)-5-fluoro-2-((6-methoxy-5-(1H-1,2,3-triazol-1-yl)pyridin-3-yl)amino)nicotinamide | 456 | 1.07 | |
| Example 2-167 | 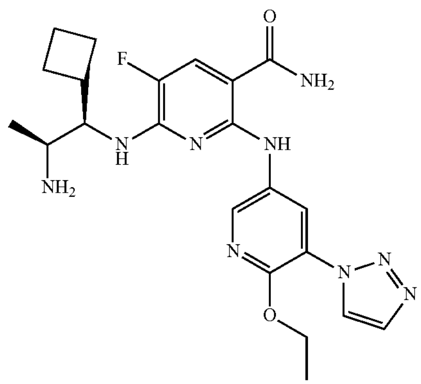 [SMILES: CCOc1ncc(Nc2nc(N[C@H](C3CCC3)[C@H](C)N)c(F)cc2C(N)=O)cc1-n1ccnn1] | 6-(((1R,2S)-2-amino-1-cyclobutylpropyl)amino)-2-((6-ethoxy-5-(1H-1,2,3-triazol-1-yl)pyridin-3-yl)amino)-5-fluoronicotinamide | 470 | 1.17 | 1H-NMR (DMSO-d6) δ: 11.66 (1H, s), 8.95 (1H, d, J = 2.7 Hz), 8.68-8.65 (1H, m), 8.22 (1H, d, J = 2.7 Hz), 8.01-7.98 (1H, m), 7.93 (1H, d, J = 12.3 Hz), 7.85-7.45 (4H, m), 7.45-7.15 (1H, m), 6.93 (1H, d, J = 8.4 Hz), 4.57-4.46 (1H, m), 4.43 (2H, q, J = 6.9 Hz), 3.46-3.25 (1H, m), 2.66-2.50 (1H, m), 1.95-1.52 (6H, m), 1.35 (3H, t, J = 6.9 Hz), 1.08 (3H, d, J = 6.6 Hz) |

TABLE 3-continued

| Example | Structure | Compound name | MS (ESI m/z): (M + H) | RT (min) | HNMR |
|---|---|---|---|---|---|
| Example 2-168 | 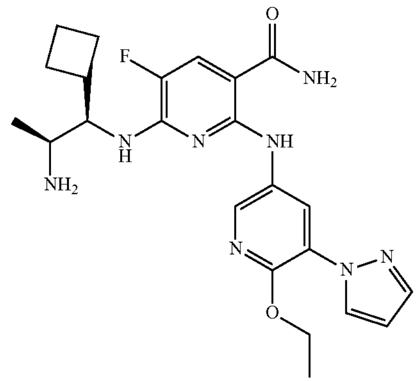 [SMILES: CCOc1ncc(Nc2nc(N[C@H](C3CCC3)[C@H](C)N)c(F)cc2C(N)=O)cc1-n1cccn1] | 6-(((1R,2S)-2-amino-1-cyclobutylpropyl)amino)-2-((6-ethoxy-5-(1H-pyrazol-1-yl)pyridin-3-yl)amino)-5-fluoronicotinamide | 469 | 1.32 | |
| Example 2-169 | 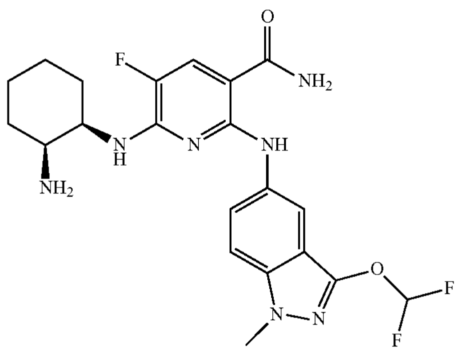 [SMILES: Cn1nc(OC(F)F)c2cc(Nc3nc(N[C@@H]4CCCC[C@@H]4N)c(F)cc3C(N)=O)ccc21] | 6-(((1R,2S)-2-aminocyclohexyl)amino)-2-((3-(difluoromethoxy)-1-methyl-1H-indazol-5-yl)amino)-5-fluoronicotinamide | 464 | 1.08 | 1H-NMR (MeOD) δ: 8.24 (1H, d, J = 1.3 Hz), 7.77 (1H, d, J = 11.9 Hz), 7.60-7.00 (1H, m), 7.44 (1H, d, J = 9.2 Hz), 7.31-7.29 (1H, m), 4.45-4.42 (1H, Hz), 3.93 (3H, s), 3.83-3.80 (1H, m), 1.87-1.67 (8H, m). |

TABLE 3-continued

| Example | Structure | Compound name | MS (ESI m/z): (M + H) | RT (min) | HNMR |
|---|---|---|---|---|---|
| Example 2-170 | 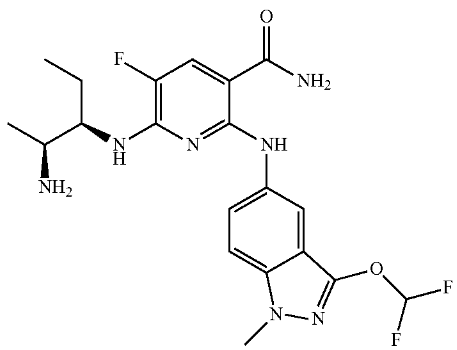 [SMILES: CC[C@@H](Nc1nc(Nc2ccc3c(c2)c(OC(F)F)nn3C)c(C(N)=O)cc1F)[C@H](C)N] | 6-(((2S,3R)-2-aminopentan-3-yl)amino)-2-((3-(difluoromethoxy)-1-methyl-1H-indazol-5-yl)amino)-5-fluoronicotinamide | 452 | 1.04 | |
| Example 2-171 | 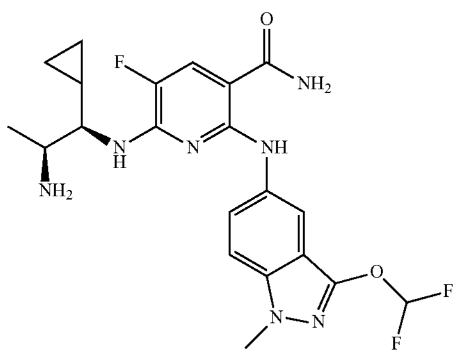 [SMILES: C[C@H](N)[C@H](Nc1nc(Nc2ccc3c(c2)c(OC(F)F)nn3C)c(C(N)=O)cc1F)C1CC1] | 6-(((1R,2S)-2-amino-1-cyclopropylpropyl)amino)-2-((3-(difluoromethoxy)-1-methyl-1H-indazol-5-yl)amino)-5-fluoronicotinamide | 464 | 1.06 | |
| Example 2-172 | 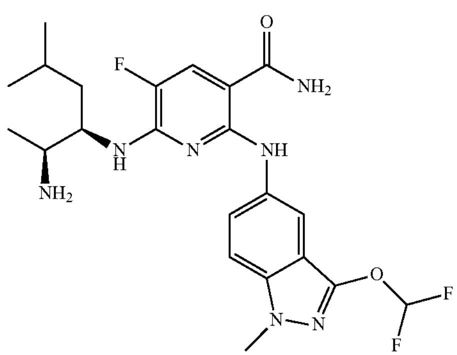 [SMILES: CC(C)C[C@@H](Nc1nc(Nc2ccc3c(c2)c(OC(F)F)nn3C)c(C(N)=O)cc1F)[C@H](C)N] | 6-(((2S,3R)-2-amino-5-methylhexan-3-yl)amino)-2-((3-(difluoromethoxy)-1-methyl-1H-indazol-5-yl)amino)-5-fluoronicotinamide | 480 | 1.19 | |

TABLE 3-continued

| Example | Structure | Compound name | MS (ESI m/z): (M + H) | RT (min) | HNMR |
|---|---|---|---|---|---|
| Example 2-173 | 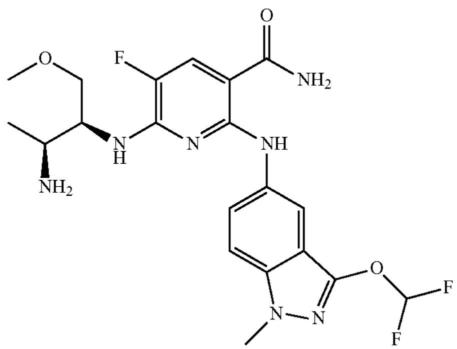 [SMILES: COC[C@@H](Nc1nc(Nc2ccc3c(c2)c(OC(F)F)nn3C)c(C(N)=O)cc1F)[C@H](C)N] | 6-(((2S,3S)-3-amino-1-methoxybutan-2-yl)amino)-2-((3-(difluoromethoxy)-1-methyl-1H-indazol-5-yl)amino)-5-fluoronicotinamide | 468 | 1 | |
| Example 2-174 | 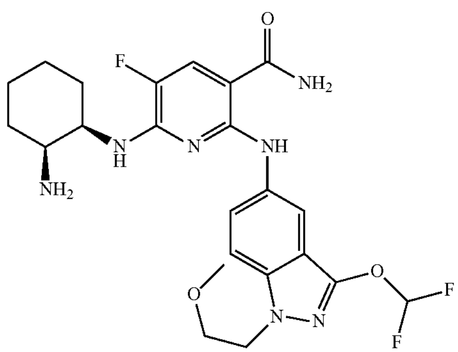 [SMILES: COCCn1nc(OC(F)F)c2cc(Nc3nc(N[C@@H]4CCCC[C@@H]4N)c(F)cc3C(N)=O)ccc21] | 6-(((1R,2S)-2-aminocyclohexyl)amino)-2-(3-(difluoromethoxy)-1-(2-methoxyethyl)-1H-indazol-5-yl)amino)-5-fluoronicotinamide | 508 | 1.14 | 1H-NMR (MeOD) δ: 8.21 (1H, d, J = 2.0 Hz), 7.77 (1H, d, J = 11.9 Hz), 7.48 (1H, d, J = 9.2 Hz), 7.36-7.25 (1H, m), 7.30-7.26 (1H, m), 4.45-4.42 (1H, m), 4.42 (2H, t, J = 5.3 Hz), 3.83-3.80 (1H, m), 3.78 (2H, t, J = 5.0 Hz), 3.28 (3H, s), 1.81-1.66 (8H, m). |

TABLE 3-continued

| Example | Structure | Compound name | MS (ESI m/z): (M + H) | RT (min) | HNMR |
|---|---|---|---|---|---|
| Example 2-175 | 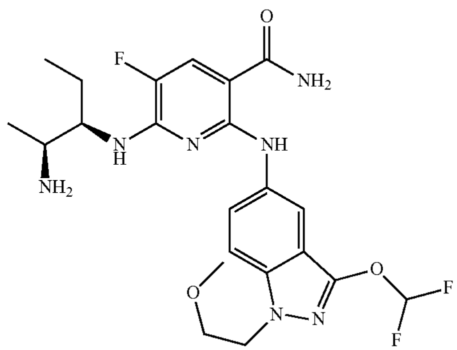 [SMILES: CC[C@@H](Nc1nc(Nc2ccc3c(c2)c(OC(F)F)nn3CCOC)c(C(N)=O)cc1F)[C@H](C)N] | 6-(((2S,3R)-2-aminopentan-3-yl)amino)-2-((3-(difluoromethoxy)-1-(2-methoxyethyl)-1H-indazol-5-yl)amino)-5-fluoronicotinamide | 496 | 1.11 | |
| Example 2-176 | 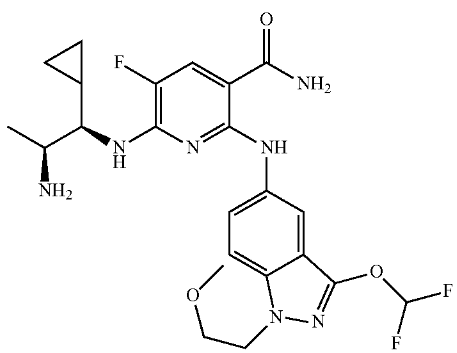 [SMILES: COCCn1nc(OC(F)F)c2cc(Nc3nc(N[C@H](C4CC4)[C@H](C)N)c(F)cc3C(N)=O)ccc21] | 6-(((1R,2S)-2-amino-1-cyclopropylpropyl)amino)-2-((3-(difluoromethoxy)-1-(2-methoxyethyl)-1H-indazol-5-yl)amino)-5-fluoronicotinamide | 508 | 1.12 | |
| Example 2-177 | 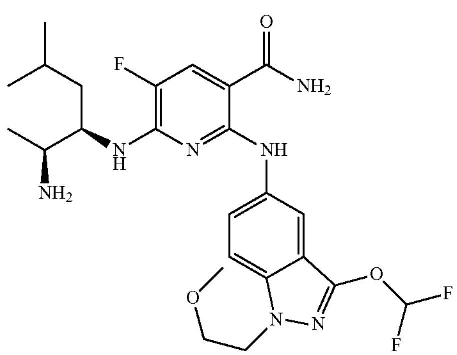 [SMILES: COCCn1nc(OC(F)F)c2cc(Nc3nc(N[C@H](CC(C)C)[C@H](C)N)c(F)cc3C(N)=O)ccc21] | 6-(((2S,3R)-2-amino-5-methylhexan-3-yl)amino)-2-((3-(difluoromethoxy)-1-(2-methoxyethyl)-1H-indazol-5-yl)amino)-5-fluoronicotinamide | 524 | 1.26 | |

TABLE 3-continued

| Example | Structure | Compound name | MS (ESI m/z): (M + H) | RT (min) | HNMR |
|---|---|---|---|---|---|
| Example 2-178 | 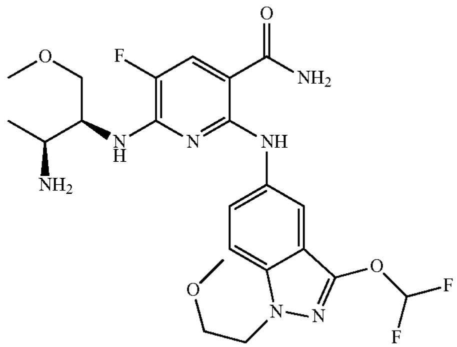 [SMILES: COCCn1nc(OC(F)F)c2cc(Nc3nc(N[C@H](COC)[C@H](C)N)c(F)cc3C(N)=O)ccc21] | 6-(((2S,3S)-3-amino-1-methoxybutan-2-yl)amino)-2-((3-(difluoromethoxy)-1-(2-methoxyethyl)-1H-indazol-5-yl)amino)-5-fluoronicotinamide | 512 | 1.07 | 1H-NMR (MeOD) δ: 7.97 (1H, d, J = 1.3 Hz), 7.77 (1H, d, J = 11.9 Hz), 7.48 (1H, d, J = 9.2 Hz), 7.36 (1H, dd, J = 9.2, 2.0 Hz), 7.13 (1H, d, J = 73.3 Hz), 4.45-4.39 (1H, m), 4.42 (2H, t, J = 5.0 Hz), 3.87 (1H, dd, J = 10.2, 3.6 Hz), 3.79 (2H, t, J = 5.0 Hz), 3.72-3.62 (2H, m), 3.42 (3H, s), 3.28 (3H, s), 1.32 (3H, d, J = 7.3 Hz). |
| Example 2-179 | 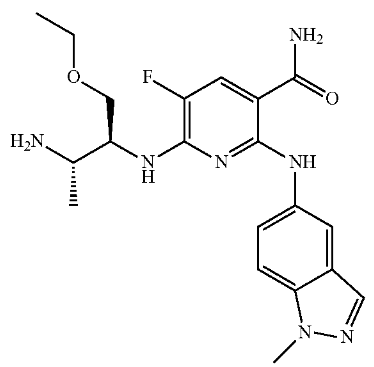 [SMILES: CCOC[C@@H](Nc1nc(Nc2ccc3c(cnn3C)c2)c(C(N)=O)cc1F)[C@H](C)N] | 6-(((2S,3S)-3-amino-1-ethoxybutan-2-yl)amino)-5-fluoro-2-((1-methyl-1H-indazol-5-yl)amino)nicotinamide | 416 | 0.93 | |

TABLE 3-continued

| Example | Structure | Compound name | MS (ESI m/z): (M + H) | RT (min) | HNMR |
|---|---|---|---|---|---|
| Example 2-180 | 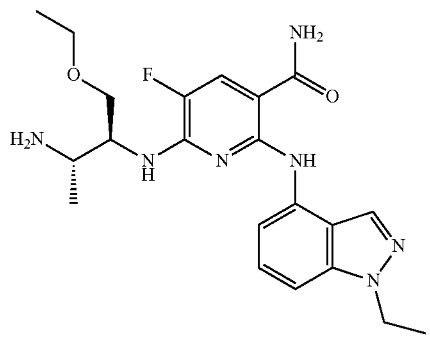 [SMILES: CCOC[C@@H](Nc1nc(Nc2cccc3c2cnn3CC)c(C(N)=O)cc1F)[C@H](C)N] | 6-(((2S,3S)-3-amino-1-ethoxybutan-2-yl)amino)-2-((1-ethyl-1H-indazol-4-yl)amino)-5-fluoronicotinamide | 430 | 1.04 | |
| Example 2-181 | 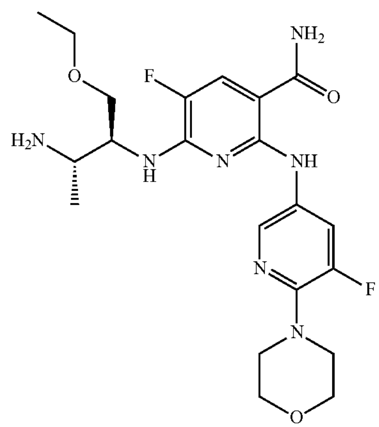 [SMILES: CCOC[C@@H](Nc1nc(Nc2cnc(N3CCOCC3)c(F)c2)c(C(N)=O)cc1F)[C@H](C)N] | 6-(((2S,3S)-3-amino-1-ethoxybutan-2-yl)amino)-5-fluoro-2-((5-fluoro-6-morpholinopyridin-3-yl)amino)nicotinamide | 466 | 0.99 | |

TABLE 3-continued

| Example | Structure | Compound name | MS (ESI m/z): (M + H) | RT (min) | HNMR |
|---|---|---|---|---|---|
| Example 2-182 | 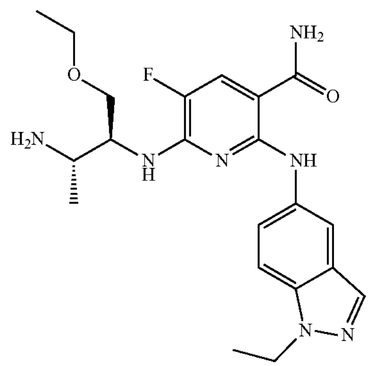 [SMILES: CCOC[C@@H](Nc1nc(Nc2ccc3c(cnn3CC)c2)c(C(N)=O)cc1F)[C@H](C)N] | 6-(((2S,3S)-3-amino-1-ethoxybutan-2-yl)amino)-2-((1-ethyl-1H-indazol-5-yl)amino)-5-fluoronicotinamide | 430 | 1 | |
| Example 2-183 | 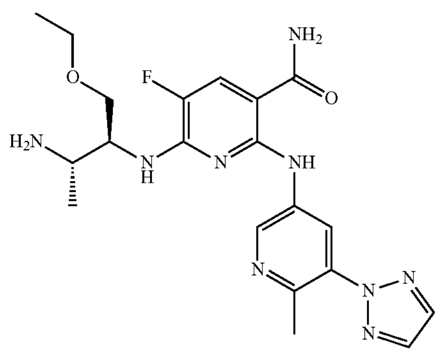 [SMILES: CCOC[C@@H](Nc1nc(Nc2cnc(C)c(-n3nccn3)c2)c(C(N)=O)cc1F)[C@H](C)N] | 6-(((2S,3S)-3-amino-1-ethoxybutan-2-yl)amino)-5-fluoro-2-((6-methyl-5-(2H-1,2,3-triazol-2-yl)pyridin-3-yl)amino)nicotinamide | 444 | 0.95 | |

TABLE 3-continued

| Example | Structure | Compound name | MS (ESI m/z): (M + H) | RT (min) | HNMR |
|---|---|---|---|---|---|
| Example 2-184 | 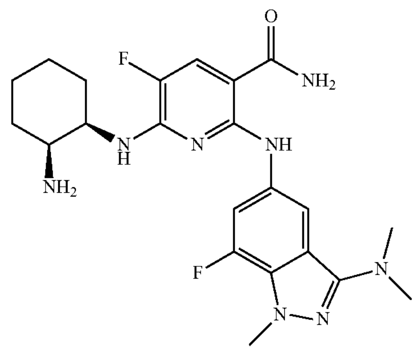 [SMILES: CN(C)c1nn(C)c2c(F)cc(Nc3nc(N[C@@H]4CCCC[C@@H]4N)c(F)cc3C(N)=O)cc12] | 6-(((1R,2S)-2-aminocyclohexyl)amino)-2-((3-(dimethylamino)-7-fluoro-1-methyl-1H-indazol-5-yl)amino)-5-fluoronicotinamide | 459 | 1.1 | 1H-NMR (MeOD) δ: 7.81 (2H, m), 7.60 (1H, br s), 4.31-4.28 (1H, m), 4.04 (3H, br s), 3.78-3.77 (1H, m), 3.06 (6H, br s), 2.00-1.55 (8H, m). |
| Example 2-185 | 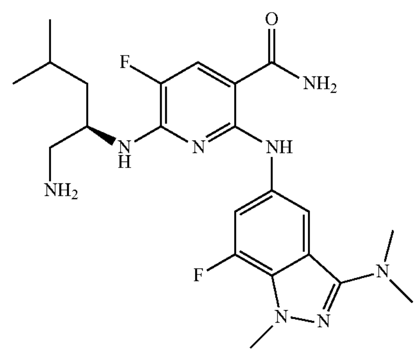 [SMILES: CC(C)C[C@H](CN)Nc1nc(Nc2cc(F)c3c(c2)c(N(C)C)nn3C)c(C(N)=O)cc1F] | (R)-6-((1-amino-4-methylpentan-2-yl)amino)-2-((3-(dimethylamino)-7-fluoro-1-methyl-1H-indazol-5-yl)amino)-5-fluoronicotinamide | 461 | 1.15 | |
| Example 2-186 | 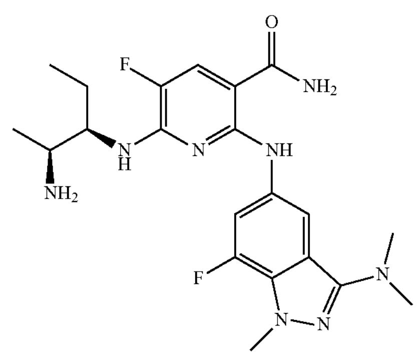 [SMILES: CC[C@@H](Nc1nc(Nc2cc(F)c3c(c2)c(N(C)C)nn3C)c(C(N)=O)cc1F)[C@H](C)N] | 6-(((2S,3R)-2-aminopentan-3-yl)amino)-2-((3-(dimethylamino)-7-fluoro-1-methyl-1H-indazol-5-yl)amino)-5-fluoronicotinamide | 447 | 1.05 | |

TABLE 3-continued

| Example | Structure | Compound name | MS (ESI m/z): (M + H) | RT (min) | HNMR |
|---|---|---|---|---|---|
| Example 2-187 | 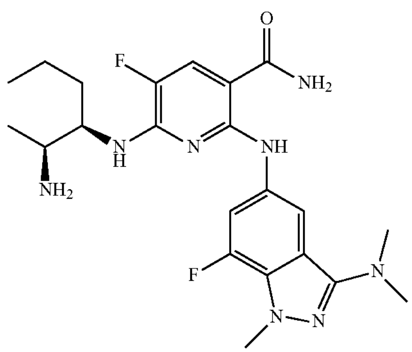 [SMILES: CCC[C@@H](Nc1nc(Nc2cc(F)c3c(c2)c(N(C)C)nn3C)c(C(N)=O)cc1F)[C@H](C)N] | 6-(((2S,3R)-2-aminohexan-3-yl)amino)-2-((3-(dimethylamino)-7-fluoro-1-methyl-1H-indazol-5-yl)amino)-5-fluoronicotinamide | 461 | 1.13 | |
| Example 2-188 | 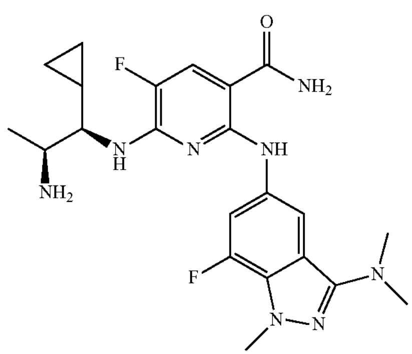 [SMILES: C[C@H](N)[C@H](Nc1nc(Nc2cc(F)c3c(c2)c(N(C)C)nn3C)c(C(N)=O)cc1F)C1CC1] | 6-(((1R,2S)-2-amino-1-cyclopropylpropyl)amino)-2-((3-(dimethylamino)-7-fluoro-1-methyl-1H-indazol-5-yl)amino)-5-fluoronicotinamide | 459 | 1.07 | 1H-NMR (MeOD) δ: 7.81-7.77 (2H, m), 7.47 (1H, br s), 4.21-4.10 (1H, m), 4.07 (3H, br s), 3.67-3.58 (1H, m), 3.40-3.34 (6H, m), 1.35 (3H, d, J = 8.6 Hz), 1.15-1.00 (1H, m), 0.81-0.72 (1H, m), 0.66-0.57 (1H, m), 0.50-0.35 (2H, m). |

TABLE 3-continued

| Example | Structure | Compound name | MS (ESI m/z): (M + H) | RT (min) | HNMR |
|---|---|---|---|---|---|
| Example 2-189 | 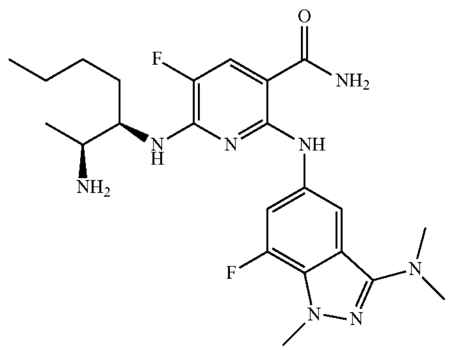 [SMILES: CCCC[C@@H](Nc1nc(Nc2cc(F)c3c(c2)c(N(C)C)nn3C)c(C(N)=O)cc1F)[C@H](C)N] | 6-(((2S,3R)-2-aminoheptan-3-yl)amino)-2-((3-(dimethylamino)-7-fluoro-1-methyl-1H-indazol-5-yl)amino)-5-fluoronicotinamide | 475 | 1.2 | |
| Example 2-190 | 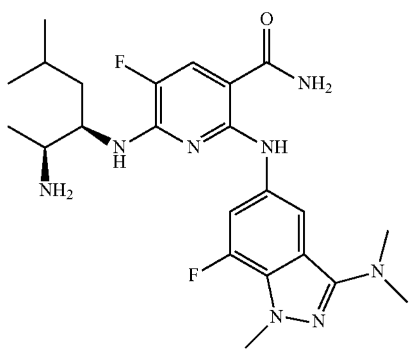 [SMILES: CC(C)C[C@@H](Nc1nc(Nc2cc(F)c3c(c2)c(N(C)C)nn3C)c(C(N)=O)cc1F)[C@H](C)N] | 6-(((2S,3R)-2-amino-5-methylhexan-3-yl)amino)-2-((3-(dimethylamino)-7-fluoro-1-methyl-1H-indazol-5-yl)amino)-5-fluoronicotinamide | 475 | 1.22 | |
| Example 2-191 | 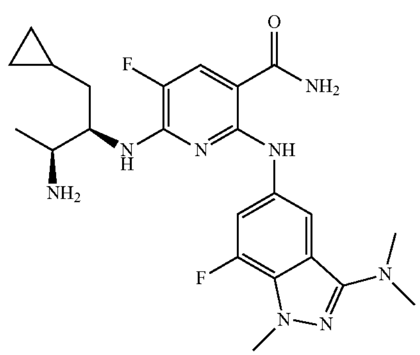 [SMILES: C[C@H](N)[C@@H](CC1CC1)Nc1nc(Nc2cc(F)c3c(c2)c(N(C)C)nn3C)c(C(N)=O)cc1F] | 6-(((2R,3S)-3-amino-1-cyclopropylbutan-2-yl)amino)-2-((3-(dimethylamino)-7-fluoro-1-methyl-1H-indazol-5-yl)amino)-5-fluoronicotinamide | 473 | 1.14 | |

TABLE 3-continued

| Example | Structure | Compound name | MS (ESI m/z): (M + H) | RT (min) | HNMR |
|---|---|---|---|---|---|
| Example 2-192 | 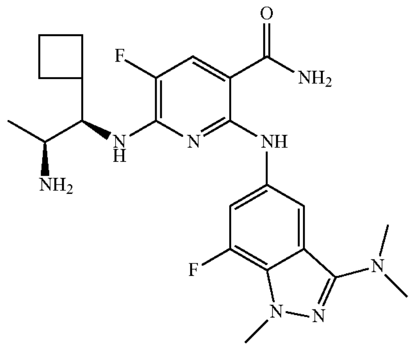 [SMILES: C[C@H](N)[C@H](Nc1nc(Nc2cc(F)c3c(c2)c(N(C)C)nn3C)c(C(N)=O)cc1F)C1CCC1] | 6-(((1R,2S)-2-amino-1-cyclobutylpropyl)amino)-2-((3-(dimethylamino)-7-fluoro-1-methyl-1H-indazol-5-yl)amino)-5-fluoronicotinamide | 471 | 1.16 | 1H-NMR (MeOD) δ: 7.76 (1H, d, J = 13.2 Hz), 7.69 (1H, d, J = 16.2 Hz), 7.52 (1H, s), 4.39-4.36 (1H, m), 4.03 (3H, s), 3.67-3.58 (1H, m), 3.21-3.11 (6H, m), 2.70-2.55 (1H, m), 1.96-1.85 (4H, m), 1.32 (3H, s), 1.20 (2H, d, J = 7.3 Hz). |
| Example 2-193 | 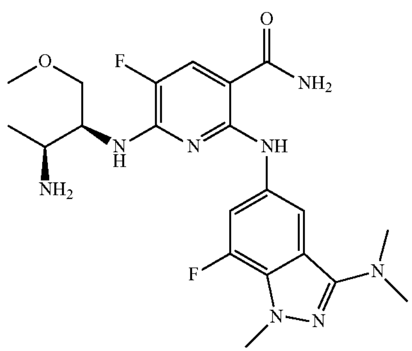 [SMILES: COC[C@@H](Nc1nc(Nc2cc(F)c3c(c2)c(N(C)C)nn3C)c(C(N)=O)cc1F)[C@H](C)N] | 6-(((2S,3S)-3-amino-1-methoxybutan-2-yl)amino)-2-((3-(dimethylamino)-7-fluoro-1-methyl-1H-indazol-5-yl)amino)-5-fluoronicotinamide | 463 | 1.02 | 1H-NMR (MeOD) δ: 7.77 (1H, d, J = 11.9 Hz), 7.54 (1H, d, J = 15.2 Hz), 7.49 (1H, d, J = 13.9 Hz), 4.37-4.32 (1H, m), 3.99 (3H, s), 3.67-3.59 (1H, m), 3.56-3.51 (2H, m), 3.41 (3H, s), 3.07 (6H, br s), 1.33 (3H, s). |

TABLE 3-continued

| Example | Structure | Compound name | MS (ESI m/z): (M + H) | RT (min) | HNMR |
|---|---|---|---|---|---|
| Example 2-194 | 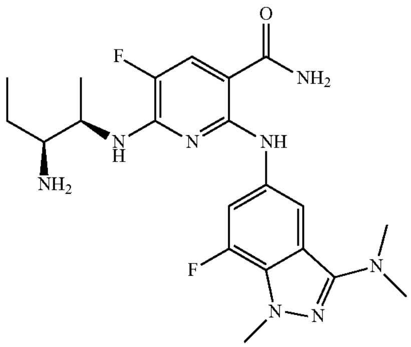 [SMILES: CC[C@H](N)[C@@H](C)Nc1nc(Nc2cc(F)c3c(c2)c(N(C)C)nn3C)c(C(N)=O)cc1F] | 6-(((2R,3S)-3-aminopentan-2-yl)amino)-2-((3-(dimethylamino)-7-fluoro-1-methyl-1H-indazol-5-yl)amino)-5-fluoronicotinamide | 447 | 1.05 | 1H-NMR (MeOD) δ: 7.76 (1H, d, J = 12.5 Hz), 7.74 (1H, d, J = 13.0 Hz), 7.52 (1H, s), 4.42-4.36 (1H, m), 4.04 (3H, s), 3.42-3.36 (1H, m), 3.26 (6H, s), 1.73-1.53 (2H, m), 1.30 (3H, d, J = 6.6 Hz), 0.81 (3H, t, J = 7.6 Hz). |
| Example 2-195 | 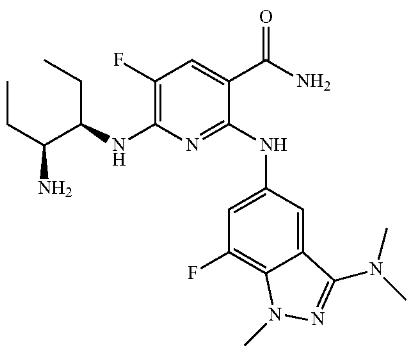 [SMILES: CC[C@H](N)[C@@H](CC)Nc1nc(Nc2cc(F)c3c(c2)c(N(C)C)nn3C)c(C(N)=O)cc1F] | 6-(((3R,4S)-4-aminohexan-3-yl)amino)-2-((3-(dimethylamino)-7-fluoro-1-methyl-1H-indazol-5-yl)amino)-5-fluoronicotinamide | 461 | 1.12 | |
| Example 2-196 | 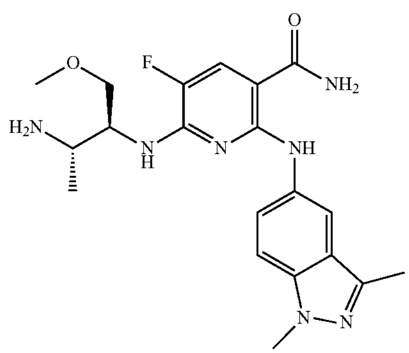 [SMILES: COC[C@@H](Nc1nc(Nc2ccc3c(c2)c(C)nn3C)c(C(N)=O)cc1F)[C@H](C)N] | 6-(((2S,3S)-3-amino-1-methoxybutan-2-yl)amino)-2-((1,3-dimethyl-1H-indazol-5-yl)amino)-5-fluoronicotinamide | 416 | 0.9 | |

TABLE 3-continued

| Example | Structure | Compound name | MS (ESI m/z): (M + H) | RT (min) | HNMR |
|---|---|---|---|---|---|
| Example 2-197 | 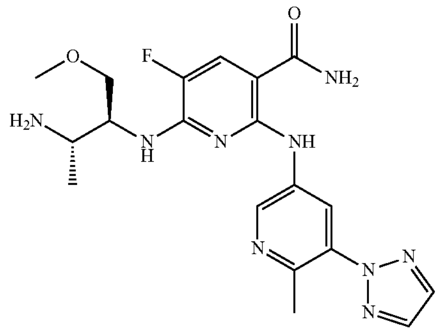 [SMILES: COC[C@@H](Nc1nc(Nc2cnc(C)c(-n3nccn3)c2)c(C(N)=O)cc1F)[C@H](C)N] | 6-(((2S,3S)-3-amino-1-methoxybutan-2-yl)amino)-5-fluoro-2-((6-methyl-5-(2H-1,2,3-triazol-2-yl)pyridin-3-yl)amino)nicotinamide | 430 | 0.88 | 1H-NMR (MeOD) δ: 9.41 (1H, d, J = 2.6 Hz), 8.98 (1H, s), 8.19 (2H, s), 7.91 (1H, d, J = 11.9 Hz), 3.85-3.62 (4H, m), 3.39 (3H, s), 2.94 (3H, s), 1.37 (3H, d, J = 6.6 Hz) |
| Example 2-198 | 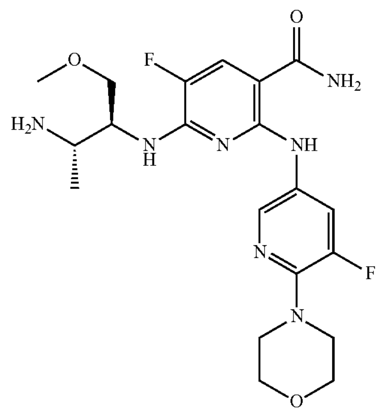 [SMILES: COC[C@@H](Nc1nc(Nc2cnc(N3CCOCC3)c(F)c2)c(C(N)=O)cc1F)[C@H](C)N] | 6-(((2S,3S)-3-amino-1-methoxybutan-2-yl)amino)-5-fluoro-2-((5-fluoro-6-morpholinopyridin-3-yl)amino)nicotinamide | 452 | 0.93 | |

TABLE 3-continued

| Example | Structure | Compound name | MS (ESI m/z): (M + H) | RT (min) | HNMR |
|---|---|---|---|---|---|
| Example 2-199 | 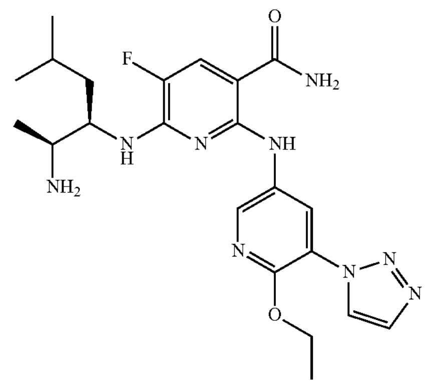 [SMILES: CCOc1ncc(Nc2nc(N[C@H](CC(C)C)[C@H](C)N)c(F)cc2C(N)=O)cc1-n1ccnn1] | 6-(((2S,3R)-2-amino-5-methylhexan-3-yl)amino)-2-((6-ethoxy-5-(1H-1,2,3-triazol-1-yl)pyridin-3-yl)amino)-5-fluoronicotinamide | 472 | 1.17 | |
| Example 2-200 | 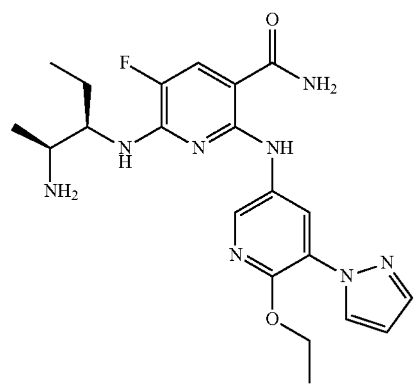 [SMILES: CCOc1ncc(Nc2nc(N[C@H](CC)[C@H](C)N)c(F)cc2C(N)=O)cc1-n1cccn1] | 6-(((2S,3R)-2-aminopentan-3-yl)amino)-2-((6-ethoxy-5-(1H-pyrazol-1-yl)pyridin-3-yl)amino)-5-fluoronicotinamide | 443 | 1.17 | |

TABLE 3-continued

| Example | Structure | Compound name | MS (ESI m/z): (M + H) | RT (min) | HNMR |
|---|---|---|---|---|---|
| Example 2-201 | 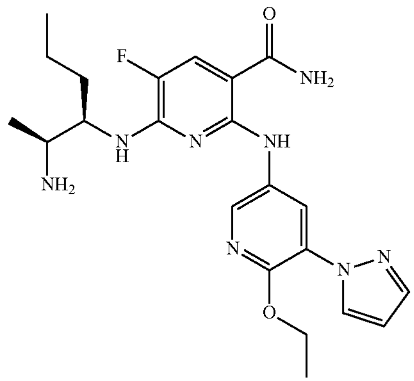 [SMILES: CCC[C@@H](Nc1nc(Nc2cnc(OCC)c(-n3cccn3)c2)c(C(N)=O)cc1F)[C@H](C)N] | 6-(((2S,3R)-2-aminohexan-3-yl)amino)-2-((6-ethoxy-5-(1H-pyrazol-1-yl)pyridin-3-yl)amino)-5-fluoronicotinamide | 457 | 1.25 | |
| Example 2-202 | 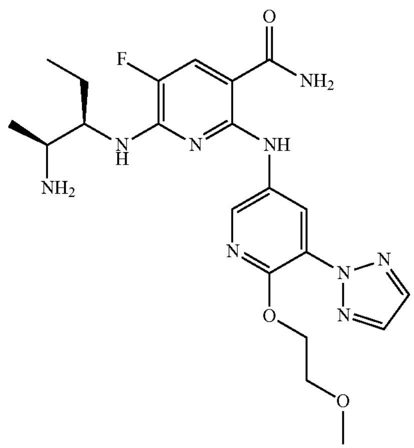 [SMILES: CC[C@@H](Nc1nc(Nc2cnc(OCCOC)c(-n3nccn3)c2)c(C(N)=O)cc1F)[C@H](C)N] | 6-(((2S,3R)-2-aminopentan-3-yl)amino)-5-fluoro-2-((6-(2-methoxyethoxy)-5-(2H-1,2,3-triazol-2-yl)pyridin-3-yl)amino)nicotinamide | 474 | 0.95 | |

TABLE 3-continued

| Example | Structure | Compound name | MS (ESI m/z): (M + H) | RT (min) | HNMR |
|---|---|---|---|---|---|
| Example 2-203 | 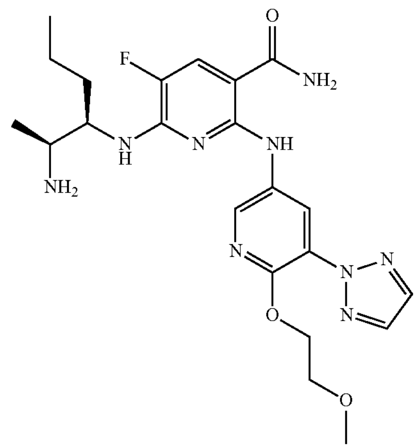 [SMILES: CCC[C@@H](Nc1nc(Nc2cnc(OCCOC)c(-n3nccn3)c2)c(C(N)=O)cc1F)[C@H](C)N] | 6-(((2S,3R)-2-aminohexan-3-yl)amino)-5-fluoro-2-((6-(2-methoxyethoxy)-5-(2H-1,2,3-triazol-2-yl)pyridin-3-yl)amino)nicotinamide | 488 | 1.02 | |
| Example 2-204 | 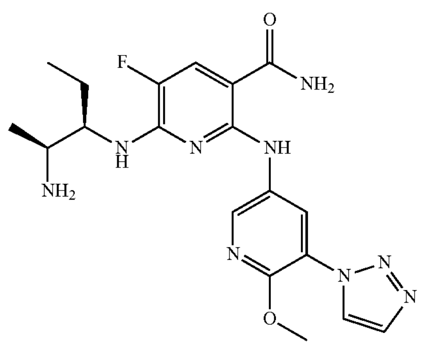 [SMILES: CC[C@@H](Nc1nc(Nc2cnc(OC)c(-n3ccnn3)c2)c(C(N)=O)cc1F)[C@H](C)N] | 6-(((2S,3R)-2-aminopentan-3-yl)amino)-5-fluoro-2-((6-methoxy-5-(1H-1,2,3-triazol-1-yl)pyridin-3-yl)amino)nicotinamide | 430 | 0.92 | |

| Example | Structure | Compound name | MS (ESI m/z): (M + H) | RT (min) | HNMR |
|---|---|---|---|---|---|
| Example 2-205 | 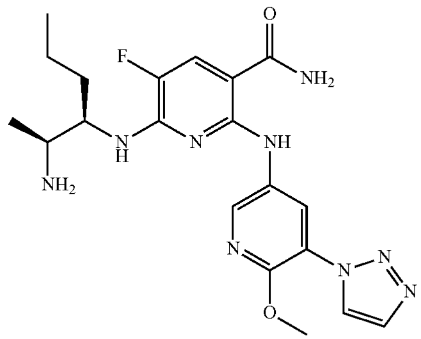 [SMILES: CCC[C@@H](Nc1nc(Nc2cnc(OC)c(-n3ccnn3)c2)c(C(N)=O)cc1F)[C@H](C)N] | 6-(((2S,3R)-2-aminohexan-3-yl)amino)-5-fluoro-2-((6-methoxy-5-(1H-1,2,3-triazol-1-yl)pyridin-3-yl)amino)nicotinamide | 444 | 1 | 1H-NMR (DMSO-d6) δ: 11.63 (1H, s), 8.83 (1H, d, J = 2.6 Hz), 8.64 (1H, s), 8.27 (1H, d, J = 2.6 Hz), 7.98 (1H, s), 7.94 (1H, d, J = 12.3 Hz), 7.86-7.50 (4H, m), 7.45-7.15 (1H, m), 7.05 (1H, d, J = 9.0 Hz), 4.47-4.32 (1H, m), 3.40-3.25 (1H, m), 3.96 (3H, s), 1.60-1.42 (2H, m), 1.40-1.10 (2H, m), 1.06 (3H, d, J = 6.6 Hz), 0.75 (3H, t, J = 7.7 Hz) |
| Example 2-206 | 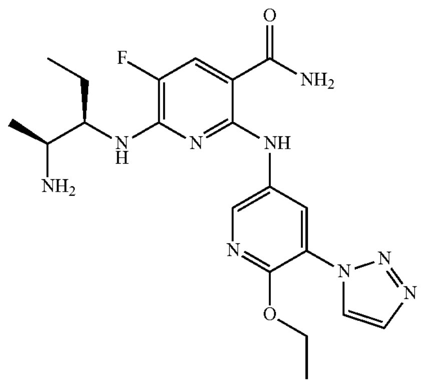 [SMILES: CCOc1ncc(Nc2nc(N[C@H](CC)[C@H](C)N)c(F)cc2C(N)=O)cc1-n1ccnn1] | 6-(((2S,3R)-2-aminopentan-3-yl)amino)-2-((6-ethoxy-5-(1H-1,2,3-triazol-1-yl)pyridin-3-yl)amino)-5-fluoronicotinamide | 444 | 1.01 | |

TABLE 3-continued

| Example | Structure | Compound name | MS (ESI m/z): (M + H) | RT (min) | HNMR |
|---|---|---|---|---|---|
| Example 2-207 | 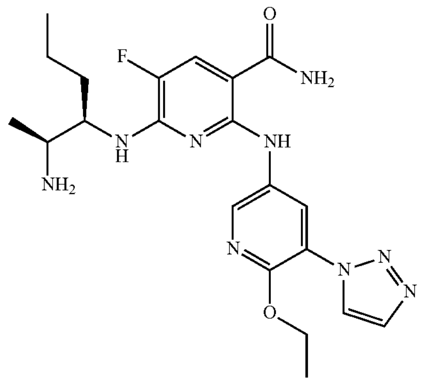 [SMILES: CCC[C@@H](Nc1nc(Nc2cnc(OCC)c(-n3ccnn3)c2)c(C(N)=O)cc1F)[C@H](C)N] | 6-(((2S,3R)-2-aminohexan-3-yl)amino)-2-((6-ethoxy-5-(1H-1,2,3-triazol-1-yl)pyridin-3-yl)amino)-5-fluoronicotinamide | 458 | 1.09 | |
| Example 2-208 | 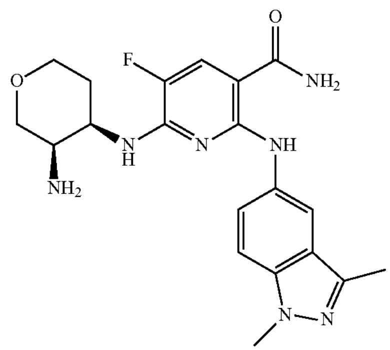 [SMILES: Cc1nn(C)c2ccc(Nc3nc(N[C@@H]4CCOC[C@@H]4N)c(F)cc3C(N)=O)cc12] | 6-(((3R,4R)-3-aminotetrahydro-2H-pyran-4-yl)amino)-2-((1,3-dimethyl-1H-indazol-5-yl)amino)-5-fluoronicotinamide | 414 | 0.79 | 1H-NMR (MeOD) δ: 7.78-7.63 (3H, m), 7.60-7.51 (1H, m), 4.24 (1H, td, J = 8.3, 4.4 Hz), 4.10-4.00 (1H, m), 4.05 (3H, s), 3.74-3.53 (3H, m), 2.60 (3H, s), 2.10-1.53 (3H, m) |

TABLE 3-continued

| Example | Compound name | Structure | MS (ESI m/z): (M + H) | RT (min) | HNMR |
|---|---|---|---|---|---|
| Example 2-209 | 6-(((3R,4R)-3-aminotetrahydro-2H-pyran-4-yl)amino)-5-fluoro-2-((3-fluoro-1-methyl-1H-indazol-5-yl)amino)nicotinamide | 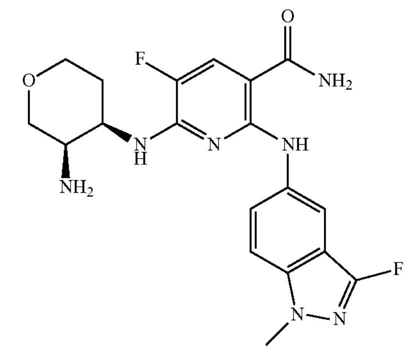 [SMILES: Cn1nc(F)c2cc(Nc3nc(N[C@@H]4CCOC[C@@H]4N)c(F)cc3C(N)=O)ccc21] | 418 | 0.87 | |
| Example 2-210 | 6-(((3R,4R)-3-aminotetrahydro-2H-pyran-4-yl)amino)-5-fluoro-2-((3-methoxy-1-methyl-1H-indazol-5-yl)amino)nicotinamide | 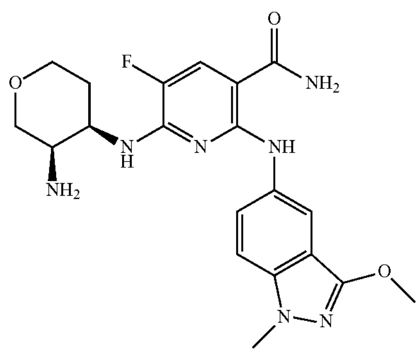 [SMILES: COc1nn(C)c2ccc(Nc3nc(N[C@@H]4CCOC[C@@H]4N)c(F)cc3C(N)=O)cc12] | 430 | 0.84 | 1H-NMR (MeOD) δ: 8.10 (1H, d, J = 2.0 Hz), 7.75 (1H, d, J = 11.9 Hz), 7.31 (1H, d, J = 9.2 Hz), 7.21 (1H, dd, J = 8.6, 2.0 Hz), 4.40 (1H, td, J = 8.4, 4.2 Hz), 4.15-4.05 (4H, m), 3.98-3.55 (7H, m), 2.14-1.80 (2H, m) |
| Example 2-211 | 6-(((3R,4R)-3-aminotetrahydro-2H-pyran-4-yl)amino)-5-fluoro-2-((7-fluoro-3-methoxy-1-methyl-1H-indazol-5-yl)amino)nicotinamide | 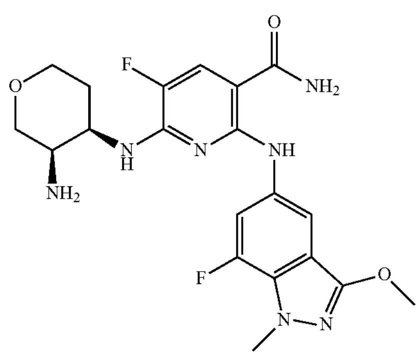 [SMILES: COc1nn(C)c2c(F)cc(Nc3nc(N[C@@H]4CCOC[C@@H]4N)c(F)cc3C(N)=O)cc12] | 448 | 0.93 | 1H-NMR (MeOD) δ: 8.29 (1H, d, J = 1.7 Hz), 8.25 (1H, d, J = 11.9 Hz), 7.63 (1H, dd, J = 11.9, 1.7 Hz), 4.93 (1H, td, J = 8.1, 4.6 Hz), 4.65-4.12 (11H, m), 2.65-2.37 (2H, m) |

TABLE 3-continued

| Example | Structure | Compound name | MS (ESI m/z): (M + H) | RT (min) | HNMR |
|---|---|---|---|---|---|
| Example 2-212 | 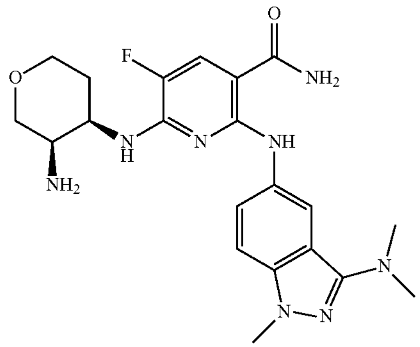 [SMILES: CN(C)c1nn(C)c2ccc(Nc3nc(N[C@@H]4CCOC[C@@H]4N)c(F)cc3C(N)=O)cc12] | 6-(((3R,4R)-3-aminotetrahydro-2H-pyran-4-yl)amino)-2-((3-(dimethylamino)-1-methyl-1H-indazol-5-yl)amino)-5-fluoronicotinamide | 443 | 0.81 | |
| Example 2-213 | 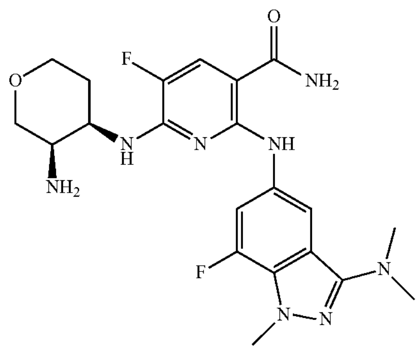 [SMILES: CN(C)c1nn(C)c2c(F)cc(Nc3nc(N[C@@H]4CCOC[C@@H]4N)c(F)cc3C(N)=O)cc12] | 6-(((3R,4R)-3-aminotetrahydro-2H-pyran-4-yl)amino)-2-((3-(dimethylamino)-7-fluoro-1-methyl-1H-indazol-5-yl)amino)-5-fluoronicotinamide | 461 | 0.9 | |
| Example 2-214 | 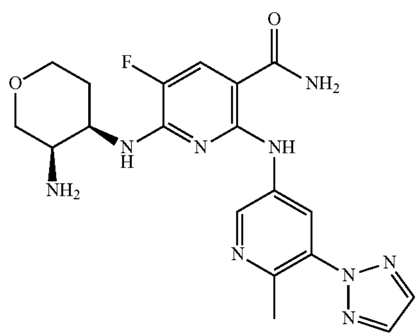 [SMILES: Cc1ncc(Nc2nc(N[C@@H]3CCOC[C@@H]3N)c(F)cc2C(N)=O)cc1-n1nccn1] | 6-(((3R,4R)-3-aminotetrahydro-2H-pyran-4-yl)amino)-5-fluoro-2-((6-methyl-5-(2H-1,2,3-triazol-2-yl)pyridin-3-yl)amino)nicotinamide | 428 | 0.75 | 1H-NMR (MeOD) δ: 9.26 (1H, d, J = 2.5 Hz), 8.88 (1H, d, J = 2.5 Hz), 8.20 (2H, s), 7.90 (1H, d, J = 11.9 Hz), 4.64-4.53 (1H, m), 4.14-4.04 (1H, m), 3.90-3.50 (4H, m), 2.90 (3H, s), 2.20-1.86 (2H, m) |

TABLE 3-continued

| Example | Structure | Compound name | MS (ESI m/z): (M + H) | RT (min) | HNMR |
|---|---|---|---|---|---|
| Example 2-215 | 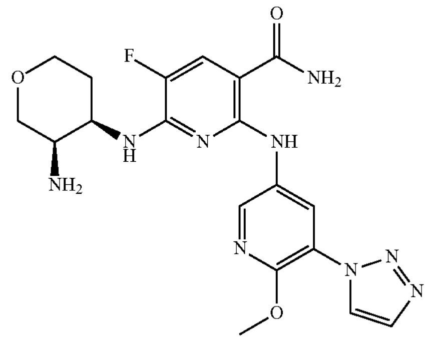 [SMILES: COc1ncc(Nc2nc(N[C@@H]3CCOC[C@@H]3N)c(F)cc2C(N)=O)cc1-n1ccnn1] | 6-(((3R,4R)-3-aminotetrahydro-2H-pyran-4-yl)amino)-5-fluoro-2-((6-methoxy-5-(1H-1,2,3-triazol-1-yl)pyridin-3-yl)amino)nicotinamide | 444 | 0.79 | 1H-NMR (MeOD) δ: 8.82 (1H, d, J = 2.6 Hz), 8.60 (1H, d, J = 1.0 Hz), 8.17 (1H, d, J = 2.6 Hz), 7.95 (1H, d, J = 1.0 Hz), 7.79 (1H, d, J = 11.9 Hz), 4.56-4.44 (1H, m), 4.12-3.96 (1H, m), 4.06 (3H, s), 3.80-3.60 (3H, m), 3.45-3.35 (1H, m), 2.12-1.82 (2H, m) |
| Example 2-216 | 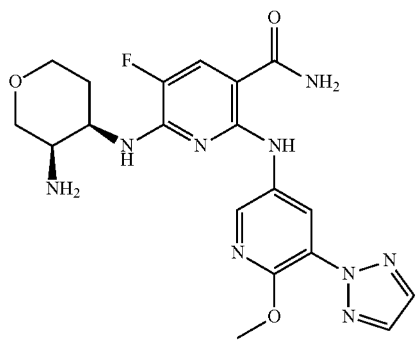 [SMILES: COc1ncc(Nc2nc(N[C@@H]3CCOC[C@@H]3N)c(F)cc2C(N)=O)cc1-n1nccn1] | 6-(((3R,4R)-3-aminotetrahydro-2H-pyran-4-yl)amino)-5-fluoro-2-((6-methoxy-5-(2H-1,2,3-triazol-2-yl)pyridin-3-yl)amino)nicotinamide | 444 | 0.79 | 1H-NMR (MeOD) δ: 8.38 (1H, d, J = 2.5 Hz), 8.25 (1H, d, J = 2.5 Hz), 8.02 (2H, s), 7.78 (1H, d, J = 11.9 Hz), 4.40-4.30 (1H, m), 4.08-3.95 (1H, m), 3.97 (3H, s), 3.80-3.67 (2H, m), 3.62-3.40 (2H, m), 2.10-1.76 (2H, m) |

TABLE 3-continued

| Example | Structure | Compound name | MS (ESI m/z): (M + H) | RT (min) | HNMR |
|---|---|---|---|---|---|
| Example 2-217 | 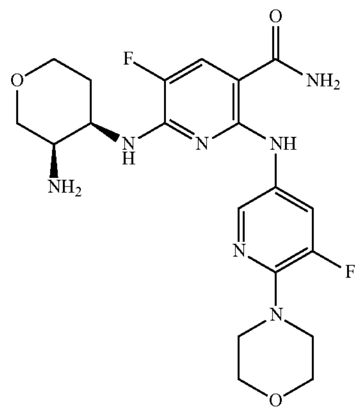 [SMILES: NC(=O)c1cc(F)c(N[C@@H]2CCOC[C@@H]2N)nc1Nc1cnc(N2CCOCC2)c(F)c1] | 6-(((3R,4R)-3-aminotetrahydro-2H-pyran-4-yl)amino)-5-fluoro-2-((5-fluoro-6-morpholinopyridin-3-yl)amino)nicotinamide | 450 | 0.81 | 1H-NMR (MeOD) δ: 8.28 (1H, d, J = 2.3 Hz), 8.24 (1H, dd, J = 14.9, 2.3 Hz), 7.82 (1H, d, J = 11.9 Hz), 4.50-4.40 (1H, m), 4.18-3.65 (9H, m), 3.58-3.50 (4H, m), 2.20-1.83 (2H, m) |
| Example 2-218 | 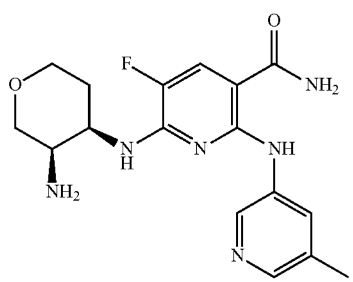 [SMILES: Cc1cncc(Nc2nc(N[C@@H]3CCOC[C@@H]3N)c(F)cc2C(N)=O)c1] | 6-(((3R,4R)-3-aminotetrahydro-2H-pyran-4-yl)amino)-5-fluoro-2-((5-methylpyridin-3-yl)amino)nicotinamide | 361 | 0.5 | 1H-NMR (MeOD) δ: 9.22 (1H, d, J = 2.0 Hz), 8.28-8.20 (2H, m), 7.89 (1H, d, J = 11.6 Hz), 4.60-4.45 (1H, m), 4.18-4.08 (1H, m), 4.06-3.97 (1H, m), 3.88-3.76 (3H, m), 2.53 (3H, s), 2.23-1.85 (2H, m) |
| Example 2-219 | 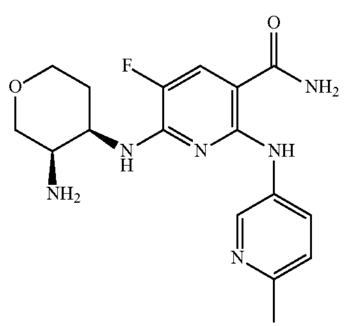 [SMILES: Cc1ccc(Nc2nc(N[C@@H]3CCOC[C@@H]3N)c(F)cc2C(N)=O)cn1] | 6-(((3R,4R)-3-aminotetrahydro-2H-pyran-4-yl)amino)-5-fluoro-2-((6-methylpyridin-3-yl)amino)nicotinamide | 361 | 0.48 | 1H-NMR (MeOD) δ: 9.15 (1H, d, J = 2.3 Hz), 8.47 (1H, dd, J = 8.8, 2.3 Hz), 7.89 (1H, d, J = 11.9 Hz), 7.81 (1H, d, J = 8.8 Hz), 4.57-4.46 (1H, m), 4.18-4.08 (1H, m), 4.06-3.72 (4H, m), 2.73 (3H, s), 2.23-1.87 (2H, m) |

| Example | Structure | Compound name | MS (ESI m/z): (M + H) | RT (min) | HNMR |
|---|---|---|---|---|---|
| Example 2-220 | 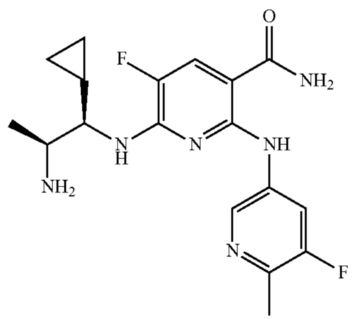 [SMILES: Cc1ncc(Nc2nc(N[C@H](C3CC3)[C@H](C)N)c(F)cc2C(N)=O)cc1F] | 6-(((1R,2S)-2-amino-1-cyclopropylpropyl)amino)-5-fluoro-2-((5-fluoro-6-methylpyridin-3-yl)amino)nicotinamide | 377 | 0.83 | 1H-NMR (DMSO-d6) δ: 11.92 (1H, s), 8.54 (1H, s), 8.15-7.70 (6H, m), 7.46-7.26 (2H, m), 3.74-3.60 (1H, m), 3.58-3.42 (1H, m), 2.43 (3H, d, J = 2.4 Hz), 1.30 (3H, d, J = 6.6 Hz), 1.20-1.06 (1H, m), 0.70-0.58 (1H, m), 0.56-0.38 (2H, m), 0.34-0.22 (1H, m) |
| Example 2-221 | 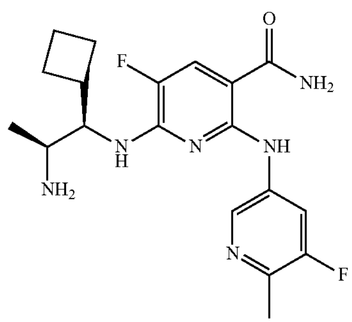 [SMILES: Cc1ncc(Nc2nc(N[C@H](C3CCC3)[C@H](C)N)c(F)cc2C(N)=O)cc1F] | 6-(((1R,2S)-2-amino-1-cyclobutylpropyl)amino)-5-fluoro-2-((5-fluoro-6-methylpyridin-3-yl)amino)nicotinamide | 391 | 0.92 | 1H-NMR (DMSO-d6) δ: 11.91 (1H, s), 8.53 (1H, s), 8.31-8.20 (1H, m), 8.00-7.75 (5H, m), 7.47-7.27 (1H, m), 7.05 (1H, d, J = 8.7 Hz), 4.44-4.30 (1H, m), 3.42-3.26 (1H, m), 2.77-2.59 (1H, m), 2.44 (3H, d, J = 2.1 Hz), 2.13-1.65 (6H, m), 1.20 (3H, d, J = 6.6 Hz) |
| Example 2-222 | 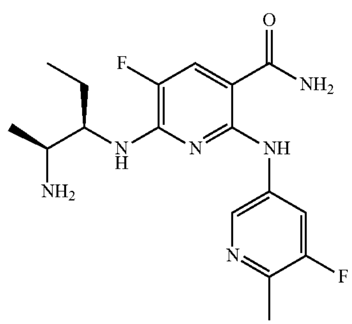 [SMILES: CC[C@@H](Nc1nc(Nc2cnc(C)c(F)c2)c(C(N)=O)cc1F)[C@H](C)N] | 6-(((2S,3R)-2-aminopentan-3-yl)amino)-5-fluoro-2-((5-fluoro-6-methylpyridin-3-yl)amino)nicotinamide | 365 | 0.8 | 1H-NMR (DMSO-d6) δ: 11.92 (1H, s), 8.60 (1H, s), 8.20-8.10 (1H, m), 8.05-7.75 (5H, m), 7.50-7.27 (1H, m), 7.13 (1H, d, J = 8.4 Hz), 4.35-4.21 (1H, m), 3.50-3.36 (1H, m), 2.43 (3H, d, J = 2.4 Hz), 1.80-1.50 (2H, m), 1.25 (3H, d, J = 6.6 Hz), 0.90 (3H, t, J = 7.4 Hz) |

TABLE 3-continued

| Example | Structure | Compound name | MS (ESI m/z): (M + H) | RT (min) | HNMR |
|---|---|---|---|---|---|
| Example 2-223 | 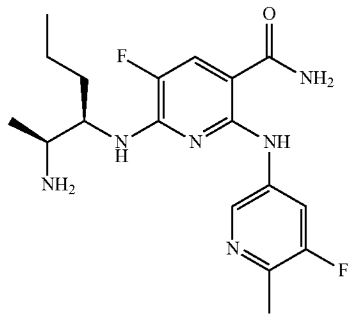 [SMILES: CCC[C@@H](Nc1nc(Nc2cnc(C)c(F)c2)c(C(N)=O)cc1F)[C@H](C)N] | 6-(((2S,3R)-2-aminohexan-3-yl)amino)-5-fluoro-2-((5-fluoro-6-methylpyridin-3-yl)amino)nicotinamide | 379 | 0.89 | 1H-NMR (DMSO-d6) δ: 11.89 (1H, s), 8.53 (1H, s), 8.18-8.06 (1H, m), 8.04-7.78 (5H, m), 7.48-7.26 (1H, m), 7.13 (1H, d, J = 9.3 Hz), 4.28-4.14 (1H, m), 3.50-3.34 (1H, m), 2.41 (3H, d, J = 2.7 Hz), 1.68-1.54 (2H, m), 1.50-1.30 (2H, m), 1.24 (3H, d, J = 6.6 Hz), 0.86 (3H, t, J = 7.2 Hz) |
| Example 2-224 | 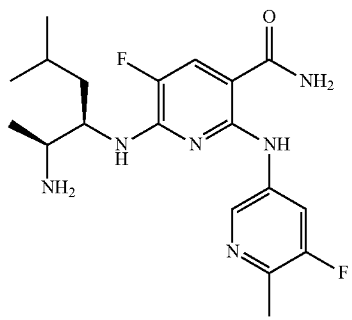 [SMILES: Cc1ncc(Nc2nc(N[C@H](CC(C)C)[C@H](C)N)c(F)cc2C(N)=O)cc1F] | 6-(((2S,3R)-2-amino-5-methylhexan-3-yl)amino)-5-fluoro-2-((5-fluoro-6-methylpyridin-3-yl)amino)nicotinamide | 393 | 0.97 | 1H-NMR (DMSO-d6) δ: 11.87 (1H, s), 8.46 (1H, s), 8.16-8.06 (1H, m), 8.00-7.70 (5H, m), 7.48-7.24 (1H, m), 7.14 (1H, d, J = 7.8 Hz), 4.33-4.20 (1H, m), 3.46-3.30 (1H, m), 2.40 (3H, d, J = 2.7 Hz), 1.70-1.54 (2H, m), 1.44-1.30 (1H, m), 1.23 (3H, d, J = 6.6 Hz), 0.91 (3H, d, J = 6.6 Hz), 0.80 (3H, d, J = 6.6 Hz) |
| Example 2-225 | 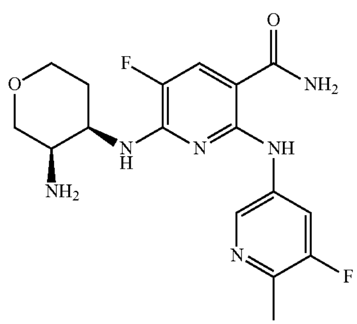 [SMILES: Cc1ncc(Nc2nc(N[C@@H]3CCOC[C@@H]3N)c(F)cc2C(N)=O)cc1F] | 6-(((3R,4R)-3-aminotetrahydro-2H-pyran-4-yl)amino)-5-fluoro-2-((5-fluoro-6-methylpyridin-3-yl)amino)nicotinamide | 379 | 0.72 | |

TABLE 3-continued

| Example | Structure | Compound name | MS (ESI m/z): (M + H) | RT (min) | HNMR |
|---|---|---|---|---|---|
| Example 2-226 | 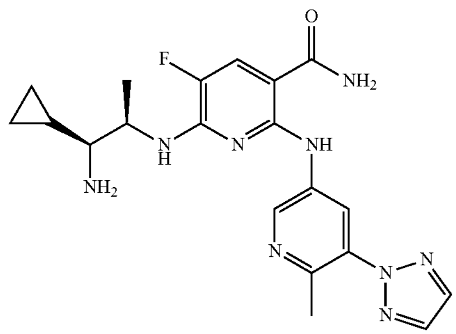 [SMILES: Cc1ncc(Nc2nc(N[C@H](C)[C@@H](N)C3CC3)c(F)cc2C(N)=O)cc1-n1nccn1] | 6-(((1S,2R)-1-amino-1-cyclopropylpropan-2-yl)amino)-5-fluoro-2-((6-methyl-5-(2H-1,2,3-triazol-2-yl)pyridin-3-yl)amino)nicotinamide | 426 | 0.84 | |
| Example 2-227 | 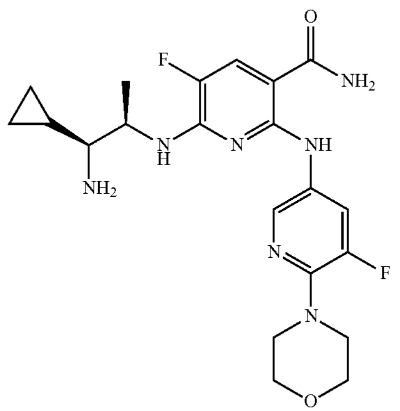 [SMILES: C[C@@H](Nc1nc(Nc2cnc(N3CCOCC3)c(F)c2)c(C(N)=O)cc1F)[C@@H](N)C1CC1] | 6-(((1S,2R)-1-amino-1-cyclopropylpropan-2-yl)amino)-5-fluoro-2-((5-fluoro-6-morpholinopyridin-3-yl)amino)nicotinamide | 448 | 0.9 | |
| Example 2-228 | 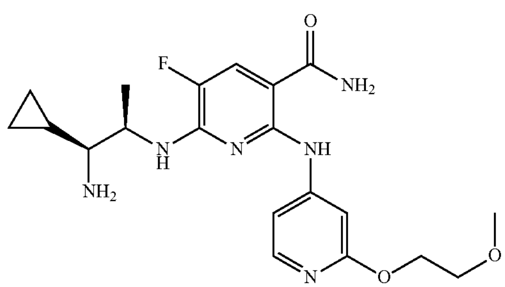 [SMILES: COCCOc1cc(Nc2nc(N[C@H](C)[C@@H](N)C3CC3)c(F)cc2C(N)=O)ccn1] | 6-(((1S,2R)-1-amino-1-cyclopropylpropan-2-yl)amino)-5-fluoro-2-((2-(2-methoxyethoxy)pyridin-4-yl)amino)nicotinamide | 419 | 0.63 | |

TABLE 3-continued

| Example | Structure | Compound name | MS (ESI m/z): (M + H) | RT (min) | HNMR |
|---|---|---|---|---|---|
| Example 2-229 | 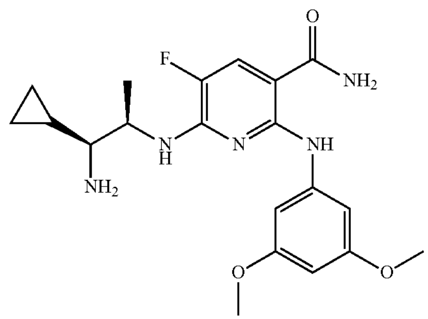 [SMILES: COc1cc(Nc2nc(N[C@H](C)[C@@H](N)C3CC3)c(F)cc2C(N)=O)cc(OC)c1] | 6-(((1S,2R)-1-amino-1-cyclopropylpropan-2-yl)amino)-2-((3,5-dimethoxyphenyl)amino)-5-fluoronicotinamide | 404 | 0.96 | |
| Example 2-230 | 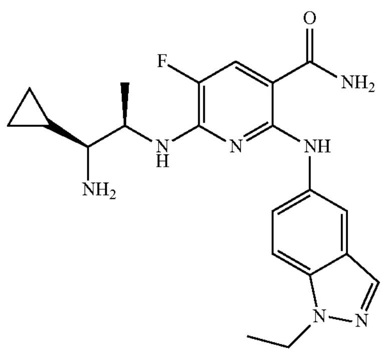 [SMILES: CCn1ncc2cc(Nc3nc(N[C@H](C)[C@@H](N)C4CC4)c(F)cc3C(N)=O)ccc21] | 6-(((1S,2R)-1-amino-1-cyclopropylpropan-2-yl)amino)-2-((1-ethyl-1H-indazol-5-yl)amino)-5-fluoronicotinamide | 412 | 0.9 | |
| Example 2-231 | 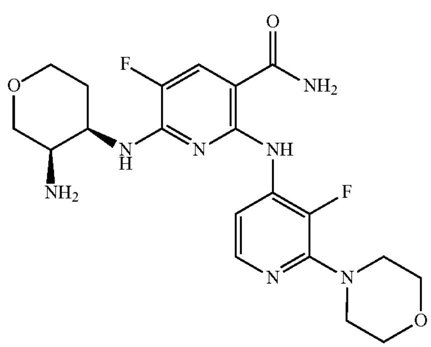 [SMILES: NC(=O)c1cc(F)c(N[C@@H]2CCOC[C@@H]2N)nc1Nc1ccnc(N2CCOCC2)c1F] | 6-(((3R,4R)-3-aminotetrahydro-2H-pyran-4-yl)amino)-5-fluoro-2-((3-fluoro-2-morpholinopyridin-4-yl)amino)nicotinamide | 450 | 0.65 | 1H-NMR (MeOD) δ: 8.37 (1H, dd, J = 6.9, 6.6 Hz), 7.96-7.90 (2H, m), 4.56-4.46 (1H, m), 4.17-4.08 (1H, m), 4.07-3.71 (8H, m), 3.61-3.55 (4H, m), 2.25-1.82 (2H, m) |

TABLE 3-continued

| Example | Structure | Compound name | MS (ESI m/z): (M + H) | RT (min) | HNMR |
|---|---|---|---|---|---|
| Example 2-232 | 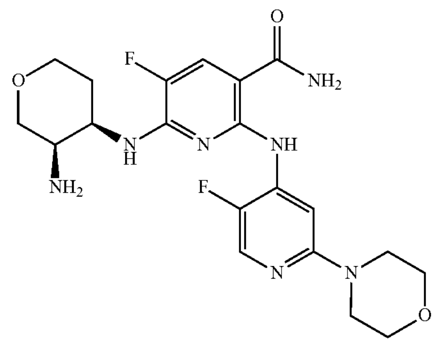 [SMILES: NC(=O)c1cc(F)c(N[C@@H]2CCOC[C@@H]2N)nc1Nc1cc(N2CCOCC2)ncc1F] | 6-(((3R,4R)-3-aminotetrahydro-2H-pyran-4-yl)amino)-5-fluoro-2-((5-fluoro-2-morpholinopyridin-4-yl)amino)nicotinamide | 450 | 0.57 | 1H-NMR (MeOD) δ: 8.02 (1H, d, J = 5.0 Hz), 7.99-7.90 (2H, m), 4.51-4.41 (1H, m), 4.22-4.10 (1H, m), 4.09-3.79 (6H, m), 3.72-3.49 (6H, m), 2.25-1.93 (2H, m) |
| Example 2-233 | 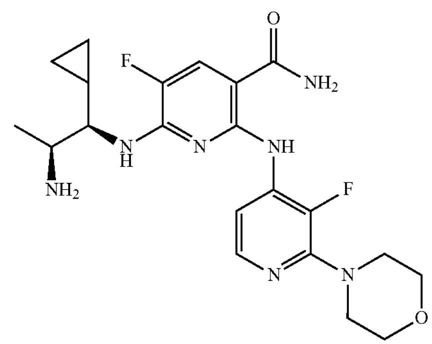 [SMILES: C[C@H](N)[C@H](Nc1nc(Nc2ccnc(N3CCOCC3)c2F)c(C(N)=O)cc1F)C1CC1] | 6-(((1R,2S)-2-amino-1-cyclopropylpropyl)amino)-5-fluoro-2-((3-fluoro-2-morpholinopyridin-4-yl)amino)nicotinamide | 448 | 0.74 | 1H-NMR (MeOD) δ: 8.33 (1H, dd, J = 6.6, 6.6 Hz), 7.99-7.93 (1H, m), 7.91 (1H, d, J = 11.9 Hz), 3.90-3.62 (6H, m), 3.60-3.54 (4H, m), 1.46 (3H, d, J = 6.6 Hz), 1.20-1.06 (1H, m), 0.84-0.73 (1H, m), 0.69-0.55 (2H, m), 0.48-0.37 (1H, m) |
| Example 2-234 | 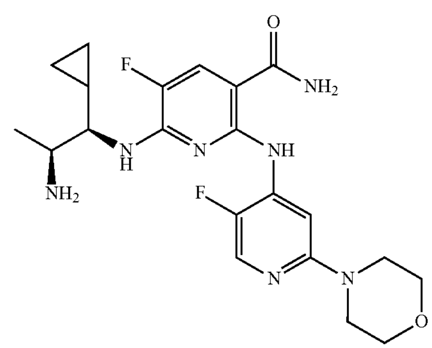 [SMILES: C[C@H](N)[C@H](Nc1nc(Nc2cc(N3CCOCC3)ncc2F)c(C(N)=O)cc1F)C1CC1] | 6-(((1R,2S)-2-amino-1-cyclopropylpropyl)amino)-5-fluoro-2-((5-fluoro-2-morpholinopyridin-4-yl)amino)nicotinamide | 448 | 0.67 | 1H-NMR (MeOD) δ: 8.01 (1H, d, J = 4.6 Hz), 7.96-7.89 (2H, m), 4.22-4.16 (1H, m), 3.91-3.84 (4H, m), 3.74-3.64 (1H, m), 3.58-3.50 (4H, m), 1.42 (3H, d, J = 6.6 Hz), 1.20-1.07 (1H, m), 0.76-0.61 (2H, m), 0.57-0.48 (1H, m), 0.39-0.30 (1H, m) |

TABLE 3-continued

| Example | Structure | Compound name | MS (ESI m/z): (M + H) | RT (min) | HNMR |
|---|---|---|---|---|---|
| Example 2-235 | 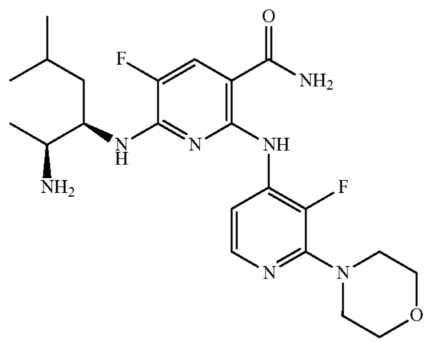 [SMILES: CC(C)C[C@@H](Nc1nc(Nc2ccnc(N3CCOCC3)c2F)c(C(N)=O)cc1F)[C@H](C)N] | 6-(((2S,3R)-2-amino-5-methylhexan-3-yl)amino)-5-fluoro-2-((3-fluoro-2-morpholinopyridin-4-yl)amino)nicotinamide | 464 | 0.87 | 1H-NMR (MeOD) δ: 8.46 (1H, dd, J = 6.9, 6.6 Hz), 7.97-7.91 (2H, m), 4.63-4.50 (1H, m), 3.90-3.83 (4H, m), 3.62-3.55 (5H, m), 1.81-1.62 (2H, m), 1.56-1.44 (1H, m),1.38 (3H, d, J = 6.6 Hz), 1.01 (3H, d, J = 6.6 Hz), 0.94 (3H, d, J = 6.6 Hz) |
| Example 2-236 | 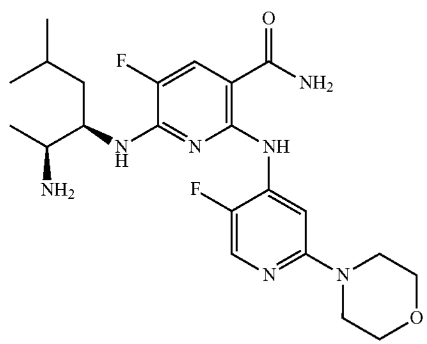 [SMILES: CC(C)C[C@@H](Nc1nc(Nc2cc(N3CCOCC3)ncc2F)c(C(N)=O)cc1F)[C@H](C)N] | 6-(((2S,3R)-2-amino-5-methylhexan-3-yl)amino)-5-fluoro-2-((5-fluoro-2-morpholinopyridin-4-yl)amino)nicotinamide | 464 | 0.8 | 1H-NMR (MeOD) δ: 8.03 (1H, d, J = 5.3 Hz), 7.99-7.92 (2H, m), 4.55-4.46 (1H, m), 3.91-3.84 (4H, m), 3.66-3.47 (5H, m), 1.83-1.69 (2H, m), 1.38-1.51 (1H, m), 1.34 (3H, d, J = 6.6 Hz), 1.01 (3H, d, J = 6.6 Hz), 0.94 (3H, d, J = 5.9 Hz) |

TABLE 3-continued

| Example | Structure | Compound name | MS (ESI m/z): (M + H) | RT (min) | HNMR |
|---|---|---|---|---|---|
| Example 2-237 | 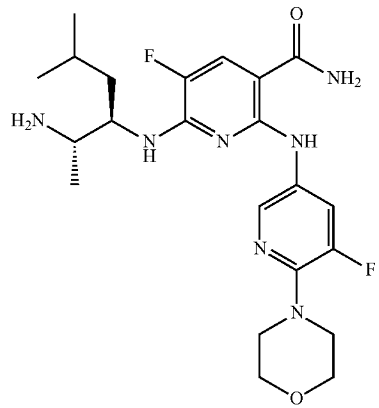 [SMILES: CC(C)C[C@@H](Nc1nc(Nc2cnc(N3CCOCC3)c(F)c2)c(C(N)=O)cc1F)[C@H](C)N] | 6-(((2S,3R)-2-amino-5-methylhexan-3-yl)amino)-5-fluoro-2-((5-fluoro-6-morpholinopyridin-3-yl)amino)nicotinamide | 464 | 1.04 | |
| Example 2-238 | 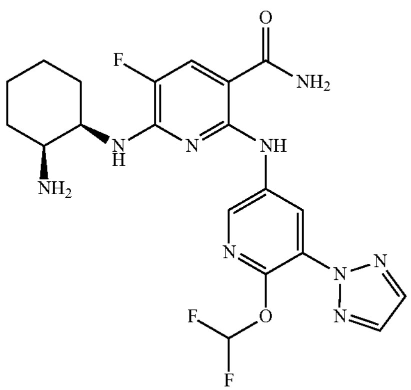 [SMILES: NC(=O)c1cc(F)c(N[C@@H]2CCCC[C@@H]2N)nc1Nc1cnc(OC(F)F)c(-n2nccn2)c1] | 6-(((1R,2S)-2-aminocyclohexyl)amino)-2-((6-(difluoromethoxy)-5-(2H-1,2,3-triazol-2-yl)pyridin-3-yl)amino)-5-fluoronicotinamide | 478 | 1.03 | 1H-NMR (DMSO-d6) δ: 11.87 (1H, s), 8.83-8.78 (1H, m), 8.36-8.32 (1H, m), 8.23 (2H, s), 8.02-7.92 (1H, m), 7.95-7.20 (6H, m), 6.94 (1H, d, J = 7.2 Hz), 4.24-4.10 (1H, m), 3.50-3.40 (1H, m), 1.85-1.65 (2H, m), 1.65-1.45 (4H, m), 1.40-1.15 (2H, m) |

TABLE 3-continued

| Example | Structure | Compound name | MS (ESI m/z): (M + H) | RT (min) | HNMR |
|---|---|---|---|---|---|
| Example 2-239 | 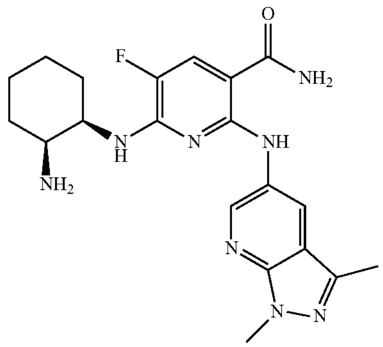 [SMILES: Cc1nn(C)c2ncc(Nc3nc(N[C@@H]4CCCC[C@@H]4N)c(F)cc3C(N)=O)cc12] | 6-(((1R,2S)-2-aminocyclohexyl)amino)-2-((1,3-dimethyl-1H-pyrazolo[3,4-b]pyridin-5-yl)amino)-5-fluoronicotinamide | 413 | 0.84 | |
| Example 2-240 | 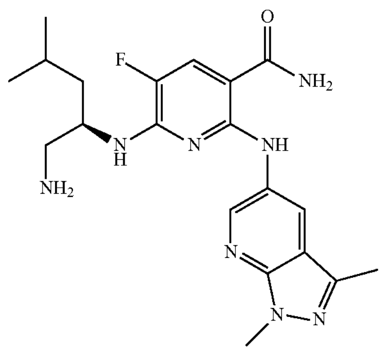 [SMILES: Cc1nn(C)c2ncc(Nc3nc(N[C@@H](CN)CC(C)C)c(F)cc3C(N)=O)cc12] | (R)-6-((1-amino-4-methylpentan-2-yl)amino)-2-((1,3-dimethyl-1H-pyrazolo[3,4-b]pyridin-5-yl)amino)-5-fluoronicotinamide | 415 | 0.93 | |
| Example 2-241 | 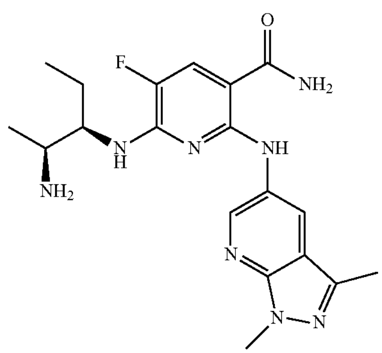 [SMILES: CC[C@@H](Nc1nc(Nc2cnc3c(c2)c(C)nn3C)c(C(N)=O)cc1F)[C@H](C)N] | 6-(((2S,3R)-2-aminopentan-3-yl)amino)-2-((1,3-dimethyl-1H-pyrazolo[3,4-b]pyridin-5-yl)amino)-5-fluoronicotinamide | 401 | 0.82 | |

TABLE 3-continued

| Example | Structure | Compound name | MS (ESI m/z): (M + H) | RT (min) | HNMR |
|---|---|---|---|---|---|
| Example 2-242 | 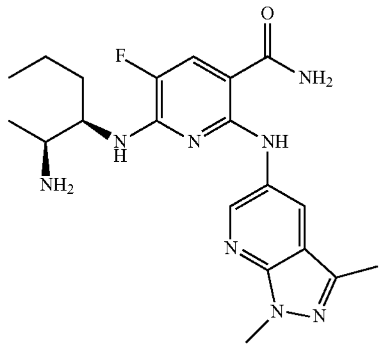 [SMILES: CCC[C@@H](Nc1nc(Nc2cnc3c(c2)c(C)nn3C)c(C(N)=O)cc1F)[C@H](C)N] | 6-(((2S,3R)-2-aminohexan-3-yl)amino)-2-((1,3-dimethyl-1H-pyrazolo[3,4-b]pyridin-5-yl)amino)-5-fluoronicotinamide | 415 | 0.89 | |
| Example 2-243 | 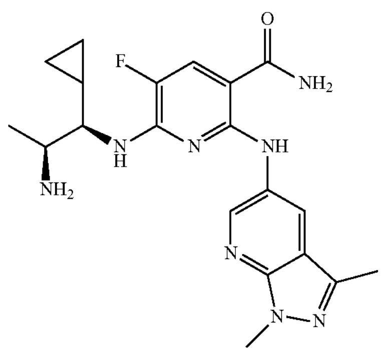 [SMILES: Cc1nn(C)c2ncc(Nc3nc(N[C@H](C4CC4)[C@H](C)N)c(F)cc3C(N)=O)cc12] | 6-(((1R,2S)-2-amino-1-cyclopropylpropyl)amino)-2-((1,3-dimethyl-1H-pyrazolo[3,4-b]pyridin-5-yl)amino)-5-fluoronicotinamide | 413 | 0.83 | 1H-NMR (MeOD) δ: 8.73 (1H, d, J = 2.6 Hz), 8.09 (1H, d, J = 2.6 Hz), 7.76 (1H, d, J = 12.6 Hz), 4.83-4.71 (1H, m), 4.03 (3H, s), 3.57-3.50 (1H, m), 2.54 (3H, s), 1.26 (3H, d, J = 6.6 Hz), 1.05-1.00 (1H, m), 0.73-0.66 (1H, m), 0.61-0.52 (1H, m), 0.35-0.28 (2H, m). |

TABLE 3-continued

| Example | Structure | Compound name | MS (ESI m/z): (M + H) | RT (min) | HNMR |
|---|---|---|---|---|---|
| Example 2-244 | 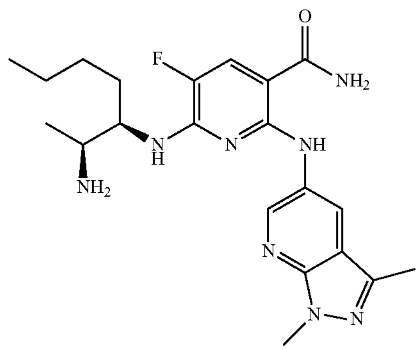 [SMILES: CCCC[C@@H](Nc1nc(Nc2cnc3c(c2)c(C)nn3C)c(C(N)=O)cc1F)[C@H](C)N] | 6-(((2S,3R)-2-aminoheptan-3-yl)amino)-2-((1,3-dimethyl-1H-pyrazolo[3,4-b]pyridin-5-yl)amino)-5-fluoronicotinamide | 429 | 0.96 | |
| Example 2-245 | 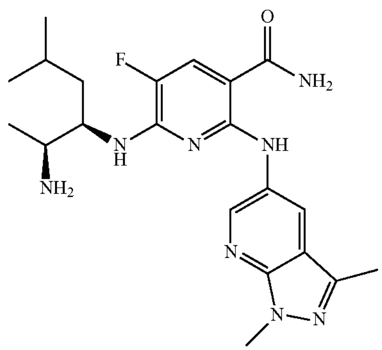 [SMILES: Cc1nn(C)c2ncc(Nc3nc(N[C@H](CC(C)C)[C@H](C)N)c(F)cc3C(N)=O)cc12] | 6-(((2S,3R)-2-amino-5-methylhexan-3-yl)amino)-2-((1,3-dimethyl-1H-pyrazolo[3,4-b]pyridin-5-yl)amino)-5-fluoronicotinamide | 429 | 0.94 | |
| Example 2-246 | 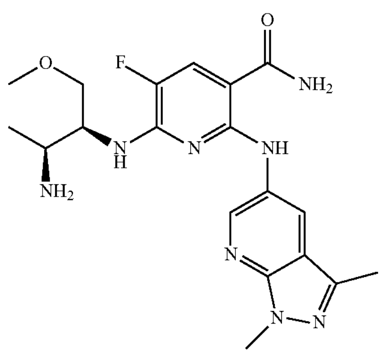 [SMILES: COC[C@@H](Nc1nc(Nc2cnc3c(c2)c(C)nn3C)c(C(N)=O)cc1F)[C@H](C)N] | 6-(((2S,3S)-3-amino-1-methoxybutan-2-yl)amino)-2-((1,3-dimethyl-1H-pyrazolo[3,4-b]pyridin-5-yl)amino)-5-fluoronicotinamide | 417 | 0.77 | |

TABLE 3-continued

| Example | Structure | Compound name | MS (ESI m/z): (M + H) | RT (min) | HNMR |
|---|---|---|---|---|---|
| Example 2-247 | 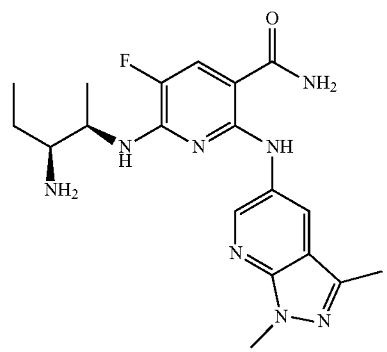 [SMILES: CC[C@H](N)[C@@H](C)Nc1nc(Nc2cnc3c(c2)c(C)nn3C)c(C(N)=O)cc1F] | 6-(((2R,3S)-3-aminopentan-2-yl)amino)-2-((1,3-dimethyl-1H-pyrazolo[3,4-b]pyridin-5-yl)amino)-5-fluoronicotinamide | 399 | 0.78 | |
| Example 2-248 | 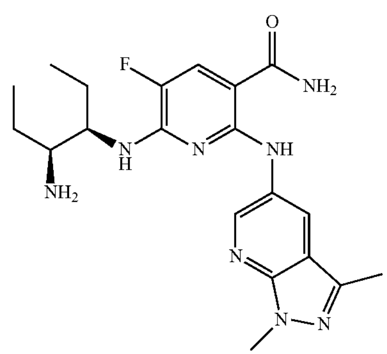 [SMILES: CC[C@H](N)[C@@H](CC)Nc1nc(Nc2cnc3c(c2)c(C)nn3C)c(C(N)=O)cc1F] | 6-(((3R,4S)-4-aminohexan-3-yl)amino)-2-((1,3-dimethyl-1H-pyrazolo[3,4-b]pyridin-5-yl)amino)-5-fluoronicotinamide | 415 | 0.85 | |

TABLE 3-continued

| Example | Structure | Compound name | MS (ESI m/z): (M + H) | RT (min) | HNMR |
|---|---|---|---|---|---|
| Example 2-249 | 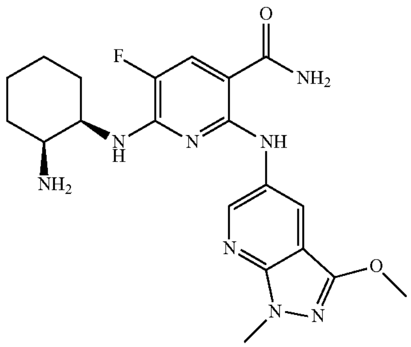 [SMILES: COc1nn(C)c2ncc(Nc3nc(N[C@@H]4CCCC[C@@H]4N)c(F)cc3C(N)=O)cc12] | 6-(((1R,2S)-2-aminocyclohexyl)amino)-5-fluoro-2-((3-methoxy-1-methyl-1H-pyrazolo[3,4-b]pyridin-5-yl)amino)nicotinamide | 429 | 0.89 | |
| Example 2-250 | 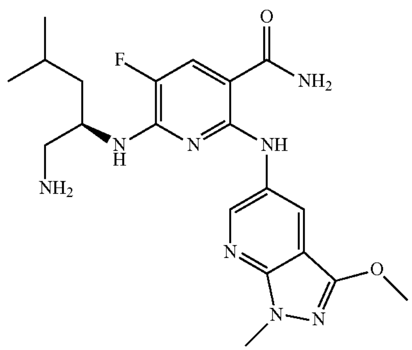 [SMILES: COc1nn(C)c2ncc(Nc3nc(N[C@@H](CN)CC(C)C)c(F)cc3C(N)=O)cc12] | (R)-6-((1-amino-4-methylpentan-2-yl)amino)-5-fluoro-2-((3-methoxy-1-methyl-1H-pyrazolo[3,4-b]pyridin-5-yl)amino)nicotinamide | 431 | 0.98 | |
| Example 2-251 | 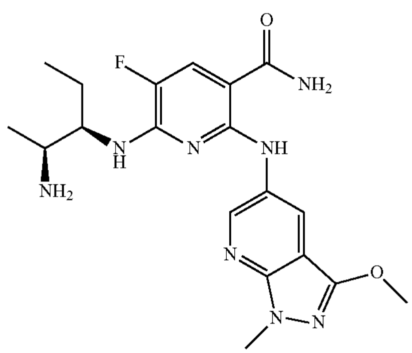 [SMILES: CC[C@@H](Nc1nc(Nc2cnc3c(c2)c(OC)nn3C)c(C(N)=O)cc1F)[C@H](C)N] | 6-(((2S,3R)-2-aminopentan-3-yl)amino)-5-fluoro-2-((3-methoxy-1-methyl-1H-pyrazolo[3,4-b]pyridin-5-yl)amino)nicotinamide | 417 | 0.87 | 1H-NMR (MeOD) δ: 8.59 (1H, d, J = 2.6 Hz), 8.23 (1H, d, J = 2.6 Hz), 7.77 (1H, d, J = 11.9 Hz), 4.21-4.18 (1H, m), 4.07 (3H, s), 3.94 (3H, s), 3.51-3.45 (1H, m), 1.72-1.56 (2H, m), 1.24 (3H, d, J = 7.3 Hz), 1.02 (3H, t, J = 7.3 Hz). |

TABLE 3-continued

| Example | Structure | Compound name | MS (ESI m/z): (M + H) | RT (min) | HNMR |
|---|---|---|---|---|---|
| Example 2-252 | 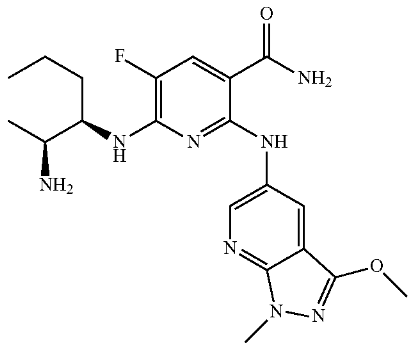 [SMILES: CCC[C@@H](Nc1nc(Nc2cnc3c(c2)c(OC)nn3C)c(C(N)=O)cc1F)[C@H](C)N] | 6-(((2S,3R)-2-aminohexan-3-yl)amino)-5-fluoro-2-((3-methoxy-1-methyl-1H-pyrazolo[3,4-b]pyridin-5-yl)amino)nicotinamide | 431 | 0.94 | 1H-NMR (MeOD) δ: 8.58 (1H, d, J = 2.6 Hz), 8.24 (1H, d, J = 2.0 Hz), 7.77 (1H, d, J = 11.9 Hz), 4.32-4.26 (1H, m), 4.06 (3H, s), 3.92 (3H, s), 3.49-3.40 (1H, m), 1.62-1.32 (4H, m), 1.24 (3H, d, J = 7.3 Hz), 0.93 (3H, t, J = 7.3 Hz). |
| Example 2-253 | 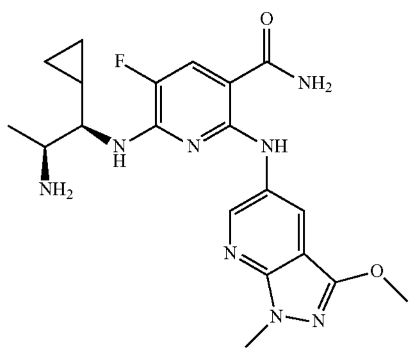 [SMILES: COc1nn(C)c2ncc(Nc3nc(N[C@H](C4CC4)[C@H](C)N)c(F)cc3C(N)=O)cc12] | 6-(((1R,2S)-2-amino-1-cyclopropylpropyl)amino)-5-fluoro-2-((3-methoxy-1-methyl-1H-pyrazolo[3,4-b]pyridin-5-yl)amino)nicotinamide | 429 | 0.88 | |

TABLE 3-continued

| Example | Structure | Compound name | MS (ESI m/z): (M + H) | RT (min) | HNMR |
|---|---|---|---|---|---|
| Example 2-254 | 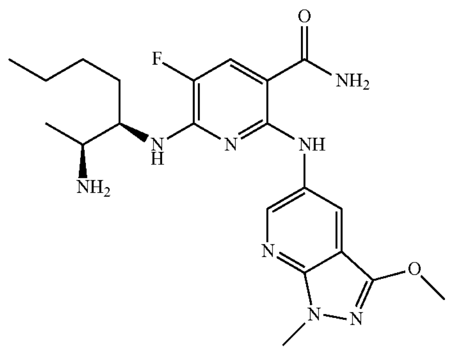 [SMILES: CCCC[C@@H](Nc1nc(Nc2cnc3c(c2)c(OC)nn3C)c(C(N)=O)cc1F)[C@H](C)N] | 6-(((2S,3R)-2-aminoheptan-3-yl)amino)-5-fluoro-2-((3-methoxy-1-methyl-1H-pyrazolo[3,4-b]pyridin-5-yl)amino)nicotinamide | 445 | 1 | |
| Example 2-255 | 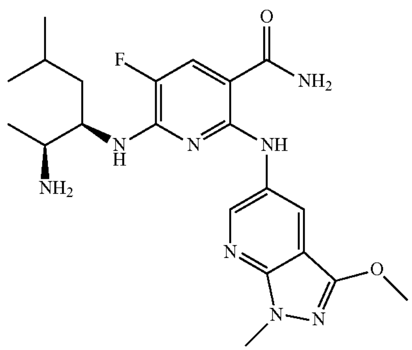 [SMILES: COc1nn(C)c2ncc(Nc3nc(N[C@H](CC(C)C)[C@H](C)N)c(F)cc3C(N)=O)cc12] | 6-(((2S,3R)-2-amino-5-methylhexan-3-yl)amino)-5-fluoro-2-((3-methoxy-1-methyl-1H-pyrazolo[3,4-b]pyridin-5-yl)amino)nicotinamide | 445 | 1 | |
| Example 2-256 | 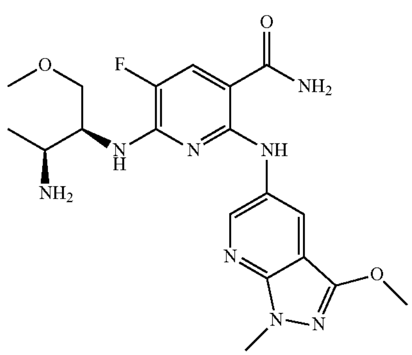 [SMILES: COC[C@@H](Nc1nc(Nc2cnc3c(c2)c(OC)nn3C)c(C(N)=O)cc1F)[C@H](C)N] | 6-(((2S,3S)-3-amino-1-methoxybutan-2-yl)amino)-5-fluoro-2-((3-methoxy-1-methyl-1H-pyrazolo[3,4-b]pyridin-5-yl)amino)nicotinamide | 433 | 0.82 | |

TABLE 3-continued

| Example | Structure | Compound name | MS (ESI m/z): (M + H) | RT (min) | HNMR |
|---|---|---|---|---|---|
| Example 2-257 | 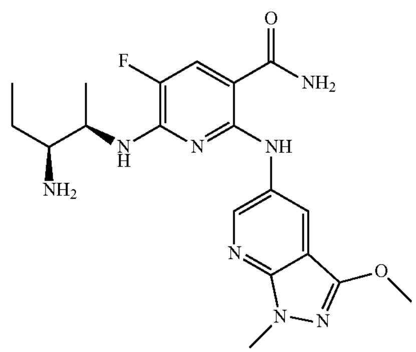 [SMILES: CC[C@H](N)[C@@H](C)Nc1nc(Nc2cnc3c(c2)c(OC)nn3C)c(C(N)=O)cc1F] | 6-(((2R,3S)-3-aminopentan-2-yl)amino)-5-fluoro-2-((3-methoxy-1-methyl-1H-pyrazolo[3,4-b]pyridin-5-yl)amino)nicotinamide | 417 | 0.83 | |
| Example 2-258 | 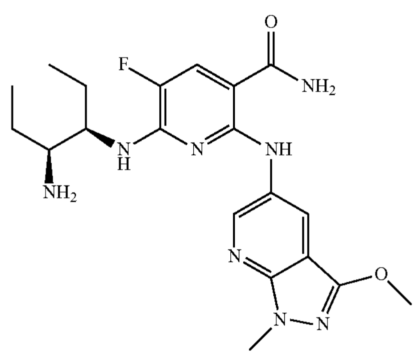 [SMILES: CC[C@H](N)[C@@H](CC)Nc1nc(Nc2cnc3c(c2)c(OC)nn3C)c(C(N)=O)cc1F] | 6-(((3R,4S)-4-aminohexan-3-yl)amino)-5-fluoro-2-((3-methoxy-1-methyl-1H-pyrazolo[3,4-b]pyridin-5-yl)amino)nicotinamide | 431 | 0.89 | |

TABLE 3-continued

| Example | Structure | Compound name | MS (ESI m/z): (M + H) | RT (min) | HNMR |
|---|---|---|---|---|---|
| Example 2-259 | 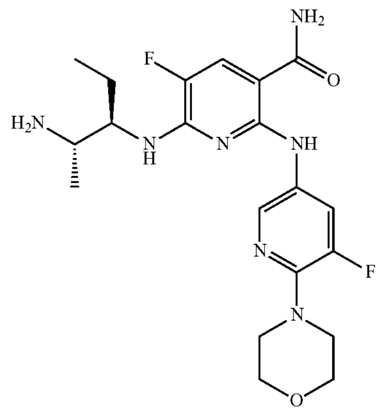 [SMILES: CC[C@@H](Nc1nc(Nc2cnc(N3CCOCC3)c(F)c2)c(C(N)=O)cc1F)[C@H](C)N] | 6-(((2S,3R)-2-aminopentan-3-yl)amino)-5-fluoro-2-((5-fluoro-6-morpholinopyridin-3-yl)amino)nicotinamide | 436 | 0.89 | |
| Example 2-260 | 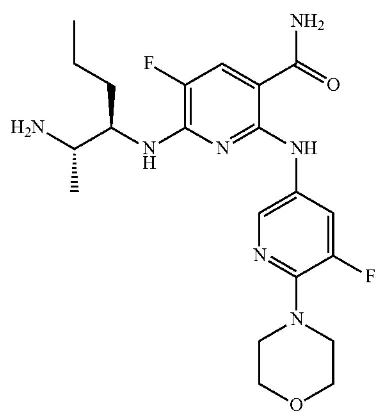 [SMILES: CCC[C@@H](Nc1nc(Nc2cnc(N3CCOCC3)c(F)c2)c(C(N)=O)cc1F)[C@H](C)N] | 6-(((2S,3R)-2-aminohexan-3-yl)amino)-5-fluoro-2-((5-fluoro-6-morpholinopyridin-3-yl)amino)nicotinamide | 450 | 0.95 | |

TABLE 3-continued

| Example | Structure | Compound name | MS (ESI m/z): (M + H) | RT (min) | HNMR |
|---|---|---|---|---|---|
| Example 2-261 | 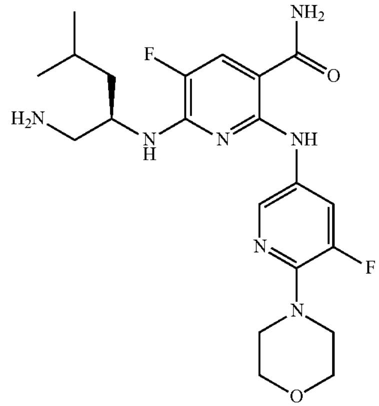 [SMILES: CC(C)C[C@H](CN)Nc1nc(Nc2cnc(N3CCOCC3)c(F)c2)c(C(N)=O)cc1F] | (R)-6-((1-amino-4-methylpentan-2-yl)amino)-5-fluoro-2-((5-fluoro-6-morpholinopyridin-3-yl)amino)nicotinamide | 450 | 1 | |
| Example 2-262 | 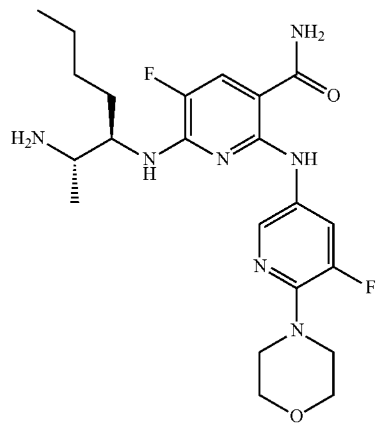 [SMILES: CCCC[C@@H](Nc1nc(Nc2cnc(N3CCOCC3)c(F)c2)c(C(N)=O)cc1F)[C@H](C)N] | 6-(((2S,3R)-2-aminoheptan-3-yl)amino)-5-fluoro-2-((5-fluoro-6-morpholinopyridin-3-yl)amino)nicotinamide | 464 | 1.03 | |

TABLE 3-continued

| Example | Structure | Compound name | MS (ESI m/z): (M + H) | RT (min) | HNMR |
|---|---|---|---|---|---|
| Example 2-263 | 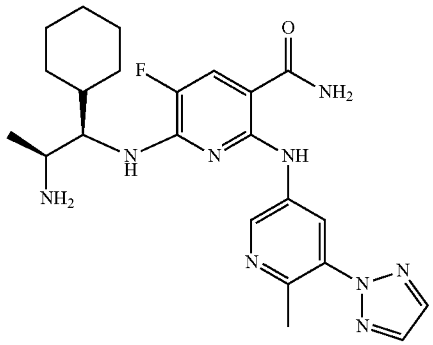 [SMILES: Cc1ncc(Nc2nc(N[C@H](C3CCCCC3)[C@H](C)N)c(F)cc2C(N)=O)cc1-n1nccn1] | 6-(((1R,2S)-2-amino-1-cyclohexylpropyl)amino)-5-fluoro-2-((6-methyl-5-(2H-1,2,3-triazol-2-yl)pyridin-3-yl)amino)nicotinamide | 468 | 1.06 | |
| Example 2-264 | 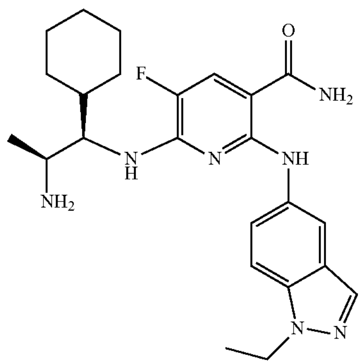 [SMILES: CCn1ncc2cc(Nc3nc(N[C@H](C4CCCCC4)[C@H](C)N)c(F)cc3C(N)=O)ccc21] | 6-(((1R,2S)-2-amino-1-cyclohexylpropyl)amino)-2-((1-ethyl-1H-indazol-5-yl)amino)-5-fluoronicotinamide | 454 | 1.11 | |

TABLE 3-continued

| Example | Structure | Compound name | MS (ESI m/z): (M + H) | RT (min) | HNMR |
|---|---|---|---|---|---|
| Example 2-265 | 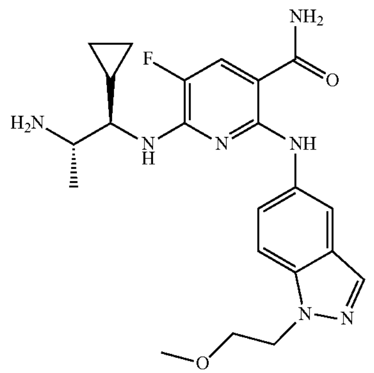 [SMILES: COCCn1ncc2cc(Nc3nc(N[C@H](C4CC4)[C@H](C)N)c(F)cc3C(N)=O)ccc21] | 6-(((1R,2S)-2-amino-1-cyclopropylpropyl)amino)-5-fluoro-2-((1-(2-methoxyethyl)-1H-indazol-5-yl)amino)nicotinamide | 442 | 0.87 | 1H-NMR (MeOD) δ: 7.96 (1H, s), 7.86 (1H, s), 7.74 (1H, d, J = 12.1 Hz), 7.56 (1H, d, J = 8.9 Hz), 7.42-7.32 (1H, m), 4.56 (2H, t, J = 5.1 Hz), 3.82 (2H, t, J = 4.8 Hz), 3.67-3.45 (2H, m), 3.28 (3H, s), 1.28 (3H, d, J = 6.9 Hz), 1.13-0.98 (1H, m), 0.80-0.55 (2H, m), 0.43 (2H, d, J = 4.6 Hz). |
| Example 2-266 | 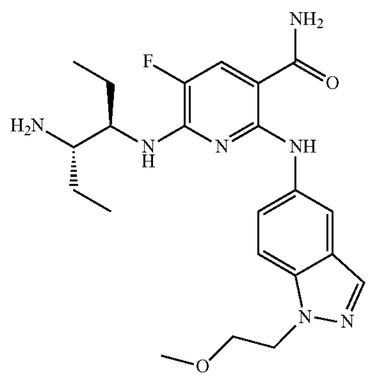 [SMILES: CC[C@H](N)[C@@H](CC)Nc1nc(Nc2ccc3c(cnn3CCOC)c2)c(C(N)=O)cc1F] | 6-(((3R,4S)-4-aminohexan-3-yl)amino)-5-fluoro-2-((1-(2-methoxyethyl)-1H-indazol-5-yl)amino)nicotinamide | 444 | 0.9 | |
| Example 2-267 | 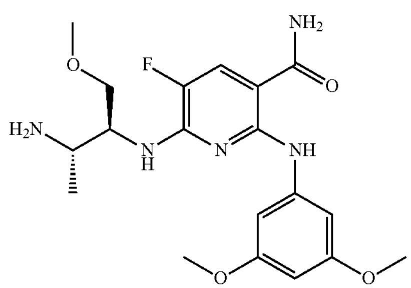 [SMILES: COC[C@@H](Nc1nc(Nc2cc(OC)cc(OC)c2)c(C(N)=O)cc1F)[C@H](C)N] | 6-(((2S,3S)-3-amino-1-methoxybutan-2-yl)amino)-2-((3,5-dimethoxyphenyl)amino)-5-fluoronicotinamide | 408 | 0.92 | 1H-NMR (MeOD) δ: 7.76 (1H, d, J = 11.9 Hz), 6.75 (2H, d, J = 2.3 Hz), 6.19 (1H, t, J = 2.3 Hz), 4.51-4.44 (1H, m), 3.91-3.83 (1H, m), 3.77 (6H, s), 3.68-3.60 (1H, m), 3.43 (3H, s), 3.40-3.34 (1H, m), 1.39 (3H, d, J = 6.9 Hz), |

TABLE 3-continued

| Example | Structure | Compound name | MS (ESI m/z): (M + H) | RT (min) | HNMR |
|---|---|---|---|---|---|
| Example 2-268 | 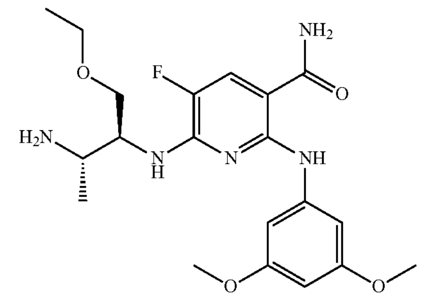 [SMILES: CCOC[C@@H](Nc1nc(Nc2cc(OC)cc(OC)c2)c(C(N)=O)cc1F)[C@H](C)N] | 6-(((2S,3S)-3-amino-1-ethoxybutan-2-yl)amino)-2-((3,5-dimethoxyphenyl)amino)-5-fluoronicotinamide | 422 | 0.99 | |
| Example 2-269 | 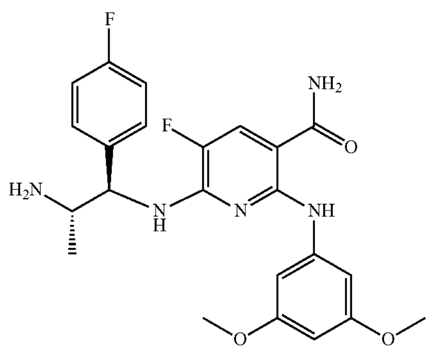 [SMILES: COc1cc(Nc2nc(N[C@H](c3ccc(F)cc3)[C@H](C)N)c(F)cc2C(N)=O)cc(OC)c1] | 6-(((1R,2S)-2-amino-1-(4-fluorophenyl)propyl)amino)-2-((3,5-dimethoxyphenyl)amino)-5-fluoronicotinamide | 458 | 1.04 | |
| Example 2-270 | 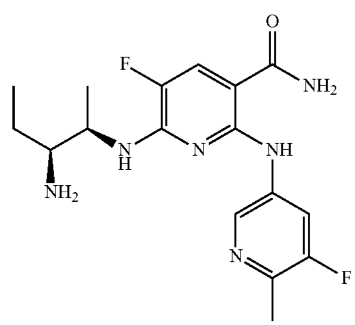 [SMILES: CC[C@H](N)[C@@H](C)Nc1nc(Nc2cnc(C)c(F)c2)c(C(N)=O)cc1F] | 6-(((2R,3S)-3-aminopentan-2-yl)amino)-5-fluoro-2-((5-fluoro-6-methylpyridin-3-yl)amino)nicotinamide | 365 | 0.79 | 1H-NMR (DMSO-d6) δ: 11.89 (1H, s), 8.55 (1H, s), 8.20-8.02 (4H, m), 7.99 (1H, d, J = 12.6 Hz), 7.98-7.70 (1H, m), 7.46-7.20 (2H, m), 4.40-4.26 (1H, m), 3.32-3.17 (1H, m), 2.43 (3H, d, J = 2.7 Hz), 1.72-1.57 (2H, m), 1.26 (3H, d, J = 7.2 Hz), 0.89 (3H, t, J = 7.4 Hz) |

TABLE 3-continued

| Example | Structure | Compound name | MS (ESI m/z): (M + H) | RT (min) | HNMR |
|---|---|---|---|---|---|
| Example 2-271 | 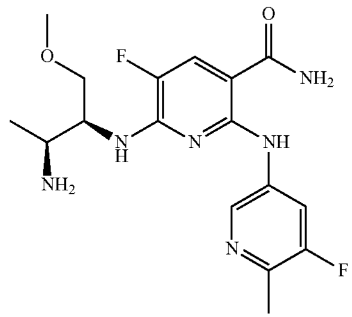 [SMILES: COC[C@@H](Nc1nc(Nc2cnc(C)c(F)c2)c(C(N)=O)cc1F)[C@H](C)N] | 6-(((2S,3S)-3-amino-1-methoxybutan-2-yl)amino)-5-fluoro-2-((5-fluoro-6-methylpyridin-3-yl)amino)nicotinamide | 381 | 0.76 | 1H-NMR (DMSO-d6) δ: 11.78 (1H, s), 8.39 (1H, s), 8.10-8.02 (1H, m), 7.97 (1H, d, J = 12.3 Hz), 7.90-7.72 (4H, m), 7.50-7.25 (1H, m), 7.06 (1H, d, J = 8.7 Hz), 4.46-4.34 (1H, m), 3.60-3.40 (3H, m), 3.30 (3H, s), 2.39 (3H, d, J = 2.7 Hz), 1.26 (3H, d, J = 6.6 Hz) |
| Example 2-272 | 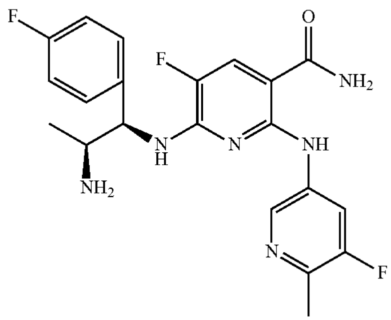 [SMILES: Cc1ncc(Nc2nc(N[C@H](c3ccc(F)cc3)[C@H](C)N)c(F)cc2C(N)=O)cc1F] | 6-(((1R,2S)-2-amino-1-(4-fluorophenyl)propyl)amino)-5-fluoro-2-((5-fluoro-6-methylpyridin-3-yl)amino)nicotinamide | 431 | 0.92 | 1H-NMR (DMSO-d6) δ: 11.81 (1H, s), 8.36 (1H, s), 8.02-7.80 (6H, m), 7.75 (1H, d, J = 7.8 Hz), 7.60-7.50 (2H, m), 7.48-7.26 (1H, m), 7.25-7.14 (1H, m), 5.38-5.28 (2H, m), 3.80-3.60 (1H, m), 2.43 (3H, d, J = 2.4 Hz), 1.26 (3H, d, J = 6.6 Hz) |
| Example 2-273 | 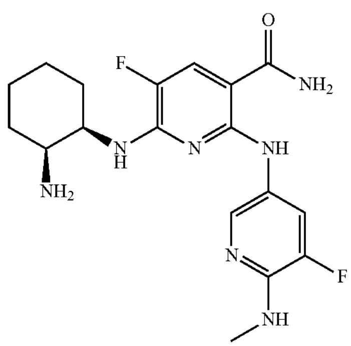 [SMILES: CNc1ncc(Nc2nc(N[C@@H]3CCCC[C@@H]3N)c(F)cc2C(N)=O)cc1F] | 6-(((1R,2S)-2-aminocyclohexyl)amino)-5-fluoro-2-((5-fluoro-6-(methylamino)pyridin-3-yl)amino)nicotinamide | 392 | 0.68 | 1H-NMR (DMSO-d6) δ: 11.23 (1H, s), 8.06-7.65 (7H, m), 7.45-7.10 (1H, m), 6.86 (1H, d, J = 6.6 Hz), 4.26-4.11 (1H, m), 3.40-3.22 (1H, m), 2.92 (3H, s), 1.90-1.75 (2H, m), 1.75-1.52 (4H, m), 1.50-1.33 (2H, m) |

TABLE 3-continued

| Example | Structure | Compound name | MS (ESI m/z): (M + H) | RT (min) | HNMR |
|---|---|---|---|---|---|
| Example 2-274 | 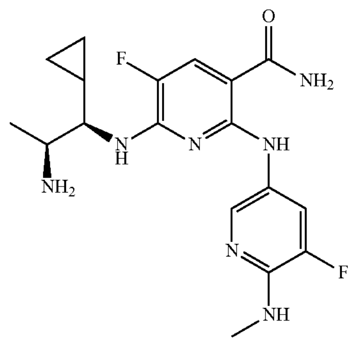 [SMILES: CNc1ncc(Nc2nc(N[C@H](C3CC3)[C@H](C)N)c(F)cc2C(N)=O)cc1F] | 6-(((1R,2S)-2-amino-1-cyclopropylpropyl)amino)-5-fluoro-2-((5-fluoro-6-(methylamino)pyridin-3-yl)amino)nicotinamide | 392 | 0.67 | |
| Example 2-275 | 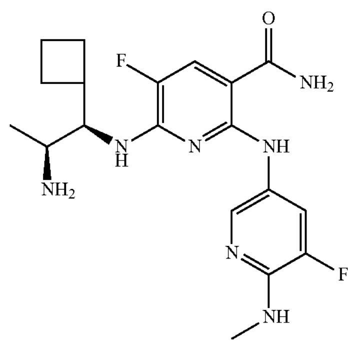 [SMILES: CNc1ncc(Nc2nc(N[C@H](C3CCC3)[C@H](C)N)c(F)cc2C(N)=O)cc1F] | 6-(((1R,2S)-2-amino-1-cyclobutylpropyl)amino)-5-fluoro-2-((5-fluoro-6-(methylamino)pyridin-3-yl)amino)nicotinamide | 406 | 0.77 | 1H-NMR (DMSO-d6) δ: 11.46 (1H, s), 8.50-8.22 (1H, m), 8.10-7.50 (6H, m), 7.45-7.12 (1H, m), 7.02-6.87 (1H, m), 4.46-4.32 (1H, m), 3.40-3.22 (1H, m), 2.97 (3H, s), 2.75-2.55 (1H, m), 2.07-1.60 (6H, m), 1.19 (3H, d, J = 6.6 Hz) |
| Example 2-276 | 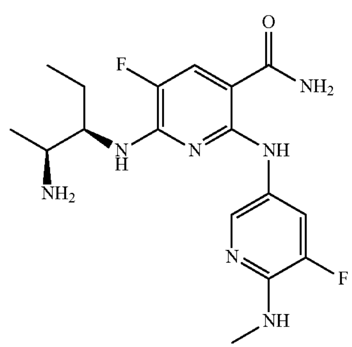 [SMILES: CC[C@@H](Nc1nc(Nc2cnc(NC)c(F)c2)c(C(N)=O)cc1F)[C@H](C)N] | 6-(((2S,3R)-2-aminopentan-3-yl)amino)-5-fluoro-2-((5-fluoro-6-(methylamino)pyridin-3-yl)amino)nicotinamide | 380 | 0.65 | 1H-NMR (DMSO-d6) δ: 11.40 (1H, s), 8.40-8.16 (1H, m), 8.10-7.65 (6H, m), 7.40-7.12 (1H, m), 7.07-6.92 (1H, m), 4.28-4.07 (1H, m), 3.40-3.25 (1H, m), 2.93 (3H, s), 1.80-1.63 (1H, m), 1.63-1.44 (1H, m), 1.21 (3H, d, J = 6.9 Hz), 0.86 (3H, t, J = 6.6 Hz) |

TABLE 3-continued

| Example | Structure | Compound name | MS (ESI m/z): (M + H) | RT (min) | HNMR |
|---|---|---|---|---|---|
| Example 2-277 | 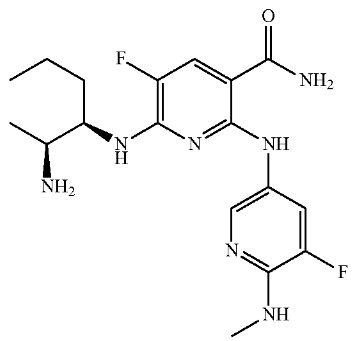 [SMILES: CCC[C@@H](Nc1nc(Nc2cnc(NC)c(F)c2)c(C(N)=O)cc1F)[C@H](C)N] | 6-(((2S,3R)-2-aminohexan-3-yl)amino)-5-fluoro-2-((5-fluoro-6-(methylamino)pyridin-3-yl)amino)nicotinamide | 394 | 0.74 | 1H-NMR (DMSO-d6) δ: 11.44 (1H, s), 8.48-8.24 (1H, m), 8.15-7.60 (6H, m), 7.40-7.16 (1H, m), 7.10-6.94 (1H, m), 4.36-4.19 (1H, m), 3.40-3.25 (1H, m), 2.95 (3H, s), 1.70-1.48 (2H, m), 1.45-1.23 (2H, m), 1.21 (3H, d, J = 6.6 Hz), 0.83 (3H, t, J = 7.2 Hz) |
| Example 2-278 | 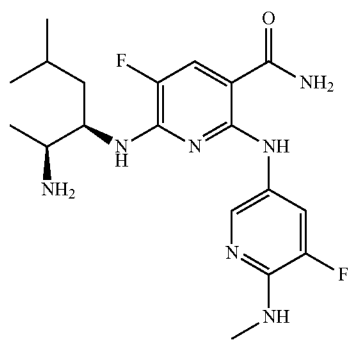 [SMILES: CNc1ncc(Nc2nc(N[C@H](CC(C)C)[C@H](C)N)c(F)cc2C(N)=O)cc1F] | 6-(((2S,3R)-2-amino-5-methylhexan-3-yl)amino)-5-fluoro-2-((5-fluoro-6-(methylamino)pyridin-3-yl)amino)nicotinamide | 408 | 0.82 | 1H-NMR (DMSO-d6) δ: 11.21 (1H, s), 8.12-7.60 (8H, m), 6.98-6.88 (1H, m), 4.28-4.14 (1H, m), 3.40-3.25 (1H, m), 2.87 (3H, s), 1.64-1.49 (2H, m), 1.40-1.20 (1H, m), 1.16 (3H, d, J = 7.2 Hz), 0.89 (3H, d, J = 6.6 Hz), 0.76 (3H, d, J = 6.6 Hz) |
| Example 2-279 | 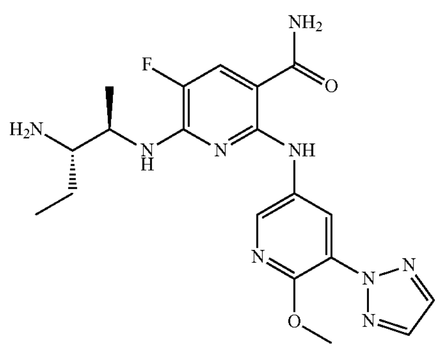 [SMILES: CC[C@H](N)[C@@H](C)Nc1nc(Nc2cnc(OC)c(-n3nccn3)c2)c(C(N)=O)cc1F] | 6-(((2R,3S)-3-aminopentan-2-yl)amino)-5-fluoro-2-((6-methoxy-5-(2H-1,2,3-triazol-2-yl)pyridin-3-yl)amino)nicotinamide | 430 | 0.82 | |

TABLE 3-continued

| Example | Structure | Compound name | MS (ESI m/z): (M + H) | RT (min) | HNMR |
|---|---|---|---|---|---|
| Example 2-280 | 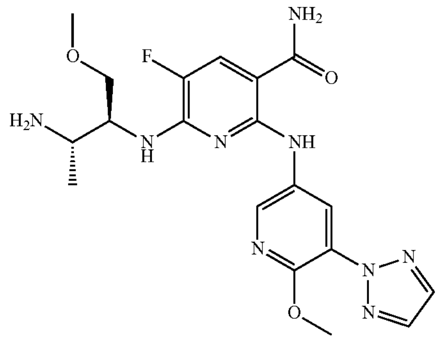 [SMILES: COC[C@@H](Nc1nc(Nc2cnc(OC)c(-n3nccn3)c2)c(C(N)=O)cc1F)[C@H](C)N] | 6-(((2S,3S)-3-amino-1-methoxybutan-2-yl)amino)-5-fluoro-2-((6-methoxy-5-((2H-1,2,3-triazol-2-yl)pyridin-3-yl)amino)nicotinamide | 446 | 0.81 | |
| Example 2-281 | 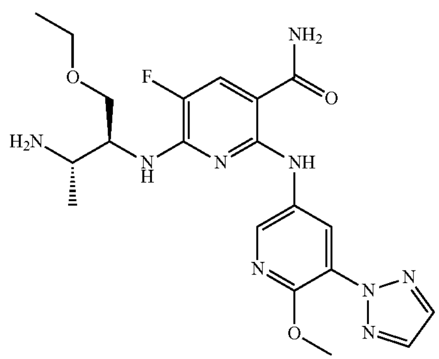 [SMILES: CCOC[C@@H](Nc1nc(Nc2cnc(OC)c(-n3nccn3)c2)c(C(N)=O)cc1F)[C@H](C)N] | 6-(((2S,3S)-3-amino-1-ethoxybutan-2-yl)amino)-5-fluoro-2-((6-methoxy-5-(2H-1,2,3-triazol-2-yl)pyridin-3-yl)amino)nicotinamide | 460 | 0.88 | |
| Example 2-282 | 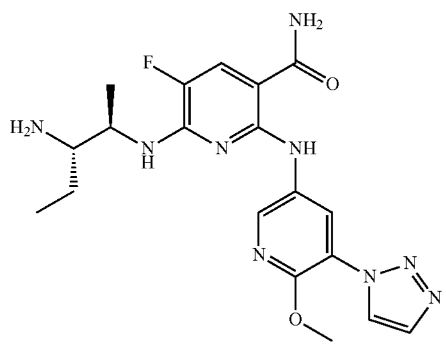 [SMILES: CC[C@H](N)[C@@H](C)Nc1nc(Nc2cnc(OC)c(-n3ccnn3)c2)c(C(N)=O)cc1F] | 6-(((2R,3S)-3-aminopentan-2-yl)amino)-5-fluoro-2-((6-methoxy-5-(1H-1,2,3-triazol-1-yl)pyridin-3-yl)amino)nicotinamide | 430 | 0.84 | |

TABLE 3-continued

| Example | Structure | Compound name | MS (ESI m/z): (M + H) | RT (min) | HNMR |
|---|---|---|---|---|---|
| Example 2-283 | 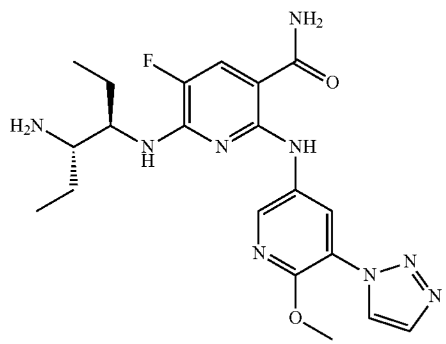 [SMILES: CC[C@H](N)[C@@H](CC)Nc1nc(Nc2cnc(OC)c(-n3ccnn3)c2)c(C(N)=O)cc1F] | 6-(((3R,4S)-4-aminohexan-3-yl)amino)-5-fluoro-2-((6-methoxy-5-(1H-1,2,3-triazol-1-yl)pyridin-3-yl)amino)nicotinamide | 444 | 0.89 | |
| Example 2-284 | 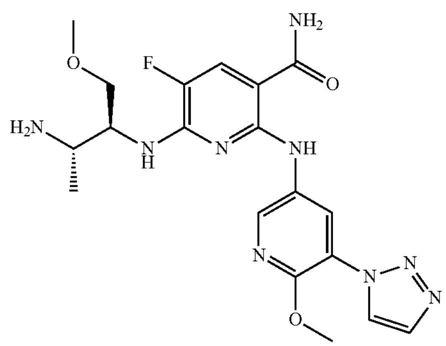 [SMILES: COC[C@@H](Nc1nc(Nc2cnc(OC)c(-n3ccnn3)c2)c(C(N)=O)cc1F)[C@H](C)N] | 6-(((2S,3S)-3-amino-1-methoxybutan-2-yl)amino)-5-fluoro-2-((6-methoxy-5-(1H-1,2,3-triazol-1-yl)pyridin-3-yl)amino)nicotinamide | 446 | 0.82 | |

| Example | Structure | Compound name | MS (ESI m/z): (M + H) | RT (min) | HNMR |
|---|---|---|---|---|---|
| Example 2-285 | 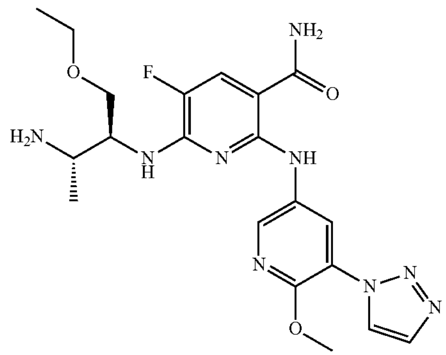 [SMILES: CCOC[C@@H](Nc1nc(Nc2cnc(OC)c(-n3ccnn3)c2)c(C(N)=O)cc1F)[C@H](C)N] | 6-(((2S,3S)-3-amino-1-ethoxybutan-2-yl)amino)-5-fluoro-2-(((6-methoxy-5-(1H-1,2,3-triazol-1-yl)pyridin-3-yl)amino)nicotinamide | 460 | 0.89 | |
| Example 2-286 | 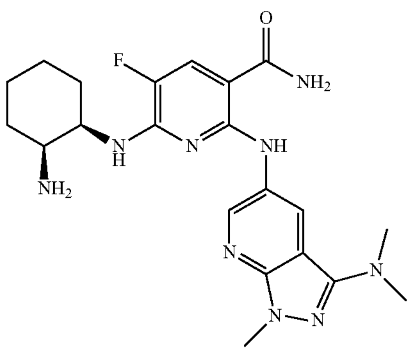 [SMILES: CN(C)c1nn(C)c2ncc(Nc3nc(N[C@@H]4CCCC[C@@H]4N)c(F)cc3C(N)=O)cc12] | 6-(((1R,2S)-2-aminocyclohexyl)amino)-2-((3-(dimethylamino)-1-methyl-1H-pyrazolo[3,4-b]pyridin-5-yl)amino)-5-fluoronicotinamide | 442 | 0.87 | |

TABLE 3-continued

| Example | Structure | Compound name | MS (ESI m/z): (M + H) | RT (min) | HNMR |
|---|---|---|---|---|---|
| Example 2-287 | 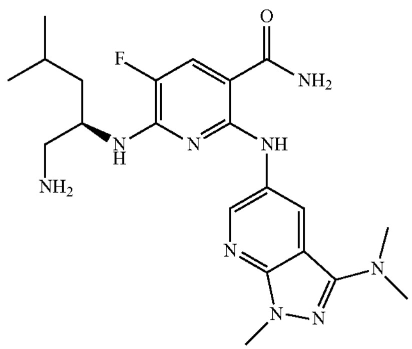 [SMILES: CC(C)C[C@H](CN)Nc1nc(Nc2cnc3c(c2)c(N(C)C)nn3C)c(C(N)=O)cc1F] | (R)-6-((1-amino-4-methylpentan-2-yl)amino)-2-((3-(dimethylamino)-1-methyl-1H-pyrazolo[3,4-b]pyridin-5-yl)amino)-5-fluoronicotinamide | 444 | 0.95 | |
| Example 2-288 | 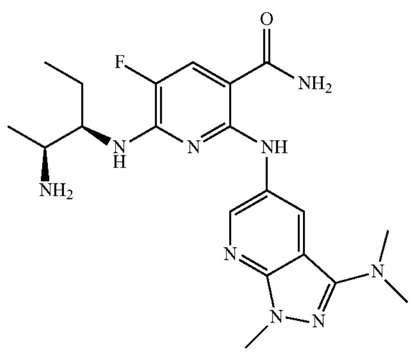 [SMILES: CC[C@@H](Nc1nc(Nc2cnc3c(c2)c(N(C)C)nn3C)c(C(N)=O)cc1F)[C@H](C)N] | 6-(((2S,3R)-2-aminopentan-3-yl)amino)-2-((3-(dimethylamino)-1-methyl-1H-pyrazolo[3,4-b]pyridin-5-yl)amino)-5-fluoronicotinamide | 430 | 0.84 | |
| Example 2-289 | 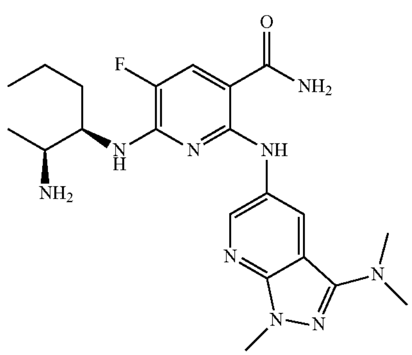 [SMILES: CCC[C@@H](Nc1nc(Nc2cnc3c(c2)c(N(C)C)nn3C)c(C(N)=O)cc1F)[C@H](C)N] | 6-(((2S,3R)-2-aminohexan-3-yl)amino)-2-((3-(dimethylamino)-1-methyl-1H-pyrazolo[3,4-b]pyridin-5-yl)amino)-5-fluoronicotinamide | 444 | 0.91 | |

TABLE 3-continued
| Example | Structure | Compound name | MS (ESI m/z): (M + H) | RT (min) | HNMR |
|---|---|---|---|---|---|
| Example 2-290 | 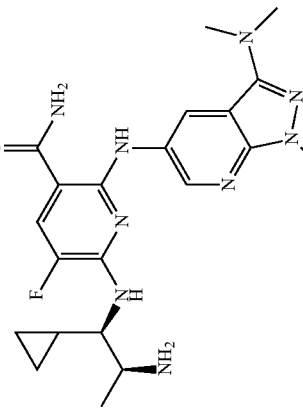 | 6-(((1R,2S)-2-amino-1-cyclopropylpropyl)amino)-2-((3-(dimethylamino)-1-methyl-1H-pyrazolo[3,4-b]pyridin-5-yl)amino)-5-fluoronicotinamide | 442 | 0.86 | |
| Example 2-291 | 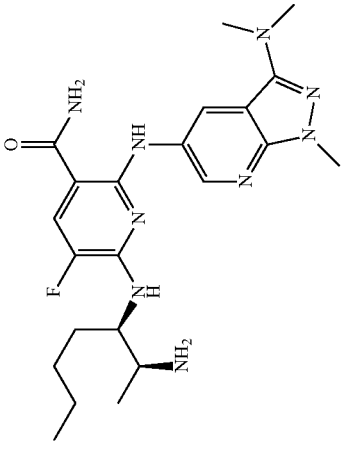 | 6-(((2S,3R)-2-aminoheptan-3-yl)amino)-2-((3-(dimethylamino)-1-methyl-1H-pyrazolo[3,4-b]pyridin-5-yl)amino)-5-fluoronicotinamide | 458 | 0.98 | |

TABLE 3-continued

| Example | Structure | Compound name | MS (ESI m/z): (M + H) | RT (min) | HNMR |
|---|---|---|---|---|---|
| Example 2-292 | 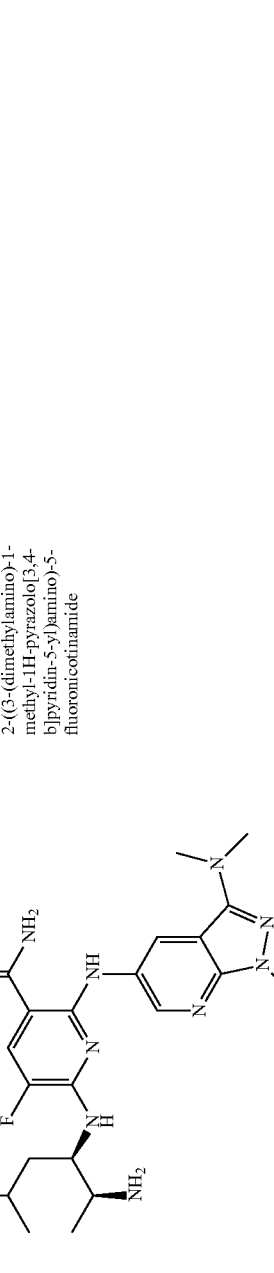 | 6-(((2S,3R)-2-amino-5-methylhexan-3-yl)amino)-2-((3-(dimethylamino)-1-methyl-1H-pyrazolo[3,4-b]pyridin-5-yl)amino)-5-fluoronicotinamide | 458 | 0.97 | |
| Example 2-293 | 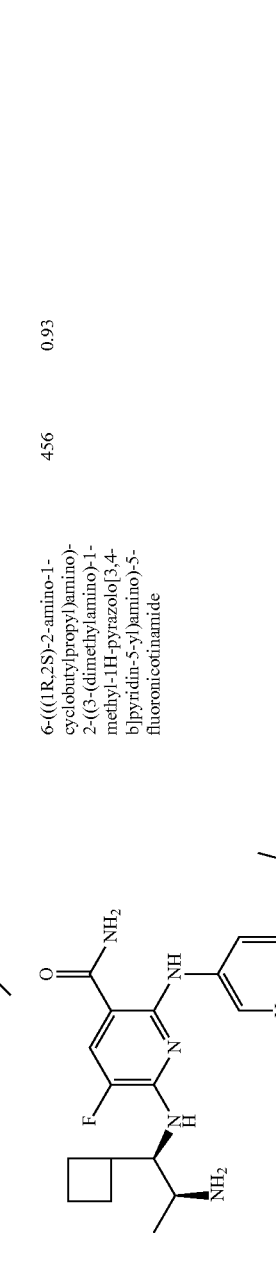 | 6-(((1R,2S)-2-amino-1-cyclobutylpropyl)amino)-2-((3-(dimethylamino)-1-methyl-1H-pyrazolo[3,4-b]pyridin-5-yl)amino)-5-fluoronicotinamide | 456 | 0.93 | |
| Example 2-294 | 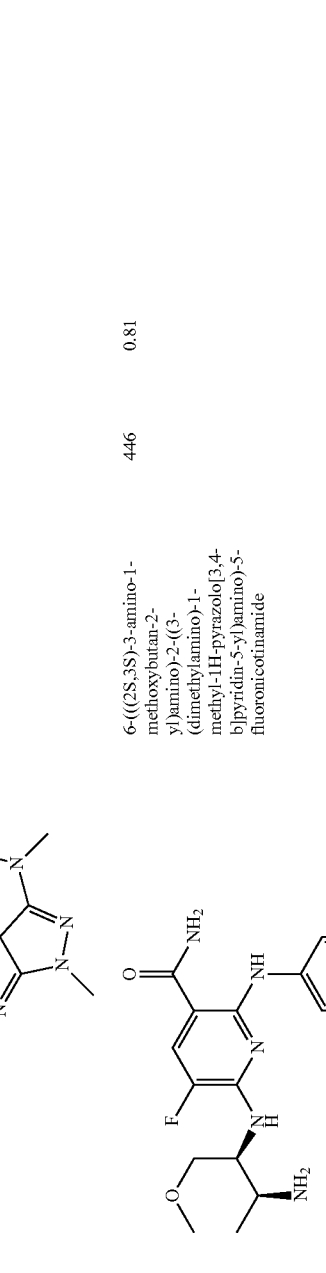 | 6-(((2S,3S)-3-amino-1-methoxybutan-2-yl)amino)-2-((3-(dimethylamino)-1-methyl-1H-pyrazolo[3,4-b]pyridin-5-yl)amino)-5-fluoronicotinamide | 446 | 0.81 | |

TABLE 3-continued

| Example | Structure | Compound name | MS (ESI m/z): (M + H) | RT (min) | HNMR |
|---|---|---|---|---|---|
| Example 2-295 | 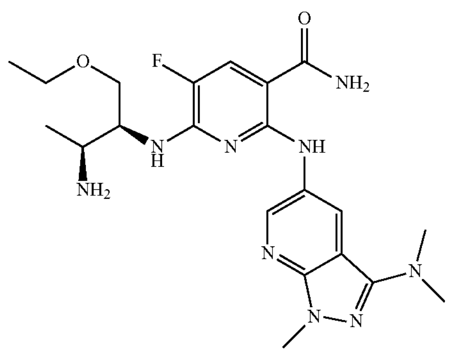 [SMILES: CCOC[C@@H](Nc1nc(Nc2cnc3c(c2)c(N(C)C)nn3C)c(C(N)=O)cc1F)[C@H](C)N] | 6-(((2S,3S)-3-amino-1-ethoxybutan-2-yl)amino)-2-((3-(dimethylamino)-1-methyl-1H-pyrazolo[3,4-b]pyridin-5-yl)amino)-5-fluoronicotinamide | 460 | 0.87 | |
| Example 2-296 | 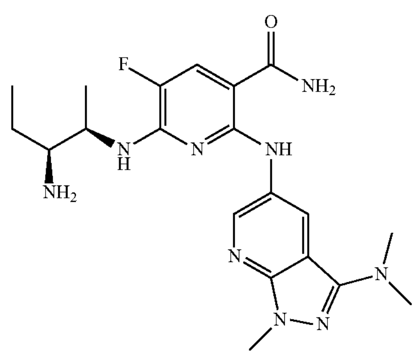 [SMILES: CC[C@H](N)[C@@H](C)Nc1nc(Nc2cnc3c(c2)c(N(C)C)nn3C)c(C(N)=O)cc1F] | 6-(((2R,3S)-3-aminopentan-2-yl)amino)-2-((3-(dimethylamino)-1-methyl-1H-pyrazolo[3,4-b]pyridin-5-yl)amino)-5-fluoronicotinamide | 430 | 0.81 | |

TABLE 3-continued

| Example | Structure | Compound name | MS (ESI m/z): (M + H) | RT (min) | HNMR |
|---|---|---|---|---|---|
| Example 2-297 | 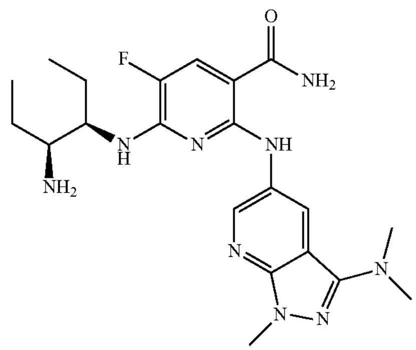 [SMILES: CC[C@H](N)[C@@H](CC)Nc1nc(Nc2cnc3c(c2)c(N(C)C)nn3C)c(C(N)=O)cc1F] | 6-(((3R,4S)-4-aminohexan-3-yl)amino)-2-((3-(dimethylamino)-1-methyl-1H-pyrazolo[3,4-b]pyridin-5-yl)amino)-5-fluoronicotinamide | 444 | 0.87 | |
| Example 2-298 | 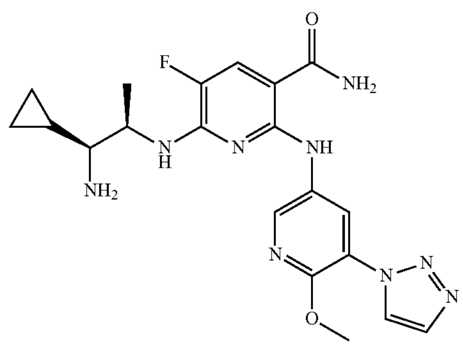 [SMILES: COc1ncc(Nc2nc(N[C@H](C)[C@@H](N)C3CC3)c(F)cc2C(N)=O)cc1-n1ccnn1] | 6-(((1S,2R)-1-amino-1-cyclopropylpropan-2-yl)amino)-5-fluoro-2-((6-methoxy-5-(1H-1,2,3-triazol-1-yl)pyridin-3-yl)amino)nicotinamide | 442 | 0.86 | |
| Example 2-299 | 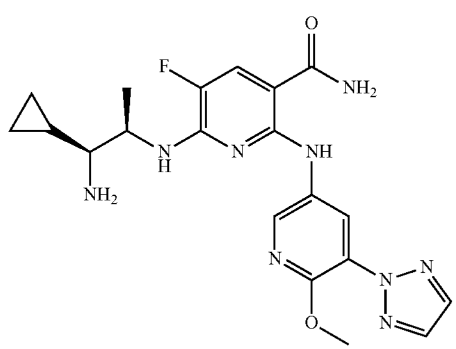 [SMILES: COc1ncc(Nc2nc(N[C@H](C)[C@@H](N)C3CC3)c(F)cc2C(N)=O)cc1-n1nccn1] | 6-(((1S,2R)-1-amino-1-cyclopropylpropan-2-yl)amino)-5-fluoro-2-((6-methoxy-5-(2H-1,2,3-triazol-2-yl)pyridin-3-yl)amino)nicotinamide | 442 | 0.86 | |

TABLE 3-continued

| Example | Structure | Compound name | MS (ESI m/z): (M + H) | RT (min) | HNMR |
|---|---|---|---|---|---|
| Example 2-300 | 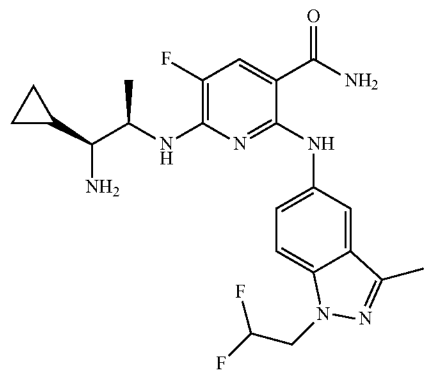 [SMILES: Cc1nn(CC(F)F)c2ccc(Nc3nc(N[C@H](C)[C@@H](N)C4CC4)c(F)cc3C(N)=O)cc12] | 6-(((1S,2R)-1-amino-1-cyclopropylpropan-2-yl)amino)-2-((1-(2,2-difluoroethyl)-3-methyl-1H-indazol-5-yl)amino)-5-fluoronicotinamide | 462 | 0.94 | |
| Example 2-301 | 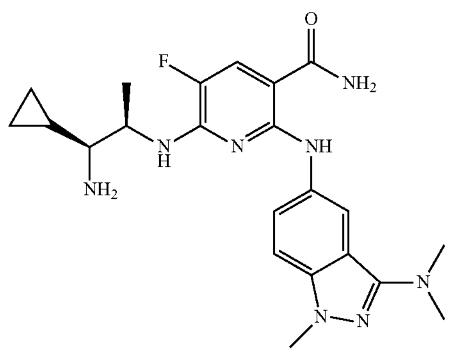 [SMILES: C[C@@H](Nc1nc(Nc2ccc3c(c2)c(N(C)C)nn3C)c(C(N)=O)cc1F)[C@@H](N)C1CC1] | 6-(((1S,2R)-1-amino-1-cyclopropylpropan-2-yl)amino)-2-((3-(dimethylamino)-1-methyl-1H-indazol-5-yl)amino)-5-fluoronicotinamide | 441 | 0.86 | |

TABLE 3-continued

| Example | Structure | Compound name | MS (ESI m/z): (M + H) | RT (min) | HNMR |
|---|---|---|---|---|---|
| Example 2-302 | 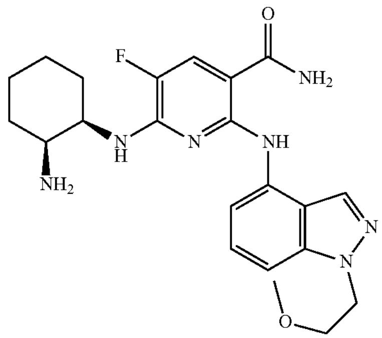 [SMILES: COCCn1ncc2c(Nc3nc(N[C@@H]4CCCC[C@@H]4N)c(F)cc3C(N)=O)cccc21] | 6-(((1R,2S)-2-aminocyclohexyl)amino)-5-fluoro-2-((1-(2-methoxyethyl)-1H-indazol-4-yl)amino)nicotinamide | 442 | 0.93 | 1H-NMR (MeOD) δ: 8.11 (1H, s), 7.86 (1H, d, J = 7.9 Hz), 7.82 (1H, t, J = 6.9 Hz), 7.39-7.34 (1H, m), 7.20 (1H, d, J = 7.9 Hz), 4.55 (2H, t, J = 5.3 Hz), 4.38-4.37 (1H, m), 3.90-3.87 (1H, m), 3.83 (2H, t, J = 5.3 Hz), 3.27 (3H, s), 1.93-1.75 (8H, m). |
| Example 2-303 | 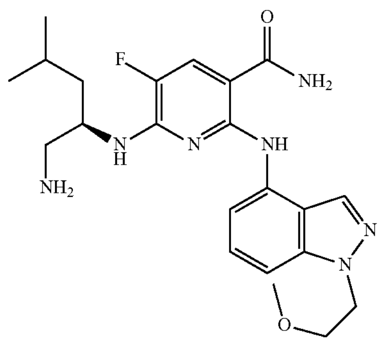 [SMILES: COCCn1ncc2c(Nc3nc(N[C@@H](CN)CC(C)C)c(F)cc3C(N)=O)cccc21] | (R)-6-((1-amino-4-methylpentan-2-yl)amino)-5-fluoro-2-((1-(2-methoxyethyl)-1H-indazol-4-yl)amino)nicotinamide | 444 | 1.01 | |
| Example 2-304 | 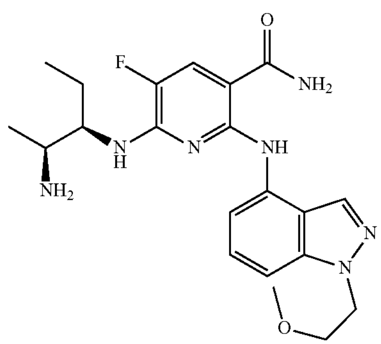 [SMILES: CC[C@@H](Nc1nc(Nc2cccc3c2cnn3CCOC)c(C(N)=O)cc1F)[C@H](C)N] | 6-(((2S,3R)-2-aminopentan-3-yl)amino)-5-fluoro-2-((1-(2-methoxyethyl)-1H-indazol-4-yl)amino)nicotinamide | 430 | 0.89 | |

TABLE 3-continued

| Example | Structure | Compound name | MS (ESI m/z): (M + H) | RT (min) | HNMR |
|---|---|---|---|---|---|
| Example 2-305 | 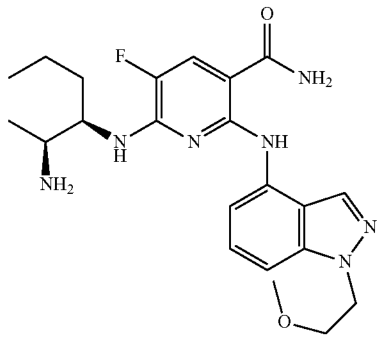 [SMILES: CCC[C@@H](Nc1nc(Nc2cccc3c2cnn3CCOC)c(C(N)=O)cc1F)[C@H](C)N] | 6-(((2S,3R)-2-aminohexan-3-yl)amino)-5-fluoro-2-((1-(2-methoxyethyl)-1H-indazol-4-yl)amino)nicotinamide | 444 | 0.97 | |
| Example 2-306 | 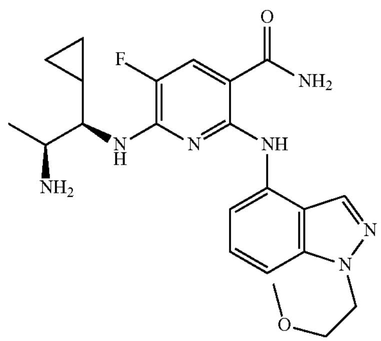 [SMILES: COCCn1ncc2c(Nc3nc(N[C@H](C4CC4)[C@H](C)N)c(F)cc3C(N)=O)cccc21] | 6-(((1R,2S)-2-amino-1-cyclopropylpropyl)amino)-5-fluoro-2-((1-(2-methoxyethyl)-1H-indazol-4-yl)amino)nicotinamide | 442 | 0.9 | |
| Example 2-307 | 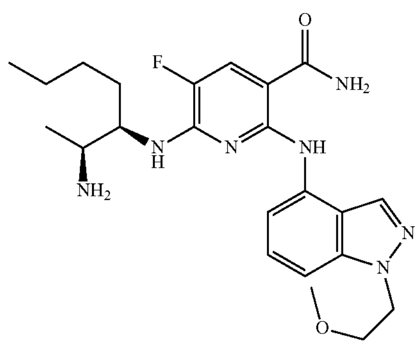 [SMILES: CCCC[C@@H](Nc1nc(Nc2cccc3c2cnn3CCOC)c(C(N)=O)cc1F)[C@H](C)N] | 6-(((2S,3R)-2-aminoheptan-3-yl)amino)-5-fluoro-2-((1-(2-methoxyethyl)-1H-indazol-4-yl)amino)nicotinamide | 458 | 1.05 | |

TABLE 3-continued

| Example | Structure | Compound name | MS (ESI m/z): (M + H) | RT (min) | HNMR |
|---|---|---|---|---|---|
| Example 2-308 | 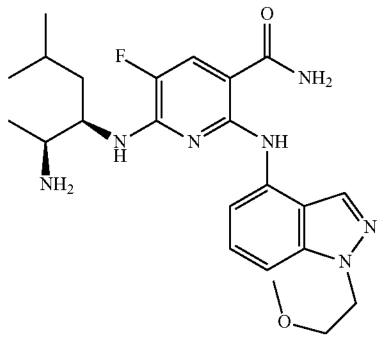 [SMILES: COCCn1ncc2c(Nc3nc(N[C@H](CC(C)C)[C@H](C)N)c(F)cc3C(N)=O)cccc21] | 6-(((2S,3R)-2-amino-5-methylhexan-3-yl)amino)-5-fluoro-2-((1-(2-methoxyethyl)-1H-indazol-4-yl)amino)nicotinamide | 458 | 1.03 | |
| Example 2-309 | 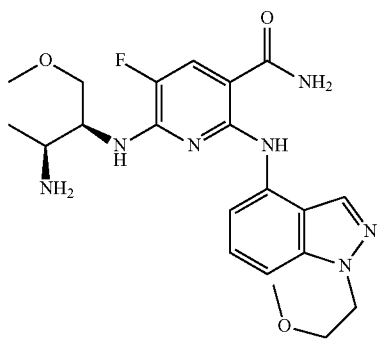 [SMILES: COCCn1ncc2c(Nc3nc(N[C@H](COC)[C@H](C)N)c(F)cc3C(N)=O)cccc21] | 6-(((2S,3S)-3-amino-1-methoxybutan-2-yl)amino)-5-fluoro-2-((1-(2-methoxyethyl)-1H-indazol-4-yl)amino)nicotinamide | 446 | 0.85 | |
| Example 2-310 | 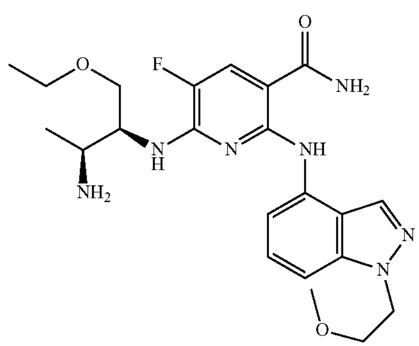 [SMILES: CCOC[C@@H](Nc1nc(Nc2cccc3c2cnn3CCOC)c(C(N)=O)cc1F)[C@H](C)N] | 6-(((2S,3S)-3-amino-1-ethoxybutan-2-yl)amino)-5-fluoro-2-((1-(2-methoxyethyl)-1H-indazol-4-yl)amino)nicotinamide | 460 | 0.92 | |

TABLE 3-continued

| Example | Structure | Compound name | MS (ESI m/z): (M + H) | RT (min) | HNMR |
|---|---|---|---|---|---|
| Example 2-311 | 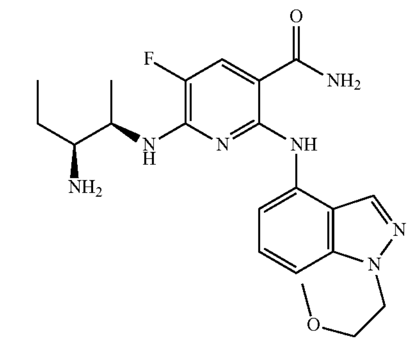 [SMILES: CC[C@H](N)[C@@H](C)Nc1nc(Nc2cccc3c2cnn3CCOC)c(C(N)=O)cc1F] | 6-(((2R,3S)-3-aminopentan-2-yl)amino)-5-fluoro-2-((1-(2-methoxyethyl)-1H-indazol-4-yl)amino)nicotinamide | 430 | 0.88 | |
| Example 2-312 | 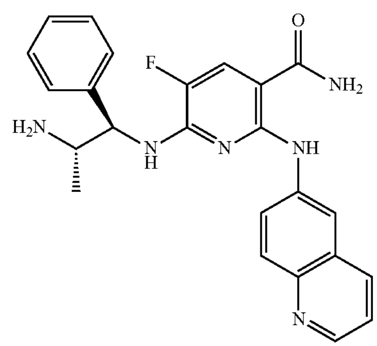 [SMILES: C[C@H](N)[C@H](Nc1nc(Nc2ccc3ncccc3c2)c(C(N)=O)cc1F)c1ccccc1] | 6-(((1R,2S)-2-amino-1-phenylpropyl)amino)-5-fluoro-2-(quinolin-6-ylamino)nicotinamide | 431 | 0.73 | |
| Example 2-313 | 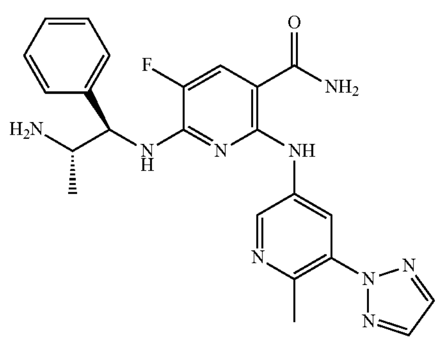 [SMILES: Cc1ncc(Nc2nc(N[C@H](c3ccccc3)[C@H](C)N)c(F)cc2C(N)=O)cc1-n1nccn1] | 6-(((1R,2S)-2-amino-1-phenylpropyl)amino)-5-fluoro-2-((6-methyl-5-(2H-1,2,3-triazol-2-yl)pyridin-3-yl)amino)nicotinamide | 462 | 0.91 | 1H-NMR (MeOD) δ: 9.20 (1H, d, J = 2.3 Hz), 8.84 (1H, d, J = 2.3 Hz), 8.15 (2H, s), 7.89 (1H, d, J = 11.9 Hz), 7.45-7.26 (5H, m), 5.76 (1H, d, J = 6.6 Hz), 3.99-3.90 (1H, m), 2.87 (3H, s), 1.41 (3H, d, J = 6.6 Hz) |

TABLE 3-continued

| Example | Structure | Compound name | MS (ESI m/z): (M + H) | RT (min) | HNMR |
|---|---|---|---|---|---|
| Example 2-314 | 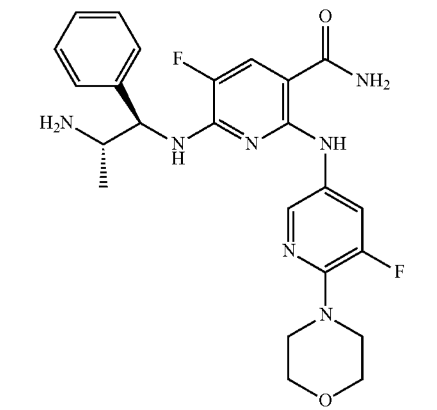 [SMILES: C[C@H](N)[C@H](Nc1nc(Nc2cnc(N3CCOCC3)c(F)c2)c(C(N)=O)cc1F)c1ccccc1] | 6-(((1R,2S)-2-amino-1-phenylpropyl)amino)-5-fluoro-2-((5-fluoro-6-morpholinopyridin-3-yl)amino)nicotinamide | 484 | 0.96 | |
| Example 2-315 | 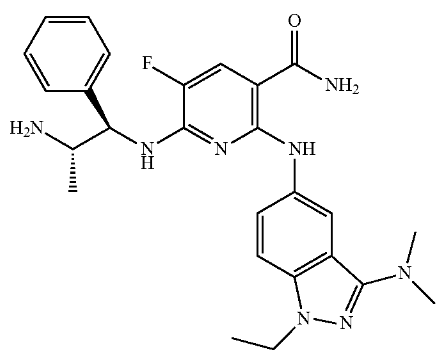 [SMILES: CCn1nc(N(C)C)c2cc(Nc3nc(N[C@H](c4ccccc4)[C@H](C)N)c(F)cc3C(N)=O)ccc21] | 6-(((1R,2S)-2-amino-1-phenylpropyl)amino)-2-((3-(dimethylamino)-1-methyl-1H-indazol-5-yl)amino)-5-fluoronicotinamide | 477 | 0.93 | |

TABLE 3-continued

| Example | Structure | Compound name | MS (ESI m/z): (M + H) | RT (min) | HNMR |
|---|---|---|---|---|---|
| Example 2-316 | 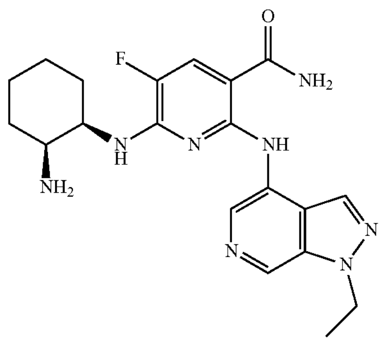 [SMILES: CCn1ncc2c(Nc3nc(N[C@@H]4CCCC[C@@H]4N)c(F)cc3C(N)=O)cncc21] | 6-(((1R,2S)-2-aminocyclohexyl)amino)-2-((1-ethyl-1H-pyrazolo[3,4-c]pyridin-4-yl)amino)-5-fluoronicotinamide | 413 | 0.68 | |
| Example 2-317 | 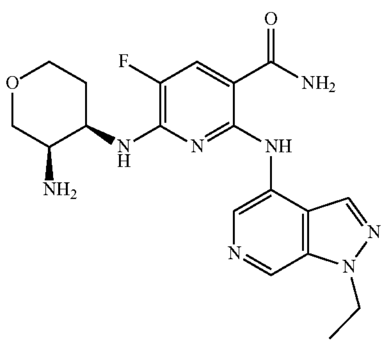 [SMILES: CCn1ncc2c(Nc3nc(N[C@@H]4CCOC[C@@H]4N)c(F)cc3C(N)=O)cncc21] | 6-(((3R,4R)-3-aminotetrahydro-2H-pyran-4-yl)amino)-2-((1-ethyl-1H-pyrazolo[3,4-c]pyridin-4-yl)amino)-5-fluoronicotinamide | 415 | 0.58 | |
| Example 2-318 | 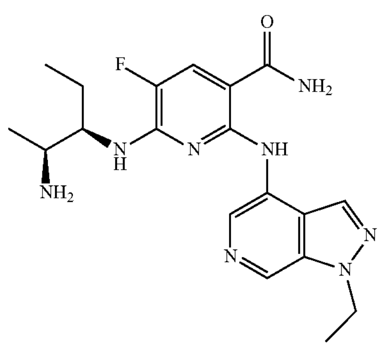 [SMILES: CC[C@@H](Nc1nc(Nc2cncc3c2cnn3CC)c(C(N)=O)cc1F)[C@H](C)N] | 6-(((2S,3R)-2-aminopentan-3-yl)amino)-2-((1-ethyl-1H-pyrazolo[3,4-c]pyridin-4-yl)amino)-5-fluoronicotinamide | 401 | 0.65 | |

TABLE 3-continued

| Example | Structure | Compound name | MS (ESI m/z): (M + H) | RT (min) | HNMR |
|---|---|---|---|---|---|
| Example 2-319 | 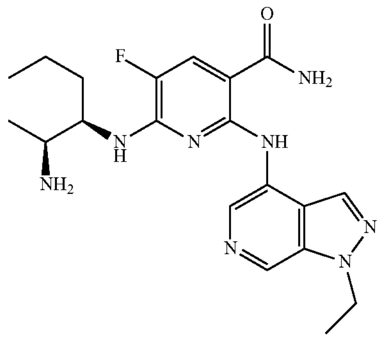 [SMILES: CCC[C@@H](Nc1nc(Nc2cncc3c2cnn3CC)c(C(N)=O)cc1F)[C@H](C)N] | 6-(((2S,3R)-2-aminohexan-3-yl)amino)-2-((1-ethyl-1H-pyrazolo[3,4-c]pyridin-4-yl)amino)-5-fluoronicotinamide | 415 | 0.73 | |
| Example 2-320 | 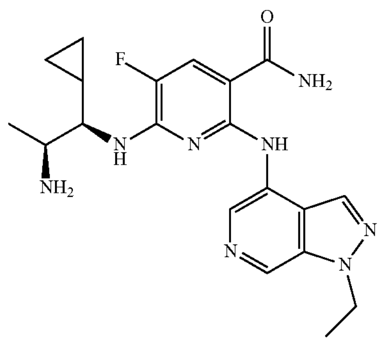 [SMILES: CCn1ncc2c(Nc3nc(N[C@H](C4CC4)[C@H](C)N)c(F)cc3C(N)=O)cncc21] | 6-(((1R,2S)-2-amino-1-cyclopropylpropyl)amino)-2-((1-ethyl-1H-pyrazolo[3,4-c]pyridin-4-yl)amino)-5-fluoronicotinamide | 413 | 0.66 | |
| Example 2-321 | 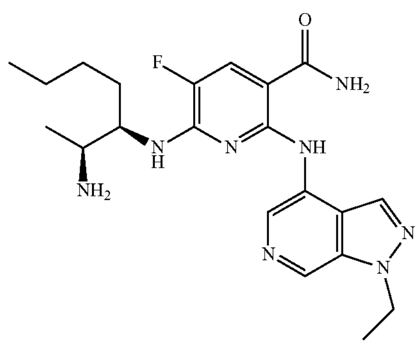 [SMILES: CCCC[C@@H](Nc1nc(Nc2cncc3c2cnn3CC)c(C(N)=O)cc1F)[C@H](C)N] | 6-(((2S,3R)-2-aminoheptan-3-yl)amino)-2-((1-ethyl-1H-pyrazolo[3,4-c]pyridin-4-yl)amino)-5-fluoronicotinamide | 429 | 0.81 | |

TABLE 3-continued

| Example | Structure | Compound name | MS (ESI m/z): (M + H) | RT (min) | HNMR |
|---|---|---|---|---|---|
| Example 2-322 | 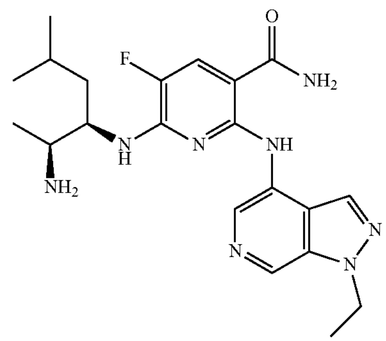 [SMILES: CCn1ncc2c(Nc3nc(N[C@H](CC(C)C)[C@H](C)N)c(F)cc3C(N)=O)cncc21] | 6-(((2S,3R)-2-amino-5-methylhexan-3-yl)amino)-2-((1-ethyl-1H-pyrazolo[3,4-c]pyridin-4-yl)amino)-5-fluoronicotinamide | 429 | 0.8 | |
| Example 2-323 | 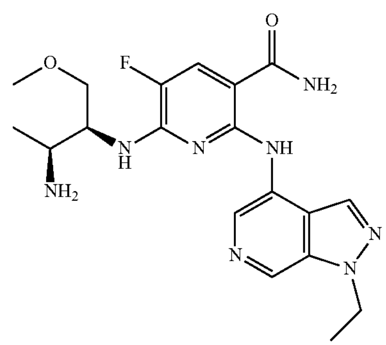 [SMILES: CCn1ncc2c(Nc3nc(N[C@H](COC)[C@H](C)N)c(F)cc3C(N)=O)cncc21] | 6-(((2S,3S)-3-amino-1-methoxybutan-2-yl)amino)-2-((1-ethyl-1H-pyrazolo[3,4-c]pyridin-4-yl)amino)-5-fluoronicotinamide | 417 | 0.61 | |
| Example 2-324 | 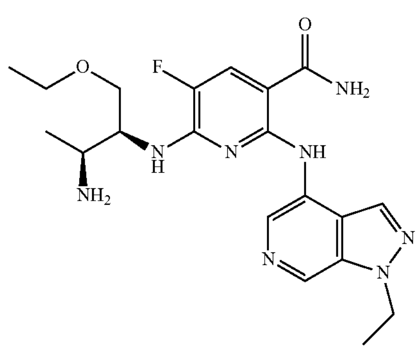 [SMILES: CCOC[C@@H](Nc1nc(Nc2cncc3c2cnn3CC)c(C(N)=O)cc1F)[C@H](C)N] | 6-(((2S,3S)-3-amino-1-ethoxybutan-2-yl)amino)-2-((1-ethyl-1H-pyrazolo[3,4-c]pyridin-4-yl)amino)-5-fluoronicotinamide | 431 | 0.67 | |

TABLE 3-continued

| Example | Structure | Compound name | MS (ESI m/z): (M + H) | RT (min) | HNMR |
|---|---|---|---|---|---|
| Example 2-325 | 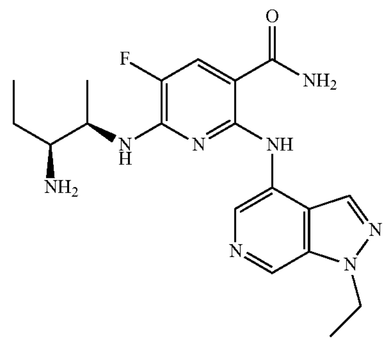 [SMILES: CC[C@H](N)[C@@H](C)Nc1nc(Nc2cncc3c2cnn3CC)c(C(N)=O)cc1F] | 6-(((2R,3S)-3-aminopentan-2-yl)amino)-2-((1-ethyl-1H-pyrazolo[3,4-c]pyridin-4-yl)amino)-5-fluoronicotinamide | 401 | 0.62 | |
| Example 2-326 | 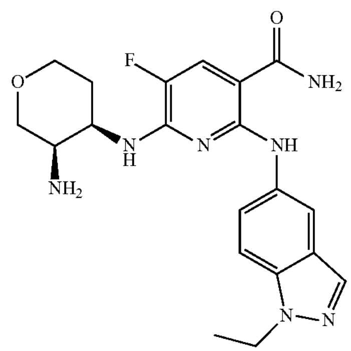 [SMILES: CCn1ncc2cc(Nc3nc(N[C@@H]4CCOC[C@@H]4N)c(F)cc3C(N)=O)ccc21] | 6-(((3R,4R)-3-aminotetrahydro-2H-pyran-4-yl)amino)-2-((1-ethyl-1H-indazol-5-yl)amino)-5-fluoronicotinamide | 414 | 0.82 | 1H-NMR (MeOD) δ: 7.99 (1H, s), 7.92 (1H, d, J = 1.3 Hz), 7.75 (1H, d, J = 11.9 Hz), 7.56 (1H, d, J = 9.2 Hz), 7.44 (1H, dd, J = 8.9, 1.7 Hz), 4.47 (2H, q, J = 7.3 Hz), 4.28 (1H, td, J = 8.4, 4.6 Hz), 4.06 (1H, dd, J = 11.9, 4.6 Hz), 3.80-3.51 (3H, m), 3.46-3.39 (1H, m), 2.11-1.94 (1H, m), 1.89-1.80 (1H, m), 1.47 (3H, t, J = 7.3 Hz). |
| Example 2-327 | 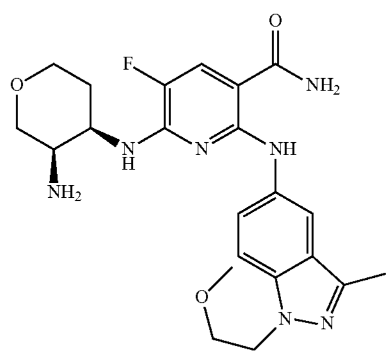 [SMILES: COCCn1nc(C)c2cc(Nc3nc(N[C@@H]4CCOC[C@@H]4N)c(F)cc3C(N)=O)ccc21] | 6-(((3R,4R)-3-aminotetrahydro-2H-pyran-4-yl)amino)-5-fluoro-2-((1-(2-methoxyethyl)-3-methyl-1H-indazol-5-yl)amino)nicotinamide | 458 | 0.81 | |

TABLE 3-continued

| Example | Structure | Compound name | MS (ESI m/z): (M + H) | RT (min) | HNMR |
|---|---|---|---|---|---|
| Example 2-328 | 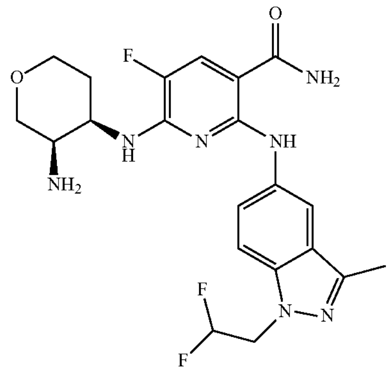 [SMILES: Cc1nn(CC(F)F)c2ccc(Nc3nc(N[C@@H]4CCOC[C@@H]4N)c(F)cc3C(N)=O)cc12] | 6-(((3R,4R)-3-aminotetrahydro-2H-pyran-4-yl)amino)-2-((1-(2,2-difluoroethyl)-3-methyl-1H-indazol-5-yl)amino)-5-fluoronicotinamide | 464 | 0.86 | 1H-NMR (MeOD) δ: 7.74 (1H, d, J = 11.9 Hz), 7.63 (1H, dd, J = 8.9, 1.7 Hz), 7.60 (1H, s), 7.53 (1H, d, J = 8.6 Hz), 6.22 (1H, tt, J = 55.5, 3.6 Hz), 4.75 (2H, td, J = 14.7, 3.5 Hz), 4.23-4.14 (1H, m), 4.08-4.00 (1H, m), 3.69-3.59 (3H, m), 3.58-3.48 (1H, m), 2.54 (3H, s), 2.04-1.94 (1H, m), 1.86-1.78 (1H, m). |
| Example 2-329 | 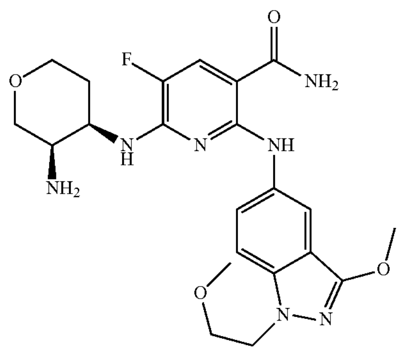 [SMILES: COCCn1nc(OC)c2cc(Nc3nc(N[C@@H]4CCOC[C@@H]4N)c(F)cc3C(N)=O)ccc21] | 6-(((3R,4R)-3-aminotetrahydro-2H-pyran-4-yl)amino)-5-fluoro-2-((3-methoxy-1-(2-methoxyethyl)-1H-indazol-5-yl)amino)nicotinamide | 474 | 0.86 | |

TABLE 3-continued

| Example | Structure | Compound name | MS (ESI m/z): (M + H) | RT (min) | HNMR |
|---|---|---|---|---|---|
| Example 2-330 | 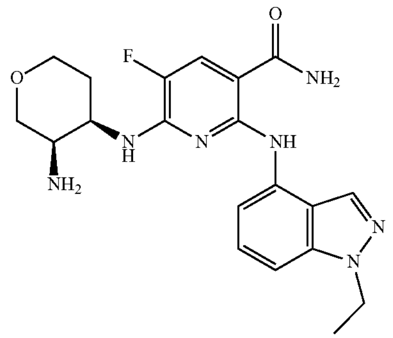 [SMILES: CCn1ncc2c(Nc3nc(N[C@@H]4CCOC[C@@H]4N)c(F)cc3C(N)=O)cccc21] | 6-((3R,4R)-3-aminotetrahydro-2H-pyran-4-yl)amino)-2-((1-ethyl-1H-indazol-4-yl)amino)-5-fluoronicotinamide | 414 | 0.82 | 1H-NMR (MeOD) δ: 8.08 (1H, s), 7.83 (1H, d, J = 12.6 Hz), 7.80 (1H, d, J = 7.9 Hz), 4.51-4.42 (2H, m), 7.20 (1H, d, J = 7.9 Hz), 4.51-4.42 (2H, m), 4.45-4.35 (1H, m), 4.12-4.08 (1H, m), 3.93-3.89 (2H, m), 3.69-3.53 (2H, m), 2.09-1.87 (2H, m), 1.48 (3H, t, J = 6.9 Hz). |
| Example 2-331 | 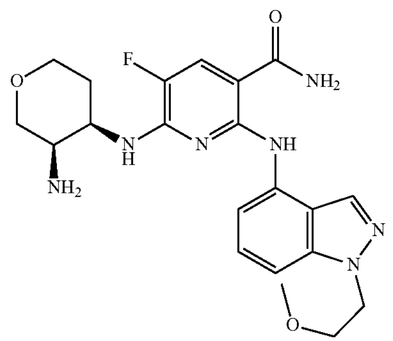 [SMILES: COCCn1ncc2c(Nc3nc(N[C@@H]4CCOC[C@@H]4N)c(F)cc3C(N)=O)cccc21] | 6-((3R,4R)-3-aminotetrahydro-2H-pyran-4-yl)amino)-5-fluoro-2-((1-(2-methoxyethyl)-1H-indazol-4-yl)amino)nicotinamide | 444 | 0.82 | 1H-NMR (MeOD) δ: 8.08 (1H, s), 7.82 (1H, d, J = 11.9 Hz), 7.71 (1H, d, J = 7.3 Hz), 7.37 (1H, t, J = 7.9 Hz), 7.23 (1H, d, J = 8.6 Hz), 4.55 (2H, t, J = 5.3 Hz), 4.39-4.32 (1H, m), 4.12-4.03 (1H, m), 3.90-3.83 (2H, m), 3.88-3.80 (2H, m), 3.64-3.55 (2H, m), 3.36 (3H, s), 2.07-1.99 (2H, m). |

TABLE 3-continued

| Example | Structure | Compound name | MS (ESI m/z): (M + H) | RT (min) | HNMR |
|---|---|---|---|---|---|
| Example 2-332 | 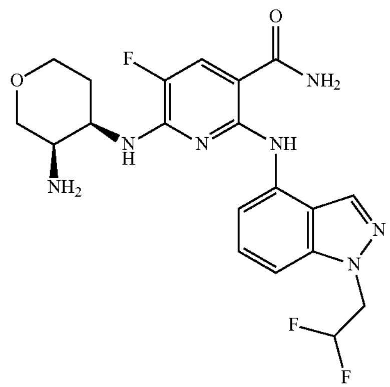 [SMILES: NC(=O)c1cc(F)c(N[C@@H]2CCOC[C@@H]2N)nc1Nc1cccc2c1cnn2CC(F)F] | 6-(((3R,4R)-3-aminotetrahydro-2H-pyran-4-yl)amino)-2-((1-(2,2-difluoroethyl)-1H-indazol-4-yl)amino)-5-fluoronicotinamide | 450 | 0.86 | 1H-NMR (MeOD) δ: 8.15 (1H, s), 7.83 (1H, d, J = 12.6 Hz), 7.80 (1H, d, J = 7.9 Hz), 7.42 (1H, t, J = 7.9 Hz), 7.24 (1H, d, J = 8.6 Hz), 6.48-6.05 (1H, m), 4.84-4.78 (2H, m), 4.42-4.34 (1H, m), 4.14-4.02 (1H, m), 3.92-3.85 (2H, m), 3.70-3.51 (2H, m), 1.93-1.84 (2H, m). |
| Example 2-333 | 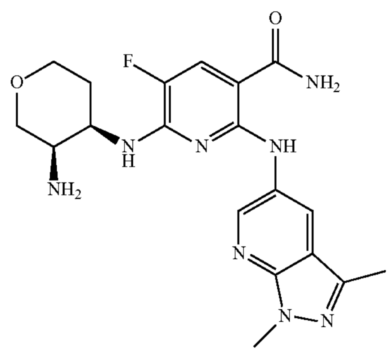 [SMILES: Cc1nn(C)c2ncc(Nc3nc(N[C@@H]4CCOC[C@@H]4N)c(F)cc3C(N)=O)cc12] | 6-(((3R,4R)-3-aminotetrahydro-2H-pyran-4-yl)amino)-2-(((1,3-dimethyl-1H-pyrazolo[3,4-b]pyridin-5-yl)amino)-5-fluoronicotinamide | 415 | 0.73 | |

TABLE 3-continued

| Example | Structure | Compound name | MS (ESI m/z): (M + H) | RT (min) | HNMR |
|---|---|---|---|---|---|
| Example 2-334 | 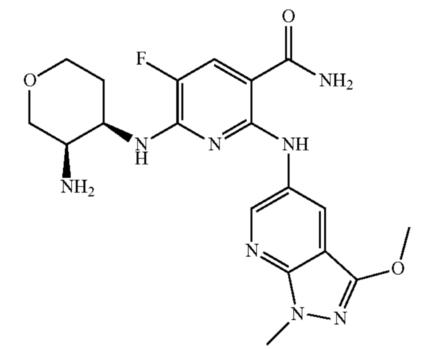 [SMILES: COc1nn(C)c2ncc(Nc3nc(N[C@@H]4CCOC[C@@H]4N)c(F)cc3C(N)=O)cc12] | 6-(((3R,4R)-3-aminotetrahydro-2H-pyran-4-yl)amino)-5-fluoro-2-((3-methoxy-1-methyl-1H-pyrazolo[3,4-b]pyridin-5-yl)amino)nicotinamide | 431 | 0.77 | |
| Example 2-335 | 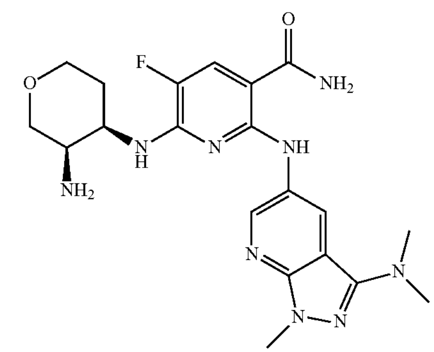 [SMILES: CN(C)c1nn(C)c2ncc(Nc3nc(N[C@@H]4CCOC[C@@H]4N)c(F)cc3C(N)=O)cc12] | 6-(((3R,4R)-3-aminotetrahydro-2H-pyran-4-yl)amino)-2-((3-(dimethylamino)-1-methyl-1H-pyrazolo[3,4-b]pyridin-5-yl)amino)-5-fluoronicotinamide | 444 | 0.76 | |
| Example 2-336 | 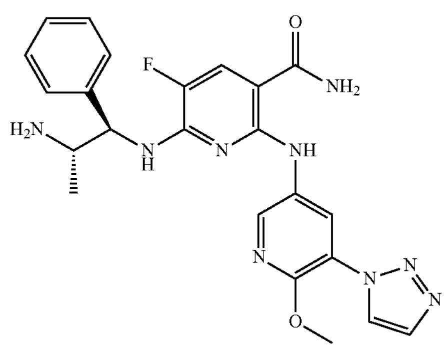 [SMILES: COc1ncc(Nc2nc(N[C@H](c3ccccc3)[C@H](C)N)c(F)cc2C(N)=O)cc1-n1ccnn1] | 6-(((1R,2S)-2-amino-1-phenylpropyl)amino)-5-fluoro-2-((6-methoxy-5-(1H-1,2,3-triazol-1-yl)pyridin-3-yl)amino)nicotinamide | 478 | 0.93 | |

TABLE 3-continued

| Example | Structure | Compound name | MS (ESI m/z): (M + H) | RT (min) | HNMR |
|---|---|---|---|---|---|
| Example 2-337 | 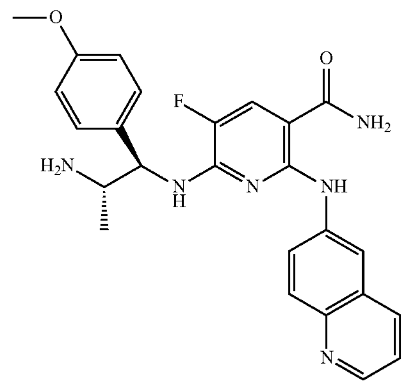 [SMILES: COc1ccc([C@@H](Nc2nc(Nc3ccc4ncccc4c3)c(C(N)=O)cc2F)[C@H](C)N)cc1] | 6-(((1R,2S)-2-amino-1-(4-methoxyphenyl)propyl)amino)-5-fluoro-2-(quinolin-6-ylamino)nicotinamide | 461 | 0.73 | |
| Example 2-338 | 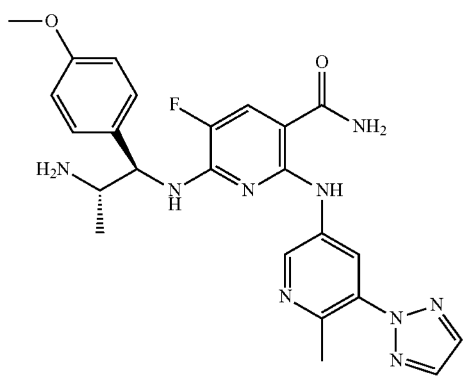 [SMILES: COc1ccc([C@@H](Nc2nc(Nc3cnc(C)c(-n4nccn4)c3)c(C(N)=O)cc2F)[C@H](C)N)cc1] | 6-(((1R,2S)-2-amino-1-(4-methoxyphenyl)propyl)amino)-5-fluoro-2-((6-methyl-5-(2H-1,2,3-triazol-2-yl)pyridin-3-yl)amino)nicotinamide | 492 | 0.85 | 1H-NMR (MeOD) δ: 9.09 (1H, d, J = 2.0 Hz), 8.85 (1H, d, J = 2.0 Hz), 8.15 (2H, s), 7.88 (1H, d, J = 11.9 Hz), 7.30 (2H, d, J = 8.6 Hz), 6.88 (2H, d, J = 8.6 Hz), 5.65 (1H, d, J = 6.6 Hz), 3.91-3.85 (1H, m), 3.75 (3H, s), 2.82 (3H, s), 1.39 (3H, d, J = 7.3 Hz) |

TABLE 3-continued

| Example | Structure | Compound name | MS (ESI m/z): (M + H) | RT (min) | HNMR |
|---|---|---|---|---|---|
| Example 2-339 | 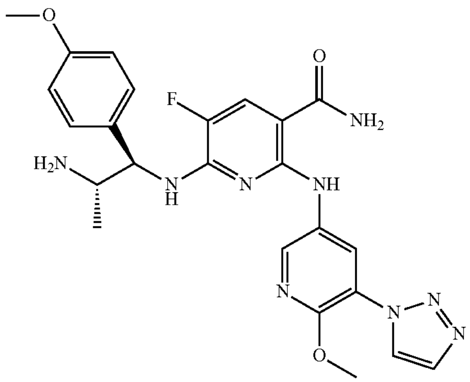 [SMILES: COc1ccc([C@@H](Nc2nc(Nc3cnc(OC)c(-n4ccnn4)c3)c(C(N)=O)cc2F)[C@H](C)N)cc1] | 6-(((1R,2S)-2-amino-1-(4-methoxyphenyl)propyl)amino)-5-fluoro-2-((6-methoxy-5-(1H-1,2,3-triazol-1-yl)pyridin-3-yl)amino)nicotinamide | 508 | 0.91 | |
| Example 2-340 | 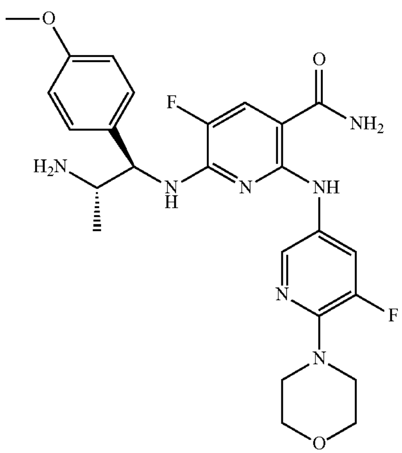 [SMILES: COc1ccc([C@@H](Nc2nc(Nc3cnc(N4CCOCC4)c(F)c3)c(C(N)=O)cc2F)[C@H](C)N)cc1] | 6-(((1R,2S)-2-amino-1-(4-methoxyphenyl)propyl)amino)-5-fluoro-2-((5-fluoro-6-morpholinopyridin-3-yl)amino)nicotinamide | 514 | 0.96 | |

TABLE 3-continued

| Example | Structure | Compound name | MS (ESI m/z): (M + H) | RT (min) | HNMR |
|---|---|---|---|---|---|
| Example 2-341 | 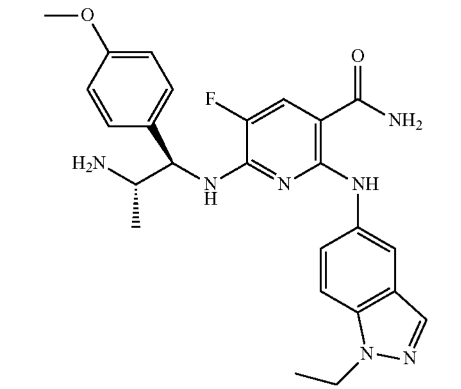 [SMILES: CCn1ncc2cc(Nc3nc(N[C@H](c4ccc(OC)cc4)[C@H](C)N)c(F)cc3C(N)=O)ccc21] | 6-(((1R,2S)-2-amino-1-(4-methoxyphenyl)propyl)amino)-2-((1-ethyl-1H-indazol-5-yl)amino)-5-fluoronicotinamide | 478 | 0.97 | 1H-NMR (MeOD) δ: 7.97 (1H, s), 7.87 (1H, d, J = 1.3 Hz), 7.75 (1H, d, J = 11.9 Hz), 7.50 (1H, d, J = 8.6 Hz), 7.36-7.27 (3H, m), 6.96 (2H, d, J = 8.6 Hz), 5.38 (1H, d, J = 5.7 Hz), 4.48 (2H, q, J = 7.2 Hz), 3.81-3.72 (4H, m), 1.49 (3H, t, J = 7.2 Hz), 1.30 (3H, d, J = 6.6 Hz) |
| Example 2-342 | 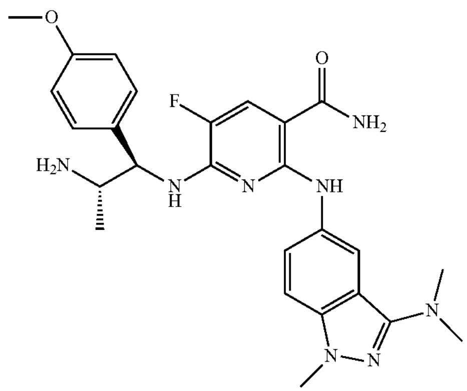 | 6-(((1R,2S)-2-amino-1-(4-methoxyphenyl)propyl)amino)-2-((3-(dimethylamino)-1-methyl-1H-indazol-5-yl)amino)-5-fluoronicotinamide | 507 | 0.94 | |

TABLE 3-continued

| Example | Structure | Compound name | MS (ESI m/z): (M + H) | RT (min) | HNMR |
|---|---|---|---|---|---|
| Example 2-343 | 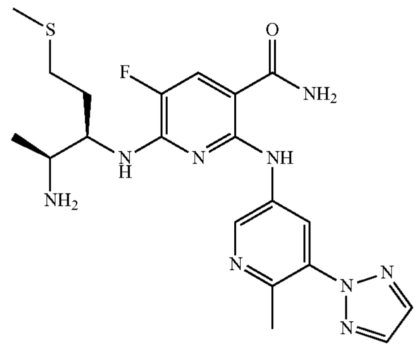 [SMILES: CSCC[C@@H](Nc1nc(Nc2cnc(C)c(-n3nccn3)c2)c(C(N)=O)cc1F)[C@H](C)N] | 6-(((3R,4S)-4-amino-1-(methylthio)pentan-3-yl)amino)-5-fluoro-2-((6-methyl-5-(2H-1,2,3-triazol-2-yl)pyridin-3-yl)amino)nicotinamide | 460 | 0.87 | |
| Example 2-344 | 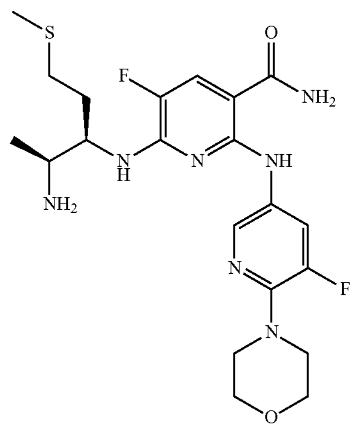 [SMILES: CSCC[C@@H](Nc1nc(Nc2cnc(N3CCOCC3)c(F)c2)c(C(N)=O)cc1F)[C@H](C)N] | 6-(((3R,4S)-4-amino-1-(methylthio)pentan-3-yl)amino)-5-fluoro-2-((5-fluoro-6-morpholinopyridin-3-yl)amino)nicotinamide | 482 | 0.94 | |

TABLE 3-continued

| Example | Structure | Compound name | MS (ESI m/z): (M + H) | RT (min) | HNMR |
|---|---|---|---|---|---|
| Example 2-345 | 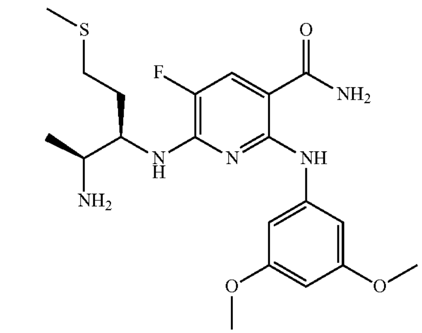 [SMILES: COc1cc(Nc2nc(N[C@H](CCSC)[C@H](C)N)c(F)cc2C(N)=O)cc(OC)c1] | 6-(((3R,4S)-4-amino-1-(methylthio)pentan-3-yl)amino)-2-((3,5-dimethoxyphenyl)amino)-5-fluoronicotinamide | 453 | 0.72 | |
| Example 2-346 | 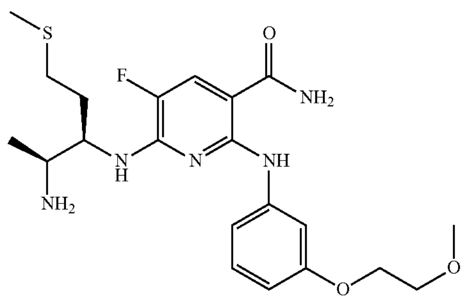 [SMILES: COCCOc1cccc(Nc2nc(N[C@H](CCSC)[C@H](C)N)c(F)cc2C(N)=O)c1] | 6-(((3R,4S)-4-amino-1-(methylthio)pentan-3-yl)amino)-5-fluoro-2-((2-(2-methoxyethoxy)pyridin-4-yl)amino)nicotinamide | 438 | 1 | |
| Example 2-347 | 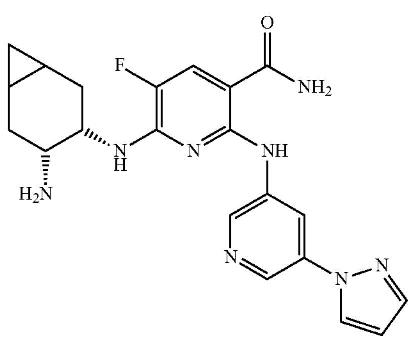 | 2-((5-(1H-pyrazol-1-yl)pyridin-3-yl)amino)-6-(((3S,4R)-4-aminobicyclo[4.1.0]heptan-3-yl)amino)-5-fluoronicotinamide | 423 | 0.87 | |

TABLE 3-continued

| Example | Structure | Compound name | MS (ESI m/z): (M + H) | RT (min) | HNMR |
|---|---|---|---|---|---|
| Example 2-348 | 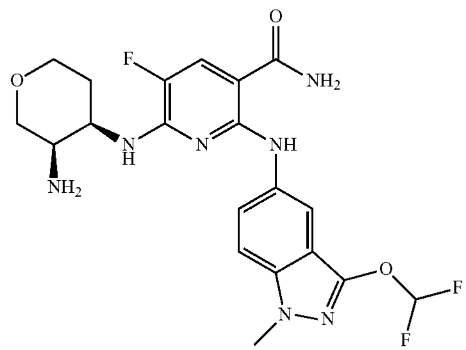 [SMILES: Cn1nc(OC(F)F)c2cc(Nc3nc(N[C@@H]4CCOC[C@@H]4N)c(F)cc3C(N)=O)ccc21] | 6-(((3R,4R)-3-aminotetrahydro-2H-pyran-4-yl)amino)-2-((3-(difluoromethoxy)-1-methyl-1H-indazol-5-yl)amino)-5-fluoronicotinamide | 466 | 0.91 | 1H-NMR (MeOD) δ: 8.14 (1H, d, J = 1.3 Hz), 7.77 (1H, d, J = 11.9 Hz), 7.45 (1H, d, J = 8.6 Hz), 7.31 (1H, dd, J = 8.6, 2.6 Hz), 7.31 (1H, d, J = 147.0 Hz), 4.44 (1H, td, J = 8.3, 4.0 Hz), 4.09 (1H, dd, J = 11.6, 4.3 Hz), 3.93 (3H, s), 3.86-3.74 (2H, m), 3.77-3.65 (2H, m), 2.04-2.00 (2H, m). |
| Example 2-349 | 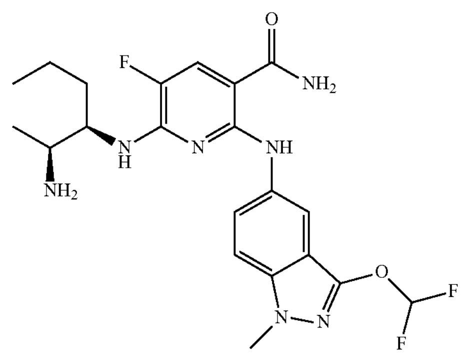 [SMILES: CCC[C@@H](Nc1nc(Nc2ccc3c(c2)c(OC(F)F)nn3C)c(C(N)=O)cc1F)[C@H](C)N] | 6-(((2S,3R)-2-aminohexan-3-yl)amino)-2-((3-(difluoromethoxy)-1-methyl-1H-indazol-5-yl)amino)-5-fluoronicotinamide | 466 | 1.08 | |
| Example 2-350 | 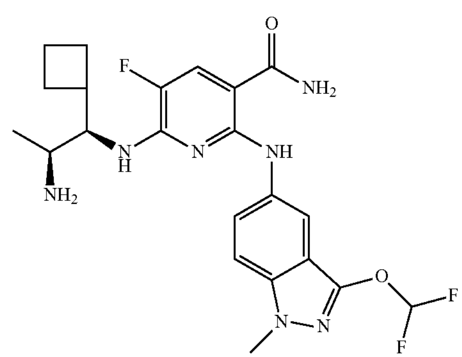 [SMILES: C[C@H](N)[C@H](Nc1nc(Nc2ccc3c(c2)c(OC(F)F)nn3C)c(C(N)=O)cc1F)C1CCC1] | 6-(((1R,2S)-2-amino-1-cyclobutylpropyl)amino)-2-((3-(difluoromethoxy)-1-methyl-1H-indazol-5-yl)amino)-5-fluoronicotinamide | 478 | 1.09 | |

TABLE 3-continued

| Example | Structure | Compound name | MS (ESI m/z): (M + H) | RT (min) | HNMR |
|---|---|---|---|---|---|
| Example 2-351 | 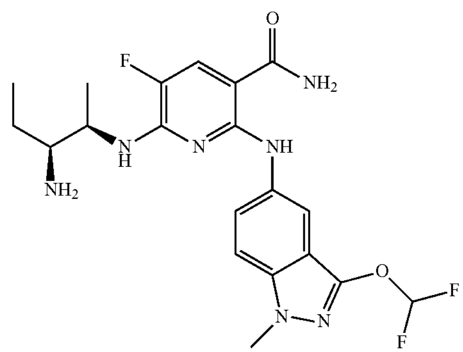 [SMILES: CC[C@H](N)[C@@H](C)Nc1nc(Nc2ccc3c(c2)c(OC(F)F)nn3C)c(C(N)=O)cc1F] | 6-(((2R,3S)-3-aminopentan-2-yl)amino)-2-((3-(difluoromethoxy)-1-methyl-1H-indazol-5-yl)amino)-5-fluoronicotinamide | 452 | 0.98 | |
| Example 2-352 | 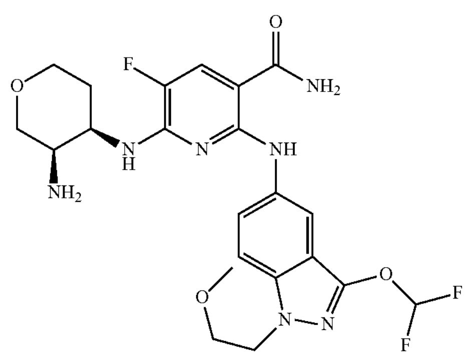 [SMILES: COCCn1nc(OC(F)F)c2cc(Nc3nc(N[C@@H]4CCOC[C@@H]4N)c(F)cc3C(N)=O)ccc21] | 6-(((3R,4R)-3-aminotetrahydro-2H-pyran-4-yl)amino)-2-((3-(difluoromethoxy)-1-(2-methoxyethyl)-1H-indazol-5-yl)amino)-5-fluoronicotinamide | 510 | 0.94 | 1H-NMR (MeOD) δ: 8.08 (1H, s), 7.77 (1H, d, J = 11.9 Hz), 7.49 (1H, d, J = 8.6 Hz), 7.34-7.30 (1H, m), 7.32 (1H, d, J = 147.0 Hz), 4.43 (2H, t, J = 5.3 Hz), 4.40-4.37 (1H, m), 4.08 (1H, dd, J = 11.2, 4.6 Hz), 3.79 (2H, t, J = 5.3 Hz), 3.77-3.72 (2H, m), 3.72-3.65 (2H, m), 3.35 (3H, s), 2.09-1.98 (2H, m). |

TABLE 3-continued

| Example | Structure | Compound name | MS (ESI m/z): (M + H) | RT (min) | HNMR |
|---|---|---|---|---|---|
| Example 2-353 | 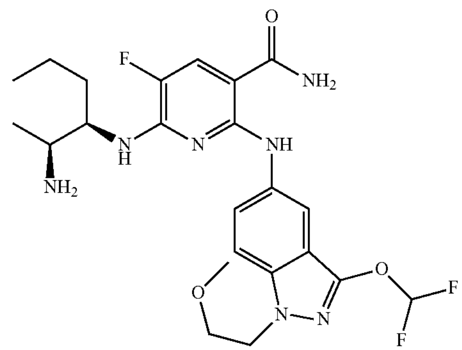 [SMILES: CCC[C@@H](Nc1nc(Nc2ccc3c(c2)c(OC(F)F)nn3CCOC)c(C(N)=O)cc1F)[C@H](C)N] | 6-(((2S,3R)-2-aminohexan-3-yl)amino)-2-((3-(difluoromethoxy)-1-(2-methoxyethyl)-1H-indazol-5-yl)amino)-5-fluoronicotinamide | 510 | 1.1 | |
| Example 2-354 | 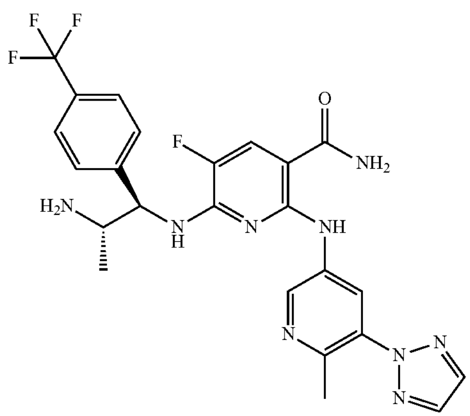 [SMILES: Cc1ncc(Nc2nc(N[C@H](c3ccc(C(F)(F)F)cc3)[C@H](C)N)c(F)cc2C(N)=O)cc1-n1nccn1] | 6-(((1R,2S)-2-amino-1-(4-(trifluoromethyl)phenyl)propyl)amino)-5-fluoro-2-(((6-methyl-5-(2H-1,2,3-triazol-2-yl)pyridin-3-yl)amino)nicotinamide | 530 | 1.02 | |

TABLE 3-continued

| Example | Structure | Compound name | MS (ESI m/z): (M + H) | RT (min) | HNMR |
|---|---|---|---|---|---|
| Example 2-355 | 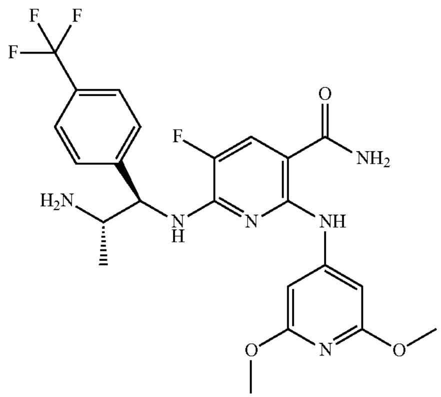 [SMILES: COc1cc(Nc2nc(N[C@H](c3ccc(C(F)(F)F)cc3)[C@H](C)N)c(F)cc2C(N)=O)cc(OC)n1] | 6-(((1R,2S)-2-amino-1-(4-(trifluoromethyl)phenyl)propyl)amino)-2-((2,6-dimethoxypyridin-4-yl)amino)-5-fluoronicotinamide | 509 | 1.15 | |
| Example 2-356 | 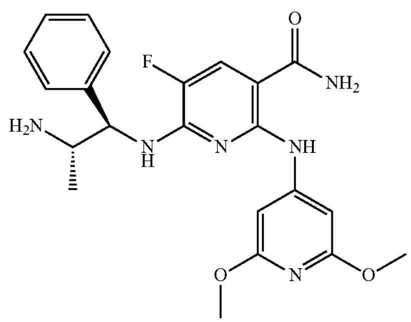 [SMILES: COc1cc(Nc2nc(N[C@H](c3ccccc3)[C@H](C)N)c(F)cc2C(N)=O)cc(OC)n1] | 6-(((1R,2S)-2-amino-1-phenylpropyl)amino)-2-((2,6-dimethoxypyridin-4-yl)amino)-5-fluoronicotinamide | 441 | 0.99 | |

TABLE 3-continued

| Example | Structure | Compound name | MS (ESI m/z): (M + H) | RT (min) | HNMR |
|---|---|---|---|---|---|
| Example 2-357 | 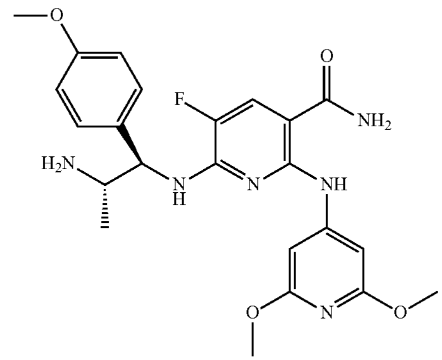 | 6-(((1R,2S)-2-amino-1-(4-methoxyphenyl)propyl)amino)-2-((2,6-dimethoxypyridin-4-yl)amino)-5-fluoronicotinamide | 471 | 1 | |
| Example 2-358 | 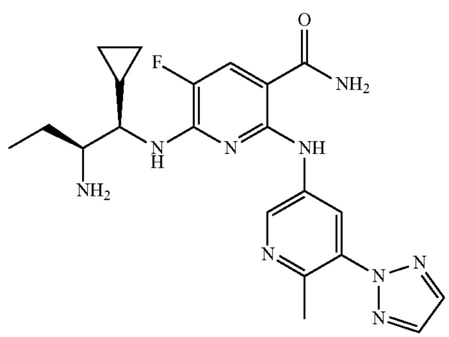 [SMILES: CC[C@H](N)[C@H](Nc1nc(Nc2cnc(C)c(-n3nccn3)c2)c(C(N)=O)cc1F)C1CC1] | 6-(((1R,2S)-2-amino-1-cyclopropylbutyl)amino)-5-fluoro-2-((6-methyl-5-(2H-1,2,3-triazol-2-yl)pyridin-3-yl)amino)nicotinamide | 440 | 0.89 | 1H-NMR (DMSO-d6) δ: 11.87 (1H, s), 8.65 (1H, s), 8.41 (1H, s), 8.21 (2H, s), 7.97 (5H, m), 7.45-7.32 (1H, m), 7.26 (1H, d, J = 7.9 Hz), 3.75-3.65 (1H, m), 3.40-3.36 (1H, m), 2.50 (3H, m), 1.65-1.45 (2H, m), 1.11-0.90 (1H, m), 0.75 (3H, t, J = 7.3 Hz), 0.60-0.16 (4H, m) |

TABLE 3-continued

| Example | Structure | Compound name | MS (ESI m/z): (M + H) | RT (min) | HNMR |
|---|---|---|---|---|---|
| Example 2-359 | 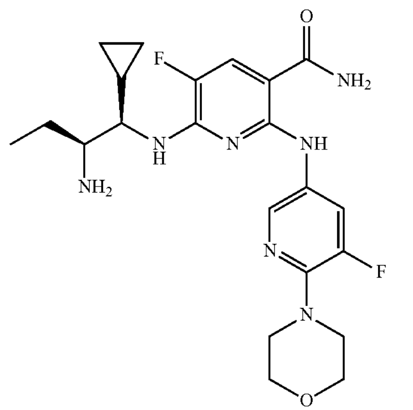 [SMILES: CC[C@H](N)[C@H](Nc1nc(Nc2cnc(N3CCOCC3)c(F)c2)c(C(N)=O)cc1F)C1CC1] | 6-(((1R,2S)-2-amino-1-cyclopropylbutyl)amino)-5-fluoro-2-((5-fluoro-6-morpholinopyridin-3-yl)amino)nicotinamide | 462 | 0.95 | |
| Example 2-360 | 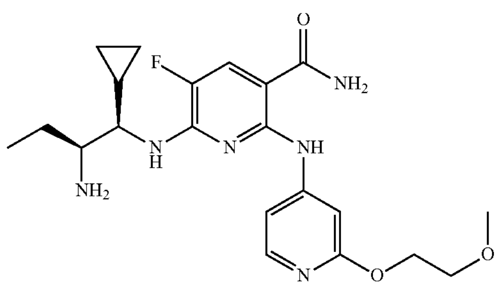 [SMILES: CC[C@H](N)[C@H](Nc1nc(Nc2ccnc(OCCOC)c2)c(C(N)=O)cc1F)C1CC1] | 6-(((1R,2S)-2-amino-1-cyclopropylbutyl)amino)-5-fluoro-2-((2-(2-methoxyethoxy)pyridin-4-yl)amino)nicotinamide | 433 | 0.72 | |
| Example 2-361 | 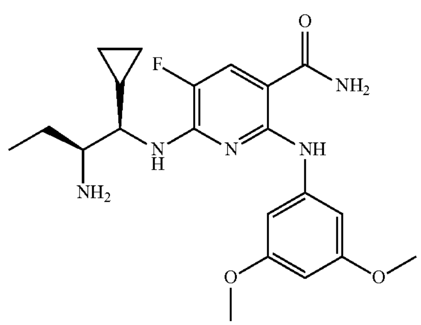 [SMILES: CC[C@H](N)[C@H](Nc1nc(Nc2cc(OC)cc(OC)c2)c(C(N)=O)cc1F)C1CC1] | 6-(((1R,2S)-2-amino-1-cyclopropylbutyl)amino)-2-((3,5-dimethoxyphenyl)amino)-5-fluoronicotinamide | 418 | 1.03 | |

TABLE 3-continued

| Example | Structure | Compound name | MS (ESI m/z): (M + H) | RT (min) | HNMR |
|---|---|---|---|---|---|
| Example 2-362 | 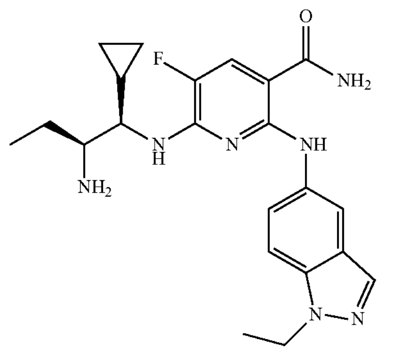 [SMILES: CC[C@H](N)[C@H](Nc1nc(Nc2ccc3c(cnn3CC)c2)c(C(N)=O)cc1F)C1CC1] | 6-(((1R,2S)-2-amino-1-cyclopropylbutyl)amino)-2-((1-ethyl-1H-indazol-5-yl)amino)-5-fluoronicotinamide | 426 | 0.95 | |
| Example 2-363 | 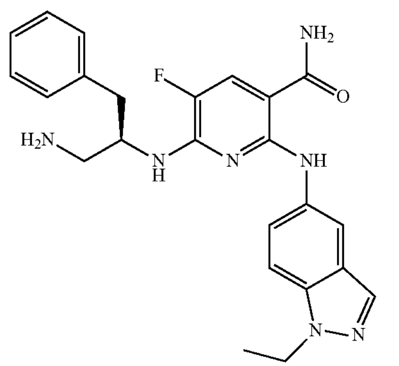 [SMILES: CCn1ncc2cc(Nc3nc(N[C@@H](CN)Cc4ccccc4)c(F)cc3C(N)=O)ccc21] | (R)-6-((1-amino-3-phenylpropan-2-yl)amino)-2-((1-ethyl-1H-indazol-5-yl)amino)-5-fluoronicotinamide | 448 | 1.02 | |

TABLE 3-continued

| Example | Structure | Compound name | MS (ESI m/z): (M + H) | RT (min) | HNMR |
|---|---|---|---|---|---|
| Example 2-364 | 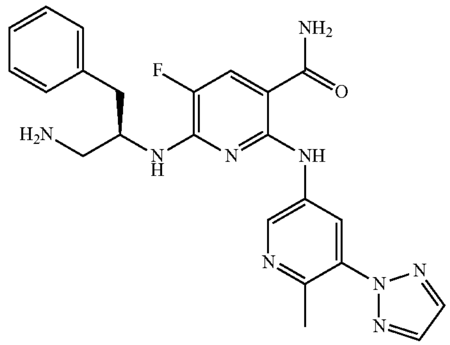 [SMILES: Cc1ncc(Nc2nc(N[C@@H](CN)Cc3ccccc3)c(F)cc2C(N)=O)cc1-n1nccn1] | (R)-6-((1-amino-3-phenylpropan-2-yl)amino)-5-fluoro-2-((6-methyl-5-(2H-1,2,3-triazol-2-yl)pyridin-3-yl)amino)nicotinamide | 462 | 0.96 | |
| Example 2-365 | 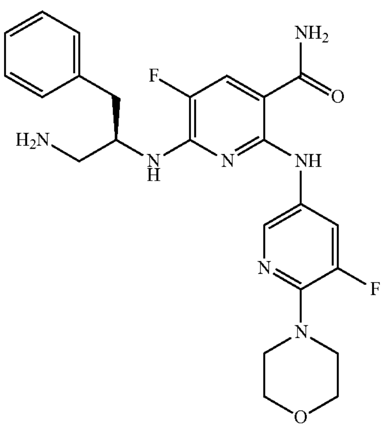 [SMILES: NC[C@@H](Cc1ccccc1)Nc1nc(Nc2cnc(N3CCOCC3)c(F)c2)c(C(N)=O)cc1F] | (R)-6-((1-amino-3-phenylpropan-2-yl)amino)-5-fluoro-2-((5-fluoro-6-morpholinopyridin-3-yl)amino)nicotinamide | 484 | 1.01 | 1H-NMR (MeOD) δ: 8.66 (1H, s), 7.90 (1H, dd, J = 14.4, 2.1 Hz), 7.72 (1H, d, J = 11.9 Hz), 7.21-7.10 (5H, m), 4.87 (2H, 溶媒ピークと重なっている), 3.92-3.86 (4H, m), 3.63-3.53 (4H, m), 3.19-2.82 (3H, m). |

| Example | Structure | Compound name | MS (ESI m/z): (M + H) | RT (min) | HNMR |
|---|---|---|---|---|---|
| Example 2-366 | 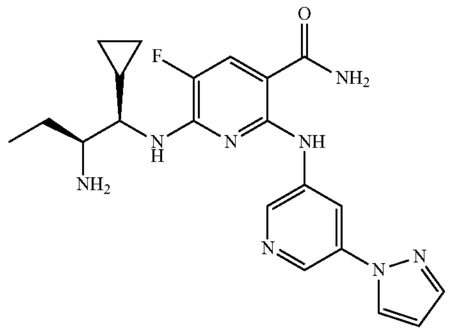 [SMILES: CC[C@H](N)[C@H](Nc1nc(Nc2cncc(-n3cccn3)c2)c(C(N)=O)cc1F)C1CC1] | 2-((5-(1H-pyrazol-1-yl)pyridin-3-yl)amino)-6-(((1R,2S)-2-amino-1-cyclopropylbutyl)amino)-5-fluoronicotinamide | 425 | 0.87 | |
| Example 2-367 | 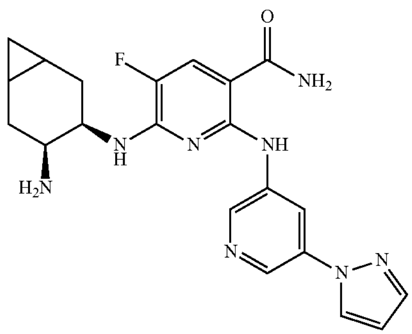 [SMILES: NC(=O)c1cc(F)c(N[C@@H]2CC3CC3C[C@@H]2N)nc1Nc1cncc(-n2cccn2)c1] | 2-((5-(1H-pyrazol-1-yl)pyridin-3-yl)amino)-6-(((3R,4S)-4-aminobicyclo[4.1.0]heptan-3-yl)amino)-5-fluoronicotinamide | 423 | 0.88 | |
| Example 2-368 | 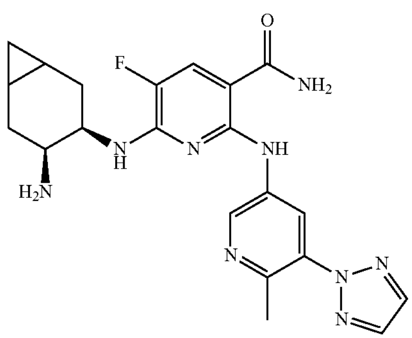 [SMILES: Cc1ncc(Nc2nc(N[C@@H]3CC4CC4C[C@@H]3N)c(F)cc2C(N)=O)cc1-n1nccn1] | 6-(((3R,4S)-4-aminobicyclo[4.1.0]heptan-3-yl)amino)-5-fluoro-2-(((6-methyl-5-(2H-1,2,3-triazol-2-yl)pyridin-3-yl)amino)nicotinamide | 438 | 0.9 | |

TABLE 3-continued

| Example | Compound name | MS (ESI m/z): (M + H) | RT (min) | HNMR |
|---|---|---|---|---|
| Example 2-369 | 6-(((1R,2S)-2-aminocyclohexyl)amino)-2-((1-ethyl-6-fluoro-1H-indazol-4-yl)amino)-5-fluoronicotinamide | 430 | 1.04 | |
| Example 2-370 | 6-(((3R,4R)-3-aminotetrahydro-2H-pyran-4-yl)amino)-2-((1-ethyl-6-fluoro-1H-indazol-4-yl)amino)-5-fluoronicotinamide | 432 | 0.93 | 1H-NMR (MeOD) δ: 8.10 (1H, s), 7.92 (1H, dd, J = 2.0, 12.0 Hz), 7.87 (1H, d, J = 11.9 Hz), 6.89 (1H, d, J = 7.9 Hz), 4.60-4.50 (1H, m), 4.38 (2H, q, J = 7.3 Hz), 4.20-4.10 (1H, m), 4.08-4.00 (2H, m), 3.87-3.66 (2H, m), 2.00-1.90 (2H, m), 1.45 (3H, t, J = 7.3 Hz). |
| Example 2-371 | 6-(((2S,3R)-2-aminopentan-3-yl)amino)-2-((1-ethyl-6-fluoro-1H-indazol-4-yl)amino)-5-fluoronicotinamide | 418 | 1.01 | |

TABLE 3-continued

| Example | Structure | Compound name | MS (ESI m/z): (M + H) | RT (min) | HNMR |
|---|---|---|---|---|---|
| Example 2-372 | 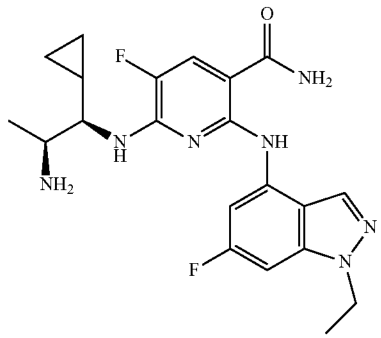 [SMILES: CCn1ncc2c(Nc3nc(N[C@H](C4CC4)[C@H](C)N)c(F)cc3C(N)=O)cc(F)cc21] | 6-(((1R,2S)-2-amino-1-cyclopropylpropyl)amino)-2-((1-ethyl-6-fluoro-1H-indazol-4-yl)amino)-5-fluoronicotinamide | 430 | 1.01 | |
| Example 2-373 | 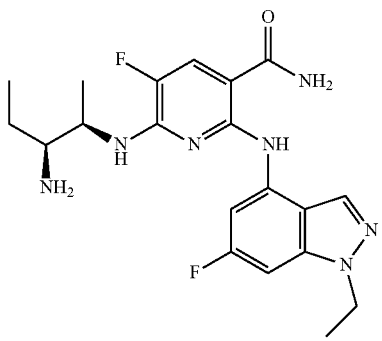 [SMILES: CC[C@H](N)[C@@H](C)Nc1nc(Nc2cc(F)cc3c2cnn3CC)c(C(N)=O)cc1F] | 6-(((2R,3S)-3-aminopentan-2-yl)amino)-2-((1-ethyl-6-fluoro-1H-indazol-4-yl)amino)-5-fluoronicotinamide | 418 | 0.97 | |
| Example 2-374 | 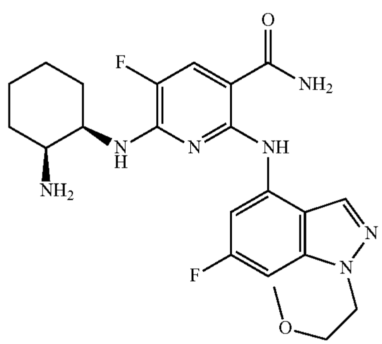 [SMILES: COCCn1ncc2c(Nc3nc(N[C@@H]4CCCC[C@@H]4N)c(F)cc3C(N)=O)cc(F)cc21] | 6-(((1R,2S)-2-aminocyclohexyl)amino)-5-fluoro-2-((6-fluoro-1-(2-methoxyethyl)-1H-indazol-4-yl)amino)nicotinamide | 460 | 0.98 | 1H-NMR (MeOD) δ: 8.11 (1H, s), 7.94 (1H, dd, J = 12.6, 2.0 Hz), 7.86 (1H, d, J = 11.9 Hz), 6.88 (1H, d, J = 9.2 Hz), 4.49 (2H, t, J = 5.3 Hz), 4.48-4.42 (1H, m), 4.05-4.00 (1H, m), 3.80 (2H, t, J = 5.3 Hz), 3.27 (3H, s), 2.01-1.60 (8H, m), |

TABLE 3-continued

| Example | Structure | Compound name | MS (ESI m/z): (M + H) | RT (min) | HNMR |
|---|---|---|---|---|---|
| Example 2-375 | 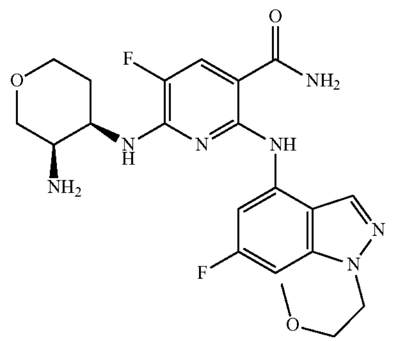 [SMILES: COCCn1ncc2c(Nc3nc(N[C@@H]4CCOC[C@@H]4N)c(F)cc3C(N)=O)cc(F)cc21] | 6-(((3R,4R)-3-aminotetrahydro-2H-pyran-4-yl)amino)-5-fluoro-2-((6-fluoro-1-(2-methoxyethyl)-1H-indazol-4-yl)amino)nicotinamide | 462 | 0.86 | 1H-NMR (MeOD) δ: 8.11 (1H, s), 7.92-7.84 (1H, m), 7.87 (1H, d, J = 13.2 Hz), 6.90 (1H, d, J = 8.6 Hz), 4.57-4.49 (1H, m), 4.49 (2H, t, J = 5.0 Hz), 4.19-4.11 (1H, m), 4.07-3.99 (2H, m), 3.87-3.62 (2H, m), 3.80 (2H, t, J = 5.0 Hz), 3.27 (3H, s), 2.02-1.87 (2H, m). |
| Example 2-376 | 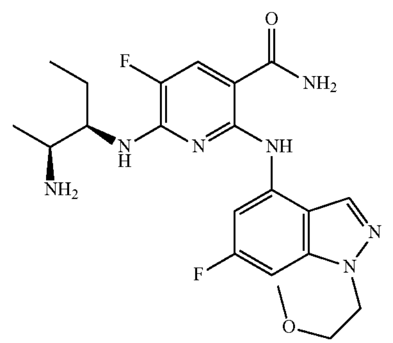 [SMILES: CC[C@@H](Nc1nc(Nc2cc(F)cc3c2cnn3CCOC)c(C(N)=O)cc1F)[C@H](C)N] | 6-(((2S,3R)-2-aminopentan-3-yl)amino)-5-fluoro-2-((6-fluoro-1-(2-methoxyethyl)-1H-indazol-4-yl)amino)nicotinamide | 448 | 0.95 | 1H-NMR (MeOD) δ: 8.11 (1H, s), 7.91 (1H, dd, J = 12.6, 1.9 Hz), 7.85 (1H, d, J = 11.9 Hz), 6.88 (1H, d, J = 8.6 Hz), 4.49 (2H, t, J = 5.0 Hz), 4.21-4.18 (1H, m), 3.80 (2H, t, J = 5.0 Hz), 3.51-3.45 (1H, m), 3.27 (3H, s), 2.20 (3H, d, J = 7.3 Hz), 1.64-1.54 (2H, m), 1.10 (3H, t, J = 7.6 Hz). |
| Example 2-377 | 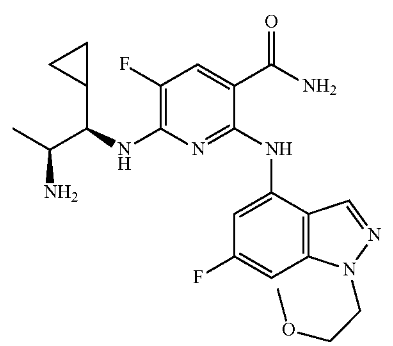 [SMILES: COCCn1ncc2c(Nc3nc(N[C@H](C4CC4)[C@H](C)N)c(F)cc3C(N)=O)cc(F)cc21] | 6-(((1R,2S)-2-amino-1-cyclopropylpropyl)amino)-5-fluoro-2-((6-fluoro-1-(2-methoxyethyl)-1H-indazol-4-yl)amino)nicotinamide | 460 | 0.95 | 1H-NMR (MeOD) δ: 8.10 (1H, s), 7.84 (1H, d, J = 12.0 Hz), 7.78 (1H, dd, J = 13.9, 2.0 Hz), 6.88 (1H, d, J = 10.0 Hz), 4.48 (2H, t, J = 5.3 Hz), 4.14-4.05 (1H, m), 3.80 (2H, t, J = 5.3 Hz), 3.79-3.74 (1H, m), 3.27 (3H, s), 1.45 (3H, d, J = 5.0 Hz), 1.17-1.11 (1H, m), 0.87-0.78 (1H, m), 0.67-0.60 (1H, m), 0.60-0.45 (2H, m). |

TABLE 3-continued

| Example | Structure | Compound name | MS (ESI m/z): (M + H) | RT (min) | HNMR |
|---|---|---|---|---|---|
| Example 2-378 | 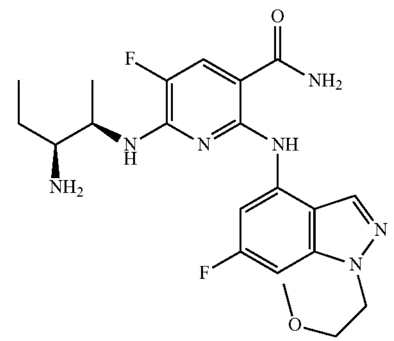 [SMILES: CC[C@H](N)[C@@H](C)Nc1nc(Nc2cc(F)cc3c2cnn3CCOC)c(C(N)=O)cc1F] | 8-(((2R,3S)-3-aminopentan-2-yl)amino)-5-fluoro-2-((6-fluoro-1-(2-methoxyethyl)-1H-indazol-4-yl)amino)nicotinamide | 448 | 0.93 | |
| Example 2-379 | 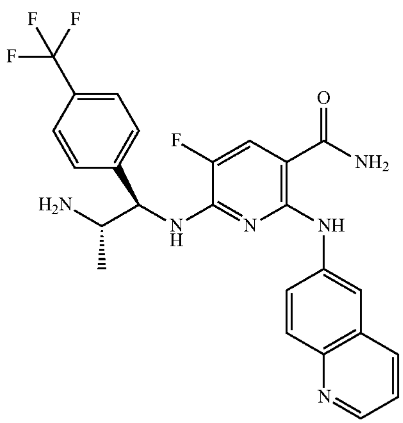 [SMILES: C[C@H](N)[C@H](Nc1nc(Nc2ccc3ncccc3c2)c(C(N)=O)cc1F)c1ccc(C(F)(F)F)cc1] | 6-(((1R,2S)-2-amino-1-(4-(trifluoromethyl)phenyl)propyl)amino)-5-fluoro-2-(quinolin-6-ylamino)nicotinamide | 499 | 0.87 | |

TABLE 3-continued

| Example | Structure | Compound name | MS (ESI m/z): (M + H) | RT (min) | HNMR |
|---|---|---|---|---|---|
| Example 2-380 | 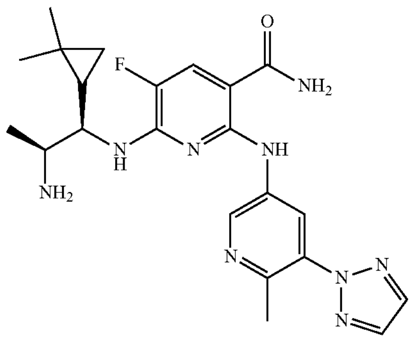 [SMILES: Cc1ncc(Nc2nc(N[C@H](C3CC3(C)C)[C@H](C)N)c(F)cc2C(N)=O)cc1-n1nccn1] | 6-(((1R,2S)-2-amino-1-((S)-2,2-dimethylcyclopropyl)propyl)amino)-5-fluoro-2-((6-methyl-5-(2H-1,2,3-triazol-2-yl)pyridin-3-yl)amino)nicotinamide | 454 | 1 | |
| Example 2-381 | 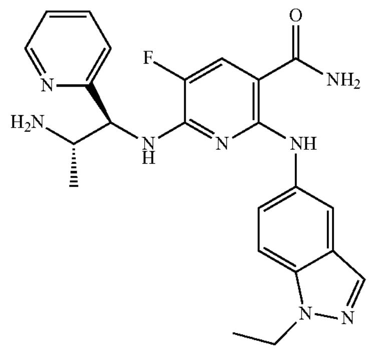 [SMILES: CCn1ncc2cc(Nc3nc(N[C@H](c4ccccn4)[C@H](C)N)c(F)cc3C(N)=O)ccc21] | 6-(((1S,2S)-2-amino-1-(pyridin-2-yl)propyl)amino)-2-((1-ethyl-1H-indazol-5-yl)amino)-5-fluoronicotinamide | 449 | 0.88 | |
| Example 2-382 | 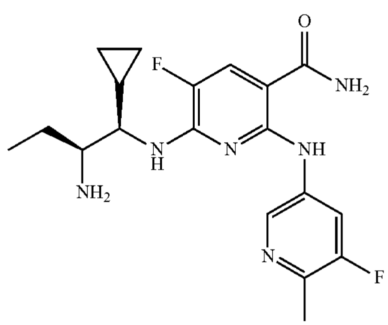 [SMILES: CC[C@H](N)[C@H](Nc1nc(Nc2cnc(C)c(F)c2)c(C(N)=O)cc1F)C1CC1] | 6-(((1R,2S)-2-amino-1-cyclopropylbutyl)amino)-5-fluoro-2-((5-fluoro-6-methylpyridin-3-yl)amino)nicotinamide | 391 | 0.88 | |

TABLE 3-continued

| Example | Structure | Compound name | MS (ESI m/z): (M + H) | RT (min) | HNMR |
|---|---|---|---|---|---|
| Example 2-383 | 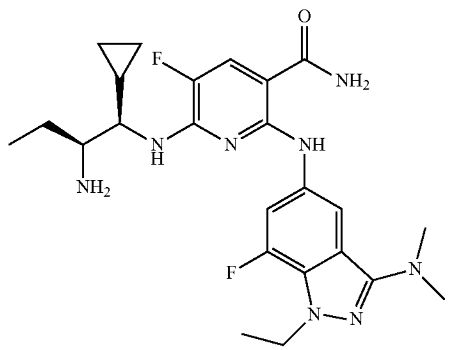 [SMILES: CC[C@H](N)[C@H](Nc1nc(Nc2cc(F)c3c(c2)c(N(C)C)nn3CC)c(C(N)=O)cc1F)C1CC1] | 6-(((1R,2S)-2-amino-1-cyclopropylbutyl)amino)-2-((3-(dimethylamino)-7-fluoro-1-methyl-1H-indazol-5-yl)amino)-5-fluoronicotinamide | 473 | 1.04 | |
| Example 2-384 | 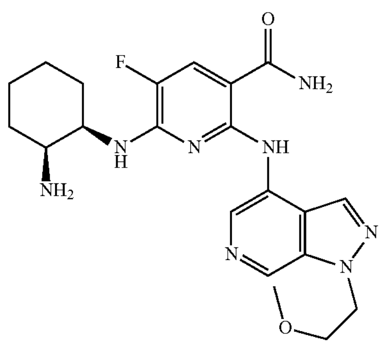 [SMILES: COCCn1ncc2c(Nc3nc(N[C@@H]4CCCC[C@@H]4N)c(F)cc3C(N)=O)cncc21] | 6-(((1R,2S)-2-aminocyclohexyl)amino)-5-fluoro-2-((1-(2-methoxyethyl)-1H-pyrazolo[3,4-c]pyridin-4-yl)amino)nicotinamide | 443 | 0.71 | |
| Example 2-385 | 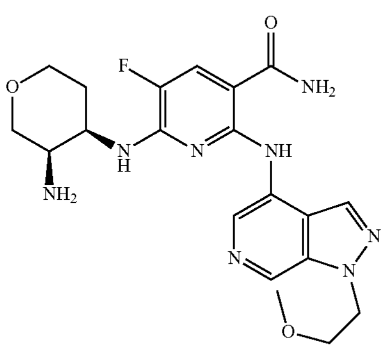 [SMILES: COCCn1ncc2c(Nc3nc(N[C@@H]4CCOC[C@@H]4N)c(F)cc3C(N)=O)cncc21] | 6-(((3R,4R)-3-aminotetrahydro-2H-pyran-4-yl)amino)-5-fluoro-2-((1-(2-methoxyethyl)-1H-pyrazolo[3,4-c]pyridin-4-yl)amino)nicotinamide | 445 | 0.59 | |

TABLE 3-continued

| Example | Structure | Compound name | MS (ESI m/z): (M + H) | RT (min) | HNMR |
|---|---|---|---|---|---|
| Example 2-386 | 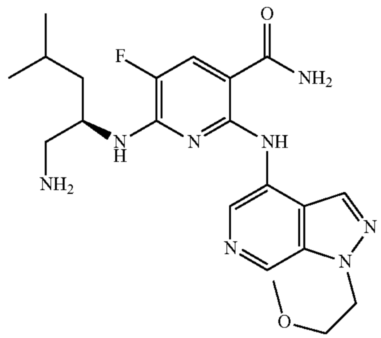 [SMILES: COCCn1ncc2c(Nc3nc(N[C@@H](CN)CC(C)C)c(F)cc3C(N)=O)cncc21] | (R)-6-((1-amino-4-methylpentan-2-yl)amino)-5-fluoro-2-((1-(2-methoxyethyl)-1H-pyrazolo[3,4-c]pyridin-4-yl)amino)nicotinamide | 445 | 0.76 | |
| Example 2-387 | 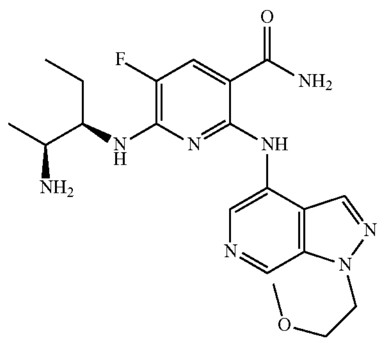 [SMILES: CC[C@@H](Nc1nc(Nc2cncc3c2cnn3CCOC)c(C(N)=O)cc1F)[C@H](C)N] | 6-(((2S,3R)-2-aminopentan-3-yl)amino)-5-fluoro-2-((1-(2-methoxyethyl)-1H-pyrazolo[3,4-c]pyridin-4-yl)amino)nicotinamide | 431 | 0.65 | |
| Example 2-388 | 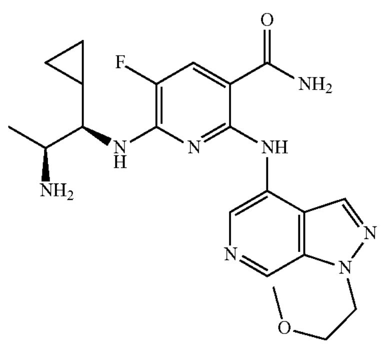 [SMILES: COCCn1ncc2c(Nc3nc(N[C@H](C4CC4)[C@H](C)N)c(F)cc3C(N)=O)cncc21] | 6-(((1R,2S)-2-amino-1-cyclopropylpropyl)amino)-5-fluoro-2-((1-(2-methoxyethyl)-1H-pyrazolo[3,4-c]pyridin-4-yl)amino)nicotinamide | 443 | 0.68 | |

TABLE 3-continued

| Example | Structure | Compound name | MS (ESI m/z): (M + H) | RT (min) | HNMR |
|---|---|---|---|---|---|
| Example 2-389 | 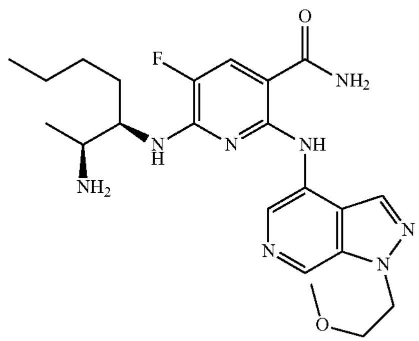 [SMILES: CCCC[C@@H](Nc1nc(Nc2cncc3c2cnn3CCOC)c(C(N)=O)cc1F)[C@H](C)N] | 6-(((2S,3R)-2-aminoheptan-3-yl)amino)-5-fluoro-2-((1-(2-methoxyethyl)-1H-pyrazolo[3,4-c]pyridin-4-yl)amino)nicotinamide | 459 | 0.78 | |
| Example 2-390 | 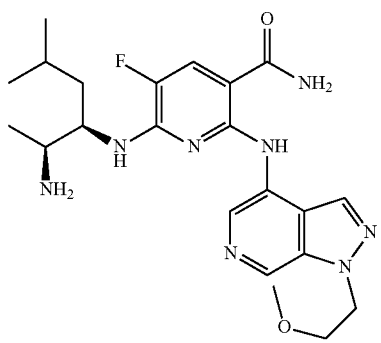 [SMILES: COCCn1ncc2c(Nc3nc(N[C@H](CC(C)C)[C@H](C)N)c(F)cc3C(N)=O)cncc21] | 6-(((2S,3R)-2-amino-5-methylhexan-3-yl)amino)-5-fluoro-2-((1-(2-methoxyethyl)-1H-pyrazolo[3,4-c]pyridin-4-yl)amino)nicotinamide | 459 | 0.76 | |
| Example 2-391 | 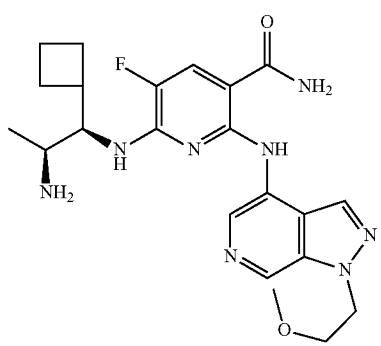 [SMILES: COCCn1ncc2c(Nc3nc(N[C@H](C4CCC4)[C@H](C)N)c(F)cc3C(N)=O)cncc21] | 6-(((1R,2S)-2-amino-1-cyclobutylpropyl)amino)-5-fluoro-2-((1-(2-methoxyethyl)-1H-pyrazolo[3,4-c]pyridin-4-yl)amino)nicotinamide | 457 | 0.74 | |

TABLE 3-continued

| Example | Structure | Compound name | MS (ESI m/z): (M + H) | RT (min) | HNMR |
|---|---|---|---|---|---|
| Example 2-392 | 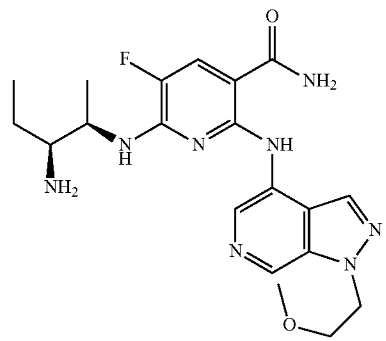 [SMILES: CC[C@H](N)[C@@H](C)Nc1nc(Nc2cncc3c2cnn3CCOC)c(C(N)=O)cc1F] | 6-(((2R,3S)-3-aminopentan-2-yl)amino)-5-fluoro-2-((1-(2-methoxyethyl)-1H-pyrazolo[3,4-c]pyridin-4-yl)amino)nicotinamide | 431 | 0.63 | |
| Example 2-393 | 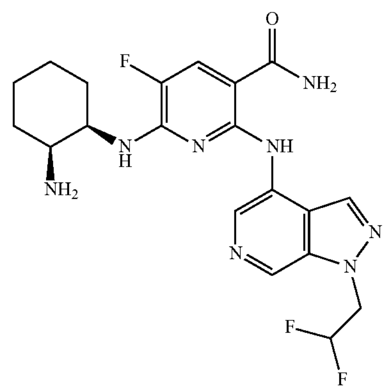 [SMILES: NC(=O)c1cc(F)c(N[C@@H]2CCCC[C@@H]2N)nc1Nc1cncc2c1cnn2CC(F)F] | 6-(((1R,2S)-2-aminocyclohexyl)amino)-2-((1-(2,2-difluoroethyl)-1H-pyrazolo[3,4-c]pyridin-4-yl)amino)-5-fluoronicotinamide | 449 | 0.72 | 1H-NMR (MeOD) δ: 9.25 (1H, s), 9.00 (1H, s), 8.54 (1H, s), 7.95 (1H, d, J = 11.9 Hz), 6.38 (1H, tt, J = 54.8, 2.9 Hz), 4.78-4.68 (2H, m), 4.56-4.51 (1H, m), 3.86-3.81 (1H, m), 1.98-1.55 (8H, m). |

TABLE 3-continued

| Example | Structure | Compound name | MS (ESI m/z): (M + H) | RT (min) | HNMR |
|---|---|---|---|---|---|
| Example 2-394 | 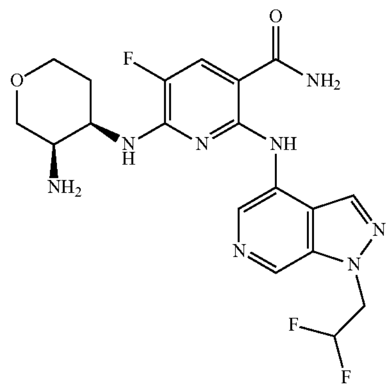 [SMILES: NC(=O)c1cc(F)c(N[C@@H]2CCOC[C@@H]2N)nc1Nc1cncc2c1cnn2CC(F)F] | 6-(((3R,4R)-3-aminotetrahydro-2H-pyran-4-yl)amino)-2-((1-(2,2-difluoroethyl)-1H-pyrazolo[3,4-c]pyridin-4-yl)amino)-5-fluoronicotinamide | 451 | 0.62 | |
| Example 2-395 | 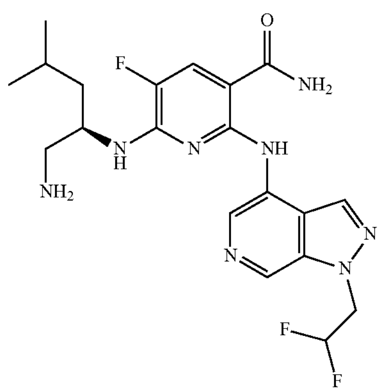 [SMILES: CC(C)C[C@H](CN)Nc1nc(Nc2cncc3c2cnn3CC(F)F)c(C(N)=O)cc1F] | (R)-6-((1-amino-4-methylpentan-2-yl)amino)-2-((1-(2,2-difluoroethyl)-1H-pyrazolo[3,4-c]pyridin-4-yl)amino)-5-fluoronicotinamide | 451 | 0.82 | |

TABLE 3-continued

| Example | Structure | Compound name | MS (ESI m/z): (M + H) | RT (min) | HNMR |
|---|---|---|---|---|---|
| Example 2-396 | 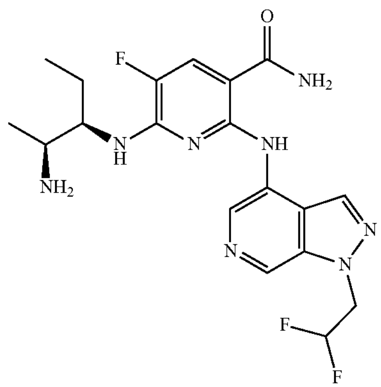 [SMILES: CC[C@@H](Nc1nc(Nc2cncc3c2cnn3CC(F)F)c(C(N)=O)cc1F)[C@H](C)N] | 6-(((2S,3R)-2-aminopentan-3-yl)amino)-2-((1-(2,2-difluoroethyl)-1H-pyrazolo[3,4-c]pyridin-4-yl)amino)-5-fluoronicotinamide | 437 | 0.7 | |
| Example 2-397 | 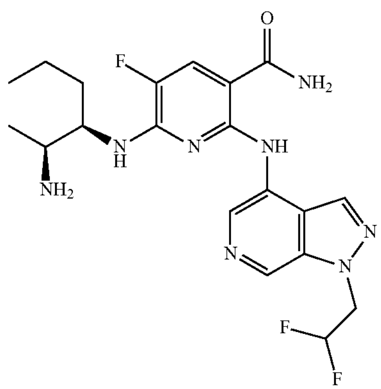 [SMILES: CCC[C@@H](Nc1nc(Nc2cncc3c2cnn3CC(F)F)c(C(N)=O)cc1F)[C@H](C)N] | 6-(((2S,3R)-2-aminohexan-3-yl)amino)-2-((1-(2,2-difluoroethyl)-1H-pyrazolo[3,4-c]pyridin-4-yl)amino)-5-fluoronicotinamide | 451 | 0.78 | |

| Example | Structure | Compound name | MS (ESI m/z): (M + H) | RT (min) | HNMR |
|---|---|---|---|---|---|
| Example 2-398 | 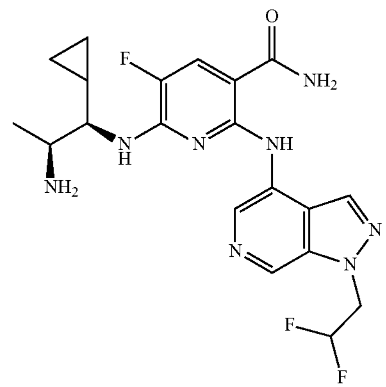 [SMILES: C[C@H](N)[C@H](Nc1nc(Nc2cncc3c2cnn3CC(F)F)c(C(N)=O)cc1F)C1CC1] | 6-(((1R,2S)-2-amino-1-cyclopropylpropyl)amino)-2-((1-(2,2-difluoroethyl)-1H-pyrazolo[3,4-c]pyridin-4-yl)amino)-5-fluoronicotinamide | 449 | 0.72 | |
| Example 2-399 | 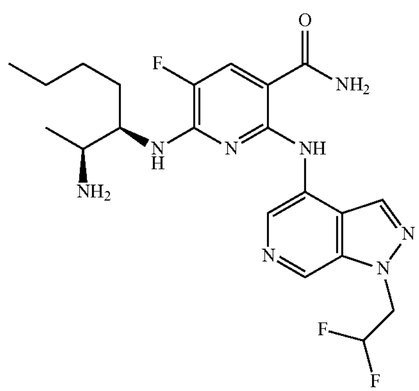 [SMILES: CCCC[C@@H](Nc1nc(Nc2cncc3c2cnn3CC(F)F)c(C(N)=O)cc1F)[C@H](C)N] | 6-(((2S,3R)-2-aminoheptan-3-yl)amino)-2-((1-(2,2-difluoroethyl)-1H-pyrazolo[3,4-c]pyridin-4-yl)amino)-5-fluoronicotinamide | 465 | 0.83 | |

| Example | Structure | Compound name | MS (ESI m/z): (M + H) | RT (min) | HNMR |
|---|---|---|---|---|---|
| Example 2-400 | 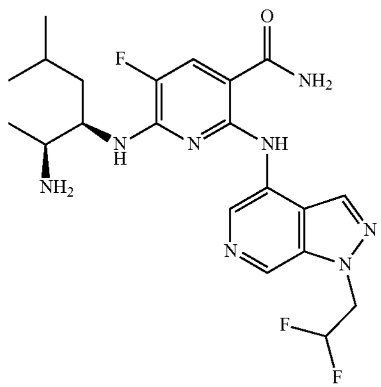 [SMILES: CC(C)C[C@@H](Nc1nc(Nc2cncc3c2cnn3CC(F)F)c(C(N)=O)cc1F)[C@H](C)N] | 6-(((2S,3R)-2-amino-5-methylhexan-3-yl)amino)-2-((1-(2,2-difluoroethyl)-1H-pyrazolo[3,4-c]pyridin-4-yl)amino)-5-fluoronicotinamide | 465 | 0.82 | |
| Example 2-401 | 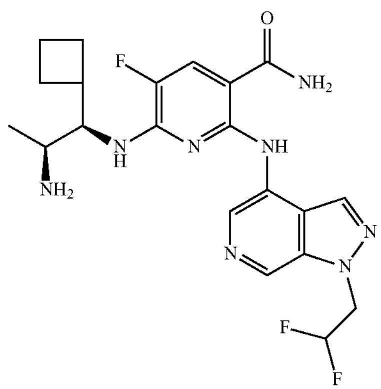 [SMILES: C[C@H](N)[C@H](Nc1nc(Nc2cncc3c2cnn3CC(F)F)c(C(N)=O)cc1F)C1CCC1] | 6-(((1R,2S)-2-amino-1-cyclobutylpropyl)amino)-2-((1-(2,2-difluoroethyl)-1H-pyrazolo[3,4-c]pyridin-4-yl)amino)-5-fluoronicotinamide | 463 | 0.79 | |

TABLE 3-continued

| Example | Structure | Compound name | MS (ESI m/z): (M + H) | RT (min) | HNMR |
|---|---|---|---|---|---|
| Example 2-402 | 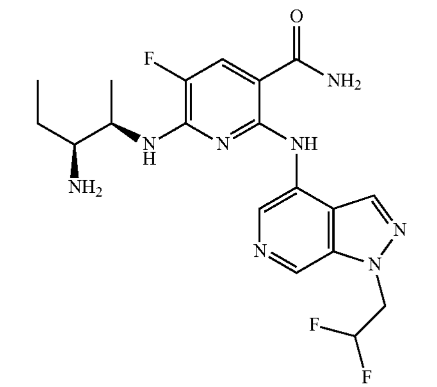 [SMILES: CC[C@H](N)[C@@H](C)Nc1nc(Nc2cncc3c2cnn3CC(F)F)c(C(N)=O)cc1F] | 6-(((2R,3S)-3-aminopentan-2-yl)amino)-2-((1-(2,2-difluoroethyl)-1H-pyrazolo[3,4-c]pyridin-4-yl)amino)-5-fluoronicotinamide | 437 | 0.66 | |
| Example 2-403 | 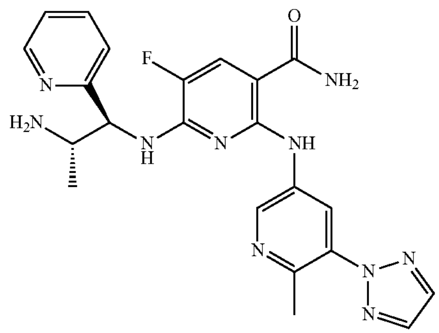 [SMILES: Cc1ncc(Nc2nc(N[C@H](c3ccccn3)[C@H](C)N)c(F)cc2C(N)=O)cc1-n1nccn1] | 6-(((1S,2S)-2-amino-1-(pyridin-2-yl)propyl)amino)-5-fluoro-2-((6-methyl-5-(2H-1,2,3-triazol-2-yl)pyridin-3-yl)amino)nicotinamide | 463 | 0.85 | |
| Example 2-404 | 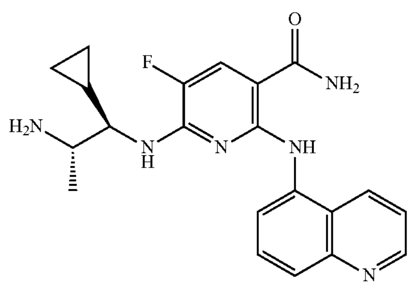 [SMILES: C[C@H](N)[C@H](Nc1nc(Nc2cccc3ncccc23)c(C(N)=O)cc1F)C1CC1] | 6-(((1R,2S)-2-amino-1-cyclopropylpropyl)amino)-5-fluoro-2-(quinolin-5-ylamino)nicotinamide | 395 | 0.68 | |

TABLE 3-continued

| Example | Structure | Compound name | MS (ESI m/z): (M + H) | RT (min) | HNMR |
|---|---|---|---|---|---|
| Example 2-405 | 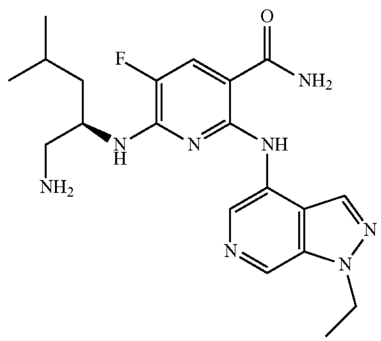 [SMILES: CCn1ncc2c(Nc3nc(N[C@@H](CN)CC(C)C)c(F)cc3C(N)=O)cncc21] | (R)-6-((1-amino-4-methylpentan-2-yl)amino)-2-((1-ethyl-1H-pyrazolo[3,4-c]pyridin-4-yl)amino)-5-fluoronicotinamide | 415 | 0.78 | |
| Example 2-406 | 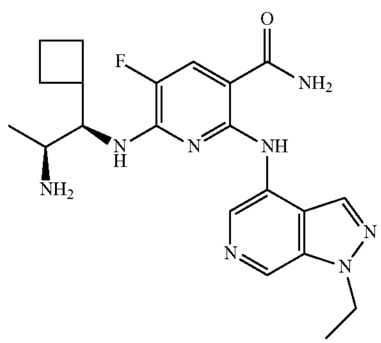 [SMILES: CCn1ncc2c(Nc3nc(N[C@H](C4CCC4)[C@H](C)N)c(F)cc3C(N)=O)cncc21] | 6-(((1R,2S)-2-amino-1-cyclobutylpropyl)amino)-2-((1-ethyl-1H-pyrazolo[3,4-c]pyridin-4-yl)amino)-5-fluoronicotinamide | 427 | 0.75 | |
| Example 2-407 | 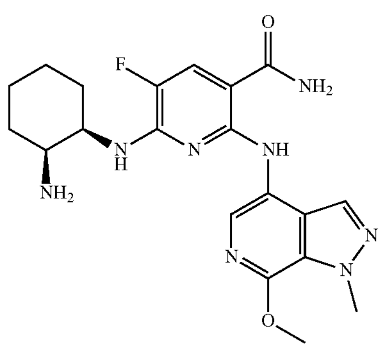 [SMILES: COc1ncc(Nc2nc(N[C@@H]3CCCC[C@@H]3N)c(F)cc2C(N)=O)c2cnn(C)c12] | 6-(((1R,2S)-2-aminocyclohexyl)amino)-5-fluoro-2-((7-methoxy-1-methyl-1H-pyrazolo[3,4-c]pyridin-4-yl)amino)nicotinamide | 429 | 0.91 | |

TABLE 3-continued

| Example | Structure | Compound name | MS (ESI m/z): (M + H) | RT (min) | HNMR |
|---|---|---|---|---|---|
| Example 2-408 | 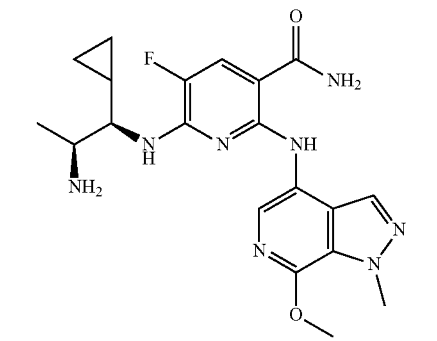 [SMILES: COc1ncc(Nc2nc(N[C@H](C3CC3)[C@H](C)N)c(F)cc2C(N)=O)c2cnn(C)c12] | 6-(((1R,2S)-2-amino-1-cyclopropylpropyl)amino)-5-fluoro-2-((7-methoxy-1-methyl-1H-pyrazolo[3,4-c]pyridin-4-yl)amino)nicotinamide | 429 | 0.89 | |
| Example 2-409 | 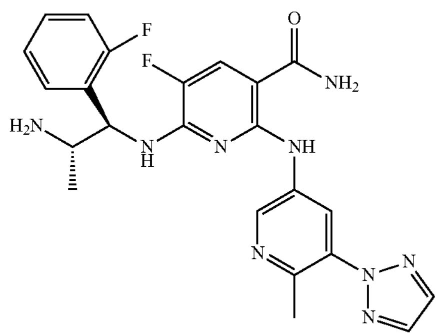 [SMILES: Cc1ncc(Nc2nc(N[C@H](c3ccccc3F)[C@H](C)N)c(F)cc2C(N)=O)cc1-n1nccn1] | 6-(((1R,2S)-2-amino-1-(2-fluorophenyl)propyl)amino)-5-fluoro-2-((6-methyl-5-(2H-1,2,3-triazol-2-yl)pyridin-3-yl)amino)nicotinamide | 480 | 0.92 | |
| Example 2-410 | 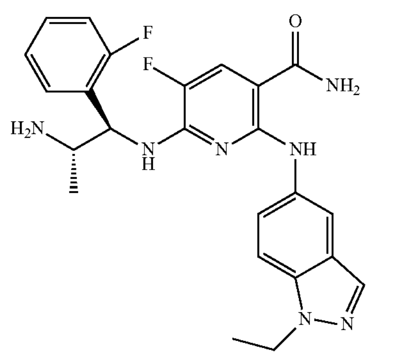 [SMILES: CCn1ncc2cc(Nc3nc(N[C@H](c4ccccc4F)[C@H](C)N)c(F)cc3C(N)=O)ccc21] | 6-(((1R,2S)-2-amino-1-(2-fluorophenyl)propyl)amino)-2-((1-ethyl-1H-indazol-5-yl)amino)-5-fluoronicotinamide | 466 | 0.98 | |

TABLE 3-continued

| Example | Structure | Compound name | MS (ESI m/z): (M + H) | RT (min) | HNMR |
|---|---|---|---|---|---|
| Example 2-411 | 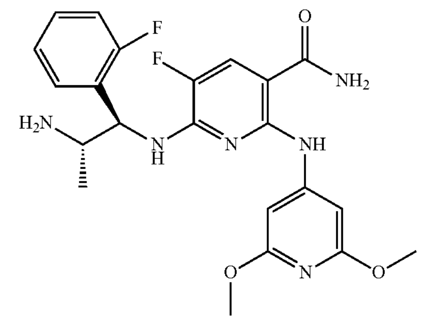 [SMILES: COc1cc(Nc2nc(N[C@H](c3ccccc3F)[C@H](C)N)c(F)cc2C(N)=O)cc(OC)n1] | 6-(((1R,2S)-2-amino-1-(2-fluorophenyl)propyl)amino)-2-((2,6-dimethoxypyridin-4-yl)amino)-5-fluoronicotinamide | 459 | 1.04 | |
| Example 2-412 | 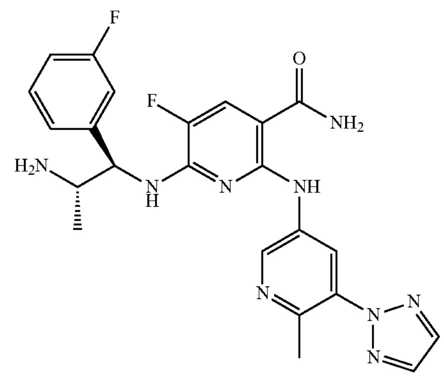 [SMILES: Cc1ncc(Nc2nc(N[C@H](c3cccc(F)c3)[C@H](C)N)c(F)cc2C(N)=O)cc1-n1nccn1] | 6-(((1R,2S)-2-amino-1-(3-fluorophenyl)propyl)amino)-5-fluoro-2-((6-methyl-5-(2H-1,2,3-triazol-2-yl)pyridin-3-yl)amino)nicotinamide | 479 | 0.9 | |

TABLE 3-continued

| Example | Structure | Compound name | MS (ESI m/z): (M + H) | RT (min) | HNMR |
|---|---|---|---|---|---|
| Example 2-413 | 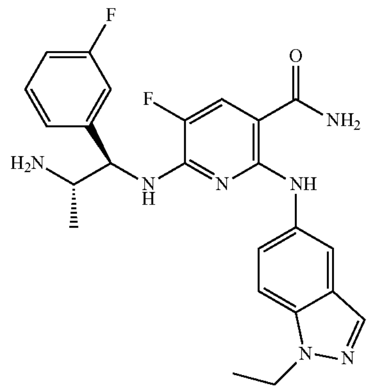 [SMILES: CCn1ncc2cc(Nc3nc(N[C@H](c4cccc(F)c4)[C@H](C)N)c(F)cc3C(N)=O)ccc21] | 6-(((1R,2S)-2-amino-1-(3-fluorophenyl)propyl)amino)-2-((1-ethyl-1H-indazol-5-yl)amino)-5-fluoronicotinamide | 466 | 0.96 | |
| Example 2-414 | 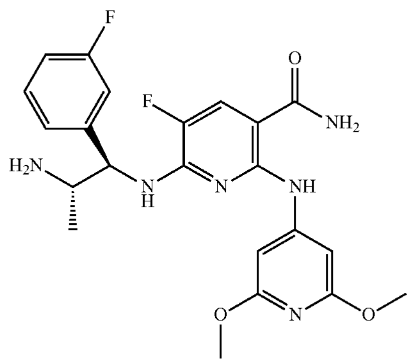 [SMILES: COc1cc(Nc2nc(N[C@H](c3cccc(F)c3)[C@H](C)N)c(F)cc2C(N)=O)cc(OC)n1] | 6-(((1R,2S)-2-amino-1-(3-fluorophenyl)propyl)amino)-2-((2,6-dimethoxypyridin-4-yl)amino)-5-fluoronicotinamide | 459 | 1 | |

TABLE 3-continued

| Example | Structure | Compound name | MS (ESI m/z): (M + H) | RT (min) | HNMR |
|---|---|---|---|---|---|
| Example 2-415 | 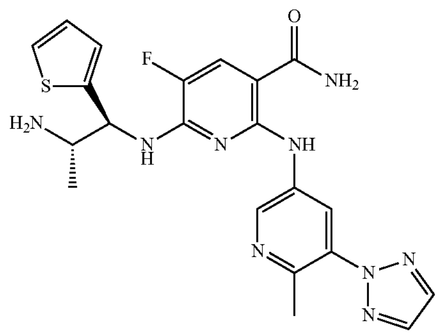 [SMILES: Cc1ncc(Nc2nc(N[C@H](c3cccs3)[C@H](C)N)c(F)cc2C(N)=O)cc1-n1nccn1] | 6-(((1S,2S)-2-amino-1-(thiophen-2-yl)propyl)amino)-5-fluoro-2-((6-methyl-5-(2H-1,2,3-triazol-2-yl)pyridin-3-yl)amino)nicotinamide | 468 | 0.88 | |
| Example 2-416 | 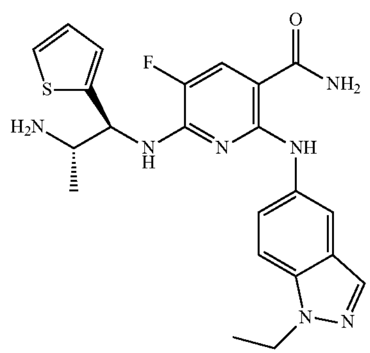 [SMILES: CCn1ncc2cc(Nc3nc(N[C@H](c4cccs4)[C@H](C)N)c(F)cc3C(N)=O)ccc21] | 6-(((1S,2S)-2-amino-1-(thiophen-2-yl)propyl)amino)-2-((1-ethyl-1H-indazol-5-yl)amino)-5-fluoronicotinamide | 454 | 0.94 | |
| Example 2-417 | 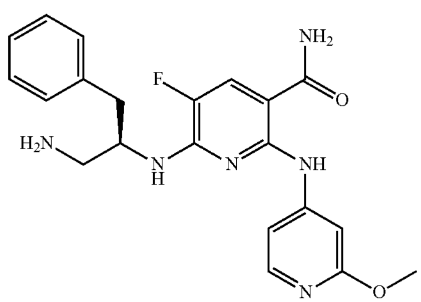 [SMILES: COc1cc(Nc2nc(N[C@@H](CN)Cc3ccccc3)c(F)cc2C(N)=O)ccn1] | (R)-6-((1-amino-3-phenylpropan-2-yl)amino)-5-fluoro-2-((2-methoxypyridin-4-yl)amino)nicotinamide | 411 | 0.74 | |

TABLE 3-continued

| Example | Structure | Compound name | MS (ESI m/z): (M + H) | RT (min) | HNMR |
|---|---|---|---|---|---|
| Example 2-418 | 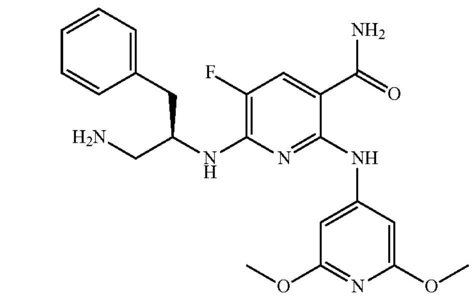 [SMILES: COc1cc(Nc2nc(N[C@@H](CN)Cc3ccccc3)c(F)cc2C(N)=O)cc(OC)n1] | (R)-6-((1-amino-3-phenylpropan-2-yl)amino)-2-((2,6-dimethoxypyridin-4-yl)amino)-5-fluoronicotinamide | 441 | 1.06 | |
| Example 2-419 | 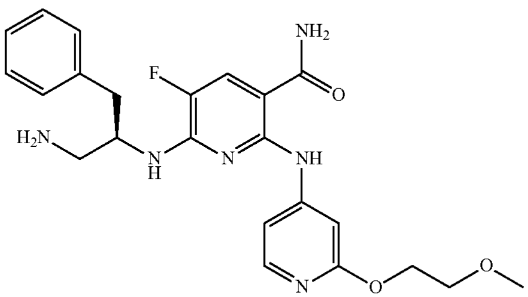 [SMILES: COCCOc1cc(Nc2nc(N[C@@H](CN)Cc3ccccc3)c(F)cc2C(N)=O)ccn1] | (R)-6-((1-amino-3-phenylpropan-2-yl)amino)-5-fluoro-2-((2-(2-methoxyethoxy)pyridin-4-yl)amino)nicotinamide | 455 | 0.78 | |
| Example 2-420 | 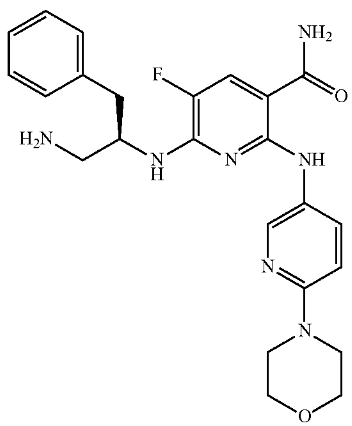 [SMILES: NC[C@@H](Cc1ccccc1)Nc1nc(Nc2ccc(N3CCOCC3)nc2)c(C(N)=O)cc1F] | (R)-6-((1-amino-3-phenylpropan-2-yl)amino)-5-fluoro-2-((6-morpholinopyridin-3-yl)amino)nicotinamide | 466 | 0.79 | 1H-NMR (MeOD) δ: 8.81 (1H, s), 7.90 (1H, dd, J = 9.6, 2.3 Hz), 7.70 (1H, d, J = 11.9 Hz), 7.20 (1H, d, J = 9.9 Hz), 7.15-7.09 (5H, m), 4.87 (2H, ピークと重なっている), 3.95-3.84 (4H, m), 3.71-3.63 (4H, m), 3.18-2.94 (2H, m), 2.87-2.74 (1H, m). |

TABLE 3-continued

| Example | Structure | Compound name | MS (ESI m/z): (M + H) | RT (min) | HNMR |
|---|---|---|---|---|---|
| Example 2-421 | 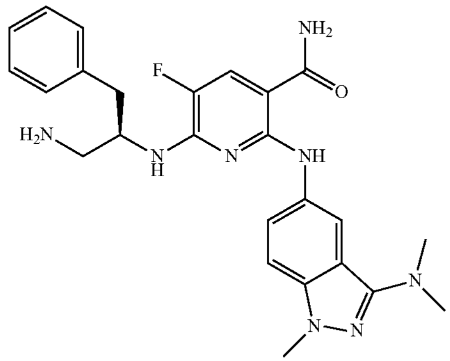 [SMILES: CN(C)c1nn(C)c2ccc(Nc3nc(N[C@@H](CN)Cc4ccccc4)c(F)cc3C(N)=O)cc12] | (R)-6-((1-amino-3-phenylpropan-2-yl)amino)-2-((3-(dimethylamino)-1-methyl-1H-indazol-5-yl)amino)-5-fluoronicotinamide | 477 | 0.99 | |
| Example 2-422 | 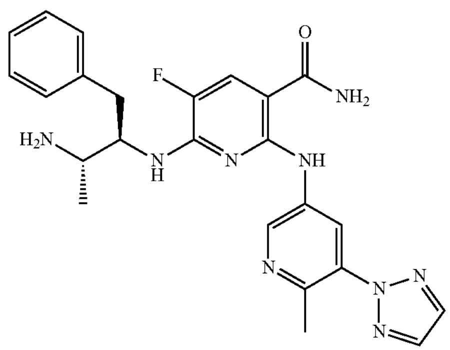 [SMILES: Cc1ncc(Nc2nc(N[C@H](Cc3ccccc3)[C@H](C)N)c(F)cc2C(N)=O)cc1-n1nccn1] | 6-(((2R,3S)-3-amino-1-phenylbutan-2-yl)amino)-5-fluoro-2-((6-methyl-5-(2H-1,2,3-triazol-2-yl)pyridin-3-yl)amino)nicotinamide | 476 | 0.96 | |

TABLE 3-continued

| Example | Structure | Compound name | MS (ESI m/z): (M + H) | RT (min) | HNMR |
|---|---|---|---|---|---|
| Example 2-423 | 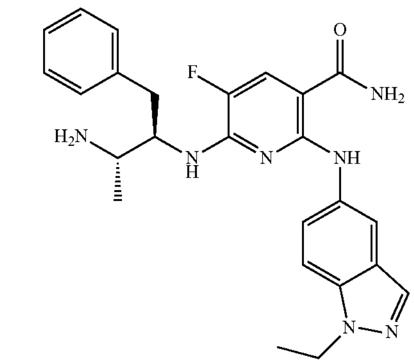 [SMILES: CCn1ncc2cc(Nc3nc(N[C@H](Cc4ccccc4)[C@H](C)N)c(F)cc3C(N)=O)ccc21] | 6-(((2R,3S)-3-amino-1-phenylbutan-2-yl)amino)-2-((1-ethyl-1H-indazol-5-yl)amino)-5-fluoronicotinamide | 462 | 1.01 | |
| Example 2-424 | 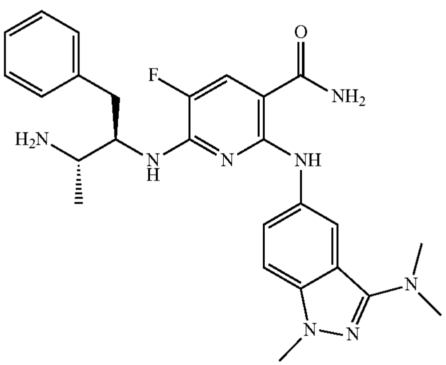 [SMILES: C[C@H](N)[C@@H](Cc1ccccc1)Nc1nc(Nc2ccc3c(c2)c(N(C)C)nn3C)c(C(N)=O)cc1F] | 6-(((2R,3S)-3-amino-1-phenylbutan-2-yl)amino)-2-((3-(dimethylamino)-1-methyl-1H-indazol-5-yl)amino)-5-fluoronicotinamide | 491 | 1 | |

TABLE 3-continued

| Example | Structure | Compound name | MS (ESI m/z): (M + H) | RT (min) | HNMR |
|---|---|---|---|---|---|
| Example 2-425 | 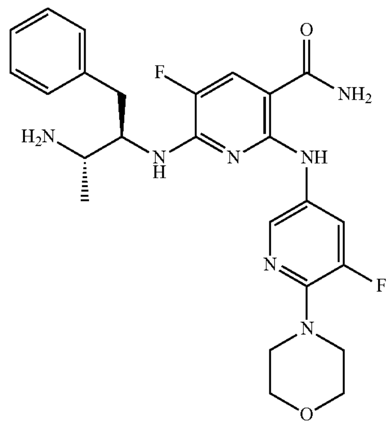 [SMILES: C[C@H](N)[C@@H](Cc1ccccc1)Nc1nc(Nc2cnc(N3CCOCC3)c(F)c2)c(C(N)=O)cc1F] | 6-(((2R,3S)-3-amino-1-phenylbutan-2-yl)amino)-5-fluoro-2-((5-fluoro-6-morpholinopyridin-3-yl)amino)nicotinamide | 498 | 1.01 | |
| Example 2-426 | 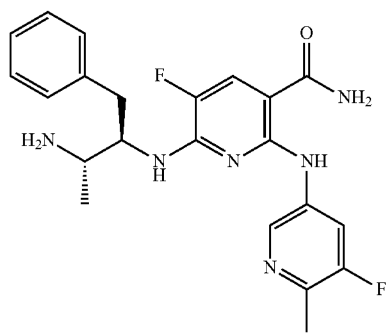 [SMILES: Cc1ncc(Nc2nc(N[C@H](Cc3ccccc3)[C@H](C)N)c(F)cc2C(N)=O)cc1F] | 6-(((2R,3S)-3-amino-1-phenylbutan-2-yl)amino)-5-fluoro-2-((5-fluoro-6-methylpyridin-3-yl)amino)nicotinamide | 427 | 0.95 | |

TABLE 3-continued

| Example | Structure | Compound name | MS (ESI m/z): (M + H) | RT (min) | HNMR |
|---|---|---|---|---|---|
| Example 2-427 | 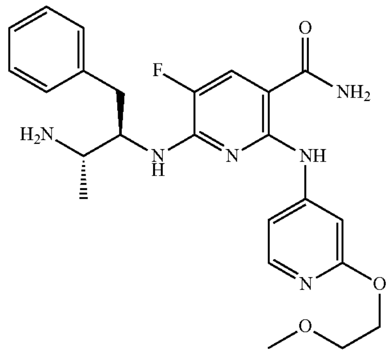 [SMILES: COCCOc1cc(Nc2nc(N[C@H](Cc3ccccc3)[C@H](C)N)c(F)cc2C(N)=O)ccn1] | 6-(((2R,3S)-3-amino-1-phenylbutan-2-yl)amino)-5-fluoro-2-((2-(2-methoxyethoxy)pyridin-4-yl)amino)nicotinamide | 469 | 0.79 | |
| Example 2-428 | 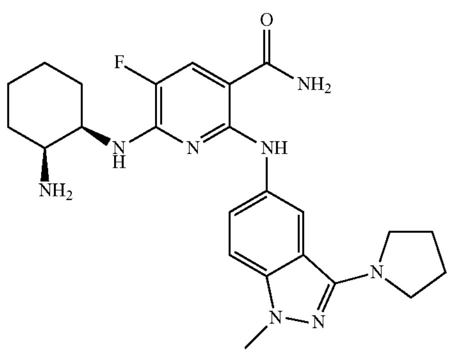 [SMILES: Cn1nc(N2CCCC2)c2cc(Nc3nc(N[C@@H]4CCCC[C@@H]4N)c(F)cc3C(N)=O)ccc21] | 6-(((1R,2S)-2-aminocyclohexyl)amino)-5-fluoro-2-((1-methyl-3-(pyrrolidin-1-1)-1H-indazol-5-yl)amino)nicotinamide | 467 | 0.92 | |

TABLE 3-continued

| Example | Structure | Compound name | MS (ESI m/z): (M + H) | RT (min) | HNMR |
|---|---|---|---|---|---|
| Example 2-429 | 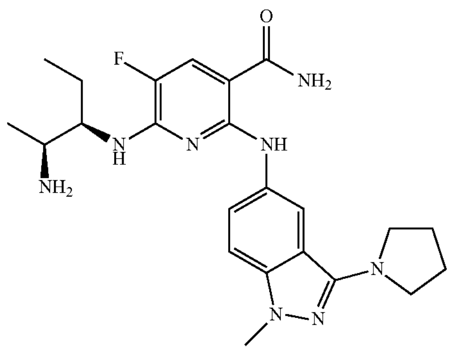 [SMILES: CC[C@@H](Nc1nc(Nc2ccc3c(c2)c(N2CCCC2)nn3C)c(C(N)=O)cc1F)[C@H](C)N] | 6-(((2S,3R)-2-aminopentan-3-yl)amino)-5-fluoro-2-((1-methyl-3-(pyrrolidin-1-yl)-1H-indazol-5-yl)amino)nicotinamide | 455 | 0.89 | |
| Example 2-430 | 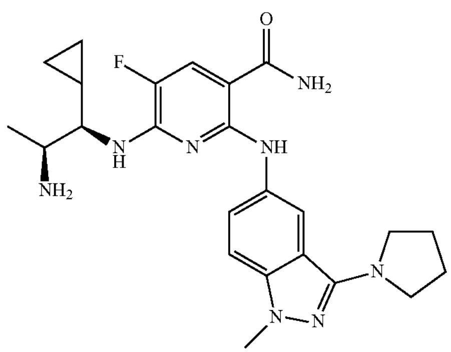 [SMILES: C[C@H](N)[C@H](Nc1nc(Nc2ccc3c(c2)c(N2CCCC2)nn3C)c(C(N)=O)cc1F)C1CC1] | 6-(((1R,2S)-2-amino-1-cyclopropylpropyl)amino)-5-fluoro-2-((1-methyl-3-(pyrrolidin-1-yl)-1H-indazol-5-yl)amino)nicotinamide | 467 | 0.91 | |
| Example 2-431 | 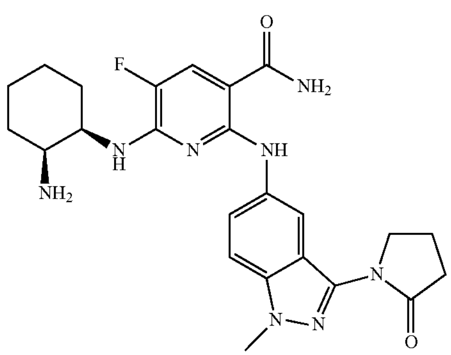 [SMILES: Cn1nc(N2CCCC2=O)c2cc(Nc3nc(N[C@@H]4CCCC[C@@H]4N)c(F)cc3C(N)=O)ccc21] | 6-(((1R,2S)-2-aminocyclohexyl)amino)-5-fluoro-2-((1-methyl-3-(2-oxopyrrolidin-1-yl)-1H-indazol-5-yl)amino)nicotinamide | 481 | 0.87 | |

TABLE 3-continued

| Example | Structure | Compound name | MS (ESI m/z): (M + H) | RT (min) | HNMR |
|---|---|---|---|---|---|
| Example 2-432 | 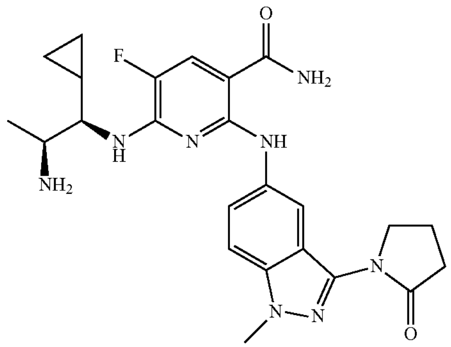 [SMILES: C[C@H](N)[C@H](Nc1nc(Nc2ccc3c(c2)c(N2CCCC2=O)nn3C)c(C(N)=O)cc1F)C1CC1] | 6-(((1R,2S)-2-amino-1-cyclopropylpropyl)amino)-5-fluoro-2-((1-methyl-3-(2-oxopyrrolidin-1-yl)-1H-indazol-5-yl)amino)nicotinamide | 481 | 0.93 | |
| Example 2-433 | 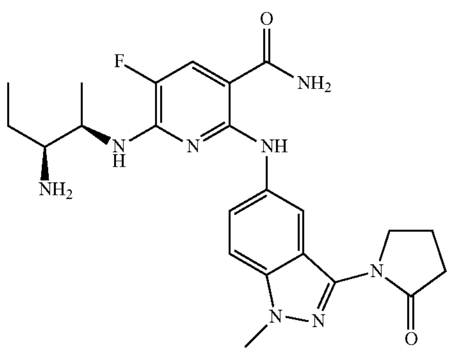 [SMILES: CC[C@H](N)[C@@H](C)Nc1nc(Nc2ccc3c(c2)c(N2CCCC2=O)nn3C)c(C(N)=O)cc1F] | 6-(((2R,3S)-3-aminopentan-2-yl)amino)-5-fluoro-2-((1-methyl-3-(2-oxopyrrolidin-1-yl)-1H-indazol-5-yl)amino)nicotinamide | 469 | 0.86 | |
| Example 2-434 | 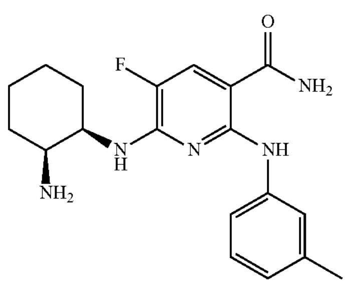 [SMILES: Cc1cccc(Nc2nc(N[C@@H]3CCCC[C@@H]3N)c(F)cc2C(N)=O)c1] | 6-(((1R,2S)-2-aminocyclohexyl)amino)-5-fluoro-2-(m-tolylamino)nicotinamide | 358 | 1.05 | 1H-NMR (MeOD) δ: 7.74 (1H, d, J = 11.9 Hz), 7.42-7.36 (1H, m), 7.29 (1H, s), 7.18 (1H, dd, J = 7.9, 7.9 Hz), 6.87-6.81 (1H, m), 4.42-4.32 (1H, m), 3.86-3.78 (1H, m), 2.34 (3H, s), 1.94-1.52 (8H, m) |

| Example | Structure | Compound name | MS (ESI m/z): (M + H) | RT (min) | HNMR |
|---|---|---|---|---|---|
| Example 2-435 | 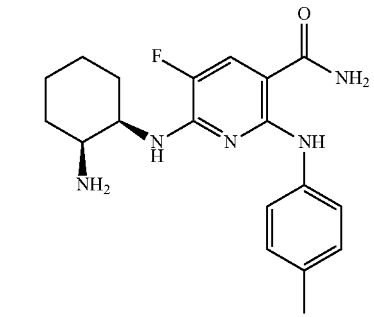 [SMILES: Cc1ccc(Nc2nc(N[C@@H]3CCCC[C@@H]3N)c(F)cc2C(N)=O)cc1] | 6-(((1R,2S)-2-aminocyclohexyl)amino)-5-fluoro-2-(p-tolylamino)nicotinamide | 358 | 1.04 | 1H-NMR (MeOD) δ: 7.72 (1H, d, J = 11.9 Hz), 7.40 (2H, d, J = 8.6 Hz), 7.12 (2H, d, J = 8.6 Hz), 4.34-4.25 (1H, m), 3.88-3.80 (1H, m), 2.30 (3H, s), 1.92-1.53 (8H, m) |
| Example 2-436 | 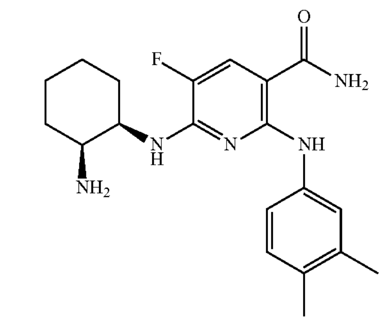 [SMILES: Cc1ccc(Nc2nc(N[C@@H]3CCCC[C@@H]3N)c(F)cc2C(N)=O)cc1C] | 6-(((1R,2S)-aminocyclohexyl)amino)-2-((3,4-dimethylphenyl)amino)-5-fluoronicotinamide | 372 | 1.1 | 1H-NMR (MeOD) δ: 7.72 (1H, d, J = 11.9 Hz), 7.32-7.27 (1H, m), 7.24-7.20 (1H, m), 7.09-7.03 (1H, m), 4.37-4.29 (1H, m), 3.83-3.75 (1H, m), 2.26 (3H, s), 2.22 (3H, s), 1.89-1.53 (8H, m) |
| Example 2-437 | 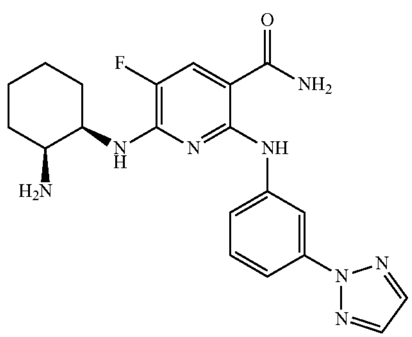 [SMILES: NC(=O)c1cc(F)c(N[C@@H]2CCCC[C@@H]2N)nc1Nc1cccc(-n2nccn2)c1] | 2-((3-(2H-1,2,3-triazol-2-yl)phenyl)amino)-6-(((1R,2S)-aminocyclohexyl)amino)-5-fluoronicotinamide | 411 | 1.03 | |

TABLE 3-continued

| Example | Structure | Compound name | MS (ESI m/z): (M + H) | RT (min) | HNMR |
|---|---|---|---|---|---|
| Example 2-438 | 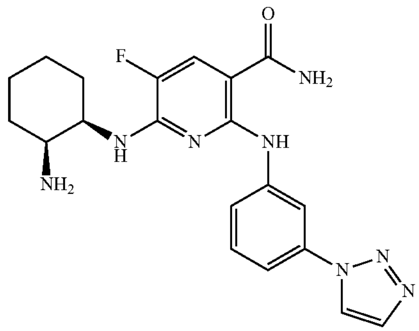 [SMILES: NC(=O)c1cc(F)c(N[C@@H]2CCCC[C@@H]2N)nc1Nc1cccc(-n2ccnn2)c1] | 2-(3-(1H-1,2,3-triazol-2-yl)phenyl)amino)-6-(((1R,2S)-2-aminocyclohexyl)amino)-5-fluoronicotinamide | 411 | 0.89 | 1H-NMR (MeOD) δ: 8.89-8.85 (1H, m), 8.58 (1H, d, J = 1.0 Hz), 7.94 (1H, d, J = 1.3 Hz), 7.80 (1H, d, J = 11.9 Hz), 7.51-7.44 (1H, m), 7.36-7.31 (1H, m), 7.26-7.21 (1H, m), 4.75-4.67 (1H, m), 3.86-3.78 (1H, m), 1.88-1.45 (8H, m) |
| Example 2-439 | 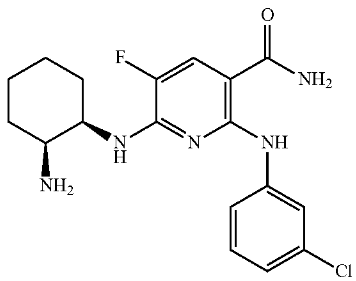 [SMILES: NC(=O)c1cc(F)c(N[C@@H]2CCCC[C@@H]2N)nc1Nc1cccc(Cl)c1] | 6-(((1R,2S)-2-aminocyclohexyl)amino)-2-((3-chlorophenyl)amino)-5-fluoronicotinamide | 378 380 | 1.1 | 1H-NMR (MeOD) δ: 7.99-7.96 (1H, m), 7.77 (1H, d, J = 11.9 Hz), 7.29-7.17 (2H, m), 6.99-6.93 (1H, m), 4.45-4.36 (1H, m), 3.89-3.83 (1H, m), 2.03-1.54 (8H, m) |
| Example 2-440 | 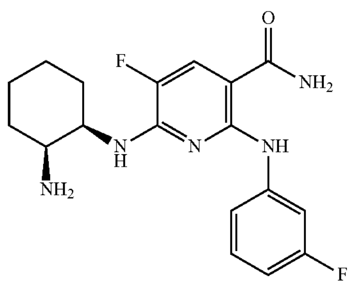 [SMILES: NC(=O)c1cc(F)c(N[C@@H]2CCCC[C@@H]2N)nc1Nc1cccc(F)c1] | 6-(((1R,2S)-2-aminocyclohexyl)amino)-5-fluoro-2-((3-fluorophenyl)amino)nicotinamide | 362 | 1.07 | 1H-NMR (MeOD) δ: 7.80-7.70 (2H, m), 7.30-7.21 (1H, m), 7.10-7.04 (1H, m), 6.73-6.65 (1H, m), 4.42-4.33 (1H, m), 3.98-3.89 (1H, m), 1.97-1.51 (8H, m) |

TABLE 3-continued

| Example | Structure | Compound name | MS (ESI m/z): (M + H) | RT (min) | HNMR |
|---|---|---|---|---|---|
| Example 2-441 | 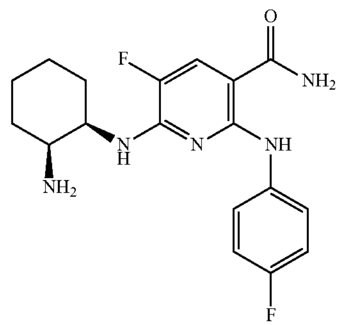 [SMILES: NC(=O)c1cc(F)c(N[C@@H]2CCCC[C@@H]2N)nc1Nc1ccc(F)cc1] | 6-(((1R,2S)-2-aminocyclohexyl)amino)-5-fluoro-2-((4-fluorophenyl)amino)nicotinamide | 362 | 1.02 | 1H-NMR (MeOD) δ: 7.74 (1H, d, J = 11.9 Hz), 7.54-7.47 (2H, m), 7.10-7.01 (2H, m), 4.33-4.24 (1H, m), 3.87-3.79 (1H, m), 1.92-1.52 (8H, m) |
| Example 2-442 | 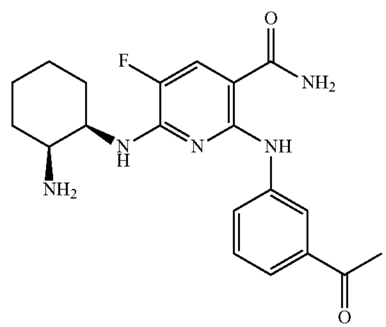 [SMILES: CC(=O)c1cccc(Nc2nc(N[C@@H]3CCCC[C@@H]3N)c(F)cc2C(N)=O)c1] | 2-((3-acetylphenyl)amino)-6-(((1R,2S)-2-aminocyclohexyl)amino)-5-fluoronicotinamide | 386 | 0.93 | 1H-NMR (MeOD) δ: 8.58-8.53 (1H, m), 7.78 (1H, d, J = 11.9 Hz), 7.68-7.62 (1H, m), 7.54-7.48 (1H, m), 7.47-7.39 (1H, m), 4.66-4.58 (1H, m), 3.85-3.76 (1H, m), 2.62 (3H, s), 1.94-1.52 (8H, m) |
| Example 2-443 | 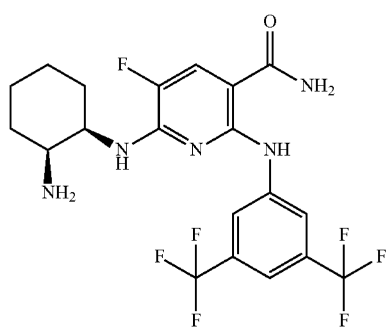 [SMILES: NC(=O)c1cc(F)c(N[C@@H]2CCCC[C@@H]2N)nc1Nc1cc(C(F)(F)F)cc(C(F)(F)F)c1] | 6-(((1R,2S)-2-aminocyclohexyl)amino)-2-(3,5-bis(trifluoromethyl)phenyl)amino)-5-fluoronicotinamide | 480 | 1.33 | 1H-NMR (MeOD) δ: 8.19 (2H, s), 7.83 (1H, d, J = 11.9 Hz), 7.47 (1H, s), 4.60-4.51 (1H, m), 3.70-3.60 (1H, m), 1.95-1.50 (8H, n) |

TABLE 3-continued

| Example | Structure | Compound name | MS (ESI m/z): (M + H) | RT (min) | HNMR |
|---|---|---|---|---|---|
| Example 2-444 | 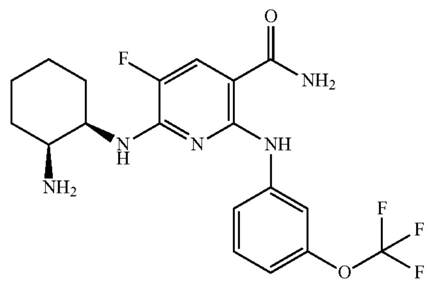 [SMILES: NC(=O)c1cc(F)c(N[C@@H]2CCCC[C@@H]2N)nc1Nc1cccc(OC(F)(F)F)c1] | 6-(((1R,2S)-2-aminocyclohexyl)amino)-5-fluoro-2-((3-(trifluoromethoxy)phenyl)amino)nicotinamide | 428 | 1.19 | 1H-NMR (MeOD) δ: 7.85-7.75 (2H, m), 7.40-7.29 (2H, m), 6.90-6.84 (1H, m), 4.47-4.38 (1H, m), 3.88-3.80 (1H, m), 1.98-1.51 (8H, m) |
| Example 2-445 | 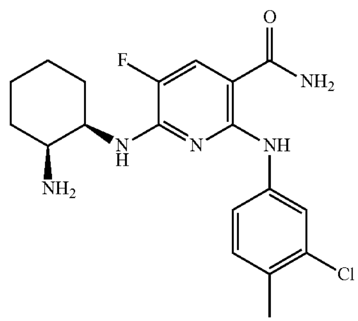 [SMILES: Cc1ccc(Nc2nc(N[C@@H]3CCCC[C@@H]3N)c(F)cc2C(N)=O)cc1Cl] | 6-(((1R,2S)-2-aminocyclohexyl)amino)-2-((3-chloro-4-methylphenyl)amino)-5-fluoronicotinamide | 392 394 | 1.17 | 1H-NMR (MeOD) δ: 7.94-7.91 (1H, m), 7.75 (1H, d, J = 11.9 Hz), 7.21-7.09 (2H, m), 4.44-4.34 (1H, m), 3.88-3.81 (1H, m), 2.31 (3H, s), 1.99-1.55 (8H, m) |
| Example 2-446 | 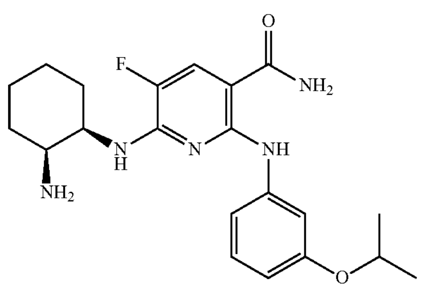 [SMILES: CC(C)Oc1cccc(Nc2nc(N[C@@H]3CCCC[C@@H]3N)c(F)cc2C(N)=O)c1] | 6-(((1R,2S)-2-aminocyclohexyl)amino)-5-fluoro-2-((3-isopropoxyphenyl)amino)nicotinamide | 402 | 1.12 | 1H-NMR (MeOD) δ: 7.74 (1H, d, J = 11.9 Hz), 7.43-7.40 (1H, m), 7.22-7.12 (1H, m), 6.93-6.87 (1H, m), 6.59-6.53 (1H, m), 4.65-4.55 (1H, m), 4.40-4.32 (1H, m), 3.97-3.91 (1H, m), 2.12-1.53 (8H, m), 1.36-1.29 (6H, m) |

TABLE 3-continued

| Example | Structure | Compound name | MS (ESI m/z): (M + H) | RT (min) | HNMR |
|---|---|---|---|---|---|
| Example 2-447 | 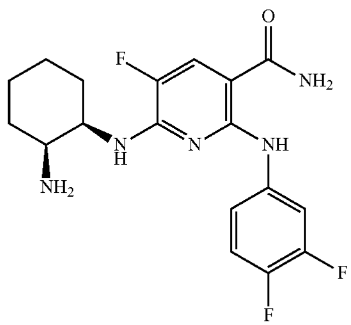 [SMILES: NC(=O)c1cc(F)c(N[C@@H]2CCCC[C@@H]2N)nc1Nc1ccc(F)c(F)c1] | 6-(((1R,2S)-2-aminocyclohexyl)amino)-2-((3,4-difluorophenyl)amino)-5-fluoronicotinamide | 380 | 1.06 | 1H-NMR (MeOD) δ: 7.90-7.78 (1H, m), 7.76 (1H, d, J = 11.9 Hz), 7.20-7.02 (1H, m), 7.10-7.03 (1H, m), 4.40-4.31 (1H, m), 3.87-3.82 (1H, m), 2.00-1.55 (8H, m) |
| Example 2-448 | 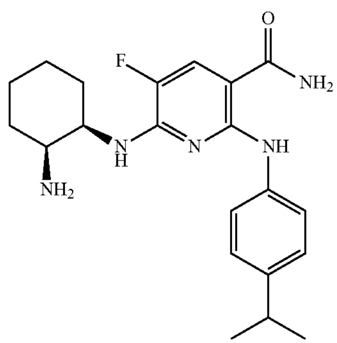 [SMILES: CC(C)c1ccc(Nc2nc(N[C@@H]3CCCC[C@@H]3N)c(F)cc2C(N)=O)cc1] | 6-(((1R,2S)-2-aminocyclohexyl)amino)-2-fluoro-2-((4-isopropylphenyl)amino)nicotinamide | 386 | 1.19 | 1H-NMR (MeOD) δ: 7.72 (1H, d, J = 11.9 Hz), 7.46-7.40 (2H, m), 7.21-7.13 (2H, m), 4.33-4.25 (1H, m), 3.92-3.85 (1H, m), 2.92-2.80 (1H, m), 1.90-1.52 (8H, m), 1.24 (6H, d, J = 6.9 Hz) |
| Example 2-449 | 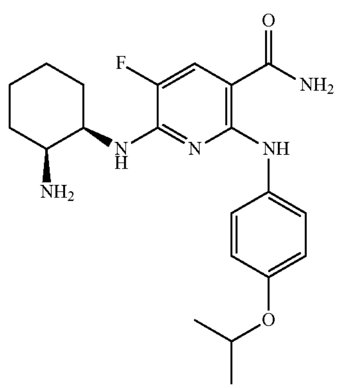 [SMILES: CC(C)Oc1ccc(Nc2nc(N[C@@H]3CCCC[C@@H]3N)c(F)cc2C(N)=O)cc1] | 6-(((1R,2S)-2-aminocyclohexyl)amino)-5-fluoro-2-((4-isopropoxyphenyl)amino)nicotinamide | 402 | 1.1 | 1H-NMR (MeOD) δ: 7.71 (1H, d, J = 11.9 Hz), 7.41-7.34 (2H, m), 6.92-6.83 (2H, m), 4.62-4.47 (1H, m), 4.27-4.18 (1H, m), 3.82-3.77 (1H, m), 1.90-1.51 (8H, m), 1.30 (6H, d, J = 5.9 Hz) |

TABLE 3-continued

| Example | Structure | Compound name | MS (ESI m/z): (M + H) | RT (min) | HNMR |
|---------|-----------|---------------|----------------------|----------|------|
| Example 2-450 | 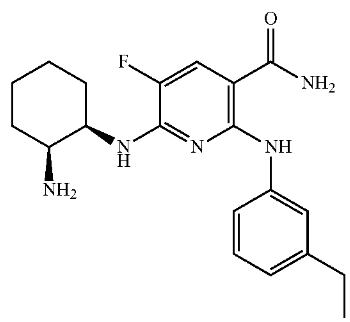 [SMILES: CCc1cccc(Nc2nc(N[C@@H]3CCCC[C@@H]3N)c(F)cc2C(N)=O)c1] | 6-(((1R,2S)-2-aminocyclohexyl)amino)-2-((3-ethylphenyl)amino)-5-fluoronicotinamide | 372 | 1.12 | 1H-NMR (MeOD) δ: 7.73 (1H, d, J = 11.9 Hz), 7.46 (1H, d, J = 7.9 Hz), 7.27-7.18 (2H, m), 6.86 (1H, d, J = 7.9 Hz), 4.43-4.34 (1H, m), 3.82-3.77 (1H, m), 2.63 (2H, q, J = 7.5 Hz), 1.92-1.50 (8H, m), 1.24 (3H, t, J = 7.4 Hz) |
| Example 2-451 | 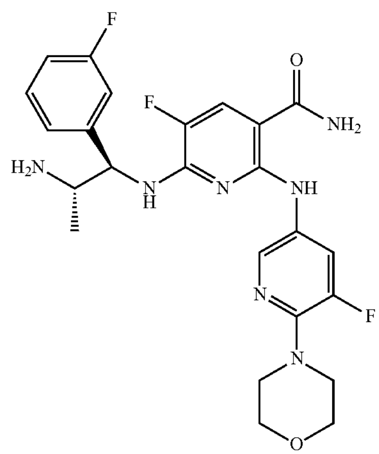 [SMILES: C[C@H](N)[C@H](Nc1nc(Nc2cnc(N3CCOCC3)c(F)c2)c(C(N)=O)cc1F)c1cccc(F)c1] | 6-(((1R,2S)-2-amino-1-(3-fluorophenyl)propyl)amino)-5-fluoro-2-((5-fluoro-6-morpholinopyridin-3-yl)amino)nicotinamide | 502 | 0.96 | |

TABLE 3-continued

| Example | Structure | Compound name | MS (ESI m/z): (M + H) | RT (min) | HNMR |
|---|---|---|---|---|---|
| Example 2-452 | 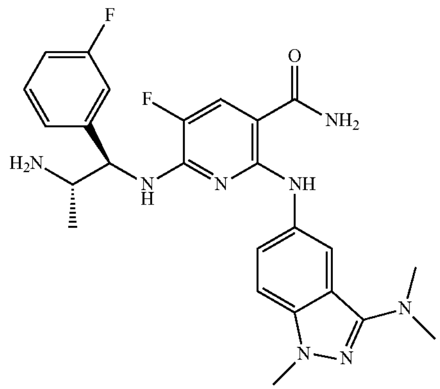 [SMILES: C[C@H](N)[C@H](Nc1nc(Nc2ccc3c(c2)c(N(C)C)nn3C)c(C(N)=O)cc1F)c1cccc(F)c1] | 6-(((1R,2S)-2-amino-1-(3-fluorophenyl)propyl)amino)-2-((3-(dimethylamino)-1-methyl-1H-indazol-5-yl)amino)-5-fluoronicotinamide | 495 | 0.93 | |
| Example 2-453 | 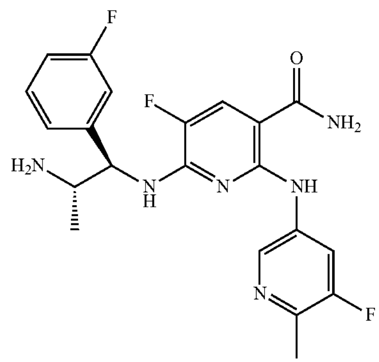 [SMILES: Cc1ncc(Nc2nc(N[C@H](c3cccc(F)c3)[C@H](C)N)c(F)cc2C(N)=O)cc1F] | 6-(((1R,2S)-2-amino-1-(3-fluorophenyl)propyl)amino)-5-fluoro-2-((5-fluoro-6-methylpyridin-3-yl)amino)nicotinamide | 431 | 0.87 | |

TABLE 3-continued

| Example | Structure | Compound name | MS (ESI m/z): (M + H) | RT (min) | HNMR |
|---|---|---|---|---|---|
| Example 2-454 | 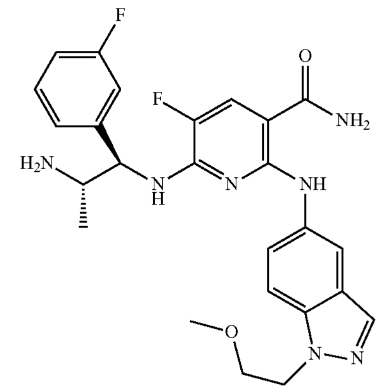 [SMILES: COCCn1ncc2cc(Nc3nc(N[C@H](c4cccc(F)c4)[C@H](C)N)c(F)cc3C(N)=O)ccc21] | 6-(((1R,2S)-2-amino-1-(3-fluorophenyl)propyl)amino)-5-fluoro-2-((1-(2-methoxyethyl)-1H-indazol-5-yl)amino)nicotinamide | 496 | 0.93 | |
| Example 2-455 | 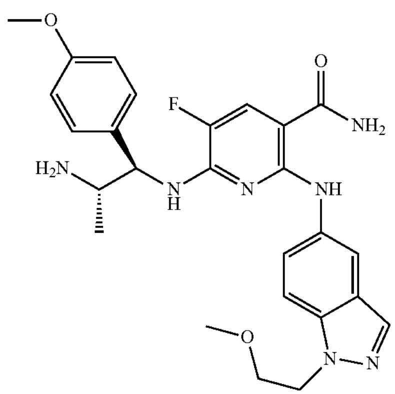 [SMILES: COCCn1ncc2cc(Nc3nc(N[C@H](c4ccc(OC)cc4)[C@H](C)N)c(F)cc3C(N)=O)ccc21] | 6-(((1R,2S)-2-amino-1-(4-methoxyphenyl)propyl)amino)-5-fluoro-2-((1-(2-methoxyethyl)-1H-indazol-5-yl)amino)nicotinamide | 508 | 0.92 | |

TABLE 3-continued

| Example | Structure | Compound name | MS (ESI m/z): (M + H) | RT (min) | HNMR |
|---|---|---|---|---|---|
| Example 2-456 | 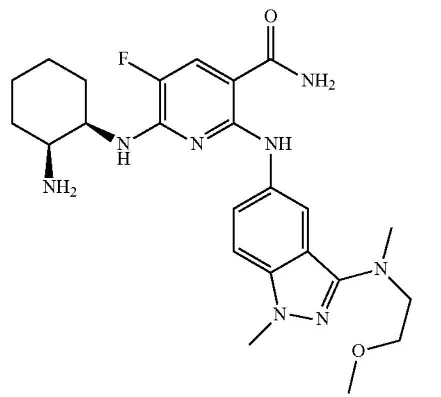 [SMILES: COCCN(C)c1nn(C)c2ccc(Nc3nc(N[C@@H]4CCCC[C@@H]4N)c(F)cc3C(N)=O)cc12] | 6-(((1R,2S)-2-aminocyclohexyl)amino)-5-fluoro-2-((3-((2-methoxyethyl)(methyl)amino)-1-methyl-1H-indazol-5-yl)amino)nicotinamide | 485 | 0.94 | 1H-NMR (MeOD) δ: 8.12 (1H, d, J = 9.9 Hz), 7.78 (1H, d, J = 7.5 Hz), 7.76 (1H, d, J = 3.5 Hz), 7.58 (1H, d, J = 9.9 Hz), 4.32-4.23 (1H, m), 3.92-3.85 (1H, m), 3.90 (3H, s), 3.77-3.53 (4H, m), 3.39 (3H, s), 3.34 (3H, s), 1.87-1.45 (8H, m). |
| Example 2-457 | 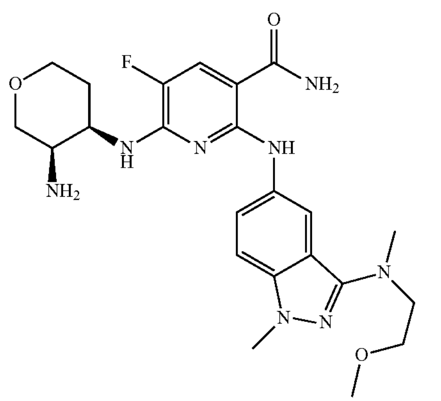 [SMILES: COCCN(C)c1nn(C)c2ccc(Nc3nc(N[C@@H]4CCOC[C@@H]4N)c(F)cc3C(N)=O)cc12] | 6-(((3R,4R)-3-aminotetrahydro-2H-pyran-4-yl)amino)-5-fluoro-2-((3-((2-methoxyethyl)(methyl)amino)-1-methyl-1H-indazol-5-yl)amino)nicotinamide | 487 | 0.83 | |

TABLE 3-continued

| Example | Structure | Compound name | MS (ESI m/z): (M + H) | RT (min) | HNMR |
|---|---|---|---|---|---|
| Example 2-458 | 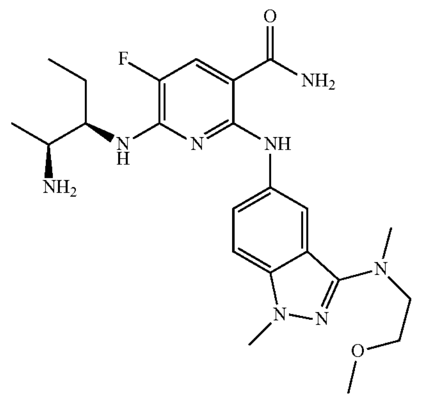 [SMILES: CC[C@@H](Nc1nc(Nc2ccc3c(c2)c(N(C)CCOC)nn3C)c(C(N)=O)cc1F)[C@H](C)N] | 6-(((2S,3R)-2-aminopentan-3-yl)amino)-5-fluoro-2-((3-((2-methoxyethyl)(methyl)amino)-1-methyl-1H-indazol-5-yl)amino)nicotinamide | 473 | 0.89 | |
| Example 2-459 | 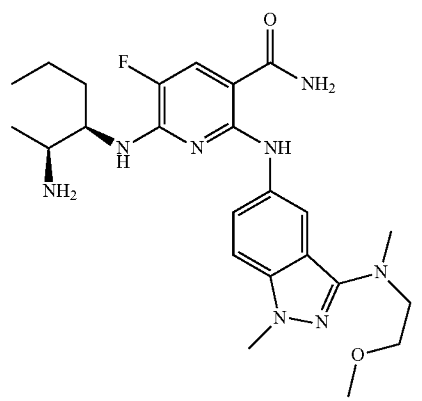 [SMILES: CCC[C@@H](Nc1nc(Nc2ccc3c(c2)c(N(C)CCOC)nn3C)c(C(N)=O)cc1F)[C@H](C)N] | 6-(((2S,3R)-2-aminohexan-3-yl)amino)-5-fluoro-2-((3-((2-methoxyethyl)(methyl)amino)-1-methyl-1H-indazol-5-yl)amino)nicotinamide | 487 | 0.95 | |

TABLE 3-continued

| Example | Structure | Compound name | MS (ESI m/z): (M + H) | RT (min) | HNMR |
|---|---|---|---|---|---|
| Example 2-460 | 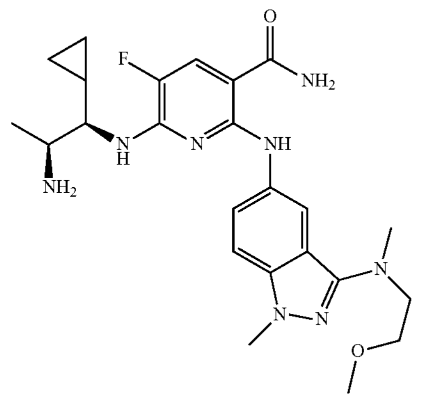 [SMILES: COCCN(C)c1nn(C)c2ccc(Nc3nc(N[C@H](C4CC4)[C@H](C)N)c(F)cc3C(N)=O)cc12] | 6-(((1R,2S)-2-amino-1-cyclopropylpropyl)amino)-5-fluoro-2-((3-((2-methoxyethyl)(methyl)amino)-1-methyl-1H-indazol-5-yl)amino)nicotinamide | 485 | 0.9 | |
| Example 2-461 | 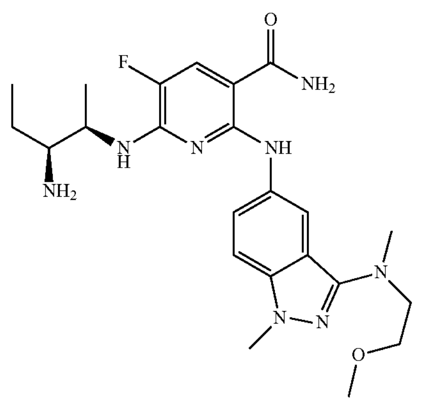 [SMILES: CC[C@H](N)[C@@H](C)Nc1nc(Nc2ccc3c(c2)c(N(C)CCOC)nn3C)c(C(N)=O)cc1F] | 6-(((2R,3S)-3-aminopentan-2-yl)amino)-5-fluoro-2-((3-((2-methoxyethyl)(methyl)amino)-1-methyl-1H-indazol-5-yl)amino)nicotinamide | 473 | 0.86 | |

TABLE 3-continued
| Example | Structure | Compound name | MS (ESI m/z): (M + H) | RT (min) | HNMR |
|---|---|---|---|---|---|
| Example 2-462 | 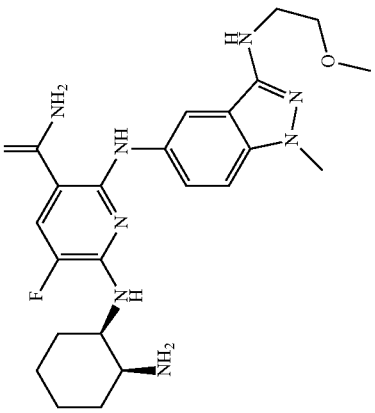 | 6-(((1R,2S)-2-aminocyclohexyl)amino)-5-fluoro-2-((3-((2-methoxyethyl)amino)-1-methyl-1H-indazol-5-yl)amino)nicotinamide | 471 | 0.87 | |
| Example 2-463 | 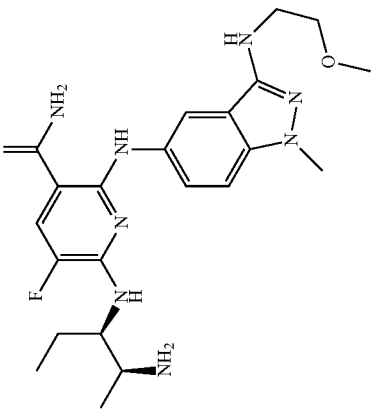 | 6-(((2S,3R)-2-aminopentan-3-yl)amino)-5-fluoro-2-((3-((2-methoxyethyl)amino)-1-methyl-1H-indazol-5-yl)amino)nicotinamide | 459 | 0.85 | |

TABLE 3-continued

| Example | Structure | Compound name | MS (ESI m/z): (M + H) | RT (min) | HNMR |
|---|---|---|---|---|---|
| Example 2-464 | 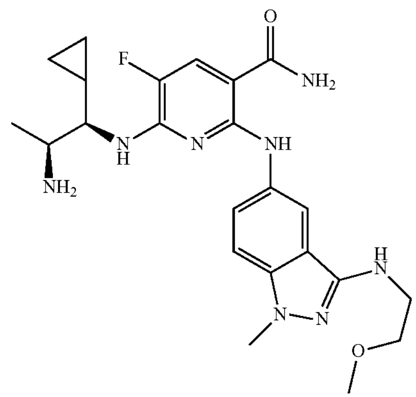 [SMILES: COCCNc1nn(C)c2ccc(Nc3nc(N[C@H](C4CC4)[C@H](C)N)c(F)cc3C(N)=O)cc12] | 6-(((1R,2S)-2-amino-1-cyclopropylpropyl)amino)-5-fluoro-2-((3-((2-methoxyethyl)amino)-1-methyl-1H-indazol-5-yl)amino)nicotinamide | 471 | 0.85 | |
| Example 2-465 | 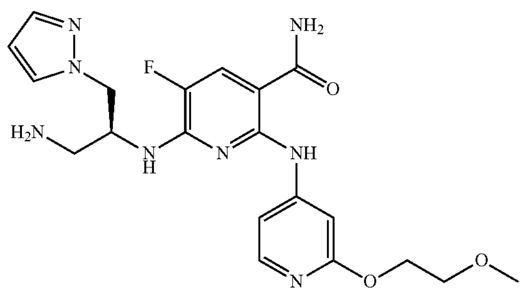 [SMILES: COCCOc1cc(Nc2nc(N[C@@H](CN)Cn3cccn3)c(F)cc2C(N)=O)ccn1] | (S)-6-((1-amino-3-(1H-pyrazol-1-yl)propan-2-yl)amino)-5-fluoro-2-((2-(2-methoxyethoxy)pyridin-4-yl)amino)nicotinamide | 445 | 0.61 | |
| Example 2-466 | 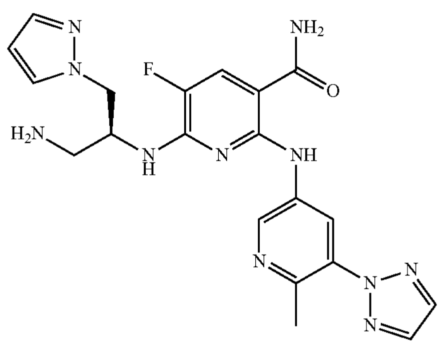 [SMILES: Cc1ncc(Nc2nc(N[C@@H](CN)Cn3cccn3)c(F)cc2C(N)=O)cc1-n1nccn1] | (S)-6-((1-amino-3-(1H-pyrazol-1-yl)propan-2-yl)amino)-5-fluoro-2-((6-methyl-5-(2H-1,2,3-triazol-2-yl)pyridin-3-yl)amino)nicotinamide | 452 | 0.76 | |

TABLE 3-continued

| Example | Structure | Compound name | MS (ESI m/z): (M + H) | RT (min) | HNMR |
|---|---|---|---|---|---|
| Example 2-467 | 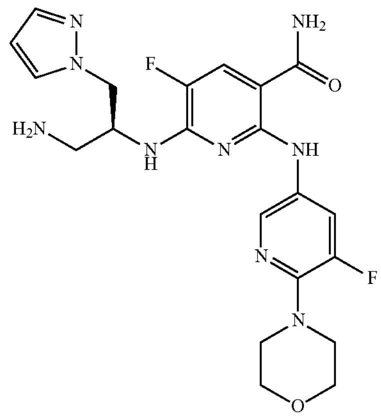 [SMILES: NC[C@@H](Cn1cccn1)Nc1nc(Nc2cnc(N3CCOCC3)c(F)c2)c(C(N)=O)cc1F] | (S)-6-((1-amino-3-(1H-pyrazol-1-yl)propan-2-yl)amino)-5-fluoro-2-((5-fluoro-6-morpholinopyridin-3-yl)amino)nicotinamide | 474 | 0.82 | |
| Example 2-468 | 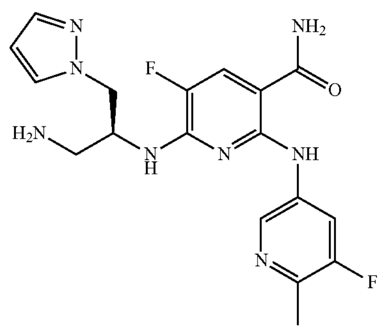 [SMILES: Cc1ncc(Nc2nc(N[C@@H](CN)Cn3cccn3)c(F)cc2C(N)=O)cc1F] | (S)-6-((1-amino-3-(1H-pyrazol-1-yl)propan-2-yl)amino)-5-fluoro-2-((5-fluoro-6-methylpyridin-3-yl)amino)nicotinamide | 403 | 0.71 | |

TABLE 3-continued

| Example | Structure | Compound name | MS (ESI m/z): (M + H) | RT (min) | HNMR |
|---|---|---|---|---|---|
| Example 2-469 | 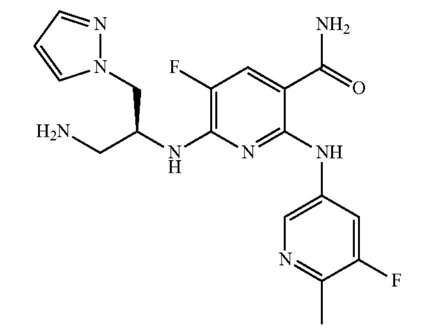 [SMILES: Cc1ncc(Nc2nc(N[C@@H](CN)Cn3cccn3)c(F)cc2C(N)=O)cc1F] | (S)-6-((1-amino-3-(1H-pyrazol-1-yl)propan-2-yl)amino)-5-fluoro-2-((5-fluoro-6-methylpyridin-3-yl)amino)nicotinamide | 438 | 0.85 | |
| Example 2-470 | 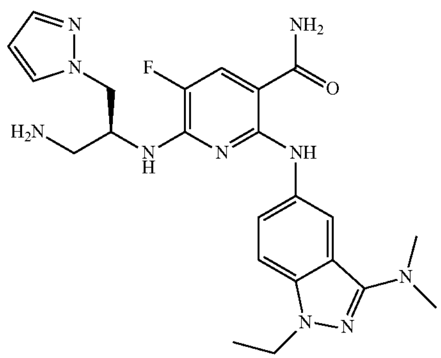 [SMILES: CCn1nc(N(C)C)c2cc(Nc3nc(N[C@@H](CN)Cn4cccn4)c(F)cc3C(N)=O)ccc21] | (S)-6-((1-amino-3-(1H-pyrazol-1-yl)propan-2-yl)amino)-2-((3-(dimethylamino)-1-methyl-1H-indazol-5-yl)amino)-5-fluoronicotinamide | 467 | 0.82 | |
| Example 2-471 | 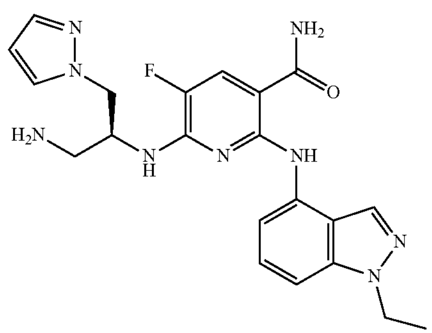 [SMILES: CCn1ncc2c(Nc3nc(N[C@@H](CN)Cn4cccn4)c(F)cc3C(N)=O)cccc21] | (S)-6-((1-amino-3-(1H-pyrazol-1-yl)propan-2-yl)amino)-2-((1-ethyl-1H-indazol-4-yl)amino)-5-fluoronicotinamide | 438 | 0.88 | |

TABLE 3-continued

| Example | Structure | Compound name | MS (ESI m/z): (M + H) | RT (min) | HNMR |
|---|---|---|---|---|---|
| Example 2-472 | 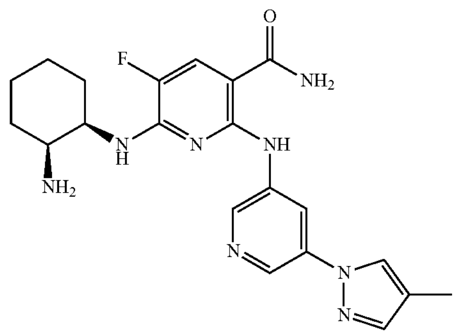 [SMILES: Cc1cnn(-c2cncc(Nc3nc(N[C@@H]4CCCC[C@@H]4N)c(F)cc3C(N)=O)c2)c1] | 6-(((1R,2S)-2-aminocyclohexyl)amino)-5-fluoro-2-((5-(4-methyl-1H-pyrazol-1-yl)pyridin-3-yl)amino)nicotinamide | 425 | 0.91 | 1H-NMR (MeOD) δ: 9.35-9.31 (1H, m), 8.82-8.67 (2H, m), 8.27 (1H, s), 7.89 (1H, s), 7.74 (1H, s), 4.74-4.64 (1H, m), 3.80-3.71 (1H, m), 2.20 (3H, s), 1.96-1.47 (8H, m) |
| Example 2-473 | 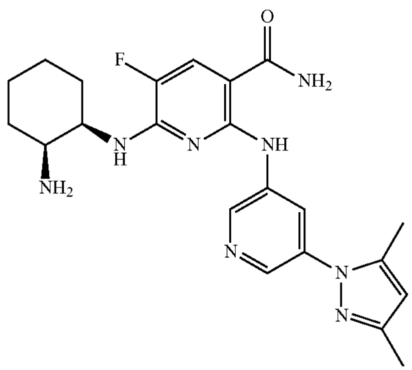 [SMILES: Cc1cc(C)n(-c2cncc(Nc3nc(N[C@@H]4CCCC[C@@H]4N)c(F)cc3C(N)=O)c2)n1] | 6-(((1R,2S)-2-aminocyclohexyl)amino)-2-((5-(3,5-dimethyl-1H-pyrazol-1-yl)pyridin-3-yl)amino)-5-fluoronicotinamide | 439 | 0.91 | 1H-NMR (MeOD) δ: 8.87-8.78 (2H, m), 8.40 (1H, s), 7.88 (1H, d, J = 11.9 Hz), 6.21 (1H, s), 4.43-4.34 (1H, m), 3.74-3.64 (1H, m), 2.41 (3H, s), 2.30 (3H, s), 1.90-1.36 (8H, m) |
| Example 2-474 | 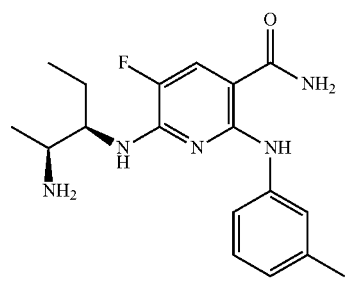 [SMILES: CC[C@@H](Nc1nc(Nc2cccc(C)c2)c(C(N)=O)cc1F)[C@H](C)N] | 6-(((2S,3R)-2-aminopentan-3-yl)amino)-5-fluoro-2-(m-tolylamino)nicotinamide | 346 | 0.99 | 1H-NMR (MeOD) δ: 7.74 (1H, d, J = 12.2 Hz), 7.40-7.34 (1H, m), 7.26-7.17 (2H, m), 6.87 (1H, d, J = 7.6 Hz), 4.30-4.19 (1H, m), 3.58-3.47 (1H, m), 2.34 (3H, s), 1.82-1.55 (2H, m), 1.26 (3H, d, J = 6.9 Hz), 1.06 (3H, t, J = 7.3 Hz) |

TABLE 3-continued

| Example | Structure | Compound name | MS (ESI m/z): (M + H) | RT (min) | HNMR |
|---|---|---|---|---|---|
| Example 2-475 | 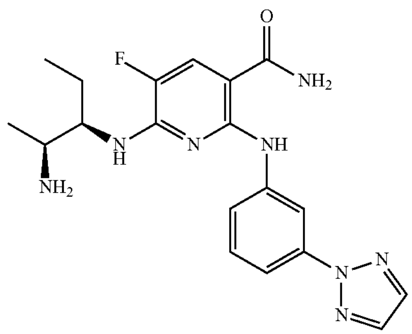 [SMILES: CC[C@@H](Nc1nc(Nc2cccc(-n3nccn3)c2)c(C(N)=O)cc1F)[C@H](C)N] | 2-(3-(2H-1,2,3-triazol-2-yl)phenyl)amino)-6-(((2S,3R)-2-aminopentan-3-yl)amino)-5-fluoronicotinamide | 399 | 1 | 1H-NMR (MeOD) δ: 9.04-9.01 (1H, m), 7.98 (2H, s), 7.81 (1H, d, J = 11.9 Hz), 7.71-7.64 (1H, m), 7.47-7.38 (1H, m), 7.16-7.10 (1H, m), 4.83-4.73 (1H, m), 3.70-3.60 (1H, m), 1.87-1.60 (2H, m), 1.27 (3H, d, J = 6.6 Hz), 1.05 (3H, t, J = 7.3 Hz) |
| Example 2-476 | 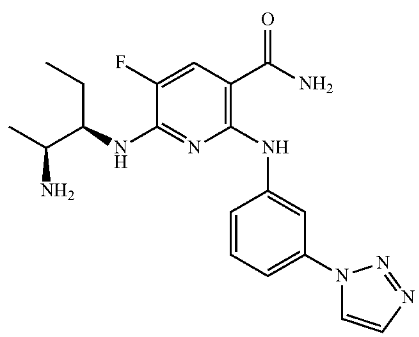 [SMILES: CC[C@@H](Nc1nc(Nc2cccc(-n3ccnn3)c2)c(C(N)=O)cc1F)[C@H](C)N] | 2-(3-(1H-1,2,3-triazol-1-yl)phenyl)amino)-6-(((2S,3R)-2-aminopentan-3-yl)amino)-5-fluoronicotinamide | 399 | 0.87 | 1H-NMR (MeOD) δ: 9.13-9.09 (1H, m), 8.64-8.59 (1H, m), 7.96-7.94 (1H, m), 7.81 (1H, d, J = 12.2 Hz), 7.52-7.44 (1H, m), 7.36-7.30 (1H, m), 7.24-7.13 (1H, m), 4.83-4.73 (1H, m), 3.82-3.68 (1H, m), 1.88-1.55 (2H, m), 1.31 (3H, d, J = 6.9 Hz), 0.94 (3H, t, J = 7.4 Hz) |
| Example 2-477 | 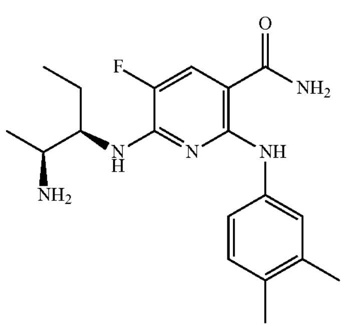 [SMILES: CC[C@@H](Nc1nc(Nc2ccc(C)c(C)c2)c(C(N)=O)cc1F)[C@H](C)N] | 6-(((2S,3R)-2-aminopentan-3-yl)amino)-2-((3,4-dimethylphenyl)amino)-5-fluoronicotinamide | 360 | 1.05 | 1H-NMR (MeOD) δ: 7.73 (1H, d, J = 11.9 Hz), 7.30-7.23 (1H, m), 7.19-7.14 (1H, m), 7.13-7.07 (1H, m), 4.24-4.14 (1H, m), 3.56-3.43 (1H, m), 2.27 (3H, s), 2.24 (3H, s), 1.78-1.55 (2H, m), 1.23 (3H, d, J = 6.6 Hz), 1.05 (3H, t, J = 7.4 Hz) |

TABLE 3-continued

| Example | Structure | Compound name | MS (ESI m/z): (M + H) | RT (min) | HNMR |
|---|---|---|---|---|---|
| Example 2-478 | 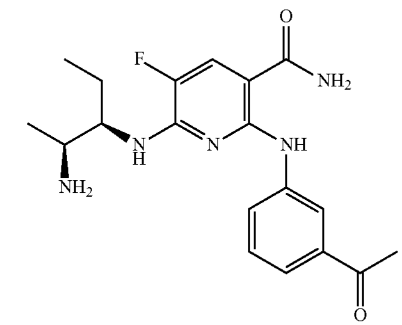 [SMILES: CC[C@@H](Nc1nc(Nc2cccc(C(C)=O)c2)c(C(N)=O)cc1F)[C@H](C)N] | 2-((3-acetylphenyl)amino)-6-(((2S,3R)-2-aminopentan-3-yl)amino)-5-fluoronicotinamide | 374 | 0.9 | 1H-NMR (MeOD) δ: 8.82-8.76 (1H, m), 7.79 (1H, d, J = 11.9 Hz), 7.69-7.63 (1H, m), 7.49-7.37 (2H, m), 4.68-4.58 (1H, m), 3.72-3.60 (1H, m), 2.65 (3H, s), 1.88-1.56 (2H, m), 1.33 (3H, d, J = 6.6 Hz), 1.00 (3H, t, J = 7.3 Hz) |
| Example 2-479 | 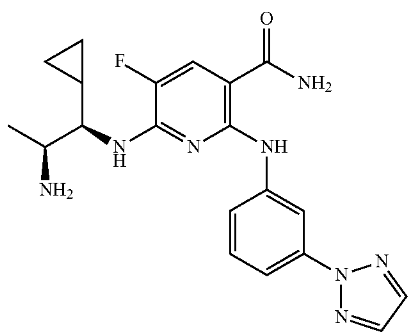 [SMILES: C[C@H](N)[C@H](Nc1nc(Nc2cccc(-n3nccn3)c2)c(C(N)=O)cc1F)C1CC1] | 2-((3-(2H-1,2,3-triazol-2-yl)phenyl)amino)-6-(((1R,2S)-2-amino-1-cyclopropylpropyl)amino)-5-fluoronicotinamide | 411 | 1.01 | 1H-NMR (MeOD) δ: 8.79-8.75 (1H, m), 7.98 (2H, s), 7.80 (1H, d, J = 11.9 Hz), 7.70-7.65 (1H, m), 7.42 (1H, dd, J = 8.3 Hz, 8.3 Hz), 7.17-7.11 (1H, m), 3.96 (1H, dd, J = 4.0 Hz, 9.9 Hz), 3.86-3.74 (1H, m), 1.34 (3H, d, J = 6.9 Hz), 1.19-1.07 (1H, m), 0.78-0.57 (2H, m), 0.57-0.37 (2H, m) |
| Example 2-480 | 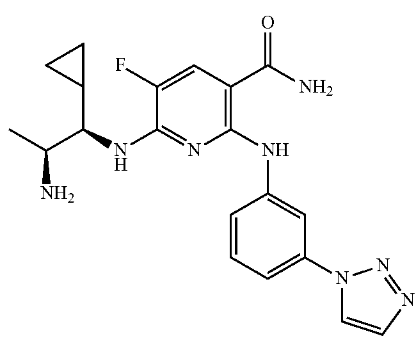 [SMILES: C[C@H](N)[C@H](Nc1nc(Nc2cccc(-n3ccnn3)c2)c(C(N)=O)cc1F)C1CC1] | 2-((3-(1H-1,2,3-triazol-1-yl)phenyl)amino)-6-(((1R,2S)-2-amino-1-cyclopropylpropyl)amino)-5-fluoronicotinamide | 411 | 0.89 | 1H-NMR (MeOD) δ: 9.03-9.00 (1H, m), 8.61 (1H, d, J = 1.0 Hz), 7.96 (1H, d, J = 1.0 Hz), 7.80 (1H, d, J = 12.2 Hz), 7.47 (1H, dd, J = 7.9 Hz, 8.3 Hz), 7.35-7.29 (1H, m), 7.19-7.12 (1H, m), 4.09 (1H, dd, J = 5.3 Hz, 9.6 Hz), 3.91-3.79 (1H, m), 1.39 (3H, d, J = 6.9 Hz), 1.20-1.04 (1H, m), 0.76-0.48 (2H, m), 0.48-0.38 (1H, m), 0.36-0.25 (1H, m) |

| Example | Structure | Compound name | MS (ESI m/z): (M + H) | RT (min) | HNMR |
|---|---|---|---|---|---|
| Example 2-481 | 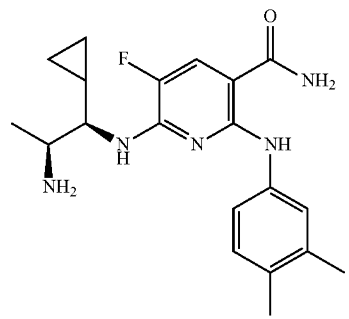 [SMILES: Cc1ccc(Nc2nc(N[C@H](C3CC3)[C@H](C)N)c(F)cc2C(N)=O)cc1C] | 6-(((1R,2S)-2-amino-1-cyclopropylpropyl)amino)-2-((3,4-dimethylphenyl)amino)-5-fluoronicotinamide | 372 | 1.07 | 1H-NMR (MeOD) δ: 7.71 (1H, d, J = 11.9 Hz), 7.24-7.17 (1H, m), 7.14-7.11 (1H, m), 7.09-7.04 (1H, m), 3.69-3.58 (1H, m), 3.53 (1H, dd, J = 4.5 Hz, 9.7 Hz), 2.25 (3H, s), 2.23 (3H, s), 1.33 (3H, d, J = 6.9 Hz), 1.17-1.02 (1H, m), 0.82-0.57 (2H, m), 0.50-0.37 (2H, m) |
| Example 2-482 | 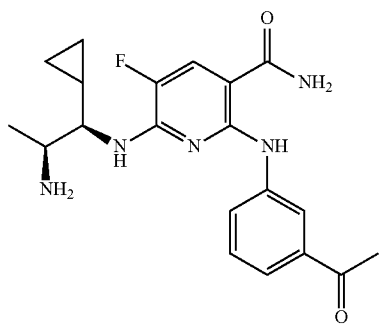 [SMILES: CC(=O)c1cccc(Nc2nc(N[C@H](C3CC3)[C@H](C)N)c(F)cc2C(N)=O)c1] | 2-(3-acetylphenyl)amino)-6-(((1R,2S)-2-amino-1-cyclopropylpropyl)amino)-5-fluoronicotinamide | 386 | 0.93 | 1H-NMR (MeOD) δ: 8.75-8.71 (1H, n), 7.77 (1H, d, J = 12.2 Hz), 7.68-7.62 (1H, m), 7.47-7.34 (2H, m), 3.96 (1H, dd, J = 5.1 Hz, 9.7 Hz), 3.83-3.70 (1H, m), 2.64 (3H, s), 1.41 (3H, d, J = 6.9 Hz), 1.22-1.07 (1H, m), 0.80-0.66 (1H, m), 0.64-0.52 (2H, m), 0.40-0.26 (1H, m) |
| Example 2-483 | 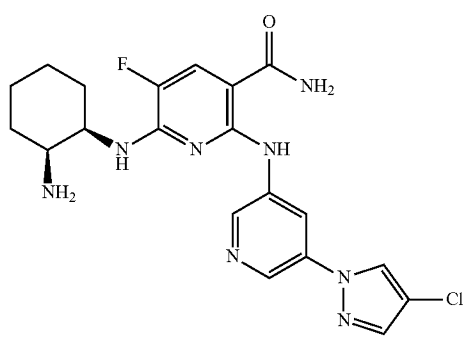 [SMILES: NC(=O)c1cc(F)c(N[C@@H]2CCCC[C@@H]2N)nc1Nc1cncc(-n2cc(Cl)cn2)c1] | 6-(((1R,2S)-2-aminocyclohexyl)amino)-2-((5-(4-chloro-1H-pyrazol-1-yl)pyridin-3-yl)amino)-5-fluoronicotinamide | 445 447 | 1 | 1H-NMR (DMSO-d6) δ: 11.96 (1H, s), 8.94 (1H, s), 8.83-8.47 (1H, m), 8.77 (1H, s), 8.04-7.66 (7H, m), 7.52-7.31 (1H, m), 7.01 (1H, d, J = 6.3 Hz), 4.40-4.26 (1H, m), 3.62-3.51 (1H, m), 1.93-1.28 (8H, m) |

TABLE 3-continued

| Example | Structure | Compound name | MS (ESI m/z): (M + H) | RT (min) | HNMR |
|---|---|---|---|---|---|
| Example 2-484 | 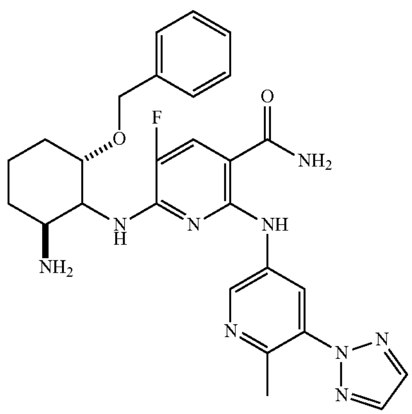 [SMILES: Cc1ncc(Nc2nc(NC3[C@@H](OCc4ccccc4)CCC[C@@H]3N)c(F)cc2C(N)=O)cc1-n1nccn1] | Mixture of 6-((2-amino-6-(benzyloxy)cyclohexyl)amino)-5-fluoro-2-((6-methyl-5-(2H-1,2,3-triazol-2-yl)pyridin-3-yl)amino)nicotinamide (1S,2S,6S),(1R,2R,6R) | 532 | 1.1 | 1H-NMR (DMSO-d6) δ: 11.75 (1H, s), 8.91-8.85 (1H, m), 8.33-8.27 (1H, m), 8.18 (2H, s), 7.99 (1H, d, J = 12.0 Hz), 7.90-7.72 (4H, m), 7.50-7.30 (1H, m), 7.30-7.12 (5H, m), 6.81 (1H, d, J = 7.8 Hz), 4.66-4.54 (1H, m), 4.44 (1H, d, J = 11.7 Hz), 4.35 (1H, d, J = 11.7 Hz), 3.71-3.56 (2H, m), 2.40 (3H, s), 1.95-1.72 (2H, m), 1.65-1.40 (4H, m) |
| Example 2-485 | 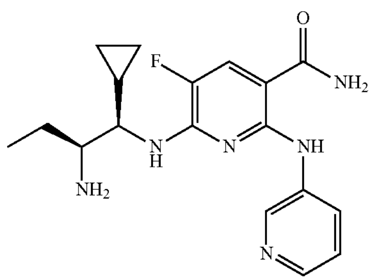 [SMILES: CC[C@H](N)[C@H](Nc1nc(Nc2cccnc2)c(C(N)=O)cc1F)C1CC1] | 6-(((1R,2S)-2-amino-1-cyclopropylbutyl)amino)-5-fluoro-2-(pyridin-3-ylamino)nicotinamide | 359 | 0.57 | |
| Example 2-486 | 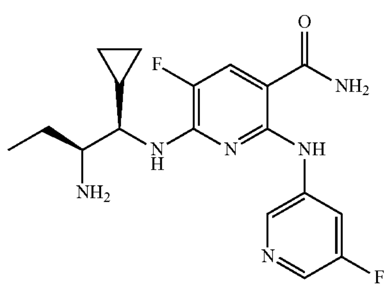 [SMILES: CC[C@H](N)[C@H](Nc1nc(Nc2cncc(F)c2)c(C(N)=O)cc1F)C1CC1] | 6-(((1R,2S)-2-amino-1-cyclopropylbutyl)amino)-5-fluoro-2-((5-fluoropyridin-3-yl)amino)nicotinamide | 377 | 0.85 | |

TABLE 3-continued

| Example | Structure | Compound name | MS (ESI m/z): (M + H) | RT (min) | HNMR |
|---|---|---|---|---|---|
| Example 2-487 | 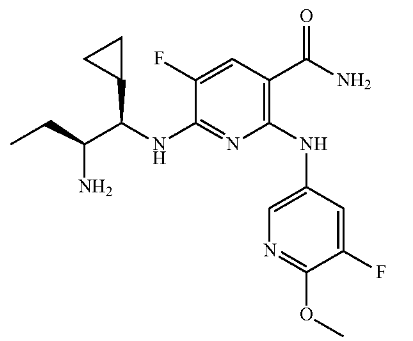 [SMILES: CC[C@H](N)[C@H](Nc1nc(Nc2cnc(OC)c(F)c2)c(C(N)=O)cc1F)C1CC1] | 6-(((1R,2S)-2-amino-1-cyclopropylbutyl)amino)-5-fluoro-2-((5-fluoro-6-methoxypyridin-3-yl)amino)nicotinamide | 407 | 0.96 | |
| Example 2-488 | 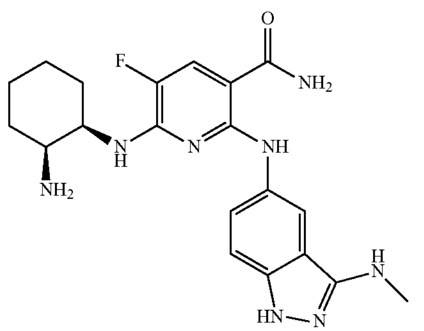 [SMILES: CNc1n[nH]c2ccc(Nc3nc(N[C@@H]4CCCC[C@@H]4N)c(F)cc3C(N)=O)cc12] | 6-(((1R,2S)-2-aminocyclohexyl)amino)-5-fluoro-2-((3-(methylamino)-1H-indazol-5-yl)amino)nicotinamide | 413 | 0.68 | |
| Example 2-489 | 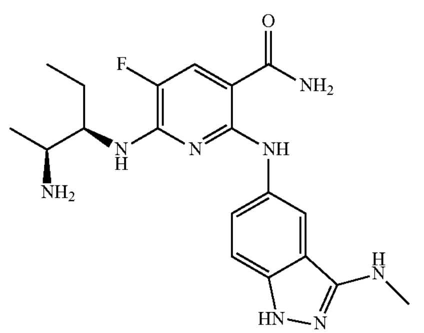 [SMILES: CC[C@@H](Nc1nc(Nc2ccc3[nH]nc(NC)c3c2)c(C(N)=O)cc1F)[C@H](C)N] | 6-(((2S,3R)-2-aminopentan-3-yl)amino)-5-fluoro-2-((3-(methylamino)-1H-indazol-5-yl)amino)nicotinamide | 401 | 0.66 | |

| Example | Structure | Compound name | MS (ESI m/z): (M + H) | RT (min) | HNMR |
|---|---|---|---|---|---|
| Example 2-490 | 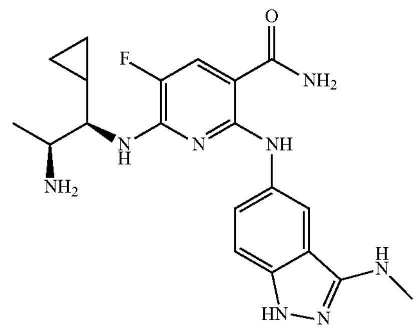 [SMILES: CNc1n[nH]c2ccc(Nc3nc(N[C@H](C4CC4)[C@H](C)N)c(F)cc3C(N)=O)cc12] | 6-(((1R,2S)-2-amino-1-cyclopropylpropyl)amino)-5-fluoro-2-((3-(methylamino)-1H-indazol-5-yl)amino)nicotinamide | 413 | 0.67 | |
| Example 2-491 | 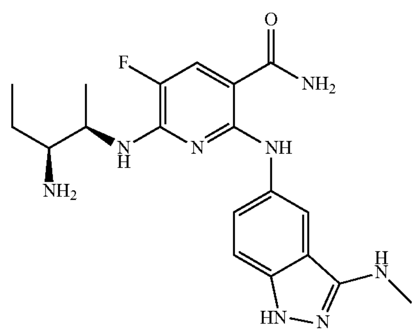 [SMILES: CC[C@H](N)[C@@H](C)Nc1nc(Nc2ccc3[nH]nc(NC)c3c2)c(C(N)=O)cc1F] | 6-(((2R,3S)-3-aminopentan-2-yl)amino)-5-fluoro-2-((3-(methylamino)-1H-indazol-5-yl)amino)nicotinamide | 401 | 0.62 | |
| Example 2-492 | 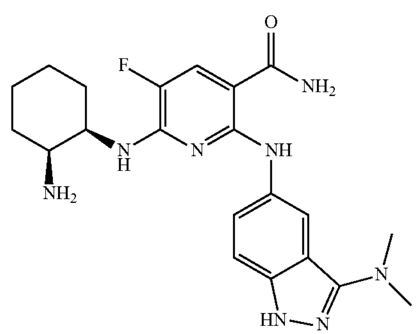 [SMILES: CN(C)c1n[nH]c2ccc(Nc3nc(N[C@@H]4CCCC[C@@H]4N)c(F)cc3C(N)=O)cc12] | 6-(((1R,2S)-2-aminocyclohexyl)amino)-2-((3-(dimethylamino)-1H-indazol-5-yl)amino)-5-fluoronicotinamide | 427 | 0.8 | |

TABLE 3-continued

| Example | Structure | Compound name | MS (ESI m/z): (M + H) | RT (min) | HNMR |
|---|---|---|---|---|---|
| Example 2-493 | 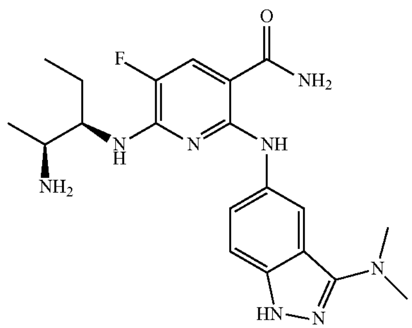 [SMILES: CC[C@@H](Nc1nc(Nc2ccc3[nH]nc(N(C)C)c3c2)c(C(N)=O)cc1F)[C@H](C)N] | 6-(((2S,3R)-2-aminopentan-3-yl)amino)-2-((3-(dimethylamino)-1H-indazol-5-yl)amino)-5-fluoronicotinamide | 415 | 0.78 | |
| Example 2-494 | 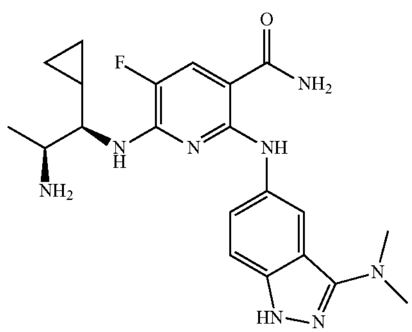 [SMILES: C[C@H](N)[C@H](Nc1nc(Nc2ccc3[nH]nc(N(C)C)c3c2)c(C(N)=O)cc1F)C1CC1] | 6-(((1R,2S)-2-amino-1-cyclopropylpropyl)amino)-2-((3-(dimethylamino)-1H-indazol-5-yl)amino)-5-fluoronicotinamide | 427 | 0.79 | |
| Example 2-495 | 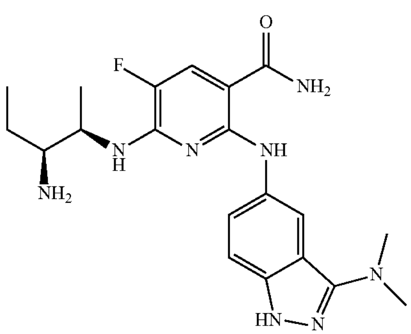 [SMILES: CC[C@H](N)[C@@H](C)Nc1nc(Nc2ccc3[nH]nc(N(C)C)c3c2)c(C(N)=O)cc1F] | 6-(((2R,3S)-3-aminopentan-2-yl)amino)-2-((3-(dimethylamino)-1H-indazol-5-yl)amino)-5-fluoronicotinamide | 415 | 0.73 | |

TABLE 3-continued

| Example | Structure | Compound name | MS (ESI m/z): (M + H) | RT (min) | HNMR |
|---|---|---|---|---|---|
| Example 2-496 | 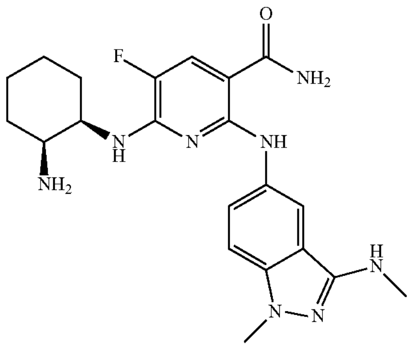 [SMILES: CNc1nn(C)c2ccc(Nc3nc(N[C@@H]4CCCC[C@@H]4N)c(F)cc3C(N)=O)cc12] | 6-(((1R,2S)-2-aminocyclohexyl)amino)-5-fluoro-2-((1-methyl-3-(methylamino)-1H-indazol-5-yl)amino)nicotinamide | 427 | 0.81 | 1H-NMR (MeOD) δ: 8.06 (1H, d, J = 9.2 Hz), 7.86 (1H, s), 7.77 (1H, d, J = 12.6 Hz), 7.54 (1H, d, J = 9.2 Hz), 4.35-4.28 (1H, m), 3.77-3.71 (1H, m), 3.75 (3H, s), 3.34 (3H, s), 1.85-1.48 (8H, m). |
| Example 2-497 | 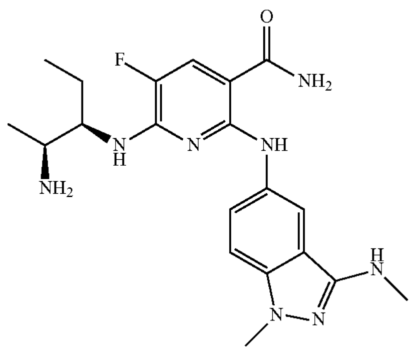 [SMILES: CC[C@@H](Nc1nc(Nc2ccc3c(c2)c(NC)nn3C)c(C(N)=O)cc1F)[C@H](C)N] | 6-(((2S,3R)-2-aminopentan-3-yl)amino)-5-fluoro-2-((1-methyl-3-(methylamino)-1H-indazol-5-yl)amino)nicotinamide | 415 | 0.79 | |
| Example 2-498 | 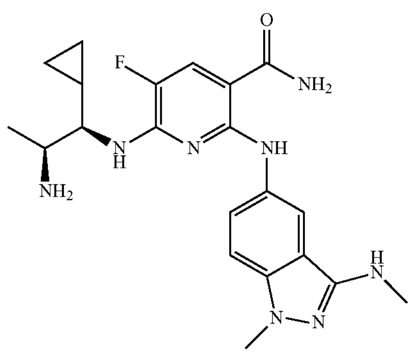 [SMILES: CNc1nn(C)c2ccc(Nc3nc(N[C@H](C4CC4)[C@H](C)N)c(F)cc3C(N)=O)cc12] | 6-(((1R,2S)-2-amino-1-cyclopropylpropyl)amino)-5-fluoro-2-((1-methyl-3-(methylamino)-1H-indazol-5-yl)amino)nicotinamide | 427 | 0.79 | |

TABLE 3-continued

| Example | Structure | Compound name | MS (ESI m/z): (M + H) | RT (min) | HNMR |
|---|---|---|---|---|---|
| Example 2-499 | 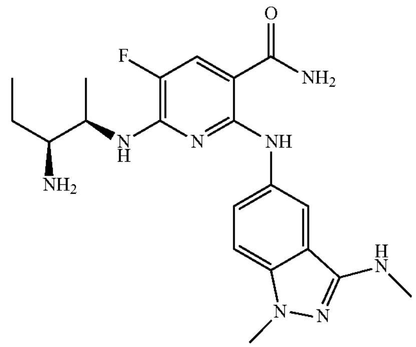 [SMILES: CC[C@H](N)[C@@H](C)Nc1nc(Nc2ccc3c(c2)c(NC)nn3C)c(C(N)=O)cc1F] | 6-(((2R,3S)-3-aminopentan-2-yl)amino)-5-fluoro-2-((1-methyl-3-(methylamino)-1H-indazol-5-yl)amino)nicotinamide | 413 | 0.74 | |
| Example 2-500 | 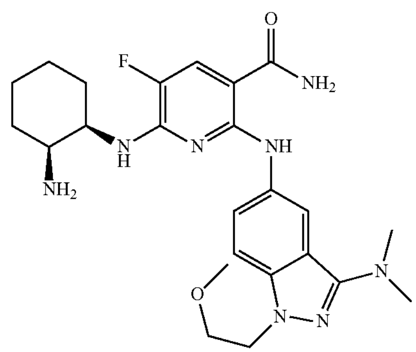 [SMILES: COCCn1nc(N(C)C)c2cc(Nc3nc(N[C@@H]4CCCC[C@@H]4N)c(F)cc3C(N)=O)ccc21] | 6-(((1R,2S)-2-aminocyclohexyl)amino)-2-((3-(dimethylamino)-1-(2-methoxyethyl)-1H-indazol-5-yl)amino)-5-fluoronicotinamide | 485 | 0.95 | |

TABLE 3-continued

| Example | Structure | Compound name | MS (ESI m/z): (M + H) | RT (min) | HNMR |
|---|---|---|---|---|---|
| Example 2-501 | 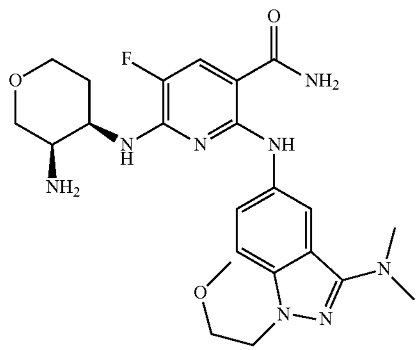 [SMILES: COCCn1nc(N(C)C)c2cc(Nc3nc(N[C@@H]4CCOC[C@@H]4N)c(F)cc3C(N)=O)ccc21] | 6-(((3R,4R)-3-aminotetrahydro-2H-pyran-4-yl)amino)-2-((3-(dimethylamino)-1-(2-methoxyethyl)-1H-indazol-5-yl)amino)-5-fluoronicotinamide | 487 | 0.84 | 1H-NMR (MeOD) δ: 8.00-7.45 (4H, m), 4.57-4.40 (1H, m), 4.28-4.00 (2H, m), 3.85-3.75 (2H, m), 3.73-3.65 (1H, m), 3.61-3.43 (4H, m), 3.35 (6H, s), 3.13 (3H, s), 2.10-1.77 (2H, m). |
| Example 2-502 | 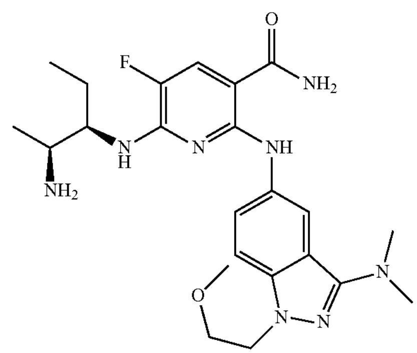 [SMILES: CC[C@@H](Nc1nc(Nc2ccc3c(c2)c(N(C)C)nn3CCOC)c(C(N)=O)cc1F)[C@H](C)N] | 6-(((2S,3R)-2-aminopentan-3-yl)amino)-2-((3-(dimethylamino)-1-(2-methoxyethyl)-1H-indazol-5-yl)amino)-5-fluoronicotinamide | 473 | 0.92 | |
| Example 2-503 | 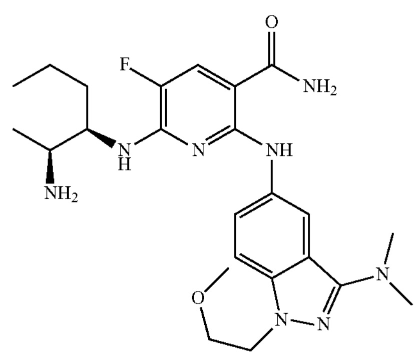 [SMILES: CCC[C@@H](Nc1nc(Nc2ccc3c(c2)c(N(C)C)nn3CCOC)c(C(N)=O)cc1F)[C@H](C)N] | 6-(((2S,3R)-2-aminohexan-3-yl)amino)-2-((3-(dimethylamino)-1-(2-methoxyethyl)-1H-indazol-5-yl)amino)-5-fluoronicotinamide | 487 | 0.98 | |

TABLE 3-continued
| Example | Structure | Compound name | MS (ESI m/z): (M + H) | RT (min) | HNMR |
|---|---|---|---|---|---|
| Example 2-504 | 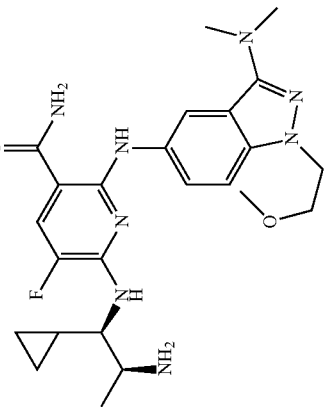 | 6-(((1R,2S)-2-amino-1-cyclopropylpropyl)amino)-2-((3-(dimethylamino)-1-(2-methoxyethyl)-1H-indazol-5-yl)amino)-5-fluoronicotinamide | 485 | 0.93 | |
| Example 2-505 | 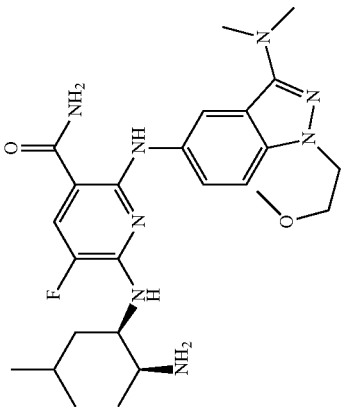 | 6-(((2S,3R)-2-amino-5-methylhexan-3-yl)amino)-2-((3-(dimethylamino)-1-(2-methoxyethyl)-1H-indazol-5-yl)amino)-5-fluoronicotinamide | 501 | 1.06 | |

TABLE 3-continued

| Example | Structure | Compound name | MS (ESI m/z): (M + H) | RT (min) | HNMR |
|---|---|---|---|---|---|
| Example 2-506 | 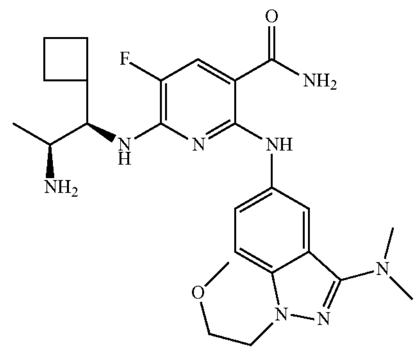 [SMILES: COCCn1nc(N(C)C)c2cc(Nc3nc(N[C@H](C4CCC4)[C@H](C)N)c(F)cc3C(N)=O)ccc21] | 6-(((1R,2S)-2-amino-1-cyclobutylpropyl)amino)-2-((3-(dimethylamino)-1-(2-methoxyethyl)-1H-indazol-5-yl)amino)-5-fluoronicotinamide | 499 | 1.01 | |
| Example 2-507 | 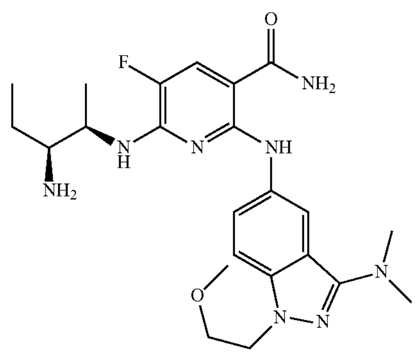 [SMILES: CC[C@H](N)[C@@H](C)Nc1nc(Nc2ccc3c(c2)c(N(C)C)nn3CCOC)c(C(N)=O)cc1F] | 6-(((2R,3S)-3-aminopentan-2-yl)amino)-2-((3-(dimethylamino)-1-(2-methoxyethyl)-1H-indazol-5-yl)amino)-5-fluoronicotinamide | 473 | 0.88 | |

TABLE 3-continued

| Example | Structure | Compound name | MS (ESI m/z): (M + H) | RT (min) | HNMR |
|---|---|---|---|---|---|
| Example 2-508 | 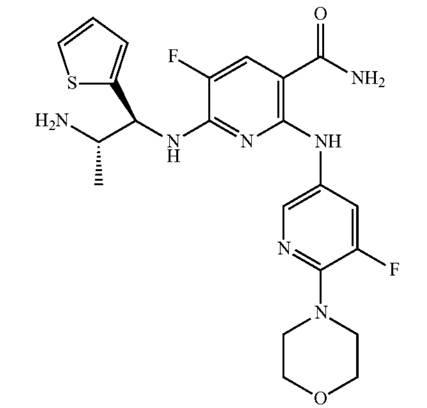 [SMILES: C[C@H](N)[C@H](Nc1nc(Nc2cnc(N3CCOCC3)c(F)c2)c(C(N)=O)cc1F)c1cccs1] | 6-(((1S,2S)-2-amino-1-(thiophen-2-yl)propyl)amino)-5-fluoro-2-((5-fluoro-6-morpholinopyridin-3-yl)amino)nicotinamide | 490 | 0.89 | 1H-NMR (MeOD) δ: 8.55 (1H, s), 7.86-7.76 (2H, m), 7.39 (1H, d, J = 5.0 Hz), 7.23 (1H, d, J = 3.6 Hz), 7.03 (1H, dd, J = 5.0, 3.6 Hz), 5.80 (1H, d, J = 7.9 Hz), 3.88-3.84 (5H, m), 3.52-3.47 (4H, m), 1.49 (3H, d, J = 6.6 Hz). |
| Example 2-509 | 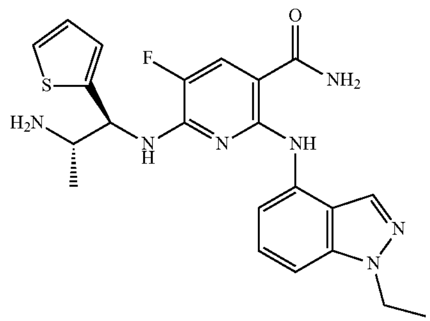 [SMILES: CCn1ncc2c(Nc3nc(N[C@H](c4cccs4)[C@H](C)N)c(F)cc3C(N)=O)cccc21] | 6-(((1S,2S)-2-amino-1-(thiophen-2-yl)propyl)amino)-2-((1-ethyl-1H-indazol-4-yl)amino)-5-fluoronicotinamide | 454 | 0.92 | |

TABLE 3-continued
| Example | Structure | Compound name | MS (ESI m/z): (M + H) | RT (min) | HNMR |
|---|---|---|---|---|---|
| Example 2-510 | 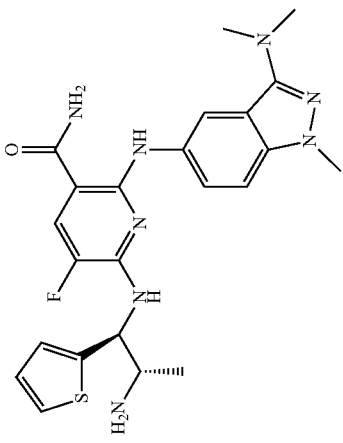 | 6-(((1S,2S)-2-amino-1-(thiophen-2-yl)propyl)amino)-2-((3-(dimethylamino)-1-methyl-1H-indazol-5-yl)amino)-5-fluoronicotinamide | 483 | 0.87 | |
| Example 2-511 | 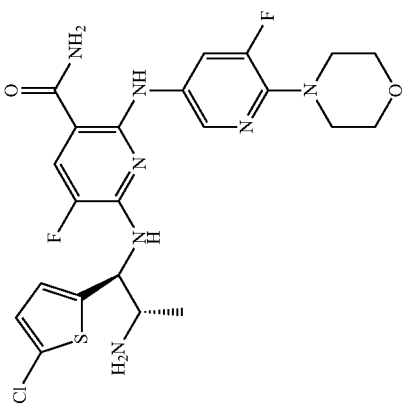 | 6-(((1S,2S)-2-amino-1-(5-chlorothiophen-2-yl)propyl)amino)-5-fluoro-2-((5-fluoro-6-morpholinopyridin-3-yl)amino)nicotinamide | 524 | 1.04 | |

TABLE 3-continued

| Example | Structure | Compound name | MS (ESI m/z): (M + H) | RT (min) | HNMR |
|---|---|---|---|---|---|
| Example 2-512 | 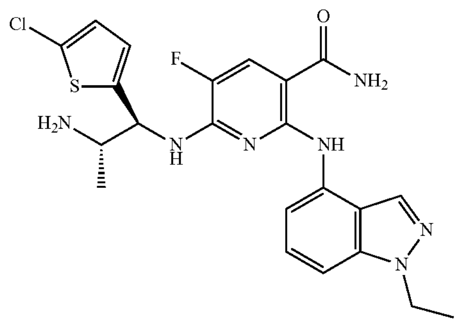 [SMILES: CCn1ncc2c(Nc3nc(N[C@H](c4ccc(Cl)s4)[C@H](C)N)c(F)cc3C(N)=O)cccc21] | 6-(((1S,2S)-2-amino-1-(5-chlorothiophen-2-yl)propyl)amino)-2-((1-ethyl-1H-indazol-4-yl)amino)-5-fluoronicotinamide | 488 | 1.07 | |
| Example 2-513 | 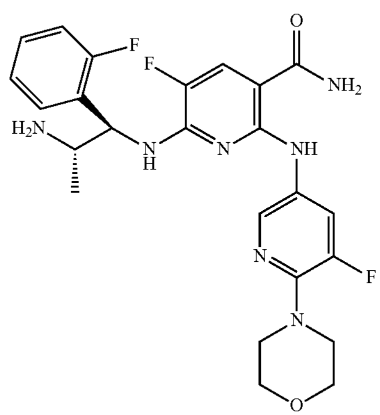 [SMILES: C[C@H](N)[C@H](Nc1nc(Nc2cnc(N3CCOCC3)c(F)c2)c(C(N)=O)cc1F)c1ccccc1F] | 6-(((1R,2S)-2-amino-1-(2-fluorophenyl)propyl)amino)-5-fluoro-2-((5-fluoro-6-morpholinopyridin-3-yl)amino)nicotinamide | 502 | 0.96 | |
| Example 2-514 | 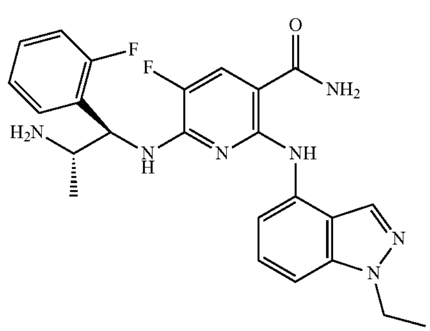 [SMILES: CCn1ncc2c(Nc3nc(N[C@H](c4ccccc4F)[C@H](C)N)c(F)cc3C(N)=O)cccc21] | 6-(((1R,2S)-2-amino-1-(2-fluorophenyl)propyl)amino)-2-((1-ethyl-1H-indazol-4-yl)amino)-5-fluoronicotinamide | 466 | 1 | |

| Example | Structure | TABLE 3-continued Compound name | MS (ESI m/z): (M + H) | RT (min) | HNMR |
|---|---|---|---|---|---|
| Example 2-515 | 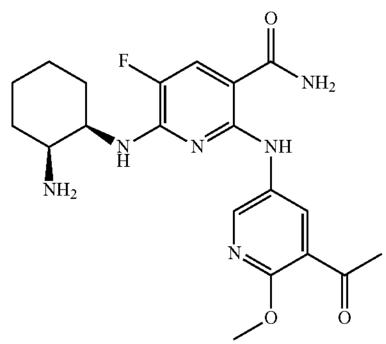 [SMILES: COc1ncc(Nc2nc(N[C@@H]3CCCC[C@@H]3N)c(F)cc2C(N)=O)cc1C(C)=O] | 2-((5-acetyl-6-methoxypyridin-3-yl)amino)-6-(((1R,2S)-2-aminocyclohexyl)amino)-5-fluoronicotinamide | 417 | 0.96 | 1H-NMR (MeOD) δ: 8.65 (1H, d, J = 3.0 Hz), 8.29 (1H, d, J = 2.6 Hz), 7.77 (1H, d, J = 11.9 Hz), 4.55-4.42 (1H, m), 4.05 (3H, s), 3.77-3.66 (1H, m), 2.65 (3H, s), 1.92-1.48 (8H, m) |
| Example 2-516 | 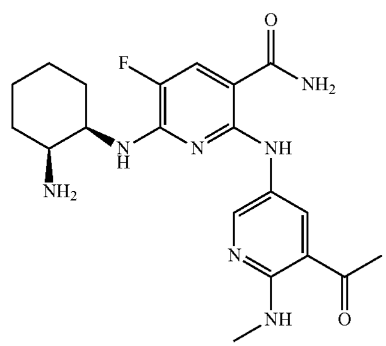 [SMILES: CNc1ncc(Nc2nc(N[C@@H]3CCCC[C@@H]3N)c(F)cc2C(N)=O)cc1C(C)=O] | 2-((5-acetyl-6-(methylamino)pyridin-3-yl)amino)-6-(((1R,2S)-2-aminocyclohexyl)amino)-5-fluoronicotinamide | 416 | 0.76 | 1H-NMR (MeOD) δ: 8.66 (1H, d, J = 2.3 Hz), 8.57 (1H, d, J = 2.6 Hz), 7.83 (1H, d, J = 11.9 Hz), 4.62-4.52 (1H, m), 3.74-3.65 (1H, m), 3.19 (3H, s), 2.69 (3H, s), 1.93-1.47 (8H, m) |

TABLE 3-continued

| Example | Structure | Compound name | MS (ESI m/z): (M + H) | RT (min) | HNMR |
|---|---|---|---|---|---|
| Example 2-517 | 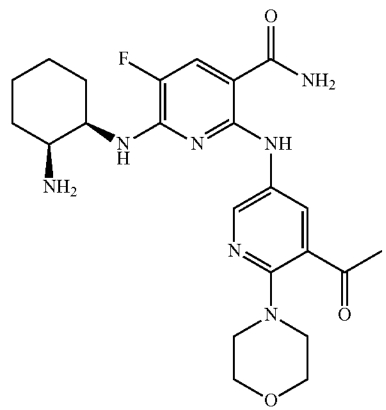 [SMILES: CC(=O)c1cc(Nc2nc(N[C@@H]3CCCC[C@@H]3N)c(F)cc2C(N)=O)cnc1N1CCOCC1] | 2-((5-acetyl-6-morpholinopyridin-3-yl)amino)-6-(((1R,2S)-2-aminocyclohexyl)amino)-5-fluoronicotinamide | 472 | 0.90 | 1H-NMR (MeOD) δ: 8.62-8.57 (1H, m), 8.37 (1H, d, J = 2.6 Hz), 7.80 (1H, d, J = 11.9 Hz), 4.57-4.44 (1H, m), 3.90-3.84 (4H, m), 3.79-3.71 (1H, m), 3.40-3.30 (4H, m), 2.68 (3H, s), 1.98-1.50 (8H, m). |
| Example 2-518 | 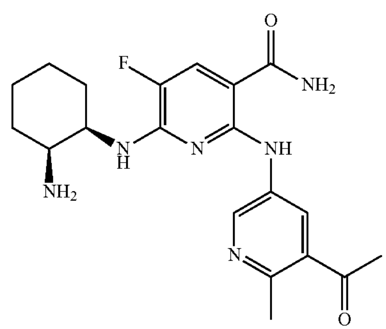 [SMILES: CC(=O)c1cc(Nc2nc(N[C@@H]3CCCC[C@@H]3N)c(F)cc2C(N)=O)cnc1C] | 2-((5-acetyl-6-methylpyridin-3-yl)amino)-6-(((1R,2S)-2-aminocyclohexyl)amino)-5-fluoronicotinamide | 401 | 0.74 | 1H-NMR (MeOD) δ: 9.40 (1H, d, J = 2.6 Hz), 8.73 (1H, d, J = 2.3 Hz), 7.91 (1H, d, J = 11.6 Hz), 4.63-4.54 (1H, n), 3.77-3.68 (1H, s), 2.83 (3H, s), 2.71 (3H, s), 2.04-1.64 (8H, m). |

TABLE 3-continued

| Example | Structure | Compound name | MS (ESI m/z): (M + H) | RT (min) | HNMR |
|---|---|---|---|---|---|
| Example 2-519 | 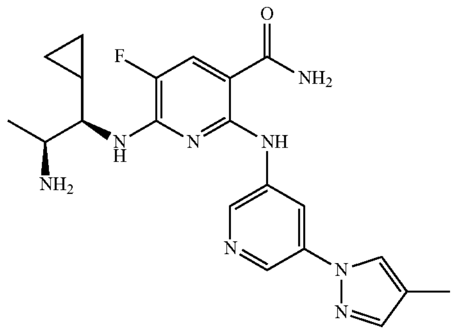 [SMILES: Cc1cnn(-c2cncc(Nc3nc(N[C@H](C4CC4)[C@H](C)N)c(F)cc3C(N)=O)c2)c1] | 6-(((1R,2S)-2-amino-1-cyclopropylpropyl)amino)-5-fluoro-2-((5-(4-methyl-1H-pyrazol-1-yl)pyridin-3-yl)amino)nicotinamide | 425 | 0.93 | 1H-NMR (MeOD) δ: 9.21-9.19 (1H, m), 8.83 (1H, s), 8.73 (1H, s), 8.27 (1H, s), 7.89 (1H, d, J = 11.9 Hz), 7.76 (1H, s), 3.98 (1H, dd, J = 4.6 Hz, 9.6 Hz), 3.82-3.70 (1H, m), 2.21 (3H, s), 1.43 (3H, d, J = 6.6 Hz), 1.25-1.09 (1H, m), 0.77-0.66 (1H, m), 0.65-0.48 (2H, m), 0.43-0.32 (1H, m) |
| Example 2-520 | 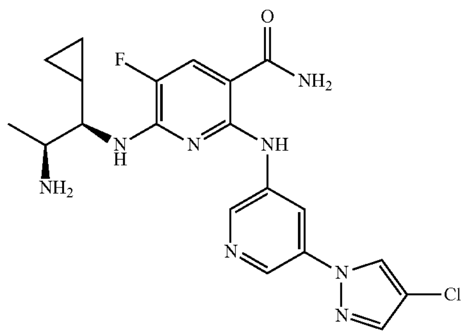 [SMILES: C[C@H](N)[C@H](Nc1nc(Nc2cncc(-n3cc(Cl)cn3)c2)c(C(N)=O)cc1F)C1CC1] | 6-(((1R,2S)-2-amino-1-cyclopropylpropyl)amino)-2-((5-(4-chloro-1H-pyrazol-1-yl)pyridin-3-yl)amino)-5-fluoronicotinamide | 445 | 1.00 | 1H-NMR (MeOD) δ: 9.09-9.05 (1H, m), 9.04-8.94 (1H, m), 8.82-8.74 (1H, m), 8.67 (1H, s), 7.92 (1H, s), 7.89 (1H, d, J = 11.9 Hz), 3.96 (1H, dd, J = 5.3 Hz, 9.2 Hz), 3.78-3.64 (1H, m), 1.43 (3H, d, J = 6.6 Hz), 1.23-1.06 (1H, m), 0.80-0.30 (4H, m) |
| Example 2-521 | 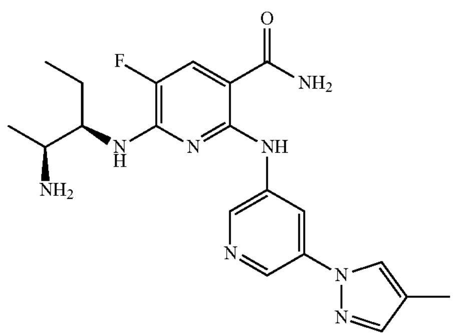 [SMILES: CC[C@@H](Nc1nc(Nc2cncc(-n3cc(C)cn3)c2)c(C(N)=O)cc1F)[C@H](C)N] | 6-(((2S,3R)-2-aminopentan-3-yl)amino)-5-fluoro-2-((5-(4-methyl-1H-pyrazol-1-yl)pyridin-3-yl)amino)nicotinamide | 413 | 0.92 | 1H-NMR (MeOD) δ: 9.59 (1H, dd, J = 2.0 Hz, 2.3 Hz), 8.78-8.71 (2H, m), 8.28 (1H, s), 7.90 (1H, d, J = 11.9 Hz), 7.77 (1H, s), 4.78-4.71 (1H, m), 3.70-3.59 (1H, m), 2.21 (3H, s), 1.88-1.60 (2H, m), 1.34 (3H, d, J = 6.9 Hz), 1.01 (3H, t, J = 7.3 Hz) |

TABLE 3-continued

| Example | Structure | Compound name | MS (ESI m/z): (M + H) | RT (min) | HNMR |
|---|---|---|---|---|---|
| Example 2-522 | 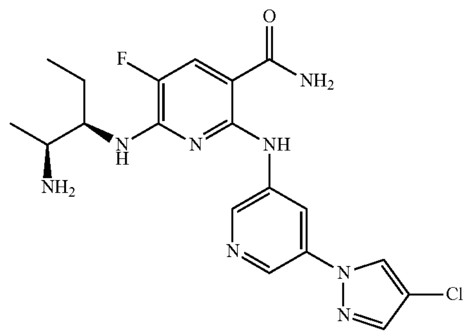 [SMILES: CC[C@@H](Nc1nc(Nc2cncc(-n3cc(Cl)cn3)c2)c(C(N)=O)cc1F)[C@H](C)N] | 6-(((2S,3R)-2-aminopentan-3-yl)amino)-2-((5-(4-chloro-1H-pyrazol-1-yl)pyridin-3-yl)amino)-5-fluoronicotinamide | 433 435 | 0.99 | 1H-NMR (MeOD) δ: 9.39-9.34 (1H, m), 8.78-8.72 (1H, m), 8.72-8.66 (1H, m), 8.66-8.63 (1H, m), 7.93-7.84 (2H, m), 4.75-4.65 (1H, m), 3.68-3.55 (1H, m), 1.90-1.58 (2H, m), 1.32 (3H, d, J = 6.9 Hz), 1.02 (3H, t, J = 7.3 Hz) |
| Example 2-523 | 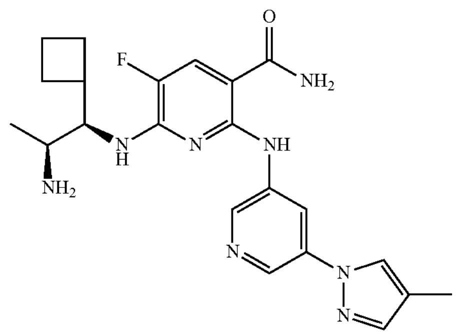 [SMILES: Cc1cnn(-c2cncc(Nc3nc(N[C@H](C4CCC4)[C@H](C)N)c(F)cc3C(N)=O)c2)c1] | 6-(((1R,2S)-2-amino-1-cyclobutylpropyl)amino)-5-fluoro-2-((5-(4-methyl-1H-pyrazol-1-yl)pyridin-3-yl)amino)nicotinamide | 439 | 1.03 | 1H-NMR (MeOD) δ: 9.60-9.56 (1H, m), 8.71-8.61 (2H, m), 8.32 (1H, s), 7.88 (1H, d, J = 11.9 Hz), 7.80 (1H, s), 4.78-4.71 (1H, m), 3.72-3.61 (1H, m), 2.78-2.61 (1H, m), 2.21 (3H, s), 2.16-1.66 (6H, m), 1.32 (3H, d, J = 6.6 Hz) |
| Example 2-524 | 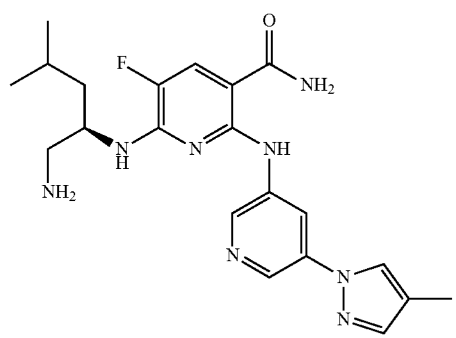 [SMILES: Cc1cnn(-c2cncc(Nc3nc(N[C@@H](CN)CC(C)C)c(F)cc3C(N)=O)c2)c1] | (R)-6-((1-amino-4-methylpentan-2-yl)amino)-5-fluoro-2-((5-(4-methyl-1H-pyrazol-1-yl)pyridin-3-yl)amino)nicotinamide | 427 | 1.03 | 1H-NMR (MeOD) δ: 9.67-9.62 (1H, m), 8.89-8.83 (1H, m), 8.78-8.74 (1H, m), 8.30 (1H, s), 7.90 (1H, d, J = 11.9 Hz), 7.78 (1H, s), 3.41-3.28 (2H, m), 3.15-3.04 (1H, m), 2.21 (3H, s), 1.78-1.62 (2H, m), 1.57-1.42 (1H, m), 0.91 (3H, d, J = 6.3 Hz), 0.82 (3H, d, J = 6.3 Hz) |

TABLE 3-continued

| Example | Structure | Compound name | MS (ESI m/z): (M + H) | RT (min) | HNMR |
|---|---|---|---|---|---|
| Example 2-525 | 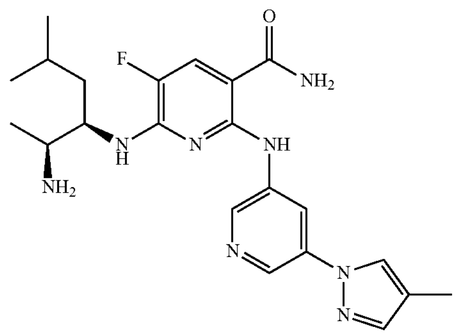 [SMILES: Cc1cnn(-c2cncc(Nc3nc(N[C@H](CC(C)C)[C@H](C)N)c(F)cc3C(N)=O)c2)c1] | 6-(((2S,3R)-2-amino-5-methylhexan-3-yl)amino)-5-fluoro-2-((5-(4-methyl-1H-pyrazol-1-yl)pyridin-3-yl)amino)nicotinamide | 441 | 1.05 | 1H-NMR (MeOD) δ: 9.60-9.55 (1H, m), 8.79-8.70 (2H, m), 8.29 (1H, s), 7.90 (1H, d, J = 11.9 Hz), 7.79 (1H, s), 4.78-4.71 (1H, m), 3.73-3.61 (1H, m), 2.21 (3H, s), 1.82-1.58 (2H, m), 1.52-1.37 (1H, m), 1.36 (3H, d, J = 6.6 Hz), 0.92 (3H, d, J = 6.6 Hz), 0.81 (3H, d, J = 6.6 Hz) |
| Example 2-526 | 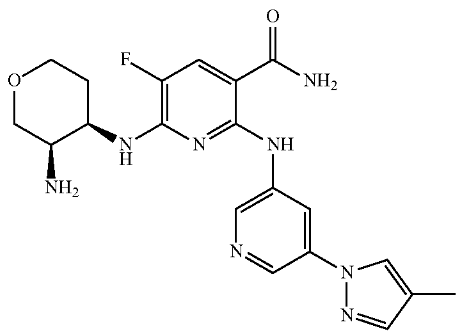 [SMILES: Cc1cnn(-c2cncc(Nc3nc(N[C@@H]4CCOC[C@@H]4N)c(F)cc3C(N)=O)c2)c1] | 6-(((3R,4R)-3-aminotetrahydro-2H-pyran-4-yl)amino)-5-fluoro-2-((5-(4-methyl-1H-pyrazol-1-yl)pyridin-3-yl)amino)nicotinamide | 427 | 0.80 | 1H-NMR (MeOD) δ: 9.18-9.13 (1H, m), 8.75-8.66 (2H, m), 8.27 (1H, s), 7.88 (1H, d, J = 11.9 Hz), 7.73 (1H, s), 4.46-4.56 (1H, m), 4.14-4.02 (1H, m), 3.86-3.77 (2H, m), 3.73-3.62 (1H, m), 3.58-3.48 (1H, m), 2.21 (3H, s), 2.17-2.04 (1H, m), 2.00-1.88 (1H, m) |
| Example 2-527 | 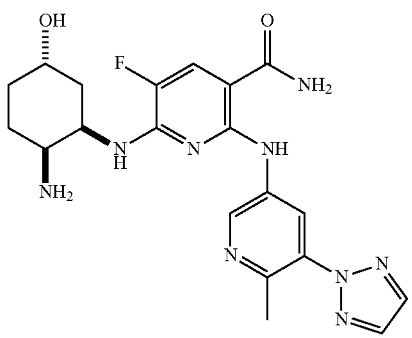 | Mixture of 6-((2-amino-5-hydroxycyclohexyl)amino)-5-fluoro-2-((6-methyl-5-(2H-1,2,3-triazol-2-yl)pyridin-3-yl)amino)nicotinamide (1R,2S,5S), (1S,2R,5R) | 442 | 0.62 | |

TABLE 3-continued

| Example | Structure | Compound name | MS (ESI m/z): (M + H) | RT (min) | HNMR |
|---|---|---|---|---|---|
| Example 2-528 | 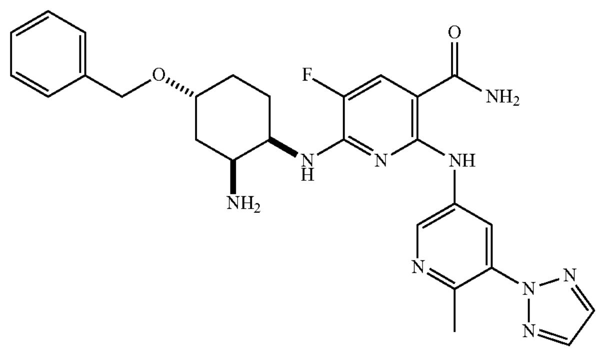 | Mixture of 6-((2-amino-4-(benzyloxy)cyclohexyl)amino)-5-fluoro-2-((6-methyl-5-(2H-1,2,3-triazol-2-yl)pyridin-3-yl)amino)nicotinamide (1R,2S,4R),(1S,2R,4S) | 532 | 1.16 | |
| Example 2-529 | 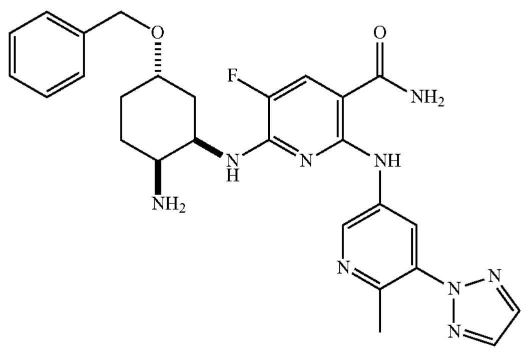 | Mixture of 6-((2-amino-5-(benzyloxy)cyclohexyl)amino)-5-fluoro-2-((6-methyl-5-(2H-1,2,3-triazol-2-yl)pyridin-3-yl)amino)nicotinamide (1S,2R,5R),(1R,2S,5S) | 532 | 1.08 | 1H-NMR (DMSO-d6) δ: 11.91 (1H, s), 8.72-8.67 (1H, m), 8.49-8.42 (1H, m), 8.16 (2H, s), 7.98 (1H, s), 7.98 (1H, d, J = 12.6 Hz), 7.98-7.80 (4H, m), 7.50-7.28 (1H, m), 7.26-7.18 (5H, m), 6.94 (1H, d, J = 6.6 Hz), 4.60-4.48 (1H, m), 4.45 (1H, d, J = 12.6 Hz), 4.38 (1H, d, J = 12.6 Hz), 3.70-3.50 (2H, m), 2.54 (3H, s), 2.15-1.98 (1H, m), 1.95-1.45 (5H, m) |
| Example 2-530 | 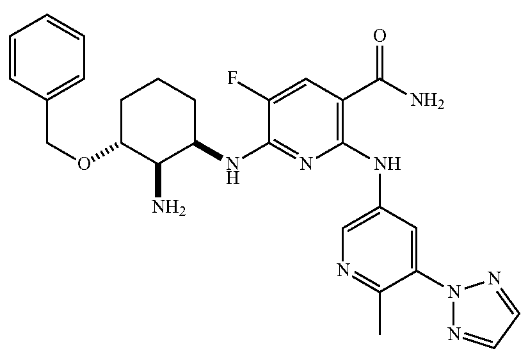 | Mixture of 6-((2-amino-3-(benzyloxy)cyclohexyl)amino)-5-fluoro-2-((6-methyl-5-(2H-1,2,3-triazol-2-yl)pyridin-3-yl)amino)nicotinamide (1R,2R,3R),(1S,2S,3S) | 532 | 1.13 | 1H-NMR (DMSO-d6) δ: 11.93 (1H, s), 8.73-8.69 (2H, m), 8.69-8.65 (1H, m), 8.24 (2H, s), 8.13-7.82 (5H, m), 7.48-7.26 (6H, m), 6.82 (1H, d, J = 7.2 Hz), 4.84-4.71 (1H, m), 4.64 (1H, d, J = 11.1 Hz), 4.50 (1H, d, J = 11.1 Hz), 4.00-3.85 (1H, m), 3.38-3.25 (1H, m), 2.52 (3H, s), 2.22-2.08 (1H, m), 1.88-1.74 (1H, m), 1.60-1.37 (2H, m), 1.37-1.20 (1H, m) |

TABLE 3-continued

| Example | Structure | Compound name | MS (ESI m/z): (M + H) | RT (min) | HNMR |
|---|---|---|---|---|---|
| Example 2-531 | 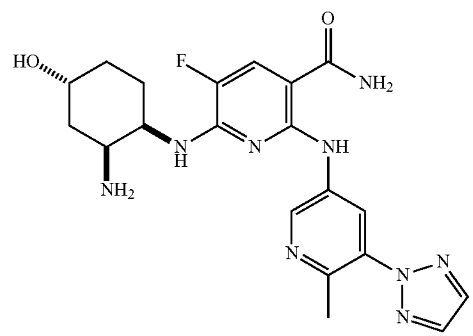 | Mixture of 6-((2-amino-4-hydroxycyclohexyl)amino)-5-fluoro-2-((6-methyl-5-(2H-1,2,3-triazol-2-yl)pyridin-3-yl)amino)nicotinamide (1R,2S,4R), (1S,2R,4S) | 442 | 0.73 | |
| Example 2-532 | 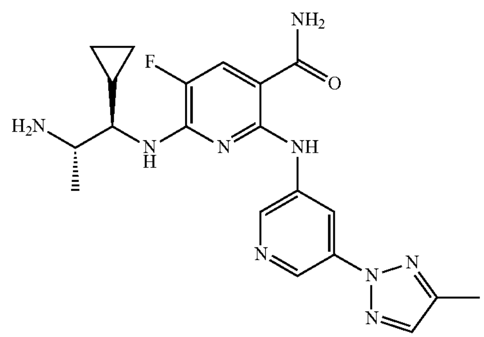 [SMILES: Cc1cnn(-c2cncc(Nc3nc(N[C@H](C4CC4)[C@H](C)N)c(F)cc3C(N)=O)c2)n1] | 6-(((1R,2S)-2-amino-1-cyclopropylpropyl)amino)-5-fluoro-2-((5-(4-methyl-2H-1,2,3-triazol-2-yl)pyridin-3-yl)amino)nicotinamide | 426 | 0.93 | |

TABLE 3-continued

| Example | Structure | Compound name | MS (ESI m/z): (M + H) | RT (min) | HNMR |
|---|---|---|---|---|---|
| Example 2-533 | 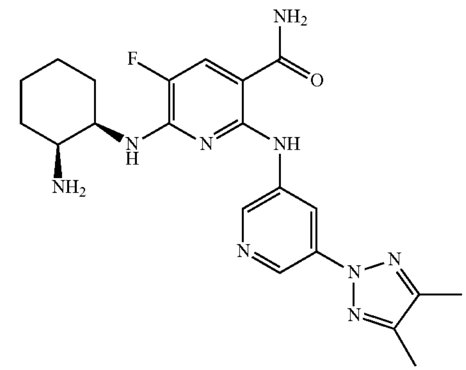 [SMILES: Cc1nn(-c2cncc(Nc3nc(N[C@@H]4CCCC[C@@H]4N)c(F)cc3C(N)=O)c2)nc1C] | 6-(((1S,2R)-2-aminocyclohexyl)amino)-2-((5-(4,5-dimethyl-2H-1,2,3-triazol-2-yl)pyridin-3-yl)amino)-5-fluoronicotinamide | 440 | 0.99 | |
| Example 2-534 | 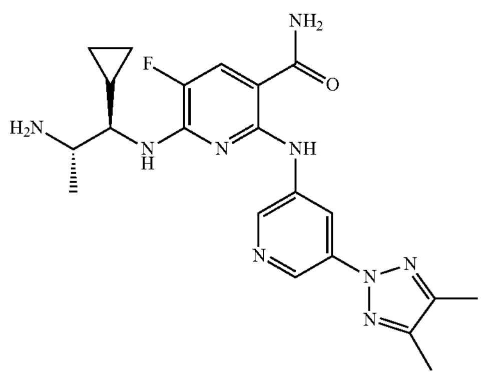 [SMILES: Cc1nn(-c2cncc(Nc3nc(N[C@H](C4CC4)[C@H](C)N)c(F)cc3C(N)=O)c2)nc1C] | 6-(((1R,2S)-2-amino-1-cyclopropylpropyl)amino)-2-((5-(4,5-dimethyl-2H-1,2,3-triazol-2-yl)pyridin-3-yl)amino)-5-fluoronicotinamide | 440 | 0.99 | |

TABLE 3-continued

| Example | Structure | Compound name | MS (ESI m/z): (M + H) | RT (min) | HNMR |
|---|---|---|---|---|---|
| Example 2-535 | 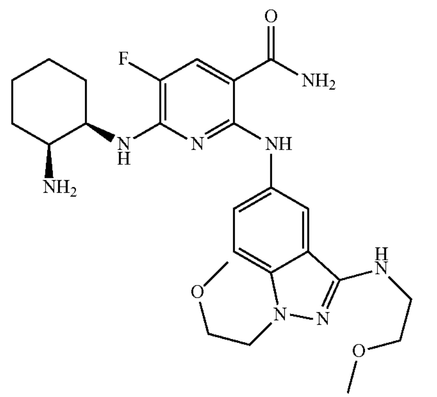 [SMILES: COCCNc1nn(CCOC)c2ccc(Nc3nc(N[C@@H]4CCCC[C@@H]4N)c(F)cc3C(N)=O)cc12] | 6-(((1R,2S)-2-aminocyclohexyl)amino)-5-fluoro-2-((1-(2-methoxyethyl)-3-((2-methoxyethyl)amino)-1H-indazol-5-yl)amino)nicotinamide | 515 | 0.88 | |
| Example 2-536 | 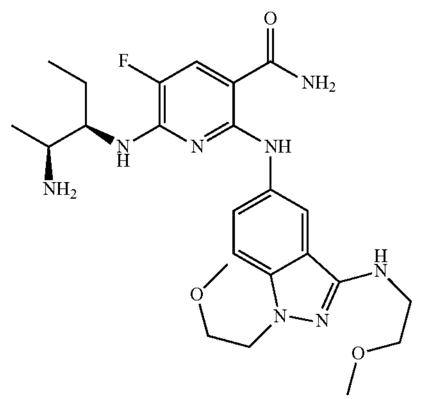 [SMILES: CC[C@@H](Nc1nc(Nc2ccc3c(c2)c(NCCOC)nn3CCOC)c(C(N)=O)cc1F)[C@H](C)N] | 6-(((2S,3R)-2-aminopentan-3-yl)amino)-5-fluoro-2-((1-(2-methoxyethyl)-3-((2-methoxyethyl)amino)-1H-indazol-5-yl)amino)nicotinamide | 503 | 0.86 | |

| Example | Structure | Compound name | MS (ESI m/z): (M + H) | RT (min) | HNMR |
|---|---|---|---|---|---|
| Example 2-537 | 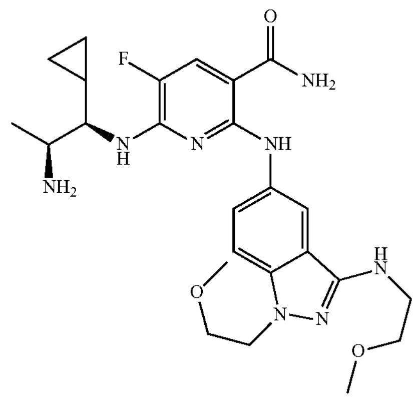 [SMILES: COCCNc1nn(CCOC)c2ccc(Nc3nc(N[C@H](C4CC4)[C@H](C)N)c(F)cc3C(N)=O)cc12] | 6-(((1R,2S)-2-amino-1-cyclopropylpropyl)amino)-5-fluoro-2-((1-(2-methoxyethyl)-3-((2-methoxyethyl)amino)-1H-indazol-5-yl)amino)nicotinamide | 515 | 0.88 | |
| Example 2-538 | 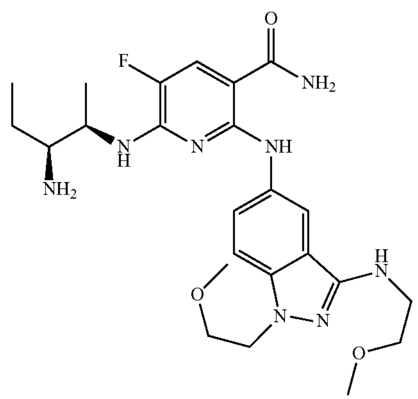 [SMILES: CC[C@H](N)[C@@H](C)Nc1nc(Nc2ccc3c(c2)c(NCCOC)nn3CCOC)c(C(N)=O)cc1F] | 6-(((2R,3S)-3-aminopentan-2-yl)amino)-5-fluoro-2-((1-(2-methoxyethyl)-3-((2-methoxyethyl)amino)-1H-indazol-5-yl)amino)nicotinamide | 503 | 0.83 | |

TABLE 3-continued

| Example | Structure | Compound name | MS (ESI m/z): (M + H) | RT (min) | HNMR |
|---|---|---|---|---|---|
| Example 2-539 | 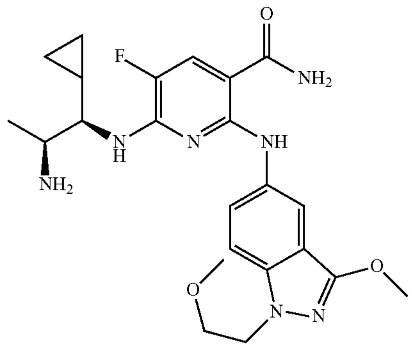 [SMILES: COCCn1nc(OC)c2cc(Nc3nc(N[C@H](C4CC4)[C@H](C)N)c(F)cc3C(N)=O)ccc21] | 6-(((1R,2S)-2-amino-1-cyclopropylpropyl)amino)-5-fluoro-2-((3-methoxy-1-(2-methoxyethyl)-1H-indazol-5-yl)amino)nicotinamide | 472 | 0.94 | |
| Example 2-540 | 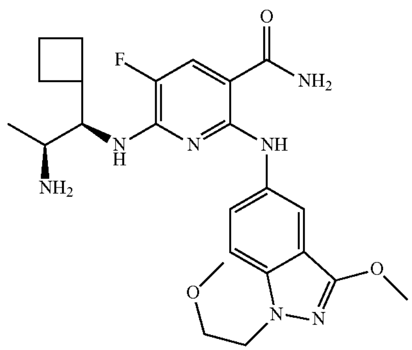 [SMILES: COCCn1nc(OC)c2cc(Nc3nc(N[C@H](C4CCC4)[C@H](C)N)c(F)cc3C(N)=O)ccc21] | 6-(((1R,2S)-2-amino-1-cyclobutylpropyl)amino)-5-fluoro-2-((3-methoxy-1-(2-methoxyethyl)-1H-indazol-5-yl)amino)nicotinamide | 486 | 1.04 | |
| Example 2-541 | 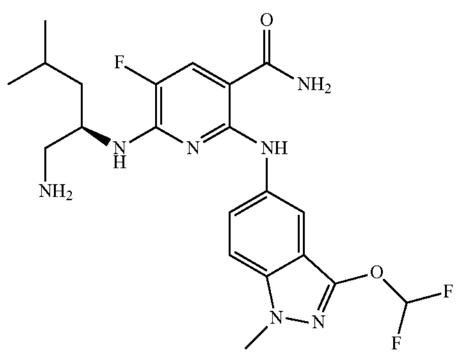 [SMILES: CC(C)C[C@H](CN)Nc1nc(Nc2ccc3c(c2)c(OC(F)F)nn3C)c(C(N)=O)cc1F] | (R)-6-((1-amino-4-methylpentan-2-yl)amino)-2-((3-(difluoromethoxy)-1-methyl-1H-indazol-5-yl)amino)-5-fluoronicotinamide | 466 | 1.09 | |

| Example | Structure | Compound name | MS (ESI m/z): (M + H) | RT (min) | HNMR |
|---|---|---|---|---|---|
| Example 2-542 | 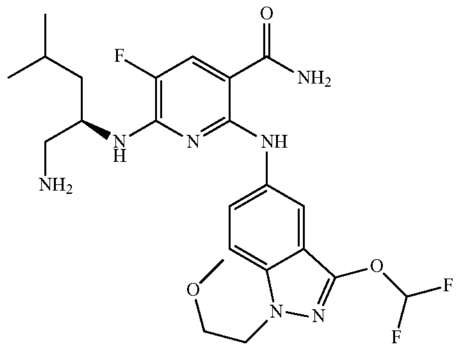 [SMILES: COCCn1nc(OC(F)F)c2cc(Nc3nc(N[C@@H](CN)CC(C)C)c(F)cc3C(N)=O)ccc21] | (R)-6-((1-amino-4-methylpentan-2-yl)amino)-2-((3-(difluoromethoxy)-1-(2-methoxyethyl)-1H-indazol-5-yl)amino)-5-fluoronicotinamide | 510 | 1.12 | |
| Example 2-543 | 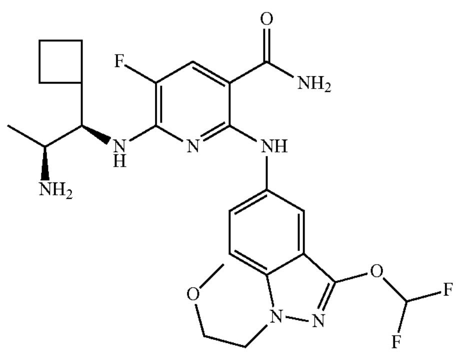 [SMILES: COCCn1nc(OC(F)F)c2cc(Nc3nc(N[C@H](C4CCC4)[C@H](C)N)c(F)cc3C(N)=O)ccc21] | 6-(((1R,2S)-2-amino-1-cyclobutylpropyl)amino)-2-((3-(difluoromethoxy)-1-(2-methoxyethyl)-1H-indazol-5-yl)amino)-5-fluoronicotinamide | 522 | 1.11 | |

TABLE 3-continued

| Example | Structure | Compound name | MS (ESI m/z): (M + H) | RT (min) | HNMR |
|---|---|---|---|---|---|
| Example 2-544 | 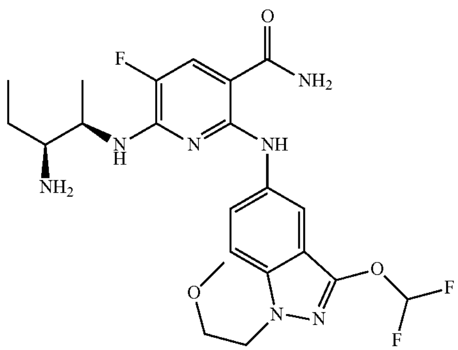 [SMILES: CC[C@H](N)[C@@H](C)Nc1nc(Nc2ccc3c(c2)c(OC(F)F)nn3CCOC)c(C(N)=O)cc1F] | 6-(((2R,3S)-3-aminopentan-2-yl)amino)-2-((3-(difluoromethoxy)-1-(2-methoxyethyl)-1H-indazol-5-yl)amino)-5-fluoronicotinamide | 497 | 0.97 | |
| Example 2-545 | 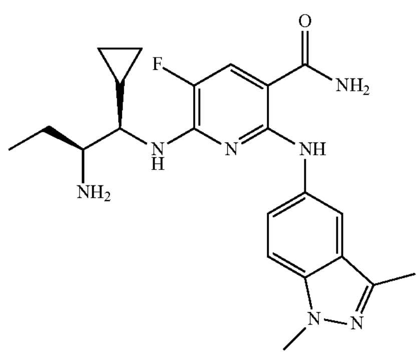 [SMILES: CC[C@H](N)[C@H](Nc1nc(Nc2ccc3c(c2)c(C)nn3C)c(C(N)=O)cc1F)C1CC1] | 6-(((1R,2S)-2-amino-1-cyclopropylbutyl)amino)-2-((1,3-dimethyl-1H-indazol-5-yl)amino)-5-fluoronicotinamide | 426 | 0.91 | |
| Example 2-546 | 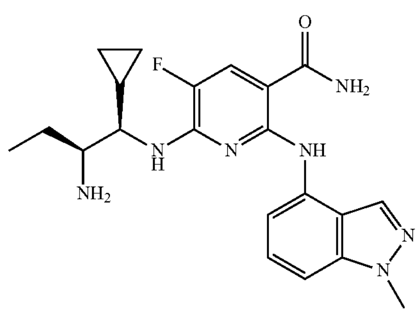 [SMILES: CC[C@H](N)[C@H](Nc1nc(Nc2cccc3c2cnn3C)c(C(N)=O)cc1F)C1CC1] | 6-(((1R,2S)-2-amino-1-cyclopropylbutyl)amino)-5-fluoro-2-((1-methyl-1H-indazol-4-yl)amino)nicotinamide | 412 | 0.93 | |

TABLE 3-continued

| Example | Structure | Compound name | MS (ESI m/z): (M + H) | RT (min) | HNMR |
|---|---|---|---|---|---|
| Example 2-547 | 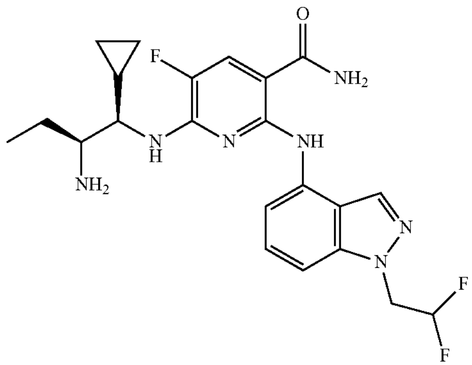 [SMILES: CC[C@H](N)[C@H](Nc1nc(Nc2cccc3c2cnn3CC(F)F)c(C(N)=O)cc1F)C1CC1] | 6-(((1R,2S)-2-amino-1-cyclopropylbutyl)amino)-2-((1-(2,2-difluoroethyl)-1H-indazol-4-yl)amino)-5-fluoronicotinamide | 462 | 0.99 | |
| Example 2-548 | 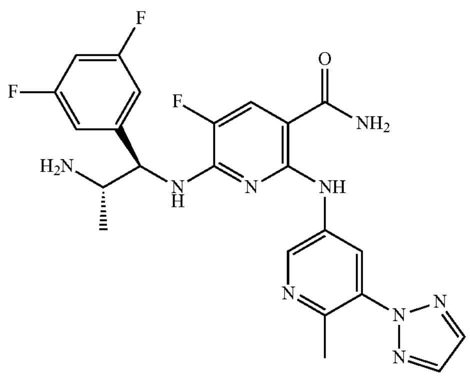 [SMILES: Cc1ncc(Nc2nc(N[C@H](c3cc(F)cc(F)c3)[C@H](C)N)c(F)cc2C(N)=O)cc1-n1nccn1] | 6-(((1R,2S)-2-amino-1-(3,5-difluorophenyl)propyl)amino)-5-fluoro-2-((6-methyl-5-(2H-1,2,3-triazol-2-yl)pyridin-3-yl)amino)nicotinamide | 498 | 0.92 | |

TABLE 3-continued
| Example | Structure | Compound name | MS (ESI m/z): (M + H) | RT (min) | HNMR |
|---|---|---|---|---|---|
| Example 2-549 | 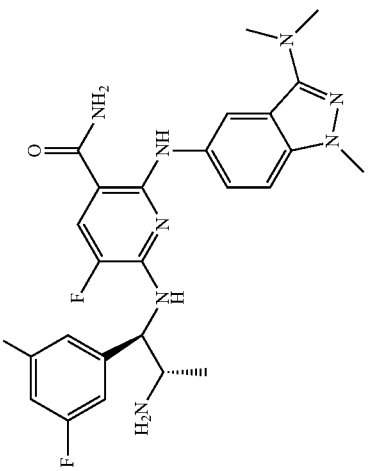 | 6-(((1R,2S)-2-amino-1-(3,5-difluorophenyl)propyl)amino)-2-((3-(dimethylamino)-1-methyl-1H-indazol-5-yl)amino)-5-fluoronicotinamide | 513 | 0.95 | |
| Example 2-550 | 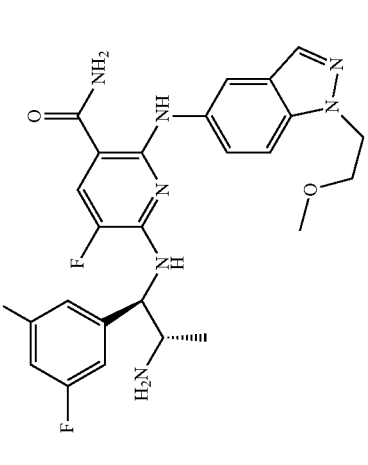 | 6-(((1R,2S)-2-amino-1-(3,5-difluorophenyl)propyl)amino)-5-fluoro-2-((1-(2-methoxyethyl)-1H-indazol-5-yl)amino)nicotinamide | 514 | 0.95 | |

TABLE 3-continued

| Example | Structure | Compound name | MS (ESI m/z): (M + H) | RT (min) | HNMR |
|---|---|---|---|---|---|
| Example 2-551 | 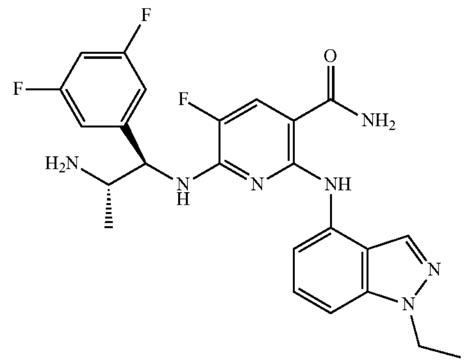 [SMILES: CCn1ncc2c(Nc3nc(N[C@H](c4cc(F)cc(F)c4)[C@H](C)N)c(F)cc3C(N)=O)cccc21] | 6-(((1R,2S)-2-amino-1-[3,5-difluorophenyl)propyl)amino)-2-((1-ethyl-1H-indazol-4-yl)amino)-5-fluoronicotinamide | 484 | 1.01 | |
| Example 2-552 | 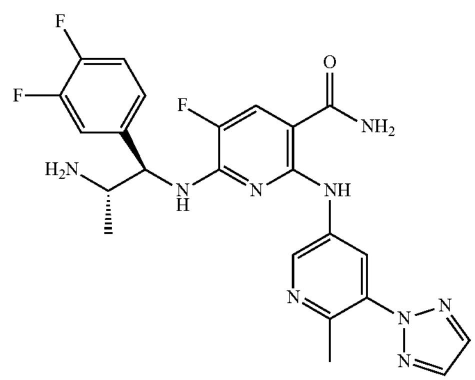 [SMILES: Cc1ncc(Nc2nc(N[C@H](c3ccc(F)c(F)c3)[C@H](C)N)c(F)cc2C(N)=O)cc1-n1nccn1] | 6-(((1R,2S)-2-amino-1-(3,4-difluorophenyl)propyl)amino)-5-fluoro-2-((6-methyl-5-(2H-1,2,3-triazol-2-yl)pyridin-3-yl)amino)nicotinamide | 498 | 0.96 | |

TABLE 3-continued
| Example | Structure | Compound name | MS (ESI m/z): (M + H) | RT (min) | HNMR |
|---|---|---|---|---|---|
| Example 2-553 | 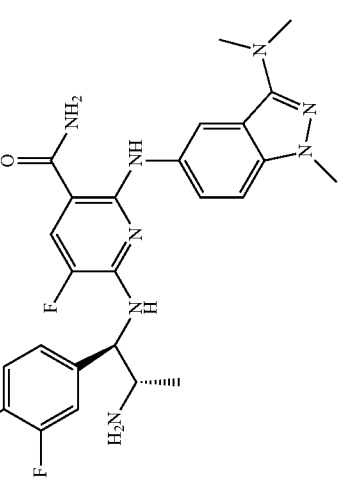 | 6-(((1R,2S)-2-amino-1-(3,4-difluorophenyl)propyl)amino)-2-((3-(dimethyl)amino)-1-methyl-1H-indazol-5-yl)amino)-5-fluoronicotinamide | 513 | 0.96 | |
| Example 2-554 | 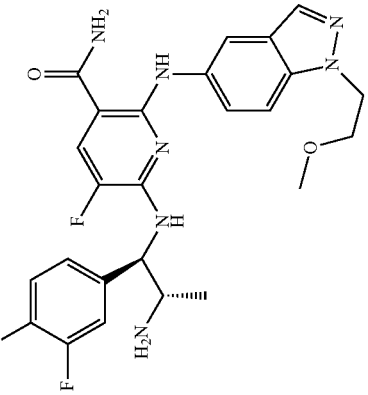 | 6-(((1R,2S)-2-amino-1-(3,4-difluorophenyl)propyl)amino)-5-fluoro-2-((1-(2-methoxyethyl)-1H-indazol-5-yl)amino)nicotinamide | 515 | 0.93 | |

TABLE 3-continued

| Example | Structure | Compound name | MS (ESI m/z): (M + H) | RT (min) | HNMR |
|---|---|---|---|---|---|
| Example 2-555 | 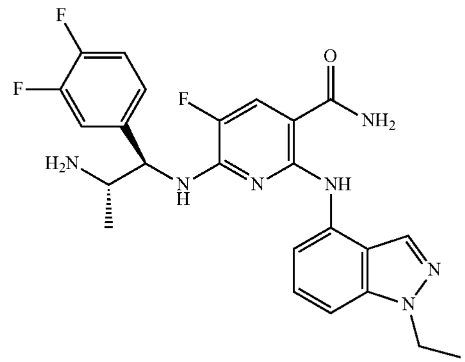 [SMILES: CCn1ncc2c(Nc3nc(N[C@H](c4ccc(F)c(F)c4)[C@H](C)N)c(F)cc3C(N)=O)cccc21] | 6-(((1R,2S)-2-amino-1-(3,4-difluorophenyl)propyl)amino)-2-((1-ethyl-1H-indazol-4-yl)amino)-5-fluoronicotinamide | 484 | 1.02 | |
| Example 2-556 | 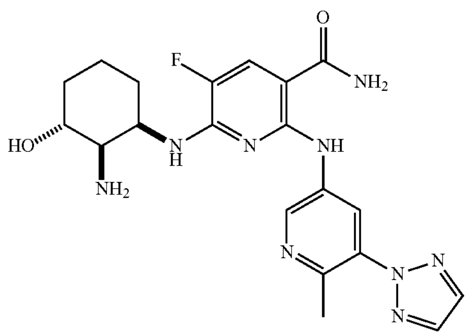 | Mixture of 6-((2-amino-3-hydroxycyclohexyl)amino)-5-fluoro-2-((6-methyl-5-(2H-1,2,3-triazol-2-yl)pyridin-3-yl)amino)nicotinamide (1R,2R,3R), (1S,1S,3S) | 442 | 0.8 | 1H-NMR (DMSO-d6) δ: 11.89 (1H, s), 8.72-8.68 (1H, m), 8.59-8.54 (1H, m), 8.21 (2H, s), 8.02-7.75 (6H, m), 7.50-7.25 (1H, m), 6.63 (1H, d, J = 7.8 Hz), 4.82-4.70 (1H, m), 4.00-3.85 (1H, m), 3.10-2.96 (1H, m), 2.45 (3H, s), 2.00-1.20 (6H, m) |
| Example 2-557 | 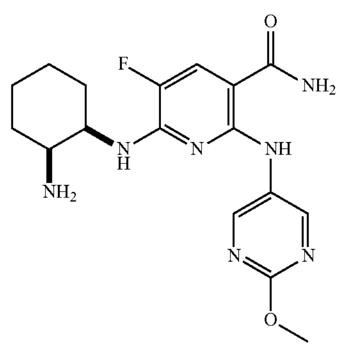 | Mixture of 6-((2-aminocyclohexyl)amino)-5-fluoro-2-((2-methoxypyrimidin-5-yl)amino)nicotinamide (1R,2S), (1S,2R) | 376 | 0.78 | |

TABLE 3-continued

| Example | Structure | Compound name | MS (ESI m/z): (M + H) | RT (min) | HNMR |
|---|---|---|---|---|---|
| Example 2-558 | 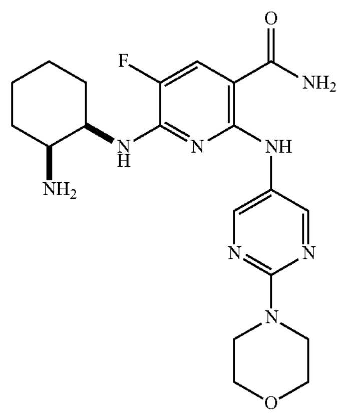 | Mixture of 6-((2-aminocyclohexyl)amino)-5-fluoro-2-((2-morpholinopyrimidin-5-yl)amino)nicotinamide (1R,2S), (1S,2R) | 431 | 0.85 | |
| Example 2-559 | 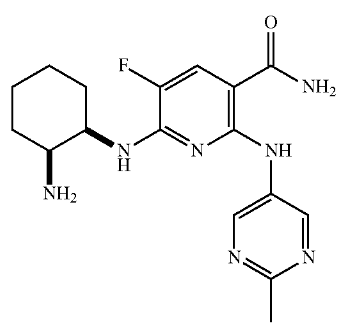 | Mixture of 6-((2-aminocyclohexyl)amino)-5-fluoro-2-((2-methylpyrimidin-5-yl)amino)nicotinamide (1R,2S), (1S,2R) | 360 | 0.73 | |

TABLE 3-continued

| Example | Structure | Compound name | MS (ESI m/z): (M + H) | RT (min) | HNMR |
|---|---|---|---|---|---|
| Example 2-560 | 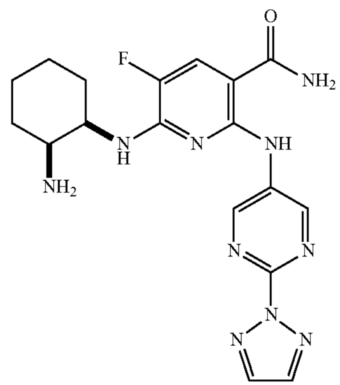 | Mixture of 2-((2-(2H-1,2,3-triazol-2-yl)pyrimidin-5-yl)amino)-6-((2-aminocyclohexyl)amino)-5-fluoronicotinamide (1S,2R), (1R,2S) | 413 | 0.76 | |
| Example 2-561 | 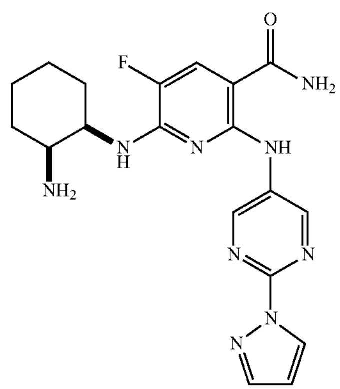 | Mixture of 2-((2-(1H-pyrazol-1-yl)pyrimidin-5-yl)amino)-6-((2-aminocyclohexyl)amino)-5-fluoronicotinamide (1S,2R), (1R,2S) | 412 | 0.85 | |

TABLE 3-continued
| Example | Structure | Compound name | MS (ESI m/z): (M + H) | RT (min) | HNMR |
|---|---|---|---|---|---|
| Example 2-562 | 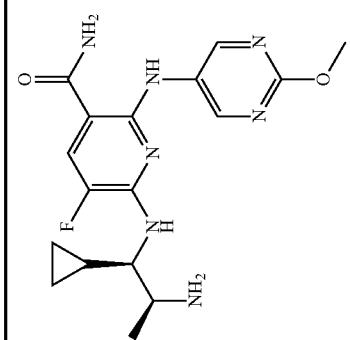 | 6-(((1R,2S)-2-amino-1-cyclopropylpropyl)amino)-5-fluoro-2-((2-methoxypyrimidin-5-yl)amino)nicotinamide | 376 | 0.75 | |
| Example 2-563 | 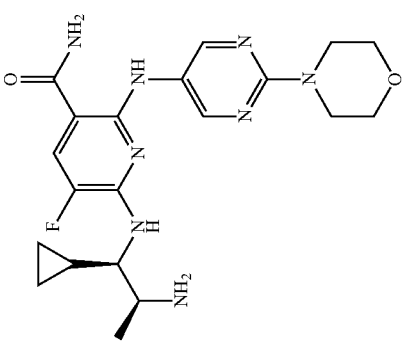 | 6-(((1R,2S)-2-amino-1-cyclopropylpropyl)amino)-5-fluoro-2-((2-morpholinopyrimidin-5-yl)amino)nicotinamide | 431 | 0.83 | |

TABLE 3-continued

| Example | Structure | Compound name | MS (ESI m/z): (M + H) | RT (min) | HNMR |
|---|---|---|---|---|---|
| Example 2-564 | 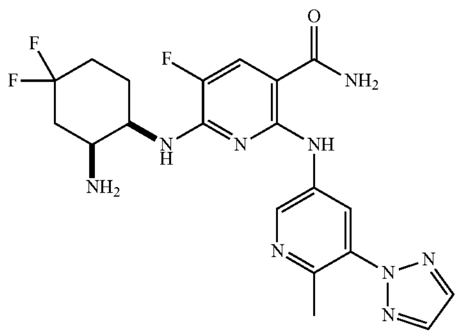 | Mixture of 6-((2-amino-4,4-difluorocyclohexyl)amino)-5-fluoro-2-((6-methyl-5-(2H-1,2,3-triazol-2-yl)pyridin-3-yl)amino)nicotinamide (1R,2S), (1S,2R) | 462 | 0.9 | |
| Example 2-565 | 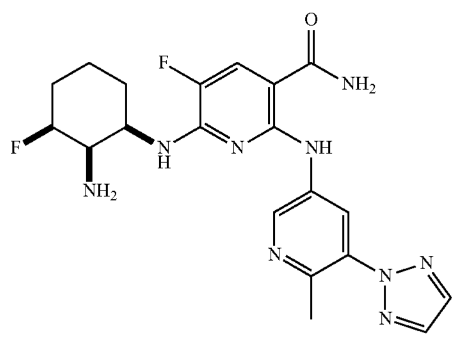 | Mixture of 6-((2-amino-3-fluorocyclohexyl)amino)-5-fluoro-2-((6-methyl-5-(2H-1,2,3-triazol-2-yl)pyridin-3-yl)amino)nicotinamide (1R,2R,3S), (1S,2S,3R) | 444 | 0.85 | |

Example 3

Example 4-1

[Formula 156]

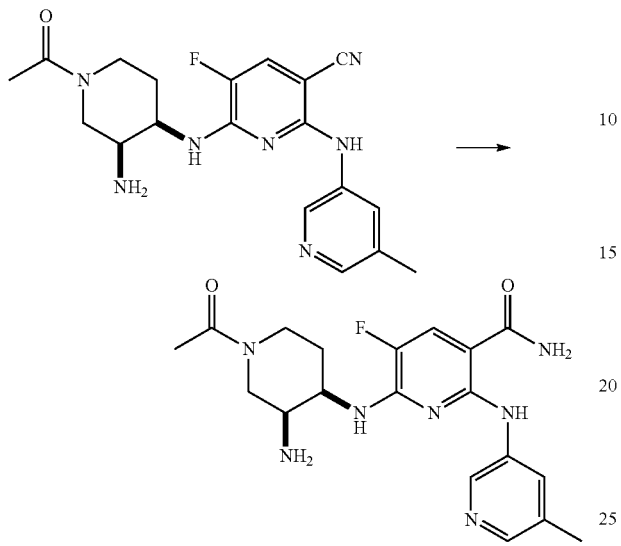

A 5M sodium hydroxide aqueous solution (0.038 ml) and a 30% hydrogen peroxide solution (0.008 ml) were added to a DMSO/EtOH (0.1 ml/0.1 ml) solution containing 6-((1-acetyl-3-aminopiperidin-4-yl)amino)-5-fluoro-2-((5-methylpyridin-3-yl)amino)nicotinonitrile hydrochloride (6 mg), followed by stirring at room temperature for 30 minutes. Water was added to the reaction solution, followed by extraction with ethyl acetate. The organic layers were washed with saturated saline and dried over anhydrous sodium sulfate. The solvent was distilled away under reduced pressure. Ethyl acetate (0.5 ml) and 4M hydrochloric acid/1,4-dioxane (0.004 ml) were added to the obtained residue, followed by stirring at room temperature for 0.5 hours. The solvent was removed under reduced pressure. The obtained residue was washed with ethyl acetate. A yellow solid of 6-((1-acetyl-3-aminopiperidin-4-yl)amino)-5-fluoro-2-((5-methylpyridin-3-yl)amino)nicotinamide hydrochloride (3.2 mg) was thus obtained.
(Table 4 (Example 4-1) lists MS data.)

Example 4

The compounds shown in table 4 were obtained as described in Example 3.

TABLE 4

| Example | Structure | Compound name | MS(ESI m/z): (M + H) | RT (min) |
|---|---|---|---|---|
| Example 4-1 | 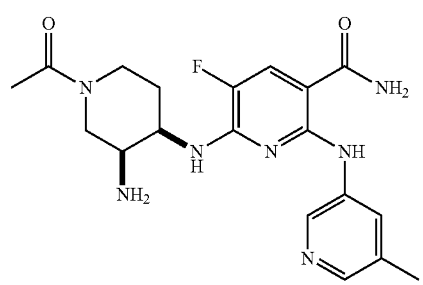 | Mixture of 6-((1-acetyl-3-aminopiperidin-4-yl)amino)-5-fluoro-2-((5-methylpyridin-3-yl)amino)nicotinamide (3S,4R) (3R,4S) | 402 | 0.51 |
| Example 4-2 | 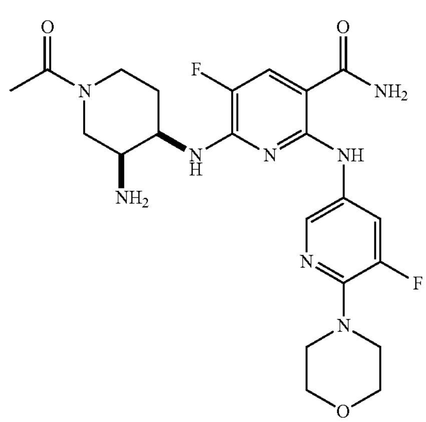 | Mixture of 6-((1-acetyl-3-aminopiperidin-4-yl)amino)-5-fluoro-2-((5-fluoro-6-morpholinopyridin-3-yl)amino)nicotinamide (3S,4R) (3R,4S) | 491 | 0.8 |

TABLE 4-continued

| Example | Structure | Compound name | MS(ESI m/z): (M + H) | RT (min) |
|---|---|---|---|---|
| Example 4-3 | 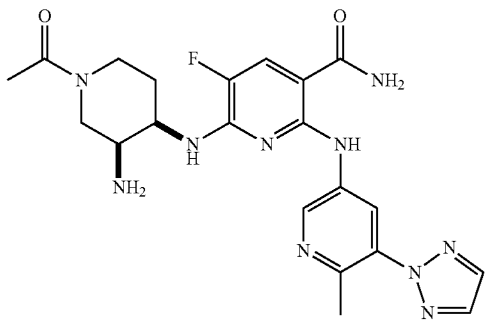 | Mixture of 6-((1-acetyl-3-aminopiperidin-4-yl)amino)-5-fluoro-2-((6-methyl-5-(2H-1,2,3-triazol-2-yl)pyridin-3-yl)amino)nicotinamide (3S,4R) (3R,4S) | 469 | 0.74 |
| Example 4-4 | 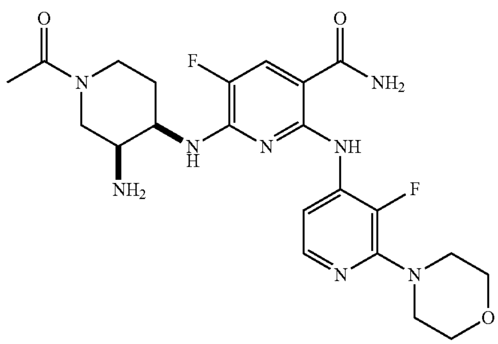 | Mixture of 6-((1-acetyl-3-aminopiperidin-4-yl)amino)-5-fluoro-2-((3-fluoro-2-morpholinopyridin-4-yl)amino)nicotinamide (3S,4R) (3R,4S) | 491 | 0.65 |

Next, the usefulness of representative compounds of the present invention will be described in the following Test Examples.

Test Example 1

Syk Enzyme Assay

A glutathione S-transferase (GST)-linked full-length human Syk protein (Carna Biosciences), which had been generated using a Baculovirus expression system, was used in the Syk enzyme assay.

7.5 μl of a reaction solution (0.83 nM Syk, 20 mM HEPES, 10 mM $MgCl_2$, 50 mM NaCl, 2 mM DTT, 0.05% BSA, pH 7.0) containing a Syk protein and a predetermined concentration of a test compound was shaken for 2 minutes, and it was then left at rest at room temperature for 13 minutes. Thereafter, 0.5 μM substrate peptide (Biotin-EDPDYEWPSA-$NH_2$) and 5 μL of a solution containing 67.5 μM ATP were added to the reaction solution, and the obtained mixture was then shaken for 2 minutes. The reaction solution was further left at rest at room temperature for 40 minutes, so as to carry out an enzyme reaction.

Thereafter, 50 μL of a reaction termination solution [60 nM APC-SA, 0.45 μg/mL Eu-PT66, 30 mM HEPES (pH 7.0), 150 mM KF, 30 mM EDTA, 0.15% BSA, 0.075% Tween20] containing Allophycocyanin-Streptavidin (APC-SA; PerkinElmer) and an Eu-W1024-labeled anti-phosphotyrosine PT66 antibody (Eu-PT66; PerkinElmer) was added to the reaction solution to terminate the enzyme reaction. At the same time, the reaction solution was left at rest at room temperature for 1 hour, so as to carry out an antigen-antibody reaction. Thereafter, using EnVision (PerkinElmer), the level of time-resolved fluorescence was measured at 615 nm and 665 nm, so that the phosphorylation of the substrate peptide was measured.

Table 5 shows the results. The following are used in Table 5 to denote standards for evaluating $IC_{50}$ of Syk-inhibitory activity.

A: Up to 10 nM
B: 10 to 50 nM
C: 50 to 100 nM

The set of numbers (XYZ-xyz) given in each Example number column indicates the corresponding Example number (Example XYZ-xyz) in Table 5.

TABLE 5

| Example 2-1 | A | Example 2-150 | A | Example 2-197 | B |
|---|---|---|---|---|---|
| Example 2-10 | A | Example 2-151 | A | Example 2-199 | A |
| Example 2-100 | A | Example 2-152 | A | Example 2-2 | A |
| Example 2-101 | A | Example 2-153 | A | Example 2-20 | A |
| Example 2-102 | C | Example 2-154 | A | Example 2-200 | B |
| Example 2-103 | C | Example 2-155 | A | Example 2-201 | B |
| Example 2-104 | C | Example 2-156 | A | Example 2-202 | C |
| Example 2-105 | B | Example 2-157 | A | Example 2-203 | B |
| Example 2-106 | B | Example 2-158 | A | Example 2-204 | B |
| Example 2-107 | C | Example 2-159 | A | Example 2-205 | B |
| Example 2-108 | C | Example 2-16 | B | Example 2-206 | B |
| Example 2-11 | A | Example 2-160 | A | Example 2-207 | A |
| Example 2-111 | B | Example 2-161 | B | Example 2-208 | A |
| Example 2-112 | B | Example 2-162 | B | Example 2-209 | A |
| Example 2-113 | B | Example 2-163 | B | Example 2-21 | A |
| Example 2-114 | A | Example 2-164 | B | Example 2-210 | A |
| Example 2-115 | B | Example 2-165 | B | Example 2-211 | A |
| Example 2-116 | B | Example 2-166 | B | Example 2-212 | A |
| Example 2-117 | C | Example 2-167 | B | Example 2-213 | A |
| Example 2-118 | C | Example 2-168 | B | Example 2-214 | A |
| Example 2-119 | B | Example 2-169 | A | Example 2-215 | B |
| Example 2-12 | A | Example 2-17 | A | Example 2-216 | B |
| Example 2-120 | A | Example 2-170 | A | Example 2-217 | C |
| Example 2-121 | A | Example 2-171 | A | Example 2-218 | B |
| Example 2-122 | B | Example 2-172 | A | Example 2-219 | B |
| Example 2-123 | A | Example 2-173 | A | Example 2-22 | A |
| Example 2-124 | A | Example 2-174 | A | Example 2-220 | B |

TABLE 5-continued

| Example | Grade | Example | Grade | Example | Grade | Example | Grade | Example | Grade | Example | Grade |
|---|---|---|---|---|---|---|---|---|---|---|---|
| Example 2-125 | A | Example 2-175 | A | Example 2-221 | A | Example 2-406 | A | Example 2-458 | A | Example 2-509 | A |
| Example 2-126 | A | Example 2-176 | A | Example 2-222 | B | Example 2-407 | B | Example 2-459 | B | Example 2-51 | A |
| Example 2-127 | A | Example 2-177 | A | Example 2-223 | A | Example 2-408 | C | Example 2-46 | A | Example 2-510 | A |
| Example 2-128 | B | Example 2-178 | A | Example 2-224 | A | Example 2-409 | A | Example 2-460 | A | Example 2-511 | B |
| Example 2-129 | B | Example 2-179 | B | Example 2-225 | B | Example 2-41 | A | Example 2-461 | B | Example 2-512 | A |
| Example 2-13 | A | Example 2-18 | A | Example 2-226 | C | Example 2-410 | A | Example 2-462 | B | Example 2-513 | B |
| Example 2-130 | A | Example 2-180 | B | Example 2-228 | C | Example 2-411 | A | Example 2-463 | B | Example 2-514 | A |
| Example 2-131 | A | Example 2-182 | A | Example 2-229 | B | Example 2-412 | B | Example 2-464 | B | Example 2-515 | B |
| Example 2-132 | A | Example 2-183 | C | Example 2-23 | A | Example 2-413 | A | Example 2-469 | B | Example 2-518 | A |
| Example 2-133 | A | Example 2-184 | A | Example 2-230 | B | Example 2-414 | A | Example 2-47 | A | Example 2-519 | A |
| Example 2-134 | A | Example 2-185 | A | Example 2-231 | B | Example 2-415 | A | Example 2-472 | A | Example 2-52 | A |
| Example 2-135 | B | Example 2-186 | A | Example 2-233 | B | Example 2-416 | A | Example 2-473 | B | Example 2-520 | A |
| Example 2-136 | B | Example 2-187 | A | Example 2-234 | C | Example 2-418 | B | Example 2-474 | A | Example 2-521 | B |
| Example 2-137 | A | Example 2-188 | A | Example 2-235 | A | Example 2-42 | B | Example 2-475 | A | Example 2-522 | B |
| Example 2-138 | A | Example 2-189 | A | Example 2-236 | B | Example 2-421 | B | Example 2-476 | A | Example 2-523 | A |
| Example 2-139 | A | Example 2-19 | A | Example 2-237 | B | Example 2-422 | B | Example 2-477 | A | Example 2-524 | A |
| Example 2-14 | B | Example 2-190 | A | Example 2-238 | B | Example 2-423 | A | Example 2-478 | A | Example 2-525 | A |
| Example 2-140 | B | Example 2-191 | B | Example 2-239 | B | Example 2-424 | A | Example 2-479 | A | Example 2-526 | A |
| Example 2-141 | B | Example 2-192 | A | Example 2-24 | A | Example 2-426 | B | Example 2-48 | A | Example 2-528 | C |
| Example 2-142 | B | Example 2-193 | B | Example 2-240 | A | Example 2-427 | B | Example 2-480 | A | Example 2-53 | A |
| Example 2-148 | A | Example 2-194 | A | Example 2-241 | B | Example 2-428 | A | Example 2-481 | A | Example 2-531 | B |
| Example 2-149 | A | Example 2-195 | B | Example 2-242 | B | Example 2-429 | A | Example 2-482 | A | Example 2-532 | A |
| Example 2-15 | A | Example 2-196 | A | Example 2-243 | B | Example 2-43 | A | Example 2-483 | A | Example 2-533 | C |
| Example 2-244 | B | Example 2-303 | A | Example 2-351 | A | Example 2-430 | B | Example 2-484 | B | Example 2-534 | C |
| Example 2-245 | A | Example 2-304 | A | Example 2-352 | A | Example 2-431 | B | Example 2-485 | B | Example 2-535 | B |
| Example 2-248 | C | Example 2-305 | A | Example 2-353 | A | Example 2-434 | A | Example 2-486 | B | Example 2-536 | B |
| Example 2-249 | A | Example 2-306 | A | Example 2-354 | B | Example 2-435 | A | Example 2-488 | A | Example 2-537 | B |
| Example 2-25 | A | Example 2-307 | A | Example 2-355 | A | Example 2-436 | A | Example 2-489 | B | Example 2-539 | A |
| Example 2-250 | A | Example 2-308 | A | Example 2-356 | B | Example 2-437 | A | Example 2-49 | A | Example 2-54 | A |
| Example 2-251 | B | Example 2-309 | B | Example 2-357 | B | Example 2-438 | A | Example 2-490 | B | Example 2-540 | A |
| Example 2-252 | A | Example 2-31 | A | Example 2-358 | B | Example 2-439 | A | Example 2-491 | B | Example 2-541 | A |
| Example 2-253 | A | Example 2-310 | C | Example 2-359 | C | Example 2-44 | A | Example 2-492 | A | Example 2-542 | A |
| Example 2-254 | A | Example 2-311 | A | Example 2-36 | B | Example 2-440 | A | Example 2-493 | A | Example 2-543 | A |
| Example 2-255 | A | Example 2-312 | A | Example 2-360 | B | Example 2-441 | A | Example 2-494 | A | Example 2-544 | B |
| Example 2-256 | C | Example 2-313 | A | Example 2-361 | B | Example 2-442 | A | Example 2-495 | A | Example 2-545 | A |
| Example 2-257 | C | Example 2-314 | A | Example 2-362 | A | Example 2-444 | A | Example 2-496 | A | Example 2-546 | A |
| Example 2-258 | B | Example 2-315 | B | Example 2-363 | B | Example 2-445 | A | Example 2-497 | C | Example 2-547 | A |
| Example 2-259 | C | Example 2-316 | A | Example 2-364 | C | Example 2-446 | A | Example 2-498 | A | Example 2-548 | B |
| Example 2-26 | A | Example 2-317 | A | Example 2-365 | C | Example 2-447 | A | Example 2-499 | B | Example 2-549 | B |
| Example 2-260 | B | Example 2-318 | A | Example 2-366 | B | Example 2-448 | B | Example 2-5 | A | Example 2-55 | A |
| Example 2-261 | B | Example 2-319 | A | Example 2-369 | A | Example 2-449 | A | Example 2-50 | A | Example 2-550 | A |
| Example 2-262 | B | Example 2-32 | A | Example 2-37 | A | Example 2-45 | A | Example 2-500 | B | Example 2-551 | B |
| Example 2-264 | B | Example 2-320 | A | Example 2-370 | A | Example 2-450 | A | Example 2-501 | B | Example 2-552 | A |
| Example 2-265 | A | Example 2-321 | A | Example 2-371 | A | Example 2-553 | A | Example 3-4 | C | | |
| Example 2-266 | A | Example 2-322 | A | Example 2-372 | A | Example 2-554 | A | | | | |
| Example 2-267 | A | Example 2-323 | B | Example 2-373 | A | Example 2-555 | A | | | | |
| Example 2-268 | B | Example 2-324 | B | Example 2-374 | A | Example 2-563 | C | | | | |
| Example 2-269 | A | Example 2-325 | A | Example 2-375 | A | Example 2-564 | B | | | | |
| Example 2-27 | A | Example 2-326 | A | Example 2-376 | A | Example 2-57 | A | | | | |
| Example 2-270 | B | Example 2-327 | A | Example 2-377 | A | Example 2-58 | B | | | | |
| Example 2-272 | B | Example 2-328 | A | Example 2-378 | A | Example 2-59 | B | | | | |
| Example 2-273 | A | Example 2-329 | A | Example 2-38 | A | Example 2-6 | A | | | | |
| Example 2-274 | B | Example 2-33 | B | Example 2-380 | A | Example 2-60 | B | | | | |
| Example 2-275 | B | Example 2-330 | A | Example 2-381 | A | Example 2-61 | B | | | | |
| Example 2-276 | B | Example 2-331 | A | Example 2-382 | B | Example 2-62 | B | | | | |
| Example 2-277 | B | Example 2-332 | A | Example 2-383 | A | Example 2-63 | B | | | | |
| Example 2-278 | B | Example 2-333 | B | Example 2-384 | A | Example 2-64 | B | | | | |
| Example 2-279 | B | Example 2-334 | A | Example 2-385 | B | Example 2-65 | B | | | | |
| Example 2-28 | A | Example 2-335 | B | Example 2-386 | A | Example 2-66 | B | | | | |
| Example 2-286 | B | Example 2-336 | A | Example 2-387 | B | Example 2-67 | B | | | | |
| Example 2-287 | B | Example 2-337 | C | Example 2-388 | A | Example 2-68 | B | | | | |
| Example 2-288 | B | Example 2-338 | B | Example 2-389 | B | Example 2-69 | B | | | | |
| Example 2-289 | A | Example 2-339 | C | Example 2-39 | A | Example 2-7 | A | | | | |
| Example 2-29 | A | Example 2-34 | B | Example 2-390 | A | Example 2-70 | A | | | | |
| Example 2-290 | B | Example 2-341 | A | Example 2-391 | A | Example 2-71 | A | | | | |
| Example 2-291 | B | Example 2-342 | B | Example 2-393 | A | Example 2-72 | A | | | | |
| Example 2-292 | A | Example 2-343 | B | Example 2-394 | A | Example 2-73 | A | | | | |
| Example 2-293 | A | Example 2-345 | B | Example 2-395 | A | Example 2-74 | A | | | | |
| Example 2-3 | A | Example 2-346 | A | Example 2-396 | A | Example 2-75 | A | | | | |
| Example 2-30 | A | Example 2-348 | A | Example 2-397 | A | Example 2-76 | B | | | | |
| Example 2-300 | B | Example 2-349 | A | Example 2-398 | A | Example 2-77 | B | | | | |
| Example 2-301 | C | Example 2-35 | B | Example 2-399 | A | Example 2-78 | A | | | | |
| Example 2-302 | A | Example 2-350 | A | Example 2-4 | A | Example 2-79 | A | | | | |
| Example 2-40 | A | Example 2-451 | A | Example 2-502 | B | Example 2-8 | A | | | | |
| Example 2-400 | A | Example 2-452 | B | Example 2-503 | B | Example 2-80 | A | | | | |
| Example 2-401 | A | Example 2-453 | A | Example 2-504 | B | Example 2-81 | B | | | | |
| Example 2-402 | A | Example 2-454 | A | Example 2-505 | B | Example 2-82 | A | | | | |
| Example 2-403 | B | Example 2-455 | A | Example 2-506 | B | Example 2-83 | A | | | | |
| Example 2-404 | A | Example 2-456 | A | Example 2-507 | C | Example 2-84 | A | | | | |
| Example 2-405 | A | Example 2-457 | A | Example 2-508 | A | Example 2-85 | B | | | | |

TABLE 5-continued

| Example | Grade |
|---|---|
| Example 2-86 | A |
| Example 2-87 | A |
| Example 2-89 | A |
| Example 2-9 | A |
| Example 2-90 | B |
| Example 2-91 | B |
| Example 2-92 | B |
| Example 2-96 | A |
| Example 2-97 | C |
| Example 2-98 | A |
| Example 2-99 | A |
| Example 3-1 | B |
| Example 3-3 | A |

Test Example 2

Selectivity of Kinase Inhibition

The concentrations of test compounds were adjusted to 100 nM. The test compounds were examined using Profiler Pro kits (Caliper) in terms of activity against each of 191 types of kinases excluding Syk. As a result, highly selective compounds (Example 2-1, Example 2-28, and Example 2-77) having kinase inhibitory rates of 75% or more with respect to only 0-1 type of kinases other than Syk and a compound (Example 2-76) having a kinase inhibitory rate of 75% or more with respect to 8 types of kinases were obtained.

Test Example 3

TNFα Generation Assay

THP-1 cells ($2\times10^5$ cells/ml), which were human monocytoid cells, were cultured in the presence of 10 ng/ml IFN-γ (Roche) for 2 days, and they were induced to differentiate into macrophage-like cells. The differentiation-induced THP-1 cells were recovered, and the cells ($1\times10^6$ cell/ml) were then allowed to react with a predetermined concentration of test compound at room temperature for 30 minutes. On the other hand, 100 μl of human IgG (10 μg/ml, SIGMA-ALDRICH) diluted with PBS was added to a 96-well plate, and it was then incubated at room temperature overnight. Thereafter, the resultant was washed with PBS twice to produce a human IgG-coated plate. A cell fluid that contained a compound was plated on the obtained human IgG-coated plate ($5\times10^4$ cells/well), and it was then cultured for 7 hours. Thereafter, the cultured solution was recovered, and the amount of TNFα secreted into the culture solution was then measured by the AlphaLISA method (PerkinElmer).

Table 6 shows the results. The following are used in Table 6 to denote standards for evaluating $IC_{50}$ of TNFα generation inhibitory activity.

A: Up to 65 nM
B: 65 to 130 nM
C: 130 to 200 nM

TABLE 6

| Example | Grade | Example | Grade | Example | Grade |
|---|---|---|---|---|---|
| Example 2-1 | B | Example 2-196 | B | Example 2-28 | B |
| Example 2-10 | A | Example 2-20 | B | Example 2-29 | B |
| Example 2-100 | C | Example 2-207 | B | Example 2-302 | C |
| Example 2-101 | C | Example 2-208 | A | Example 2-306 | C |
| Example 2-106 | C | Example 2-209 | B | Example 2-31 | B |
| Example 2-11 | C | Example 2-21 | C | Example 2-311 | C |
| Example 2-114 | C | Example 2-210 | A | Example 2-316 | B |
| Example 2-121 | C | Example 2-211 | B | Example 2-317 | B |
| Example 2-122 | C | Example 2-213 | B | Example 2-319 | B |
| Example 2-123 | B | Example 2-214 | B | Example 2-32 | C |
| Example 2-125 | B | Example 2-215 | C | Example 2-320 | B |
| Example 2-126 | B | Example 2-216 | C | Example 2-321 | C |
| Example 2-127 | C | Example 2-218 | B | Example 2-322 | B |
| Example 2-129 | C | Example 2-219 | C | Example 2-325 | C |
| Example 2-130 | B | Example 2-22 | C | Example 2-326 | A |
| Example 2-131 | B | Example 2-220 | C | Example 2-327 | C |
| Example 2-132 | C | Example 2-221 | C | Example 2-328 | A |
| Example 2-133 | B | Example 2-222 | C | Example 2-329 | B |
| Example 2-134 | C | Example 2-223 | C | Example 2-33 | C |
| Example 2-135 | C | Example 2-224 | C | Example 2-330 | B |
| Example 2-136 | C | Example 2-225 | C | Example 2-332 | B |
| Example 2-137 | B | Example 2-229 | C | Example 2-334 | B |
| Example 2-138 | A | Example 2-23 | B | Example 2-348 | C |
| Example 2-139 | B | Example 2-230 | B | Example 2-36 | C |
| Example 2-141 | C | Example 2-233 | C | Example 2-362 | B |
| Example 2-142 | B | Example 2-235 | B | Example 2-366 | C |
| Example 2-148 | B | Example 2-239 | C | Example 2-37 | B |
| Example 2-149 | B | Example 2-24 | C | Example 2-370 | C |
| Example 2-150 | C | Example 2-240 | C | Example 2-372 | C |
| Example 2-151 | C | Example 2-242 | C | Example 2-374 | C |
| Example 2-152 | C | Example 2-243 | C | Example 2-375 | B |
| Example 2-153 | C | Example 2-249 | B | Example 2-376 | B |
| Example 2-159 | B | Example 2-25 | C | Example 2-377 | B |
| Example 2-162 | C | Example 2-251 | C | Example 2-378 | B |
| Example 2-17 | B | Example 2-252 | C | Example 2-38 | B |
| Example 2-170 | C | Example 2-253 | B | Example 2-381 | B |
| Example 2-172 | C | Example 2-254 | C | Example 2-39 | A |
| Example 2-173 | B | Example 2-255 | C | Example 2-4 | B |
| Example 2-174 | C | Example 2-26 | C | Example 2-40 | A |
| Example 2-179 | C | Example 2-265 | B | Example 2-404 | B |
| Example 2-18 | B | Example 2-266 | B | Example 2-406 | C |
| Example 2-180 | C | Example 2-267 | B | Example 2-409 | C |
| Example 2-182 | B | Example 2-268 | C | Example 2-41 | B |
| Example 2-184 | B | Example 2-269 | B | Example 2-410 | B |
| Example 2-185 | C | Example 2-27 | B | Example 2-413 | B |
| Example 2-186 | B | Example 2-270 | B | Example 2-414 | B |
| Example 2-187 | B | Example 2-272 | C | Example 2-415 | C |
| Example 2-188 | A | Example 2-273 | B | Example 2-416 | A |
| Example 2-19 | C | Example 2-274 | C | Example 2-42 | B |
| Example 2-193 | C | Example 2-275 | C | Example 2-428 | C |
| Example 2-43 | C | Example 2-75 | C | | |
| Example 2-434 | B | Example 2-76 | C | | |
| Example 2-436 | C | Example 2-77 | C | | |
| Example 2-437 | B | Example 2-78 | B | | |
| Example 2-438 | A | Example 2-79 | C | | |
| Example 2-439 | B | Example 2-8 | A | | |
| Example 2-44 | B | Example 2-80 | B | | |
| Example 2-440 | C | Example 2-82 | C | | |
| Example 2-441 | C | Example 2-83 | C | | |
| Example 2-442 | B | Example 2-84 | C | | |
| Example 2-45 | C | Example 2-87 | C | | |
| Example 2-454 | B | Example 2-9 | B | | |
| Example 2-46 | B | Example 2-91 | C | | |
| Example 2-47 | B | Example 2-96 | C | | |
| Example 2-472 | A | Example 2-98 | C | | |
| Example 2-474 | C | | | | |
| Example 2-475 | B | | | | |
| Example 2-476 | B | | | | |
| Example 2-477 | C | | | | |
| Example 2-478 | B | | | | |
| Example 2-479 | B | | | | |
| Example 2-48 | B | | | | |
| Example 2-480 | B | | | | |
| Example 2-481 | B | | | | |
| Example 2-482 | B | | | | |
| Example 2-49 | C | | | | |
| Example 2-496 | C | | | | |
| Example 2-5 | B | | | | |
| Example 2-508 | B | | | | |
| Example 2-51 | C | | | | |
| Example 2-518 | B | | | | |
| Example 2-519 | C | | | | |
| Example 2-52 | C | | | | |
| Example 2-521 | B | | | | |
| Example 2-522 | C | | | | |
| Example 2-539 | C | | | | |
| Example 2-54 | C | | | | |
| Example 2-546 | C | | | | |
| Example 2-57 | B | | | | |

TABLE 6-continued

| | |
|---|---|
| Example 2-58 | C |
| Example 2-6 | C |
| Example 2-66 | C |
| Example 2-67 | C |
| Example 2-69 | C |
| Example 2-7 | B |
| Example 2-70 | C |
| Example 2-71 | A |
| Example 2-72 | C |
| Example 2-73 | C |
| Example 2-74 | B |

Test Example 4

Antibody-Dependent Phagocytosis Assay

THP-1 cells ($2 \times 10^5$ cells/ml), which were human monocytoid cells, were cultured in the presence of 10 ng/ml IFNγ for 2 days, and they were induced to differentiate into macrophage-like cells. The differentiation-induced THP-1 cells were recovered, and the cells ($5 \times 10^4$ cells/well) were then allowed to react with a predetermined concentration of test compound at room temperature for 30 minutes. Thereafter, *Escherichia coli* (Life Technologies) labeled with a pH-sensitive dye (pH-rodo) was subjected to opsonization using an anti-*Escherichia coli* antibody (Life Technologies). Then, the resultant was added to the THP-1 cells obtained above, followed by incubation at 37° C. for 3 hours. Opsonized *Escherichia coli* and cell-permeable fluorescent dye (Calcein AM) were simultaneously added thereto, followed by quantitative determination of phagocytosis of opsonized *Escherichia coli* in viable cells using an IN Cell Analyzer.

The test results are listed in Table 7 below. The following are used in Table 7 to denote standards for evaluating $IC_{50}$ upon phagocytosis inhibition.
A: Up to 1 μM
B: 1 to 3 μM
C: 3 to 6 μM

TABLE 7

| | | | | | |
|---|---|---|---|---|---|
| Example 2-1 | A | Example 2-184 | A | Example 2-358 | B |
| Example 2-2 | A | Example 2-188 | A | Example 2-365 | A |
| Example 2-4 | B | Example 2-192 | B | Example 2-375 | B |
| Example 2-13 | A | Example 2-193 | B | Example 2-376 | A |
| Example 2-17 | A | Example 2-194 | B | Example 2-380 | B |
| Example 2-18 | A | Example 2-197 | C | Example 2-393 | B |
| Example 2-21 | A | Example 2-205 | B | Example 2-394 | C |
| Example 2-22 | A | Example 2-213 | A | Example 2-397 | B |
| Example 2-23 | A | Example 2-214 | B | Example 2-399 | B |
| Example 2-28 | A | Example 2-216 | B | Example 2-405 | B |
| Example 2-31 | A | Example 2-217 | B | Example 2-406 | B |
| Example 2-36 | B | Example 2-218 | B | Example 2-409 | B |
| Example 2-40 | A | Example 2-221 | A | Example 2-420 | A |
| Example 2-44 | A | Example 2-224 | B | Example 2-427 | B |
| Example 2-48 | A | Example 2-231 | B | | |
| Example 2-50 | A | Example 2-235 | A | | |
| Example 2-51 | A | Example 2-236 | B | | |
| Example 2-52 | A | Example 2-238 | A | | |
| Example 2-70 | B | Example 2-252 | A | | |
| Example 2-66 | A | Example 2-265 | A | | |
| Example 2-74 | A | Example 2-267 | B | | |
| Example 2-76 | B | Example 2-270 | B | | |
| Example 2-77 | A | Example 2-272 | A | | |
| Example 2-85 | A | Example 2-275 | B | | |
| Example 2-87 | B | Example 2-291 | B | | |
| Example 2-89 | B | Example 2-292 | B | | |
| Example 2-91 | B | Example 2-302 | B | | |
| Example 2-96 | A | Example 2-305 | B | | |
| Example 2-98 | A | Example 2-306 | B | | |
| Example 2-100 | B | Example 2-312 | A | | |

TABLE 7-continued

| | | | |
|---|---|---|---|
| Example 2-113 | B | Example 2-313 | C |
| Example 2-114 | B | Example 2-316 | A |
| Example 2-116 | B | Example 2-317 | B |
| Example 2-121 | B | Example 2-318 | B |
| Example 2-123 | A | Example 2-319 | A |
| Example 2-124 | A | Example 2-320 | A |
| Example 2-126 | A | Example 2-321 | B |
| Example 2-127 | A | Example 2-322 | A |
| Example 2-128 | B | Example 2-323 | B |
| Example 2-135 | B | Example 2-324 | A |
| Example 2-136 | B | Example 2-325 | A |
| Example 2-142 | A | Example 2-330 | A |
| Example 2-158 | A | Example 2-331 | B |
| Example 2-162 | B | Example 2-332 | A |
| Example 2-163 | B | Example 2-338 | A |
| Example 2-166 | B | Example 2-343 | B |
| Example 2-169 | A | Example 2-346 | B |
| Example 2-170 | B | Example 2-348 | A |
| Example 2-174 | A | Example 2-349 | B |
| Example 2-178 | B | Example 2-352 | A |

Test Example 5

Ames Test

Four *Salmonella typhimurium* strains (TA100, TA1535, TA98, and TA1537) and one *Escherichia coli* strain (WP2uvrA) were used for the Ames test.

A solution containing a test compound (0.1 ml) was added to a test tube. 0.1 M Na-phosphate buffer was added to the tube for no metabolic activation (S9(−)) or an S-9 mix (Kikkoman) (0.5 ml) was added to the tube for metabolic activation (S9(+)). Further, a precultured bacterial cell suspension (0.1 ml) was added to the tube, followed by shaking at 37° C. for 20 minutes. Thereafter, 2-ml top agar (a solution prepared by mixing 5 mM L-histidine and a 5 mM D-biotin preparation solution at a volume ratio of 99:1 in a Bacto™ Agar aqueous solution for *salmonella* or a solution prepared by mixing a 5 mM L-tryptophan aqueous solution and a 5 mM D-biotin preparation solution at a volume ratio of 99:1 in a Bacto™ Agar aqueous solution for *Escherichia coli*) was added, followed by sufficient stirring. The content of the tube was poured onto a minimal glucose agar plate medium and cultured at 37° C. for 48 hours.

Colony count was performed using an auto colony counter. The average of colony counts for two plates was defined as the measurement value.

When the average number of revertant colonies per plate for a test compound was at least two times that for a negative control (DMSO solvent alone) and increased in a dose-dependent manner, such test compound was determined to yield a positive test result.

As a result, the following compounds were found to yield negative test results.

Example 2-1, Example 2-28, Example 2-48, Example 2-76, Example 2-77, Example 2-184, Example 2-188, Example 2-213, Example 2-220, Example 2-221, Example 2-235, Example 2-192, Example 2-302, Example 2-358

Test Example 6

Micronucleus Test Using Culture Cells

CHL cells (from Chinese hamster lung) were seeded on a 96 well plate (5000 cells/well) and cultured at 37° C. and 5% $CO_2$ for 24 hours. Thereafter, CHL cells were divided into a no metabolic activation (S9(−)) group and a metabolic activation (S9(+)) group. Phosphate buffered saline (hereinafter abbreviated as PBS(−)) or S-9 mix (Kikkoman) was added to each group. Test substances were separately added, followed by culture at 37° C. and 5% $CO_2$ for 6 hours. Then, each mixture was washed with PBS(−) and a culture solution (100 μL) was again added thereto, followed by culture at 37° C. and 5% $CO_2$ for 18 hours. Cells were fixed with ethanol, followed by removal of the supernatant. PBS(−) containing 2 μg/mL Hoechst 33342 (Invitrogen) and 2 μg/mL CellMask (Invitrogen) (100 μL) was added for staining at room temperature for 30 minutes. Cells were washed with PBS(−), PBS(−) (100 μL) was added thereto, and cells having micronuclei were detected using an IN Cell Analyzer (GE). At least 1000 cells were analyzed per condition for calculation of the frequency of micronuclei. In addition, a cell toxicity test using CellTiter-Glo (Promega) was conducted at the same time as the micronucleus test.

The mutagenicity of each test compound was assessed according to the criteria described below. Dunnett's statistical analysis was conducted for a statistical significance test.
Positive: Statistically significant increase and dose relationship
Negative: No significant increase
False positive: Significant increase and no dose relationship or Significant increase and strong cell toxicity (survival rate: 50% or less)

Compounds listed in Table 8 were tested according to the above standards. As a result, each compound was found to yield a negative test result.

TABLE 8

| Example 2-1 | Example 2-154 | Example 2-322 |
| Example 2-2 | Example 2-156 | Example 2-325 |
| Example 2-4 | Example 2-158 | Example 2-331 |
| Example 2-13 | Example 2-162 | Example 2-332 |
| Example 2-21 | Example 2-163 | Example 2-338 |
| Example 2-22 | Example 2-169 | Example 2-346 |
| Example 2-23 | Example 2-170 | Example 2-348 |
| Example 2-24 | Example 2-171 | Example 2-349 |
| Example 2-25 | Example 2-172 | Example 2-352 |
| Example 2-30 | Example 2-174 | Example 2-358 |
| Example 2-31 | Example 2-184 | Example 2-370 |
| Example 2-41 | Example 2-188 | Example 2-373 |
| Example 2-50 | Example 2-192 | Example 2-374 |
| Example 2-52 | Example 2-194 | Example 2-376 |
| Example 2-59 | Example 2-197 | Example 2-380 |
| Example 2-63 | Exampld 2-208 | Example 2-393 |
| Example 2-65 | Example 2-214 | Example 2-394 |
| Example 2-76 | Example 2-216 | Example 2-397 |
| Example 2-77 | Example 2-217 | Example 2-434 |
| Example 2-78 | Example 2-218 | Example 2-435 |
| Example 2-83 | Example 2-223 | Example 2-436 |
| Example 2-85 | Example 2-224 | Example 2-439 |
| Example 2-87 | Example 2-235 | Example 2-441 |
| Example 2-89 | Example 2-236 | Example 2-444 |
| Example 2-91 | Example 2-238 | Example 2-448 |
| Example 2-96 | Example 2-252 | Example 2-473 |
| Example 2-98 | Example 2-265 | Example 2-483 |
| Example 2-100 | Example 2-268 | |
| Example 2-101 | Example 2-270 | |
| Example 2-113 | Example 2-272 | |
| Example 2-114 | Example 2-275 | |
| Example 2-116 | Example 2-291 | |
| Example 2-121 | Example 2-292 | |
| Example 2-123 | Example 2-305 | |
| Example 2-124 | Example 2-306 | |
| Example 2-126 | Example 2-312 | |
| Example 2-127 | Example 2-316 | |
| Example 2-135 | Example 2-318 | |
| Example 2-136 | Example 2-319 | |
| Example 2-142 | Example 2-320 | |

Test Example 7

Rat-Type-II-Collagen-Induced Arthritis

The compounds were tested to examine effects upon rat type II collagen arthritis. Equivalent volumes of 0.05 mol/L acetic acid in which a 3 mg/mL bovine type II collagen solution (Collagen Gijutsu Kenshu-Kai) had been dissolved and Freund's incomplete adjuvant (Wako Pure Chemical Industries, Ltd.) were mixed to prepare an emulsion. A portion of the emulsion (0.5 ml) was intradermally injected into the tail bases of 6- to 8-week-old female Lewis rats (Charles River Laboratories Japan, Inc.) (Day 0). Each rat was subjected to the same treatment on Day 7 after the initial inoculation so as to induce arthritis. Each test compound was orally administered from Day 7 to Day 20 once daily. At a given time during the period from Day 7 to Day 21, the rat hindlimb volume was determined using a plethysmometer (UGO BASILE), and the result was designated as an arthritis index. The following compound group significantly inhibited hindlimb swelling on Day 20 compared with the control group in the case of oral administration at 10 mg/kg/day (Student's t-test): Example 2-1, Example 2-76, and Example 2-184.

Test Example 8

Mouse Thrombocytopenia Model

Test compounds were tested to examine effects upon mouse thrombocytopenia. Each test compound (50 mg/kg) was administered to 5- to 7-week-old female BALB/c mice (Charles River Laboratories Japan, Inc.). One hour thereafter, an anti-mouse CD41 (Integrin can) antibody (SCB) (1 μg (200 μl)) was intravenously administered to each mouse so as to induce thrombocytopenia. Four hours after administration of the anti-CD41 antibody, blood sampling from the postcava was performed. The platelet count was determined using an automated hematology analyzer.

As a result, the groups to which the following compounds had been administered showed the improvement of platelet count (50% or more improvement) compared with the control group:
Example 2-1, Example 2-2, Example 2-18, Example 2-28, Example 2-48, Example 2-76, Example 2-77, Example 2-87, Example 2-89, Example 2-91, Example 2-100, Example 2-123, Example 2-142, Example 2-174, Example 2-184, Example 2-188, Example 2-192, Example 2-193, Example 2-213, Example 2-251, Example 2-252, Example 2-265, Example 2-267, Example 2-302, Example 2-326, Example 2-328, Example 2-330, Example 2-331, Example 2-348, Example 2-352, Example 2-358, Example 2-415, Example 2-456, Example 2-473, and Example 2-483.

The invention claimed is:
1. A nicotinamide derivative represented by the following formula (I) or a salt thereof:

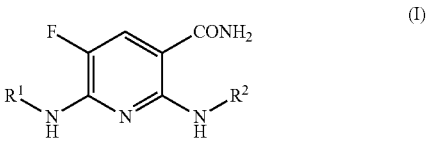

(I)

wherein
$R^1$ is a substituent represented by the following formula (II-1), (III-1), or (IV-1):

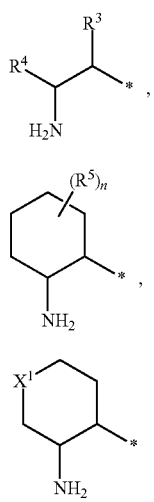

(II-1)

(III-1)

(IV-1)

wherein
$R^3$ is a hydrogen atom, or a $C_{1-6}$ alkyl, $C_{3-8}$ cycloalkyl, phenyl, pyridyl or thienyl group, each of which optionally has at least one substituent selected from a substituent group $\alpha_{1-1}$, substituent group $\alpha_{1-1}$: a halogen atom and $C_{1-6}$ alkyl, $C_{3-8}$ cycloalkyl, $C_{1-6}$ alkoxy, $C_{1-6}$ alkylthio, phenyl, and pyrazolyl groups, each of which optionally has at least one halogen atom:

$R^4$ represents a hydrogen atom, $C_{1-6}$ alkyl group, or $C_{3-8}$ cycloalkyl group, $R^5$ represents a hydroxy group, a halogen atom, or a $C_{1-6}$ alkyl or $C_{1-6}$ alkoxy group, each of which optionally has at least one phenyl group, n represents an integer of 0-2, when n is 2, $R^5$ may be the same or different, and two $R^5$s may, together with a carbon atom to which they bind, form a $C_{3-8}$ cycloalkane ring, $X^1$ represents an oxygen atom or —N($R^6$)— wherein $R^6$ represents a hydrogen atom, formyl group, C2-C12 alkanoyl group or aroyl group, and "*" represents a binding site, and $R^2$ is a substituent represented by the following formula (V-1), a substituent represented by the following formula (VI-1) or (VI-2), or a substituent represented by the following formula (VII-1):

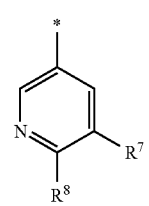

(V-1)

wherein $R^7$ and $R^8$, which may be the same or different, are each a substituent selected from a substituent group $\alpha_{3-2}$, substituent group $\alpha_{3-2}$: a halogen atom and $C_{1-6}$ alkyl, $C_{3-8}$ cycloalkyl, $C_{1-6}$ alkoxy, (di)$C_{1-6}$ alkylamino, pyrazolyl, triazolyl, and morpholinyl groups, each of which optionally has at least one substituent selected from a substituent group $\beta_{3-2}$;

substituent group $\beta_{3-2}$: a halogen atom and a $C_{1-6}$ alkyl group;

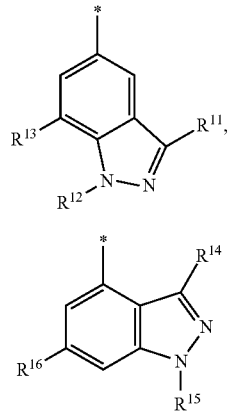

(VI-1)

(VI-2)

wherein $R^{11}$ is a substituent selected from a substituent group $\alpha_{4-2}$, $R^{12}$, $R^{13}$, $R^{14}$ and $R^{16}$, which may be the same or different, are each a hydrogen atom or a substituent selected from a substituent group $\alpha_{4-2}$, and $R^{15}$ is a substituent selected from a substituent group $\alpha_{4-2-1}$, substituent group $\alpha_{4-2}$: a halogen atom and $C_{1-6}$ alkyl, $C_{1-6}$ alkoxy, and (di)$C_{1-6}$ alkylamino groups, each of which optionally has at least one substituent selected from a substituent group $\beta_{4-2}$;

substituent group $\alpha_{4-2-1}$: a halogen atom, $C_{1-6}$ alkoxy which optionally has at least one substituent selected from a substituent group $\beta_{4-2}$ and $C_{1-6}$ alkyl which has at least one substituent selected from a substituent group $\beta_{4-2}$;

substituent group $\beta_{4-2}$: a halogen atom and a $C_{1-6}$ alkoxy group;

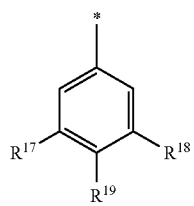

(VII-1)

wherein $R^{17}$, $R^{18}$, and $R^{19}$, which may be the same or different, are each a hydrogen atom or a substituent selected from a substituent group $\alpha_{5-2}$, substituent group $\alpha_{5-2}$: a halogen atom, a $C_{1-6}$ alkoxy group, and $C_{1-6}$ alkyl and triazolyl groups each of which optionally has at least one halogen atom, provided that, when $R^2$ is a substituent represented by the formula (VII-1), $R^1$ is a substituent represented by the formula (II-1):

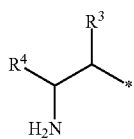
(II-1)

wherein R³ is a $C_{1-6}$ alkyl, $C_{3-8}$ cycloalkyl, phenyl, pyridyl or thienyl group, each of which optionally has at least one substituent selected from a substituent group $\alpha_{1-1}$, substituent group $\alpha_{1-1}$: a halogen atom and $C_{1-6}$ alkyl, $C_{3-8}$ cycloalkyl, $C_{1-6}$ alkoxy, $C_{1-6}$ alkylthio, phenyl, and pyrazolyl groups, each of which optionally has at least one halogen atom;

R⁴ represents $C_{1-6}$ alkyl group, or $C_{3-8}$ cycloalkyl group.

2. The nicotinamide derivative or a salt thereof according to claim 1, wherein R¹ is a substituent represented by the following formula (II-2), (III-2), or (IV-2):

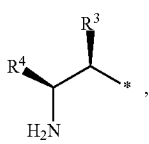
(II-2)

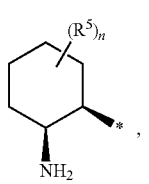
(III-2)

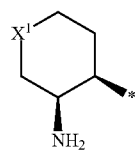
(IV-2)

wherein R³, R⁴, R⁵, n, and X¹ have the same definitions as those described in claim 1.

3. The nicotinamide derivative or a salt thereof according to claim 1, wherein R⁴ represents a hydrogen atom or a $C_{1-3}$ alkyl group.

4. The nicotinamide derivative or a salt thereof according to claim 1, wherein n is an integer of 0.

5. The nicotinamide derivative or a salt thereof according to claim 1, wherein X¹ represents an oxygen atom.

6. The nicotinamide derivative or a salt thereof according to claim 1, wherein R² is a substituent represented by formula (V-1)

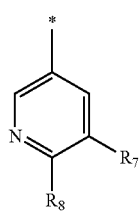
(VI-1)

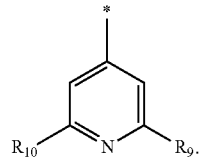
(VI-2)

7. The nicotinamide derivative or a salt thereof according to claim 1, wherein R² is a substituent represented by formula (VI-1) or (VI-2).

8. The nicotinamide derivative or a salt thereof according to claim 1, wherein R² is a substituent represented by formula (VII-1).

9. The nicotinamide derivative or a salt thereof according to claim 1, wherein the nicotinamide derivative is represented by the following formula (I-1)

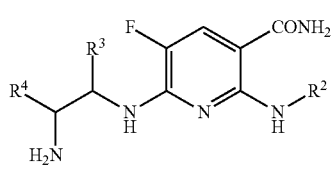
(I-1)

wherein R², R³, and R⁴ have the same definitions as R², R³, and R⁴ described in claim 1.

10. The nicotinamide derivative or a salt thereof according to claim 1, wherein the nicotinamide derivative is represented by the following formula (I-3):

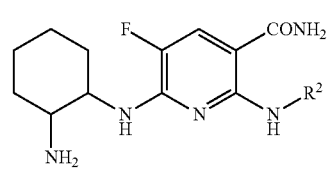
(I-3)

wherein R² has the same definition as R² described in claim 1.

11. The nicotinamide derivative or a salt thereof according to claim 1, wherein the nicotinamide derivative is represented by the following formula (I-5):

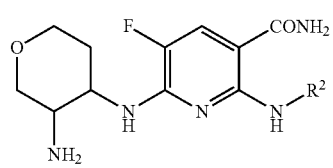
(I-5)

wherein R² has the same definition as R² described in claim 1.

12. A pharmaceutical composition, comprising the nicotinamide derivative or a salt thereof according to claim 1; and a pharmaceutically acceptable carrier.

13. A method for treating a disease, comprising: administering the pharmaceutical composition according to claim 12 to a human in need thereof, wherein the disease is selected from the group consisting of rheumatoid arthritis and idiopathic thrombocytopenic purpurea.

14. A compound which is selected from a group consisting of:

- 6-(((1R,2S)-2-aminocyclohexyl)amino)-2-((3-(dimethylamino)-1-methyl-1H-indazol-5-yl)amino)-5-fluoronicotinamide;
- 6-(((1R,2S)-2-amino-1-cyclobutylpropyl)amino)-5-fluoro-2-((1-methyl-1H-indazol-6-yl)amino)nicotinamide;
- 6-(((2R,3S)-3-aminopentan-2-yl)amino)-2-((1-ethyl-1H-indazol-4-yl)amino)-5-fluoronicotinamide;
- 6-(((3R,4S)-4-aminohexan-3-yl)amino)-2-((1-ethyl-1H-indazol-4-yl)amino)-5-fluoronicotinamide;
- 6-(((2S,3R)-2-amino-5-methylhexan-3-yl)amino)-2-((1-ethyl-1H-indazol-6-yl)amino)-5-fluoronicotinamide;
- 6-(((1R,2S)-2-amino-1-cyclobutylpropyl)amino)-5-fluoro-2-((6-methoxy-5-(2H-1,2,3-triazol-2-yl)pyridin-3-yl)amino)nicotinamide;
- 6-(((2S,3R)-2-amino-5-methylhexan-3-yl)amino)-5-fluoro-2-((1-methyl-1H-indazol-4-yl)amino)nicotinamide;
- 6-(((2S,3S)-3-amino-1-methoxybutan-2-yl)amino)-2-((3-(dimethylamino)-1-methyl-1H-indazol-5-yl)amino)-5-fluoronicotinamide;
- 6-(((2S,3S)-3-amino-1-methoxybutan-2-yl)amino)-5-fluoro-2-((3-methoxy-1-methyl-1H-indazol-5-yl)amino)nicotinamide;
- 6-4(1R,2S)-2-aminocyclohexyl)amino)-5-fluoro-2-((3-methoxy-1-(2-methoxyethyl)-1H-indazol-5-yl)amino)nicotinamide;
- (R)-6-((1-amino-4-methylpentan-2-yl)amino)-5-fluoro-2-((3-methoxy-1-(2-methoxyethyl)-1H-indazol-5-yl)amino)nicotinamide;
- 6-(((2S,3R)-2-aminopentan-3-yl)amino)-5-fluoro-2-((3-methoxy-1-(2-methoxyethyl)-1H-indazol-5-yl)amino)nicotinamide;
- 6-(((2S,3R)-2-aminohexan-3-yl)amino)-5-fluoro-2-((3-methoxy-1-(2-methoxyethyl)-1H-indazol-5-yl)amino)nicotinamide;
- 6-(((2S,3R)-2-amino-5-methylhexan-3-yl)amino)-5-fluoro-2-((3-methoxy-1-(2-methoxyethyl)-1H-indazol-5-yl)amino)nicotinamide;
- 6-(((lR,2S)-2-aminocyclohexyl)amino)-2-((3-(dimethylamino)-2-methyl-2H-indazol-5-yl)amino)-5-fluoronicotinamide;
- (R)-6-((1-amino-4-methylpentan-2-yl)amino)-5-fluoro-2-((1-(2-methoxyethyl)-3-methyl-1H-indazol-5-yl)amino)nicotinamide;
- 6-(((2S,3R)-2-aminopentan-3-yl)amino)-5-fluoro-2-((1-(2-methoxyethyl)-3-methyl-1H-indazol-5-yl)amino)nicotinamide;
- 6-(((2S,3R)-2-aminohexan-3-yl)amino)-5-fluoro-2-((1-(2-methoxyethyl)-3-methyl-1H-indazol-5-yl)amino)nicotinamide;
- 6-(((1R,2S)-2-amino-1-cyclopropylpropyl)amino)-5-fluoro-2-((1-(2-methoxyethyl)-3-methyl-1H-indazol-5-yl)amino)nicotinamide;
- 6-(((2S,3R)-2-amino-5-methylhexan-3-yl)amino)-5-fluoro-2-((1-(2-methoxyethyl)-3-methyl-1H-indazol-5-yl)amino)nicotinamide;
- (R)-6-((1-amino-4-methylpentan-2-yl)amino)-2-((1-(2,2-difluoroethyl)-3-methyl-1H-indazol-5-yl)amino)-5-fluoronicotinamide;
- 6-(((2S,3R)-2-aminohexan-3-yl)amino)-2-((1-(2,2-difluoroethyl)-3-methyl-1H-indazol-5-yl)amino)-5-fluoronicotinamide;
- 6-(((2S,3S)-3-amino-1-methoxybutan-2-yl)amino)-2-((1-(2,2-difluoroethyl)-3-methyl-1H-indazol-5-yl)amino)-5-fluoronicotinamide;
- 6-(((2S,3R)-2-aminopentan-3-yl)amino)-2-((7-chloro-1-methyl-1H-indazol-5-yl)amino)-5-fluoronicotinamide;
- 6-(((2S,3S)-3-amino-1-methoxybutan-2-yl)amino)-2-((7-chloro-1-methyl-1H-indazol-5-yl)amino)-5-fluoronicotinamide;
- 6-(((2S,3R)-2-amino-5-methylhexan-3-yl)amino)-2-((3-(dimethylamino)-2-methyl-2H-indazol-5-yl)amino)-5-fluoronicotinamide;
- 6-(((1R,2S)-2-aminocyclohexyl)amino)-5-fluoro-2-((7-fluoro-3-methoxy-1-methyl-1H-indazol-5-yl)amino)nicotinamide;
- (R)-6-((1-amino-4-methylpentan-2-yl)amino)-5-fluoro-2-((7-fluoro-3-methoxy-1-methyl-1H-indazol-5-yl)amino)nicotinamide;
- 6-(((2S,3R)-2-aminopentan-3-yl)amino)-5-fluoro-2-((7-fluoro-3-methoxy-1-methyl-1H-indazol-5-yl)amino)nicotinamide;
- 6-(((2S,3R)-2-aminohexan-3-yl)amino)-5-fluoro-2-((7-fluoro-3-methoxy-1-methyl-1H-indazol-5-yl)amino)nicotinamide;
- 6-(((1R,2S)-2-amino-1-cyclopropylpropyl)amino)-5-fluoro-2-((7-fluoro-3-methoxy-1-methyl-1H-indazol-5-yl)amino)nicotinamide;
- 6-(((2S,3R)-2-aminoheptan-3-yl)amino)-5-fluoro-2-((7-fluoro-3-methoxy-1-methyl-1H-indazol-5-yl)amino)nicotinamide;
- 6-(((2S,3R)-2-amino-5-methylhexan-3-yl)amino)-5-fluoro-2-((7-fluoro-3-methoxy-1-methyl-1H-indazol-5-yl)amino)nicotinamide;
- 6-(((2R,3S)-3-amino-1-cyclopropylbutan-2-yl)amino)-5-fluoro-2-((7-fluoro-3-methoxy-1-methyl-1H-indazol-5-yl)amino)nicotinamide;
- 6-(((1R,2S)-2-amino-1-cyclobutylpropyl)amino)-5-fluoro-2-((7-fluoro-3-methoxy-1-methyl-1H-indazol-5-yl)amino)nicotinamide;
- 6-(((2S,3S)-3-amino-1-methoxybutan-2-yl)amino)-5-fluoro-2-((7-fluoro-3-methoxy-1-methyl-1H-indazol-5-yl)amino)nicotinamide;
- 6-(((3R,4S)-4-aminohexan-3-yl)amino)-5-fluoro-2-((7-fluoro-3-methoxy-1-methyl-1H-indazol-5-yl)amino)nicotinamide;
- 6-(((1R,2S)-2-aminocyclohexyl)amino)-2-((3-(difluoromethoxy)-1-methyl-1H-indazol-5-yl)amino)-5-fluoronicotinamide;
- 6-(((2S,3R)-2-aminopentan-3-yl)amino)-2-((5,6-dimethylpyridin-3-yl)amino)-5-fluoronicotinamide;
- 6-(((2S,3R)-2-aminopentan-3-yl)amino)-2-((3-(difluoromethoxy)-1-methyl-1H-indazol-5-yl)amino)-5-fluoronicotinamide;
- 6-(((1R,2S)-2-amino-1-cyclopropylpropyl)amino)-2-((3-(difluoromethoxy)-1-methyl-1H-indazol-5-yl)amino)-5-fluoronicotinamide;
- 6-(((2S,3R)-2-amino-5-methylhexan-3-yl)amino)-2-((3-(difluoromethoxy)-1-methyl-1H-indazol-5-yl)amino)-5-fluoronicotinamide;
- 6-(((2S,3S)-3-amino-1-methoxybutan-2-yl)amino)-2-((3-(difluoromethoxy)-1-methyl-1H-indazol-5-yl)amino)-5-fluoronicotinamide;
- 6-(((lR,2S)-2-aminocyclohexyl)amino)-2-((3-(difluoromethoxy)-1-(2-methoxyethyl)-1H-indazol-5-yl)amino)-5-fluoronicotinamide;
- 6-(((2S,3R)-2-aminopentan-3-yl)amino)-2-((3-(difluoromethoxy)-1-(2-methoxyethyl)-1H-indazol-5-yl)amino)-5-fluoronicotinamide;

6-(((1R,2S)-2-amino-1-cyclopropylpropyl)amino)-2-((3-(difluoromethoxy)-1-(2-methoxyethyl)-1H-indazol-5-yl)amino)-5-fluoronicotinamide;

6-(((2S,3R)-2-amino-5-methylhexan-3-yl)amino)-2-((3-(difluoromethoxy)-1-(2-methoxyethyl)-1H-indazol-5-yl)amino)-5-fluoronicotinamide;

6-(((2S,3S)-3-amino-1-methoxybutan-2-yl)amino)-2-((3-(difluoromethoxy)-1-(2-methoxyethyl)-1H-indazol-5-yl)amino)-5-fluoronicotinamide;

6-(((2S,3R)-2-amino-5-methylhexan-3-yl)amino)-2-((5,6-dimethylpyridin-3-yl)amino)-5-fluoronicotinamide;

6-(((2S,3S)-3-amino-1-ethoxybutan-2-yl)amino)-2-((1-ethyl-1H-indazol-5-yl)amino)-5-fluoronicotinamide;

6-(((1R,2S)-2-aminocyclohexyl)amino)-2-((3-(dimethylamino)-7-fluoro-1-methyl-1H-indazol-5-yl)amino)-5-fluoronicotinamid;

(R)-6-((1-amino-4-methylpentan-2-yl)amino)-2-((3-(dimethylamino)-7-fluoro-1-methyl-1H-indazol-5-yl)amino)-5-fluoronicotinamide;

6-(((2S,3R)-2-aminopentan-3-yl)amino)-2-((3-(dimethylamino)-7-fluoro-1-methyl-1H-indazol-5-yl)amino)-5-fluoronicotinamide;

6-(((2S,3R)-2-aminohexan-3-yl)amino)-2-((3-(dimethylamino)-7-fluoro-1-methyl-1H-indazol-5-yl)amino)-5-fluoronicotinamide;

6-(((1R,2S)-2-amino-1-cyclopropylpropyl)amino)-2-((3-(dimethylamino)-7-fluoro-1-methyl-1H-indazol-5-yl)amino)-5-fluoronicotinamide;

6-(((2S,3R)-2-aminoheptan-3-yl)amino)-2-((3-(dimethylamino)-7-fluoro-1-methyl-1H-indazol-5-yl)amino)-5-fluoronicotinamide;

6-(((2S,3R)-2-aminoheptan-3-yl)amino)-2-((5,6-dimethylpyridin-3-yl)amino)-5-fluoronicotinamide;

6-(((2S,3R)-2-amino-5-methylhexan-3-yl)amino)-2-((3-(dimethylamino)-7-fluoro-1-methyl-1H-indazol-5-yl)amino)-5-fluoronicotinamide;

6-(((1R,2S)-2-amino-1-cyclobutylpropyl)amino)-2-((3-(dimethylamino)-7-fluoro-1-methyl-1H-indazol-5-yl)amino)-5-fluoronicotinamide;

6-(((2R,3S)-3-aminopentan-2-yl)amino)-2-((3-(dimethylamino)-7-fluoro-1-methyl-1H-indazol-5-yl)amino)-5-fluoronicotinamide;

6-(((2S,3S)-3-amino-1-methoxybutan-2-yl)amino)-2-((1,3-dimethyl-1H-indazol-5-yl)amino)-5-fluoronicotinamide;

6-(((2S,3R)-2-amino-5-methylhexan-3-yl)amino)-2-((6-ethoxy-5-(1H-1,2,3-triazol-1-yl)pyridin-3-yl)amino)-5-fluoronicotinamide;

6-(((2R,3S)-3-amino-1-cyclopropylbutan-2-yl)amino)-2-((3-(dimethylamino)-1-methyl-1H-indazol-5-yl)amino)-5-fluoronicotinamide;

6-4(1R,2S)-2-aminocyclohexyl)amino)-2-((1-(2,2-difluoroethyl)-1H-indazol-4-yl)amino)-5-fluoronicotinamide;

6-(((2S,3R)-2-aminohexan-3-yl)amino)-2-((6-ethoxy-5-(1H-1,2,3-triazol-1-yl)pyridin-3-yl)amino)-5-fluoronicotinamide;

6-(((3R,4R)-3-aminotetrahydro-2H-pyran-4-yl)amino)-2-((1,3-dimethyl-1H-indazol-5-yl)amino)-5-fluoronicotinamide;

6-(((3R,4R)-3-aminotetrahydro-2H-pyran-4-yl)amino)-5-fluoro-2-((3-fluoro-1-methyl-1H-indazol-5-yl)amino)nicotinamide;

6-(((2R,3S)-3-amino-1-cyclopropylbutan-2-yl)amino)-2-((1-(2,2-difluoroethyl)-1H-indazol-4-yl)amino)-5-fluoronicotinamide;

6-(((3R,4R)-3-aminotetrahydro-2H-pyran-4-yl)amino)-5-fluoro-2-((3-methoxy-1-methyl-1H-indazol-5-yl)amino)nicotinamide;

6-(((3R,4R)-3-aminotetrahydro-2H-pyran-4-yl)amino)-5-fluoro-2-((7-fluoro-3-methoxy-1-methyl-1H-indazol-5-yl)amino)nicotinamide;

6-(((3R,4R)-3-aminotetrahydro-2H-pyran-4-yl)amino)-2-((3-(dimethylamino)-1-methyl-1H-indazol-5-yl)amino)-5-fluoronicotinamide;

6-(((3R,4R)-3-aminotetrahydro-2H-pyran-4-yl)amino)-2-((3-(dimethylamino)-7-fluoro-1-methyl-1H-indazol-5-yl)amino)-5-fluoronicotinamide;

6-(((3R,4R)-3-aminotetrahydro-2H-pyran-4-yl)amino)-5-fluoro-2-((6-methyl-5-(2H-1,2,3-triazol-2-yl)pyridin-3-yl)amino)nicotinamide;

6-(((2S,3R)-2-amino-5-methylhexan-3-yl)amino)-2-((1-(2,2-difluoroethyl)-1H-indazol-4-yl)amino)-5-fluoronicotinamide;

6-(((1R,2S)-2-amino-1-cyclobutylpropyl)amino)-5-fluoro-2-((5-fluoro-6-methylpyridin-3-yl)amino)nicotinamide;

6-(((2S,3R)-2-aminohexan-3-yl)amino)-5-fluoro-2-((5-fluoro-6-methylpyridin-3-yl)amino)nicotinamide;

6-(((2S,3R)-2-amino-5-methylhexan-3-yl)amino)-5-fluoro-2-((5-fluoro-6-methylpyridin-3-yl)amino)nicotinamide;

6-(((2S,3R)-2-aminopentan-3-yl)amino)-2-((1-(2,2-difluoroethyl)-1H-indazol-4-yl)amino)-5-fluoronicotinamide;

6-(((2S,3R)-2-amino-5-methylhexan-3-yl)amino)-5-fluoro-2-((3-fluoro-2-morpholinopyridin-4-yl)amino)nicotinamide;

2-((5-(1H-pyrazol-1-yl)pyridin-3-yl)amino)-6-(((1R,2S)-2-amino-1-cyclobutylpropyl)amino)-5-fluoronicotinamide;

(R)-6-((1-amino-4-methylpentan-2-yl)amino)-2-((1,3-dimethyl-1H-pyrazolo[3,4-b]pyridin-5-yl)amino)-5-fluoronicotinamide;

6-(((2S,3R)-2-amino-5-methylhexan-3-yl)amino)-2-((1,3-dimethyl-1H-pyrazolo[3,4-b]pyridin-5-yl)amino)-5-fluoronicotinamide;

6-(((1R,2S)-2-aminocyclohexyl)amino)-5-fluoro-2-((3-methoxy-1-methyl-1H-pyrazolo[3,4-b]pyridin-5-yl)amino)nicotinamide;

6-(((1R,2S)-2-amino-1-cyclobutylpropyl)amino)-5-fluoro-2-(m-tolylamino)nicotinamide (R)-6-((1-amino-4-methylpentan-2-yl)amino)-5-fluoro-2-((3-methoxy-1-methyl-1H-pyrazolo[3,4-b]pyridin-5-yl)amino)nicotinamide;

6-(((2S,3R)-2-aminohexan-3-yl)amino)-5-fluoro-2-((3-methoxy-1-methyl-1H-pyrazolo[3,4-b]pyridin-5-yl)amino)nicotinamide;

6-(((1R,2S)-2-amino-1-cyclopropylpropyl)amino)-5-fluoro-2-((3-methoxy-1-methyl-1H-pyrazolo[3,4-b]pyridin-5-yl)amino)nicotinamide;

6-(((2S,3R)-2-aminoheptan-3-yl)amino)-5-fluoro-2-((3-methoxy-1-methyl-1H-pyrazolo[3,4-b]pyridin-5-yl)amino)nicotinamide;

6-(((2S,3R)-2-amino-5-methylhexan-3-yl)amino)-5-fluoro-2-((3-methoxy-1-methyl-1H-pyrazolo[3,4-b]pyridin-5-yl)amino)nicotinamide;

6-(((1R,2S)-2-amino-1-cyclobutylpropyl)amino)-2-((3,5-dimethylphenyl)amino)-5-fluoronicotinamide;

6-(((1R,2S)-2-amino-1-cyclopropylpropyl)amino)-5-fluoro-2-1-(2-methoxyethyl)-1H-indazol-5-yl)amino)nicotinamide;

6-(((3R,4S)-4-aminohexan-3-yl)amino)-5-fluoro-2-((1-(2-methoxyethyl)-1H-indazol-5-yl)amino)nicotinamide;
6-(((2S,3S)-3-amino-1-methoxybutan-2-yl)amino)-2-((3,5-dimethoxyphenyl)amino)-5-fluoronicotinamide;
6-(((1R,2S)-2-amino-1-(4-fluorophenyl)propyl)amino)-2-((3,5-dimethoxyphenyl)amino)-5-fluoronicotinamide;
6-(((1R,2S)-2-amino-1-cyclobutylpropyl)amino)-5-fluoro-2-((3-methoxyphenyl)amino)nicotinamide;
6-(((1R,2S)-2-aminocyclohexyl)amino)-5-fluoro-2-((5-fluoro-6-(methylamino)pyridin-3-yl)amino)nicotinamide;
6-(((1R,2S)-2-amino-1-cyclobutylpropyl)amino)-2-((3,5-dimethoxyphenyl)amino)-5-fluoronicotinamide;
6-(((2S,3R)-2-aminohexan-3-yl)amino)-2-((3-(dimethylamino)-1-methyl-1H-pyrazolo[3,4-b]pyridin-5-yl)amino)-5-fluoronicotinamide;
6-(((1R,2S)-2-amino-1-cyclobutylpropyl)amino)-2-((3,4-dimethoxyphenyl)amino)-5-fluoronicotinamide;
6-(((2S,3R)-2-amino-5-methylhexan-3-yl)amino)-2-((3-(dimethylamino)-1-methyl-1H-pyrazolo[3,4-b]pyridin-5-yl)amino)-5-fluoronicotinamide;
6-(((1R,2S)-2-amino-1-cyclobutylpropyl)amino)-2-((3-(dimethylamino)-1-methyl-1H-pyrazolo[3,4-b]pyridin-5-yl)amino)-5-fluoronicotinamide;
6-(((2S,3R)-2-amino-5-methylhexan-3-yl)amino)-2-((3-(dimethylamino)-1-methyl-1H-indazol-5-yl)amino)-5-fluoronicotinamide;
6-(((1S,2R)-1-amino-1-cyclopropylpropan-2-yl)amino)-2-((1-(2,2-difluoroethyl)-3-methyl-1H-indazol-5-yl)amino)-5-fluoronicotinamide;
6-(((1R,2S)-2-aminocyclohexyl)amino)-5-fluoro-2(1-(2-methoxyethyl)-1H-indazol-4-yl)amino)nicotinamide;
(R)-6-((1-amino-4-methylpentan-2-yl)amino)-5-fluoro-2-((1-(2-methoxyethyl)-1H-indazol-4-yl)amino)nicotinamide;
6-(((2S,3R)-2-aminopentan-3-yl)amino)-5-fluoro-2-((1-(2-methoxyethyl)-1H-indazol-4-yl)amino)nicotinamide;
6-(((2S,3R)-2-aminohexan-3-yl)amino)-5-fluoro-2-((1-(2-methoxyethyl)-1H-indazol-4-yl)amino)nicotinamide;
6-(((1R,2S)-2-amino-1-cyclopropylpropyl)amino)-5-fluoro-2-((1-(2-methoxyethyl)-1H-indazol-4-yl)amino)nicotinamide;
6-(((2S,3R)-2-aminoheptan-3-yl)amino)-5-fluoro-2-((1-(2-methoxyethyl)-1H-indazol-4-yl)amino)nicotinamide;
6-(((2S,3R)-2-amino-5-methylhexan-3-yl)amino)-5-fluoro-2-((1-(2-methoxyethyl)-1H-indazol-4-yl)amino)nicotinamide;
6-(((2S,3R)-2-aminopentan-3-yl)amino)-5-fluoro-2-((6-methyl-5-(2H-1,2,3-triazol-2-yl)pyridin-3-yl)amino)nicotinamide;
6-(((2R,3S)-3-aminopentan-2-yl)amino)-5-fluoro-2-((1-(2-methoxyethyl)-1H-indazol-4-yl)amino)nicotinamide;
6-(((1R,2S)-2-amino-1-phenylpropyl)amino)-5-fluoro-2-(quinolin-6-ylamino)nicotinamide;
6-(((1R,2S)-2-amino-1-phenylpropyl)amino)-5-fluoro-2-((6-methyl-5-(2H-1,2,3-triazol-2-yl)pyridin-3-yl)amino)nicotinamide;
6-(((1R,2S)-2-amino-1-phenylpropyl)amino)-5-fluoro-2-((5-fluoro-6-morpholinopyridin-3-yl)amino)nicotinamide;

6-(((1R,2S)-2-aminocyclohexyl)amino)-2-((1-ethyl-1H-pyrazolo[3,4-c]pyridin-4-yl)amino)-5-fluoronicotinamide;
6-(((3R,4R)-3-aminotetrahydro-2H-pyran-4-yl)amino)-2-((1-ethyl-1H-pyrazolo[3,4-c]pyridin-4-yl)amino)-5-fluoronicotinamide;
6-(((2S,3R)-2-aminopentan-3-yl)amino)-2-(1-ethyl-1H-pyrazolo[3,4-c]pyridin-4-yl)amino)-5-fluoronicotinamide;
6-(((2S,3R)-2-aminohexan-3-yl)amino)-2-((1-ethyl-1H-pyrazolo[3,4-c]pyridin-4-yl)amino)-5-fluoronicotinamide;
6-(((1R,2S)-2-amino-1-(4-fluorophenyl)propyl)amino)-5-fluoro-2-((6-methyl-5-(2H-1,2,3-triazol-2-yl)pyridin-3-yl)amino)nicotinamide;
6-(((1R,2S)-2-amino-1-cyclopropylpropyl)amino)-2-((1-ethyl-1H-pyrazolo[3,4-c]pyridin-4-yl)amino)-5-fluoronicotinamide;
6-(((2S,3R)-2-aminoheptan-3-yl)amino)-2-(1-ethyl-1H-pyrazolo[3,4-c]pyridin-4-yl)amino)-5-fluoronicotinamide;
6-(((2S,3R)-2-amino-5-methylhexan-3-yl)amino)-2-((1-ethyl-1H-pyrazolo[3,4-c]pyridin-4-yl)amino)-5-fluoronicotinamide;
6-(((2R,3S)-3-aminopentan-2-yl)amino)-2-((1-ethyl-1H-pyrazolo[3,4-c]pyridin-4-yl)amino)-5-fluoronicotinamide;
6-(((3R,4R)-3-aminotetrahydro-2H-pyran-4-yl)amino)-2-((1-ethyl-1H-indazol-5-yl)amino)-5-fluoronicotinamide;
6-(((3R,4R)-3-aminotetrahydro-2H-pyran-4-yl)amino)-5-fluoro-2-((1-(2-methoxyethyl)-3-methyl-1H-indazol-5-yl)amino)nicotinamide;
6-(((3R,4R)-3-aminotetrahydro-2H-pyran-4-yl)amino)-2-((1-(2,2-difluoroethyl)-3-methyl-1H-indazol-5-yl)amino)-5-fluoronicotinamide;
6-(((3R,4R)-3-aminotetrahydro-2H-pyran-4-yl)amino)-5-fluoro-2-((3-methoxy-1-(2-methoxyethyl)-1H-indazol-5-yl)amino)nicotinamide;
6-(((3R,4R)-3-aminotetrahydro-2H-pyran-4-yl)amino)-2-((1-ethyl-1H-indazol-4-yl)amino)-5-fluoronicotinamide;
6-(((3R,4R)-3-aminotetrahydro-2H-pyran-4-yl)amino)-5-fluoro-2-((1-(2-methoxyethyl)-1H-indazol-4-yl)amino)nicotinamide;
6-(((3R,4R)-3-aminotetrahydro-2H-pyran-4-yl)amino)-2-((1-(2,2-difluoroethyl)-1H-indazol-4-yl)amino)-5-fluoronicotinamide;
6-(((3R,4R)-3-aminotetrahydro-2H-pyran-4-yl)amino)-5-fluoro-2-((3-methoxy-1-methyl-1H-pyrazolo[3,4-b]pyridin-5-yl)amino)nicotinamide;
6-4(1R,2S)-2-amino-1-phenylpropyl)amino)-5-fluoro-2-((6-methoxy-5-(H-1,2,3-triazol-1-yl)pyridin-3-yl)amino)nicotinamide;
6-4(1R,2S)-2-amino-1-(4-methoxyphenyl)propyl)amino)-2-((1-ethyl-1H-indazol-5-yl)amino)-5-fluoronicotinamide;
6-(((3R,4S)-4-amino-1-(methylthio)pentan-3-yl)amino)-5-fluoro-2-((2-(2-methoxyethoxy)pyridin-4-yl)amino)nicotinamide;
6-(((3R,4R)-3-aminotetrahydro-2H-pyran-4-yl)amino)-2-((3-(difluoromethoxy)-1-methyl-1H-indazol-5-yl)amino)-5-fluoronicotinamide;
6-(((2S,3R)-2-aminohexan-3-yl)amino)-2-((3-(difluoromethoxy)-1-methyl-1H-indazol-5-yl)amino)-5-fluoronicotinamide;

6-(((1R,2S)-2-amino-1-cyclobutylpropyl)amino)-2-((3-(difluoromethoxy)-1-methyl-1H-indazol-5-yl)amino)-5-fluoronicotinamide;
6-(((2R,3S)-3-aminopentan-2-yl)amino)-2-((3-(difluoromethoxy)-1-methyl-1H-indazol-5-yl)amino)-5-fluoronicotinamide;
6-(((3R,4R)-3-aminotetrahydro-2H-pyran-4-yl)amino)-2-((3-(difluoromethoxy)-1-(2-methoxyethyl)-1H-indazol-5-yl)amino)-5-fluoronicotinamide;
6-(((2S,3R)-2-aminohexan-3-yl)amino)-2-((3-(difluoromethoxy)-1-(2-methoxyethyl)-1H-indazol-5-yl)amino)-5-fluoronicotinamide;
6-4(1R,2S)-2-amino-1-(4-(trifluoromethyl)phenyl)propyl)amino)-2-((2,6-dimethoxypyridin-4-yl)amino)-5-fluoronicotinamide;
6-(((1R,2S)-2-amino-1-cyclopropylbutyl)amino)-2-((1-ethyl-1H-indazol-5-yl)amino)-5-fluoronicotinamide;
6-(((1R,2S)-2-aminocyclohexyl)amino)-2-((1-ethyl-6-fluoro-1H-indazol-4-yl)amino)-5-fluoronicotinamide;
6-(((2S,3R)-2-amino-5-methylhexan-3-yl)amino)-5-fluoro-2-((1-methyl-1H-indazol-6-yl)amino)nicotinamide;
6-(((3R,4R)-3-aminotetrahydro-2H-pyran-4-yl)amino)-2-((1-ethyl-6-fluoro-1H-indazol-4-yl)amino)-5-fluoronicotinamide;
6-(((2S,3R)-2-aminopentan-3-yl)amino)-2-((1-ethyl-6-fluoro-1H-indazol-4-yl)amino)-5-fluoronicotinamide;
6-(((1R,2S)-2-amino-1-cyclopropylpropyl)amino)-2-((1-ethyl-6-fluoro-1H-indazol-4-yl)amino)-5-fluoronicotinamide;
6-(((2R,3S)-3-aminopentan-2-yl)amino)-2-((1-ethyl-6-fluoro-1H-indazol-4-yl)amino)-5-fluoronicotinamide;
6-4(1R,2S)-2-aminocyclohexyl)amino)-5-fluoro-2-((6-fluoro-1-(2-methoxyethyl)-1H-indazol-4-yl)amino)nicotinamide;
6-(((3R,4R)-3-aminotetrahydro-2H-pyran-4-yl)amino)-5-fluoro-2-((6-fluoro-1-(2-methoxyethyl)-1H-indazol-4-yl)amino)nicotinamide;
6-(((2S,3R)-2-aminopentan-3-yl)amino)-5-fluoro-2-((6-fluoro-1-(2-methoxyethyl)-1H-indazol-4-yl)amino)nicotinamide;
6-(((1R,2S)-2-amino-1-cyclopropylpropyl)amino)-5-fluoro-2-((6-fluoro-1-(2-methoxyethyl)-1H-indazol-4-yl)amino)nicotinamide;
6-(((2R,3S)-3-aminopentan-2-yl)amino)-5-fluoro-2-((6-fluoro-1-(2-methoxyethyl)-1H-indazol-4-yl)amino)nicotinamide;
6-(((2S,3R)-2-aminoheptan-3-yl)amino)-5-fluoro-2-((1-methyl-1H-indazol-6-yl)amino)nicotinamide;
6-(((1R,2S)-2-amino-1-((S)-2,2-dimethylcyclopropyl)propyl)amino)-5-fluoro-2-((6-methyl-5-(2H-1,2,3-triazol-2-yl)pyridin-3-yl)amino)nicotinamide;
6-(((1S,2S)-2-amino-1-(pyridin-2-yl)propyl)amino)-2-((1-ethyl-1H-indazol-5-yl)amino)-5-fluoronicotinamide;
6-(((1R,2S)-2-amino-1-cyclopropylbutyl)amino)-2-((3-(dimethylamino)-7-fluoro-1-methyl-1H-indazol-5-yl)amino)-5-fluoronicotinamide;
6-4(1R,2S)-2-aminocyclohexyl)amino)-5-fluoro-2-((1-(2-(methoxyethyl)-1H-pyrazolo[3,4-c]pyridin-4-yl)amino)nicotinamide;
(R)-6-((1-amino-4-methylpentan-2-yl)amino)-5-fluoro-2-((1-(2-methoxyethyl)-1H-pyrazolo[3,4-c]pyridin-4-yl)amino)nicotinamide;
6-4(1R,2S)-2-amino-1-cyclopropylpropyl)amino)-5-fluoro-2-((1-(2-methoxyethyl)-1H-pyrazolo[3,4-c]pyridin-4-yl)amino)nicotinamide;
6-(((2R,3S)-3-aminopentan-2-yl)amino)-5-fluoro-2-((1-methyl-1H-indazol-6-yl)amino)nicotinamide;
6-(((2S,3R)-2-amino-5-methylhexan-3-yl)amino)-5-fluoro-2-((1-(2-methoxyethyl)-1H-pyrazolo[3,4-c]pyridin-4-yl)amino)nicotinamide;
6-(((1R,2S)-2-amino-1-cyclobutylpropyl)amino)-5-fluoro-2-((1-(2-methoxyethyl)-1H-pyrazolo[3,4-c]pyridin-4-yl)amino)nicotinamide;
6-4(1R,2S)-2-aminocyclohexyl)amino)-2-((1-(2,2-difluoroethyl)-1H-pyrazolo[3,4-c]pyridin-4-yl)amino)-5-fluoronicotinamide;
6-(((3R,4R)-3-aminotetrahydro-2H-pyran-4-yl)amino)-2-((1-(2,2-difluoroethyl)-1H-pyrazolo[3,4-c]pyridin-4-yl)amino)-5-fluoronicotinamide;
(R)-6-((1-amino-4-methylpentan-2-yl)amino)-2-((1-(2,2-difluoroethyl)-1H-pyrazolo[3,4-c]pyridin-4-yl)amino)-5-fluoronicotinamide;
6-4(2S,3R)-2-aminopentan-3-yl)amino)-2-((1-(2,2-difluoroethyl)-1H-pyrazolo[3,4-c]pyridin-4-yl)amino)-5-fluoronicotinamide;
6-(((2S,3R)-2-aminohexan-3-yl)amino)-2-((1-(2,2-difluoroethyl)-1H-pyrazolo[3,4-c]pyridin-4-yl)amino)-5-fluoronicotinamide;
6-(((1R,2S)-2-amino-1-cyclopropylpropyl)amino)-2-((1-(2,2-difluoroethyl)-1H-pyrazolo[3,4-c]pyridin-4-yl)amino)-5-fluoronicotinamide;
6-4(2S,3R)-2-aminoheptan-3-yl)amino)-2-((1-(2,2-difluoroethyl)-1H-pyrazolo[3,4-c]pyridin-4-yl)amino)-5-fluoronicotinamide;
6-(((2S,3R)-2-aminopentan-3-yl)amino)-2-((3-(dimethylamino)-1-methyl-1H-indazol-5-yl)amino)-5-fluoronicotinamide;
6-(((2R,3S)-3-aminopentan-2-yl)amino)-5-fluoro-2-((1-methyl-1H-indazol-5-yl)amino)nicotinamide;
6-(((2S,3R)-2-amino-5-methylhexan-3-yl)amino)-2-((1-(2,2-difluoroethyl)-1H-pyrazolo[3,4-c]pyridin-4-yl)amino)-5-fluoronicotinamide;
6-(((1R,2S)-2-amino-1-cyclobutylpropyl)amino)-2-((1-(2,2-difluoroethyl)-1H-pyrazolo[3,4-c]pyridin-4-yl)amino)-5-fluoronicotinamide;
6-(((2R,3S)-3-aminopentan-2-yl)amino)-2-((1-(2,2-difluoroethyl)-1H-pyrazolo[3,4-c]pyridin-4-yl)amino)-5-fluoronicotinamide;
6-(((1R,2S)-2-amino-1-cyclopropylpropyl)amino)-5-fluoro-2-(quinolin-5-ylamino)nicotinamide;
(R)-6-((1-amino-4-methylpentan-2-yl)amino)-2-((1-ethyl-1H-pyrazolo[3,4-c]pyridin-4-yl)amino)-5-fluoronicotinamide;
6-(((1R,2S)-2-amino-1-cyclobutylpropyl)amino)-2-((1-ethyl-1H-pyrazolo[3,4-c]pyridin-4-yl)amino)-5-fluoronicotinamide;
6-(((1R,2S)-2-amino-1-(2-fluorophenyl)propyl)amino)-5-fluoro-2-((6-methyl-5-(2H-1,2,3-triazol-2-yl)pyridin-3-yl)amino)nicotinamide;
6-(((2R,3S)-3-aminopentan-2-yl)amino)-2-((5-cyclopropylpyridin-3-yl)amino)-5-fluoronicotinamide;
6-(((1R,2S)-2-amino-1-(2-fluorophenyl)propyl)amino)-2-((1-ethyl-1H-indazol-5-yl)amino)-5-fluoronicotinamide;
6-(((1R,2S)-2-amino-1-(2-fluorophenyl)propyl)amino)-2-((2,6-dimethoxypyridin-4-yl)amino)-5-fluoronicotinamide;
6-(((1R,2S)-2-amino-1-(3-fluorophenyl)propyl)amino)-2-((1-ethyl-1H-indazol-5-yl)amino)-5-fluoronicotinamide;

6-(((1R,2S)-2-amino-1-(3-fluorophenyl)propyl)amino)-2-((2,6-dimethoxypyridin-4-yl)amino)-5-fluoronicotinamide;
6-(((1S,2S)-2-amino-1-(thiophen-2-yl)propyl)amino)-5-fluoro-2-((6-methyl-5-(2H-1,2,3-triazol-2-yl)pyridin-3-yl)amino)nicotinamide;
6-(((1S,2S)-2-amino-1-(thiophen-2-yl)propyl)amino)-2-((1-ethyl-1H-indazol-5-yl)amino)-5-fluoronicotinamide;
6-(((2R,3S)-3-amino-1-phenylbutan-2-yl)amino)-2-((1-ethyl-1H-indazol-5-yl)amino)-5-fluoronicotinamide;
6-(((2R,3S)-3-amino-1-phenylbutan-2-yl)amino)-2-((3-(dimethylamino)-1-methyl-1H-indazol-5-yl)amino)-5-fluoronicotinamide;
6-(((2S,3R)-2-aminopentan-3-yl)amino)-5-fluoro-2-((1-methyl-3-(pyrrolidin-1-yl)-1H-indazol-5-yl)amino)nicotinamide;
6-(((3R,4S)-4-aminohexan-3-yl)amino)-5-fluoro-2-((2-(2-methoxyethoxy)pyridin-4-yl)amino)nicotinamide;
6-(((1R,2S)-2-aminocyclohexyl)amino)-5-fluoro-2-(m-tolylamino)nicotinamide;
6-(((1R,2S)-2-aminocyclohexyl)amino)-5-fluoro-2-(p-tolylamino)nicotinamide;
6-(((1R,2S)-2-aminocyclohexyl)amino)-2-((3,4-dimethylphenyl)amino)-5-fluoronicotinamide;
2-((3-(2H-1,2,3-triazol-2-yl)phenyl)amino)-6-(((1R,2S)-2-aminocyclohexyl)amino)-5-fluoronicotinamide;
2-((3-(1H-1,2,3-triazol-1-yl)phenyl)amino)-6-(((1R,2S)-2-aminocyclohexyl)amino)-5-fluoronicotinamide;
6-(((1R,2S)-2-aminocyclohexyl)amino)-2-((3-chlorophenyl)amino)-5-fluoronicotinamide;
6-(((1R,2S)-2-amino-1-cyclopropylpropyl)amino)-5-fluoro-2-(m-tolylamino)nicotinamide;
6-(((1R,2S)-2-aminocyclohexyl)amino)-5-fluoro-2-((3-fluorophenyl)amino)nicotinamide;
6-(((1R,2S)-2-aminocyclohexyl)amino)-5-fluoro-2-((4-fluorophenyl)amino)nicotinamide;
2-((3-acetylphenyl)amino)-6-(((1R,2S)-2-aminocyclohexyl)amino)-5-fluoronicotinamide;
6-(((1R,2S)-2-aminocyclohexyl)amino)-5-fluoro-2-((3-(trifluoromethoxy)phenyl)amino)nicotinamide;
6-(((1R,2S)-2-aminocyclohexyl)amino)-5-fluoro-2-((3-chloro-4-methylphenyl)amino)nicotinamide;
6-(((1R,2S)-2-aminocyclohexyl)amino)-5-fluoro-2-((3-isopropoxyphenyl)amino)nicotinamide;
6-(((1R,2S)-2-aminocyclohexyl)amino)-2-((3,4-difluorophenyl)amino)-5-fluoronicotinamide;
6-(((1R,2S)-2-aminocyclohexyl)amino)-5-fluoro-2-((4-isopropoxyphenyl)amino)nicotinamide;
6-(((1R,2S)-2-amino-1-cyclopropylpropyl)amino)-2-((3,5-dimethylphenyl)amino)-5-fluoronicotinamide;
6-(((1R,2S)-2-aminocyclohexyl)amino)-2-((3-ethylphenyl)amino)-5-fluoronicotinamide 6-(((1R,2S)-2-amino-1-(3-fluorophenyl)propyl)amino)-5-fluoro-2-((5-fluoro-6-morpholinopyridin-3-yl)amino)nicotinamide;
6-(((1R,2S)-2-amino-1-(3-fluorophenyl)propyl)amino)-2-(3-(dimethylamino)-1-methyl-1H-indazol-5-yl)amino)-5-fluoronicotinamide;
6-(((1R,2S)-2-amino-1-(3-fluorophenyl)propyl)amino)-5-fluoro-2-((5-fluoro-6-methylpyridin-3-yl)amino)nicotinamide;
6-(((1R,2S)-2-amino-1-(3-fluorophenyl)propyl)amino)-5-fluoro-2-((1-(2-methoxyethyl)-1H-indazol-5-yl)amino)nicotinamide;
6-(((1R,2S)-2-amino-1-(4-methoxyphenyl)propyl)amino)-5-fluoro-2-((1-(2-methoxyethyl)-1H-indazol-5-yl)amino)nicotinamide;
6-(((1R,2S)-2-aminocyclohexyl)amino)-5-fluoro-2-((3-((2-methoxyethyl)(methyl)amino)-1-methyl-1H-indazol-5-yl)amino)nicotinamide;
6-(((3R,4R)-3-aminotetrahydro-2H-pyran-4-yl)amino)-5-fluoro-2-((3-((2-methoxyethyl)(methyl)amino)-1-methyl-1H-indazol-5-yl)amino)nicotinamide;
6-(((2S,3R)-2-aminopentan-3-yl)amino)-5-fluoro-2-((3-((2-methoxyethyl)(methyl)amino)-1-methyl-1H-indazol-5-yl)amino)nicotinamide;
6-(((1R,2S)-2-amino-1-cyclopropylpropyl)amino)-5-fluoro-2-((3-methoxyphenyl)amino)nicotinamide;
6-(((1R,2S)-2-amino-1-cyclopropylpropyl)amino)-5-fluoro-2-((3-((2-methoxyethyl)(methyl)amino)-1-methyl-1H-indazol-5-yl)amino)nicotinamide;
6-(((1R,2S)-2-amino-1-cyclopropylpropyl)amino)-2-((3,5-dimethoxyphenyl)amino)-5-fluoronicotinamide;
6-(((1R,2S)-2-aminocyclohexyl)amino)-5-fluoro-2-((5-(4-methyl-1H-pyrazol-1-yl)pyridin-3-yl)amino)nicotinamide;
6-(((2S,3R)-2-aminopentan-3-yl)amino)-5-fluoro-2-(m-tolylamino)nicotinamide;
2-((3-(2H-1,2,3-triazol-2-yl)phenyl)amino)-6-(((2S,3R)-2-aminopentan-3-yl)amino)-5-fluoronicotinamide;
2-((3-(1H-1,2,3-triazol-1-yl)phenyl)amino)-6-(((2S,3R)-2-aminopentan-3-yl)amino)-5-fluoronicotinamide;
6-(((2S,3R)-2-aminopentan-3-yl)amino)-2-((3,4-dimethylphenyl)amino)-5-fluoronicotinamide;
2-((3-acetylphenyl)amino)-6-(((2S,3R)-2-aminopentan-3-yl)amino)-5-fluoronicotinamide;
2-((3-(2H-1,2,3-triazol-2-yl)phenyl)amino)-6-(((1R,2S)-2-amino-1-cyclopropylpropyl)amino)-5-fluoronicotinamide;
6-(((1R,2S)-2-amino-1-cyclopropylpropyl)amino)-2-((3,4-dimethoxyphenyl)amino)-5-fluoronicotinamide;
2-((3-(1H-1,2,3-triazol-1-yl)phenyl)amino)-6-(((1R,2S)-2-amino-1-cyclopropylpropyl)amino)-5-fluoronicotinamide;
6-(((1R,2S)-2-amino-1-cyclopropylpropyl)amino)-2-((3,4-dimethylphenyl)amino)-5-fluoronicotinamide;
2-((3-acetylphenyl)amino)-6-(((1R,2S)-2-amino-1-cyclopropylpropyl)amino)-5-fluoronicotinamide;
6-4(1R,2S)-2-aminocyclohexyl)amino)-2-((5-(4-chloro-1H-pyrazol-1-yl)pyridin-3-yl)amino)-5-fluoronicotinamide;
6-(((1R,2S)-2-aminocyclohexyl)amino)-5-fluoro-2-((3-(methylamino)-1H-indazol-5-yl)amino)nicotinamide;
6-4(1R,2S)-2-amino-1-cyclopropylpropyl)amino)-5-fluoro-2-((3-methoxy-4-methylphenyl)amino)nicotinamide;
6-(((1R,2S)-2-aminocyclohexyl)amino)-2-((3-(dimethylamino)-1H-indazol-5-yl)amino)-5-fluoronicotinamide;
6-(((2S,3R)-2-aminopentan-3-yl)amino)-2-((3-(dimethylamino)-1H-indazol-5-yl)amino)-5-fluoronicotinamide;
6-(((1R,2S)-2-amino-1-cyclopropylpropyl)amino)-2-((3-(dimethylamino)-1H-indazol-5-yl)amino)-5-fluoronicotinamide;
6-(((2R,3S)-3-aminopentan-2-yl)amino)-2-((3-(dimethylamino)-1H-indazol-5-yl)amino)-5-fluoronicotinamide;
6-(((1R,2S)-2-aminocyclohexyl)amino)-5-fluoro-2-((1-methyl-3-(methylamino)-1H-indazol-5-yl)amino)nicotinamide;
6-(((1R,2S)-2-amino-1-cyclopropylpropyl)amino)-5-fluoro-2-((1-methyl-3-(methylamino)-1H-indazol-5-yl)amino)nicotinamide;

6-(((1R,2S)-2-amino-1-cyclobutylpropyl)amino)-5-fluoro-2-((2-methoxypyridin-4-yl)amino)nicotinamide;
6-(((2R,3S)-3-amino-1-cyclopropylbutan-2-yl)amino)-2-((1-ethyl-3-methoxy-1H-indazol-5-yl)amino)-5-fluoronicotinamide;
6-(((1S,2S)-2-amino-1-(thiophen-2-yl)propyl)amino)-5-fluoro-2-((5-fluoro-6-morpholinopyridin-3-yl)amino)nicotinamide;
6-(((1S,2S)-2-amino-1-(thiophen-2-yl)propyl)amino)-2-((1-ethyl-1H-indazol-4-yl)amino)-5-fluoronicotinamide;
6-(((2S,3R)-2-amino-5-methylhexan-3-yl)amino)-2-((1-ethyl-3-methoxy-1H-indazol-5-yl)amino)-5-fluoronicotinamide;
6-(((1S,2S)-2-amino-1-(thiophen-2-yl)propyl)amino)-2-((3-(dimethylamino)-1-methyl-1H-indazol-5-yl)amino)-5-fluoronicotinamide;
6-(((1S,2S)-2-amino-1-(5-chlorothiophen-2-yl)propyl)amino)-2-((1-ethyl-1H-indazol-4-yl)amino)-5-fluoronicotinamide;
6-(((1R,2S)-2-amino-1-(2-fluorophenyl)propyl)amino)-2-((1-ethyl-1H-indazol-4-yl)amino)5-fluoronicotinamide;
2-((5-acetyl-6-methylpyridin-3-yl)amino)-6-(((1R,2S)-2-aminocyclohexyl)amino)-5-fluoronicotinamide;
6-(((1R,2S)-2-amino-1-cyclopropylpropyl)amino)-5-fluoro-2-((5-(4-methyl-1H-pyrazol-1-yl)pyridin-3-yl)amino)nicotinamide;
6-(((2S,3R)-2-aminopentan-3-yl)amino)-2-((1-ethyl-3-methoxy-1H-indazol-5-yl)amino)-5-fluoronicotinamide;
6-(((1R,2S)-2-amino-1-cyclopropylpropyl)amino)-2-((5-(4-chloro-1H-pyrazol-1-yl)pyridin-3-yl)amino)-5-fluoronicotinamide;
6-(((1R,2S)-2-amino-1-cyclobutylpropyl)amino)-5-fluoro-2-((5-(4-methyl-1H-pyrazol-1-yl)pyridin-3-yl)amino)nicotinamide;
(R)-6-((1-amino-4-methylpentan-2-yl)amino)-5-fluoro-2-((5-(4-methyl-1H-pyrazol-1-yl)pyridin-3-yl)amino)nicotinamide;
6-(((2S,3R)-2-amino-5-methylhexan-3-yl)amino)-5-fluoro-2-((5-(4-methyl-1H-pyrazol-1-yl)pyridin-3-yl)amino)nicotinamide;
6-(((3R,4R)-3-aminotetrahydro-2H-pyran-4-yl)amino)-5-fluoro-2-((5-(4-methyl-1H-pyrazol-1-yl)pyridin-3-yl)amino)nicotinamide;
6-(((2R,3S)-3-amino-1-cyclopropylbutan-2-yl)amino)-2-((1-(2,2-difluoroethyl)-3-methoxy-1H-indazol-5-yl)amino)-5-fluoronicotinamide;
6-(((1R,2S)-2-amino-1-cyclopropylpropyl)amino)-5-fluoro-2-((5-(4-methyl-2H-1,2,3-triazol-2-yl)pyridin-3-yl)amino)nicotinamide;
6-(((1R,2S)-2-amino-1-cyclopropylpropyl)amino)-5-fluoro-2-((3-methoxy-1-(2-methoxyethyl)-1H-indazol-5-yl)amino)nicotinamide;
6-(((2S,3R)-2-amino-5-methylhexan-3-yl)amino)-2-((1-(2,2-difluoroethyl)-3-methoxy-1H-indazol-5-yl)amino)-5-fluoronicotinamide;
6-(((1R,2S)-2-amino-1-cyclobutylpropyl)amino)-5-fluoro-2-((3-methoxy-1-(2-methoxyethyl)-1H-indazol-5-yl)amino)nicotinamide;
(R)-6-((1-amino-4-methylpentan-2-yl)amino)-2-((3-(difluoromethoxy)-1-methyl-1H-indazol-5-yl)amino)-5-fluoronicotinamide;
(R)-6-((1-amino-4-methylpentan-2-yl)amino)-2-((3-(difluoromethoxy)-1-(2-methoxyethyl)-1H-indazol-5-yl)amino)-5-fluoronicotinamide;
6-(((1R,2S)-2-amino-1-cyclobutylpropyl)amino)-2-((3-(difluoromethoxy)-1-(2-methoxyethyl)-1H-indazol-5-yl)amino)-5-fluoronicotinamide;
6-(((1R,2S)-2-amino-1-cyclopropylbutyl)amino)-2-((1,3-dimethyl-1H-indazol-5-yl)amino)-5-fluoronicotinamide;
6-(((1R,2S)-2-amino-1-cyclopropylbutyl)amino)-5-fluoro-2-((1-methyl-1H-indazol-4-yl)amino)nicotinamide;
6-(((1R,2S)-2-amino-1-cyclopropylbutyl)amino)-2-((1-(2,2-difluoroethyl)-1H-indazol-4-yl)amino)-5-fluoronicotinamide;
6-(((2S,3R)-2-aminopentan-3-yl)amino)-2-((1-(2,2-difluoroethyl)-3-methoxy-1H-indazol-5-yl)amino)-5-fluoronicotinamide;
6-(((1R,2S)-2-amino-1-(3,5-difluorophenyl)propyl)amino)-5-fluoro-2-((1-(2-methoxyethyl)-1H-indazol-5-yl)amino)nicotinamide;
6-(((1R,2S)-2-amino-1-(3,4-difluorophenyl)propyl)amino)-5-fluoro-2-((6-methyl-5-(2H-1,2,3-triazol-2-yl)pyridin-3-yl)amino)nicotinamide;
6-(((1R,2S)-2-amino-1-(3,4-difluorophenyl)propyl)amino)-2-((3-(dimethylamino)-1-methyl-1H-indazol-5-yl)amino)-5-fluoronicotinamide;
6-(((1R,2S)-2-amino-1-(3,4-difluorophenyl)propyl)amino)-5-fluoro-2-((1-(2-methoxyethyl)-1H-indazol-5-yl)amino)nicotinamide;
6-(((1R,2S)-2-amino-1-(3,4-difluorophenyl)propyl)amino)-2-((1-ethyl-1H-indazol-4-yl)amino)-5-fluoronicotinamide;
6-4(2S,3R)-2-aminopentan-3-yl)amino)-5-fluoro-2-((3-methoxybenzo[d]isoxazol-5-yl)amino)nicotinamide;
6-(((1R,2S)-2-amino-1-cyclobutylpropyl)amino)-2-((2,6-dimethoxypyridin-4-yl)amino)-5-fluoronicotinamide;
6-(((1R,2S)-2-amino-1-cyclobutylpropyl)amino)-5-fluoro-2-((2-(2-methoxyethoxy)pyridin-4-yl)amino)nicotinamide;
2-((5-(1H-pyrazol-1-yl)pyridin-3-yl)amino)-6-(((2S,3R)-2-amino-5-methylhexan-3-yl)amino)-5-fluoronicotinamide;
6-(((1R,2S)-2-amino-1-cyclopropylpropyl)amino)-2-((1-(2,2-difluoroethyl)-1H-indazol-5-yl)amino)-5-fluoronicotinamide;
6-(((1R,2S)-2-amino-1-cyclopropylpropyl)amino)-2-((3-(dimethylamino)-1-methyl-1H-indazol-5-yl)amino)-5-fluoronicotinamide;
6-(((1R,2S)-2-amino-1-cyclopropylpropyl)amino)-2-((1-ethyl-3-methoxy-1H-indazol-5-yl)amino)-5-fluoronicotinamide;
6-(((1R,2S)-2-amino-1-cyclopropylpropyl)amino)-2-((1-(2,2-difluoroethyl)-3-methoxy-1H-indazol-5-yl)amino)-5-fluoronicotinamide;
6-(((1R,2S)-2-amino-1-cyclopropylpropyl)amino)-2-((1-(2,2-difluoroethyl)-1H-indazol-4-yl)amino)-5-fluoronicotinamide;
6-(((1R,2S)-2-amino-1-cyclopropylpropyl)amino)-5-fluoro-2-((5-fluoro-6-morpholinopyridin-3-yl)amino)nicotinamide;
(R)-6-((1-amino-4-methylpentan-2-yl)amino)-5-fluoro-2-((3-methoxy-1-methyl-1H-indazol-5-yl)amino)nicotinamide;
(R)-6-((1-amino-3-cyclopropylpropan-2-yl)amino)-5-fluoro-2-((3-methoxy-1-methyl-1H-indazol-5-yl)amino)nicotinamide;

6-(((1R,2S)-2-amino-1-cyclobutylpropyl)amino)-5-fluoro-2-(quinolin-6-ylamino)nicotinamide;

6-(((2S,3R)-2-aminohexan-3-yl)amino)-5-fluoro-2-((3-methoxy-1-methyl-1H-indazol-5-yl)amino)nicotinamide;

6-(((1R,2S)-2-amino-1-cyclobutylpropyl)amino)-5-fluoro-2-((3-methoxy-1-methyl-1H-indazol-5-yl)amino)nicotinamide;

6-(((2S,3R)-2-aminoheptan-3-yl)amino)-5-fluoro-2-((3-methoxy-1-methyl-1H-indazol-5-yl)amino)nicotinamide;

6-(((2R,3S)-3-aminopentan-2-yl)amino)-5-fluoro-2-((3-methoxy-1-methyl-1H-indazol-5-yl)amino)nicotinamide;

(R)-6-((1-amino-4-methylpentan-2-yl)amino)-2-((3-(dimethylamino)-1-methyl-1H-indazol-5-yl)amino)-5-fluoronicotinamide;

6-(((2S,3R)-2-aminohexan-3-yl)amino)-2-((3-(dimethylamino)-1-methyl-1H-indazol-5-yl)amino)-5-fluoronicotinamide;

6-(((1R,2S)-2-amino-1-cyclobutylpropyl)amino)-2-((3-(dimethylamino)-1-methyl-1H-indazol-5-yl)amino)-5-fluoronicotinamide;

6-(((1R,2S)-2-amino-1-cyclobutylpropyl)amino)-2-((1-ethyl-1H-indazol-5-yl)amino)-5-fluoronicotinamide;

6-(((2S,3R)-2-aminohexan-3-yl)amino)-2-((1-ethyl-1H-indazol-4-yl)amino)-5-fluoronicotinamide;

6-(((1R,2S)-2-amino-1-cyclobutylpropyl)amino)-2-((1-ethyl-1H-indazol-4-yl)amino)-5-fluoronicotinamide;

6-(((2S,3R)-2-aminoheptan-3-yl)amino)-2-((1-ethyl-1H-indazol-4-yl)amino)-5-fluoronicotinamide; and mixture of 6-((1-acetyl-3-aminopiperidin-4-yl)amino)-5-fluoro-2-((6-methyl-5-(2H-1,2,3-triazol-2-yl)pyridin-3-yl)amino)nicotinamide(3S,4R) (3R,4S).

* * * * *